(12) United States Patent
Venkatraman et al.

(10) Patent No.: US 12,428,415 B2
(45) Date of Patent: Sep. 30, 2025

(54) MATRIPTASE 2 INHIBITORS AND USES THEREOF

(71) Applicant: Disc Medicine, Inc., Watertown, MA (US)

(72) Inventors: Srikanth Venkatraman, Edison, NJ (US); Subhendu Mukherjee, Serampore (IN); Rajeev Goswami, Dehradun (IN); Venkateshwar Rao Gummadi, Bangalore (IN); A. Bharathi Raja, Krishnagiri Dist. (IN); Murtuza Hadianawala, Rajkot (IN)

(73) Assignee: Disc Medicine, Inc., Watertown, MA (US)

( * ) Notice: Subject to any disclaimer, the term of this patent is extended or adjusted under 35 U.S.C. 154(b) by 972 days.

(21) Appl. No.: 17/282,176

(22) PCT Filed: Oct. 2, 2019

(86) PCT No.: PCT/US2019/054196
§ 371 (c)(1),
(2) Date: Apr. 1, 2021

(87) PCT Pub. No.: WO2020/072580
PCT Pub. Date: Apr. 9, 2020

(65) Prior Publication Data
US 2023/0043159 A1    Feb. 9, 2023

Related U.S. Application Data

(60) Provisional application No. 62/740,057, filed on Oct. 2, 2018.

(51) Int. Cl.
| | | |
|---|---|---|
| *C07D 471/04* | (2006.01) | |
| *C07D 209/42* | (2006.01) | |
| *C07D 233/28* | (2006.01) | |
| *C07D 401/06* | (2006.01) | |
| *C07D 401/12* | (2006.01) | |
| *C07D 401/14* | (2006.01) | |
| *C07D 403/12* | (2006.01) | |
| *C07D 403/14* | (2006.01) | |
| *C07D 405/12* | (2006.01) | |
| *C07D 409/06* | (2006.01) | |
| *C07D 409/12* | (2006.01) | |
| *C07D 413/04* | (2006.01) | |
| *C07D 413/10* | (2006.01) | |
| *C07D 413/14* | (2006.01) | |
| *C07D 417/04* | (2006.01) | |
| *C07D 417/12* | (2006.01) | |
| *C07D 471/08* | (2006.01) | |

(52) U.S. Cl.
CPC ......... *C07D 471/04* (2013.01); *C07D 209/42* (2013.01); *C07D 233/28* (2013.01); *C07D 401/06* (2013.01); *C07D 401/12* (2013.01); *C07D 401/14* (2013.01); *C07D 403/12* (2013.01); *C07D 403/14* (2013.01); *C07D 405/12* (2013.01); *C07D 409/06* (2013.01); *C07D 409/12* (2013.01); *C07D 413/04* (2013.01); *C07D 413/10* (2013.01); *C07D 413/14* (2013.01); *C07D 417/04* (2013.01); *C07D 417/12* (2013.01); *C07D 471/08* (2013.01)

(58) Field of Classification Search
CPC .. C07D 209/08; C07D 209/12; C07D 209/22; C07D 209/40; C07D 209/42; C07D 233/28; C07D 401/06; C07D 401/12; C07D 401/14; C07D 403/04; C07D 403/06; C07D 403/12; C07D 403/14; C07D 405/12; C07D 409/06; C07D 409/12; C07D 413/04; C07D 413/06; C07D 413/10; C07D 413/12; C07D 413/14; C07D 417/04; C07D 417/12; C07D 471/04; C07D 471/08; C07D 487/08
See application file for complete search history.

(56) References Cited

U.S. PATENT DOCUMENTS

| | | | | |
|---|---|---|---|---|
| 5,877,199 A | * | 3/1999 | Birdsall | ............... C07D 209/18 548/441 |
| 6,201,006 B1 | * | 3/2001 | Koo | ..................... C07D 403/14 548/518 |
| 7,045,544 B2 | | 5/2006 | Erguden et al. | |
| 8,293,915 B2 | | 10/2012 | Tully et al. | |
| 8,304,419 B2 | | 11/2012 | Chong et al. | |
| 9,365,853 B2 | | 6/2016 | Richter et al. | |
| 2002/0013314 A1 | | 1/2002 | Zhu et al. | |
| 2015/0005277 A1 | | 1/2015 | Wang et al. | |

FOREIGN PATENT DOCUMENTS

| | | |
|---|---|---|
| CN | 101857631 A | 10/2010 |
| CN | 105175309 A | 12/2015 |
| CN | 106998692 A | 8/2017 |
| JP | H0578344 A | 3/1993 |

(Continued)

OTHER PUBLICATIONS

PubChem et al., CID 67761733, publ. Nov. 30, 2012, pp. 1-8 (Year: 2012).*

(Continued)

*Primary Examiner* — Sarah Pihonak
(74) *Attorney, Agent, or Firm* — Wolf, Greenfield & Sacks, P.C.

(57) ABSTRACT

The present invention provides compounds for inhibiting matriptase 2, or a mutant thereof, and compositions and methods of use thereof.

32 Claims, No Drawings

(56) References Cited

FOREIGN PATENT DOCUMENTS

| JP | H06227971 A | 8/1994 | | |
|---|---|---|---|---|
| JP | H10-67682 A | 3/1998 | | |
| JP | H11246554 A | 9/1999 | | |
| JP | 2002-532479 A | 10/2002 | | |
| JP | 2004-537564 A | 12/2004 | | |
| JP | 2006-511562 A | 4/2006 | | |
| JP | 2007-532657 A | 11/2007 | | |
| JP | 2009-502767 A | 1/2009 | | |
| JP | 2010-529965 A | 9/2010 | | |
| WO | WO 95/33720 A1 | 12/1995 | | |
| WO | WO 00/35886 A2 | 6/2000 | | |
| WO | WO 01/00657 A2 | 1/2001 | | |
| WO | WO 01/97794 A2 | 12/2001 | | |
| WO | WO 03/010141 A2 | 2/2003 | | |
| WO | 2004056768 A2 | 7/2004 | | |
| WO | WO-2004094372 A2 * | 11/2004 | ........... | C07D 209/08 |
| WO | WO 2005/099709 A2 | 10/2005 | | |
| WO | WO 2007/010144 A1 | 1/2007 | | |
| WO | WO 2008/154271 A1 | 12/2008 | | |
| WO | WO 2009/095163 A2 | 8/2009 | | |
| WO | WO 2011/016528 A1 | 2/2011 | | |
| WO | 2017071653 A1 | 5/2017 | | |
| WO | WO 2017/156177 A1 | 9/2017 | | |
| WO | 2018112648 A1 | 6/2018 | | |
| WO | WO 2020/072580 A1 | 4/2020 | | |

OTHER PUBLICATIONS

Extended European Search Report for Application No. 19869116.4, mailed May 25, 2022.

International Search Report and Written Opinion for Application No. PCT/US2019/054196, mailed Jan. 6, 2020.

International Preliminary Report on Patentability for Application No. PCT/US2019/054196, mailed Apr. 15, 2021.

Goswami et al., Structure-guided discovery of 2-aryl/pyridin-2-yl-1H-indole derivatives as potent and selective hepsin inhibitors. Bioorg Med Chem Lett. Nov. 15, 2015;25(22):5309-14. doi: 10.1016/j.bmcl.2015.09.042. Epub Sep. 21, 2015.

Kettle et al., N-Benzylindole-2-carboxylic acids: potent functional antagonists of the CCR2b chemokine receptor. Bioorg Med Chem Lett. Jan. 19, 2004;14(2):405-8. doi: 10.1016/j.bmcl.2003.10.049.

Reddy et al., Catalyst-free Synthesis of 6-Hydroxy Indoles via the Condensation of Carboxymethyl Cyclohexadienones and Amines. J Org Chem. Aug. 18, 2017;82(16):8426-8437. doi: 10.1021/acs.joc.7b01136. Epub Jul. 28, 2017.

Astcian et al., "Design, Synthesis, and Biological Evaluation of Indole Biphenylcarboxylic Acids as PPARγ Antagonists," ACS Medicinal Chemistry Letters 6(9):998-1003 (2015).

Potter et al., "Structure-Guided Design of α-Amino Acid-Derived Pin1 Inhibitors," Bioorganic and Medicinal Chemistry Letters 20(2):586-590 (2010).

Sall et al., "Platelet Glycoprotein IIb-IIIa Receptor (GPIIb-IIIa) Antagonists Derived from Amidinoindoles," Bioorganic and Medicinal Chemistry Letters 6(1):81-86 (1996).

St-Georges et al., "Modulating the Selectivity of Matriptase-2 Inhibitors with Unnatural Amino Acids," European Journal of Medicinal Chemistry 129:110-123 (2017).

Zhou et al., "Discovery of a First-in-Class, Potent, Selective, and Orally Bioavailable Inhibitor of the p97 AAA ATPase (CB-5083)," Journal of Medicinal Chemistry 58:9480-9497 (2015).

Wu et al., Novel solid-phase synthesis of 1,2-dialkoxyindoles. Org Lett. Aug. 7, 2003;5(16):2935-8. doi: 10.1021/o1035153g.

* cited by examiner

MATRIPTASE 2 INHIBITORS AND USES THEREOF

CROSS-REFERENCE TO RELATED APPLICATIONS

This present application is a U.S. national stage filing under 35 U.S.C. § 371 of International Application No. PCT/US2019/054196, filed Oct. 2, 2019, which claims the benefit of priority to U.S. Provisional Application No. 62/740,057, filed Oct. 2, 2018, each of which is incorporated herein by reference in its entirety.

TECHNICAL FIELD OF THE INVENTION

The present invention relates to compounds and methods useful for inhibition of Matriptase 2 ("Mat-2"), or a mutant thereof. The invention also provides pharmaceutically acceptable compositions comprising compounds of the present invention and methods of using said compositions in the treatment of various disorders.

BACKGROUND OF THE INVENTION

Matriptase-2 is a cell surface serine protease with a modular structure. Mutations in matriptase-2 cause iron-refractory iron deficiency anemia (IRIDA), an iron deficiency disorder where the level of hepcidin is inappropriately high. The enzyme activity of matriptase-2 reduces hepcidin expression through the suppression of bone morphogenetic protein (BMP)/sons of mothers against decapentaplegic homologue protein (SMAD) signaling. Loss of or inhibition of matriptase-2 activity leads to an increase in hepcidin production by the liver.

SUMMARY OF THE INVENTION

It has now been found that compounds of the present invention, and pharmaceutically acceptable compositions thereof, are effective as Matriptase 2 inhibitors. In one aspect, the present invention provides a compound of Formula I:

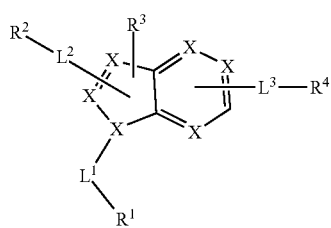

I or a pharmaceutically acceptable salt thereof, wherein each variable is as defined and described herein.

Compounds of the present invention, and pharmaceutically acceptable compositions thereof, are useful for treating a variety of diseases, disorders or conditions associated with relative or absolute hepcidin deficiency, or diseases, disorders, or conditions in which regulating iron metabolism by increasing hepcidin production by the liver may be therapeutically useful. Such diseases, disorders, or conditions include those described herein.

DETAILED DESCRIPTION OF CERTAIN EMBODIMENTS

1. General Description of Certain Embodiments of the Invention

Compounds of the present invention, and pharmaceutical compositions thereof, are useful as inhibitors of Matriptase 2, or a mutant thereof. Without wishing to be bound by any particular theory, it is believed that compounds of the present invention, and pharmaceutical compositions thereof, may inhibit the activity of Matriptase 2, or a mutant thereof, and thus treat certain diseases, disorders, or conditions associated with relative or absolute hepcidin deficiency, or diseases, disorders, or conditions in which regulating iron metabolism by increasing hepcidin production by the liver may be therapeutically useful, such as those described herein.

It has now been found that compounds of this invention, and pharmaceutically acceptable compositions thereof, are effective as Matripase 2 inhibitors. In one aspect, the present invention provides a compound of Formula I:

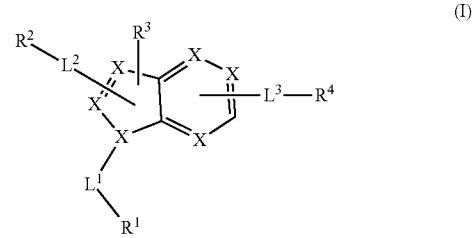

(I)

or a pharmaceutically acceptable salt thereof, wherein
  each X is independently C or N;
  $L^1$ is a bond, or an optionally substituted bivalent $C_{1-8}$ saturated or unsaturated, straight or branched hydrocarbon chain, wherein 1, 2, or 3 methylene units of the hydrocarbon chain are optionally and independently replaced by —S(O)$_2$—, —C(O)—, or —O—;
  $R^1$ is H, or an optionally substituted ring selected from phenyl, a 5-6 membered heteroaromatic ring having 1-4 heteroatoms independently selected from nitrogen, oxygen, and sulfur, a 8-10 membered bicyclic aromatic carbocyclic ring, and a 8-10 membered bicyclic heteroaromatic ring having 1-4 heteroatoms independently selected from nitrogen, oxygen, and sulfur;
  $L^2$ is an optionally substituted bivalent $C_{1-8}$ saturated or unsaturated, straight or branched hydrocarbon chain, wherein 1, 2, or 3 methylene units of the hydrocarbon chain are optionally and independently replaced by —NR—C(O)—, —C(O)—NR—, —C(O)—, —S(O)$_2$—, —C(O)—O—, —O—C(O)—, —NR—S(O)$_2$—, —S(O)$_2$—NR—, or -Cy-;
  -Cy- is an optionally substituted bivalent ring selected from phenyl, a 4-6 membered monocyclic heterocyclic ring having 1-4 heteroatoms independently selected from nitrogen, oxygen, and sulfur, and a 4-6 membered monocyclic heteroaromatic ring having 1-4 heteroatoms independently selected from nitrogen, oxygen, and sulfur;
  $R^2$ is H, or an optionally substituted ring selected from a 4-7 membered monocyclic carbocyclic ring, a 4-7 membered monocyclic heterocyclic ring having 1-4 heteroatoms independently selected from nitrogen, oxygen, and sulfur, a 7-10 membered bicyclic carbocyclic ring, a 7-10 membered bicyclic heterocarboxylic ring having 1-4 heteroatoms independently selected from nitrogen, oxygen, and sulfur, phenyl, 5-6 membered monocyclic heteroaromatic ring having 1-4 heteroatoms independently selected from nitrogen, oxygen, and sulfur, a 8-10 membered bicyclic aromatic ring, a 8-10 membered bicyclic heteroaromatic ring having 1-4 heteroatoms independently selected from nitrogen, oxygen, and sulfur, and adamantly;

$R^3$ is H, halogen, —CN, —C(O)H, —NH$_2$, —NO$_2$, —COOH, —CONH$_2$, —NH—C(O)—O—C$_{1-6}$aliphatic, C$_{1-6}$aliphatic, or —C(O)—C$_{1-6}$aliphatic, wherein the C$_{1-6}$aliphatic is optionally substituted;

$L^3$ is bond, or an optionally substituted bivalent C$_{1-8}$ saturated or unsaturated, straight or branched hydrocarbon chain, wherein 1, 2, or 3 methylene units of the hydrocarbon chain are optionally replaced by —CO—;

$R^4$ is —NHR, —C(N═R)—NHR, —NH—C(N═R)—NHR, —F, or —OH; and each R is independently H, —C$_{1-8}$alkyl, —OC$_{1-8}$alkyl, —C(O)—C$_{1-8}$alkyl, —C(O)—OC$_{1-8}$alkyl, 4-7 membered monocyclic carbocyclyl, —O-(4-7 membered monocyclic carbocyclyl), —C(O)-(4-7 membered monocyclic carbocyclyl), —C(O)—O-(4-7 membered monocyclic carbocyclyl), phenyl, —O-phenyl, —C(O)-phenyl, —C(O)—O-phenyl, 8-10 membered bicyclic aryl, —O-(8-10 membered bicyclic aryl), —C(O)-(8-10 membered bicyclic aryl), or —C(O)—O-(8-10 membered bicyclic aryl), wherein each of the C$_{1-8}$alkyl, 4-7 membered monocyclic carbocyclyl, phenyl, and 8-10 membered bicyclic aryl is optionally and independently substituted.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic C$_3$-C$_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bicyclic ring" or "bicyclic ring system" refers to any bicyclic ring system, i.e. carbocyclic or heterocyclic, saturated or having one or more units of unsaturation, having one or more atoms in common between the two rings of the ring system. Thus, the term includes any permissible ring fusion, such as ortho-fused or spirocyclic. As used herein, the term "heterobicyclic" is a subset of "bicyclic" that requires that one or more heteroatoms are present in one or both rings of the bicycle. Such heteroatoms may be present at ring junctions and are optionally substituted, and may be selected from nitrogen (including N-oxides), oxygen, sulfur (including oxidized forms such as sulfones and sulfonates), phosphorus (including oxidized forms such as phosphates), boron, etc. In some embodiments, a bicyclic group has 7-12 ring members and 0-4 heteroatoms independently selected from nitrogen, oxygen, or sulfur. As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bicyclic rings include:

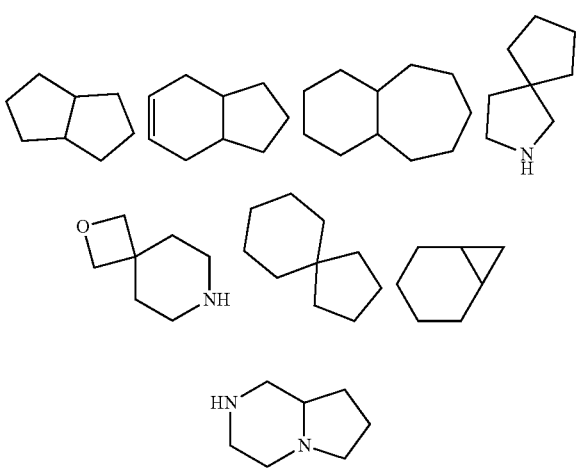

Exemplary bridged bicyclics include:

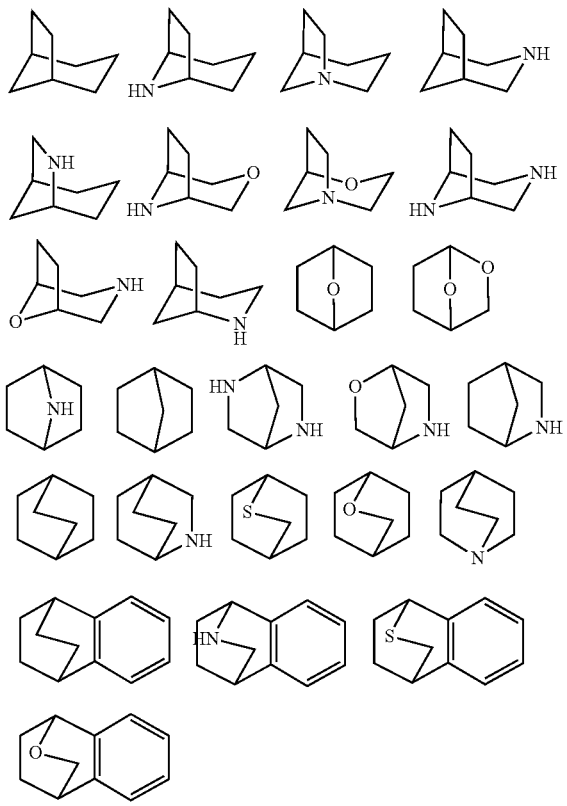

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

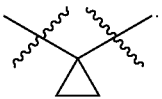 [SMILES: *C1(*)CC1]

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl, pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Each optional substituent on a substitutable carbon is a monovalent substituent independently selected from halogen; —(CH$_2$)$_{0-4}$R$^\circ$; —(CH$_2$)$_{0-4}$OR$^\circ$; —O(CH$_2$)$_{0-4}$R$^\circ$, —O—(CH$_2$)$_{0-4}$C(O)OR$^\circ$; —(CH$_2$)$_{0-4}$CH(OR$^\circ$)$_2$; —(CH$_2$)$_{0-4}$SR$^\circ$; —(CH$_2$)$_{0-4}$Ph, which may be substituted with R$^\circ$; —(CH$_2$)$_{0-4}$O(CH$_2$)$_{0-1}$Ph which may be substituted with R$^\circ$; —CH=CHPh, which may be substituted with R$^\circ$; —(CH$_2$)$_{0-4}$O(CH$_2$)$_{0-1}$-pyridyl which may be substituted with R$^\circ$; —NO$_2$; —CN; —N$_3$; —(CH$_2$)$_{0-4}$N(R$^\circ$)$_2$; —(CH$_2$)$_{0-4}$N(R$^\circ$)C(O)R$^\circ$; —N(R$^\circ$)C(S)R$^\circ$; —(CH$_2$)$_{0-4}$N(R$^\circ$)C(O)NR$^\circ$$_2$; —N(R$^\circ$)C(S)NR$^\circ$$_2$; —(CH$_2$)$_{0-4}$N(R$^\circ$)C(O)OR$^\circ$; —N(R$^\circ$)N(R$^\circ$)C(O)R$^\circ$; —N(R$^\circ$)N(R$^\circ$)C(O)NR$^\circ$$_2$; —N(R$^\circ$)N(R$^\circ$)C(O)OR$^\circ$; —(CH$_2$)$_{0-4}$C(O)R$^\circ$; —C(S)R$^\circ$; —(CH$_2$)$_{0-4}$C(O)OR$^\circ$; —(CH$_2$)$_{0-4}$C(O)SR$^\circ$; —(CH$_2$)$_{0-4}$C(O)OSiR$^\circ$$_3$; —(CH$_2$)$_{0-4}$OC(O)R$^\circ$; —OC(O)(CH$_2$)$_{0-4}$SR—, SC(S)SR$^\circ$; —(CH$_2$)$_{0-4}$SC(O)R$^\circ$; —(CH$_2$)$_{0-4}$C(O)NR$^\circ$$_2$; —C(S)NR$^\circ$$_2$; —C(S)SR$^\circ$; —SC(S)SR$^\circ$, —(CH$_2$)$_{0-4}$OC(O) NR$^\circ$$_2$; —C(O)N(OR$^\circ$)R$^\circ$; —C(O)C(O)R$^\circ$; —C(O)CH$_2$C(O) R$^\circ$; —C(NOR$^\circ$)R$^\circ$; —(CH$_2$)$_{0-4}$SSR$^\circ$; —(CH$_2$)$_{0-4}$S(O)$_2$R$^\circ$; —(CH$_2$)$_{0-4}$S(O)$_2$OR$^\circ$; —(CH$_2$)$_{0-4}$OS(O)$_2$R$^\circ$; —S(O)$_2$NR$^\circ$$_2$; —S(O)(NR$^\circ$)R$^\circ$; —S(O)$_2$N=C(NR$^\circ$$_2$)$_2$; —(CH$_2$)$_{0-4}$S(O) R$^\circ$; —N(R$^\circ$)S(O)$_2$NR$^\circ$$_2$; —N(R$^\circ$)S(O)$_2$R$^\circ$; —N(OR$^\circ$)R$^\circ$; —C(NH)NR$^\circ$$_2$; —P(O)$_2$R$^\circ$; —P(O)R$^\circ$$_2$; —OP(O)R$^\circ$$_2$; —OP(O)(OR$^\circ$)$_2$; SiR$^\circ$$_3$; —(C$_{1-4}$ straight or branched alkylene)O—N(R$^\circ$)$_2$; or —(C$_{1-4}$ straight or branched alkylene)C(O)O—N(R$^\circ$)$_2$.

Each R$^\circ$ is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R$^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted by a divalent substituent on a saturated carbon atom of R$^\circ$ selected from =O and =S; or each R$^\circ$ is optionally substituted with a monovalent substituent independently selected from halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C (O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$.

Each R$^\bullet$ is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, and wherein each R$^\bullet$ is unsubstituted or where preceded by halo is substituted only with one or more halogens; or wherein an optional substituent on a saturated carbon is a divalent substituent independently selected from =O, =S, =NNR*$_2$, =NNHC(O)R*, =NNHC(O)OR*, =NNHS (O)$_2$R*, =NR*, =NOR*, —O(C(R*$_2$))$_{2-3}$O—, or —S(C (R*$_2$))$_{2-3}$S—, or a divalent substituent bound to vicinal substitutable carbons of an "optionally substituted" group is —O(CR*$_2$)$_{2-3}$O—, wherein each independent occurrence of R* is selected from hydrogen, C$_{1-6}$ aliphatic or an unsubstituted 5-6-membered saturated, partially unsaturated, or aryl ring having 0-4 heteroatoms independently selected from nitrogen, oxygen, or sulfur.

When R* is C$_{1-6}$ aliphatic, R* is optionally substituted with halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, and wherein each R$^\bullet$ is unsubstituted or where preceded by halo is substituted only with one or more halogens.

An optional substituent on a substitutable nitrogen is independently —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S (O)$_2$R$^\dagger$; wherein each R$^\dagger$ is independently hydrogen, C$_{1-6}$ aliphatic, unsubstituted —OPh, or an unsubstituted 5-6-membered saturated, partially unsaturated, or aryl ring having 0-4 heteroatoms independently selected from nitrogen, oxygen, or sulfur, or, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur; wherein when R† is C$_{1-6}$ aliphatic, R† is optionally substituted with halogen, —R˙, -(haloR˙), —OH, —OR˙, —O(haloR˙), —CN, —C(O)OH, —C(O)OR˙, —NH$_2$, —NHR˙, —NR˙$_2$, or —NO$_2$, wherein each R˙ is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, and wherein each R˙ is unsubstituted or where preceded by halo is substituted only with one or more halogens.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention. In certain embodiments, a compound of the invention comprises one or more deuterium atoms.

As used herein, the term "inhibitor" is defined as a compound that binds to and/or inhibits Matriptase 2, or a mutant thereof, with measurable affinity. In certain embodiments, an inhibitor has an IC$_{50}$ and/or binding constant of less than about 100 µM, less than about 50 µM, less than about 20 µM, less than about 10 µM, or less than about 5 µM.

The terms "measurable affinity" and "measurably inhibit," as used herein, means a measurable change in Matriptase 2, or a mutant thereof, activity between a sample comprising a compound of the present invention, or composition thereof, and Matriptase 2, or a mutant thereof, and an equivalent sample comprising Matriptase 2, or a mutant thereof, in the absence of said compound, or composition thereof.

3. Description of Exemplary Embodiments

In one aspect, the present invention provides a compound of Formula I:

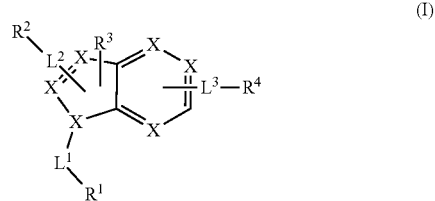

or a pharmaceutically acceptable salt thereof, wherein
each X is independently C or N;
L$^1$ is a bond, or an optionally substituted bivalent C$_{1-8}$ saturated or unsaturated, straight or branched hydrocarbon chain, wherein 1, 2, or 3 methylene units of the hydrocarbon chain are optionally and independently replaced by —S(O)$_2$—, —C(O)—, or —O—;
R$^1$ is H, or an optionally substituted ring selected from phenyl, a 5-6 membered heteroaromatic ring having 1-4 heteroatoms independently selected from nitrogen, oxygen, and sulfur, a 8-10 membered bicyclic aromatic carbocyclic ring, and a 8-10 membered bicyclic heteroaromatic ring having 1-4 heteroatoms independently selected from nitrogen, oxygen, and sulfur;
L$^2$ is an optionally substituted bivalent C$_{1-8}$ saturated or unsaturated, straight or branched hydrocarbon chain, wherein 1, 2, or 3 methylene units of the hydrocarbon chain are optionally and independently replaced by —NR—C(O)—, —C(O)—NR—, —C(O)—, —S(O)$_2$—, —C(O)—O—, —O—C(O)—, —NR—S(O)$_2$—, —S(O)$_2$—NR—, or -Cy-;
-Cy- is an optionally substituted bivalent ring selected from phenyl, and a 4-6 membered monocyclic heteroaromatic ring having 1-4 heteroatoms independently selected from nitrogen, oxygen, and sulfur;
R$^2$ is H, or an optionally substituted ring selected from a 4-7 membered monocyclic carbocyclic ring, a 4-7 membered monocyclic heterocyclic ring having 1-4 heteroatoms independently selected from nitrogen, oxygen, and sulfur, a 7-10 membered bicyclic carbocyclic ring, a 7-10 membered bicyclic heterocarboxylic ring having 1-4 heteroatoms independently selected from nitrogen, oxygen, and sulfur, phenyl, 5-6 membered monocyclic heteroaromatic ring having 1-4 heteroatoms independently selected from nitrogen, oxygen, and sulfur, a 8-10 membered bicyclic aromatic ring, a 8-10 membered bicyclic heteroaromatic ring having 1-4 heteroatoms independently selected from nitrogen, oxygen, and sulfur, and adamantly;

$R^3$ is H, halogen, —CN, —C(O)H, —NH$_2$, —NO$_2$, —COOH, —CONH$_2$, —NH—C(O)—O—C$_{1-6}$aliphatic, C$_{1-6}$aliphatic, or —C(O)—C$_{1-6}$aliphatic, wherein the C$_{1-6}$aliphatic is optionally substituted;

$L^3$ is a bond, or an optionally substituted bivalent C$_{1-8}$ saturated or unsaturated, straight or branched hydrocarbon chain, wherein 1, 2, or 3 methylene units of the hydrocarbon chain are optionally replaced by —CO—;

$R^4$ is —NHR, —C(N—R)—NHR, —NH—C(N—R)—NHR, —F, or —OH; and each R is independently H, —C$_{1-8}$alkyl, —OC$_{1-8}$alkyl, —C(O)—C$_{1-8}$alkyl, —C(O)—OC$_{1-8}$alkyl, 4-7 membered monocyclic carbocyclyl, —O-(4-7 membered monocyclic carbocyclyl), —C(O)-(4-7 membered monocyclic carbocyclyl), —C(O)—O-(4-7 membered monocyclic carbocyclyl), phenyl, —O-phenyl, —C(O)-phenyl, —C(O)—O-phenyl, 8-10 membered bicyclic aryl, —O-(8-10 membered bicyclic aryl), —C(O)-(8-10 membered bicyclic aryl), or —C(O)—O-(8-10 membered bicyclic aryl), wherein each of the C$_{1-8}$alkyl, 4-7 membered monocyclic carbocyclyl, phenyl, and 8-10 membered bicyclic aryl is optionally and independently substituted.

As defined generally above, each X is independently C or N.

In some embodiments, X is C. In some embodiments, X is N.

In some embodiments, each X is indecently C or N such that

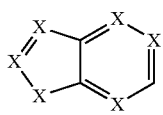

is selected from the following

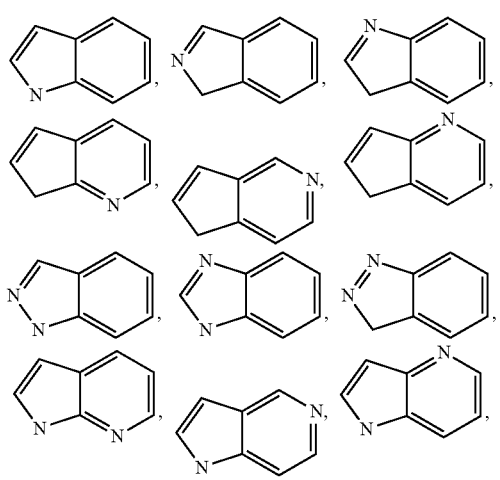

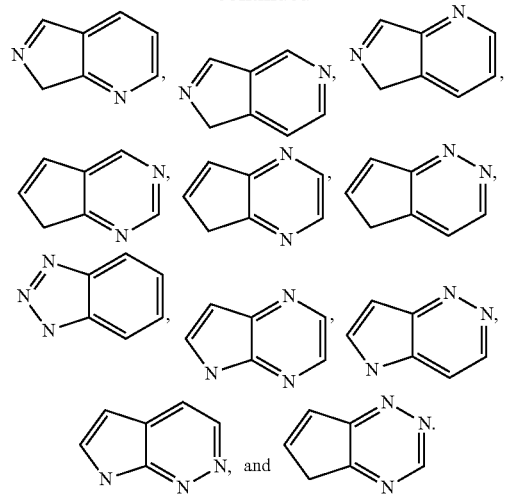

In some embodiments, each X is independently selected from those depicted in Table A, below.

As defined generally above, $L^1$ is a bond, or an optionally substituted C$_{1-8}$ bivalent hydrocarbon chain, wherein 1, 2, or 3 methylene units of the hydrocarbon chain are optionally and independently replaced by —S(O)$_2$—, —C(O)—, or —O—.

In some embodiments, $L^1$ is a bond.

In some embodiments, $L^1$ is an optionally substituted C$_{1-8}$ bivalent hydrocarbon chain, wherein 1, 2, or 3 methylene units of the hydrocarbon chain are optionally and independently replaced by —S(O)$_2$—, —C(O)—, or —O—. In some embodiments, $L^1$ is an optionally substituted C$_{1-8}$ bivalent hydrocarbon chain, wherein 1 methylene unit of the hydrocarbon chain is optionally replaced by —S(O)$_2$—, —C(O)—, or —O—. In some embodiments, $L^1$ is an optionally substituted C$_{1-8}$ bivalent hydrocarbon chain, wherein 2 methylene units of the hydrocarbon chain are optionally and independently replaced by —S(O)$_2$—, —C(O)—, or —O—. In some embodiments, $L^1$ is an optionally substituted C$_{1-8}$ bivalent hydrocarbon chain, wherein 3 methylene units of the hydrocarbon chain are optionally and independently replaced by —S(O)$_2$—, —C(O)—, or —O—.

In some embodiments, $L^1$ is an optionally substituted C$_{1-8}$ bivalent hydrocarbon chain, wherein 1 methylene unit of the hydrocarbon chain is replaced by —S(O)$_2$—. In some embodiments, $L^1$ is an optionally substituted C$_{1-8}$ bivalent hydrocarbon chain, wherein 1 methylene unit of the hydrocarbon chain is replaced by —C(O)—. In some embodiments, $L^1$ is an optionally substituted C$_{1-8}$ bivalent hydrocarbon chain, wherein 1 methylene unit of the hydrocarbon chain is replaced by —O—.

In some embodiments, $L^1$ is —(CH$_2$)—. In some embodiments, $L^1$ is —(CH$_2$)$_2$—. In some embodiments, $L^1$ is —(CH$_2$)$_3$—. In some embodiments, $L^1$ is —S(O)$_2$CH$_2$—. In some embodiments, $L^1$ is —S(O)$_2$(CH$_2$)$_2$—. In some embodiments, $L^1$ is —S(O)$_2$—. In some embodiments, $L^1$ is —CH$_2$S(O)$_2$—. In some embodiments, $L^1$ is —(CH$_2$)$_2$—S(O)$_2$—.

In some embodiments, $L^1$ is selected from those depicted in Table A, below.

As defined generally above, $R^1$ is H, or an optionally substituted ring selected from phenyl, a 5-6 membered heteroaromatic ring having 1-4 heteroatoms independently selected from nitrogen, oxygen, and sulfur, a 8-10 membered bicyclic aromatic carbocyclic ring, and a 8-10 membered bicyclic heteroaromatic ring having 1-4 heteroatoms independently selected from nitrogen, oxygen, and sulfur.

In some embodiments, $R^1$ is H. In some embodiments, $R^1$ is an optionally substituted ring selected from phenyl, a 5-6 membered heteroaromatic ring having 1-4 heteroatoms independently selected from nitrogen, oxygen, and sulfur, a 8-10 membered bicyclic aromatic carbocyclic ring, and a 8-10 membered bicyclic heteroaromatic ring having 1-4 heteroatoms independently selected from nitrogen, oxygen, and sulfur.

In some embodiments, $R^1$ is optionally substituted phenyl. In some embodiments, $R^1$ is unsubstituted phenyl. In some embodiments, $R^1$ is

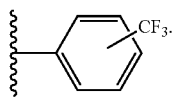

In some embodiments, $R^1$ is

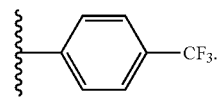

In some embodiments, $R^1$ is

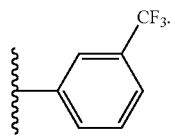 [SMILES: *c1cccc(C(F)(F)F)c1]

In some embodiments, $R^1$ is

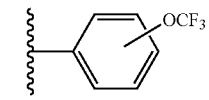

In some embodiments, $R^1$ is

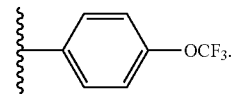

In some embodiments, $R^1$ is

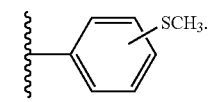

In some embodiments, $R^1$ is

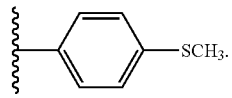

In some embodiments, $R^1$ is

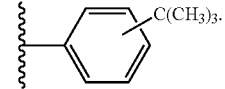

In some embodiments, $R^1$ is

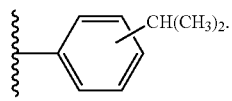

In some embodiments, $R^1$ is

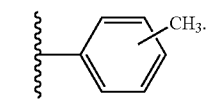

In some embodiments, $R^1$ is

wherein halogen is F, Cl, or Br. In some embodiments, $R^1$ is

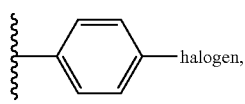

wherein halogen is F, Cl or Br. In some embodiments, $R^1$ is

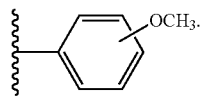

In some embodiments, $R^1$ is

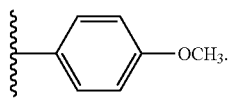 [SMILES: *c1ccc(OC)cc1]

In some embodiments, $R^1$ is

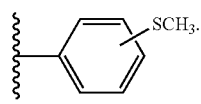

In some embodiments, $R^1$ is

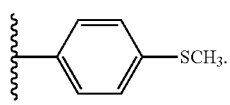

In some embodiments, $R^1$ is

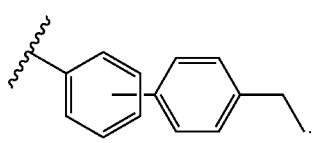

In some embodiments, $R^1$ is

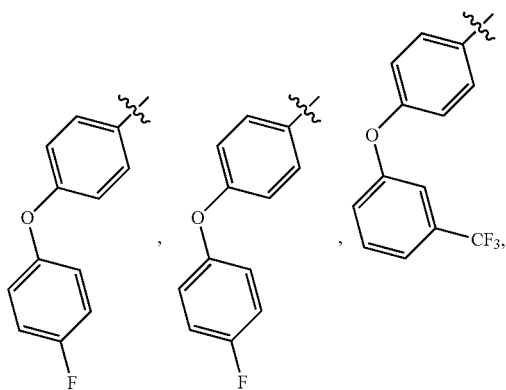

-continued

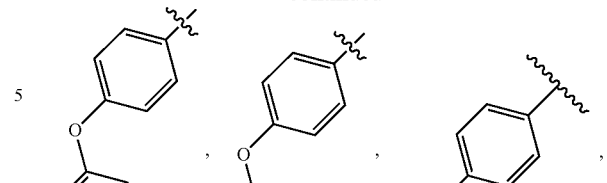

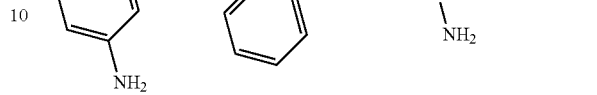

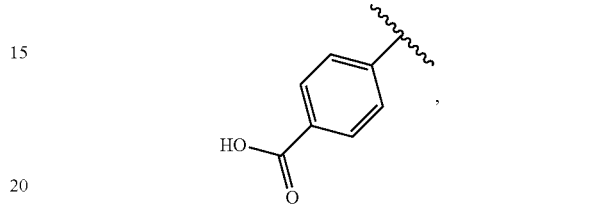

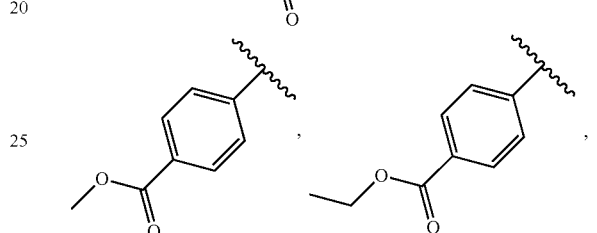

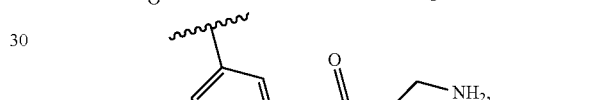

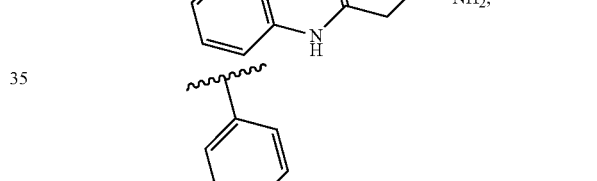

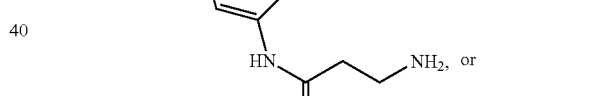

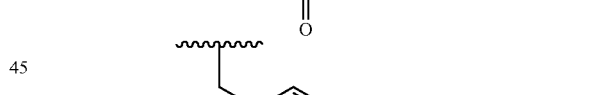

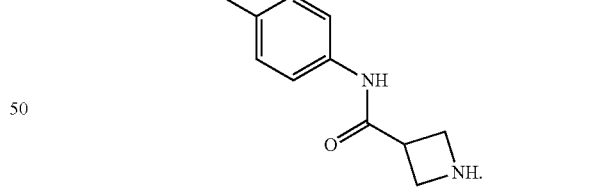

In some embodiments, $R^1$ is an optionally substituted 5-6 membered heteroaromatic ring having 1-4 heteroatoms independently selected from nitrogen, oxygen, and sulfur. In some embodiments, $R^1$ is an optionally substituted 5-membered heteroaromatic ring having 1, 2, 3, or 4 heteroatoms independently selected from nitrogen, oxygen, and sulfur. In some embodiments, $R^1$ is an optionally substituted 6-membered heteroaromatic ring having 1, 2, 3, or 4 heteroatoms independently selected from nitrogen, oxygen, and sulfur.

In some embodiments, $R^1$ is optionally substituted pyridyl. In some embodiments, $R^1$ is unsubstituted pyridyl. In some embodiments, $R^1$ is In some embodiments, R¹ is

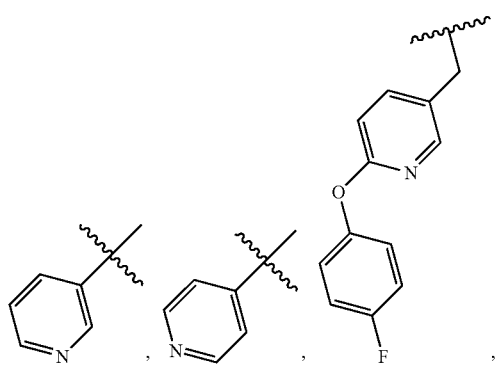, or

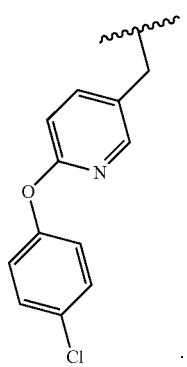

In some embodiments, R¹ is

In some embodiments, R¹ is an optionally substituted 8-10 membered bicyclic aromatic carbocyclic ring. In some embodiments, R¹ is an optionally substituted 8-membered bicyclic aromatic carbocyclic ring. In some embodiments, R¹ is an optionally substituted 9-membered bicyclic aromatic carbocyclic ring. In some embodiments, R¹ is an optionally substituted 10-membered bicyclic aromatic carbocyclic ring. In some embodiments, R¹ is a 10-membered bicyclic aromatic carbocyclic ring, optionally substituted by —CH₂—R¹¹, —O—R¹¹, —N—R¹¹, —S—R¹¹, —NR—C(O)—R¹¹, —C(O)—NR—R¹¹, —C(O)—R¹¹, —S(O)₂—R¹¹, —C(O)—O—R¹¹, —O—C(O)—R¹¹, —NR—S(O)₂—R¹¹, or —S(O)₂—NR—R¹¹, wherein R¹¹ is optionally substituted phenyl or a 5-6 membered heteroaromatic ring having 1-4 heteroatoms independently selected from nitrogen, oxygen, and sulfur. In some embodiments, R¹ is

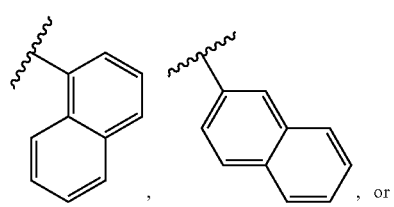

In some embodiments, R¹ is

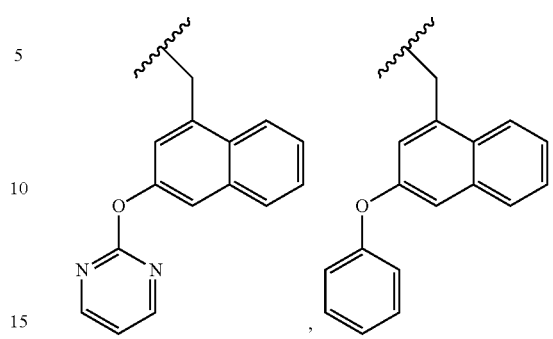, or

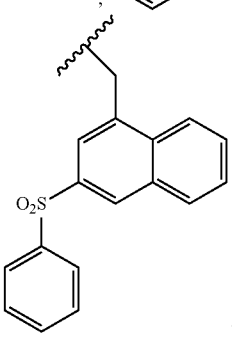

In some embodiments, R¹ is an optionally substituted 8-10 membered bicyclic heteroaromatic ring having 1-4 heteroatoms independently selected from nitrogen, oxygen, and sulfur. In some embodiments, R¹ is an optionally substituted 8-membered bicyclic heteroaromatic ring having 1, 2, 3, or 4 heteroatoms independently selected from nitrogen, oxygen, and sulfur. In some embodiments, R¹ is an optionally substituted 9-membered bicyclic heteroaromatic ring having 1, 2, 3, or 4 heteroatoms independently selected from nitrogen, oxygen, and sulfur. In some embodiments, R¹ is an optionally substituted 10-membered bicyclic heteroaromatic ring having 1, 2, 3, or 4 heteroatoms independently selected from nitrogen, oxygen, and sulfur.

In some embodiments, R¹ is

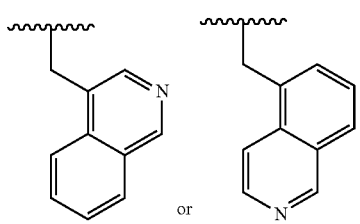

In some embodiments, R¹ is selected from those depicted in Table A, below.

As defined generally above, L² is an optionally substituted C₁₋₈ bivalent hydrocarbon chain, wherein 1, 2, or 3 methylene units of the hydrocarbon chain are optionally and independently replaced by —NR—C(O)—, —C(O)—NR—, —C(O)—, —S(O)₂—, —C(O)—O—, —O—C(O)—, —NR—S(O)₂—, —S(O)₂—NR—, or -Cy-.

In some embodiments, L² is an optionally substituted C₁₋₈ bivalent hydrocarbon chain, wherein 1, 2, or 3 methylene units of the hydrocarbon chain are optionally and independently replaced by —NR—C(O)—, —C(O)—NR—, —C(O)—, —C(O)—O—, or —O—C(O)—. In some embodiments, a $C_{1-8}$ bivalent hydrocarbon chain is substituted by —OH.

In some embodiments, $L^2$ is an optionally substituted $C_{1-8}$ bivalent hydrocarbon chain, wherein 1, 2, or 3 methylene units of the hydrocarbon chain are optionally and independently replaced by —S(O)$_2$—, —NR—S(O)$_2$—, or —S(O)$_2$—NR—.

In some embodiments, $L^2$ is an optionally substituted $C_{1-8}$ bivalent hydrocarbon chain, wherein 1, 2, or 3 methylene units of the hydrocarbon chain are optionally and independently replaced by -Cy-.

In some embodiments, $L^2$ is an optionally substituted $C_{1-8}$ bivalent hydrocarbon chain, wherein 1, 2, or 3 methylene units of the hydrocarbon chain are optionally and independently replaced by —NR—C(O)—, —C(O)—NR—, —NR—S(O)$_2$—, or —S(O)$_2$—NR—.

In some embodiments, $L^2$ is an optionally substituted $C_{1-8}$ bivalent hydrocarbon chain, wherein 1, 2, or 3 methylene units of the hydrocarbon chain are optionally and independently replaced by —C(O)— or —S(O)$_2$—.

In some embodiments, $L^2$ is an optionally substituted $C_{1-8}$ bivalent hydrocarbon chain, wherein 1, 2, or 3 methylene units of the hydrocarbon chain are optionally and independently replaced by —C(O)—O— or —O—C(O)—.

In some embodiments, $L^2$ is

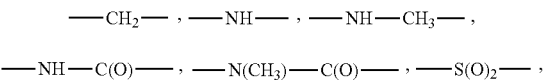

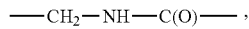

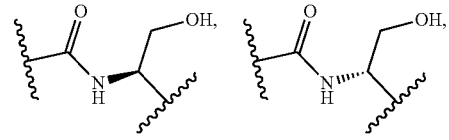

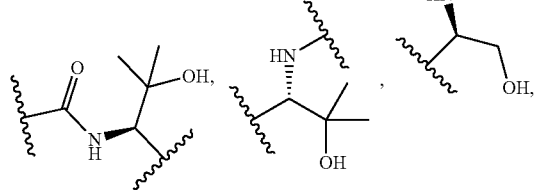

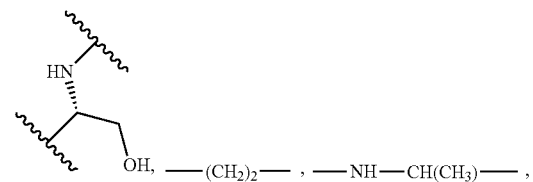

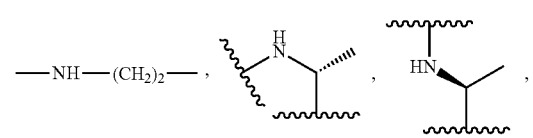

-continued

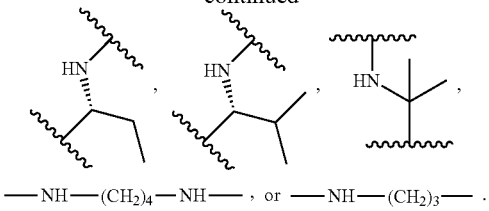

—NH—(CH$_2$)$_4$—NH—, or —NH—(CH$_2$)$_3$—.

In some embodiments, $L^2$ is selected from those depicted in Table A, below.

As defined generally above, -Cy- is an optionally substituted bivalent ring selected from phenyl, a 4-6 membered monocyclic heterocyclic ring having 1-4 heteroatoms independently selected from nitrogen, oxygen, and sulfur, and a 4-6 membered monocyclic heteroaromatic ring having 1-4 heteroatoms independently selected from nitrogen, oxygen, and sulfur.

In some embodiments, -Cy- is optionally substituted phenylene. In some embodiments, -Cy- is unsubstituted phenylene.

In some embodiments, -Cy- is optionally substituted pyridylene. In some embodiments, -Cy- is unsubstituted pyridylene.

In some embodiments, -Cy- is an optionally substituted 4-6 membered monocyclic heteroaromatic ring having 1-4 heteroatoms independently selected from nitrogen, oxygen, and sulfur. In some embodiments, -Cy- is an optionally substituted 4-membered monocyclic heteroaromatic ring having 1, 2, 3, or 4 heteroatoms independently selected from nitrogen, oxygen, and sulfur. In some embodiments, -Cy- is an optionally substituted 5-membered monocyclic heteroaromatic ring having 1, 2, 3, or 4 heteroatoms independently selected from nitrogen, oxygen, and sulfur. In some embodiments, -Cy- is an optionally substituted 6-membered monocyclic heteroaromatic ring having 1, 2, 3, or 4 heteroatoms independently selected from nitrogen, oxygen, and sulfur.

In some embodiments, -Cy- is an optionally substituted 4-6 membered monocyclic heterocyclic ring having 1-4 heteroatoms independently selected from nitrogen, oxygen, and sulfur. In some embodiments, -Cy- is an optionally substituted 4-membered monocyclic heterocyclic ring having 1, 2, 3, or 4 heteroatoms independently selected from nitrogen, oxygen, and sulfur. In some embodiments, -Cy- is an optionally substituted 5-membered monocyclic heterocyclic ring having 1, 2, 3, or 4 heteroatoms independently selected from nitrogen, oxygen, and sulfur. In some embodiments, -Cy- is an optionally substituted 6-membered monocyclic heterocyclic ring having 1, 2, 3, or 4 heteroatoms independently selected from nitrogen, oxygen, and sulfur.

In some embodiments, -Cy- is an optionally substituted bivalent ring which is oxadiazole. In some embodiments, -Cy- is an optionally substituted bivalent ring which is thiadizaole.

In some embodiments, -Cy- is selected from those depicted in Table A, below.

As defined generally above, $R^2$ is H, or an optionally substituted ring selected from a 4-7 membered monocyclic carbocyclic ring, a 4-7 membered monocyclic heterocyclic ring having 1-4 heteroatoms independently selected from nitrogen, oxygen, and sulfur, a 7-10 membered bicyclic carbocyclic ring, a 7-10 membered bicyclic heterocarboxylic ring having 1-4 heteroatoms independently selected from nitrogen, oxygen, and sulfur, phenyl, 5-6 membered monocyclic heteroaromatic ring having 1-4 heteroatoms independently selected from nitrogen, oxygen, and sulfur, a 8-10 membered bicyclic aromatic ring, a 8-10 membered bicyclic heteroaromatic ring having 1-4 heteroatoms independently selected from nitrogen, oxygen, and sulfur, and adamantyl.

In some embodiments, R² is H. In some embodiments, R² is an optionally substituted ring selected from a 4-7 membered monocyclic carbocyclic ring, a 4-7 membered monocyclic heterocyclic ring having 1-4 heteroatoms independently selected from nitrogen, oxygen, and sulfur, a 7-10 membered bicyclic carbocyclic ring, a 7-10 membered bicyclic heterocarboxylic ring having 1-4 heteroatoms independently selected from nitrogen, oxygen, and sulfur, phenyl, 5-6 membered monocyclic heteroaromatic ring having 1-4 heteroatoms independently selected from nitrogen, oxygen, and sulfur, a 8-10 membered bicyclic aromatic ring, a 8-10 membered bicyclic heteroaromatic ring having 1-4 heteroatoms independently selected from nitrogen, oxygen, and sulfur, and adamantyl.

In some embodiments, R² is an optionally substituted 4-7 membered monocyclic carbocyclic ring.

In some embodiments, R² is an optionally substituted 4-7 membered monocyclic heterocyclic ring having 1-4 heteroatoms independently selected from nitrogen, oxygen, and sulfur. In some embodiments, R² is an optionally substituted 4-membered monocyclic heterocyclic ring having 1, 2, 3, or 4 heteroatoms independently selected from nitrogen, oxygen, and sulfur. In some embodiments, R² is an optionally substituted 5-membered monocyclic heterocyclic ring having 1, 2, 3, or 4 heteroatoms independently selected from nitrogen, oxygen, and sulfur. In some embodiments, R² is an optionally substituted 6-membered monocyclic heterocyclic ring having 1, 2, 3, or 4 heteroatoms independently selected from nitrogen, oxygen, and sulfur. In some embodiments, R² is an optionally substituted 7-membered monocyclic heterocyclic ring having 1, 2, 3, or 4 heteroatoms independently selected from nitrogen, oxygen, and sulfur.

In some embodiments, R² is an optionally substituted 7-10 membered bicyclic carbocyclic ring.

In some embodiments, R² is an optionally substituted 7-10 membered bicyclic heterocarboxylic ring having 1-4 heteroatoms independently selected from nitrogen, oxygen, and sulfur. In some embodiments, R² is an optionally substituted 7-membered bicyclic heterocarboxylic ring having 1, 2, 3, or 4 heteroatoms independently selected from nitrogen, oxygen, and sulfur. In some embodiments, R² is an optionally substituted 8-membered bicyclic heterocarboxylic ring having 1, 2, 3, or 4 heteroatoms independently selected from nitrogen, oxygen, and sulfur. In some embodiments, R² is an optionally substituted 9-membered bicyclic heterocarboxylic ring having 1, 2, 3, or 4 heteroatoms independently selected from nitrogen, oxygen, and sulfur. In some embodiments, R² is an optionally substituted 10-membered bicyclic heterocarboxylic ring having 1, 2, 3, or 4 heteroatoms independently selected from nitrogen, oxygen, and sulfur.

In some embodiments, R² is optionally substituted phenyl.

In some embodiments, R² is an optionally substituted 5-6 membered monocyclic heteroaromatic ring having 1-4 heteroatoms independently selected from nitrogen, oxygen, and sulfur. In some embodiments, R² is an optionally substituted 5-membered monocyclic heteroaromatic ring having 1, 2, 3, or 4 heteroatoms independently selected from nitrogen, oxygen, and sulfur. In some embodiments, R² is an optionally substituted 6-membered monocyclic heteroaromatic ring having 1, 2, 3, or 4 heteroatoms independently selected from nitrogen, oxygen, and sulfur.

In some embodiments, R² is an optionally substituted 8-10 membered bicyclic aromatic ring.

In some embodiments, R² is an optionally substituted 8-10 membered bicyclic heteroaromatic ring having 1-4 heteroatoms independently selected from nitrogen, oxygen, and sulfur. In some embodiments, R² is an optionally substituted 8-membered bicyclic heteroaromatic ring having 1, 2, 3, or 4 heteroatoms independently selected from nitrogen, oxygen, and sulfur. In some embodiments, R² is an optionally substituted 9-membered bicyclic heteroaromatic ring having 1, 2, 3, or 4 heteroatoms independently selected from nitrogen, oxygen, and sulfur. In some embodiments, R² is an optionally substituted 10-membered bicyclic heteroaromatic ring having 1, 2, 3, or 4 heteroatoms independently selected from nitrogen, oxygen, and sulfur.

In some embodiments, R² is optionally substituted adamantyl.

In some embodiments, R² is selected from:

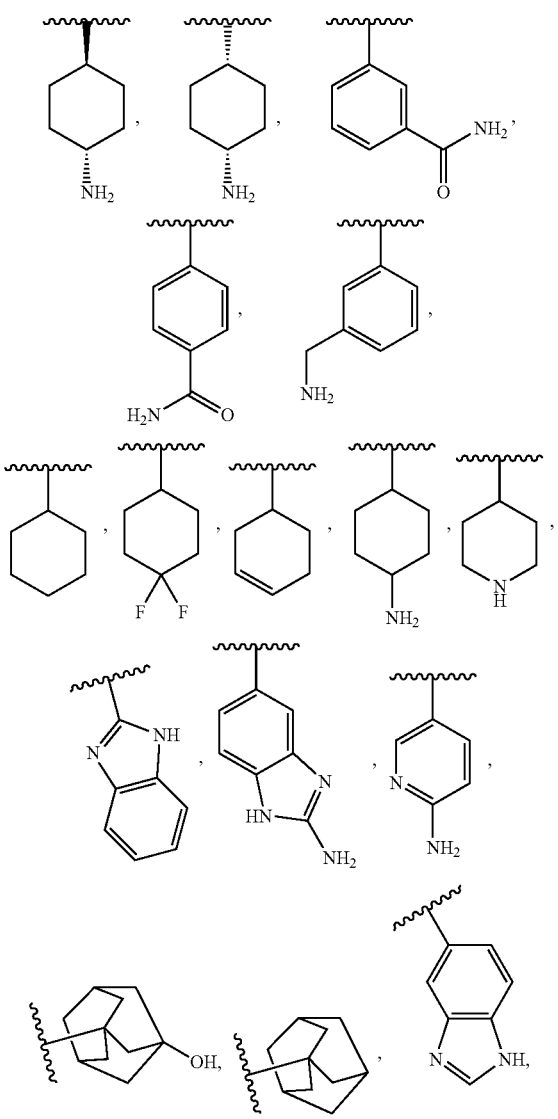

-continued
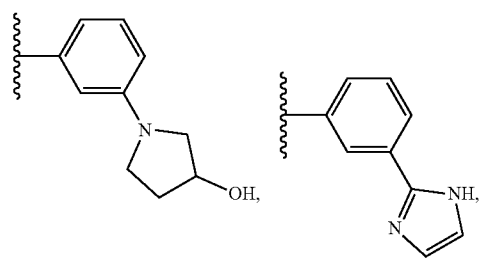
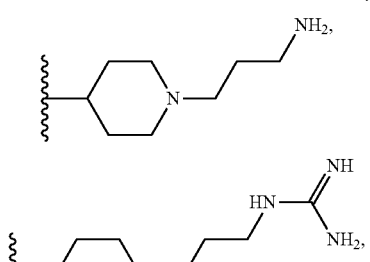
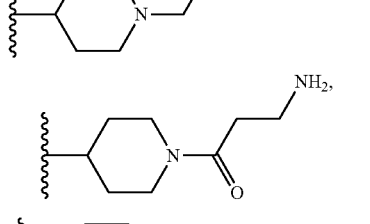
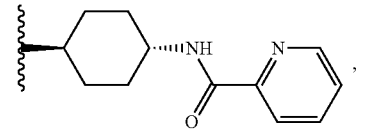
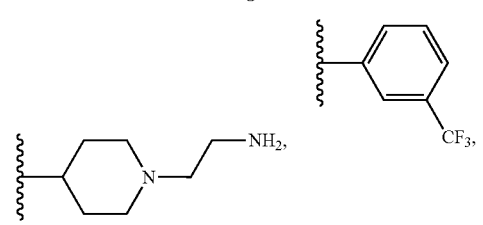
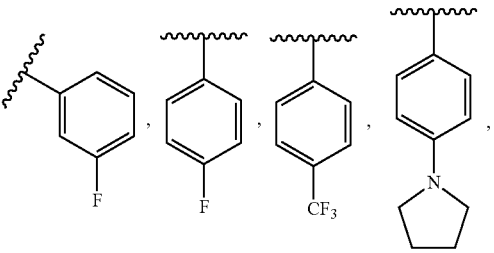
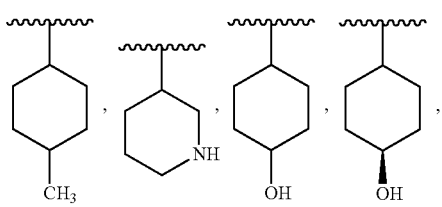
-continued
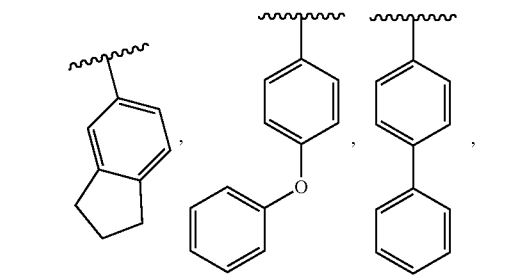
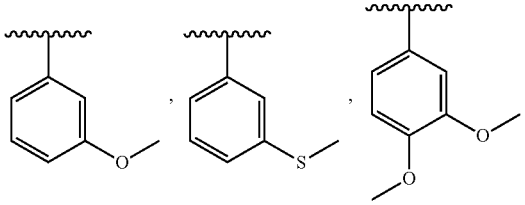
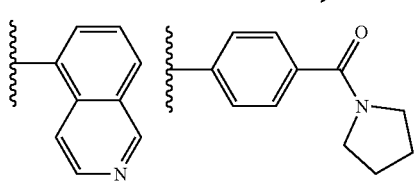
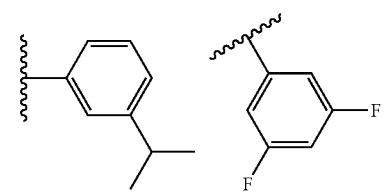
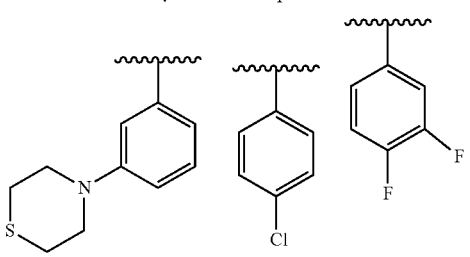
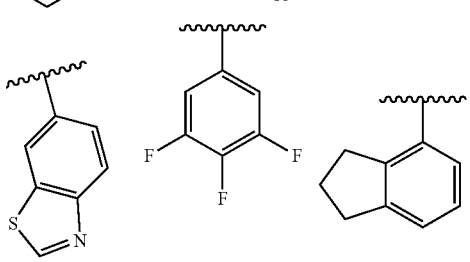
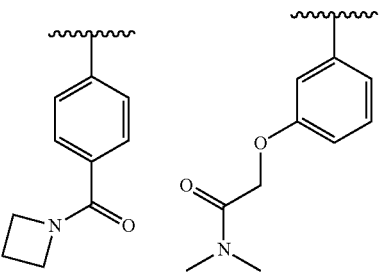

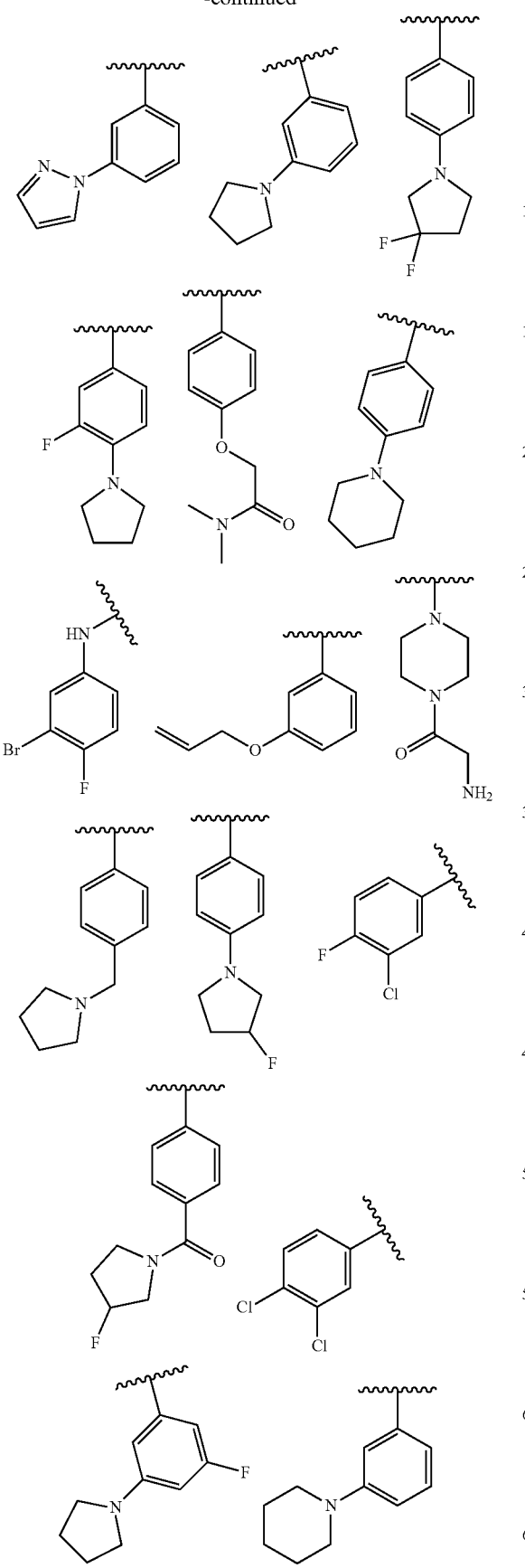
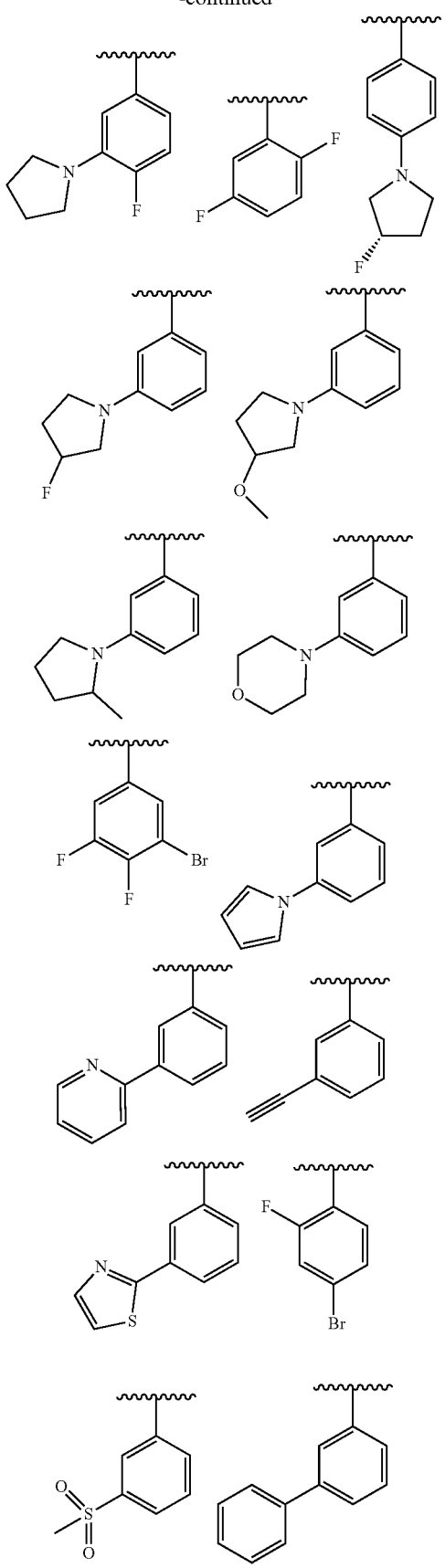

-continued
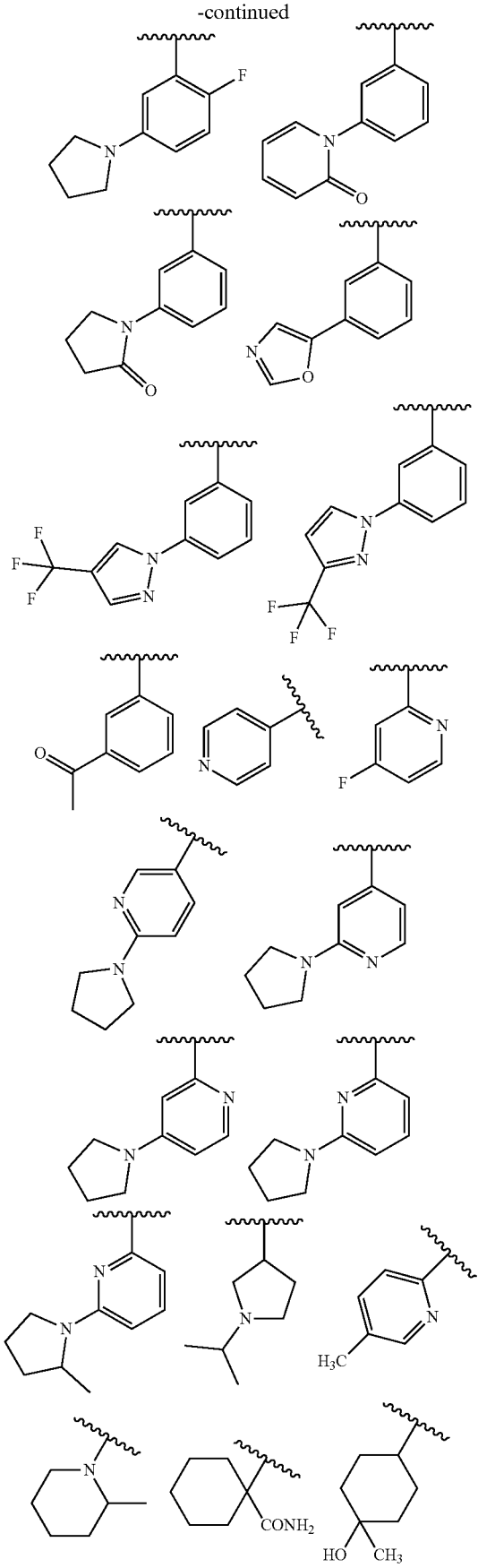
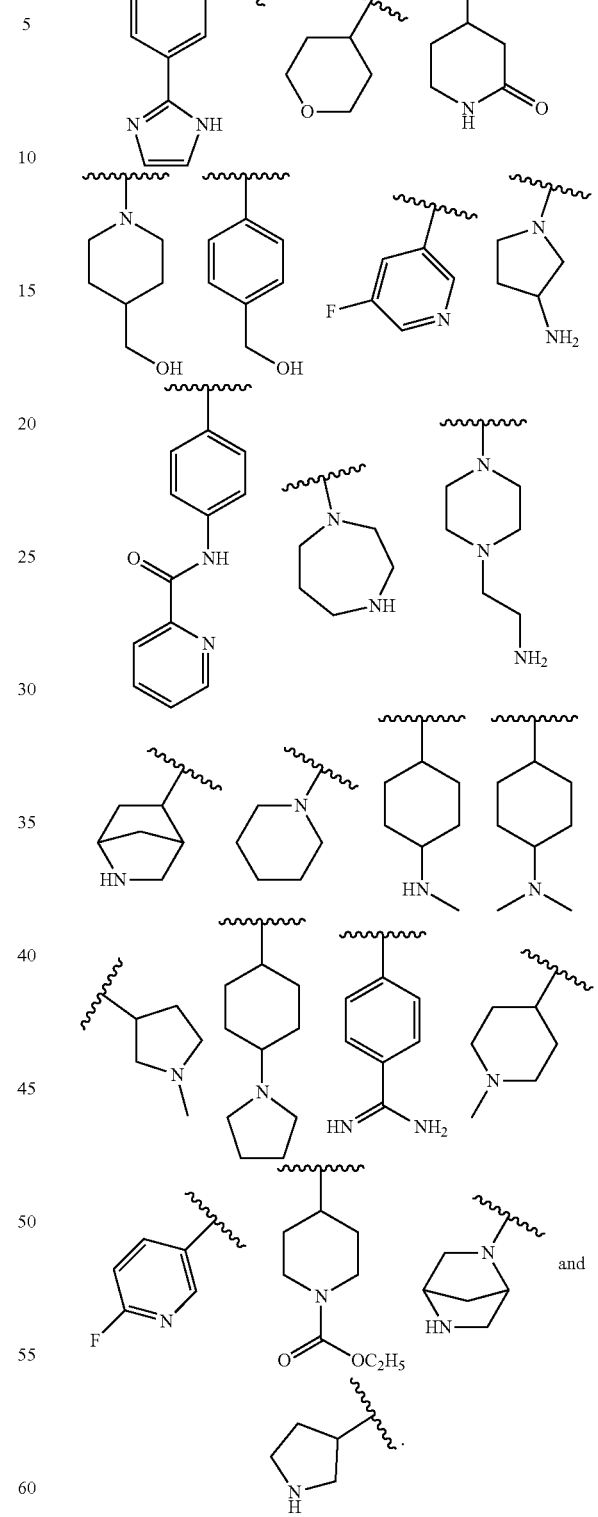
In some embodiments, $R^2$ is selected from those depicted in Table A, below.
As defined generally above, $R^3$ is H, —OH, halogen, —CN, —C(O)H, —NH$_2$, —NO$_2$, —COOH, —CONH$_2$, —NH—C(O)—O—C$_{1-6}$aliphatic, C$_{1-6}$aliphatic, or —C(O)—C$_{1-6}$aliphatic, wherein the C$_{1-6}$aliphatic is optionally substituted.

In some embodiments, R$^3$ is H. In some embodiments, R$^3$ is halogen. In some embodiments, R$^3$ is —CN. In some embodiments, R$^3$ is —C(O)H. In some embodiments, R$^3$ is —NH$_2$. In some embodiments, R$^3$ is —NO$_2$. In some embodiments, R$^3$ is —COOH. In some embodiments, R$^3$ is —CONH$_2$. In some embodiments, R$^3$ is —NH—C(O)—O—C$_{1-6}$aliphatic, wherein the C$_{1-6}$aliphatic is optionally substituted. In some embodiments, R$^3$ is C$_{1-6}$aliphatic, wherein the C$_{1-6}$ aliphatic is optionally substituted. In some embodiments, R$^3$ is —C(O)—C$_{1-6}$aliphatic, wherein the C$_{1-6}$aliphatic is optionally substituted.

In some embodiments, R$^3$ is —OH. In some embodiments, R$^3$ is —NH$_2$. In some embodiments, R$^3$ is —NO$_2$. In some embodiments, R$^3$ is —COOH. In some embodiments, R$^3$ is —NH—C(O)—O—C$_2$H$_5$. In some embodiments, R$^3$ is —CH$_2$—OCH$_3$.

In some embodiments, R$^3$ is selected from those depicted in Table A, below.

As defined generally above, L$^3$ is a bond, or an optionally substituted C$_{1-8}$ bivalent hydrocarbon chain, wherein 1, 2, or 3 methylene units of the hydrocarbon chain are optionally replaced by —CO—.

In some embodiments, L$^3$ is a bond.

In some embodiments, L$^3$ is an optionally substituted C$_{1-8}$ bivalent hydrocarbon chain, wherein 1, 2, or 3 methylene units of the hydrocarbon chain are optionally replaced by —CO—. In some embodiments, L$^3$ is an optionally substituted C$_{1-8}$ bivalent hydrocarbon chain, wherein 1 methylene unit of the hydrocarbon chain is optionally replaced by —CO—. In some embodiments, L$^3$ is an optionally substituted C$_{1-8}$ bivalent hydrocarbon chain, wherein 2 methylene units of the hydrocarbon chain are optionally replaced by —CO—. In some embodiments, L$^3$ is an optionally substituted C$_{1-8}$ bivalent hydrocarbon chain, wherein 3 methylene units of the hydrocarbon chain are optionally replaced by —CO—.

In some embodiments, L3 is —CH$_2$—.

In some embodiments, L$^3$ is selected from those depicted in Table A, below.

As defined generally above, R$^4$ is —NHR, —C(N—R)—NHR, —NH—C(N—R)—NHR, —F, or —OH.

In some embodiments, R$^4$ is —NHR. In some embodiments, R$^4$ is —C(N—R)—NHR. In some embodiments, R$^4$ is —NH—C(N—R)—NHR. In some embodiments, R$^4$ is —F. In some embodiments, R$^4$ is —OH.

In some embodiments, R$^4$ is —NH$_2$. In some embodiments, R$^4$ is selected from:

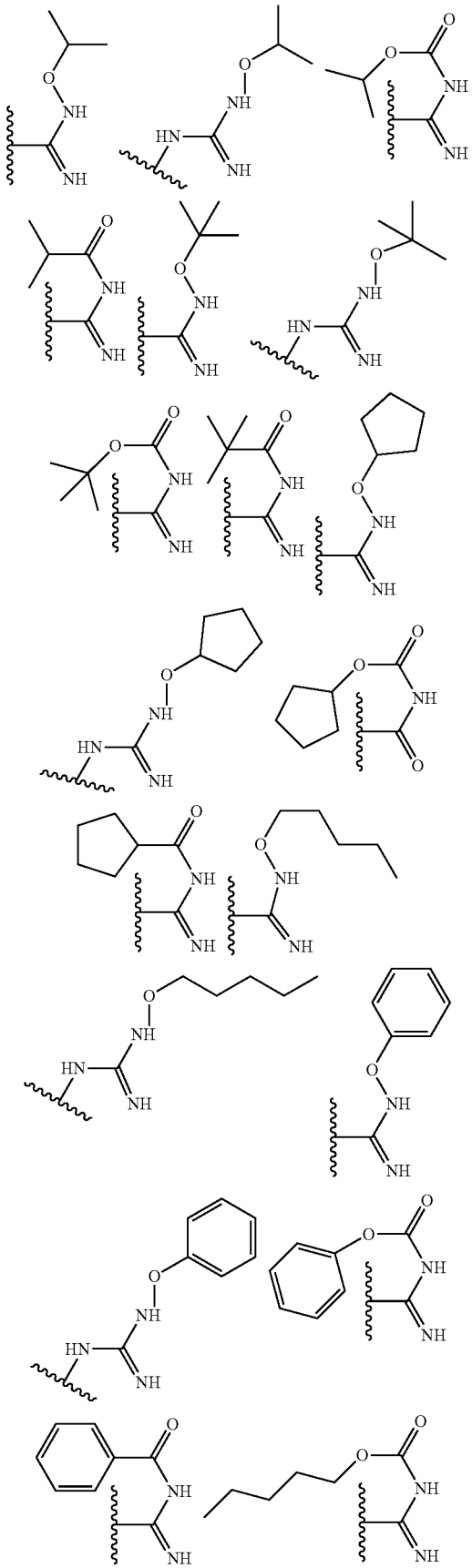

-continued

-continued

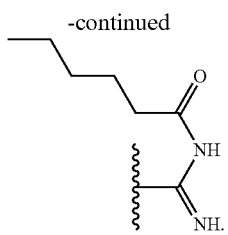

In some embodiments, $R^4$ is selected from those depicted in Table A, below.

As defined generally above, each R is independently H, —$C_{1-8}$alkyl, —$OC_{1-8}$alkyl, —C(O)—$C_{1-8}$alkyl, —C(O)—$OC_{1-8}$alkyl, 4-7 membered monocyclic carbocyclyl, —O-(4-7 membered monocyclic carbocyclyl), —C(O)-(4-7 membered monocyclic carbocyclyl), —C(O)—O-(4-7 membered monocyclic carbocyclyl), phenyl, —O-phenyl, —C(O)-phenyl, —C(O)—O-phenyl, 8-10 membered bicyclic aryl, —O-(8-10 membered bicyclic aryl), —C(O)-(8-10 membered bicyclic aryl), or —C(O)—O-(8-10 membered bicyclic aryl), wherein each of the $C_{1-8}$alkyl, 4-7 membered monocyclic carbocyclyl, phenyl, and 8-10 membered bicyclic aryl is optionally and independently substituted.

In some embodiments, R is H. In some embodiments, R is —OH.

In some embodiments, R is optionally substituted —$C_{1-8}$alkyl. In some embodiments, R is optionally substituted —$OC_{1-8}$alkyl. In some embodiments, R is optionally substituted —C(O)—$C_{1-8}$alkyl. In some embodiments, R is optionally substituted —C(O)—$OC_{1-8}$alkyl. In some embodiments, $C_{1-8}$alkyl is $C_{1-6}$alkyl. In some embodiments, $C_{1-8}$alkyl is isopropyl. In some embodiments, $C_{1-8}$alkyl is tert-butyl. In some embodiments, $C_{1-8}$alkyl is neopentyl.

In some embodiments, R is optionally substituted 4-7 membered monocyclic carbocyclyl. In some embodiments, R is optionally substituted —O-(4-7 membered monocyclic carbocyclyl). In some embodiments, R is optionally substituted —C(O)-(4-7 membered monocyclic carbocyclyl). In some embodiments, R is optionally substituted —C(O)—O-(4-7 membered monocyclic carbocyclyl). In some embodiments, 4-7 membered monocyclic carbocyclyl is cyclopentyl. In some embodiments, 4-7 membered monocyclic carbocyclyl is cyclohexyl.

In some embodiments, R is optionally substituted phenyl. In some embodiments, R is optionally substituted —O-phenyl. In some embodiments, R is optionally substituted —C(O)-phenyl. In some embodiments, R is optionally substituted —C(O)—O-phenyl.

In some embodiments, R is optionally substituted 8-10 membered bicyclic aryl. In some embodiments, R is optionally substituted —O-(8-10 membered bicyclic aryl). In some embodiments, R is optionally substituted —C(O)-(8-10 membered bicyclic aryl). In some embodiments, R is optionally substituted —C(O)—O-(8-10 membered bicyclic aryl).

In some embodiments, R is selected from those depicted in Table A, below.

In some embodiments, a compound of formula I is of formula II:

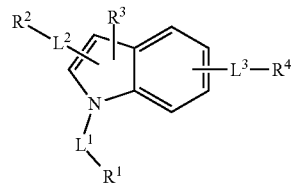

(II)

wherein each of $L^1$, $L^2$, $L^3$, $R^1$, $R^2$, $R^3$, $R^4$, -Cy-, and R is as defined above and described in embodiments herein, both singly and in combination.

In some embodiments, a compound of formula I is selected from formulas II-a to II-f:

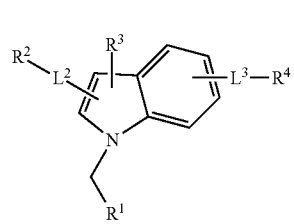

(II-a)

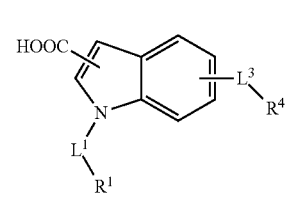

(II-b)

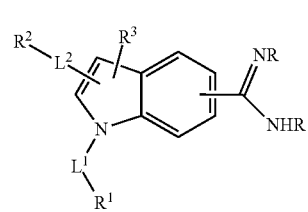

(II-c)

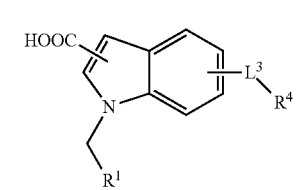

(II-d)

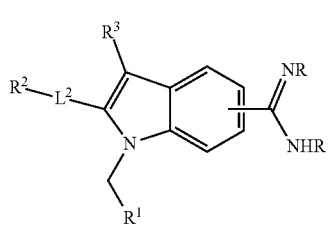

(II-e)

(II-f)

or a pharmaceutically acceptable salt thereof, wherein each of $L^1$, $L^2$, $L^3$, $R^1$, $R^2$, $R^3$, $R^4$, -Cy-, and R is as defined above and described in embodiments herein, both singly and in combination.

In some embodiments, a compound of formula I is of formula III:

(III)

wherein each of $L^1$, $L^2$, $L^3$, $R^1$, $R^2$, $R^3$, $R^4$, -Cy-, and R is as defined above and described in embodiments herein, both singly and in combination.

In some embodiments, a compound of formula I is selected from formulas III-a to III-f:

(III-a)

(III-b)

(III-c)

(III-d)

(III-e)

(III-f)

or a pharmaceutically acceptable salt thereof, wherein each of $L^1$, $L^2$, $L^3$, $R^1$, $R^2$, $R^3$, $R^4$, -Cy-, and R is as defined above and described in embodiments herein, both singly and in combination.

In some embodiments, a compound of formula I is of formula IV:

(IV)

wherein each of $L^1$, $L^2$, $L^3$, $R^1$, $R^2$, $R^3$, $R^4$, -Cy-, and R is as defined above and described in embodiments herein, both singly and in combination.

In some embodiments, a compound of formula I is selected from formulas IV-a to IV-f:

(IV-a)

-continued

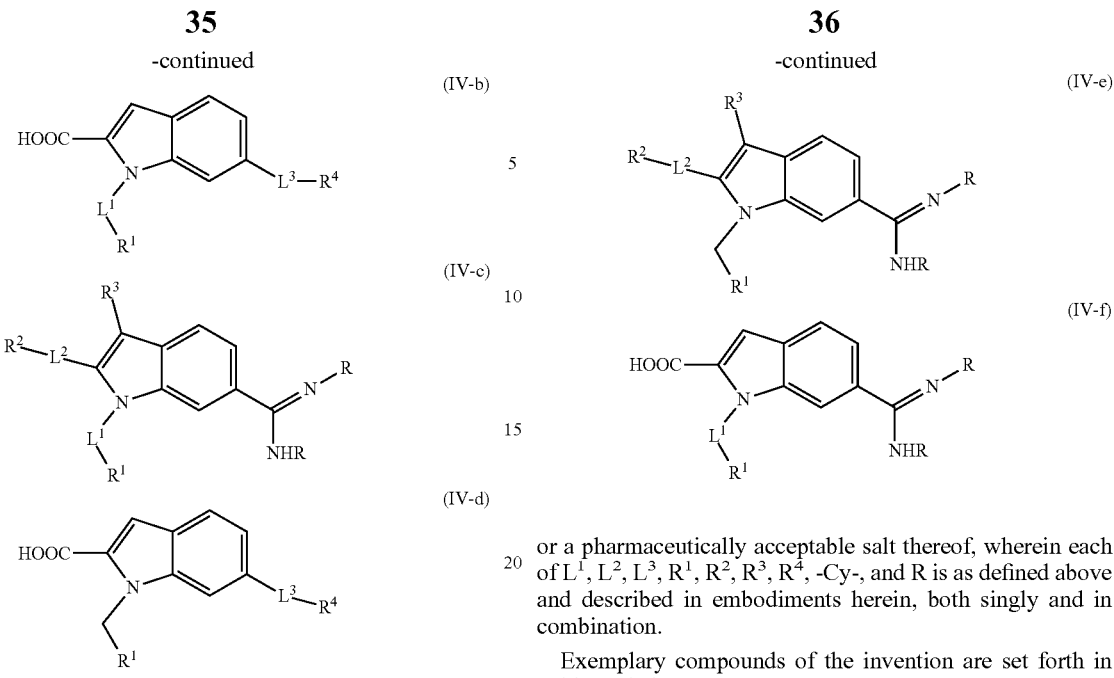

or a pharmaceutically acceptable salt thereof, wherein each of $L^1$, $L^2$, $L^3$, $R^1$, $R^2$, $R^3$, $R^4$, -Cy-, and R is as defined above and described in embodiments herein, both singly and in combination.

Exemplary compounds of the invention are set forth in Table A, below.

TABLE A

| Cpd. ID. | Structure | HPLC Rt- min | % Purity- Indole | M + H | Assay Used | Mar-2 % inhibition at 1 uM |
|---|---|---|---|---|---|---|
| I-1 | 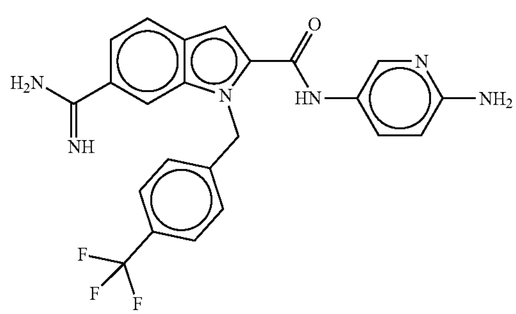 | NA | NA | NA | A | A |
| I-2 | 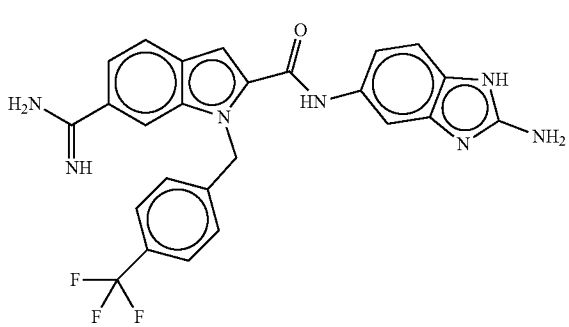 | NA | NA | NA | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-3 | 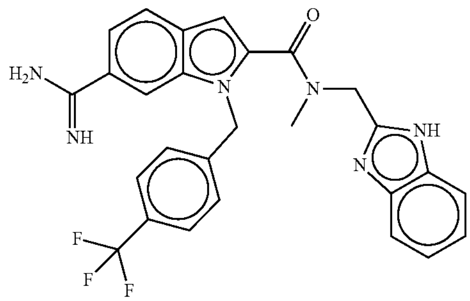 | | NA | NA | A | A |
| I-4 | 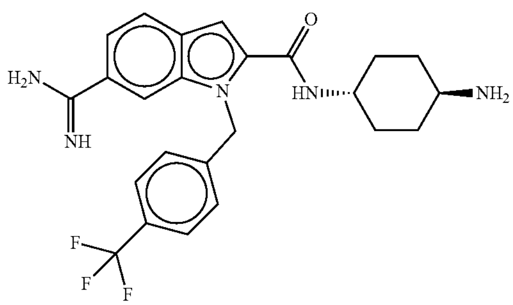 | 6.8 | 97.2 | 458.2 | A | B |
| I-5 | 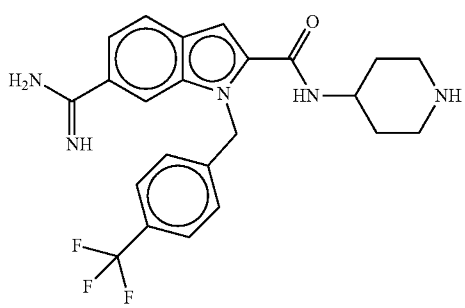 | 7.6 | 92.6 | 444.1 | A | B |
| I-6 | 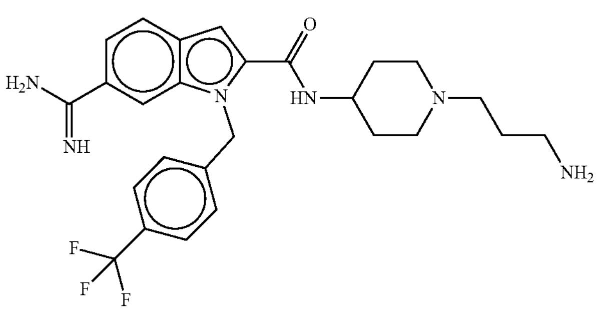 | 6.1 | 95.2 | 501.2 | A | B |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-7 | 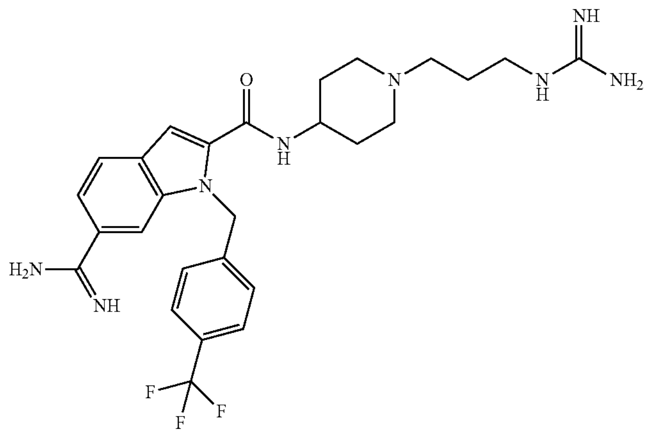 [SMILES: N=C(N)NCCCN1CCC(NC(=O)c2cc3ccc(C(=N)N)cc3n2Cc2ccc(C(F)(F)F)cc2)CC1] | | | 543.3 | ND | ND |
| I-8 | 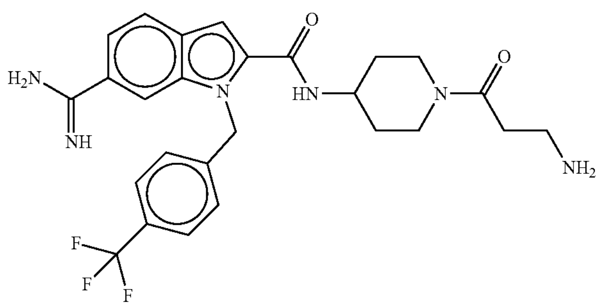 | 6.8 | 92.3 | 515.2 | A | B |
| I-9 | 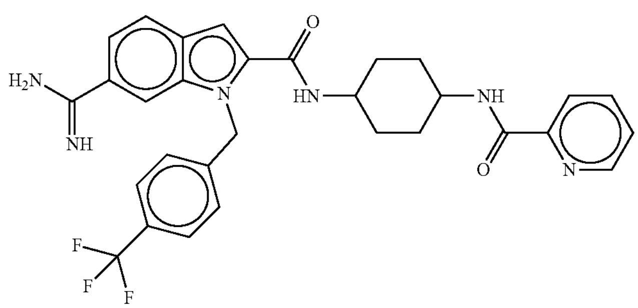 | 8.7 | 97.8 | 563.2 | A | B |
| I-10 | 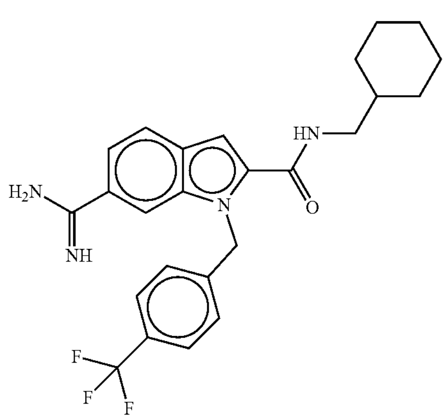 | 3.8 | 95 | 457.1 | A | B |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-11 | 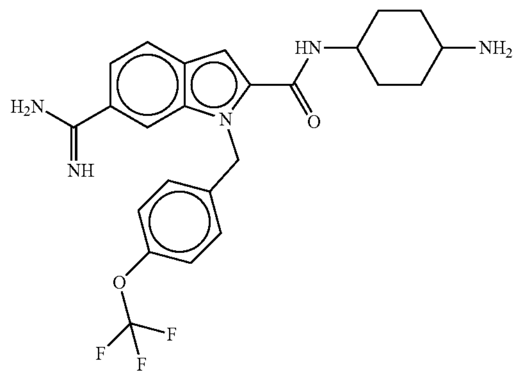 | 6.7 | 90.2 | 474.1 | A | B |
| I-12 | 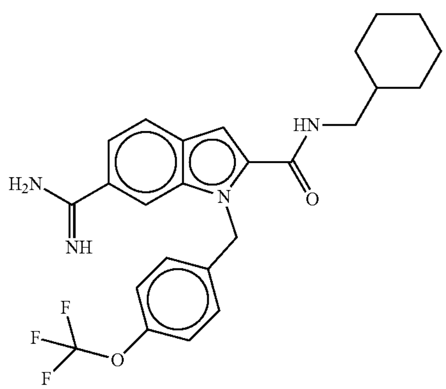 | 4.1 | 98.8 | 473.3 | A | A |
| I-13 | 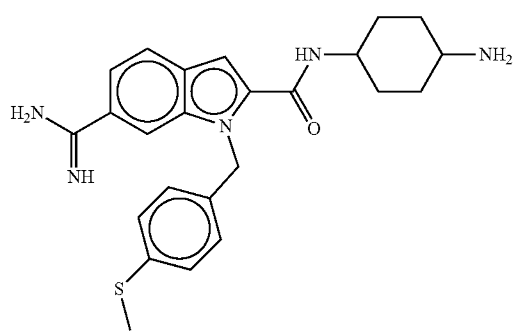 | 7.4 | 88.7 | 436.1 | A | C |
| I-14 | 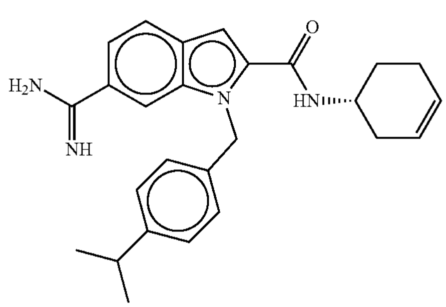 | NA | NA | 415.1 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-15 | 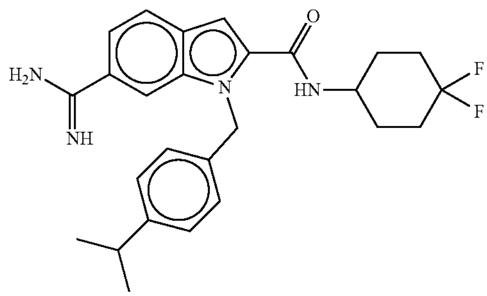 | 7.3 | 87.4 | 453.2 | A | A |
| I-16 | 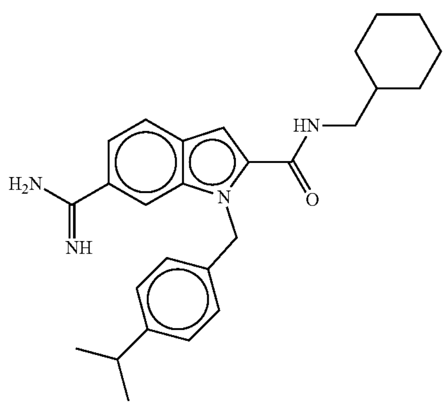 | 4.2 | 92.6 | 431.3 | A | A |
| I-17 | 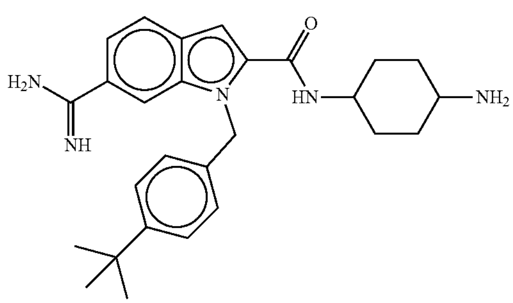 | 6.9 | 95.7 | 446.2 | A | C |
| I-18 | 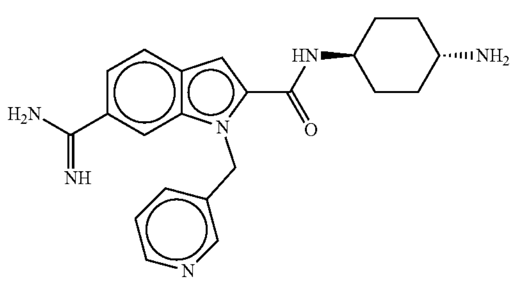 | NA | NA | 391.2 | A | B |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-19 | 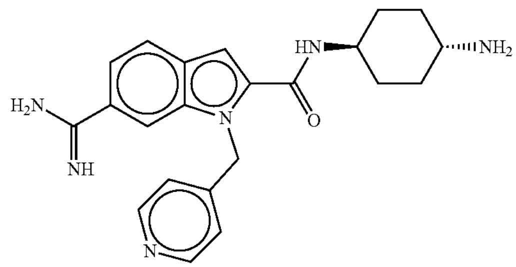 | 5.7 | 93.2 | 391.2 | A | B |
| I-20 | 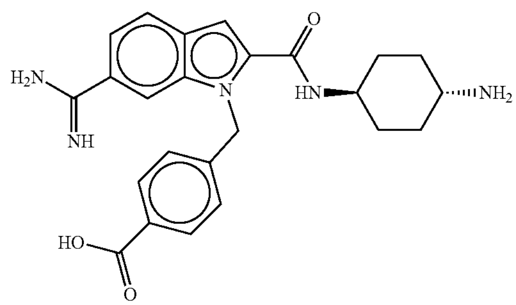 | 4.3 | 90.1 | 434.2 | A | B |
| I-21 | 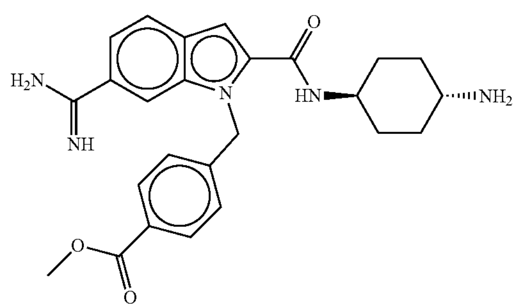 | 4.4 | 96.7 | 448.2 | A | C |
| I-22 | 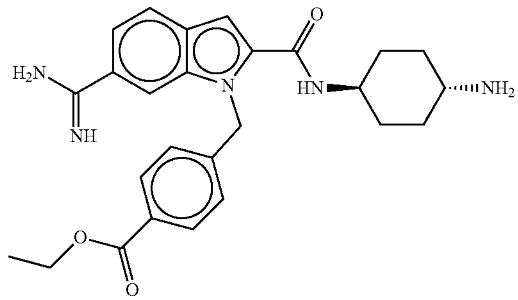 | 4.6 | 96.2 | 462.2 | A | B |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-23 | 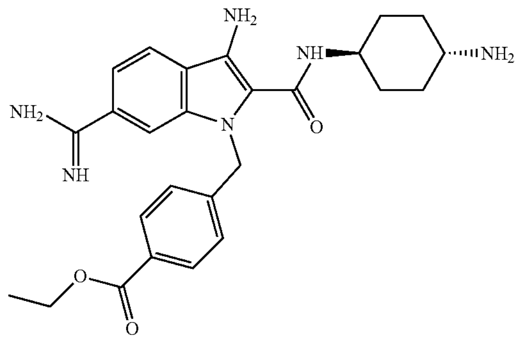 [SMILES: CCOC(=O)c1ccc(Cn2c(C(=O)N[C@H]3CC[C@H](N)CC3)c(N)c3ccc(C(=N)N)cc32)cc1] | | | 477.2 | ND | ND |
| I-24 | 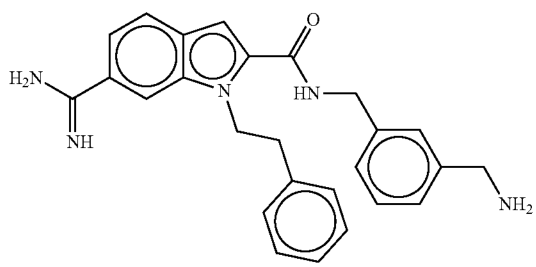 | 5.6 | 95.4 | 426.2 | A | A |
| I-25 | 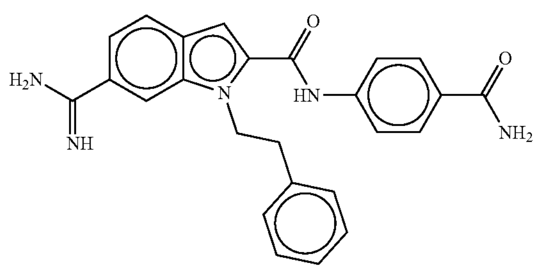 | 5 | 95.2 | 426.2 | A | A |
| I-26 | 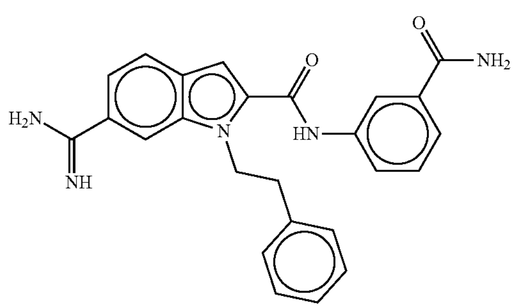 | 5.1 | 94.1 | 426.2 | A | A |
| I-27 | 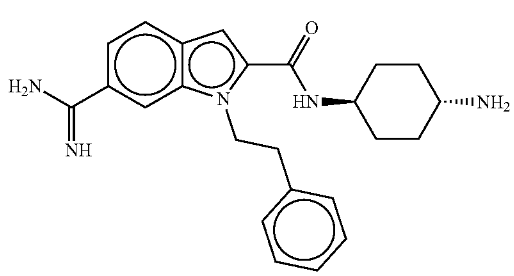 | 6.3 | 98.1 | 404.2 | A | C |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-28 | 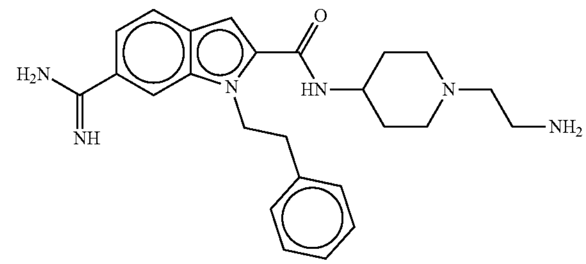 | 4.2 | 94.7 | 433.3 | A | B |
| I-29 | 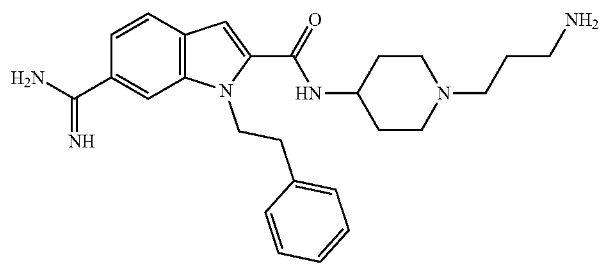 [SMILES: N=C(N)c1ccc2cc(C(=O)NC3CCN(CCCN)CC3)n(CCc3ccccc3)c2c1] | | | 447.3 | ND | ND |
| I-30 | 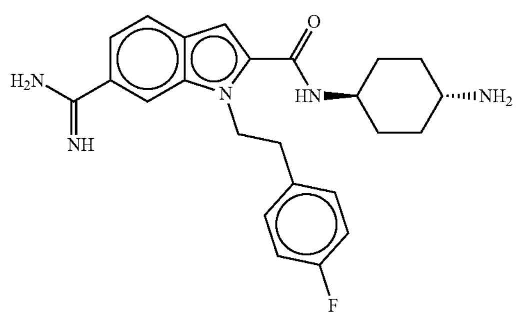 | 4.5 | 96.4 | 422.2 | A | B |
| I-31 | 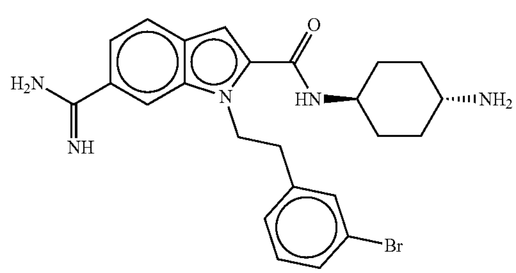 | 5 | 96.7 | 484 | A | B |
| I-32 | 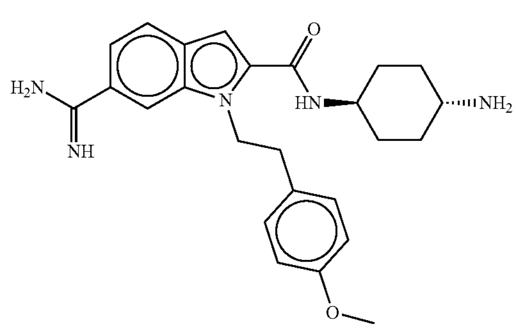 | 5.4 | 91.1 | 434.2 | A | B |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-33 | 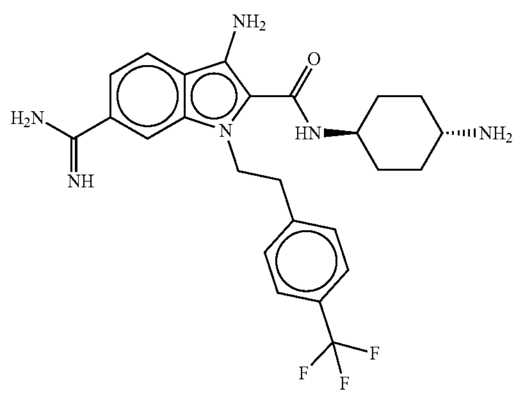 | 4.7 | 95.7 | 487.2 | A | A |
| I-34 | 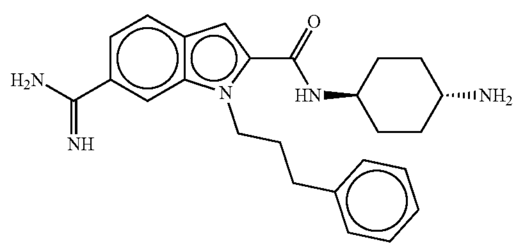 | 6.4 | 99.1 | 418.2 | A | B |
| I-35 | 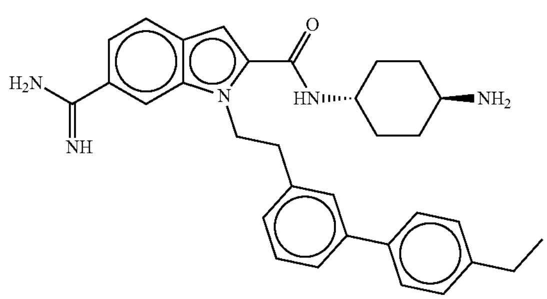 | 6 | 98.5 | 508.2 | A | B |
| I-36 | 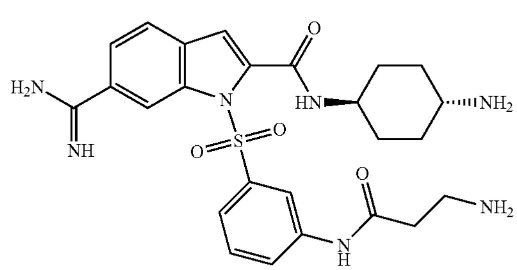 [SMILES: N=C(N)c1ccc2cc(C(=O)N[C@H]3CC[C@H](N)CC3)n(S(=O)(=O)c3cccc(NC(=O)CCN)c3)c2c1] | | | 526.2 | ND | ND |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-37 | 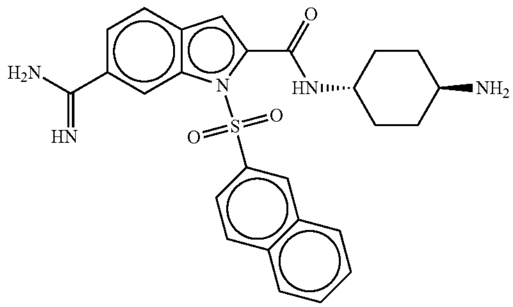 | 4.8 | 98.5 | 490.3 | B | A |
| I-38 | 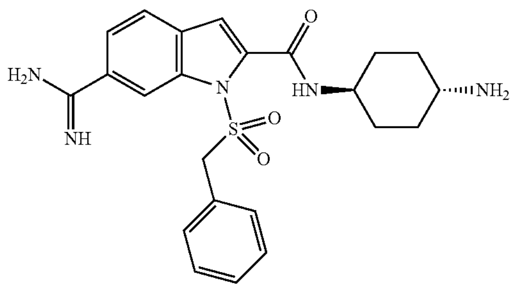 [SMILES: N=C(N)c1ccc2cc(C(=O)N[C@H]3CC[C@H](N)CC3)n(S(=O)(=O)Cc3ccccc3)c2c1] | | | 454.2 | ND | ND |
| I-39 | 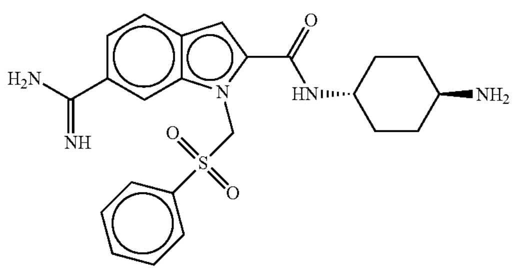 | 4.2 | 93.1 | 454.1 | A | B |
| I-40 | 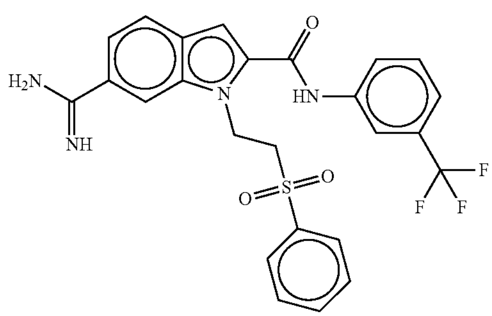 | 3.6 | 97.3 | | A | A |
| I-41 | 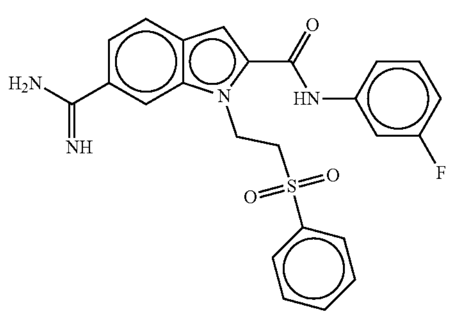 | 6.3 | 93.5 | 465 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-42 | 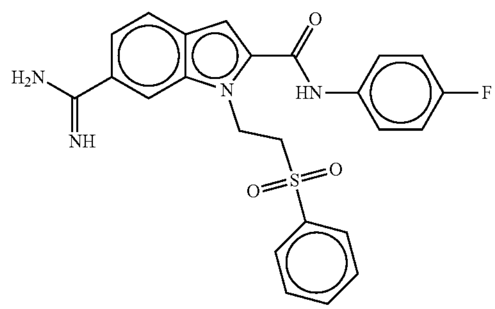 | 7 | 94.1 | 465 | A | A |
| I-43 | 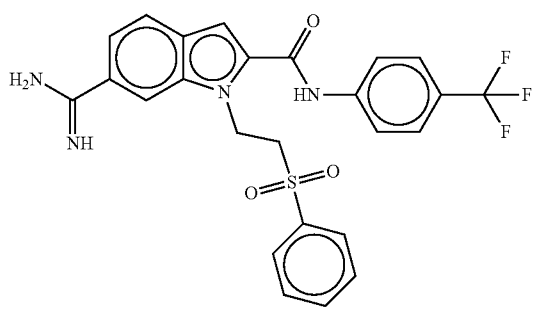 | 6.9 | 95.4 | 514.9 | A | A |
| I-44 | 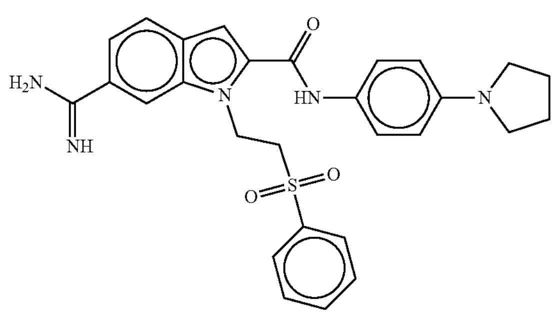 | 6.8 | 98.7 | 516.55 | A | A |
| I-45 | 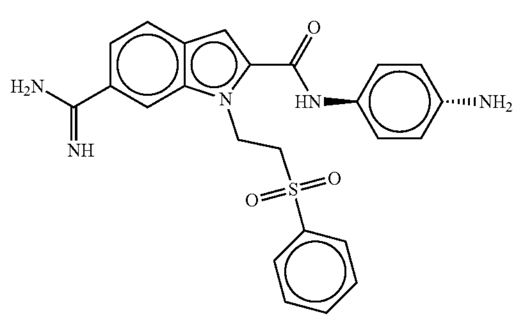 | 4.4 | 98.9 | 468.2 | A | C |

TABLE A-continued

Exemplary Compounds

| Cpd. ID. | Structure | HPLC Rt- min | % Purity- Indole | M + H | Assay Used | Mar-2 % inhibition at 1 uM |
|---|---|---|---|---|---|---|
| I-46 | 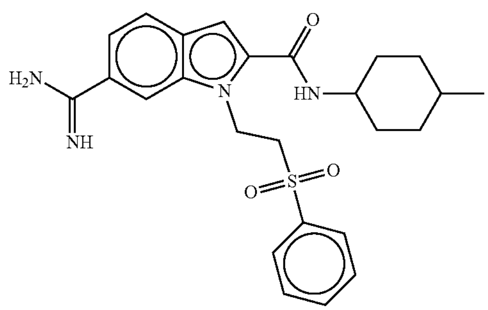 | 3.6 | 96.9 | 467.2 | A | A |
| I-47 | 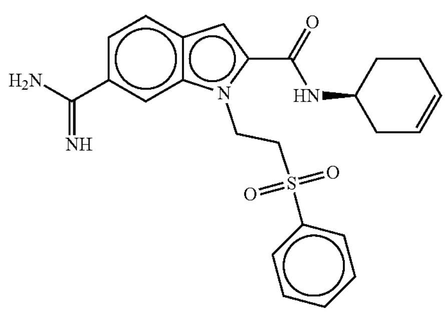 | 3.3 | 96.2 | 451.3 | A | A |
| I-48 | 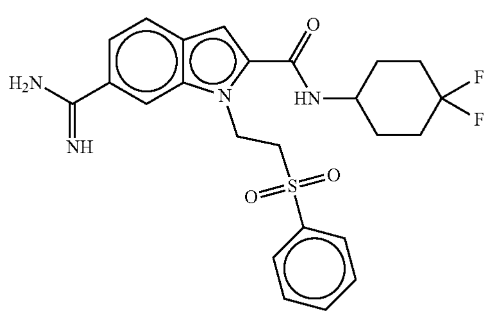 | 6.1 | 95.7 | 489.1 | A | B |
| I-49 | 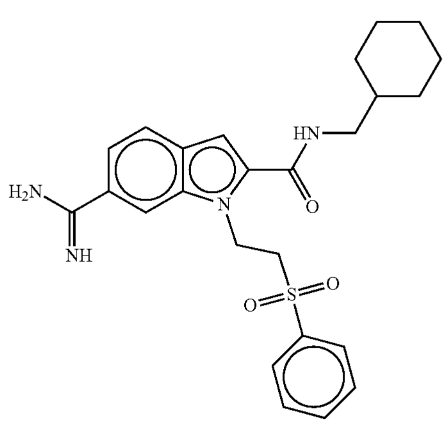 | 7.2 | 98.8 | 467.2 | A | A |

TABLE A-continued

Exemplary Compounds

| Cpd. ID. | Structure | HPLC Rt- min | % Purity- Indole | M + H | Assay Used | Mar-2 % inhibition at 1 uM |
|---|---|---|---|---|---|---|
| I-50 | 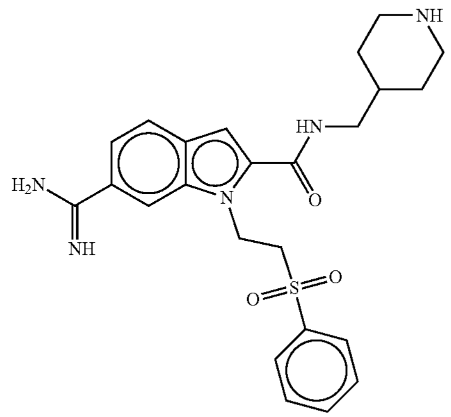 | 4.5 | 90.1 | 568.2 | A | C |
| I-51 | 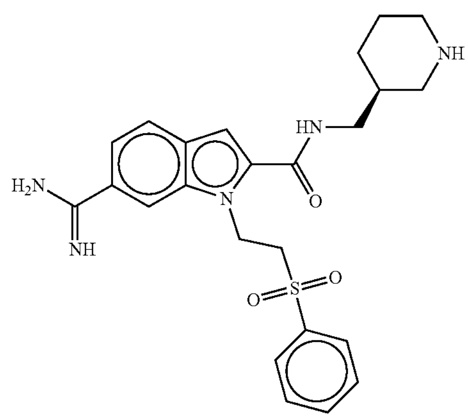 | 4.6 | 98.7 | 468 | A | B |
| I-52 | 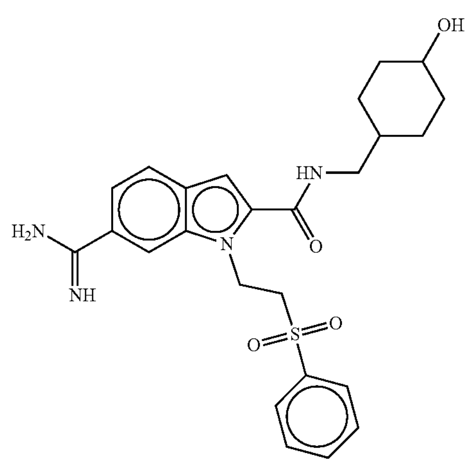 | 5.5 | 76.3 | 483.2 | A | A |

TABLE A-continued
Exemplary Compounds
| Cpd. ID. | Structure | HPLC Rt- min | % Purity- Indole | M + H | Assay Used | Mar-2 % inhibition at 1 uM |
|---|---|---|---|---|---|---|
| I-53 | 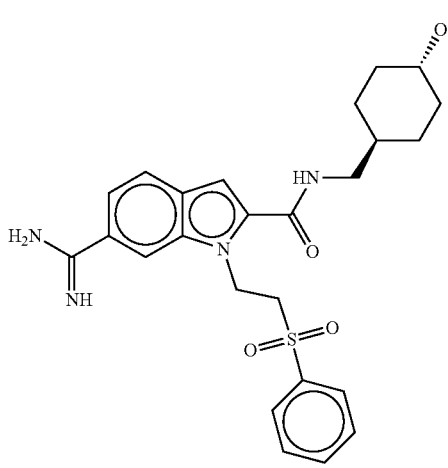 | 5.5 | 96 | 468.2 | A | A |
| I-54 | 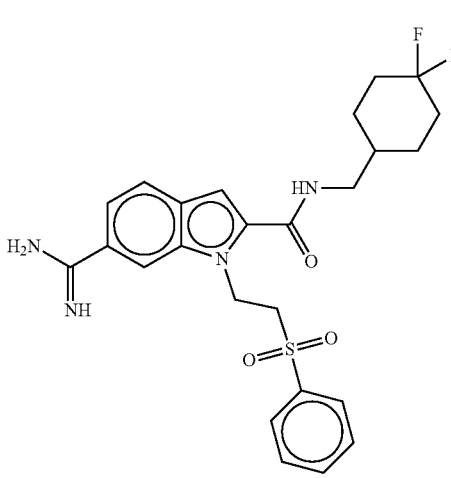 | 6.2 | 98 | 503.2 | A | A |
| I-55 | 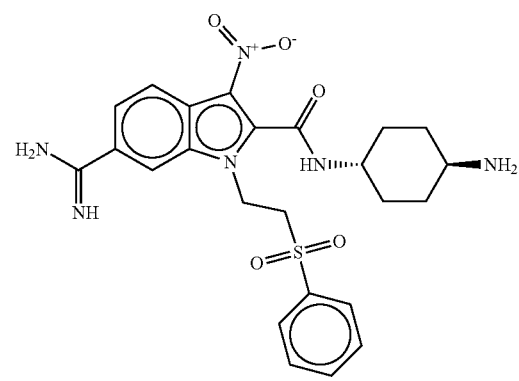 | NA | NA | 513.2 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-56 | 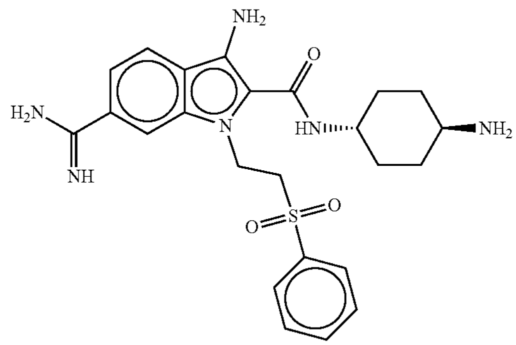 | NA | NA | 483.2 | A | B |
| I-57 | 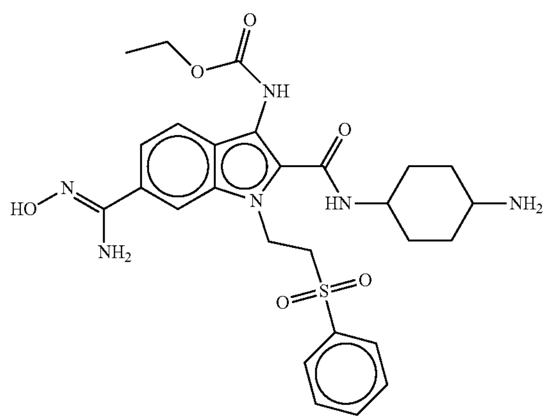 | 4.5 | 90.1 | 571 | A | A |
| I-58 | 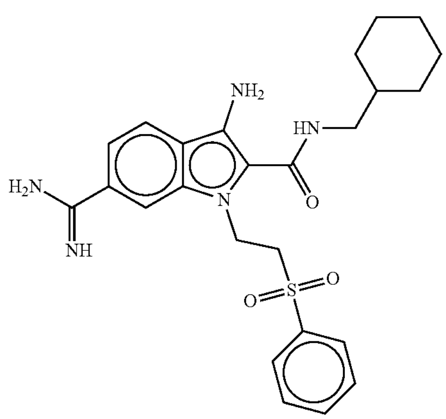 | 6.4 | 93.5 | 482.2 | A | A |
| I-59 | 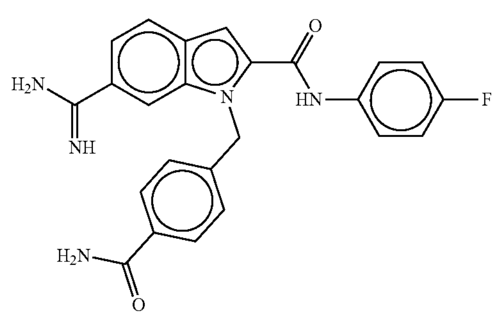 | 3 | 98.1 | 430.1 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-60 | 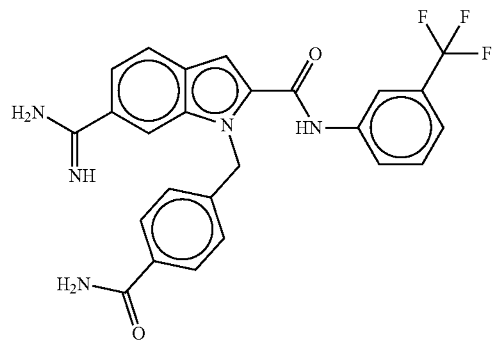 | 5.7 | 95.5 | 480.2 | A | A |
| I-61 | 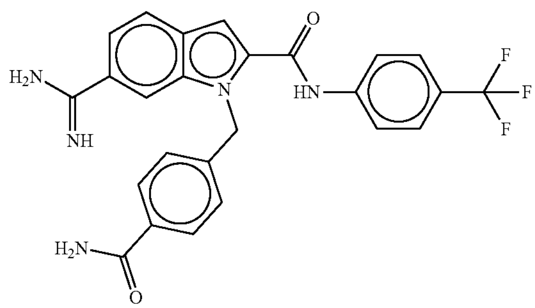 | 5.6 | 90.5 | 480.2 | A | A |
| I-62 | 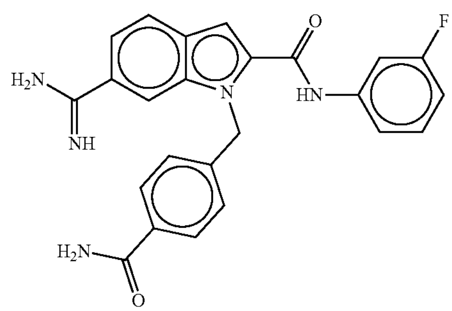 | 5.2 | 97.3 | 430.2 | A | A |
| I-63 | 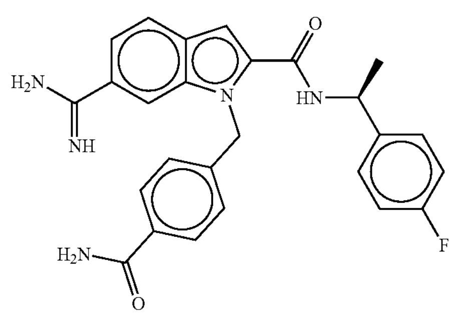 | 3.9 | 91.8 | 458.2 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-64 | 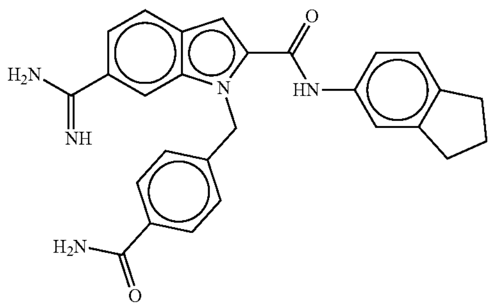 | 6.3 | 89.9 | 452.2 | A | A |
| I-65 | 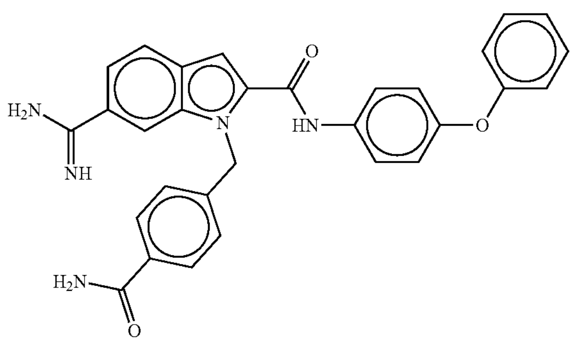 | 3.2 | 92.5 | 504.3 | A | A |
| I-66 | 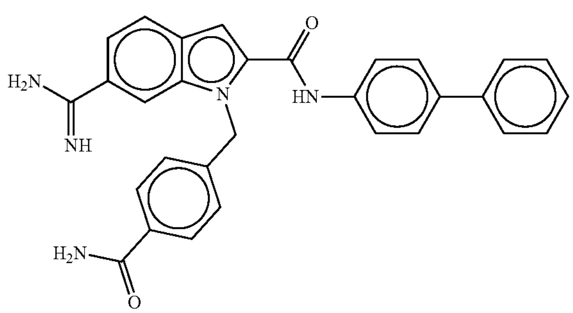 | 6.2 | 91.8 | 488.2 | A | A |
| I-67 | 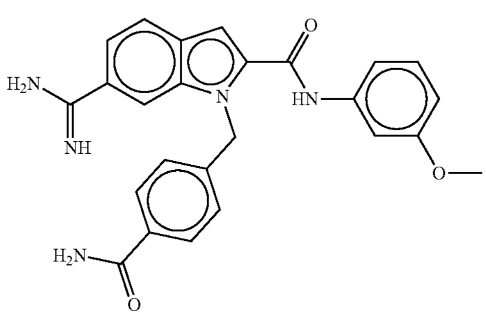 | 6 | 92.6 | 442 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-68 | 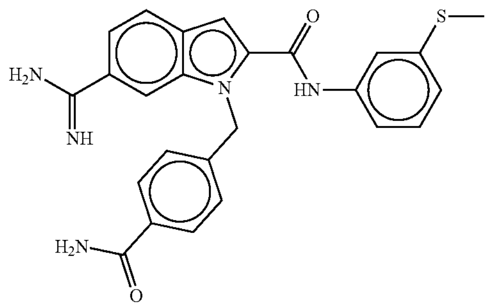 | 6.3 | 93.8 | 457.9 | A | A |
| I-69 | 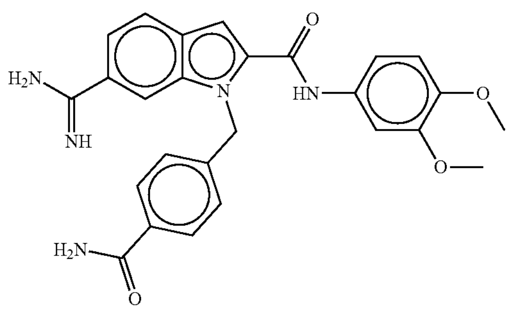 | 11.7 | 89.2 | 471.8 | A | A |
| I-70 | 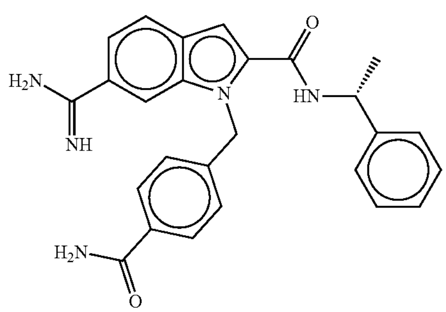 | 2.8 | 91.2 | 439.8 | A | A |
| I-71 | 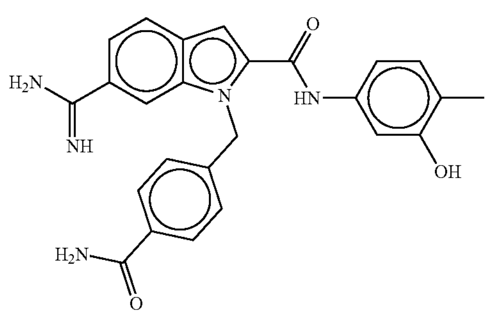 | 4.9 | 93 | 441.9 | A | A |

TABLE A-continued
Exemplary Compounds
| Cpd. ID. | Structure | HPLC Rt-min | % Purity-Indole | M + H | Assay Used | Mar-2 % inhibition at 1 uM |
|---|---|---|---|---|---|---|
| I-72 | 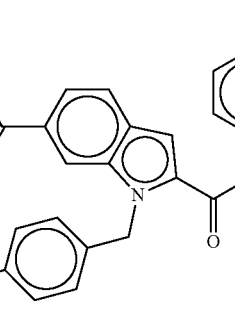 | 6.1 | 95.7 | 440.2 | A | A |
| I-73 | 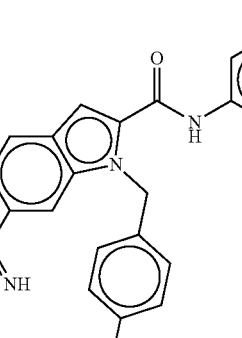 | 4.7 | 87.9 | 463.2 | A | B |
| I-74 | 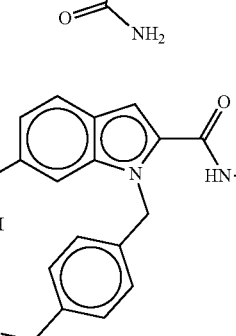 | 4.7 | 89.5 | 452.7 | A | A |
| I-75 | 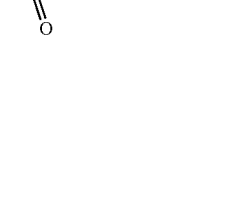 | 6.2 | 95 | 458.2 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-76 | 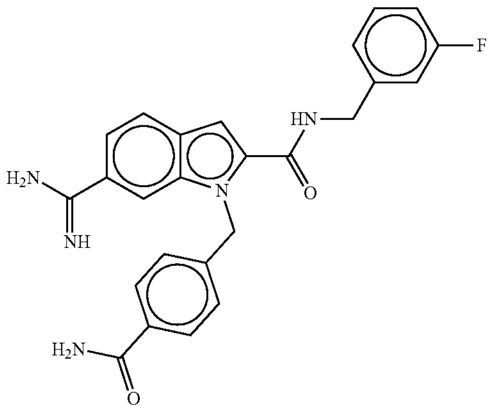 | 2.7 | 96.1 | 444.2 | A | A |
| I-77 | 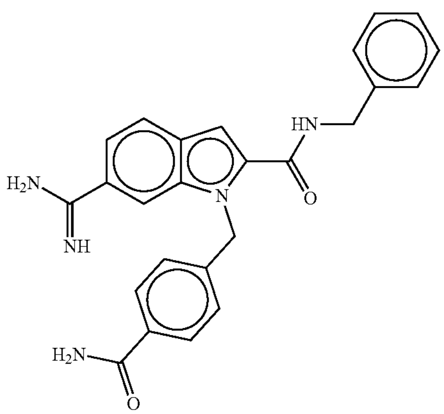 | 6.2 | 90.2 | 426.65 | A | A |
| I-78 | 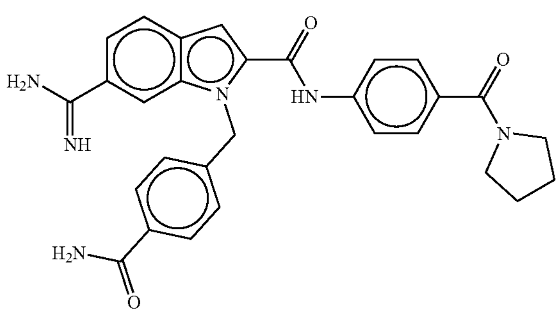 | 5.8 | 96.7 | 509.4 | A | A |
| I-79 | 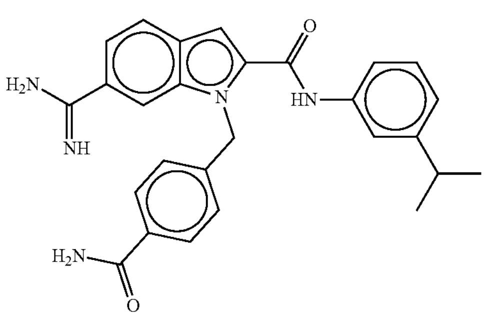 | 3.9 | 93.1 | 454.3 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-80 | 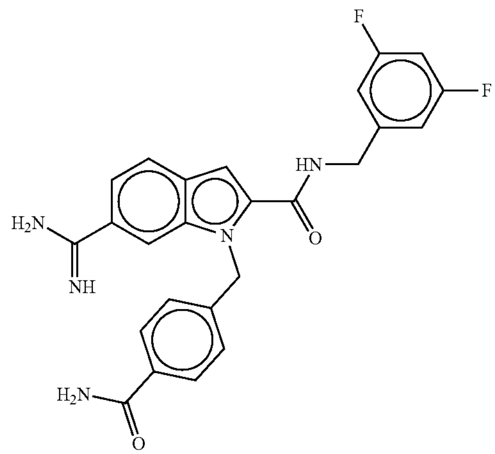 | 3.5 | 99.3 | 462.2 | A | A |
| I-81 | 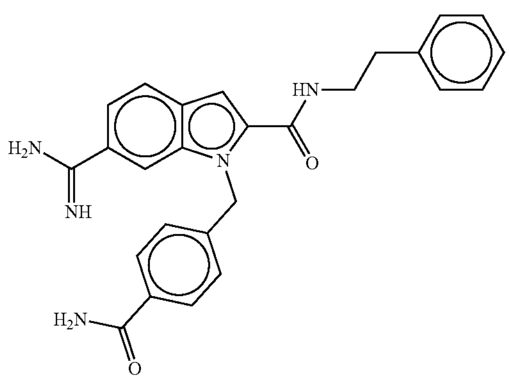 | 5.9 | 97.9 | 440.2 | A | A |
| I-82 | 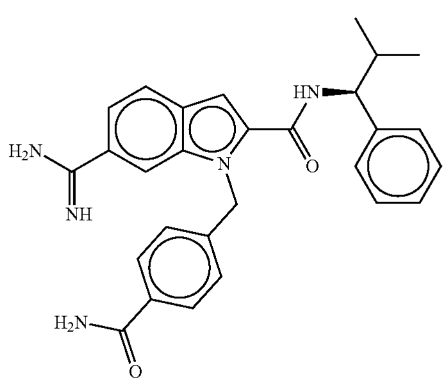 | 2.9 | 89.6 | 467.9 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-83 | 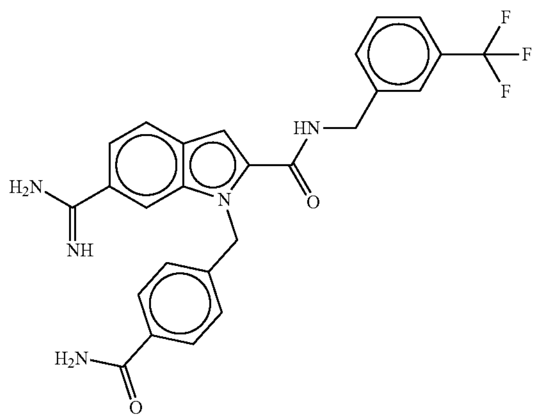 | 2.9 | 99.1 | 494.5 | A | A |
| I-84 | 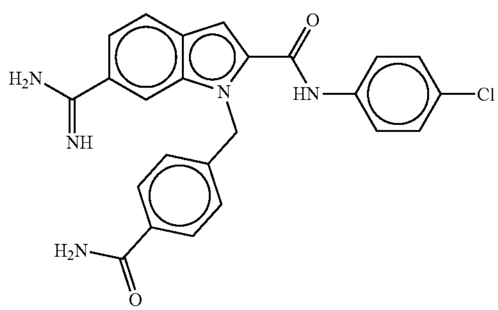 | 3.3 | 96.2 | 446.25 | A | A |
| I-85 | 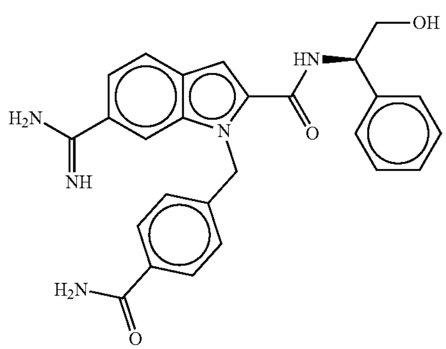 | 5.5 | 94.9 | 456.4 | A | A |
| I-86 | 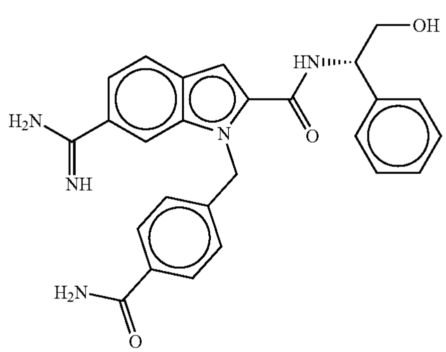 | 5.3 | 92.7 | 456.2 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-87 | 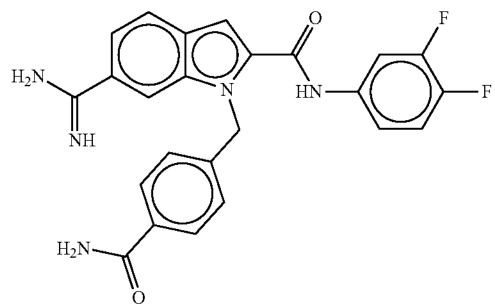 | 3.6 | 96.3 | 447.8 | A | A |
| I-88 | 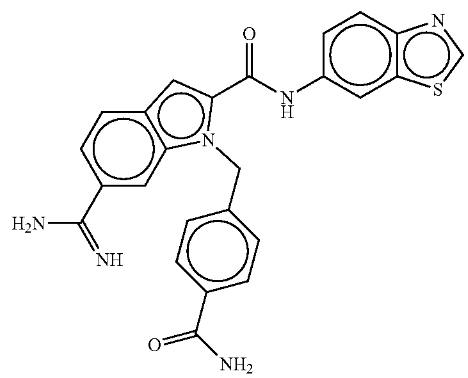 | 5.6 | 87.1 | 469.2 | A | A |
| I-89 | 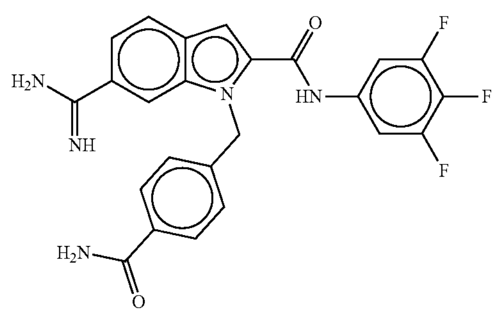 | 3.2 | 97.1 | 466.3 | A | A |
| I-90 | 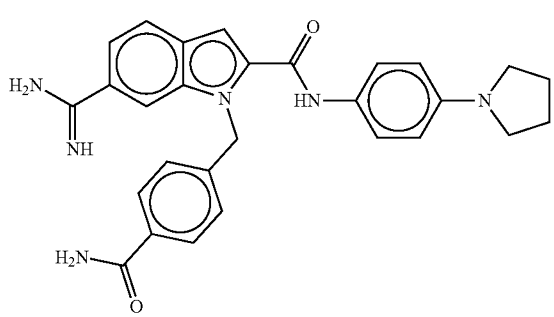 | 3.2 | 92.5 | 481.2 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-91 | 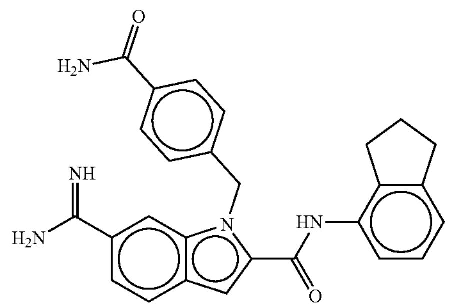 | 6.2 | 90 | 452.3 | A | A |
| I-92 | 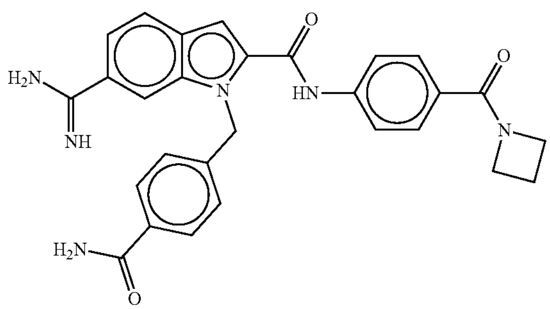 | 5.5 | 96.4 | 495.2 | A | A |
| I-93 | 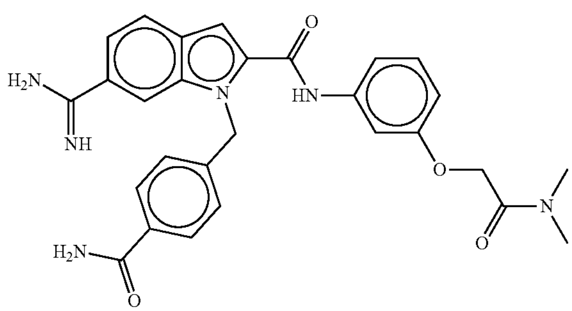 | 5.5 | 95.2 | 535.1 | A | A |
| I-94 | 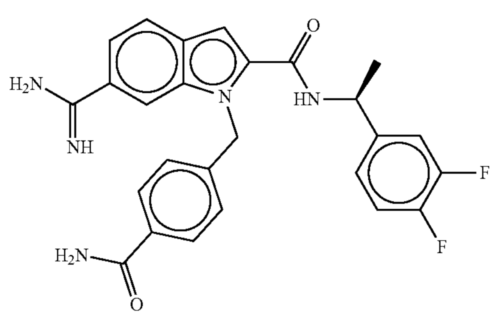 | 3.1 | 98.4 | 476.2 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-95 | 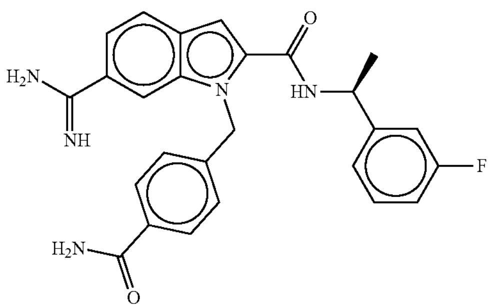 | 3.1 | 96.6 | 458.2 | A | A |
| I-96 | 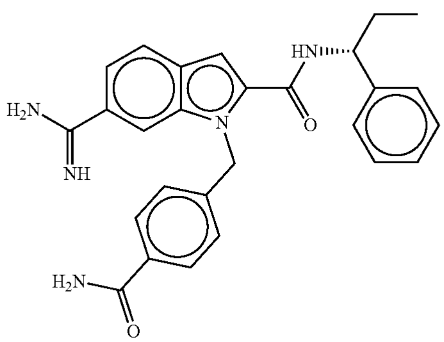 | 6.3 | 97.3 | 454.2 | A | B |
| I-97 | 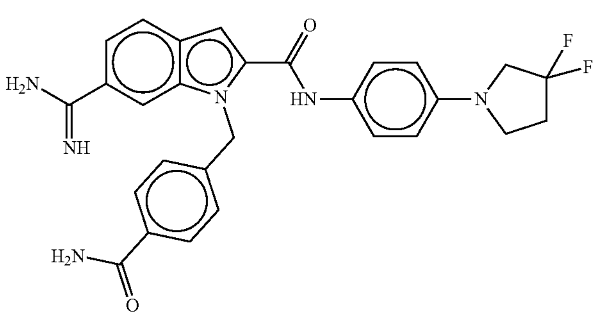 | 6.4 | 97.6 | 517.4 | A | B |
| I-98 | 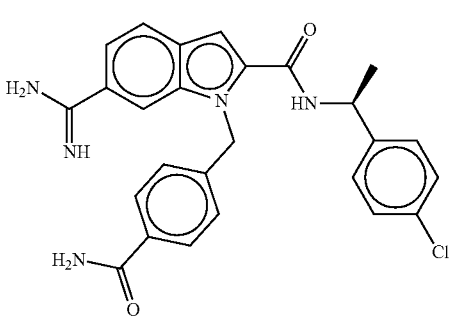 | 3.2 | 90.8 | 474.3 | A | A |

TABLE A-continued
Exemplary Compounds
| Cpd. ID. | Structure | HPLC Rt-min | % Purity-Indole | M + H | Assay Used | Mar-2 % inhibition at 1 uM |
|---|---|---|---|---|---|---|
| I-99 | 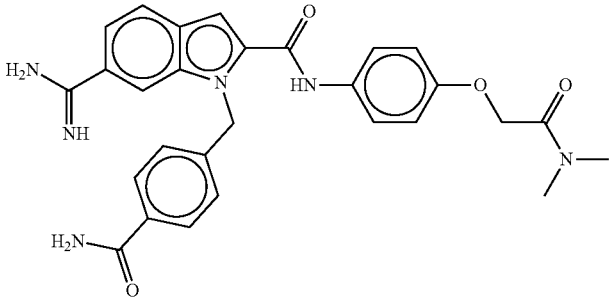 | 2.7 | 97 | 513.2 | A | B |
| I-100 | 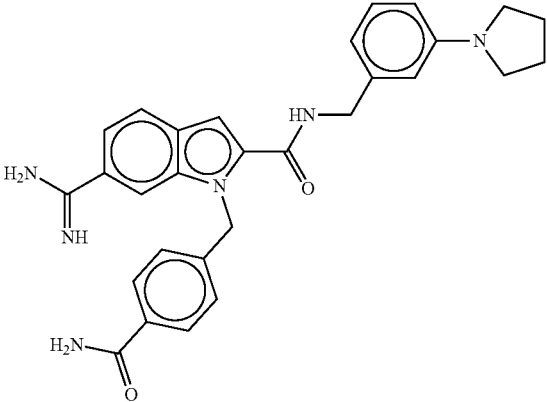 | NA | NA | 495.2 | A | B |
| I-101 | 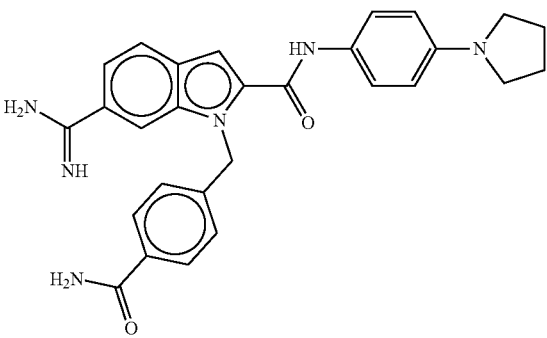 |  |  | 481.2 | ND | ND |
| I-102 | 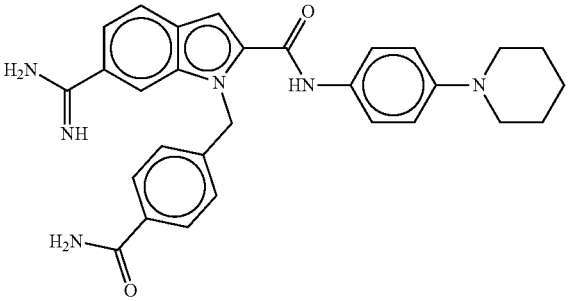 | 5.1 | 99.2 | 495.15 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-103 | 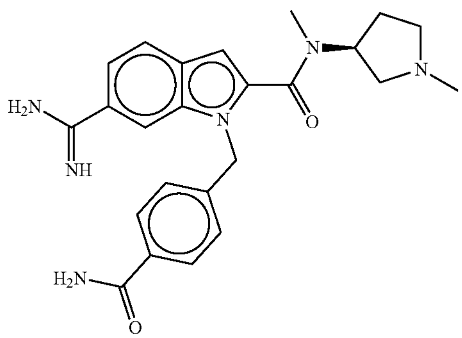 | 4.4 | 94.3 | 433.3 | A | A |
| I-104 | 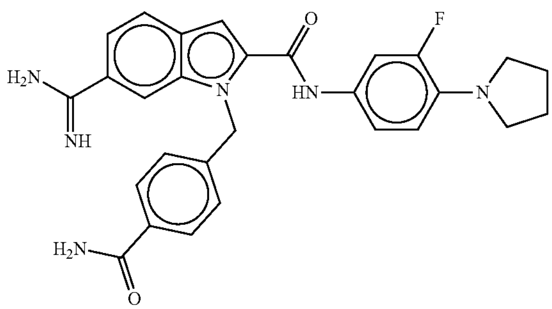 | 6.6 | 97.8 | 499.6 | A | A |
| I-105 | 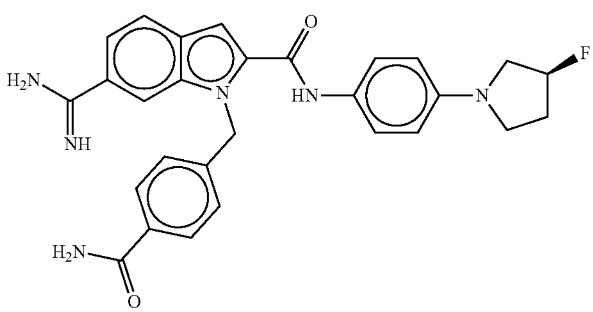 | 5.9 | 97.5 | 499.4 | A | B |
| I-106 | 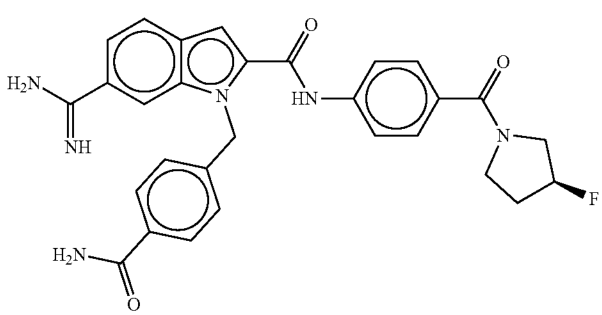 | 3.2 | 99.8 | 527.4 | A | A |

TABLE A-continued
Exemplary Compounds
| Cpd. ID. | Structure | HPLC Rt-min | % Purity-Indole | M + H | Assay Used | Mar-2 % inhibition at 1 uM |
|---|---|---|---|---|---|---|
| I-107 | 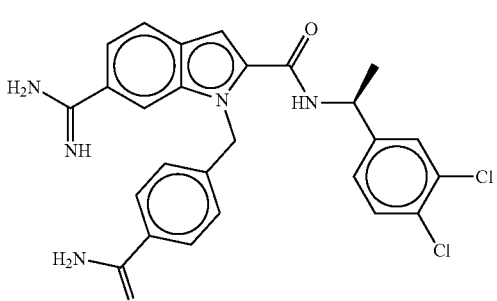 | 3.8 | 96.4 | 508.45 | A | A |
| I-108 | 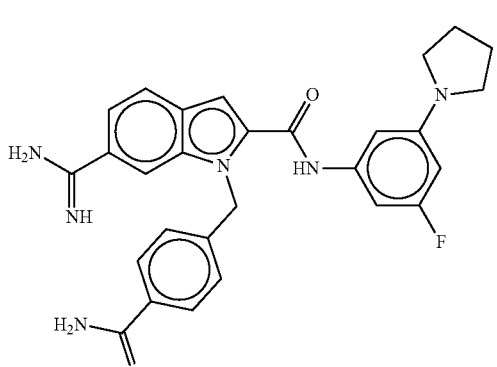 | 6.6 | 94.7 | 499.2 | A | A |
| I-109 | 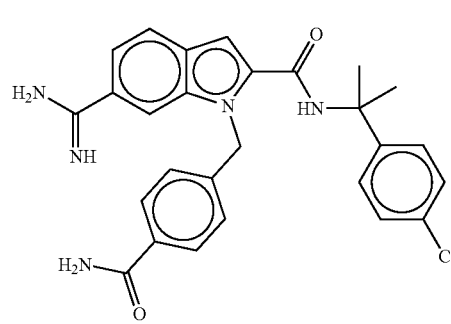 | 6.2 | 98 | 487.8 | A | A |
| I-110 | 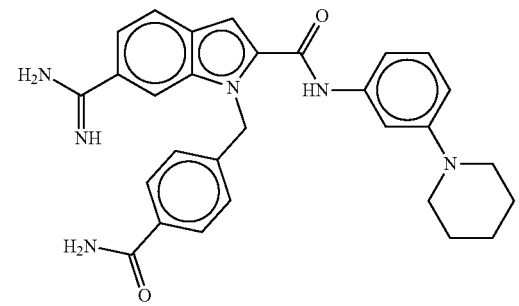 | 5.3 | 98.4 | 495.4 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-111 | 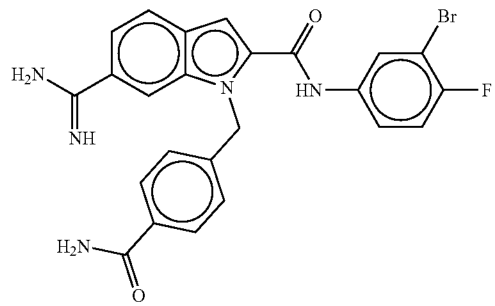 | 6.5 | 93.2 | 508.1 | A | A |
| I-112 | 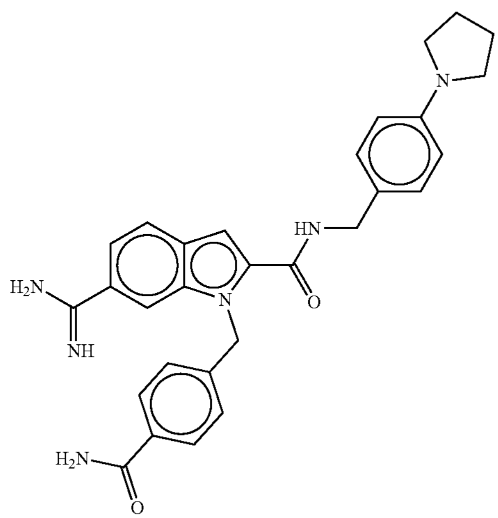 | NA | NA | 495.2 | A | B |
| I-113 | 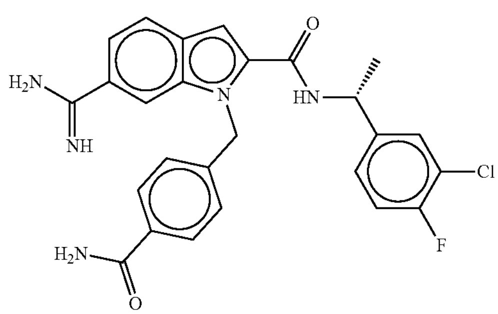 | 6.4 | 94 | 491.8 | A | A |
| I-114 | 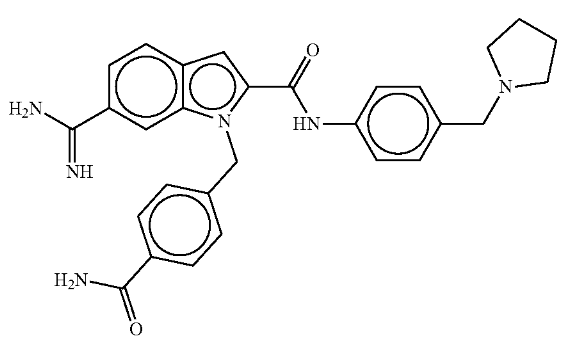 | 4.8 | 97.9 | 495.3 | A | B |

TABLE A-continued
Exemplary Compounds
| Cpd. ID. | Structure | HPLC Rt-min | % Purity-Indole | M + H | Assay Used | Mar-2 % inhibition at 1 uM |
|---|---|---|---|---|---|---|
| I-115 | 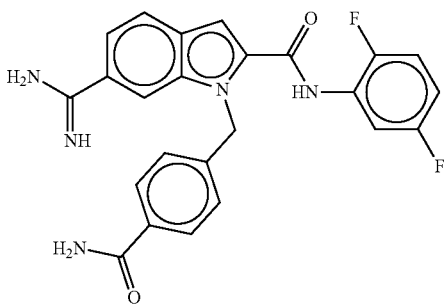 | 5.6 | 96.3 | 448.3 | A | A |
| I-116 | 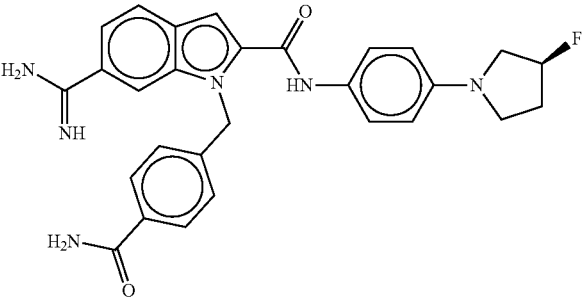 | 6.2 | 98.3 | 499.5 | A | B |
| I-117 | 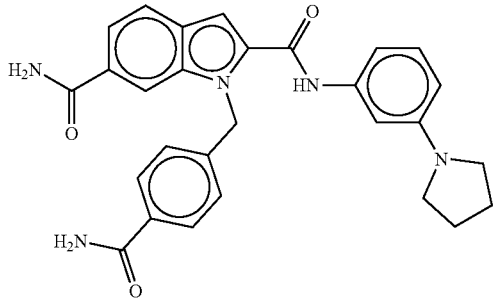 | 6.9 | 98.5 | 481.9 | A | A |
| I-118 | 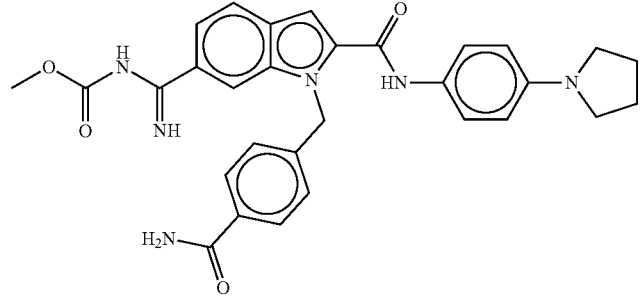 | 3.8 | 97.4 | 538.8 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-119 | 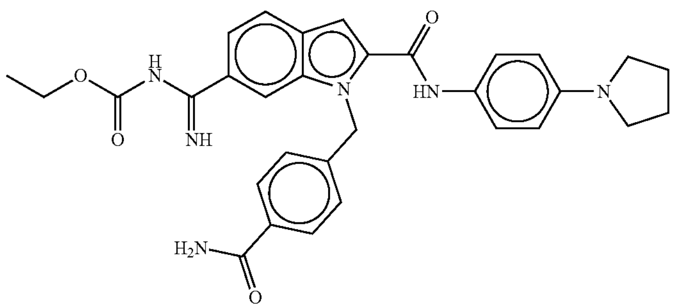 | 6 | 96.9 | 552.9 | A | A |
| I-120 | 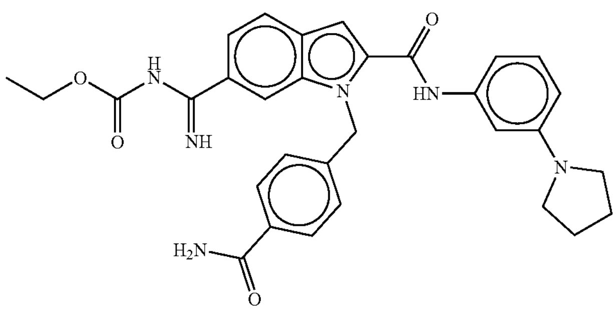 | 6.7 | 96 | 552.9 | A | A |
| I-121 | 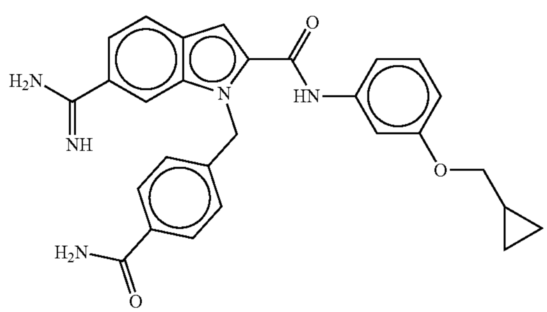 | 6.2 | 98.8 | 482.55 | A | A |
| I-122 | 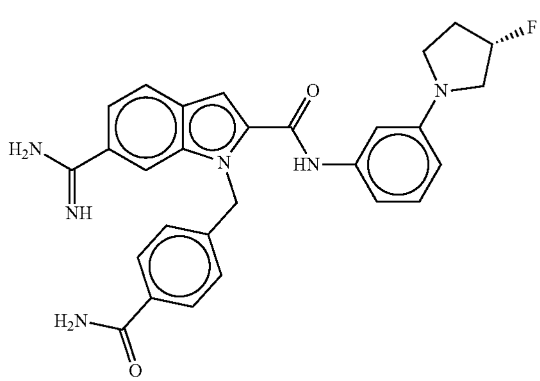 | 6.1 | 94.1 | 499.5 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-123 | 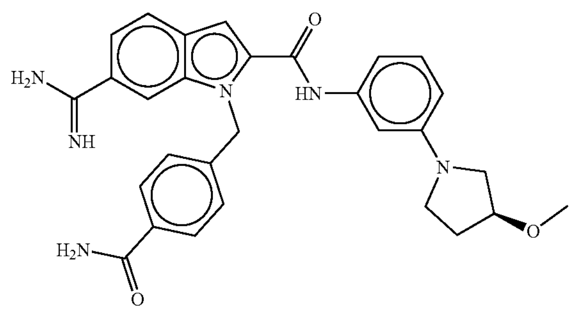 | 6.3 | 94.4 | 511.55 | A | A |
| I-124 | 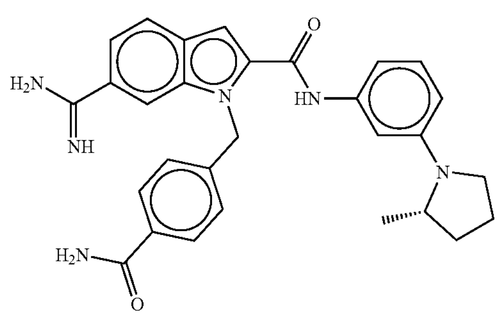 | 3.3 | 96.6 | 494.9 | A | A |
| I-125 | 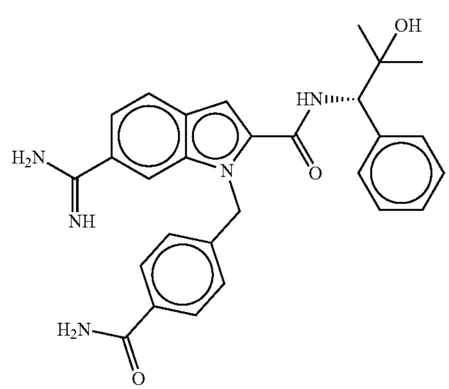 | 5.6 | 93.3 | 484.5 | A | B |
| I-126 | 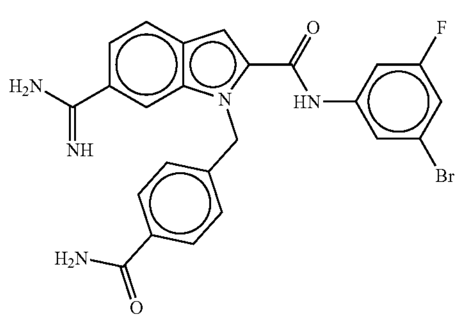 | 6.3 | 95.1 | 509.7 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-127 | 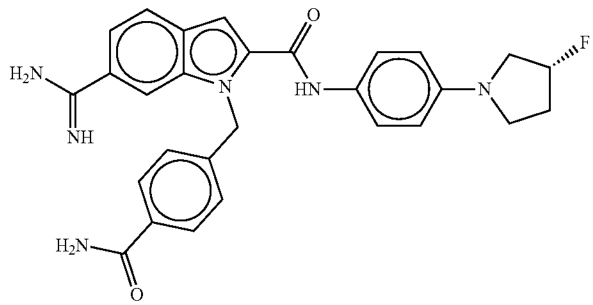 | 6.2 | 94 | 499.25 | A | B |
| I-128 | 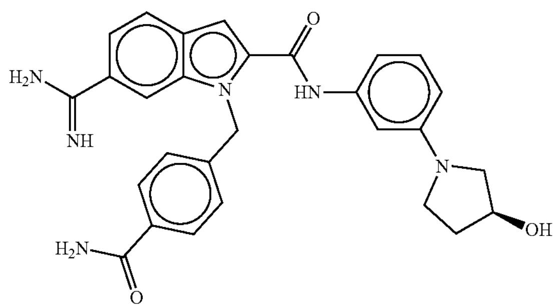 | 5.8 | 90.6 | 497.5 | A | A |
| I-129 | 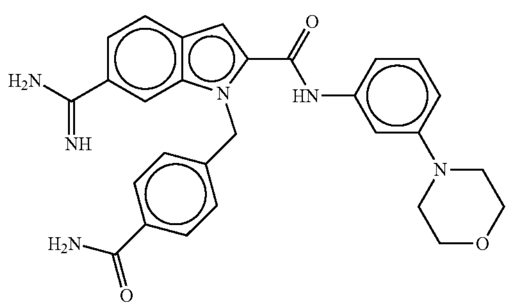 | 5.6 | 92.8 | 497.4 | A | A |
| I-130 | 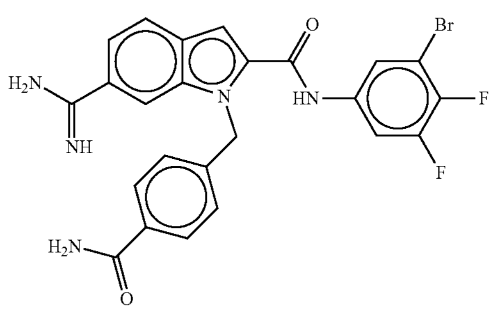 | 3.9 | 99.3 | 526.2 | A | A |

TABLE A-continued
Exemplary Compounds
| Cpd. ID. | Structure | HPLC Rt-min | % Purity-Indole | M + H | Assay Used | Mar-2 % inhibition at 1 uM |
|---|---|---|---|---|---|---|
| I-131 | 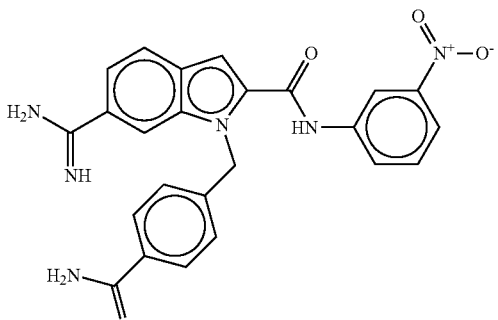 | 3.5 | 99.4 | 456.9 | A | A |
| I-132 | 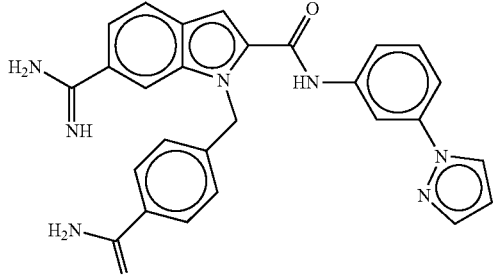 | 5.6 | 97.8 | 478.2 | A | B |
| I-133 | 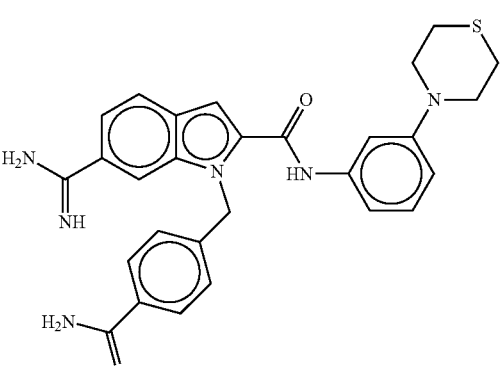 | 3.7 | 98.3 | 513.2 | A | A |
| I-134 | 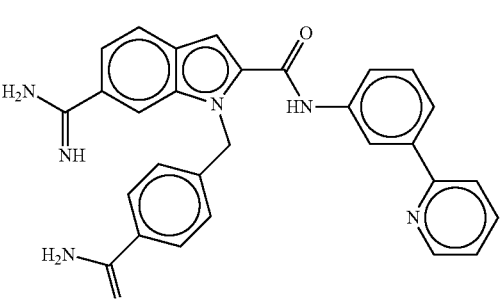 | 5.5 | 98.1 | 488.95 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-135 | 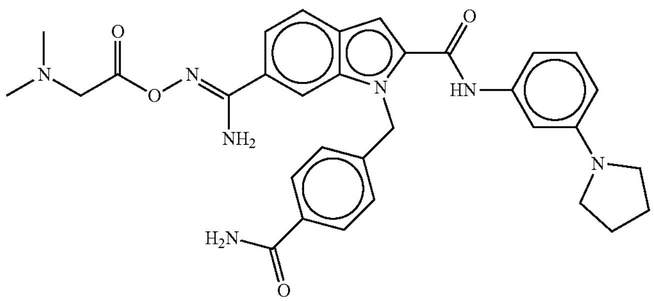 | 3.9 | 93.1 | 582.4 | A | A |
| I-136 | 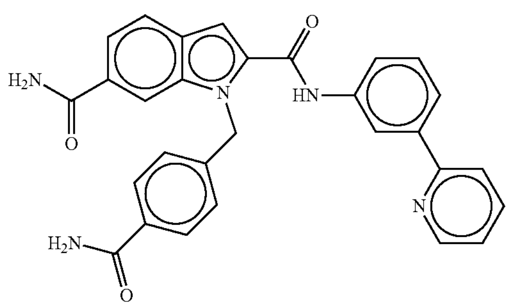 | 6.2 | 99.4 | 489.95 | A | A |
| I-137 | 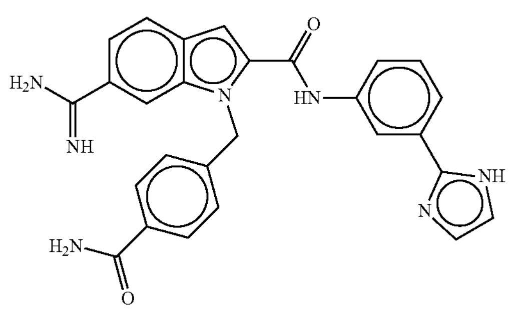 | 4.9 | 94.8 | 478.4 | A | B |
| I-138 | 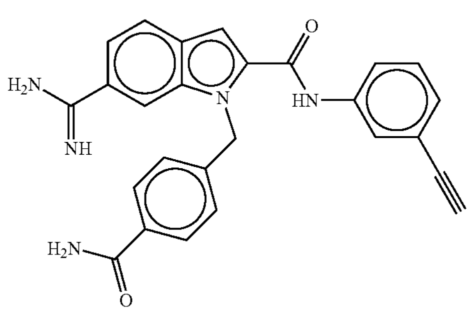 | 6.1 | 92.4 | 436.1 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-139 | 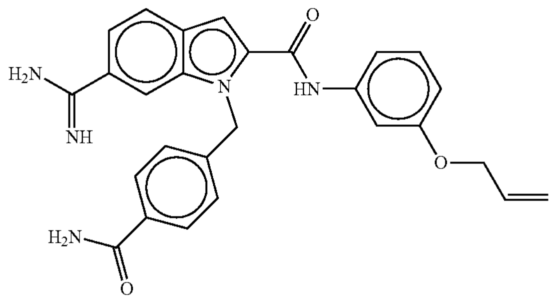 | 3.1 | 97.7 | 468.2 | A | A |
| I-140 | 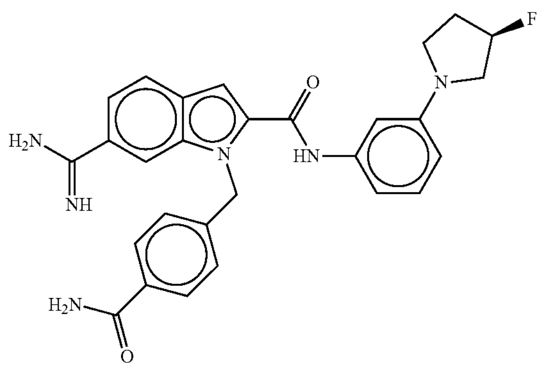 | NA | NA | 499.2 | A | A |
| I-141 | 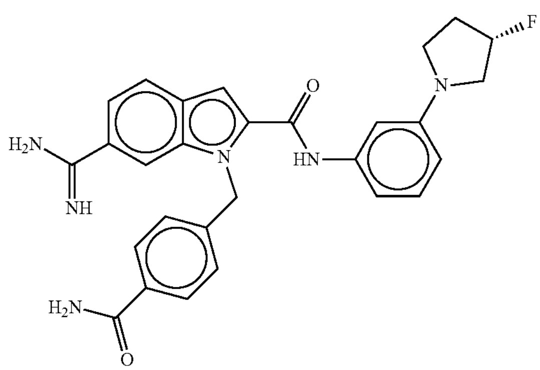 | NA | NA | 499.2 | A | A |
| I-142 | 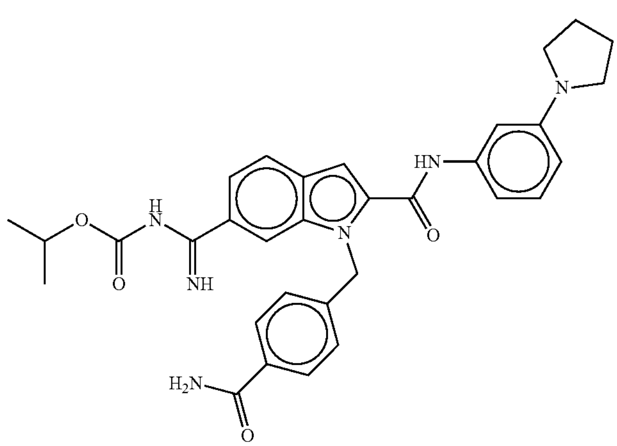 | 6.8 | 93.2 | 567.5 | A | B |

TABLE A-continued
Exemplary Compounds
| Cpd. ID. | Structure | HPLC Rt-min | % Purity-Indole | M + H | Assay Used | Mar-2 % inhibition at 1 uM |
|---|---|---|---|---|---|---|
| I-143 | 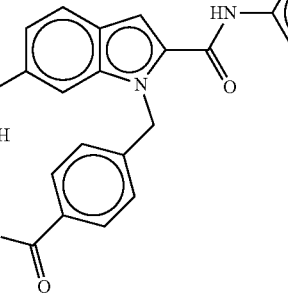 | 3.8 | 97.2 | 615.5 | A | A |
| I-144 | 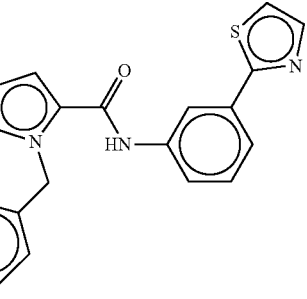 | 3.6 | 98.2 | 495.1 | A | A |
| I-145 | 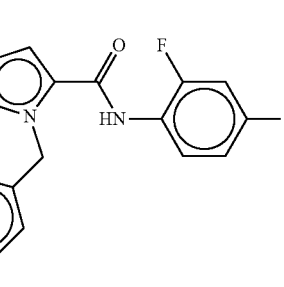 | 6.2 | 94.5 | 508 | A | A |
| I-146 | 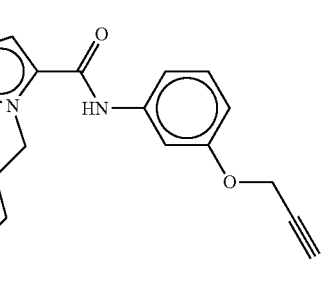 | 5.9 | 93.7 | 466 | A | B |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-147 | 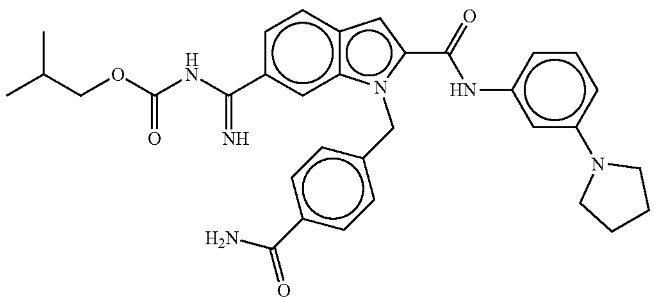 | 4.5 | 97.9 | 581.5 | A | A |
| I-148 | 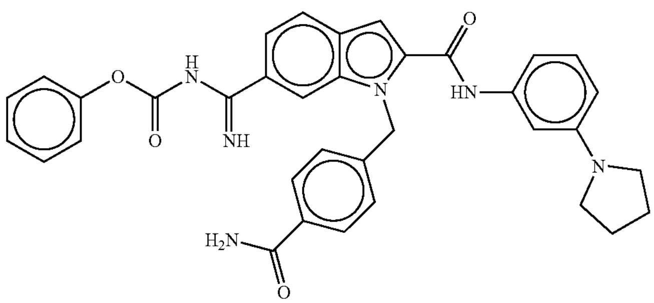 | 4.3 | 95.1 | 601.6 | A | A |
| I-149 | 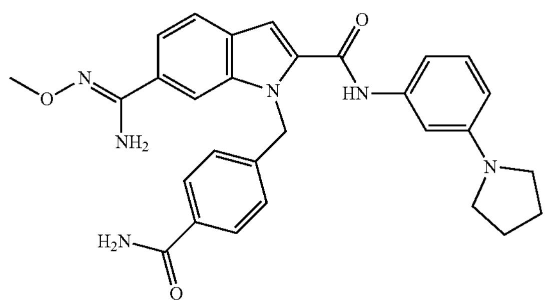 [SMILES: CO/N=C(\N)c1ccc2cc(C(=O)Nc3cccc(N4CCCC4)c3)n(Cc3ccc(C(N)=O)cc3)c2c1] | | | 511.2 | ND | ND |
| I-150 | 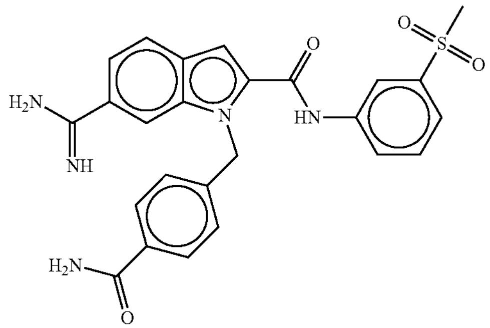 | 5.4 | 97.3 | 490.3 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-151 | 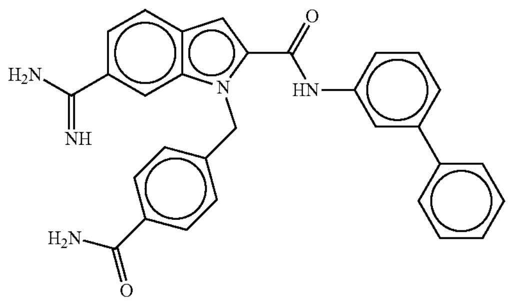 | 3.9 | 98.2 | 488.6 | A | A |
| I-152 | 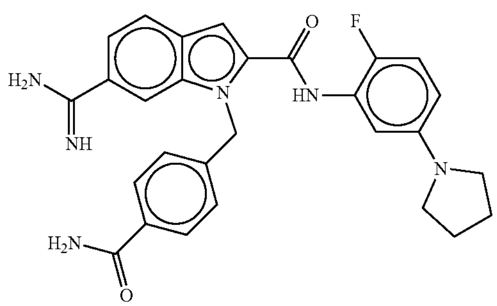 | 3.2 | 94.9 | 499.3 | A | A |
| I-153 | 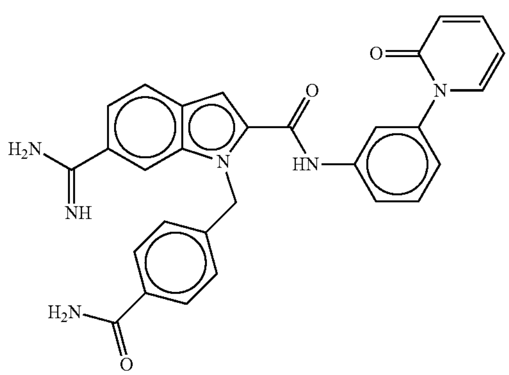 | 5.5 | 96.6 | 505.3 | A | B |
| I-154 | 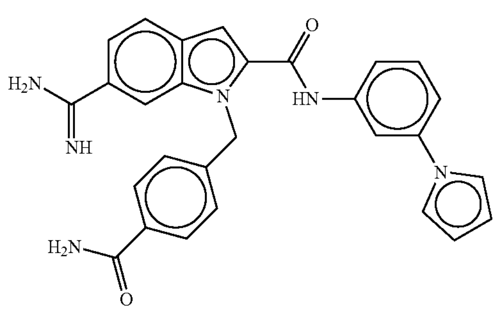 | 3.2 | 96.5 | 477.2 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-155 | 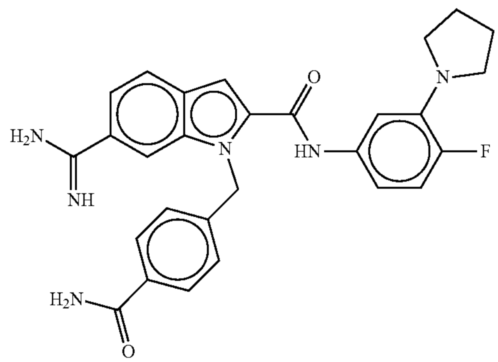 | 6.6 | 90.7 | 499.7 | A | A |
| I-156 | 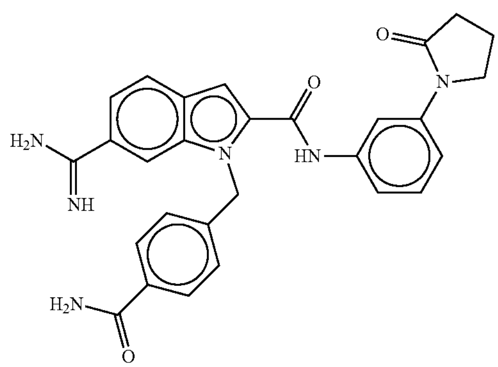 | 5.5 | 90.5 | 495.35 | A | A |
| I-157 | 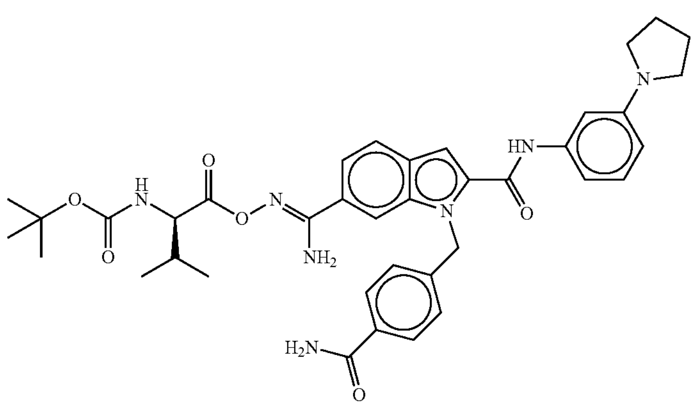 | 4.5 | 90.9 | 695.9 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-158 | 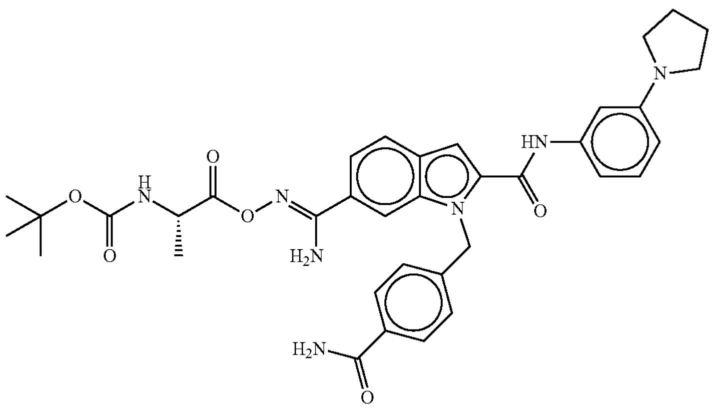 | 4.1 | 92.2 | 668.05 | A | A |
| I-159 | 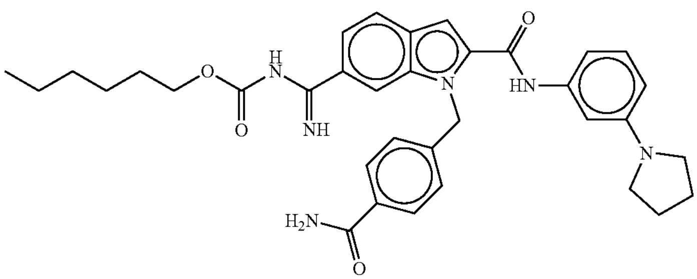 | 4.2 | 96.8 | 609.15 | A | A |
| I-160 | 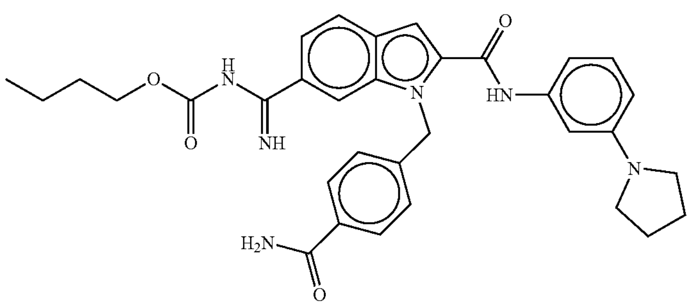 | 6.9 | 98.3 | 581.5 | A | A |
| I-161 | 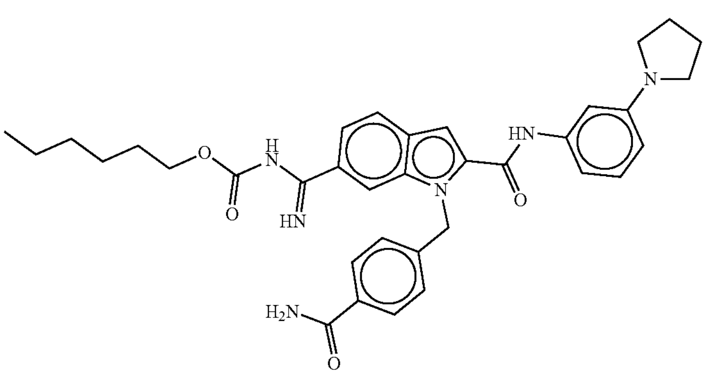 | 3.8 | 98.5 | 594.9 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-162 | 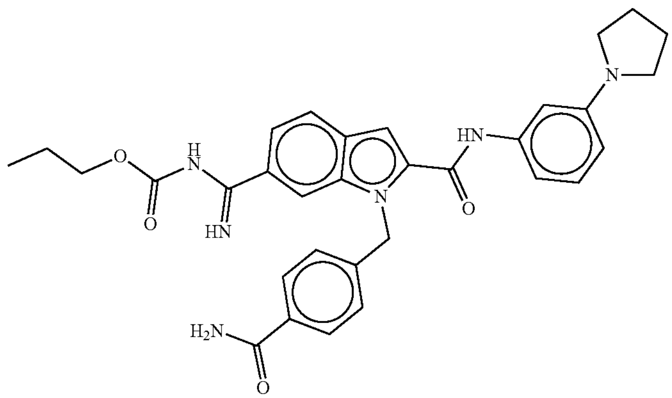 | 4 | 91.5 | 567.6 | A | A |
| I-163 | 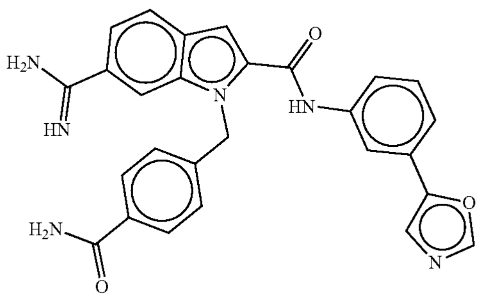 | 3.1 | 90.6 | 479.3 | A | A |
| I-164 | 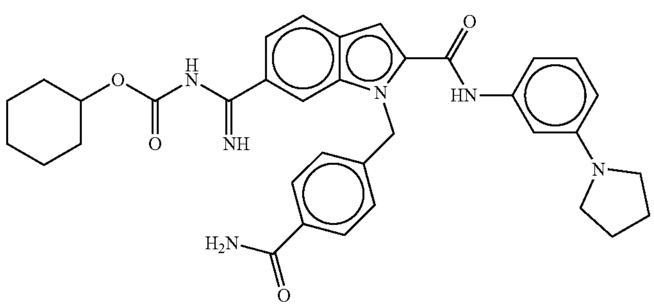 | 7.1 | 92.7 | 607.5 | A | A |
| I-165 | 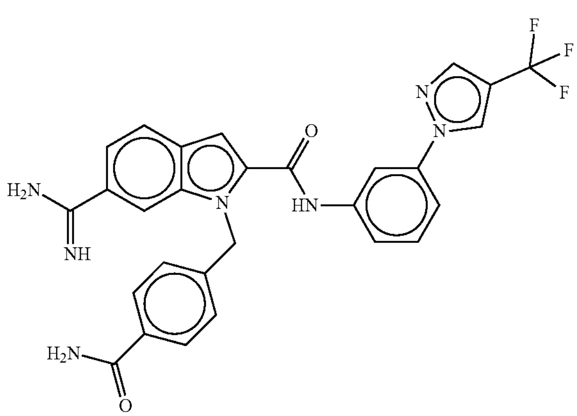 | 3.9 | 99.5 | 546.5 | A | A |

TABLE A-continued
Exemplary Compounds
| Cpd. ID. | Structure | HPLC Rt-min | % Purity-Indole | M + H | Assay Used | Mar-2 % inhibition at 1 uM |
|---|---|---|---|---|---|---|
| I-166 | 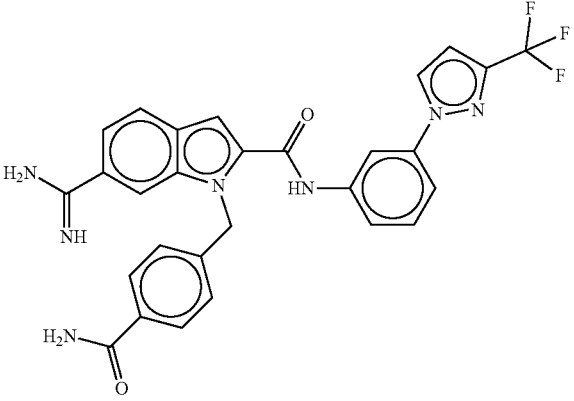 | 2.6 | 96.6 | 546.2 | A | A |
| I-167 | 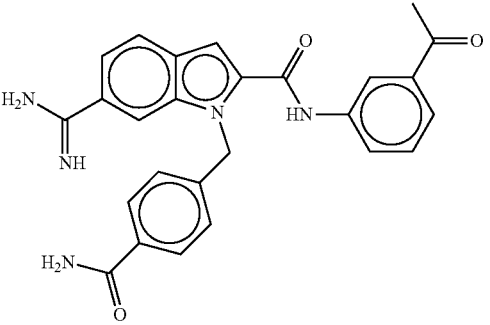 | | | 546.2 | ND | ND |
| I-168 | 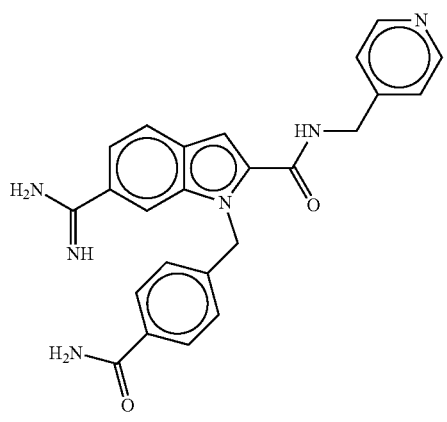 | 4.3 | 91.9 | 427.2 | A | B |
| I-169 | 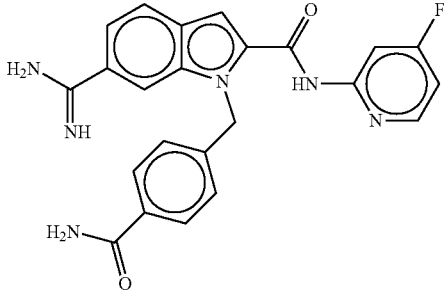 | 5.9 | 95.2 | 430.9 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-170 | 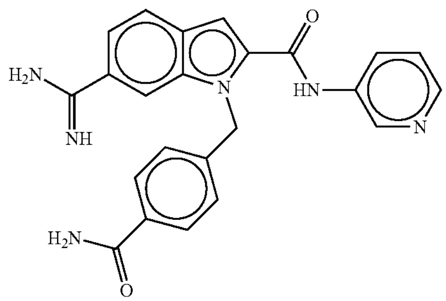 | 6.8 | 87.2 | 413.6 | A | A |
| I-171 | 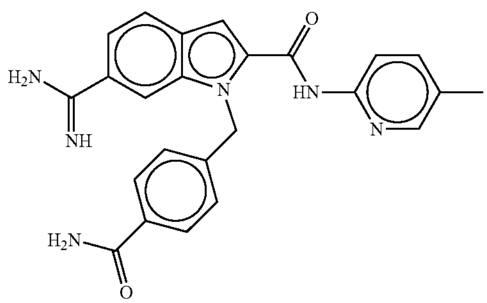 | 5.6 | 95.1 | 425.05 | A | A |
| I-172 | 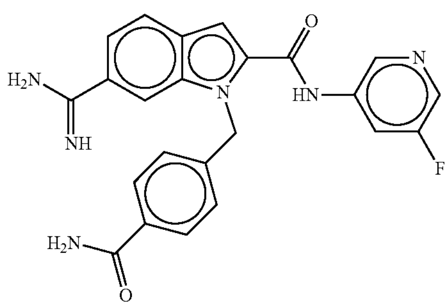 | 2.7 | 94.1 | 431.2 | A | A |
| I-173 | 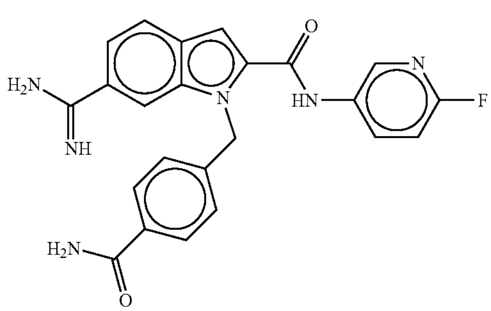 | 5.7 | 90.6 | 430.8 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-174 | 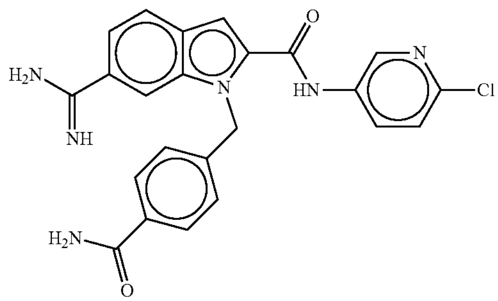 | 5.9 | 95.7 | 447.05 | A | A |
| I-175 | 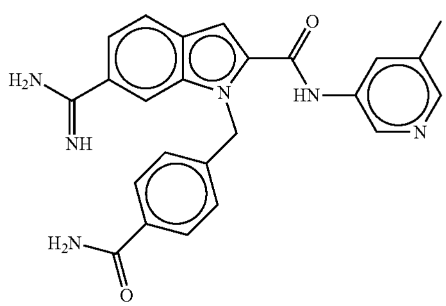 | 4.8 | 92.1 | 427.2 | A | B |
| I-176 | 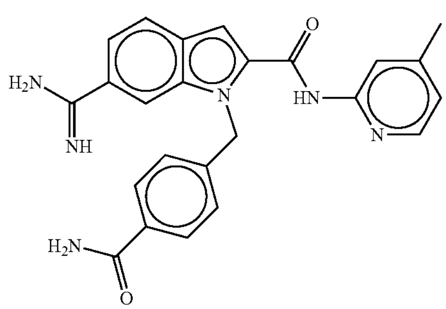 | 5.4 | 95.5 | 427.1 | A | A |
| I-177 | 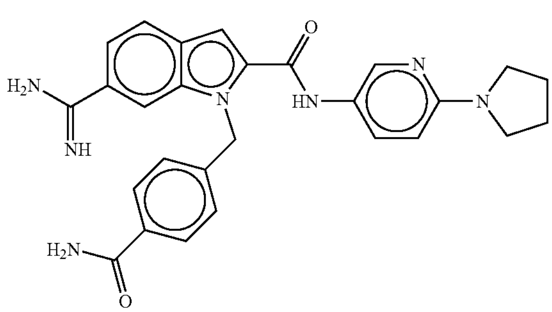 | 4.9 | 97.7 | 482.2 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-178 | 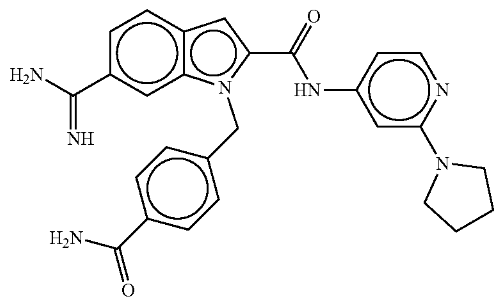 | 5 | 96.1 | 482.2 | A | A |
| I-179 | 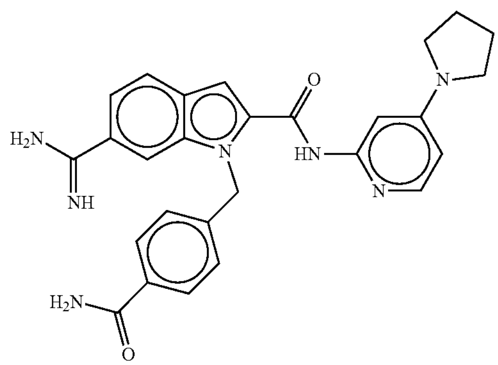 | 5.1 | 97.6 | 481.9 | A | A |
| I-180 | 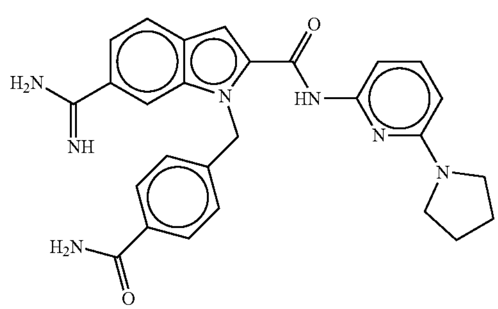 | 5.8 | 93.5 | 482.2 | A | B |
| I-181 | 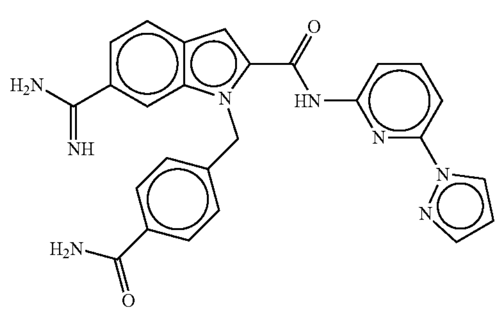 | 6.1 | 97.5 | 479.3 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-182 | 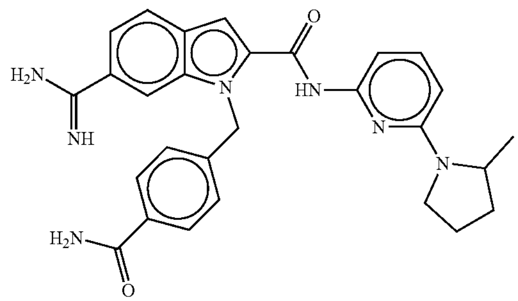 | | | 496.2 | ND | ND |
| I-183 | 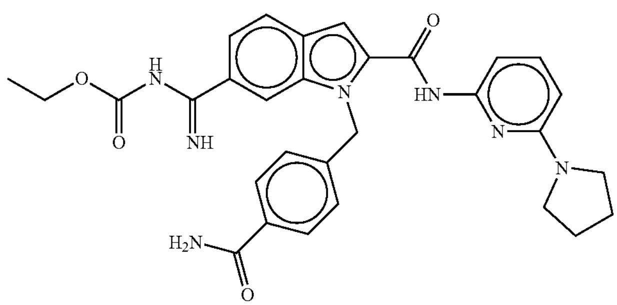 | 5.9 | 97.5 | 554.2 | A | A |
| I-184 | 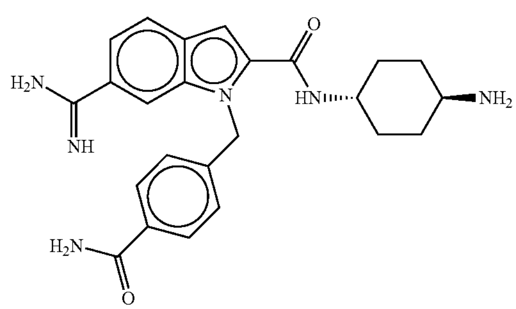 | 4.2 | 89.5 | 433.1 | A | B |
| I-185 | 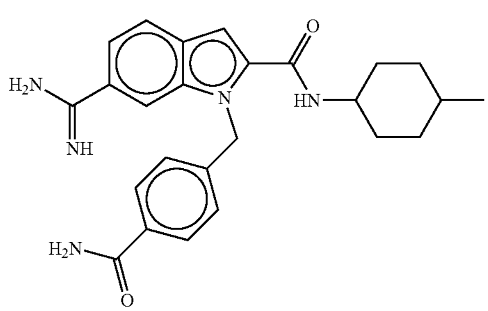 | 5.8 | 91.3 | 432.3 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-186 | 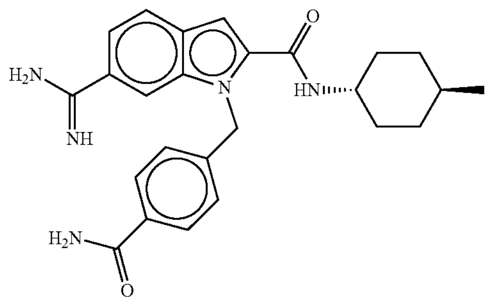 | NA | NA | 432.3 | A | A |
| I-187 | 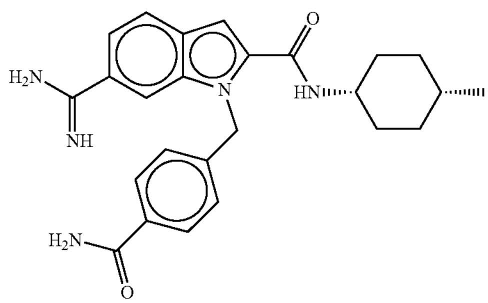 | | | 432.3 | ND | ND |
| I-188 | 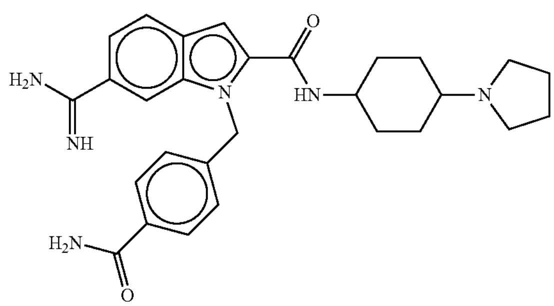 | 4.5 | 91.7 | 487.5 | A | B |
| I-189 | 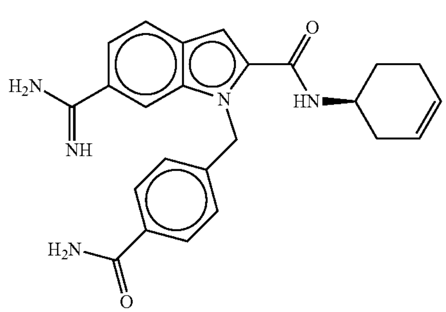 | 3.4 | 97 | 416.3 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-190 | 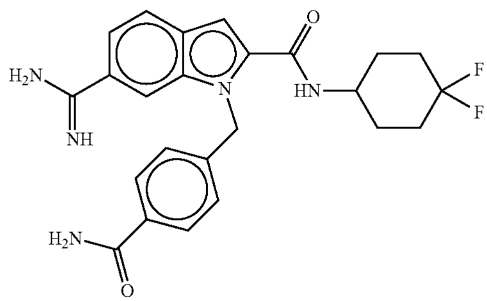 | 3.3 | 97.5 | 454.1 | A | A |
| I-191 | 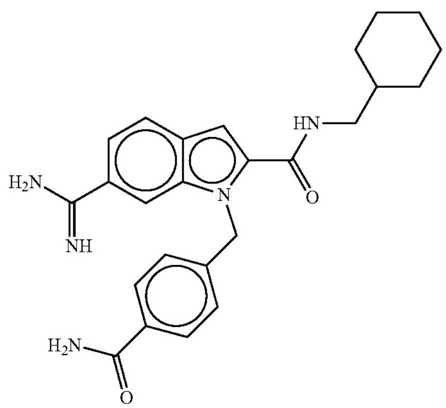 | 3.1 | 92 | 432.1 | A | A |
| I-192 | 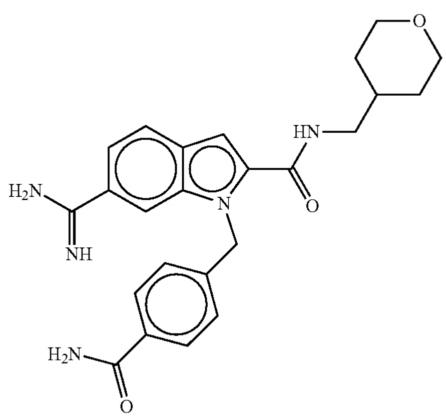 | 5 | 93.2 | 439.9 | A | A |
| I-193 | 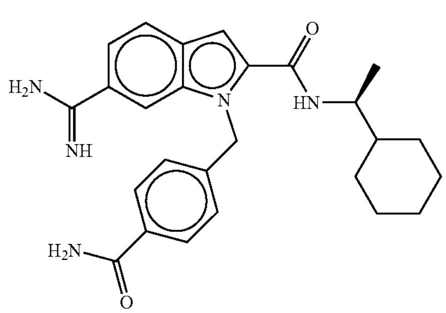 | 2.9 | 95 | 445.9 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-194 | 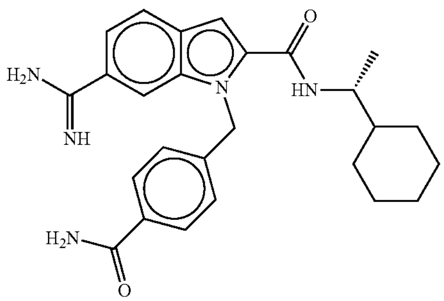 | 2.9 | 90.5 | 446.65 | A | A |
| I-195 | 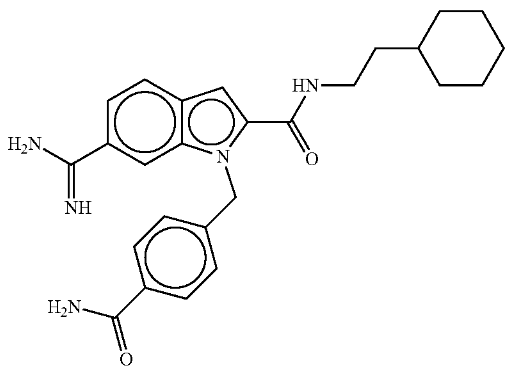 | 6.6 | 94 | 446.2 | A | A |
| I-196 | 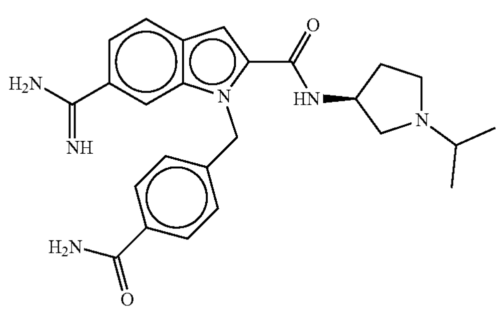 | 4.4 | 93.9 | 447.2 | A | A |
| I-197 | 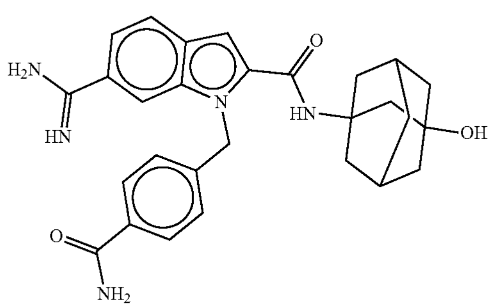 | 2.7 | 90.9 | 486.2 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-198 | 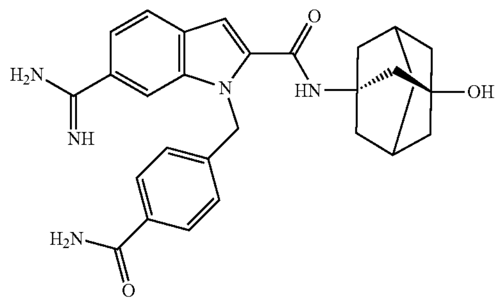 [SMILES: N=C(N)c1ccc2cc(C(=O)N[C@]34CC5CC(C[C@@](O)(C5)C3)C4)n(Cc3ccc(C(N)=O)cc3)c2c1] | 2.7 | 93.4 | 485.9 | A | A |
| I-199 | 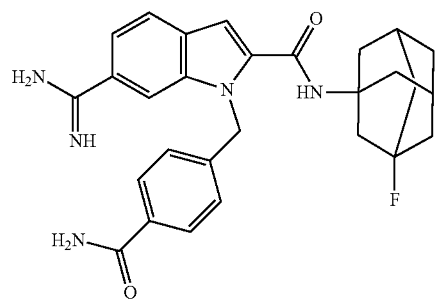 [SMILES: N=C(N)c1ccc2cc(C(=O)NC34CC5CC(CC(F)(C5)C3)C4)n(Cc3ccc(C(N)=O)cc3)c2c1] | | | 488.2 | ND | ND |
| I-200 | 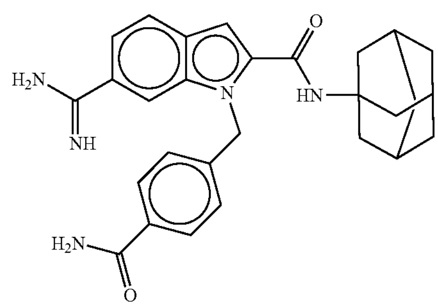 | 4 | 95.7 | 469.9 | A | A |
| I-201 | 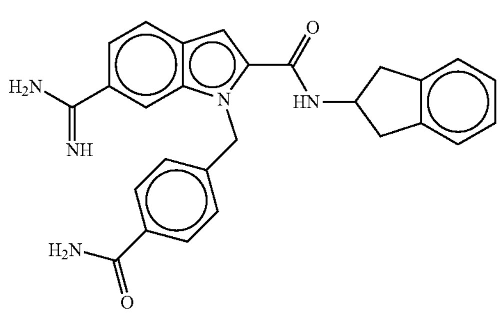 | 3.6 | 91.8 | 453 | A | A |

TABLE A-continued
Exemplary Compounds
| Cpd. ID. | Structure | HPLC Rt-min | % Purity-Indole | M + H | Assay Used | Mar-2 % inhibition at 1 uM |
|---|---|---|---|---|---|---|
| I-202 | 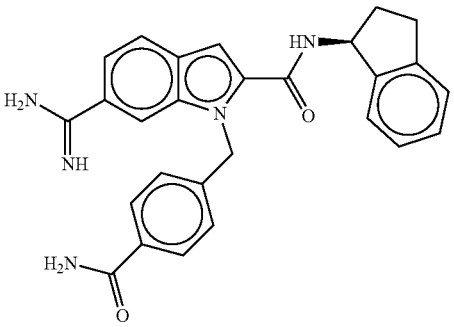 | 6 | 97 | 452.1 | A | A |
| I-203 | 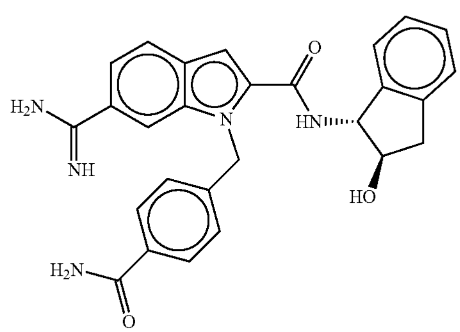 | 5.5 | 98.7 | 467.8 | A | A |
| I-204 | 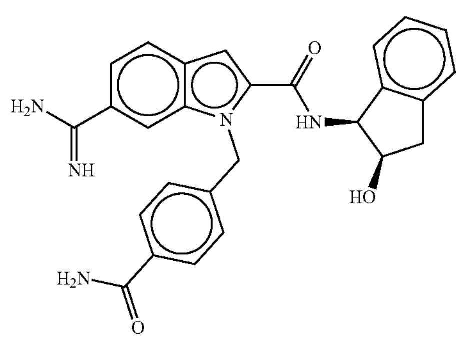 | 5.3 | 95.4 | 468.5 | A | A |
| I-205 | 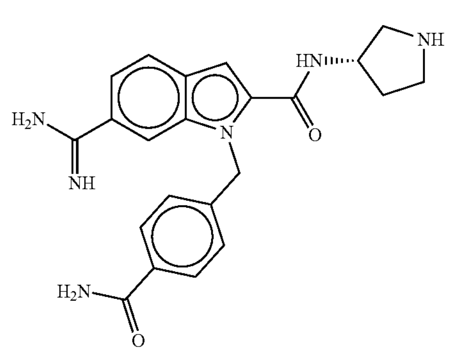 | 4.2 | 84.3 | 405.2 | A | B |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-206 | 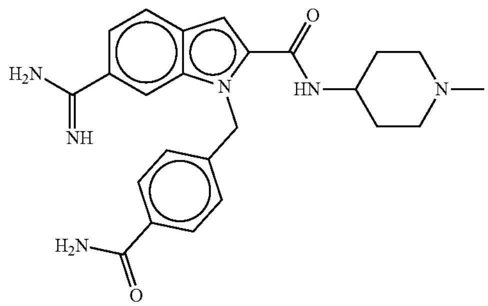 | 4.2 | 90.6 | 433.2 | A | B |
| I-207 | 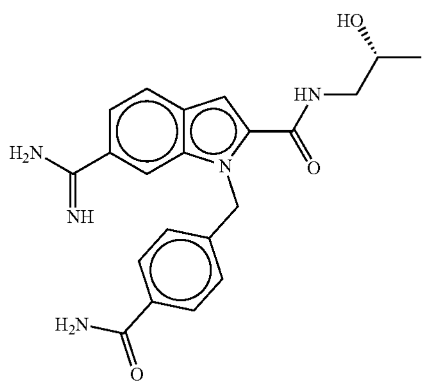 | 4.7 | 94 | 393.9 | A | A |
| I-208 | 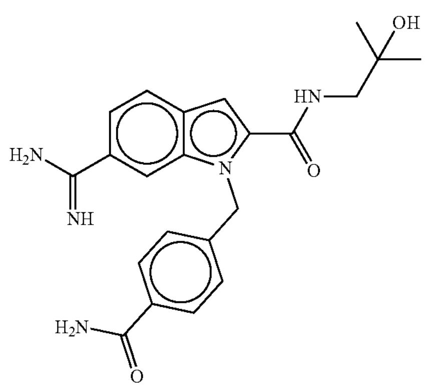 | 4.4 | 91.3 | 408.2 | A | A |
| I-209 | 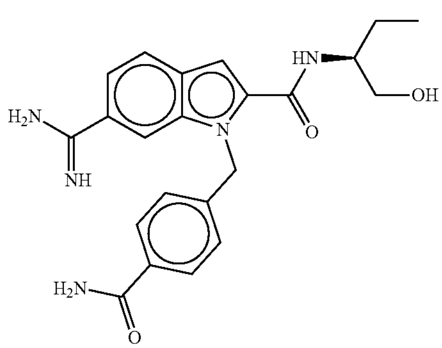 | NA | NA | NA | A | A |

TABLE A-continued
Exemplary Compounds
| Cpd. ID. | Structure | HPLC Rt-min | % Purity-Indole | M + H | Assay Used | Mar-2 % inhibition at 1 uM |
|---|---|---|---|---|---|---|
| I-210 | 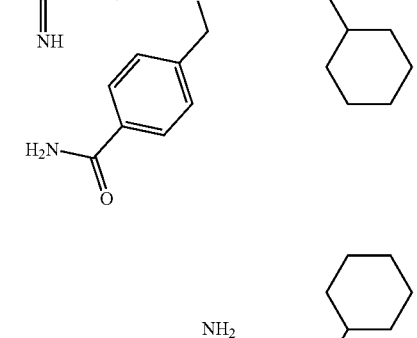 | | | 447.2 | ND | ND |
| I-211 | 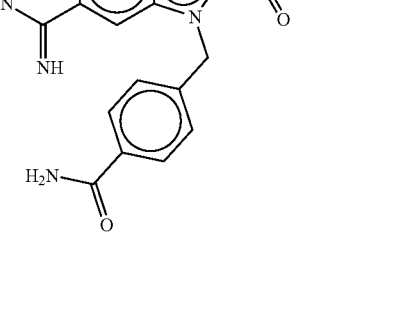 | 6.2 | 96.2 | 448 | A | A |
| I-212 | 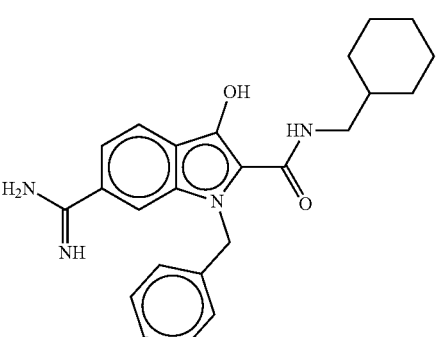 | 3.2 | 95.2 | 448.2 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-213 | 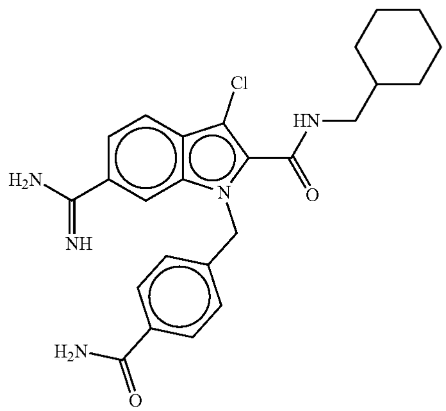 | 3.8 | 98.6 | 466.2 | A | A |
| I-214 | 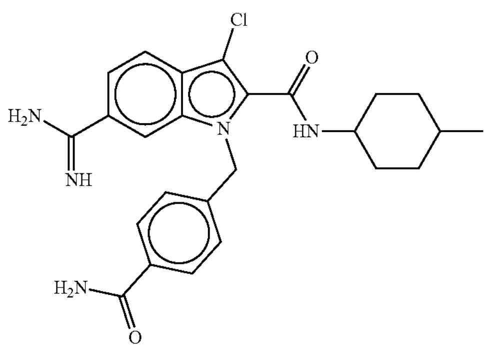 | 6.6 | 90.9 | 466.1 | A | A |
| I-215 | 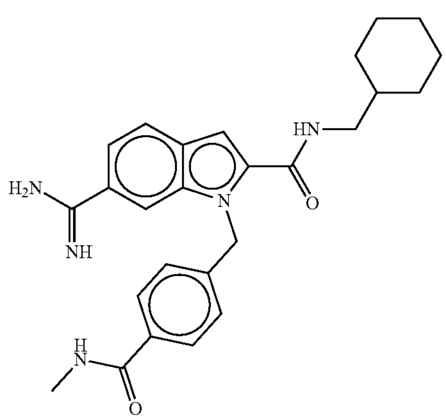 | 3.6 | 91.7 | 446.2 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-216 | 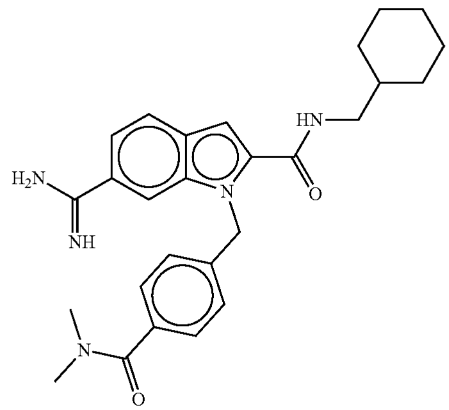 | 3.8 | 91.4 | 460.3 | A | A |
| I-217 | 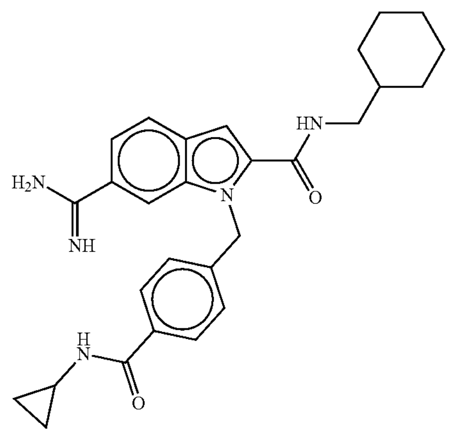 | 3.4 | 95.2 | 472.2 | A | A |
| I-218 | 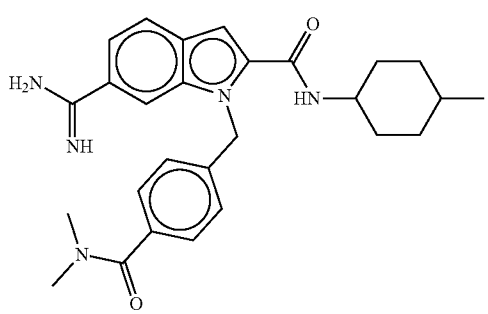 | 6.5 | 94 | 460.2 | A | A |
| I-219 | 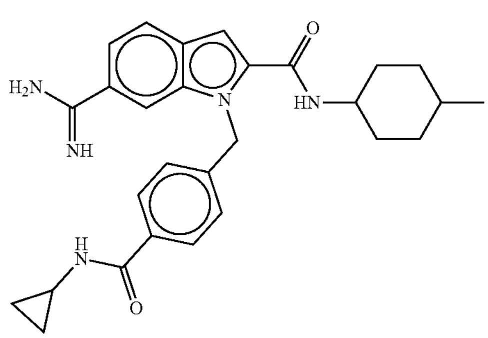 | 6.5 | 88.9 | 472.2 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-220 | 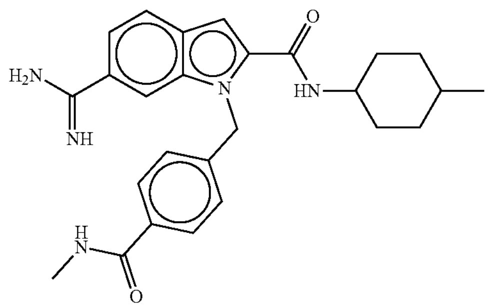 | 6.3 | 89 | 446.2 | A | A |
| I-221 | 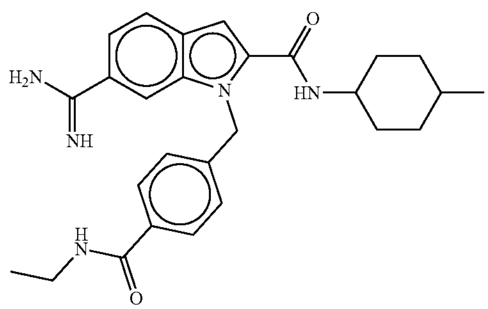 | 3.9 | 97.4 | 460 | A | A |
| I-222 | 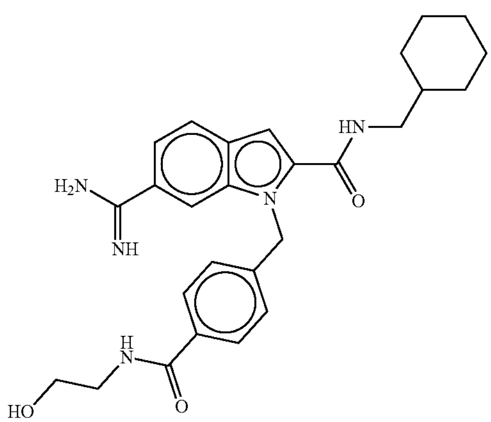 | 6 | 91.9 | 476.2 | A | A |
| I-223 | 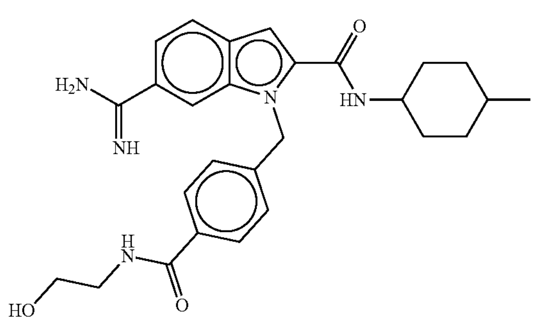 | 6.1 | 96.9 | 476.2 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-224 | 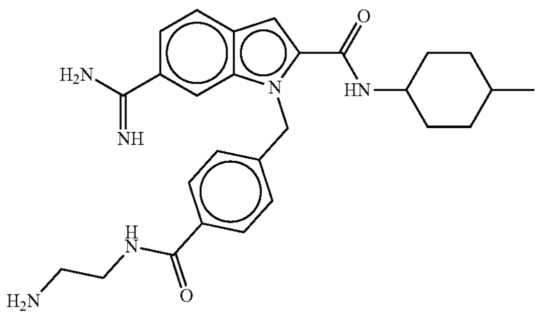 | 5.5 | 92.5 | 475.2 | A | A |
| I-225 | 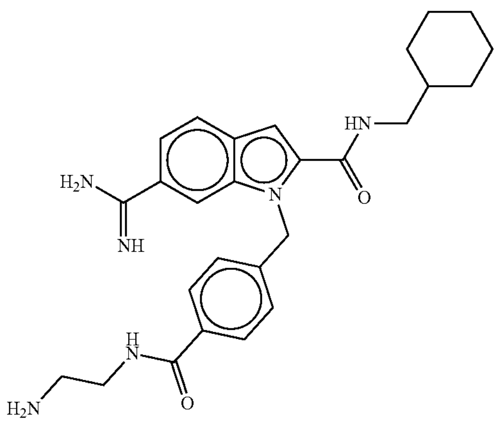 | 5.4 | 95.2 | 475.2 | A | A |
| I-226 | 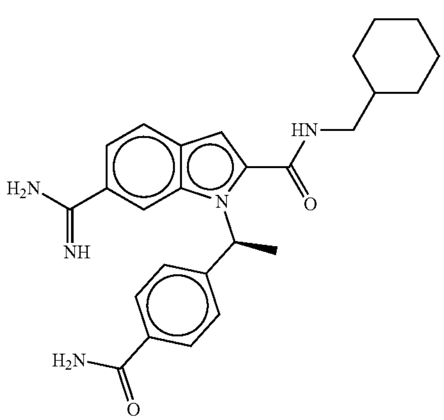 | 6.5 | 84.3 | 446.2 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-227 | 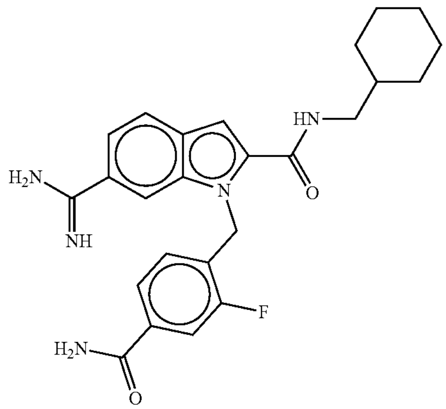 | 3.1 | 98 | 450.1 | A | A |
| I-228 | 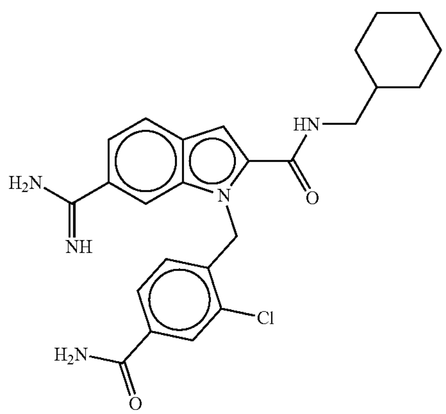 | 6.3 | 97.5 | 466 | A | A |
| I-229 | 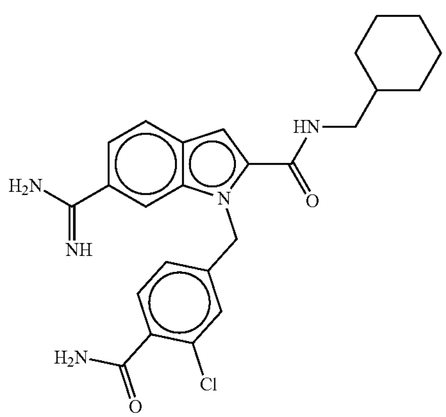 | 2.9 | 94.5 | 467.55 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-230 | 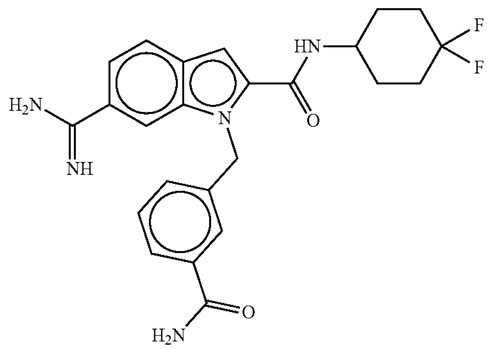 | 3.4 | 95.4 | 454.1 | A | A |
| I-231 | 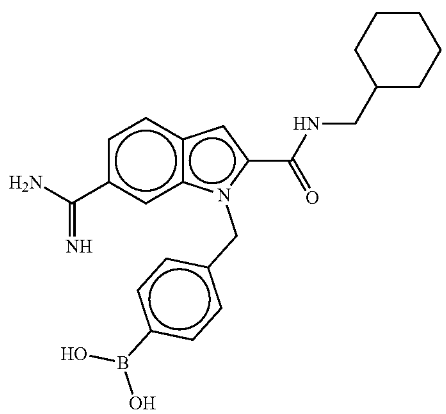 | NA | NA | 433.2 | A | A |
| I-232 | 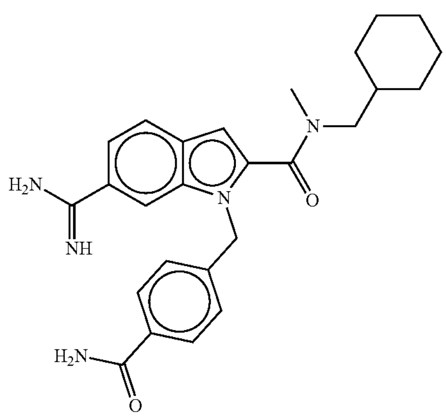 | 3.7 | 96.4 | 446.3 | A | A |
| I-233 | 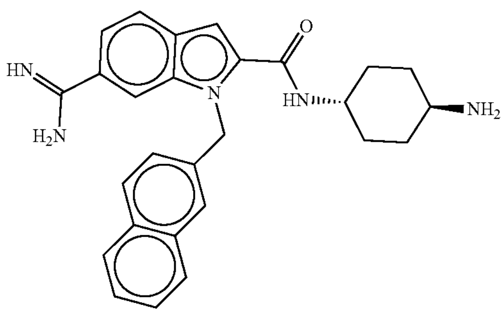 | 5 | 98.3 | 440 | B | B |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-234 | 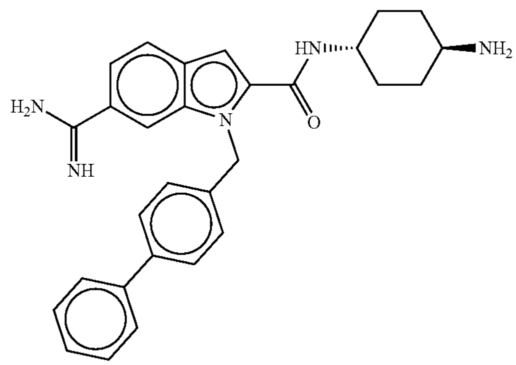 | 6.9 | 95.2 | 466.2 | A | B |
| I-235 | 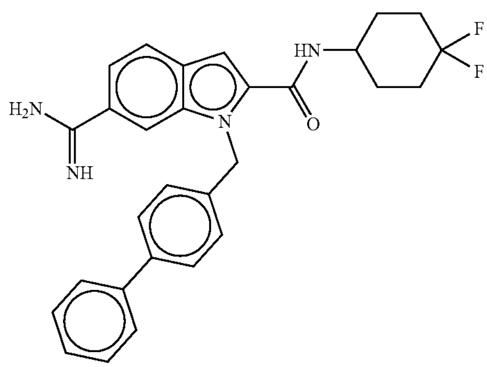 | 3.9 | 92.7 | 487.1 | A | A |
| I-236 | 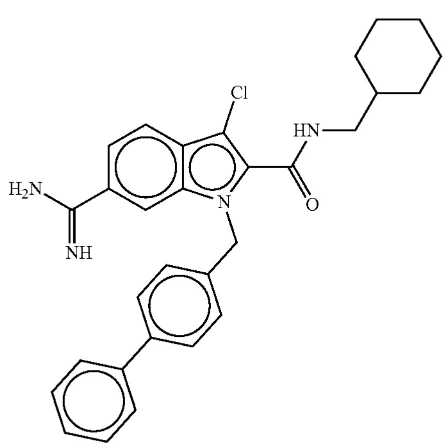 | 7.4 | 95.1 | 499.3 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-237 | 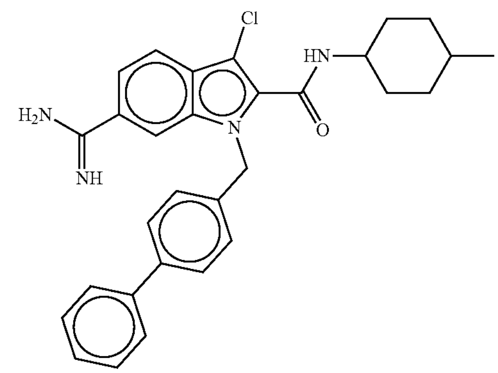 | 4.3 | 87.9 | 499.2 | A | A |
| I-238 | 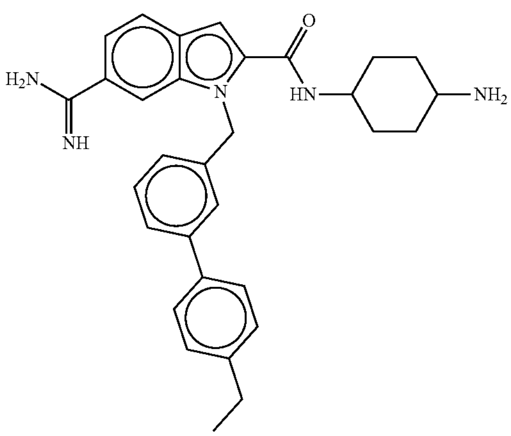 | 5.1 | 96 | 494.3 | A | B |
| I-239 | 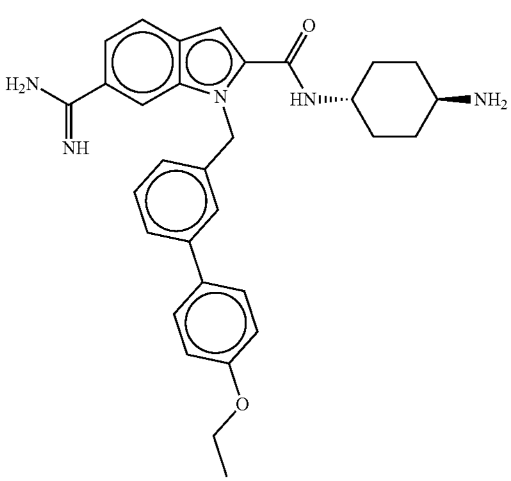 | 5 | 91 | 510.3 | A | B |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-240 | 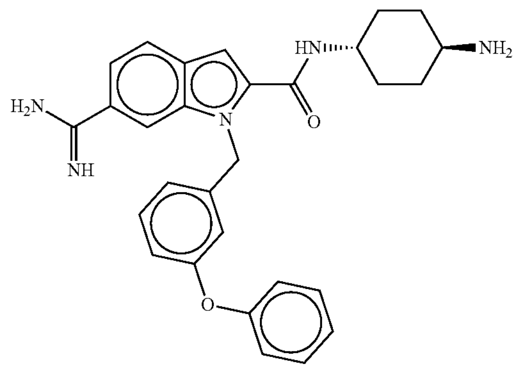 | 5.7 | 98.5 | 482.2 | A | C |
| I-241 | 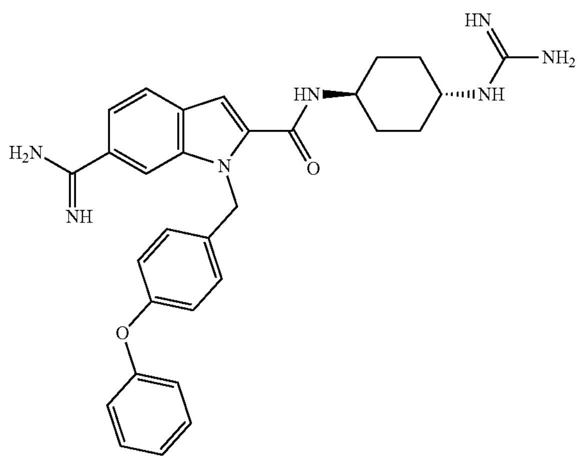 [SMILES: N=C(N)N[C@H]1CC[C@H](NC(=O)c2cc3ccc(C(=N)N)cc3n2Cc2ccc(Oc3ccccc3)cc2)CC1] | | | 524.3 | ND | ND |
| I-242 | 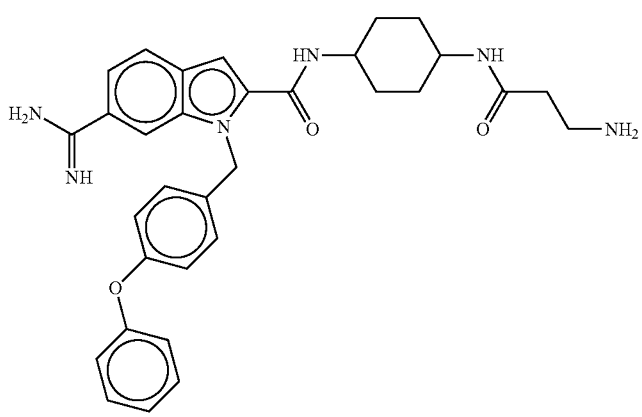 | 7.1 | 93.5 | 553.2 | A | B |

TABLE A-continued

Exemplary Compounds

| Cpd. ID. | Structure | HPLC Rt- min | % Purity- Indole | M + H | Assay Used | Mar-2 % inhibition at 1 uM |
|---|---|---|---|---|---|---|
| I-243 | 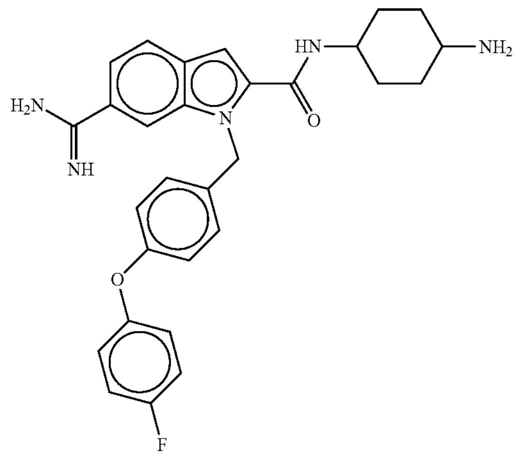 | 7.1 | 93.8 | 500.2 | A | C |
| I-244 | 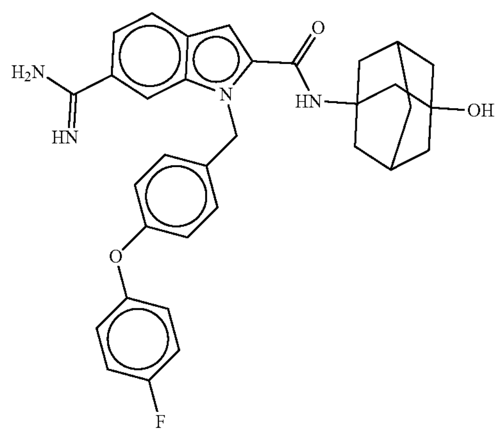 | 8.9 | 98 | 553.2 | A | B |
| I-245 | 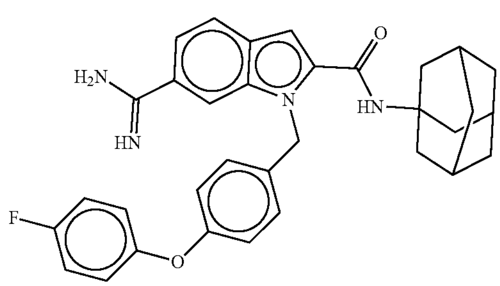 | 10.6 | 98.9 | 537.2 | A | B |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-246 | 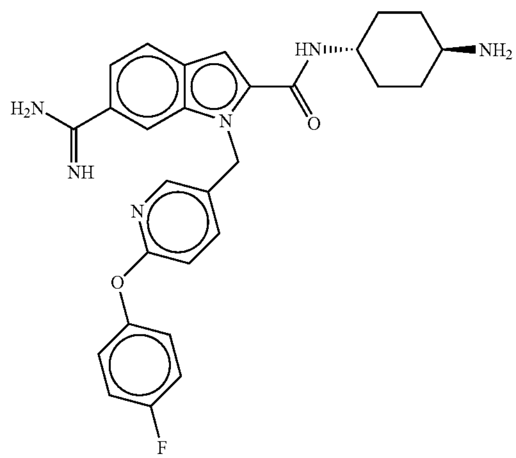 | 4.7 | 97.6 | 501.2 | A | C |
| I-247 | 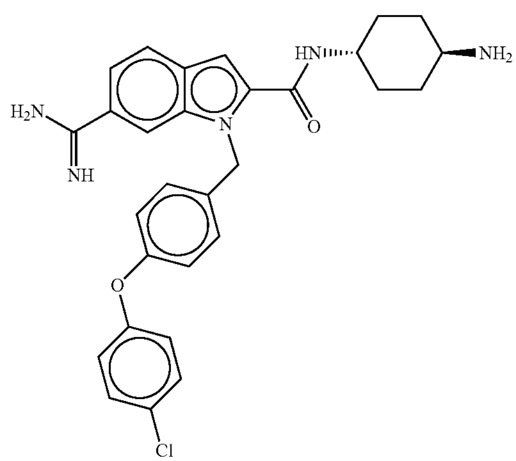 | 7.7 | 96.2 | 516.1 | A | C |
| I-248 | 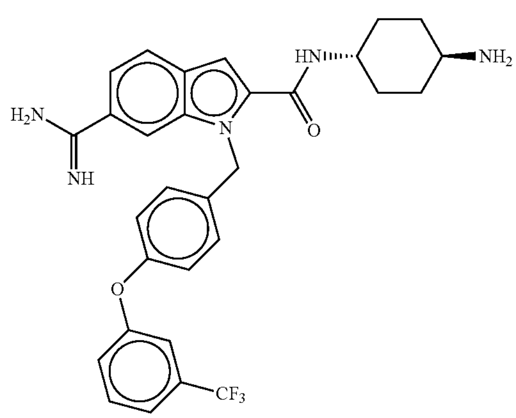 | 7.34 | 92.5 | 516.2 | A | B |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-249 | 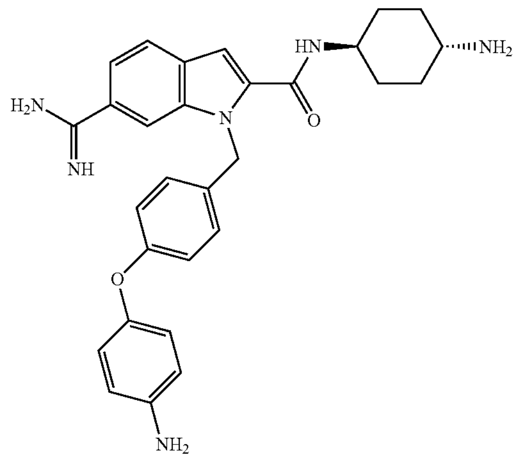 [SMILES: N=C(N)c1ccc2cc(C(=O)N[C@H]3CC[C@H](N)CC3)n(Cc3ccc(Oc4ccc(N)cc4)cc3)c2c1] | | | 497.3 | ND | ND |
| I-250 | 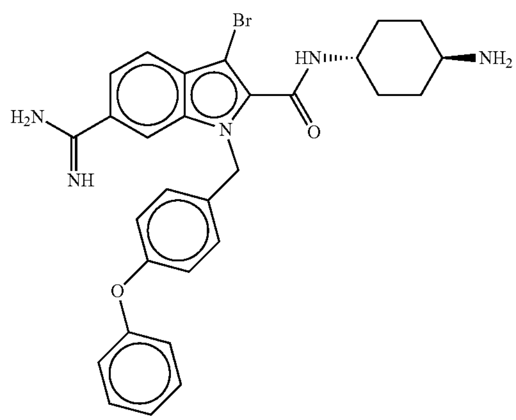 | 4.8 | 98.9 | 561.9 | A | B |
| I-251 | 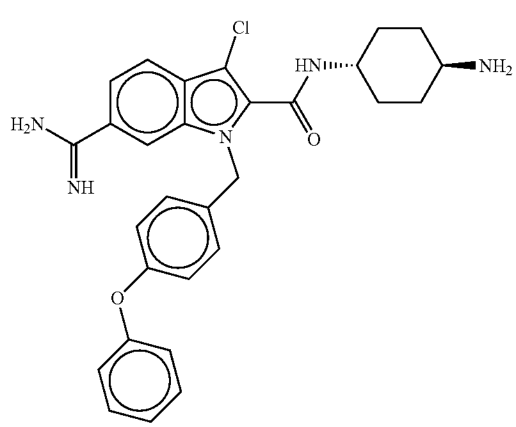 | 5.37 | 97 | 516.2 | A | B |

TABLE A-continued

Exemplary Compounds

| Cpd. ID. | Structure | HPLC Rt- min | % Purity- Indole | M + H | Assay Used | Mar-2 % inhibition at 1 uM |
|---|---|---|---|---|---|---|
| I-252 | 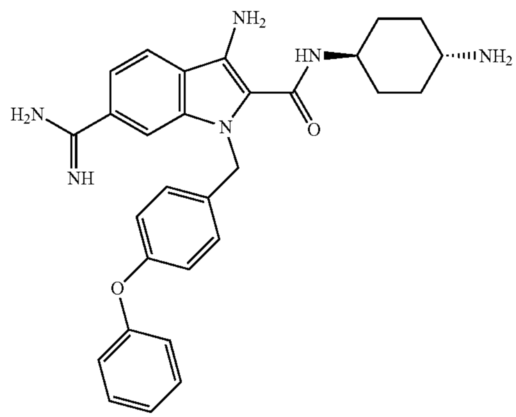 [SMILES: N=C(N)c1ccc2c(N)c(C(=O)N[C@H]3CC[C@H](N)CC3)n(Cc3ccc(Oc4ccccc4)cc3)c2c1] | | | 497.3 | ND | ND |
| I-253 | 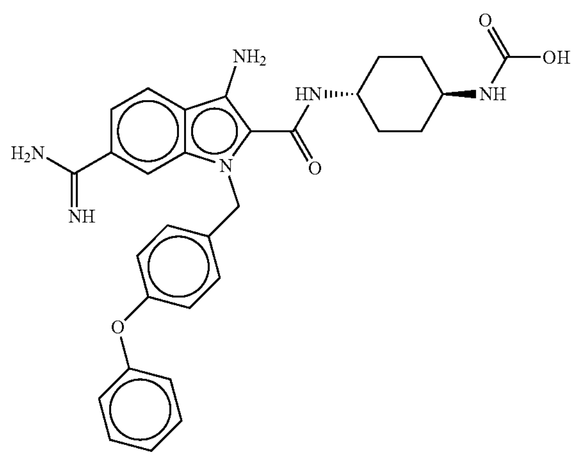 | 6.7 | 87.1 | 541.2 | A | A |
| I-254 | 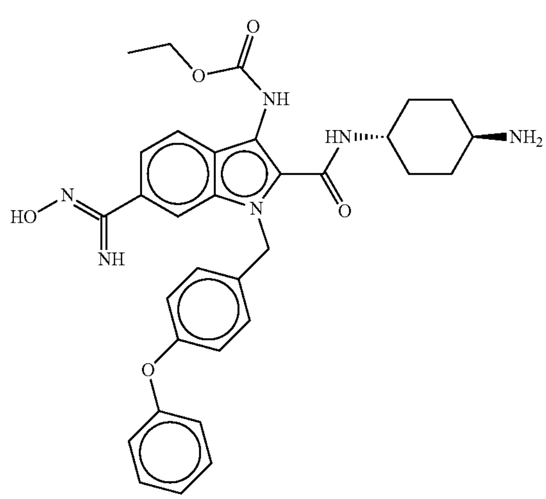 | 5 | 97.3 | 585.3 | A | B |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-255 | 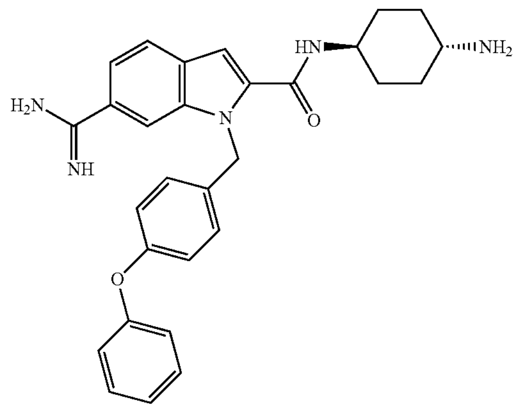 [SMILES: N=C(N)c1ccc2cc(C(=O)N[C@H]3CC[C@H](N)CC3)n(Cc3ccc(Oc4ccccc4)cc3)c2c1] | | | 482.2 | ND | ND |
| I-256 | 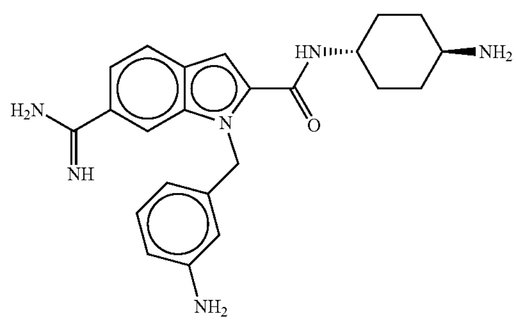 | 4.3 | 94.6 | 405.1 | A | B |
| I-257 | 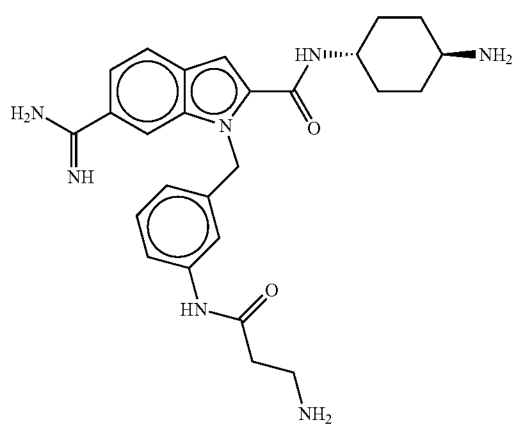 | 4 | 97.1 | 476.2 | A | C |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-258 | 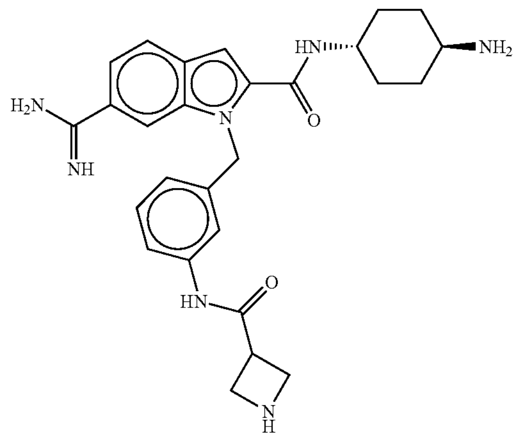 | 4.2 | 94.3 | 488.1 | A | C |
| I-259 | 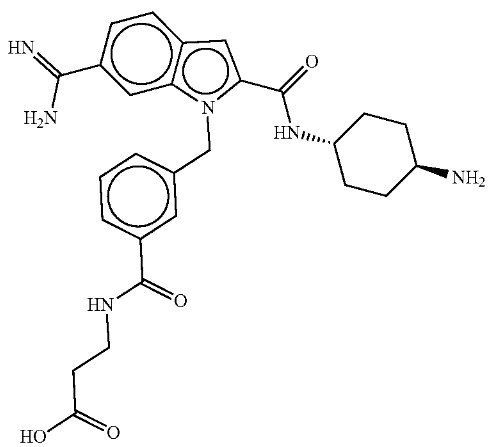 | 4.5 | 96 | 505.3 | A | B |
| I-260 | 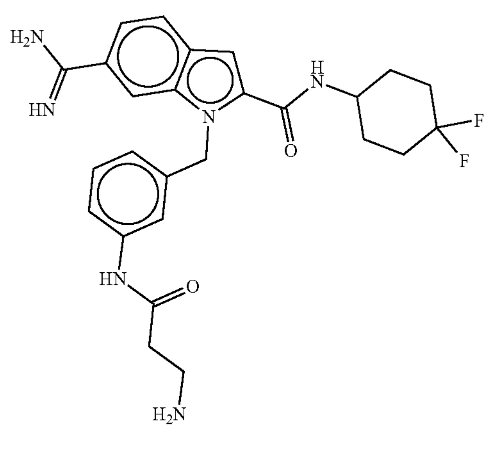 | 5.8 | 89.3 | 497.1 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-261 | 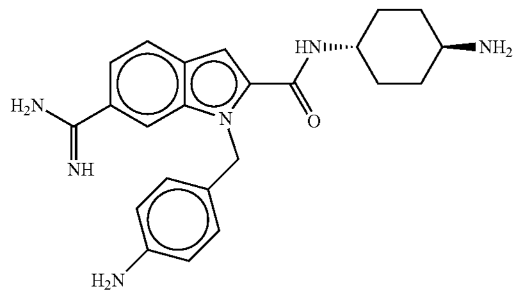 | 5.6 | 91.6 | 405.2 | A | B |
| I-262 | 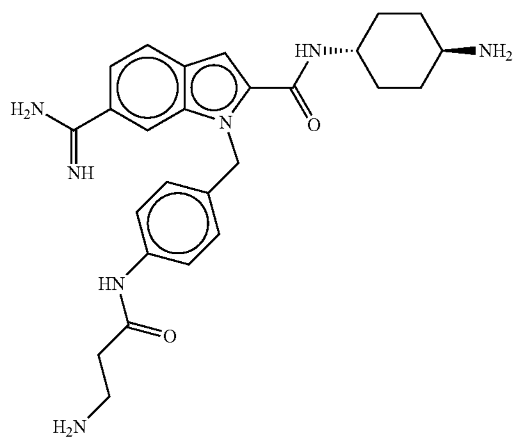 | 4.1 | 85.9 | 476 | A | B |
| I-s263 | 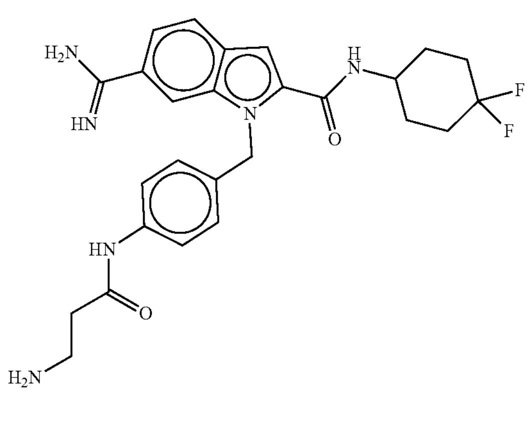 | 5.1 | 92.3 | 497.2 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-264 | 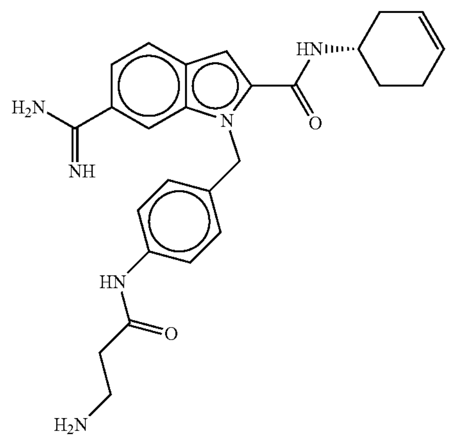 | 5.3 | 81.9 | 459.2 | A | A |
| I-265 | 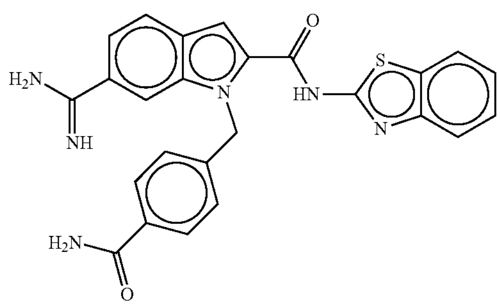 | 2.9 | 86.9 | 469.1 | A | A |
| I-266 | 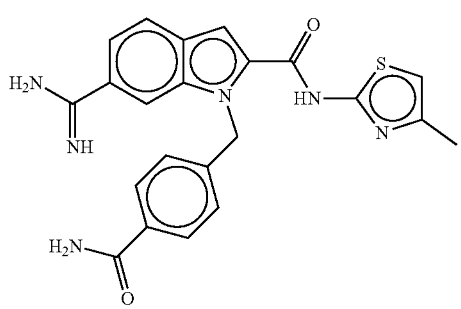 | 5.8 | 93.8 | 433 | A | A |
| I-267 | 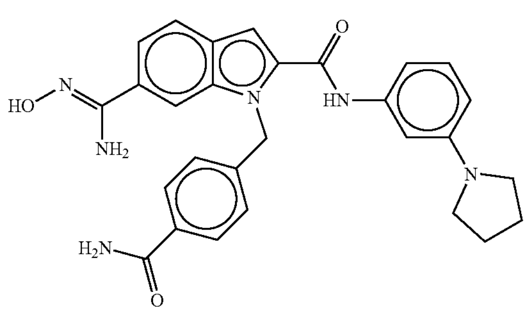 | 3.8 | 94.7 | 496.8 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-268 | 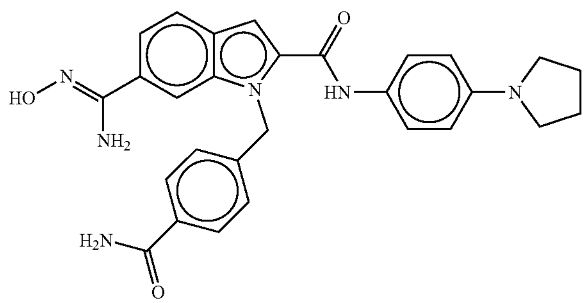 | 3.7 | 99.8 | 497.2 | A | A |
| I-269 | 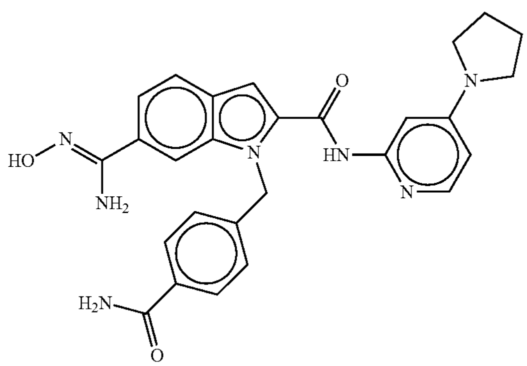 | 2.8 | 98.2 | 498.4 | A | A |
| I-270 | 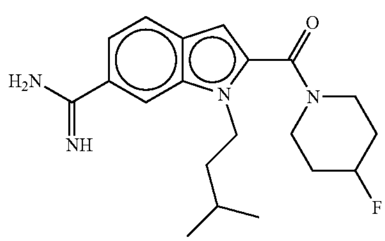 | 3.6 | 97 | 359.1 | A | A |
| I-271 | 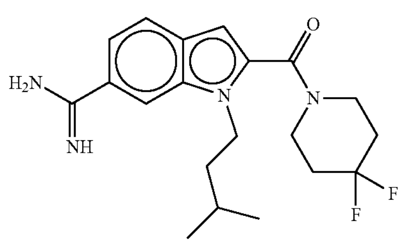 | 3.3 | 91.1 | 377.2 | A | A |
| I-272 | 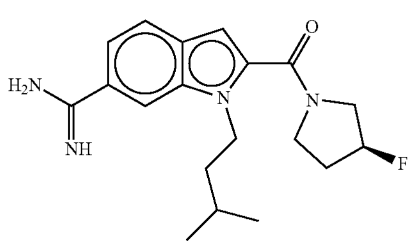 | 2.9 | 96.6 | 345.2 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-273 | 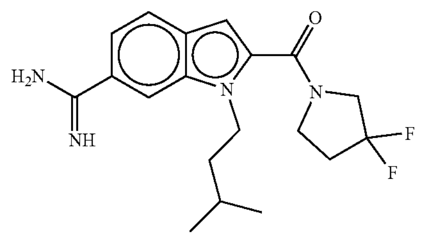 | 6.2 | 93.8 | 363.2 | A | A |
| I-274 | 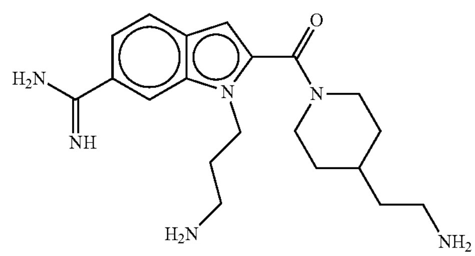 | 5.8 | 97.5 | 357.2 | A | B |
| I-275 | 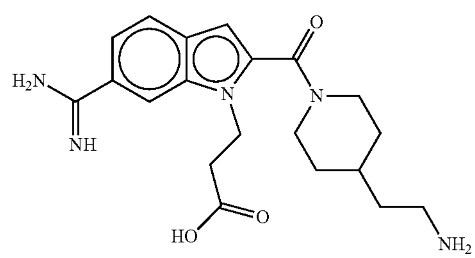 | | | 386.2 | ND | ND |
| I-276 | 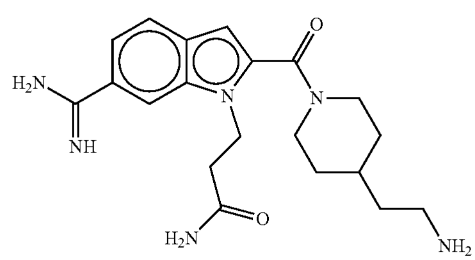 | 4.1 | 90.2 | 385.2 | A | B |
| I-277 | 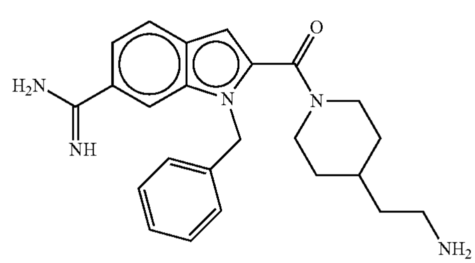 | | | 404.2 | ND | ND |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-278 | 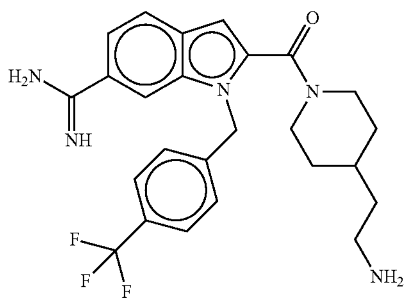 | NA | NA | 472.2 | A | A |
| I-279 | 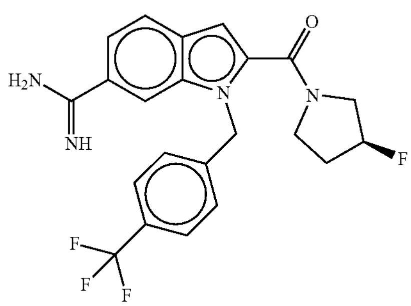 | 8.3 | 98 | 433.1 | A | A |
| I-280 | 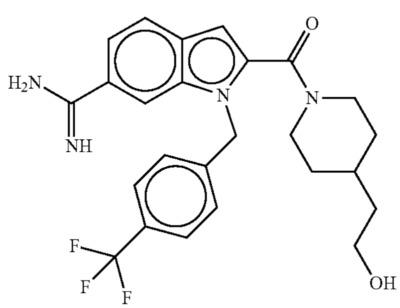 | NA | NA | 473.2 | A | A |
| I-281 | 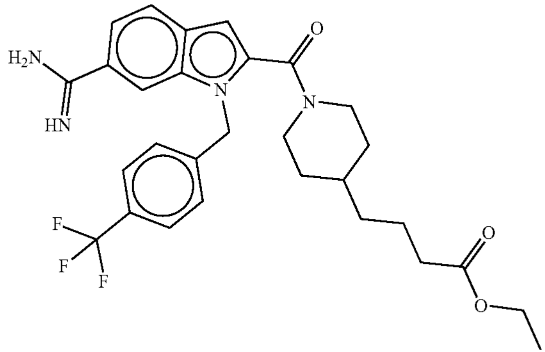 | 9.3 | 98.4 | 543.2 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-282 | 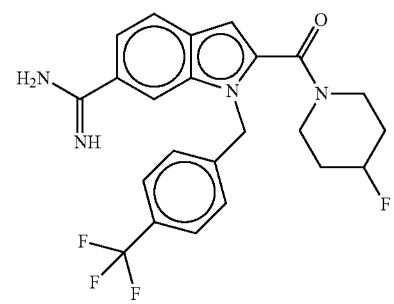 | 3.4 | 83.5 | 447.2 | A | A |
| I-283 | 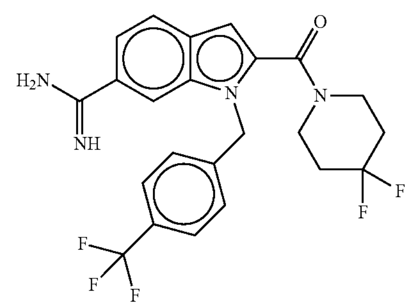 | 3.4 | 93.6 | 465.1 | A | A |
| I-284 | 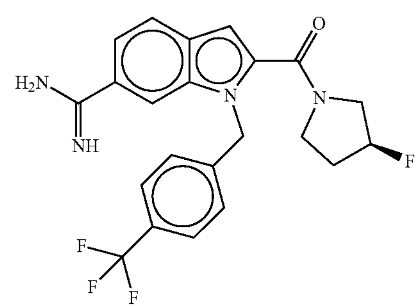 | 6.7 | 88.1 | 433.1 | A | A |
| I-285 | 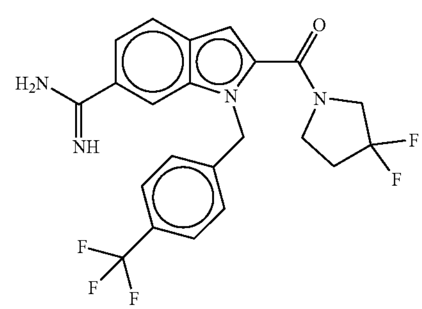 | 6.5 | 85.9 | 451.1 | A | A |

TABLE A-continued

Exemplary Compounds

| Cpd. ID. | Structure | HPLC Rt- min | % Purity- Indole | M + H | Assay Used | Mar-2 % inhibition at 1 uM |
|---|---|---|---|---|---|---|
| I-286 | 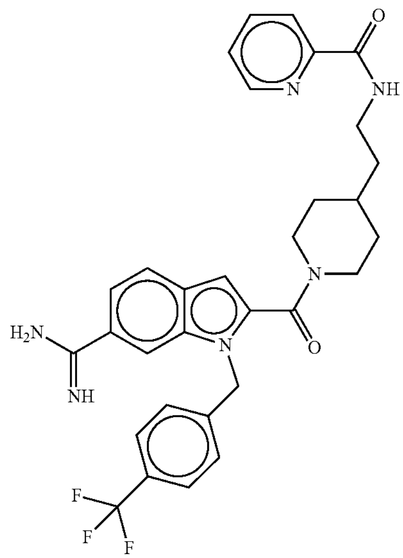 | 8.5 | 94.9 | 578.2 | A | A |
| I-287 | 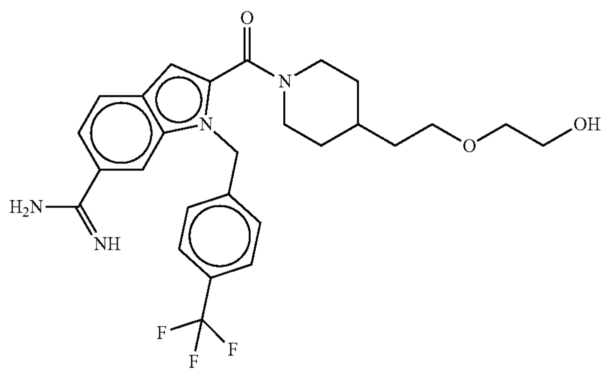 | NA | NA | 517.2 | A | A |
| I-288 | 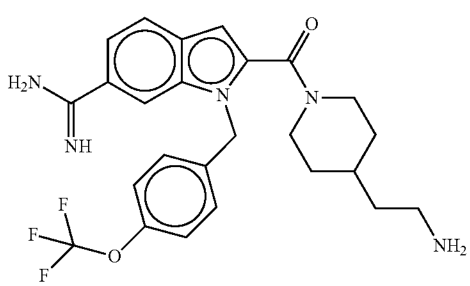 | 6.7 | 96.8 | 487.1 | A | A |
| I-289 | 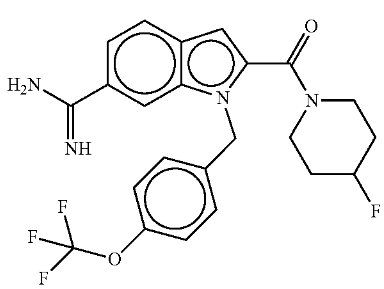 | 6.9 | 98.7 | 493.1 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-290 | 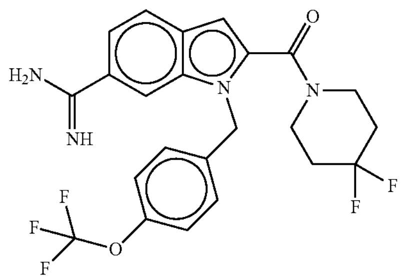 | 3.9 | 98 | 481.3 | A | A |
| I-291 | 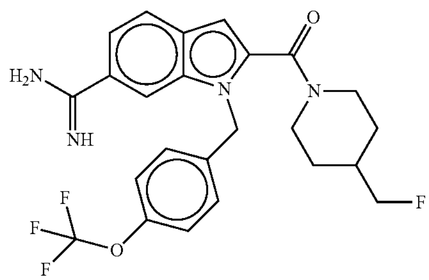 | 3.4 | 95.2 | 477.2 | A | A |
| I-292 | 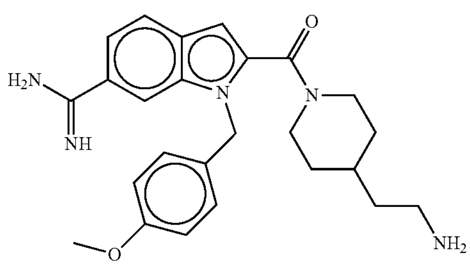 | | | 434.2 | NA | NA |
| I-293 | 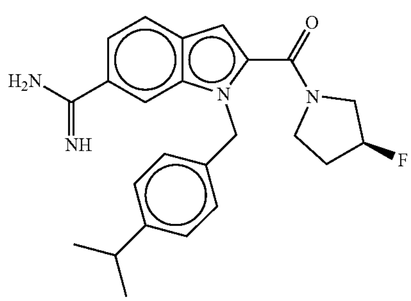 | 7 | 98.1 | 407.3 | A | A |
| I-294 | 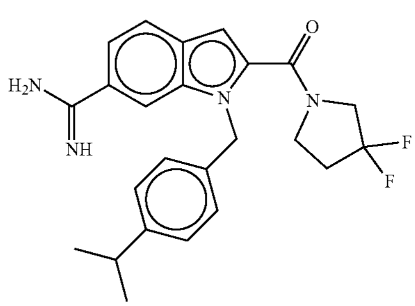 | 3.5 | 93.6 | 425.2 | A | A |

TABLE A-continued
Exemplary Compounds
| Cpd. ID. | Structure | HPLC Rt-min | % Purity-Indole | M + H | Assay Used | Mar-2 % inhibition at 1 uM |
|---|---|---|---|---|---|---|
| I-295 | 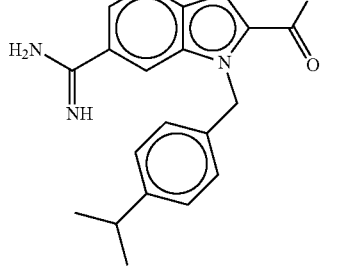 | 3.7 | 98 | 421.3 | A | A |
| I-296 | 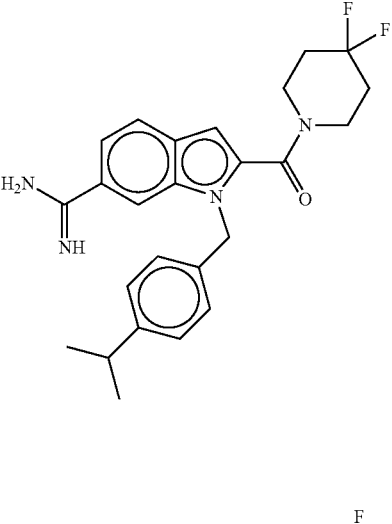 | 4.1 | 98.3 | 439.3 | A | A |
| I-297 | 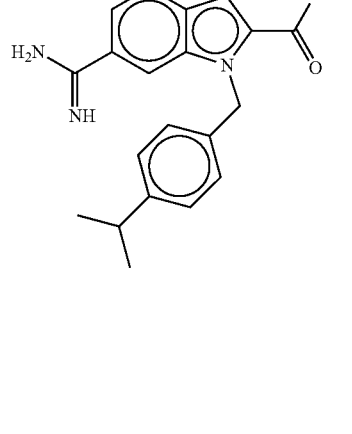 | 3.6 | 97.1 | 435.4 | A | A |

TABLE A-continued
Exemplary Compounds
| Cpd. ID. | Structure | HPLC Rt- min | % Purity- Indole | M + H | As- say Used | Mar-2 % inhibi- tion at 1 uM |
|---|---|---|---|---|---|---|
| I-298 | 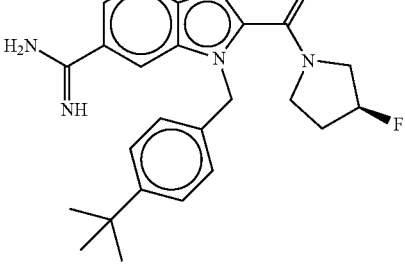 | 6.6 | 92.8 | 421.3 | A | B |
| I-299 | 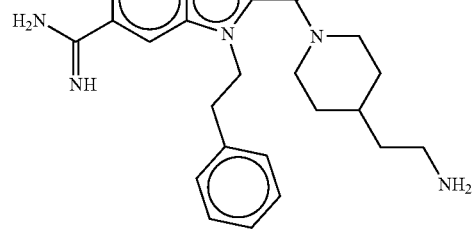 | 6.3 | 90.7 | 418.2 | A | B |
| I-300 | 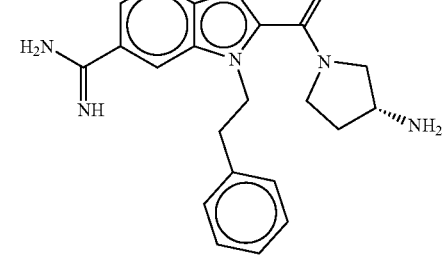 | 4.5 | 94.9 | 376.1 | A | B |
| I-301 | 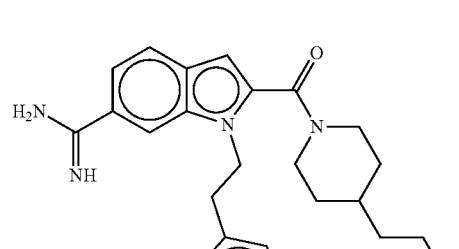 | 4.6 | 97 | 436.2 | A | B |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-302 | 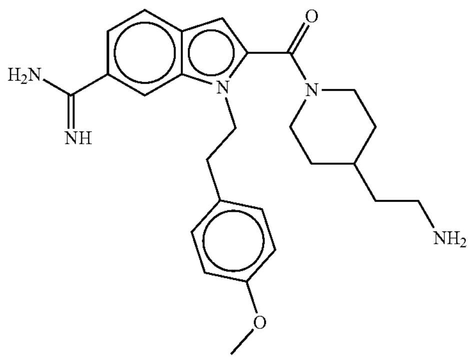 | 5.5 | 86.1 | 448.2 | A | B |
| I-303 | 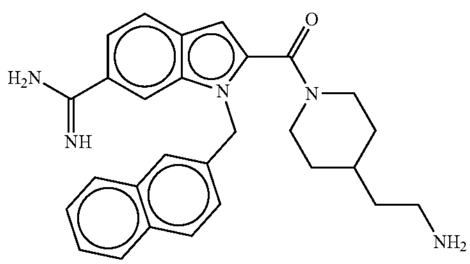 | | | 454.2 | ND | ND |
| I-304 | 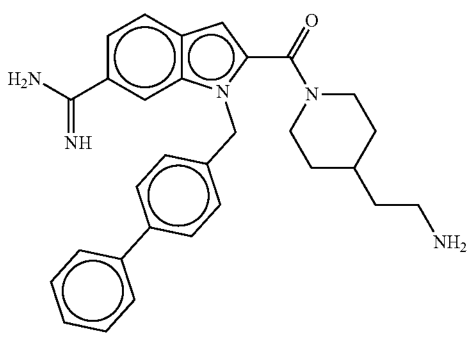 | | | 480.3 | ND | ND |
| I-305 | 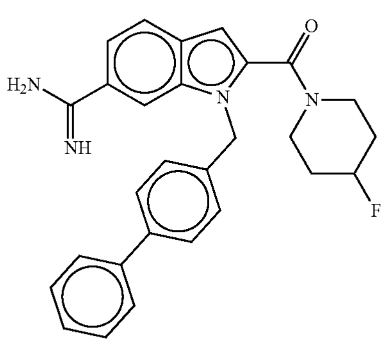 | | | 455.2 | ND | ND |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-306 | 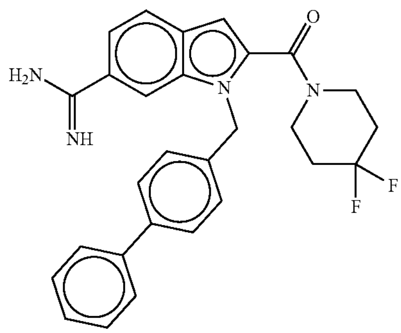 | 3.6 | 98.3 | 473.2 | A | A |
| I-307 | 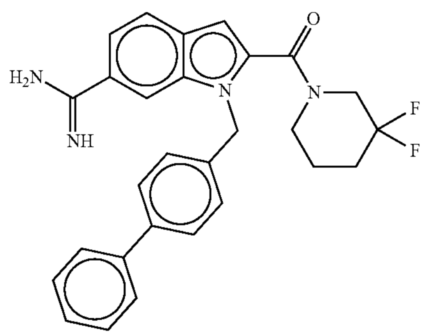 | 4 | 95.6 | 473.2 | A | A |
| I-308 | 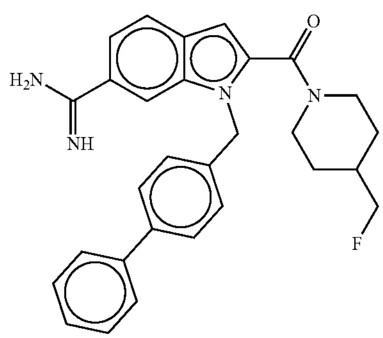 | 4 | 91.1 | 469.2 | A | A |
| I-309 | 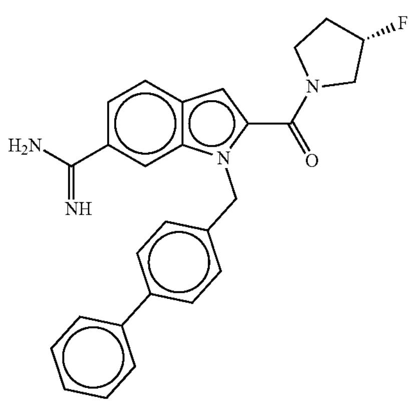 | 3.8 | 95.8 | 441.2 | A | A |

TABLE A-continued
Exemplary Compounds
| Cpd. ID. | Structure | HPLC Rt-min | % Purity-Indole | M + H | Assay Used | Mar-2 % inhibition at 1 uM |
|---|---|---|---|---|---|---|
| I-310 | 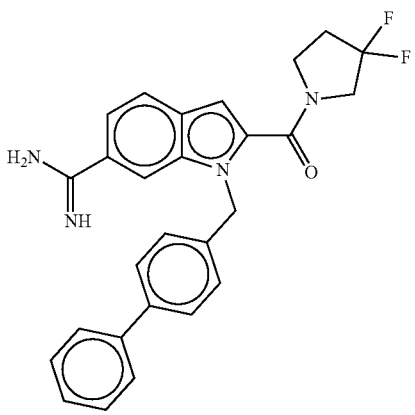 | 3.4 | 97 | 459 | A | A |
| I-311 | 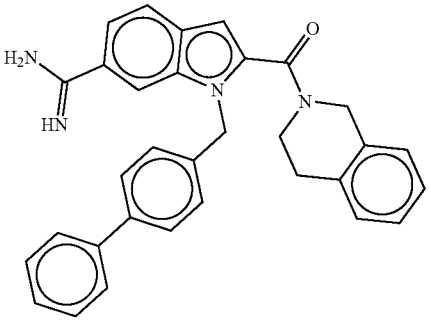 | 4.4 | 87.7 | 485.4 | A | A |
| I-312 | 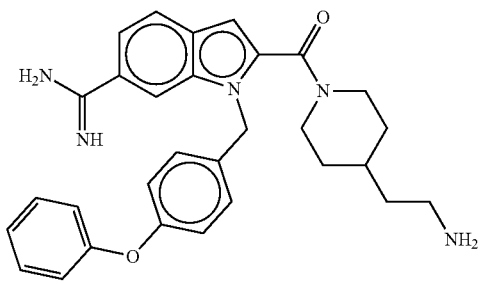 | | | 496.3 | NA | NA |
| I-313 | 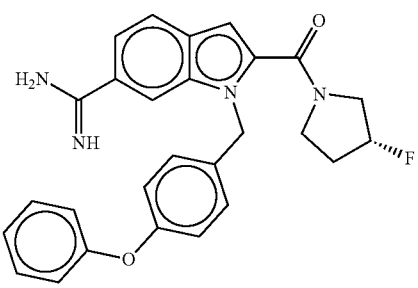 | 6.4 | 93.8 | 457.2 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-314 | 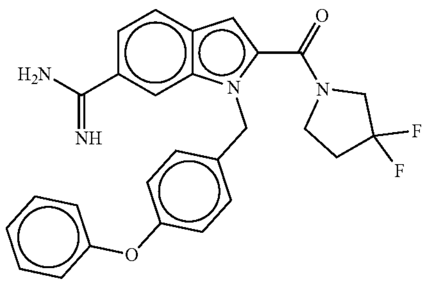 | 3.5 | 91 | 475.1 | A | A |
| I-315 | 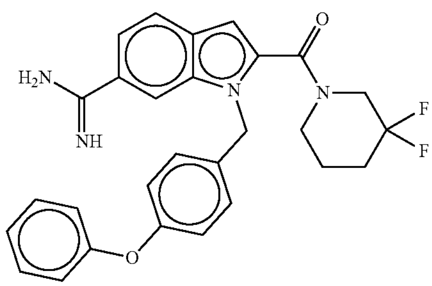 | 6.7 | 97.1 | 489.2 | A | A |
| I-316 | 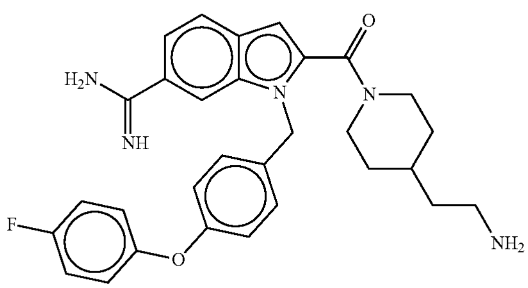 | 6 | 95.5 | 514.2 | A | A |
| I-317 | 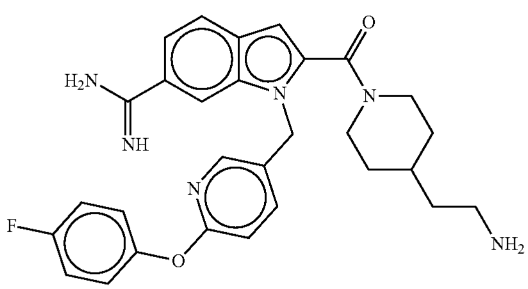 | 4.7 | 99.1 | 515.2 | A | B |
| I-318 | 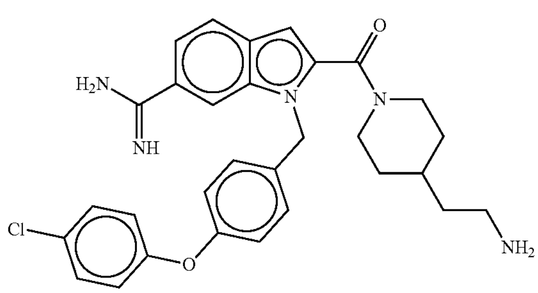 | | | 530.2 | ND | ND |

TABLE A-continued
Exemplary Compounds
| Cpd. ID. | Structure | HPLC Rt-min | % Purity-Indole | M + H | Assay Used | Mar-2 % inhibition at 1 uM |
|---|---|---|---|---|---|---|
| I-319 | 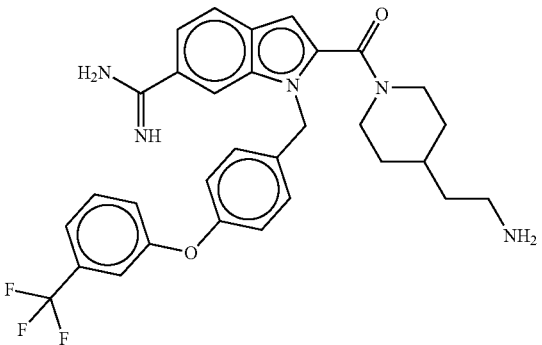 | 7.5 | 99.5 | 564.2 | A | B |
| I-320 | 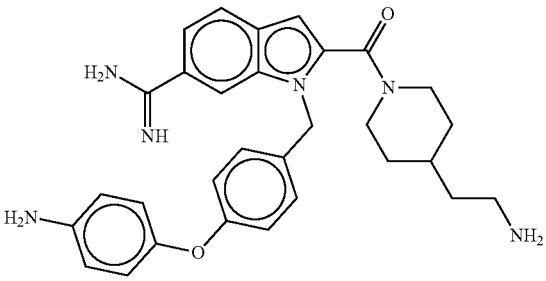 |  |  | 511.3 | ND | ND |
| I-321 | 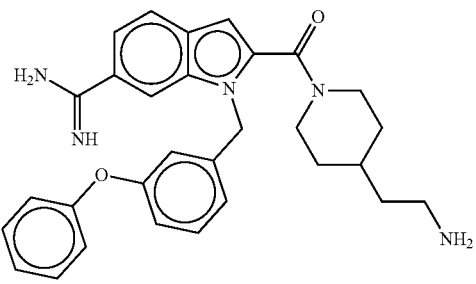 | 6.8 | 98.1 | 496.2 | A | B |
| I-322 | 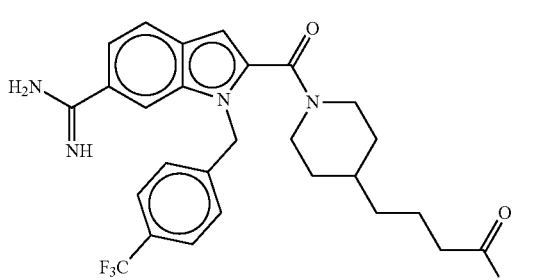 | 7.9 | 98.8 | 514.2 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-323 | 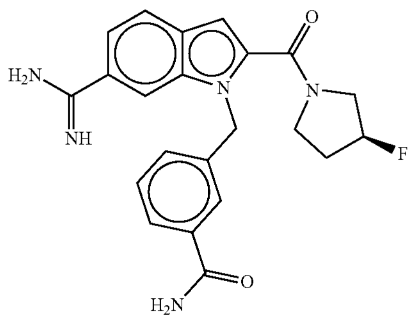 | 5 | 96 | 408.1 | A | A |
| I-324 | 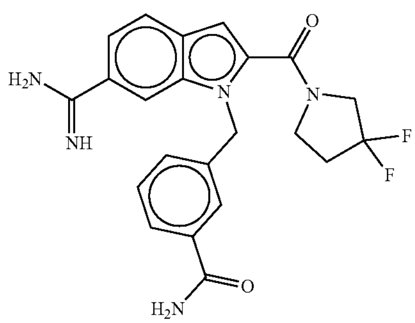 | 5.3 | 95 | 426.3 | A | A |
| I-325 | 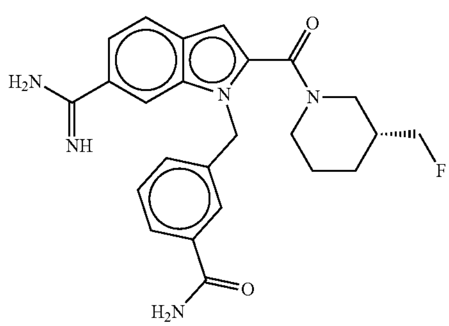 | 5.5 | 97.7 | 436.2 | A | A |
| I-326 | 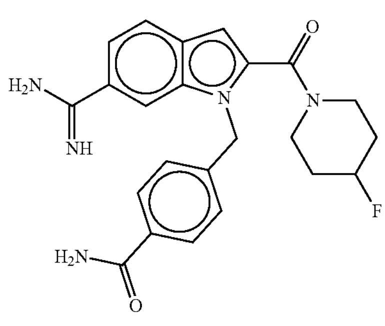 | 5.3 | 85.4 | 421.9 | A | A |

TABLE A-continued
Exemplary Compounds
| Cpd. ID. | Structure | HPLC Rt-min | % Purity-Indole | M + H | Assay Used | Mar-2 % inhibition at 1 uM |
|---|---|---|---|---|---|---|
| I-327 | 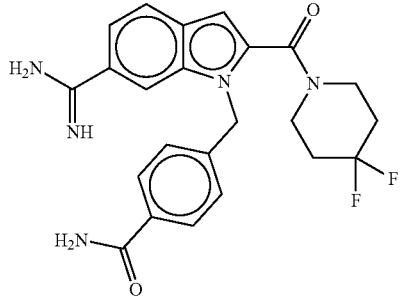 | 5.5 | 95.6 | 440.2 | A | A |
| I-328 | 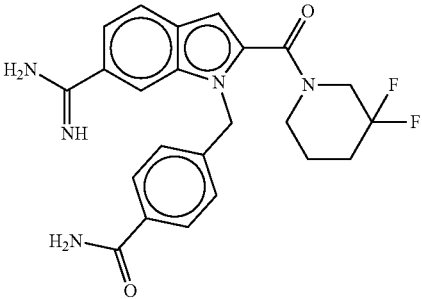 | | | 440.2 | A | A |
| I-329 | 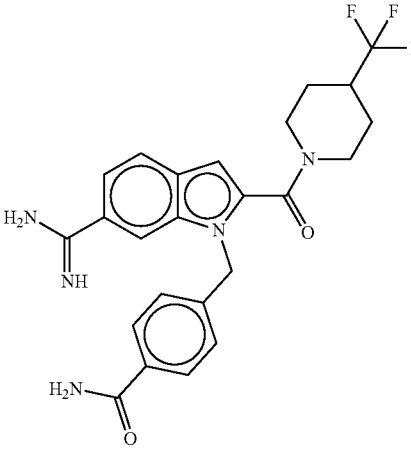 | 6.3 | 98.2 | 472.1 | A | A |
| I-330 | 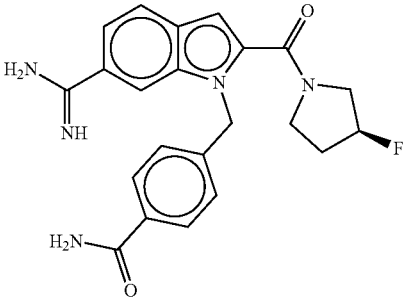 | 3.9 | 95.7 | 407.9 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-331 | 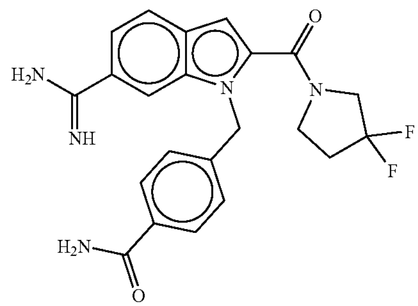 | 5.3 | 95.1 | 425.9 | A | A |
| I-332 | 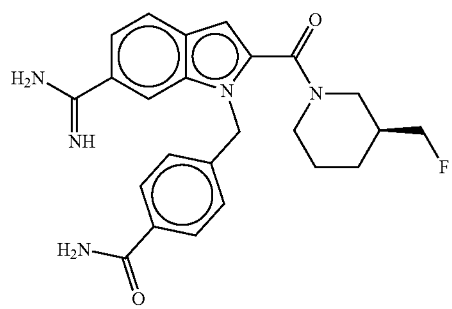 | 5.3 | 98.3 | 436.2 | A | A |
| I-333 | 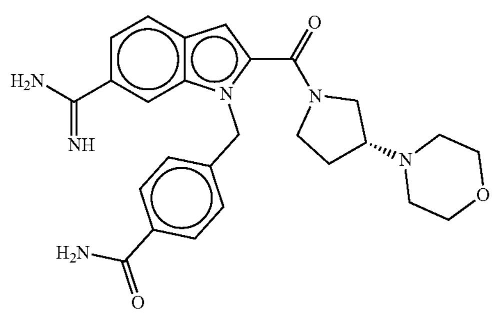 | NA | NA | 475.2 | A | A |
| I-334 | 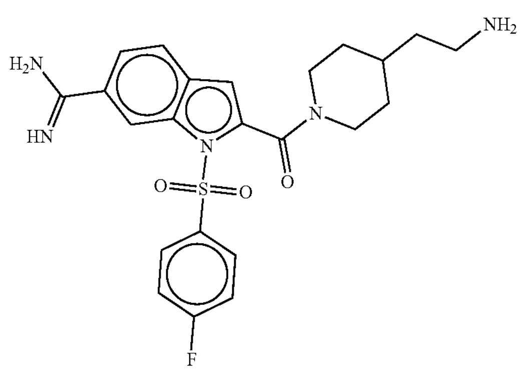 | | | 472.2 | ND | ND |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-335 | 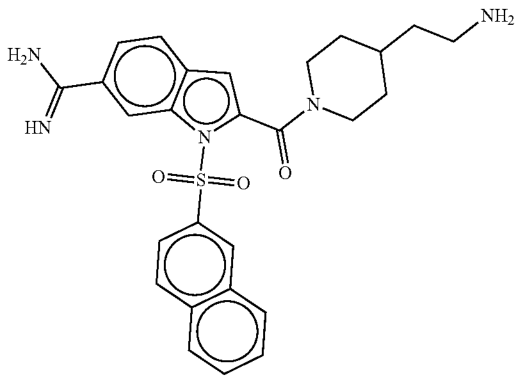 | 5.7 | 90 | 504.1 | A | A |
| I-336 | 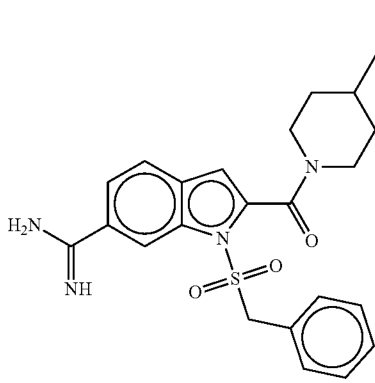 | 6.8 | 91.7 | 468.1 | A | A |
| I-337 | 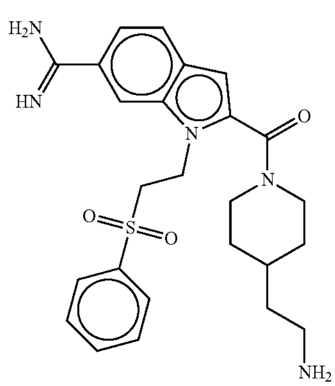 | 5.9 | 97.8 | 508 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-338 | 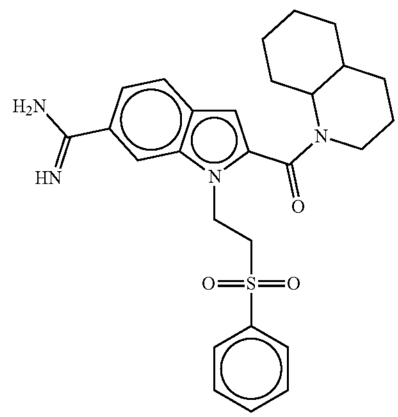 | 6.1 | 99.4 | 493.2 | A | A |
| I-339 | 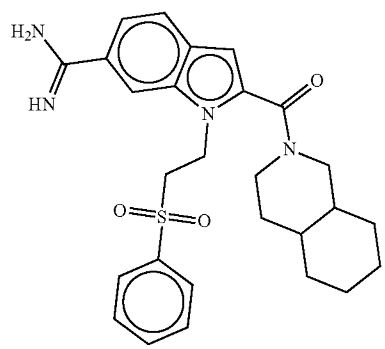 | 6.2 | 99.6 | 493.2 | A | A |
| I-340 | 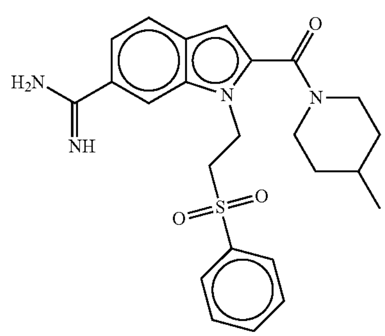 | 3.7 | 98 | 453.4 | A | A |
| I-341 | 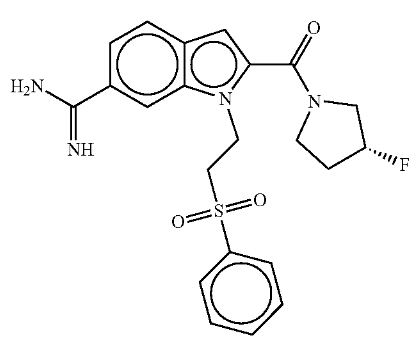 | 3.3 | 86.6 | 443 | A | A |

TABLE A-continued

Exemplary Compounds

| Cpd. ID. | Structure | HPLC Rt- min | % Purity- Indole | M + H | Assay Used | Mar-2 % inhibition at 1 uM |
|---|---|---|---|---|---|---|
| I-342 | 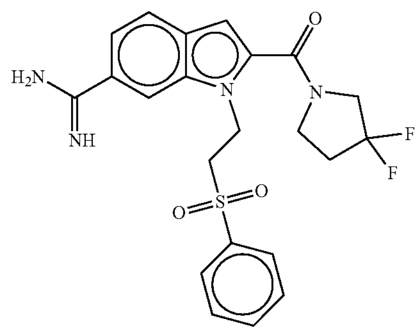 | 6 | 96.7 | 460.9 | A | A |
| I-343 | 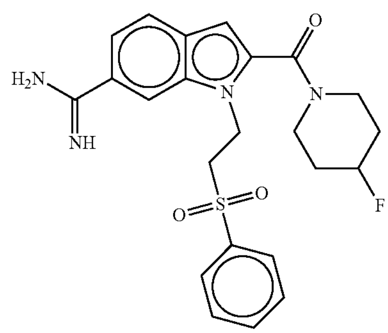 | 6.6 | 98.8 | 457 | A | A |
| I-344 | 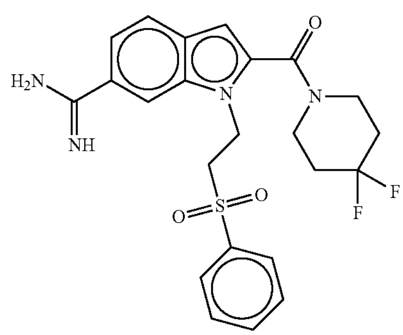 | 3.1 | 97.1 | 475.1 | A | A |
| I-345 | 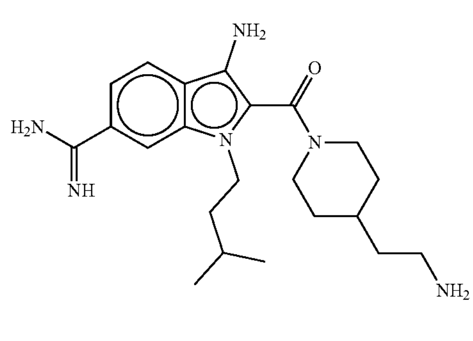 | 4.4 | 97.7 | 399.3 | A | B |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-346 | 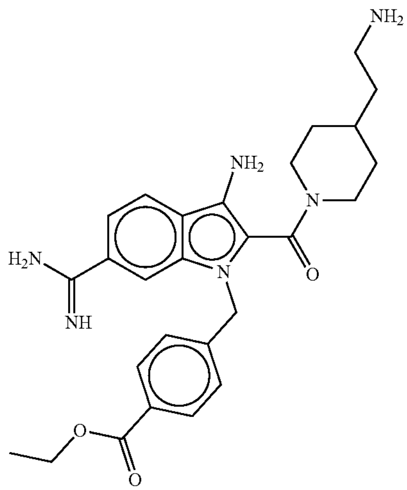 | 4.5 | 92.9 | 491.4 | A | A |
| I-347 | 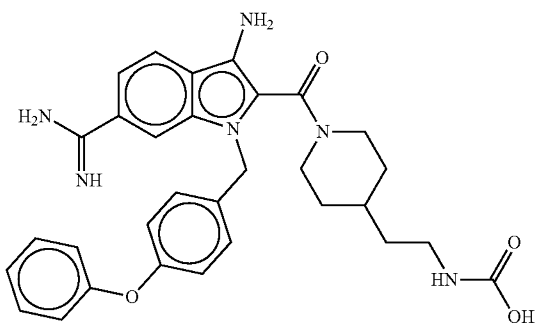 | 4.7 | 94 | 551.3 | A | A |
| I-348 | 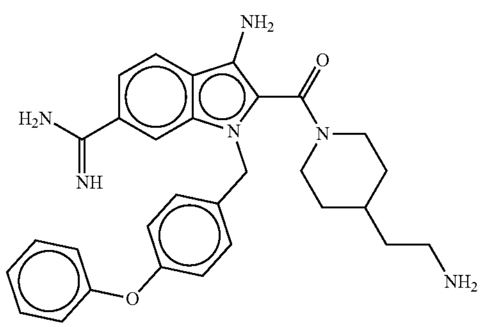 | 4.8 | 97.9 | 511.2 | A | A |
| I-349 | 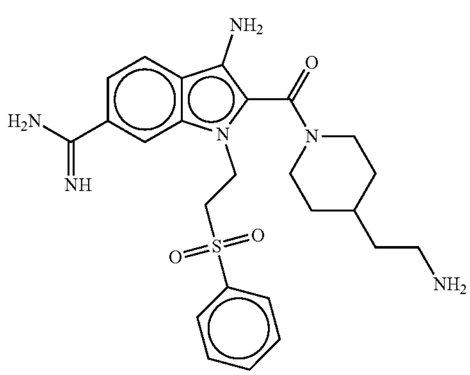 | NA | NA | 497.2 | A | B |

TABLE A-continued
Exemplary Compounds
| Cpd. ID. | Structure | HPLC Rt-min | % Purity-Indole | M + H | Assay Used | Mar-2 % inhibition at 1 uM |
|---|---|---|---|---|---|---|
| I-350 | 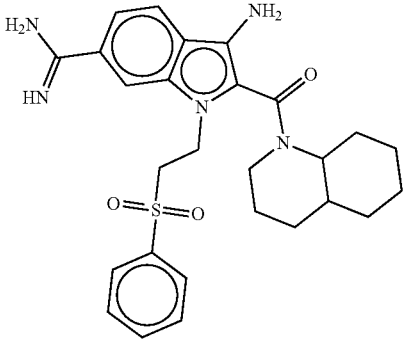 | NA | NA | 508.2 | NA | NA |
| I-351 | 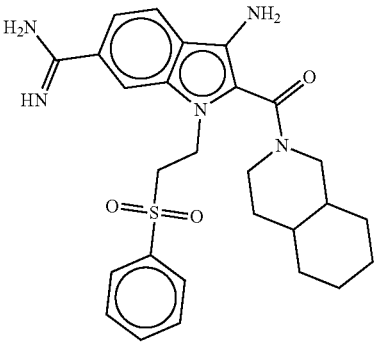 | 5.8 | 95.1 | 508.2 | A | A |
| I-352 | 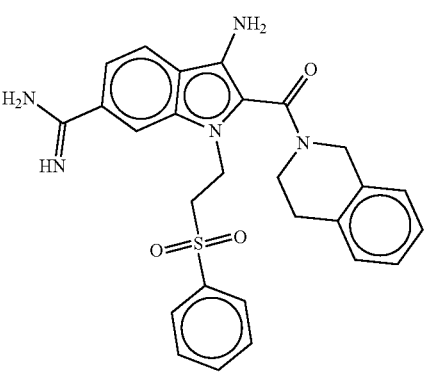 | 5.5 | 97 | 502.1 | A | A |
| I-353 | 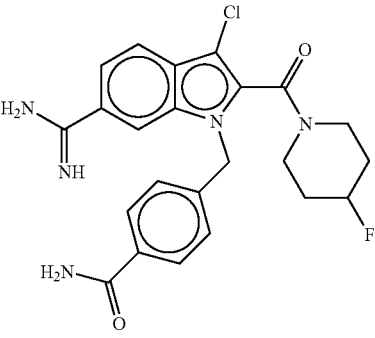 | 4.1 | 97.5 | 489 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-354 | 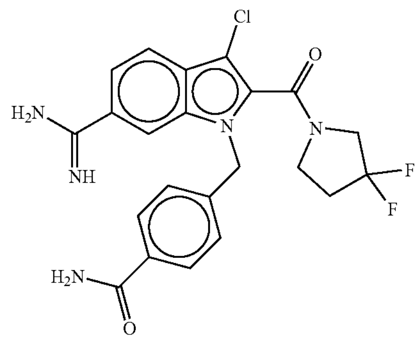 | 5.6 | 97.4 | 460 | A | A |
| I-355 | 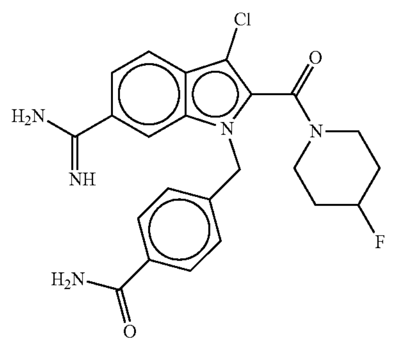 | 6.1 | 94.3 | 456.1 | A | A |
| I-356 | 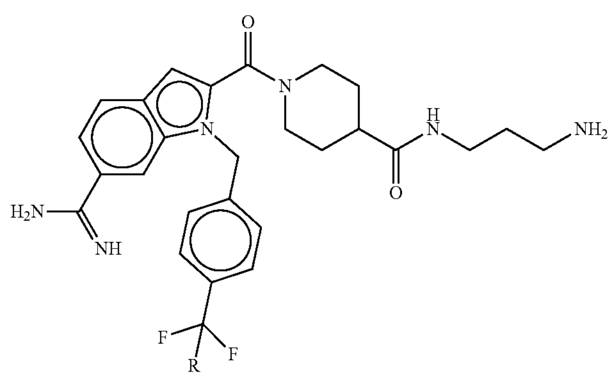 | 6.6 | 79.7 | 529.2 | A | A |
| I-357 | 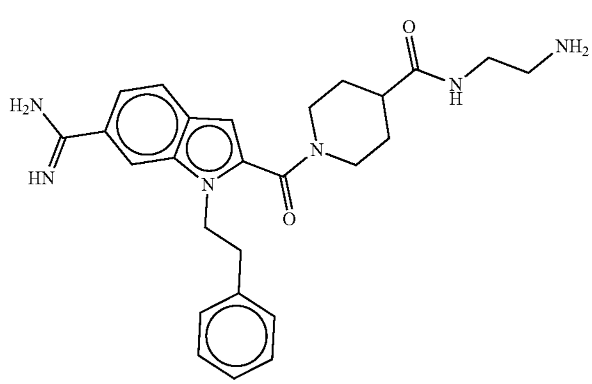 | 4.4 | 94.7 | 461.2 | A | A |

TABLE A-continued

Exemplary Compounds

| Cpd. ID. | Structure | HPLC Rt- min | % Purity- Indole | M + H | Assay Used | Mar-2 % inhibition at 1 uM |
|---|---|---|---|---|---|---|
| I-358 | 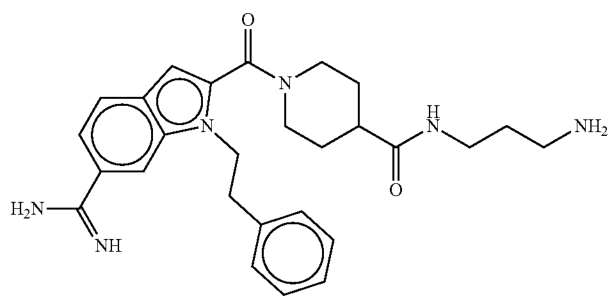 | 4.5 | 96.7 | 475.2 | A | B |
| I-359 | 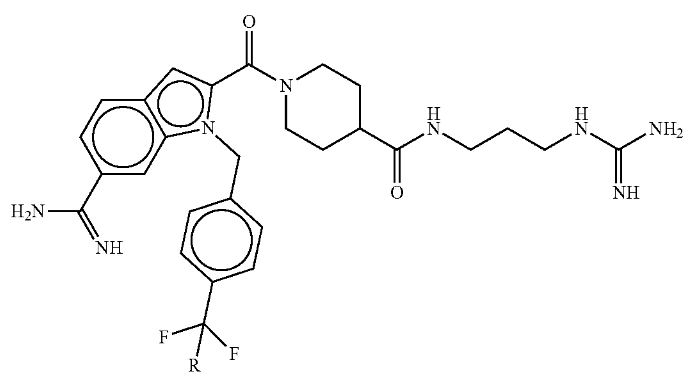 | NA | NA | 571.2 | A | B |
| I-360 | 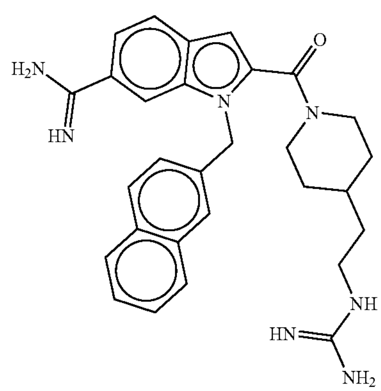 | 6.7 | 99.6 | 496.2 | A | B |
| I-361 | 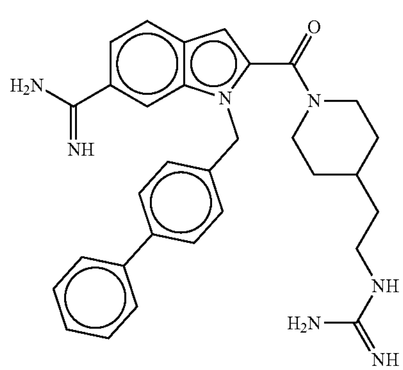 | 7 | 94.4 | 522.2 | A | A |

TABLE A-continued
Exemplary Compounds
| Cpd. ID. | Structure | HPLC Rt- min | % Purity- Indole | M + H | Assay Used | Mar-2 % inhibition at 1 uM |
|---|---|---|---|---|---|---|
| I-362 | 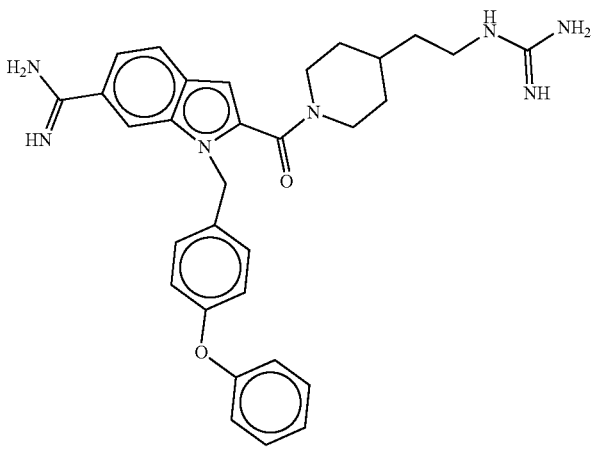 | | | 538.3 | ND | ND |
| I-363 | 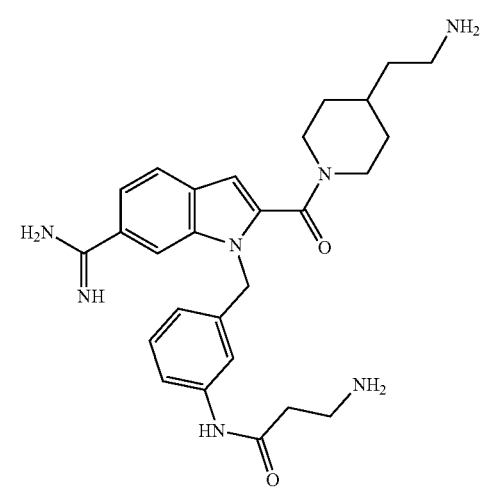 [SMILES: N=C(N)c1ccc2cc(C(=O)N3CCC(CCN)CC3)n(Cc3cccc(NC(=O)CCN)c3)c2c1] | | | 490.3 | ND | ND |
| I-364 | 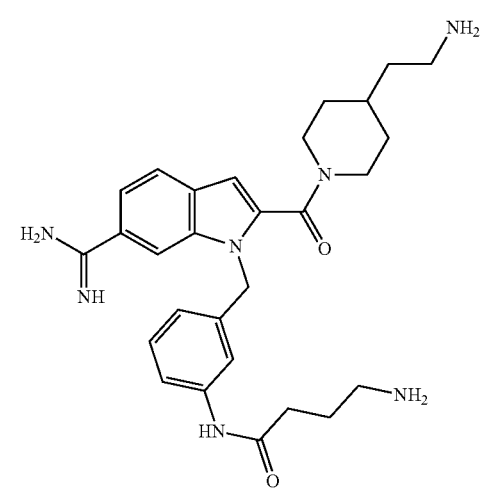 [SMILES: N=C(N)c1ccc2cc(C(=O)N3CCC(CCN)CC3)n(Cc3cccc(NC(=O)CCCN)c3)c2c1] | | | 504.3 | ND | ND |

TABLE A-continued
Exemplary Compounds
| Cpd. ID. | Structure | HPLC Rt-min | % Purity-Indole | M + H | Assay Used | Mar-2 % inhibition at 1 uM |
|---|---|---|---|---|---|---|
| I-365 | 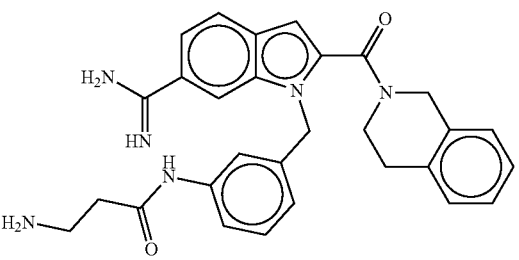 | 6 | 95.3 | 495.2 | A | A |
| I-366 | 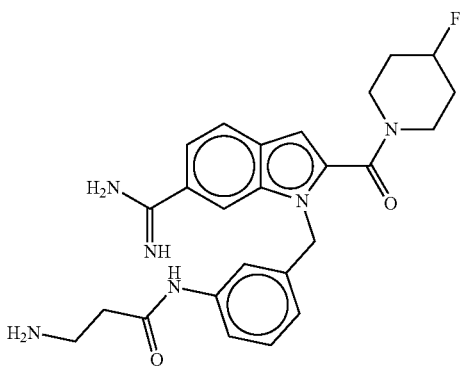 | 5.4 | 97.4 | 465.2 | A | A |
| I-367 | 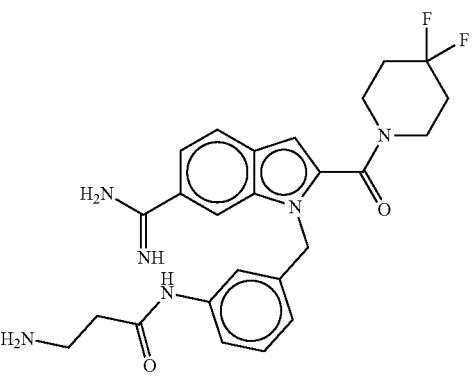 | 5.8 | 93.9 | 483.1 | A | A |
| I-368 | 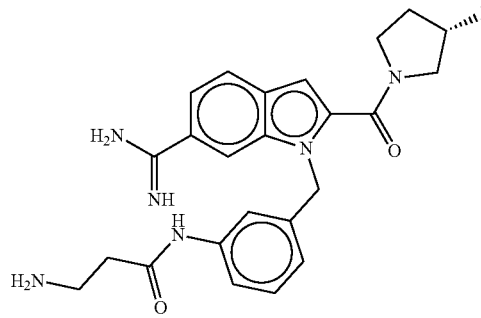 | 5.2 | 95.9 | 451.1 | A | A |

TABLE A-continued
Exemplary Compounds
| Cpd. ID. | Structure | HPLC Rt-min | % Purity-Indole | M + H | Assay Used | Mar-2 % inhibition at 1 uM |
|---|---|---|---|---|---|---|
| I-369 | 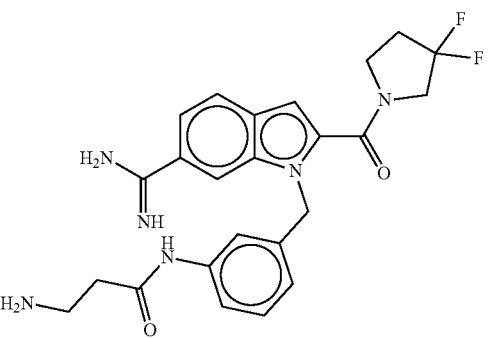 | 5.5 | 86.5 | 469.2 | A | A |
| I-370 | 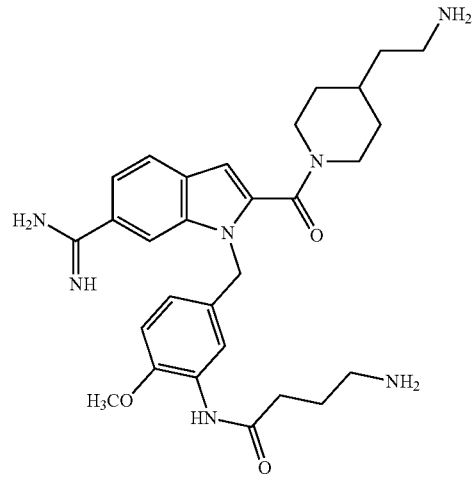 [SMILES: COc1ccc(Cn2c(C(=O)N3CCC(CCN)CC3)cc3ccc(C(=N)N)cc32)cc1NC(=O)CCCN] | | | 520.3 | ND | ND |
| I-371 | 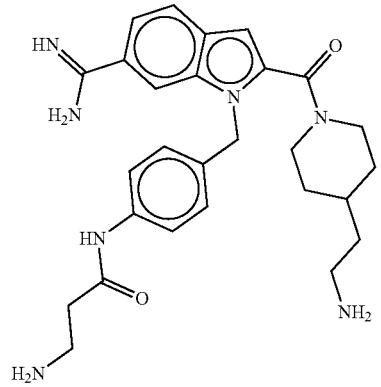 | | | 490.3 | ND | ND |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-372 | 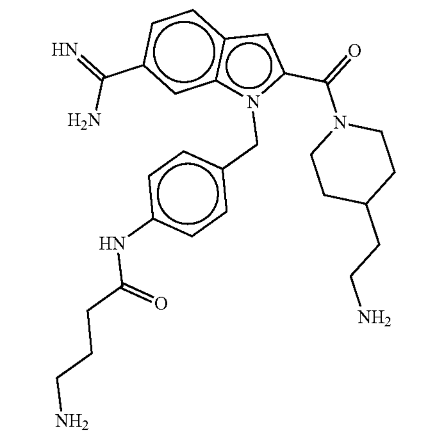 | 4.1 | 95.3 | 504.2 | A | B |
| I-373 | 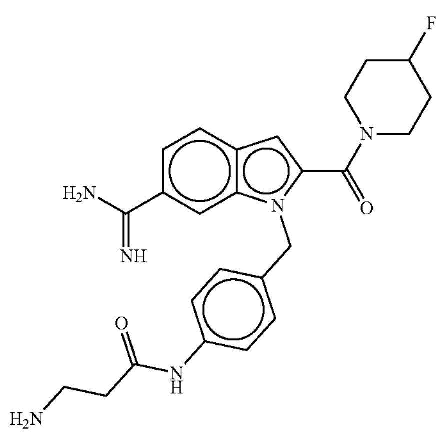 | 4.8 | 94.2 | 465.5 | A | A |
| I-374 | 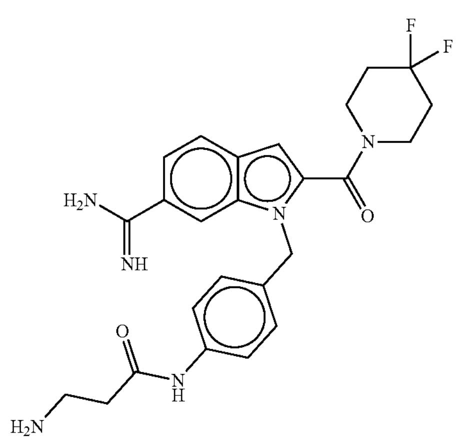 | 4.8 | 94.3 | 483.2 | A | A |

TABLE A-continued
Exemplary Compounds
| Cpd. ID. | Structure | HPLC Rt- min | % Purity- Indole | M + H | Assay Used | Mar-2 % inhibition at 1 uM |
|---|---|---|---|---|---|---|
| I-375 | 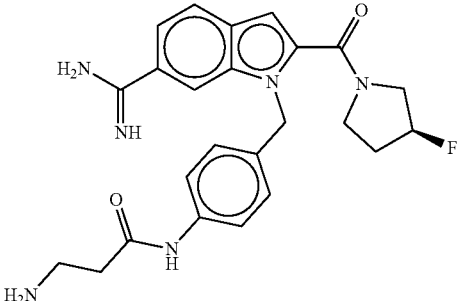 | 4.6 | 88.9 | 451.2 | A | A |
| I-376 | 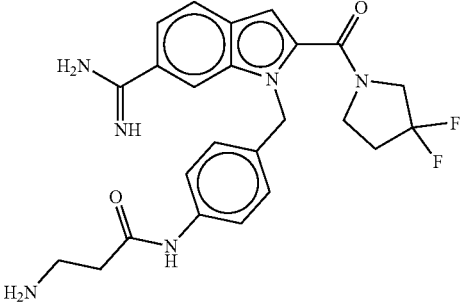 | 5.4 | 93.4 | 469 | A | A |
| I-377 | 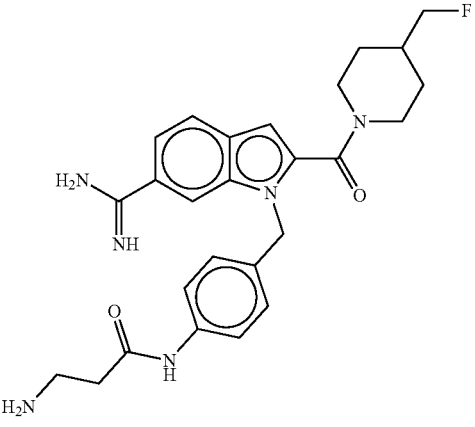 | 4.9 | 85.8 | 749.1 | A | A |
| I-378 | 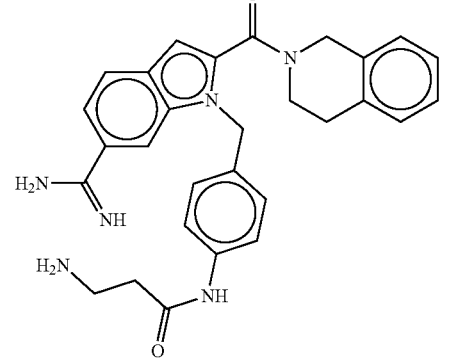 | 5.1 | 82.8 | 495.2 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-379 | 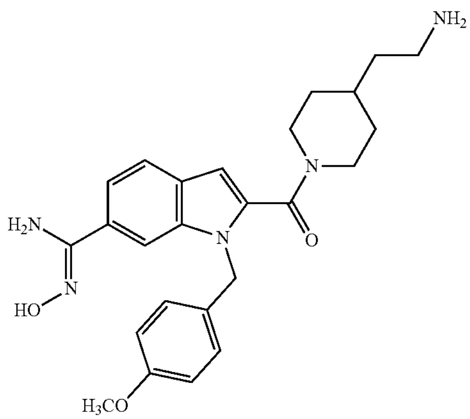 [SMILES: COc1ccc(Cn2c(C(=O)N3CCC(CCN)CC3)cc3ccc(/C(N)=N/O)cc32)cc1] | | | 488.2 | ND | ND |
| I-380 | 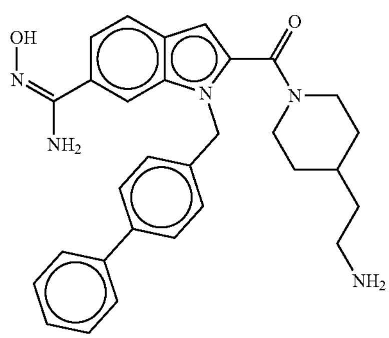 | 6.9 | 96.4 | 496.3 | A | A |
| I-381 | 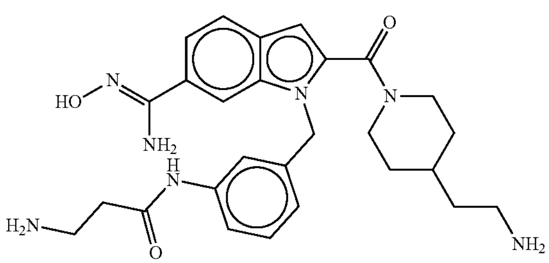 | 4.4 | 98 | 506.1 | A | A |
| I-382 | 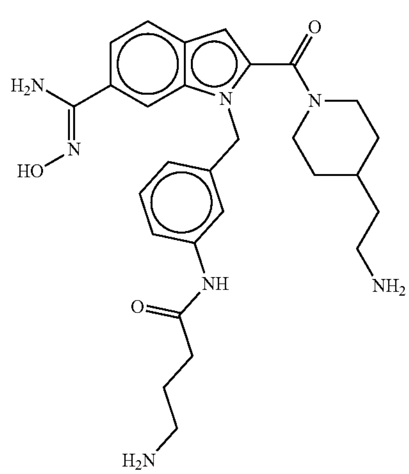 | 4.1 | 96.3 | 520.2 | A | A |

TABLE A-continued
Exemplary Compounds
| Cpd. ID. | Structure | HPLC Rt-min | % Purity-Indole | M + H | Assay Used | Mar-2 % inhibition at 1 uM |
|---|---|---|---|---|---|---|
| I-383 | 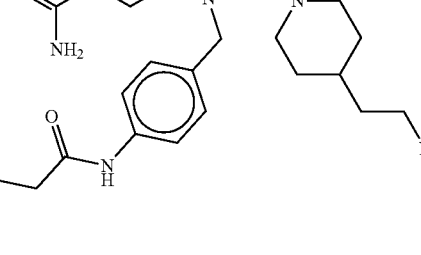 | 4.3 | 96.1 | 506.2 | A | A |
| I-384 | 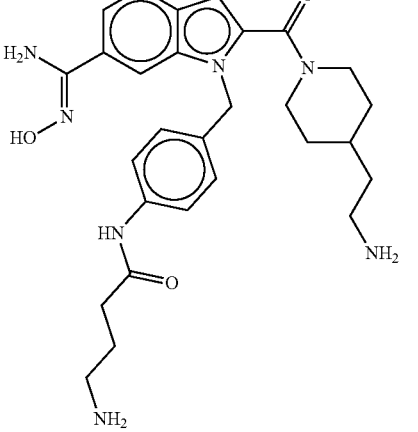 | 4.3 | 96.8 | 520.2 | A | B |
| I-385 | 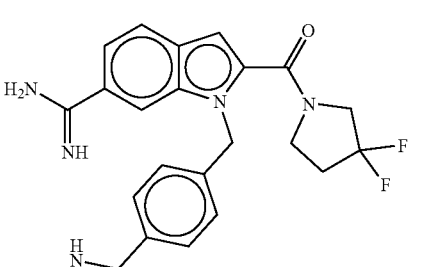 | 3.3 | 96.9 | 454.2 | A | A |
| I-386 | 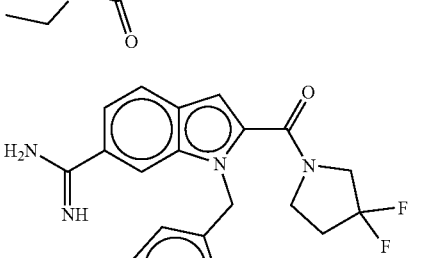 | 5.6 | 91.1 | 454.1 | A | A |

TABLE A-continued
Exemplary Compounds
| Cpd. ID. | Structure | HPLC Rt-min | % Purity-Indole | M + H | Assay Used | Mar-2 % inhibition at 1 uM |
|---|---|---|---|---|---|---|
| I-387 | 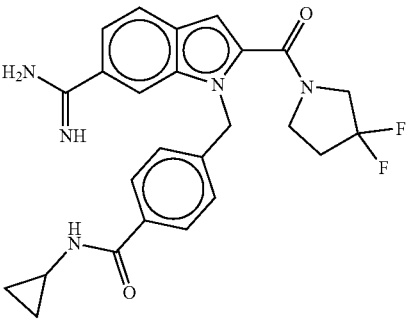 | 3.4 | 88.6 | 466.2 | A | A |
| I-388 | 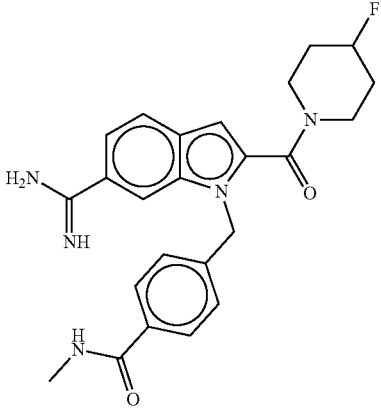 | 5.3 | 96.4 | 436.1 | A | A |
| I-389 | 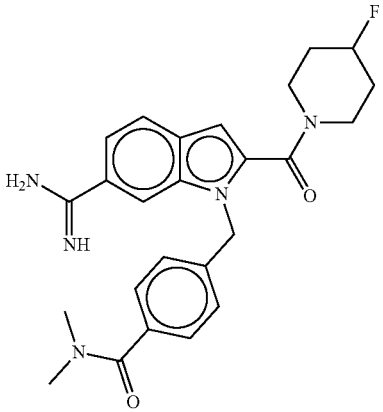 | 5.5 | 95.2 | 450.2 | A | A |

TABLE A-continued
Exemplary Compounds
| Cpd. ID. | Structure | HPLC Rt-min | % Purity-Indole | M + H | Assay Used | Mar-2 % inhibition at 1 uM |
|---|---|---|---|---|---|---|
| I-390 | 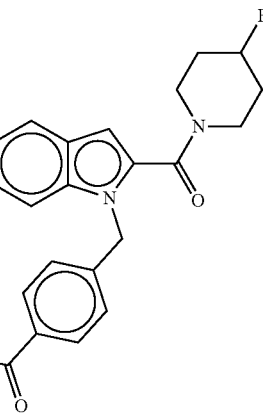 | 5.5 | 96.3 | 450.2 | A | A |
| I-391 | 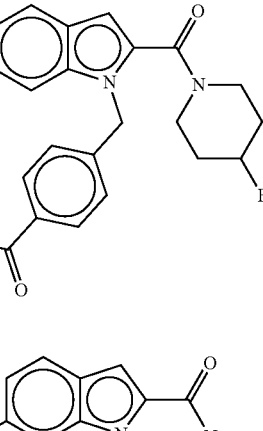 | 5.5 | 98 | 462.2 | A | A |
| I-392 | 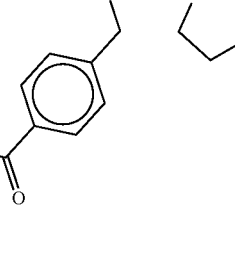 | 4.7 | 91 | 469.2 | A | A |
| I-393 | 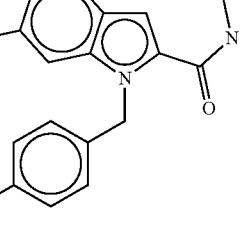 | 4.7 | 94.6 | 465.2 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-394 | 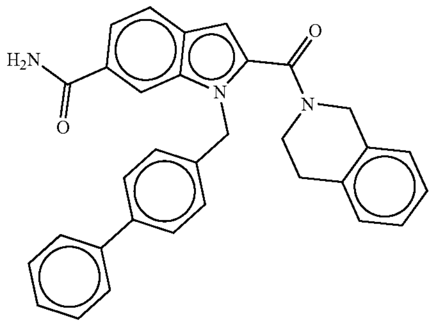 | 5.6 | 89.3 | 486.2 | A | A |
| I-395 | 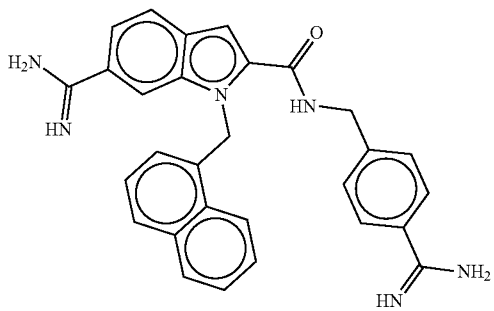 | 4.9 | 99.5 | 475.2 | B | D |
| I-396 | 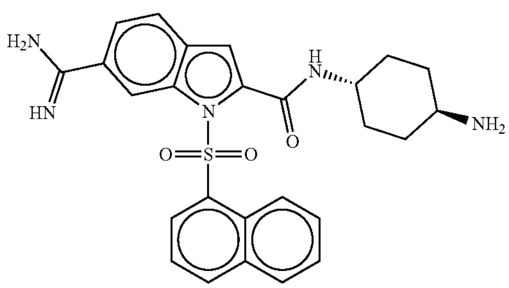 | 4.6 | 99.6 | 490.3 | B | B |
| I-397 | 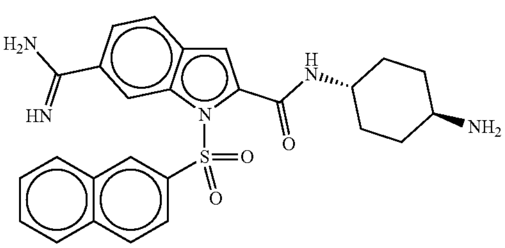 | | | 490.3 | A | B |
| I-398 | 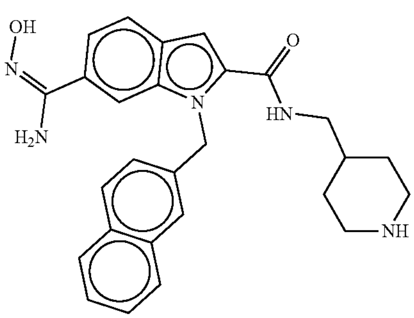 | 5.1 | 99.8 | 456.2 | A | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-399 | 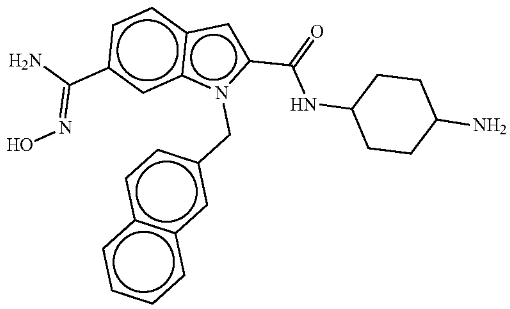 | 5.3 | 98.4 | 456.3 | A | A |
| I-400 | 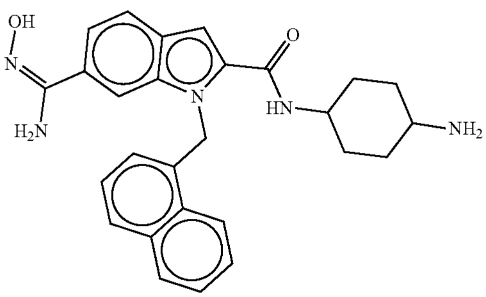 | 5.1 | 98.5 | 456.3 | A | B |
| I-401 | 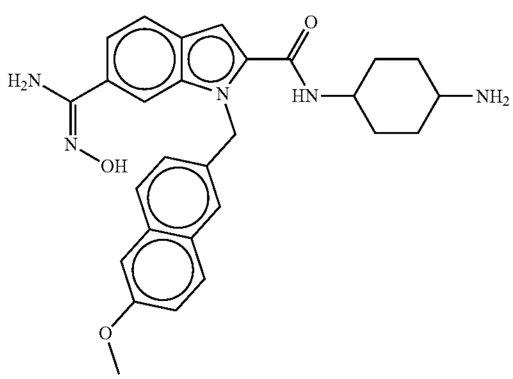 | 4.9 | 98.1 | 486.3 | A | A |
| I-402 | 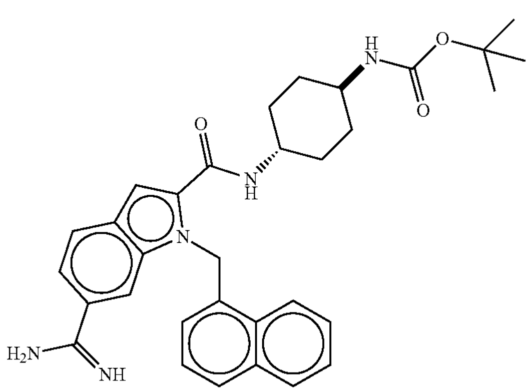 | 6.8 | 99.1 | 540.25 | B | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-403 | 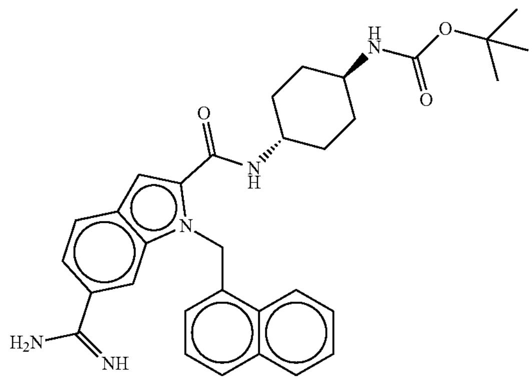 | 6.8 | 98.3 | 540.1 | B | A |
| I-404 | 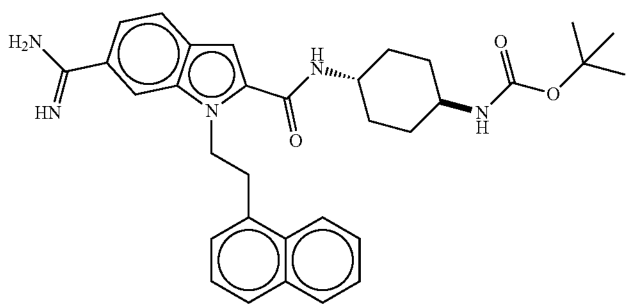 | 5.4 | 98.5 | 554.2 | B | A |
| I-405 | 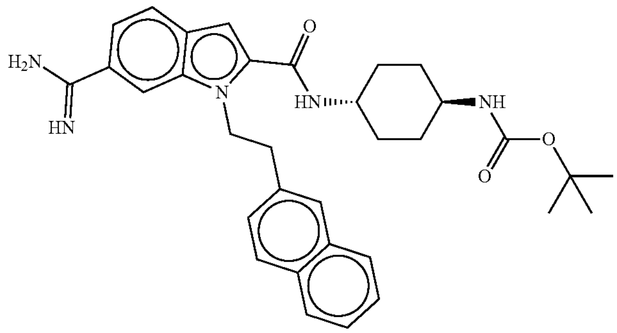 | 4.9 | 97.7 | 554.4 | B | B |
| I-406 | 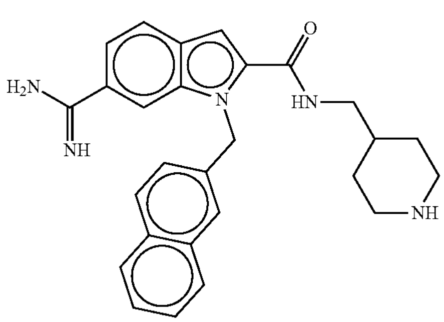 | 5.1 | 95.2 | 440.4 | A | B |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-407 | 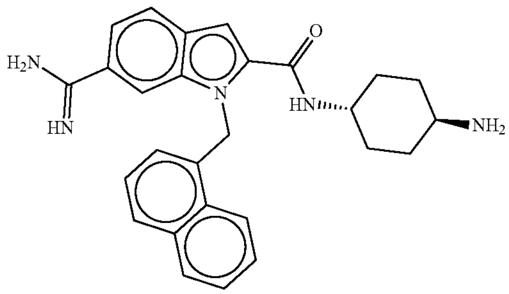 | 5 | 97.8 | 440.4 | B | D |
| I-408 | 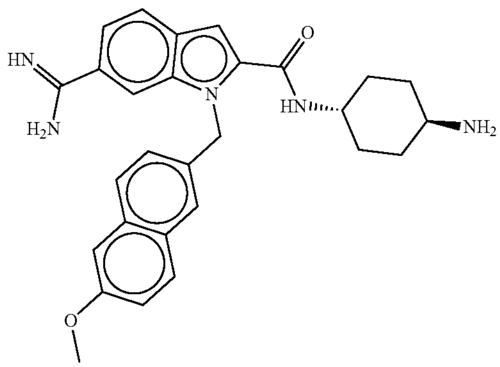 | 5 | 95.1 | 470.4 | A | C |
| I-409 | 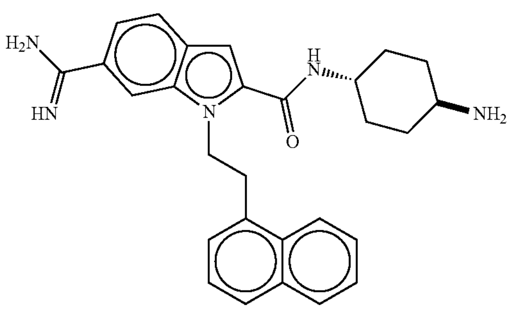 | 4.9 | 97.9 | 454.2 | B | B |
| I-410 | 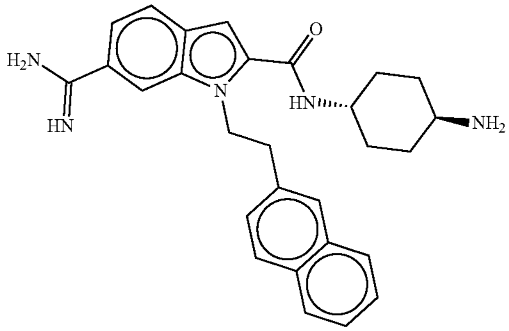 | 4.9 | 98.2 | 454.3 | B | B |

TABLE A-continued

Exemplary Compounds

| Cpd. ID. | Structure | HPLC Rt- min | % Purity- Indole | M + H | Assay Used | Mar-2 % inhibition at 1 uM |
|---|---|---|---|---|---|---|
| I-411 | 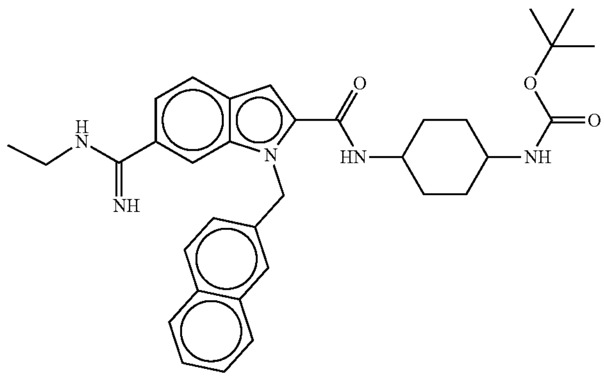 | 6.1 | 98.3 | 568.9 | B | A |
| I-412 | 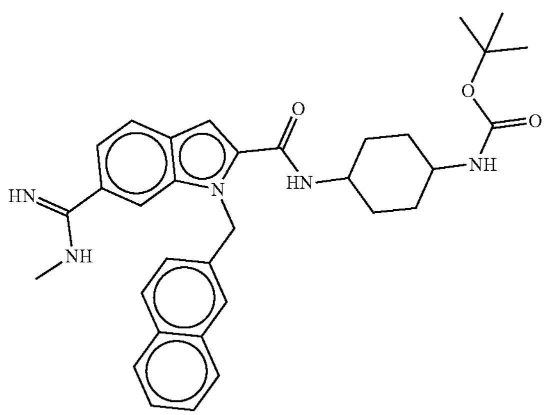 | 10.7 | 89.3 | 554.35 | B | B |
| I-413 | 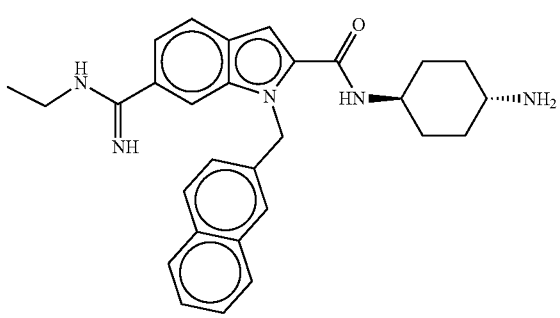 | 4.6 | 96.4 | 468.04 | B | B |
| I-414 | 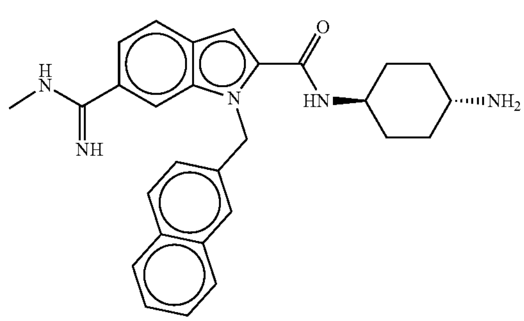 | 4.8 | 97.8 | 454.45 | B | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-415 | 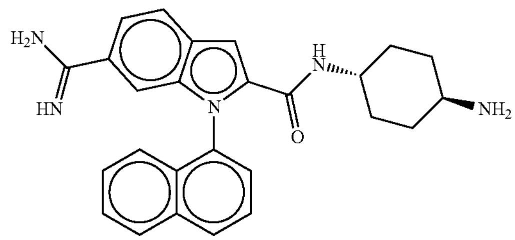 | 4.6 | 95.5 | 426.3 | B | B |
| I-416 | 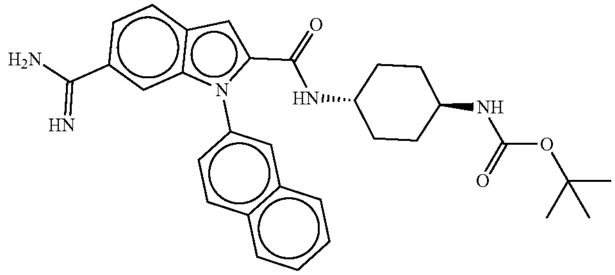 | 4.7 | 98.6 | 525.95 | B | A |
| I-417 | 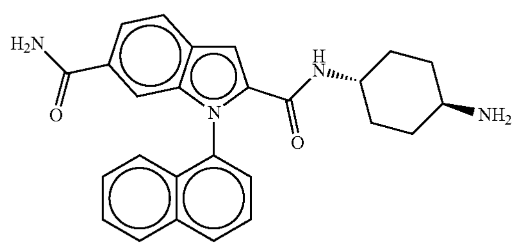 | 5 | 99.6 | 427.2 | B | A |
| I-418 | 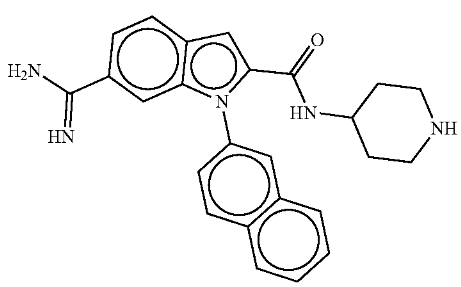 | 4.8 | 99.4 | 426.2 | B | D |
| I-419 | 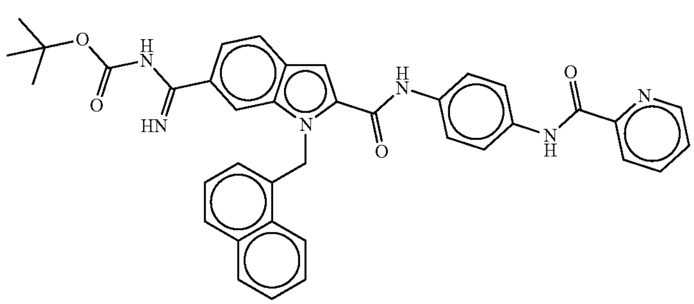 | 5.8 | 94 | 639.4 | B | A |

TABLE A-continued

Exemplary Compounds

| Cpd. ID. | Structure | HPLC Rt- min | % Purity- Indole | M + H | Assay Used | Mar-2 % inhibition at 1 uM |
|---|---|---|---|---|---|---|
| I-420 | 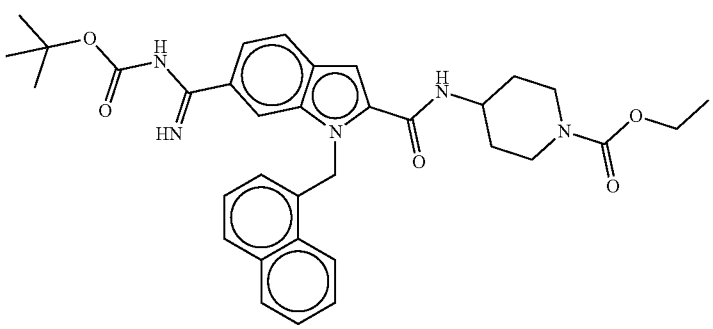 | 5.1 | 92.2 | 598.4 | B | A |
| I-421 | 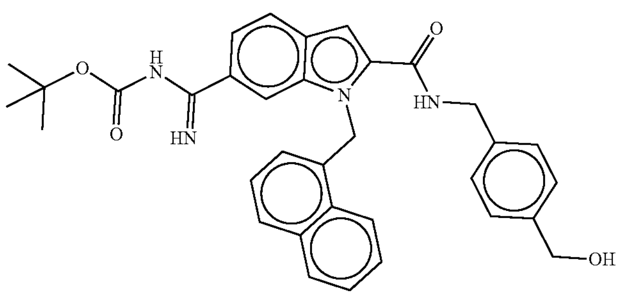 | 6.1 | 97.5 | 563.25 | B | A |
| I-422 | 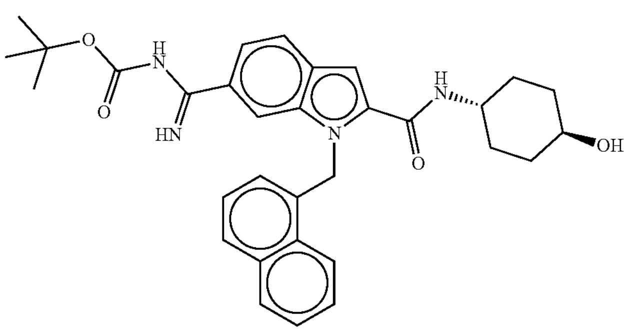 | 11.7 | 96.3 | 541.4 | B | B |
| I-423 | 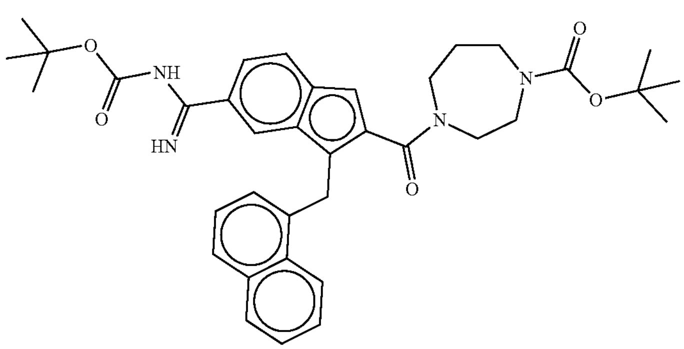 | 14.1 | 97.2 | 626.6 | B | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-424 | 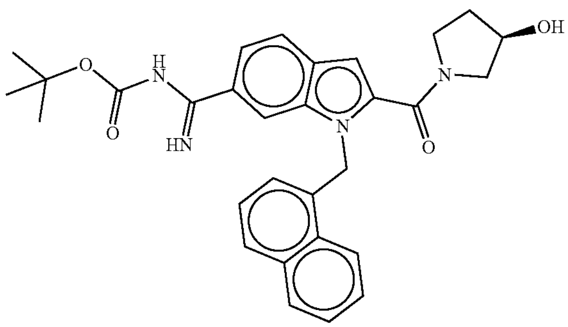 | 11 | 99.2 | 513.4 | B | A |
| I-425 | 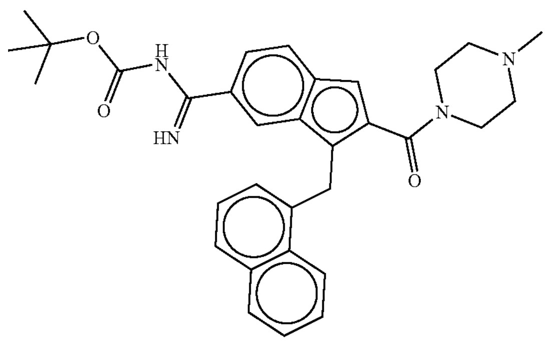 | 11.8 | 98.4 | 526.5 | B | A |
| I-426 | 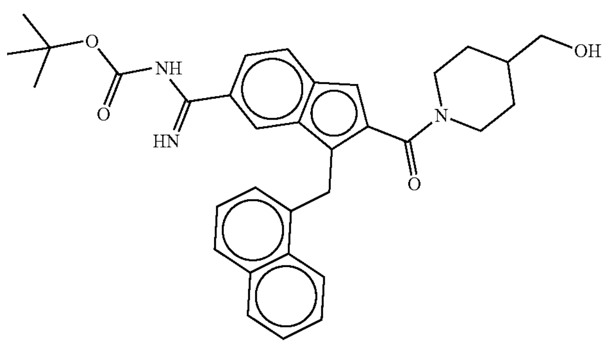 | 11.3 | 98.4 | 541.3 | B | A |
| I-427 | 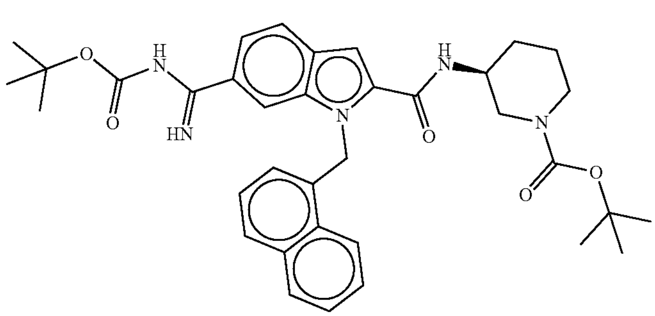 | 14.3 | 98.9 | 626.6 | B | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-428 | 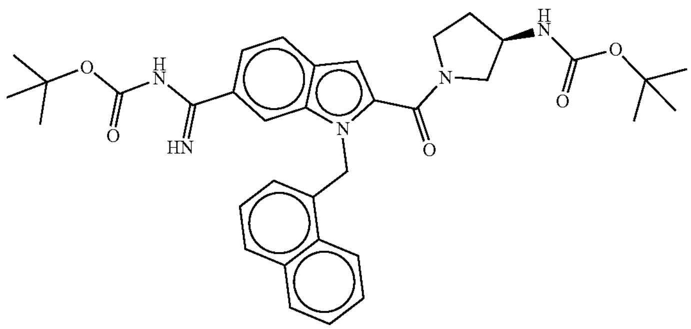 | 13.4 | 98.2 | 612.4 | B | A |
| I-429 | 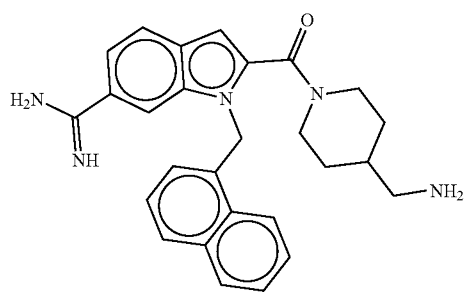 | 4.5 | 97.4 | 440.3 | B | C |
| I-430 | 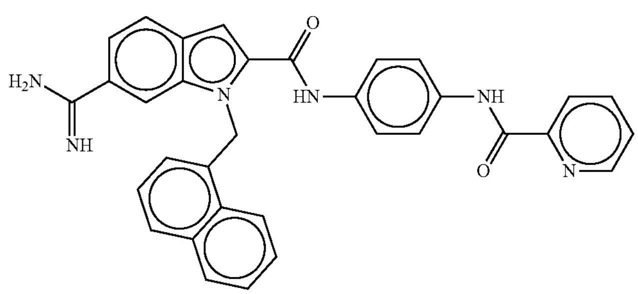 | 6.6 | 98.4 | 539.4 | B | C |
| I-431 | 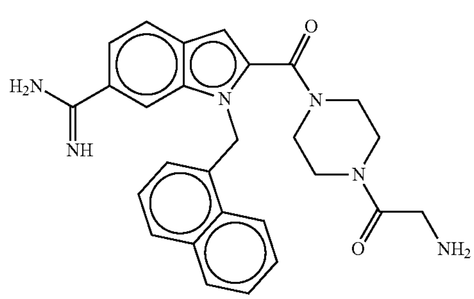 | 4.7 | 96.7 | 469.4 | B | C |

TABLE A-continued

Exemplary Compounds

| Cpd. ID. | Structure | HPLC Rt- min | % Purity- Indole | M + H | Assay Used | Mar-2 % inhibition at 1 uM |
|---|---|---|---|---|---|---|
| I-432 | 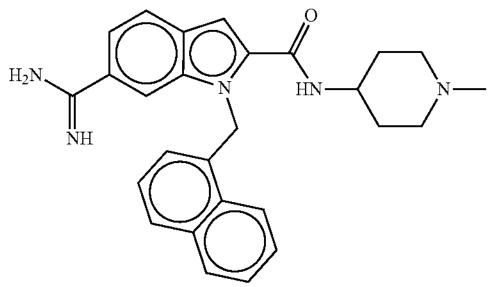 | 5.1 | 97.5 | 440.3 | B | D |
| I-433 | 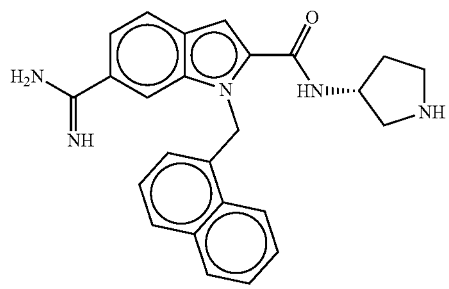 | 4.4 | 97.1 | 412.1 | B | D |
| I-434 | 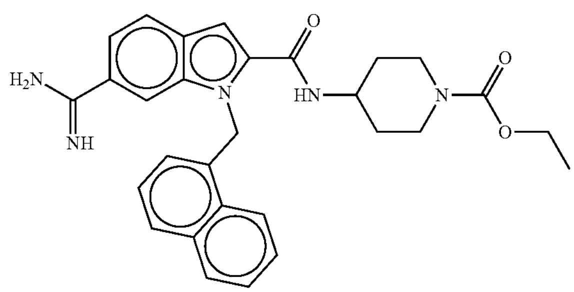 | 5.8 | 97.6 | 498.7 | B | D |
| I-435 | 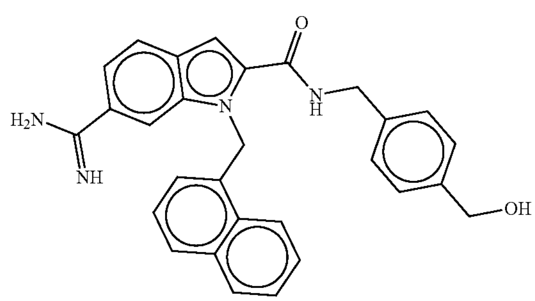 | 6.3 | 90.7 | 463.45 | B | C |
| I-436 | 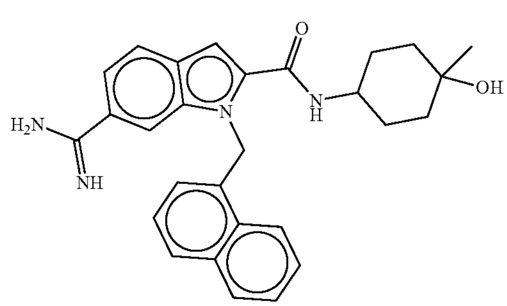 | 5.2 | 84.7 | 455.2 | B | C |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-437 | 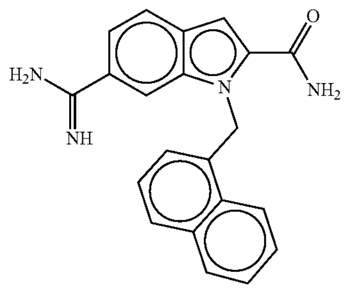 | 5.7 | 99.7 | 343.1 | B | D |
| I-438 | 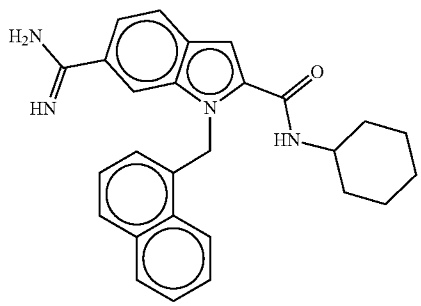 | 3.4 | 99.4 | 425.1 | B | B |
| I-439 | 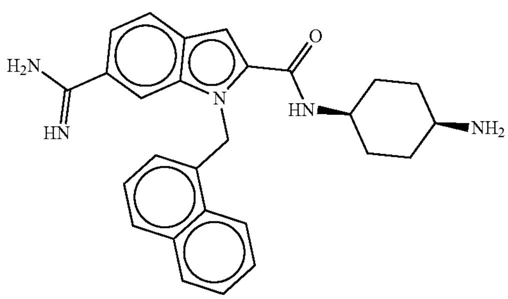 | 4.8 | 98.7 | 440.4 | B | D |
| I-440 | 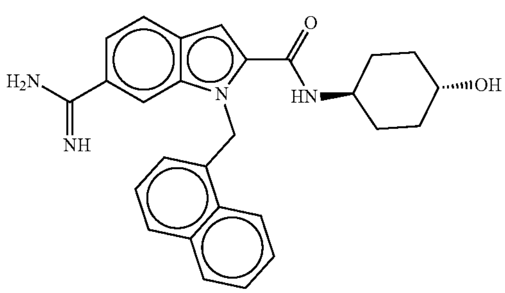 | 5.3 | 98.5 | 441.26 | B | D |
| I-441 | 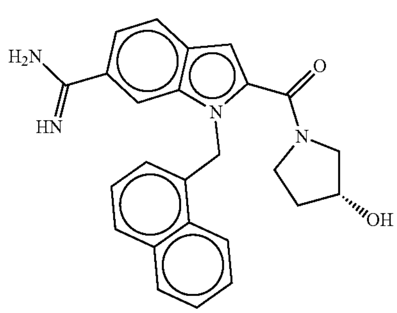 | 5.3 | 98.2 | 513.2 | B | B |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-442 | 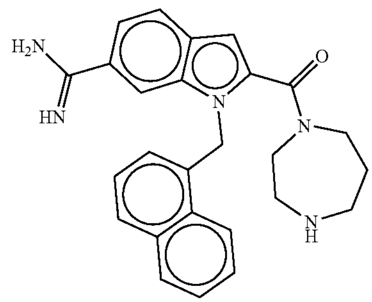 | 4.6 | 98.7 | 426.3 | B | C |
| I-443 | 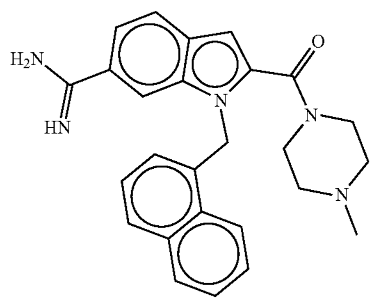 | 4.9 | 98.1 | 426.3 | B | A |
| I-444 | 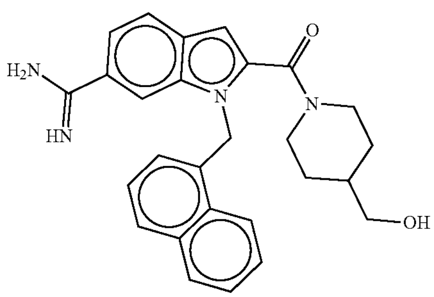 | 5.4 | 97.5 | 441.6 | B | B |
| I-445 | 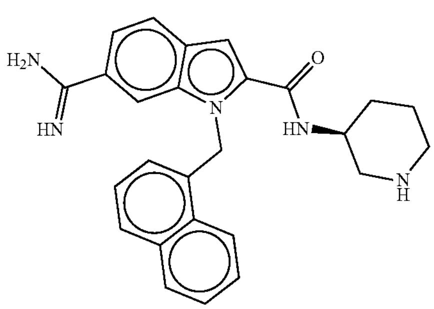 | 4.7 | 99.8 | 426.3 | B | D |

TABLE A-continued
Exemplary Compounds
| Cpd. ID. | Structure | HPLC Rt-min | % Purity-Indole | M + H | Assay Used | Mar-2 % inhibition at 1 uM |
|---|---|---|---|---|---|---|
| I-446 | 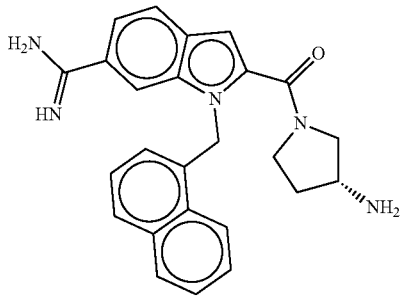 | 4.6 | 98.7 | 412.3 | B | C |
| I-447 | 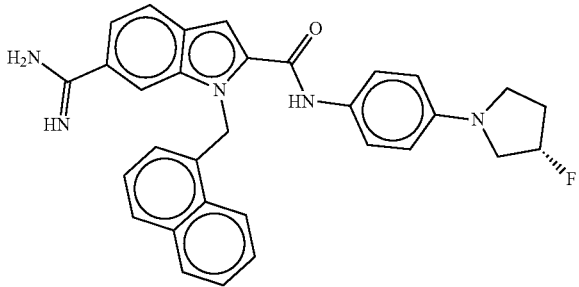 | 6.1 | 95.8 | 506.65 | B | B |
| I-448 | 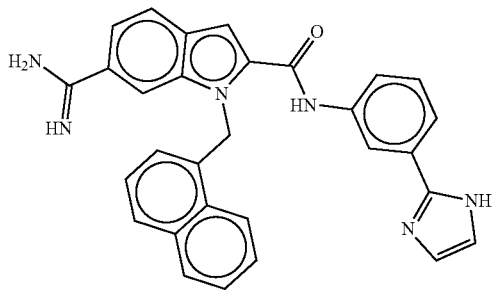 | 6.9 | 94.2 | 485 | B | B |
| I-449 | 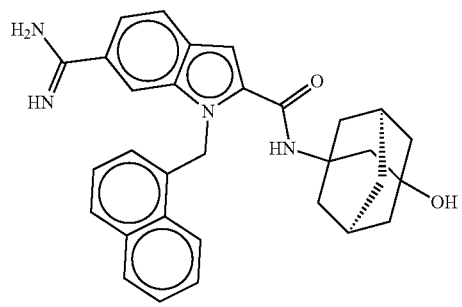 | 8.1 | 99.1 | 493.65 | B | B |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-450 | 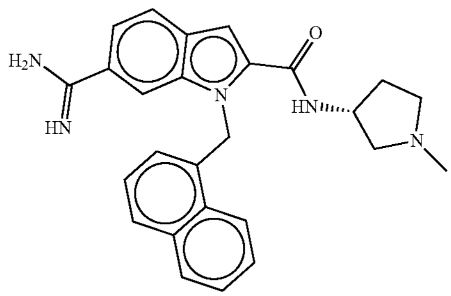 | 4.7 | 99.9 | 426.2 | B | D |
| I-451 | 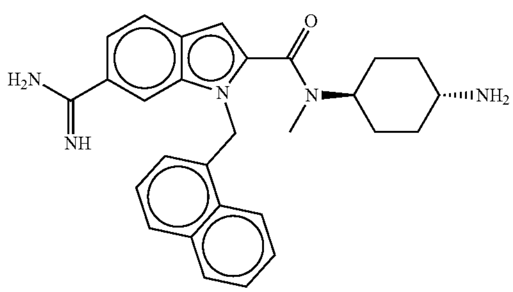 | 4.5 | 99.2 | 454.5 | B | C |
| I-452 | 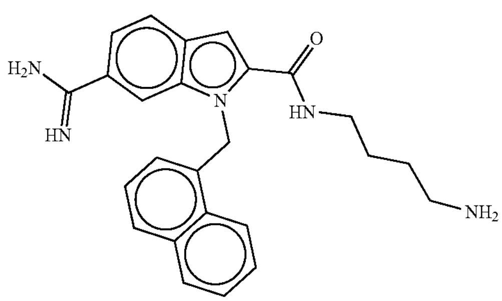 | 4.5 | 98.5 | 414.4 | B | D |
| I-453 | 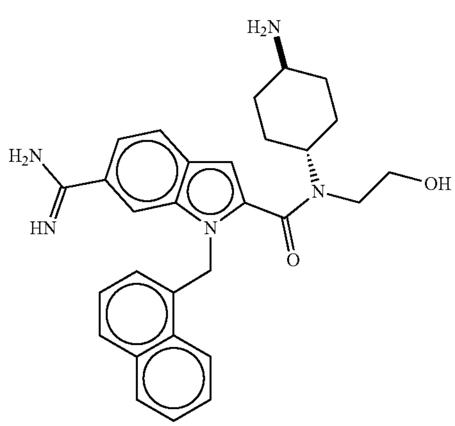 | 4.6 | 96.6 | 484.65 | B | C |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-454 | 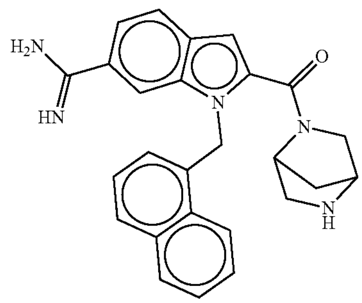 | 4.8 | 96.6 | 424.3 | B | D |
| I-455 | 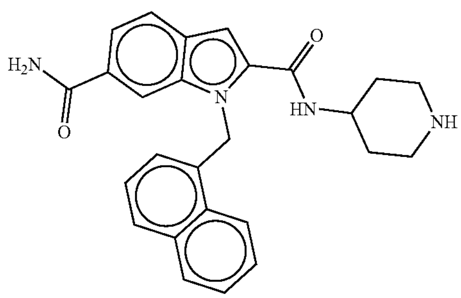 | 6.2 | 97.3 | 428 | B | A |
| I-456 | 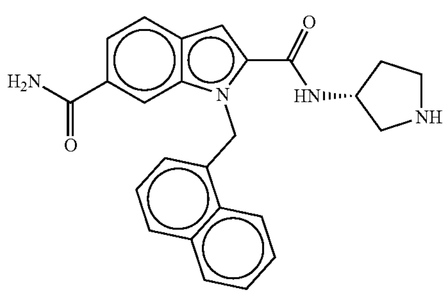 | 5.8 | 99.1 | 413 | B | A |
| I-457 | 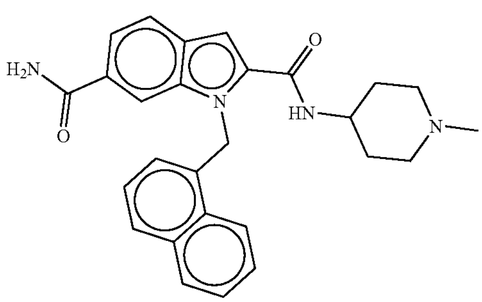 | 5 | 93.6 | 441.4 | B | A |
| I-458 | 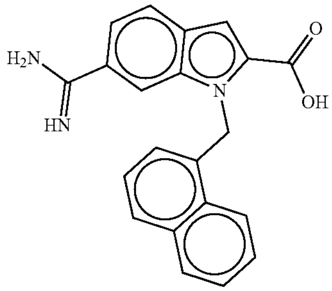 | 5.4 | 98 | 342 | B | D |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-459 | 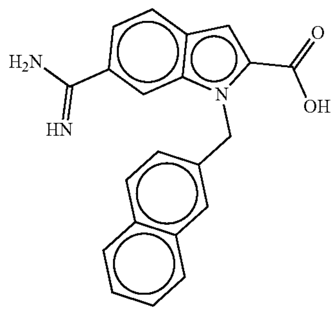 | 6 | 96.9 | 344.2 | B | B |
| I-460 | 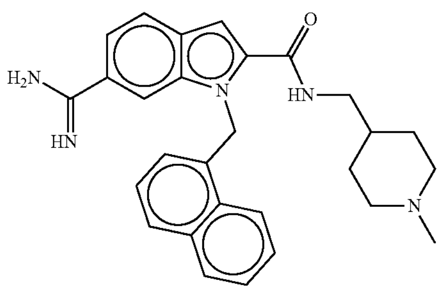 | 5.1 | 99.7 | 453.9 | B | D |
| I-461 | 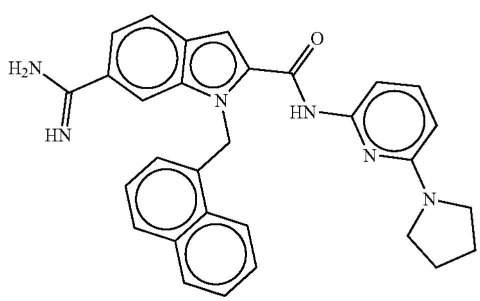 | | | 488.95 | B | B |
| I-462 | 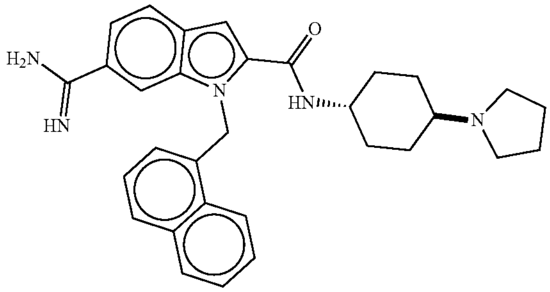 | 5.2 | 98.9 | 494.2 | B | D |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-463 | 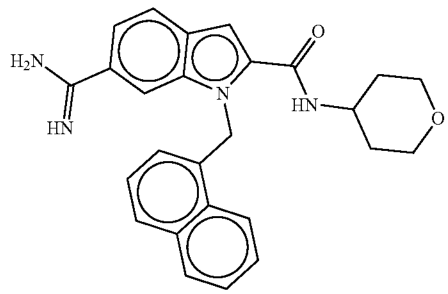 | 5.5 | 98.3 | 427.1 | B | C |
| I-464 | 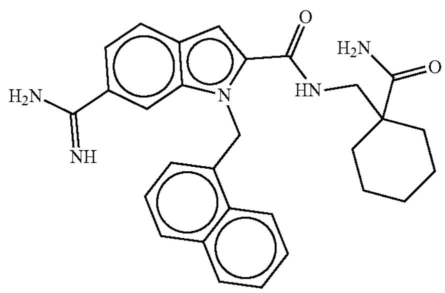 | 5.6 | 97.9 | 482.6 | B | C |
| I-465 | 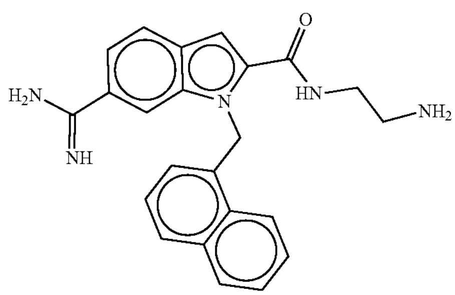 | 5.3 | 99.2 | 386.2 | B | D |
| I-466 | 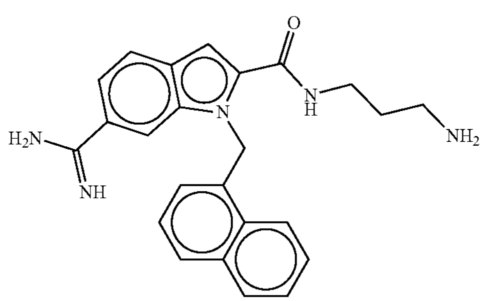 | 5 | 99.7 | 400.4 | B | D |
| I-467 | 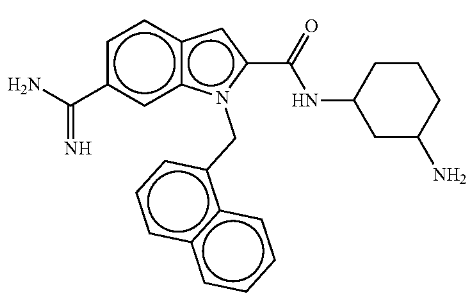 | 5.3 | 99 | 440.3 | B | D |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-468 | 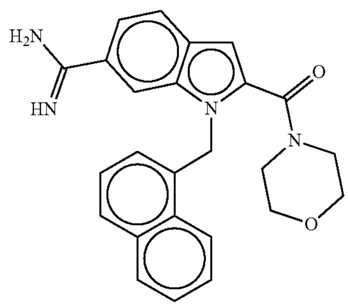 | 6.1 | 94.1 | 412.9 | B | B |
| I-469 | 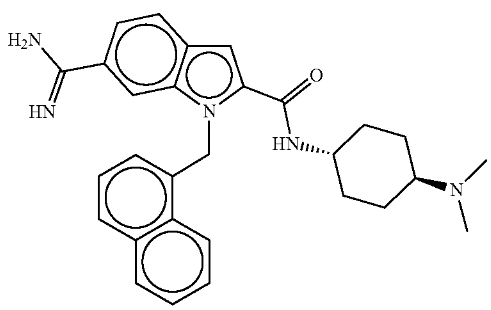 | 5 | 98.6 | 468.3 | B | D |
| I-470 | 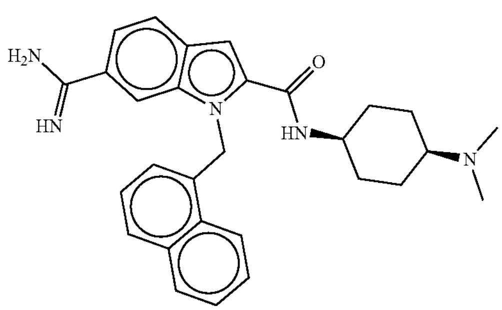 | 5 | 99.3 | 468.3 | B | D |
| I-471 | 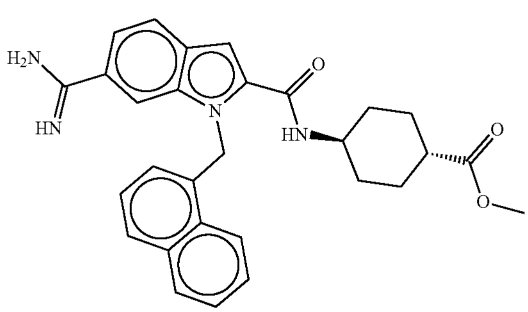 | 5.8 | 95.6 | 483.3 | B | B |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-472 | 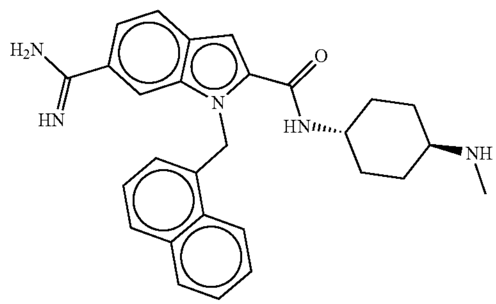 | 4.4 | 97.9 | 454.2 | B | D |
| I-473 | 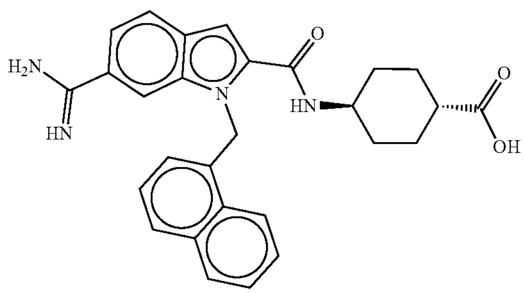 | 4.8 | 96.4 | 469.2 | B | B |
| I-474 | 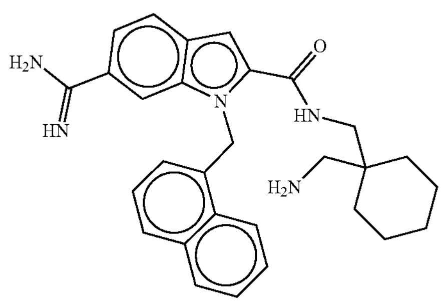 | | | 468.3 | B | D |
| I-475 | 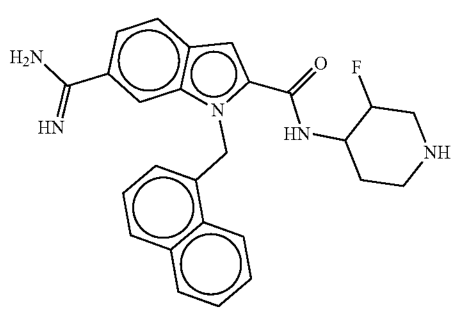 | | | 444.1 | B | D |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-476 | 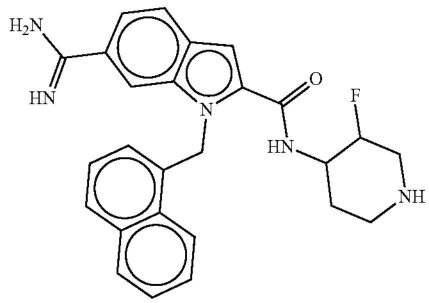 | | | 444 | B | D |
| I-477 | 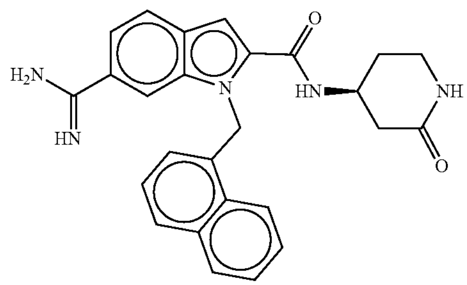 | 5.6 | 98.6 | 440.1 | B | C |
| I-478 | 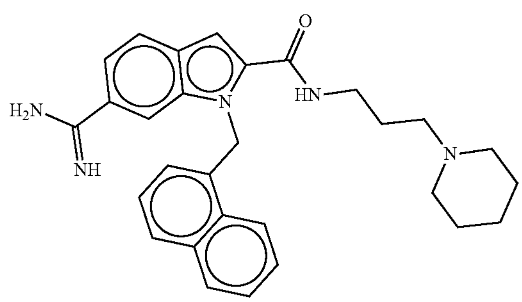 | 5.3 | 99.1 | 468.3 | B | D |
| I-479 | 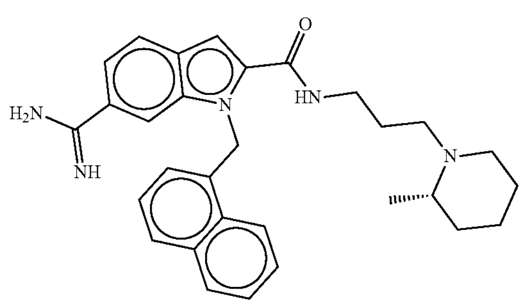 | 6.5 | 98.1 | 482.25 | B | C |
| I-480 | 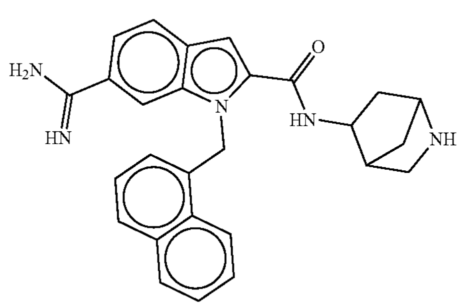 | 4.5 | 98.2 | 438.2 | B | D |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-481 | 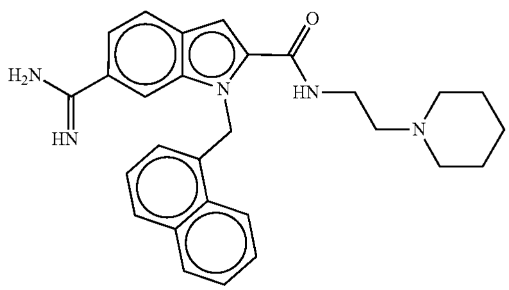 | 5.3 | 99.1 | 454.2 | B | D |
| I-482 | 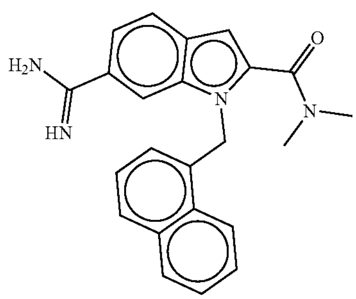 | | | 371.15 | B | B |
| I-483 | 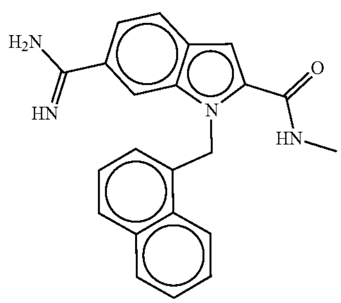 | | | 357.1 | B | C |
| I-484 | 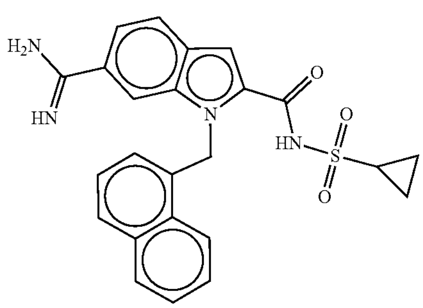 | | | 447.2 | B | B |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-485 | 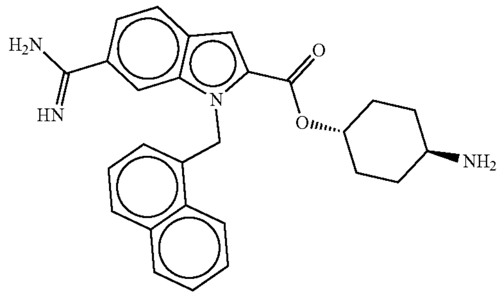 | 5.2 | 98.3 | 440.85 | B | D |
| I-486 | 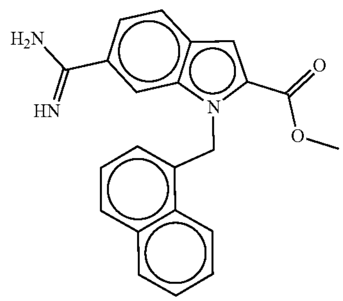 | 5.2 | 96 | 358 | B | B |
| I-487 | 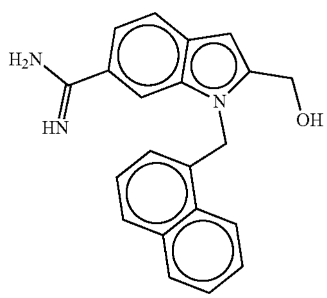 | 5.3 | 98.7 | 330.1 | B | C |
| I-488 | 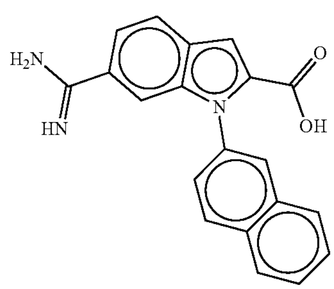 | 4.7 | 99.6 | 330.1 | B | A |
| I-489 | 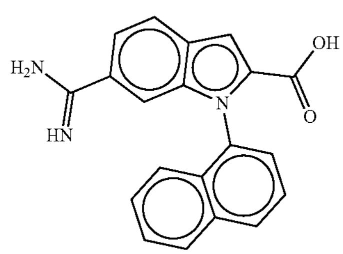 | 5.5 | 99.5 | 330.1 | B | A |

TABLE A-continued
Exemplary Compounds
| Cpd. ID. | Structure | HPLC Rt-min | % Purity-Indole | M + H | Assay Used | Mar-2 % inhibition at 1 uM |
|---|---|---|---|---|---|---|
| I-490 | 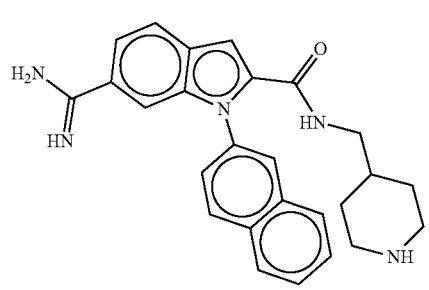 | 4.9 | 98.1 | 426.2 | B | C |
| I-491 | 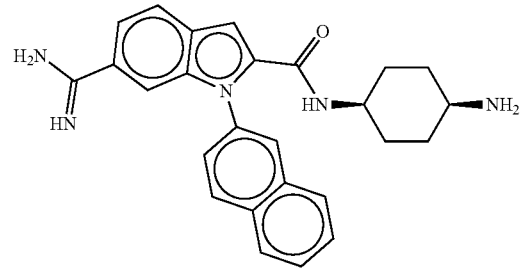 | 4.6 | 98.5 | 425.8 | B | C |
| I-492 | 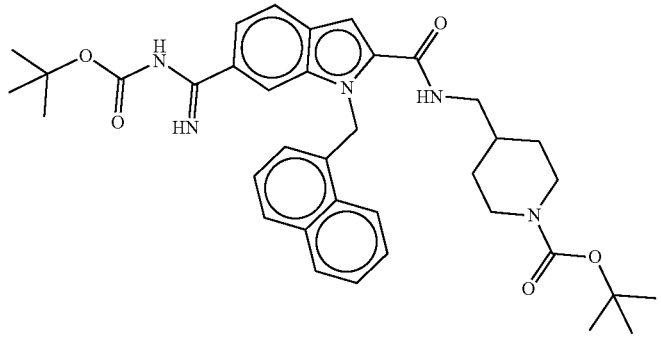 | 6.6 | 98.2 | 640.5 | B | B |
| I-493 | 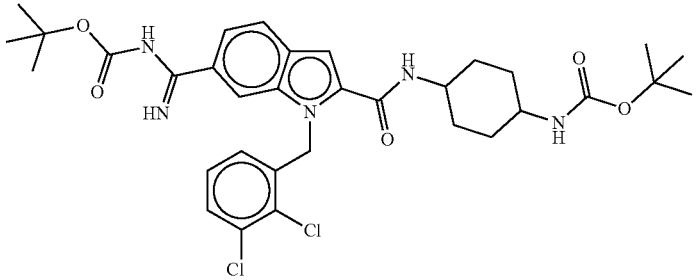 | 14.3 | 90.5 | 658.5 | B | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-494 | 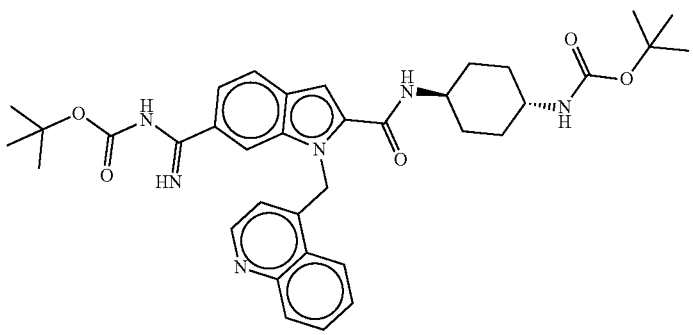 | 4.5 | 97.7 | 641.5 | B | A |
| I-495 | 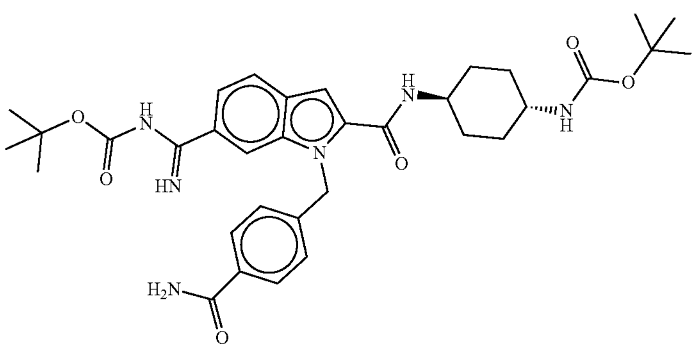 | 4.4 | 97.3 | 633.9 | B | A |
| I-496 | 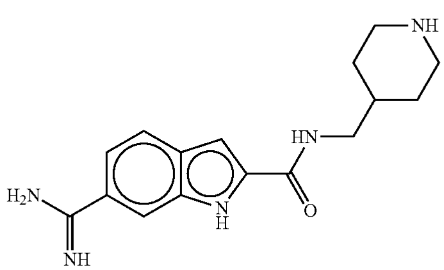 | 4.2 | 98.9 | 300 | B | A |
| I-497 | 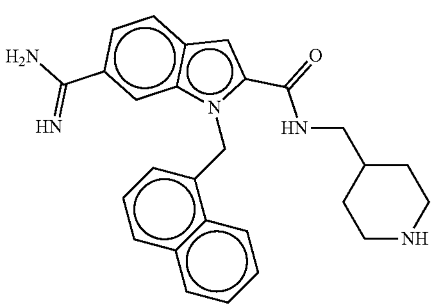 | 4.7 | 99 | 440.2 | B | D |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-498 | 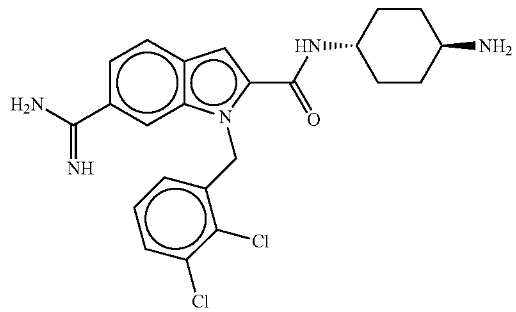 | 4.4 | 98.9 | 458.2 | B | B |
| I-499 | 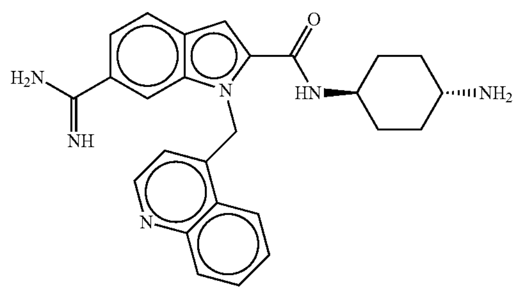 | 4.4 | 98 | 441.1 | B | C |
| I-500 | 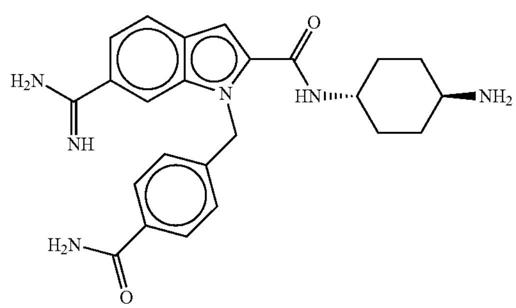 | 4.4 | 99.2 | 433.5 | B | B |
| I-501 | 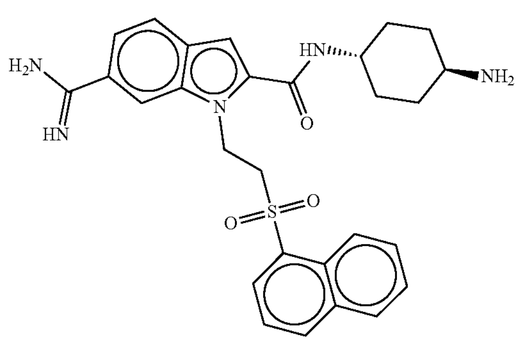 | 5 | 99.1 | 518.3 | B | A |

TABLE A-continued

Exemplary Compounds

| Cpd. ID. | Structure | HPLC Rt- min | % Purity- Indole | M + H | As- say Used | Mar-2 % inhibi- tion at 1 uM |
|---|---|---|---|---|---|---|
| I-502 | 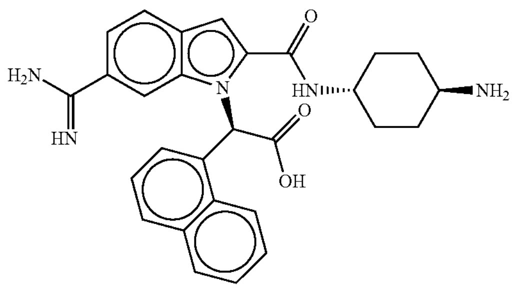 | 4.9 | 96.8 | 484.3 | B | A |
| I-503 | 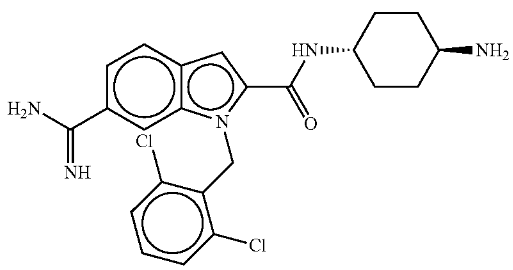 | 4.6 | 97.1 | 458.1 | B | A |
| I-504 | 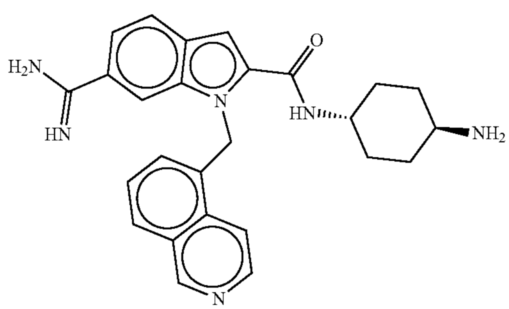 | 3.9 | 95.1 | 441.3 | B | C |
| I-505 | 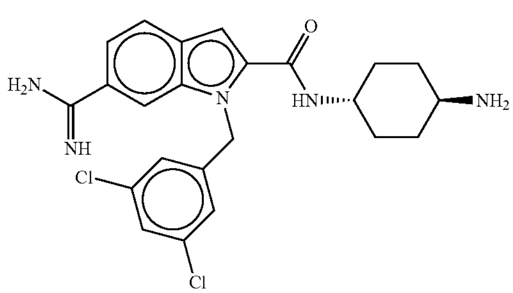 | 5.3 | 97.7 | 458.2 | B | B |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-506 | 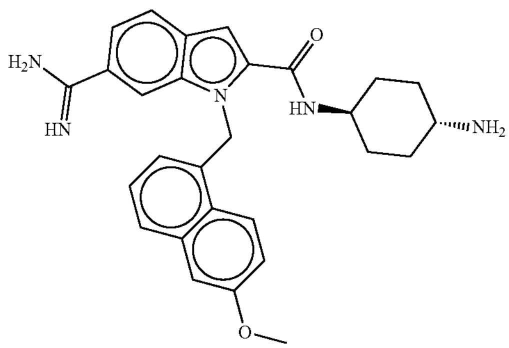 | 4.3 | 99.4 | 470.3 | B | D |
| I-507 | 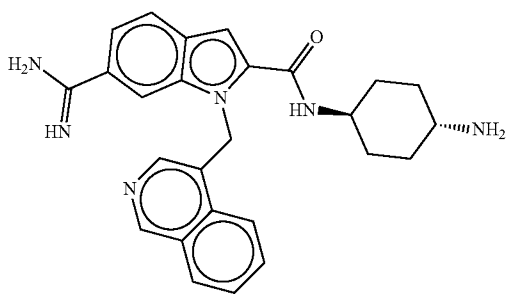 | 4.3 | 99.7 | 441.3 | B | C |
| I-508 | 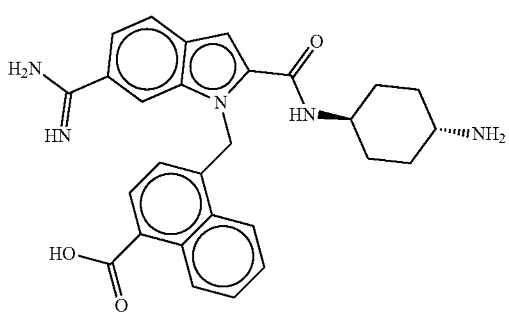 | 4.7 | 98.1 | 484.2 | B | B |
| I-509 | 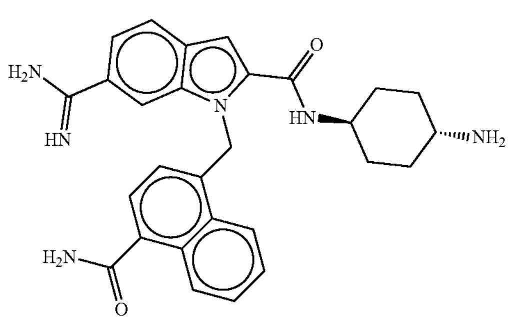 | 5.3 | 95.1 | 483.6 | B | C |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-510 | 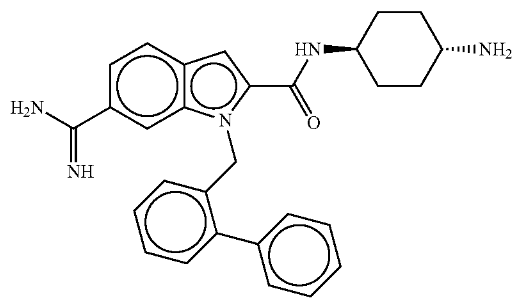 | 4.9 | 98.8 | 466.25 | B | A |
| I-511 | 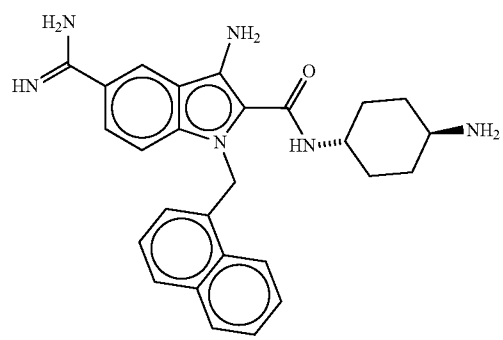 | 5.8 | 94.4 | 455.2 | B | D |
| I-512 | 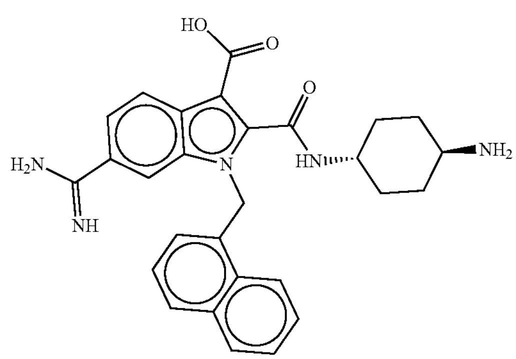 | 4.6 | 99.5 | 482.3 | B | C |
| I-513 | 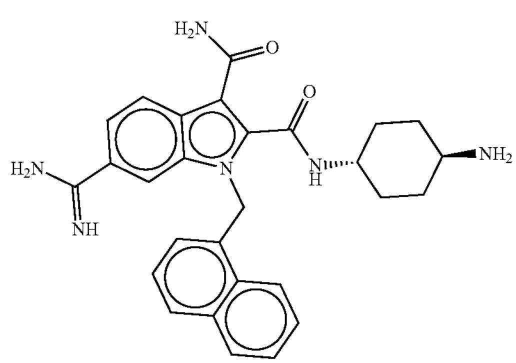 | 4.6 | 97.6 | 481.4 | B | B |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-514 | 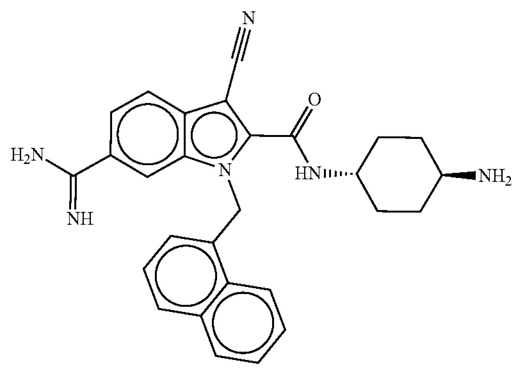 | 4.9 | 99.5 | 465.2 | B | A |
| I-515 | 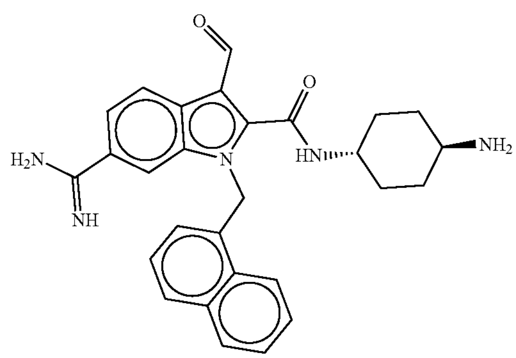 | 5.1 | 98.9 | 468.3 | B | B |
| I-516 | 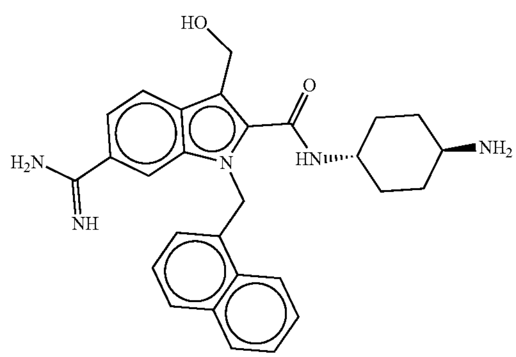 | 8.17 | 89.7 | 470.2 | B | A |
| I-517 | 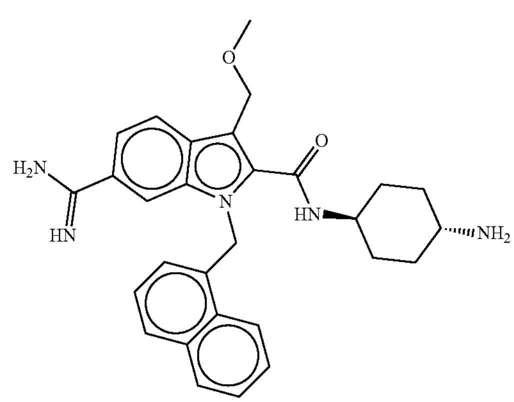 | 5 | 97.2 | 484.4 | B | C |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-518 | 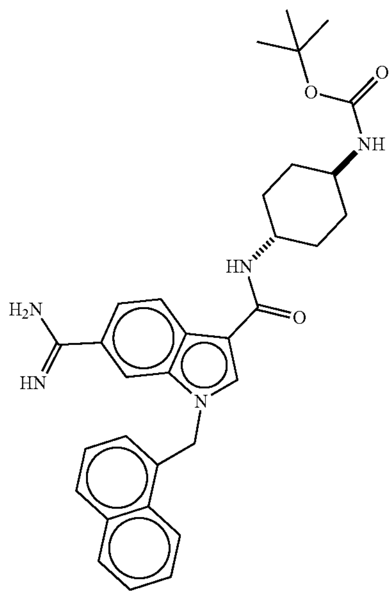 | 9.2 | 94.4 | 540 | B | A |
| I-519 | 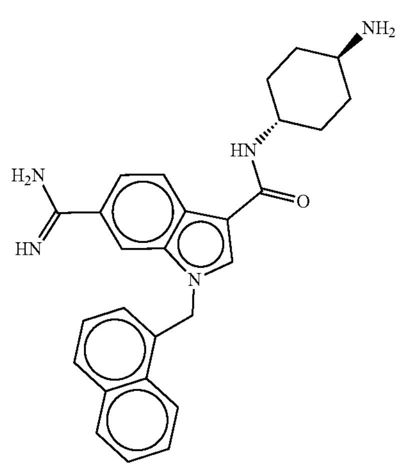 | 5 | 95 | 440.2 | B | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-520 | 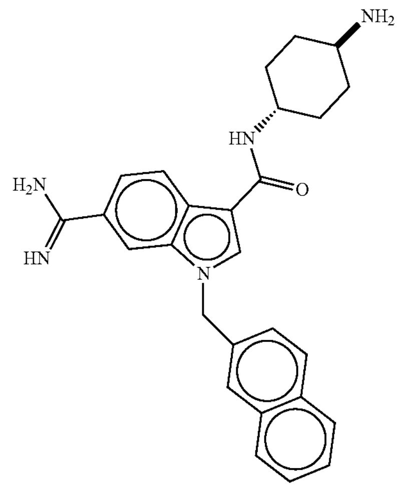 | 4.9 | 98.7 | 440.4 | B | A |
| I-521 | 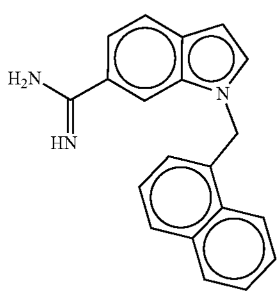 | 6.5 | 99.1 | 300.2 | B | C |
| I-522 | 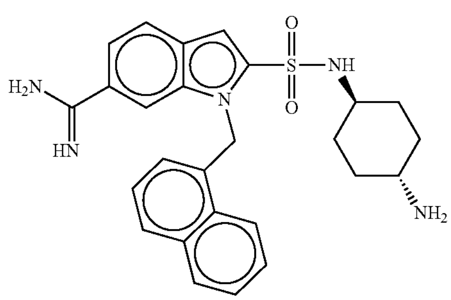 | 5.5 | 99 | 474.5 | B | C |
| I-523 | 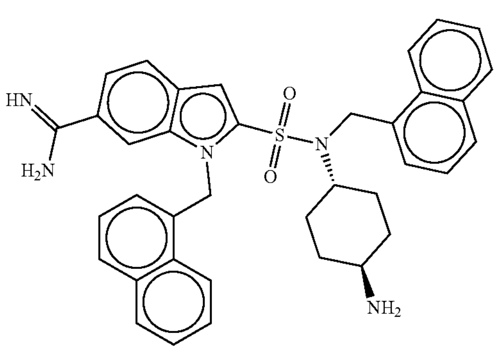 | 5.8 | 98.2 | 615.85 | B | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-524 | 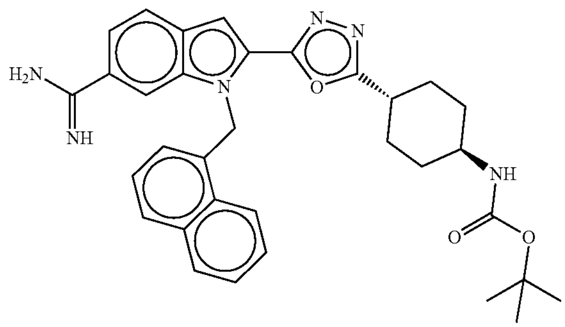 | 7 | 91.4 | 565.4 | B | B |
| I-525 | 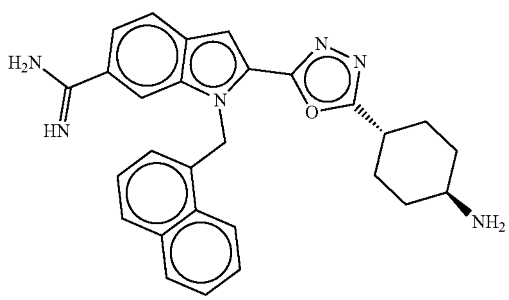 | 5.2 | 95.3 | 465.2 | B | D |
| I-526 | 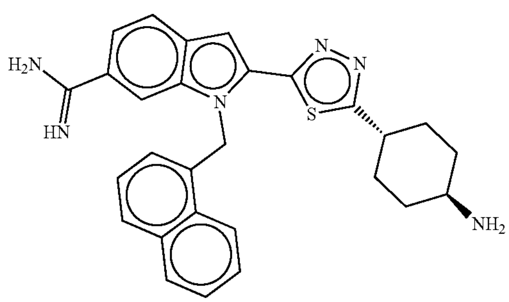 | 4.4 | 96.5 | 481.3 | B | D |
| I-527 | 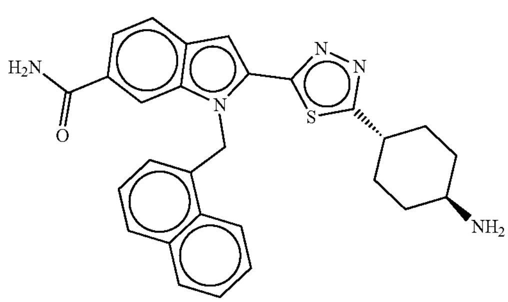 | 6 | 98.7 | 482.3 | B | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-528 | 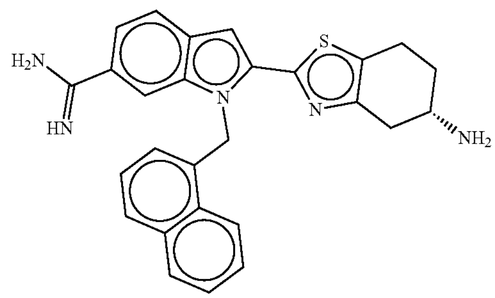 | 5.2 | 96.8 | 452.3 | B | B |
| I-529 | 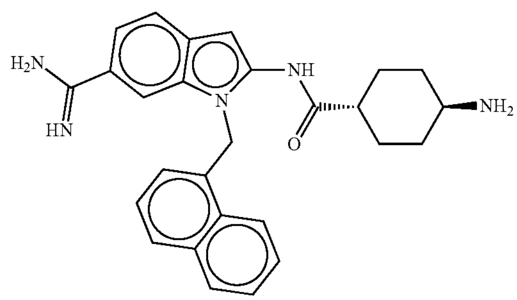 | 5.2 | 98.1 | 440.3 | B | C |
| I-530 | 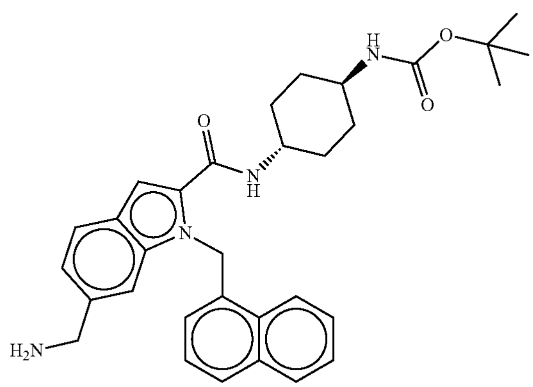 | 6.1 | 95.2 | 528.4 | B | A |
| I-531 | 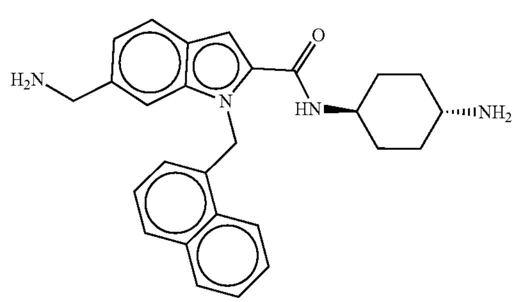 | 5.6 | 99.5 | 428.3 | B | C |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-532 | 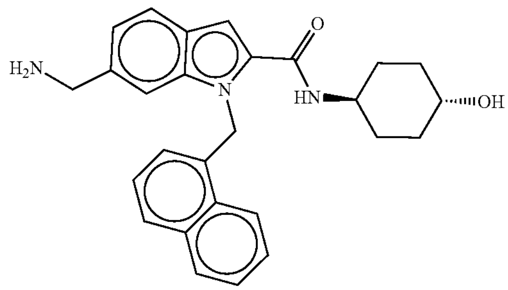 | 5.3 | 97.9 | 411.2 | B | B |
| I-533 | 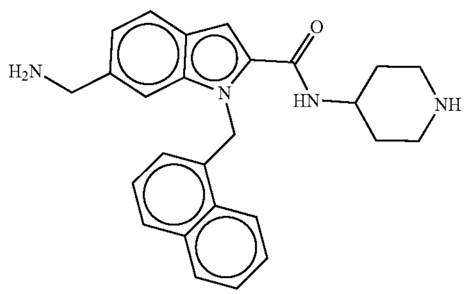 | 4.8 | 97.8 | 413.35 | B | B |
| I-534 | 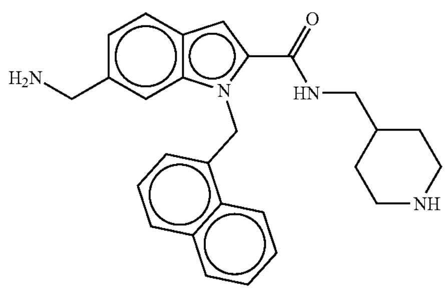 | 4.7 | 99.7 | 427.3 | B | B |
| I-535 | 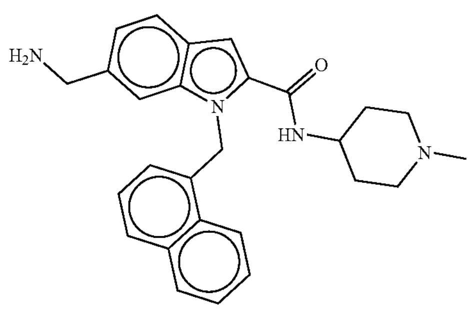 | 5 | 99 | 426.95 | B | B |
| I-536 | 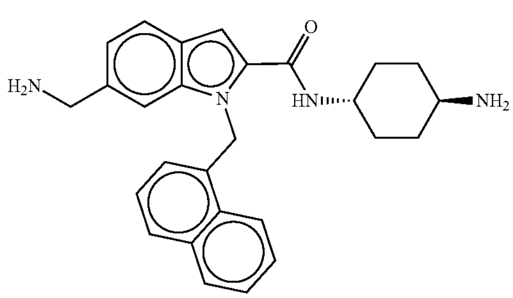 | 5 | 99.5 | 414.4 | B | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-537 | 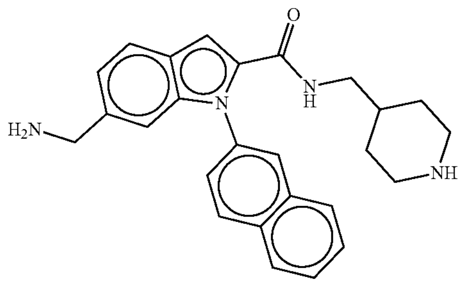 | 4.9 | 98 | 412.95 | B | A |
| I-538 | 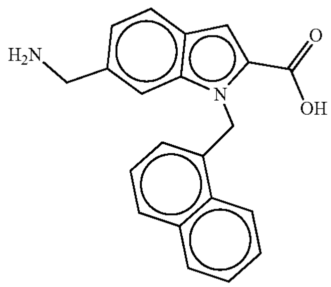 | 5.9 | 96.6 | 331.1 | B | B |
| I-539 | 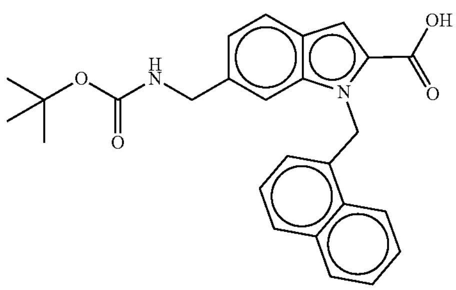 | 6.7 | 97.8 | 429.2 | B | A |
| I-540 | 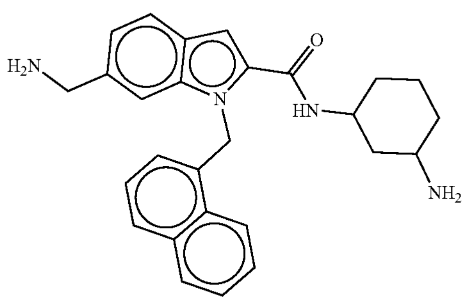 | 5.3 | 98.6 | 427.4 | B | B |
| I-541 | 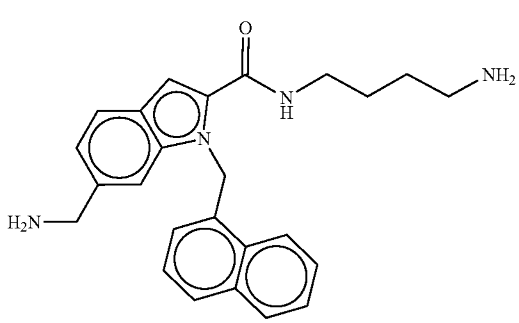 | 5.3 | 98 | 401.2 | B | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-542 | 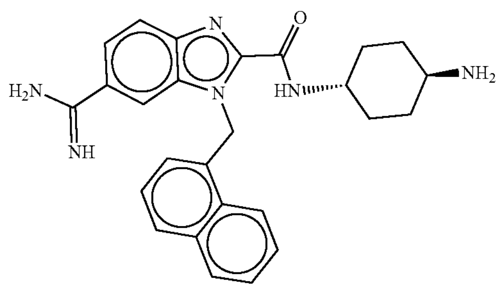 | 4.6 | 99.1 | 441.1 | B | D |
| I-543 | 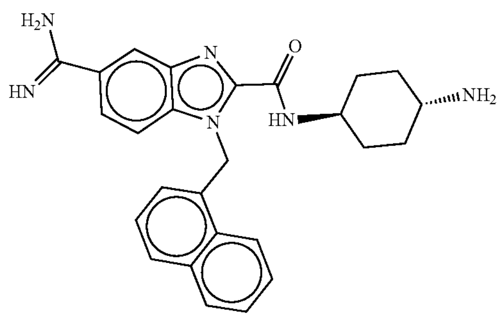 | | | 441.2 | B | A |
| I-544 | 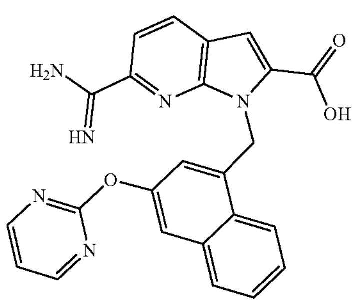 [SMILES: N=C(N)c1ccc2cc(C(=O)O)n(Cc3cc(Oc4ncccn4)cc4ccccc34)c2n1] | 5.751 | 97.09 | 439.10 | B | B |
| I-545 | 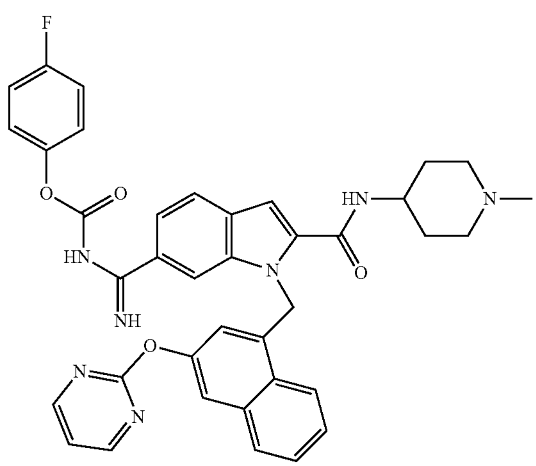 [SMILES: CN1CCC(NC(=O)c2cc3ccc(C(=N)NC(=O)Oc4ccc(F)cc4)cc3n2Cc2cc(Oc3ncccn3)cc3ccccc23)CC1] | 13.30 | 86.312 | 672.25 | B | B |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-546 | 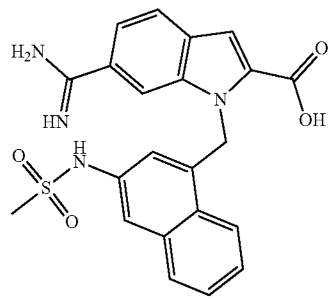 [SMILES: CS(=O)(=O)Nc1cc(Cn2c(C(=O)O)cc3ccc(C(=N)N)cc32)c2ccccc2c1] | 5.065 | 95.22 | 437.15 | B | D |
| I-547 | 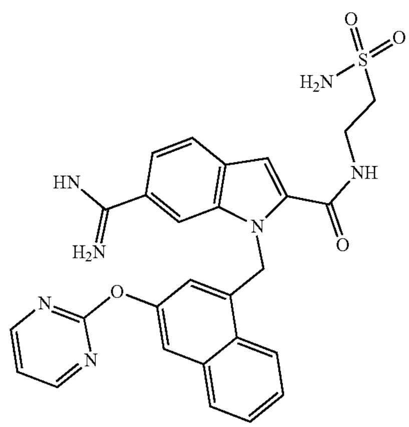 [SMILES: N=C(N)c1ccc2cc(C(=O)NCCS(N)(=O)=O)n(Cc3cc(Oc4ncccn4)cc4ccccc34)c2c1] | 5.039 | 99.40 | 544.2 | B | D |
| I-548 | 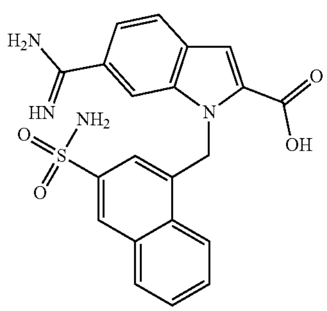 [SMILES: N=C(N)c1ccc2cc(C(=O)O)n(Cc3cc(S(N)(=O)=O)cc4ccccc34)c2c1] | 5.26 | 98.07 | 423.1 | B | B |
| I-549 | 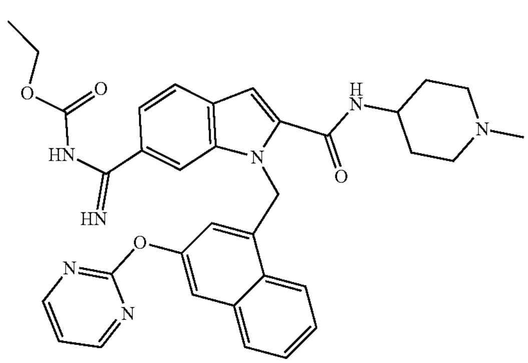 [SMILES: CCOC(=O)NC(=N)c1ccc2cc(C(=O)NC3CCN(C)CC3)n(Cc3cc(Oc4ncccn4)cc4ccccc34)c2c1] | 4.854 | 95.06 | 606.3 | B | B |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-550 | 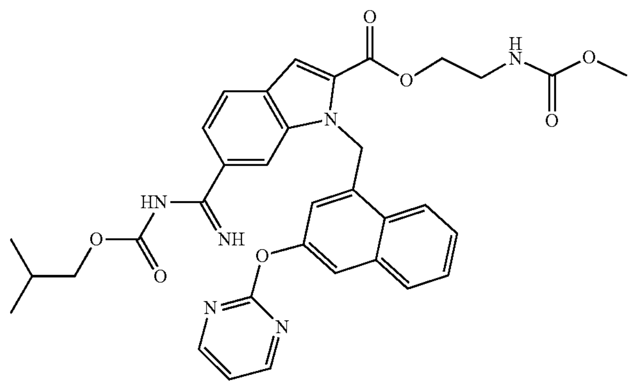 [SMILES: COC(=O)NCCOC(=O)c1cc2ccc(C(=N)NC(=O)OCC(C)C)cc2n1Cc1cc(Oc2ncccn2)cc2ccccc12] | 13.68 | 95.19 | 639.20 | B | A |
| I-551 | 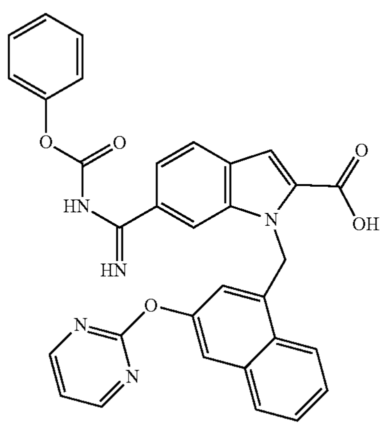 [SMILES: N=C(NC(=O)Oc1ccccc1)c1ccc2cc(C(=O)O)n(Cc3cc(Oc4ncccn4)cc4ccccc34)c2c1] | 7.193 | 90.09 | 558.15 | B | A |
| I-552 | 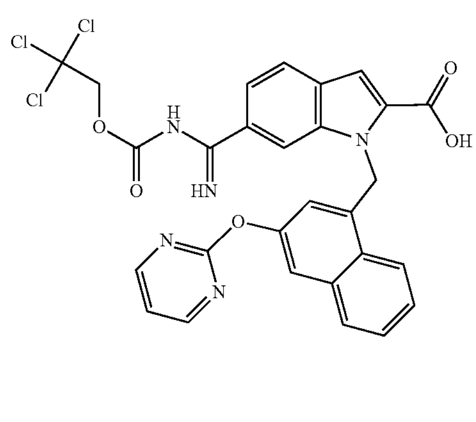 [SMILES: N=C(NC(=O)OCC(Cl)(Cl)Cl)c1ccc2cc(C(=O)O)n(Cc3cc(Oc4ncccn4)cc4ccccc34)c2c1] | 7.489 | 95.645 | 614.05 | B | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-553 | 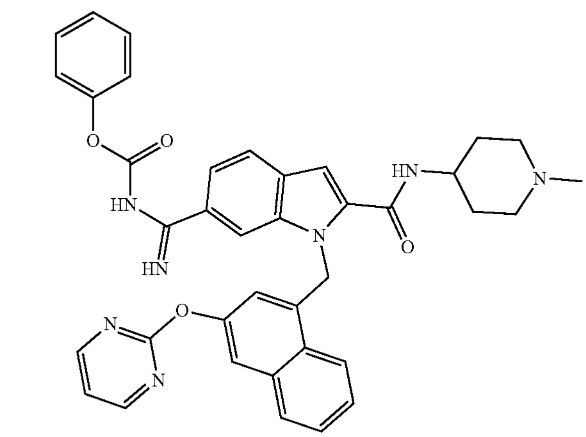 [SMILES: CN1CCC(NC(=O)c2cc3ccc(C(=N)NC(=O)Oc4ccccc4)cc3n2Cc2cc(Oc3ncccn3)cc3ccccc23)CC1] | 13.055 | 95.05 | 654.25 | B | A |
| I-554 | 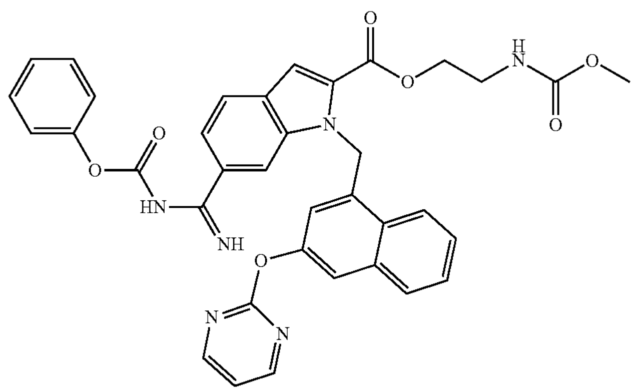 [SMILES: COC(=O)NCCOC(=O)c1cc2ccc(C(=N)NC(=O)Oc3ccccc3)cc2n1Cc1cc(Oc2ncccn2)cc2ccccc12] | 13.59 | 95.01 | 659.20 | B | A |
| I-555 | 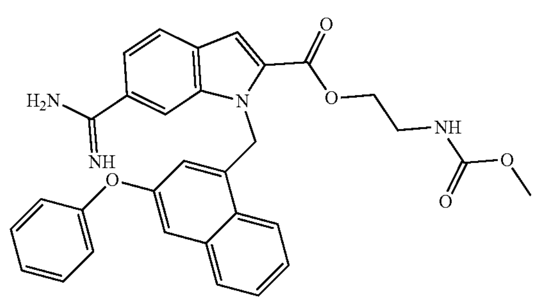 [SMILES: COC(=O)NCCOC(=O)c1cc2ccc(C(=N)N)cc2n1Cc1cc(Oc2ccccc2)cc2ccccc12] | 6.737 | 96.72 | 537.25 | B | B |
| I-556 | 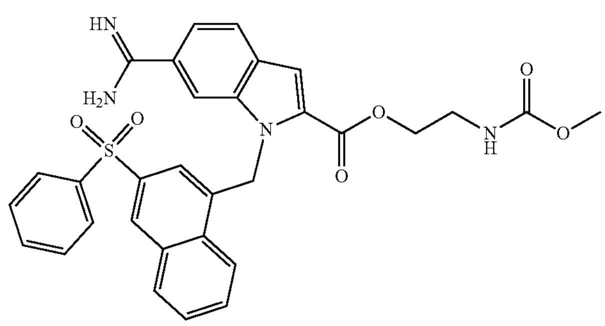 [SMILES: COC(=O)NCCOC(=O)c1cc2ccc(C(=N)N)cc2n1Cc1cc(S(=O)(=O)c2ccccc2)cc2ccccc12] | 4.284 | 99.36 | 585.15 | B | B |

TABLE A-continued

Exemplary Compounds

| Cpd. ID. | Structure | HPLC Rt- min | % Purity- Indole | M + H | As- say Used | Mar-2 % inhibi- tion at 1 uM |
|---|---|---|---|---|---|---|
| I-557 | 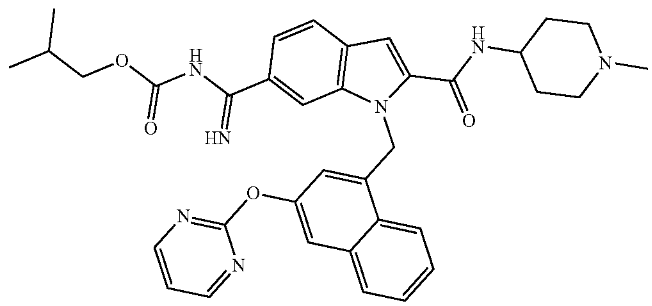 [SMILES: CC(C)COC(=O)NC(=N)c1ccc2cc(C(=O)NC3CCN(C)CC3)n(Cc3cc(Oc4ncccn4)cc4ccccc34)c2c1] | 12.941 | 96.77 | 632.35 | B | A |
| I-558 | 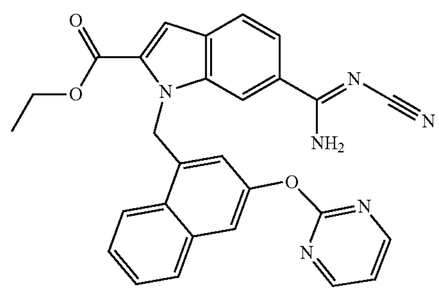 [SMILES: CCOC(=O)c1cc2ccc(/C(N)=N/C#N)cc2n1Cc1cc(Oc2ncccn2)cc2ccccc12] | 12.13 | 98.96 | 491.2 | B | A |
| I-559 | 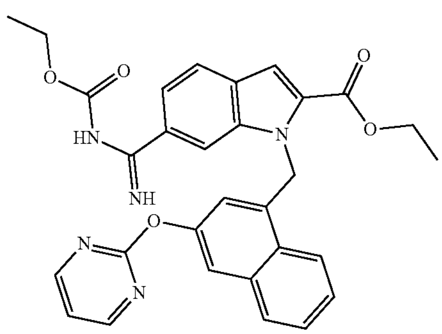 [SMILES: CCOC(=O)NC(=N)c1ccc2cc(C(=O)OCC)n(Cc3cc(Oc4ncccn4)cc4ccccc34)c2c1] | 14.38 | 97.75 | 538.4 | B | B |
| I-560 | 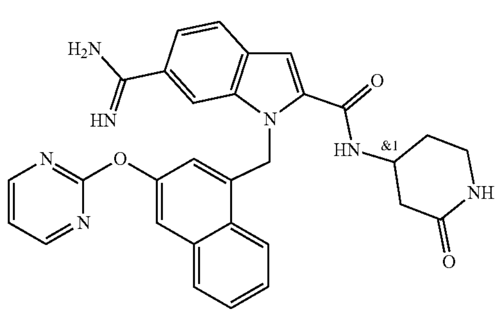 [SMILES: N=C(N)c1ccc2cc(C(=O)NC3CCNC(=O)C3)n(Cc3cc(Oc4ncccn4)cc4ccccc34)c2c1] | 6.253 | 95.70 | 534.2 | B | C |

TABLE A-continued

Exemplary Compounds

| Cpd. ID. | Structure | HPLC Rt- min | % Purity- Indole | M + H | Assay Used | Mar-2 % inhibition at 1 uM |
|---|---|---|---|---|---|---|
| I-561 | 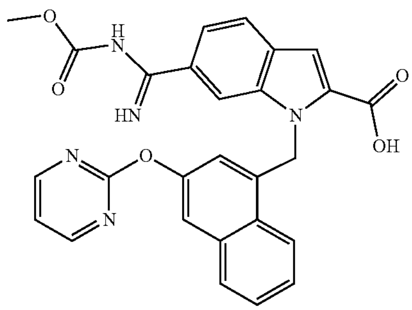 [SMILES: COC(=O)NC(=N)c1ccc2cc(C(=O)O)n(Cc3cc(Oc4ncccn4)cc4ccccc34)c2c1] | 6.218 | 96.319 | 496.15 | B | B |
| I-562 | 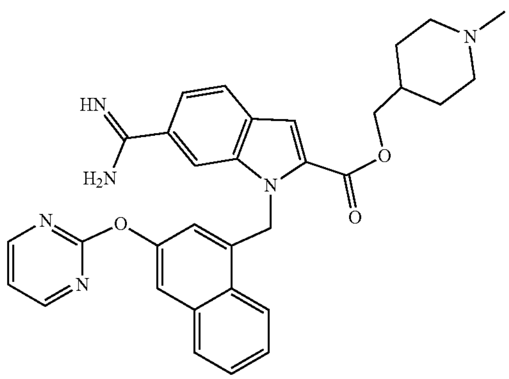 [SMILES: CN1CCC(COC(=O)c2cc3ccc(C(=N)N)cc3n2Cc2cc(Oc3ncccn3)cc3ccccc23)CC1] | 5.323 | 98.7 | 549.1 | B | C |
| I-563 | 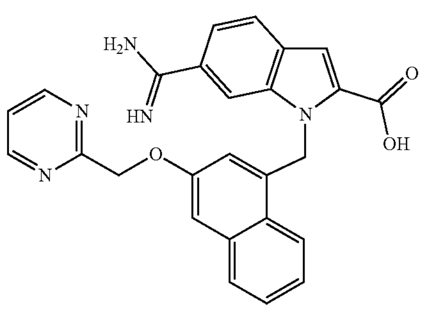 [SMILES: N=C(N)c1ccc2cc(C(=O)O)n(Cc3cc(OCc4ncccn4)cc4ccccc34)c2c1] | 5.69 | 95.17 | 452.2 | B | C |
| I-564 | 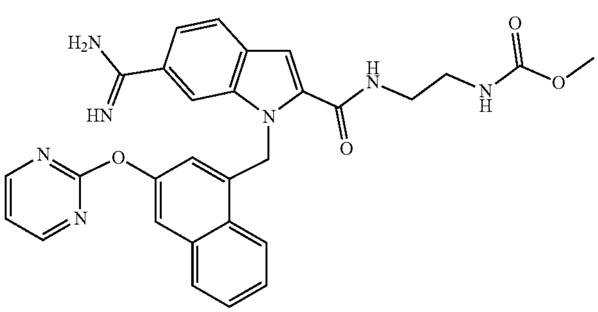 [SMILES: COC(=O)NCCNC(=O)c1cc2ccc(C(=N)N)cc2n1Cc1cc(Oc2ncccn2)cc2ccccc12] | 5.203 | 97.85 | 538.3 | B | D |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-565 | 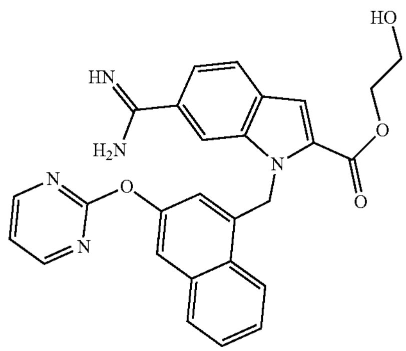 [SMILES: N=C(N)c1ccc2cc(C(=O)OCCO)n(Cc3cc(Oc4ncccn4)cc4ccccc34)c2c1] | 6.971 | 97.35 | 482.15 | B | D |
| I-566 | 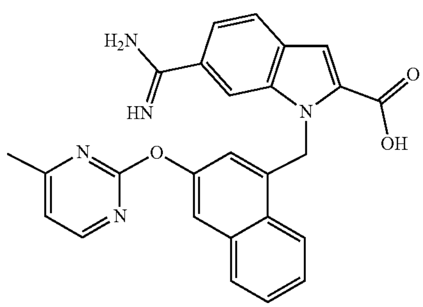 [SMILES: Cc1ccnc(Oc2cc(Cn3c(C(=O)O)cc4ccc(C(=N)N)cc43)c3ccccc3c2)n1] | 5.25 | 98.38 | 452.15 | B | B |
| I-567 | 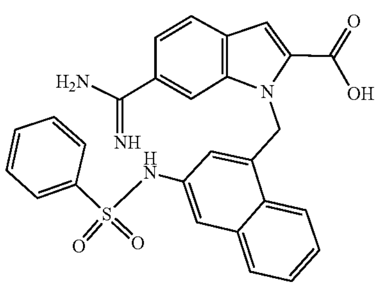 [SMILES: N=C(N)c1ccc2cc(C(=O)O)n(Cc3cc(NS(=O)(=O)c4ccccc4)cc4ccccc34)c2c1] | 5.420 | 98.2 | 499.0 | B | D |
| I-568 | 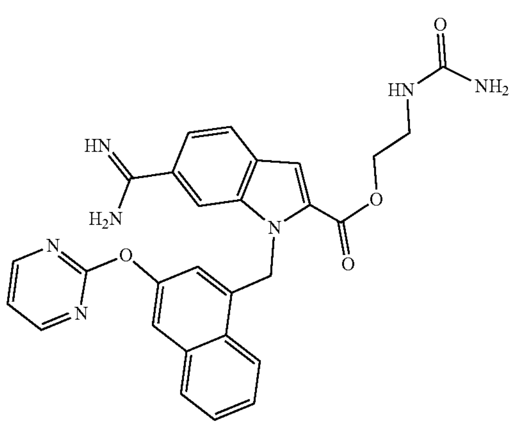 [SMILES: N=C(N)c1ccc2cc(C(=O)OCCNC(N)=O)n(Cc3cc(Oc4ncccn4)cc4ccccc34)c2c1] | 5.07 | 98.9 | 524.2 | B | D |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-569 | 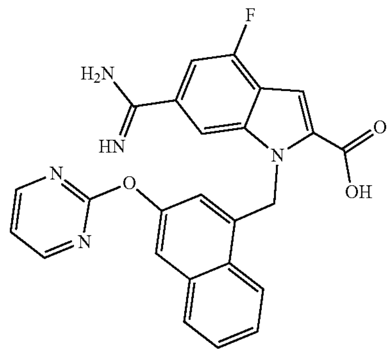 [SMILES: N=C(N)c1cc(F)c2cc(C(=O)O)n(Cc3cc(Oc4ncccn4)cc4ccccc34)c2c1] | 5.247 | 97 | 456.1 | B | D |
| I-570 | 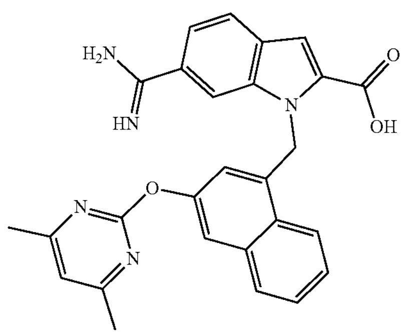 [SMILES: Cc1cc(C)nc(Oc2cc(Cn3c(C(=O)O)cc4ccc(C(=N)N)cc43)c3ccccc3c2)n1] | 6.081 | 95.34 | 466.20 | B | B |
| I-571 | 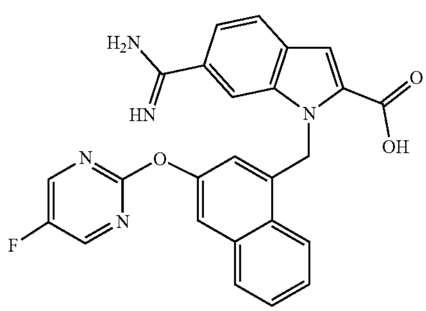 [SMILES: N=C(N)c1ccc2cc(C(=O)O)n(Cc3cc(Oc4ncc(F)cn4)cc4ccccc34)c2c1] | 5.890 | 98.02 | 456.10 | B | C |
| I-572 | 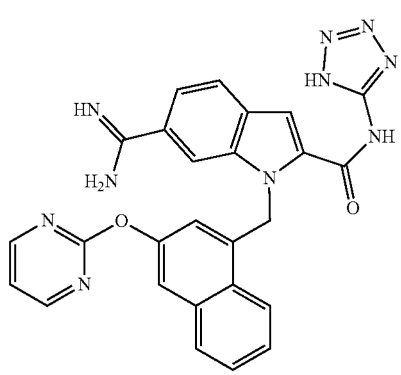 [SMILES: N=C(N)c1ccc2cc(C(=O)Nc3nnn[nH]3)n(Cc3cc(Oc4ncccn4)cc4ccccc34)c2c1] | 5.72 | 99.07 | 505.20 | B | C |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-573 | 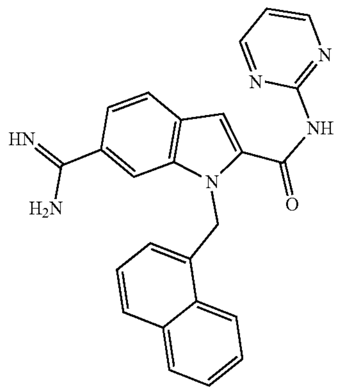 [SMILES: N=C(N)c1ccc2cc(C(=O)Nc3ncccn3)n(Cc3cccc4ccccc34)c2c1] | 5.809 | 97.469 | 421.20 | B | C |
| I-574 | 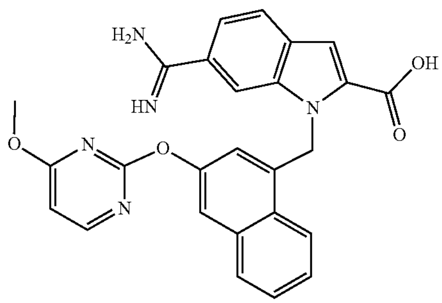 [SMILES: COc1ccnc(Oc2cc(Cn3c(C(=O)O)cc4ccc(C(=N)N)cc43)c3ccccc3c2)n1] | 5.962 | 96.81 | 468.2 | B | B |
| I-575 | 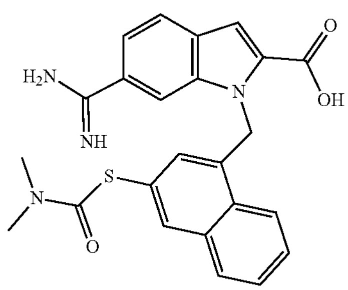 [SMILES: CN(C)C(=O)Sc1cc(Cn2c(C(=O)O)cc3ccc(C(=N)N)cc32)c2ccccc2c1] | 3.030 | 99.92 | 447.15 | B | A |
| I-576 | 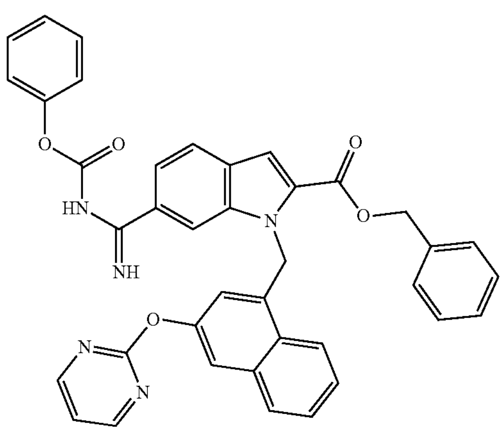 [SMILES: N=C(NC(=O)Oc1ccccc1)c1ccc2cc(C(=O)OCc3ccccc3)n(Cc3cc(Oc4ncccn4)cc4ccccc34)c2c1] | 15.343 | 86.662 | 648.15 | B | A |

TABLE A-continued

Exemplary Compounds

| Cpd. ID. | Structure | HPLC Rt- min | % Purity- Indole | M + H | Assay Used | Mar-2 % inhibition at 1 uM |
|---|---|---|---|---|---|---|
| I-577 | 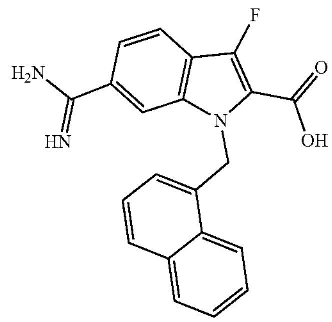 [SMILES: N=C(N)c1ccc2c(F)c(C(=O)O)n(Cc3cccc4ccccc34)c2c1] | 5.285 | 99.0 | 360.15 | B | C |
| I-578 | 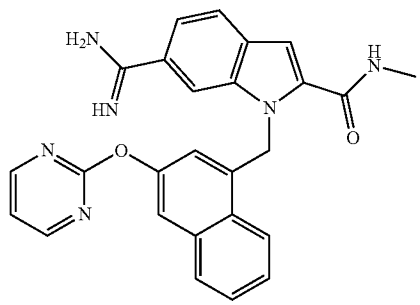 [SMILES: CNC(=O)c1cc2ccc(C(=N)N)cc2n1Cc1cc(Oc2ncccn2)cc2ccccc12] | 5.941 | 99.12 | 451.15 | B | D |
| I-579 | 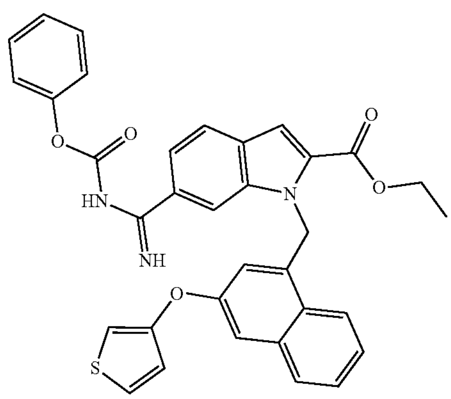 [SMILES: CCOC(=O)c1cc2ccc(C(=N)NC(=O)Oc3ccccc3)cc2n1Cc1cc(Oc2ccsc2)cc2ccccc12] | 16.36 | 88.59 | 590.20 | B | A |
| I-580 | 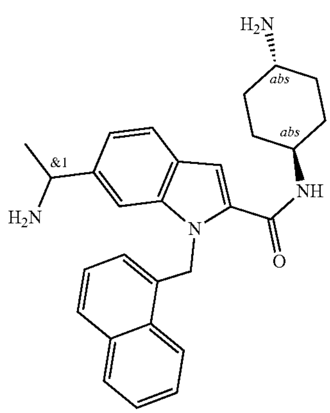 [SMILES: CC(N)c1ccc2cc(C(=O)N[C@H]3CC[C@H](N)CC3)n(Cc3cccc4ccccc34)c2c1] | 5.309 | 98.51 | 439.15 | B | A |

TABLE A-continued
Exemplary Compounds
| Cpd. ID. | Structure | HPLC Rt- min | % Purity- Indole | M + H | Assay Used | Mar-2 % inhibition at 1 uM |
|---|---|---|---|---|---|---|
| I-581 | 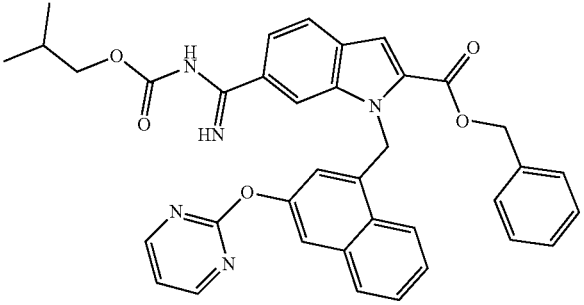 [SMILES: CC(C)COC(=O)NC(=N)c1ccc2cc(C(=O)OCc3ccccc3)n(Cc3cc(Oc4ncccn4)cc4ccccc34)c2c1] | 15.714 | 98.915 | 628.30 | B | B |
| I-582 | 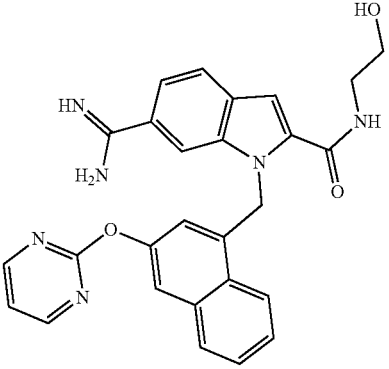 [SMILES: N=C(N)c1ccc2cc(C(=O)NCCO)n(Cc3cc(Oc4ncccn4)cc4ccccc34)c2c1] | 5.50 | 97.87 | 481.20 | B | D |
| I-583 | 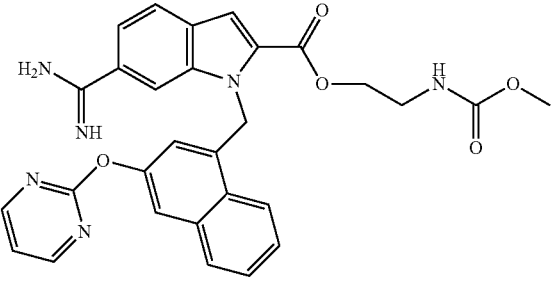 [SMILES: COC(=O)NCCOC(=O)c1cc2ccc(C(=N)N)cc2n1Cc1cc(Oc2ncccn2)cc2ccccc12] | 5.416 | 98.91 | 539.30 | B | D |
| I-584 | 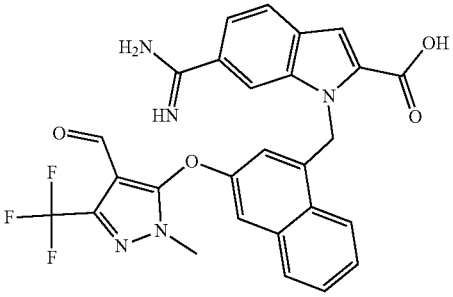 [SMILES: Cn1nc(C(F)(F)F)c(C=O)c1Oc1cc(Cn2c(C(=O)O)cc3ccc(C(=N)N)cc32)c2ccccc2c1] | 6.33 | 82.35 | 536.2 | B | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-585 | 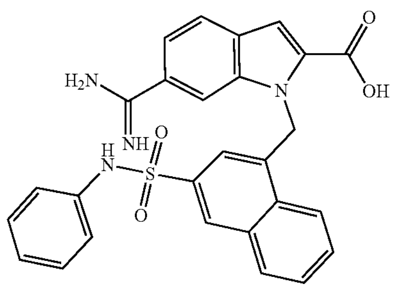 [SMILES: N=C(N)c1ccc2cc(C(=O)O)n(Cc3cc(S(=O)(=O)Nc4ccccc4)cc4ccccc34)c2c1] | 5.37 | 97.89 | 499.1 | B | C |
| I-586 | 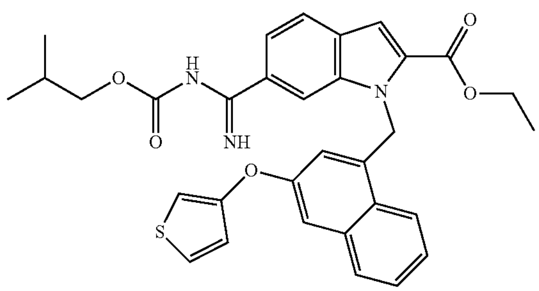 [SMILES: CCOC(=O)c1cc2ccc(C(=N)NC(=O)OCC(C)C)cc2n1Cc1cc(Oc2ccsc2)cc2ccccc12] | 4.05 | 95.57 | 570.20 | B | B |
| I-587 | 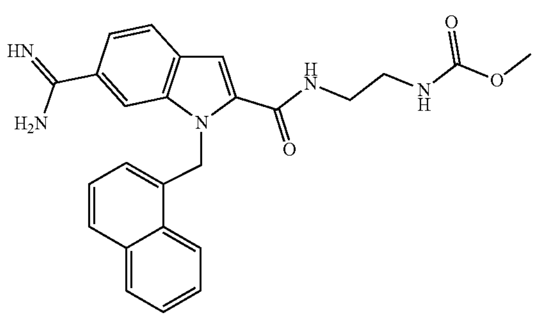 [SMILES: COC(=O)NCCNC(=O)c1cc2ccc(C(=N)N)cc2n1Cc1cccc2ccccc12] | 5.294 | 99.45 | 444.20 | B | D |
| I-588 | 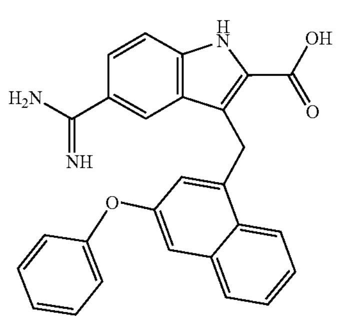 [SMILES: N=C(N)c1ccc2[nH]c(C(=O)O)c(Cc3cc(Oc4ccccc4)cc4ccccc34)c2c1] | 6.6 | 96.23 | 436.1 | B | B |

TABLE A-continued
Exemplary Compounds
| Cpd. ID. | Structure | HPLC Rt-min | % Purity-Indole | M + H | Assay Used | Mar-2 % inhibition at 1 uM |
|---|---|---|---|---|---|---|
| I-589 | 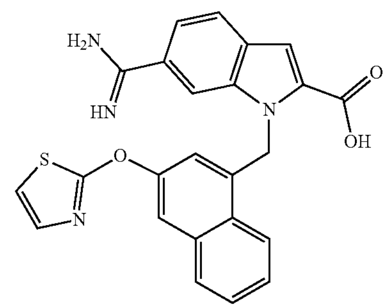 [SMILES: N=C(N)c1ccc2cc(C(=O)O)n(Cc3cc(Oc4nccs4)cc4ccccc34)c2c1] | 5.388 | 98.21 | 443.2 | B | D |
| I-590 | 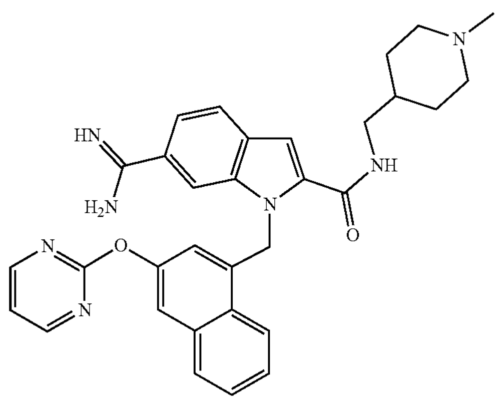 [SMILES: CN1CCC(CNC(=O)c2cc3ccc(C(=N)N)cc3n2Cc2cc(Oc3ncccn3)cc3ccccc23)CC1] | 5.99 | 99.24 | 548.4 | B | D |
| I-591 | 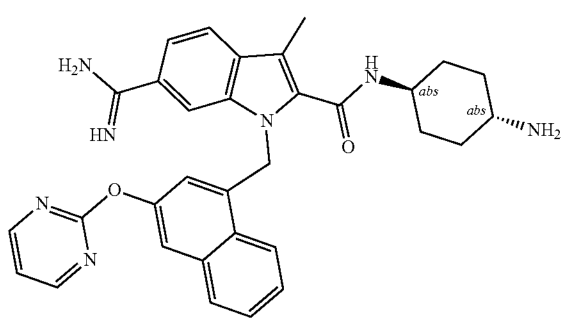 [SMILES: Cc1c(C(=O)N[C@H]2CC[C@H](N)CC2)n(Cc2cc(Oc3ncccn3)cc3ccccc23)c2cc(C(=N)N)ccc12] | 5.944 | 99.135 | 548.4 | B | D |
| I-592 | 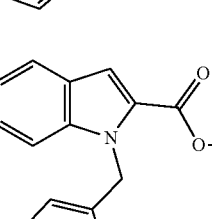 | 5.47 | 99.20 | 470.15 | B | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-593 | 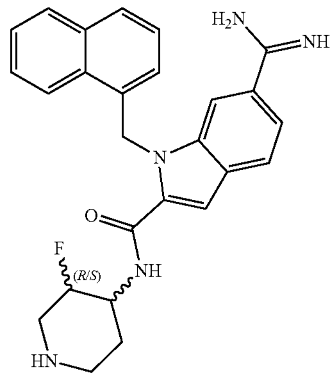 [SMILES: N=C(N)c1ccc2cc(C(=O)NC3CCNCC3F)n(Cc3cccc4ccccc34)c2c1] | | 99.6 | 444.1 | B | D |
| I-594 | 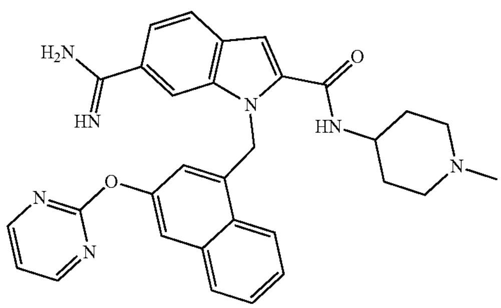 [SMILES: CN1CCC(NC(=O)c2cc3ccc(C(=N)N)cc3n2Cc2cc(Oc3ncccn3)cc3ccccc23)CC1] | 4.593 | 96.66 | 534.25 | B | D |
| I-595 | 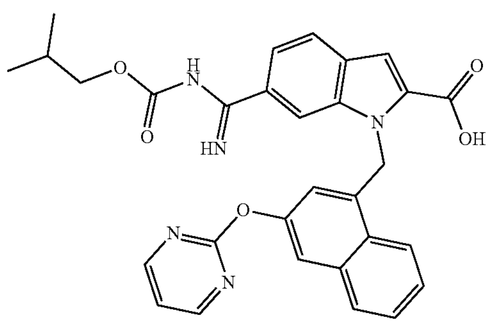 [SMILES: CC(C)COC(=O)NC(=N)c1ccc2cc(C(=O)O)n(Cc3cc(Oc4ncccn4)cc4ccccc34)c2c1] | 7.624 | 97.366 | 538.25 | B | B |
| I-596 | 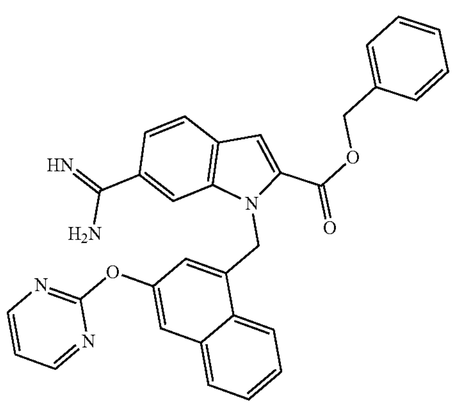 [SMILES: N=C(N)c1ccc2cc(C(=O)OCc3ccccc3)n(Cc3cc(Oc4ncccn4)cc4ccccc34)c2c1] | 3.416 | 98.47 | 528.15 | B | B |

TABLE A-continued
Exemplary Compounds
| Cpd. ID. | Structure | HPLC Rt-min | % Purity-Indole | M + H | Assay Used | Mar-2 % inhibition at 1 uM |
|---|---|---|---|---|---|---|
| I-597 | 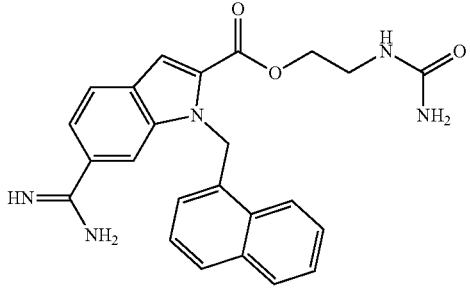 [SMILES: N=C(N)c1ccc2cc(C(=O)OCCNC(N)=O)n(Cc3cccc4ccccc34)c2c1] | 5.505 | 98.49 | 430.15 | B | D |
| I-598 | 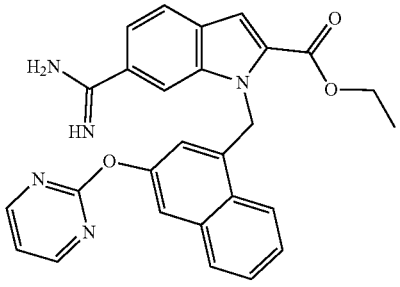 [SMILES: CCOC(=O)c1cc2ccc(C(=N)N)cc2n1Cc1cc(Oc2ncccn2)cc2ccccc12] | 4.684 | 97.80 | 466.2 | B | D |
| I-599 | 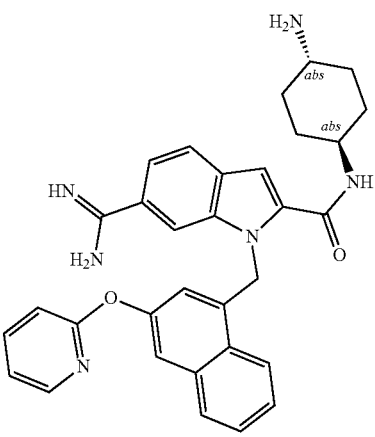 [SMILES: N=C(N)c1ccc2cc(C(=O)N[C@H]3CC[C@H](N)CC3)n(Cc3cc(Oc4ccccn4)cc4ccccc34)c2c1] | 5.347 | 99.21 | 533.25 | B | D |
| I-600 | 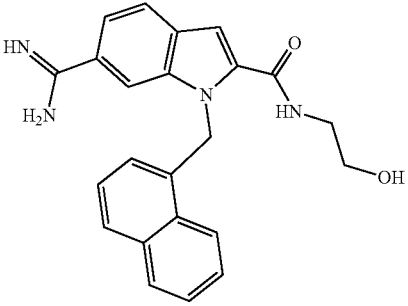 [SMILES: N=C(N)c1ccc2cc(C(=O)NCCO)n(Cc3cccc4ccccc34)c2c1] | 5.443 | 98 | 387.2 | B | D |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-601 | 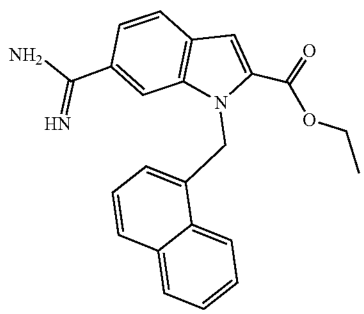 [SMILES: CCOC(=O)c1cc2ccc(C(=N)N)cc2n1Cc1cccc2ccccc12] | 6.41 | 99.14 | 372.15 | B | C |
| I-602 | 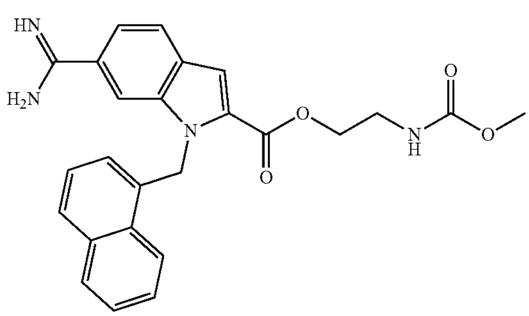 [SMILES: COC(=O)NCCOC(=O)c1cc2ccc(C(=N)N)cc2n1Cc1cccc2ccccc12] | 6.350 | 99 | 445.2 | B | C |
| I-603 | 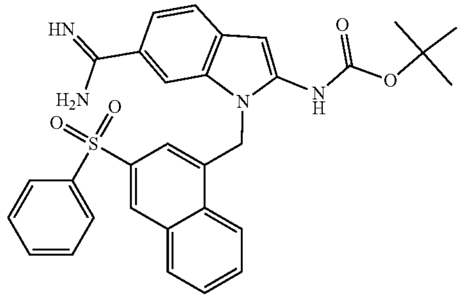 [SMILES: CC(C)(C)OC(=O)Nc1cc2ccc(C(=N)N)cc2n1Cc1cc(S(=O)(=O)c2ccccc2)cc2ccccc12] | 5.250 | 83.86 | 555.4 | B | B |
| I-604 | 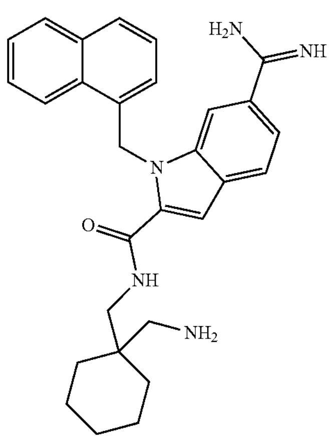 [SMILES: N=C(N)c1ccc2cc(C(=O)NCC3(CN)CCCCC3)n(Cc3cccc4ccccc34)c2c1] | | 97.6 | 468.3 | B | D |

TABLE A-continued
Exemplary Compounds
| Cpd. ID. | Structure | HPLC Rt-min | % Purity-Indole | M + H | Assay Used | Mar-2 % inhibition at 1 uM |
|---|---|---|---|---|---|---|
| I-605 | 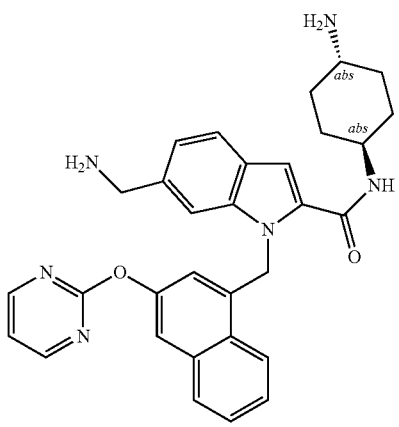 [SMILES: NCc1ccc2cc(C(=O)N[C@H]3CC[C@H](N)CC3)n(Cc3cc(Oc4ncccn4)cc4ccccc34)c2c1] | 5.282 | 99.16 | 521.35 | B | C |
| I-606 | 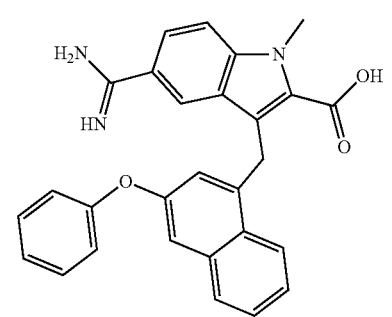 [SMILES: Cn1c(C(=O)O)c(Cc2cc(Oc3ccccc3)cc3ccccc23)c2cc(C(=N)N)ccc21] | 4.68 | 98.79 | 450.15 | B | B |
| I-607 | 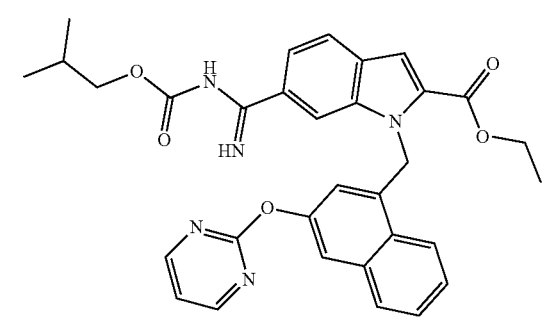 [SMILES: CCOC(=O)c1cc2ccc(C(=N)NC(=O)OCC(C)C)cc2n1Cc1cc(Oc2ncccn2)cc2ccccc12] | 15.775 | 99.14 | 566.3 | B | A |
| I-608 | 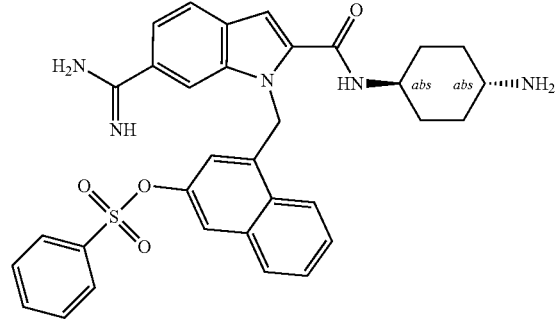 [SMILES: N=C(N)c1ccc2cc(C(=O)N[C@H]3CC[C@H](N)CC3)n(Cc3cc(OS(=O)(=O)c4ccccc4)cc4ccccc34)c2c1] | 4.939 | 99 | 596.2 | B | D |

TABLE A-continued

Exemplary Compounds

| Cpd. ID. | Structure | HPLC Rt-min | % Purity-Indole | M + H | Assay Used | Mar-2 % inhibition at 1 uM |
| --- | --- | --- | --- | --- | --- | --- |
| I-609 | 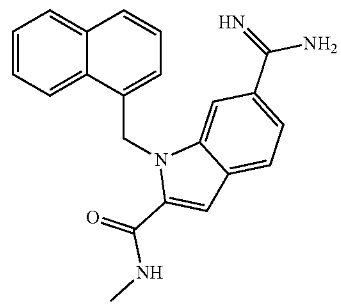 [SMILES: CNC(=O)c1cc2ccc(C(=N)N)cc2n1Cc1cccc2ccccc12] | | 98.3 | 357.1 | B | C |
| I-610 | 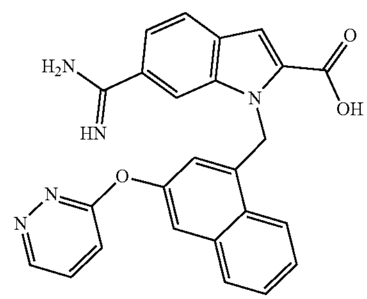 [SMILES: N=C(N)c1ccc2cc(C(=O)O)n(Cc3cc(Oc4cccnn4)cc4ccccc34)c2c1] | 5.78 | 98.45 | 438.2 | B | B |
| I-611 | 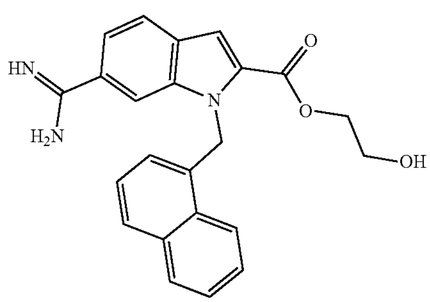 [SMILES: N=C(N)c1ccc2cc(C(=O)OCCO)n(Cc3cccc4ccccc34)c2c1] | 5.357 | 99.186 | 388.5 | B | C |
| I-612 | 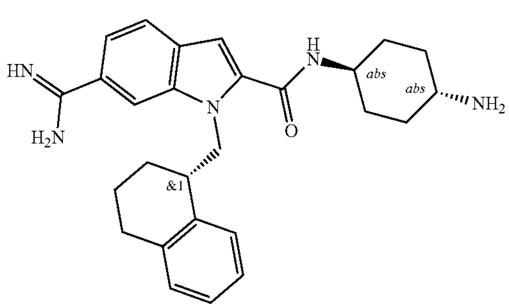 [SMILES: N=C(N)c1ccc2cc(C(=O)N[C@H]3CC[C@H](N)CC3)n(C[C@H]3CCCc4ccccc43)c2c1] | 4.662 | 99.203 | 444.4 | B | B |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-613 | 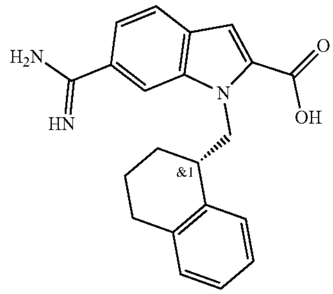 [SMILES: N=C(N)c1ccc2cc(C(=O)O)n(C[C@H]3CCCc4ccccc43)c2c1] | 6.189 | 99.296 | 348.4 | B | B |
| I-614 | 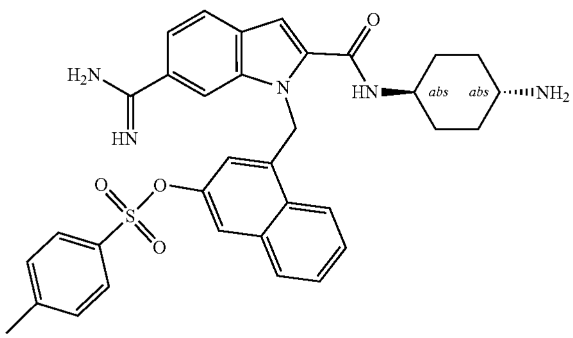 [SMILES: Cc1ccc(S(=O)(=O)Oc2cc(Cn3c(C(=O)N[C@H]4CC[C@H](N)CC4)cc4ccc(C(=N)N)cc43)c3ccccc3c2)cc1] | 5.627 | 97.99 | 610.50 | B | D |
| I-615 | 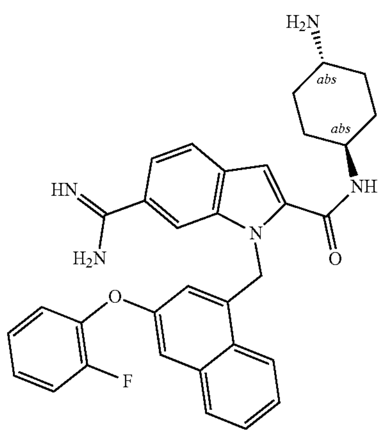 [SMILES: N=C(N)c1ccc2cc(C(=O)N[C@H]3CC[C@H](N)CC3)n(Cc3cc(Oc4ccccc4F)cc4ccccc34)c2c1] | 4.990 | 98.00 | 550.25 | B | D |
| I-616 | 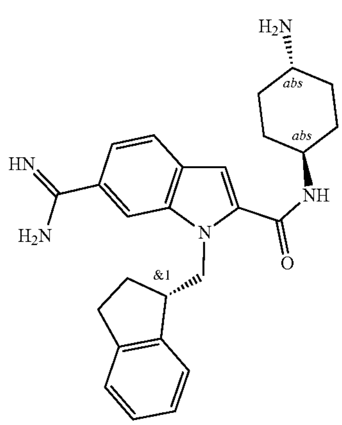 [SMILES: N=C(N)c1ccc2cc(C(=O)N[C@H]3CC[C@H](N)CC3)n(C[C@H]3CCc4ccccc43)c2c1] | 4.59 | 99.0 | 430.3 | B | B |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-617 | 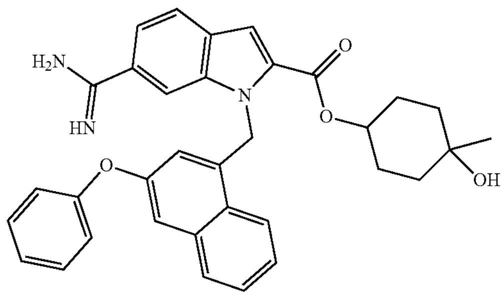 [SMILES: CC1(O)CCC(OC(=O)c2cc3ccc(C(=N)N)cc3n2Cc2cc(Oc3ccccc3)cc3ccccc23)CC1] | 7.201 | 96.126 | 548.5 | B | A |
| I-618 | 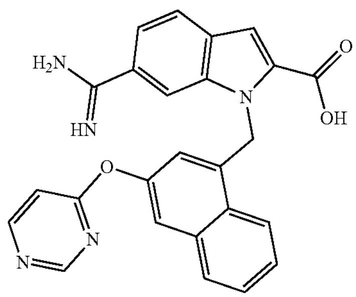 [SMILES: N=C(N)c1ccc2cc(C(=O)O)n(Cc3cc(Oc4ccncn4)cc4ccccc34)c2c1] | 5.69 | 96.41 | 437.7 | B | C |
| I-619 | 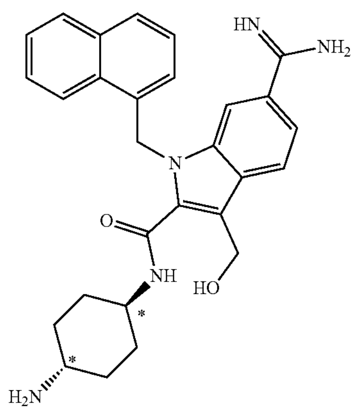 [SMILES: N=C(N)c1ccc2c(CO)c(C(=O)N[C@H]3CC[C@H](N)CC3)n(Cc3cccc4ccccc34)c2c1] | 8.17 | 89.7 | 470.2 | B | A |
| I-620 | 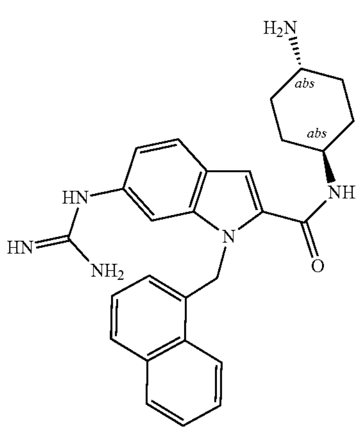 [SMILES: N=C(N)Nc1ccc2cc(C(=O)N[C@H]3CC[C@H](N)CC3)n(Cc3cccc4ccccc34)c2c1] | 5.58 | 99.46 | 455.3 | B | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-621 | | 5.836 | 99.28 | 500.1 | B | D |
| I-622 | | 6.36 | 95.88 | 536.25 | B | A |
| I-623 | | 5.913 | 98.58 | 438.10 | B | C |
| I-624 | | | 96.7 | 371.15 | B | B |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-625 | 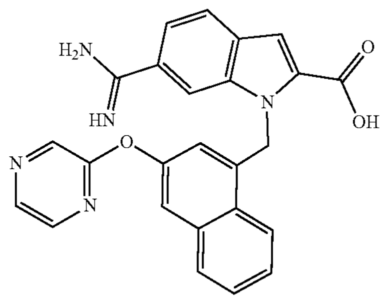 [SMILES: N=C(N)c1ccc2cc(C(=O)O)n(Cc3cc(Oc4cnccn4)cc4ccccc34)c2c1] | 5.181 | 98.89 | 438.1 | B | C |
| I-626 | 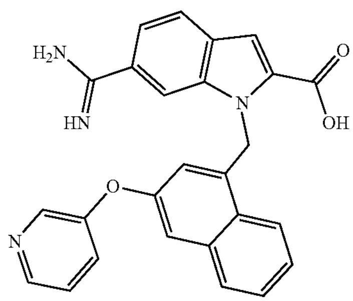 [SMILES: N=C(N)c1ccc2cc(C(=O)O)n(Cc3cc(Oc4cccnc4)cc4ccccc34)c2c1] | 5.134 | 96.80 | 437.4 | B | B |
| I-627 | 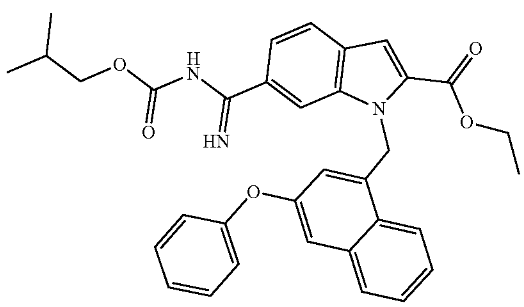 [SMILES: CCOC(=O)c1cc2ccc(C(=N)NC(=O)OCC(C)C)cc2n1Cc1cc(Oc2ccccc2)cc2ccccc12] | 4.05 | 95.60 | 564.20 | B | A |
| I-628 | 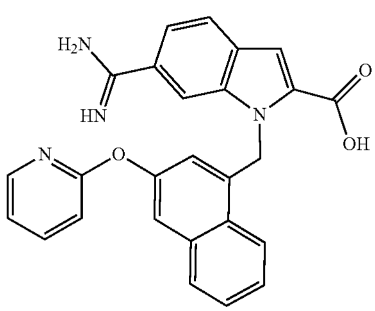 [SMILES: N=C(N)c1ccc2cc(C(=O)O)n(Cc3cc(Oc4ccccn4)cc4ccccc34)c2c1] | 3.26 | 98.83 | 437.4 | B | D |

TABLE A-continued
Exemplary Compounds
| Cpd. ID. | Structure | HPLC Rt-min | % Purity-Indole | M + H | Assay Used | Mar-2 % inhibition at 1 uM |
|---|---|---|---|---|---|---|
| I-629 | 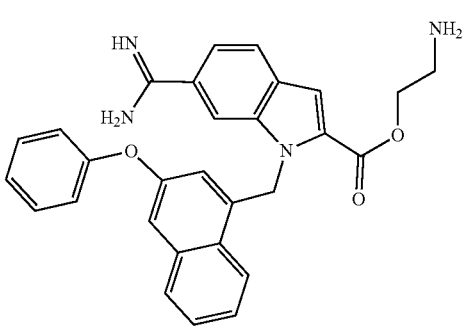 [SMILES: N=C(N)c1ccc2cc(C(=O)OCCN)n(Cc3cc(Oc4ccccc4)cc4ccccc34)c2c1] | 5.076 | 97.93 | 479.2 | B | D |
| I-630 | 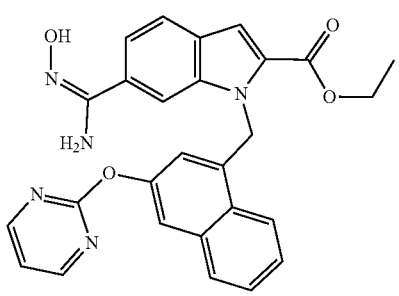 [SMILES: CCOC(=O)c1cc2ccc(/C(N)=N\O)cc2n1Cc1cc(Oc2ncccn2)cc2ccccc12] | 4.621 | 96.29 | 482.4 | B | A |
| I-631 | 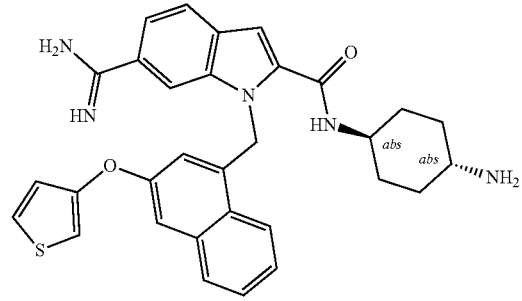 [SMILES: N=C(N)c1ccc2cc(C(=O)N[C@H]3CC[C@H](N)CC3)n(Cc3cc(Oc4ccsc4)cc4ccccc34)c2c1] | 4.94 | 99.71 | 538.5 | B | D |
| I-632 | 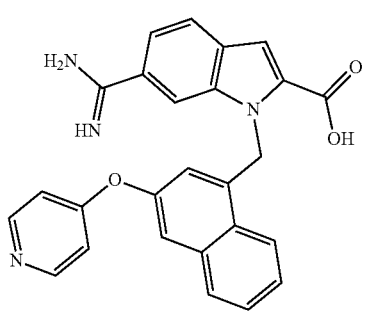 [SMILES: N=C(N)c1ccc2cc(C(=O)O)n(Cc3cc(Oc4ccncc4)cc4ccccc34)c2c1] | 4.784 | 99.26 | 437.15 | B | C |

TABLE A-continued
Exemplary Compounds
| Cpd. ID. | Structure | HPLC Rt- min | % Purity- Indole | M + H | Assay Used | Mar-2 % inhibition at 1 uM |
|---|---|---|---|---|---|---|
| I-633 | 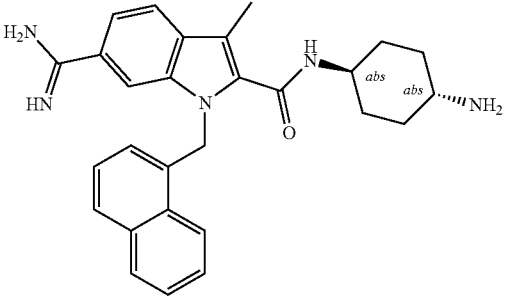 [SMILES: Cc1c(C(=O)N[C@H]2CC[C@H](N)CC2)n(Cc2cccc3ccccc23)c2cc(C(=N)N)ccc12] | 5.78 | 99.92 | 454.2 | B | D |
| I-634 | 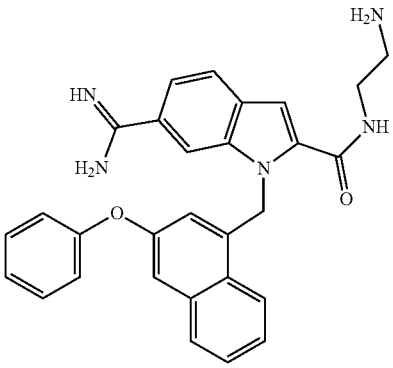 [SMILES: N=C(N)c1ccc2cc(C(=O)NCCN)n(Cc3cc(Oc4ccccc4)cc4ccccc34)c2c1] | 6.23 | 98.42 | 478.4 | B | D |
| I-635 | 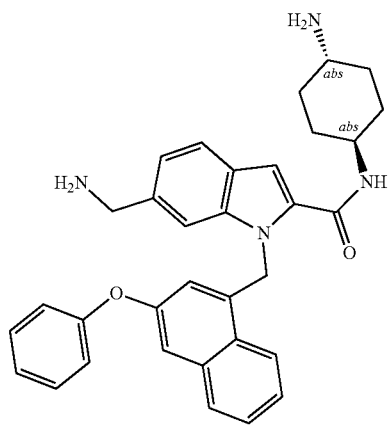 [SMILES: NCc1ccc2cc(C(=O)N[C@H]3CC[C@H](N)CC3)n(Cc3cc(Oc4ccccc4)cc4ccccc34)c2c1] | 5.754 | 99.23 | 519.3 | B | C |
| I-636 | 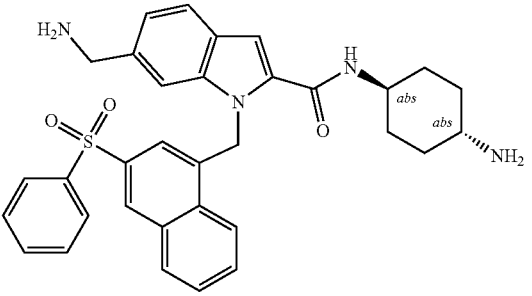 [SMILES: NCc1ccc2cc(C(=O)N[C@H]3CC[C@H](N)CC3)n(Cc3cc(S(=O)(=O)c4ccccc4)cc4ccccc34)c2c1] | 5.28 | 99.07 | 565.20 | B | B |

TABLE A-continued
Exemplary Compounds
| Cpd. ID. | Structure | HPLC Rt-min | % Purity-Indole | M + H | Assay Used | Mar-2 % inhibition at 1 uM |
|---|---|---|---|---|---|---|
| I-637 | 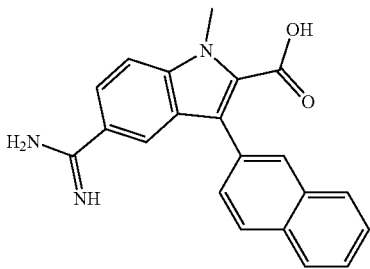 [SMILES: Cn1c(C(=O)O)c(-c2ccc3ccccc3c2)c2cc(C(=N)N)ccc21] | 4.949 | 99.50 | 344.0 | B | A |
| I-638 | 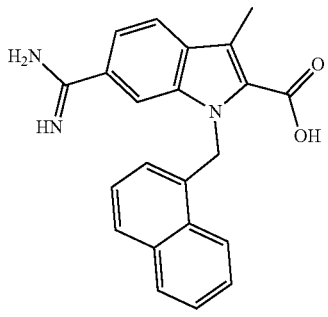 [SMILES: Cc1c(C(=O)O)n(Cc2cccc3ccccc23)c2cc(C(=N)N)ccc12] | 5.03 | 99.23 | 358.1 | B | C |
| I-639 | 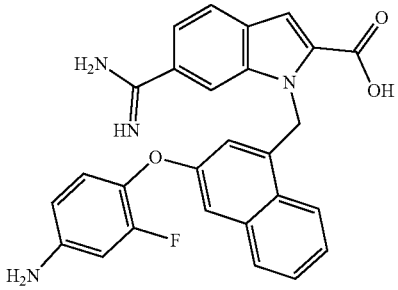 [SMILES: N=C(N)c1ccc2cc(C(=O)O)n(Cc3cc(Oc4ccc(N)cc4F)cc4ccccc34)c2c1] | 6.063 | 98.50 | 469.20 | B | C |
| I-640 | 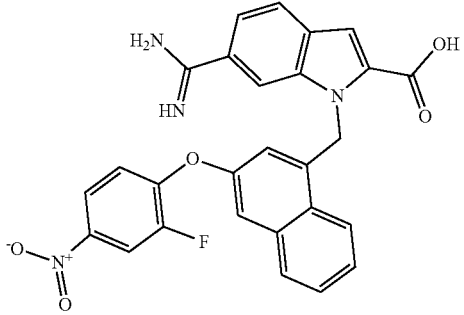 | 4.75 | 98.30 | 499.05 | B | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-641 | 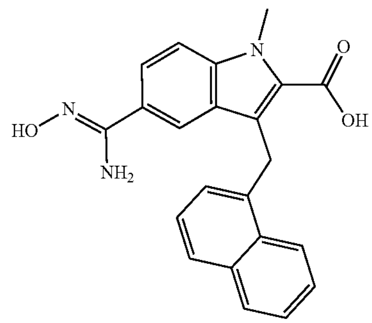 [SMILES: Cn1c(C(=O)O)c(Cc2cccc3ccccc23)c2cc(/C(N)=N/O)ccc21] | 5.021 | 99.93 | 374.1 | B | A |
| I-642 | 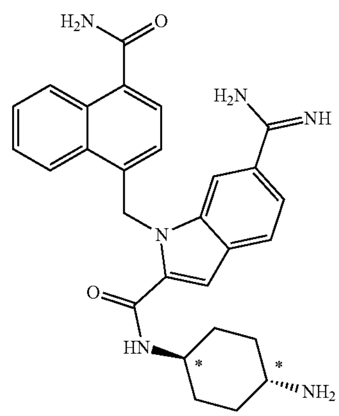 [SMILES: N=C(N)c1ccc2cc(C(=O)N[C@H]3CC[C@H](N)CC3)n(Cc3ccc(C(N)=O)c4ccccc34)c2c1] | 5.3 | 95.1 | 483.6 | B | C |
| I-643 | 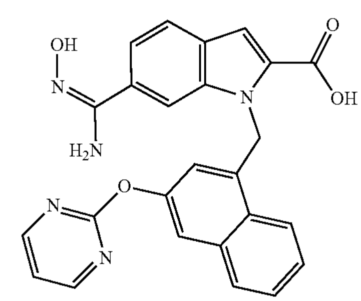 [SMILES: N/C(=N/O)c1ccc2cc(C(=O)O)n(Cc3cc(Oc4ncccn4)cc4ccccc34)c2c1] | 5.779 | 97.41 | 454.3 | B | A |
| I-644 | 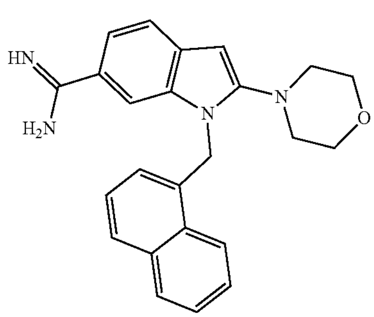 [SMILES: N=C(N)c1ccc2cc(N3CCOCC3)n(Cc3cccc4ccccc34)c2c1] | 5.27 | 99.3 | 385.1 | B | B |

TABLE A-continued
Exemplary Compounds
| Cpd. ID. | Structure | HPLC Rt-min | % Purity-Indole | M + H | Assay Used | Mar-2 % inhibition at 1 uM |
|---|---|---|---|---|---|---|
| I-645 | 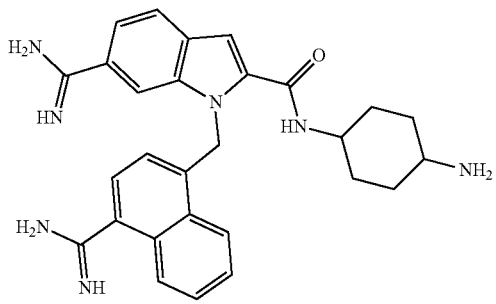 [SMILES: N=C(N)c1ccc2cc(C(=O)NC3CCC(N)CC3)n(Cc3ccc(C(=N)N)c4ccccc34)c2c1] | 0.84 | 95.63 | 482.2 | B | B |
| I-646 | 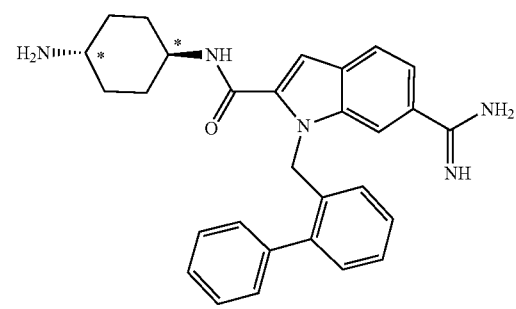 [SMILES: N=C(N)c1ccc2cc(C(=O)N[C@H]3CC[C@H](N)CC3)n(Cc3ccccc3-c3ccccc3)c2c1] | 4.9 | 98.8 | 466.2 | B | A |
| I-647 | 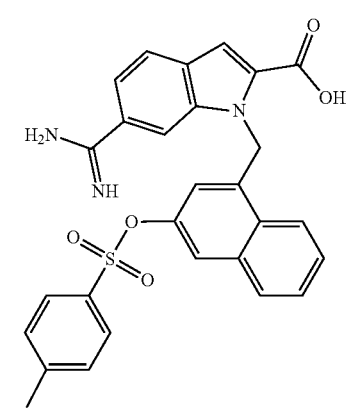 [SMILES: Cc1ccc(S(=O)(=O)Oc2cc(Cn3c(C(=O)O)cc4ccc(C(=N)N)cc43)c3ccccc3c2)cc1] | 5.25 | 99.66 | 514.45 | B | D |
| I-648 | 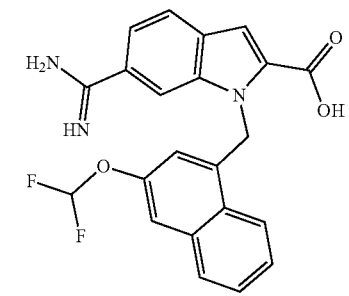 [SMILES: N=C(N)c1ccc2cc(C(=O)O)n(Cc3cc(OC(F)F)cc4ccccc34)c2c1] | 6.028 | 96.94 | 409.95 | B | C |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-649 | 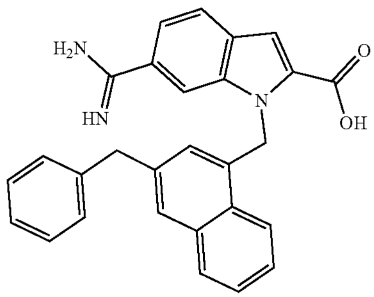 [SMILES: N=C(N)c1ccc2cc(C(=O)O)n(Cc3cc(Cc4ccccc4)cc4ccccc34)c2c1] | 6.567 | 98.82 | 434.6 | B | A |
| I-650 | 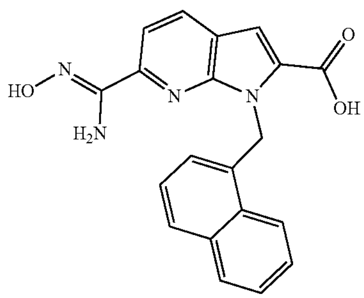 [SMILES: N/C(=N\O)c1ccc2cc(C(=O)O)n(Cc3cccc4ccccc34)c2n1] | 6.316 | 94.00 | 361.40 | B | A |
| I-651 | 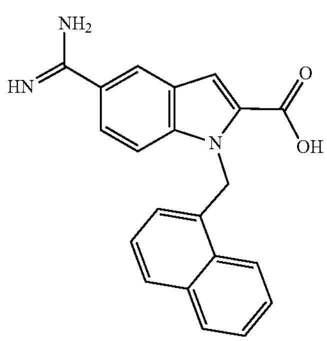 [SMILES: N=C(N)c1ccc2c(c1)cc(C(=O)O)n2Cc1cccc2ccccc12] | 6.170 | 97.20 | 344.50 | B | A |
| I-652 | 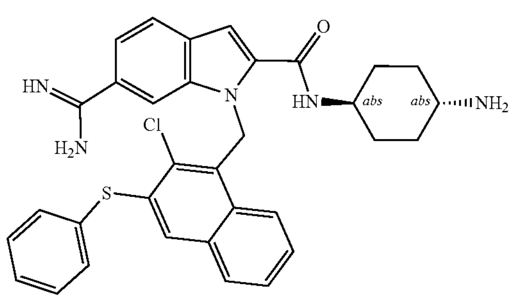 [SMILES: N=C(N)c1ccc2cc(C(=O)N[C@H]3CC[C@H](N)CC3)n(Cc3c(Cl)c(Sc4ccccc4)cc4ccccc34)c2c1] | 5.299 | 98.2 | 582.5 | B | C |

TABLE A-continued

Exemplary Compounds

| Cpd. ID. | Structure | HPLC Rt- min | % Purity- Indole | M + H | Assay Used | Mar-2 % inhibition at 1 uM |
|---|---|---|---|---|---|---|
| I-653 | 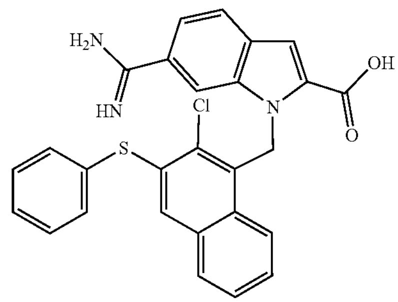 [SMILES: N=C(N)c1ccc2cc(C(=O)O)n(Cc3c(Cl)c(Sc4ccccc4)cc4ccccc34)c2c1] | 5.672 | 97.76 | 486.3 | B | A |
| I-654 | 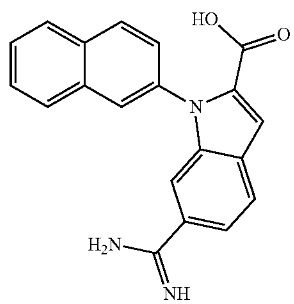 [SMILES: N=C(N)c1ccc2cc(C(=O)O)n(-c3ccc4ccccc4c3)c2c1] | 4.7 | 99.6 | 330.1 | B | A |
| I-655 | 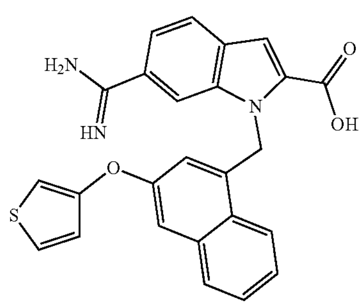 [SMILES: N=C(N)c1ccc2cc(C(=O)O)n(Cc3cc(Oc4ccsc4)cc4ccccc34)c2c1] | 6.135 | 97.12 | 442.3 | B | C |
| I-656 | 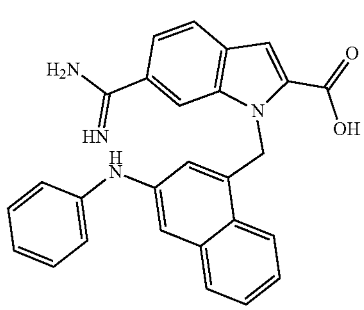 [SMILES: N=C(N)c1ccc2cc(C(=O)O)n(Cc3cc(Nc4ccccc4)cc4ccccc34)c2c1] | 6.115 | 96.72 | 435.5 | B | C |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-657 | 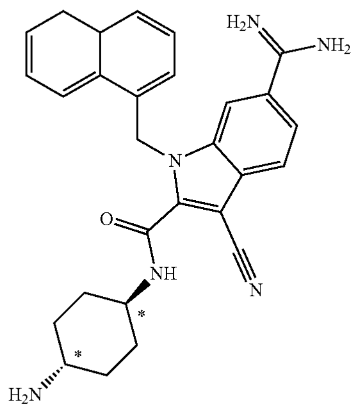 [SMILES: N#Cc1c(C(=O)N[C@H]2CC[C@H](N)CC2)n(CC2=CC=CC3CC=CC=C23)c2cc(C(=N)N)ccc12] | 4.9 | 99.5 | 465.2 | B | A |
| I-658 | 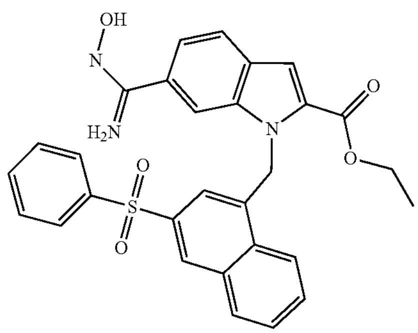 [SMILES: CCOC(=O)c1cc2ccc(C(=N)NO)cc2n1Cc1cc(S(=O)(=O)c2ccccc2)cc2ccccc12] | 6.473 | 98.85 | 528.4 | B | A |
| I-659 | 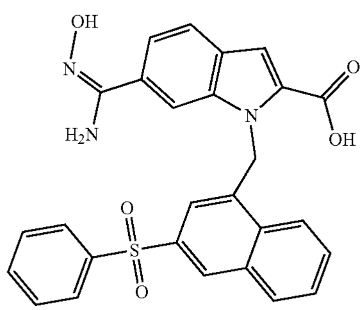 [SMILES: N/C(=N/O)c1ccc2cc(C(=O)O)n(Cc3cc(S(=O)(=O)c4ccccc4)cc4ccccc34)c2c1] | 7.244 | 94.75 | 500.4 | B | A |
| I-660 | 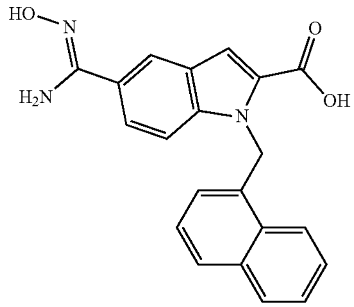 [SMILES: N/C(=N\O)c1ccc2c(c1)cc(C(=O)O)n2Cc1cccc2ccccc12] | 3.536 | 97.23 | 360.4 | B | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-661 | 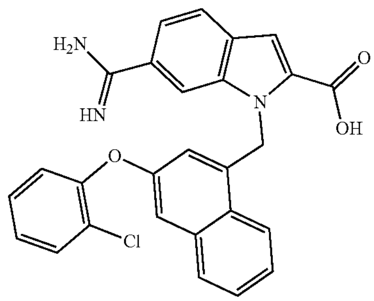 [SMILES: N=C(N)c1ccc2cc(C(=O)O)n(Cc3cc(Oc4ccccc4Cl)cc4ccccc34)c2c1] | 4.84 | 97.3 | 470.02 | B | B |
| I-662 | 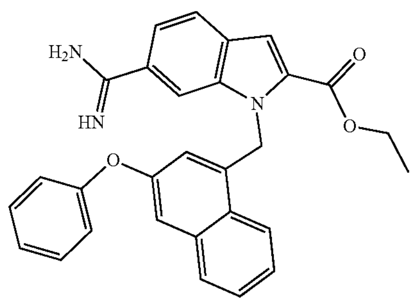 [SMILES: CCOC(=O)c1cc2ccc(C(=N)N)cc2n1Cc1cc(Oc2ccccc2)cc2ccccc12] | 6.771 | 95.49 | 464.2 | B | B |
| I-663 | 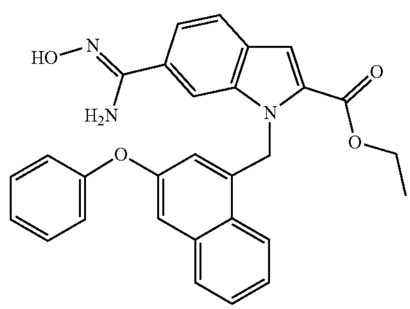 [SMILES: CCOC(=O)c1cc2ccc(/C(N)=N/O)cc2n1Cc1cc(Oc2ccccc2)cc2ccccc12] | 6.786 | 97.84 | 480.2 | B | A |
| I-664 | 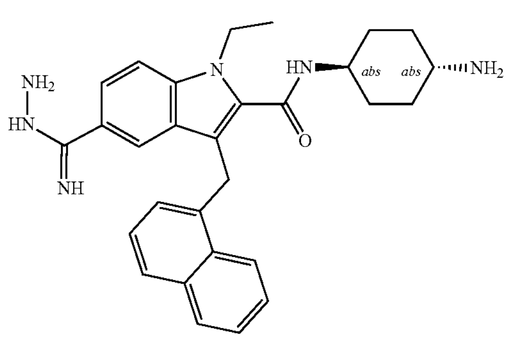 [SMILES: CCn1c(C(=O)N[C@H]2CC[C@H](N)CC2)c(Cc2cccc3ccccc23)c2cc(C(=N)NN)ccc21] | 5.653 | 95.32 | 483.3 | B | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-665 | 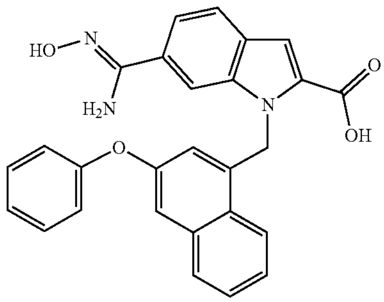 [SMILES: N/C(=N\O)c1ccc2cc(C(=O)O)n(Cc3cc(Oc4ccccc4)cc4ccccc34)c2c1] | 6.194 | 97.26 | 452.30 | B | A |
| I-666 | 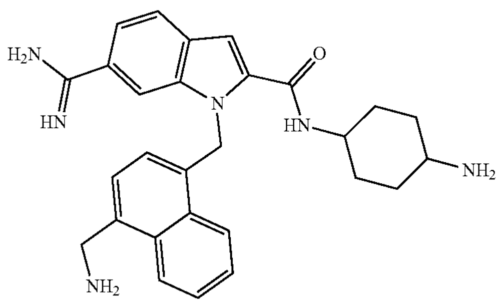 [SMILES: N=C(N)c1ccc2cc(C(=O)NC3CCC(N)CC3)n(Cc3ccc(CN)c4ccccc34)c2c1] | 0.85 | 98.78 | 469.3 | B | C |
| I-667 | 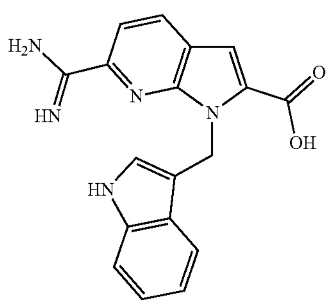 [SMILES: N=C(N)c1ccc2cc(C(=O)O)n(Cc3c[nH]c4ccccc34)c2n1] | 5.186 | 98.55 | 332.2 | B | B |
| I-668 | 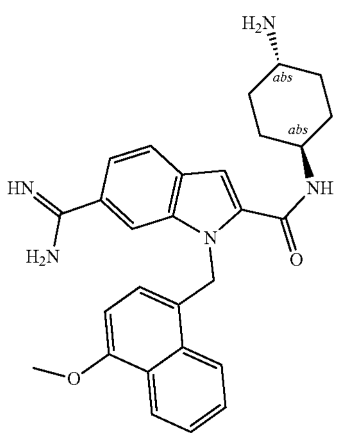 [SMILES: COc1ccc(Cn2c(C(=O)N[C@H]3CC[C@H](N)CC3)cc3ccc(C(=N)N)cc32)c2ccccc12] | 5.268 | 98.98 | 470.25 | B | D |

TABLE A-continued
Exemplary Compounds
| Cpd. ID. | Structure | HPLC Rt-min | % Purity-Indole | M + H | Assay Used | Mar-2 % inhibition at 1 uM |
|---|---|---|---|---|---|---|
| I-669 | 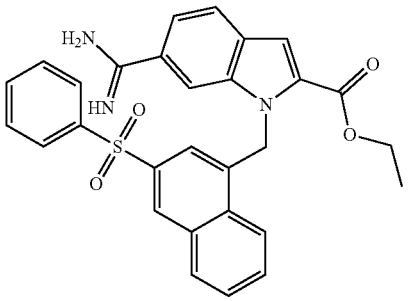 [SMILES: CCOC(=O)c1cc2ccc(C(=N)N)cc2n1Cc1cc(S(=O)(=O)c2ccccc2)cc2ccccc12] | 6.383 | 98.44 | 512.20 | B | B |
| I-670 | 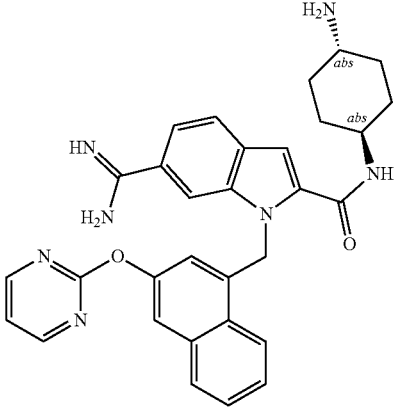 [SMILES: N=C(N)c1ccc2cc(C(=O)N[C@H]3CC[C@H](N)CC3)n(Cc3cc(Oc4ncccn4)cc4ccccc34)c2c1] | 5.077 | 97.93 | 534.5 | B | D |
| I-671 | 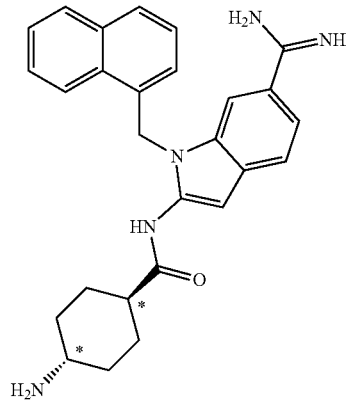 [SMILES: N=C(N)c1ccc2cc(NC(=O)[C@H]3CC[C@H](N)CC3)n(Cc3cccc4ccccc34)c2c1] | 5.2 | 98.1 | 440.3 | B | C |

TABLE A-continued
Exemplary Compounds
| Cpd. ID. | Structure | HPLC Rt-min | % Purity-Indole | M + H | Assay Used | Mar-2 % inhibition at 1 uM |
|---|---|---|---|---|---|---|
| I-672 | 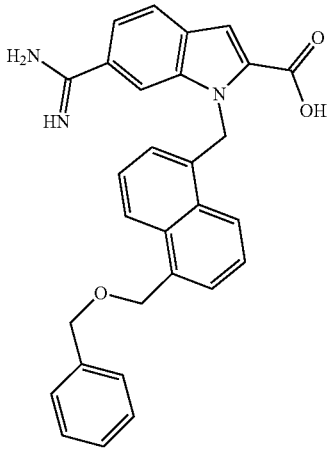 [SMILES: N=C(N)c1ccc2cc(C(=O)O)n(Cc3cccc4c(COCc5ccccc5)cccc34)c2c1] | 6.627 | 98.69 | 464.2 | B | D |
| I-673 | 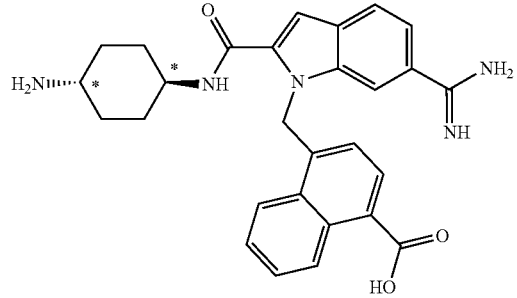 [SMILES: N=C(N)c1ccc2cc(C(=O)N[C@H]3CC[C@H](N)CC3)n(Cc3ccc(C(=O)O)c4ccccc34)c2c1] | 4.7 | 98.1 | 484.2 | B | B |
| I-674 | 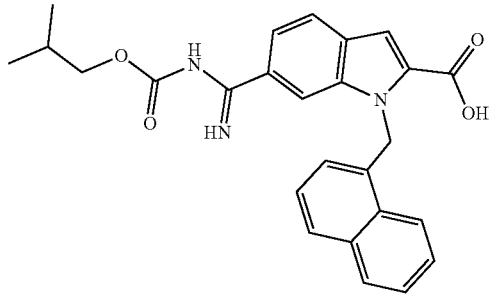 [SMILES: CC(C)COC(=O)NC(=N)c1ccc2cc(C(=O)O)n(Cc3cccc4ccccc34)c2c1] | 5.430 | 92.36 | 445.25 | B | B |
| I-675 | 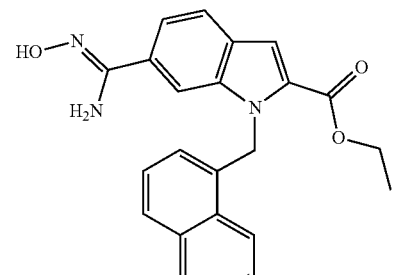 | 5.54 | 99.91 | 388.2 | B | A |

TABLE A-continued
Exemplary Compounds
| Cpd. ID. | Structure | HPLC Rt-min | % Purity-Indole | M + H | Assay Used | Mar-2 % inhibition at 1 uM |
|---|---|---|---|---|---|---|
| I-676 | 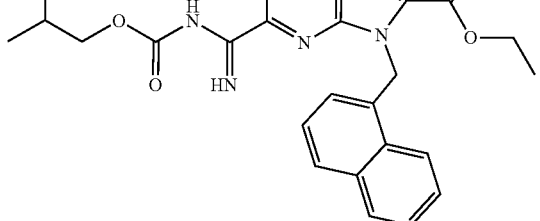 | 16.056 | 97.51 | 473.10 | B | A |
| I-677 | 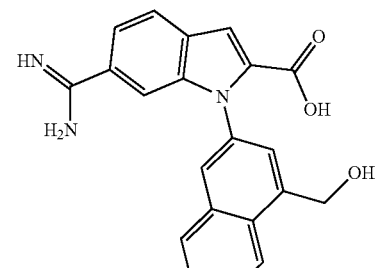 | 5.094 | 96.65 | 360.0 | B | C |
| I-678 | 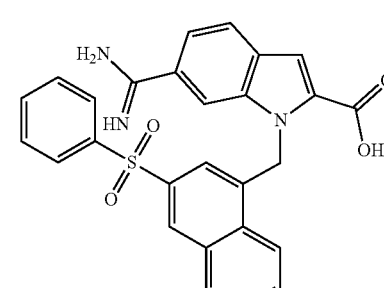 | 5.807 | 98.97 | 484.00 | B | C |
| I-679 | 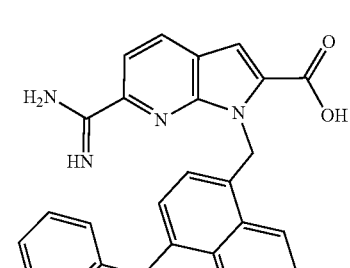 | 6.524 | 96.34 | 437.05 | B | B |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-680 | 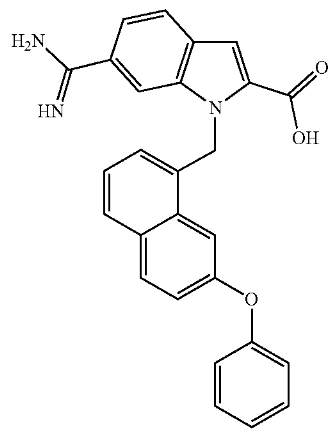 [SMILES: N=C(N)c1ccc2cc(C(=O)O)n(Cc3cccc4ccc(Oc5ccccc5)cc34)c2c1] | 6.23 | 99.4 | 436.05 | B | B |
| I-681 | 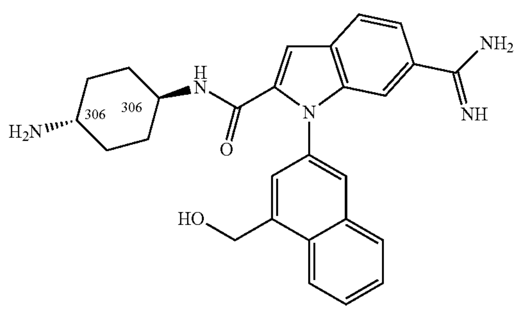 [SMILES: N=C(N)c1ccc2cc(C(=O)N[C@H]3CC[C@H](N)CC3)n(-c3cc(CO)c4ccccc4c3)c2c1] | 4.646 | 95.42 | 456.3 | B | D |
| I-682 | 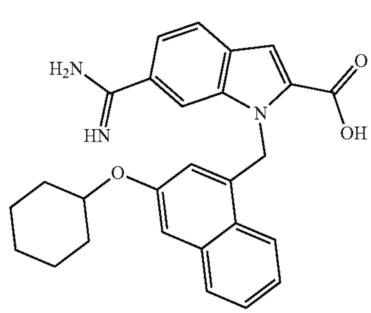 [SMILES: N=C(N)c1ccc2cc(C(=O)O)n(Cc3cc(OC4CCCCC4)cc4ccccc34)c2c1] | 6.664 | 97.40 | 442.0 | B | B |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-683 | 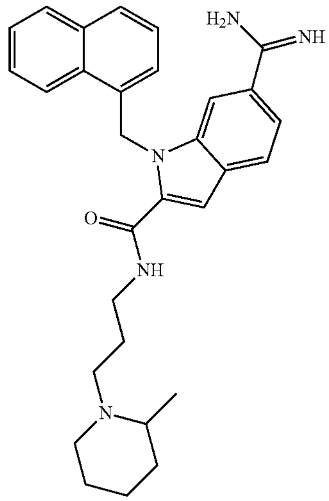 [SMILES: CC1CCCCN1CCCNC(=O)c1cc2ccc(C(=N)N)cc2n1Cc1cccc2ccccc12] | 6.5 | 98.1 | 482.25 | B | C |
| I-684 | 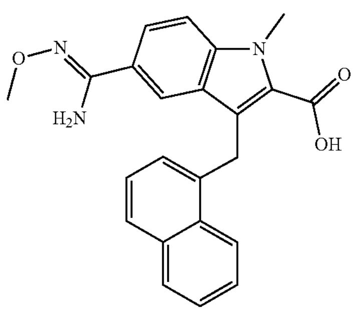 [SMILES: CO/N=C(\N)c1ccc2c(c1)c(Cc1cccc3ccccc13)c(C(=O)O)n2C] | 5.72 | 99.3 | 388.2 | B | A |
| I-685 | 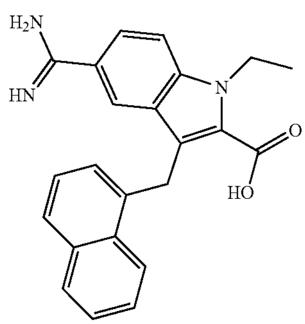 [SMILES: CCn1c(C(=O)O)c(Cc2cccc3ccccc23)c2cc(C(=N)N)ccc21] | 5.089 | 99.08 | 372.2 | B | C |
| I-686 | 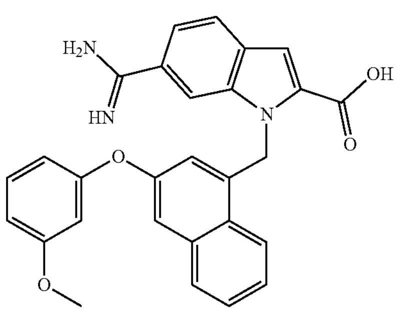 [SMILES: COc1cccc(Oc2cc(Cn3c(C(=O)O)cc4ccc(C(=N)N)cc43)c3ccccc3c2)c1] | 6.73 | 98.1 | 466.05 | B | C |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-687 | 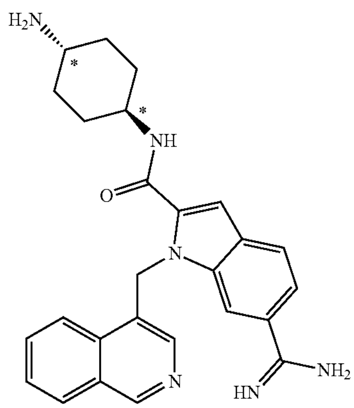 [SMILES: N=C(N)c1ccc2cc(C(=O)N[C@H]3CC[C@H](N)CC3)n(Cc3cncc4ccccc34)c2c1] | 4.3 | 99.7 | 441.3 | B | C |
| I-688 | 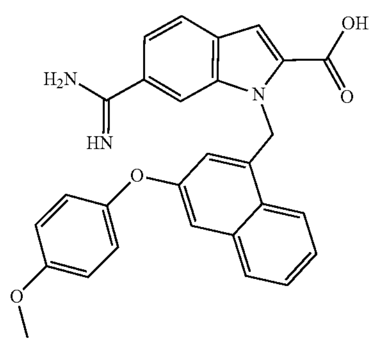 [SMILES: COc1ccc(Oc2cc(Cn3c(C(=O)O)cc4ccc(C(=N)N)cc43)c3ccccc3c2)cc1] | 5.29 | 99.96 | 466.2 | B | C |
| I-689 | 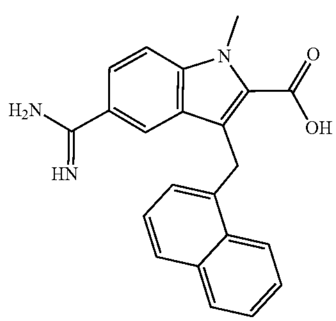 [SMILES: Cn1c(C(=O)O)c(Cc2cccc3ccccc23)c2cc(C(=N)N)ccc21] | 1.08 | 99.53 | 358.03 | B | D |
| I-690 | 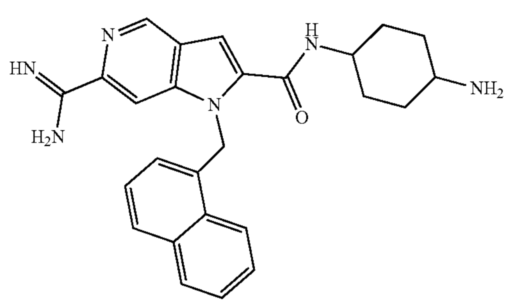 [SMILES: N=C(N)c1cc2c(cn1)cc(C(=O)NC1CCC(N)CC1)n2Cc1cccc2ccccc12] | 7.79 | 99.77 | 441.3 | B | D |

TABLE A-continued
Exemplary Compounds
| Cpd. ID. | Structure | HPLC Rt-min | % Purity-Indole | M + H | Assay Used | Mar-2 % inhibition at 1 uM |
|---|---|---|---|---|---|---|
| I-691 | 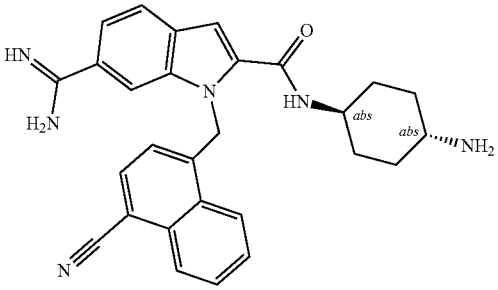 [SMILES: N#Cc1ccc(Cn2c(C(=O)N[C@H]3CC[C@H](N)CC3)cc3ccc(C(=N)N)cc32)c2ccccc12] | 5.61 | 96.60 | 465.3 | B | D |
| I-692 | 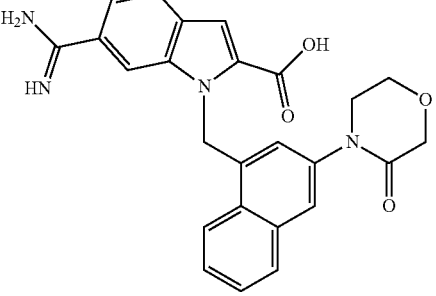 | 5.122 | 95.65 | 443.25 | B | A |
| I-693 | 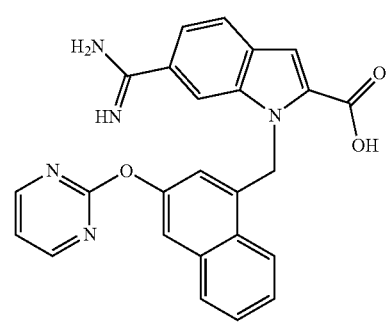 [SMILES: N=C(N)c1ccc2cc(C(=O)O)n(Cc3cc(Oc4ncccn4)cc4ccccc34)c2c1] | 5.164 | 99.39 | 438.1 | B | D |
| I-694 | 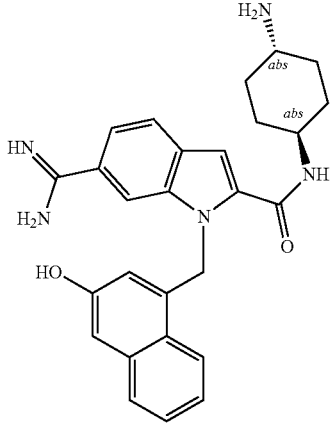 [SMILES: N=C(N)c1ccc2cc(C(=O)N[C@H]3CC[C@H](N)CC3)n(Cc3cc(O)cc4ccccc34)c2c1] | 5.010 | 98.045 | 456.0 | B | D |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-695 | 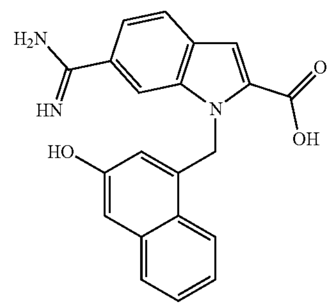 [SMILES: N=C(N)c1ccc2cc(C(=O)O)n(Cc3cc(O)cc4ccccc34)c2c1] | 5.505 | 96.73 | 360.1 | B | D |
| I-696 | 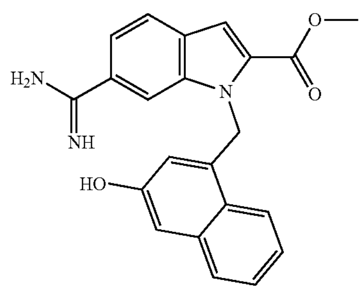 [SMILES: COC(=O)c1cc2ccc(C(=N)N)cc2n1Cc1cc(O)cc2ccccc12] | 6.133 | 98.32 | 374.1 | B | C |
| I-697 | 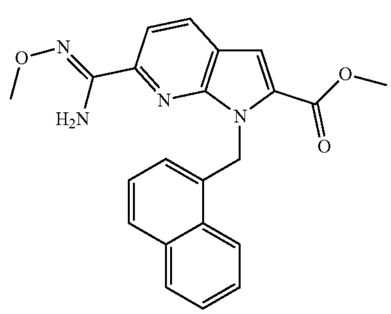 | 4.637 | 97.59 | 389.15 | B | A |
| I-698 | 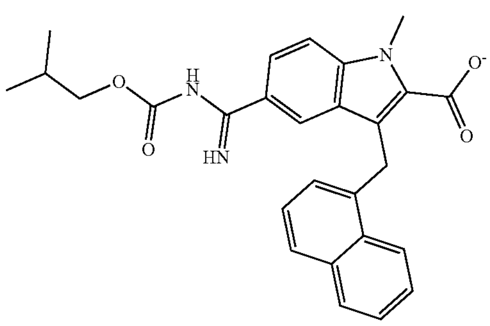 [SMILES: CC(C)COC(=O)NC(=N)c1ccc2c(c1)c(Cc1cccc3ccccc13)c(C(=O)[O-])n2C] | 5.460 | 94.07 | 458.5 | B | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-699 | 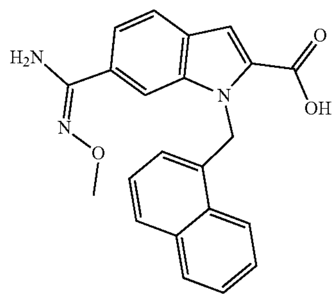 [SMILES: CO/N=C(/N)c1ccc2cc(C(=O)O)n(Cc3cccc4ccccc34)c2c1] | 5.955 | 99.70 | 374.1 | B | A |
| I-700 | 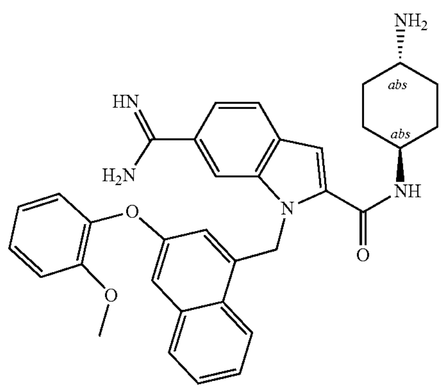 [SMILES: COc1ccccc1Oc1cc(Cn2c(C(=O)N[C@H]3CC[C@H](N)CC3)cc3ccc(C(=N)N)cc32)c2ccccc2c1] | 5.528 | 95.51 | 560.25 | B | C |
| I-701 | 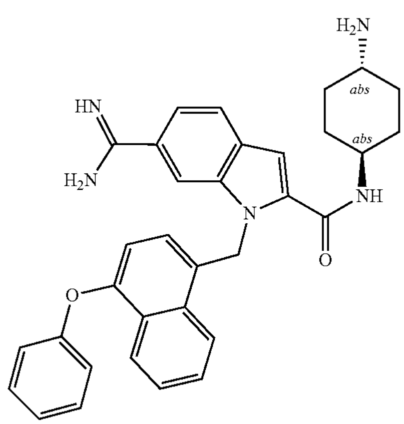 [SMILES: N=C(N)c1ccc2cc(C(=O)N[C@H]3CC[C@H](N)CC3)n(Cc3ccc(Oc4ccccc4)c4ccccc34)c2c1] | 5.284 | 98.57 | 532.3 | B | D |

TABLE A-continued
Exemplary Compounds
| Cpd. ID. | Structure | HPLC Rt-min | % Purity-Indole | M + H | Assay Used | Mar-2 % inhibition at 1 uM |
|---|---|---|---|---|---|---|
| I-702 | 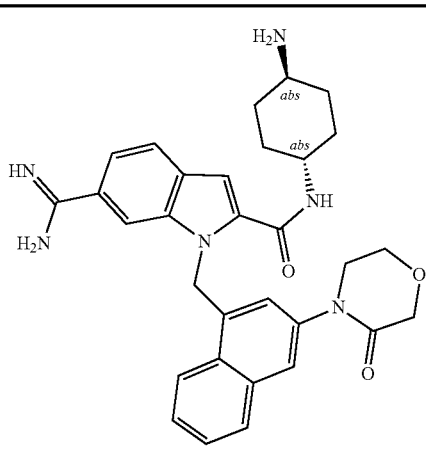 | 4.996 | 99.02 | 539.25 | B | B |
| I-703 | 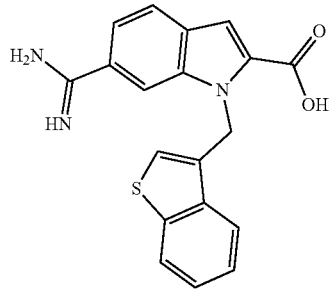 [SMILES: N=C(N)c1ccc2cc(C(=O)O)n(Cc3csc4ccccc34)c2c1] | 5.884 | 98.45 | 350.25 | B | C |
| I-704 | 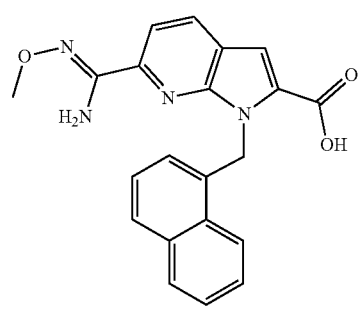 [SMILES: CO/N=C(\N)c1ccc2cc(C(=O)O)n(Cc3cccc4ccccc34)c2n1] | 5.553 | 96.33 | 375.05 | B | A |
| I-705 | 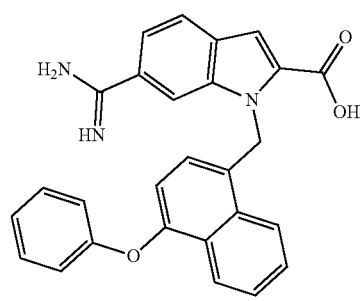 [SMILES: N=C(N)c1ccc2cc(C(=O)O)n(Cc3ccc(Oc4ccccc4)c4ccccc34)c2c1] | 6.599 | 97.63 | 436.2 | B | C |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-706 | 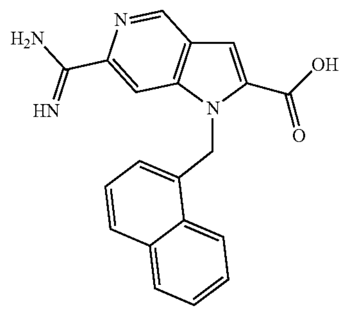 [SMILES: N=C(N)c1cc2c(cn1)cc(C(=O)O)n2Cc1cccc2ccccc12] | 6.115 | 94.43 | 344.95 | B | B |
| I-707 | 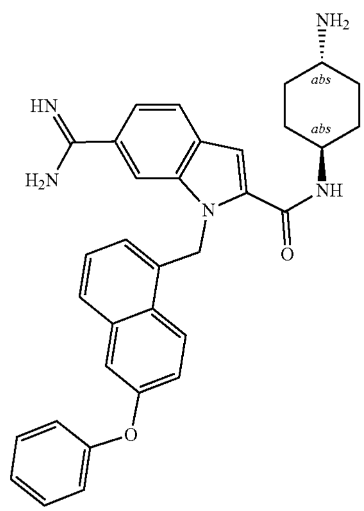 [SMILES: N=C(N)c1ccc2cc(C(=O)N[C@H]3CC[C@H](N)CC3)n(Cc3cccc4cc(Oc5ccccc5)ccc34)c2c1] | 5.751 | 98.76 | 532.20 | B | D |
| I-708 | 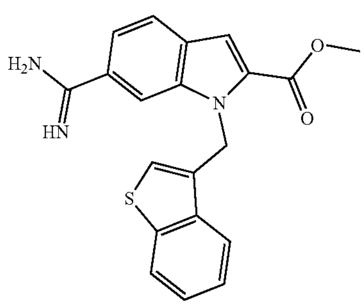 [SMILES: COC(=O)c1cc2ccc(C(=N)N)cc2n1Cc1csc2ccccc12] | 6.004 | 96.61 | 364.0 | B | B |
| I-709 | 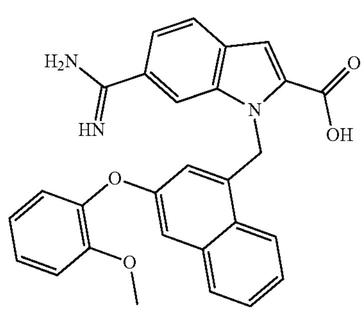 [SMILES: COc1ccccc1Oc1cc(Cn2c(C(=O)O)cc3ccc(C(=N)N)cc32)c2ccccc2c1] | 6.426 | 98.52 | 466.25 | B | B |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-710 | 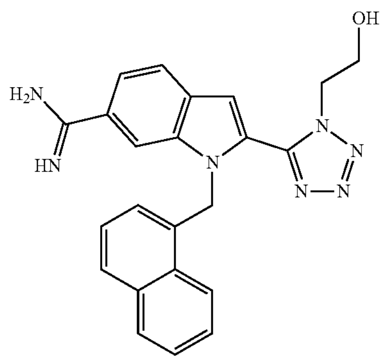 [SMILES: N=C(N)c1ccc2cc(-c3nnnn3CCO)n(Cc3cccc4ccccc34)c2c1] | 5.039 | 99.9 | 412.2 | B | D |
| I-711 | 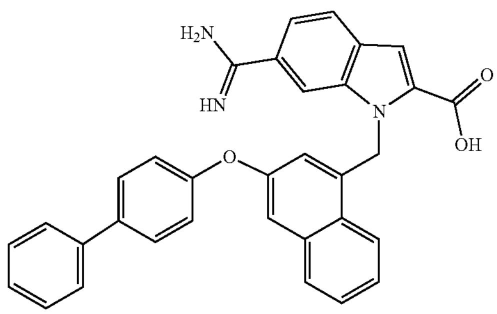 [SMILES: N=C(N)c1ccc2cc(C(=O)O)n(Cc3cc(Oc4ccc(-c5ccccc5)cc4)cc4ccccc34)c2c1] | 6.542 | 98.498 | 512.2 | B | B |
| I-712 | 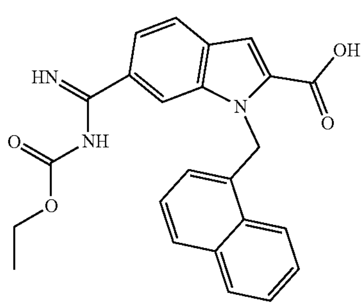 [SMILES: CCOC(=O)NC(=N)c1ccc2cc(C(=O)O)n(Cc3cccc4ccccc34)c2c1] | 3.852 | 95.02 | 416.15 | B | A |
| I-713 | 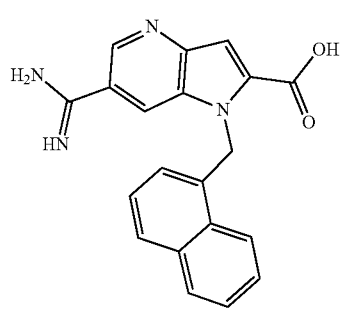 [SMILES: N=C(N)c1cnc2cc(C(=O)O)n(Cc3cccc4ccccc34)c2c1] | 4.76 | 98.6 | 345.1 | B | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-714 | 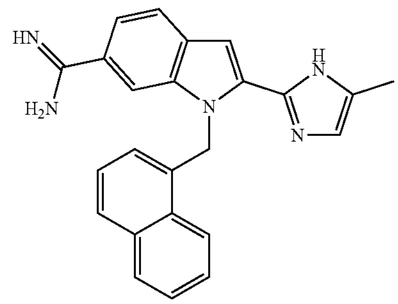 [SMILES: Cc1cnc(-c2cc3ccc(C(=N)N)cc3n2Cc2cccc3ccccc23)[nH]1] | 5.746 | 99.86 | 380.05 | B | D |
| I-715 | 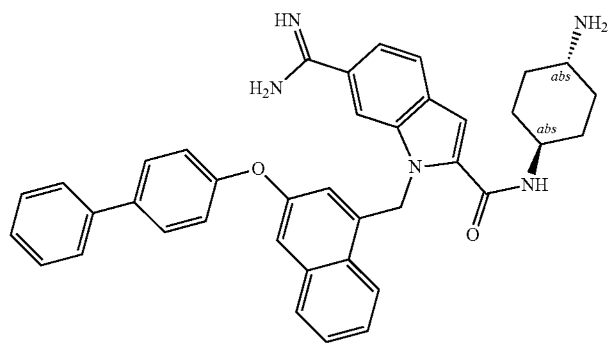 | 5.664 | 95.347 | 608.3 | B | A |
| I-716 | 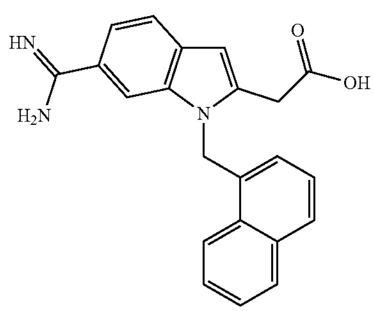 [SMILES: N=C(N)c1ccc2cc(CC(=O)O)n(Cc3cccc4ccccc34)c2c1] | 5.80 | 95.14 | 358.2 | B | D |
| I-717 | 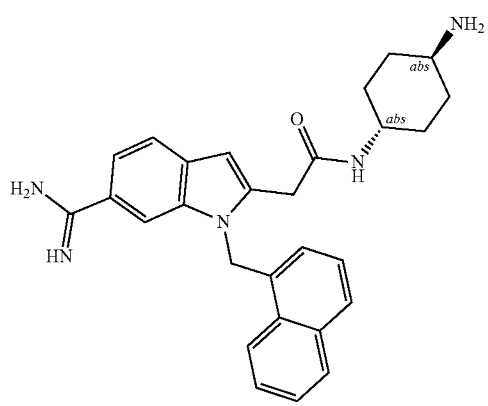 [SMILES: N=C(N)c1ccc2cc(CC(=O)N[C@H]3CC[C@H](N)CC3)n(Cc3cccc4ccccc34)c2c1] | 5.03 | 96.4 | 454.3 | B | D |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-718 | 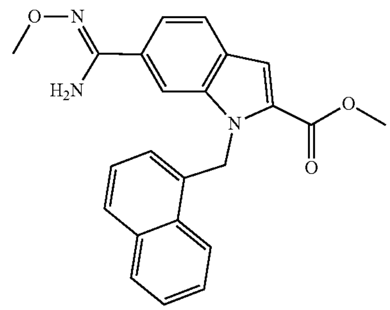 | | 95 | 387.95 | B | A |
| I-719 | 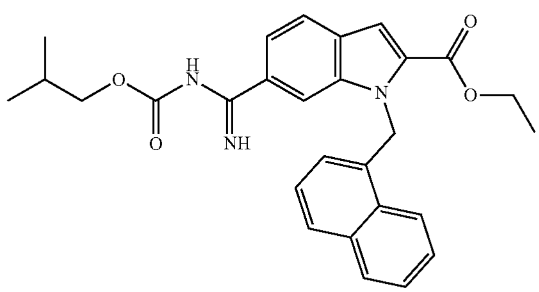 [SMILES: CCOC(=O)c1cc2ccc(C(=N)NC(=O)OCC(C)C)cc2n1Cc1cccc2ccccc12] | 7.230 | 96.72 | 472.2 | B | A |
| I-720 | 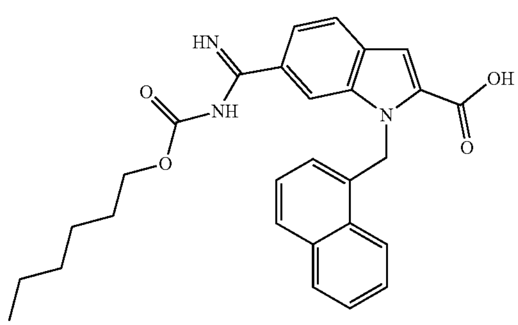 [SMILES: CCCCCCOC(=O)NC(=N)c1ccc2cc(C(=O)O)n(Cc3cccc4ccccc34)c2c1] | 7.086 | 97.12 | 472.2 | B | A |
| I-721 | 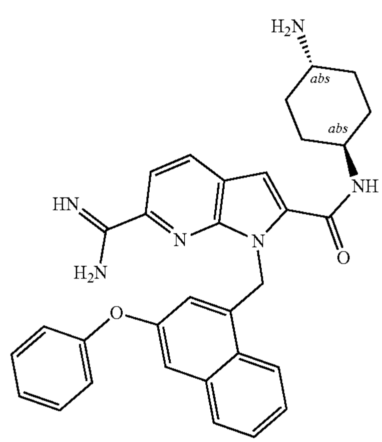 [SMILES: N=C(N)c1ccc2cc(C(=O)N[C@H]3CC[C@H](N)CC3)n(Cc3cc(Oc4ccccc4)cc4ccccc34)c2n1] | 5.620 | 95.43 | 533.20 | B | D |

TABLE A-continued
Exemplary Compounds
| Cpd. ID. | Structure | HPLC Rt- min | % Purity- Indole | M + H | Assay Used | Mar-2 % inhibition at 1 uM |
|---|---|---|---|---|---|---|
| I-722 | 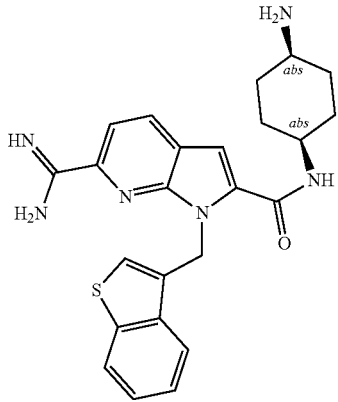 [SMILES: N=C(N)c1ccc2cc(C(=O)N[C@H]3CC[C@@H](N)CC3)n(Cc3csc4ccccc34)c2n1] | 5.114 | 96.00 | 447.10 | B | D |
| I-723 | 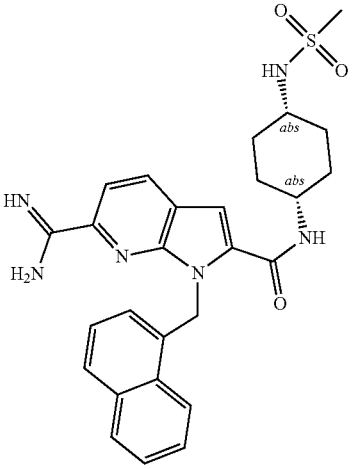 [SMILES: CS(=O)(=O)N[C@H]1CC[C@@H](NC(=O)c2cc3ccc(C(=N)N)nc3n2Cc2cccc3ccccc23)CC1] | 5.484 | 96.14 | 519.20 | B | D |
| I-724 | 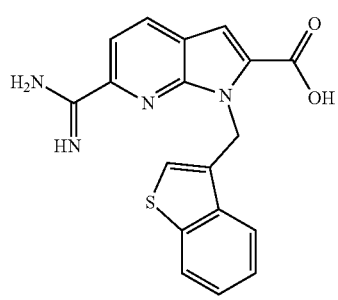 [SMILES: N=C(N)c1ccc2cc(C(=O)O)n(Cc3csc4ccccc34)c2n1] | 5.894 | 97.53 | 350.95 | B | C |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-725 | 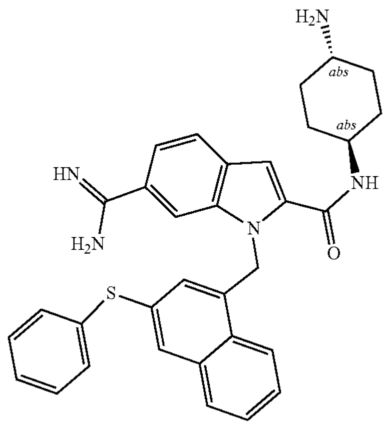 [SMILES: N=C(N)c1ccc2cc(C(=O)N[C@H]3CC[C@H](N)CC3)n(Cc3cc(Sc4ccccc4)cc4ccccc34)c2c1] | 5.740 | 98.97 | 548.35 | B | D |
| I-726 | 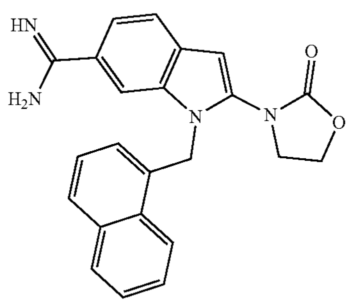 [SMILES: N=C(N)c1ccc2cc(N3CCOC3=O)n(Cc3cccc4ccccc34)c2c1] | 6.641 | 99.52 | 385.0 | B | B |
| I-727 | 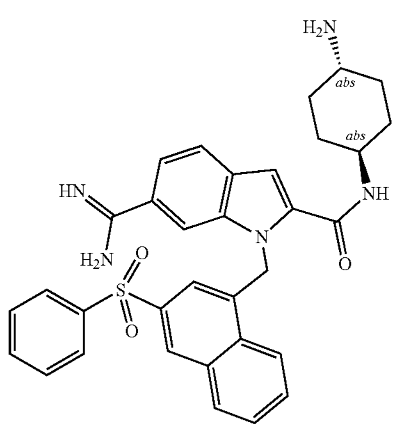 [SMILES: N=C(N)c1ccc2cc(C(=O)N[C@H]3CC[C@H](N)CC3)n(Cc3cc(S(=O)(=O)c4ccccc4)cc4ccccc34)c2c1] | 5.035 | 98.35 | 580.20 | B | D |

TABLE A-continued

Exemplary Compounds

| Cpd. ID. | Structure | HPLC Rt- min | % Purity- Indole | M + H | Assay Used | Mar-2 % inhibition at 1 uM |
|---|---|---|---|---|---|---|
| I-728 | 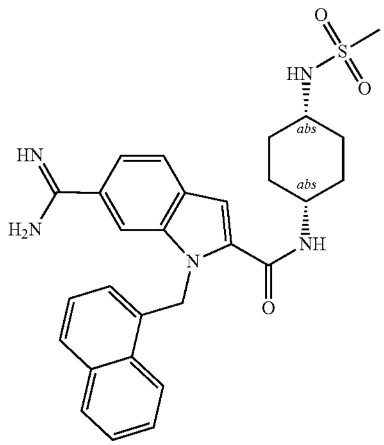 [SMILES: CS(=O)(=O)N[C@H]1CC[C@@H](NC(=O)c2cc3ccc(C(=N)N)cc3n2Cc2cccc3ccccc23)CC1] | 6.07 | 97.24 | 518.2 | B | D |
| I-729 | 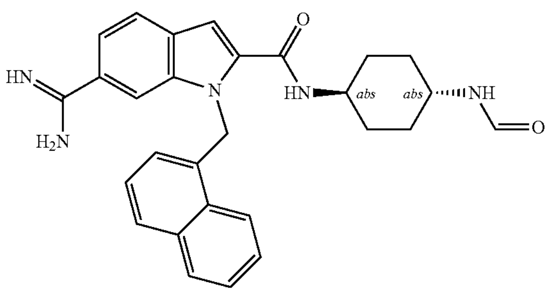 [SMILES: N=C(N)c1ccc2cc(C(=O)N[C@H]3CC[C@H](NC=O)CC3)n(Cc3cccc4ccccc34)c2c1] | 2.90 | 96.47 | 468.2 | B | C |
| I-730 | 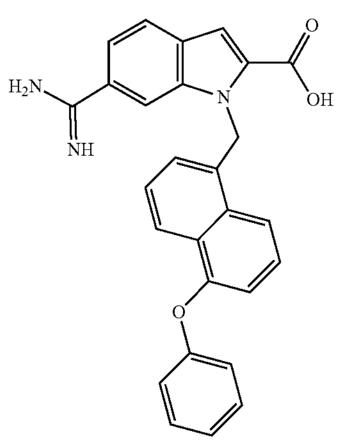 [SMILES: N=C(N)c1ccc2cc(C(=O)O)n(Cc3cccc4c(Oc5ccccc5)cccc34)c2c1] | 3.51 | 98.6 | 436.2 | B | C |

TABLE A-continued
Exemplary Compounds
| Cpd. ID. | Structure | HPLC Rt- min | % Purity- Indole | M + H | Assay Used | Mar-2 % inhibition at 1 uM |
|---|---|---|---|---|---|---|
| I-731 | 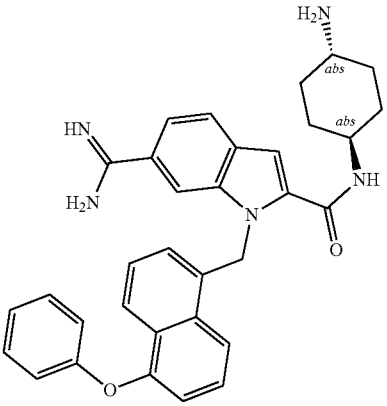 [SMILES: N=C(N)c1ccc2cc(C(=O)N[C@H]3CC[C@H](N)CC3)n(Cc3cccc4c(Oc5ccccc5)cccc34)c2c1] | 5.30 | 96.7 | 532.2 | B | D |
| I-732 | 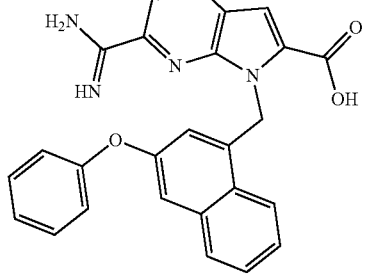 | 6.180 | 99.37 | 437.20 | B | B |
| I-733 | 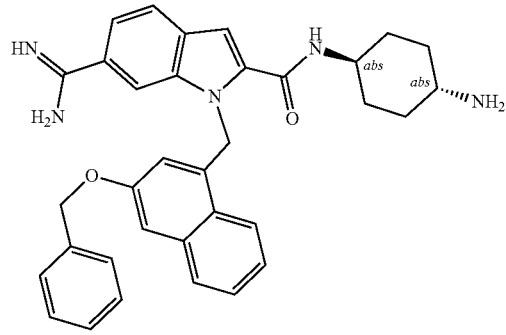 [SMILES: N=C(N)c1ccc2cc(C(=O)N[C@H]3CC[C@H](N)CC3)n(Cc3cc(OCc4ccccc4)cc4ccccc34)c2c1] | 5.575 | 96.985 | 546.3 | B | D |
| I-734 | 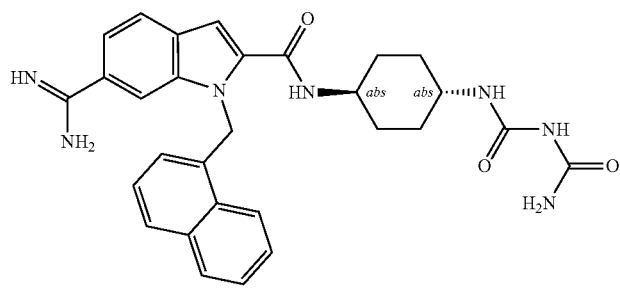 [SMILES: N=C(N)c1ccc2cc(C(=O)N[C@H]3CC[C@H](NC(=O)NC(N)=O)CC3)n(Cc3cccc4ccccc34)c2c1] | 5.81 | 85.28 | 526.4 | B | C |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-735 | 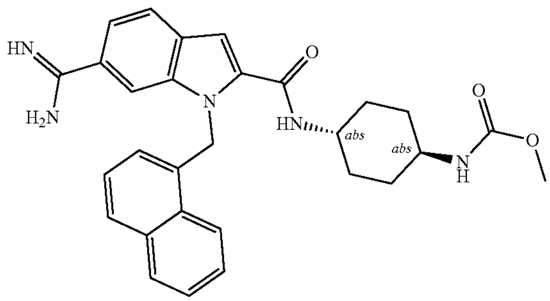 [SMILES: COC(=O)N[C@H]1CC[C@H](NC(=O)c2cc3ccc(C(=N)N)cc3n2Cc2cccc3ccccc23)CC1] | 6.09 | 99.09 | 498.2 | B | B |
| I-736 | 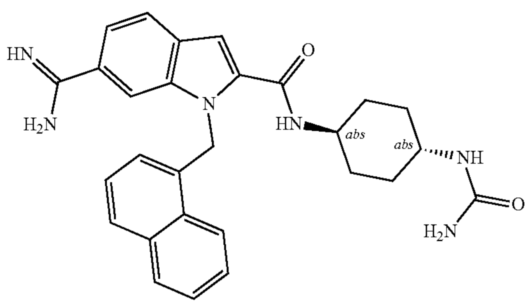 [SMILES: N=C(N)c1ccc2cc(C(=O)N[C@H]3CC[C@H](NC(N)=O)CC3)n(Cc3cccc4ccccc34)c2c1] | 51.8 | 98.89 | 483.2 | B | C |
| I-737 | 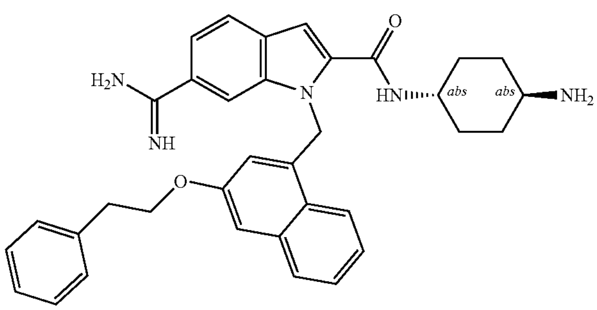 [SMILES: N=C(N)c1ccc2cc(C(=O)N[C@H]3CC[C@H](N)CC3)n(Cc3cc(OCCc4ccccc4)cc4ccccc34)c2c1] | 5.690 | 98.488 | 560.4 | B | D |
| I-738 | 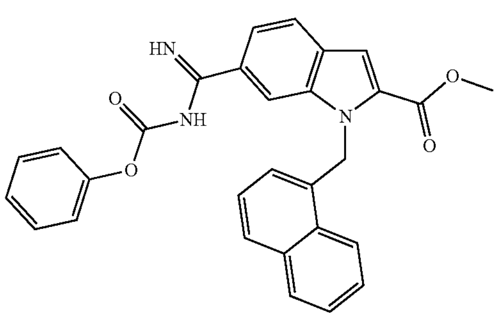 [SMILES: COC(=O)c1cc2ccc(C(=N)NC(=O)Oc3ccccc3)cc2n1Cc1cccc2ccccc12] | 15.907 | 96.19 | 478.20 | B | A |

TABLE A-continued
Exemplary Compounds
| Cpd. ID. | Structure | HPLC Rt-min | % Purity-Indole | M + H | Assay Used | Mar-2 % inhibition at 1 uM |
|---|---|---|---|---|---|---|
| I-739 | 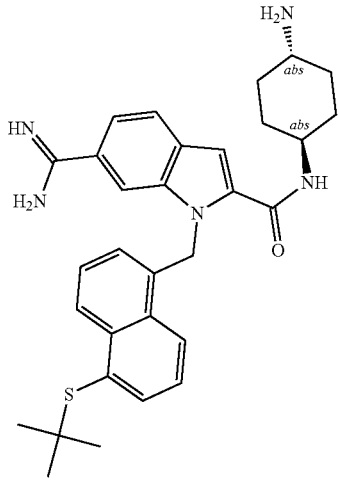 [SMILES: CC(C)(C)Sc1cccc2c(Cn3c(C(=O)N[C@H]4CC[C@H](N)CC4)cc4ccc(C(=N)N)cc43)cccc12] | 6.388 | 99.81 | 528.3 | B | D |
| I-740 | 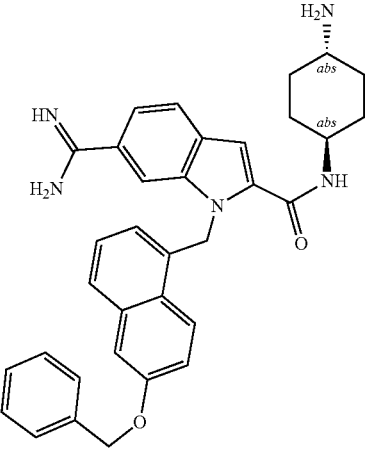 [SMILES: N=C(N)c1ccc2cc(C(=O)N[C@H]3CC[C@H](N)CC3)n(Cc3cccc4cc(OCc5ccccc5)ccc34)c2c1] | 5.309 | 99.25 | 546.25 | B | D |
| I-741 | 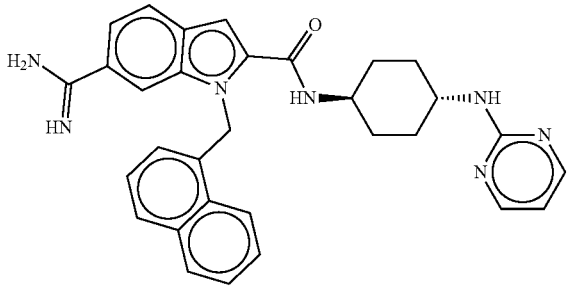 | 5.814 | 98.36 | 518.3 | B | C |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-742 | 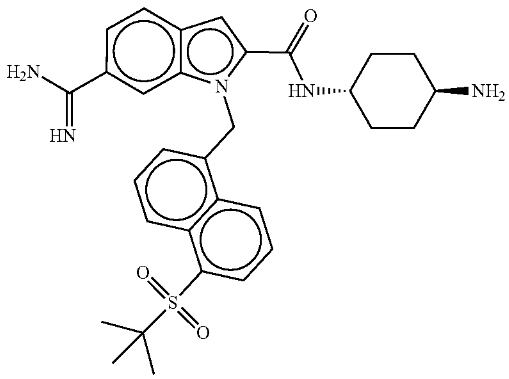 | 5.884 | 99.89 | 560.3 | B | C |
| I-743 | 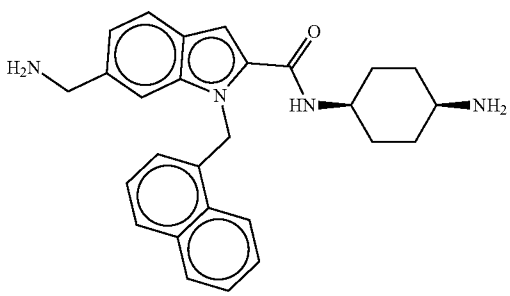 | 6.239 | 98.36 | 427.40 | B | C |
| I-744 | 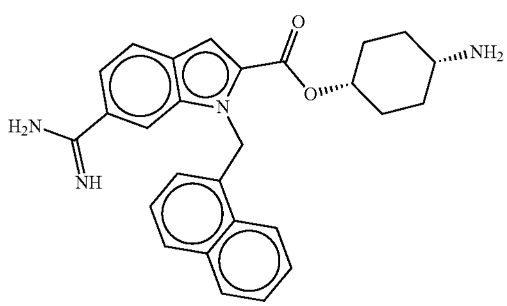 | 5.09 | 99.14 | 441.4 | B | D |
| I-745 | 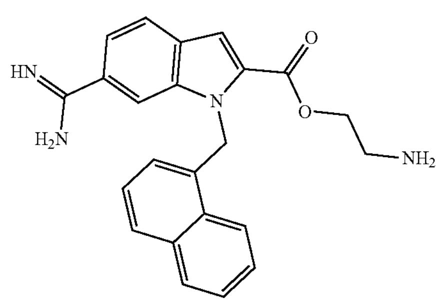 [SMILES: N=C(N)c1ccc2cc(C(=O)OCCN)n(Cc3cccc4ccccc34)c2c1] | 4.89 | 99.09 | 387.2 | B | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-746 | 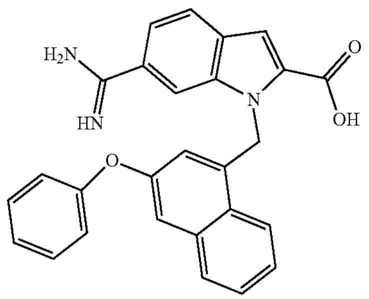 [SMILES: N=C(N)c1ccc2cc(C(=O)O)n(Cc3cc(Oc4ccccc4)cc4ccccc34)c2c1] | 7.592 | 99.42 | 436.3 | B | C |
| I-747 | 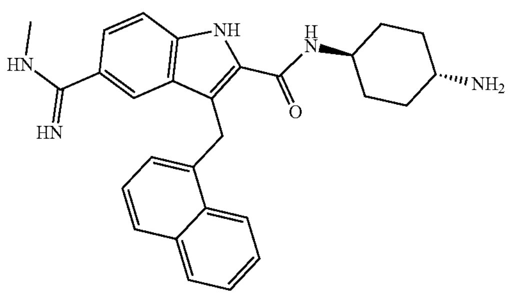 [SMILES: CNC(=N)c1ccc2[nH]c(C(=O)N[C@H]3CC[C@H](N)CC3)c(Cc3cccc4ccccc34)c2c1] | 4.87 | 98.16 | 454.2 | B | A |
| I-748 | 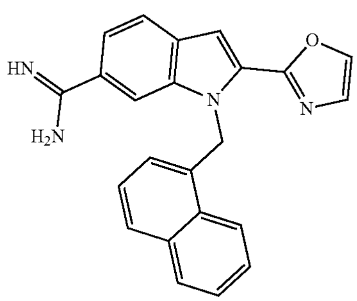 [SMILES: N=C(N)c1ccc2cc(-c3ncco3)n(Cc3cccc4ccccc34)c2c1] | 5.33 | 99.74 | 367.1 | B | D |
| I-749 | 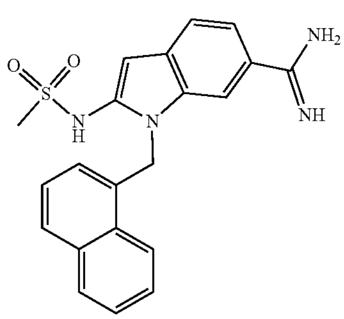 [SMILES: CS(=O)(=O)Nc1cc2ccc(C(=N)N)cc2n1Cc1cccc2ccccc12] | 6.522 | 98.05 | 392.95 | B | C |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-750 | 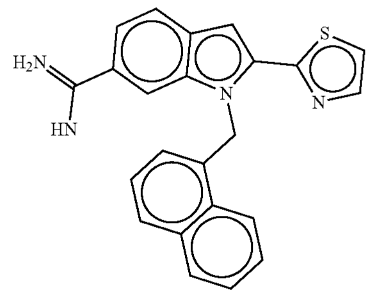 | 5.391 | 99.97 | 383.2 | B | C |
| I-751 | 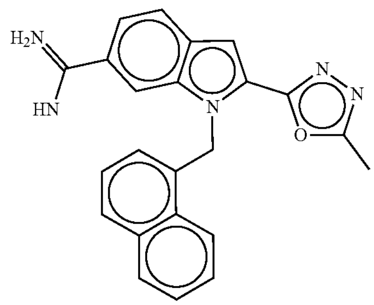 | 5.148 | 97.52 | 382.0 | B | C |
| I-752 | 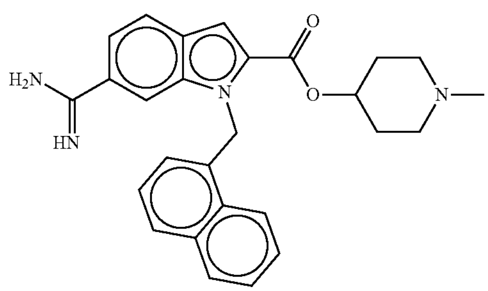 | 5.03 | 93.0 | 441.2 | B | D |
| I-753 | 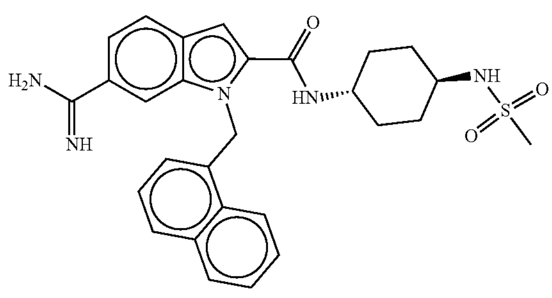 | 5.45 | 97.3 | 518.3 | B | C |
| I-754 | 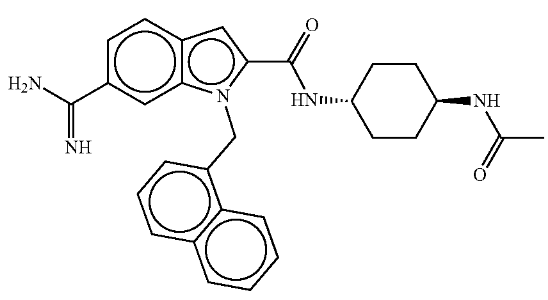 | 5.39 | 96.5 | 482.2 | B | C |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-755 | 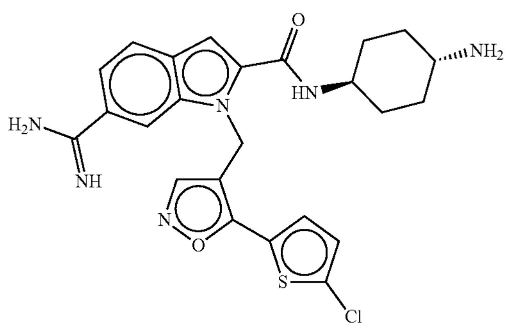 | 4.924 | 98.87 | 497.3 | B | B |
| I-756 | 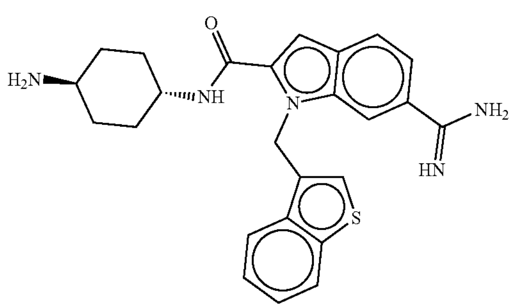 | 4.54 | 99.18 | 446.3 | B | D |
| I-757 | 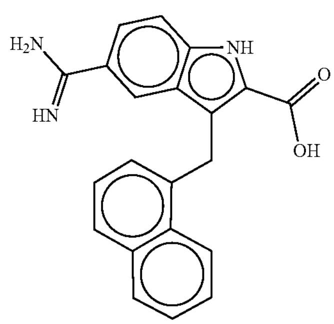 | 6.69 | 98.18 | 344.3 | B | D |
| I-758 | 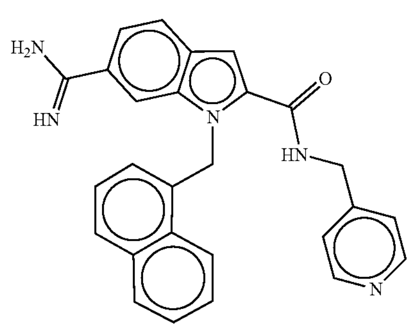 | 4.90 | 98.34 | 434.25 | B | C |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-759 | 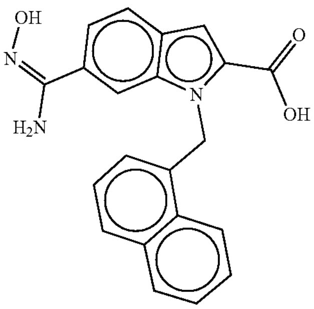 | 5.481 | 98.11 | 360.00 | B | A |
| I-760 | 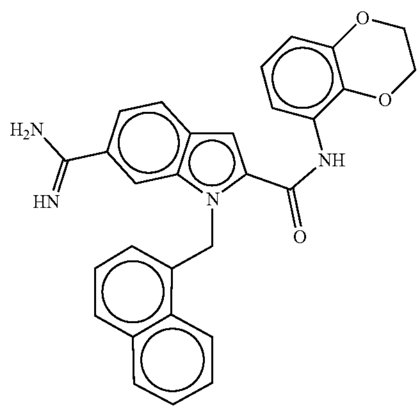 | 6.245 | 98.54 | 477.3 | B | A |
| I-761 | 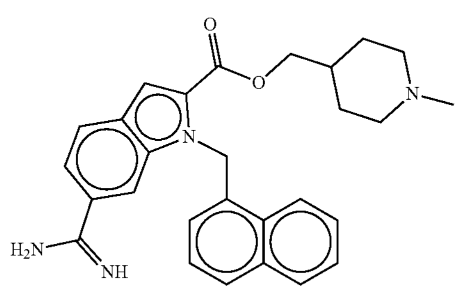 | 5.08 | 98.57 | 455.2 | B | D |
| I-762 | 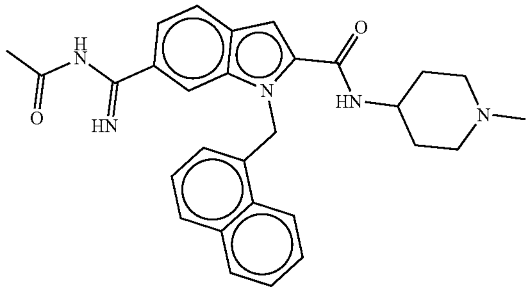 | 6.89 | 98.85 | 483.3 | B | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-763 | 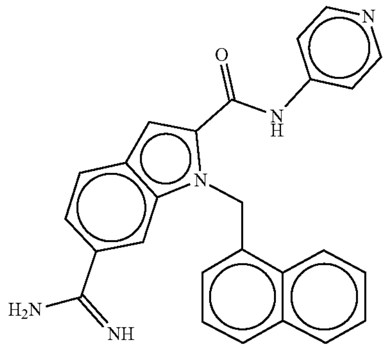 | 5.03 | 98.27 | 420.3 | B | C |
| I-764 | 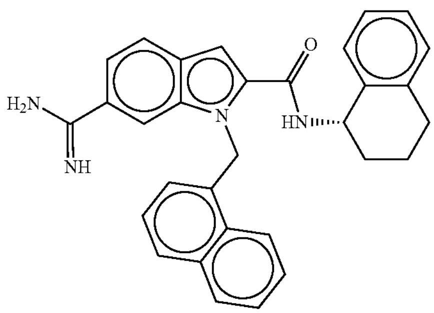 | 5.372 | 98.69 | 473.4 | B | A |
| I-765 | 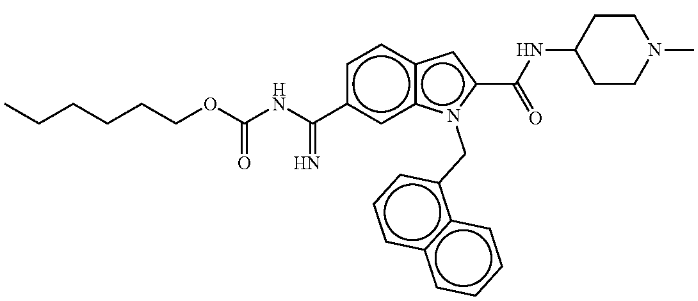 | 5.708 | 96.31 | 568.30 | B | A |
| I-766 | 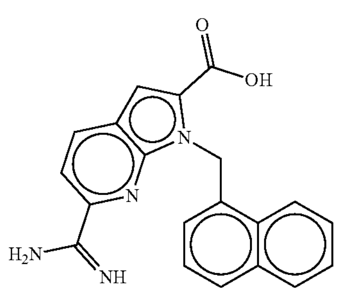 | 6.750 | 98.21 | 345.30 | B | D |

TABLE A-continued
Exemplary Compounds
| Cpd. ID. | Structure | HPLC Rt-min | % Purity-Indole | M + H | Assay Used | Mar-2 % inhibition at 1 uM |
|---|---|---|---|---|---|---|
| I-767 | 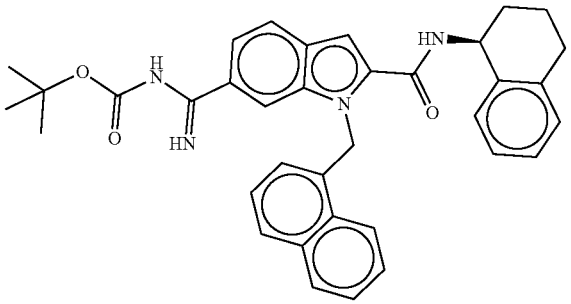 | 14.854 | 92.61 | 573.00 | B | A |
| I-768 | 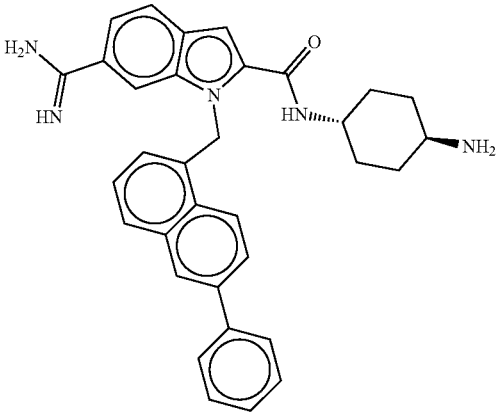 | 4.89 | 98.28 | 516.2 | B | D |
| I-769 | 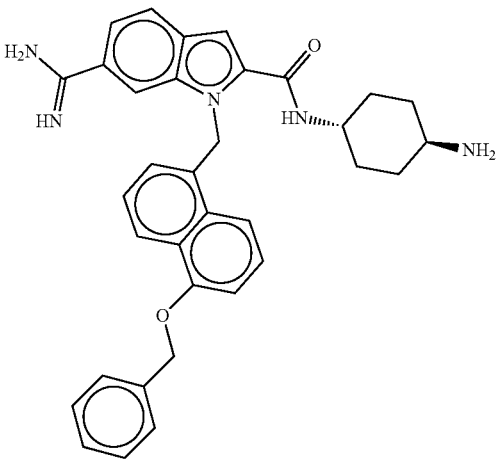 | 4.95 | 98.59 | 546.3 | B | D |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-770 | 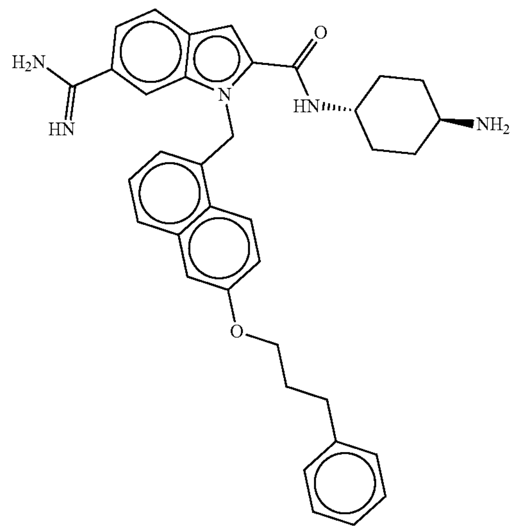 | 5.15 | 97.01 | 574.2 | B | C |
| I-771 | 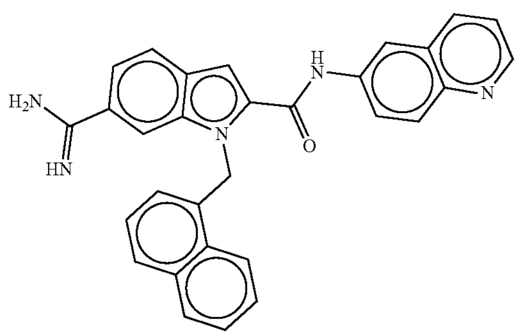 | 5.431 | 95.906 | 470.0 | B | B |
| I-772 | 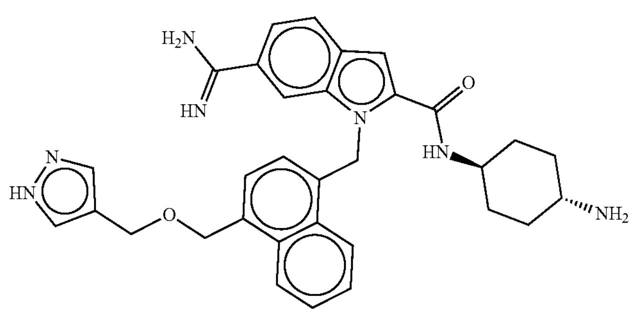 | 4.39 | 98.34 | 550.2 | B | D |
| I-773 | 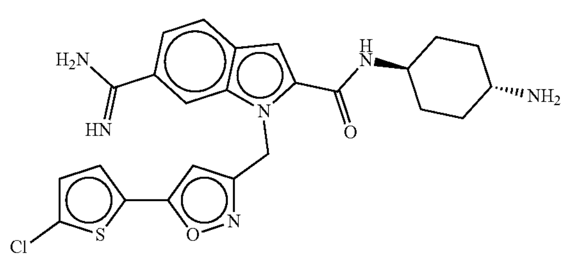 | 5.008 | 97.24 | 497.1 | B | C |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-774 | 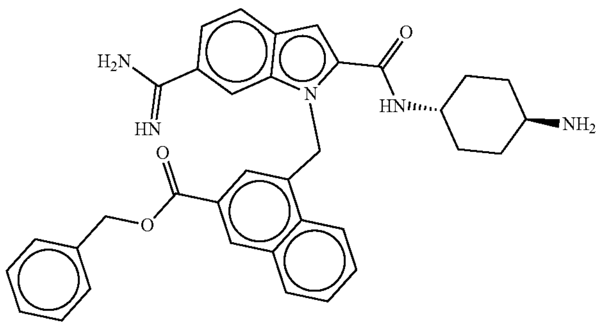 | 5.104 | 97.31 | 574.1 | B | D |
| I-775 | 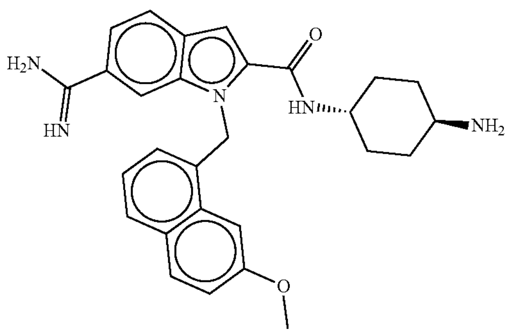 | 4.82 | 98.8 | 470.2 | B | D |
| I-776 | 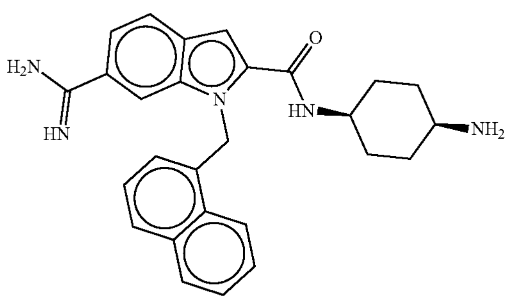 | 4.593 | 93.56 | 441.10 | B | D |
| I-777 | 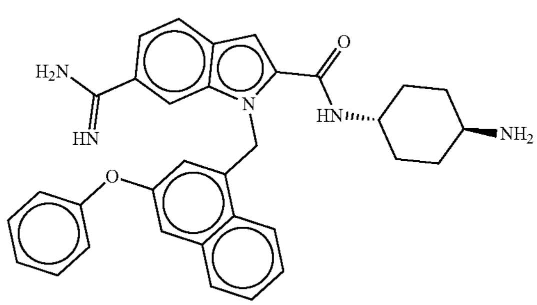 | 5.661 | 99.35 | 532.3 | B | D |

TABLE A-continued
Exemplary Compounds
| Cpd. ID. | Structure | HPLC Rt-min | % Purity-Indole | M + H | Assay Used | Mar-2 % inhibition at 1 uM |
|---|---|---|---|---|---|---|
| I-778 | 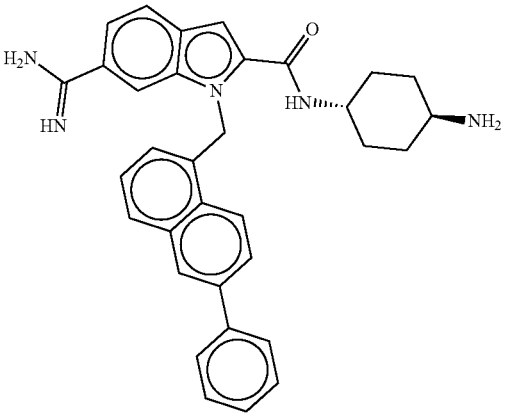 | 4.901 | 99.32 | 516.2 | B | C |
| I-779 | 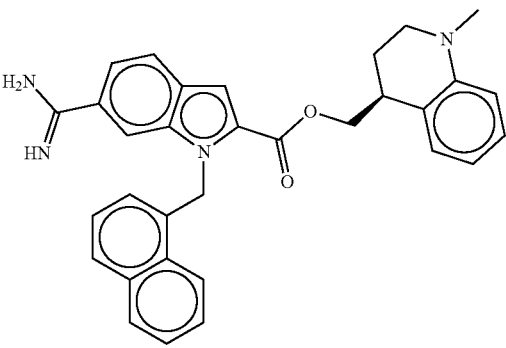 | 6.295 | 95.52 | 503.1 | B | B |
| I-780 | 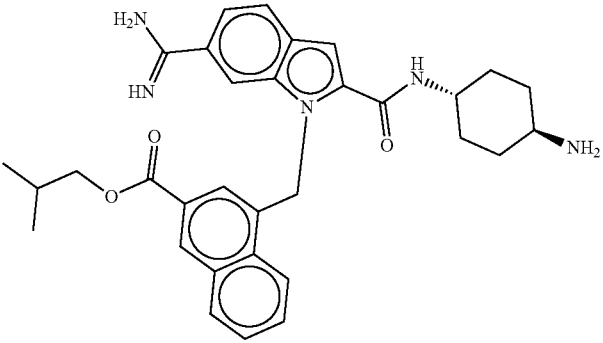 | 4.819 | 98.72 | 540.1 | B | D |
| I-781 | 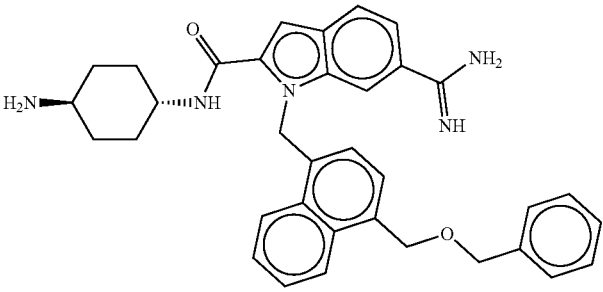 | 6.43 | 98.06 | 560.2 | B | D |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-782 | 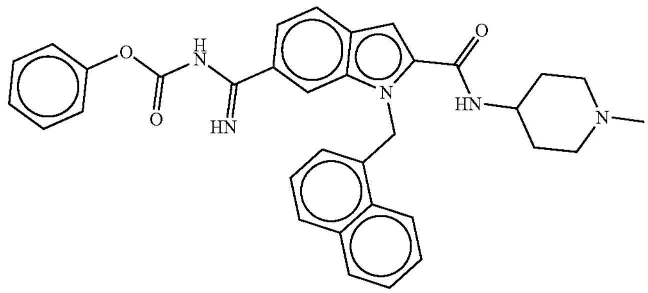 | 5.521 | 86.50 | 560.2 | B | C |
| I-783 | 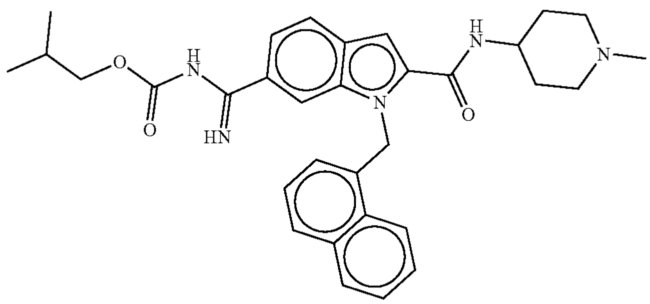 | 5.992 | 94.35 | 540.2 | B | A |
| I-784 | 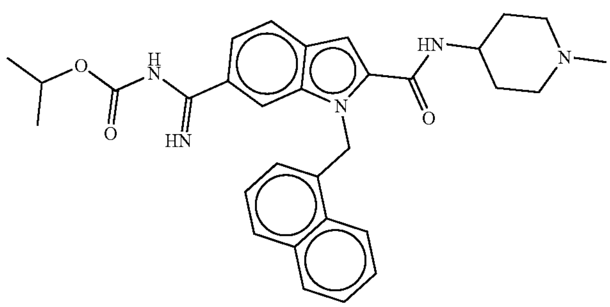 | 4.615 | 94.2 | 526.40 | B | B |
| I-785 | 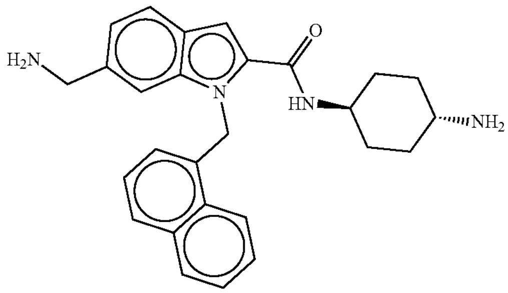 | 4.336 | 95.28 | 428.0 | B | C |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-786 | 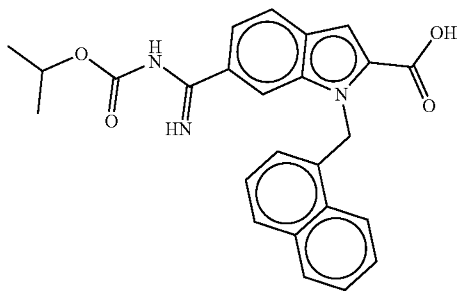 | 6.604 | 96.91 | 430.25 | B | A |
| I-787 | 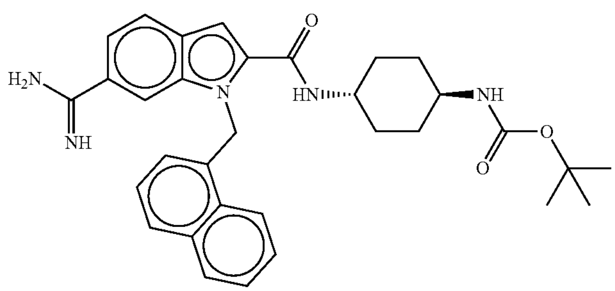 | 6.096 | 96.50 | 540.40 | B | A |
| I-788 | 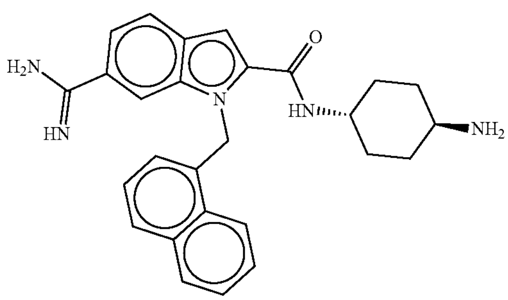 | 4.849 | 96.86 | 441.10 | B | C |
| I-789 | 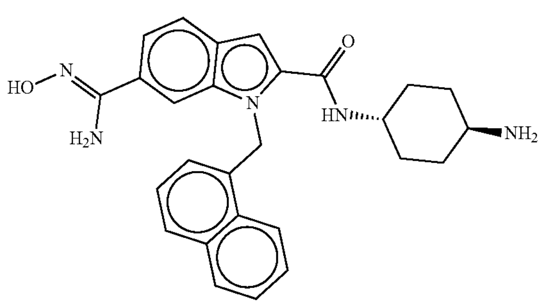 | 5.123 | 95.25 | 457.20 | B | A |

TABLE A-continued
Exemplary Compounds
| Cpd. ID. | Structure | HPLC Rt-min | % Purity-Indole | M + H | Assay Used | Mar-2 % inhibition at 1 uM |
|---|---|---|---|---|---|---|
| I-790 | 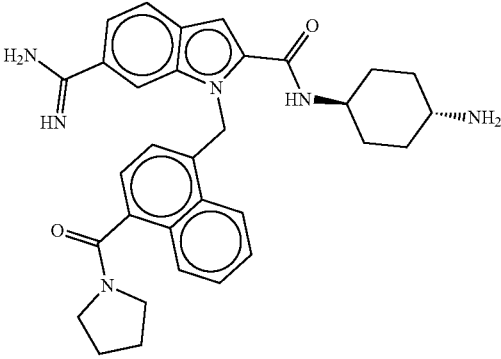 | 4.70 | 98.80 | 537.3 | B | B |
| I-791 | 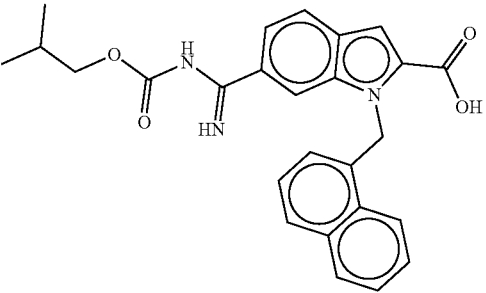 | 3.501 | 98.06 | 444.25 | B | A |
| I-792 | 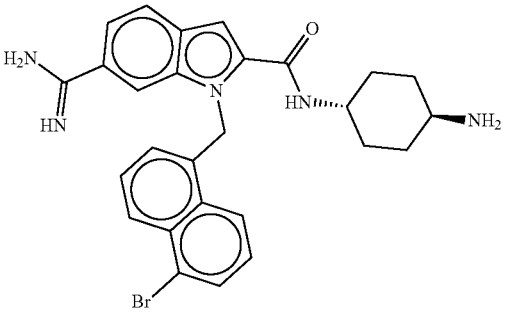 | 4.960 | 98.13 | 520.0 | B | D |
| I-793 | 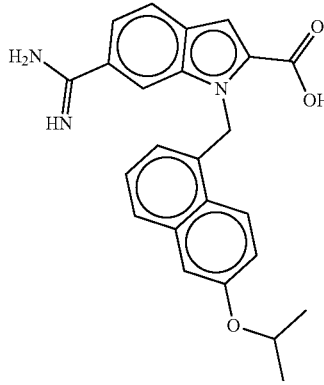 | 5.38 | 99.09 | 402.2 | B | C |

TABLE A-continued
Exemplary Compounds
| Cpd. ID. | Structure | HPLC Rt-min | % Purity-Indole | M + H | Assay Used | Mar-2 % inhibition at 1 uM |
|---|---|---|---|---|---|---|
| I-794 | 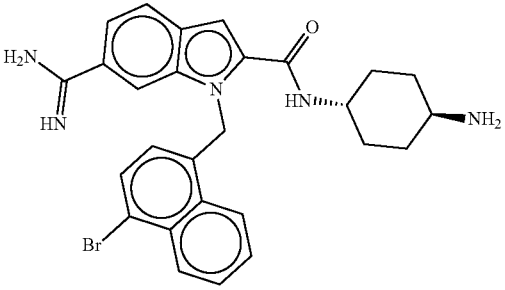 | 5.019 | 98.17 | 518.15 | B | D |
| I-795 | 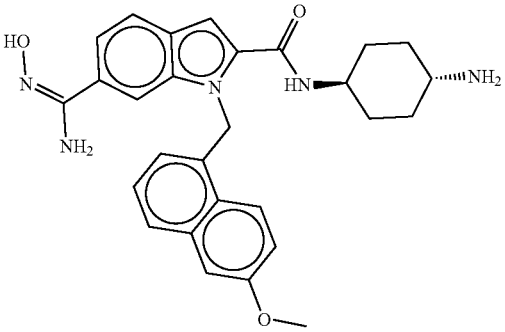 | 4.49 | 99.17 | 486.2 | B | A |
| I-796 | 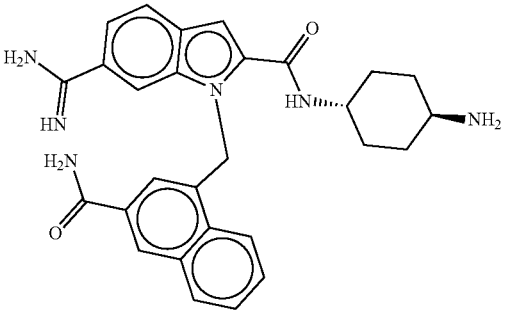 | 4.697 | 96.39 | 483.3 | B | C |
| I-797 | 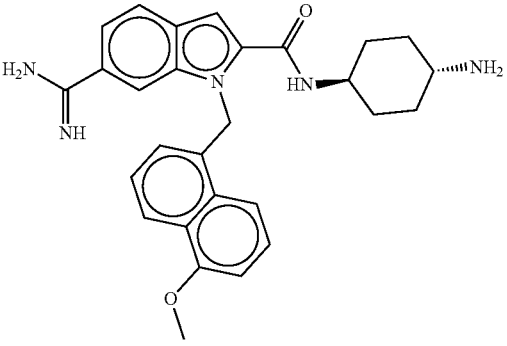 | 4.501 | 97.08 | 470.10 | B | D |

TABLE A-continued

Exemplary Compounds

| Cpd. ID. | Structure | HPLC Rt- min | % Purity- Indole | M + H | Assay Used | Mar-2 % inhibition at 1 uM |
|---|---|---|---|---|---|---|
| I-798 | 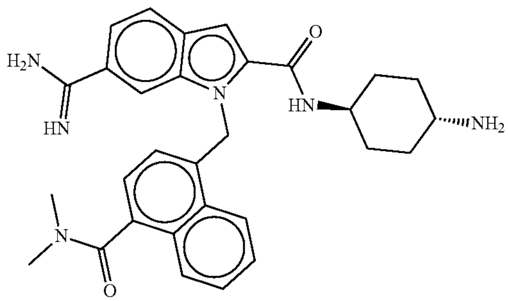 | 5.502 | 98.4 | 511.25 | B | C |
| I-799 | 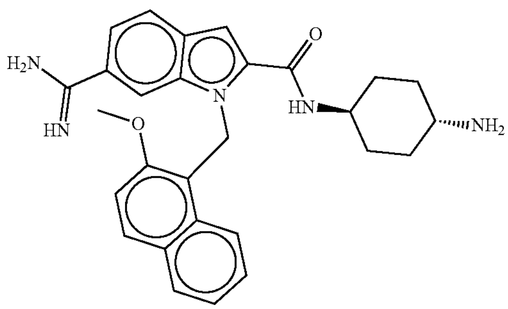 | 5.467 | 99.3 | 470.2 | B | A |
| I-800 | 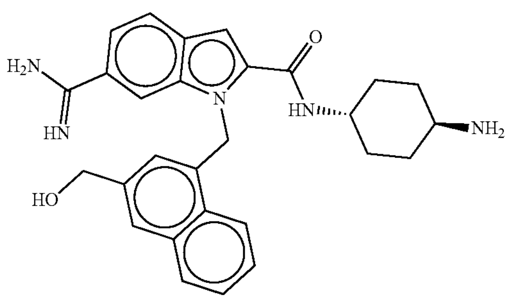 | 5.527 | 98.10 | 470.3 | B | B |
| I-801 | 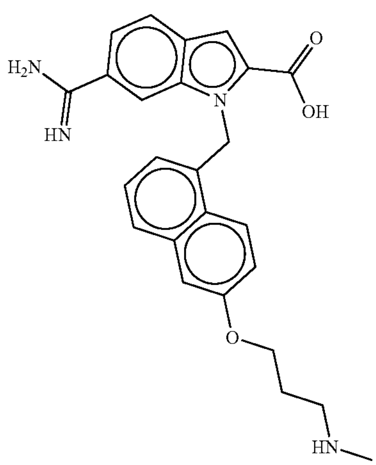 | 4.80 | 95.06 | 431.1 | B | C |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-802 | 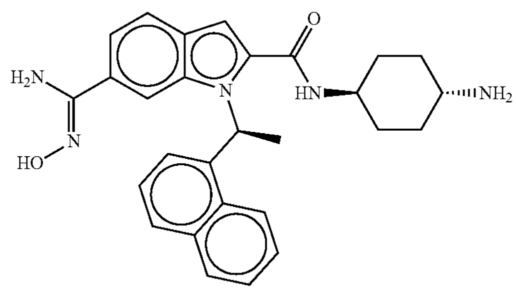 | 5.781 | 96.58 | 470.2 | B | A |
| I-803 | 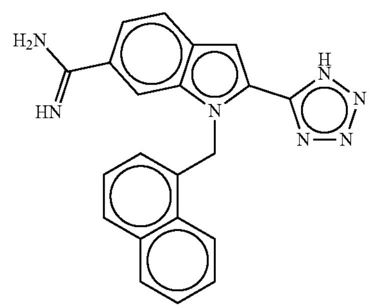 | 5.221 | 95.77 | 368.15 | B | D |
| I-804 | 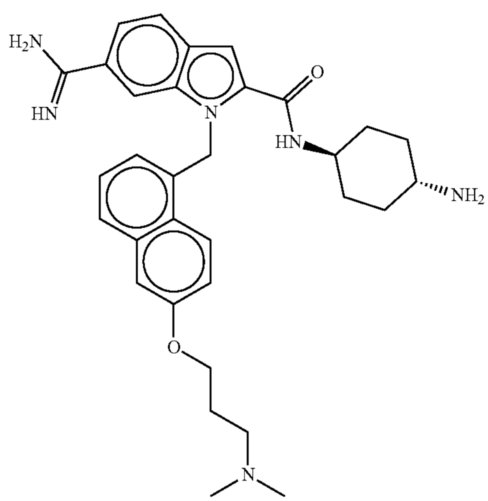 | 5.34 | 98.70 | 541.3 | B | D |
| I-805 | 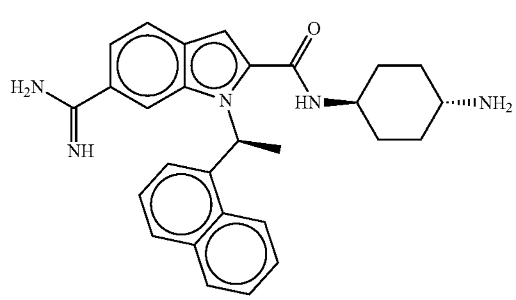 | 6.132 | 98.18 | 454.1 | B | A |

TABLE A-continued
Exemplary Compounds
| Cpd. ID. | Structure | HPLC Rt-min | % Purity-Indole | M + H | Assay Used | Mar-2 % inhibition at 1 uM |
|---|---|---|---|---|---|---|
| I-806 | 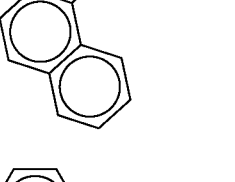 | 4.635 | 99.80 | 484.1 | B | C |
| I-807 | 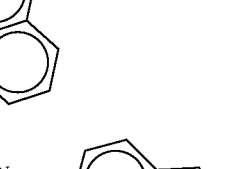 | 4.615 | 98.13 | 470.1 | B | D |
| I-808 | 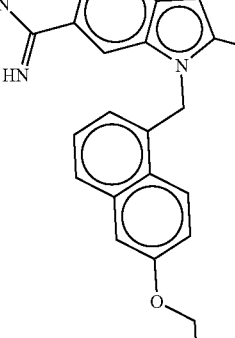 | 5.10 | 99.71 | 445.2 | B | C |
| I-809 | 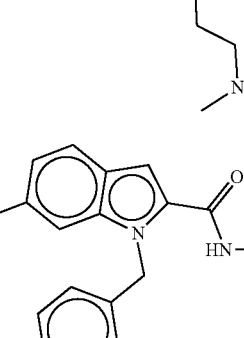 | 5.75 | 98.62 | 442.25 | B | B |

TABLE A-continued

Exemplary Compounds

| Cpd. ID. | Structure | HPLC Rt- min | % Purity- Indole | M + H | Assay Used | Mar-2 % inhibition at 1 uM |
|---|---|---|---|---|---|---|
| I-810 | 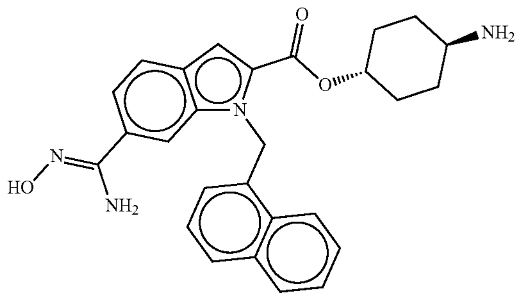 | 5.021 | 98.69 | 457.15 | B | B |
| I-811 | 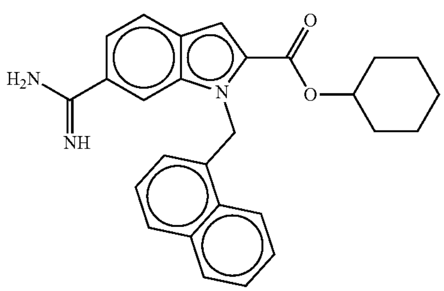 | 6.795 | 95.48 | 426.10 | B | B |
| I-812 | 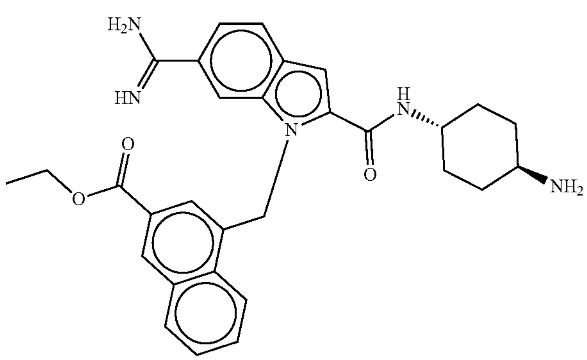 | 6.026 | 97.04 | 512.3 | B | D |
| I-813 | 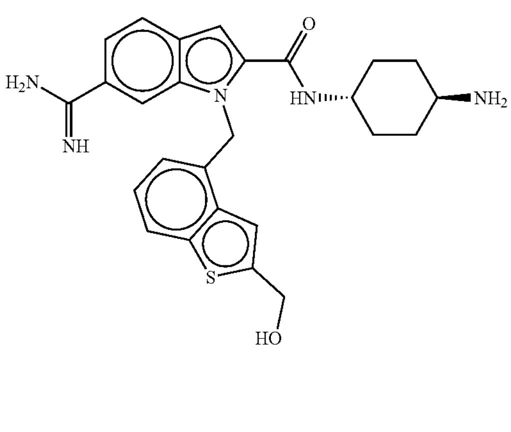 | 4.793 | 97.05 | 476.20 | B | C |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-814 | 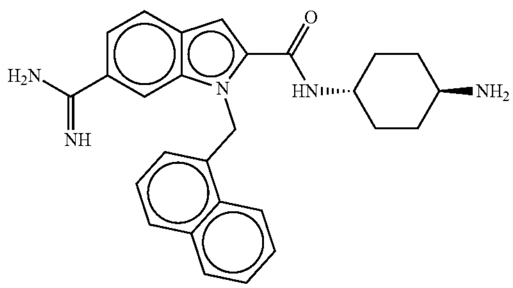 | 5.153 | 99.796 | 444.25 | B | B |
| I-815 | 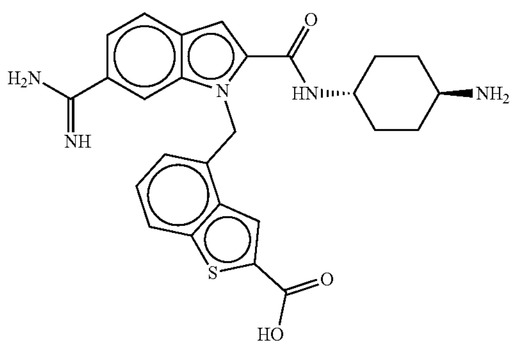 | 4.834 | 97.55 | 490.30 | B | C |
| I-816 | 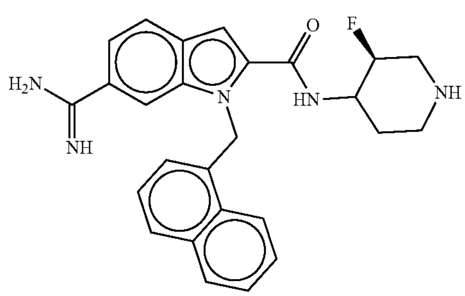 | | | 444 | B | D |
| I-817 | 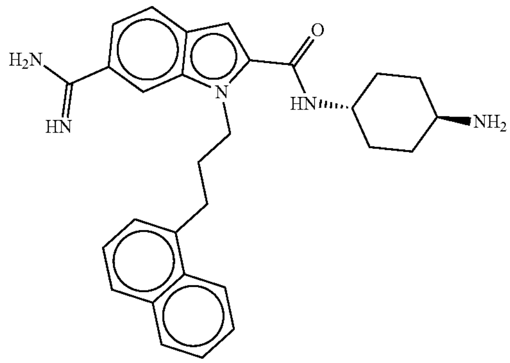 | 6.07 | 98.16 | 468.2 | B | A |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-818 | 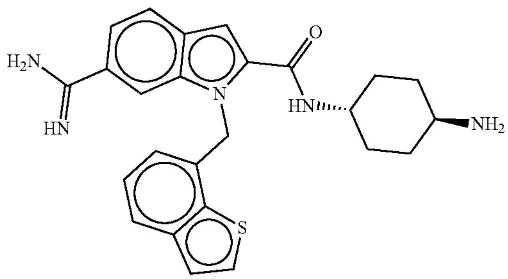 | 5.68 | 98.86 | 446.3 | B | C |
| I-819 | 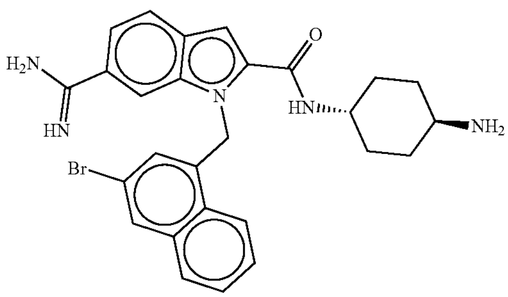 | 6.024 | 98.11 | 520.2 | B | D |
| I-820 | 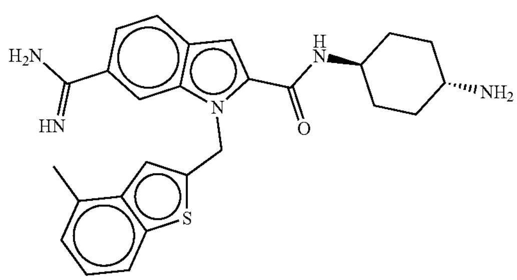 | 4.677 | 99.20 | 460.15 | B | B |
| I-821 | 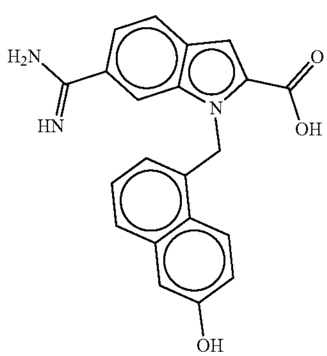 | 5.08 | 98.2 | 360.1 | B | D |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-822 | 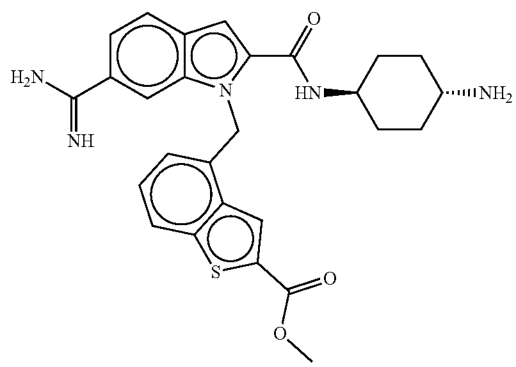 | 5.043 | 99.84 | 504.10 | B | C |
| I-823 | 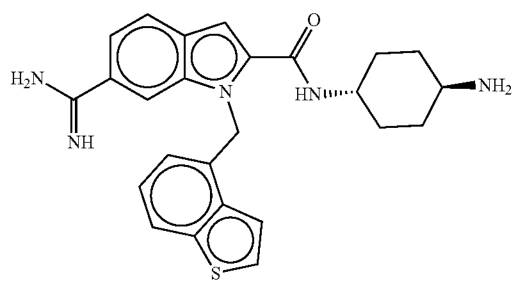 | 5.206 | 99.64 | 446.10 | B | C |
| I-824 | 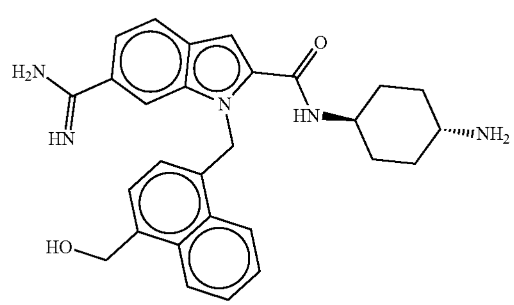 | 5.04 | 99.5 | 470.4 | B | D |
| I-825 | 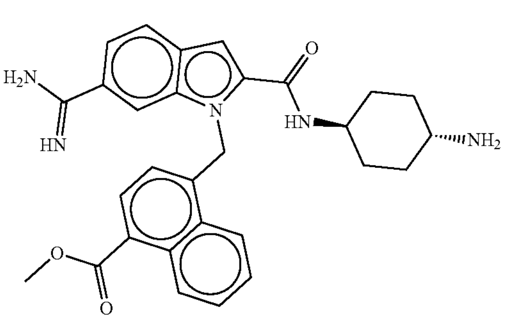 | 5.35 | 99.8 | 498.1 | B | D |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-826 | 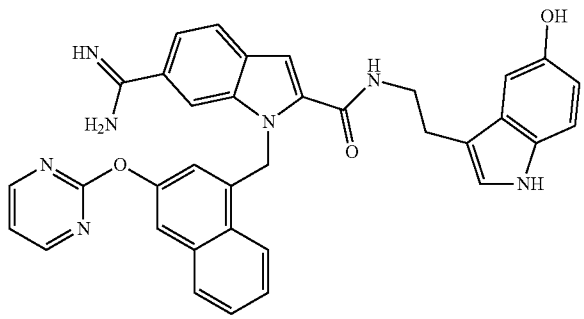 [SMILES: N=C(N)c1ccc2cc(C(=O)NCCc3c[nH]c4ccc(O)cc34)n(Cc3cc(Oc4ncccn4)cc4ccccc34)c2c1] | 6.01 | 96.13 | 596.3 | B | B |
| I-827 | 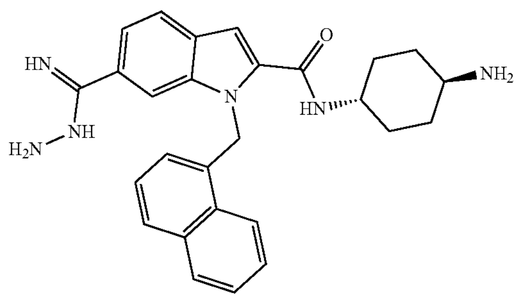 [SMILES: N=C(NN)c1ccc2cc(C(=O)N[C@H]3CC[C@H](N)CC3)n(Cc3cccc4ccccc34)c2c1] | 5.60 | 93.2 | 455.3 | B | B |
| I-828 | 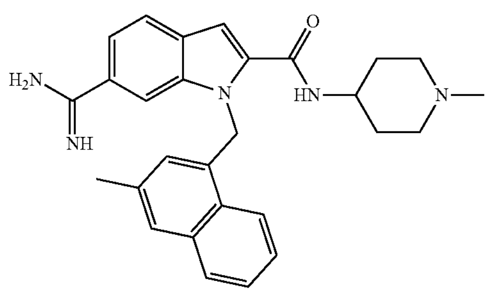 [SMILES: Cc1cc(Cn2c(C(=O)NC3CCN(C)CC3)cc3ccc(C(=N)N)cc32)c2ccccc2c1] | | | | | |
| I-829 | 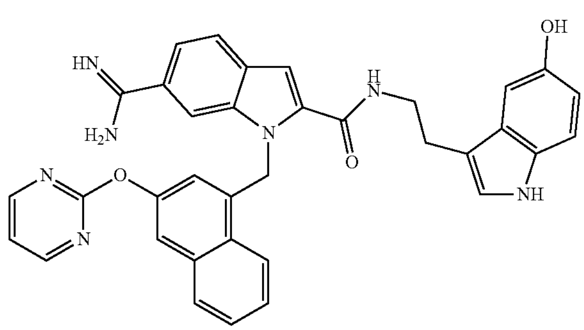 [SMILES: N=C(N)c1ccc2cc(C(=O)NCCc3c[nH]c4ccc(O)cc34)n(Cc3cc(Oc4ncccn4)cc4ccccc34)c2c1] | | | | | |

TABLE A-continued

Exemplary Compounds

| Cpd. ID. | Structure | HPLC Rt- min | % Purity- Indole | M + H | Assay Used | Mar-2 % inhibition at 1 uM |
|---|---|---|---|---|---|---|
| I-830 | 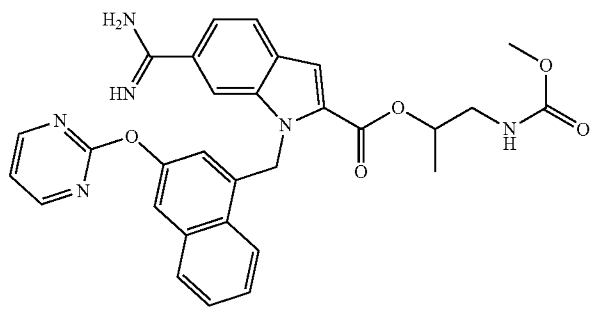 [SMILES: COC(=O)NCC(C)OC(=O)c1cc2ccc(C(=N)N)cc2n1Cc1cc(Oc2ncccn2)cc2ccccc12] | | | | | |
| I-831 | 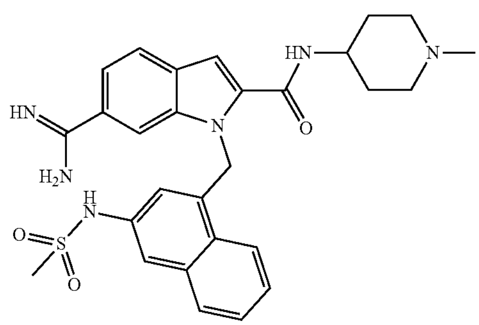 [SMILES: CN1CCC(NC(=O)c2cc3ccc(C(=N)N)cc3n2Cc2cc(NS(C)(=O)=O)cc3ccccc23)CC1] | | | | | |
| I-832 | 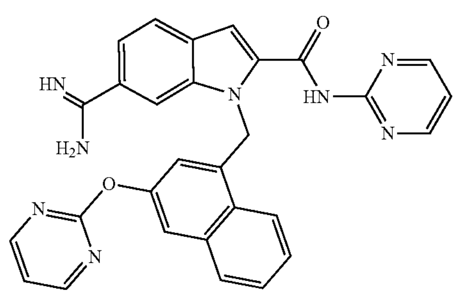 [SMILES: N=C(N)c1ccc2cc(C(=O)Nc3ncccn3)n(Cc3cc(Oc4ncccn4)cc4ccccc34)c2c1] | | | | | |
| I-833 | 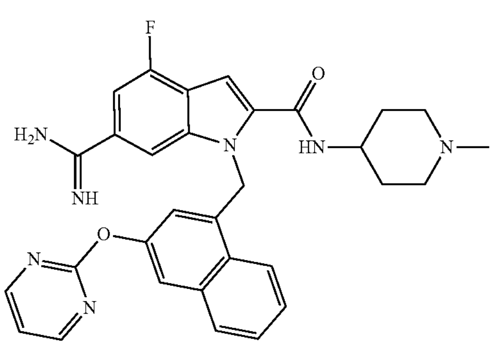 [SMILES: CN1CCC(NC(=O)c2cc3c(F)cc(C(=N)N)cc3n2Cc2cc(Oc3ncccn3)cc3ccccc23)CC1] | | | | | |

TABLE A-continued

Exemplary Compounds

| Cpd. ID. | Structure | HPLC Rt- min | % Purity- Indole | M + H | Assay Used | Mar-2 % inhibition at 1 uM |
|---|---|---|---|---|---|---|
| I-834 | 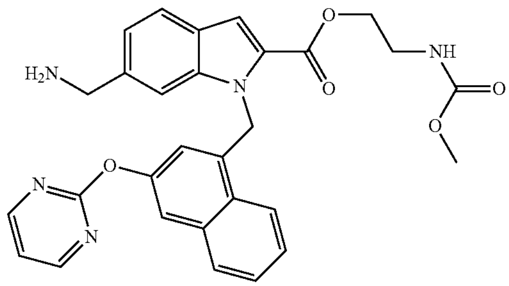 [SMILES: COC(=O)NCCOC(=O)c1cc2ccc(CN)cc2n1Cc1cc(Oc2ncccn2)cc2ccccc12] | | | | | |
| I-835 | 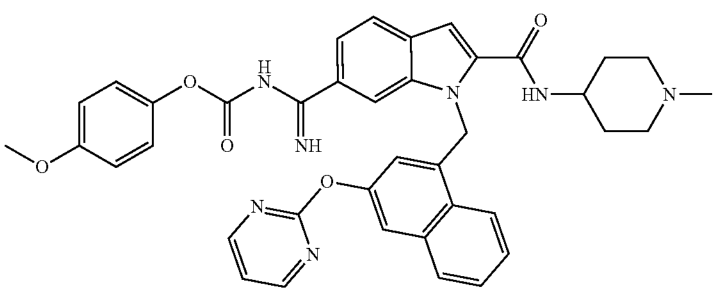 | | | | | |
| I-836 | 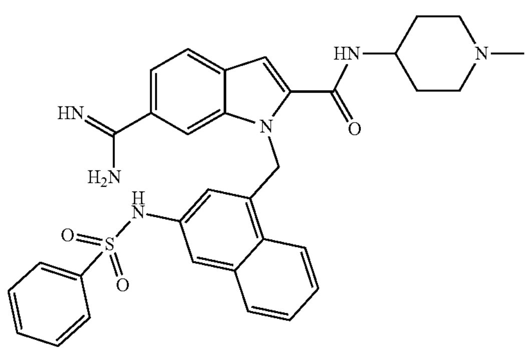 [SMILES: CN1CCC(NC(=O)c2cc3ccc(C(=N)N)cc3n2Cc2cc(NS(=O)(=O)c3ccccc3)cc3ccccc23)CC1] | | | | | |
| I-837 | 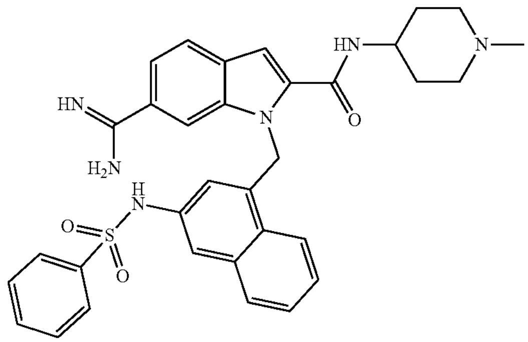 [SMILES: CN1CCC(NC(=O)c2cc3ccc(C(=N)N)cc3n2Cc2cc(NS(=O)(=O)c3ccccc3)cc3ccccc23)CC1] | | | | | |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-838 | 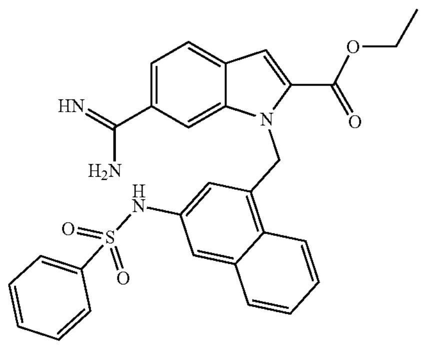 [SMILES: CCOC(=O)c1cc2ccc(C(=N)N)cc2n1Cc1cc(NS(=O)(=O)c2ccccc2)cc2ccccc12] | | | | | |
| I-839 | 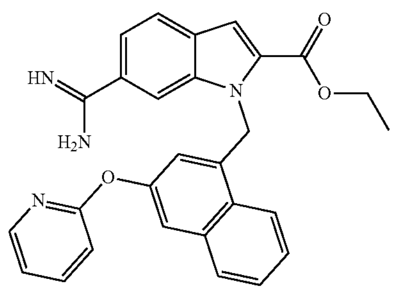 [SMILES: CCOC(=O)c1cc2ccc(C(=N)N)cc2n1Cc1cc(Oc2ccccn2)cc2ccccc12] | | | | | |
| I-840 | 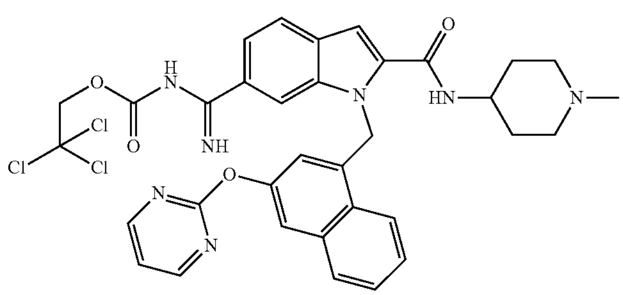 [SMILES: CN1CCC(NC(=O)c2cc3ccc(C(=N)NC(=O)OCC(Cl)(Cl)Cl)cc3n2Cc2cc(Oc3ncccn3)cc3ccccc23)CC1] | | | | | |
| I-841 | 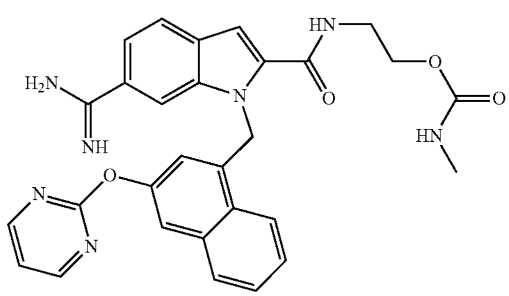 [SMILES: CNC(=O)OCCNC(=O)c1cc2ccc(C(=N)N)cc2n1Cc1cc(Oc2ncccn2)cc2ccccc12] | | | | | |

TABLE A-continued

Exemplary Compounds

| Cpd. ID. | Structure | HPLC Rt-min | % Purity-Indole | M + H | Assay Used | Mar-2 % inhibition at 1 uM |
|---|---|---|---|---|---|---|
| I-842 | 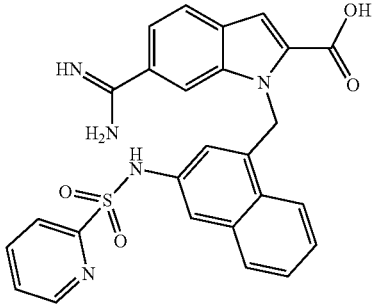 [SMILES: N=C(N)c1ccc2cc(C(=O)O)n(Cc3cc(NS(=O)(=O)c4ccccn4)cc4ccccc34)c2c1] | | | | | |
| I-843 | 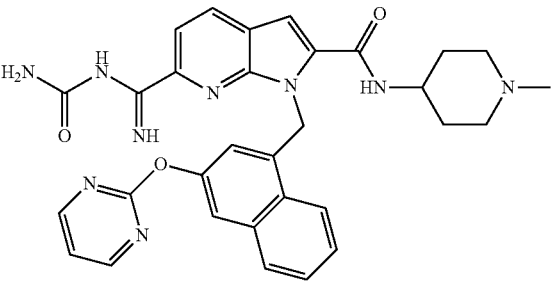 [SMILES: CN1CCC(NC(=O)c2cc3ccc(C(=N)NC(N)=O)nc3n2Cc2cc(Oc3ncccn3)cc3ccccc23)CC1] | | | | | |
| I-844 | 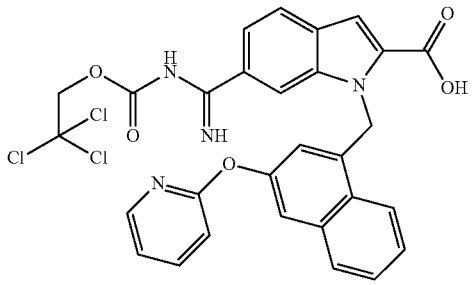 [SMILES: N=C(NC(=O)OCC(Cl)(Cl)Cl)c1ccc2cc(C(=O)O)n(Cc3cc(Oc4ccccn4)cc4ccccc34)c2c1] | | | | | |

Definition of % inhibition (I) range at 1 uM:
0% ≤ I < 25% = A;
25% ≤ I < 50% = B;
50% ≤ I < 75% = C;
75% ≤ I ≤ 100% = D.

In some embodiments, the present invention provides a compound set forth in Table A, above, or a pharmaceutically acceptable salt thereof.

In some embodiments, the present invention provides a compound described in the examples below, or a pharmaceutically acceptable salt thereof.

In some embodiments, a compound of the invention is not:

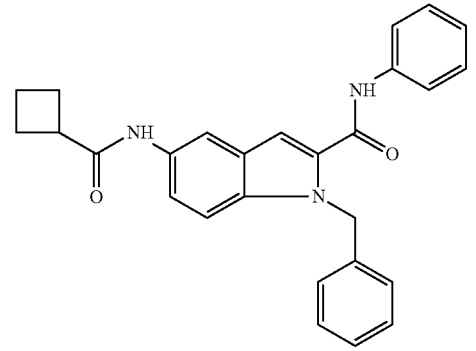

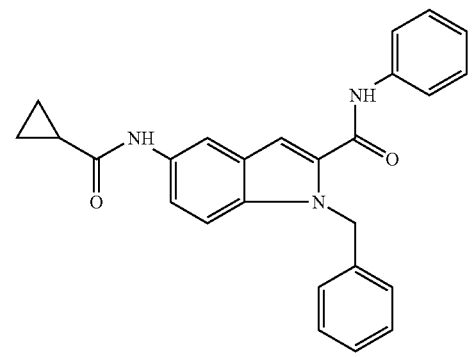

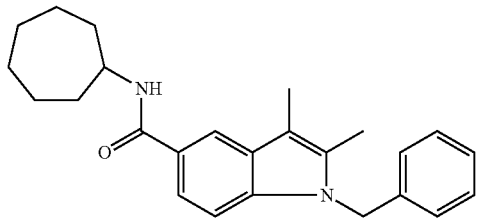

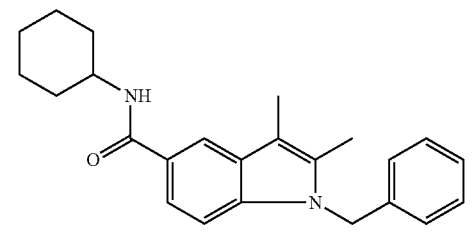

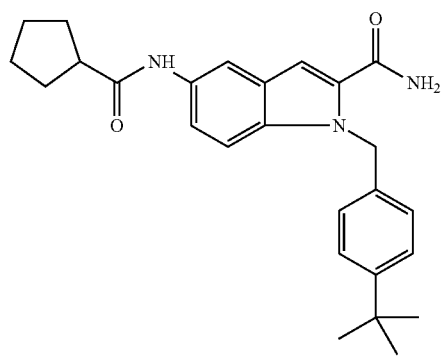

-continued

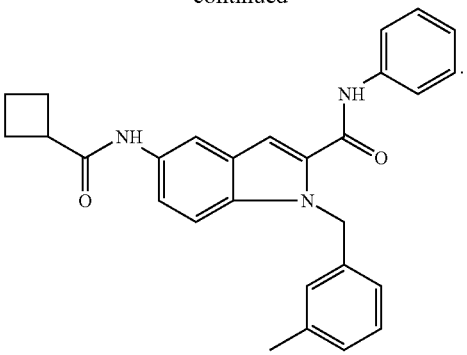

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit Matriptase 2, or a mutant thereof, in a biological sample or in a patient. In certain embodiments, the amount of compound in compositions of this invention is such that is effective to measurably inhibit Matriptase 2, or a mutant thereof, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of Matriptase 2, or a mutant thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the inhibition of Matriptase 2, or a mutant thereof.

The activity of a compound utilized in this invention as an inhibitor of Matriptase 2, or a mutant thereof, may be assayed in vitro, in vivo or in a cell line. In vitro assays include assays that determine inhibition of Matriptase 2, or a mutant thereof. Alternate in vitro assays quantitate the ability of the inhibitor to bind to Matriptase 2, or a mutant thereof. Detailed conditions for assaying a compound utilized in this invention as an inhibitor of Matriptase 2, or a mutant thereof, are set forth in the Examples below.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

As used herein, the terms "low hepcidin" disorders, diseases, and/or conditions as used herein means any disease or other deleterious condition in which absolute or relative hepcidin deficiency is known to play a role, or in which an increase in hepcidin may be therapeutically useful.

Provided compounds are inhibitors of Matriptase 2, or a mutant thereof, and are therefore useful for treating low hepcidin disorders, diseases, and/or conditions. Accordingly, in certain embodiments, the present invention provides a method for treating a low hepcidin disorder, disease, and/or condition, comprising the step of administering to a patient in need thereof a compound of the present invention, or pharmaceutically acceptable composition thereof.

Without wishing to be bound by any specific theory, inhibition of Matriptase-2 has been found to lead to increased hepcidin production by the liver. Accordingly, in some embodiments, the present invention provides a method for increasing hepcidin production by the liver in a patient, comprising the step of administering to the patient a compound of the present invention, or pharmaceutically acceptable composition thereof. In some embodiments, the present invention provides a method for treating absolute and/or relative hepcidin deficiency in a patient, comprising the step of administering to the patient a compound of the present invention, or pharmaceutically acceptable composition thereof. In some embodiments, the present invention provides a method for treating hepcidin underproduction in a patient, comprising the step of administering to the patient a compound of the present invention, or pharmaceutically acceptable composition thereof. In some embodiments, the present invention provides a method for treating excess or increased iron absorption or accumulation in a patient, comprising the step of administering to the patient a compound of the present invention, or pharmaceutically acceptable composition thereof in order to increase hepcidin production by the liver. In some embodiments, the present invention provides a method for treating ineffective erythropoiesis in a patient, comprising the step of administering to the patient a compound of the present invention, or pharmaceutically acceptable composition thereof.

In some embodiments, the present invention provides a method for treating one or more iron overload disorder, disease, and/or condition, comprising the step of administering to a patient in need thereof a compound of the present invention, or pharmaceutically acceptable composition thereof.

As used herein, the term "iron overload disorder, disease, and/or condition" refers to a condition, disease, or disorder associated with excessive iron levels or iron overload. Large amounts of free iron in the bloodstream can lead to cell damage, especially in the liver, heart and endocrine glands. The causes of excess iron may be genetic, for example the iron excess may be caused by a genetic condition such as hemochromatosis type 1 (classical hemochromatosis), hemochromatosis type 2A or 2B (juvenile hemochromatosis), hemochromatosis type 3, African iron overload, neonatal hemochromatosis, aceruloplasminemia, or congenital atransferrinemia. Examples of non-genetic causes of iron excess include dietary iron overload (including African iron overload), transfusional iron overload (due to a blood transfusion given to patients with thalassaemia or other congenital hematological disorders), hemodialysis, chronic liver disease (such as hepatitis C, cirrhosis, non-alcoholic steatohepatitis), porphyria cutanea tarda, post-portacaval shunting, dysmetabolic overload syndrome, iron tablet overdose (such as that caused by consumption by children of iron tablets intended for adults), or any other cause of acute or chronic iron overload.

In some embodiments, an iron overload disorder, disease, and/or condition is Hemochromatosis Type 1. In some embodiments, an iron overload disorder, disease, and/or condition is Hemochromatosis Type 2a. In some embodiments, an iron overload disorder, disease, and/or condition is Hemochromatosis Type 2b. In some embodiments, an iron overload disorder, disease, and/or condition is Hemochromatosis Type 3.

In some embodiments, an iron overload disorder, disease, and/or condition is hepcidin deficiency. In some embodiments, an iron overload disorder, disease, and/or condition is Transfusional iron overload. In some embodiments, an iron overload disorder, disease, and/or condition is African iron overload. In some embodiments, an iron overload disorder, disease, and/or condition is Iron overload cardiomyopathy.

In some embodiments, the present invention provides a method for treating one or more iron loading anemia, comprising the step of administering to a patient in need thereof a compound of the present invention, or pharmaceutically acceptable composition thereof. In some embodiments, an Iron Loading Anemia is beta thalassemia, HbE/beta thalassemia, or other variants thereof, including but not limited to: thalassemia major, thalassemia intermedia, thalassemia minor, non-transfusion dependent thalassemia, and transfusion-dependent thalassemia. In some embodiments, an iron loading anemia is associated with, and/or caused by, alpha thalassemia. In some embodiments, an iron loading anemia is congenital dyserythropoietic anemia Type I and/or Type II. In some embodiments, an iron loading anemia is pyruvate kinase deficiency. In some embodiments, an iron loading anemia is myelodyplasia including but not limited to myelodysplastic syndrome (MDS), RARS and/or SF3B1 associated MDS.

In some embodiments, the present invention provides a method for treating one or more hematological disease, disorder, and/or condition, comprising the step of administering to a patient in need thereof a compound of the present invention, or pharmaceutically acceptable composition thereof. In some embodiments, a hematological disease, disorder, and/or condition is sickle cell disease. In some embodiments, a hematological disease, disorder, and/or condition is sickle cell anemia. In some embodiments, a hematological disease, disorder, and/or condition is polycythemia vera. In some embodiments, a hematological disease, disorder, and/or condition is sideroblastic anemia. In some embodiments, a hematological disease, disorder, and/or condition is bone marrow transplantation.

In some embodiments, the present invention provides a method for treating one or more liver disease, comprising the step of administering to a patient in need thereof a compound of the present invention, or pharmaceutically acceptable composition thereof. In some embodiments, a liver disease is Hepatitis B. In some embodiments, a liver disease is Hepatitis C or other forms of viral hepatitis. In some embodiments, a liver disease is alcoholic liver disease. In some embodiments, a liver disease is cirrhosis of the liver. In some embodiments, a liver disease is hepatocellular carcinoma. In some embodiments, a liver disease is non-alcoholic steatohepatitis (NASH).

In some embodiments, the present invention provides a method for treating one or more metabolic disease, comprising the step of administering to a patient in need thereof a compound of the present invention, or pharmaceutically acceptable composition thereof. In some embodiments, a metabolic disease is metabolic syndrome. In some embodiments, a metabolic disease is insulin resistance. In some embodiments, a metabolic disease is Type II diabetes. In some embodiments, a metabolic disease is porphyria. In some embodiments, a metabolic disease is porphyria cutanea tarda. In some embodiments, a metabolic disease is Wilson's Disease. In some embodiments, a metabolic disease is acute iron overdose.

In some embodiments, the present invention provides a method for treating one or more neurodegenerative disorder, comprising the step of administering to a patient in need thereof a compound of the present invention, or pharmaceutically acceptable composition thereof. In some embodiments, a neurodegenerative disorder is selected from the group consisting of Huntington's Disease (HD); Parkinson's Disease (PD); amyotrophic lateral sclerosis (ALS); fronto-temporal dementia (FTD); corticobasal degeneration (CBD); progressive supranuclear palsy (PSP); dementia with Lewy Bodies (DLB); and multiple sclerosis (MS).

In some embodiments, the present invention provides a method for treating one or more infectious disease, comprising the step of administering to a patient in need thereof a compound of the present invention, or pharmaceutically acceptable composition thereof. In some embodiments, an infectious disease is a siderophilic infection.

The compounds and compositions, according to the method of the present invention, may be administered using any amount and any route of administration effective for treating or lessening the severity of a low hepcidin disease, disorder, and/or condition, or any amount and any route of administration effective for increasing hepcidin production by the liver. The exact amount required will vary from subject to subject, depending on the species, age, and general condition of the subject, the severity of the disease or condition, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the disease or disorder being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

In some embodiments, the invention relates to a method of inhibiting matriptase 2 activity, or a mutant thereof, in a biological sample comprising the step of contacting said biological sample with a compound of this invention, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

In some embodiments, the present invention provides a method of treating a disclosed disease or condition comprising administering to a patient in need thereof an effective amount of a compound disclosed herein or a pharmaceutically acceptable salt thereof and co-administering simultaneously or sequentially an effective amount of one or more additional therapeutic agents. In some embodiments, the method includes co-administering one additional therapeutic agent. In some embodiments, the method includes co-administering two or more additional therapeutic agents. In some embodiments, the combination of the disclosed compound and the additional therapeutic agent or agents acts synergistically. In some embodiments, an additional therapeutic agent is an iron chelating compound, or a pharmaceutically acceptable salt thereof. In some embodiments, an iron chelating compound, or a pharmaceutically acceptable salt thereof, is selected from the group consisting of deferasirox, deferiprone and deferoxamine.

In some embodiments, the present invention provides a method of treating a disclosed disease or condition comprising administering to a patient in need thereof an effective amount of a compound disclosed herein or a pharmaceutically acceptable salt thereof, and an iron chelating compound or a pharmaceutically acceptable salt thereof. In some embodiments, a patient is a patient with iron overload. In some embodiments, a patient is a patient with cardiac iron overload or iron overload related cardiomyopathy. In some embodiments, an iron chelating compound, or a pharmaceutically acceptable salt thereof, is selected from the group consisting of deferasirox, deferiprone and deferoxamine.

EXEMPLIFICATION

General Synthetic Methods

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein. General Modes of Preparation:

The general synthetic methods used in each General Procedure follow and include an illustration of a compound that was synthesized using the designated General Procedure. None of the specific conditions and reagents noted herein are to be construed as limiting the scope of the invention and are provided for illustrative purposes only.

Compounds of this invention may be made by synthetic chemical processes, examples of which are shown herein. It is meant to be understood that the order of the steps in the processes may be varied, that reagents, solvents and reaction conditions may be substituted for those specifically mentioned, and that vulnerable moieties may be protected and deprotected, as necessary.

Unless otherwise stated, work-up includes distribution of the reaction mixture between the organic and aqueous phase indicated within parentheses, separation of layers and drying the organic layer over anhydrous sodium sulphate, filtration and distillation of the solvent under reduced pressure. Purification, unless otherwise mentioned, includes purification by silica gel chromatographic techniques, generally using ethyl acetate/petroleum ether mixture of a suitable polarity as the mobile phase.

The following abbreviations refer respectively to the definitions below:

ACN—Acetonitrile; br—Broad; ° C.—Degree Celsius; $CHCl_3$-Chloroform; $CD_3OD$—Deuterated Methanol; DMSO—$d^6$—Deuterated dimethylsulfoxide; DCM—Dichloromethane; DIPEA—Diisopropylethylamine; DMF—N, N-Dimethylformamide; d—Doublet; dd—Doublet of doublet; EDC·HCl—1-(3-Dimethylaminopropyl)-3-ethyl-carbodiimide hydrochloride; mg—Miligram; g—Gram; h—Hours; $^1H$—Proton; HCl—Hydrochloric acid; HPLC—High-Performance Liquid Chromatography; $H_2$—Hydrogen; HOBt—1-Hydroxy benzotriazole; $K_2CO_3$—Potassium carbonate; LCMS—Liquid chromatography mass spectroscopy; $LiOH·H_2O$—Lithium hydroxide monohydrate; M—Molar; MHz—Mega hertz (frequency); MeOH—Methanol; mL—MilliLiter; min—Minutes; mol—Moles; $M^+$—Molecular ion; M—Multiplet; $N_2$—Nitrogen; $NH_3$—Ammonia; NBS—N-Bromosuccinimide; NCS—N-Chlorosuccinimide; NMR—Nuclear Magnetic Resonance; NaOH—Sodium Hydroxide; RT—Room temperature; s—Singlet; t—Triplet; TLC—Thin Layer Chromatography; TFA—Trifluoroacetic acid; TEA—Triethylamine; THF—Tetrahydrofuran; %—Percentage; μ—Micron; and δ—Delta; Zn—Zinc; mmol—millimoles.

Analysis for the compounds of the present invention unless mentioned, was conducted in the general methods well known to the person skilled in the art. Having described the invention with reference to certain preferred embodiments, other embodiments will become apparent to one skilled in the art from consideration of the specification. The invention is further defined by reference to the following examples, describing in detail the analysis of the compounds of the invention.

LCMS data has been recorded in +ve mode unless otherwise mentioned.

It will be apparent to those skilled in the art that many modifications, both to materials and methods, may be practiced without departing from the scope of the invention.

was added 1-(bromomethyl)-4-(trifluoromethyl)benzene (6.14 g, 25.67 mmol) and potassium carbonate (3.55 g, 25.67 mmol) and stirred at room temperature for 8 h. After reaction completion, mixture was quenched with ice-cold water and precipitated product was filtered off. Thus obtained solid was further washed with water and dried under vacuum to give crude compound which was purified by column chromatography using silica-gel as an adsorbent and eluted with 30-40% ethylacetate/hexane to afford the title compound (7.4 g). LCMS: 373.1 (M+1)$^+$.

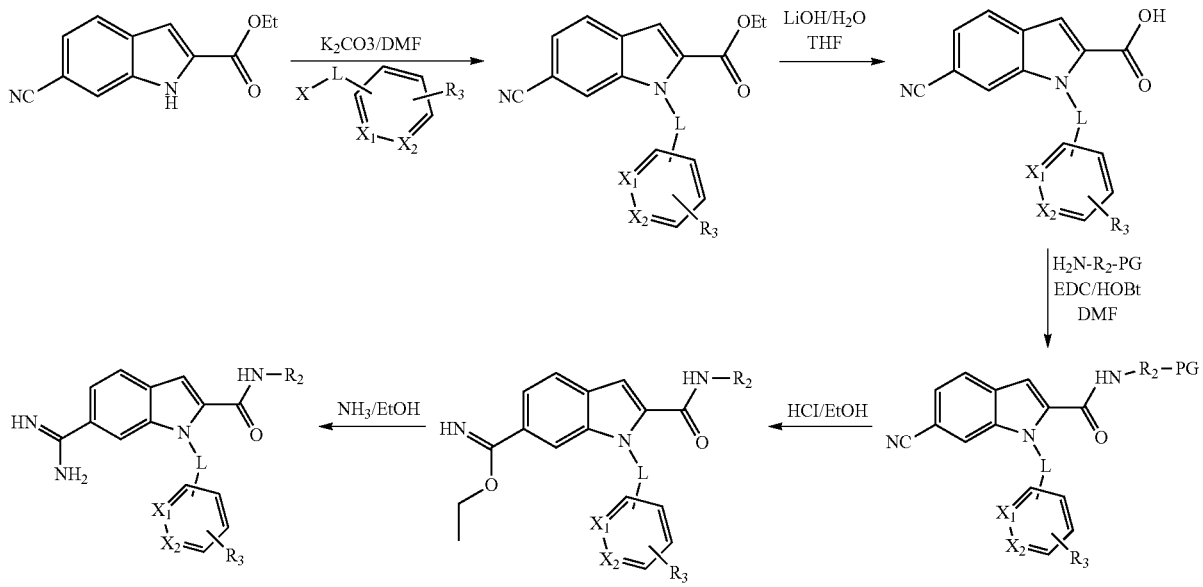

General synthetic Scheme 1

PG = optional protecting group; X = Br or Cl; $X_1$, $X_2$, $R_2$ and $R_3$ as defined in Formula (I)

Example 1: Synthesis of Compound I-1

N-(6-aminopyridin-3-yl)-6-carbamimidoyl-1-(4-(trifluoromethyl)benzyl)-1H-indole-2-carboxamide

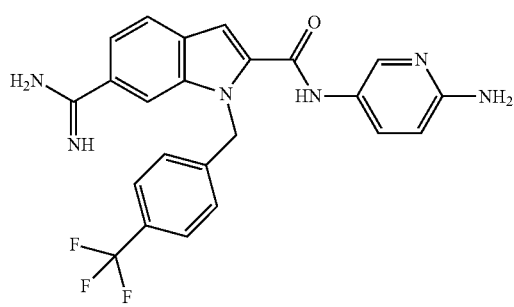 [SMILES: N=C(N)c1ccc2cc(C(=O)Nc3ccc(N)nc3)n(Cc3ccc(C(F)(F)F)cc3)c2c1]

Step-1: Ethyl 6-cyano-1-(4-(trifluoromethyl)benzyl)-1H-indole-2-carboxylate Ethyl 6-cyano-1H-indole-2-carboxylate (5.0 g, 23.34 mmol), dissolved in 150 mL of N,N-dimethylformamide,

Step-2: 6-Cyano-1-(4-(trifluoromethyl)benzyl)-1H-indole-2-carboxylic Acid

Product of step-1 of example-1 (7.0 g, 18.8 mmol) was dissolved in 100 mL mixture of tetrahydrofuran/methanol/water (1:1:1) and added lithium hydroxide (1.57 g, 65.8 mmol) at room temperature. Resulting mixture was stirred at room temperature for 4 h. Mixture was acidified with saturated aqueous solution of citric acid and extracted with ethyl acetate followed by washed with brine and dried over anhydrous sodium sulphate and then solvent was evaporated under vacuum to get the title compound (5.2 g). LCMS: 345.1 (M+1)$^+$.

Step-3: tert-Butyl (5-(6-cyano-1-(4-(trifluoromethyl)benzyl)-1H-indole-2-carboxamido)pyridin-2-yl)carbamate Product of step-2 of example-1 (350 mg, 1.01 mmol), dissolved in 5 mL of N,N-dimethylformamide, was added Butyl (5-aminopyridin-2-yl)carbamate (234 mg, 1.1 mmol), EDCI·HCl (292 mg, 1.52 mmol), HOBt (137 mg, 1.01 mmol) and DIEA (526 mg, 4.066 mmol) to the reaction mixture and resulted solution was stirred at RT for overnight. Reaction mixture was quenched with water, extracted with ethyl acetate followed by washed with brine and water and dried over sodium sulphate. Solvent was evaporated under vacuum to give crude compound which was purified by column chromatography using silica-gel as an adsorbent and eluted with 20% ethylacetate/hexane and afforded the title compound (380 mg). LCMS: 536.2 (M+1)$^+$.

Step-4: Ethyl 2-((6-aminopyridin-3-yl)carbamoyl)-1-(4-(trifluoromethyl)benzyl)-1H-indole-6-carbimidate Product was step-3 of example-1 (350 mg, 0.65 mmol) was dissolved in 50 mL of ethanolic-HCl (ethanol was saturated with HCl gas at −20° C.) and kept in a glass sealed tube for 12 h at RT. After reaction completion, solvent was evaporated under vacuum to afford the title compound (205 mg). LCMS: 482.2 (M+1)$^+$.

Step-5: N-(6-aminopyridin-3-yl)-6-carbamimidoyl-1-(4-(trifluoromethyl)benzyl)-1H-indole-2-carboxamide Product of step-4 of example-1 (200 mg, 0.41 mmol) was dissolved in 50 mL of ethanolic-ammonia (ethanol was saturated with ammonia gas at −70° C.) and kept for overnight in a steel bomb at RT. After reaction completion, solvent was evaporated under vacuum to give crude product which was purified by preparative High-performance liquid chromatography instrument with a Agilent XDB C18 reverse phase column (21.2×150 mm, 5 micron). The mobile phases were 30% acetonitrile in water (0.1% TFA) to 100% acetonitrile (0.1% TFA) which afforded the title compound (110 mg). LCMS: 452.2 (M+1)$^+$, $^1$H NMR (300 MHz, DMSO-d$_6$): δ 5.98 (s, 2H), 6.93 (d, 2H), 7.22 (d, 1H), 7.51 (m, 4H), 7.81 (brs, 1H), 8.05 (m, 2H), 8.41 (s, 1H), 8.41 (s, 1H), 9.11 (brs, 2H), 9.25 (brs, 2H), 10.75 (brs, 1H).

The following compounds listed in table-1, table-2 and table-3 were prepared according to Scheme-1 by following similar procedure as described above for example-1 using appropriate reagents with suitable modifications known to the one skilled in the art.

TABLE 1

| Cpd. ID. | R$_1$ | R$_2$ | R$_3$ | L | LCMS (M + 1)$^+$ | $^1$H NMR |
|---|---|---|---|---|---|---|
| I-1 | H | 6-aminopyridin-3-yl | —CF$_3$ | CH$_2$ | 452.2 | δ 5.98 (s, 2H), 6.93 (d, 2H), 7.22 (d, 1H), 7.51(m, 4H), 7.81 (brs, 1H), 8.05 (m, 2H), 8.41 (s, 1H), 8.41 (s, 1H), 9.11 (brs, 2H), 9.25 (brs, 2H), 10.75 (brs, 1H). |
| I-2 | H | 2-amino-1H-benzimidazol-5-yl | —CF$_3$ | CH$_2$ | 492.2 | δ 5.98 (s, 2H), 7.21 (d, 2H), 7.32 (d, 1H), 7.47 (m, 1H), 7.62 (m, 4H), 7.95 (d, 1H), 8.11 (d, 1H), 8.21 (s, 1H), 8.35 (brs, 1H), 8.51 (brs, 2H), 9.15 (brs, 2H), 9.24 (brs, 2H), 10.71(s, 1H). |
| I-3 | —CH$_3$ | (1H-benzimidazol-2-yl)methyl | —CF$_3$ | CH$_2$ | 458.2 | δ 3.12 (s, 3H), 4.92 (s, 2H), 5.68 (s, 2H), 7.18 (d, 4H), 7.42 (m, 4H), 7.62 (m, 2H), 7.91 (m, 2H), 8.12 (brs, 1H), 8.87 (brs, 2H), 9.21 (brs, 2H). |

TABLE 1-continued

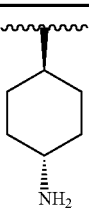

| Cpd. ID. | R₁ | R₂ | R₃ | L | LCMS (M + 1)⁺ | ¹H NMR |
|---|---|---|---|---|---|---|
| I-4 | H | 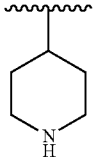 | —CF₃ | CH₂ | 458.2 | δ 1.32 (m, 4H), 1.75 (m, 4H), 2.92 (m, 1H), 3.65 (m, 1H), 5.98 (s, 2H), 7.21 (d, 2H), 7.32 (brs, 1H), 7.55 (d, 1H), 7.62 (d, 2H), 7.82 (m, 3H), 8.21 (s, 1H), 8.62 (d, 1H), 9.08 (brs, 2H), 9.24 (brs, 2H); HPLC: 97.17% (Retention Time = 6.79 min). |
| I-5 | H | 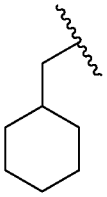 | —CF₃ | CH₂ | 444.2 | δ 1.68 (m, 2H), 1.83 (m, 2H), 2.92 (m, 2H), 3.32 (m, 2H), 3.92 (m, 1H), 5.98 (s, 2H), 7.25 (d, 2H), 7.38 (s, 1H), 7.55 (m, 3H), 7.92 (d, 1H), 8.41 (s, 1H), 8.85 (m, 2H), 9.18 (brs, 2H), 9.35 (brs, 2H); HPLC: 92.63% (Retention Time = 7.63 min). |
| I-10 | H |  | —CF₃ | CH₂ | 457.2 | δ 0.87 (m, 2H), 1.09 (d, 3H), 1.56 (m, 6H), 3.03 (m, 2H), 5.97 (s, 2H), 7.17 (d, 2H), 7.29 (s, 1H), 7.58 (d, 2H), 7.93 (d, 1H), 8.22 (s, 1H), 8.73 (m, 1H), 9.00 (brs, 2H), 9.24 (brs, 2H); HPLC: 95.02% (Retention Time = 3.82 min). |
| I-11 | H | 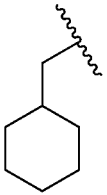 | —OCF₃ | CH₂ | 474.2 | δ 1.4H), 2.96 (m, 1H), 3.62 (m, 1H), 5.97 (s, 2H), 7.17 (d, 2H), 7.29 (d, 3H), 7.53 (m, 1H), 7.81 (m, 4H), 8.22 (s, 1H), 8.58 (d, 1H), 9.00 (brs, 2H), 9.24 (brs, 2H); HPLC: 90.18% (Retention Time = 6.7 min). |
| I-12 | H |  | —OCF₃ | CH₂ | 473.2 | δ 0.87 (m, 2H), 1.09 (d, 3H), 1.56 (m, 6H), 3.05 (m, 2H), 5.89 (s, 2H), 7.12 (d, 2H), 7.25 (d, 3H), 7.53 (m, 1H), 7.90 (d, 1H), 8.22 (s, 1H), 8.73 (m, 1H), 8.99 (brs, 2H), 9.24 (brs, 2H); HPLC: 98.78% (Retention Time = 4.05 min). |
| I-13 | H | 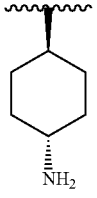 | —SCH₃ | CH₂ | 436.2 | δ 1.32 (m, 4H), 1.75 (m, 4H), 2.41 (s, 3H), 2.96 (m, 1H), 3.62 (m, 1H), 5.82 (s, 2H), 7.05 (d, 2H), 7.12 (d, 3H), 7.22 (s, 1H), 7.52 (m, 1H), 7.83 (d, 1H), 7.93 (m, 3H), 8.22 (s, 1H), 9.22 (brs, 2H), 9.24 (brs, 2H); HPLC: 88.69% (Retention Time = 7.36 min). |

TABLE 1-continued

| Cpd. ID. | R₁ | R₂ | R₃ | L | LCMS (M + 1)⁺ | ¹H NMR |
|---|---|---|---|---|---|---|
| I-14 | H | cyclohexenyl-CH< | —C(CH₃)₂ | CH₂ | 415.2 | δ 1.13 (d, 6H), 1.51 (m, 1H), 1.81(m, 1H), 2.12 (m, 2H), 2.28 (m, 2H), 2.45 (m, 1H), 3.91 (m, 1H), 5.65 (m, 2H), 5.83 (s, 2H), 7.02 (d, 2H), 7.13 (d, 2H), 7.23 (s, 1H), 7.52 (d, 1H), 7.88 (d, 1H), 8.24 (s, 1H), 8.63 (m, 1H), 9.00 (brs, 2H), 9.26 (brs, 2H). |
| I-15 | H | 4,4-difluorocyclohexyl-CH< | —C(CH₃)₂ | CH₂ | 453.2 | δ 1.13 (d, 6H), 1.51 (m, 2H), 1.81(m, 3H), 2.12 (m, 3H), 2.81 (m, 1H), 3.91 (m, 1H), 5.83 (s, 2H), 7.02 (d, 2H), 7.13 (d, 2H), 7.54 (d, 1H), 7.88 (d, 1H), 8.24 (s, 1H), 8.63 (m, 1H), 9.00 (brs, 2H), 9.26 (brs, 2H); HPLC: 87.34% (Retention Time = 7.27 min). |
| I-16 | H | cyclohexyl-CH₂-CH< | —C(CH₃)₂ | CH₂ | 431.3 | δ 0.87 (m, 2H), 1.11 (d, 6H), 1.12(m, 3H), 1.60 (m, 6H), 2.78 (m, 1H), 3.05 (m, 2H), 5.83 (s, 2H), 6.97 (d, 2H), 7.10 (d, 2H), 7.19 (m, 1H), 7.52 (d, 1H), 7.88 (d, 1H) 8.22 (s, 1H), 8.70 (m, 1H), 8.86 (brs, 2H), 9.24 (brs, 2H); HPLC: 92.57% (Retention Time = 4.15 min). |
| I-17 | H | trans-4-aminocyclohexyl-CH< | —C(CH₃)₃ | CH₂ | 446.3 | δ 1.40(s, 9H), 1.42 (m, 4H), 1.81(m, 4H), 2.95 (m, 1H), 3.71 (m, 1H), 5.83 (s, 2H), 6.97 (d, 2H), 7.20 (m, 3H), 7.53 (d, 1H), 7.83 (m, 3H), 8.21 (s, 1H), 8.58 (d, 1H), 9.20 (brs, 2H), 9.22 (brs, 2H); HPLC: 95.69% (Retention Time = 6.89 min). |
| I-24 | H | 3-(aminomethyl)benzyl | —H | (CH₂)₂ | 426.2 | δ 3.04 (m, 2H), 4.03 (m, 2H), 4.5 (d, 2H), 4.8 (m, 2H), 7.21 (m, 5H), 7.35 (m, 4H), 7.50 (m, 1H), 7.85 (d, 1H), 8.15 (m, 4H), 9.05 (brs, 2H), 9.25 (brs, 2H); HPLC: 95.36% (Retention Time = 5.59 min). |
| I-25 | H | 4-carbamoylbenzyl | —H | (CH₂)₂ | 426.2 | δ 3.04 (m, 2H), 4.91 (m, 2H), 7.21 (m, 6H), 7.45 (s, 1H), 7.55 (m, 1H), 7.82 (m, 6H), 8.15 (s, 1H), 8.90 (brs, 2H), 9.30 (brs, 2H), 10.30 (s, 1H); HPLC: 95.18% (Retention Time = 4.96 min). |

TABLE 1-continued

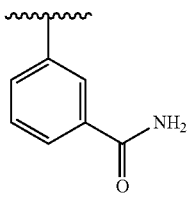 [SMILES: *c1cccc(C(N)=O)c1]

| Cpd. ID. | R₁ | R₂ | R₃ | L | LCMS (M + 1)⁺ | ¹H NMR |
|---|---|---|---|---|---|---|
| I-26 | H | 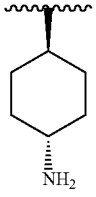 | —H | (CH₂)₂ | 426.2 | δ 3.11 (m, 2H), 4.84 (m, 2H), 7.14 (m, 5H), 7.42 (m, 3H), 7.54 (d, 1H), 7.63 (d, 1H), 7.91 (m, 2H), 8.01 (brs, 1H), 8.16 (s, 1H), 8.26 (s, 1H), 9.09 (brs, 2H), 9.31 (brs, 2H), 10.50 (s, 1H); HPLC: 94.08% (Retention Time = 5.069 min). |
| I-27 | H | 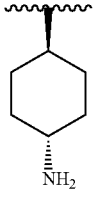 | —H | (CH₂)₂ | 404.2 | CD3OD δ 1.51 (m, 5H), 2.05 (m, 4H), 3.19(m, 3H), 3.81 (m, 2H), 7.01 (m, 2H), 7.03 (s, 1H), 7.12 (m, 4H), 7.43 (m, 1H), 7.79 (d, 1H), 7.89 (s, 1H); HPLC: 98.05% (Retention Time = 6.313 min). |
| I-30 | H | 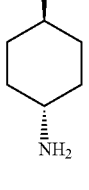 | —F | (CH₂)₂ | 422.2 | δ 1.42 (m, 4H), 1.81(m, 4H), 2.95 (m, 3H), 3.71 (m, 1H), 4.81 (m, 2H), 7.05 (m, 2H), 7.15 (m, 3H), 7.48 (d, 1H), 7.83 (m, 3H), 8.13 (s, 1H), 8.45 (d, 1H), 9.08 (brs, 2H), 9.28 (brs, 2H); HPLC: 96.43% (Retention Time = 4.461 min). |
| I-31 | H | 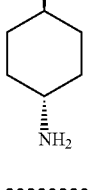 | —Br | (CH₂)₂ | 482.2 | δ 1.38 (m, 4H), 1.92 (m, 4H), 3.12 (m, 3H), 3.7 (m, 1H), 4.75 (m, 2H), 7.15 (m, 3H), 7.39 (m, 3H), 7.82 (m, 3H), 8.18 (s, 1H), 8.45 (d, 1H), 9.08 (brs, 2H), 9.25 (brs, 2H); HPLC: 96.72% (Retention Time = 5.029 min). |
| I-32 | H | 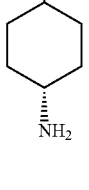 | —OCH₃ | (CH₂)₂ | 434.3 | δ 1.38 (m, 4H), 1.92 (m, 4H), 2.98 (m, 3H), 3.71 (m, 3H), 4.75 (m, 2H), 6.81 (d, 2H), 7.39 (m, 3H), 7.48 (d, 1H), 7.82 (d, 1H), 7.91 (m, 3H), 8.11 (s, 1H), 8.46 (d, 1H), 9.08 (brs, 2H), 9.27 (brs, 2H); HPLC: 91.07% (Retention Time = 5.432 min). |
| I-34 | H | | —H | (CH₂)₃ | 418.2 | δ 1.28 (m, 4H), 1.85 (m, 4H), 2.01 (m, 2H), 2.52 (m, 3H), 3.54 (m, 1H), 4.65 (m, 2H), 7.12 (m, 3H), 7.22 (m, 2H), 7.44 (d, 1H), 7.79 (d, 1H), 8.09 (brs, 1H), 8.51 (d, 1H); HPLC: 99.07% (Retention Time = 6.417 min). |

TABLE 1-continued
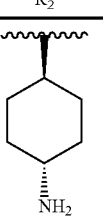
| Cpd. ID. | R₁ | R₂ | R₃ | L | LCMS (M + 1)⁺ | ¹H NMR |
|---|---|---|---|---|---|---|
| I-35 | H | 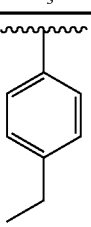 | 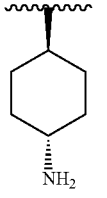 [SMILES: *[C@H]1CC[C@H](N)CC1] | (CH₂)₂ | 508.3 | δ 1.18 (m, 7H), 1.82 (m, 4H), 2.52 (m, 3H), 3.14 (m, 2H), 3.71 (m, 1H), 4.65 (m, 2H), 6.91 (m, 3H), 7.81 (m, 3H), 7.49 (m, 3H), 7.81 (m, 4H), 8.18 (brs, 1H), 8.49 (d, 1H), 9.19 (brs, 3H); HPLC: 98.51% (Retention Time = 5.998 min). |
| I-38 | —H | 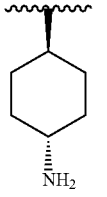 | —H | —SO₂CH₂ | 454.2 | CD3OD δ 1.51(m, 4H), 2.15 (m, 4H) 3.13 (m, 1H), 3.85 (m, 1H), 5.25 9s, 2H), 7.11 (s, 1H), 7.12 (m, 3H), 7.25 (m, 2H), 7.48 (m, 2H), 7.75 (d, 1H). |
| I-39 | H | 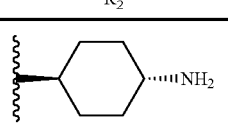 | H | —CH₂SO₂ | 454.2 | δ 1.33(m, 4H), 1.82 (m, 4H) 2.96 (m, 1H), 3.71 (m, 1H), 7.11 (s, 1H), 6.33 (s, 2H), 7.28 (s, 1H), 7.42 (m, 4H), 7.65 (m, 1H), 7.85 (m, 3H), 8.08 (s, 1H), 8.52 (d, 1H), 9.15 (m, 3H); HPLC: 93.09% (Retention Time = 4.23 min). |
TABLE 2
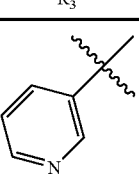
| Cpd. ID. | R₂ | R₃' | L | LCMS (M + 1)⁺ | ¹H NMR |
|---|---|---|---|---|---|
| I-18 | 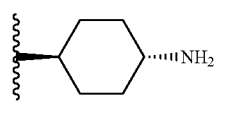 [SMILES: *[C@H]1CC[C@H](N)CC1] | 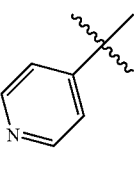 [SMILES: *c1ccncc1] | CH₂ | 391.2 | δ 1.35 (m, 4H), 1.83 (m, 4H), 2.95 (m, 1H), 3.71 (m, 1H), 5.95 (s, 2H), 7.15 (d, 2H), 7.48 (s, 1H), 7.66 (d, 1H), 7.80 (m, 2H), 7.92 (d, 1H), 8.15 (s, 1H), 8.58 (d, 2H), 8.65 (d, 1H), 9.12 (brs, 2H), 9.22 (brs, 2H). |
| I-19 | 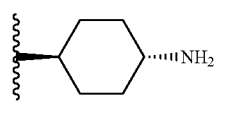 [SMILES: *[C@H]1CC[C@H](N)CC1] | 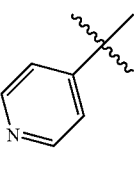 [SMILES: *c1ccncc1] | CH₂ | 391.2 | δ 1.35 (m, 4H), 1.83 (m, 4H), 2.95 (m, 1H), 3.71 (m, 1H), 5.95 (s, 2H), 7.15 (d, 2H), 7.38 (s, 1H), 7.53 (d, 1H), 7.75 (m, 2H), 7.92 (d, 1H), 8.15 (s, 1H), 8.58 (d, 2H), 8.65 (d, 1H), 9.12 (brs, 2H), 9.22 (brs, 2H); HPLC: |

TABLE 2-continued

| Cpd. ID. | R₂ | R₃' | L | LCMS (M + 1)⁺ | ¹H NMR |
|---|---|---|---|---|---|
| | | | | | 93.22% (Retention Time = 5.738 min). |
| I-37 | trans-4-aminocyclohexyl | 2-naphthyl | —SO₂— | 490.2 | δ 1.42 (m, 4H), 1.98 (m, 4H), 3.03 (m, 1H), 3.71 (m, 1H), 7.11 (s, 1H), 7.63 (m, 3H), 7.83 (m, 3H), 8.08 (d, 1H), 8.12 (m, 3H), 8.49 (s, 1H), 8.79 (m, 2H), 9.19 (brs, 2H), 9.42 (brs, 2H); HPLC: 98.49% (Retention Time = 4.824 min). |
| I-243 | cis-4-aminocyclohexyl | 4-(4-fluorophenoxy)phenyl | CH₂ | 500.2 | δ 1.32 (m, 4H), 1.82 (m, 2H), 1.95 (m, 2H), 2.95 (m, 1H), 3.71 (m, 1H), 5.82 (s, 2H), 6.88 (d, 2H), 6.98 (m, 2H), 7.12 (m, 5H), 7.55 (d, 1H), 7.88 (d, 1H), 7.98 (m, 2H), 8.28 (s, 1H), 8.64 (d, 1H), 9.21 (brs, 2H), 9.32 (brs, 2H); HPLC: 93.848% (Retention Time = 7.131 min). |
| I-244 | 3-hydroxyadamantyl | 4-(4-fluorophenoxy)phenyl | CH₂ | 553.3 | δ 1.48 (m, 6H), 1.88 (m, 6H), 2.15 (m, 2H), 4.51 (s, 1H), 5.79 (s, 2H), 6.84 (d, 2H), 6.97 (m, 2H), 7.15 (m, 5H), 7.53 (d, 1H), 7.82 (d, 1H), 8.09 (s, 1H), 8.31 (s, 1H), 8.96 (brs, 2H), 9.28 (brs, 2H); HPLC: 98.0% (Retention Time = 8.857 min). |
| I-245 | 3-hydroxyadamantyl | 4-(4-fluorophenoxy)phenyl | CH₂ | 537.3 | δ 1.45 (m, 2H), 1.68 (m, 8H), 1.92 (m, 5H), 5.79 (s, 2H), 6.84 (d, 2H), 6.97 (m, 2H), 7.08 (brs, 1H), 7.15 (m, 2H), 7.24 (d, 1H), 7.42 (s, 1H), 7.58 (d, 1H), 7.85 (d, 1H), 8.31 (m, 2H), 9.08 (brs, 2H), 9.33 (brs, 2H); HPLC: 98.92% (Retention Time = 10.588 min). |

TABLE 2-continued

| Cpd. ID. | R₂ | R₃' | L | LCMS (M + 1)⁺ | ¹H NMR |
|---|---|---|---|---|---|
| I-246 | cyclohexyl-NH₂ | 5-(4-fluorophenoxy)pyridin-2-yl | CH₂ | 501.2 | δ 1.32 (m, 4H), 1.95 (m, 4H), 3.15 (m, 1H), 3.71 (m, 1H), 5.82 (s, 2H), 7.02 (d, 1H), 7.15 (m, 2H), 7.25 (m, 4H), 7.58 (m, 2H), 7.88 (m, 2H), 8.05 (m, 1H), 8.35 (s, 1H), 8.64 (d, 1H), 9.14 (brs, 2H), 9.32 (brs, 2H); HPLC: 97.62% (Retention Time = 4.705 min). |
| I-247 | cyclohexyl-NH₂ | 4-(4-chlorophenoxy)phenyl | CH₂ | 516.2 | δ 1.41 (m, 4H), 1.83 (m, 4H), 2.96 (m, 1H), 3.71 (m, 1H), 5.85 (s, 2H), 6.91 (m, 3H), 7.15 (m, 3H), 7.35 (d, 2H), 7.55 (d, 1H), 7.81 (m, 4H), 8.25 (s, 1H), 8.61 (d, 1H), 9.12 (brs, 2H), 9.25 (brs, 2H); HPLC: 96.19% (Retention Time = 7.746 min). |
| I-248 | cyclohexyl-NH₂ | 4-(3-trifluoromethylphenoxy)phenyl | CH₂ | 516.2 | δ 1.31 (m, 4H), 1.83 (m, 4H), 2.96 (m, 1H), 3.52 (m, 1H), 5.85 (s, 2H), 7.12 (d, 1H), 7.15 (m, 3H), 7.45 (d, 1H), 7.55 (m, 3H), 7.81 (m, 3H), 8.25 (s, 1H), 8.61 (s, 1H), 9.05 (brs, 2H), 9.25 (brs, 2H); HPLC: 92.54% (Retention Time = 7.347 min). |
| I-249 | cyclohexyl-NH₂ | 4-(4-aminophenoxy)phenyl | CH₂ | 497.3 | δ 1.31 (m, 4H), 1.83 (m, 4H), 2.96 (m, 1H), 3.72 (m, 1H), 5.82 (s, 2H), 6.95 (m, 4H), 7.15 (m, 4H), 7.45 (s, 1H), 7.55 (d, 1H), 7.85 (m, 3H), 8.25 (s, 1H), 8.61 (d, 1H), 8.61 (d, 1H), 9.15 (brs, 2H), 9.28 (brs, 2H). |

TABLE 2-continued

*[Structure: indole core with H₂N-C(=NH)- at 6-position, 2-carboxamide HN-R₂, N-substituted with L-R₃']*

| Cpd. ID. | R₂ | R₃' | L | LCMS (M + 1)⁺ | ¹H NMR |
|---|---|---|---|---|---|
| I-255 | *trans-cyclohexyl-NH₂* | *4-phenoxyphenyl* | CH₂ | 482.2 | δ 1.31 (m, 4H), 1.83 (m, 4H), 2.96 (m, 1H), 3.52 (m, 1H), 5.83 (s, 2H), 6.65 (s, 1H), 6.85 (m, 2H), 6.93 (m, 2H), 7.12 (m, 1H), 7.25 (m, 2H), 7.45 (m, 2H), 7.55 (m, 1H), 8.85 (m, 3H), 8.21 (s, 1H), 8.65 (d, 1H), 9.18 (brs, 2H), 9.25 (brs, 2H). |

TABLE 3

*[Structure: indole core with H₂N-C(=NH)- at 6-position, 2-carboxamide HN-R₂, N-substituted with 4-(aminocarbonyl)benzyl]*

| Cpd. ID. | R₂ | LCMS (M + 1)⁺ | ¹H NMR |
|---|---|---|---|
| I-74 | *5-benzimidazolyl* | 452.2 | δ 5.96 (s, 2H), 7.12 (d, 2H), 7.31 (brs, 1H), 7.50 (m, 4H), 7.74 (d, 2H), 7.86 (brs, 1H), 7.97 (d, 1H), 8.04 (s, 1H), 8.20 (brs, 2H), 8.91 (brs, 2H), 9.24 (brs, 2H), 10.61 (s, 1H), 13.01 (brs, 1H); HPLC: 89.45% (Retention Time = 4.718 min). |
| I-85 | *2-hydroxy-1-phenylethyl* | 456.2 | δ 3.64 (m, 2H), 5.00 (m, 1H), 5.86 (s, 2H), 7.07 (d, 2H), 7.21 (m, 1H), 7.30 (m, 5H), 7.43 (brs, 1H), 7.53 (d, 1H), 7.70 (d, 2H), 7.89 (m, 2H), 8.15 (s, 1H), 9.17 (d, 1H); HPLC: 94.87% (Retention Time = 5.506 min). |
| I-86 | *2-hydroxy-1-phenylethyl (enantiomer)* | 456.2 | δ 3.66 (m, 2H), 5.02 (m, 1H), 5.87 (s, 2H), 7.07 (d, 2H), 7.23 (m, 1H), 7.30 (m, 5H), 7.44 (brs, 1H), 7.54 (d, 1H), 7.71 (d, 2H), 7.89 (brs, 1H), 7.94 (d, 1H), 8.16 (s, 1H), 8.95 (brs, 2H), 9.07 (d, 1H), 9.23 (brs, 2H); HPLC: 92.65% (Retention Time = 5.291 min). |

TABLE 3-continued

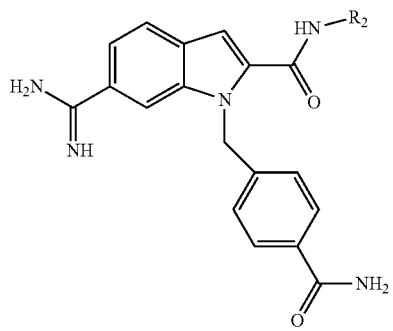

| Cpd. ID. | R₂ | LCMS (M + 1)⁺ ¹H NMR |
|---|---|---|
| I-125 | (structure: 2-methyl-1-phenyl-propan-2-ol substituent with OH) | 484.2 δ 0.99 (s, 3H), 1.11 (s, 3H), 4.65 (s, 1H), 4.91 (d, 1H), 7.04 (d, 2H), 7.22 (m, 5H), 7.38 (s, 1H), 7.41 (d, 2H), 7.54 (d, 1H), 7.68 (d, 2H), 7.88 (brs, 1H), 7.93 (d, 1H), 8.18 (s, 1H), 8.73 (d, 1H), 8.90 (brs, 2H), 9.23 (brs, 2H), 10.41 (brs, 1H); HPLC: 93.29% (Retention Time = 5.627 min). |
| I-128 | (structure: phenyl with 3-hydroxypyrrolidin-1-yl) | 497.2 δ 1.87 (m, 1H), 2.02 (m, 1H), 3.04 (d, 1H), 3.23 (m, 2H), 3.38 (m, 2H), 5.95 (s, 2H), 6.27 (d, 1H), 6.27 (d, 1H), 6.94 (m, 2H), 7.08 (m, 3H), 7.32 (brs, 1H), 7.50 (s, 1H), 7.56 (d, 2H), 7.74 (d, 2H), 7.88 (brs, 1H), 8.19 (s, 1H), 8.93 (brs, 2H), 9.25 (brs, 2H), 10.35 (brs, 1H); HPLC: 90.58% (Retention Time = 5.801 min). |
| I-137 | (structure: phenyl with 1H-imidazol-2-yl) | 478.2 δ 5.97 (s, 2H), 7.10 (d, 2H), 7.34 (brs, 1H), 7.59 (m, 2H), 7.72 (m, 2H), 7.75 (m, 6H), 7.88 (s, 1H), 8.01 (d, 1H), 8.20 (s, 1H), 8.51 (s, 1H), 8.96 (brs, 2H), 9.26 (brs, 2H), 10.89 (brs, 1H); HPLC: 94.83% (Retention Time = 4.861 min). |

Example 2: Synthesis of Compound I-6

N-(1-(3-Aminopropyl)piperidin-4-yl)-6-carbamimidoyl-1-(4-(trifluoromethyl)benzyl)-1H indole-2-carboxamide

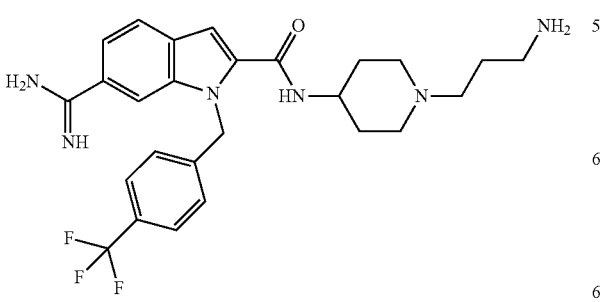

Step-1: tert-butyl 4-(6-cyano-1-(4-(trifluoromethyl)benzyl)-1H-indole-2-carboxamido)-piperidine-1-carboxylate The product of step-2 of example 1 and tert-butyl 4-aminopiperidine-1-carboxylate were treated together to afford the title compound following the procedure described in step-3 of example 1. LCMS: 527.2 (M+1)⁺.

Step-2: 6-cyano-N-(piperidin-4-yl)-1-(4-(trifluoromethyl)benzyl)-1H-indole-2-carboxamide The product of step-1 of example-2 (884 mg, 1.68 mmol) was treated with 30 mL of ethanolic-HCl to afford 665 mg of the title compound following the procedure described in step-4 of example-1 but reaction was done at 0° C. for 2 h. LCMS: 427.2 (M+1)⁺.

Step-3: tert-butyl (3-(4-(6-cyano-1-(4-(trifluoromethyl)benzyl)-1H-indole-2-carboxamido)-piperidin-1-yl)propyl)carbamate The product of step-2 of example-2 (550 mg, 1.28 mmol) was treated with tert-butyl (3-bromopropyl)carbamate (305 mg, 1.28 mmol) to afford 525 mg of the title compound following the procedure described in step-1 of example-1. LCMS: 584.3 (M+1)⁺.

Step-4: Ethyl 2-((1-(3-aminopropyl)piperidin-4-yl) carbamoyl)-1-(4-(trifluoromethyl)benzyl)-1H-indole-6-carbimidate The product of step-3 of example-2 (450 mg, 0.77 mmol) was treated with 50 mL of ethanolic-HCl to afford 215 mg of the title compound following the procedure described in step-4 of example-1. LCMS: 530.3 (M+1)⁺.

Step-5: N-(1-(3-Aminopropyl)piperidin-4-yl)-6-carbamimidoyl-1-(4-(trifluoromethyl)benzyl)-1H-indole-2-carboxamide The product of step-4 of example-2 (200 mg, 0.37 mmol) was treated with 30 mL of ethanolic-NH₃ to afford 95 mg of the title compound following the procedure described in step-5 of example-1. LCMS: 501.2 (M+1)⁺, ¹H NMR (300 MHz, DMSO-d₆): δ 1.72 (m, 2H), 1.91 (m, 4H), 2.83 (m, 2H), 3.45 (m, 2H), 3.92 (m, 1H), 5.95 (s, 2H), 7.21 (d, 2H), 7.35 (s, 1H), 7.52 (d, 1H), 7.62 (d, 2H), 7.91 (m, 4H), 8.21 (s, 1H), 8.82 (d, 1H), 9.15 (brs, 2H), 9.24 (brs, 2H), 9.89 (brs, 1H); HPLC: 95.18% (Retention Time=6.081 min).

Example 3: Synthesis of Compound I-7

6-Carbamimidoyl-N-(1-(3-guanidinopropyl)piperidin-4-yl)-1-(4-(trifluoromethyl)benzyl)-1H-indole-2-carboxamide

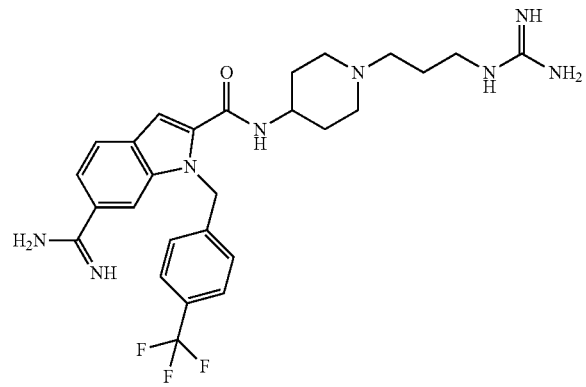 [SMILES: N=C(N)NCCCN1CCC(NC(=O)c2cc3ccc(C(=N)N)cc3n2Cc2ccc(C(F)(F)F)cc2)CC1]

Step-1: N-(1-(3-aminopropyl)piperidin-4-yl)-6-cyano-1-(4-(trifluoromethyl)benzyl)-1H-indole-2-carboxamide The product of step-3 of example-2 (550 mg, 1.28 mmol) was treated with 20 mL of ethanolic-HCl to afford 520 mg of the title compound following the procedure described in step-2 of example-2. LCMS: 484.2 (M+1)⁺.

Step-2: 6-Cyano-N-(1-(3-guanidinopropyl)piperidin-4-yl)-1-(4-(trifluoromethyl)benzyl)-1H-indole-2-carboxamide The product of step-1 of example-3 (498 mg, 1.03 mmol) was dissolved in 15 mL of N,N-dimethylformamide and treated with 1H-pyrazole-1-carboxamidine hydrochloride (329 mg, 2.25 mmol) and N,N-diisopropylethylamine (452 mg, 3.50 mmol) and resulted mixture was stirred for 24 h at room temperature. The solvent was evaporated under vacuum to give 250 mg of the title compound which was used as such without further purification. LCMS: 526.2 (M+1)⁺.

Step-3: Ethyl 2-((1-(3-guanidinopropyl)piperidin-4-yl)carbamoyl)-1-(4-(trifluoromethyl)benzyl)-1H-indole-6-carbimidate The product of step-2 of example-3 (250 mg, 0.47 mmol) was treated with 50 mL of ethanolic-HCl to afford 180 mg of the title compound following the procedure described in step-4 of example-1. LCMS: 572.3 (M+1)⁺.

Step-4: 6-Carbamimidoyl-N-(1-(3-guanidinopropyl) piperidin-4-yl)-1-(4-(trifluoromethyl)benzyl)-1H-indole-2-carboxamide The product of step-3 of example-3 (170 mg, 0.29 mmol) was treated with 30 mL of ethanolic-NH₃ to afford 40 mg of the title compound following the procedure described in step-5 of example-1. LCMS: 543.3 (M+1)⁺, ¹H NMR (300 MHz, DMSO-d₆): δ 1.72 (m, 6H), 3.01 (m, 3H), 3.18 (m, 3H), 2.98 (m, 3H), 3.96 (brs, 2H), 5.95 (s, 2H), 7.21 (d, 2H), 7.35 (s, 1H), 7.52 (d, 1H), 7.62 (d, 2H), 7.88 (m, 1H), 7.9 (d, 1H), 8.21 (s, 1H), 8.85 (d, 1H), 9.05 (brs, 2H), 9.24 (brs, 2H), 9.89 (brs, 1H).

Example 4: Synthesis of Compound I-8

N-(1-(3-aminopropanoyl)piperidin-4-yl)-6-carbamimidoyl-1-(4-(trifluoromethyl)benzyl)-1H-indole-2-carboxamide

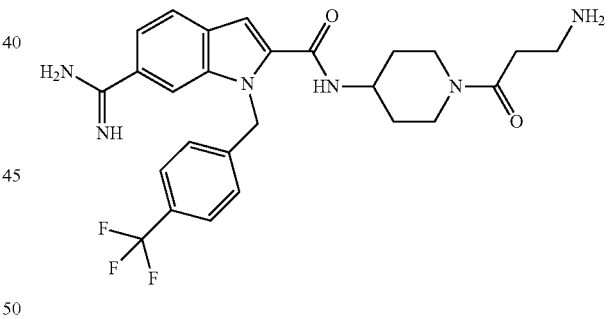

Step-1: tert-butyl (3-(4-(6-cyano-1-(4-(trifluoromethyl)benzyl)-1H-indole-2-carboxamido)-piperidin-1-yl)-3-oxopropyl)carbamate The product of step-2 of example-2 (553 mg, 1.3 mmol) and 3-((tert-butoxycarbonyl)amino)propanoic acid (245 mg, 1.3 mmol) were treated together to afford 380 mg of the title compound following the procedure described in step-3 of example-1. LCMS: 598.3 (M+1)⁺.

Step-2: Ethyl 2-((1-(3-aminopropanoyl)piperidin-4-yl)carbamoyl)-1-(4-(trifluoromethyl)benzyl)-1H-indole-6-carbimidate The product of step-1 of example-4 (304 mg, 0.51 mmol) was treated with 50 mL of ethanolic-HCl to afford 65 mg of the title compound following the procedure described in step-4 of example-1. LCMS: 544.2 (M+1)+.

Step-3: N-(1-(3-Aminopropanoyl)piperidin-4-yl)-6-carbamimidoyl-1-(4-(trifluoromethyl)-benzyl)-1H-indole-2-carboxamide The product of step-2 of example-4 (167 mg, 0.28 mmol) was treated with 30 mL of ethanolic-NH₃ to afford 80 mg of the title compound following the procedure described in step-5 of example-1. LCMS: 515.2 (M+1)+, ¹H NMR (300 MHz, DMSO-d₆): δ 1.35 (m, 2H), 1.75 (m, 2H), 2.72 (m, 4H), 2.95 (m, 4H), 3.78 (m, 1H), 5.95 (s, 2H), 7.23 (d, 2H), 7.35 (s, 1H), 7.58 (d, 1H), 7.66 (d, 2H), 7.85 (m, 2H), 8.41 (s, 1H), 8.75 (d, 1H), 9.18 (brs, 2H), 9.35 (brs, 2H); HPLC: 92.34% (Retention Time=6.841 min).

Example 5: Synthesis of Compound I-9

6-carbamimidoyl-N-((1r,4r)-4-(picolinamido)cyclohexyl)-1-(4-(trifluoromethyl)-1H-indole-2-carboxamide

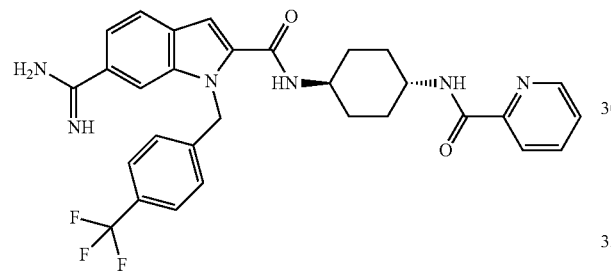

Step-1: tert-butyl ((1r,4r)-4-(6-cyano-1-(4-(trifluoromethyl)benzyl)-1H-indole-2-carboxamido) cyclohexyl)carbamate The product of step-2 of example-1 (430 mg, 1.25 mmol) and tert-butyl ((1r,4r)-4-aminocyclohexyl) carbamate (268 mg, 1.25 mmol) were treated together to afford 520 mg of the title compound following the procedure described in step-3 of example-1. LCMS: 541.2 (M+1)+.

Step-2: N-((1r,4r)-4-aminocyclohexyl)-6-cyano-1-(4-(trifluoromethyl)benzyl)-1H-indole-2-carboxamide The product of step-1 of example-5 (275 mg, 0.51 mmol) was treated with 20 mL of ethanolic-HCl to afford 115 mg of the title compound following the procedure described in step-2 of example-6. LCMS: 441.2 (M+1)+.

Step-3: 6-cyano-N-((1r,4r)-4-(picolinamido)cyclohexyl)-1-(4-(trifluoromethyl)benzyl)-1H-indole-2-carboxamide The product of step-2 of example-5 (572 mg, 1.3 mmol) and picolinic acid (160 mg, 1.3 mmol) were treated together to afford 420 mg of the title compound following the procedure described in step-3 of example-1. LCMS: 546.3 (M+1)+.

Step-4: Ethyl 2-(((1r,4r)-4-(picolinamido)cyclohexyl)carbamoyl)-1-(4-(trifluoromethyl)benzyl)-1H-indole-6-carbimidate The product of step-3 of example-5 (275 mg, 0.51 mmol) was treated with 50 mL of ethanolic-HCl to afford 95 mg of the title compound following the procedure described in step-4 of example-1. LCMS: 592.2 (M+1)+.

Step-5: 6-Carbamimidoyl-N-((1r,4r)-4-(picolinamido)cyclohexyl)-1-(4-(trifluoromethyl)benzyl)-1H-indole-2-carboxamide The product of step-4 of example-5 (95 mg, 0.16 mmol) was treated with 30 mL of ethanolic-NH₃ to afford 20 mg of the title compound following the procedure described in step-5 of example-1. LCMS: 563.2 (M+1)+, ¹H NMR (300 MHz, CD₃OD): δ 1.48 (m, 4H), 1.93 (m, 4H), 3.82 (m, 2H), 5.93 (s, 2H), 7.18 (d, 3H), 7.52 (m, 4H), 7.91 (m, 2H), 8.22 (m, 2H), 8.61 (m, 1H); HPLC: 97.78% (Retention Time=8.714 min).

Example 6: Synthesis of Compound I-20

4-((2-(((1r,4r)-4-aminocyclohexyl)carbamoyl)-6-carbamimidoyl-1H-indol-1-yl)methyl)benzoic Acid

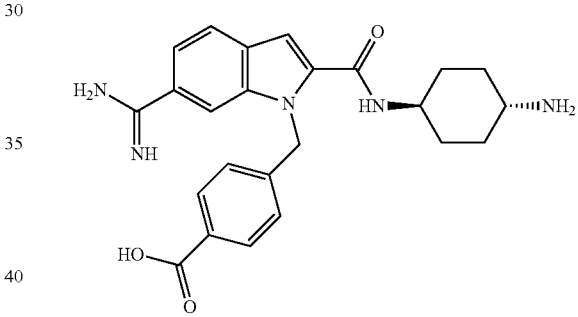

Step-1: 6-Cyano-1H-indole-2-carboxylic Acid

Ethyl 6-cyano-1H-indole-2-carboxylate (710 mg, 3.31 mmol) and lithium hydroxide (486 mg, 11.58 mmol) were treated together to afford 480 mg of the title compound following the procedure described in step-2 of example-1. LCMS: 187.1 (M+1)+.

Step-2: tert-Butyl ((1r,4r)-4-(6-cyano-1H-indole-2-carboxamido)cyclohexyl)carbamate The product of step-1 of example-6 (480 mg, 2.56 mmol) and tert-butyl((1r, 4r)-4-aminocyclohexyl)-carbamate (547 mg, 2.56 mmol) were treated together to afford 325 mg of the title compound following the procedure described in step-3 of example-1. LCMS: 383.2 (M+1)+.

Step-3: 4-((2-(((1r,4r)-4-((tert-Butoxycarbonyl)amino)cyclohexyl)carbamoyl)-6-cyano-1H-indol-1-yl)methyl)benzoic Acid The product of step-2 of example-6 (325 mg, 0.84 mmol) and 4-(bromomethyl)benzoic acid (179 mg, 0.84 mmol)

were treated together to afford 198 mg of the title compound following the procedure described in step-1 of example-1. LCMS: 517.2 (M+1)⁺.

Step-4: 4-((2-(((1r,4r)-4-Aminocyclohexyl)carbamoyl)-6-(ethoxy(imino)methyl)-1H-indol-1-yl)methyl) benzoic Acid The product of step-3 of example-6 (198 mg, 0.38 mmol) was treated with 30 mL of ethanolic-HCl to afford 82 mg of the title compound following the procedure described in step-4 of example-1. LCMS: 463.2 (M+1)⁺.

Step-5: 4-((3-Amino-2-(((1r,4r)-4-aminocyclohexyl)carbamoyl)-6-carbamimidoyl-1H-indol-1-yl)methyl) benzoic Acid The product of step-4 of example-6 (80 mg, 0.17 mmol) was treated with 20 mL of ethanolic-NH₃ to afford 14 mg of the title compound following the procedure described in step-5 of example-1. LCMS: 434.2 (M+1)⁺, ¹H NMR (300 MHz, DMSO-d₆): δ 1.32 (m, 4H), 1.83 (m, 4H), 2.95 (m, 1H), 3.63 (m, 1H), 5.91 (s, 2H), 7.11 (d, 2H), 7.27 (s, 1H), 7.52 (d, 1H), 7.80 (m, 5H), 8.19 (s, 1H), 8.62 (d, 1H), 9.11 (brs, 2H), 9.25 (brs, 2H), 12.91 (brs, 1H); HPLC: 90.14% (Retention Time=4.327 min).

Example 7: Synthesis of Compound I-21

Methyl 4-((2-(((1r,4r)-4-aminocyclohexyl)carbamoyl)-6-carbamimidoyl-1H-indol-1-yl)methyl)-benzoate

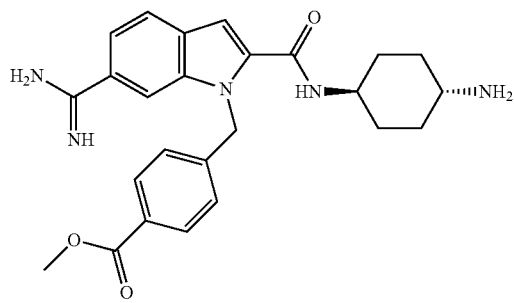 [SMILES: COC(=O)c1ccc(Cn2c(C(=O)N[C@H]3CC[C@H](N)CC3)cc3ccc(C(=N)N)cc32)cc1]

Step-1: Methyl 4-((2-(((1r,4r)-4-((tert-butoxycarbonyl)amino)cyclohexyl)carbamoyl)-6-cyano-1H-indol-1-yl)methyl)benzoate The product of step-2 of example-6 (300 mg, 0.78 mmol) and methyl 4-(bromomethyl)benzoate (177 mg, 0.78 mmol) were treated together to afford 380 mg of the title compound following the procedure described in step-1 of example-1. LCMS: 531.2 (M+1)⁺.

Step-2: Methyl 4-((2-(((1r,4r)-4-aminocyclohexyl)carbamoyl)-6-(ethoxy(imino)methyl)-1H-indol-1-yl) methyl)benzoate The product of step-1 of example-7 (350 mg, 0.65 mmol) was treated with 50 mL of ethanolic-HCl to afford 153 mg of the title compound following the procedure described in step-4 of example-1. LCMS: 477.2 (M+1)⁺.

Step-3: Methyl 4-((2-(((1r,4r)-4-aminocyclohexyl)carbamoyl)-6-carbamimidoyl-1H-indol-1-yl)methyl) benzoate The product of step-2 of example-7 (150 mg, 0.28 mmol) was treated with 30 mL of ethanolic-NH₃ to afford 42 mg of the title compound following the procedure described in step-5 of example-1. LCMS: 448.2 (M+1)⁺, ¹H NMR (300 MHz, DMSO-d₆): δ 1.32 (m, 4H), 1.82 (m, 4H), 2.96 (m, 1H), 3.52 (m, 1H), 3.81 (m, 3H), 5.96 (s, 2H), 7.13 (d, 2H), 7.32 (s, 1H), 7.55 (d, 1H), 7.82 (m, 5H), 8.19 (s, 1H), 8.65 (d, 1H), 9.24 (brs, 3H); HPLC: 96.693% (Retention Time=5.524 min).

Example 8: Synthesis of Compound I-22

Ethyl 4-((2-(((1r,4r)-4-aminocyclohexyl)carbamoyl)-6-carbamimidoyl-1H-indol-1-yl)methyl)-benzoate

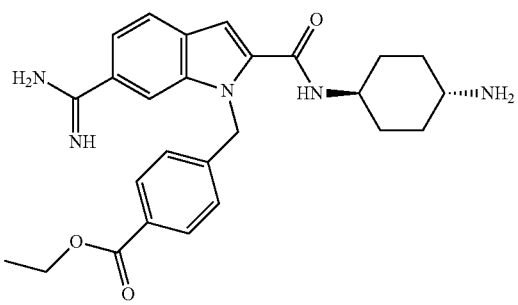 [SMILES: CCOC(=O)c1ccc(Cn2c(C(=O)N[C@H]3CC[C@H](N)CC3)cc3ccc(C(=N)N)cc32)cc1]

This compound was prepared by following the procedure described in step-1 to step-3 of example-7 using ethyl 4-(bromomethyl)benzoate. LCMS: 462.2 (M+1)⁺, ¹H NMR (300 MHz, DMSO-d₆): δ 1.32 (m, 3H), 1.41 (m, 4H), 1.82 (m, 4H), 2.96 (m, 1H), 3.52 (m, 1H), 4.26 (m, 2H), 5.96 (s, 2H), 7.13 (d, 2H), 7.32 (s, 1H), 7.86 (m, 6H), 8.21 (s, 1H), 8.62 (d, 1H), 9.24 (brs, 3H); HPLC: 96.18% (Retention Time=4.601 min).

Example 9: Synthesis of Compound I-23

Ethyl 4-((3-amino-2-(((1r,4r)-4-aminocyclohexyl)carbamoyl)-6-carbamimidoyl-1H-indol-1-yl)-methyl)benzoate

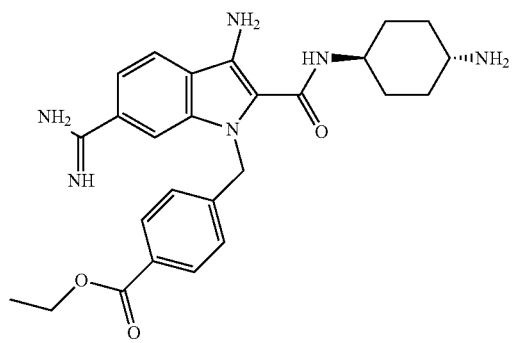 [SMILES: CCOC(=O)c1ccc(Cn2c(C(=O)N[C@H]3CC[C@H](N)CC3)c(N)c3ccc(C(=N)N)cc32)cc1]

Step-1: tert-Butyl ((1r,4r)-4-(6-cyano-3-nitro-1H-indole-2-carboxamido)cyclohexyl)carbamate The product of step-2 of example-6 (535 mg, 1.39 mmol) was dissolved in 10 mL of acetic acid and cooled it to 0° C. Copper(II) nitrate trihydrate (401 mg, 1.66) was added and stirred for 3 h. Reaction mixture was quenched with cold-water and extracted with ethyl acetate, followed by washed with brine and dried over sodium sulphate. Solvent was evaporated to give crude product which was purified with column chromatography using silica-gel as an adsorbent and elution with hexane:ethyl acetate (7:3) afforded 310 mg of the title compound. LCMS: 428.2 (M+1)$^+$.

Step-2: Ethyl 4-((2-(((1r,4r)-4-((tert-butoxycarbonyl)amino)cyclohexyl)carbamoyl)-6-cyano-3-nitro-1H-indol-1-yl)methyl)benzoate The product of step-1 of example-9 (310 mg, 0.72 mmol) and ethyl 4-(bromomethyl)benzoate (174 mg, 0.72 mmol) were treated together to afford 213 mg of the title compound following the procedure described in step-1 of example-1. LCMS: 590.2 (M+1)$^+$.

Step-3: Ethyl 4-((3-amino-2-(((1r,4r)-4-((tert-butoxycarbonyl)amino)cyclohexyl)carbamoyl)-6-cyano-1H-indol-1-yl)methyl)benzoate The product of step-2 of example-9 (200 mg, 0.33 mmol) was dissolved in 10 mL of glacial acetic acid and added zinc (107 mg, 1.65 mmol) in portions at room temperature. Reaction mixture was stirred at RT for 6 h. Contents were filtered through celite pad and filtrate was concentrated under vacuum to afford crude compound which was purified by column chromatography using silica-gel as an adsorbent and eluted with hexane:ethylacetate (6:4) and afforded the title compound (152 mg). LCMS: 560.3 (M+1)$^+$.

Step-4: Ethyl 4-((3-amino-2-(((1r,4r)-4-aminocyclohexyl)carbamoyl)-6-(ethoxy(imino)methyl)-1H-indol-1-yl)methyl)benzoate The product of step-3 of example-9 (150 mg, 0.27 mmol) was treated with 40 mL of ethanolic-HCl to afford 111 mg of the title compound following the procedure described in step-4 of example-1. LCMS: 506.3 (M+1)$^+$.

Step-5: Ethyl 4-((3-amino-2-(((1r,4r)-4-aminocyclohexyl)carbamoyl)-6-carbamimidoyl-1H-indol-1-yl)methyl)benzoate The product of step-4 of example-9 (108 mg, 0.21 mmol) was treated with 30 mL of ethanolic-NH$_3$ to afford 29 mg of the title compound following the procedure described in step-5 of example-1. LCMS: 477.2 (M+1)$^+$, $^1$H NMR (300 MHz, DMSO-d$_6$): δ 1.32 (m, 3H), 1.41 (m, 5H), 1.85 (m, 4H), 3.0 (m, 1H), 3.62 (m, 2H), 4.26 (m, 2H), 3.62 (m, 2H), 7.12 (d, 2H), 7.42 (m, 1H), 7.76 (m, 5H), 7.88 (d, 1H), 8.42 (m, 2H), 8.85 (brs, 2H), 9.19 (brs, 2H).

Example 10: Synthesis of Compound I-28

N-(1-(2-Aminoethyl)piperidin-4-yl)-6-carbamimidoyl-1-phenethyl-1H-indole-2-carboxamide

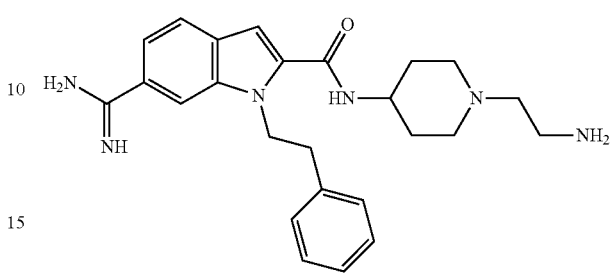

Step-1: Ethyl 6-cyano-1-phenethyl-1H-indole-2-carboxylate

Ethyl 6-cyano-1H-indole-2-carboxylate (2500 mg, 11.67 mmol) and (2-bromoethyl)benzene (2160 mg, 11.67 mmol) were treated together to afford 3100 mg of the title compound following the procedure described in step-1 of example-1. LCMS: 319.1 (M+1)$^+$.

Step-2: 6-Cyano-1-phenethyl-1H-indole-2-carboxylic Acid

The product of step-1 of example-10 (3000 mg, 9.42 mmol) and lithium hydroxide (792 mg, 32.97 mmol) were treated together to afford 2100 mg of the title compound following the procedure described in step-2 of example-1. LCMS: 291.1 (M+1)$^+$.

Step-3: tert-Butyl 4-(6-cyano-1-phenethyl-1H-indole-2-carboxamido)piperidine-1-carboxylate The product of step-2 of example-10 (390 mg, 1.34 mmol) and tert-butyl 4-aminopiperidine-1-carboxylate (205 mg, 1.5 mmol) were treated together to afford 378 mg of the title compound following the procedure described in step-3 of example-1. LCMS: 473.2 (M+1)$^+$.

Step-4: 6-Cyano-1-phenethyl-N-(piperidin-4-yl)-1H-indole-2-carboxamide

The product of step-3 of example-10 (350 mg, 0.73 mmol) was treated with 20 mL of ethanolic-HCl to afford 212 mg of the title compound following the procedure described in step-2 of example-2. LCMS: 373.2 (M+1)$^+$.

Step-5: tert-Butyl (2-(4-(6-cyano-1-phenethyl-1H-indole-2-carboxamido)piperidin-1-yl)ethyl)carbamate The product of step-4 of example-10 (200 mg, 0.53 mmol) and tert-butyl (2-bromoethyl)carbamate (118 mg, 0.53 mmol) were treated together to afford 226 mg of the title compound following the procedure described in step-1 of example-1. LCMS: 516.3 (M+1)$^+$.

Step-6: Ethyl 2-((1-(2-aminoethyl)piperidin-4-yl)carbamoyl)-1-phenethyl-1H-indole-6-carbimidate The product of step-5 of example-10 (220 mg, 0.42 mmol) was treated with 50 mL of ethanolic-HCl to afford 105 mg of the title compound following the procedure described in step-4 of example-1. LCMS: 462.3 (M+1)⁺.

Step-7: N-(1-(2-aminoethyl)piperidin-4-yl)-6-carbamimidoyl-1-phenethyl-1H-indole-2-carboxamide The product of step-6 of example-10 (105 mg, 0.22 mmol) was treated with 50 mL of ethanolic-NH₃ to afford 43 mg of the title compound following the procedure described in step-5 of example-1. LCMS: 433.3 (M+1)⁺, ¹H NMR (300 MHz, DMSO-d₆): δ 1.62 (m, 2H), 1.19 (m, 2H), 2.12 (m, 3H), 3.00 (m, 4H), 3.33 (m, 4H), 3.62 (m, 2H), 4.12 (m, 1H), 4.81 (m, 2H), 7.35 (m, 3H), 7.51 (d, 1H), 7.85 (d, 1H), 8.05 (m, 2H), 8.70 (m, 1H), 9.07 (brs, 2H), 9.24 (brs, 2H), 9.91 (brs, 1H); HPLC: 94.7% (Retention Time=4.194 min).

Example 11: Synthesis of Compound I-29

N-(1-(3-Aminopropyl)piperidin-4-yl)-6-carbamimidoyl-1-phenethyl-1H-indole-2-carboxamide

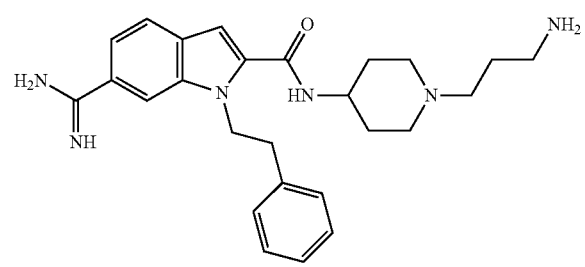 [SMILES: N=C(N)c1ccc2cc(C(=O)NC3CCN(CCCN)CC3)n(CCc3ccccc3)c2c1]

Step-1: tert-Butyl (3-(4-(6-cyano-1-phenethyl-1H-indole-2-carboxamido)piperidin-1-yl)propyl)carbamate The product of step-4 of example-10 (380 mg, 1.01 mmol) and tert-butyl (3-bromopropyl)carbamate (239 mg, 1.01 mmol) were treated together to afford 350 mg of the title compound following the procedure described in step-1 of example-1. LCMS: 530.3 (M+1)⁺.

Step-2: Ethyl 2-((1-(3-aminopropyl)piperidin-4-yl)carbamoyl)-1-phenethyl-1H-indole-6-carbimidate The product of step-1 of example-11 (350 mg, 0.66 mmol) was treated with 50 mL of ethanolic-HCl to afford 253 mg of the title compound following the procedure described in step-4 of example-1. LCMS: 476.3 (M+1)⁺.

Step-3: N-(1-(3-Aminopropyl)piperidin-4-yl)-6-carbamimidoyl-1-phenethyl-1H-indole-2-carboxamide The product of step-2 of example-11 (250 mg, 0.55 mmol) was treated with 50 mL of ethanolic-NH₃ to afford 135 mg of the title compound following the procedure described in step-5 of example-1. LCMS: 447.3 (M+1)⁺, ¹H NMR (300 MHz, DMSO-d₆): δ 1.62 (m, 2H), 1.19 (m, 4H), 2.85 (m, 4H), 3.05 (m, 6H), 4.05 (m, 1H), 4.73 (m, 2H), 7.15 (m, 5H), 7.51 (d, 1H), 7.85 (m, 3H), 8.15 (d, 1H), 8.70 (d, 1H), 9.07 (brs, 2H), 9.24 (brs, 2H), 9.69 (brs, 1H).

Example 12: Synthesis of Compound I-33

3-Amino-N-((1r,4r)-4-aminocyclohexyl)-6-carbamimidoyl-1-(4-(trifluoromethyl)-phenethyl)-1H-indole-2-carboxamide

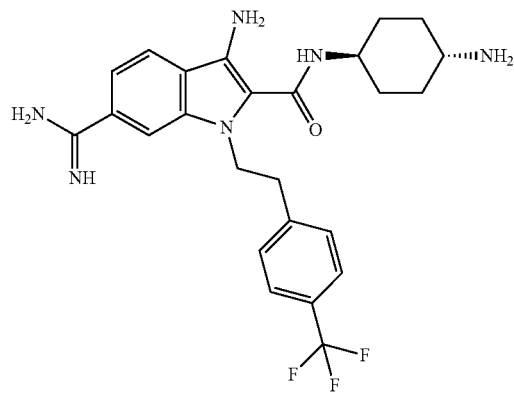 [SMILES: N=C(N)c1ccc2c(N)c(C(=O)N[C@H]3CC[C@H](N)CC3)n(CCc3ccc(C(F)(F)F)cc3)c2c1]

Step-1: tert-Butyl ((1r,4r)-4-(6-cyano-3-nitro-1-(4-(trifluoromethyl)phenethyl)-1H-indole-2-carboxamido)cyclohexyl)carbamate The product of step-1 of example-9 (580 mg, 1.35 mmol) and 1-(2-bromoethyl)-4-(trifluoromethyl)benzene (340 mg, 1.35 mmol) were treated together to afford 550 mg of the title compound following the procedure described in step-1 of example-1. LCMS: 600.2 (M+1)⁺.

Step-2: tert-Butyl ((1r,4r)-4-(3-amino-6-cyano-1-(4-(trifluoromethyl)phenethyl)-1H-indole-2-carboxamido)cyclohexyl)carbamate The product of step-1 of example-12 (455 mg, 0.75 mmol) and zinc (246 mg, 3.79 mmol) were treated together to afford 345 mg of the title compound following the procedure described in step-3 of example-9. LCMS: 570.3 (M+1)⁺.

Step-3: Ethyl-3-amino-2-(((1r,4r)-4-aminocyclohexyl)carbamoyl)-1-(4-(trifluoromethyl)-phenethyl)-1H-indole-6-carbimidate The product of step-2 of example-12 (345 mg, 0.60 mmol) was treated with 50 mL of ethanolic-HCl to afford 180 mg of the title compound following the procedure described in step-4 of example-1. LCMS: 516.2 (M+1)⁺.

Step-4: 3-Amino-N-((1r,4r)-4-aminocyclohexyl)-6-carbamimidoyl-1-(4-(trifluoromethyl)-phenethyl)-1H-indole-2-carboxamide The product of step-3 of example-12 (180 mg, 0.34 mmol) was treated with 50 mL of ethanolic-NH₃ to afford 65 mg of the title compound following the procedure described in step-5 of example-1. LCMS: 487.2 (M+1)⁺, ¹H NMR (300 MHz, DMSO-d₆): δ 1.38 (m, 4H), 1.92 (m, 4H), 2.93 (m, 3H), 3.05 (m, 1H), 3.75 (m, 3H), 3.72 (m, 1H), 4.65 (m, 2H), 7.35 (m, 3H), 7.59 (d, 2H), 7.82 (m, 3H), 8.52 (d, 1H), 8.89 (brs, 2H), 9.19 (brs, 2H); HPLC: 95.67% (Retention Time=4.682 min).

Example 13: Synthesis of Compound I-36

N-((1r,4r)-4-Aminocyclohexyl)-1-((3-(3-aminopropanamido)phenyl)sulfonyl)-6-carbamimidoyl-1H-indole-2-carboxamide

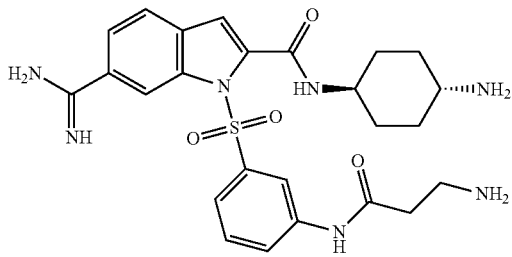 [SMILES: N=C(N)c1ccc2cc(C(=O)N[C@H]3CC[C@H](N)CC3)n(S(=O)(=O)c3cccc(NC(=O)CCN)c3)c2c1]

Step-1: Ethyl 6-cyano-1-((3-nitrophenyl)sulfonyl)-1H-indole-2-carboxylate

Ethyl 6-cyano-1H-indole-2-carboxylate (780 mg, 3.64 mmol) and 3-nitrobenzene-1-sulfonyl chloride (2011 mg, 9.1 mmol) were treated together to afford 660 mg of the title compound following the procedure described in step-1 of example-1. LCMS: 401.1 (M+1)$^+$.

Step-2: 6-Cyano-1-((3-nitrophenyl)sulfonyl)-1H-indole-2-carboxylic Acid

The product of step-1 of example-13 (550 mg, 1.37 mmol) and lithium hydroxide (201 mg, 4.79 mmol) were treated together to afford 425 mg of the title compound following the procedure described in step-2 of example-1. LCMS: 372.1 (M+1)$^+$.

Step-3: tert-Butyl ((1r,4r)-4-(6-cyano-1-((3-nitrophenyl)sulfonyl)-1H-indole-2-carboxamido)-cyclohexyl)carbamate The product of step-2 of example-13 (400 mg, 1.07 mmol) and tert-butyl ((1r,4r)-4-aminocyclohexyl)carbamate (230 mg, 1.07 mmol) were treated together to afford 368 mg of the title compound following the procedure described in step-3 of example-1. LCMS: 568.2 (M+1)$^+$.

Step-4: tert-Butyl ((1r,4r)-4-(1-((3-aminophenyl)sulfonyl)-6-cyano-1H-indole-2-carboxamido)-cyclohexyl)carbamate The product of step-3 of example-13 (360 mg, 0.63 mmol) was treated with zinc (205 mg, 3.16 mmol) to afford 210 mg of the title compound following the procedure described in step-3 of example 9. LCMS: 538.2 (M+1)$^+$.

Step-5: tert-Butyl ((1r,4r)-4-(1-((3-(3-(tert-butyl carbamate)-propanamido)phenyl)sulfonyl)-6-cyano-1H-indole-2-carboxamido)cyclohexyl)carbamate The product of step-4 of example-13 (200 mg, 0.37 mmol) and 3-(((tert-butoxycarbonyl)amino)propanoic acid (70 mg, 0.37 mmol) were treated together to afford 185 mg of the title compound following the procedure described in step-3 of example-1. LCMS: 709.3 (M+1)$^+$.

Step-6: Ethyl-2-(((1r,4r)-4-aminocyclohexyl)carbamoyl)-1-((3-(3-aminopropanamido)phenyl)-sulfonyl)-1H-indole-6-carbimidate The product of step-5 of example-1 (185 mg, 0.26 mmol) was treated with 50 mL of ethanolic-HCl to afford 88 mg of the title compound following the procedure described in step-4 of example-1. LCMS: 555.2 (M+1)$^+$.

Step-7: N-((1r,4r)-4-Aminocyclohexyl)-1-((3-(3-aminopropanamido)phenyl)sulfonyl)-6-carbamimidoyl-1H-indole-2-carboxamide The product of step-6 of example-13 (85 mg, 0.15 mmol) was treated with 50 mL of ethanolic-NH$_3$ to afford 18 mg of the title compound following the procedure described in step-5 of example-1. LCMS: 526.2 (M+1)$^+$.

General synthetic scheme 2:

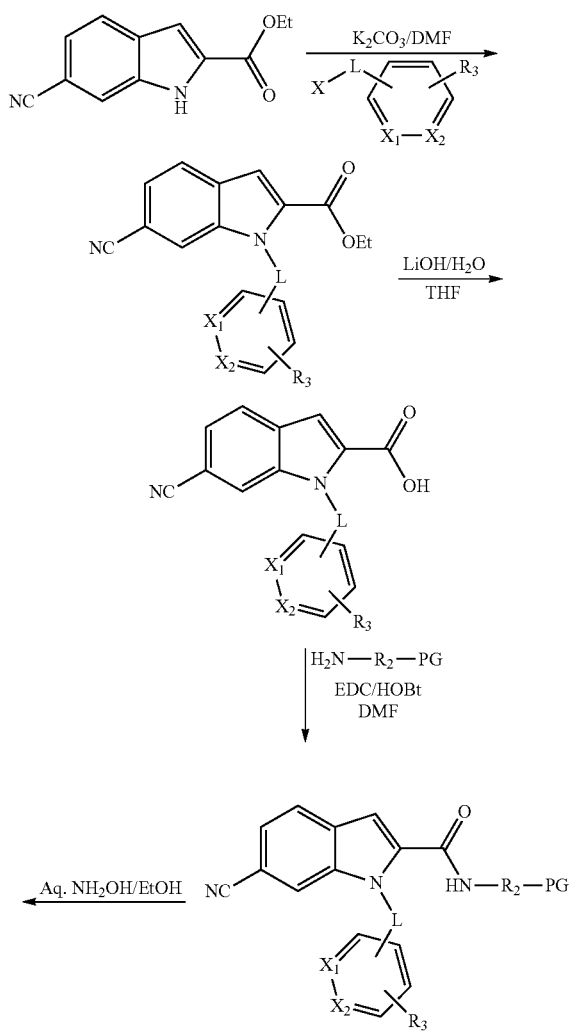

-continued

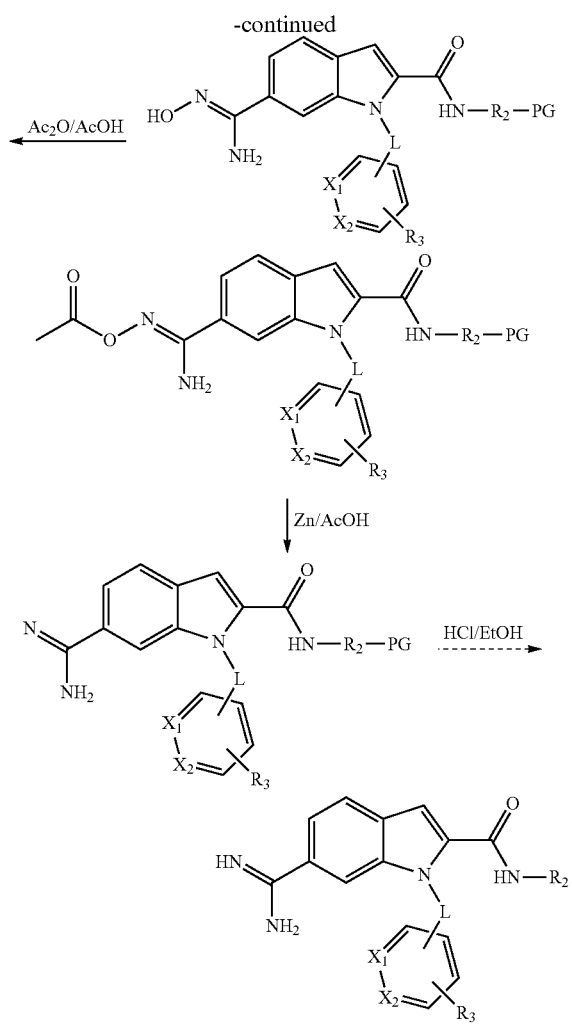

X = Br or Cl; PG = optional protecting group;
----▶ = optional step only when PG is present Example 14: Synthesis of Compound I-40

6-Carbamimidoyl-1-(2-(phenylsulfonyl)ethyl)-N-(3-(trifluoromethyl)phenyl)-1H-indole-2-carboxamide

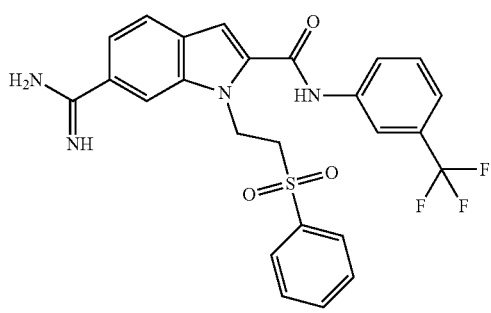 [SMILES: N=C(N)c1ccc2cc(C(=O)Nc3cccc(C(F)(F)F)c3)n(CCS(=O)(=O)c3ccccc3)c2c1]

Step-1: Ethyl 6-cyano-1-(2-(phenylsulfonyl)ethyl)-1H-indole-2-carboxylate

Ethyl 6-cyano-1H-indole-2-carboxylate (3.5 g, 16.33 mmol) and ((2-bromoethyl)sulfonyl)benzene (4.68 mg, 16.33 mmol) were treated together to afford 5.2 g of the title compound following the procedure described in step-1 of example-1. LCMS: 383.1 (M+1)$^+$.

Step-2: 6-Cyano-1-(2-(phenylsulfonyl)ethyl)-1H-indole-2-carboxylic Acid

The product of step-1 of example-14 (5.1 g, 13.33 mmol) and lithium hydroxide (1.12 g, 46.65 mmol) were treated together to afford 4.1 g of the title compound following the procedure described in step-2 of example-1. LCMS: 355.1 (M+1)$^+$.

Step-3: 6-Cyano-1-(2-(phenylsulfonyl)ethyl)-N-(3-(trifluoromethyl)phenyl)-1H-indole-2-carboxamide The product of step-2 of example-14 (578 mg, 1.63 mmol) and 3-(trifluoromethyl)aniline (262 mg, 1.63 mmol) were treated together to afford 645 mg of the title compound following the procedure described in step-3 of example-1. LCMS: 498.1 (M+1)$^+$.

Step-4: 6-(N'-hydroxycarbamimidoyl)-1-(2-(phenylsulfonyl)ethyl)-N-(3-(trifluoromethyl)-phenyl)-1H-indole-2-carboxamide The product of step-3 of example-14 (550 mg, 1.10 mmol) was dissolved in 10 mL of ethanol and added aqueous hydroxylamine solution (1.3 mL) and resulting mixture was refluxed for 4 h at 80° C. Solvent was evaporated under vacuum to afford the title compound (425 mg) which was used for the next step without further purification. LCMS: 531.1 (M+1)$^+$.

Step-5: 6-(N'-acetoxycarbamimidoyl)-1-(2-(phenylsulfonyl)ethyl)-N-(3-(trifluoromethyl)phenyl)-1H-indole-2-carboxamide The product of step-4 of example-14 (570 mg, 1.07 mmol) was dissolved in 5 mL of acetic acid and added acetic anhydride (0.87 mg, 8.56 mmol) and resulting mixture was stirred at RT for 2 h. Solvent was evaporated under vacuum to afford the title compound (560 mg) which was used for the next step without further purification. LCMS: 573.1 (M+1)$^+$.

Step-6: 6-Carbamimidoyl-1-(2-(phenylsulfonyl)ethyl)-N-(3-(trifluoromethyl)phenyl)-1H-indole-2-carboxamide The product of step-5 of example-14 (450 mg, 0.78 mmol) was dissolved in 5 mL of acetic acid and added zinc (408 mg, 6.24 mmol) in portions and resulting mixture was stirred at RT for 6 h. Reaction mixture was filtered through celite pad and resulting filtrate was concentrated under vacuum to give crude product which was purified with reversed-phase preparative HPLC and afforded the title compound (275 mg). LCMS: 573.1 (M+1)$^+$, $^1$H NMR (300 MHz, DMSO-d$_6$): δ 4.00 (m, 2H), 4.92 (m, 2H), 7.45 (s, 1H), 7.49 (m, 2H), 7.59 (m, 3H), 7.63 (m, 1H), 7.90 (m, 3H), 7.96 (m, 2H), 8.21 (s, 1H), 9.09 (brs, 2H), 9.32 (brs, 2H), 10.76 (s, 1H); HPLC: 97.32% (Retention Time=3.595 min).

The following compounds listed in table-4 were prepared according to Scheme-2 by following similar procedure as described above for example-14 using appropriate reagents with suitable modifications known to the one skilled in the art.

TABLE 4

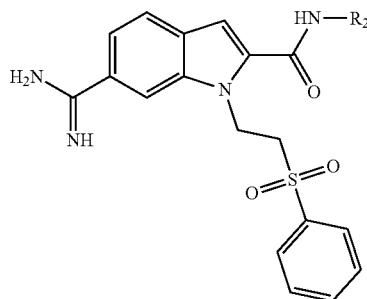

| Cpd. ID. | R₂ | LCMS (M + 1)⁺ | ¹H NMR |
|---|---|---|---|
| I-41 | 3-fluorophenyl | 465.1 | δ 3.98 (m, 2H), 4.92 (m, 2H), 6.97 (m, 1H), 7.42 (m, 2H), 7.51 (m, 2H), 7.59 (m, 2H), 7.69 (m, 2H), 7.90 (m, 3H), 8.00 (s, 1H), 9.25 (brs, 2H), 9.33 (brs, 2H), 10.76 (s, 1H); HPLC: 93.52% (Retention Time = 6.336 min). |
| I-42 | 4-fluorophenyl | 465.1 | δ 3.97 (m, 2H), 4.91 (m, 2H), 7.21 (m, 2H), 7.38 (s, 1H), 7.51 (d, 2H), 7.60 (m, 2H), 7.72 (m, 2H), 7.88 (m, 3H), 7.97 (s, 1H), 9.21 (brs, 2H), 9.32 (brs, 2H), 10.6 (s, 1H); HPLC: 94.07% (Retention Time = 7.022 min). |
| I-43 | 4-(trifluoromethyl)phenyl | 515.1 | δ 4.08 (m, 2H), 5.02 (m, 2H), 7.53 (s, 1H), 7.60 (d, 1H), 7.69 (m, 2H), 7.83 (m, 3H), 7.99 (m, 6H), 9.23 (brs, 2H), 9.40 (brs, 2H), 10.88 (brs, 1H); HPLC: 95.35% (Retention Time = 6.922 min). |
| I-44 | 4-(pyrrolidin-1-yl)phenyl | 516.2 | δ 1.91 (m, 4H), 3.20 (m, 4H), 3.95 (m, 2H), 4.89 (m, 2H), 6.53 (m, 2H), 7.30 (s, 1H), 7.49 (d, 3H), 7.57 (m, 2H), 7.73 (m, 1H), 7.84 (m, 4H), 8.98 (brs, 2H), 9.28 (brs, 2H), 10.18 (brs, 1H); HPLC: 98.7% (Retention Time = 6.79 min). |
| I-45 | trans-4-aminocyclohexyl | 468.2 | δ 1.41 (m, 4H), 1.85 (m, 5H), 2.90 (m, 1H), 3.54 (m, 1H), 3.85 (m, 2H), 4.87 (m, 2H), 7.18 (s, 1H), 7.47 (d, 1H), 7.59 (m, 2H), 7.71 (m, 1H), 7.81 (m, 3H), 7.95 (m, 2H), 8.54 (d, 1H), 9.23 (d, 3H); HPLC: 98.89% (Retention Time = 4.35 min). |
| I-46 | 4-methylcyclohexyl | 467.2 | δ 0.88 (m, 3H), 1.50 (m, 4H), 1.65 (m, 5H), 3.90 (m, 3H), 4.87 (m, 2H), 7.14 (d, 1H), 7.47 (d, 1H), 7.61 (m, 2H), 7.74 (m, 2H), 7.81 (m, 3H), 8.35 (m, 1H), 9.06 (brs, 2H), 9.27 (brs, 2H); HPLC: 96.87% (Retention Time = 3.598 min). |

TABLE 4-continued

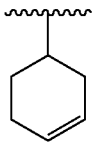

| Cpd. ID. | R$_2$ | LCMS (M + 1)$^+$ | $^1$H NMR |
|---|---|---|---|
| I-47 | 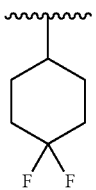 | 451.2 | δ 1.54 (m, 2H), 1.81 (m, 2H), 2.22 (m, 2H), 3.92 (m, 3H), 4.88 (m, 2H), 5.67 (m, 2H), 7.16 (s, 1H), 7.47 (d, 1H), 7.59 (m, 2H), 7.71 (m, 1H), 7.81 (m, 3H), 8.52 (m, 1H), 8.92 (d, 1H), 8.92 (brs, 2H), 9.27 (brs, 2H); HPLC: 96.25% (Retention Time = 3.256 min). |
| I-48 | 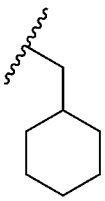 [SMILES: *CC1CCCCC1] | 489.2 | δ 1.61 (m, 2H), 1.84 (m, 3H), 2.04 (m, 4H), 3.91 (m, 3H), 4.89 (m, 2H), 7.16 (s, 1H), 7.47 (d, 1H), 7.61 (m, 2H), 7.72 (m, 1H), 7.81 (m, 3H), 8.54 (m, 1H), 9.00 (brs, 2H), 9.27 (brs, 2H); HPLC: 95.67% (Retention Time = 6.084 min). |
| I-49 | 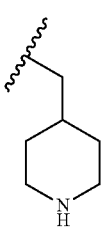 | 467.2 | δ 0.89 (m, 2H), 1.15 (m, 3H), 1.63 (m, 6H), 3.05 (m, 2H), 3.92 (m, 2H), 4.87 (m, 2H), 7.13 (s, 1H), 7.47 (d, 1H), 7.58 (m, 2H), 7.71 (m, 1H), 7.80 (m, 4H), 8.68 (m, 1H), 9.14 (brs, 2H), 9.29 (brs, 2H); HPLC: 98.85% (Retention Time = 7.193 min). |
| I-50 | 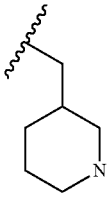 | 468.2 | δ 1.34 (m, 2H), 1.84 (m, 3H), 2.86 (m, 2H), 3.16 (m, 2H), 3.30 (m, 2H), 3.95 (m, 2H), 4.93 (m, 2H), 7.16 (s, 1H), 7.51 (d, 1H), 7.63 (m, 2H), 7.73 (m, 1H), 7.81 (m, 3H), 8.49 (brs, 1H), 8.69 (brs, 1H), 8.84 (m, 1H), 9.27 (brs, 3H); HPLC: 90.13% (Retention Time = 4.522 min). |
| I-51 | 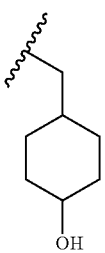 | 468.2 | δ 1.20 (m, 1H), 1.60 (m, 1H), 1.78 (m, 2H), 1.96 (m, 1H), 2.66 (m, 2H), 3.15 (m, 2H), 3.93 (m, 2H), 4.91 (m, 2H), 7.14 (s, 1H), 7.47 (d, 1H), 7.56 (m, 2H), 7.69 (m, 1H), 7.79 (m, 3H), 7.83 (s, 1H), 8.45 (m, 1H), 8.79 (m, 1H), 8.84 (m, 1H), 9.22 (brs, 2H), 9.29 (brs, 2H); HPLC: 98.74% (Retention Time = 4.635 min). |
| I-52 | | 468.2 | δ 1.40 (m, 1H), 1.60 (m, 4H), 3.11 (m, 2H), 3.44 (m, 4H), 3.75 (m, 1H), 3.94 (m, 2H), 4.33 (brs, 1H), 4.90 (m, 2H), 7.16 (s, 1H), 7.49 (d, 1H), 7.63 (m, 2H), 7.73 (m, 2H), 7.83 (m, 3H), 8.70 (m, 1H), 9.02 (brs, 2H), 9.30 (brs, 2H); HPLC: 76.34% (Retention Time = 5.455 min). |

TABLE 4-continued

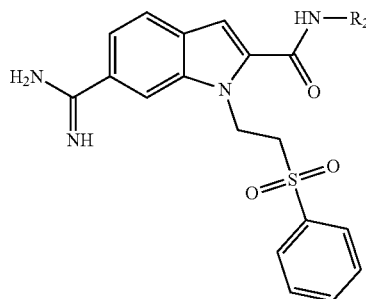

| Cpd. ID. | R$_2$ | LCMS (M + 1)$^+$ | $^1$H NMR |
|---|---|---|---|
| I-53 | (trans-4-hydroxycyclohexyl)methyl | 468.2 | δ 1.38 (m, 1H), 1.58 (m, 4H), 2.49 (m, 1H), 3.08 (m, 2H), 3.90 (m, 4H), 4.87 (m, 4H), 7.11 (s, 1H), 7.45 (d, 1H), 7.57 (m, 2H), 7.69 (m, 2H), 7.83 (m, 3H), 8.66 (m, 1H); HPLC: 95.96% (Retention Time = 5.498 min). |
| I-54 | (4,4-difluorocyclohexyl)methyl | 503.2 | δ 1.91 (m, 2H), 1.70 (m, 5H), 2.01 (m, 2H), 3.14 (m, 2H), 3.93 (m, 2H), 4.90 (m, 2H), 7.14 (s, 1H), 7.48 (d, 1H), 7.60 (m, 2H), 7.71 (m, 1H), 7.81 (m, 3H), 8.78 (brs, 1H), 9.03 (brs, 2H), 9.28 (brs, 2H), 10.18 (brs, 1H); HPLC: 98% (Retention Time = 6.214 min). |

Example 15: Synthesis of Compound I-55

N-((1r,4r)-4-Aminocyclohexyl)-6-carbamimidoyl-3-nitro-1-(2-(phenylsulfonyl)ethyl)-1H-indole-2-carboxamide

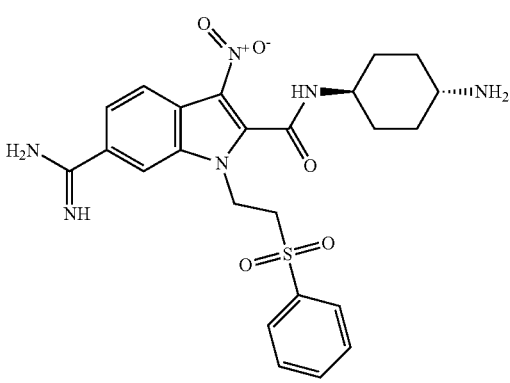

Step-1: tert-Butyl-((1r,4r)-4-(6-cyano-3-nitro-1-(2-(phenylsulfonyl)ethyl)-1H-indole-2-carboxamido)-cyclohexyl)carbamate The product of step-1 of example-9 (688 mg, 1.60 mmol) and ((2-bromoethyl)sulfonyl)benzene (395 mg, 1.60 mmol) were treated together to afford 780 mg of the title compound following the procedure described in step-1 of example-1. LCMS: 596.2 (M+1)$^+$.

Step-2: Ethyl-2-(((1r,4r)-4-aminocyclohexyl)carbamoyl)-3-nitro-1-(2-(phenylsulfonyl)ethyl)-1H-indole-6-carbimidate The product of step-1 of example-15 (650 mg, 1.09 mmol) was treated with 60 mL of ethanolic-HCl to afford 380 mg of the title compound following the procedure described in step-4 of example-1. LCMS: 542.2 (M+1)$^+$.

Step-3: N-((1r,4r)-4-Aminocyclohexyl)-6-carbamimidoyl-3-nitro-1-(2-(phenylsulfonyl)ethyl)-1H-indole-2-carboxamide The product of step-2 of example-15 (250 mg, 0.46 mmol) was treated with 50 mL of ethanolic-NH$_3$ to afford 135 mg of the title compound following the procedure described in step-5 of example-1. LCMS: 513.2 (M+1)$^+$, $^1$H NMR (300 MHz, DMSO-d$_6$): δ 1.21 (m, 2H), 1.38 (m, 2H), 1.85 (m, 4H), 3.05 (m, 1H), 3.55 (m, 1H), 4.01 (m, 2H), 4.55 (m, 2H), 7.65 (m, 2H), 7.81 (m, 6H), 8.20 (brs, 1H), 8.52 (d, 1H), 9.12 (d, 1H), 8.25 (brs, 2H), 9.45 (brs, 2H).

Example 16: Synthesis of Compound I-56

3-Amino-N-((1r,4r)-4-aminocyclohexyl)-6-carbamimidoyl-1-(2-(phenylsulfonyl)ethyl)-1H-indole-2-carboxamide

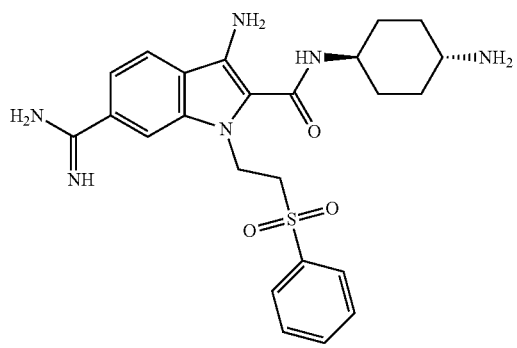 [SMILES: N=C(N)c1ccc2c(N)c(C(=O)N[C@H]3CC[C@H](N)CC3)n(CCS(=O)(=O)c3ccccc3)c2c1]

Step-1: tert-Butyl ((1r,4r)-4-(3-amino-6-cyano-1-(2-(phenylsulfonyl)ethyl)-1H-indole-2-carboxamido)cyclohexyl)carbamate The product of step-1 of example-15 (335 mg, 0.56 mmol) and zinc (182 mg, 2.80 mmol) were treated together to afford 180 mg of the title compound following the procedure described in step-3 of example-9. LCMS: 566.2 $(M+1)^+$.

Step-2: Ethyl 3-amino-2-(((1r,4r)-4-aminocyclohexyl)carbamoyl)-1-(2-(phenylsulfonyl)ethyl)-1H-indole-6-carbimidate The product of step-1 of example-16 (175 mg, 0.30 mmol) was treated with 40 mL of ethanolic-HCl to afford 105 mg of the title compound following the procedure described in step-4 of example-1. LCMS: 512.2 $(M+1)^+$.

Step-3: tert-Butyl ((1r,4r)-4-(3-amino-6-carbamimidoyl-1-(2-(phenylsulfonyl)ethyl)-1H-indole-2-carboxamido)cyclohexyl)carbamate The product of step-2 of example-16 (105 mg, 0.20 mmol) was treated with 30 mL of ethanolic-NH₃ to afford 43 mg of the title compound following the procedure described in step-5 of example-1. LCMS: 483.2 $(M+1)^+$, $^1$H NMR (300 MHz, DMSO-$d_6$): δ 1.45 (m, 4H), 1.91 (m, 4H), 3.08 (m, 1H), 3.52 (m, 1H), 3.79 (m, 2H), 4.67 (m, 2H), 7.37 (d, 1H), 7.65 (m, 2H), 7.73 (m, 2H), 7.83 (m, 6H), 7.91 (d, 1H), 9.12 (brs, 2H), 9.28 (brs, 2H).

Example 17: Synthesis of Compound I-17

Ethyl (2-(((1r,4r)-4-aminocyclohexyl)carbamoyl)-6-((Z)—N'-hydroxycarbamimidoyl)-1-(2-(phenylsulfonyl)ethyl)-1H-indol-3-yl)carbamate

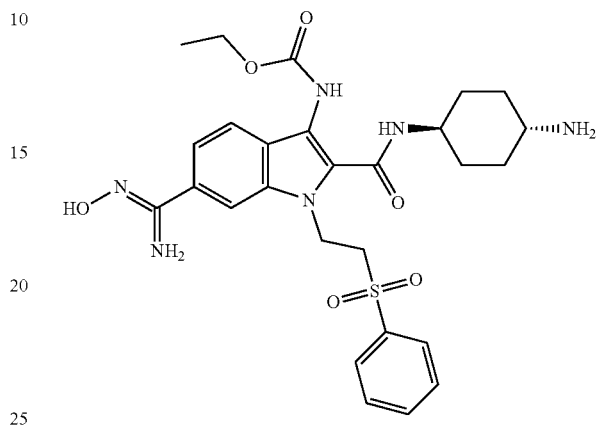

Step-1: tert-Butyl ((1r,4r)-4-(3-(ethylcarbamate)-6-cyano-1-(2-(phenylsulfonyl)ethyl)-1H-indole-2-carboxamido)cyclohexyl)carbamate The product of step-1 of example-16 (630 mg, 1.11 mmol) and Ethyl chloroformate (119 mg, 1.11 mmol) were treated together to afford 553 mg of the title compound following the procedure described in step-1 of example-1. LCMS: 638.3 $(M+1)^+$.

Step-2: tert-Butyl ((1r,4r)-4-(3-(ethylcarbamate)-6-((Z)—N'-hydroxycarbamimidoyl)-1-(2-(phenylsulfonyl)-ethyl)-1H-indole-2-carboxamido)cyclohexyl)carbamate The product of step-1 of example-17 (540 mg, 0.84 mmol) and aqueous hydroxylamine (2.7 mL) were treated together to afford 329 mg of the title compound following the procedure described in step-4 of example-14. LCMS: 671.3 $(M+1)^+$.

Step-3: Ethyl (2-(((1r,4r)-4-aminocyclohexyl)carbamoyl)-6-((Z)—N'-hydroxycarbamimidoyl)-1-(2-(phenylsulfonyl)ethyl)-1H-indol-3-yl)carbamate The product of step-2 of example-17 (315 mg, 0.46 mmol) was treated with 30 mL of ethanolic-HCl to afford 180 mg of the title compound following the procedure described in step-2 of example-2. LCMS: 571.2 $(M+1)^+$, $^1$H NMR (300 MHz, DMSO-$d_6$): δ 1.45 (m, 7H), 1.91 (m, 4H), 3.08 (m, 1H), 3.52 (m, 1H), 3.89 (m, 2H), 4.67 (m, 2H), 7.37 (d, 1H), 7.56 (m, 3H), 7.73 (m, 2H), 7.83 (m, 5H), 8.05 (d, 1H), 8.93 (brs, 1H), 11.11 (brs, 1H), 12.80 (brs, 1H); HPLC: 90.09% (Retention Time=4.488 min).

Example 18: Synthesis of Compound I-58

3-Amino-6-carbamimidoyl-N-(cyclohexylmethyl)-1-(2-(phenylsulfonyl)ethyl)-1H-indole-2-carboxamide

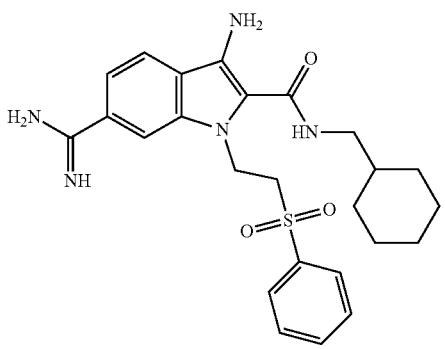 [SMILES: N=C(N)c1ccc2c(N)c(C(=O)NCC3CCCCC3)n(CCS(=O)(=O)c3ccccc3)c2c1]

Step-1: 6-Cyano-N-(cyclohexylmethyl)-1H-indole-2-carboxamide

The product of step-1 of example-6 (1.0 g, 5.34 mmol) and cyclohexylmethanamine (603 mg, 5.34 mmol) were treated together to afford 1.25 g of the title compound following the procedure described in step-3 of example-1. LCMS: 282.2 (M+1)$^+$.

Step-2: 6-Cyano-N-(cyclohexylmethyl)-3-nitro-1H-indole-2-carboxamide

The product of step-1 of example-18 (610 mg, 2.16 mmol) and copper(II) nitrate trihydrate (622 mg, 2.59 mmol) were treated together to afford 352 mg of the title compound following the procedure described in step-1 of example-9. LCMS: 327.1 (M+1)$^+$.

Step-3: 6-Cyano-N-(cyclohexylmethyl)-3-nitro-1-(2-(phenylsulfonyl)ethyl)-1H-indole-2-carboxamide The product of step-2 of example-18 (345 mg, 1.05 mmol) and ((2-bromoethyl)sulfonyl)benzene (389 mg, 1.57 mmol) were treated together to afford 356 mg of the title compound following the procedure described in step-1 of example-1. LCMS: 495.2 (M+1)$^+$.

Step-4: 3-Amino-6-cyano-N-(cyclohexylmethyl)-1-(2-(phenylsulfonyl)ethyl)-1H-indole-2-carboxamide The product of step-3 of example-18 (350 mg, 0.70 mmol) and zinc (229 mg, 3.5 mmol) were treated together to afford 195 mg of the title compound following the procedure described in step-3 of example-9. LCMS: 465.2 (M+1)$^+$.

Step-5: Ethyl 3-amino-2-((cyclohexylmethyl)carbamoyl)-1-(2-(phenylsulfonyl)ethyl)-1H-indole-6-carbimidate The product of step-4 of example-18 (190 mg, 0.40 mmol) was treated with ethanolic-HCl to afford 133 mg of the title compound following the procedure described in step-4 of example-1. LCMS: 511.2 (M+1)$^+$.

Step-6: 3-Amino-6-carbamimidoyl-N-(cyclohexylmethyl)-1-(2-(phenylsulfonyl)ethyl)-1H-indole-2-carboxamide The product of step-5 of example-18 (125 mg, 0.24 mmol) was treated with ethanolic-NH$_3$ to afford 38 mg of the title compound following the procedure described in step-5 of example-1. LCMS: 482.2 (M+1)$^+$, $^1$H NMR (300 MHz, DMSO-d$_6$): δ 0.92 (m, 2H), 1.11 (m, 3H), 1.52 (m, 1H), 1.66 (m, 4H), 3.08 (m, 2H), 3.77 (m, 2H), 4.67 (m, 2H), 5.03 (brs, 2H), 7.37 (d, 1H), 7.60 (m, 2H), 7.73 (m, 2H), 7.83 (m, 2H), 7.91 (d, 2H), 8.10 (m, 1H), 8.92 (brs, 2H), 9.25 (brs, 2H); HPLC: 93.49% (Retention Time=6.417 min).

Example 19: Synthesis of Compound I-59

6-Carbamimidoyl-1-(4-carbamoylbenzyl)-N-(4-fluorophenyl)-1H-indole-2-carboxamide

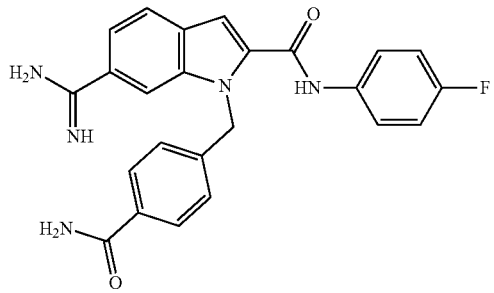 [SMILES: N=C(N)c1ccc2cc(C(=O)Nc3ccc(F)cc3)n(Cc3ccc(C(N)=O)cc3)c2c1]

Step-1: Ethyl 1-(4-carbamoylbenzyl)-6-cyano-1H-indole-2-carboxylate

Ethyl 6-cyano-1H-indole-2-carboxylate (4.0 g, 18.67 mmol) and 4-(bromomethyl)benzamide (4.8 g, 22.4 mmol) were treated together to afford 5.26 g of the title compound following the procedure described in step-1 of example 1. LCMS: 348.1 (M+1)$^+$.

Step-2: 1-(4-Carbamoylbenzyl)-6-cyano-1H-indole-2-carboxylic Acid

The product of step-1 of example 19 (1.2 g, 3.44 mmol) and lithium hydroxide (505 mg, 12.04 mmol) were treated together to afford 882 mg of the title compound following the procedure described in step-2 of example 1. LCMS: 320.1 (M+1)$^+$.

Step-3: 1-(4-carbamoylbenzyl)-6-cyano-N-(4-fluorophenyl)-1H-indole-2-carboxamide The product of step-2 of example 19 (500 mg, 1.56 mmol) and 4-fluoroaniline (174 mg, 1.56 mmol) were treated together to afford 385 mg of the title compound following the procedure described in step-3 of example 1. LCMS: 413.1 (M+1)$^+$.

Step-4: 1-(4-carbamoylbenzyl)-N-(4-fluorophenyl)-6-(N'-hydroxycarbamimidoyl)-1H-indole-2-carboxamide The product of step-3 of example 19 (360 mg, 0.87 mmol) and aqueous hydroxylamine (1.8 mL) were treated together to afford 310 mg of the title compound following the procedure described in step-4 of example 40. LCMS: 446.2 (M+1)⁺.

Step-5: 6-(N'-acetoxycarbamimidoyl)-1-(4-carbamoylbenzyl)-N-(4-fluorophenyl)-1H-indole-2-carboxamide The product of step-4 of example 19 (285 mg, 0.64 mmol) and acetic anhydride (261 mg, 2.56 mmol) were treated together to afford 240 mg of the title compound following the procedure described in step-5 of example 14. LCMS: 488.2 (M+1)⁺.

Step-6: 6-Carbamimidoyl-1-(4-carbamoylbenzyl)-N-(4-fluorophenyl)-1H-indole-2-carboxamide The product of step-5 of example 19 (230 mg, 0.47 mmol) and zinc (125 mg, 1.89 mmol) were treated together to afford 128 mg of the title compound following the procedure described in step-6 of example 14. LCMS: 430.2 (M+1)⁺, ¹H NMR (300 MHz, DMSO-$d_6$): δ 5.94 (s, 2H), 7.10 (d, 2H), 7.18 (m, 2H), 7.34 (brs, 1H), 7.52 (brs, 1H), 7.57 (d, 1H), 7.74 (m, 4H), 7.89 (brs, 1H), 7.98 (d, 1H), 8.21 (brs, 1H), 9.01 (brs, 2H), 9.27 (s, 2H), 10.65 (brs, 1H); HPLC: 98.09% (Retention Time=3.018 min).

The following compounds listed in table-5 and table-6 were prepared according to Scheme-2 by following similar procedure as described above for example-19 using appropriate reagents with suitable modifications known to the one skilled in the art.

TABLE 5

| Cpd. ID. | R₂ | LCMS (M + 1)⁺ | ¹H NMR |
|---|---|---|---|
| I-60 | 3-CF₃-phenyl | 480.2 | δ 6.02 (s, 2H), 7.25 (d, 2H), 7.48 (d, 1H), 7.59 (m, 2H), 7.67 (brs, 1H), 7.71 (d, 2H), 7.99 (m, 2H), 8.20 (brs, 2H), 9.17 (m, 4H), 9.29 (brs, 2H), 10.91 (brs, 1H); HPLC: 95.48% (Retention Time = 5.739 min). |
| I-61 | 4-CF₃-phenyl | 480.2 | δ 6.02 (s, 2H), 7.25 (d, 2H), 7.61 (d, 1H), 7.68 (s, 1H), 7.71 (m, 5H), 7.96 (d, 2H), 8.02 (d, 1H), 8.22 (brs, 1H), 9.20 (m, 3H), 9.30 (brs, 2H), 10.93 (brs, 1H); HPLC: 90.47% (Retention Time = 5.632 min). |
| I-62 | 3-F-phenyl | 430.2 | δ 6.02 (s, 2H), 6.96 (m, 1H), 7.28 (d, 2H), 7.41 (m, 1H), 7.57 (m, 3H), 7.70 (m, 3H), 7.98 (d, 1H), 8.22 (brs, 1H); HPLC: 97.26% (Retention Time = 5.232 min). |
| I-63 | 1-(4-F-phenyl)ethyl | 458.2 | δ 1.44 (m, 3H), 5.10 (m, 1H), 5.87 (s, 2H), 7.03 (d, 2H), 7.10 (m, 2H), 7.31 (m, 4H), 7.55 (d, 1H), 7.73 (d, 2H), 7.93 (m, 2H), 8.19 (s, 1H), 8.95 (brs, 2H), 9.16 (d, 1H), 9.24 (brs, 2H); HPLC: 91.78% (Retention Time = 3.935 min). |

TABLE 5-continued

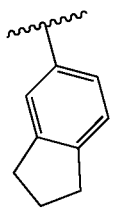 [SMILES: *c1ccc2c(c1)CCC2]

| Cpd. ID. | R₂ | LCMS (M + 1)⁺ | ¹H NMR |
|---|---|---|---|
| I-64 | 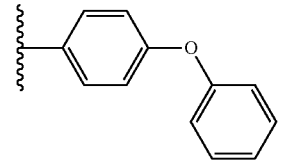 [SMILES: *c1ccc(Oc2ccccc2)cc1] | 452.2 | δ 1.92 (m, 2H), 2.68 (m, 2H), 2.86 (m, 2H), 5.94 (s, 2H), 7.11 (m, 5H), 7.34 (brs, 1H), 7.48 (s, 1H), 7.57 (d, 1H), 7.76 (d, 2H), 7.90 (brs, 1H), 7.96 (d, 1H), 8.24 (brs, 1H), 8.99 (brs, 2H), 9.28 (brs, 2H), 10.27 (brs, 1H); HPLC: 89.92% (Retention Time = 6.261 min). |
| I-65 | 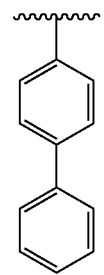 [SMILES: *c1ccc(-c2ccccc2)cc1] | 504.2 | δ 5.94 (s, 2H), 6.97 (m, 3H), 7.09 (m, 3H), 7.32 (brs, 1H), 7.35 (m, 3H), 7.50 (s, 1H), 7.55 (d, 1H), 7.74 (d, 4H), 7.89 (brs, 1H), 7.94 (d, 1H), 8.20 (brs, 1H), 10.61 (brs, 1H); HPLC: 92.49% (Retention Time = 3.238 min). |
| I-66 | 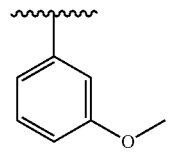 [SMILES: *c1cccc(OC)c1] | 488.2 | δ 5.96 (s, 2H), 7.12 (d, 2H), 7.34 (m, 2H), 7.45 (m, 3H), 7.57 (m, 2H), 7.67 (m, 5H), 7.75 (d, 2H), 7.82 (d, 3H), 7.84 (brs, 1H), 7.99 (d, 1H), 8.22 (brs, 1H), 8.91 (brs, 2H), 9.26 (brs, 2H), 10.61 (brs, 1H); HPLC: 91.77% (Retention Time = 6.153 min). |
| I-67 | 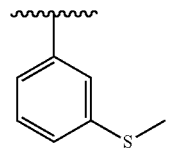 [SMILES: *c1cccc(SC)c1] | 442.2 | δ 3.74 (s, 3H), 5.90 (s, 2H), 6.68 (m, 1H), 7.10 (d, 2H), 7.23 (m, 2H), 7.33 (m, 2H), 7.41 (brs, 1H), 7.47 (s, 1H), 7.69 (s, 1H), 7.75 (d, 2H), 7.81 (d, 1H), 8.20 (brs, 1H), 9.12 (brs, 2H), 9.27 (brs, 2H), 10.42 (brs, 1H); HPLC: 92.58% (Retention Time = 5.984 min). |
| I-68 | 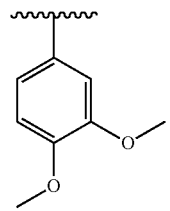 [SMILES: *c1ccc(OC)c(OC)c1] | 456.2 | δ 2.45 (s, 3H), 5.93 (s, 2H), 6.93 (d, 1H), 7.08 (d, 2H), 7.23 (m 2H) 7.45 (m 2H) 7.66 (brs, 1H), 7.72 (d, 2H), 7.88 (m, 1H), 8.19 (d, 1H), 9.01 (brs, 2H), 9.25 (brs, 2H), 10.56 (brs, 1H); HPLC: 93.76% (Retention Time = 6.256 min). |
| I-69 | | 472.2 | δ 3.73 (s, 6H), 5.95 (s, 2H), 6.91 (d, 1H), 7.13 (d, 2H), 7.29 (m, 2H), 7.39 (m, 1H), 7.46 (m, 1H), 7.55 (d, 2H), 7.88 (m, 1H), 7.92 (d, 1H), 8.17 (brs, 1H), 9.28 (brs, 2H), 10.42 (brs, 1H); HPLC: 89.19% (Retention Time = 11.717 min). |

TABLE 5-continued

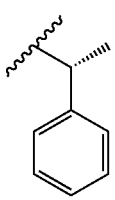

| Cpd. ID. | R₂ | LCMS (M + 1)⁺ | ¹H NMR |
|---|---|---|---|
| I-70 | 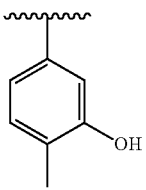 [SMILES: *c1ccc(C)c(O)c1] | 440.2 | δ 1.44 (d, 3H), 5.1 (m, 1H), 5.88 (s, 2H), 7.04 (d, 2H), 7.23 (m, 1H), 7.30 (m, 4H), 7.35 (brs, 1H), 7.38 (s, 2H), 7.54 (d, 1H), 7.72 (d, 1H), 7.90 (m, 2H), 8.18 (brs, 1H), 8.95 (brs, 2H), 9.21 (d, 1H), 9.26 (brs, 2H); HPLC: 91.23% (Retention Time = 2.78 min). |
| I-71 | 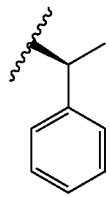 [SMILES: *[C@@H](C)c1ccccc1] | 442.2 | δ 2.07 (s, 3H), 5.94 (s, 2H), 6.99 (s, 2H), 7.11 (d, 2H), 7.33 (s, 1H), 7.38 (s, 1H), 7.49 (s, 1H), 7.56 (d, 1H), 7.74 (d, 1H), 7.89 (s, 1H), 7.96 (d, 1H), 8.20 (s, 1H), 9.00 (brs, 2H), 9.26 (brs, 2H), 9.41 (s, 1H), 10.4 (s, 1H); HPLC: 93.04% (Retention Time = 4.949 min). |
| I-72 | 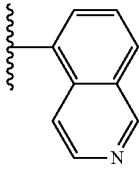 [SMILES: *c1cccc2cnccc12] | 440.2 | δ 1.44 (d, 3H), 5.11 (m, 1H), 5.87 (s, 2H), 7.04 (d, 2H), 7.21 (m, 1H), 7.30 (m, 4H), 7.32 (brs, 1H), 7.38 (s, 2H), 7.54 (d, 1H), 7.72 (d, 1H), 7.90 (m, 2H), 8.18 (brs, 1H), 8.93 (brs, 2H), 9.14 (d, 1H), 9.23 (brs, 2H); HPLC: 95.71% (Retention Time = 6.119 min). |
| I-73 | 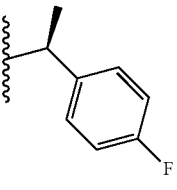 [SMILES: *[C@@H](C)c1ccc(F)cc1] | 463.2 | δ 5.96 (s, 2H), 7.10 (d, 2H), 7.37 (brs, 1H), 7.56 (d, 1H), 7.60 (d, 1H), 7.70 (m, 2H), 7.80 (m, 3H), 7.94 (brs, 1H), 8.03 (d, 1H), 8.08 (d, 1H), 8.29 (brs, 1H), 8.44 (d, 1H), 8.95 (brs, 2H), 9.28 (brs, 2H), 9.39 (brs, 1H); HPLC: 87.91% (Retention Time = 4.704 min). |
| I-75 | 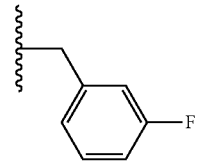 [SMILES: *Cc1cccc(F)c1] | 458.2 | δ 1.42 (d, 3H), 5.1 (m, 1H), 5.87 (s, 2H), 7.03 (m, 4H), 7.30 (m, 4H), 7.54 (d, 1H), 7.72 (d, 2H), 7.90 (m, 2H), 8.18 (brs, 1H), 8.93 (brs, 2H), 9.14 (d, 1H), 9.23 (brs, 2H); HPLC: 94.97% (Retention Time = 6.236 min). |
| I-76 | | 444.2 | δ 4.45 (d, 2H), 5.94 (s, 2H), 7.01 (m, 4H), 7.31 (m, 2H), 7.37 (s, 1H), 7.54 (d, 1H), 7.74 (d, 2H), 7.87 (brs, 1H), 7.93 (d, 1H), 8.19 (s, 1H), 8.89 (brs, 2H), 9.23 (brs, 2H), 9.33 (m, 1H); HPLC: 96.13% (Retention Time = 2.712 min). |

TABLE 5-continued

[Structure: indene core with H₂N-C(=NH)- (amidine) group, HN-R₂ amide, and benzyl group bearing -C(=O)-NH₂]

| Cpd. ID. | R₂ | LCMS (M + 1)⁺ | ¹H NMR |
|---|---|---|---|
| I-77 | benzyl (CH₂-phenyl) | 426.2 | δ 4.45 (d, 2H), 5.97 (s, 2H), 7.06 (d, 2H), 7.23 (d, 2H), 7.30 (m, 5H), 7.56 (d, 1H), 7.76 (d, 2H), 7.94 (m, 2H), 8.22 (brs, 1H), 8.92 (brs, 2H), 9.25 (brs, 2H), 9.34 (m, 1H); HPLC: 90.23% (Retention Time = 6.194 min). |
| I-78 | 4-(pyrrolidin-1-ylcarbonyl)phenyl | 509.2 | δ 1.84 (m, 4H), 3.41 (m, 4H), 5.95 (s, 2H), 7.10 (d, 2H), 7.31 (brs, 1H), 7.52 (m, 4H), 7.75 (m, 4H), 7.87 (brs, 1H), 7.99 (d, 1H), 8.21 (brs, 1H), 8.93 (brs, 2H), 9.26 (brs, 2H); HPLC: 96.67% (Retention Time = 5.828 min). |
| I-79 | 3-isopropylphenyl | 454.2 | δ 1.19 (m, 6H), 2.86 (m, 1H), 5.96 (s, 2H), 6.99 (m, 1H), 7.10 (d, 1H), 7.31 (m, 2H), 7.44 (m, 1H), 7.57 (m, 3H), 7.65 (m, 1H), 7.77 (d, 1H), 7.93 (m, 2H), 8.19 (d, 1H), 8.95 (d, 2H), 9.26 (d, 2H), 10.51 (brs, 1H); HPLC: 93.09% (Retention Time = 3.885 min). |
| I-80 | 3,5-difluorobenzyl | 462.2 | δ 4.45 (d, 2H), 5.94 (s, 2H), 6.94 (d, 2H), 7.04 (m, 2H), 7.31 (brs, 2H), 7.39 (s, 1H), 7.54 (m, 1H), 7.73 (d, 2H), 7.86 (brs, 462.2 1H), 7.94 (d, 1H), 8.18 (s, 1H), 8.89 (brs, 2H), 9.23 (brs, 2H), 9.38 (m, 1H); HPLC: 99.33% (Retention Time = 3.464 min). |
| I-81 | 2-phenylethyl | 462.2 | δ 2.78 (m, 2H), 3.48 (m, 2H), 5.93 (s, 2H), 7.06 (d, 2H), 7.16 (m, 3H), 7.23 (m, 3H), 7.28 (brs, 1H), 7.54 (d, 1H), 7.76 (d, 2H), 7.91 (m, 2H), 8.16 (s, 1H), 8.86 (m, 1H), 8.92 (brs, 2H), 9.23 (brs, 2H); HPLC: 97.89% (Retention Time = 5.911 min). |
| I-82 | 3-methyl-2-phenylbutyl | 468.2 | δ 0.68 (d, 3H), 0.92 (d, 3H), 4.58 (m, 1H), 2.48 (m, 1H), 5.82 (d, 2H), 7.03 (m, 3H), 7.23 (m, 8H), 7.53 (d, 1H), 7.67 (d, 2H), 7.87 (brs, 1H), 7.92 (d, 1H), 8.18 (s, 1H), 8.95 (brs, 2H), 9.09 (d, 1H), 9.23 (brs, 2H); HPLC: 89.62% (Retention Time = 2.908 min). |
| I-83 | 3-(trifluoromethyl)benzyl | 468.2 | δ 4.52 (d, 2H), 5.95 (s, 2H), 7.04 (d, 2H), 7.33 (brs, 1H), 7.38 (s, 1H), 7.46 (m, 5H), 7.73 (d, 2H), 7.89 (brs, 1H), 7.94 (d, 1H), 8.19 (brs, 1H), 8.94 (brs, 2H), 9.24 (brs, 2H), 9.40 (m, 1H); HPLC: 99.08% (Retention Time = 2.884 min). |

TABLE 5-continued

| Cpd. ID. | R₂ | LCMS (M + 1)⁺ | ¹H NMR |
|---|---|---|---|
| I-84 | 4-Cl-phenyl | 446.1 | δ 5.94 (s, 2H), 7.10 (d, 2H), 7.35 (brs, 1H), 7.41 (m, 2H), 7.54 (s, 1H), 7.57 (m, 1H), 7.75 (m, 4H), 7.89 (brs, 1H), 7.99 (d, 1H), 8.21 (s, 1H), 8.96 (brs, 2H), 9.27 (brs, 2H), 10.71 (s, 1H); HPLC: 96.173% (Retention Time = 3.279 min). |
| I-87 | 3,4-diF-phenyl | 448.1 | δ 5.92 (s, 2H), 7.08 (d, 2H), 7.33 (brs, 1H), 7.44 (m, 4H), 7.73 (d, 2H), 7.84 (m, 2H), 7.98 (d, 1H), 8.20 (s, 1H), 8.98 (brs, 2H), 9.25 (brs, 2H), 10.78 (brs, 1H); HPLC: 96.26% (Retention Time = 3.586 min). |
| I-88 | benzothiazol-6-yl | 469.1 | δ 5.97 (s, 2H), 7.12 (d, 2H), 7.31 (brs, 1H), 7.58 (m, 2H), 7.74 (m, 3H), 7.87 (brs, 1H), 7.99 (m, 2H), 8.21 (s, 1H), 8.64 (d, 1H), 9.00 (brs, 2H), 9.27 (brs, 2H), 9.30 (s, 1H) 10.83 (brs, 1H); HPLC: 87.07% (Retention Time = 5.59 min). |
| I-89 | 3,4,5-triF-phenyl | 466.1 | δ 5.92 (s, 2H), 7.07 (d, 2H), 7.32 (brs, 1H), 7.53 (m, 2H), 7.65 (m, 2H), 7.73 (d, 2H), 7.88 (brs, 1H), 7.99 (d, 1H), 8.20 (s, 1H), 8.97 (brs, 2H), 9.26 (brs, 2H), 10.88 (brs, 1H); HPLC: 97.15% (Retention Time = 3.249 min). |
| I-90 | 4-(pyrrolidin-1-yl)phenyl | 481.2 | δ 1.92 (m, 4H), 3.35 (m, 4H), 5.96 (s, 2H), 6.48 (d, 2H), 7.10 (d, 2H), 7.31 (brs, 1H), 7.42 (m, 4H), 7.75 (d, 2H), 7.87 (brs, 1H), 7.95 (d, 1H), 8.18 (s, 1H), 8.90 (brs, 2H), 9.29 (brs, 2H), 10.40 (s, 1H); HPLC: 92.5% (Retention Time = 3.176 min). |
| I-91 | 2,3-dihydro-1H-inden-4-yl | 452.2 | δ 1.92 (m, 2H), 2.68 (m, 2H), 2.87 (m, 2H), 5.94 (s, 2H), 7.11 (d, 4H), 7.33 (brs, 1H), 7.46 (s, 1H), 7.56 (d, 1H), 7.76 (d, 2H), 7.91 (m, 2H), 8.23 (s, 1H), 10.27 (brs, 1H); HPLC: 90.02% (Retention Time = 6.249 min). |
| I-92 | 4-(azetidine-1-carbonyl)phenyl | 495.2 | δ 2.24 (m, 2H), 4.01 (m, 2H), 4.32 (m, 2H), 5.96 (s, 2H), 7.11 (d, 2H), 7.34 (brs, 1H), 7.59 (m 4H), 7.75 (d 2H), 7.80 (d, 2H), 7.83 (brs, 1H), 8.00 (d, 1H), 8.24 (s, 2H), 9.00 (brs, 2H), 9.29 (brs, 2H), 10.80 (s, 1H); HPLC: 96.38% (Retention Time = 5.454 min). |
| I-93 | 3-(2-(dimethylamino)-2-oxoethoxy)phenyl | 513.2 | δ 2.99 (s, 3H), 3.14 (s, 3H), 4.83 (s, 2H), 6.03 (s, 2H), 6.76 (m, 1H), 7.20 (d, 2H), 7.26 (d, 2H), 7.40 (m, 2H), 7.46 (s, 1H), 7.53 (brs, 1H), 7.58 (d, 1H), 7.77 (d, 2H), 7.96 (d, 1H), 8.09 (s, 1H); HPLC: 95.16% (Retention Time = 5.498 min). |

TABLE 5-continued

| Cpd. ID. | R₂ | LCMS (M + 1)⁺ | ¹H NMR |
|---|---|---|---|
| I-94 | (1-(3,4-difluorophenyl)ethyl) | 476.2 | δ 1.42 (m, 3H), 5.08 (m, 1H), 5.85 (s, 2H), 7.03 (d, 2H), 7.14 (brs, 1H), 7.31 (m, 4H), 7.55 (d, 1H), 7.72 (d, 2H), 7.90 (m, 2H), 8.19 (s, 1H), 8.98 (brs, 2H), 9.16 (d, 1H), 9.24 (brs, 2H); HPLC: 98.37% (Retention Time = 3.123 min). |
| I-95 | (1-(3-fluorophenyl)ethyl) | 458.2 | δ 1.44 (d, 3H), 5.10 (m, 1H), 5.88 (s, 2H), 7.03 (d, 2H), 7.14 (m, 2H), 7.31 (m, 2H), 7.41 (s, 2H), 7.55 (d, 1H), 7.72 (d, 2H), 7.90 (brs, 1H), 7.93 (d, 1H), 8.20 (brs, 1H), 8.97 (brs, 2H), 9.19 (d, 1H), 9.26 (brs, 2H); HPLC: 96.55% (Retention Time = 3.073 min). |
| I-96 | (1-phenylpropyl) | 454.2 | δ 0.87 (m, 3H), 1.80 (m, 2H), 4.89 (m, 1H), 5.85 (s, 2H), 7.07 (d, 2H), 7.21 (m, 1H), 7.31 (m, 6H), 7.53 (d, 1H), 7.70 (d, 2H), 7.87 (brs, 1H), 8.17 (s, 1H), 9.11 (d, 1H); HPLC: 97.36% (Retention Time = 6.276 min). |
| I-97 | (4-(3,3-difluoropyrrolidin-1-yl)phenyl) | 517.2 | δ 2.41 (m, 2H), 3.44 (s, 4H), 5.93 (s, 2H), 6.58 (d, 2H), 7.09 (d, 2H), 7.43 (brs, 1H), 7.53 (m, 3H), 7.71 (d, 2H), 7.93 (d, 1H), 8.11 (s, 1H), 8.86 (s, 2H), 9.28 (brs, 2H), 10.37 (s, 1H); HPLC: 97.56% (Retention Time = 6.406 min). |
| I-98 | (1-(4-chlorophenyl)ethyl) | 474.2 | δ 1.44 (m, 3H), 5.04 (m, 1H), 5.87 (s, 2H), 7.03 (d, 2H), 7.32 (m, 6H), 7.55 (d, 1H), 7.73 (d, 2H), 7.93 (m, 1H), 8.19 (s, 1H), 8.92 (brs, 2H), 9.16 (d, 1H), 9.24 (brs, 2H); HPLC: 90.81% (Retention Time = 3.207 min). |
| I-99 | (4-(2-(dimethylamino)-2-oxoethoxy)phenyl) | 513.2 | δ 2.66 (s, 3H), 2.83 (s, 3H), 4.76 (s, 2H), 5.94 (s, 2H), 6.88 (d, 2H), 7.09 (d, 2H), 7.31 (brs, 1H), 7.55 (m, 3H), 7.73 (d, 2H), 7.87 (brs, 1H), 7.97 (d, 1H), 8.20 (s, 1H), 8.92 (brs, 2H), 9.24 (brs, 2H), 10.46 (s, 1H); HPLC: 97.01% (Retention Time = 2.729 min). |
| I-100 | (3-(pyrrolidin-1-yl)phenethyl) | 495.2 | δ 1.90 (m, 4H), 3.12 (m, 4H), 4.37 (m, 2H), 5.97 (s, 2H), 6.39 (m, 2H), 7.03 (m, 3H), 7.35 (m, 2H), 7.55 (d, 1H), 7.73 (d, 2H), 7.90 (m, 2H), 8.17 (s, 1H), 8.91 (brs, 2H), 9.23 (m, 3H). |

TABLE 5-continued

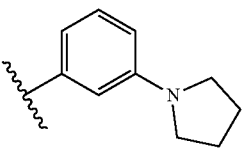 [SMILES: *c1cccc(N2CCCC2)c1]

| Cpd. ID. | R₂ | LCMS (M + 1)⁺ | ¹H NMR |
|---|---|---|---|
| I-101 |  | 481.2 | δ 1.92 (m, 4H), 3.19 (m, 4H), 5.94 (s, 2H), 6.29 (d, 2H), 6.95 (s, 1H), 7.01 (d, 1H), 7.07 (m, 2H), 7.32 (brs, 1H), 7.48 (s, 1H), 7.55 (d, 1H), 7.75 (d, 2H), 7.87 (brs, 1H), 7.95 (d, 1H), 8.17 (s, 1H), 8.87 (brs, 2H), 9.23 (s, 2H), 10.34 (brs, 1H). |
| I-102 |  | 495.2 | δ 1.52 (m, 2H), 1.63 (m, 4H), 3.12 (m, 4H), 5.94 (s, 2H), 6.97 (brs, 1H), 7.12 (d, 2H), 7.32 (s, 1H), 7.46 (s, 1H), 7.55 (d, 3H), 7.73 (d, 2H), 7.87 (brs, 1H), 7.97 (d, 1H), 8.19 (s, 1H), 8.97 (brs, 2H), 9.24 (brs, 2H), 10.41 (brs, 1H); HPLC: 99.18% (Retention Time = 5.13 min). |
| I-104 | 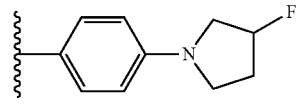 [SMILES: *c1ccc(N2CCC(F)C2)cc1] | 499.2 | δ 1.85 (m, 4H), 3.25 (m, 4H), 5.94 (s, 2H), 6.71 (m, 1H), 7.10 (d, 2H), 7.28 (m, 2H), 7.45 (brs, 1H), 7.51 (m, 2H), 7.73 (d, 2H), 7.87 (brs, 1H), 7.94 (d, 1H), 8.17 (s, 1H), 9.00 (brs, 2H), 9.23 (s, 2H), 10.45 (brs, 1H); HPLC: 97.83% (Retention Time = 6.589 min). |
| I-105 | 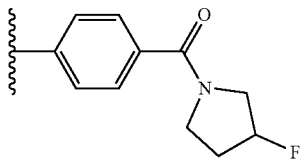 [SMILES: *c1ccc(C(=O)N2CCC(F)C2)cc1] | 499.2 | δ 2.24 (m, 2H), 3.44 (m, 4H), 5.38 (m, 1H), 5.94 (s, 2H), 6.56 (d, 2H), 7.10 (d, 2H), 7.32 (brs, 1H), 7.51 (s, 1H), 7.54 (d, 3H), 7.73 (d, 2H), 7.87 (brs, 1H), 7.94 (d, 1H), 8.17 (s, 1H), 8.85 (brs, 2H), 9.23 (s, 2H), 10.30 (brs, 1H); HPLC: 97.53% (Retention Time = 5.88 min). |
| I-106 | 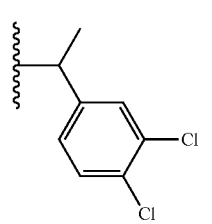 [SMILES: *C(C)c1ccc(Cl)c(Cl)c1] | 527.2 | δ 2.13 (m, 2H), 3.66 (m, 4H), 5.31 (m, 1H), 5.95 (s, 2H), 7.10 (d, 2H), 7.33 (brs, 1H), 7.57 (m, 4H), 7.74 (d, 2H), 7.79 (m, 2H), 7.88 (brs, 1H), 7.99 (d, 1H), 8.96 (d, 2H), 9.26 (brs, 2H), 10.76 (brs, 1H); HPLC: 99.76% (Retention Time = 3.192 min). |
| I-107 | 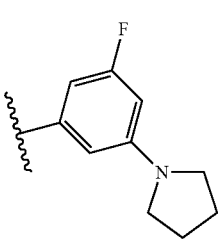 [SMILES: *c1cc(F)cc(N2CCCC2)c1] | 527.2 | δ 1.42 (d, 3H), 5.10 (m, 1H), 5.86 (s, 2H), 7.01 (m, 2H), 7.13 (s, 1H), 7.26 (m, 2H), 7.33 (brs, 1H), 7.54 (m, 3H), 7.72 (d, 2H), 7.89 (brs, 1H), 7.93 (d, 1H), 8.18 (brs, 1H), 9.00 (brs, 2H), 9.25 (m, 2H); HPLC: 96.45% (Retention Time = 3.809 min). |
| I-108 |  | 499.2 | δ 1.95 (m, 4H), 3.18 (m, 4H), 5.92 (s, 2H), 6.06 (d, 1H), 6.73 (s, 1H), 6.93 (m, 1H), 7.08 (d, 2H), 7.29 (brs, 1H), 7.49 (s, 1H), 7.55 (d, 1H), 7.73 (d, 2H), 7.85 (brs, 1H), 7.95 (d, 1H), 8.17 (s, 1H), 8.90 (brs, 2H), 9.23 (brs, 2H), 10.46 (brs, 1H); HPLC: 94.68% (Retention Time = 6.566 min). |

TABLE 5-continued

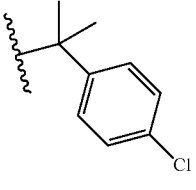 [SMILES: *C(C)(C)c1ccc(Cl)cc1]

| Cpd. ID. | R₂ | LCMS (M + 1)⁺ | ¹H NMR |
|---|---|---|---|
| I-109 | 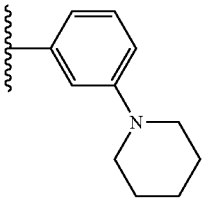 [SMILES: *c1cccc(N2CCCCC2)c1] | 499.2 | δ 1.60 (s, 6H), 5.78 (s, 2H), 7.03 (d, 2H), 7.22 (m, 4H), 7.39 (brs, 1H), 7.55 (d, 1H), 7.71 (m, 4H), 7.92 (d, 1H), 8.20 (brs, 1H), 8.87 (d, 2H), 9.23 (s, 2H); HPLC: 98.01% (Retention Time = 6.207 min). |
| I-110 | 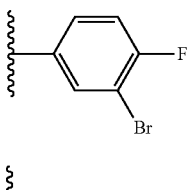 | 495.2 | δ 1.57 (m, 2H), 1.71 (m, 4H), 3.12 (m, 4H), 5.94 (s, 2H), 6.97 (brs, 1H), 7.10 (d, 2H), 7.32 (m, 3H), 7.53 (s, 1H), 7.59 (m, 1H), 7.74 (d, 2H), 7.88 (brs, 1H), 7.97 (d, 1H), 8.19 (s, 1H), 9.07 (brs, 2H), 9.26 (brs, 2H), 10.60 (brs, 1H); HPLC: 98.38% (Retention Time = 5.321 min). |
| I-111 | 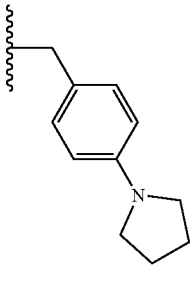 [SMILES: *Cc1ccc(N2CCCC2)cc1] | 508.1 | δ 5.93 (s, 2H), 7.10 (d, 2H), 7.32 (brs, 1H), 7.58 (m, 1H), 7.69 (m, 2H), 7.71 (m, 2H), 7.87 (brs, 2H), 8.01 (d, 1H), 8.12 (m, 1H), 8.20 (s, 1H), 9.00 (brs, 2H), 9.25 (brs, 2H), 10.73 (brs, 1H); HPLC: 93.19% (Retention Time = 6.496 min). |
| I-112 | 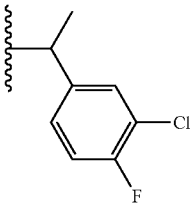 [SMILES: *C(C)c1ccc(F)c(Cl)c1] | 495.2 | CD₃OD<br>δ 2.08 (m, 4H), 3.38 (m, 4H), 4.43 (s, 2H), 5.99 (s, 2H), 6.71 (d, 1H), 7.04 (m, 3H), 7.22 (s, 1H), 7.55 (d, 1H), 7.75 (d, 2H), 7.75 (d, 2H), 7.90 (d, 1H), 8.09 (s, 1H). |
| I-113 | 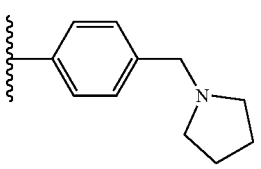 [SMILES: *c1ccc(CN2CCCC2)cc1] | 492.1 | δ 1.42 (d, 3H), 5.10 (m, 1H), 5.84 (s, 2H), 7.03 (d, 2H), 7.29 (m, 3H), 7.36 (s, 1H), 7.52 (m, 2H), 7.70 (d, 2H), 7.89 (m, 2H), 8.15 (s, 1H), 9.16 (d, 1H); HPLC: 93.96% (Retention Time = 6.382 min). |
| I-114 | | 495.2 | δ 1.67 (m, 4H), 2.40 (m, 4H), 3.52 (s, 2H), 5.94 (s, 2H), 7.14 (d, 2H), 7.25 (d, 2H), 7.32 (brs, 1H), 7.49 (s, 1H), 7.55 (d, 1H), 7.65 (d, 2H), 7.73 (d, 2H), 7.88 (brs, 1H), 7.95 (d, 1H), 8.20 (brs, 1H), 10.56 (brs, 1H); HPLC: 97.89% (Retention Time = 4.784 min). |

TABLE 5-continued

| Cpd. ID. | R₂ | LCMS (M + 1)⁺ | ¹H NMR |
|---|---|---|---|
| I-115 | 2,5-difluorophenyl | 448.1 | δ 5.96 (s, 2H), 7.12 (m, 1H), 7.18 (d, 2H), 7.34 (m, 2H), 7.53 (m, 3H), 7.76 (d, 1H), 7.91 (brs, 1H), 8.19 (brs, 1H); HPLC: 96.34% (Retention Time = 5.636 min). |
| I-116 | 4-[(3S)-3-fluoropyrrolidin-1-yl]phenyl | 499.2 | δ 2.24 (m, 2H), 3.44 (m, 4H), 5.40 (m, 1H), 5.97 (s, 2H), 6.57 (d, 2H), 7.14 (d, 2H), 7.35 (brs, 1H), 7.54 (s, 1H), 7.56 (d, 3H), 7.76 (d, 2H), 7.90 (brs, 1H), 7.97 (d, 1H), 8.20 (d, 1H), 8.85 (brs, 2H), 9.26 (m, 2H), 10.34 (brs, 1H); HPLC: 98.26% (Retention Time = 6.179 min). |
| I-121 | 3-(cyclopropylmethoxy)phenyl | 482.2 | δ 0.31 (m, 2H), 0.56 (m, 2H), 1.22 (m, 1H), 3.78 (d, 2H), 5.95 (s, 2H), 6.68 (d, 1H), 7.11 (d, 2H), 7.23 (m, 1H), 7.33 (m, 2H), 7.39 (brs, 1H), 7.51 (s, 1H), 7.58 (d, 1H), 7.75 (d, 2H), 7.89 (d, 1H), 8.21 (s, 2H), 9.07 (brs, 2H), 9.26 (brs, 2H), 10.54 (brs, 1H); HPLC: 98.8% (Retention Time = 6.16 min). |
| I-122 | 3-(3-fluoropyrrolidin-1-yl)phenyl | 499.2 | δ 2.24 (m, 2H), 3.44 (m, 4H), 5.40 (m, 1H), 5.95 (s, 2H), 6.35 (d, 1H), 7.00 (s, 2H), 7.08 (m, 4H), 7.31 (s, 2H), 7.49 (s, 1H), 7.58 (d, 1H), 7.74 (d, 2H), 7.79 (brs, 1H), 7.94 (d, 1H), 8.19 (s, 1H), 9.26 (m, 2H), 10.41 (brs, 1H); HPLC: 94.11% (Retention Time = 6.127 min). |
| I-123 | 3-(3-methoxypyrrolidin-1-yl)phenyl | 511.2 | δ 2.05 (m, 2H), 3.25 (s, 3H), 3.39 (m, 4H), 4.09 (m, 1H), 5.95 (s, 2H), 6.30 (d, 1H), 6.98 (s, 1H), 7.04 (m, 4H), 7.32 (s, 1H), 7.48 (s, 1H), 7.56 (d, 1H), 7.75 (d, 2H), 7.89 (brs, 1H), 7.93 (d, 2H), 8.19 (s, 1H), 10.41 (brs, 1H); HPLC: 94.36% (Retention Time = 6.304 min). |
| I-124 | 3-(2-methylpyrrolidin-1-yl)phenyl | 495.2 | δ 1.14 (m, 3H), 1.71 (m, 1H), 1.98 (m, 2H), 2.55 (m, 2H), 3.83 (m, 2H), 5.97 (s, 2H), 7.13 (d, 4H), 7.32 (s, 2H), 7.53 (s, 1H), 7.59 (d, 1H), 7.75 (d, 2H), 7.90 (brs, 1H), 7.96 (d, 1H), 8.30 (s, 1H), 9.06 (brs, 2H), 9.36 (brs, 2H), 10.51 (brs, 1H); HPLC: 96.59% (Retention Time = 3.283 min). |
| I-126 | 3-bromo-5-fluorophenyl | 508.1 | δ 5.94 (s, 2H), 7.09 (d, 2H), 7.30 (m, 2H), 7.57 (d, 2H), 7.64 (d, 1H), 7.75 (d, 2H), 7.84 (s, 1H), 8.89 (s, 1H), 8.01 (d, 1H), 8.21 (s, 1H), 8.95 (s, 2H), 9.27 (brs, 2H), 10.85 (brs, 1H); HPLC: 95.08% (Retention Time = 6.285 min). |

TABLE 5-continued

| Cpd. ID. | R₂ | LCMS (M + 1)⁺ | ¹H NMR |
|---|---|---|---|
| I-127 | 4-(3-fluoropyrrolidin-1-yl)phenyl | 499.2 | δ 2.18 (m, 2H), 3.44 (m, 4H), 5.36 (m, 1H), 5.95 (s, 2H), 6.55 (d, 2H), 7.13 (d, 2H), 7.31 (brs, 1H), 7.53 (s, 1H), 7.55 (d, 3H), 7.74 (d, 2H), 7.87 (brs, 1H), 7.92 (d, 1H), 8.17 (s, 1H), 9.61 (brs, 3H), 10.34 (brs, 1H); HPLC: 94% (Retention Time = 6.168 min). |
| I-129 | 3-morpholinophenyl | 497.2 | δ 3.08 (m, 4H), 3.75 (m, 4H), 5.95 (s, 2H), 6.72 (d, 1H), 7.10 (d, 2H), 7.19 (m, 2H), 7.34 (s, 2H), 7.50 (s, 1H), 7.57 (m, 1H), 7.75 (d, 2H), 7.89 (brs, 1H), 7.98 (d, 1H), 8.19 (s, 1H), 8.97 (brs, 2H), 9.26 (brs, 2H), 10.33 (brs, 1H); HPLC: 92.81% (Retention Time = 5.608 min). |
| I-130 | 3-bromo-4,5-difluorophenyl | 526.1 | δ 5.94 (s, 2H), 7.09 (d, 2H), 7.34 (brs, 1H), 7.58 (m, 2H), 7.75 (d, 2H), 7.82 (m, 3H), 8.01 (d, 1H), 8.21 (s, 1H), 8.98 (brs, 2H), 9.27 (brs, 2H), 10.85 (brs, 1H); HPLC: 99.28% (Retention Time = 3.935 min). |
| I-131 | 3-nitrophenyl | 457.2 | δ 5.98 (s, 2H), 7.11 (d, 2H), 7.59 (brs, 1H), 7.59 (m, 3H), 7.76 (d, 2H), 7.78 (brs, 1H), 7.98 (d, 1H), 8.01 (d, 1H), 8.15 (d, 1H), 8.22 (s, 1H), 8.75 (m, 1H), 8.92 (brs, 2H), 9.27 (brs, 2H), 11.01 (brs, 1H); HPLC: 99.38% (Retention Time = 3.527 min). |
| I-132 | 3-(1H-pyrazol-1-yl)phenyl | 478.2 | δ 5.97 (s, 2H), 7.11 (m, 2H), 7.32 (brs, 1H), 7.46 (m, 1H), 7.60 (m, 3H), 7.67 (m, 1H), 7.77 (m, 3H), 7.88 (brs, 1H), 8.01 (d, 1H), 8.20 (brs, 1H), 8.36 (m, 1H), 8.44 (d, 1H), 8.91 (brs, 2H), 9.26 (brs, 2H), 10.75 (brs, 1H); HPLC: 97.82% (Retention Time = 5.634 min). |
| I-133 | 3-thiomorpholinophenyl | 513.2 | δ 2.68 (m, 4H), 3.50 (m, 4H), 5.95 (s, 2H), 6.72 (d, 1H), 7.10 (d, 2H), 7.19 (m, 2H), 7.30 (m, 2H), 7.50 (s, 1H), 7.57 (m, 1H), 7.75 (d, 2H), 7.89 (brs, 1H), 7.98 (d, 1H), 8.19 (s, 1H), 8.91 (brs, 2H), 9.25 (brs, 2H), 10.41 (brs, 1H); HPLC: 98.29% (Retention Time = 3.667 min). |

TABLE 5-continued

| Cpd. ID. | R₂ | LCMS (M + 1)⁺ | ¹H NMR |
|---|---|---|---|
| I-134 | 3-(pyridin-2-yl)phenyl | 489.2 | δ 5.98 (s, 2H), 7.12 (d, 2H), 7.32 (brs, 1H), 7.38 (m, 1H), 7.48 (m, 1H), 7.58 (m, 2H), 7.78 (m, 2H), 7.80 (m, 3H), 7.84 (brs, 1H), 7.92 (m, 1H), 8.02 (d, 1H), 8.20 (s, 1H), 8.68 (d, 1H), 8.95 (brs, 2H), 9.27 (brs, 2H), 10.71 (brs, 1H); HPLC: 98.07% (Retention Time = 5.528 min). |
| I-138 | 3-ethynylphenyl | 436.2 | δ 4.22 (s, 1H), 5.95 (s, 2H), 7.11 (d, 2H), 7.22 (d, 1H), 7.33 (brs, 1H), 7.39 (m, 1H), 7.55 (s, 1H), 7.59 (m, 1H), 7.77 (m, 3H), 7.88 (m, 3H), 7.99 (d, 1H), 8.21 (s, 1H), 8.91 (brs, 1H), 9.25 (brs, 2H), 10.66 (brs, 1H); HPLC: 92.38% (Retention Time = 6.114 min). |
| I-139 | 3-(allyloxy)phenyl | 468.2 | δ 4.54 (d, 2H), 5.25 (m, 1H), 5.38 (m, 1H), 5.95 (s, 2H), 6.01 (m, 1H), 6.71 (m, 1H), 7.12 (d, 2H), 7.22 (m, 1H), 7.32 (m, 2H), 7.43 (s, 1H), 7.52 (s, 1H), 7.58 (d, 1H), 7.75 (d, 2H), 7.89 (brs, 1H), 7.97 (d, 1H), 8.22 (brs, 1H), 9.19 (brs, 2H), 9.28 (brs, 2H), 10.56 (brs, 1H); HPLC: 97.72% (Retention Time = 3.082 min). |
| I-140 | 3-((S)-3-fluoropyrrolidin-1-yl)phenyl | 499.2 | δ 2.25 (m, 2H), 3.44 (m, 4H), 5.41 (m, 1H), 5.98 (s, 2H), 6.36 (d, 1H), 7.00 (s, 1H), 7.14 (m, 3H), 7.35 (brs, 1H), 7.53 (s, 1H), 7.59 (d, 1H), 7.77 (d, 2H), 7.90 (brs, 1H), 7.99 (d, 1H), 8.22 (s, 1H), 8.97 (brs, 2H), 9.28 (brs, 2H), 10.41 (brs, 1H). |
| I-141 | 3-((R)-3-fluoropyrrolidin-1-yl)phenyl | 499.2 | δ 2.29 (m, 2H), 3.44 (m, 4H), 5.41 (m, 1H), 5.97 (s, 2H), 6.36 (d, 1H), 7.00 (s, 1H), 7.14 (m, 4H), 7.19 (brs, 1H), 7.50 (s, 1H), 7.58 (d, 1H), 7.77 (d, 2H), 7.90 (brs, 1H), 7.95 (d, 1H), 8.21 (s, 1H), 10.41 (brs, 1H). |
| I-144 | 3-(thiazol-2-yl)phenyl | 495.2 | δ 5.98 (s, 2H), 7.12 (d, 1H), 7.32 (brs, 1H), 7.48 (m, 1H), 7.60 (m, 2H), 7.69 (m, 2H), 7.75 (d, 1H), 7.77 (d, 2H), 7.81 (d, 1H), 7.86 (m, 1H), 7.94 (d, 1H), 8.00 (d, 1H), 8.20 (brs, 1H), 8.45 (s, 1H), 8.89 (brs, 2H), 9.26 (brs, 2H), 10.78 (brs, 1H); HPLC: 98.19% (Retention Time = 3.551 min). |

TABLE 5-continued

| Cpd. ID. | R₂ | LCMS (M + 1)⁺ | ¹H NMR |
|---|---|---|---|
| I-145 | (3-fluoro-4-linked-5-bromophenyl) | 508.1 | δ 5.97 (s, 2H), 7.14 (d, 2H), 7.22 (m, 1H), 7.36 (brs, 1H), 7.54 (m, 4H), 7.78 (d, 2H), 7.92 (brs, 1H), 8.02 (d, 1H), 8.25 (s, 1H), 8.94 (brs, 2H), 9.30 (s, 2H), 10.64 (brs, 1H); HPLC: 94.52% (Retention Time = 6.199 min). |
| I-146 | (3-(prop-2-yn-1-yloxy)phenyl) | 466.2 | δ 3.60 (m, 1H), 4.78 (d, 2H), 5.96 (s, 2H), 6.78 (m, 1H), 7.12 (d, 2H), 7.26 (m, 1H), 7.30 (brs, 1H), 7.37 (d, 1H), 7.53 (s, 1H), 7.58 (d, 1H), 7.75 (d, 2H), 7.88 (brs, 1H), 8.01 (d, 1H), 8.22 (s, 1H), 8.93 (brs, 2H) 9.27 (brs, 2H), 10.61 (brs, 1H); HPLC: 93.72% (Retention Time = 5.91 min). |
| I-150 | (3-(methylsulfonyl)phenyl) | 490.2 | δ 3.21 (s, 3H), 5.97 (s, 2H), 7.12 (d, 2H), 7.32 (brs, 1H), 7.62 (m, 5H), 7.67 (d, 2H), 7.88 (br, 1H), 8.05 (m, 2H), 8.20 (s, 1H), 8.39 (s, 1H), 8.95 (brs, 2H), 9.27 (brs, 2H), 10.95 (s, 1H); HPLC: 97.34% (Retention Time = 5.398 min). |
| I-151 | (biphenyl-3-yl) | 488.2 | δ 5.95 (s, 2H), 7.15 (d, 2H), 7.32 (brs, 1H), 7.43 (m, 4H), 7.51 (m, 2H), 7.62 (d, 1H), 7.72 (d, 2H), 7.87 (d, 1H), 8.05 (s, 1H), 8.19 (s, 1H), 10.60 (s, 1H); HPLC: 98.19% (Retention Time = 3.928 min). |
| I-152 | (4-fluoro-3-(pyrrolidin-1-yl)phenyl) | 499.2 | δ 1.93 (m, 4H), 3.17 (m, 4H), 5.94 (s, 2H), 6.37 (m, 1H), 6.58 (m, 1H), 7.08 (m, 3H), 7.33 (brs, 1H), 7.53 (s, 1H), 7.56 (d, 2H), 7.78 (brs, 1H), 7.96 (d, 1H), 8.21 (s, 1H), 8.95 (brs, 2H) 9.26 (brs, 2H), 10.30 (brs, 1H); HPLC: 94.93% (Retention Time = 3.196 min). |
| I-153 | (3-(2-oxopyridin-1(2H)-yl)phenyl) | 505.2 | δ 5.95 (s, 2H), 6.30 (m, 1H), 6.50 (m, 1H), 7.24 (m, 3H), 7.32 (brs, 1H), 7.52 (m, 2H), 7.59 (d, 2H), 7.65 (d, 1H), 7.76 (m, 3H), 7.87 (d, 2H), 8.01 (d, 1H), 8.20 (s, 1H), 8.96 (brs, 2H), 9.26 (brs, 2H), 10.80 (brs, 1H); HPLC: 96.58% (Retention Time = 5.543 min). |

TABLE 5-continued

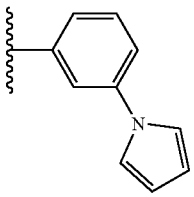 [SMILES: *c1cccc(-n2cccc2)c1]

| Cpd. ID. | R₂ | LCMS (M + 1)⁺ | ¹H NMR |
|---|---|---|---|
| I-154 | 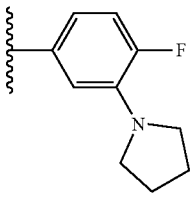 [SMILES: *c1ccc(F)c(N2CCCC2)c1] | 477.2 | δ 5.96 (s, 2H), 6.28 (m, 2H), 7.14 (m, 2H), 7.21 (m, 2H), 7.27 (m, 2H), 7.41 (m, 1H), 7.56 (m, 2H), 7.59 (m, 2H), 7.75 (d, 2H), 7.87 (brs, 1H), 7.93 (d, 1H), 8.20 (s, 1H), 8.88 (brs, 2H), 9.26 (brs, 1H), 10.85 (s, 1H); HPLC: 96.49% (Retention Time = 3.164 min). |
| I-155 | 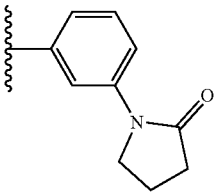 [SMILES: *c1cccc(N2CCCC2=O)c1] | 499.2 | δ 1.88 (m, 4H), 3.30 (m, 4H), 5.94 (s, 2H), 6.90 (m, 2H), 7.14 (m, 4H), 7.27 (s, 2H), 7.32 (brs, 1H), 7.44 (s, 1H), 7.59 (d, 2H), 7.88 (brs, 1H), 7.96 (d, 1H), 8.20 (s, 1H), 9.01 (brs, 2H) 9.26 (brs, 2H), 10.49 (brs, 1H); HPLC: 90.72% (Retention Time = 6.585 min). |
| I-156 | 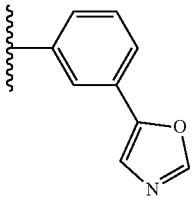 [SMILES: *c1cccc(-c2cnco2)c1] | 495.2 | δ 2.06 (m, 2H), 3.83 (s, 2H), 5.94 (s, 2H), 7.11 (d, 2H), 7.36 (m, 3H), 7.57 (s, 3H), 7.74 (d, 2H), 7.88 (brs, 1H), 7.94 (d, 1H), 8.07 (brs, 1H), 8.08 (s, 1H), 8.20 (s, 1H), 8.92 (brs, 2H) 9.26 (brs, 2H), 10.61 (brs, 1H); HPLC: 90.51% (Retention Time = 5.523 min). |
| I-163 | 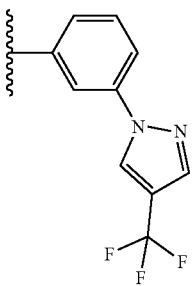 [SMILES: *c1cccc(-n2cc(C(F)(F)F)cn2)c1] | 479.2 | δ 5.97 (s, 2H), 7.11 (d, 2H), 7.32 (brs, 1H), 7.44 (m, 2H), 7.58 (m, 2H), 7.67 (s, 1H), 7.77 (m, 2H), 7.88 (brs, 1H), 8.16 (d, 1H), 8.20 (d, 1H), 8.47 (d, 2H), 8.92 (brs, 2H), 9.26 (brs, 2H), 10.79 (brs, 1H); HPLC: 90.61% (Retention Time = 3.114 min). |
| I-165 |  | 546.2 | δ 5.97 (s, 2H), 7.11 (d, 2H), 7.32 (brs, 1H), 7.50 (m, 1H), 7.58 (m, 3H), 7.74 (m, 3H), 7.77 (brs, 1H), 8.01 (d, 1H), 8.21 (d, 2H), 8.23 (s, 1H), 8.94 (brs, 2H), 9.17 (s, 1H), 9.26 (brs, 2H), 10.81 (brs, 1H); HPLC: 99.46% (Retention Time = 3.901 min). |

TABLE 5-continued

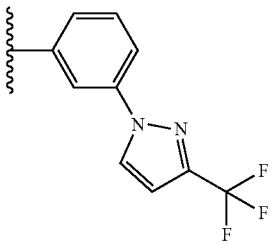 [SMILES: *c1cccc(-n2ccc(C(F)(F)F)n2)c1]

| Cpd. ID. | R₂ | LCMS (M + 1)⁺ | ¹H NMR |
|---|---|---|---|
| I-166 | 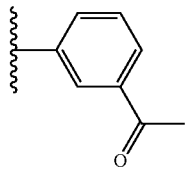 [SMILES: *c1cccc(C(C)=O)c1] | 546.2 | δ 5.97 (s, 2H), 7.04 (s, 1H), 7.05 (d, 2H) 7.30 (brs, 1H), 7.53 (m, 4H), 7.73 (d, 2H), 7.82 (d, 1H), 7.85 (brs, 1H), 8.01 (d, 1H), 8.18 (s, 1H), 8.31 (s, 1H), 8.69 (s, 1H), 8.91 (brs, 2H), 9.24 (brs, 2H); HPLC: 96.62% (Retention Time = 2.574 min). |
| I-167 | 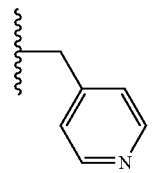 [SMILES: *Cc1ccncc1] | 546.2 | δ 2.58 (s, 3H), 5.96 (s, 2H), 7.11 (d, 2H), 7.32 (brs, 1H), 7.52 (m, 1H), 7.58 (m, 2H), 7.73 (m, 3H), 7.87 (brs, 1H), 7.99 (d, 2H), 8.21 (s, 1H), 8.32 (s, 1H), 9.00 (brs, 2H), 9.26 (brs, 2H), 10.98 (brs, 1H). |
| I-168 | 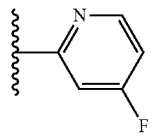 [SMILES: *c1cc(F)ccn1] | 427.2 | δ 4.54 (d, 2H), 5.92 (s, 2H), 7.02 (d, 2H), 7.41 (m, 3H), 7.58 (d, 2H), 7.75 (d, 2H), 7.94 (m, 2H), 8.23 (s, 1H), 8.57 (m, 2H), 9.13 (brs, 2H), 9.27 (brs, 2H), 9.49 (brs, 1H); HPLC: 91.94% (Retention Time = 4.304 min). |
| I-169 | 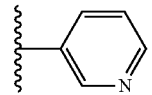 | 431.2 | δ 5.95 (s, 2H), 7.11 (d, 2H), 7.32 (brs, 1H), 7.58 (d, 1H), 7.70 (s, 1H), 7.78 (m, 3H), 7.89 (brs, 1H), 7.98 (d, 1H), 8.09 (m, 1H), 8.20 (brs, 1H), 8.42 (d, 1H), 8.96 (brs, 2H), 9.27 (brs, 2H), 11.22 (brs, 1H); HPLC: 95.21% (Retention Time = 5.883 min). |
| I-170 | 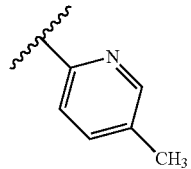 | 413.2 | δ 5.95 (s, 2H), 7.11 (d, 2H), 7.34 (brs, 1H), 7.48 (m, 1H), 7.58 (m, 2H), 7.75 (d, 2H), 7.89 (brs, 1H), 8.01 (d, 1H), 8.22 (m, 2H), 8.38 (d, 1H), 8.95 (s, 3H), 9.27 (brs, 2H), 10.87 (brs, 1H); HPLC: 87.15% (Retention Time = 6.782 min). |
| I-171 | 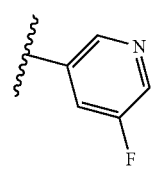 [SMILES: *c1cncc(F)c1] | 427.2 | (CD₃OD) δ 2.31 (s, 3H), 6.03 (s, 2H), 7.18 (d, 2H), 7.48 (s, 1H), 7.57 (m, 1H), 7.63 (m, 1H), 7.76 (d, 2H), 7.96 (m, 2H), 8.04 (s, 1H), 8.18 (s, 1H); HPLC: 95.12% (Retention Time = 5.551 min). |
| I-172 | | 431.2 | δ 5.95 (s, 2H), 7.11 (d, 2H), 7.32 (brs, 1H), 7.60 (d, 2H), 7.75 (d, 2H), 7.89 (brs, 1H), 8.00 (d, 1H), 8.14 (m, 1H), 8.21 (s, 1H), 8.35 (m, 1H), 8.75 (s, 1H), 9.03 (brs, 2H), 9.28 (brs, 2H), 11.0 (brs, 1H); HPLC: 94.12% (Retention Time = 2.683 min). |

TABLE 5-continued

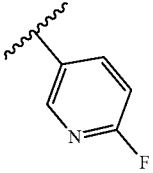 [SMILES: *c1ccc(F)nc1]

| Cpd. ID. | R₂ | LCMS (M + 1)⁺ | ¹H NMR |
|---|---|---|---|
| I-173 | 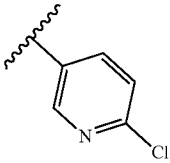 [SMILES: *c1ccc(Cl)nc1] | 431.2 | δ 5.95 (s, 2H), 7.11 (d, 2H), 7.21 (m, 1H), 7.32 (brs, 1H), 7.58 (m, 2H), 7.75 (d, 2H), 7.90 (brs, 1H), 8.00 (d, 1H), 8.22 (s, 1H), 8.28 (m, 1H), 8.55 (s, 1H), 9.06 (brs, 2H), 9.28 (brs, 2H), 10.87 (brs, 1H); HPLC: 90.57% (Retention Time = 5.733 min). |
| I-174 | 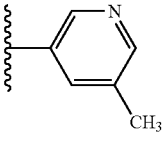 | 447.1 | δ 5.93 (s, 2H), 7.08 (d, 2H), 7.32 (brs, 1H), 7.49 (m, 1H), 7.58 (m, 2H), 7.73 (m, 2H), 7.87 (brs, 1H), 7.99 (m, 1H), 8.18 (m, 2H), 8.74 (m, 1H), 8.94 (brs, 2H), 9.25 (brs, 2H), 10.88 (brs, 1H); HPLC: 95.74% (Retention Time = 5.917 min). |
| I-175 | 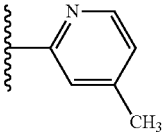 [SMILES: *c1cc(C)ccn1] | 427.1 | δ 2.53 (s, 3H), 5.95 (s, 2H), 7.09 (d, 2H), 7.32 (brs, 1H), 7.58 (m, 2H), 7.75 (d, 2H), 7.88 (brs, 1H), 8.00 (d, 1H), 8.13 (s, 1H), 8.21 (s, 1H), 8.27 (s, 1H), 8.79 (s, 1H), 9.02 (brs, 2H), 9.27 (brs, 2H), 10.87 (brs, 1H); HPLC: 92.07% (Retention Time = 4.846 min). |
| I-176 | 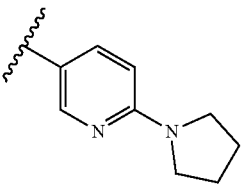 [SMILES: *c1ccc(N2CCCC2)nc1] | 427.1 | δ 2.3 (m, 3H), 5.90 (s, 2H), 7.00 (s, 1H), 7.10 (d, 2H), 7.21 (brs, 1H), 7.55 (d, 1H), 7.69 (s, 1H), 7.75 (d, 2H), 7.87 (m, 3H), 8.18 (s, 1H), 8.25 (d, 1H); HPLC: 95.5% (Retention Time = 5.413 min). |
| I-177 | 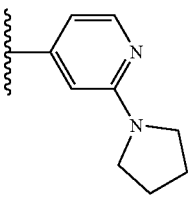 [SMILES: *c1ccnc(N2CCCC2)c1] | 482.2 | δ 2.0 (m, 4H), 3.47 (m, 4H), 5.94 (s, 2H), 6.99 (m, 1H), 7.08 (d, 2H), 7.31 (brs, 1H), 7.53 (s, 1H), 7.59 (d, 1H), 7.74 (d, 2H), 7.86 (brs, 1H), 7.98 (d, 1H), 8.03 (m, 1H), 8.20 (s, 1H), 8.97 (brs, 2H), 9.25 (brs, 2H), 10.68 (brs, 1H); HPLC: 97.67% (Retention Time = 4.906 min). |
| I-178 | 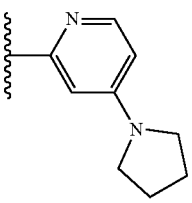 [SMILES: *c1cc(N2CCCC2)ccn1] | 482.2 | δ 2.0 (m, 4H), 3.44 (m, 4H), 5.93 (s, 2H), 7.05 (m, 3H), 7.34 (m, 2H), 7.58 (d, 1H), 7.67 (brs, 1H), 7.76 (d, 1H), 7.88 (brs, 1H), 7.91 (d, 1H), 8.02 (d, 1H), 8.21 (s, 1H), 9.02 (brs, 2H), 9.27 (brs, 2H), 11.21 (brs, 1H); HPLC: 96.07% (Retention Time = 5.001 min). |
| I-179 | | 482.2 | δ 1.93 (m, 4H), 3.26 (m, 4H), 5.96 (s, 2H), 6.30 (m, 1H), 7.10 (d, 2H), 7.26 (brs, 1H), 7.31 (brs, 1H), 7.54 (m, 1H), 7.61 (s, 1H), 7.74 (d, 2H), 7.90 (m, 3H), 8.11 (s, 1H), 10.41 (brs, 1H); HPLC: 97.64% (Retention Time = 5.087 min). |

TABLE 5-continued

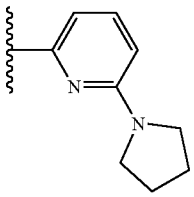 [SMILES: *c1cccc(N2CCCC2)n1]

| Cpd. ID. | R₂ | LCMS (M + 1)⁺ | ¹H NMR |
|---|---|---|---|
| I-180 | 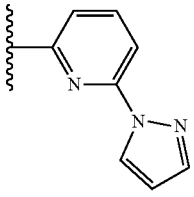 [SMILES: *c1cccc(-n2cccn2)n1] | 482.2 | δ 1.96 (m, 4H), 3.42 (m, 4H), 5.97 (s, 2H), 6.25 (d, 2H), 7.12 (d, 2H), 7.26 (d, 1H), 7.50 (brs, 1H), 7.52 (m, 1H), 7.58 (d, 1H), 7.66 (s, 1H), 7.90 (brs, 1H), 7.98 (d, 1H), 8.21 (s, 1H), 8.96 (brs, 2H), 9.28 (brs, 2H), 10.41 (brs, 1H); HPLC: 93.47% (Retention Time = 5.776 min). |
| I-181 | 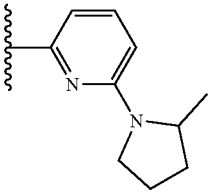 [SMILES: *c1cccc(N2CCCC2C)n1] | 479.2 | δ 5.97 (s, 2H), 6.61 (m, 1H) 7.11 (d, 2H), 7.32 (brs, 1H), 7.58 (d, 2H), 7.65 (m, 2H), 7.67 (m, 2H), 7.57 (s, 1H), 7.77 (brs, 1H), 7.98 (m, 2H), 8.22 (s, 1H), 8.57 (d, 1H), 8.97 (brs, 2H), 9.27 (brs, 2H), 11.11 (brs, 1H); HPLC: 97.49% (Retention Time = 6.088 min). |
| I-182 | 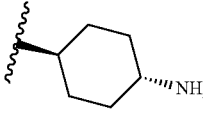 | 496.2 | δ 1.16 (d, 3H), 1.66 (m, 1H), 2.01 (m, 4H), 3.33 (m, 1H), 4.12 (m, 1H), 5.94 (s, 2H), 6.22 (d, 1H), 7.10 (d, 2H), 7.19 (d, 1H), 7.32 (brs, 1H), 7.48 (m, 1H), 7.58 (m, 1H), 7.75 (d, 2H), 7.88 (brs, 1H), 7.96 (d, 1H), 8.19 (brs, 1H), 8.88 (brs, 2H), 9.25 (brs, 2H), 10.4 (brs, 1H). |
| I-184 | 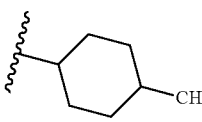 | 533.3 | δ 1.35 (m, 4H), 1.85 (m, 4H), 2.96 (m, 1H), 3.52 (m, 1H), 5.81 (s, 2H), 7.15 (d, 2H), 7.32 (brs, 1H), 7.35 (brs, 1H), 7.55 (d, 1H), 7.75 (d, 2H), 7.85 (m, 3H), 8.21 (brs, 1H), 8.65 (d, 1H), 9.08 (brs, 2H), 9.30 (brs, 2H); HPLC: 89.53% (Retention Time = 4.231 min). |
| I-185 | 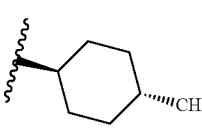 | 432.3 | δ 0.81 (m, 3H), 1.33 (m, 2H), 1.49 (m, 2H), 1.65 (m, 3H), 1.85 (m, 2H), 3.74 (m, 1H), 5.81 (s, 2H), 6.86 (s, 1H), 7.15 (d, 1H), 7.29 (brs, 1H), 7.61 (d, 1H), 7.83 (m, 3H), 7.95 (brs, 1H), 8.33 (s, 1H), 8.94 (brs, 2H), 9.30 (brs, 2H); HPLC: 91.33% (Retention Time = 5.751 min). |
| I-186 | 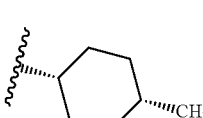 | 432.3 | δ 0.91 (m, 3H), 1.37 (m, 2H), 1.45 (m, 4H), 1.52 (m, 3H), 3.85 (m, 1H), 5.88 (s, 2H), 7.12 (d, 2H), 7.27 (s 1H), 7.34 (brs, 1H), 7.54 (d, 1H), 7.75 (d, 2H), 7.90 (m, 2H), 8.19 (s, 1H), 8.45 (d, 1H), 8.98 (brs, 2H), 9.24 (brs, 2H); |
| I-187 |  | 432.3 | δ 0.86 (m, 3H), 1.34 (m, 2H), 1.43 (m, 4H), 1.53 (m, 3H), 3.85 (m, 1H), 5.88 (s, 2H), 7.10 (d, 2H), 7.25 (m, 1H), 7.33 (brs, 1H), 7.74 (d, 1H), 7.89 (m, 3H), 8.17 (s, 1H), 8.44 (d, 1H), 8.94 (brs, 2H), 9.22 (brs, 2H). |

TABLE 5-continued

| Cpd. ID. | R₂ | LCMS (M + 1)⁺ | ¹H NMR |
|---|---|---|---|
| I-188 | cyclohexyl-pyrrolidine | 487.3 | δ 1.37 (m, 2H), 1.46 (m, 2H), 1.82 (m, 4H), 1.99 (m, 2H), 2.10 (m, 2H), 3.08 (m, 3H), 3.42 (m, 2H), 3.71 (m, 1H), 5.90 (s, 2H), 7.10 (m, 2H), 7.26 (s, 1H), 7.35 (brs, 1H), 7.54 (d, 1H), 7.74 (d, 2H), 7.90 (d, 2H), 8.19 (s, 1H), 8.65 (d, 1H), 9.01 (brs, 2H), 9.24 (brs, 2H), 9.67 (brs, 1H); HPLC: 91.75% (Retention Time = 4.459 min). |
| I-189 | cyclohexenyl | 416.3 | δ 1.52 (m, 1H), 1.81 (m, 1H), 2.09 (m, 2H), 2.21 (m, 2H), 3.92 (m, 1H), 5.64 (s, 1H), 5.91 (s, 1H), 6.95 (s, 1H), 7.10 (m, 2H), 7.27 (d, 1H), 7.34 (brs, 1H), 7.54 (d, 1H), 7.74 (d, 2H), 7.90 (d, 1H), 8.18 (s, 1H), 8.62 (d, 1H), 8.99 (brs, 2H), 9.24 (brs, 2H); HPLC: 97.03% (Retention Time = 3.364 min). |
| I-190 | 4,4-difluorocyclohexyl | 454.2 | δ 1.57 (m, 2H), 1.81 (m, 3H), 1.97 (m, 3H), 3.93 (m, 1H), 5.90 (s, 2H), 7.10 (m, 2H), 7.28 (s, 1H), 7.34 (brs, 1H), 7.54 (d, 1H), 7.74 (d, 2H), 7.90 (d, 2H), 8.19 (s, 1H), 8.65 (d, 1H), 9.01 (brs, 2H), 9.24 (brs, 2H); HPLC: 97.47% (Retention Time = 3.318 min). |
| I-191 | cyclohexylmethyl | 432.2 | δ 0.83 (m, 2H), 1.10 (m, 3H), 1.49 (m, 1H), 1.58 (m, 5H), 3.04 (m, 2H), 5.93 (s, 2H), 7.06 (m, 2H), 7.25 (s, 1H), 7.34 (brs, 1H), 7.55 (d, 1H), 7.75 (d, 2H), 7.91 (m, 2H), 8.21 (s, 1H), 8.74 (m, 1H), 9.05 (brs, 2H), 9.25 (brs, 2H); HPLC: 91.99% (Retention Time = 3.073 min). |
| I-192 | tetrahydropyranylmethyl | 434.2 | δ 1.07 (m, 2H), 1.39 (m, 2H), 1.66 (m, 1H), 3.07 (m, 2H), 3.14 (m, 2H), 3.76 (m, 2H), 5.91 (s, 2H), 7.03 (m, 2H), 7.24 (s, 1H), 7.33 (brs, 1H), 7.54 (d, 1H), 7.74 (d, 2H), 7.90 (m, 2H), 8.21 (s, 1H), 8.75 (m, 1H), 9.05 (brs, 2H), 9.24 (brs, 2H); HPLC: 93.25% (Retention Time = 4.987 min). |
| I-193 | (R)-1-cyclohexylethyl | 446.2 | δ 0.82 (m, 2H), 1.05 (m, 5H), 1.38 (m, 1H), 1.51 (m, 6H), 3.75 (m, 1H), 5.89 (s, 2H), 7.04 (m, 2H), 7.17 (brs, 1H), 7.22 (s, 1H), 7.30 (m, 1H), 7.54 (d, 1H), 7.74 (d, 1H), 7.89 (d, 2H), 8.21 (s, 1H), 8.46 (d, 1H), 9.15 (brs, 2H), 9.24 (brs, 2H); HPLC: 94.99% (Retention Time = 2.943 min). |
| I-194 | (S)-1-cyclohexylethyl | 446.2 | δ 0.82 (m, 2H), 1.05 (m, 6H), 1.57 (m, 6H), 3.75 (m, 1H), 5.89 (s, 2H), 7.06 (d, 2H), 7.22 (s, 1H), 7.30 (brs, 1H), 7.53 (m, 1H), 7.73 (d, 2H), 7.87 (m, 2H), 8.20 (s, 1H), 8.43 (d, 1H), 8.93 (brs, 2H), 9.22 (brs, 2H); HPLC: 90.54% (Retention Time = 2.949 min). |

TABLE 5-continued

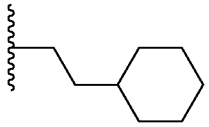 [SMILES: *CCC1CCCCC1]

| Cpd. ID. | R$_2$ | LCMS (M + 1)$^+$ | $^1$H NMR |
|---|---|---|---|
| I-195 | 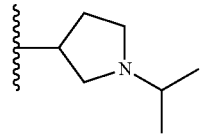 [SMILES: *C1CCN(C(C)C)C1] | 446.2 | δ 0.84 (m, 2H), 1.07 (m, 4H), 1.34 (m, 2H), 1.62 (m, 5H), 3.17 (m, 2H), 5.93 (s, 2H), 7.09 (d, 2H), 7.22 (s, 1H), 7.32 (brs, 1H), 7.53 (d, 1H), 7.74 (d, 2H), 7.86 (d, 2H), 8.15 (s, 1H), 8.71 (m, 1H); HPLC: 93.96% (Retention Time = 6.625 min). |
| I-196 | 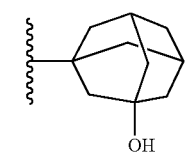 [SMILES: *C12CC3CC(C1)CC(O)(C3)C2] | 447.2 | δ 1.25 (m, 6H), 1.98 (m, 1H), 2.15 (m, 1H), 2.94 (m, 1H), 3.20 (s, 1H), 3.52 (m, 3H), 4.48 (m, 1H), 5.91 (s, 2H), 7.07 (m, 2H), 7.34 (m, 2H), 7.56 (d, 1H), 7.76 (d, 2H), 7.91 (m, 2H), 8.19 (d, 1H), 8.93 (m, 2H), 9.25 (brs, 2H), 9.88 (m, 1H); HPLC: 93.87% (Retention Time = 4.423 min). |
| I-197 | 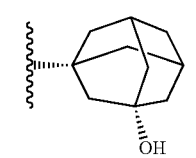 [SMILES: *[C@]12CC3CC(C1)C[C@](O)(C3)C2] | 486.2 | δ 1.45 (m, 6H), 1.85 (m, 6H), 2.15 (s, 2H), 4.55 (brs, 1H), 5.84 (s, 2H), 7.15 (m, 3H), 7.35 (brs, 1H), 7.51 (m, 1H), 7.74 (d, 2H), 7.85 (m, 2H), 8.13 (m, 1H), 8.92 (brs, 2H), 9.22 (brs, 2H); HPLC: 90.86% (Retention Time = 2.668 min). |
| I-198 | 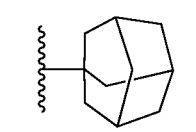 | 486.2 | δ 1.45 (m, 6H), 1.84 (m, 6H), 2.14 (s, 2H), 5.86 (s, 2H), 7.18 (m, 3H), 7.51 (d, 1H), 7.83 (m, 3H), 8.11 (brs, 1H), 8.16 (brs, 1H), 8.90 (brs, 2H), 9.21 (brs, 2H); HPLC: 93.37% (Retention Time = 2.707 min). |
| I-200 | 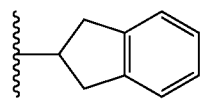 [SMILES: *C1Cc2ccccc2C1] | 470.2 | δ 1.64 (s, 6H), 2.03 (m, 9H), 5.85 (s, 2H), 7.17 (m, 3H), 7.35 (brs, 1H), 7.52 (d, 1H), 7.75 (d, 2H), 7.86 (m, 2H), 8.05 (brs, 1H), 8.19 (brs, 1H), 9.00 (brs, 2H), 9.23 (brs, 2H); HPLC: 95.67% (Retention Time = 3.979 min). |
| I-201 | 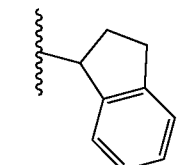 | 452.2 | δ 2.85 (m, 2H), 3.16 (m, 2H), 4.65 (m, 1H), 5.92 (s, 2H), 6.98 (s, 1H), 7.11 (m, 3H), 7.20 (m, 2H), 7.29 (s, 1H), 7.35 (brs, 1H), 7.52 (d, 1H), 7.75 (d, 2H), 7.88 (m, 2H), 8.18 (brs, 1H), 8.94 (m, 3H), 9.23 (brs, 2H); HPLC: 91.77% (Retention Time = 3.566 min). |
| I-202 | 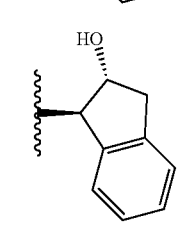 | 452.2 | δ 2.85 (m, 2H), 2.81 (m, 2H), 5.5 (m, 1H), 5.98 (d, 2H), 6.83 (d, 2H), 7.06 (m, 2H), 7.18 (m, 2H), 7.31 (s, 1H), 7.37 (brs, 1H), 7.54 (d, 1H), 7.79 (d, 2H), 7.90 (m, 2H), 8.23 (brs, 1H), 8.94 (brs, 1H), 9.10 (m, 1H), 9.30 (brs, 2H); HPLC: 96.98% (Retention Time = 5.987 min). |
| I-203 | | 468.2 | δ 2.73 (m, 1H), 3.10 (m, 2H), 4.38 (m, 1H), 5.16 (m, 1H), 5.99 (d, 2H), 6.64 (d, 1H), 7.03 (m, 1H), 7.09 (d, 2H), 7.16 (d, 2H), 7.33 (s, 1H), 7.54 (d, 1H), 7.78 (d, 1H), 7.91 (m, 2H), 8.23 (brs, 1H), 8.89 (brs, 2H), 9.03 (d, 1H), 9.23 (brs, 2H); HPLC: 98.7% (Retention Time = 5.507 min). |

TABLE 5-continued

| Cpd. ID. | R₂ | LCMS (M + 1)⁺ | ¹H NMR |
|---|---|---|---|
| I-204 | [2-hydroxyindanyl] | 468.2 | δ 2.88 (m, 1H), 3.08 (m, 2H), 4.53 (m, 1H), 5.20 (d, 1H), 5.38 (m, 1H), 5.99 (d, 2H), 6.93 (d, 1H), 7.10 (m, 5H), 7.37 (brs, 1H), 7.55 (d, 1H), 7.80 (d, 1H), 7.92 (d, 2H), 8.21 (brs, 1H), 8.53 (d, 1H), 8.89 (brs, 2H), 9.25 (brs, 2H); HPLC: 95.44% (Retention Time = 5.292 min). |
| I-205 | [3-pyrrolidinyl] | 405.2 | δ 1.93 (m, 1H), 2.14 (m, 1H), 3.07 (m, 1H), 3.22 (m, 1H), 3.27 (m, 2H), 4.44 (m, 1H), 5.90 (m, 2H), 7.08 (d, 2H), 7.33 (m, 2H), 7.54 (d, 1H), 7.74 (d, 2H), 7.90 (m, 2H), 8.81 (brs, 1H), 8.84 (m, 1H), 9.03 (brs, 2H), 9.24 (brs, 2H); HPLC: 84.25% (Retention Time = 4.151 min). |
| I-206 | [1-methylpiperidin-4-yl] | 433.2 | δ 1.68 (m, 2H), 1.95 (m, 2H), 2.75 (d, 3H), 3.04 (m, 2H), 3.35 (m, 2H), 3.85 (m, 1H), 5.90, (m, 2H), 7.08, (d, 2H), 7.3 (s, 1H), 7.37 (m, 1H), 7.54 (d, 1H), 7.74 (d, 2H), 7.90 (m, 2H), 8.19 (m, 1H), 8.79 (d, 1H), 9.00 (brs, 2H), 9.24 (brs, 2H); HPLC: 90.61% (Retention Time = 4.181 min). |
| I-207 | [2-hydroxypropyl] | 394.2 | δ 0.99 (d, 3H), 3.14 (m, 2H), 3.75 (m, 1H), 5.92 (s, 2H), 7.08 (d, 2H), 7.31 (m, 2H), 7.52 (d, 1H), 7.73 (d, 2H), 7.90 (m, 2H), 8.15 (s, 1H), 8.71 (m, 1H), 8.94 (brs, 2H), 9.22 (brs, 2H), 9.24 (brs, 2H); HPLC: 94.0% (Retention Time = 4.667 min). |
| I-208 | [2-hydroxy-2-methylpropyl] | 408.2 | δ 1.05 (m, 6H), 3.20 (m, 2H), 4.55 (brs, 1H), 5.91 (s, 2H), 7.08 (d, 2H), 7.32 (m, 2H), 7.44 (d, 1H), 7.73 (d, 2H), 7.81 (d, 1H), 7.89 (m, 1H), 7.97 (brs, 1H), 8.51 (m, 1H), 9.03 (brs, 2H), 9.24 (brs, 2H); HPLC: 91.342% (Retention Time = 4.396 min). |
| I-209 | [3-hydroxy-2-methylpropyl] | 408.2 | δ 0.80 (m, 3H), 1.35 (m, 1H), 1.64 (m, 1H), 3.34 (m, 1H), 3.39 (m, 1H), 3.82 (m, 1H), 5.93 (s, 2H), 7.15 (d, 2H), 7.31 (brs, 2H), 7.75 (d, 2H), 7.89 (d, 2H), 8.27 (s, 1H), 8.40 (d, 1H), 9.02 (brs, 2H), 9.33 (brs, 2H). |
| I-265 | [benzothiazol-2-yl] | 469.1 | δ 5.96 (s, 2H), 7.12 (d, 2H), 7.33 (brs, 1H), 7.58 (m, 2H), 7.75 (m, 3H), 7.88 (brs, 1H), 8.00 (m, 2H), 8.21 (s, 1H), 8.64 (s, 1H), 8.90 (brs, 2H), 9.26 (m, 2H), 10.92 (s, 1H); HPLC: 86.89% (Retention Time = 2.924 min). |
| I-266 | [4-methylthiazol-2-yl] | 433.1 | δ 2.30 (s, 3H), 6.00 (s, 2H), 6.83 (brs, 1H), 7.06 (d, 2H), 7.33 (s, 1H), 7.56 (d, 1H), 7.74 (m, 3H), 7.88 (brs, 1H), 7.98 (d, 1H), 8.18 (brs, 1H), 8.93 (brs, 2H), 9.26 (m, 2H); HPLC: 93.75% (Retention Time = 5.786 min). |

TABLE 6

[Structure: 1H-indole with 6-carboxamidine (H2N-C(=NH)-) at position 6, N1-R3', and 2-carboxamide C(=O)NH-R2]

| Cpd. ID. | R2 | R3' | LCMS (M + 1)+ | 1H NMR |
|---|---|---|---|---|
| I-266 | -CH2-cyclohexyl | -CH(CH3)-(4-carbamoylphenyl) | 446.2 | δ 0.85 (m, 2H), 1.17 (m, 4H), 1.51 (m, 1H), 1.63 (m, 4H), 2.03 (m, 3H), 3.06 (m, 2H), 3.15 (m, 1H), 6.33 (m, 1H), 7.09 (s, 1H), 7.27 (d, 1H), 7.41 (m, 2H), 7.56 (brs, 1H), 7.78 (m, 3H); HPLC: 84.28% (Retention Time = 6.495 min). |
| I-227 | -CH2-cyclohexyl | -CH2-(3-fluoro-4-carbamoylphenyl) | 450.2 | δ 0.82 (m, 2H), 1.08 (m, 3H), 1.47 (m, 1H), 1.60 (m, 5H), 3.01 (m, 2H), 5.96 (s, 2H), 6.46 (m, 1H), 7.28 (s, 1H), 7.48 (m, 3H), 7.67 (d, 1H), 7.89 (d, 1H), 7.99 (brs, 1H), 8.16 (s, 1H), 8.72 (m, 1H); HPLC: 98.05% (Retention Time = 3.057 min). |
| I-228 | -CH2-cyclohexyl | -CH2-(3-chloro-4-carbamoylphenyl) | 466.2 | δ 0.76 (m, 2H), 1.05 (m, 3H), 1.40 (m, 1H), 1.52 (m, 5H), 2.98 (m, 2H), 5.97 (s, 2H), 6.08 (d, 1H), 6.37 (s, 1H), 7.48 (brs, 1H), 7.58 (m, 2H), 7.95 (m, 2H), 8.03 (brs, 1H), 8.14 (brs, 1H), 8.77 (m, 1H), 9.11 (brs, 2H), 9.24 (brs, 2H); HPLC: 97.51% (Retention Time = 6.278 min). |
| I-229 | -CH2-cyclohexyl | -CH2-(2-chloro-4-carbamoylphenyl) | 466.2 | δ 0.88 (m, 2H), 1.10 (m, 3H), 1.52 (m, 1H), 1.61 (m, 5H), 3.07 (m, 2H), 5.88 (s, 2H), 7.06 (d, 1H), 7.16 (s, 1H), 7.27 (m, 2H), 7.53 (m, 2H), 7.78 (brs, 1H), 7.86 (d, 1H), 8.15 (brs, 1H), 8.77 (m, 1H); HPLC: 94.47% (Retention Time = 2.907 min). |
| I-230 | -(4,4-difluorocyclohexyl) | -CH2-(3-carbamoylphenyl) | 454.2 | δ 1.56 (m, 2H), 1.80 (m, 3H), 1.95 (m, 3H), 3.59 (m, 1H), 5.90 (s, 2H), 7.08 (s, 1H), 7.19 (m, 2H), 7.26 (s, 1H), 7.30 (m, 2H), 7.55 (d, 1H), 7.65 (s, 1H), 7.70 (d, 1H), 7.89 (m, 1H), 8.30 (brs, 1H), 8.66 (d, 1H), 8.99 (brs, 2H), 9.33 (brs, 2H); HPLC: 95.37% (Retention Time = 3.356 min). |

TABLE 6-continued

| Cpd. ID. | R₂ | R₃' | LCMS (M + 1)⁺ | ¹H NMR |
|---|---|---|---|---|
| I-231 | cyclohexylmethyl | 4-(dihydroxyboryl)benzyl | 433.2 | δ 0.83 (m, 2H), 1.08 (m, 4H), 1.47 (m, 1H), 1.59 (m, 4H), 3.04 (m, 2H), 5.88 (s, 2H), 6.98 (d, 2H), 7.21 (s, 1H), 7.54 (d, 1H), 7.65 (d, 2H), 7.87 (d, 1H), 8.02 (brs, 2H), 8.20 (s, 1H), 8.71 (m, 1H), 8.99 (brs, 2H), 9.25 (brs, 2H). |
| I-233 | 4-aminocyclohexyl | naphthalen-2-ylmethyl | 440.2 | δ 1.27 (m, 4H), 1.79 (m, 4H), 2.93 (m, 1H), 3.64 (m, 1H), 6.00 (s, 1H), 7.23 (m, 2H), 7.44 (m, 2H), 7.52 (m, 2H), 7.73 (m, 7H), 8.27 (s, 1H), 8.61 (d, 1H), 9.03 (brs, 2H), 9.25 (brs, 2H); HPLC: 98.31% (Retention Time = 5.043 min). |
| I-234 | 4-aminocyclohexyl | biphenyl-4-ylmethyl | 466.2 | δ 1.31 (m, 4H), 1.86 (m, 4H), 2.96 (m, 1H), 3.65 (m, 1H), 5.65 (s, 1H), 7.28 (d, 2H), 7.41 (m, 2H), 7.57 (m, 4H), 7.65 (d, 1H), 7.78 (d, 1H), 7.94 (m, 3H), 8.44 (s, 1H), 8.80 (d, 1H), 9.39 (brs, 2H); HPLC: 95.23% (Retention Time = 6.883 min). |
| I-235 | 4,4-difluorocyclohexyl | biphenyl-4-ylmethyl | 487.2 | δ 1.62 (m, 2H), 1.86 (m, 3H), 2.06 (m, 3H), 3.98 (m, 1H), 5.94 (s, 2H), 7.20 (d, 2H), 7.31 (s, 1H), 7.37 (m, 1H), 7.47 (m, 2H), 7.58 (m, 5H), 7.94 (d, 1H), 8.28 (s, 1H), 8.68 (d, 1H), 8.94 (brs, 2H), 9.29 (brs, 2H); HPLC: 92.73% (Retention Time = 3.851 min). |
| I-238 | 4-aminocyclohexyl | (4'-ethylbiphenyl-3-yl)methyl | 494.3 | δ 1.42 (m, 3H), 1.45 (m, 4H), 1.81 (m, 4H), 2.52 (m, 2H), 2.95 (m, 1H), 3.71 (m, 1H), 7.33 (d, 1H), 7.22 (s, 1H), 7.33 (m, 4H), 7.42 (m, 3H), 7.58 (d, 2H), 7.89 (m, 4H), 8.35 (brs, 1H), 8.71 (d, 1H), 9.13 (brs, 2H), 9.32 (brs, 2H); HPLC: 96.01% (Retention Time = 5.108 min). |

TABLE 6-continued

| Cpd. ID. | R₂ | R₃' | LCMS (M + 1)⁺ | ¹H NMR |
|---|---|---|---|---|
| I-239 | cyclohexyl-NH₂ (trans) | 3-(4-ethoxyphenyl)benzyl | 510.3 | δ 1.42 (m, 7H), 1.82 (m, 4H), 2.95 (m, 1H), 3.71 (m, 1H), 4.01 (m, 2H), 6.95 (m, 4H), 7.21 (s, 1H), 7.33 (m, 1H), 7.42 (m, 5H), 7.52 (d, 1H), 7.89 (m, 4H), 8.35 (d, 1H), 9.13 (brs, 2H), 9.32 (brs, 2H); HPLC: 91.03% (Retention Time = 5.008 min). |
| I-240 | cyclohexyl-NH₂ (trans) | 3-phenoxybenzyl | 482.2 | δ 1.32 (m, 4H), 1.82 (m, 4H), 2.96 (m, 1H), 3.71 (m, 1H), 5.82 (s, 2H), 6.88 (m, 4H), 7.12 (m, 3H), 7.22 (brs, 1H), 7.33 (m, 2H), 7.53 (d, 1H), 7.83 (m, 3H), 8.24 (s, 1H), 8.58 (d, 1H), 8.88 (brs, 2H), 9.28 (brs, 2H); HPLC: 98.51% (Retention Time = 5.74 min). |

Example 20: Synthesis of Compound I-103

6-Carbamimidoyl-1-(4-carbamoylbenzyl)-N-methyl-N-(1-methylpyrrolidin-3-yl)-1H-indole-2-carboxamide

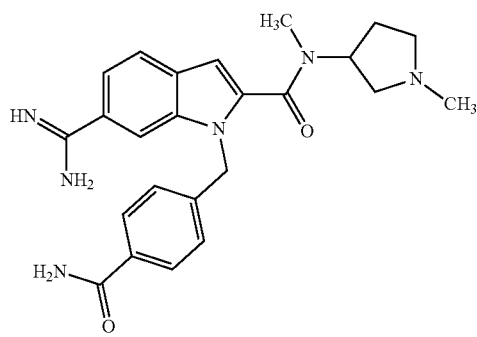 [SMILES: CN1CCC(N(C)C(=O)c2cc3ccc(C(=N)N)cc3n2Cc2ccc(C(N)=O)cc2)C1]

Step-1: 1-(4-Carbamoylbenzyl)-6-cyano-N-methyl-N-(1-methylpyrrolidin-3-yl)-1H-indole-2-carboxamide The product of step-2 of example 19 (500 mg, 1.56 mmol) and N,1-dimethylpyrrolidin-3-amine (178 mg, 1.56 mmol) were treated together to afford 385 mg of the title compound following the procedure described in step-3 of example 1. LCMS: 413.1 (M+1)⁺.

Step-2: 1-(4-Carbamoylbenzyl)-6-(N'-hydroxycarbamimidoyl)-N-methyl-N-(1-methylpyrrolidin-3-yl)-1H-indole-2-carboxamide The product of step-1 of example 20 (360 mg, 0.87 mmol) and aqueous hydroxylamine (1.7 mL) were treated together to afford 310 mg of the title compound following the procedure described in step-4 of example 14. LCMS: 448.2 (M+1)⁺.

Step-3: 6-(N'-Acetoxycarbamimidoyl)-1-(4-carbamoylbenzyl)-N-methyl-N-(1-methylpyrrolidin-3-yl)-1H-indole-2-carboxamide The product of step-2 of example 20 (280 mg, 0.62 mmol) and acetic anhydride (260 mg, 2.54 mmol) were treated together to afford 240 mg of the title compound following the procedure described in step-5 of example 14. LCMS: 491.2 (M+1)⁺.

Step-4: 6-Carbamimidoyl-1-(4-carbamoylbenzyl)-N-(4-fluorophenyl)-1H-indole-2-carboxamide The product of step-3 of example 20 (230 mg, 0.46 mmol) and zinc (125 mg, 1.89 mmol) were treated together to afford 108 mg of the title compound following the procedure described in step-6 of example 14. LCMS: 433.2 (M+1)⁺, ¹H NMR (300 MHz, DMSO-d₆): δ 1.94 (m, 2H), 2.40 (m, 2H), 2.60 (m, 2H), 2.94 (s, 3H), 3.05 (s, 3H), 5.76 (m, 2H), 7.00 (d, 1H), 7.20 (d, 2H), 7.26 (brs, 1H), 7.58 (d, 1H), 7.83 (d, 2H), 7.92 (d, 1H), 8.17 (m, 1H); HPLC: 94.31% (Retention Time=4.429 min).

Example 21: Synthesis of Compound I-117

1-(4-Carbamoylbenzyl)-$N^2$-(3-(pyrrolidin-1-yl)phenyl)-1H-indole-2,6-dicarboxamide

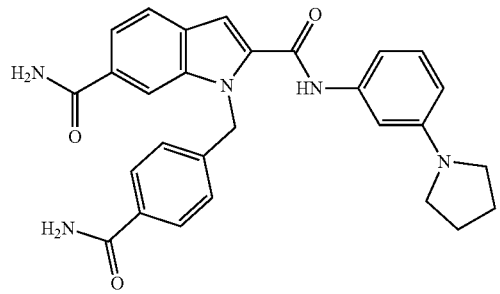 [SMILES: NC(=O)c1ccc(Cn2c(C(=O)Nc3cccc(N4CCCC4)c3)cc3ccc(C(N)=O)cc32)cc1]

Step-1: 1-(4-Carbamoylbenzyl)-6-cyano-N-(3-(pyrrolidin-1-yl)phenyl)-1H-indole-2-carboxamide The product of step-2 of example-19 (500 mg, 1.56 mmol) and 3-(pyrrolidin-1-yl)aniline (254 mg, 1.56 mmol) were treated together to afford 520 mg of the title compound following the procedure described in step-3 of example-1. LCMS: 464.2 (M+1)⁺.

Step-2: 1-(4-Carbamoylbenzyl)-$N^2$-(3-(pyrrolidin-1-yl)phenyl)-1H-indole-2,6-dicarboxamide To a solution of the product of step-1 of example-21 (250 mg, 0.53 mmol) in 5 mL of the mixture of methanol and water (1:1) was added solid sodium hydroxide (65 mg, 1.6 mmol). The reaction was stirred at 50° C. Upon reaction completion, the reaction mixture was concentrated to remove methanol and acidified with 2N HCl. The aqueous mixture was extracted with ethyl acetate and dried over anhydrous sodium sulphate. Solvent was evaporated under vacuum to give crude product which was purified by reverse-phase preparative HPLC and afforded 120 mg of the title compound. LCMS: 482.2 (M+1)⁺, ¹H NMR (300 MHz, DMSO-d₆): δ 1.93 (m, 4H), 3.20 (m, 4H), 5.94 (s, 2H), 6.30 (d, 2H), 6.99 (m, 6H), 7.22 (d, 2H), 7.42 (s, 1H), 7.69 (m, 4H), 7.87 (brs, 1H), 7.97 (brs, 1H), 8.11 (s, 1H), 10.26 (brs, 1H); HPLC: 98.46% (Retention Time=6.85 min).

General synthetic scheme-2A

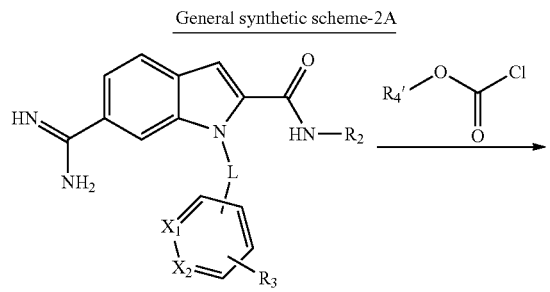

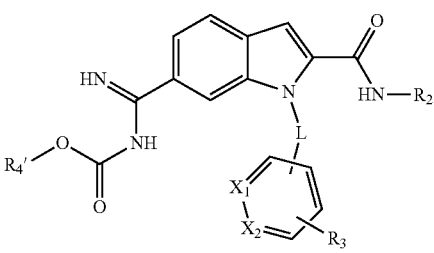

R₄' is an appropriate partial substituent of R₄; R₄ is as defined in formula (I)

Example 22: Synthesis of Compound I-118

Methyl ((1-(4-carbamoylbenzyl)-2-((4-(pyrrolidin-1-yl)phenyl)carbamoyl)-1H-indol-6-yl)(imino)methyl)carbamate

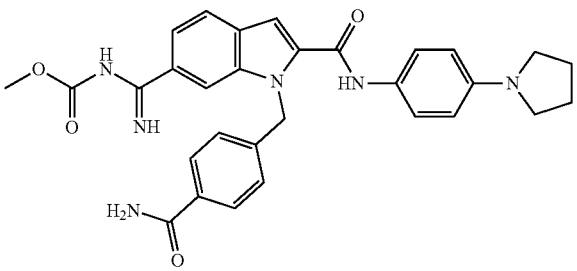 [SMILES: COC(=O)NC(=N)c1ccc2cc(C(=O)Nc3ccc(N4CCCC4)cc3)n(Cc3ccc(C(N)=O)cc3)c2c1]

Step-1: Methyl ((1-(4-carbamoylbenzyl)-2-((4-(pyrrolidin-1-yl)phenyl)carbamoyl)-1H-indol-6-yl)(imino)methyl)carbamate Compound I-90 (300 mg, 0.64 mmol) and potassium carbonate (355 mg, 2.57 mmol) were dissolved in 10 mL of DMF and added methyl carbonochloridate (95 mg, 0.96 mmol) drop wise at 0° C. and stirred the mixture at RT for 8 h. After reaction completion, mixture was quenched with ice-cold water and extracted with ethyl acetate followed with brine and dried over anhydrous sodium sulphate. Solvent was evaporated under vacuum to give crude product which was purified with reverse-phase HPLC and afforded the title compound (120 mg, Yield: 70%-80%). LCMS 539.2 (M+1)⁺, ¹H NMR (300 MHz, DMSO-d₆): δ 1.92 (m, 4H), 3.18 (m, 4H), 3.61 (s, 3H), 5.96 (s, 2H), 6.49 (d, 2H), 7.07 (d, 2H), 7.30 (brs, 1H), 7.39 (s, 1H), 7.50 (d, 2H), 7.73 (d, 2H), 7.80 (s, 2H), 7.87 (brs, 1H), 8.24 (s, 1H), 9.20 (brs, 2H), 10.22 (brs, 1H); HPLC: 97.37% (Retention Time, 3.765 min).

The following compounds listed in table-7 were prepared according to Scheme-2 followed by Scheme-2A by following similar procedure as described above for example-22 using appropriate reagents with suitable modifications known to the one skilled in the art.

TABLE 7

[Structure: indole core with HN-R2 amide at 2-position, R4'-NH-C(=NH)- amidine at 6-position, and N1-CH2-phenyl-C(=O)NH2 benzamide]

| Cpd. ID. | R₂ | R₄' | LCMS (M + 1)⁺ | ¹H NMR |
|---|---|---|---|---|
| I-119 | 4-(pyrrolidin-1-yl)phenyl | ethyl isobutyrate (–C(CH₃)₂–C(=O)–O–Et) | 553.2 | δ 1.19 (m, 3H), 1.92 (m, 4H), 3.18 (m, 4H), 4.04 (m, 2H), 5.96 (s, 2H), 6.49 (d, 2H), 7.07 (d, 2H), 7.30 (brs, 1H), 7.39 (s, 1H), 7.49 (d, 2H), 7.73 (d, 2H), 7.80 (s, 2H), 7.86 (brs, 1H), 8.23 (s, 1H), 9.2 (br, 2H), 10.21 (brs, 1H); HPLC: 96.94% (Retention Time = 5.974 min). |
| I-120 | 3-(pyrrolidin-1-yl)phenyl | ethyl isobutyrate | 553.2 | δ 1.19 (m, 3H), 1.94 (m, 4H), 3.20 (m, 4H), 4.03 (m, 2H), 5.96 (s, 2H), 6.28 (d, 1H), 6.97 (s, 1H), 7.01 (m, 4H), 7.30 (brs, 1H), 7.44 (m, 1H), 7.73 (d, 2H), 7.81 (s, 2H), 7.86 (brs, 1H), 8.24 (s, 1H), 9.1 (brs, 2H), 10.34 (brs, 1H); HPLC: 95.99% (Retention Time = 6.717 min). |
| I-142 | 3-(pyrrolidin-1-yl)phenyl | isopropyl isobutyrate | 567.2 | δ 1.23 (d, 6H), 1.94 (m, 4H), 3.17 (m, 4H), 4.82 (m, 1H), 5.98 (s, 2H), 6.29 (d, 1H), 6.98 (s, 1H), 7.08 (m, 4H), 7.30 (brs, 1H), 7.46 (s, 1H), 7.74 (d, 2H), 7.84 (s, 2H), 7.86 (brs, 1H), 8.24 (s, 1H), 9.2 (brs, 2H), 10.28 (s, 1H); HPLC: 93.15% (Retention Time = 6.804 min). |
| I-143 | 3-(pyrrolidin-1-yl)phenyl | benzyl isobutyrate | 615.3 | δ 1.96 (m, 4H), 3.21 (m, 4H), 5.13 (s, 2H), 5.98 (s, 2H), 6.33 (d, 1H), 7.00 (s, 1H), 7.04 (m, 4H), 7.34 (m, 5H), 7.47 (s, 1H), 7.75 (d, 2H), 7.84 (m, 2H), 8.29 (s, 1H), 9.2 (brs, 3H), 10.31 (s, 1H); HPLC: 97.16% (Retention Time = 3.771 min). |

TABLE 7-continued

| Cpd. ID. | R₂ | R₄' | LCMS (M + 1)⁺ | ¹H NMR |
|---|---|---|---|---|
| I-147 | 3-(pyrrolidin-1-yl)phenyl | isobutyl ester | 581.3 | δ 0.90 (d, 6H), 1.91 (m, 5H), 3.20 (m, 4H), 3.80 (d, 2H), 5.96 (s, 2H), 6.28 (d, 1H), 7.01 (m, 2H), 7.07 (m, 2H), 7.29 (brs, 1H), 7.44 (s, 1H), 7.73 (d, 2H), 7.81 (s, 2H), 7.86 (brs, 1H), 8.24 (s, 1H), 9.2 (br, 2H), 10.30 (s, 1H); HPLC: 97.86% (Retention Time = 4.472 min). |
| I-148 | 3-(pyrrolidin-1-yl)phenyl | phenyl ester | 601.3 | δ 1.93 (m, 4H), 3.20 (m, 4H), 5.95 (s, 2H), 6.29 (d, 1H), 6.97 (s, 1H), 7.07 (m, 5H), 7.17 (m, 4H), 7.30 (s, 1H), 7.37 (m, 2H), 7.46 (s, 1H), 7.74 (d, 2H), 8.87 (m, 3H), 8.28 (s, 2H), 9.29 (brs, 1H); HPLC: 95.06% (Retention Time = 4.331 min). |
| I-159 | 3-(pyrrolidin-1-yl)phenyl | hexyl ester | 609.3 | δ 0.87 (m, 3H), 1.34 (m, 6H), 1.55 (m, 2H), 1.93 (m, 4H), 3.20 (m, 4H), 4.00 (m, 2H), 5.83 (s, 2H), 6.28 (d, 1H), 6.97 (brs, 1H), 7.01 (d, 1H), 7.06 (m, 2H), 7.29 (brs, 1H), 7.45 (s, 1H), 7.73 (d, 2H), 7.81 (s, 1H), 7.86 (s, 1H), 8.24 (s, 1H), 9.03 (brs, 2H), 10.30 (s, 1H); HPLC: 96.75% (Retention Time = 4.221 min). |
| I-160 | 3-(pyrrolidin-1-yl)phenyl | butyl ester | 581.3 | δ 0.90 (m, 3H), 1.34 (m, 2H), 1.55 (m, 2H), 1.93 (m, 4H), 3.18 (m, 4H), 4.13 (m, 2H), 5.96 (s, 2H), 6.28 (d, 1H), 6.97 (brs, 1H), 7.01 (d, 1H), 7.06 (m, 3H), 7.30 (brs, 1H), 7.44 (s, 1H), 7.73 (d, 2H), 7.86 (m, 3H), 8.28 (s, 1H), 9.03 (br, 2H), 10.30 (s, 1H); HPLC: 98.32% (Retention Time = 6.936 min). |

TABLE 7-continued
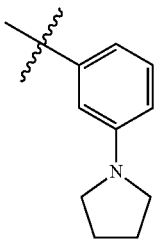 [SMILES: *c1cccc(N2CCCC2)c1]
| Cpd. ID. | R₂ | R₄' | LCMS (M + 1)⁺ | ¹H NMR |
|---|---|---|---|---|
| I-161 | 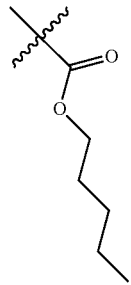 [SMILES: *C(=O)OCCCCC] | 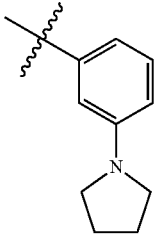 [SMILES: *c1cccc(N2CCCC2)c1] | 595.3 | δ 0.87 (m, 3H), 1.30 (m, 4H), 1.55 (m, 2H), 1.93 (m, 4H), 3.20 (m, 4H), 4.01 (m, 2H), 5.96 (s, 2H), 6.28 (d, 1H), 6.97 (brs, 1H), 7.01 (d, 1H), 7.06 (m, 3H), 7.29 (brs, 1H), 7.44 (s, 1H), 7.73 (d, 2H), 7.81 (s, 2H), 7.86 (s, 1H), 8.24 (s, 1H), 9.03 (brs, 2H), 10.30 (s, 1H); HPLC: 98.51% (Retention Time = 3.81 min). |
| I-162 | 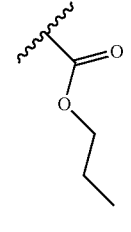 [SMILES: *C(=O)OCCC] | 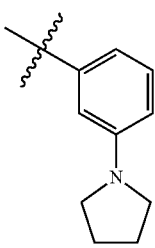 [SMILES: *c1cccc(N2CCCC2)c1] | 567.3 | δ 0.90 (m, 3H), 1.61 (m, 2H), 2.32 (m, 4H), 3.21 (m, 4H), 3.95 (m, 2H), 5.96 (s, 2H), 6.28 (d, 1H), 6.97 (s, 1H), 7.01 (d, 1H), 7.09 (m, 3H), 7.44 (s, 1H), 7.73 (d, 2H), 7.81 (s, 2H), 7.86 (m, 1H), 8.24 (s, 1H), 10.23 (s, 1H); HPLC: 91.46% (Retention Time = 3.984 min). |
| I-164 | 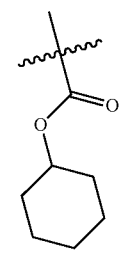 | 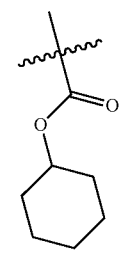 | 607.3 | δ 1.21 (m, 6H), 1.51 (m, 1H), 1.69 (m, 2H), 1.85 (m, 2H), 1.95 (m, 4H), 3.20 (m, 4H), 4.55 (m, 1H), 5.96 (s, 2H), 6.28 (d, 1H), 6.97 (s, 1H), 7.01 (m, 4H), 7.29 (s, 1H), 7.44 (s, 1H), 7.73 (d, 2H), 7.81 (m, 3H), 8.23 (s, 1H), 9.20 (brs, 2H), 10.23 (s, 1H); HPLC: 92.67% (Retention Time = 7.061 min). |

Example 23: Synthesis of Compound I-135

1-(4-Carbamoylbenzyl)-6-(N'-(2-(dimethylamino)acetoxy)carbamimidoyl)-N-(3-(pyrrolidin-1-yl)phenyl)-1H-indole-2-carboxamide

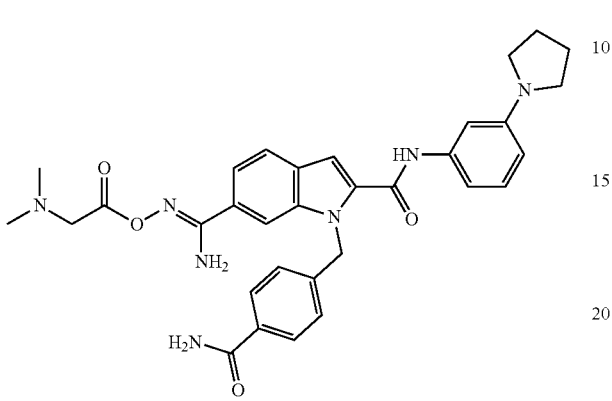

Step-1: 1-(4-Carbamoylbenzyl)-6-cyano-N-(3-(pyrrolidin-1-yl)phenyl)-1H-indole-2-carboxamide The product of step-2 of example-19 (500 mg, 1.56 mmol) and 3-(pyrrolidin-1-yl)aniline (254 mg, 1.56 mmol) were treated together to afford 520 mg of the title compound following the procedure described in step-3 of example-1. LCMS: 464.2 (M+1)$^+$.

Step-2: 1-(4-Carbamoylbenzyl)-6-(N'-hydroxycarbamimidoyl)-N-(3-(pyrrolidin-1-yl)phenyl)-1H-indole-2-carboxamide The product of step-1 of example-23 (500 mg, 0.24 mmol) and aqueous hydroxylamine (0.063 mL) were treated together to afford 350 mg of the title compound following the procedure described in step-4 of example-14. LCMS: 497.2 (M+1)$^+$.

Step-3: 1-(4-Carbamoylbenzyl)-6-(N'-(2-(dimethylamino)acetoxy)carbamimidoyl)-N-(3-(pyrrolidin-1-yl)phenyl)-1H-indole-2-carboxamide The solution of N,N-dimethylglycine (45 mg, 0.44 mmol), triethylamine (66 mg, 0.66 mmol) in 10 mL of tetrahydrofuran, at 0° C. isobutyl chloroformate (60 mg, 0.44 mmol) was added and stirred for 2 h, followed by the addition of product of step-2 of example-23 (220 mg, 0.44 mmol) and stirred at RT for 8 h. After reaction completion, the solvent was evaporated under vacuum to give crude product which was purified with reverse-phase HPLC and afforded the title compound (85 mg, Yield: 20%-30%). LCMS: 582.3 (M+1)$^+$, $^1$H NMR (300 MHz, DMSO-d$_6$): δ 1.95 (m, 4H), 2.54 (s, 6H), 3.18 (m, 6H), 5.84 (brs, 2H), 5.92 (s, 2H), 6.29 (d, 2H), 7.02 (m, 2H), 7.09 (m, 3H), 7.29 (brs, 1H), 7.40 (s, 1H), 7.52 (d, 1H), 7.68 (m, 3H), 7.84 (m, 2H), 9.61 (brs, 1H), 10.19 (brs, 1H); HPLC: 93.11% (Retention Time=3.869 min).

Example 24: Synthesis of Example I-136

1-(4-Carbamoylbenzyl)-N$^2$-(3-(pyridin-2-yl)phenyl)-1H-indole-2,6-dicarboxamide

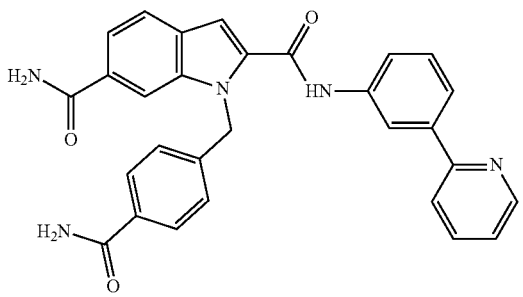 [SMILES: NC(=O)c1ccc(Cn2c(C(=O)Nc3cccc(-c4ccccn4)c3)cc3ccc(C(N)=O)cc32)cc1]

Step-1: 1-(4-Carbamoylbenzyl)-6-cyano-N-(3-(pyridin-2-yl)phenyl)-1H-indole-2-carboxamide The product of step-2 of example-19 (1.2 g, 3.76 mmol) and 3-(pyridin-2-yl)aniline (640 mg, 3.76 mmol) were treated together to afford 1230 mg of the title compound following the procedure described in step-3 of example-1. LCMS: 472.2 (M+1)$^+$.

Step-2: 1-(4-carbamoylbenzyl)-N$^2$-(3-(pyridin-2-yl)phenyl)-1H-indole-2,6-dicarboxamide The product of step-1 of example-24 (150 mg, 0.31 mmol) and sodium hydroxide (38 mg, 0.93 mmol) were treated together to afford 300 mg of the title compound following the procedure described in step-2 of example-21. LCMS: 490.2 (M+1)$^+$, $^1$H NMR (300 MHz, DMSO-d$_6$): δ 5.98 (s, 2H), 7.10 (d, 2H), 7.30 (brs, 1H), 7.35 (brs, 1H), 7.40 (m, 1H), 7.50 (m, 1H), 7.54 (s, 1H), 7.70 (m, 8H), 7.96 (m, 3H), 8.13 (s, 1H), 8.54 (s, 1H), 8.69 (d, 1H), 10.63 (brs, 1H); HPLC: 99.42% (Retention Time=6.151 min).

Example 25: Synthesis of Compound I-149

1-(4-Carbamoylbenzyl)-6-(N'-methoxycarbamimidoyl)-N-(3-(pyrrolidin-1-yl)phenyl)-1H-indole-2-carboxamide

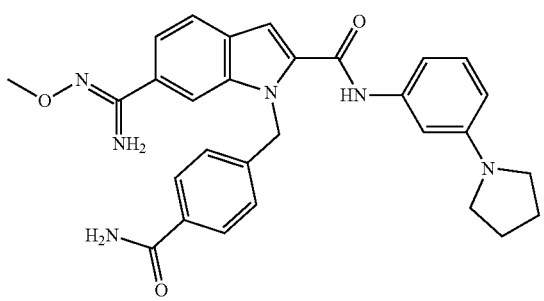

Step-1: 1-(4-Carbamoylbenzyl-6-(N'-methoxycarbamimidoyl)-N-(3-(pyrrolidin-1-yl)phenyl)-1H-indole-2-carboxamide To the solution of the product of step-2 of example-23 (300 mg, 0.6 mmol) in 10 mL of dioxane was added 0.7 N sodium hydroxide (25 mg, 0.6 mmol) aqueous solution drop wise at 0° C. and stirred for 10 minutes followed by dimethyl sulfate (1860 mg, 10 mmol) was added drop wise at the same temperature and reaction mixture was stirred for 4 h at 0° C. Solvent was evaporated under vacuum to give crude product which was purified by reverse-phase preparative HPLC and afforded 35 mg of the title compound. LCMS: 511.2 (M+1)$^+$, $^1$H NMR (300 MHz, DMSO-$d_6$): δ 1.95 (m, 4H), 3.16 (m, 7H), 5.95 (s, 2H), 6.29 (d, 1H), 7.80 (br, 2H), 7.00 (s, 1H), 7.06 (m, 2H), 7.20 (m, 3H), 7.29 (s, 1H), 7.75 (d, 3H), 7.84 (m, 2H), 10.22 (s, 1H).

Example 26: Synthesis of Compound I-157

(R)-tert-butyl (1-(((amino(1-(4-carbamoylbenzyl)-2-((3-(pyrrolidin-1-yl)phenyl)-carbamoyl)-1H-indol-6-yl)methylene)amino)oxy)-3-methyl-1-oxobutan-2-yl)carbamate

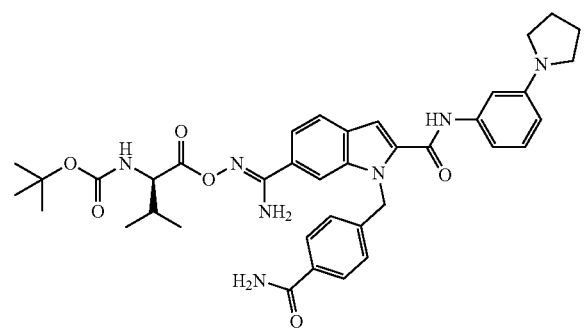 [SMILES: CC(C)[C@@H](NC(=O)OC(C)(C)C)C(=O)O/N=C(\N)c1ccc2cc(C(=O)Nc3cccc(N4CCCC4)c3)n(Cc3ccc(C(N)=O)cc3)c2c1]

Step-1: (R)-tert-butyl (1-(((amino(1-(4-carbamoylbenzyl)-2-((3-(pyrrolidin-1-yl)phenyl)-carbamoyl)-1H-indol-6-yl)methylene)amino)oxy)-3-methyl-1-oxobutan-2-yl)carbamate The product of step-2 of example-23 (230 mg, 0.46 mmol) and (R)-2-((tert-butoxycarbonyl)-amino)-3-methylbutanoic acid (100 mg, 0.46 mmol) were treated together to afford 60 mg of the title compound following the procedure described in step-3 of example-23. LCMS: 696.3 (M+1)$^+$, $^1$H NMR (300 MHz, DMSO-$d_6$): δ 0.90 (m, 6H), 1.41 (s, 9H), 1.95 (m, 4H), 3.18 (m, 4H), 4.04 (m, 1H), 5.95 (s, 2H), 6.28 (d, 1H), 6.84 (brs, 1H), 6.97 (s, 1H), 7.06 (d, 1H), 7.11 (m, 2H), 7.28 (brs, 1H), 7.34 (d, 1H), 7.43 (s, 1H), 7.51 (d, 1H), 7.72 (d, 2H), 7.81 (d, 1H), 7.85 (brs, 1H), 9.26 (brs, 2H), 10.21 (s, 1H); HPLC: 90.92% (Retention Time=4.537 min).

Example 27: Synthesis of Compound I-158

(S)-tert-butyl (1-(((amino(1-(4-carbamoylbenzyl)-2-((3-(pyrrolidin-1-yl)phenyl)carbamoyl)-1H-indol-6-yl)methylene)amino)oxy)-1-oxopropan-2-yl)carbamate

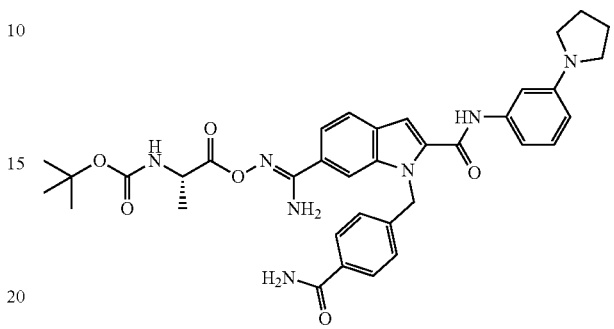

Step-1: (S)-tert-butyl (1-(((amino(1-(4-carbamoylbenzyl)-2-((3-(pyrrolidin-1-yl)phenyl)-carbamoyl)-1H-indol-6-yl)methylene)amino)oxy)-1-oxopropan-2-yl)carbamate The product of step-2 of example-23 (0.2 mg, 0.4 mmol) and (S)-Boc alanine were treated together to afford 45 mg of the title compound following the procedure described in step-3 of example-23.

Example 28: Synthesis of Compound I-183

Ethyl ((1-(4-carbamoylbenzyl)-2-((6-(pyrrolidin-1-yl)pyridin-2-yl)carbamoyl)-1H-indol-6-yl)(imino)methyl)carbamate

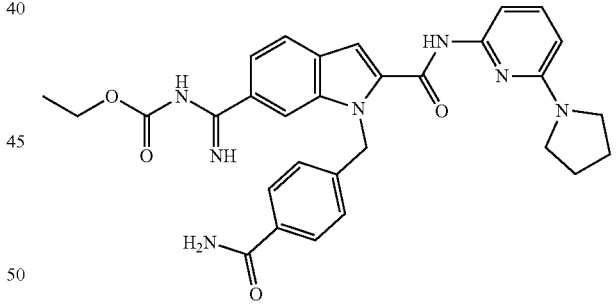

Step-1: 1-(4-Carbamoylbenzyl)-6-cyano-N-(6-(pyrrolidin-1-yl)pyridin-2-yl)-1H-indole-2-carboxamide The product of step-2 of example-19 (950 mg, 2.97 mmol) and 6-(pyrrolidin-1-yl)pyridin-2-amine (485 mg, 2.97 mmol) were treated together to afford 685 mg of the title compound following the procedure described in step-3 of example-1. LCMS: 465.2 (M+1)$^+$.

Step-2: 1-(4-Carbamoylbenzyl)-6-(N'-hydroxycarbamimidoyl)-N-(6-(pyrrolidin-1-yl)pyridin-2-yl)-1H-indole-2-carboxamide The product of step-1 of example-28 (685 mg, 1.47 mmol) and aqueous hydroxylamine (0.4 mL) were treated together to afford 520 mg of the title compound following the procedure described in step-4 of example-14. LCMS: 498.2 (M+1)+.

Step-3: 6-(N'-Acetoxycarbamimidoyl)-1-(4-carbamoylbenzyl)-N-(6-(pyrrolidin-1-yl)pyridin-2-yl)-1H-indole-2-carboxamide The product of step-2 of example-28 (520 mg, 1.04 mmol) and acetic anhydride (213 mg, 2.08 mmol) were treated together to afford 465 mg of the title compound following the procedure described in step-5 of example-14. LCMS: 540.2 (M+1)+.

Step-4: 6-Carbamimidoyl-1-(4-carbamoylbenzyl)-N-(6-(pyrrolidin-1-yl)pyridin-2-yl)-1H-indole-2-carboxamide The product of step-3 of example-28 (460 mg, 0.85 mmol) and zinc (112 mg, 1.7 mmol) were treated together to afford 60 mg of the title compound following the procedure described in step-6 of example-14. LCMS: 482.2 (M+1)+.

Step-5: Ethyl ((1-(4-carbamoylbenzyl)-2-((6-(pyrrolidin-1-yl)pyridin-2-yl)carbamoyl)-1H-indol-6-yl)(imino)methyl)carbamate The product of step-4 of example-28 (350 mg, 0.72 mmol) and ethyl carbonochloridate (78 mg, 0.72 mmol) were treated together to afford 70 mg of the title compound following the procedure described in step-1 of example 22. LCMS: 554.2 (M+1)+, $^1$H NMR (300 MHz, DMSO-$d_6$): δ 1.19 (m, 3H), 1.92 (m, 4H), 3.38 (m, 4H), 4.04 (m, 2H), 4.12 (m, 1H), 5.95 (s, 2H), 6.18 (d, 1H), 7.05 (d, 2H), 7.22 (d, 1H), 7.29 (brs, 1H), 7.46 (m, 1H), 7.59 (m, 1H), 7.72 (d, 2H), 7.80 (s, 1H), 7.85 (s, 1H), 8.24 (s, 1H), 9.01 (brs, 2H), 10.4 (brs, 1H); HPLC: 97.47% (Retention Time=5.938 min).

Example 29: Synthesis of Compound I-199

6-Carbamimidoyl-1-(4-carbamoylbenzyl)-N-(3-fluoroadamantan-1-yl)-1H-indole-2-carboxamide

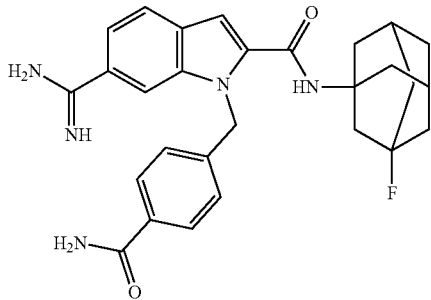 [SMILES: N=C(N)c1ccc2cc(C(=O)NC34CC5CC(CC(F)(C5)C3)C4)n(Cc3ccc(C(N)=O)cc3)c2c1]

Step-1: 1-(4-Carbamoylbenzyl)-6-cyano-N-(3-((2-methoxyethoxy)methoxy)adamantan-1-yl)-1H-indole-2-carboxamide The product of step-2 of example-19 (800 mg, 2.5 mmol) and 3-((2-methoxyethoxy)methoxy)adamantan-1-amine (640 mg, 2.5 mmol) were treated together to afford 635 mg of the title compound following the procedure described in step-3 of example-1. LCMS: 557.3 (M+1)+.

Step-2: 1-(4-Carbamoylbenzyl)-6-cyano-N-(3-hydroxyadamantan-1-yl)-1H-indole-2-carboxamide The product of step-1 of example-29 (650 mg, 1.07 mmol) was treated with 50 mL of ethanolic-HCl to afford 320 mg of the title compound following the procedure described in step-2 of example-2. LCMS: 469.2 (M+1)+.

Step-3: 1-(4-Carbamoylbenzyl)-6-cyano-N-(3-fluoroadamantan-1-yl)-1H-indole-2-carboxamide The product of step-2 of example-29 (320 mg, 0.68 mmol) was dissolved in 10 mL of dichloromethane and cooled to −78° C. Diethylaminosulfur trifluoride (165 mg, 1.02 mmol) was added and reaction mixture was stirred for 1 h at −30° C. Mixture was quenched with ice-cold water and extracted with dichloromethane, dried over sodium sulphate and solvent was evaporated under vacuum to afford 180 mg of the title compound, which was subjected to next step without further purification. LCMS: 471.2 (M+1)+.

Step-4: 1-(4-carbamoylbenzyl)-N-(3-fluoroadamantan-1-yl)-6-(N'-hydroxycarbamimidoyl)-1H-indole-2-carboxamide The product of step-3 of example-29 (180 mg, 0.38 mmol) and aqueous hydroxylamine (0.1 mL) were treated together to afford 150 mg of the title compound following the procedure described in step-4 of example-14. LCMS: 504.2 (M+1)+.

Step-5: 6-(N'-acetoxycarbamimidoyl)-1-(4-carbamoylbenzyl)-N-(3-fluoroadamantan-1-yl)-1H-indole-2-carboxamide The product of step-4 of example-29 (150 mg, 0.29 mmol) and acetic anhydride (60 mg, 0.6 mmol) were treated together to afford 120 mg of the title compound following the procedure described in step-5 of example-14. LCMS: 546.2 (M+1)+.

Step-6: 6-Carbamimidoyl-1-(4-carbamoylbenzyl)-N-((1r,3r)-3-((2-methoxyethoxy)methoxy)-adamantan-1-yl)-1H-indole-2-carboxamide The product of step-5 of example-29 (120 mg, 0.21 mmol) and zinc (30 mg, 0.45 mmol) were treated together to afford 25 mg of the title compound following the procedure described in step-6 of example-14. LCMS: 488.2 (M+1)+, $^1$H NMR (300 MHz, DMSO-$d_6$): δ 1.51 (s, 2H), 1.80 (m, 4H), 1.94 (s, 4H), 2.17 (m, 2H), 2.29 (m, 2H), 5.84 (s, 2H), 7.15 (m, 3H), 7.33 (brs, 1H), 7.52 (d, 1H), 7.75 (d, 2H), 7.87 (m, 2H), 8.19 (brs, 1H), 8.27 (brs, 1H), 8.93 (brs, 2H), 9.22 (brs, 2H).

Example 30: Synthesis of Compound I-210

3-Amino-6-carbamimidoyl-1-(4-carbamoylbenzyl)-N-(cyclohexylmethyl)-1H-indole-2-carboxamide

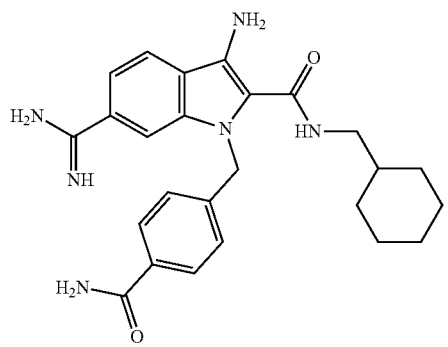

Step-1: 1-(4-carbamoylbenzyl)-6-cyano-N-(cyclohexylmethyl)-1H-indole-2-carboxamide The product of step-2 of example-18 (780 mg, 2.76 mmol) and 4-(bromomethyl)benzamide (592 mg, 2.76 mmol) were treated together to afford 645 mg of the title compound following the procedure described in step-1 of example-1. LCMS: 413.1 (M+1)$^+$.

Step-2: 1-(4-carbamoylbenzyl)-N-(cyclohexylmethyl)-6-(N'-hydroxycarbamimidoyl)-3-nitro-1H-indole-2-carboxamide The product of step-1 of example-30 (645 mg, 1.56 mmol) and aqueous hydroxylamine (0.5 mL) were treated together to afford 470 mg of the title compound following the procedure described in step-4 of example-14. LCMS: 493.2 (M+1)$^+$.

Step-3: 6-(N'-acetoxycarbamimidoyl)-1-(4-carbamoylbenzyl)-N-(cyclohexylmethyl)-3-nitro-1H-indole-2-carboxamide The product of step-2 of example-30 (470 mg, 0.95 mmol) and acetic anhydride (194 mg, 1.9 mmol) were treated together to afford 385 mg of the title compound following the procedure described in step-5 of example-14. LCMS: 535.2 (M+1)$^+$.

Step-4: 3-Amino-6-carbamimidoyl-1-(4-carbamoylbenzyl)-N-(cyclohexylmethyl)-1H-indole-2-carboxamide The product of step-3 of example-30 (385 mg, 0.71 mmol) and zinc (187 mg, 2.87 mmol) were treated together to afford 55 mg of the title compound following the procedure described in step-6 of example-14. LCMS: 447.2 (M+1)$^+$, $^1$H NMR (300 MHz, DMSO-d$_6$): δ 0.83 (m, 2H), 1.06 (m, 3H), 1.45 (m, 2H), 1.55 (m, 6H), 3.07 (m, 2H), 5.08 (brs, 2H), 5.68 (s, 2H), 6.98 (d, 2H), 7.30 (brs, 1H), 7.39 (d, 1H), 7.69 (d, 2H), 7.86 (brs, 1H), 7.92 (d, 1H), 8.06 (m, 2H).

Example 31: Synthesis of Compound I-211

3-Amino-1-(4-carbamoylbenzyl)-N$^2$-(cyclohexylmethyl)-1H-indole-2,6-dicarboxamide

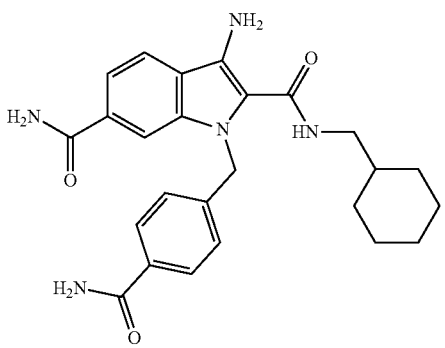 [SMILES: NC(=O)c1ccc(Cn2c(C(=O)NCC3CCCCC3)c(N)c3ccc(C(N)=O)cc32)cc1]

Step-1: 1-(4-Carbamoylbenzyl)-N2-(cyclohexylmethyl)-3-nitro-1H-indole-2,6-dicarboxamide The product of step-1 of example-81 (340 mg, 0.82 mmol) and sodium hydroxide (65 mg, 1.64 mmol) were treated together to afford 165 mg of the title compound following the procedure described in step-2 of example-21. LCMS: 478.2 (M+1)$^+$.

Step-2: 3-amino-1-(4-carbamoylbenzyl)-N$^2$-(cyclohexylmethyl)-1H-indole-2,6-dicarboxamide The product of step-1 of example-81 (165 mg, 0.34 mmol) and zinc (45 mg, 0.69 mmol) were treated together to afford 300 mg of the title compound following the procedure described in step-3 of example-9. LCMS: 448.2 (M+1)$^+$, $^1$H NMR (300 MHz, DMSO-d$_6$): δ 0.76 (m, 2H), 1.06 (m, 3H), 1.38 (m, 1H), 1.48 (m, 5H), 3.03 (m, 2H), 5.08 (brs, 2H), 5.73 (s, 2H), 7.00 (d, 1H), 7.12 (brs, 1H), 7.25 (brs, 1H), 7.41 (d, 1H), 7.78 (d, 1H), 7.98 (d, 1H), 8.04 (m, 2H), 8.95 (brs, 2H), 9.19 (brs, 2H); HPLC: 96.22% (Retention Time=6.176 min).

Example 32: Synthesis of Compound I-212

6-Carbamimidoyl-1-(4-carbamoylbenzyl)-N-(cyclohexylmethyl)-3-hydroxy-1H-indole-2-carboxamide

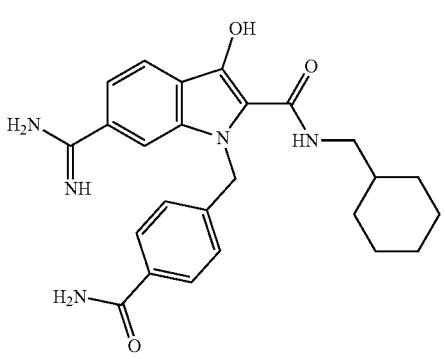 [SMILES: N=C(N)c1ccc2c(O)c(C(=O)NCC3CCCCC3)n(Cc3ccc(C(N)=O)cc3)c2c1]

Step-1: Ethyl 3-acetoxy-6-cyano-1H-indole-2-carboxylate

In a sealed tube ethyl 6-cyano-1H-indole-2-carboxylate (1.46 g, 6.82 mmol), (diacetoxyiodo)benzene (2.85 g, 8.86 mmol), palladium II acetate (75 mg, 0.34 mmol) were dissolved in 150 mL of acetic acid and mixture was slowly heated to 100° C. for 3 h. The reaction mixture was diluted with ethyl acetate and filtered it through celite pad and filtrate was washed with water and dried over sodium sulphate. Solvent was evaporated under vacuum to give crude compound which was purified with column chromatography using silica-gel as an adsorbent and eluted with hexane:ethyl acetate (7:3) to afford 645 mg of the title compound. LCMS: 273.1 (M+1)$^+$.

Step-2: Ethyl 3-acetoxy-1-(4-carbamoylbenzyl)-6-cyano-1H-indole-2-carboxylate The product of step-1 of example-212 (645 mg, 2.37 mmol) and 4-(bromomethyl)benzamide (507 mg, 2.37 mmol) were treated together to afford 745 mg of the title compound following the procedure described in step-1 of example-1. LCMS: 406.1 (M+1)$^+$.

Step-3: Ethyl 1-(4-carbamoylbenzyl)-6-cyano-3-hydroxy-1H-indole-2-carboxylate The product of step-2 of example-32 (745 mg, 1.83 mmol) was dissolved in 150 mL of toluene and treated with silica-gel (165 mg, 2.75 mmol), 4-methylbenzenesulfonic acid (380 mg, 2.2 mmol) and water (72 mg, 4.02 mmol). Mixture was heated to 80° C. for 6 h. The reaction mixture quenched with cold-water and extracted with ethyl acetate, followed by washed with water and dried over sodium sulphate. Solvent was evaporated under vacuum to give crude compound which was purified with column chromatography using silica-gel as an adsorbent and eluted with hexane:ethyl acetate (6:4) to afford 540 mg of the title compound. LCMS: 364.1 (M+1)$^+$.

Step-4: Ethyl 1-(4-carbamoylbenzyl)-6-cyano-3-((4-methoxybenzyl)oxy)-1H-indole-2-carboxylate The product of step-3 of example-32 (540 mg, 1.48 mmol), dissolved in 50 mL of tetrahydrofuran, was added 1-(bromomethyl)-4-methoxybenzene (298 mg, 1.48 mmol) and sodium hydride (60 mg, 1.48 mmol) at 0° C. Reaction mixture was stirred at room temperature for 6 h. Mixture was quenched with cold water, extracted with ethyl acetate followed by washed with brine and dried over sodium sulphate. Solvent was evaporated under vacuum to give crude compound which was purified by column chromatography using silica-gel as an adsorbent and eluted with hexane:ethylacetate (8:2) to afford 610 mg of the title compound. LCMS: 484.2 (M+1)$^+$.

Step-5: 1-(4-Carbamoylbenzyl)-6-cyano-3-((4-methoxybenzyl)oxy)-1H-indole-2-carboxylic Acid The product of step-4 of example-32 (610 mg, 1.26 mmol) and lithium hydroxide (60 mg, 2.52 mmol) were treated together to afford 385 mg of the title compound following the procedure described in step-2 of example-1. LCMS: 456.2 (M+1)$^+$.

Step-6: 1-(4-Carbamoylbenzyl)-N-(cyclohexylmethyl)-6-cyano-3-((4-methoxybenzyl)oxy)-1H-indole-2-carboxamide The product of step-5 of example-32 (385 mg, 0.84 mmol) and cyclohexylmethanamine (95 mg, 0.84 mmol) were treated together to afford 310 mg of the title compound following the procedure described in step-3 of example-1. LCMS: 551.3 (M+1)$^+$.

Step-7: 1-(4-Carbamoylbenzyl)-N-(cyclohexylmethyl)-6-(N'-hydroxycarbamimidoyl)-3-((4-methoxybenzyl)oxy)-1H-indole-2-carboxamide The product of step-6 of example-32 (310 mg, 0.56 mmol) and aqueous hydroxylamine (0.2 mL) were treated together to afford 165 mg of the title compound following the procedure described in step-4 of example-14. LCMS: 584.3 (M+1)$^+$.

Step-8: 6-(N'-acetoxycarbamimidoyl)-1-(4-carbamoylbenzyl)-N-(cyclohexylmethyl)-3-((4-methoxybenzyl)oxy)-1H-indole-2-carboxamide The product of step-7 of example-32 (165 mg, 0.28 mmol) and acetic anhydride (58 mg, 0.56 mmol) were treated together to afford 145 mg of the title compound following the procedure described in step-5 of example-14. LCMS: 626.3 (M+1)$^+$.

Step-9: 6-Carbamimidoyl-1-(4-carbamoylbenzyl)-N-(cyclohexylmethyl)-3-hydroxy-1H-indole-2-carboxamide The product of step-8 of example-32 (145 mg, 0.23 mmol), dissolved in 20 mL of methanol, was treated with 10% palladium on carbon (24 mg, 0.23 mmol) under nitrogen at room temperature for 4 h. Mixture was filtered through celite pad and filtrate was concentrated to give crude product which was purified with reversed-phase preparative column chromatography and afforded 20 mg of the title compound. LCMS: 448.2 (M+1)$^+$, $^1$H NMR (300 MHz, DMSO-d$_6$): δ 0.95 (m, 2H), 1.06 (m, 3H), 1.38 (m, 1H), 1.48 (m, 5H), 3.18 (m, 2H), 5.92 (s, 2H), 7.01 (d, 2H), 7.32 (brs, 1H), 7.43 (d, 1H), 7.72 (d, 2H), 7.88 (d, 1H), 7.88 (brs, 1H), 7.98 (m, 2H), 8.09 (s, 1H), 8.89 (brs, 2H), 9.22 (brs, 2H); HPLC: 95.18% (Retention Time=3.216 min).

General synthetic Scheme 3

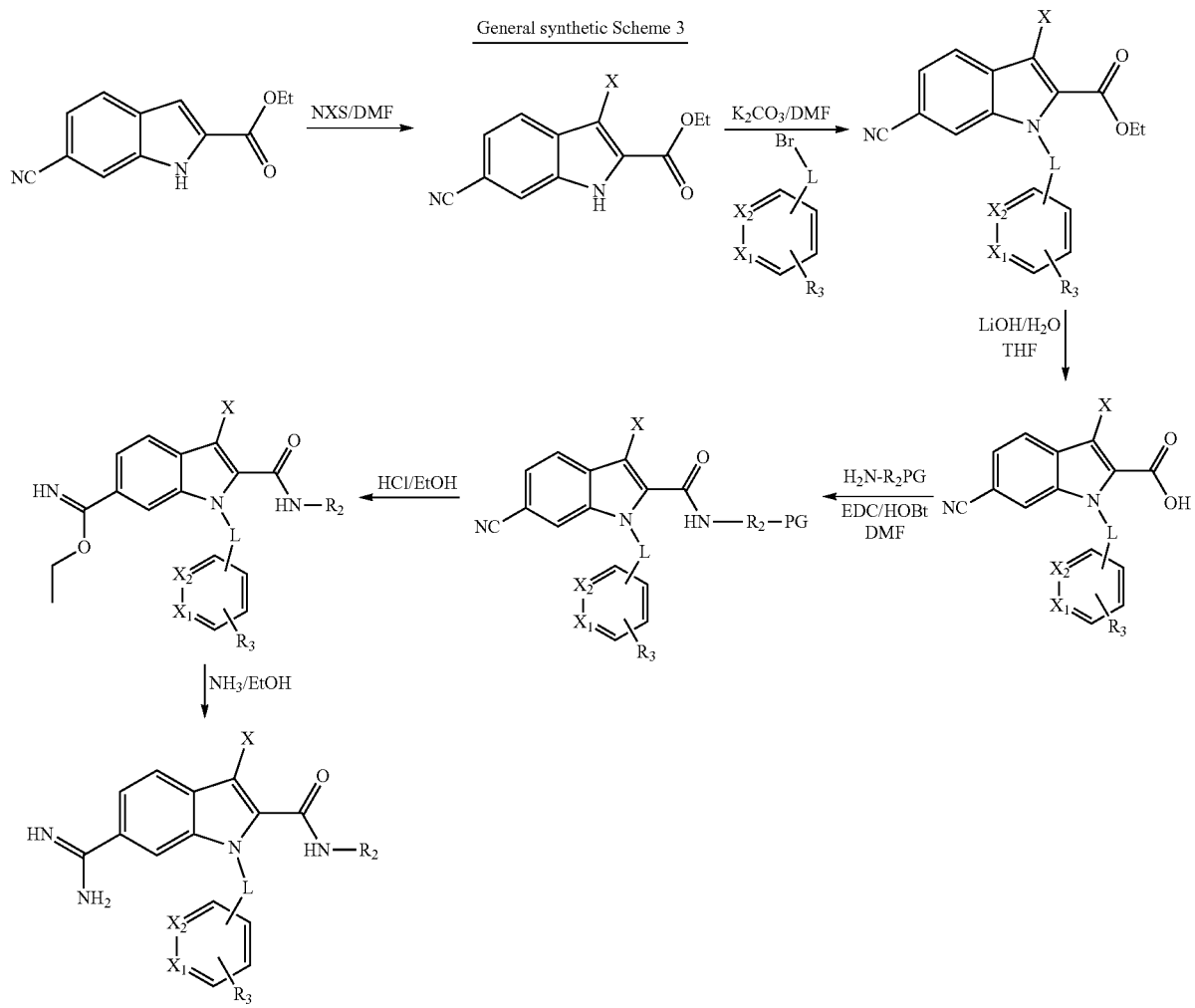

NXS = N-halosuccinimide; X = Br or Cl; PG = optional protecting group; $X_1$, $X_2$, $R_2$ and $R_3$ are as defined in formula (I)

Example 33: Synthesis of Compound 213

6-Carbamimidoyl-1-(4-carbamoylbenzyl)-3-chloro-N-(cyclohexylmethyl)-1H-indole-2-carboxamide

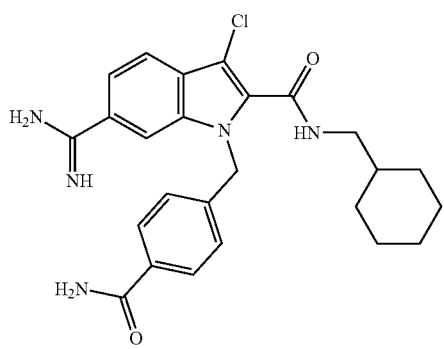

Step-1: Ethyl 3-chloro-6-cyano-1H-indole-2-carboxylate

Ethyl 6-cyano-1H-indole-2-carboxylate (1.25 g, 5.84 mmol) was dissolved in 125 mL of dimethylformamide and added N-chlorosuccinimide (932 mg, 7.0 mmol) at 0° C. in portions and stirred the mixture for 12 h at room temperature. Reaction mixture was quenched to cold water, extracted with ethylacetate, followed by washed with brine and dried over sodium sulphate. Solvent was evaporated under vacuum and resulted crude residue was purified by column chromatography using silica-gel as an adsorbent and eluted with hexane:ethylacetate (9:1) to afford 820 mg of the title compound. LCMS: 249.1 $(M+1)^+$.

Step-2: Ethyl 6-carbamimidoyl-1-(4-carbamoylbenzyl)-3-chloro-1H-indole-2-carboxylate The product of step-1 of example-33 (820 mg, 3.29 mmol) and 4-(bromomethyl)benzamide (704 mg, 3.29 mmol) were treated together to afford 1150 mg of the title compound following the procedure described in step-1 of example-1. LCMS: 399.1 $(M+1)^+$.

Step-3: 6-Carbamimidoyl-1-(4-carbamoylbenzyl)-3-chloro-1H-indole-2-carboxylic Acid The product of step-2 of example-33 (1150 mg, 2.88 mmol) and lithium hydroxide (138 mg, 5.76 mmol) were treated together to afford 735 mg of the title compound following the procedure described in step-2 of example-1. LCMS: 371.1 (M+1)$^+$.

Step-4: 1-(4-Carbamoylbenzyl)-3-chloro-6-cyano-N-(cyclohexylmethyl)-1H-indole-2-carboxamide The product of step-3 of example-33 (735 mg, 1.98 mmol) and cyclohexylmethanamine (223 mg, 1.98 mmol) were treated together to afford 630 mg of the title compound following the procedure described in step-3 of example-1. LCMS: 449.2 (M+1)$^+$.

Step-5: Ethyl 1-(4-carbamoylbenzyl)-3-chloro-2-((cyclohexylmethyl)carbamoyl)-1H-indole-6-carbimidate The product of step-4 of example-33 (630 mg, 1.4 mmol) was treated with 50 mL of ethanolic-HCl to afford 385 mg of the title compound following the procedure described in step-4 of example-1. LCMS: 495.2 (M+1)$^+$.

Step-6: 6-Carbamimidoyl-1-(4-carbamoylbenzyl)-3-chloro-N-(cyclohexylmethyl)-1H-indole-2-carboxamide The product of step-5 of example-33 (385 mg, 0.77 mmol) was treated with 50 mL of ethanolic-NH$_3$ to afford 75 mg of the title compound following the procedure described in step-5 of example-1. LCMS: 466.2 (M+1)$^+$, $^1$H NMR (300 MHz, DMSO-d$_6$): δ 0.84 (m, 2H), 1.07 (m, 3H), 1.56 (m, 6H), 3.05 (m, 2H), 5.75 (s, 2H), 7.12 (d, 2H), 7.36 (brs, 1H), 7.63 (d, 1H), 7.77 (m, 3H), 7.93 (brs, 1H), 8.26 (brs, 1H), 8.78 (m, 1H), 9.02 (brs, 2H), 9.29 (brs, 2H); HPLC: 98.64% (Retention Time=3.759 min).

The following compounds listed in table-8 were prepared according to Scheme-3 by following similar procedure as described above for example-33 using appropriate reagents with suitable modifications known to the one skilled in the art.

TABLE 8

| Cpd. ID. | R$_2$ | R$_5$ | R$_3$ | LCMS (M + 1)$^+$ | $^1$H NMR |
|---|---|---|---|---|---|
| I-214 | 4-methylcyclohexyl | Cl | 4-carbamoyl (4) | 466.2 | δ 0.85 (d, 3H), 1.26 (m, 6H), 1.65 (m, 2H), 1.75 (m, 1H), 3.52 (m, 1H), 5.75 (s, 2H), 7.21 (m, 2H), 7.37 (brs, 1H), 7.64 (m, 1H), 7.77 (m, 3H), 7.94 (brs, 1H), 8.26 (d, 1H), 8.65 (m, 1H), 9.03 (brs, 2H), 9.30 (brs, 2H); HPLC: 90.92% (Retention Time = 6.563 min). |
| I-236 | cyclohexylmethyl | Cl | phenyl (4) | 500.2 | δ 0.87 (m, 2H), 1.07 (m, 4H), 1.47 (m, 1H), 1.60 (m, 4H), 3.09 (m, 2H), 5.70 (s, 2H), 7.19 (d, 2H), 7.34 (m, 1H), 7.42 (m, 2H), 7.56 (m, 4H), 7.64 (d, 1H), 7.82 (d, 1H), 8.82 (m, 1H), 9.05 (brs, 2H), 9.32 (brs, 2H); HPLC: 95.15% (Retention Time = 7.397 min). |
| I-237 | 4-methylcyclohexylmethyl | Cl | phenyl (4) | 499.2 | δ 0.83 (m, 3H), 1.25 (m, 2H), 1.40 (m, 5H), 1.62 (m, 2H), 3.98 (m, 1H), 5.67 (s, 2H), 7.27 (d, 2H), 7.35 (m, 1H), 7.44 (m, 2H), 7.56 (m, 4H), 7.60 (d, 1H), 7.82 (m, 1H), 8.34 (d, 1H), 8.6 (m, 1H), 9.05 (brs, 2H), 9.32 (brs, 2H); HPLC: 87.94% (Retention Time = 4.346 min). |

TABLE 8-continued

| Cpd. ID. | R$_2$ | R$_5$ | R$_3$ | LCMS (M + 1)$^+$ | $^1$H NMR |
|---|---|---|---|---|---|
| I-250 | cyclohexyl-NH$_2$ | Br | phenoxy | 560.2 | δ 1.31 (m, 4H), 1.83 (m, 4H), 2.96 (m, 1H), 3.52 (m, 1H), 5.61 (s, 2H), 6.91 (d, 3H), 7.12 (m, 1H), 7.21 (d, 2H), 7.36 (m, 2H), 7.65 (d, 1H), 7.75 (m, 2H), 8.35 (brs, 2H), 8.37 (brs, 1H), 8.71 (d, 1H), 9.18 (brs, 2H), 9.35 (brs, 2H); HPLC: 98.88% (Retention Time = 4.847 min). |
| I-251 | cyclohexyl-NH$_2$ | Cl | phenoxy | 516.2 | δ 1.31 (m, 4H), 1.83 (m, 4H), 2.96 (m, 1H), 3.52 (m, 1H), 5.63 (s, 2H), 6.91 (d, 4H), 7.12 (m, 1H), 7.21 (d, 2H), 7.36 (m, 2H), 7.65 (d, 1H), 7.81 (m, 4H), 8.41 (brs, 1H), 8.85 (d, 1H), 9.18 (brs, 2H), 9.35 (brs, 2H); HPLC: 97.1% (Retention Time = 5.37 min). |

Example 34: Synthesis of Compound I-215

6-Carbamimidoyl-N-(cyclohexylmethyl)-1-(4-(methylcarbamoyl)benzyl)-1H-indole-2-carboxamide

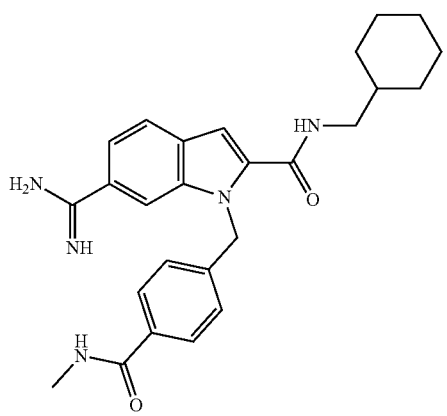 [SMILES: CNC(=O)c1ccc(Cn2c(C(=O)NCC3CCCCC3)cc3ccc(C(=N)N)cc32)cc1]

Step-1: Methyl 4-((6-cyano-2-((cyclohexylmethyl)carbamoyl)-1H-indol-1-yl)methyl)benzoate The product of step-1 of example-18 (950 mg, 3.36 mmol) and methyl 4-(bromomethyl)benzoate (771 mg, 3.36 mmol) were treated together to afford 1.16 g of the title compound following the procedure described in step-1 of example-1. LCMS: 430.2 (M+1)$^+$.

Step-2: 4-((6-Cyano-2-((cyclohexylmethyl)carbamoyl)-1H-indol-1-yl)methyl)benzoic Acid The product of step-1 of example-34 (1.16 g, 2.7 mmol) and lithium hydroxide (130 mg, 5.41 mmol) were treated together to afford 835 mg of the title compound following the procedure described in step-2 of example-1. LCMS: 417.2 (M+1)$^+$.

Step-3: 6-Cyano-N-(cyclohexylmethyl)-1-(4-(methylcarbamoyl)benzyl)-1H-indole-2-carboxamide The product of step-2 of example-34 (830 mg, 1.99 mmol) and methanamine (62 mg, 1.99 mmol) were treated together to afford 445 mg of the title compound following the procedure described in step-3 of example-1. LCMS: 429.2 (M+1)$^+$.

Step-4: Ethyl 2-((cyclohexylmethyl)carbamoyl)-1-(4-(methylcarbamoyl)benzyl)-1H-indole-6-carbimidate The product of step-3 of example-34 (445 mg, 1.03 mmol) was treated with 50 mL of ethanolic-HCl to afford 265 mg of the title compound following the procedure described in step-4 of example-1. LCMS: 475.3 (M+1)$^+$.

Step-5: 6-Carbamimidoyl-N-(cyclohexylmethyl)-1-(4-(methylcarbamoyl)benzyl)-1H-indole-2-carboxamide The product of step-4 of example-34 (265 mg, 0.55 mmol) was treated with 30 mL of ethanolic-NH₃ to afford 80 mg of the title compound following the procedure described in step-5 of example-1. LCMS: 446.2 (M+1)⁺, ¹H NMR (300 MHz, DMSO-$d_6$): δ 0.84 (m, 2H), 1.09 (m, 3H), 1.58 (m, 6H), 2.73 (d, 3H), 3.03 (m, 2H), 5.91 (s, 2H), 7.06 (d, 2H), 7.24 (brs, 1H), 7.53 (d, 1H), 7.69 (d, 2H), 7.90 (d, 1H), 8.18 (brs, 1H), 8.33 (m, 1H), 8.72 (m, 1H), 8.90 (brs, 2H), 9.22 (brs, 2H); HPLC: 91.68% (Retention Time=3.622 min).

Example 35: Synthesis of Compound I-216

6-Carbamimidoyl-N-(cyclohexylmethyl)-1-(4-(dimethylcarbamoyl)benzyl)-1H-indole-2-carboxamide

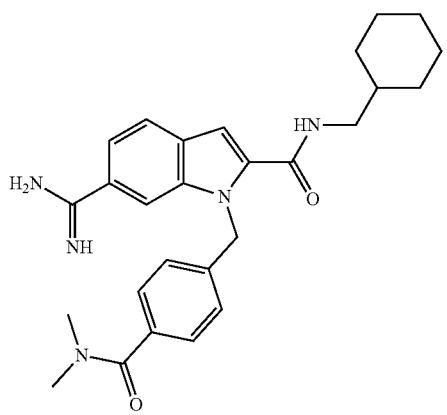 [SMILES: CN(C)C(=O)c1ccc(Cn2c(C(=O)NCC3CCCCC3)cc3ccc(C(=N)N)cc32)cc1]

This compound was prepared by reacting the product of step-2 of example-34 with dimethylamine by following a similar procedure described in step-3 to step-5 of example-34. LCMS: 460.2 (M+1)⁺, ¹H NMR (300 MHz, DMSO-$d_6$): δ 0.84 (m, 2H), 1.11 (m, 3H), 1.61 (m, 6H), 2.85 (s, 3H), 2.93 (s, 3H), 3.05 (m, 2H), 5.90 (s, 2H), 7.06 (d, 2H), 7.25 (m, 3H), 7.55 (d, 1H), 8.19 (s, 1H), 8.72 (m, 1H), 8.87 (brs, 1H), 9.23 (brs, 2H); HPLC: 91.37% (Retention Time=3.758 min).

Example 36: Synthesis of Compound I-217

6-Carbamimidoyl-N-(cyclohexylmethyl)-1-(4-(cyclopropylcarbamoyl)benzyl)-1H-indole-2-carboxamide

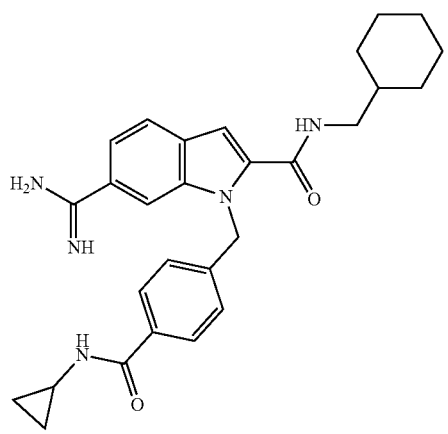 [SMILES: N=C(N)c1ccc2cc(C(=O)NCC3CCCCC3)n(Cc3ccc(C(=O)NC4CC4)cc3)c2c1]

This compound was prepared by reacting the product of step-2 of example-34 with cyclopropylamine by following a similar procedure described in step-3 to step-5 of example-34. LCMS: 472.3 (M+1)⁺, ¹H NMR (300 MHz, DMSO-$d_6$): δ 0.49 (m, 2H), 0.64 (m, 2H), 0.84 (m, 2H), 1.11 (m, 3H), 1.61 (m, 6H), 2.75 (m, 1H), 3.03 (m, 2H), 5.90 (s, 2H), 7.05 (d, 2H), 7.24 (s, 1H), 7.53 (d, 1H), 7.68 (d, 1H), 7.90 (d, 1H), 8.17 (brs, 1H), 8.34 (m, 1H), 8.71 (m, 1H), 8.88 (brs, 2H), 9.22 (brs, 2H); HPLC: 95.16% (Retention Time=3.363 min).

Example 37: Synthesis of Compound I-218

6-Carbamimidoyl-1-(4-(dimethylcarbamoyl)benzyl)-N-(4-methylcyclohexyl)-1H-indole-2-carboxamide

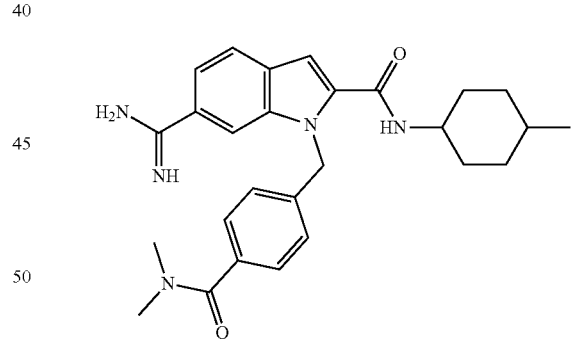

Step-1: 6-Cyano-N-(4-methylcyclohexyl)-1H-indole-2-carboxamide

The product of step-1 of example-6 (850 mg, 4.54 mmol) and 4-methylcyclohexanamine (513 mg, 4.54 mmol) were treated together to afford 530 mg of the title compound following the procedure described in step-3 of example 1. LCMS: 282.2 (M+1)⁺.

Step-2: Methyl 4-((6-cyano-2-((4-methylcyclohexyl)carbamoyl)-1H-indol-1-yl)methyl)benzoate The product of step-1 of example-37 (530 mg, 1.87 mmol) and methyl 4-(bromomethyl)benzoate (430 mg, 1.87 mmol) were treated together to afford 565 mg of the title compound following the procedure described in step-1 of example-1. LCMS: 430.2 (M+1)⁺.

Step-3: 4-((6-Cyano-2-((4-methylcyclohexyl)carbamoyl)-1H-indol-1-yl)methyl)benzoic Acid The product of step-2 of example 37 (550 mg, 1.27 mmol) and lithium hydroxide (60 mg, 2.54 mmol) were treated together to afford 410 mg of the title compound following the procedure described in step-2 of example-1. LCMS: 416.2 (M+1)⁺.

Step-4: 6-Cyano-1-(4-(dimethylcarbamoyl)benzyl)-N-(4-methylcyclohexyl)-1H-indole-2-carboxamide The product of step-3 of example 37 (410 mg, 0.98 mmol) and dimethylamine (45 mg, 0.98 mmol) were treated together to afford 270 mg of the title compound following the procedure described in step-3 of example-1. LCMS: 443.2 (M+1)⁺.

Step-5: Ethyl 1-(4-(dimethylcarbamoyl)benzyl)-2-((4-methylcyclohexyl)carbamoyl)-1H-indole-6-carbimidate The product of step-4 of example 37 (270 mg, 0.6 mmol) was treated with 50 mL of ethanolic-HCl to afford 160 mg of the title compound following the procedure described in step-4 of example-1. LCMS: 489.3 (M+1)⁺.

Step-6: 6-Carbamimidoyl-1-(4-(dimethylcarbamoyl)benzyl)-N-(4-methylcyclohexyl)-1H-indole-2-carboxamide The product of step-5 of example 37 (160 mg, 0.32 mmol) was treated with 30 mL of ethanolic-NH₃ to afford 35 mg of the title compound following the procedure described in step-5 of example-1. LCMS: 460.3 (M+1)⁺, ¹H NMR (300 MHz, DMSO-d₆): δ 0.85 (d, 3H), 1.34 (m, 6H), 1.60 (m, 4H), 2.84 (s, 3H), 2.93 (s, 3H), 3.85 (m, 1H), 5.87 (d, 2H), 7.08 (m, 2H), 7.24 (m, 1H), 7.53 (m, 1H), 7.88 (m, 1H), 8.21 (d, 1H), 8.43 (d, 1H), 8.99 (brs, 2H), 9.24 (brs, 2H); HPLC: 93.97% (Retention Time=6.536 min).

Example 38: Synthesis of Compound I-219

6-Carbamimidoyl-1-(4-(cyclopropylcarbamoyl)benzyl)-N-(4-methylcyclohexyl)-1H-indole-2-carboxamide

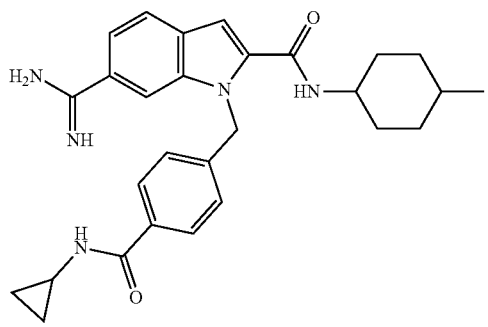 [SMILES: CC1CCC(NC(=O)c2cc3ccc(C(=N)N)cc3n2Cc2ccc(C(=O)NC3CC3)cc2)CC1]

This compound was prepared by reacting the product of step-3 of example-37 with cyclopropylamine by following a similar procedure described in step-4 to step-6 of example-37. LCMS: 472.3 (M+1)⁺, ¹H NMR (300 MHz, DMSO-d₆): δ 0.50 (m, 2H), 0.63 (m, 2H), 0.88 (m, 3H), 1.34 (m, 3H), 1.49 (m, 3H), 1.62 (m, 3H), 2.78 (m, 1H), 3.81 (m, 1H), 5.87 (s, 2H), 7.15 (d, 2H), 7.23 (d, 1H), 7.51 (d, 1H), 7.67 (d, 2H), 7.84 (m, 1H), 8.14 (m, 1H), 8.33 (d, 1H), 8.42 (d, 1H); HPLC: 88.81% (Retention Time=6.469 min).

Example 39: Synthesis of Compound I-220

6-Carbamimidoyl-1-(4-(methylcarbamoyl)benzyl)-N-(4-methylcyclohexyl)-1H-indole-2-carboxamide

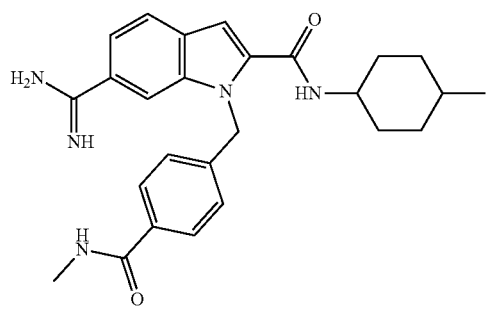 [SMILES: CNC(=O)c1ccc(Cn2c(C(=O)NC3CCC(C)CC3)cc3ccc(C(=N)N)cc32)cc1]

This compound was prepared by reacting the product of step-3 of example-37 with methylamine by following a similar procedure described in step-4 to step-6 of example-37. LCMS: 446.3 (M+1)⁺, ¹H NMR (300 MHz, DMSO-d₆): δ 0.86 (d, 3H), 1.32 (m, 3H), 1.46 (m, 3H), 1.62 (m, 3H), 2.73 (d, 3H), 3.3.78 (m, 1H), 5.88 (d, 2H), 7.12 (d, 2H), 7.25 (d, 1H), 7.53 (d, 1H), 7.70 (d, 2H), 7.88 (m, 1H), 8.16 (m, 1H), 8.34 (m, 1H), 8.44 (d, 1H), 8.91 (brs, 2H), 9.22 (brs, 2H); HPLC: 89.03% (Retention Time=6.274 min).

Example 40: Synthesis of Compound I-221

6-Carbamimidoyl-1-(4-(ethylcarbamoyl)benzyl)-N-(4-methylcyclohexyl)-1H-indole-2-carboxamide

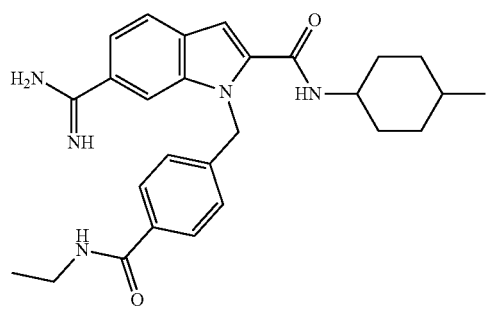 [SMILES: CCNC(=O)c1ccc(Cn2c(C(=O)NC3CCC(C)CC3)cc3ccc(C(=N)N)cc32)cc1]

This compound was prepared by reacting the product of step-3 of example-37 with ethylamine by following a similar procedure described in step-4 to step-6 of example-37. LCMS: 460.3 (M+1)⁺, ¹H NMR (300 MHz, DMSO-d₆): δ 0.90 (d, 3H), 1.05 (m, 3H), 1.34 (m, 6H), 1.61 (m, 3H), 3.23 (m, 2H), 3.85 (m, 1H), 5.87 (s, 2H), 7.12 (d, 2H), 7.26 (s, 1H), 7.53 (d, 1H), 7.70 (d, 2H), 7.89 (m, 1H), 8.17 (s, 1H), 8.37 (m, 1H), 8.44 (d, 1H), 8.92 (brs, 2H); HPLC: 97.38% (Retention Time=3.915 min).

Example 41: Synthesis of Compound I-222

6-Carbamimidoyl-N-(cyclohexylmethyl)-1-(4-((2-hydroxyethyl)carbamoyl)benzyl)-1H-indole-2-carboxamide

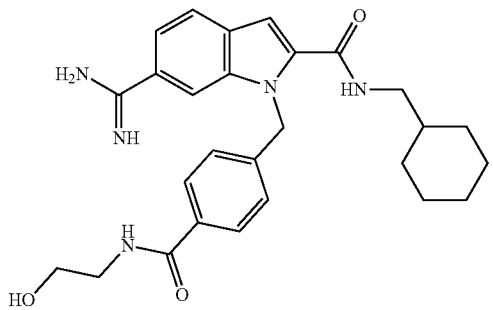 [SMILES: N=C(N)c1ccc2cc(C(=O)NCC3CCCCC3)n(Cc3ccc(C(=O)NCCO)cc3)c2c1]

This compound was prepared by reacting the product of step-2 of example-34 with 2-((2-methoxyethoxy)methoxy) ethanamine by following a similar procedure described in step-3 to step-5 of example-34. LCMS: 476.3 (M+1)$^+$, $^1$H NMR (300 MHz, DMSO-d$_6$): δ 0.82 (m, 2H), 1.09 (m, 3H), 1.61 (m, 6H), 3.03 (m, 2H), 3.25 (m, 2H), 3.43 (m, 2H), 5.91 (s, 2H), 7.06 (d, 2H), 7.24 (s, 1H), 7.53 (d, 1H), 7.72 (d, 2H), 7.90 (d, 1H), 8.17 (brs, 1H), 8.36 (m, 1H), 8.72 (m, 1H), 8.86 (brs, 2H), 9.22 (brs, 2H); HPLC: 91.88% (Retention Time=6.012 min).

Example 42: Synthesis of Compound I-223

6-Carbamimidoyl-1-(4-((2-hydroxyethyl)carbamoyl) benzyl)-N-(4-methylcyclohexyl)-1H-indole-2-carboxamide

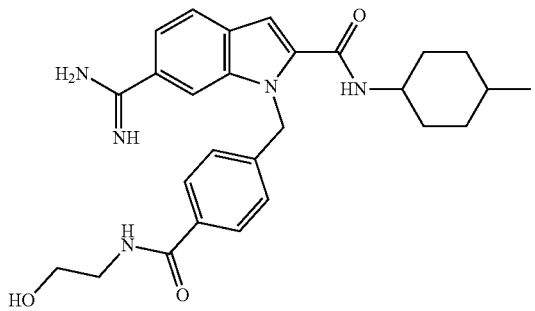 [SMILES: CC1CCC(NC(=O)c2cc3ccc(C(=N)N)cc3n2Cc2ccc(C(=O)NCCO)cc2)CC1]

This compound was prepared by reacting the product of step-3 of example-37 with 2-((2-methoxyethoxy)methoxy) ethanamine by following a similar procedure described in step-4 to step-6 of example-39. LCMS: 476.3 (M+1)$^+$, $^1$H NMR (300 MHz, DMSO-d$_6$): δ 0.90 (m, 3H), 1.37 (m, 2H), 1.46 (m, 4H), 1.63 (m, 3H), 3.25 (m, 2H), 3.44 (m, 2H), 3.91 (m, 1H), 5.90 (s, 2H), 7.14 (d, 2H), 7.27 (d, 1H), 7.74 (d, 2H), 7.89 (d, 1H), 8.24 (brs, 1H), 8.39 (m, 1H), 8.47 (d, 1H), 8.98 (brs, 2H), 9.30 (brs, 2H); HPLC: 96.87% (Retention Time=6.14 min).

Example 43: Synthesis of Compound I-224

1-(4-((2-Aminoethyl)carbamoyl)benzyl)-6-carbamimidoyl-N-(4-methylcyclohexyl)-1H-indole-2-carboxamide

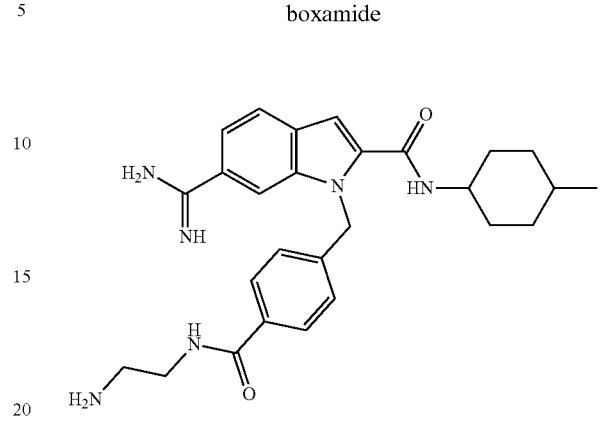

This compound was prepared by reacting the product of step-3 of example-37 with tert-butyl (2-aminoethyl)carbamate by following a similar procedure described in step-4 to step-6 of example-37. LCMS: 475.3 (M+1)$^+$, $^1$H NMR (300 MHz, DMSO-d$_6$): δ 0.91 (m, 3H), 1.34 (m, 2H), 1.47 (m, 4H), 1.63 (m, 3H), 2.93 (m, 2H), 3.35 (m, 2H), 3.88 (m, 1H), 5.89 (s, 2H), 7.16 (d, 2H), 7.28 (d, 1H), 7.54 (d, 2H), 7.74 (m, 3H), 7.90 (m, 1H), 8.15 (s, 1H), 8.45 (m, 1H), 8.54 (m, 1H), 8.97 (s, 2H), 9.23 (brs, 2H); HPLC: 92.46% (Retention Time=5.517 min).

Example 44: Synthesis of Compound I-225

1-(4-((2-Aminoethyl)carbamoyl)benzyl)-6-carbamimidoyl-N-(cyclohexylmethyl)-1H-indole-2-carboxamide

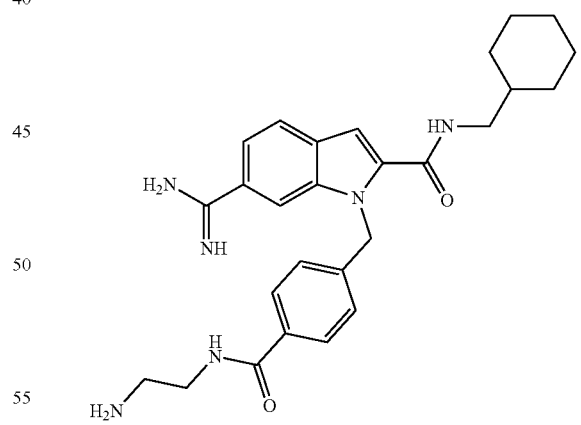

This compound was prepared by reacting the product of step-2 of example-34 with tert-butyl (2-aminoethyl)carbamate by following a similar procedure described in step-3 to step-5 of example-34. LCMS: 475.3 (M+1)$^+$, $^1$H NMR (300 MHz, DMSO-d$_6$): δ 0.83 (m, 2H), 1.07 (m, 4H), 1.47 (m, 1H), 1.60 (m, 4H), 2.94 (m, 2H), 3.05 (m, 2H), 3.34 (m, 2H), 5.92 (s, 2H), 7.11 (d, 2H), 7.27 (s, 1H), 7.54 (d, 2H), 7.73 (m, 3H), 7.90 (m, 1H), 8.16 (s, 1H), 8.56 (m, 1H), 8.74 (m, 1H), 9.03 (brs, 2H), 9.23 (brs, 2H); HPLC: 95.19% (Retention Time=5.421 min).

Example 45: Synthesis of Compound I-232

6-Carbamimidoyl-1-(4-carbamoylbenzyl)-N-(cyclohexylmethyl)-N-methyl-1H-indole-2-carboxamide

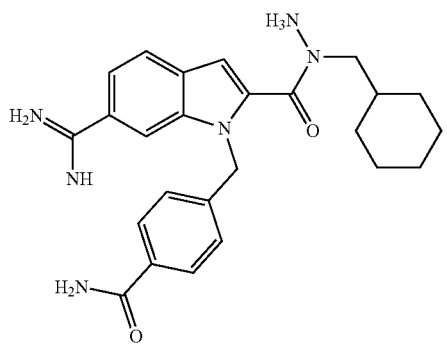 [SMILES: N=C(N)c1ccc2cc(C(=O)N(N)CC3CCCCC3)n(Cc3ccc(C(N)=O)cc3)c2c1]

Step-1: 1-(4-Carbamoylbenzyl)-6-cyano-N-(cyclohexylmethyl)-N-methyl-1H-indole-2-carboxamide The product of step-2 of example 19 (500 mg, 1.56 mmol) and 1-cyclohexyl-N-methylmethanamine (198 mg, 1.56 mmol) were treated together to afford 395 mg of the title compound following the procedure described in step-3 of example 1. LCMS: 429.2 (M+1)$^+$.

Step-2: 1-(4-Carbamoylbenzyl)-N-(cyclohexylmethyl)-6-(N'-hydroxycarbamimidoyl)-N-methyl-1H-indole-2-carboxamide The product of step-1 of example 50 (380 mg, 0.88 mmol) and aqueous hydroxylamine (1.7 mL) were treated together to afford 300 mg of the title compound following the procedure described in step-4 of example 14. LCMS: 462.2 (M+1)$^+$.

Step-3: 6-(N'-Acetoxycarbamimidoyl)-1-(4-carbamoylbenzyl)-N-(cyclohexylmethyl)-N-methyl-1H-indole-2-carboxamide The product of step-2 of example 50 (250 mg, 0.54 mmol) and acetic anhydride (260 mg, 2.54 mmol) were treated together to afford 180 mg of the title compound following the procedure described in step-5 of example 14. LCMS: 504.2 (M+1)$^+$.

Step-4: 6-Carbamimidoyl-1-(4-carbamoylbenzyl)-N-(cyclohexylmethyl)-N-methyl-1H-indole-2-carboxamide The product of step-3 of example 50 (160 mg, 0.31 mmol) and zinc (80 mg, 1.24 mmol) were treated together to afford 65 mg of the title compound following the procedure described in step-6 of example 14. LCMS: 446.2 (M+1)$^+$, $^1$H NMR (300 MHz, DMSO-d$_6$): δ 0.76 (m, 2H), 1.08 (m, 3H), 1.38 (m, 1H), 1.48 (m, 6H), 2.90 (s, 3H), 3.23 (d, 2H), 5.65 (d, 2H), 6.99 (s, 1H), 7.04 (d, 1H), 7.35 (brs, 1H), 7.56 (d, 1H), 7.79 (d, 2H), 7.86 (d, 1H), 7.92 (brs, 1H), 8.23 (d, 1H), 9.05 (brs, 2H), 9.24 (brs, 2H); HPLC: 96.43% (Retention Time=3.663 min).

Example 46: Synthesis of Compound I-226

6-Carbamimidoyl-1-(4-carbamoyl-phenethyl)-N-(cyclohexylmethyl)-1H-indole-2-carboxamide

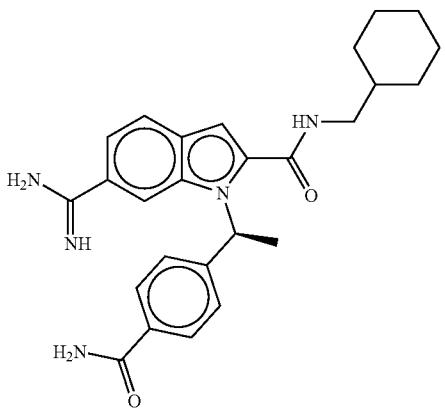

The synthesis of compound in Example I-226 was accomplished following similar procedures to example 45 using Steps 1 to Step 4 where N-methyl cyclohexylmethyl amine was replaced with cylohexyl methyl amine and Example 19 step 1. LCMS: 446.2 (M+1)$^+$ $^1$H NMR (300 MHz, DMSO-d$_6$): δ 0.85 (m, 2H), 1.17 (m, 4H), 1.51 (m, 1H), 1.63 (m, 4H), 2.03 (m, 3H), 3.06 (m, 2H), 3.15 (m, 1H), 6.33 (m, 1H), 7.09 (s, 1H), 7.27 (d, 1H), 7.41 (m, 2H), 7.56 (brs, 1H), 7.78 (m, 3H); HPLC: 84.28% (Retention Time=6.495 min).

Example 47: Synthesis of Compound I-227

6-Carbamimidoyl-1-(2-Fluoro-4-carbamoyl-benzyl)-N-(cyclohexylmethyl)-1H-indole-2-carboxamide

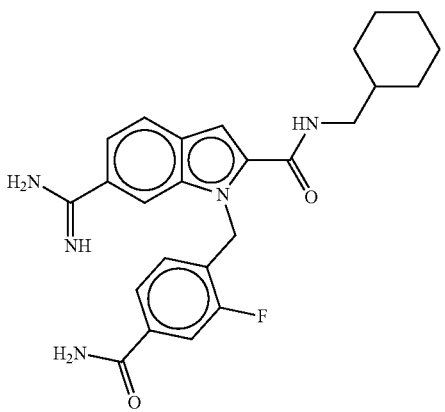

The synthesis of compound in Example I-227 was accomplished following similar procedures to example 45 using Steps 1 to Step 4 where N-methyl cyclohexylmethyl amine was replaced with cylohexyl methyl amine and Example 19 step 1. LCMS: 450.2 (M+1)$^+$ $^1$H NMR (300 MHz, DMSO-d$_6$): δ 0.82 (m, 2H), 1.08 (m, 3H), 1.47 (m, 1H), 1.60 (m, 5H), 3.01 (m, 2H), 5.96 (s, 2H), 6.46 (m, 1H), 7.28 (s, 1H), 7.48 (m, 3H), 7.67 (d, 1H), 7.89 (d, 1H), 7.99 (brs, 1H), 8.16 (s, 1H), 8.72 (m, 1H); HPLC: 98.05% (Retention Time=3.057 min).

Example 48: Synthesis of Compound I-228

6-Carbamimidoyl-1-(2-Chloro-4-carbamoyl-benzyl)-N-(cyclohexylmethyl)-1H-indole-2-carboxamide

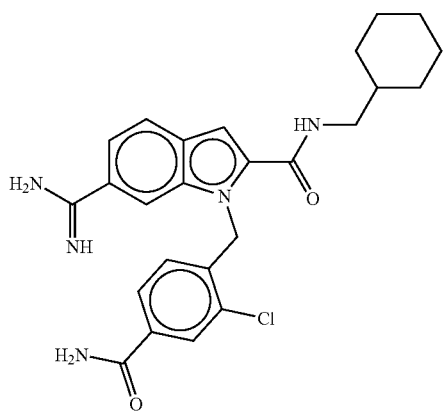

The synthesis of compound in Example I-228 was accomplished following similar procedures to example 45 using Steps 1 to Step 4 where N-methyl cyclohexylmethyl amine was replaced with cylohexyl methyl amine and Example 19 step 1 using the corresponding 2 chloro derivative. LCMS: 466.2 (M+1)+ $^1$H NMR (300 MHz, DMSO-$d_6$): δ 0.76 (m, 2H), 1.05 (m, 3H), 1.40 (m, 1H), 1.52 (m, 5H), 2.98 (m, 2H), 5.97 (s, 2H), 6.08 (d, 1H), 6.37 (s, 1H), 7.48 (brs, 1H), 7.58 (m, 2H), 7.95 (m, 2H), 8.03 (brs, 1H), 8.14 (brs, 1H), 8.77 (m, 1H), 9.11 (brs, 2H), 9.24 (brs, 2H); HPLC: 97.51% (Retention Time=6.278 min).

Example 49: Synthesis of Compound I-229

6-Carbamimidoyl-1-(3-Chloro-4-carbamoyl-benzyl)-N-(cyclohexylmethyl)-1H-indole-2-carboxamide

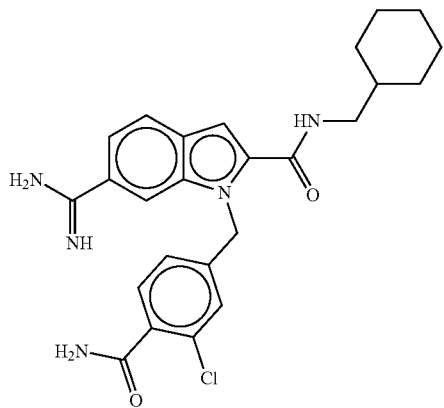

The synthesis of compound in Example I-229 was accomplished following similar procedures to example 45 using Steps 1 to Step 4 where N-methyl cyclohexylmethyl amine was replaced with cylohexyl methyl amine and Example 19 step 1 using the corresponding 3 chloro derivative. LCMS: 466.2 (M+1)+ $^1$H NMR (300 MHz, DMSO-$d_6$): δ δ 0.88 (m, 2H), 1.10 (m, 3H), 1.52 (m, 1H), 1.61 (m, 5H), 3.07 (m, 2H), 5.88 (s, 2H), 7.06 (d, 1H), 7.16 (s, 1H), 7.27 (m, 2H), 7.53 (m, 2H), 7.78 (brs, 1H), 7.86 (d, 1H), 8.15 (brs, 1H), 8.77 (m, 1H); HPLC: 94.47% (Retention Time=2.907 min).

Example 50: Synthesis of Compound I-230

6-Carbamimidoyl-1-(3-carbamoylbenzyl)-N-(4-difluorocyclohexyl)-1H-indole-2-carboxamide

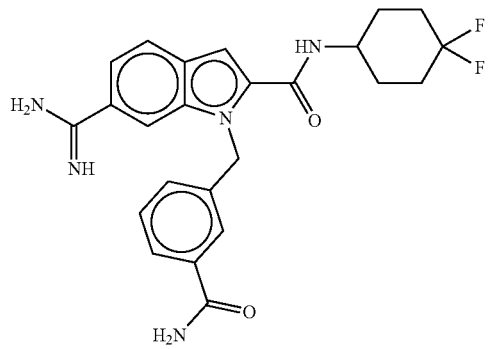

The synthesis of compound in Example I-230 was accomplished following similar procedures to example 45 using Steps 1 to Step 4 where N-methyl cyclohexylmethyl amine was replaced with 4,difluorocyclohexyl amine and Example 19 step 1 using the corresponding 3 carbamoyl derivative LCMS: 454.2 (M+1)+1.56 (m, 2H), 1.80 (m, 3H), 1.95 (m, 3H), 3.59 (m, 1H), 5.90 (s, 2H), 7.08 (s, 1H), 7.19 (m, 2H), 7.26 (s, 1H), 7.30 (m, 2H), 7.55 (d, 1H), 7.65 (s, 1H), 7.70 (d, 1H), 7.89 (m, 1H), 8.30 (brs, 1H), 8.66 (d, 1H), 8.99 (brs, 2H), 9.33 (brs, 2H); HPLC: 95.37% (Retention Time=3.356 min).

Example 51: Synthesis of Compound I-241

6-Carbamimidoyl-N-((1r,4r)-4-guanidinocyclohexyl)-1-(4-phenoxybenzyl)-1H-indole-2-carboxamide

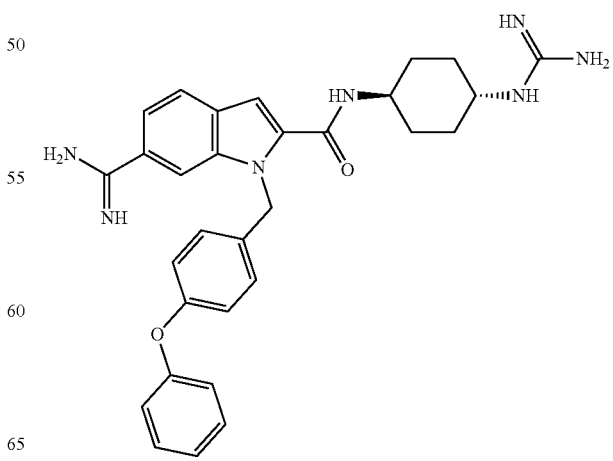

Step-1: Ethyl 6-cyano-1-(4-phenoxybenzyl)-1H-indole-2-carboxylate

Ethyl 6-cyano-1H-indole-2-carboxylate (3.2 g, 14.95 mmol) and 1-(bromomethyl)-4-phenoxybenzene (3.93 g, 14.95 mmol) were treated together to afford 4.65 g of the title compound following the procedure described in step-1 of example-1. LCMS: 397.2 (M+1)⁺.

Step-2: 6-Cyano-1-((4'-ethoxy-[1,1'-biphenyl]-3-yl)methyl)-1H-indole-2-carboxylic Acid The product of step-1 of example-51 (4.5 g, 11.33 mmol) and lithium hydroxide (544 mg, 22.67 mmol) were treated together to afford 3.28 g of the title compound following the procedure described in step-2 of example-1. LCMS: 367.2 (M+1)⁺.

Step-3: tert-Butyl ((1r,4r)-4-(6-cyano-1-(4-phenoxybenzyl)-1H-indole-2-carboxamido) cyclohexyl)carbamate The product of step-2 of example-51 (650 mg, 1.77 mmol) and tert-butyl ((1r,4r)-4-aminocyclohexyl)carbamate (378 mg, 1.77 mmol) were treated together to afford 485 mg of the title compound following the procedure described in step-3 of example-1. LCMS: 565.3 (M+1)⁺.

Step-4: N-((1r,4r)-4-Aminocyclohexyl)-6-cyano-1-(4-phenoxybenzyl)-1H-indole-2-carboxamide The product of step-3 of example-51 (840 mg, 1.48 mmol) was treated with 50 mL of ethanolic-HCl to afford 645 mg of the title compound following the procedure described in step-2 of example-2. LCMS: 465.2 (M+1)⁺.

Step-5: 6-Cyano-N-((1r,4r)-4-guanidinocyclohexyl)-1-(4-phenoxybenzyl)-1H-indole-2-carboxamide The product of step-4 of example-51 (640 mg, 1.37 mmol), dissolved in 10 mL of N,N-dimethylformamide, was treated with 1H-pyrazole-1-carboxamidine hydrochloride (405 mg, 2.76 mmol) and N,N-diisopropylethylamine (535 mg, 4.11 mmol) to afford 320 mg of the title compound following the procedure described in step-2 of example-3. LCMS: 507.3 (M+1)⁺.

Step-6: Ethyl 2-(((1r,4r)-4-guanidinocyclohexyl)carbamoyl)-1-(4-phenoxybenzyl)-1H-indole-6-carbimidate The product of step-5 of example-51 (320 mg, 0.63 mmol) was treated with 50 mL of ethanolic-HCl to afford 175 mg of the title compound following the procedure described in step-4 of example-1. LCMS: 553.3 (M+1)⁺.

Step-7: 6-Carbamimidoyl-N-((1r,4r)-4-guanidinocyclohexyl)-1-(4-phenoxybenzyl)-1H-indole-2-carboxamide The product of step-6 of example-51 (150 mg, 0.28 mmol) was treated with 30 mL of ethanolic-NH₃ to afford 80 mg of the title compound following the procedure described in step-5 of example-1. LCMS: 524.3 (M+1)⁺, ¹H NMR (300 MHz, DMSO-d₆): δ 1.32 (m, 4H), 1.82 (m, 4H), 2.45 (m, 2H), 3.71 (m, 2H), 5.82 (s, 2H), 6.88 (m, 4H), 7.12 (m, 3H), 7.22 (brs, 1H), 7.33 (m, 2H), 7.53 (m, 2H), 7.88 (d, 1H), 8.31 (s, 1H), 8.65 (d, 1H), 9.12 (brs, 2H), 9.32 (brs, 2H).

Example 52: Synthesis of Compound I-242

N-((1r,4r)-4-(3-Aminopropanamido)cyclohexyl)-6-carbamimidoyl-1-(4-phenoxybenzyl)-1H-indole-2-carboxamide

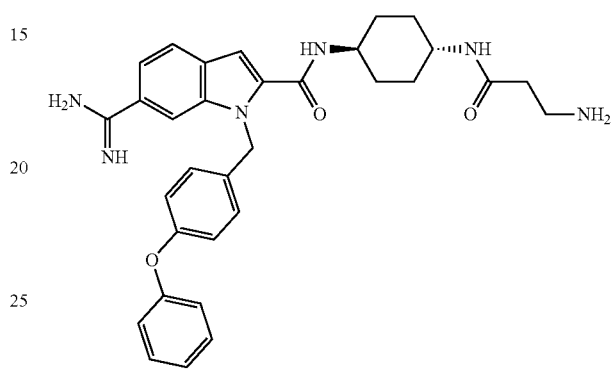

Step-1: tert-Butyl (3-(((1r,4r)-4-(6-cyano-1-(4-phenoxybenzyl)-1H-indole-2-carboxamido)-cyclohexyl)-amino)-3-oxopropyl)carbamate The product of step-4 example 51 (730 mg, 1.56 mmol) and 3-((tert-butoxycarbonyl)amino)propanoic acid (296 mg, 1.56 mmol) were treated together to afford 425 mg of the title compound following the procedure described in step-3 of example-1. LCMS: 636.3 (M+1)⁺.

Step-2: Ethyl 2-(((1r,4r)-4-(3-aminopropanamido)cyclohexyl)carbamoyl)-1-(4-phenoxybenzyl)-1H-indole-6-carbimidate The product of step-1 of example 52 (425 mg, 0.66 mmol) was treated with 50 mL of ethanolic-HCl to afford 195 mg of the title compound following the procedure described in step-4 of example 1. LCMS: 582.3 (M+1)⁺.

Step-3: N-((1r,4r)-4-(3-Aminopropanamido)cyclohexyl)-6-carbamimidoyl-1-(4-phenoxybenzyl)-1H-indole-2-carboxamide The product of step-2 of example 52 (195 mg, 0.33 mmol) was treated with 30 mL of ethanolic-NH₃ to afford 62 mg of the title compound following the procedure described in step-5 of example 1. LCMS: 553.3 (M+1)⁺, ¹H NMR (300 MHz, DMSO-d₆): δ 1.32 (m, 4H), 1.82 (m, 4H), 2.45 (m, 2H), 2.95 (m, 2H), 3.71 (m, 2H), 5.82 (s, 2H), 6.88 (m, 3H), 7.12 (m, 3H), 7.22 (m, 2H), 7.33 (m, 2H), 7.53 (d, 1H), 7.81 (m, 3H), 8.21 (d, 1H), 8.28 (d, 1H), 9.12 (brs, 2H), 9.32 (brs, 2H); HPLC: 93.49% (Retention Time=7.133 min).

Example 53: Synthesis of Compound I-252

3-amino-N-((1r,4r)-4-aminocyclohexyl)-6-carbamimidoyl-1-(4-phenoxybenzyl)-1H-indole-2-carboxamide

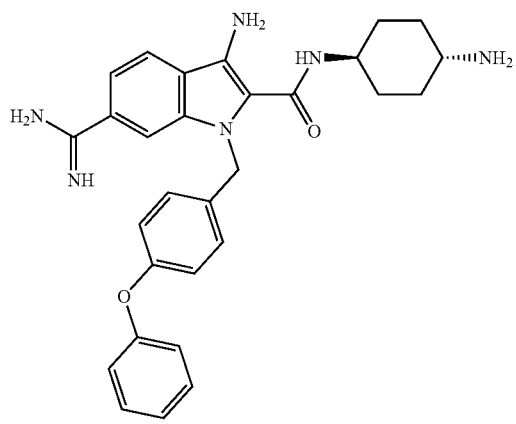 [SMILES: N=C(N)c1ccc2c(N)c(C(=O)N[C@H]3CC[C@H](N)CC3)n(Cc3ccc(Oc4ccccc4)cc3)c2c1]

Step-1: tert-Butyl ((1r,4r)-4-(6-cyano-3-nitro-1-(4-phenoxybenzyl)-1H-indole-2-carboxamido)-cyclohexyl)carbamate The product of step-1 of example-9 (980 mg, 2.29 mmol) and 1-(bromomethyl)-4-phenoxybenzene (605 mg, 2.29 mmol) were treated together to afford 760 mg of the title compound following the procedure described in step-1 of example-1. LCMS: 610.3 (M+1)$^+$.

Step-2: tert-Butyl ((1r,4r)-4-(3-amino-6-cyano-1-(4-phenoxybenzyl)-1H-indole-2-carboxamido)-cyclohexyl)carbamate The product of step-1 of example-53 (750 mg, 1.22 mmol) and zinc (160 mg, 2.45 mmol) were treated together to afford 430 mg of the title compound following the procedure described in step-3 of example-9. LCMS: 580.3 (M+1)$^+$.

Step-3: Ethyl 3-amino-2-(((1r,4r)-4-aminocyclohexyl)carbamoyl)-1-(4-phenoxybenzyl)-1H-indole-6-carbimidate The product of step-2 of example-53 (430 mg, 0.74 mmol) was treated with 50 mL of ethanolic-HCl to afford 155 mg of the title compound following the procedure described in step-4 of example-1. LCMS: 526.3 (M+1)$^+$.

Step-4: 3-Amino-N-((1r,4r)-4-aminocyclohexyl)-6-carbamimidoyl-1-(4-phenoxybenzyl)-1H-indole-2-carboxamide The product of step-3 of example-53 (155 mg, 0.29 mmol) was treated with 30 mL of ethanolic-NH$_3$ to afford 15 mg of the title compound following the procedure described in step-5 of example-1. LCMS: 497.3 (M+1)$^+$, $^1$H NMR (300 MHz, DMSO-d$_6$): δ 1.31 (m, 4H), 1.83 (m, 4H), 2.95 (m, 1H), 3.71 (m, 1H), 5.63 (s, 2H), 6.85 (d, 4H), 7.12 (m, 1H), 7.21 (d, 2H), 7.36 (m, 3H), 7.81 (m, 3H), 7.94 (d, 1H), 8.13 (d, 1H), 8.18 (brs, 1H), 9.10 (brs, 2H), 9.21 (brs, 2H).

Example 54: Synthesis of Compound I-253

((1r,4r)-4-(3-Amino-6-carbamimidoyl-1-(4-phenoxybenzyl)-1H-indole-2-carboxamido)-cyclohexyl) carbamic Acid

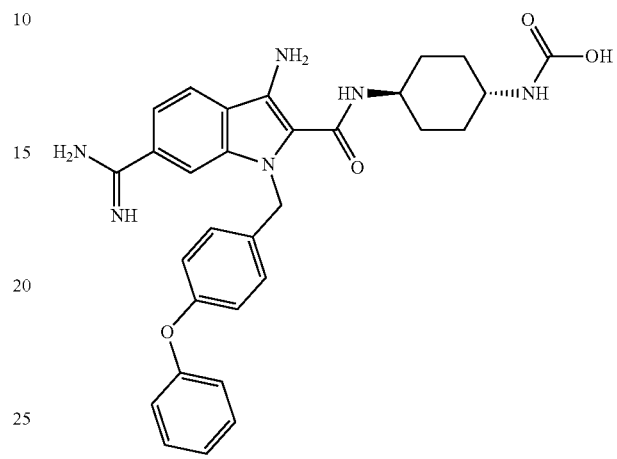

Step-1: ((1r,4r)-4-(3-Amino-6-cyano-1-(4-phenoxybenzyl)-1H-indole-2-carboxamido)-cyclohexyl)carbamic Acid The product of step-2 of example 53 (510 mg, 0.87 mmol) and sodium hydroxide (52 mg, 1.3 mmol) were treated together to afford 180 mg of the title compound following the procedure described in step-2 of example-1 without using lithium hydroxide as base. LCMS: 524.2 (M+1)$^+$.

Step-2: ((1r,4r)-4-(3-Amino-6-(ethoxy(imino)methyl)-1-(4-phenoxybenzyl)-1H-indole-2-carboxamido)-cyclohexyl)carbamic Acid The product of step-1 of example-53 (180 mg, 0.51 mmol) was treated with 30 mL of ethanolic-HCl to afford 65 mg of the title compound following the procedure described in step-4 of example-1. LCMS: 570.3 (M+1)$^+$.

Step-3: ((1r,4r)-4-(3-Amino-6-carbamimidoyl-1-(4-phenoxybenzyl)-1H-indole-2-carboxamido)-cyclohexyl)carbamic Acid The product of step-2 of example-53 (65 mg, 0.11 mmol) was treated with 20 mL of ethanolic-NH$_3$ to afford 10 mg of the title compound following the procedure described in step-5 of example-1. LCMS: 541.2 (M+1)$^+$, $^1$H NMR (300 MHz, DMSO-d$_6$): δ 1.21 (m, 2H), 1.36 (m, 2H), 1.79 (m, 4H), 2.95 (m, 1H), 3.71 (m, 1H), 5.63 (s, 2H), 6.85 (d, 4H), 7.12 (m, 3H), 7.32 (m, 3H), 7.52 (m, 1H), 7.71 (d, 1H), 7.82 (m, 2H), 8.19 (d, 1H), 8.31 (brs, 1H), 9.10 (brs, 2H), 9.21 (brs, 2H), 9.65 (brs, 1H); HPLC: 87.13% (Retention Time=6.683 min).

Example 55: Synthesis of Compound I-254

Ethyl (2-(((1r,4r)-4-aminocyclohexyl)carbamoyl)-6-((Z)—N'-hydroxycarbamimidoyl)-1-(4-phenoxybenzyl)-1H-indol-3-yl)carbamate

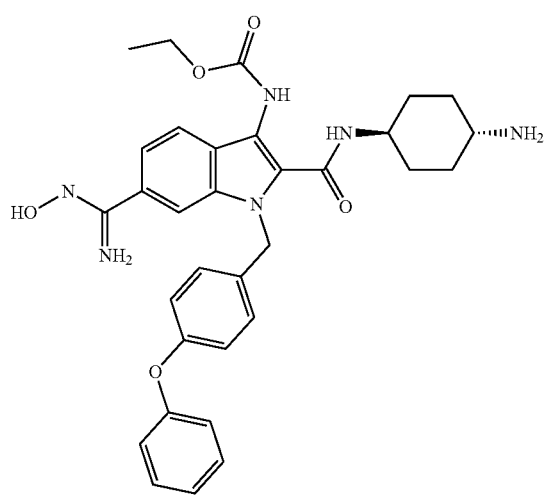 [SMILES: CCOC(=O)Nc1c(C(=O)N[C@H]2CC[C@H](N)CC2)n(Cc2ccc(Oc3ccccc3)cc2)c2cc(C(=N)NO)ccc12]

Step-1: tert-Butyl ((1r,4r)-4-(3-ethylcarbamate-6-cyano-1-(4-phenoxybenzyl)-1H-indole-2-carboxamido)cyclohexyl)carbamate The product of step-2 of example 53 (650 mg, 1.12 mmol) and ethyl carbonochloridate (121 mg, 1.12 mmol) were treated together to afford 370 mg of the title compound following the procedure described in step-1 of example-1. LCMS: 652.3 (M+1)$^+$.

Step-2: tert-Butyl ((1r,4r)-4-(3-ethylcarbamate-6-((Z)—N'-hydroxycarbamimidoyl)-1-(4-phenoxybenzyl)-1H-indole-2-carboxamido)cyclohexyl)carbamate The product of step-1 of example-55 (370 mg, 0.56 mmol) and aqueous hydroxylamine (0.2 mL) were treated together to afford 230 mg of the title compound following the procedure described in step-4 of example-14. LCMS: 613.3 (M+1)$^+$.

Step-3: Ethyl (2-(((1r,4r)-4-aminocyclohexyl)carbamoyl)-6-((Z)—N'-hydroxycarbamimidoyl)-1-(4-phenoxybenzyl)-1H-indol-3-yl)carbamate The product of step-2 of example-55 (230 mg, 0.37 mmol) was treated with 30 mL of ethanolic-HCl to afford 65 mg of the title compound following the procedure described in step-2 of example-2. LCMS: 585.3 (M+1)$^+$, $^1$H NMR (300 MHz, DMSO-d$_6$): δ 1.21 (m, 7H), 1.81 (m, 4H), 2.96 (m, 1H), 3.52 (m, 1H), 4.09 (m, 2H), 5.83 (s, 2H), 6.89 (m, 4H), 7.11 (m, 3H), 7.32 (m, 3H), 7.62 (d, 1H), 7.81 (m, 3H), 8.08 (d, 1H), 8.18 (brs, 1H), 8.88 (brs, 1H), 11.10 (brs, 1H), 12.6 (brs, 1H); HPLC: 97.32% (Retention Time=4.97 min).

Example 56: Synthesis of Compound I-256

1-(3-Aminobenzyl)-N-((1r,4r)-4-aminocyclohexyl)-6-carbamimidoyl-1H-indole-2-carboxamide

Step-1: tert-Butyl ((1r,4r)-4-(6-cyano-1-(3-nitrobenzyl)-1H-indole-2-carboxamido)-cyclohexyl)carbamate The product of step-2 of example-6 (1200 mg, 3.13 mmol) and 1-(bromomethyl)-3-nitrobenzene (676 mg, 3.13 mmol) were treated together to afford 850 mg of the title compound following the procedure described in step-1 of example-1. LCMS: 518.2 (M+1)$^+$.

Step-2: tert-Butyl ((1r,4r)-4-(1-(3-aminobenzyl)-6-cyano-1H-indole-2-carboxamido)cyclohexyl)-carbamate The product of step-1 of example-56 (850 mg, 1.64 mmol) and zinc (213 mg, 3.28 mmol) were treated together to afford 410 mg of the title compound following the procedure described in step-3 of example-9. LCMS: 488.3 (M+1)$^+$.

Step-3: Ethyl 1-(3-aminobenzyl)-2-(((1r,4r)-4-aminocyclohexyl)carbamoyl)-1H-indole-6-carbimidate The product of step-2 of example-56 (410 mg, 0.84 mmol) was treated with 50 mL of ethanolic-HCl to afford 235 mg of the title compound following the procedure described in step-4 of example-1. LCMS: 434.2 (M+1)$^+$.

Step-4: 1-(3-Aminobenzyl)-N-((1r,4r)-4-aminocyclohexyl)-6-carbamimidoyl-1H-indole-2-carboxamide The product of step-3 of example-56 (235 mg, 0.54 mmol) was treated with 30 mL of ethanolic-NH$_3$ to afford 35 mg of the title compound following the procedure described in step-5 of example-1. LCMS: 405.2 (M+1)$^+$, $^1$H NMR (300 MHz, DMSO-d$_6$): δ 1.42 (m, 4H), 1.81 (m, 4H), 2.95 (m, 1H), 3.45 (m, 1H), 5.83 (s, 2H), 6.41 (m, 3H), 6.97 (m, 1H), 7.22 (s, 1H), 7.52 (d, 1H), 7.82 (m, 4H), 8.15 (brs, 1H), 8.61 (d, 1H), 9.05 (brs, 2H), 9.25 (brs, 2H); HPLC: 94.55% (Retention Time=4.255 min).

Example 57: Synthesis of Compound I-257

N-((1r,4r)-4-aminocyclohexyl)-1-(3-(3-aminopropanamido)benzyl)-6-carbamimidoyl-1H-indole-2-carboxamide

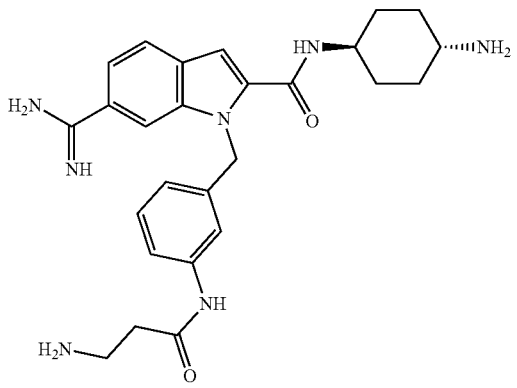 [SMILES: N=C(N)c1ccc2cc(C(=O)N[C@H]3CC[C@H](N)CC3)n(Cc3cccc(NC(=O)CCN)c3)c2c1]

This compound was prepared by treating the product of step-2 of example-56 with 3-((tert-butoxycarbonyl)amino)propanoic acid by following a similar procedure as described in step-3 to step-5 of example-1. LCMS: 476.3 (M+1)⁺, $^1$H NMR (300 MHz, DMSO-d$_6$): δ 1.32 (m, 4H), 1.83 (m, 4H), 2.63 (m, 2H), 3.11 (m, 3H), 3.71 (m, 1H), 5.84 (s, 2H), 7.14 (m, 1H), 7.27 (s, 1H), 7.32 (brs, 1H), 7.48 (m, 2H), 7.84 (m, 4H), 7.93 (m, 2H), 8.18 (s, 1H), 8.58 (d, 1H), 9.22 (d, 3H), 10.18 (brs, 1H); HPLC: 97.1% (Retention Time=4.042 min).

Example 58: Synthesis of Compound I-258

N-((1r,4r)-4-Aminocyclohexyl)-1-(3-(azetidine-3-carboxamido)benzyl)-6-carbamimidoyl-1H-indole-2-carboxamide

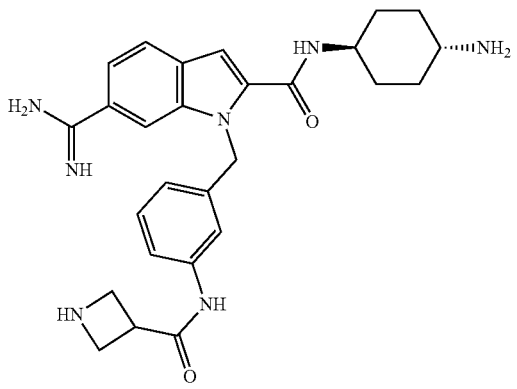 [SMILES: N=C(N)c1ccc2cc(C(=O)N[C@H]3CC[C@H](N)CC3)n(Cc3cccc(NC(=O)C4CNC4)c3)c2c1]

This compound was prepared by treating the product of step-2 of example-56 with 1-(tert-butoxycarbonyl)azetidine-3-carboxylic acid by following a similar procedure as described in step-3 to step-5 of example-1. LCMS: 488.3 (M+1)⁺, $^1$H NMR (300 MHz, DMSO-d$_6$): δ 1.42 (m, 4H), 1.81 (m, 4H), 2.95 (m, 2H), 3.55 (m, 3H), 4.05 (m, 2H), 5.83 (s, 2H), 6.71 (d, 1H), 7.22 (m, 2H), 7.51 (m, 2H), 7.82 (m, 4H), 8.15 (brs, 1H), 8.61 (d, 1H), 8.71 (brs, 1H), 9.05 (brs, 2H), 9.25 (brs, 2H), 10.21 (s, 1H); HPLC: 94.31% (Retention Time=4.177 min).

Example 59: Synthesis of Compound I-259

3-(3-((2-(((1r,4r)-4-Amiocyclohexyl)carbamoyl)-6-carbamimidoyl-1H-indol-1-yl)methyl)benzamido)propanoic Acid

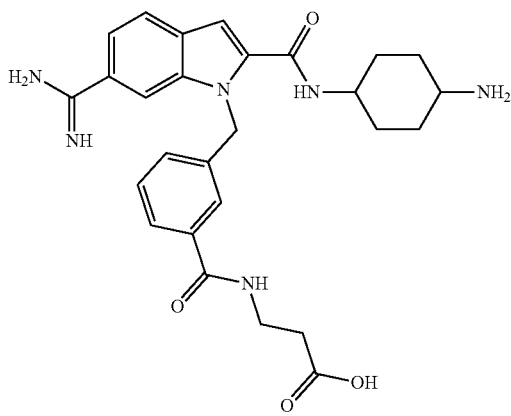 [SMILES: N=C(N)c1ccc2cc(C(=O)NC3CCC(N)CC3)n(Cc3cccc(C(=O)NCCC(=O)O)c3)c2c1]

Step-1: methyl 3-((2-(((1r,4r)-4-((tert-butoxycarbonyl)amino)cyclohexyl)carbamoyl)-6-cyano-1H-indol-1-yl)methyl)benzoate The product of step-2 of example 6 (1.2 g, 3.13 mmol) and methyl 3-(bromomethyl)benzoate (717 mg, 3.13 mmol) were treated together to afford 930 mg of the title compound following the procedure described in step-1 of example-1. LCMS: 531.2 (M+1)⁺.

Step-2: 3-((2-(((1r,4r)-4-((tert-Butoxycarbonyl)amino)cyclohexyl)carbamoyl)-6-cyano-1H-indol-1-yl)methyl)benzoic Acid The product of step-1 of example-59 (930 mg, 1.75 mmol) and lithium hydroxide (85 mg, 3.5 mmol) were treated together to afford 630 mg of the title compound following the procedure described in step-2 of example-1. LCMS: 517.2 (M+1)⁺.

Step-3: Methyl 3-(3-((2-(((1r,4r)-4-((tert-butoxycarbonyl)amino)cyclohexyl)carbamoyl)-6-cyano-1H-indol-1-yl)methyl)benzamido)propanoate The product of step-2 of example-59 (630 mg, 1.21 mmol) and methyl 3-aminopropanoate (125 mg, 1.21 mmol) were treated together to afford 340 mg of the title compound following the procedure described in step-3 of example-1. LCMS: 602.3 (M+1)⁺.

Step-4: 3-(3-((2-(((1r,4r)-4-((tert-Butoxycarbonyl)amino)cyclohexyl)carbamoyl)-6-cyano-1H-indol-1-yl)methyl)benzamido)propanoic Acid The product of step-3 of example-59 (340 mg, 0.56 mmol) and lithium hydroxide (55 mg, 2.26 mmol) were treated together to afford 210 mg of the title compound following the procedure described in step-2 of example-1. LCMS: 588.3 (M+1)+.

Step-5: 3-(3-((2-(((1r,4r)-4-Aminocyclohexyl)carbamoyl)-6-(ethoxy(imino)methyl)-1H-indol-1-yl)methyl)benzamido)propanoic Acid The product of step-4 of example-59 (200 mg, 0.34 mmol) was treated with 50 mL of ethanolic-HCl to afford 75 mg of the title compound following the procedure described in step-4 of example-1. LCMS: 534.3 (M+1)+.

Step-6: 3-(3-((2-(((1r,4r)-4-Aminocyclohexyl)carbamoyl)-6-carbamimidoyl-1H-indol-1-yl)methyl)benzamido)propanoic Acid The product of step-5 of example-59 (70 mg, 0.13 mmol) was treated with 20 mL of ethanolic-NH$_3$ to afford 23 mg of the title compound following the procedure described in step-5 of example-1. LCMS: 505.3 (M+1)+, $^1$H NMR (300 MHz, DMSO-d$_6$): δ 1.32 (m, 4H), 1.83 (m, 4H), 2.33 (m, 3H), 2.95 (m, 1H), 3.45 (m, 2H), 5.84 (s, 2H), 6.82 (s, 1H), 7.17 (d, 1H), 7.28 (s, 1H), 7.36 (m, 2H), 7.52 (m, 3H), 7.81 (m, 2H), 8.21 (s, 1H), 8.45 (m, 1H), 8.65 (d, 1H), 9.02 (brs, 2H), 9.25 (brs, 2H), 13.24 (brs, 1H); HPLC: 96.04% (Retention Time=4.45 min).

Example 60: Synthesis of Compound I-260

1-(3-(3-Aminopropanamido)benzyl)-6-carbamimidoyl-N-(4,4-difluorocyclohexyl)-1H-indole-2-carboxamide

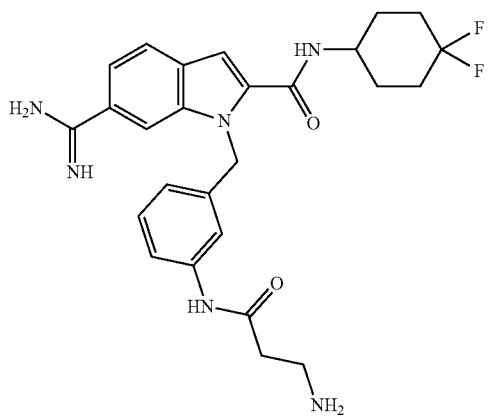 [SMILES: N=C(N)c1ccc2cc(C(=O)NC3CCC(F)(F)CC3)n(Cc3cccc(NC(=O)CCN)c3)c2c1]

Step-1: Ethyl 6-cyano-1-(3-nitrobenzyl)-1H-indole-2-carboxylate

Ethyl 6-cyano-1H-indole-2-carboxylate (1.45 g, 6.77 mmol) and 1-(bromomethyl)-3-nitrobenzene (1.46 g, 6.77 mmol) were treated together to afford 1.05 g of the title compound following the procedure described in step-1 of example-1. LCMS: 350.1 (M+1)+.

Step-2: 6-Cyano-1-(3-nitrobenzyl)-1H-indole-2-carboxylic Acid

The product of step-1 of example-60 (1.05 g, 3.0 mmol) and lithium hydroxide (145 mg, 6.0 mmol) were treated together to afford 680 mg of the title compound following the procedure described in step-2 of example-1. LCMS: 322.1 (M+1)+.

Step-3: 6-Cyano-N-(4,4-difluorocyclohexyl)-1-(3-nitrobenzyl)-1H-indole-2-carboxamide The product of step-2 of example-60 (680 mg, 2.11 mmol) and 4,4-difluorocyclohexanamine (285 mg, 2.11 mmol) were treated together to afford 570 mg of the title compound following the procedure described in step-3 of example-1. LCMS: 439.2 (M+1)+.

Step-4: 1-(3-Aminobenzyl)-6-cyano-N-(4,4-difluorocyclohexyl)-1H-indole-2-carboxamide The product of step-3 of example-60 (570 mg, 1.29 mmol) and zinc (170 mg, 2.62 mmol) were treated together to afford 410 mg of the title compound following the procedure described in step-3 of example-9. LCMS: 409.2 (M+1)+.

Step-5: tert-Butyl (3-((3-((6-cyano-2-((4,4-difluorocyclohexyl)carbamoyl)-1H-indol-1-yl)-methyl)phenyl)amino)-3-oxopropyl)carbamate The product of step-4 of example-60 (410 mg, 1.0 mmol) and 3-((tert-butoxycarbonyl)amino)propanoic acid (190 mg, 1.0 mmol) were treated together to afford 365 mg of the title compound following the procedure described in step-3 of example-1. LCMS: 580.3 (M+1)+.

Step-6: Ethyl 2-(((1r,4r)-4-aminocyclohexyl)carbamoyl)-1-(3-((2-aminoethyl)carbamoyl)-benzyl)-1H-indole-6-carbimidate The product of step-5 of example-60 (350 mg, 0.6 mmol) was treated with 50 mL of ethanolic-HCl to afford 115 mg of the title compound following the procedure described in step-4 of example-1. LCMS: 526.3 (M+1)+.

Step-7: 1-(3-(3-Aminopropanamido)benzyl)-6-carbamimidoyl-N-(4,4-difluorocyclohexyl)-1H-indole-2-carboxamide The product of step-6 of example-60 (115 mg, 0.21 mmol) was treated with 30 mL of ethanolic-NH$_3$ to afford 34 mg of the title compound following the procedure described in step-5 of example-1. LCMS: 497.3 (M+1)+, $^1$H NMR (300 MHz, DMSO-d$_6$): δ 1.61 (m, 2H), 1.83 (m, 3H), 2.03 (m, 3H), 2.63 (m, 2H), 3.04 (m, 2H), 3.95 (m, 1H), 5.83 (s, 2H), 6.71 (d, 1H), 7.17 (m, 1H), 7.28 (s, 1H), 7.36 (brs, 1H), 7.47 (d, 1H), 7.54 (m, 1H), 7.74 (brs, 3H), 7.90 (d, 1H), 8.18 (s, 1H), 8.59 (d, 1H), 9.02 (brs, 2H), 9.25 (brs, 2H); HPLC: 89.25% (Retention Time=5.796 min).

Example 61: Synthesis of Compound I-261

1-(4-Aminobenzyl)-N-((1r,4r)-4-aminocyclohexyl)-6-carbamimidoyl-1H-indole-2-carboxamide

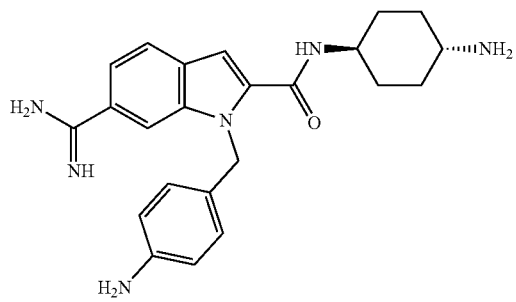 [SMILES: N=C(N)c1ccc2cc(C(=O)N[C@H]3CC[C@H](N)CC3)n(Cc3ccc(N)cc3)c2c1]

Step-1: tert-Butyl ((1r,4r)-4-(6-cyano-1-(4-nitrobenzyl)-1H-indole-2-carboxamido)-cyclohexyl)carbamate The product of step-2 of example-6 (1.2 g, 3.13 mmol) and 1-(bromomethyl)-4-nitrobenzene (676 mg, 3.13 mmol) were treated together to afford 970 mg of the title compound following the procedure described in step-1 of example-1. LCMS: 518.2 (M+1)$^+$.

Step-2: tert-Butyl ((1r,4r)-4-(1-(3-aminobenzyl)-6-cyano-1H-indole-2-carboxamido)cyclohexyl)-carbamate The product of step-1 of example-61 (970 mg, 1.87 mmol) and zinc (244 mg, 3.74 mmol) were treated together to afford 530 mg of the title compound following the procedure described in step-3 of example-9. LCMS: 488.3 (M+1)$^+$.

Step-3: Ethyl 1-(4-aminobenzyl)-2-(((1r,4r)-4-aminocyclohexyl)carbamoyl)-1H-indole-6-carbimidate The product of step-2 of example-61 (340 mg, 0.69 mmol) was treated with 50 mL of ethanolic-HCl to afford 150 mg of the title compound following the procedure described in step-4 of example-1. LCMS: 434.2 (M+1)$^+$.

Step-4: 1-(4-Aminobenzyl)-N-((1r,4r)-4-aminocyclohexyl)-6-carbamimidoyl-1H-indole-2-carboxamide The product of step-3 of example-61 (150 mg, 0.34 mmol) was treated with 30 mL of ethanolic-NH$_3$ to afford 22 mg of the title compound following the procedure described in step-5 of example-1. LCMS: 405.2 (M+1)$^+$, $^1$H NMR (300 MHz, DMSO-d$_6$): δ 1.41 (m, 4H), 1.75 (m, 4H), 2.96 (m, 1H), 3.62 (m, 1H), 5.67 (s, 2H), 6.67 (brs, 2H), 6.97 (d, 2H), 7.13 (s, 1H), 7.52 (d, 1H), 7.85 (d, 1H), 7.95 (m, 3H), 8.25 (s, 1H), 9.00 (brs, 2H), 9.24 (brs, 2H); HPLC: 91.55% (Retention Time=5.551 min).

Example 62: Synthesis of Compound I-262

N-((1r,4r)-4-Aminocyclohexyl)-1-(4-(3-aminopropanamido)benzyl)-6-carbamimidoyl-1H-indole-2-carboxamide

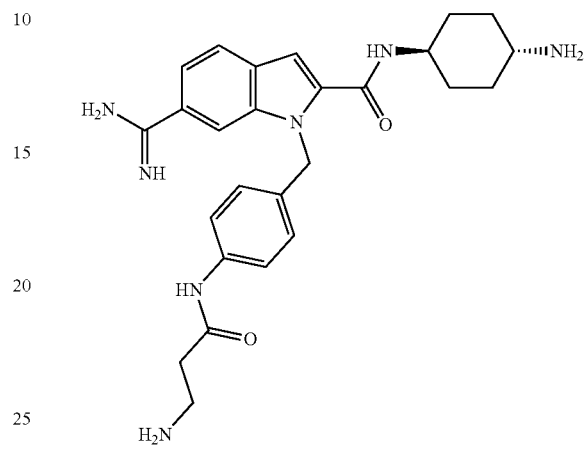

Step-1: tert-Butyl ((1r,4r)-4-(1-(4-(3-((tert-butoxycarbonyl)amino)propanamido)benzyl)-6-cyano-1H-indole-2-carboxamido)cyclohexyl)carbamate The product of step-2 of example-61 (640 mg, 1.31 mmol) and 3-((tert-butoxycarbonyl)amino)propanoic acid (248 mg, 1.31 mmol) were treated together to afford 430 mg of the title compound following the procedure described in step-3 of example-1. LCMS: 659.3 (M+1)$^+$.

Step-2: Ethyl 2-(((1r,4r)-4-aminocyclohexyl)carbamoyl)-1-(4-(3-aminopropanamido)benzyl)-1H-indole-6-carbimidate The product of step-1 of example-62 (430 mg, 0.65 mmol) was treated with 50 mL of ethanolic-HCl to afford 170 mg of the title compound following the procedure described in step-4 of example-1. LCMS: 505.3 (M+1)$^+$.

Step-3: N-((1r,4r)-4-Aminocyclohexyl)-1-(4-(3-aminopropanamido)benzyl)-6-carbamimidoyl-1H-indole-2-carboxamide The product of step-2 of example-62 (170 mg, 0.33 mmol) was treated with 30 mL of ethanolic-NH$_3$ to afford 28 mg of the title compound following the procedure described in step-5 of example-1. LCMS: 476.3 (M+1)$^+$, $^1$H NMR (300 MHz, DMSO-d$_6$): δ 1.48 (m, 4H), 1.83 (m, 4H), 2.15 (m, 2H), 3.10 (m, 2H), 3.70 (m, 1H), 5.88 (s, 2H), 7.08 (d, 2H), 7.22 (s, 1H), 7.45 (d, 2H), 7.53 (d, 2H), 7.73 (brs, 3H), 7.88 (m, 3H), 8.18 (s, 1H), 8.61 (d, 1H), 9.09 (brs, 2H), 9.23 (brs, 2H), 10.13 (s, 1H); HPLC: 85.85% (Retention Time=4.127 min).

Example 63: Synthesis of Compound I-263

1-(4-(3-Aminopropanamido)benzyl)-6-carbamimidoyl-N-(4,4-difluorocyclohexyl)-1H-indole-2-carboxamide

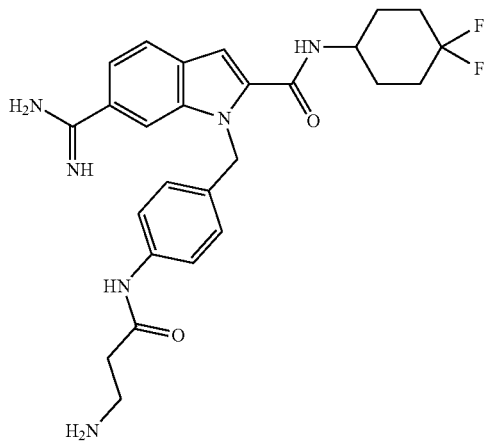 [SMILES: N=C(N)c1ccc2cc(C(=O)NC3CCC(F)(F)CC3)n(Cc3ccc(NC(=O)CCN)cc3)c2c1]

Step-1: Ethyl 6-cyano-1-(4-nitrobenzyl)-1H-indole-2-carboxylate

The product of step-2 of example-6 (1.35 g, 3.52 mmol) and 1-(bromomethyl)-4-nitrobenzene (761 mg, 3.52 mmol) were treated together to afford 955 mg of the title compound following the procedure described in step-1 of example-1. LCMS: 350.1 (M+1)$^+$.

Step-2: 6-Cyano-1-(4-nitrobenzyl)-1H-indole-2-carboxylic Acid

The product of step-1 of example-63 (950 mg, 2.71 mmol) and lithium hydroxide (130 mg, 5.42 mmol) were treated together to afford 710 mg of the title compound following the procedure described in step-2 of example-1. LCMS: 322.1 (M+1)$^+$.

Step-3: 6-Cyano-N-(4,4-difluorocyclohexyl)-1-(4-nitrobenzyl)-1H-indole-2-carboxamide The product of step-2 of example-63 (650 mg, 2.01 mmol) and 4,4-difluorocyclohexanamine (272 mg, 2.01 mmol) were treated together to afford 512 mg of the title compound following the procedure described in step-3 of example-1. LCMS: 439.2 (M+1)$^+$.

Step-4: 1-(4-Aminobenzyl)-6-cyano-N-(4,4-difluorocyclohexyl)-1H-indole-2-carboxamide The product of step-3 of example-63 (510 mg, 1.16 mmol) and zinc (151 mg, 2.32 mmol) were treated together to afford 365 mg of the title compound following the procedure described in step-3 of example-9. LCMS: 409.2 (M+1)$^+$.

Step-5: tert-Butyl (3-((4-(((6-cyano-2-((4,4-difluorocyclohexyl)carbamoyl)-1H-indol-1-yl)-methyl)phenyl)amino)-3-oxopropyl)carbamate The product of step-4 of example-63 (365 mg, 0.89 mmol) and 3-((tert-butoxycarbonyl)amino)propanoic acid (120 mg, 0.89 mmol) were treated together to afford 280 mg of the title compound following the procedure described in step-3 of example-1. LCMS: 580.3 (M+1)$^+$.

Step-6: Ethyl 1-(4-(3-aminopropanamido)benzyl)-2-((4,4-difluorocyclohexyl)carbamoyl)-1H-indole-6-carbimidate The product of step-5 of example-63 (280 mg, 0.48 mmol) was treated with 50 mL of ethanolic-HCl to afford 125 mg of the title compound following the procedure described in step-4 of example 1. LCMS: 526.3 (M+1)$^+$.

Step-7: 1-(4-(3-Aminopropanamido)benzyl)-6-carbamimidoyl-N-(4,4-difluorocyclohexyl)-1H-indole-2-carboxamide The product of step-6 of example 63 (125 mg, 0.23 mmol) was treated with 30 mL of ethanolic-NH$_3$ to afford 22 mg of the title compound following the procedure described in step-5 of example-1. LCMS: 497.3 (M+1)$^+$, $^1$H NMR (300 MHz, DMSO-d$_6$): δ 1.21 (m, 2H), 1.83 (m, 3H), 2.03 (m, 3H), 2.63 (m, 2H), 3.04 (m, 2H), 3.95 (m, 1H), 5.88 (s, 2H), 7.08 (d, 2H), 7.22 (s, 1H), 7.45 (d, 2H), 7.53 (d, 2H), 7.73 (brs, 3H), 7.88 (d, 1H), 8.61 (d, 1H), 9.04 (brs, 2H), 9.25 (brs, 2H), 10.13 (s, 1H); HPLC: 92.28% (Retention Time=5.091 min).

Example 64 Synthesis of Compound I-264

1-(4-(3-Aminopropanamido)benzyl)-6-carbamimidoyl-N-(cyclohex-3-en-1-yl)-1H-indole-2-carboxamide

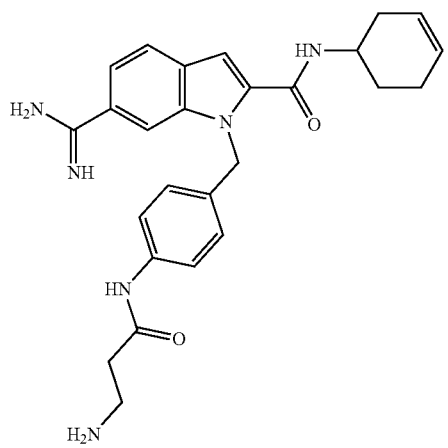 [SMILES: N=C(N)c1ccc2cc(C(=O)NC3CC=CCC3)n(Cc3ccc(NC(=O)CCN)cc3)c2c1]

Step-1: 6-Cyano-N-(cyclohex-3-en-1-yl)-1-(4-nitrobenzyl)-1H-indole-2-carboxamide The product of step-2 of example-63 (500 mg, 1.55 mmol) and cyclohex-3-enamine (150 mg, 1.55 mmol) were treated together to afford 360 mg of the title compound following the procedure described in step-3 of example-1. LCMS: 401.2 (M+1)$^+$.

Step-2: 1-(4-Aminobenzyl)-6-cyano-N-(cyclohex-3-en-1-yl)-1H-indole-2-carboxamide The product of step-1 of example-64 (360 mg, 0.89 mmol) and zinc (116 mg, 1.8 mmol) were treated together to afford 265 mg of the title compound following the procedure described in step-3 of example-9. LCMS: 371.2 (M+1)⁺.

Step-3: tert-Butyl (3-((4-((6-cyano-2-(cyclohex-3-en-1-ylcarbamoyl)-1H-indol-1-yl)methyl)phenyl)amino)-3-oxopropyl)carbamate The product of step-2 of example-64 (260 mg, 0.7 mmol) and 3-((tert-butoxycarbonyl)amino)propanoic acid (132 mg, 0.7 mmol) were treated together to afford 200 mg of the title compound following the procedure described in step-3 of example-1. LCMS: 542.3 (M+1)⁺.

Step-4: Ethyl 1-(4-(3-aminopropanamido)benzyl)-2-(cyclohex-3-en-1-ylcarbamoyl)-1H-indole-6-carbimidate The product of step-3 of example-64 (200 mg, 0.36 mmol) was treated with 30 mL of ethanolic-HCl to afford 85 mg of the title compound following the procedure described in step-4 of example-1. LCMS: 488.3 (M+1)⁺.

Step-5: 1-(4-(3-Aminopropanamido)benzyl)-6-carbamimidoyl-N-(4,4-difluorocyclohexyl)-1H-indole-2-carboxamide The product of step-4 of example-64 (85 mg, 0.17 mmol) was treated with 20 mL of ethanolic-NH₃ to afford 14 mg of the title compound following the procedure described in step-5 of example-1. LCMS: 459.2 (M+1)⁺, ¹H NMR (300 MHz, DMSO-d₆): δ 1.51 (m, 1H), 1.81 (m, 1H), 2.01 (m, 3H), 2.25 (m, 1H), 2.63 (m, 2H), 3.02 (m, 2H), 3.91 (m, 1H), 5.65 (brs, 2H), 5.79 (s, 2H), 7.09 (d, 1H), 7.23 (s, 1H), 7.45 (d, 2H), 7.52 (m, 1H), 7.71 (m, 3H), 7.88 (d, 1H), 8.60 (d, 1H), 8.96 (brs, 2H), 9.24 (brs, 2H), 10.12 (s, 1H); HPLC: 81.94% (Retention Time=5.292 min).

Example 65: Synthesis of Compound I-267

1-(4-Carbamoylbenzyl)-6-(N'-hydroxycarbamimidoyl)-N-(3-(pyrrolidin-1-yl)phenyl)-1H-indole-2-carboxamide

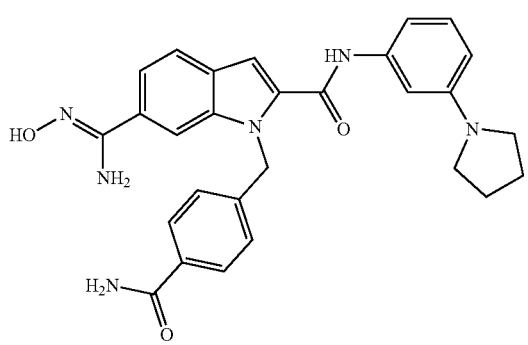 [SMILES: NC(=O)c1ccc(Cn2c(C(=O)Nc3cccc(N4CCCC4)c3)cc3ccc(/C(N)=N/O)cc32)cc1]

The crude product of step-2 of example-23 was purified by preparative High-performance liquid chromatography instrument with a Agilent XDB C18 reverse phase column (21.2×150 mm, 5 micron). The mobile phases were 30% acetonitrile in water (0.1% TFA) to 100% acetonitrile (0.1% TFA) which afforded the title compound (25 mg). LCMS: 497.2 (M+1)⁺, ¹H NMR (300 MHz, DMSO-d₆): δ 1.94 (m, 4H), 3.19 (m, 4H), 5.93 (s, 2H), 6.28 (d, 2H), 6.96 (s, 1H), 7.01 (d, 1H), 7.07 (m, 3H), 7.31 (brs, 1H), 7.44 (m, 2H), 7.73 (m, 2H), 7.87 (brs, 1H), 7.91 (d, 2H), 8.03 (s, 1H), 10.34 (brs, 1H); HPLC: 94.73% (Retention Time=3.839 min).

Example 66: Synthesis of Compound I-268

1-(4-Carbamoylbenzyl)-6-(N'-hydroxycarbamimidoyl)-N-(4-(pyrrolidin-1-yl)phenyl)-1H-indole-2-carboxamide

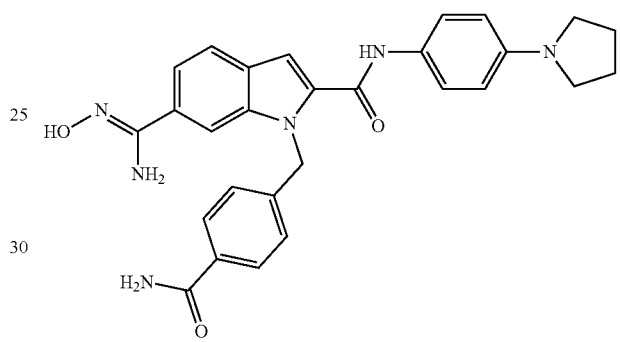

Step-1: 1-(4-Carbamoylbenzyl)-6-cyano-N-(4-(pyrrolidin-1-yl)phenyl)-1H-indole-2-carboxamide The product of step-2 of example 19 (500 mg, 1.56 mmol) and 4-(pyrrolidin-1-yl)aniline (252 mg, 1.56 mmol) were treated together to afford 375 mg of the title compound following the procedure described in step-3 of example 1. LCMS: 464.2 (M+1)⁺.

Step-2: 1-(4-Carbamoylbenzyl)-6-(N'-hydroxycarbamimidoyl)-N-(4-(pyrrolidin-1-yl)phenyl)-1H-indole-2-carboxamide The product of step-1 of example 66 (370 mg, 0.79 mmol) and aqueous hydroxylamine (1.3 mL) were treated together to afford 180 mg of the title compound following the procedure described in step-4 of example 14. LCMS: 497.2 (M+1)⁺, ¹H NMR (300 MHz, DMSO-d₆): δ 1.92 (m, 4H), 3.21 (m, 4H), 5.93 (s, 2H), 6.49 (d, 2H), 7.11 (d, 2H), 7.31 (brs, 1H), 7.43 (m, 4H), 7.73 (d, 2H), 7.87 (m, 2H), 8.01 (s, 1H), 10.24 (brs, 1H); HPLC: 99.76% (Retention Time=3.663 min).

Example 67: Synthesis of Compound I-269

1-(4-Carbamoylbenzyl)-6-(N'-hydroxycarbamimidoyl)-N-(4-(pyrrolidin-1-yl)pyridin-2-yl)-1H-indole-2-carboxamide

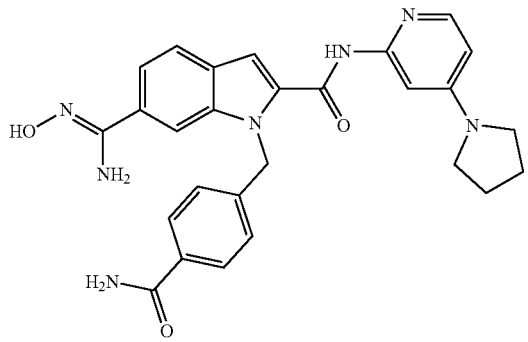 [SMILES: NC(=O)c1ccc(Cn2c(C(=O)Nc3cc(N4CCCC4)ccn3)cc3ccc(/C(N)=N/O)cc32)cc1]

Step-2: 1-(4-Carbamoylbenzyl)-6-(N'-hydroxycarbamimidoyl)-N-(4-(pyrrolidin-1-yl)pyridin-2-yl)-1H-indole-2-carboxamide The product of step-1 of example 67 (250 mg, 0.53 mmol) and aqueous hydroxylamine (1.2 mL) were treated together to afford 110 mg of the title compound following the procedure described in step-4 of example 14. LCMS: 498.2 (M+1)$^+$, $^1$H NMR (300 MHz, DMSO-d$_6$): δ 2.02 (m, 4H), 3.42 (m, 4H), 5.93 (s, 2H), 6.69 (m, 2H), 7.08 (d, 2H), 7.34 (brs, 1H), 7.53 (d, 1H), 7.70 (s, 1H), 7.78 (d, 2H), 7.88 (m, 1H), 7.92 (m, 2H), 11.85 (brs, 1H); HPLC: 98.17% (Retention Time=2.79 min).

General synthetic scheme 4

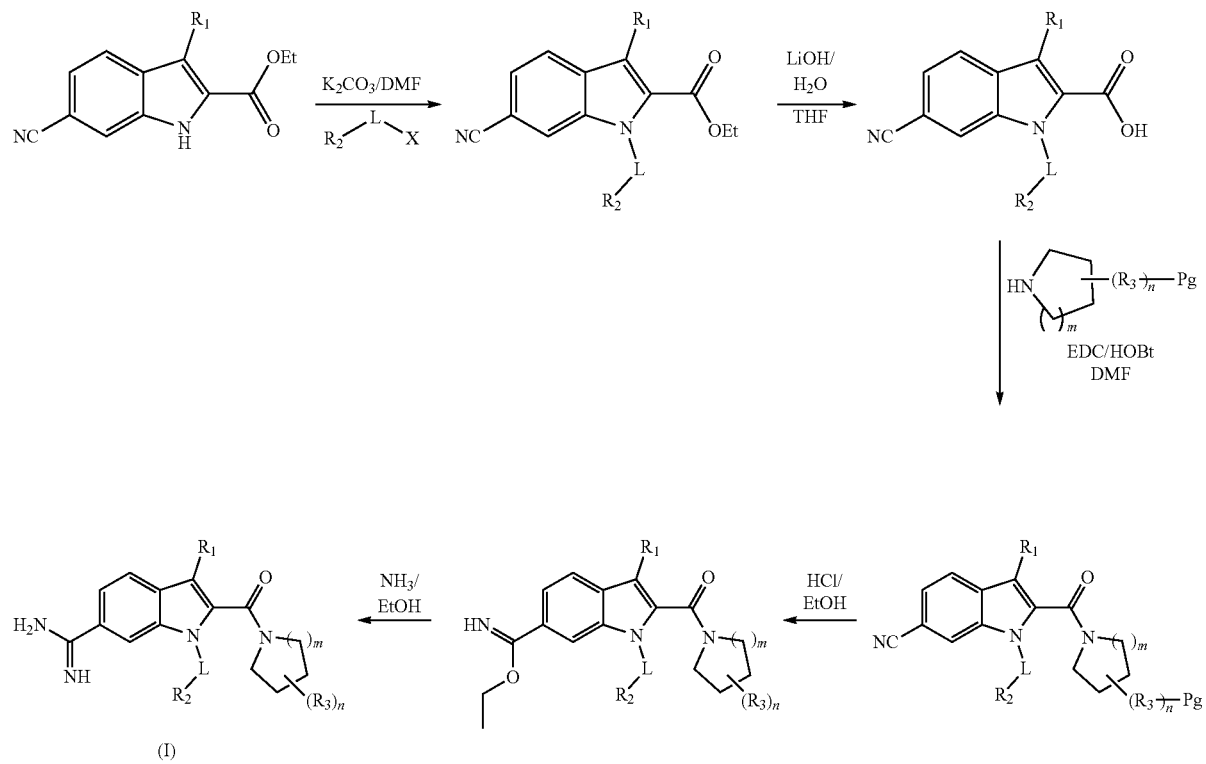

R$_1$ = H; X = Cl/Br; Pg = optional Protecting group; R$_2$, R$_3$, m and n are as defined in formula (I)

Step-1: 1-(4-Carbamoylbenzyl)-6-cyano-N-(4-(pyrrolidin-1-yl)pyridin-2-yl)-1H-indole-2-carboxamide The product of step-2 of example 19 (500 mg, 1.56 mmol) and 4-(pyrrolidin-1-yl)pyridin-2-amine (254 mg, 1.56 mmol) were treated together to afford 285 mg of the title compound following the procedure described in step-3 of example 1. LCMS: 465.2 (M+1)$^+$.

The first general approach for the synthesis of compounds of general formula (I) is depicted in general synthetic scheme-4. Ethyl 6-cyano-1H-indole-2-carboxylate was treated with various alkylating agents in presence of a suitable base (K$_2$CO$_3$) and suitable solvent (DMF) to yield alkylated derivatives. Hydrolysis of C (2) ethyl ester with aq. LiOH followed by coupling with amines using EDCI, HOBt yielded amides. The cyano group in the resultant amide derivatives were converted to the amine anlogs by treatment with ethanolic HCl and the intermediate imidate were quenched with ammonia to form compound of formula (I).

Example 68: Synthesis of Compound I-270

2-(4-Fluoropiperidine-1-carbonyl)-1-isopentyl-1H-indole-6-carboximidamide

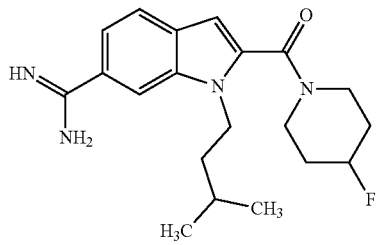 [SMILES: CC(C)CCn1c(C(=O)N2CCC(F)CC2)cc2ccc(C(=N)N)cc21]

Step-1: Ethyl 6-cyano-1-isopentyl-1H-indole-2-carboxylate

Ethyl 6-cyano-1H-indole-2-carboxylate (10.0 g, 46.71 mmol), dissolved in 250 mL of N,N-dimethylformamide (DMF), was added 1-bromo-3-methylbutane (7.0 g, 46.71 mmol) and potassium carbonate ($K_2CO_3$) (7.73 g, 56.0 mmol) and stirred at room temperature for 8 h. After reaction completion, mixture was quenched with ice-cold water and precipitated product was filtered off. Thus obtained solid was further washed with water and dried under vacuum to give crude compound which was purified by column chromatography using silica-gel as an adsorbent and eluted with 10-20% ethylacetate/hexane to afford the title compound (6.2 g). LCMS: 285.1 $(M+1)^+$.

Step-2: 6-Cyano-1-isopentyl-1H-indole-2-carboxylic Acid

Product of step-1 of example-68 (5.8 g, 19.64 mmol) was dissolved in 100 mL mixture of tetrahydrofuran/methanol/water (1:1:1) and added lithium hydroxide (LiOH) (1.9 g, 78.6 mmol) at room temperature. Resulting mixture was stirred at room temperature for 4-6 h. Mixture was acidified with saturated aqueous solution of citric acid and extracted with ethyl acetate followed by washed with brine and dried over anhydrous sodium sulphate and then solvent was evaporated under vacuum to get the title compound (3.65 g). LCMS: 257.1 $(M+1)^+$.

Step-3: 2-(4-Fluoropiperidine-1-carbonyl)-1-isopentyl-1H-indole-6-carbonitrile

Product of step-2 of example-68 (650 mg, 2.53 mmol) was dissolved in 10 mL of N,N-dimethylformamide and added 1-ethyl-3-(3-dimethylaminopropyl)carbodiimide (EDCI) (392 mg, 2.53 mmol), hydroxybenzotriazole (HOBt) (341 mg, 2.53 mmol) and N,N-diisopropylethylamine (DIPEA) (327 mg, 2.53 mmol) and stirred for 15 min at RT. 4-Fluoropiperidine (260 mg, 2.53 mmol), dissolved in 5 mL of DMF, was added to the reaction mixture and resulted solution was stirred at RT for overnight. Reaction mixture was quenched with water, extracted with ethyl acetate followed by washed with brine and water and dried over sodium sulphate. Solvent was evaporated under vacuum to give crude compound which was purified by column chromatography using silica-gel as an adsorbent and eluted with 10% ethylacetate/hexane and afforded the title compound (510 mg). LCMS: 342.2 $(M+1)^+$.

Step-4: Ethyl 2-(4-fluoropiperidine-1-carbonyl)-1-isopentyl-1H-indole-6-carbimidate Product was step-3 of example-68 (450 mg, 1.31 mmol) was dissolved in 50 mL of ethanolic-HCl (ethanol was saturated with HCl gas at $-20°$ C.) and kept in a glass sealed tube for 12 h at RT. After reaction completion, solvent was evaporated under vacuum to afford the title compound (235 mg). LCMS: 388.2 $(M+1)^+$.

Step-5: 2-(4-Fluoropiperidine-1-carbonyl)-1-isopentyl-1H-indole-6-carboximidamide Product of step-4 of example-68 (220 mg, 0.56 mmol) was dissolved in 50 mL of ethanolic-$NH_3$ (ethanol was saturated with $NH_3$ gas at $-70°$ C.) and kept for overnight in a steel bomb at RT. After reaction completion, solvent was evaporated under vacuum to give crude product which was purified by preparative High-performance liquid chromatography instrument with a Agilent XDB C18 reverse phase column (21.2×150 mm, 5 micron). The mobile phases were 30% acetonitrile in water (0.1% TFA) to 100% acetonitrile (0.1% TFA) which afforded the title compound (110 mg). LCMS: 359.2 $(M+1)^+$, $^1H$ NMR (300 MHz, DMSO-$d_6$): δ 0.90 (m, 6H), 1.49 (m, 1H), 1.61 (m, 2H), 1.71 (m, 2H), 1.81 (m, 2H), 3.72 (m, 4H), 4.33 (m, 2H), 4.90 (m, 1H), 6.84 (s, 1H), 7.51 (d, 1H), 7.81 (d, 1H), 8.11 (s, 1H), 9.06 (brs, 2H), 9.28 (brs, 2H); HPLC: 96.96% (Retention Time=3.613 min).

The following compounds listed in table-9 were prepared according to scheme-1 by following similar procedure as described above for example-68 using appropriate reagents with suitable modifications known to the one skilled in the art.

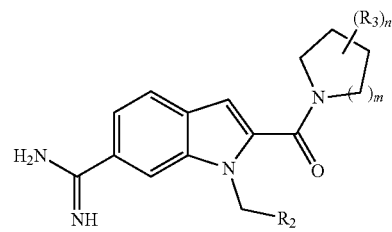

TABLE 9

| Cpd. ID. | R₂ | m | R₃ | Characteristic Data |
|---|---|---|---|---|
| I-271 | isopropyl (CH(CH₃)₂) | 2 | —F₂ | LCMS (M + 1)⁺: 377.2<br>¹H NMR: δ 0.84 (m, 6H), 1.49 (m, 1H), 1.61 (m, 2H), 2.09 (m, 4H), 3.72 (m, 4H), 4.30 (m, 2H), 6.90 (s, 1H), 7.51 (d, 1H), 7.81 (d, 1H), 8.09 (s, 1H), 8.93 (brs, 2H), 9.27 (brs, 2H); HPLC: 91.12% (Retention Time = 3.282 min). |
| I-272 | isopropyl (CH(CH₃)₂) | 1 | —F | LCMS (M + 1)⁺: 345.2<br>¹H NMR: δ 0.84 (m, 6H), 1.49 (m, 1H), 1.56 (m, 2H), 2.21 (m, 2H), 3.72 (m, 4H), 4.44 (m, 2H), 5.25 (m, 1H), 6.98 (d, 1H), 7.50 (d, 1H), 7.82 (d, 1H), 8.09 (d, 1H), 8.92 (brs, 2H), 9.27 (brs, 2H); HPLC: 96.63% (Retention Time = 2.94 min). |
| I-273 | isopropyl (CH(CH₃)₂) | 1 | —F₂ | LCMS (M + 1)⁺: 363.2<br>¹H NMR: δ 0.87 (m, 6H), 1.49 (m, 1H), 1.62 (m, 2H), 2.55 (m, 2H), 3.77 (m, 1H), 3.88 (m, 1H), 3.98 (m, 1H), 4.10 (m, 1H), 4.41 (m, 2H), 7.05 (s, 1H), 7.51 (d, 1H), 7.82 (d, 1H), 8.09 (s, 1H), 8.94 (brs, 2H), 9.28 (brs, 2H); HPLC: 93.83% (Retention Time = 6.136 min). |
| I-274 | 3-aminopropyl (H₂N-CH₂CH₂CH₂-) | 2 | —(CH₂)₂NH₂ | LCMS (M + 1)⁺: 371.2<br>¹H NMR: δ 1.49 (m, 4H), 1.91 (m, 6H), 2.72 (m, 2H), 3.00 (m, 1H), 3.71 (m, 4H), 4.52 (m, 2H), 7.25 (s, 1H), 7.51 (d, 1H), 7.81 (m, 4H), 8.21 (s, 1H), 8.63 (s, 1H), 925 (d, 3H); HPLC: 97.48% (Retention Time = 5.764 min). |
| I-275 | -CH₂CH₂C(=O)OH | 2 | —(CH₂)₂NH₂ | LCMS (M + 1)⁺: 386.2<br>¹H NMR: δ 0.81 (m, 2H), 1.49 (m, 2H), 1.65 (m, 4H), 2.82 (m, 4H), 3.15 (m, 2H), 3.95 (m, 1H), 4.50 (m, 3H), 4.8 (m, 1H), 6.75 (s, 1H), 7.51 (m, 1H), 7.71 (brs, 2H), 7.81 (d, 2H), 8.91 (brs, 2H), 9.18 (brs, 2H). |
| I-276 | -CH₂CH₂C(=O)NH₂ | 2 | —(CH₂)₂NH₂ | LCMS (M + 1)⁺: 385.2<br>¹H NMR: δ 1.21 (m, 2H), 1.49 (m, 2H), 1.61 (m, 4H), 2.55 (m, 2H), 2.8 (m, 3H), 3.15 (m, 1H), 3.95 (m, 1H), 4.45 (m, 3H), 6.73 (s, 1H), 6.87 (s, 1H), 7.51 (d, 1H), 7.32 (s, 1H), 7.70 (m, 2H), 8.15 (s, 1H), 9.15 (brs, 2H), 9.25 (brs, 2H); HPLC: 90.17% (Retention Time = 4.108 min). |
| I-277 | phenyl | 2 | —(CH₂)₂NH₂ | LCMS (M + 1)⁺: 404.2<br>¹H NMR: δ 1.40 (m, 2H), 1.67 (m, 4H), 2.52 (m, 2H), 2.84 (m, 3H), 3.15 (m, 1H), 3.95 (m, 1H), 4.68 (brs, 2H), 5.64 (s, 2H), 6.97 (s, 1H), 7.08 (d, 2H), 7.33 (m, 2H), 7.51 (d, 1H), 7.70 (m, 2H), 8.15 (s, 1H), 9.15 (brs, 2H), 9.25 (brs, 2H). |
| I-278 | 4-(trifluoromethyl)phenyl | 2 | —(CH₂)₂NH₂ | LCMS (M + 1)⁺: 472.2<br>¹H NMR: δ 0.45 (m, 1H), 0.73 (m, 1H), 1.33 (m, 3H), 1.49 (m, 1H), 1.71 (m, 1H), 2.71 (m, 4H), 3.68 (m, 3H), 4.44 (m, 1H), 5.52 (m, 2H), 6.88 (s, 1H), 7.25 (d, 2H), 7.59 (m, 1H), 7.65 (d, 2H), 7.73 (brs, 2H), 7.83 (d, 1H), 8.29 (s, 1H), 9.15 (brs, 2H), 9.25 (brs, 2H). |

TABLE 9-continued

| Cpd. ID. | R₂ | m | R₃ | Characteristic Data |
|---|---|---|---|---|
| I-279 | 4-(trifluoromethyl)phenyl | 2 | —(S)—F | LCMS (M + 1)⁺: 433.1<br>¹H NMR: δ 2.21 (m, 2H), 3.44 (m, 4H), 5.22 (m, 1H), 5.71 (s, 2H), 7.10 (s, 1H), 7.21 (m, 2H), 7.58 (m, 3H), 7.85 (d, 1H), 8.21 (s, 1H), 9.11 (brs, 2H), 9.23 (brs, 2H); HPLC: 98.0% (Retention Time = 8.305 min). |
| I-280 | 4-(trifluoromethyl)phenyl | 2 | —(CH₂)₂OH | LCMS (M + 1)⁺: 473.2<br>¹H NMR: δ 0.33 (m, 1H), 0.78 (m, 1H), 1.21 (m, 4H), 1.35 (m, 1H), 1.49 (m, 3H), 2.80 (m, 1H), 3.65 (m, 1H), 4.33 (m, 2H), 5.62 (m, 2H), 6.84 (s, 2H), 7.22 (m, 2H), 7.53 (d, 1H), 7.64 (d, 2H), 7.83 (d, 1H), 8.28 (s, 1H), 8.96 (brs, 2H), 9.23 (brs, 2H). |
| I-281 | 4-(trifluoromethyl)phenyl | 2 | —(CH₂)₃C(O)OCH₂CH₃ | LCMS (M + 1)⁺: 543.2<br>¹H NMR: δ 0.33 (m, 1H), 0.81 (m, 1H), 1.12 (m, 2H), 1.25 (m, 3H), 1.31 (m, 4H), 1.61 (m, 1H), 2.22 (m, 2H), 2.62 (m, 1H), 2.91 (m, 1H), 3.71 (m, 1H), 4.11 (m, 2H), 4.35 (m, 1H), 5.23 (d, 2H), 6.85 (s, 1H), 7.25 (d, 2H), 7.55 (m, 3H), 7.83 (d, 1H), 8.35 (brs, 1H), 9.21 (brs, 3H); HPLC: 98.397% (Retention Time = 9.335 min). |
| I-282 | 4-(trifluoromethyl)phenyl | 2 | —F | LCMS (M + 1)⁺: 447.2<br>¹H NMR: δ 1.54 (m, 2H), 2.96 (m, 2H), 3.53 (m, 4H), 4.52 9m, 1H), 5.63 (s, 2H), 6.93 (s, 1H), 7.24 (d, 2H), 7.53 (s, 1H), 7.65 (d, 2H), 7.86 (d, 1H), 8.21 (s, 1H), 9.03 (brs, 2H), 9.25 (brs, 2H); HPLC: 83.54% (Retention Time = 3.351 min). |
| I-283 | 4-(trifluoromethyl)phenyl | 2 | —F₂ | LCMS (M + 1)⁺:<br>¹H NMR: δ 1.54 (m, 2H), 1.88 (m, 2H), 3.53 (m, 4H), 5.67 (s, 2H), 6.99 (s, 1H), 7.27 (d, 2H), 7.56 (d, 2H), 7.67 (d, 2H), 7.87 (d, 1H), 8.29 (s, 1H), 8.95 (brs, 2H), 9.25 (brs, 2H); HPLC: 93.59% (Retention Time = 3.359 min). |
| I-284 | 4-(trifluoromethyl)phenyl | 1 | —F | LCMS (M + 1)⁺: 433.2<br>¹H NMR: δ 3.62 (m, 3H), 3.83 (m, 3H), 5.22 (m, 1H), 5.73 (s, 2H), 6.97 (s, 1H), 7.10 (d, 3H), 7.23 (m, 2H), 7.54 (d, 1H), 7.64 (m, 2H), 7.87 (m, 1H), 8.91 (brs, 2H), 9.24 (brs, 2H); HPLC: 88.08% (Retention Time = 6.732 min). |
| I-285 | 4-(trifluoromethyl)phenyl | 1 | —F₂ | LCMS (M + 1)⁺: 451.1<br>¹H NMR: δ 3.62 (m, 3H), 3.83 (m, 3H), 5.73 (s, 2H), 6.92 (s, 1H), 7.19 (d, 3H), 7.55 (d, 1H), 7.63 (m, 2H), 7.88 (d, 1H), 8.20 (d, 1H), 8.88 (brs, 2H), 9.24 (brs, 2H); HPLC: 85.91% (Retention Time = 6.459 min). |

TABLE 9-continued

| Cpd. ID. | R₂ | m | R₃ | Characteristic Data |
|---|---|---|---|---|
| I-286 | 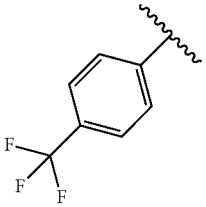 [SMILES: *c1ccc(C(F)(F)F)cc1] | 2 | 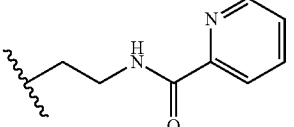 | LCMS (M + 1)⁺: 577.2<br>¹H NMR: δ 0.81 (m, 2H), 1.24 (m, 5H), 1.75 (m, 1H), 2.65 (m, 1H), 2.91 (m, 1H), 3.45 (m, 2H), 4.46 (m, 1H), 5.65 (s, 2H), 6.83 (s, 1H), 7.22 (m, 2H), 7.52 (m, 2H), 7.62 (d, 2H), 7.82 (d, 1H), 7.91 (m, 2H), 8.30 (s, 1H), 8.61 (d, 1H), 8.73 (m, 1H), 8.88 (brs, 2H), 9.18 (brs, 2H); HPLC: 94.95% (Retention Time = 8.471 min). |
| I-287 | 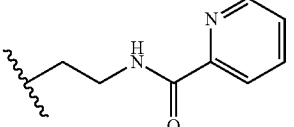 | 2 | —(CH₂)₂O(CH₂)₂OH | LCMS (M + 1)⁺: 517.2<br>¹H NMR: δ 3.46 (m, 3H), 3.51 (m, 3H), 3.72 (m, 2H), 5.65 (s, 2H), 7.02 (s, 1H), 7.21 (d, 2H), 7.55 (d, 1H), 7.61 (d, 2H), 7.86 (d, 1H), 8.19 (s, 1H), 9.10 (brs, 2H), 9.26 (brs, 2H), 10.33 (brs, 1H). |
| I-288 | 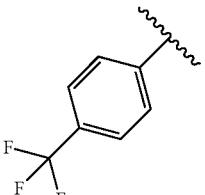 | 2 | —(CH₂)₂NH₂ | LCMS (M + 1)⁺: 488.2<br>¹H NMR: δ 0.52 (m, 4H), 0.81 (m, 2H), 1.48 (m, 2H), 1.61 (m, 2H), 2.65 (m, 2H), 3.71 (m, 2H), 4.49 (m, 1H), 5.61 (s, 2H), 6.82 (s, 1H), 7.16 (d, 2H), 7.24 (d, 2H), 7.55 (d, 1H), 7.63 (m, 3H), 7.82 (d, 2H), 8.28 1H), 9.10 (brs, 2H), 9.22 (brs, 2H); HPLC:? 96.83% (Retention Time = 6.695 min). |
| I-289 | 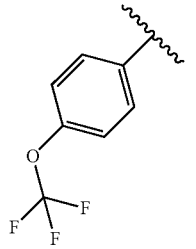 | 2 | —F | LCMS (M + 1)⁺: 463.2<br>¹H NMR: δ 1.48 (m, 2H), 1.75 (m, 2H), 3.61 (m, 4H), 4.71 (m, 1H), 5.60 (s, 2H), 6.92 (s, 1H), 7.19 (d, 2H), 7.32 (d, 2H), 7.56 (d, 1H), 7.86 (d, 1H), 8.32 (s, 1H), 8.96 (brs, 2H), 9.26 (brs, 2H); HPLC: 98.69% (Retention Time = 6.89 min). |
| I-290 | 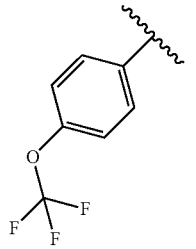 [SMILES: *c1ccc(OC(F)(F)F)cc1] | 2 | —F₂ | LCMS (M + 1)⁺: 481.2<br>¹H NMR: δ 1.48 (m, 2H), 1.85 (m, 2H), 3.61 (m, 4H), 4.71 (m, 1H), 5.59 (s, 2H), 6.97 (s, 1H), 7.19 (d, 2H), 7.31 (d, 2H), 7.55 (d, 1H), 7.86 (d, 1H), 8.32 (s, 1H), 8.94 (brs, 2H), 9.25 (brs, 2H); HPLC: 98.03% (Retention Time = 3.908 min). |
| I-291 | 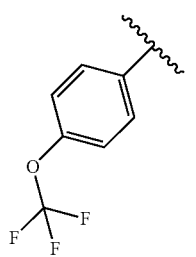 [SMILES: *c1ccc(OC(F)(F)F)cc1] | 2 | —CH₂F | LCMS (M + 1)⁺: 477.2<br>¹H NMR: δ 0.54 (m, 1H), 1.02 (m, 1H), 1.42 (m, 2H), 1.72 (m, 1H), 1.89 (m, 1H), 2.71 (m, 1H), 2.96 (m, 1H), 3.77 (m, 1H), 4.15 (m, 2H), 5.63 (s, 2H), 5.59 (s, 2H), 6.90 (s, 1H), 7.21 (d, 2H), 7.34 (d, 2H), 7.58 (m, 1H), 7.88 (d, 1H), 8.34 (s, 1H), 9.00 (brs, 2H), 9.28 (brs, 2H); HPLC: 95.23% (Retention Time = 3.421 min). |

TABLE 9-continued

| Cpd. ID. | R₂ | m | R₃ | Characteristic Data |
|---|---|---|---|---|
| I-292 | 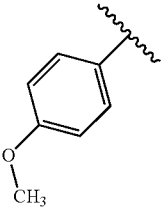 [SMILES: *c1ccc(OC)cc1] | 2 | —(CH₂)₂NH₂ | LCMS (M + 1)⁺: 434.2<br>¹H NMR: δ 0.50 (m, 1H), 0.90 (m, 1H), 1.35 (m, 3H), 1.51 (m, 3H), 1.89 (m, 1H), 2.71 (m, 4H), 3.70 (s, 3H), 4.44 (m, 1H), 5.45 (s, 2H), 6.78 (s, 1H), 6.83 (d, 2H), 7.52 (d, 1H), 7.73 (m, 4H), 8.32 (s, 1H), 9.02 (brs, 2H), 9.23 (brs, 2H). |
| I-293 | 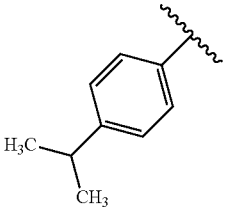 [SMILES: *c1ccc(C(C)C)cc1] | 1 | —F | LCMS (M + 1)⁺: 407.2<br>¹H NMR: δ 1.10 (d, 6H), 2.44 (m, 2H), 2.80 (m, 2H), 3.33 (m, 3H), 3.68 (m, 1H), 5.53 (d, 2H), 6.98 (d, 2H), 7.04 (d, 1H), 7.10 (m, 2H), 7.53 (d, 1H), 7.83 (m, 1H), 8.25 (d, 1H), 8.87 (brs, 2H), 9.25 (brs, 2H); HPLC: 98.1% (Retention Time = 6.996 min). |
| I-294 | 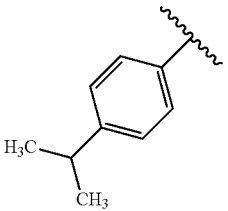 | 1 | —F₂ | LCMS (M + 1)⁺: 425.2<br>¹H NMR: δ 1.11 (d, 6H), 2.35 (m, 1H), 2.80 (m, 1H), 3.49 (m, 1H), 3.66 (m, 1H), 3.79 (m, 2H), 5.55 (d, 2H), 6.96 (m, 2H), 7.08 (m, 3H), 7.54 (d, 1H), 7.84 (d, 1H), 7.29 (s, 1H), 9.04 (brs, 2H), 9.28 (brs, 2H); HPLC: 93.59% (Retention Time = 3.512 min). |
| I-295 | 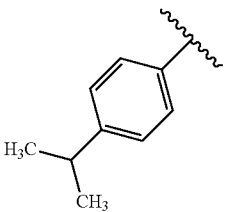 | 2 | —F | LCMS (M + 1)⁺: 421.2<br>¹H NMR: δ 1.12 (d, 6H), 1.58 (m, 2H), 1.72 (m, 2H), 2.79 (m, 1H), 3.59 (m, 4H), 4.64 (m, 1H), 5.50 (d, 2H), 6.85 (s, 1H), 6.98 (d, 2H), 7.14 (d, 2H), 7.54 (d, 1H), 7.83 (d, 1H), 8.34 (s, 1H), 8.96 (brs, 2H), 9.26 (brs, 2H); HPLC: 98.0% (Retention Time = 3.663 min). |
| I-296 | 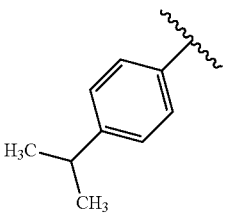 | 2 | —F₂ | LCMS (M + 1)⁺: 439.2<br>¹H NMR: δ 1.11 (d, 6H), 1.24 (m, 2H), 1.82 (m, 2H), 2.79 (m, 1H), 3.35 (m, 2H), 3.65 (m, 2H), 4.64 (m, 1H), 5.52 (s, 2H), 6.91 (s, 1H), 6.99 (d, 2H), 7.15 (d, 2H), 7.56 (d, 1H), 7.84 (d, 1H), 8.38 (s, 1H), 9.15 (brs, 2H), 9.29 (brs, 2H); HPLC: 98.25% (Retention Time = 4.072 min). |
| I-297 | 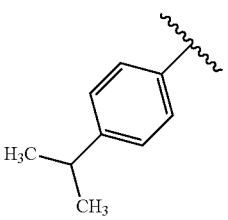 | 2 | —CH₂F | LCMS (M + 1)⁺: 435.2<br>¹H NMR: δ 1.12 (d, 6H), 1.53 (m, 2H), 1.82 (m, 2H), 2.79 (m, 1H), 3.39 (m, 2H), 3.65 (m, 1H), 4.18 (m, 1H), 4.45 (m, 1H), 5.51 (s, 2H), 6.82 (s, 1H), 6.98 (d, 2H), 7.15 (d, 2H), 7.54 (d, 1H), 7.83 (d, 1H), 8.32 (s, 1H), 8.16 (brs, 2H), 9.25 (brs, 2H); HPLC: 97.1% (Retention Time = 3.598 min). |
| I-298 | 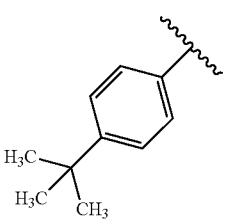 [SMILES: *c1ccc(C(C)(C)C)cc1] | 1 | —F | LCMS (M + 1)⁺: 421.2<br>¹H NMR: δ 1.17 (s, 9H), 1.59 (m, 2H), 1.89 (m, 2H), 2.65 (m, 2H), 3.33 (d, 1H), 5.60 (m, 2H), 6.95 (s, 1H), 7.07 (m, 2H), 7.30 ( m, 2H), 7.59 (m, 1H), 7.90 (d, 1H), 8.29 (d, 1H); HPLC: 92.83% (Retention Time = 6.607 min). |

TABLE 9-continued

| Cpd. ID. | R₂ | m | R₃ | Characteristic Data |
|---|---|---|---|---|
| I-299 | 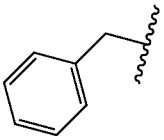 [SMILES: *Cc1ccccc1] | 2 | —(CH₂)₂NH₂ | LCMS (M + 1)⁺: 418.2<br>¹H NMR: δ 1.49 (m, 3H), 1.62 (m, 4H), 2.80 (m, 4H), 3.05 (m, 2H), 3.71 (m, 1H), 4.52 (m, 3H), 6.72 (s, 1H), 7.11 (m, 4H), 7.50 (d, 1H), 7.70 (m, 3H), 8.15 (s, 1H), 8.98 (brs, 2H), 9.26 (brs, 2H); HPLC: 90.67% (Retention Time = 6.348 min). |
| I-300 | 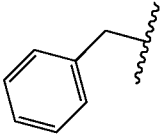 [SMILES: *Cc1ccccc1] | 1 | —(S)NH₂ | LCMS (M + 1)⁺: 376.2<br>¹H NMR: δ 1.97 (m, 1H), 2.22 (m, 1H), 3.12 (m, 3H), 3.51 (m, 4H), 3.85 (m, 1H), 4.61 (m, 2H), 6.35 (d, 1H), 7.11 (d, 1H), 7.20 (m, 4H), 7.53 (d, 1H), 7.80 (d, 1H), 8.19 (m, 4H), 9.24 (brs, 3H); HPLC: 94.87% (Retention Time = 4.465 min). |
| I-301 | 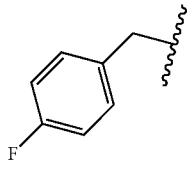 [SMILES: *Cc1ccc(F)cc1] | 2 | —(CH₂)₂NH₂ | LCMS (M + 1)⁺: 436.2<br>¹H NMR: δ 1.49 (m, 2H), 1.61 (m, 4H), 2.80 (m, 3H), 3.05 (m, 2H), 3.71 (m, 2H), 4.52 (m, 3H), 6.73 (s, 1H), 7.05 (m, 4H), 7.50 (d, 1H), 7.70 (m, 4H), 8.15 (s, 1H), 9.10 (brs, 2H), 9.32 (brs, 2H); HPLC: 96.98% (Retention Time = 4.552 min). |
| I-302 | 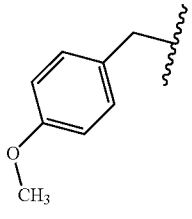 [SMILES: *Cc1ccc(OC)cc1] | 2 | —(CH₂)₂NH₂ | LCMS (M + 1)⁺: 448.3<br>¹H NMR: δ 1.05 (m, 3H), 1.49 (m, 3H), 1.60 (m, 4H), 2.80 (m, 2H), 2.95 (m, 2H), 3.71 (s, 3H), 4.50 (m, 3H), 6.73 (s, 1H), 6.80 (d, 2H), 7.13 (d, 2H), 7.50 (d, 1H), 7.80 (m, 4H), 8.15 (s, 1H), 9.15 (brs, 2H), 9.32 (brs, 2H). |
| I-303 | 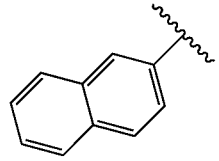 [SMILES: *c1ccc2ccccc2c1] | 2 | —(CH₂)₂NH₂ | LCMS (M + 1)⁺: 454.2<br>¹H NMR: δ 0.52 (m, 1H), 0.85 (m, 2H), 1.33 (m, 5H), 2.60 (m, 2H), 3.44 (m, 2H), 4.50 (m, 1H), 5.70 (m, 2H), 6.93 (s, 1H), 7.20 (d, 2H), 7.43 (m, 5H), 7.81 (m, 3H), 8.40 (s, 1H), 8.92 (brs, 2H), 9.22 (brs, 2H); HPLC: 86.08% (Retention Time = 5.488 min). |
| I-304 | 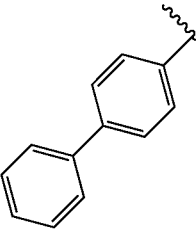 | 2 | —(CH₂)₂NH₂ | LCMS (M + 1)⁺: 480.3<br>¹H NMR: δ 0.50 (m, 1H), 0.85 (m, 1H), 1.33 (m, 4H), 1.71 (m, 1H), 2.65 (m, 3H), 2.82 (m, 1H), 3.72 (m, 1H), 4.50 (m, 1H), 5.60 (m, 2H), 6.85 (s, 1H), 7.18 (d, 2H), 7.35 (m, 1H), 7.45 (m, 2H), 7.55 (m, 7H), 7.85 (d, 1H), 8.35 (s, 1H), 9.04 (brs, 2H), 9.34 (brs, 2H). |
| I-305 | 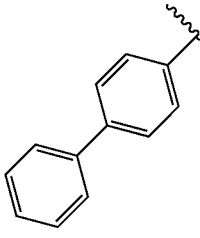 | 2 | —F | LCMS (M + 1)⁺: 455.2<br>¹H NMR: δ 1.07 (m, 2H), 1.59 (brs, 2H), 1.89 (m, 2H), 3.65 (m, 2H), 4.80 (m, 1H), 5.60 (m, 2H), 6.95 (s, 1H), 7.07 (m, H), 7.40 (m, 1H), 7.59 (m, 2H), 7.90 (d, 1H), 7.75 (d, 5H), 8.29 (s, 1H), 9.04 (brs, 2H), 9.34 (brs, 2H). |

TABLE 9-continued

| Cpd. ID. | R₂ | m | R₃ | Characteristic Data |
|---|---|---|---|---|
| I-306 | 4-biphenyl | 2 | —F₂ | LCMS (M + 1)⁺: 473.2<br>¹H NMR: δ 1.44 (m, 2H), 1.91 (m, 2H), 3.40 (m, 2H), 3.68 (m, 2H), 5.61 (s, 2H), 6.96 (s, 1H), 7.17 (d, 2H), 7.35 (m, 1H), 7.42 (m, 2H), 7.55 (m, 5H), 7.86 (d, 1H), 9.01 (brs, 2H), 9.29 (brs, 2H); HPLC: 98.3% (Retention Time = 3.602 min). |
| I-307 | 4-biphenyl | 2 | —F₂ | LCMS (M + 1)⁺: 473.2<br>¹H NMR: δ 1.41 (m, 2H), 2.11 (m, 2H), 3.62 (m, 4H), 5.60 (s, 2H), 6.93 (s, 1H), 7.18 (m, 2H), 7.35 (m, 1H), 7.44 (m, 2H), 7.56 (m, 5H), 7.86 (d, 1H), 9.01 (brs, 2H), 9.29 (brs, 2H); HPLC: 95.6% (Retention Time = 4.033 min). |
| I-308 | 4-biphenyl | 2 | —CH₂F | LCMS (M + 1)⁺: 469.2<br>¹H NMR: δ 0.5 (m, 1H), 1.0 (m, 1H), 1.38 (m, 1H), 1.65 (m, 2H), 2.72 (m, 1H), 2.95 (m, 1H), 3.78 (m, 1H), 3.98 (m, 2H), 4.51 (m, 1H), 5.62 (d, 2H), 6.89 (s, 1H), 7.19 (d, 2H), 7.38 (m, 1H), 7.40 (m, 2H), 7.59 (m, 5H), 7.88 (d, 1H), 8.38 (s, 1H), 8.91 (brs, 2H), 9.29 (brs, 2H); HPLC: 91.12% (Retention Time = 3.976 min). |
| I-309 | 4-biphenyl | 1 | —F | LCMS (M + 1)⁺: 441.2<br>¹H NMR: δ 1.57 (m, 1H), 2.05 (m, 2H), 3.56 (m, 2H), 3.64 (m, 2H), 3.68 (m, 2H), 5.64 (m, 2H), 7.09 (d, 1H), 7.17 (m, 2H), 7.33 (m, 2H), 7.53 (m, 5H), 7.85 (m, 1H), 8.29 (d, 1H), 9.00 (brs, 2H), 9.28 (brs, 2H); HPLC: 95.82% (Retention Time = 3.8 min). |
| I-310 | 4-biphenyl | 1 | —F₂ | LCMS (M + 1)⁺: 459.2<br>¹H NMR: δ 2.35 (m, 1H), 2.42 (m, 1H), 3.61 (m, 2H), 3.90 (m, 2H), 5.69 (d, 2H), 7.17 (m, 3H), 7.37 (m, 3H), 7.61 (m, 5H), 7.90 (d, 1H), 7.34 (s, 1H), 9.13 (brs, 2H), 9.32 (brs, 2H); HPLC: 96.98% (Retention Time = 3.436 min). |
| I-311 | 4-biphenyl | 2 | 1,2-phenylene (spirocyclic) | LCMS (M + 1)⁺: 485.2<br>¹H NMR: δ 2.54 (m, 1H), 2.74 (m, 1H), 3.42 (m, 1H), 3.81 (m, 1H), 4.62 (m, 1H), 4.75 (m, 1H), 5.60 (s, 2H), 7.00 (m, 4H), 7.20 (m, 4H), 7.43 (m, 4H), 7.56 (m, 3H), 7.88 (m, 1H), 8.34 (s, 1H), 8.99 (brs, 2H), 9.28 (brs, 2H); HPLC: 87.73% (Retention Time = 4.384 min). |

TABLE 9-continued

| Cpd. ID. | R₂ | m | R₃ | Characteristic Data |
|---|---|---|---|---|
| I-312 | 4-phenoxyphenyl | 2 | —(CH₂)₂NH₂ | LCMS (M + 1)⁺: 496.3<br>¹H NMR: δ 0.88 (m, 2H), 1.45 (m, 2H), 1.51 (m, 4H), 2.81 (m, 2H), 3.62 (m, 2H), 4.45 (m, 1H), 5.60 (s, 2H), 6.82 (s, 1H), 6.95 (d, 3H), 7.10 (d, 3H), 7.33 (m, 2H), 7.53 (d, 2H), 7.77 (brs, 3H), 7.81 (d, 1H), 8.32 (s, 1H), 9.02 (brs, 2H), 9.25 (brs, 2H). |
| I-313 | 4-phenoxyphenyl | 1 | —F | LCMS (M + 1)⁺: 457.2<br>¹H NMR: δ 2.28 (m, 3H), 3.48 (m, 4H), 5.60 (d, 2H), 6.87 (m, 4H), 7.10 (m, 4H), 7.33 (m, 2H), 7.53 (d, 2H), 7.83 (m, 1H), 8.28 (s, 1H), 8.96 (brs, 2H), 9.25 (brs, 2H); HPLC: 93.81% (Retention Time = 6.425 min). |
| I-314 | 4-phenoxyphenyl | 1 | —F₂ | LCMS (M + 1)⁺: 475.2<br>¹H NMR: δ 2.28 (m, 1H), 2.41 (m, 1H), 3.58 (m, 2H), 3.68 (m, 1H), 3.81 (m, 2H), 5.60 (d, 2H), 6.89 (m, 4H), 7.10 (m, 4H), 7.34 (m, 2H), 7.56 (d, 2H), 7.84 (d, 1H), 8.39 (s, 1H), 9.06 (brs, 2H), 9.37 (brs, 2H); HPLC: 91.0% (Retention Time = 3.501 min). |
| I-315 | 4-phenoxyphenyl | 2 | —F₂ | LCMS (M + 1)⁺: 489.2<br>¹H NMR: δ 1.49 (m, 2H), 2.08 (m, 2H), 3.36 (m, 2H), 3.91 (m, 2H), 5.53 (s, 2H), 6.88 (m, 5H), 7.10 (m, 3H), 7.34 (m, 2H), 7.54 (d, 2H), 7.80 (d, 1H), 8.25 (s, 1H); HPLC: 97.09% (Retention Time = 6.694 min). |
| I-316 | 4-(4-fluorophenoxy)phenyl | 2 | —(CH₂)₂NH₂ | LCMS (M + 1)⁺: 514.2<br>¹H NMR: δ 0.61 (m, 1H), 1.21 (m, 1H), 1.49 (m, 4H), 1.85 (m, 2H), 2.71 (m, 2H), 3.71 (m, 1H), 4.45 (m, 1H), 4.53 (m, 1H), 5.51 (s, 2H), 6.81 (s, 1H), 6.87 (m, 2H), 7.95 (m, 2H), 7.13 (m, 4H), 7.57 (d, 1H), 7.80 (d, 1H), 7.97 (brs, 2H), 8.40 (s, 1H), 9.32 (brs, 3H); HPLC: 95.49% (Retention Time = 5.995 min). |

TABLE 9-continued

| Cpd. ID. | R₂ | m | R₃ | Characteristic Data |
|---|---|---|---|---|
| I-317 | 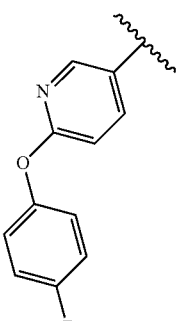 | 2 | —(CH₂)₂NH₂ | LCMS (M + 1)⁺: 515.2<br>¹H NMR: δ 1.49 (m, 4H), 1.71 (m, 2H), 2.81 (m, 4H), 3.72 (m, 2H), 4.50 (m, 1H), 5.51 (s, 2H), 6.85 (s, 1H), 6.97 (d, 1H), 7.11 (m, 2H), 7.22 (m, 2H), 7.52 (d, 1H), 7.70 (m, 3H), 7.81 (d, 1H), 8.60 (s, 1H), 8.95 (d, 2H), 9.25 (brs, 2H); HPLC: 99.15% (Retention Time = 4.707 min). |
| I-318 | 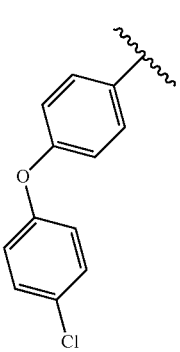 [SMILES: *c1ccc(Oc2ccc(F)cc2)cc1] | 2 | —(CH₂)₂NH₂ | LCMS (M + 1)⁺: 530.2<br>¹H NMR: δ 0.61 (m, 1H), 1.21 (m, 1H), 1.51 (m, 4H), 1.85 (m, 2H), 2.71 (m, 2H), 2.82 (m, 1H), 3.85 (m, 1H), 4.53 (m, 1H), 5.61 (s, 2H), 6.85 (s, 1H), 6.97 (m, 4H), 7.11 (m, 2H), 7.33 (d, 2H), 7.52 (d, 1H), 7.80 (d, 1H), 7.97 (brs, 2H), 8.43 (s, 1H), 9.32 (brs, 3H). |
| I-319 | 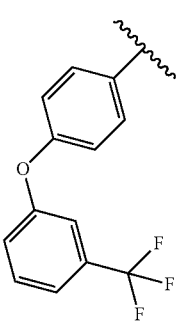 [SMILES: *c1ccc(Oc2cccc(C(F)(F)F)c2)cc1] | 2 | —(CH₂)₂NH₂ | LCMS (M + 1)⁺: 564.2<br>¹H NMR: δ 1.49 (m, 4H), 1.71 (m, 1H), 2.61 (m, 4H), 3.68 (m, 3H), 4.44 (m, 1H), 4.52 (m, 1H), 6.82 (s, 1H), 7.21 (d, 2H), 7.19 (m, 4H), 7.42 (m, 1H), 7.53 (m, 2H), 7.73 (m, 3H), 8.32 (s, 1H), 9.11 (brs, 2H), 9.25 (brs, 2H); HPLC: 99.5% (Retention Time = 7.501 min). |
| I-320 | 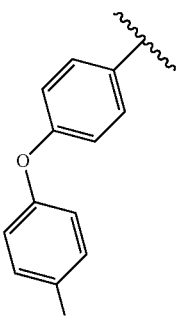 | 2 | —(CH₂)₂NH₂ | LCMS (M + 1)⁺: 511.3<br>¹H NMR: δ 0.61 (m, 2H), 0.98 (m, 2H), 1.21 (m, 1H), 1.42 (m, 4H), 2.62 (m, 3H), 3.75 (m, 1H), 4.50 (m, 2H), 5.51 (s, 2H), 6.95 (s, 1H), 6.97 (m, 4H), 7.11 (m, 4H), 7.53 (d, 1H), 7.81 (m, 3H), 8.33 (s, 1H), 9.22 (brs, 3H). |

TABLE 9-continued

| Cpd. ID. | R₂ | m | R₃ | Characteristic Data |
|---|---|---|---|---|
| I-321 | 3-phenoxyphenyl | 2 | —(CH₂)₂NH₂ | LCMS (M + 1)⁺: 496.3<br>¹H NMR: δ 0.51 (m, 1H), 0.91 (m, 1H), 1.37 (m, 6H), 2.71 (m, 4H), 4.45 (m, 1H), 6.85 (s, 1H), 6.95 (m, 4H), 7.20 (m, 1H), 7.35 (m, 3H), 7.58 (d, 1H), 7.88 (m, 3H), 8.32 (s, 1H), 9.10 (brs, 2H), 9.35 (brs, 2H); HPLC: 98.12% (Retention Time = 6.806 min). |
| I-322 | 4-(trifluoromethyl)phenyl | 2 | —(CH₂)₃C(O)NH₂ | LCMS (M + 1)⁺: 514.2<br>¹H NMR: δ 0.48 (m, 1H), 0.95 (m, 1H), 1.15 (m, 2H), 1.49 (m, 2H), 1.52 (m, 2H), 1.71 (m, 1H), 2.15 (m, 2H), 2.71 (m, 1H), 2.81 (m, 1H), 3.71 (m, 1H), 4.50 (m, 1H), 5.65 (s, 2H), 6.85 (d, 2H), 7.55 (m, 3H), 7.86 (d, 1H), 8.15 (s, 1H); HPLC: 98.79% (Retention Time = 7.879 min). |

General syntheic scheme 5

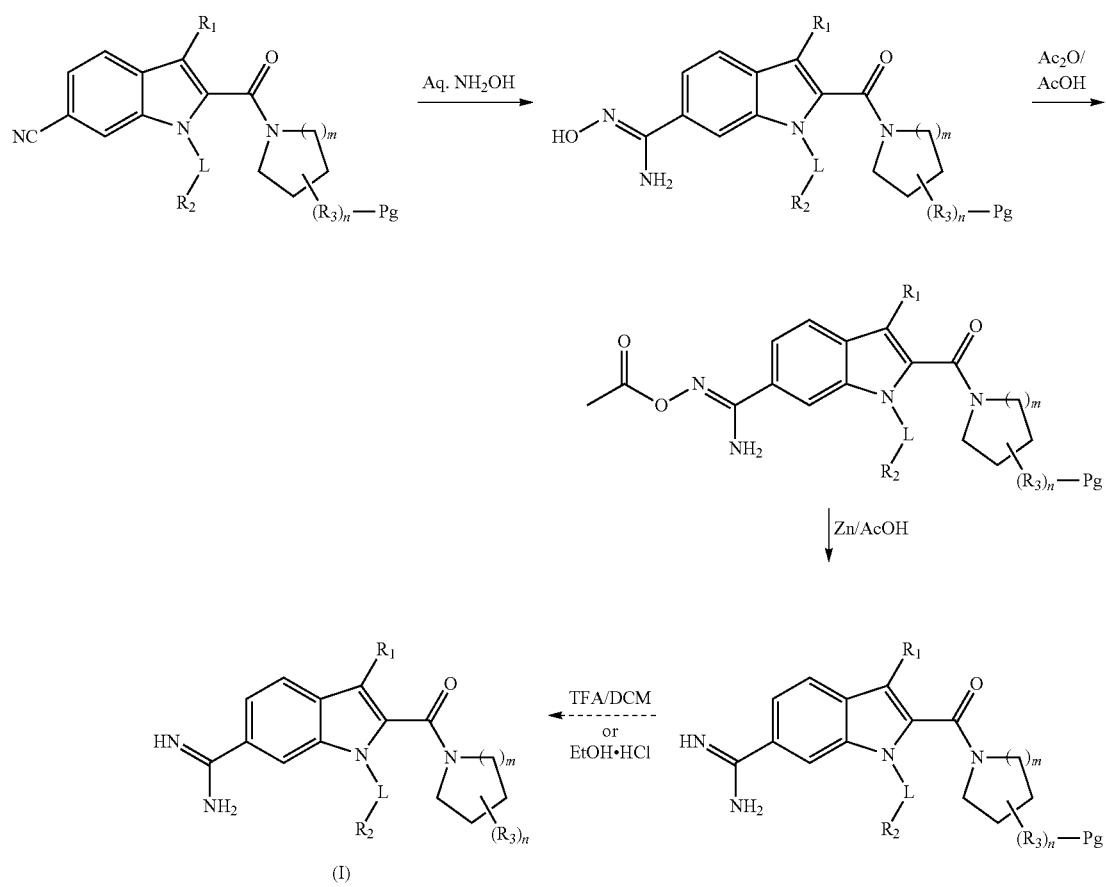

R₁ = H, Pg = optional protecting group; - - -▶ optional step when Pg is present; R₂, R₃, m and n are as defined in formula (I)

Another general approach for the synthesis of compounds of general formula (I) is depicted in general synthetic scheme-5. C (2) amide derived 6-cyano indole 2 carboxylic acid derivatives were treated with hydroxylamine to form amidoxime derivatives which were acylated with Ac₂O and reduced with Zn/AcOH to install the amidine functionality. Deprotection of acidic labile protecting with a suitable reagent (TFA/DCM or EtOH·HCl) to afforded compound of formula (I).

Example 69: Synthesis of Compound I-323

3-((6-Carbamimidoyl-2-(3-fluoropyrrolidine-1-carbonyl)-1H-indol-1-yl)methyl)benzamide

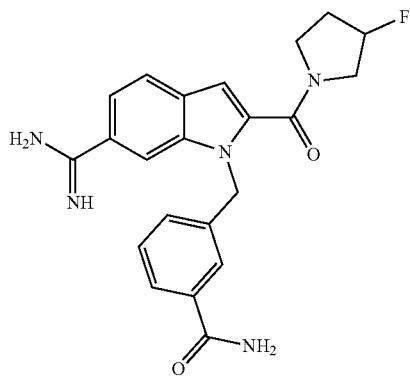 [SMILES: N=C(N)c1ccc2cc(C(=O)N3CCC(F)C3)n(Cc3cccc(C(N)=O)c3)c2c1]

Step-1: Ethyl 1-(3-carbamoylbenzyl)-6-cyano-1H-indole-2-carboxylate

Ethyl 6-cyano-1H-indole-2-carboxylate (3.57 g, 16.71 mmol) and 3-(bromomethyl)benzamide (3.56 g, 16.71 mmol) were treated together to afford the title compound following the procedure described in step-1 of example-68. LCMS: 348.1 (M+1)⁺.

Step-2: 1-(3-carbamoylbenzyl)-6-cyano-1H-indole-2-carboxylic Acid

Product of step-1 of example-69 (1.2 g, 3.45 mmol) was treated with lithium hydroxide (331 mg, 13.82 mmol) to afford the title compound (770 mg) following the procedure described in step-2 of example 1. LCMS: 320.1 (M+1)⁺.

Step-3: 3-((6-Cyano-2-(3-fluoropyrrolidine-1-carbonyl)-1H-indol-1-yl)methyl)benzamide Product of step-2 of example-69 (700 mg, 2.19 mmol) was treated with 3-fluoropyrrolidine (195 mg, 2.19 mmol) to afford the title compound (525 mg) following the procedure described in step-3 of example 1. LCMS: 391.1 (M+1)⁺.

Step-4: 3-((2-(3-fluoropyrrolidine-1-carbonyl)-6-(N'-hydroxycarbamimidoyl)-1H-indol-1-yl)methyl)benzamide The product of step-3 of example-69 (500 mg, 1.28 mmol) was dissolved in 20 mL of ethanol and added aqueous hydroxylamine solution (0.3 mL) and resulting mixture was refluxed for 4-6 h at 80° C. Solvent was evaporated under vacuum to afford the title compound (425 mg) which was used for the next step without further purification. LCMS: 424.2 (M+1)⁺.

Step-5: 3-((6-(N'-Acetoxycarbamimidoyl)-2-(3-fluoropyrrolidine-1-carbonyl)-1H-indol-1-yl)methyl)benzamide The product of step-4 of example-69 (400 mg, 0.94 mmol) was dissolved in 10 mL of acetic acid and added acetic anhydride (767 mg, 7.52 mmol) and resulting mixture was stirred at RT for 2 h. Solvent was evaporated under vacuum to afford the title compound (260 mg) which was used for the next step without further purification. LCMS: 466.2 (M+1)⁺.

Step-6: 3-((6-Carbamimidoyl-2-(3-fluoropyrrolidine-1-carbonyl)-1H-indol-1-yl)methyl)benzamide The product of step-5 of example-69 (250 mg, 0.53 mmol) was dissolved in 5 mL of acetic acid and added Zn (275 mg, 4.3 mmol) in portions and resulting mixture was stirred at RT for 6-8 h. Reaction mixture was filtered through celite pad and resulting filtrate was concentrated under vacuum to give crude product which was purified with reversed-phase preparative HPLC and afforded the title compound (75 mg). LCMS: 408.2 (M+1)⁺, ¹H NMR (300 MHz, DMSO-d₆): δ 2.05 (m, 3H), 3.43 (m, 2H), 3.57 (m, 2H), 5.67 (s, 2H), 7.10 (m, 2H), 7.26 (m, 3H), 7.55 (m, 2H), 7.72 (m, 1H), 7.85 (m, 1H), 7.88 (m, 1H), 8.24 (d, 1H), 9.04 (brs, 2H), 9.25 (brs, 2H); HPLC: 96.03% (Retention Time=5.033 min).

The following compounds listed in table-10 were prepared according to scheme-5 by following similar procedure as described above for example-69 using appropriate reagents with suitable modifications known to the one skilled in the art.

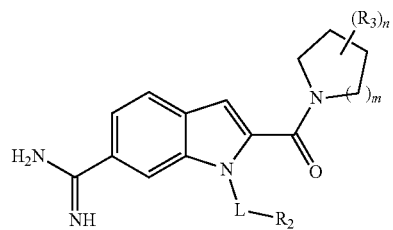

TABLE 10

| Cpd. ID. | L | R₂ | m | R₃ (binding site) | Characteristic Data |
|---|---|---|---|---|---|
| I-324 | —CH₂— | 3-carbamoylphenyl | 1 | —F₂ | LCMS (M + 1)⁺: 426.2<br>¹H NMR: δ 2.24 (m, 2H), 3.53 (m, 2H), 3.80 (m, 2H), 5.67 (s, 2H), 7.15 (m, 2H), 7.29 (m, 3H), 7.52 (m, 2H), 7.75 (m, 1H), 7.86 (m, 1H), 7.94 (m, 1H), 9.00 (brs, 2H), 9.26 (brs, 2H); HPLC: 95.0% (Retention Time = 5.282 min). |
| I-325 | —CH₂— | 3-carbamoylphenyl | 2 | —CH₂F | LCMS (M + 1)⁺: 436.2<br>¹H NMR: δ 1.28 (m, 2H), 1.52 (m, 2H), 2.63 (m, 2H), 3.53 (m, 2H), 4.12 9 (m, 1H), 4.80 (m, 2H), 5.61 (s, 2H), 6.87 (s, 1H), 7.29 (m, 1H), 7.38 (m, 2H), 7.55 (m, 2H), 7.75 (d, 1H), 7.85 (d, 1H), 7.95 (s, 1H), 8.31 (s, 1H), 8.97 (brs, 2H), 9.25 (brs, 2H); HPLC: 97.74% (Retention Time = 5.495 min). |
| I-326 | —CH₂— | 4-carbamoylphenyl | 2 | —F | LCMS (M + 1)⁺: 422.2<br>¹H NMR: δ 1.84 (m, 4H), 1.89 (m, 4H), 4.8 (d, 1H), 5.85 (s, 2H), 6.95 (s, 1H), 7.17 (m, 2H), 7.40 (s, 1H), 7.59 (d, 1H), 7.81 (d, 2H), 7.90 (d, 1H), 7.95 (brs, 1H), 8.29 (s, 1H), 8.91 (brs, 2H), 9.28 (brs, 2H); HPLC: 85.43% (Retention Time = 5.317 min). |
| I-327 | —CH₂— | 4-carbamoylphenyl | 2 | —F₂ | LCMS (M + 1)⁺: 440.2<br>¹H NMR: δ 1.07 (m, 2H), 1.59 (brs, 2H), 1.89 (brs, 2H), 3.65 (brs, 2H), 5.60 (s, 2H), 6.95 (s, 1H), 7.17 (m, 2H), 7.40 (s, 1H), 7.59 (d, 1H), 7.81 (d, 2H), 7.90 (d, 1H), 7.95 (brs, 1H), 8.29 (s, 1H), 8.91 (brs, 2H), 9.28 (brs, 2H); HPLC: 95.62% (Retention Time = 5.496 min). |
| I-328 | —CH₂— | 4-carbamoylphenyl | 2 | —F₂ | LCMS (M + 1)⁺: 440.2<br>¹H NMR: δ 1.49 (m, 1H), 1.71 (m, 1H), 2.04 (m, 2H), 3.77 (m, 3H), 4.05 (m, 1H), 5.58 (s, 2H), 6.92 (m, 1H), 7.10 (d, 2H), 7.33 (s, 1H), 7.53 (d, 1H), 7.75 (d, 2H), 7.85 (m, 2H), 8.13 (brs, 2H), 8.92 (brs, 2H), 9.25 (s, 2H); HPLC: 98.02% (Retention Time = 5.91 min). |
| I-329 | —CH₂— | 4-carbamoylphenyl | 2 | —CF₃ | LCMS (M + 1)⁺: 472.2<br>¹H NMR: δ 0.59 (m, 2H), 1.08 (m, 2H), 1.55 (m, 1H), 1.85 (m, 1H), 2.71 (m, 1H), 3.02 (m, 1H), 4.51 (m, 1H), 5.60 (d, 2H), 6.94 (s, 1H), 7.10 (d, 2H), 7.55 (d, 1H), 7.78 (d, 2H), 7.89 (d, 1H), 8.24 (s, 1H), 9.01 (brs, 2H), 9.25 (s, 2H); HPLC: 98.23% (Retention Time = 6.268 min). |
| I-330 | —CH₂— | 4-carbamoylphenyl | 1 | —(R)F | LCMS (M + 1)⁺: 408.2<br>¹H NMR: δ 1.84 (m, 4H), 1.89 (m, 4H), 4.82 (d, 1H), 5.87 (m, 2H), 6.94 (s, 1H), 7.17 (m, 2H), 7.40 (s, 1H), 7.59 (d, 1H), 7.81 (d, 2H), 7.90 (d, 1H), 7.90 (brs, 1H), 8.22 (d, 1H); HPLC: 95.65% (Retention Time = 3.86 min). |

TABLE 10-continued

| Cpd. ID. | L | R₂ | m | R₃ (binding site) | Characteristic Data |
|---|---|---|---|---|---|
| I-331 | —CH₂— | 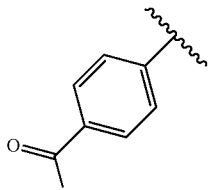 | 1 | —F₂ | LCMS (M + 1)⁺: 426.2<br>¹H NMR: δ 2.40 (m, 2H), 3.40 (m, 1H), 3.71 (m, 2H), 3.90 (m, 2H), 5.72 (m, 2H), 7.17 (m, 1H), 7.19 (brs, 1H), 7.39 (brs, 1H), 7.60 (d, 1H), 7.85 (m, 2H), 7.99 (s, 1H), 8.24 (brs, 1H), 9.14 (brs, 2H), 9.24 (brs, 2H); HPLC: 95.06% (Retention Time = 5.261 min). |
| I-332 | —CH₂— | 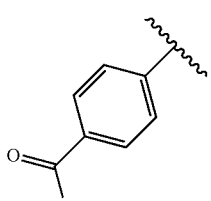 | 2 | —CH₂F | LCMS (M + 1)⁺: 436.2<br>¹H NMR: δ 1.23 (m, 2H), 1.60 (m, 2H), 2.76 (m, 2H), 3.53 (m, 2H), 4.12 (m, 1H), 4.80 (m, 2H), 5.61 (s, 2H), 6.88 (s, 1H), 7.12 (d, 2H), 7.36 (s, 1H), 7.55 (d, 1H), 7.78 (d, 1H), 7.85 (d, 1H), 7.93 (s, 1H), 8.25 (s, 1H), 9.01 (brs, 2H), 9.24 (brs, 2H); HPLC: 98.31% (Retention Time = 5.28 min). |
| I-333 | —CH₂— | 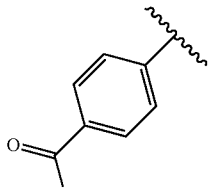 | 1 | 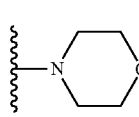 | LCMS (M + 1)⁺: 475.2<br>¹H NMR: δ 1.82 (m, 2H), 2.35 (m, 2H), 3.62 (m, 6H), 3.82 (m, 2H), 5.62 (m, 3H), 7.17 (m, 1H), 7.07 (m, 2H), 7.36 (brs, 1H), 7.53 (d, 1H), 7.75 (d, 2H), 7.86 (d, 1H), 7.90 (brs, 1H), 8.19 (s, 1H), 8.99 (brs, 2H), 9.23 (brs, 2H). |
| I-334 | —SO₂— | 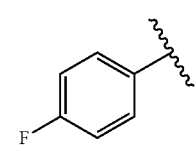 | 2 | —(CH₂)₂NH₂ | LCMS (M + 1)⁺: 472.2<br>¹H NMR: δ 1.52 (m, 5H), 1.81 (m, 1H), 2.81 (m, 3H), 3.21 (m, 1H), 3.47 (m, 2H), 4.52 (m, 1H), 7.71 (s, 1H), 7.46 (m, 2H), 7.72 (m, 1H), 7.78 (brs, 2H), 7.88 (m, 1H), 8.32 (m, 3H), 9.25 (brs, 2H), 9.45 (brs, 2H). |
| I-335 | —SO₂— | 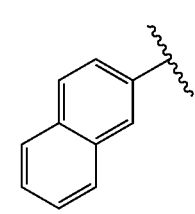 [SMILES: *c1ccc2ccccc2c1] | 2 | —(CH₂)₂NH₂ | LCMS (M + 1)⁺: 504.2<br>¹H NMR: δ 1.21 (m, 2H), 1.50 (m, 5H), 2.81 (m, 2H), 3.15 (m, 1H), 3.48 (m, 2H), 4.60 (m, 1H), 7.11 (s, 1H), 7.65 (m, 6H), 7.82 (d, 1H), 8.01 (d, 1H), 8.12 (m, 3H), 8.45 (s, 1H), 8.95 (s, 1H), 9.20 (brs, 2H), 9.42 (brs, 2H); HPLC: 90.02% (Retention Time = 5.696 min). |
| I-336 | —SO₂— | 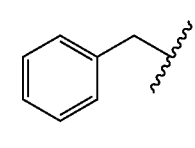 [SMILES: *Cc1ccccc1] | 2 | —(CH₂)₂NH₂ | LCMS (M + 1)⁺: 468.2<br>¹H NMR: δ 1.21 (m, 2H), 1.45 (m, 5H), 2.81 (m, 2H), 3.15 (m, 2H), 3.65 (m, 1H), 4.51 (m, 1H), 5.21 (s, 2H), 6.78 (s, 1H), 7.08 (m, 1H), 7.16 (m, 5H), 7.53 (m, 1H), 7.65 (s, 4H), 7.80 (d, 1H), 9.05 (brs, 2H), 9.22 (brs, 2H); HPLC: 91.69% (Retention Time = 6.826 min). |
| I-337 | —CH₂— | 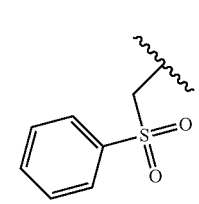 [SMILES: *CS(=O)(=O)c1ccccc1] | 2 | —(CH₂)₂NH₂ | LCMS (M + 1)⁺: 482.2<br>¹H NMR: δ 1.49 (m, 6H), 1.51 (m, 6H), 2.81 (m, 3H), 3.15 (m, 2H), 3.91 (m, 2H), 4.11 (m, 1H), 4.45 (m, 1H), 4.71 (m, 2H), 6.78 (s, 1H), 7.49 (m, 1H), 7.62 (m, 6H), 7.87 (m, 2H), 7.95 (s, 1H), 9.05 (brs, 2H), 9.25 (brs, 2H); HPLC: 97.62% (Retention Time = 4.705 min). |

TABLE 10-continued

| Cpd. ID. | L | R₂ | m | R₃ (binding site) | Characteristic Data |
|---|---|---|---|---|---|
| I-338 | —CH₂— | 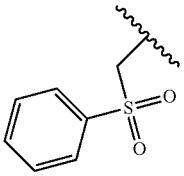 [SMILES: *CS(=O)(=O)c1ccccc1] | 2 | 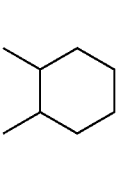 | LCMS (M + 1)⁺: 493.2<br>¹H NMR: δ 1.31 (m, 6H), 1.51 (m, 6H), 3.21 (m, 1H), 3.52 (m, 1H), 3.75 (m, 3H), 4.41 (m, 3H), 6.72 (m, 1H), 7.49 (d, 1H), 7.62 (m, 2H), 7.72 (m, 2H), 7.85 (m, 2H), 7.94 (s, 1H), 9.10 (brs, 2H), 9.25 (brs, 2H); HPLC: 99.41% (Retention Time = 6.109 min). |
| I-339 | —CH₂— | 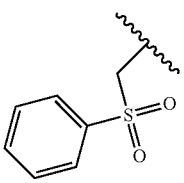 [SMILES: *CS(=O)(=O)c1ccccc1] | 2 | 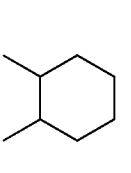 | LCMS (M + 1)⁺: 493.2<br>¹H NMR: δ 0.98 (m, 2H), 1.15 (m, 5H), 1.51 (m, 5H), 2.71 (m, 1H), 3.15 (m, 1H), 3.81 (m, 3H), 3.89 (m, 3H), 4.31 (m, 1H), 4.61 (m, 2H), 6.75 (s, 1H), 7.51 (d, 1H), 7.65 (m, 2H), 7.55 (m, 2H), 7.82 (d, 2H), 7.94 (s, 1H), 9.11 (brs, 2H), 9.25 (brs, 2H); HPLC: 99.64% (Retention Time = 6.153 min). |
| I-340 | —CH₂— | 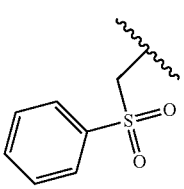 [SMILES: *CS(=O)(=O)c1ccccc1] | 2 | —CH₃ | LCMS (M + 1)⁺: 453.2<br>¹H NMR: δ 0.92 (d, 3H), 1.22 (m, 2H), 1.68 (m, 3H), 2.71 (m, 1H), 3.15 (m, 1H), 3.90 (m, 4H), 4.35 (m, 1H), 4.65 (m, 2H), 6.76 (s, 1H), 7.51 (d, 1H), 7.65 (m, 2H), 7.76 (m, 2H), 7.87 (d, 2H), 7.97 (s, 1H), 9.16 (brs, 2H), 9.27 (brs, 2H); HPLC: 97.99% (Retention Time = 3.699 min). |
| I-341 | —CH₂— | 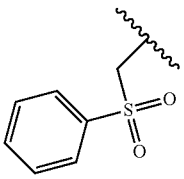 [SMILES: *CS(=O)(=O)c1ccccc1] | 1 | —F | LCMS (M + 1)⁺: 443.2<br>¹H NMR: δ 2.15 (m, 2H), 2.44 (m, 2H), 3.67 (m, 4H), 4.71 (m, 2H), 5.33 (m, 1H), 7.02 (d, 1H), 7.52 (d, 1H), 7.64 (m, 2H), 7.76 (m, 1H), 7.81 (m, 4H), 7.96 (s, 1H), 9.04 (brs, 2H), 9.30 (brs, 2H); HPLC: 86.65% (Retention Time = 3.305 min). |
| I-342 | —CH₂— | 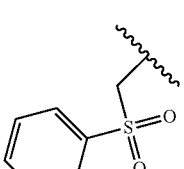 | 1 | —F₂ | LCMS (M + 1)⁺: 461.1<br>¹H NMR: δ 2.24 (m, 2H), 3.71 (m, 1H), 3.92 (m, 4H), 4.18 (m, 1H), 4.83 (m, 2H), 7.07 (d, 1H), 7.52 (d, 1H), 7.63 (m, 2H), 7.74 (m, 1H), 7.81 (m, 3H), 7.97 (brs, 1H), 9.08 (brs, 2H), 9.30 (brs, 2H); HPLC: 96.74% (Retention Time = 5.99 min). |
| I-343 | —CH₂— | 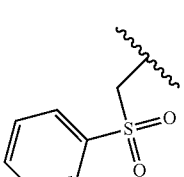 | 2 | —F | LCMS (M + 1)⁺: 457.2<br>¹H NMR: δ 1.79 (m, 4H), 3.67 (m, 4H), 3.91 (m, 2H), 4.72 (m, 2H), 4.91 (m, 1H), 6.84 (s, 1H), 7.51 (d, 1H), 7.65 (m, 2H), 7.74 (m, 2H), 7.81 (d, 1H), 7.97 (s, 1H), 9.18 (brs, 2H), 9.28 (brs, 2H); HPLC: 98.84% (Retention Time = 6.551 min). |
| I-344 | —CH₂— | 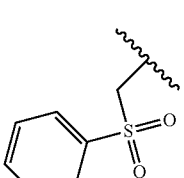 | 2 | —F₂ | LCMS (M + 1)⁺: 475.2<br>¹H NMR: δ 2.09 (m, 4H), 3.77 (m, 4H), 3.92 (m, 2H), 4.78 (m, 2H), 6.91 (s, 1H),<br>7.52 (d, 1H), 7.64 (m, 2H), 7.74 (m, 1H), 7.80 (d, 1H), 7.86 (d, 2H), 7.98 (s, 1H), 9.18 (brs, 2H), 9.29 (brs, 2H); HPLC: 97.1% (Retention Time = 3.105 min). |

General synthetic scheme - 6

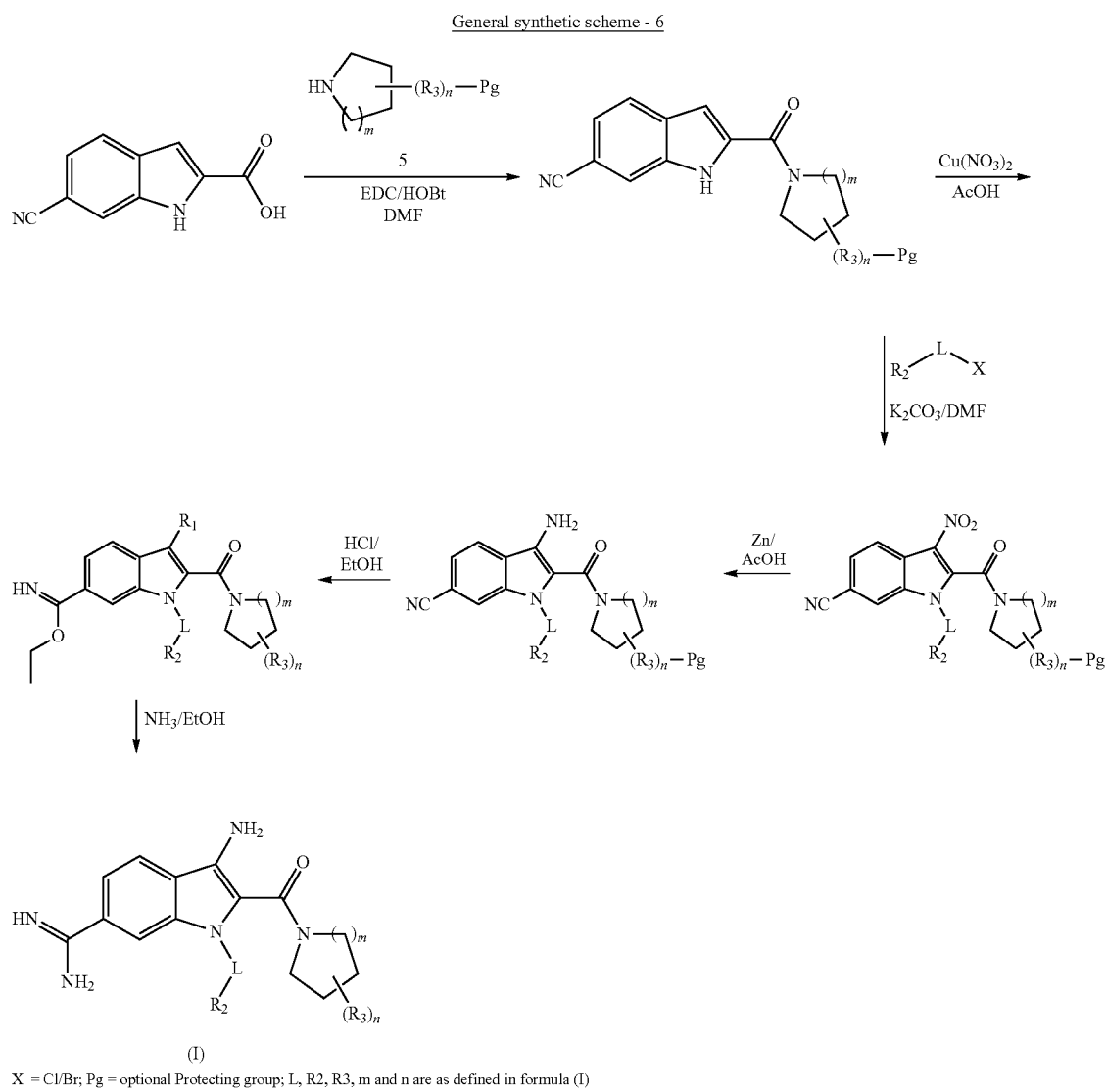

X = Cl/Br; Pg = optional Protecting group; L, R2, R3, m and n are as defined in formula (I)

Yet another general approach for the synthesis of compounds of general formula (I) is depicted in general synthetic scheme-6. 6-cyano indole 2-carboxylic acid on coupling with suitable amines under standard coupling conditions yields coupled compound which was then dissolved in acetic acid and treated with copper(II)nitrate trihydrate to get 3-nitro indole derivatives which on further treatment with alkyl halide in presence of a suitable base ($K_2CO_3$) and a suitable solvent (DMF) yielded N-alkylated analogs which upon reducing with Zn/glacial AcOH affords 3-amino derivatives. The corresponding 3-amino analogs were then treated with ethanolic HCl to get compound imidates, which was then treated with ethanolic ammonia to afford compound of formula (I).

Example 70: Synthesis of Compound I-345

3-Amino-2-(4-(2-aminoethyl)piperidine-1-carbonyl)-1-isopentyl-1H-indole-6-carboximidamide

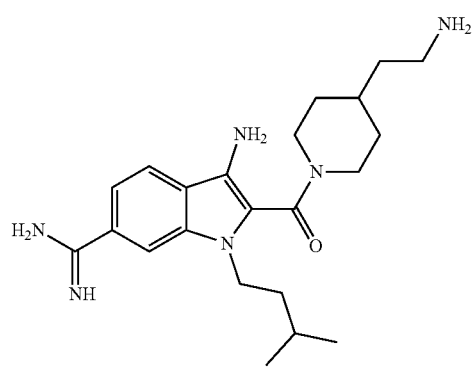 [SMILES: CC(C)CCn1c(C(=O)N2CCC(CCN)CC2)c(N)c2ccc(C(=N)N)cc21]

Step-1: tert-Butyl (2-(1-(6-cyano-1H-indole-2-carbonyl)piperidin-4-yl)ethyl)carbamate 6-Cyano-1H-indole-2-carboxylic acid (1.85 g, 9.94 mmol) and tert-butyl (2-(piperidin-4-yl)ethyl)carbamate (2.26 g, 9.94 mmol) were treated together to afford the title compound (1.77 g) following the procedure described in step-3 of example-68. LCMS: 397.2 (M+1)⁺.

Step-2: tert-Butyl (2-(1-(6-cyano-3-nitro-1H-indole-2-carbonyl)piperidin-4-yl)ethyl)carbamate The product of step-1 of example-70 (1.7 g, 4.29 mmol) was dissolved in 30 mL of acetic acid and cooled it to 0° C. Copper(II) nitrate trihydrate (401 mg, 5.16) was added and stirred for 3 h. Reaction mixture was quenched with coldwater and extracted with ethyl acetate, followed by washed with brine and dried over sodium sulphate. Solvent was evaporated to give crude product which was purified with column chromatography using silica-gel as an adsorbent and elution with hexane:ethyl acetate (7:3) afforded 610 mg of the title compound. LCMS: 442.2 (M+1)⁺.

Step-3: tert-Butyl (2-(1-(6-cyano-1-isopentyl-3-nitro-1H-indole-2-carbonyl)piperidin-4-yl)ethyl)-carbamate The product of step-2 of example-70 (600 mg, 1.36 mmol) and 1-bromo-3-methylbutane (204 mg, 1.36 mmol) were treated together to afford the title compound (1.52 g) following the procedure described in step-1 of example 1. LCMS: 512.3 (M+1)⁺.

Step-4: tert-Butyl (2-(1-(3-amino-6-cyano-1-isopentyl-1H-indole-2-carbonyl)piperidin-4-yl)ethyl)-carbamate The product of step-3 of example-70 (510 mg, 0.99 mmol) was dissolved in 10 mL of glacial acetic acid (AcOH) and added Zn (383 mg, 5.98 mmol) in portions at room temperature. Reaction mixture was stirred at RT for 6 h. Contents were filtered through celite pad and filtrate was concentrated under vacuum to afford crude compound which was purified by column chromatography using silica-gel as an adsorbent and eluted with hexane:ethylacetate (6:4) and afforded the title compound (190 mg). LCMS: 482.3 (M+1)⁺.

Step-5: Ethyl 3-amino-2-(4-(2-aminoethyl)piperidine-1-carbonyl)-1-isopentyl-1H-indole-6-carbimidate The product of step-4 of example-70 (190 mg, 0.39 mmol) was treated with 50 mL of ethanolic-HCl to afford the title compound (135 mg) following the procedure described in step-4 of example 1. LCMS: 428.3 (M+1)⁺.

Step-6: 2-(4-Fluoropiperidine-1-carbonyl)-1-isopentyl-1H-indole-6-carboximidamide The product of step-5 of example-70 (130 mg, 0.3 mmol) was treated with 50 mL of ethanolic-NH₃ to afford the title compound (35 mg) following the procedure described in step-5 of example 1. LCMS: 399.3 (M+1)⁺, ¹H NMR (300 MHz, DMSO-d₆): δ 0.81 (m, 6H), 0.98 (m, 1H), 1.48 (m, 6H), 1.65 (m, 3H), 2.81 (m, 3H), 3.11 (m, 1H), 4.01 (m, 1H), 4.21 (m, 3H), 7.38 (m, 1H), 7.71 (m, 3H), 7.82 (m, 1H), 7.93 (m, 1H), 9.00 (brs, 2H), 9.21 (brs, 2H); HPLC: 97.75% (Retention Time=4.399 min).

The following compounds listed in table-11 were prepared according to Scheme-6 by following similar procedure as described above for example 70 using appropriate reagents with suitable modifications known to the one skilled in the art.

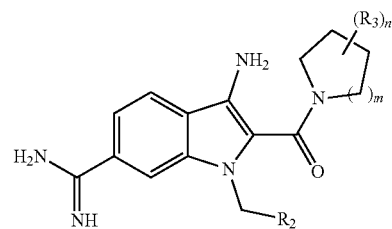

TABLE 11

| Cpd. ID. | R₂ | m | R₃ (binding site) | Characteristic Data |
|---|---|---|---|---|
| I-346 | (4-ethoxycarbonyl-phenyl-methyl) | 2 | —(CH₂)₂NH₂ | LCMS (M + 1)⁺: 491.3<br>¹H NMR: δ 1.4 (m, 4H), 1.51 (m, 7H), 2.42 (m, 1H), 3.48 (m, 4H), 4.11 (m, 1H), 4.31 (m, 1H), 4.51 (m, 2H), 7.36 (d, 1H), 7.62 (m, 2H), 7.72 (m, 2H), 7.82 (m, 3H), 9.11 (brs, 2H), 9.21 (brs, 2H); HPLC: 92.85% (Retention Time = 4.452 min). |

TABLE 11-continued

| Cpd. ID. | R$_2$ | m | R$_3$ (binding site) | Characteristic Data |
|---|---|---|---|---|
| I-347 | (4-phenoxyphenyl group) | 2 | —(CH$_2$)$_2$NHC(O)OH | LCMS (M + 1)$^+$: 555.3<br>$^1$H NMR: δ 1.31 (m, 3H), 1.48 (m, 4H), 2.76 (m, 2H), 3.25 (m, 2H), 4.44 (m, 2H), 5.48 (m, 2H), 6.85 (m, 3H), 7.12 (m, 3H), 7.31 (m, 2H), 7.35 (m, 2H), 7.52 (m, 1H), 8.35 (d, 1H), 9.98 (brs, 1H); HPLC: 94.04% (Retention Time = 4.695 min). |
| I-348 | (4-phenoxyphenyl group) | 2 | —(CH$_2$)$_2$NH$_2$ | LCMS (M + 1)$^+$: 511.3<br>$^1$H NMR: δ 1.31 (m, 3H), 1.48 (m, 4H), 2.76 (m, 4H), 3.48 (m, 2H), 5.48 (d, 2H), 6.88 (m, 4H), 7.12 (m, 2H), 7.36 (m, 3H), 7.75 (brs, 3H), 7.88 (d, 1H), 8.45 (s, 1H), 9.01 (brs, 2H), 9.24 (brs, 2H); HPLC: 97.94% (Retention Time = 4.774 min). |

General syntheic scheme 7

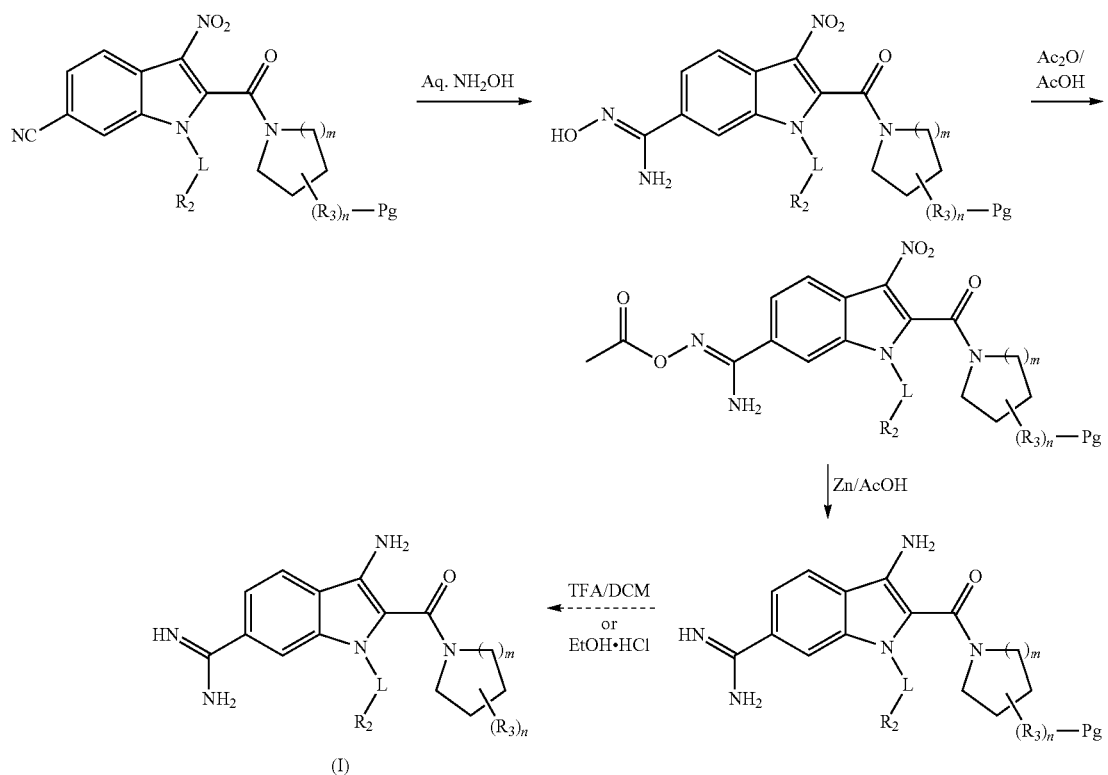

Pg = optional protecting group; L, R$_2$, R$_3$, m and n are as defined in formula (I)

Yet another general approach for the synthesis of compounds of general formula (I) is depicted in general synthetic scheme-7. 3-Nitroindole derivative described in scheme 6 upon treating with aq. hydroxylamine yielded amidoximes which on acylation in presence of acetic acid and acetic anhydride followed by reduction with, Zn/AcOH yielded amidine derivatives. The amindine analogs were then deprotected under acidic condition with either HCl or TFA to afford the compound of formula (I).

Example 71: Synthesis of Compound I-349

3-Amino-2-(4-(2-aminoethyl)piperidine-1-carbonyl)-1-(2-(phenylsulfonyl)ethyl)-1H-indole-6-carboximidamide

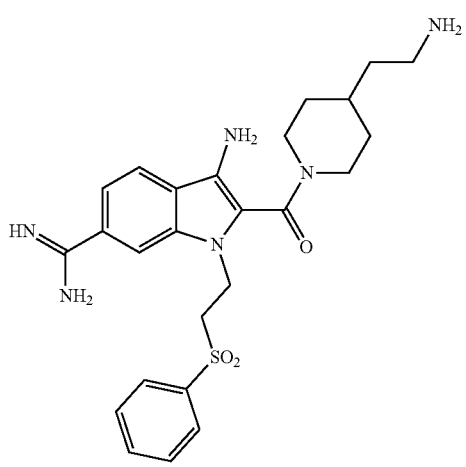 [SMILES: N=C(N)c1ccc2c(N)c(C(=O)N3CCC(CCN)CC3)n(CCS(=O)(=O)c3ccccc3)c2c1]

Step-1: tert-Butyl (2-(1-(6-cyano-1H-indole-2-carbonyl)piperidin-4-yl)ethyl)carbamate 6-Cyano-1H-indole-2-carboxylic acid (1.85 g, 9.94 mmol) and tert-butyl (2-(piperidin-4-yl)ethyl)carbamate (2.26 g, 9.94 mmol) were treated together to afford the title compound (1.77 g) following the procedure described in step-3 of example-68. LCMS: 397.2 (M+1)$^+$.

Step-2: tert-Butyl (2-(1-(6-cyano-3-nitro-1H-indole-2-carbonyl)piperidin-4-yl)ethyl)carbamate The product of step-1 of example-71 (1.7 g, 4.29 mmol) and copper(II) nitrate trihydrate (401 mg, 5.16) were treated together to afford the title compound (610 mg) following the procedure described in step-2 of example-70. LCMS: 442.2 (M+1)$^+$.

Step-3: tert-Butyl (2-(1-(6-cyano-3-nitro-1-(2-(phenylsulfonyl)ethyl)-1H-indole-2-carbonyl)piperidin-4-yl)ethyl)carbamate The product of step-2 of example-71 (600 mg, 1.36 mmol) and ((2-bromoethyl)sulfonyl)benzene (337 mg, 1.36 mmol) were treated together to afford the title compound (540 mg) following the procedure described in step-1 of example 1. LCMS: 610.2 (M+1)$^+$.

Step-4: tert-Butyl-(2-(1-(6-(N'-hydroxycarbamimidoyl)-3-nitro-1-(2-(phenylsulfonyl)ethyl)-1H-indole-2-carbonyl)piperidin-4-yl)ethyl)carbamate The product of step-3 of example-71 (540 mg, 0.88 mmol) was treated with aq NH$_2$OH solution (0.3 mL) to afford the title compound (410 mg) following the procedure described in step-4 of example-69. LCMS: 643.2 (M+1)$^+$.

Step-5: tert-Butyl-(2-(1-(6-(N'-acetoxycarbamimidoyl)-3-nitro-1-(2-(phenylsulfonyl)ethyl)-1H-indole-2-carbonyl)piperidin-4-yl)ethyl)carbamate The product of step-4 of example-71 (410 mg, 0.63 mmol) was treated with acetic anhydride (Ac$_2$O) (521 mg, 5.1 mmol) to afford the title compound (325 mg) following the procedure described in step-5 of example-69. LCMS: 685.3 (M+1)$^+$.

Step-6: tert-Butyl (2-(1-(3-amino-6-carbamimidoyl-1-(2-(phenylsulfonyl)ethyl)-1H-indole-2-carbonyl)piperidin-4-yl)ethyl)carbamate The product of step-5 of example-71 (325 mg, 0.47 mmol) was treated with zinc (365 mg, 5.7 mmol) to afford the title compound (185 mg) following the procedure described in step-6 of example 69. LCMS: 597.3 (M+1)$^+$.

Step-7: 3-Amino-2-(4-(2-aminoethyl)piperidine-1-carbonyl)-1-(2-(phenylsulfonyl)ethyl)-1H-indole-6-carboximidamide The product of step-6 of example-71 (185 mg, 0.31 mmol) was treated with 20 mL of ethanolic-HCl to afford 65 mg of the title compound following the procedure described in step-4 of example-1 except reaction was done at 0° C. for 2 h. LCMS: 497.2 (M+1)$^+$, $^1$H NMR (300 MHz, DMSO-d$_6$): δ 0.98 (m, 2H), 1.40 (m, 3H), 1.61 (m, 3H), 2.81 (m, 3H), 2.99 (m, 2H), 3.65 (m, 2H), 3.95 (m, 2H), 4.45 (brs, 2H), 4.80 (brs, 2H), 7.32 (m, 1H), 7.61 (m, 6H), 7.82 (m, 3H), 9.01 (brs, 2H), 9.24 (brs, 2H).

The following compounds listed in table-12 were prepared according to scheme-7 by following similar procedure as described above for example-71 using appropriate reagents with suitable modifications known to the one skilled in the art.

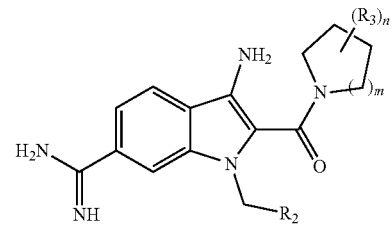

TABLE 12

| Cpd. ID. | R₂ | m | R₃ | Characteristic Data |
|---|---|---|---|---|
| I-350 | phenyl-SO₂-CH₂- | 2 | cyclohexane-fused | LCMS (M + 1)⁺: 508.2<br>¹H NMR: δ 1.4 (m, 4H), 1.51 (m, 7H), 2.42 (m, 1H), 3.48 (m, 4H), 4.11 (m, 1H), 4.31 (m, 1H), 4.51 (m, 2H), 7.36 (d, 1H), 7.62 (m, 2H), 7.72 (m, 2H), 7.82 (m, 3H), 9.11 (brs, 2H), 9.21 (brs, 2H); HPLC: 97.8% (Retention Time = 5.857 min). |
| I-351 | phenyl-SO₂-CH₂- | 2 | cyclohexane-fused | LCMS (M + 1)⁺: 508.2<br>¹H NMR: δ 0.8 (m, 5H), 1.4 (m, 7H), 2.42 (m, 1H), 3.12 (m, 1H), 3.7 (m, 2H), 3.91 (m, 1H), 4.45 (m, 2H), 4.8 (m, 1H), 7.32 (d, 1H), 7.60 (m, 2H), 7.71 (m, 2H), 7.82 (m, 3H), 8.91 (brs, 2H), 9.18 (brs, 2H); HPLC: 95.06% (Retention Time = 5.819 min). |
| I-352 | phenyl-SO₂-CH₂- | 2 | benzene-fused | LCMS (M + 1)⁺: 502.2<br>¹H NMR: δ 2.85 (m, 2H), 3.62 (m, 4H), 3.82 (m, 1H), 4.45 (m, 2H), 4.68 (s, 2H), 5.00 (m, 1H), 7.32 (d, 5H), 7.35 (m, 1H), 7.46 (m, 2H), 7.77 (m, 3H), 7.79 (s, 1H), 7.89 (d, 1H), 8.96 (brs, 2H), 9.18 (brs, 2H); HPLC: 97.02% (Retention Time = 5.524 min). |

35

General synthetic scheme-8

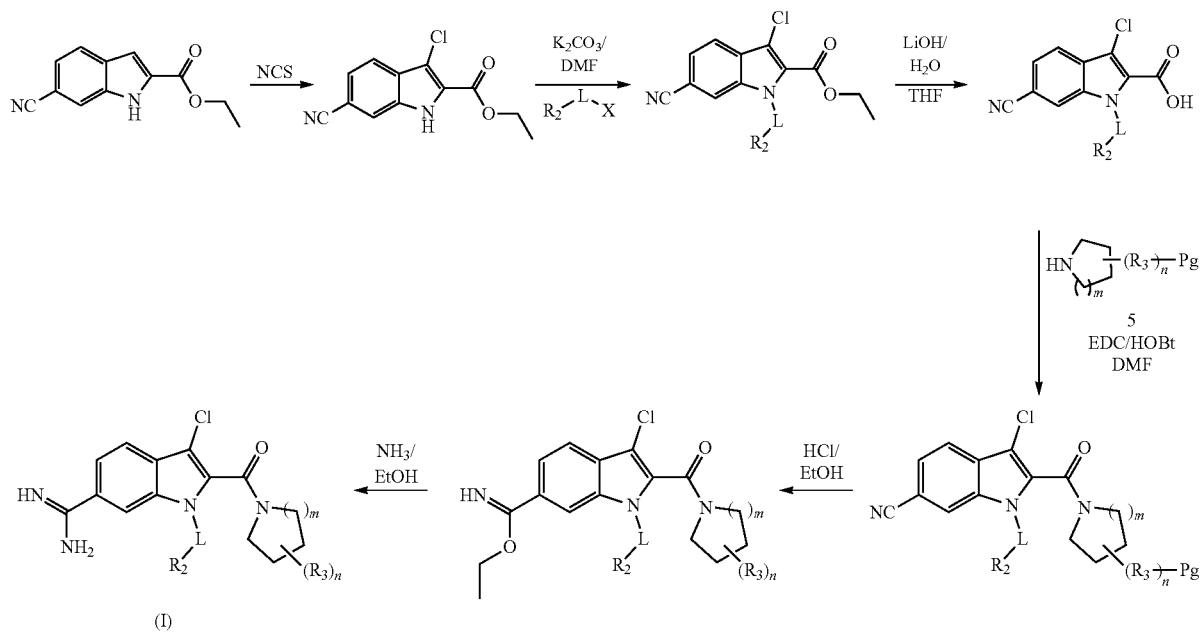

X = Br; Pg = optional Protecting group; L, R₂, R₃, m and n are as defined in formula (I)

Yet another general approach for the synthesis of compounds of general formula (I) is depicted in general synthetic scheme-8. 6-Cyno-indole 2-ethyl carboxylate upon reacting with N-chlorosuccinimide in presence of suitable solvent (DMF) yielded 3-chloro-6-cyano-indole-2 carboxylate, which upon treating with appropriate alkylating agent in presence of a suitable base ($K_2CO_3$) and a suitable solvent (DMF) gives compound N-alkylated derivatives. Hydrolysis of C(2) ethyl ester in presence of $LiOH/H_2O$ followed by coupling with cyclic yielded corresponding amides which were treated with ethanolic HCl. This intermediate imidates on further treatment with ethanolic ammonia yielded compounds of formula (I).

Example 72: Synthesis of Compound I-353

1-([1,1'-Biphenyl]-4-ylmethyl)-3-chloro-2-(4-fluoropiperidine-1-carbonyl)-1H-indole-6-carboximidamide

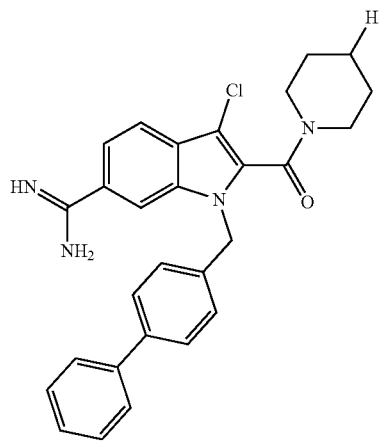 [SMILES: N=C(N)c1ccc2c(Cl)c(C(=O)N3CCCCC3)n(Cc3ccc(-c4ccccc4)cc3)c2c1]

Step-1: Ethyl 3-chloro-6-cyano-1H-indole-2-carboxylate

Ethyl 6-cyano-1H-indole-2-carboxylate (1.25 g, 5.84 mmol) was dissolved in 125 mL of dimethylformamide and added N-chlorosuccinimide (932 mg, 7.0 mmol) at 0° C. in portions and stirred the mixture for 12 h at room temperature. Reaction mixture was quenched to cold water, extracted with ethylacetate, followed by washed with brine and dried over sodium sulphate. Solvent was evaporated under vacuum and resulted crude residue was purified by column chromatography using silica-gel as an adsorbent and eluted with hexane:ethylacetate (9:1) to afford 820 mg of the title compound. LCMS: 249.1 $(M+1)^+$.

Step-2: Ethyl 1-([1,1'-biphenyl]-4-ylmethyl)-3-chloro-6-cyano-1H-indole-2-carboxylate The product of step-2 of example-72 (800 mg, 3.22 mmol) was treated with 4-(bromomethyl)-1,1'-biphenyl (792 mg, 3.22 mmol) to afford the title compound (910 mg) following the procedure described in step-1 of example-68. LCMS: 415.1 $(M+1)^+$.

Step-3: 1-([1,1'-Biphenyl]-4-ylmethyl)-3-chloro-6-cyano-1H-indole-2-carboxylic Acid The product of step-3 of example-72 (900 mg, 2.17 mmol) was treated with lithium hydroxide (417 mg, 17.4 mmol) to afford the title compound (640 mg) following the procedure described in step-2 of example-68. LCMS: 387.1 $(M+1)^+$.

Step-4: 1-([1,1'-Biphenyl]-4-ylmethyl)-3-chloro-2-(4-fluoropiperidine-1-carbonyl)-1H-indole-6-carbonitrile The product of step-3 of example-72 (640 mg, 1.65 mmol) and 4-fluoropiperidine (170 mg, 1.65 mmol) were treated together to afford the title compound (430 mg) following the procedure described in step-3 of example-68. LCMS: 472.1 $(M+1)^+$.

Step-5: Ethyl 1-([1,1'-biphenyl]-4-ylmethyl)-3-chloro-2-(4-fluoropiperidine-1-carbonyl)-1H-indole-6-carbimidate The product of step-4 of example-72 (430 mg, 0.91 mmol) was treated with 50 mL of ethanolic-HCl to afford the title compound (225 mg) following the procedure described in step-4 of example-68. LCMS: 518.2 $(M+1)^+$.

Step-6: 1-([1,1'-Biphenyl]-4-ylmethyl)-3-chloro-2-(4-fluoropiperidine-1-carbonyl)-1H-indole-6-carboximidamide The product of step-5 of example-72 (220 mg, 0.42 mmol) was treated with 50 mL of ethanolic-$NH_3$ to afford the title compound (65 mg) following the procedure described in step-5 of example-68. LCMS: 489.2 $(M+1)^+$, $^1$H NMR (300 MHz, DMSO-$d_6$): δ 1.52 (m, 2H), 1.66 (m, 2H), 2.96 (m, 1H), 3.13 (m, 1H), 3.46 (m, 1H), 3.79 (m, 2H), 5.33 (m, 1H), 5.72 (m, 1H), 7.21 (m, 2H), 7.35 (m, 1H), 7.42 (m, 2H), 7.58 (m, 3H), 7.66 (m, 1H), 7.82 (m, 1H), 8.46 (d, 1H), 9.07 (brs, 2H), 9.36 (brs, 2H); HPLC: 97.53% (Retention Time=4.135 min).

The following compounds listed in table-13 were prepared according to scheme-8 by following similar procedure as described above for example-72 using appropriate reagents with suitable modifications known to the one skilled in the art.

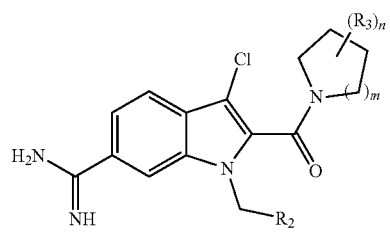

TABLE 13

| Cpd. ID. | R₂ | m | R₃ | Characteristic Data |
|---|---|---|---|---|
| I-354 | 4-carbamoylphenyl-CH₂ | 1 | —F₂ | LCMS (M + 1)⁺: 460.1<br>¹H NMR: δ 2.24 (m, 2H), 3.53 (m, 2H), 3.80 (m, 2H), 5.67 (s, 2H), 7.20 (m, 2H), 7.34 (m, 3H), 7.64 (m, 1H), 7.78 (m, 3H), 7.91 (m, 1H), 8.34 (d, 1H); HPLC: 97.43% (Retention Time = 5.578 min). |
| I-355 | 4-carbamoylphenyl-CH₂ | 2 | —F | LCMS (M + 1)⁺: 456.1<br>¹H NMR: δ 1.52 (m, 2H), 1.65 (m, 2H), 2.96 (m, 1H), 3.15 (m, 1H), 3.37 (m, 1H), 4.62 (m, 2H), 5.38 (m, 1H), 5.69 (m, 1H), 7.18 (m, 2H), 7.38 (m, 1H), 7.65 (m, 2H), 7.79 (m, 3H), 7.95 (m, 1H), 8.38 (s, 1H), 9.02 (brs, 2H), 9.33 (brs, 2H); HPLC: 94.329% (Retention Time = 6.098 min). | cyclic amines followed by further coupling with various amines yielded diamide derivatives. Treatment of diamides with ethanolic HCl followed by ethanolic ammonia yielded compounds of formula (I).

Example 73: Synthesis of Compound I-356

N-(3-Aminopropyl)-1-(6-carbamimidoyl-1-(4-(trifluoromethyl)benzyl)-1H-indole-2-carbonyl)-piperidine-4-carboxamide

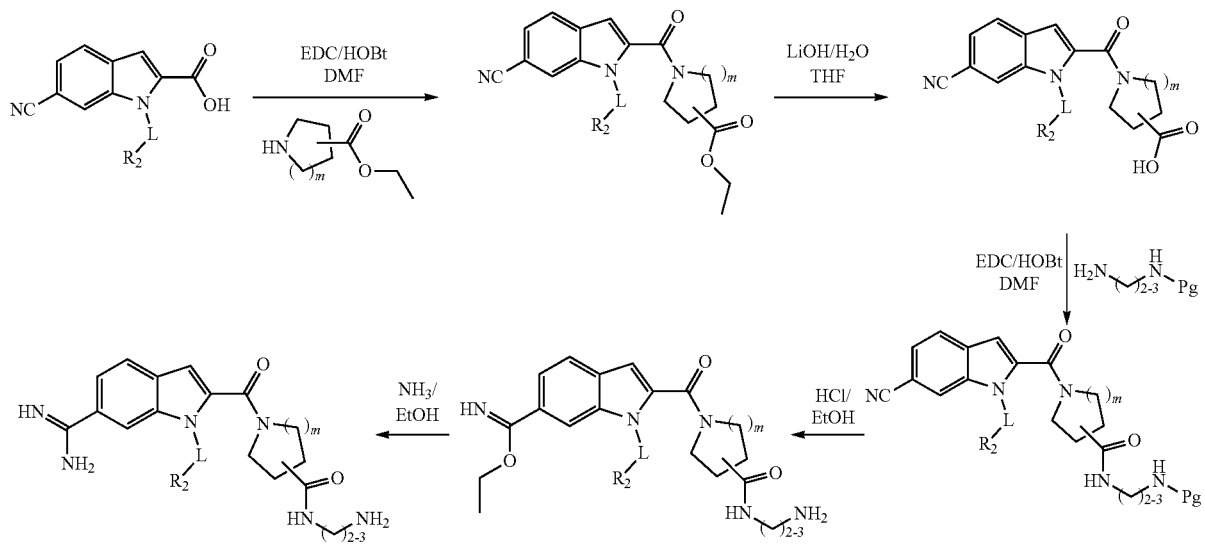

General synthetic scheme-9

Pg = Protecting group; L, R₂ and m are as defined in formula (I)

Yet another general approach for the synthesis of compounds of general formula (I) is depicted in general synthetic scheme-9. N-functionalized 6-cyano indole 2 carboxylic acids previously described were coupled with ester containing cyclic amines to yield corresponding cyclic amides. Hydrolysis of the ester functionality appended to the Step-1: Ethyl 6-cyano-1-(4-(trifluoromethyl)benzyl)-1H-indole-2-carboxylate Ethyl 6-cyano-1H-indole-2-carboxylate (10.0 g, 46.71 mmol) and 1-(bromomethyl)-4-(trifluoromethyl)benzene (7.0 g, 46.71 mmol) were treated together to afford the title compound (6.2 g) following the procedure described in step-1 of example-68. LCMS: 285.1 (M+1)⁺.

Step-2: 6-Cyano-1-(4-(trifluoromethyl)benzyl)-1H-indole-2-carboxylic Acid

The product of step-1 of example-73 (5.8 g, 19.64 mmol) was treated with LiOH (1.89 g, 78.6 mmol) to afford the title compound (3.65 g) following the procedure described in step-2 of example 68. LCMS: 257.1 (M+1)⁺.

Step-3: Ethyl 1-(6-cyano-1-(4-(trifluoromethyl)benzyl)-1H-indole-2-carbonyl)piperidine-4-carboxylate The product of step-2 of example-73 (1.55 g, 6.05 mmol) and ethyl piperidine-4-carboxylate (950 mg, 6.05 mmol) were treated together to afford the title compound (1.75 g) following the procedure described in step-3 of example-68. LCMS: 484.2 (M+1)⁺.

Step-4: 1-(6-Cyano-1-(4-(trifluoromethyl)benzyl)-1H-indole-2-carbonyl)piperidine-4-carboxylic Acid The product of step-3 of example-73 (1.7 g, 3.51 mmol) was treated with LiOH (338 mg, 14.0 mmol) in H₂O to afford the title compound (1.04 g) following the procedure described in step-2 of example 68. LCMS: 456.2 (M+1)⁺.

Step-5: tert-Butyl (3-(1-(6-cyano-1-(4-(trifluoromethyl)benzyl)-1H-indole-2-carbonyl)piperidine-4-carboxamido)propyl)carbamate The product of step-4 of example-73 (800 mg, 1.75 mmol) and tert-butyl (3-aminopropyl)carbamate (305 mg, 1.75 mmol) were treated together to afford 580 mg of the title compound following the procedure described in step-3 of example-68. LCMS: 612.3 (M+1)⁺.

Step-6: Ethyl 2-(4-((3-aminopropyl)carbamoyl)piperidine-1-carbonyl)-1-(4-(trifluoromethyl)-benzyl)-1H-indole-6-carbimidate The product of step-5 of example-73 (550 mg, 0.9 mmol) was treated with 50 mL of ethanolic-HCl to afford the title compound (340 mg) following the procedure described in step-4 of example-68. LCMS: 558.3 (M+1)⁺.

Step-7: N-(3-Aminopropyl)-1-(6-carbamimidoyl-1-(4-(trifluoromethyl)benzyl)-1H-indole-2-carbonyl)piperidine-4-carboxamide The product of step-6 of example-73 (340 mg, 0.61 mmol) was treated with 50 mL of ethanolic-NH₃ to afford the title compound (90 mg) following the procedure described in step-5 of example 68. LCMS: 529.2 (M+1)⁺, ¹H NMR (300 MHz, DMSO-d₆): δ 1.51 (m, 4H), 2.49 (m, 2H), 2.71 (m, 4H), 3.15 (m, 3H), 3.82 (m, 1H), 4.38 (m, 1H), 5.65 (s, 2H), 6.83 (s, 1H), 7.23 (m, 2H), 7.52 (d, 1H), 7.78 (m, 4H), 7.94 (m, 1H), 9.13 (brs, 2H), 9.23 (brs, 2H); HPLC: 79.68% (Retention Time 6.572 min).

The following compounds listed in Table-14 were prepared according to scheme-9 by following similar procedure as described above for example 73 using appropriate reagents with suitable modifications known to the one skilled in the art.

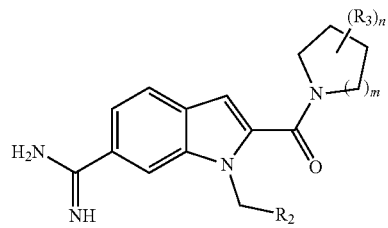

TABLE 14

| Cpd. ID. | R₂ | m | R₃ | ¹H NMR |
|---|---|---|---|---|
| I-357 | benzyl | 2 | —C(O)NH(CH₂)₂NH₂ | LCMS (M + 1)⁺: 461.3<br>¹H NMR: δ 1.51 (m, 2H), 1.65 (m, 3H), 2.71 (m, 2H), 3.15 (m, 2H), 3.82 (m, 1H), 4.51 (m, 2H), 6.73 (s, 1H), 7.13 (m, 4H), 7.50 (d, 1H), 7.80 (d, 1H), 8.14 (m, 2H), 8.97 (brs, 2H), 9.25 (brs, 2H); HPLC: 94.68% (Retention Time = 4.421 min). |
| I-358 | benzyl | 2 | —C(O)NH(CH₂)₃NH₂ | LCMS (M + 1)⁺: 475.3<br>¹H NMR: δ 1.51 (m, 2H), 1.65 (m, 3H), 2.71 (m, 2H), 3.15 (m, 4H), 3.82 (m, 1H), 4.51 (m, 2H), 6.73 (s, 1H), 7.13 (m, 4H), 7.51 (d, 1H), 7.80 (d, 1H), 8.24 (m, 1H), 8.19 (s, 1H), 8.44 (brs, 3H); HPLC: 96.72% (Retention Time = 4.455 min). |

General synthetic scheme 10

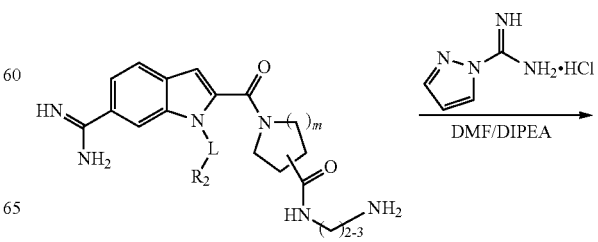

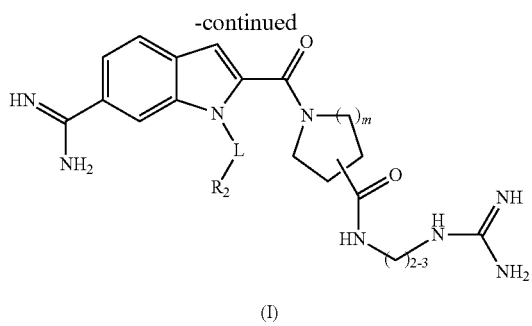

(I)

Yet another general approach for the synthesis of compounds of general formula (I) is depicted in general synthetic scheme 10. Amino analogs obtained from scheme 9 upon treating with 1H-pyrazole-1-carboxamidine hydrochloride in presence of a suitable base (DIPEA) in a suitable solvent (DMF) affords compound of formula (I).

Example 74: Synthesis of Compound I-359

1-(6-Carbamimidoyl-1-(4-(trifluoromethyl)benzyl)-1H-indole-2-carbonyl)-N-(3-guanidinopropyl)-piperidine-4-carboxamide

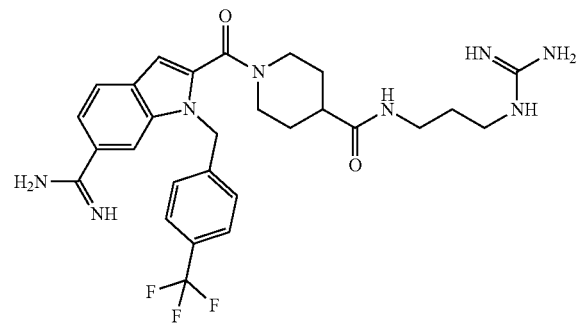 [SMILES: N=C(N)NCCCNC(=O)C1CCN(C(=O)c2cc3ccc(C(=N)N)cc3n2Cc2ccc(C(F)(F)F)cc2)CC1]

Step-1: 1-(6-Carbamimidoyl-1-(4-(trifluoromethyl)benzyl)-1H-indole-2-carbonyl)-N-(3-guanidinopropyl)piperidine-4-carboxamide The product of step-7 of example-73 (90 mg, 0.17 mmol), dissolved in 10 mL of DMF, was treated with 1H-pyrazole-1-carboxamidine hydrochloride (50 mg, 0.34 mmol) and DIPEA (88 mg, 0.68 mmol) and stirred at room temperature for 24 h. The solvent was evaporated under vacuum to give crude compound which was purified by reversed-phase preparative high performance column chromatography to afford 20 mg of the title compound. LCMS: 571.3 (M+1)$^+$, $^1$H NMR (300 MHz, DMSO-d$_6$): δ 1.49 (m, 3H), 1.71 (m, 2H), 2.31 (m, 2H), 3.12 (m, 6H), 3.85 (m, 1H), 4.45 (m, 1H), 5.65 (s, 2H), 6.95 (s, 1H), 7.22 (d, 2H), 7.50 (m, 2H), 7.63 (d, 2H), 7.83 (m, 2H), 8.22 (s, 1H), 8.89 (brs, 2H), 9.25 (brs, 2H).

The following compounds listed in table-15 were prepared according to scheme 10 followed by scheme-7 by following similar procedure as described above for example 74 using appropriate reagents with suitable modifications known to the one skilled in the art.

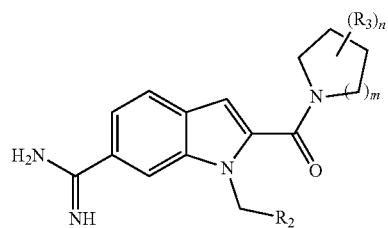

TABLE 15

| Cpd. ID. | R$_2$ | m | R$_3$ | Characteristic Data |
|---|---|---|---|---|
| I-360 | 2-naphthyl | 2 | —(CH$_2$)$_2$NHC(NH)NH$_2$ | LCMS (M + 1)$^+$: 496.3<br>$^1$H NMR: δ 0.52 (m, 4H), 1.21 (m, 2H), 1.49 (m, 2H), 2.71 (m, 4H), 4.45 (m, 1H), 5.53 (d, 2H), 6.81 (s, 1H), 7.18 (d, 1H), 7.39 (m, 1H), 7.45 (m, 2H), 7.53 (m, 2H), 7.82 (d, 4H), 8.42 (s, 1H), 9.00 (brs, 2H), 9.22 (brs, 2H); HPLC: 99.56% (Retention Time = 6.702 min). |
| I-361 | 4-biphenyl | 2 | —(CH$_2$)$_2$NHC(NH)NH$_2$ | LCMS (M + 1)$^+$: 522.3<br>$^1$H NMR: δ 0.49 (m, 1H), 0.81 (m, 1H), 1.21 (m, 3H), 1.35 (m, 2H), 1.61 (m, 1H), 2.85 (m, 3H), 3.70 (m, 1H), 4.45 (m, 1H), 5.57 (d, 2H), 6.82 (s, 1H), 7.14 (d, 3H), 7.32 (m, 2H), 7.39 (m, 2H), 7.50 (m, 1H), 7.52 (m, 5H), 7.83 (d, 1H), 8.35 (s, 1H), 9.00 (brs, 2H), 9.27 (brs, 2H); HPLC: 94.44% (Retention Time = 6.998 min). |

TABLE 15-continued
| Cpd. ID. | R$_2$ | m | R$_3$ | Characteristic Data |
|---|---|---|---|---|
| I-362 | 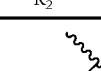 | 2 | —(CH$_2$)$_2$NHC(NH)NH$_2$ | LCMS (M + 1)$^+$: 538.3<br>$^1$H NMR: δ 0.52 (m, 2H), 0.71 (m, 1H), 0.82 (m, 2H), 1.49 (m, 2H), 1.71 (m, 2H), 3.12 (m, 2H), 3.70 (m, 2H), 4.45 (m, 2H), 5.51 (d, 2H), 6.81 (s, 1H), 7.12 (d, 4H), 7.19 (m, 3H), 7.35 (m, 2H), 7.43 (m, 1H), 7.52 (d, 1H), 7.83 (d, 1H), 8.32 (s, 1H), 8.90 (brs, 2H), 9.22 (brs, 2H). |
General synthetic scheme - 11
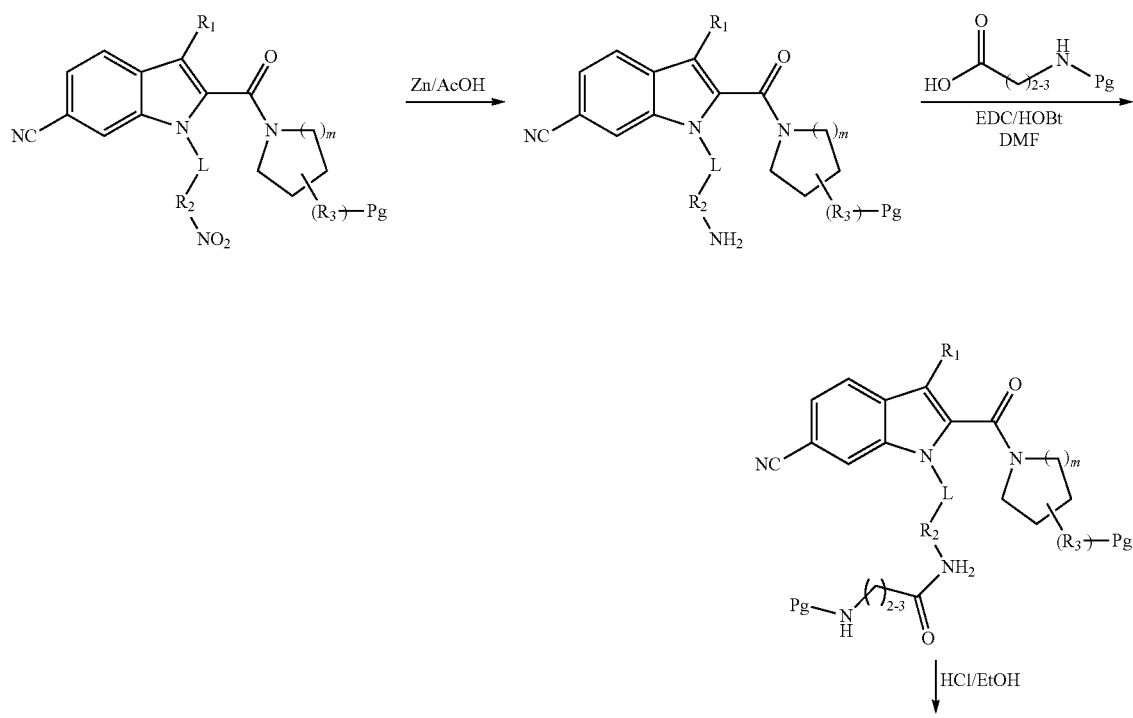
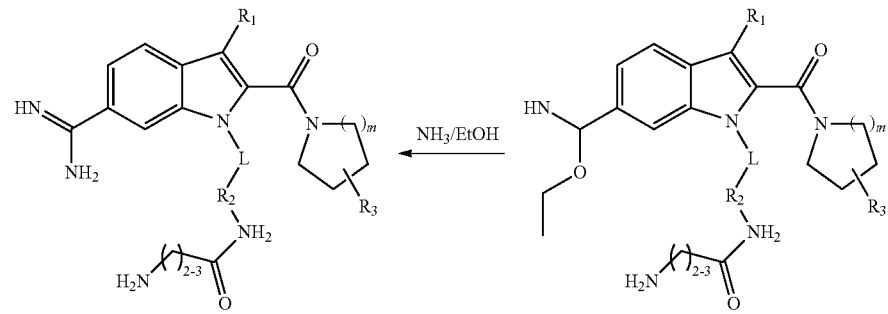
Pg = Protecting group; R$_2$ is —NO$_2$ substituted; R$_1$, R$_3$ and m are as defined in formula (I)

in general synthetic scheme-11. Nitro derivative upon reduction with Zn in presence of acetic acid Yielded amines which were coupling with the carboxylic acid under standard coupling conditions yields compound N-1 functionalized amides. Deprotection of the protecting group with ethanolic HCl also resulted in conversion of the nitrile to immediate which on treatment with ammonia yielded analogs of formula (I).

Example 75: Synthesis of Compound I-363

3-Amino-N-(3-((2-(4-(2-aminoethyl)piperidine-1-carbonyl)-6-carbamimidoyl-1H-indol-1-yl)methyl)phenyl)propenamide

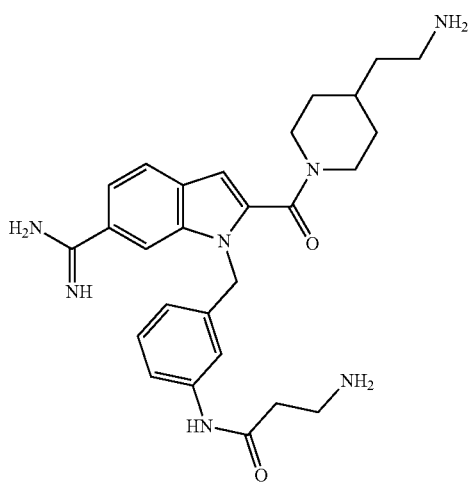 [SMILES: N=C(N)c1ccc2cc(C(=O)N3CCC(CCN)CC3)n(Cc3cccc(NC(=O)CCN)c3)c2c1]

Step-1: Ethyl 6-cyano-1-(3-nitrobenzyl)-1H-indole-2-carboxylate

Ethyl 6-cyano-1H-indole-2-carboxylate (10.0 g, 46.71 mmol) and 1-(bromomethyl)-3-nitrobenzene (10.04 g, 46.71 mmol) were treated together to afford 6.8 g of the title compound following the procedure described in step-1 of example-68. LCMS: 350.1 (M+1)$^+$.

Step-2: 6-Cyano-1-(3-nitrobenzyl)-1H-indole-2-carboxylic Acid

The product of step-1 of example-75 (1.6 g, 4.58 mmol) was treated with lithium hydroxide (440 mg, 18.33 mmol to afford 930 mg of the title compound following the procedure described in step-2 of example-68. LCMS: 322.1 (M+1)$^+$.

Step-3: Ethyl 1-(6-cyano-1-(4-(trifluoromethyl)benzyl)-1H-indole-2-carbonyl)piperidine-4-carboxylate The product of step-2 of example-75 (900 mg, 2.8 mmol) and tert-butyl (2-(piperidin-4-yl)ethyl)-carbamate (638 mg, 2.8 mmol) were treated together to afford 740 mg of the title compound following the procedure described in step-3 of example-68. LCMS: 532.2 (M+1)$^+$.

Step-4: tert-Butyl (2-(1-(1-(3-aminobenzyl)-6-cyano-1H-indole-2-carbonyl)piperidin-4-yl)ethyl) carbamate The product of step-3 of example-75 (730 mg, 1.37 mmol) was treated with zinc (350 mg, 5.48 mmol) to afford 400 mg of the title compound following the procedure described in step-4 of example 70. LCMS: 502.3 (M+1)$^+$.

Step-5: tert-Butyl (2-(1-(1-(3-(3-((tert-butoxycarbonyl)amino)propanamido)benzyl)-6-cyano-1H-indole-2-carbonyl)piperidin-4-yl)ethyl)carbamate The product of step-4 of example-75 (400 mg, 0.59 mmol) and 3-((tert-butoxycarbonyl)-amino)propanoic acid (112 mg, 0.59 mmol) were treated together to afford 320 mg of the title compound following the procedure described in step-3 of example 68. LCMS: 673.3 (M+1)$^+$.

Step-6: Ethyl 2-(4-(2-aminoethyl)piperidine-1-carbonyl)-1-(3-(3-aminopropanamido)benzyl)-1H-indole-6-carbimidate The product of step-5 of example-75 (320 mg, 0.47 mmol) was treated with 50 mL of ethanolic-HCl to afford 110 mg of the title compound following the procedure described in step-4 of example 68. LCMS: 519.3 (M+1)$^+$.

Step-7: 3-Amino-N-(3-((2-(4-(2-aminoethyl)piperidine-1-carbonyl)-6-carbamimidoyl-1H-indol-1-yl)methyl)phenyl)propanamide The product of step-6 of example-75 (110 mg, 0.21 mmol) was treated with 50 mL of ethanolic-NH$_3$ to afford 22 mg of the title compound following the procedure described in step-5 of example 68. LCMS: 490.3 (M+1)$^+$, $^1$H NMR (300 MHz, DMSO-d$_6$): δ 0.51 (m, 1H), 0.81 (m, 1H), 1.32 (m, 2H), 1.49 (m, 2H), 1.61 (m, 1H), 2.65 (m, 4H), 2.81 (m, 1H), 3.05 (m, 2H), 3.71 (m, 2H), 4.41 (m, 1H), 5.52 (d, 2H), 6.52 (s, 1H), 6.75 (m, 2H), 7.21 (m, 1H), 7.31 (s, 1H), 7.52 (m, 2H), 7.81 (m, 6H), 8.35 (s, 1H), 9.12 (brs, 2H), 9.27 (brs, 2H), 10.10 (brs, 2H).

The following compounds listed in table-16 were prepared according to scheme-11 by following similar procedure as described above for example 75 using appropriate reagents with suitable modifications known to the one skilled in the art.

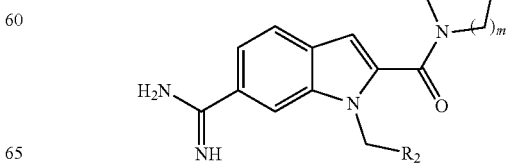

TABLE 16

| Cpd. ID. | R$_2$ | m | R$_3$ | Characteristic Data |
|---|---|---|---|---|
| I-364 | 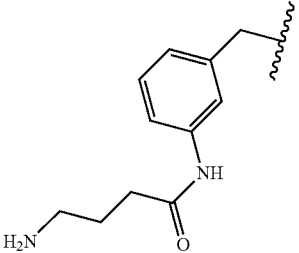 [SMILES: *Cc1cccc(NC(=O)CCCN)c1] | 2 | —(CH$_2$)$_2$NH$_2$ | LCMS (M + 1)$^+$: 504.3<br>$^1$H NMR: δ 0.49 (m, 1H), 0.81 (m, 1H), 1.35 (m, 5H), 1.51 (m, 1H), 1.71 (m, 2H), 2.31 (m, 2H), 2.71 (m, 4H), 3.45 (m, 2H), 4.44 (m, 1H), 5.51 (m, 2H), 6.51 (s, 1H), 6.71 (d, 1H), 6.81 (s, 1H), 7.15 (m, 2H), 7.48 (m, 2H), 7.71 (m, 5H), 8.30 (s, 1H), 9.07 (brs, 2H), 9.26 (brs, 2H), 10.00 (brs, 1H). |
| I-365 | 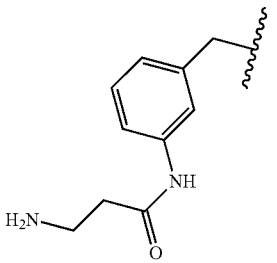 [SMILES: *Cc1cccc(NC(=O)CCN)c1] | 2 | 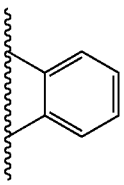 | LCMS (M + 1)$^+$: 495.2<br>$^1$H NMR: δ 2.55 (m, 4H), 2.99 (m, 2H), 3.45 (m, 1H), 3.71 (m, 1H), 4.60 (m, 1H), 4.69 (m, 1H), 5.55 (d, 2H), 6.80 (d, 1H), 7.10 (m, 6H), 17.29 (m, 1H), 7.41 (m, 1H), 7.57 (d, 1H), 7.73 (brs, 2H), 7.84 (m, 1H), 8.29 (s, 1H), 9.07 (brs, 2H), 9.26 (brs, 2H), 9.81 (m, 1H); HPLC: 95.33% (Retention Time = 5.976 min). |
| I-366 | 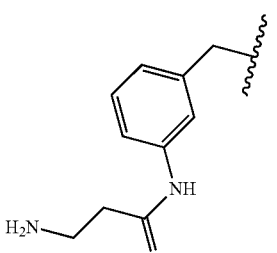 | 2 | —F | LCMS (M + 1)$^+$: 465.2<br>$^1$H NMR: δ 1.33 (m, 2H), 1.62 (m, 2H), 2.63 (m, 2H), 3.02 (m, 2H), 3.60 (m, 4H), 4.71 (m, 1H), 5.54 (s, 2H), 6.80 (d, 1H), 6.90 (s, 1H), 7.24 (m, 2H), 7.47 (d, 1H), 7.56 (d, 1H), 7.75 (brs, 2H), 7.84 (d, 1H), 8.30 (s, 1H), 9.09 (brs, 2H), 9.26 (brs, 2H), 10.13 (s, 1H); HPLC: 97.35% (Retention Time = 5.366 min). |
| I-367 | 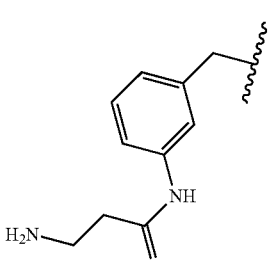 | 2 | —F$_2$ | LCMS (M + 1)$^+$: 483.2<br>$^1$H NMR: δ 1.50 (m, 2H), 1.90 (m, 2H), 2.63 (m, 2H), 3.02 (m, 2H), 3.47 (m, 4H), 5.55 (s, 2H), 6.82 (d, 1H), 6.96 (s, 1H), 7.22 (m, 1H), 7.34 (s, 1H), 7.46 (d, 1H), 7.57 (d, 1H), 7.74 (brs, 2H), 8.33 (s, 1H), 9.08 (brs, 2H), 9.27 (brs, 2H), 10.15 (s, 1H); HPLC: 93.92% (Retention Time = 5.761 min). |
| I-368 | 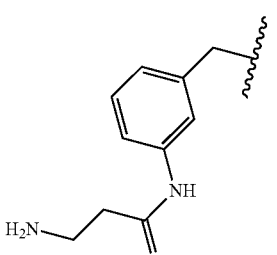 | 1 | —F | LCMS (M + 1)$^+$: 451.2<br>$^1$H NMR: δ 2.22 (m, 2H), 2.67 (m, 2H), 3.03 (m, 2H), 3.63 (m, 2H), 3.61 (m, 2H), 5.61 (m, 2H), 6.75 (m, 1H), 7.09 (d, 1H), 7.19 (m, 1H), 7.31 (d, 1H), 7.40 (d, 1H), 7.54 (m, 1H), 7.73 (m, 2H), 7.84 (m, 1H), 8.21 (d, 1H), 9.04 (brs, 2H), 9.24 (brs, 2H), 10.07 (d, 1H); HPLC: 95.95% (Retention Time = 5.237 min). |

TABLE 16-continued

| Cpd. ID. | R₂ | m | R₃ | Characteristic Data |
|---|---|---|---|---|
| I-369 | 3-aminopropanamido-phenyl-CH₂– (meta-substituted) | 1 | —F₂ | LCMS (M + 1)⁺: 469.2<br>¹H NMR: δ 2.22 (m, 2H), 2.62 (m, 2H), 3.02 (m, 2H), 3.63 (m, 2H), 3.83 (m, 2H), 5.60 (m, 2H), 6.81 (m, 1H), 7.13 (m, 3H), 7.40 (d, 1H), 7.55 (d, 1H), 7.73 (brs, 2H), 7.85 (m, 1H), 8.23 (d, 1H), 9.05 (brs, 2H), 9.26 (brs, 2H), 10.09 (d, 1H); HPLC: 86.52% (Retention Time = 5.456 min). |
| I-370 | 3-aminopropanamido-2-methoxy-phenyl-CH₂– | 2 | —(CH₂)₂NH₂ | LCMS (M + 1)⁺: 520.3<br>¹H NMR: δ 0.56 (m, 1H), 0.89 (m, 1H), 1.11 (m, 2H), 1.49 (m, 4H), 1.63 (m, 1H), 2.63 (m, 5H), 2.98 (m, 2H), 3.75 (s, 3H), 4.45 (m, 1H), 5.49 (s, 2H), 6.81 (s, 2H), 7.95 (d, 1H), 7.55 (d, 1H), 7.74 (m, 6H), 8.25 (s, 1H), 9.12 (brs, 2H), 9.27 (brs, 2H), 9.41 (brs, 1H). |
| I-371 | 4-(3-aminopropanamido)-phenyl-CH₂– | 2 | —(CH₂)₂NH₂ | LCMS (M + 1)⁺: 490.3<br>¹H NMR: δ 1.43 (m, 3H), 1.52 (m, 2H), 1.71 (m, 1H), 2.63 (m, 3H), 2.72 (m, 4H), 3.15 (m, 2H), 3.95 (m, 1H), 5.49 (s, 2H), 6.81 (s, 1H), 7.08 (d, 2H), 7.49 (m, 3H), 7.54 (m, 6H), 8.25 (s, 1H), 9.12 (brs, 2H), 9.27 (brs, 2H), 10.19 (brs, 1H). |
| I-372 | 4-(4-aminobutanamido)-phenyl-CH₂– | 2 | —(CH₂)₂NH₂ | LCMS (M + 1)⁺: 504.3<br>¹H NMR: δ 0.51 (m, 1H), 0.91 (m, 1H), 1.42 (m, 4H), 1.72 (m, 2H), 2.33 (m, 2H), 2.71 (m, 5H), 3.75 (m, 2H), 4.41 (m, 2H), 5.49 (s, 2H), 7.05 (d, 2H), 7.42 (m, 3H), 7.65 (m, 6H), 8.25 (s, 1H), 9.12 (brs, 2H), 9.27 (brs, 2H), 10.10 (brs, 1H); HPLC: 95.32% (Retention Time = 4.102 min). |
| I-373 | 4-(3-aminopropanamido)-phenyl-CH₂– | 2 | —F | LCMS (M + 1)⁺: 465.2<br>¹H NMR: δ 1.34 (m, 2H), 1.62 (m, 2H), 2.64 (m, 2H), 3.04 (m, 2H), 3.50 (m, 4H), 4.71 (m, 1H), 5.49 (s, 2H), 6.88 (s, 1H), 7.08 (d, 2H), 7.49 (d, 2H), 7.54 (d, 1H), 7.73 (m, 3H), 8.30 (s, 1H), 9.00 (brs, 2H), 9.26 (brs, 2H); HPLC: 94.18% (Retention Time = 4.799 min). |
| I-374 | 4-(3-aminopropanamido)-phenyl-CH₂– | 2 | —F₂ | LCMS (M + 1)⁺: 483.2<br>¹H NMR: δ 1.56 (m, 2H), 1.92 (m, 2H), 2.65 (m, 2H), 3.04 (m, 2H), 3.37 (m, 2H), 3.61 (m, 2H), 5.49 (s, 2H), 6.93 (s, 1H), 7.08 (d, 2H), 7.50 (m, 3H), 7.74 (m, 3H), 8.32 (s, 1H), 9.08 (brs, 2H), 9.27 (brs, 2H), 10.18 (s, 2H); HPLC: 94.34% (Retention Time = 4.828 min). |

TABLE 16-continued

| Cpd. ID. | R₂ | m | R₃ | Characteristic Data |
|---|---|---|---|---|
| I-375 | ![structure with H₂N-CH₂-CH₂-C(=O)-NH-C₆H₄-CH₂-] | 1 | —F | LCMS (M + 1)⁺: 451.2<br>¹H NMR: δ 2.22 (m, 2H), 2.67 (m, 2H), 3.03 (m, 2H), 3.52 (m, 3H), 3.61 (m, 2H), 5.58 (m, 2H), 7.05 (m, 3H), 7.46 (d, 2H), 7.54 (d, 1H), 7.76 (m, 4H), 8.25 (d, 1H), 9.11 (brs, 2H), 9.27 (brs, 2H); HPLC: 88.87% (Retention Time = 4.572 min). |
| I-376 | ![structure with H₂N-CH₂-CH₂-C(=O)-NH-C₆H₄-CH₂-] | 1 | —F₂ | LCMS (M + 1)⁺: 469.2<br>¹H NMR: δ 2.22 (m, 2H), 2.64 (m, 2H), 3.35 (m, 2H), 3.57 (m, 2H), 3.75 (m, 2H), 5.54 (d, 2H), 7.05 (m, 3H), 7.46 (d, 2H), 7.54 (d, 1H), 7.76 (m, 3H), 8.12 (d, 1H), 9.11 (brs, 2H), 9.27 (brs, 2H); HPLC: 93.35% (Retention Time = 5.363 min). |
| I-377 | ![structure with H₂N-CH₂-CH₂-C(=O)-NH-C₆H₄-CH₂-] | 2 | —CH₂F | LCMS (M + 1)⁺: 479.2<br>¹H NMR: δ 0.82 (m, 1H), 0.92 (m, 1H), 1.19 (m, 1H), 1.65 (m, 1H), 1.85 (m. 1H), 2.63 (m, 2H), 2.95 (m, 2H), 3.04 (m, 2H), 4.11 (m, 1H), 4.21 (m, 2H), 4.45 (m, 1H), 5.47 (d, 2H), 6.82 (s, 1H), 7.07 (d, 2H), 7.50 (m, 3H), 7.74 (m, 4H), 8.32 (s, 1H), 9.02 (brs, 2H), 9.26 (brs, 2H), 10.18 (brs, 1H); HPLC: 85.78% (Retention Time = 4.916 min). |
| I-378 | ![structure with H₂N-CH₂-CH₂-C(=O)-NH-C₆H₄-CH₂-] | 2 | ![fused benzene ring] | LCMS (M + 1)⁺: 495.2<br>¹H NMR: δ 2.81 (m, 4H), 3.00 (m, 2H), 4.51 (m, 1H), 4.72 (s, 1H), 5.50 (s, 2H), 6.95 (m, 2H), 7.11 (m, 5H), 7.56 (m, 2H), 7.83 (m, 4H), 8.45 (m, 1H), 8.97 (brs, 2H), 9.32 (brs, 2H); HPLC: 82.81% (Retention Time = 5.087 min). |

General synthetic scheme - 12

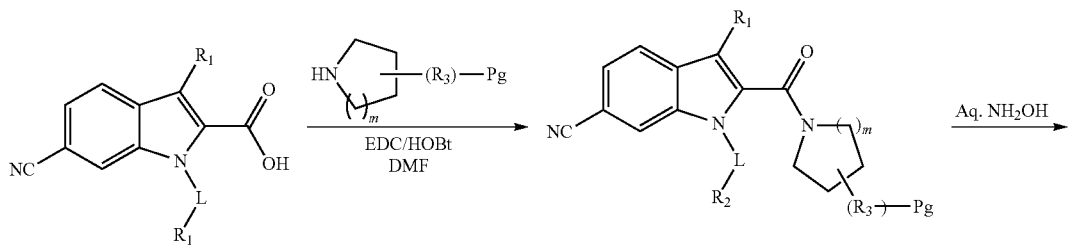

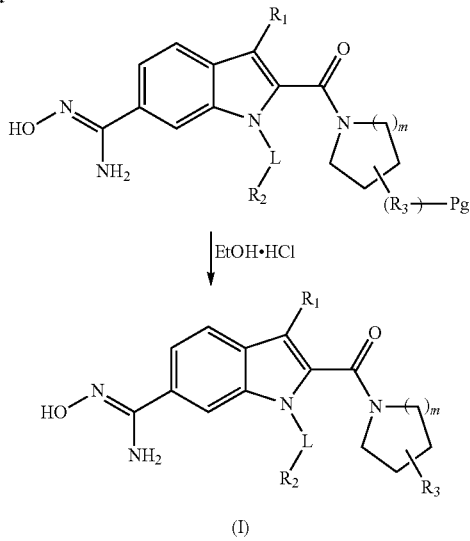

(I)

$R_1$ = H, Pg = Protecting group; $R_2$, $R_3$ and m are as defined in formula (I)

Yet another general approach for the synthesis of compounds of general formula (I) is depicted in general synthetic scheme-12. Appropriately functionalized 6-cyano indole 2 carboxylic acids were coupled functionalized cyclic amines using EDC/HOBt to yield C(2) amides which on treatment with aq. hydroxylamine followed by deprotection of acid labile protecting groups with ethanolic HCl yielded analogs of general formula (I).

Example 76: Synthesis of Compound I-379

2-(4-(2-Aminoethyl)piperidine-1-carbonyl)-N'-hydroxy-1-(4-(trifluoromethyl)benzyl)-1H-indole-6-carboximidamide

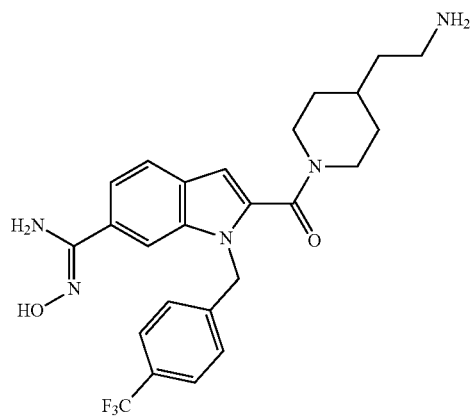 [SMILES: NCCC1CCN(C(=O)c2cc3ccc(/C(N)=N/O)cc3n2Cc2ccc(C(F)(F)F)cc2)CC1]

Step-1: tert-Butyl (2-(1-(6-cyano-1-(4-(trifluoromethyl)benzyl)-1H-indole-2-carbonyl)piperidin-4-yl)ethyl)carbamate The product of step-2 of example-73 (753 mg, 2.19 mmol) and tert-butyl (2-(piperidin-4-yl)ethyl)carbamate (500 mg, 2.19 mmol) were treated together to afford 575 mg of the title compound following the procedure described in step-3 of example 68. LCMS: 555.3 $(M+1)^+$.

Step-2: tert-Butyl-(2-(1-(6-(N'-hydroxycarbamimidoyl)-1-(4-(trifluoromethyl)benzyl)-1H-indole-2-carbonyl)piperidin-4-yl)ethyl)carbamate The product of step-1 of example-76 (500 mg, 0.9 mmol) was treated with aq $NH_2OH$ solution (0.3 mL) to afford 425 mg of the title compound following the procedure described in step-4 of example 69. LCMS: 588.3 $(M+1)^+$.

Step-3: 2-(4-(2-Aminoethyl)piperidine-1-carbonyl)-N'-hydroxy-1-(4-(trifluoromethyl)benzyl)-1H-indole-6-carboximidamide The product of step-2 of example-76 (420 mg, 0.71 mmol) was treated with 30 mL of ethanolic-HCl to afford 180 mg of the title compound following the procedure described in step-7 of example 71. LCMS: 488.2 $(M+1)^+$, $^1H$ NMR (300 MHz, DMSO-$d_6$): δ 0.66 (m, 1H), 0.95 (m, 1H), 1.31 (m, 5H), 2.61 (m, 5H), 4.21 (m, 1H), 5.61 (s, 2H), 6.91 (s, 1H), 7.32 (d, 2H), 7.41 (d, 1H), 7.60 (m, 4H), 7.85 (d, 1H), 8.20 (s, 1H), 9.00 (brs, 2H), 11.10 (brs, 1H).

The following compounds listed in table-17 were prepared according to scheme-12 by following similar procedure as described above for example 76 using appropriate reagents with suitable modifications known to the one skilled in the art.

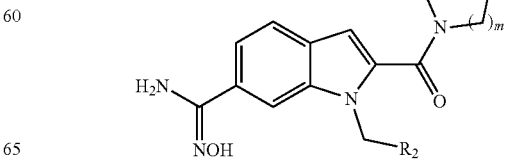

TABLE 17

| Cpd. ID. | R₂ | R₃ | m | ¹H NMR |
|---|---|---|---|---|
| I-380 | biphenyl | —(CH₂)₂NH₂ | 2 | LCMS (M + 1)⁺: 496.3<br>¹H NMR: δ 0.56 (m, 2H), 0.82 (m, 2H), 1.33 (m, 2H), 1.50 (m, 1H), 1.62 (m, 2H), 2.71 (m, 4H), 3.71 (m, 1H), 4.45 (m, 1H), 5.51 (s, 2H), 6.81 (s, 1H), 7.15 (d, 2H), 7.35 (m, 1H), 7.45 (m, 3H), 7.60 (m, 6H), 7.82 (d, 1H), 8.15 (s, 1H); HPLC: 96.43% (Retention Time = 6.943 min). |
| I-381 | 3-(H₂N-CH₂CH₂-C(O)NH)-benzyl | —(CH₂)₂NH₂ | 2 | LCMS (M + 1)⁺: 506.3<br>¹H NMR: δ 0.52 (m, 1H), 0.82 (m, 1H), 1.35 (m, 4H), 1.65 (m, 1H), 2.65 (m, 2H), 2.71 (m, 4H), 3.05 (m, 2H), 3.80 (m, 1H), 4.44 (m, 1H), 5.51 (s, 2H), 6.70 (d, 1H), 6.81 (s, 1H), 7.32 (m, 2H), 7.49 (m, 2H), 7.80 (m, 6H), 8.15 (s, 1H), 9.01 (brs, 2H), 10.15 (brs, 1H), 11.11 (brs, 1H); HPLC: 97.96% (Retention Time = 4.392 min). |
| I-382 | 3-(H₂N-CH₂CH₂CH₂-C(O)NH)-benzyl | —(CH₂)₂NH₂ | 2 | LCMS (M + 1)⁺: 520.3<br>¹H NMR: δ 0.49 (m, 1H), 0.82 (m, 1H), 1.15 (m, 1H), 1.32 (m, 4H), 1.80 (m, 2H), 2.35 (m, 2H), 2.71 (m, 4H), 3.85 (m, 1H), 4.44 (m, 2H), 5.5 (s, 2H), 6.80 (m, 2H), 7.32 (m, 2H), 7.49 (m, 2H), 7.80 (m, 6H), 8.15 (s, 1H), 8.88 (brs, 1H), 10.00 (brs, 2H), 11.11 (brs, 1H); HPLC: 96.323% (Retention Time = 4.136 min). |
| I-383 | 4-(H₂N-CH₂CH₂-C(O)NH)-benzyl | —(CH₂)₂NH₂ | 2 | LCMS (M + 1)⁺: 506.3<br>¹H NMR: δ 0.49 (m, 1H), 0.82 (m, 1H), 1.15 (m, 1H), 1.32 (m, 4H), 1.80 (m, 2H), 2.35 (m, 2H), 2.71 (m, 4H), 3.85 (m, 1H), 4.44 (m, 2H), 5.5 (s, 2H), 6.80 (m, 2H), 7.32 (m, 2H), 7.49 (m, 2H), 7.80 (m, 6H), 8.15 (s, 1H), 8.88 (brs, 2H), 10.00 (brs, 1H), 11.11 (brs, 1H); HPLC: 96.06% (Retention Time = 4.347 min). |

TABLE 17-continued
| Cpd. ID. | R$_2$ | R$_3$ | m | $^1$H NMR |
|---|---|---|---|---|
| I-384 | 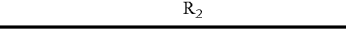 | —(CH$_2$)$_2$NH$_2$ | 2 | LCMS (M + 1)$^+$: 520.3<br>$^1$H NMR: δ 0.49 (m, 1H), 0.98 (m, 1H), 1.35 (m, 4H), 1.80 (m, 3H), 2.35 (m, 2H), 2.71 (m, 4H), 3.65 (m, 1H), 3.85 (m, 2H), 4.44 (m, 2H), 5.48 (s, 2H), 6.78 (s, 1H), 7.22 (d, 2H), 7.41 (d, 1H), 7.48 (md, 2H), 7.78 (m, 6H), 8.18 (s, 1H), 9.01 (brs, 2H), 10.02 (brs, 1H), 11.11 (brs, 1H); HPLC: 96.78% (Retention Time = 4.276 min). |
General synthetic scheme-13
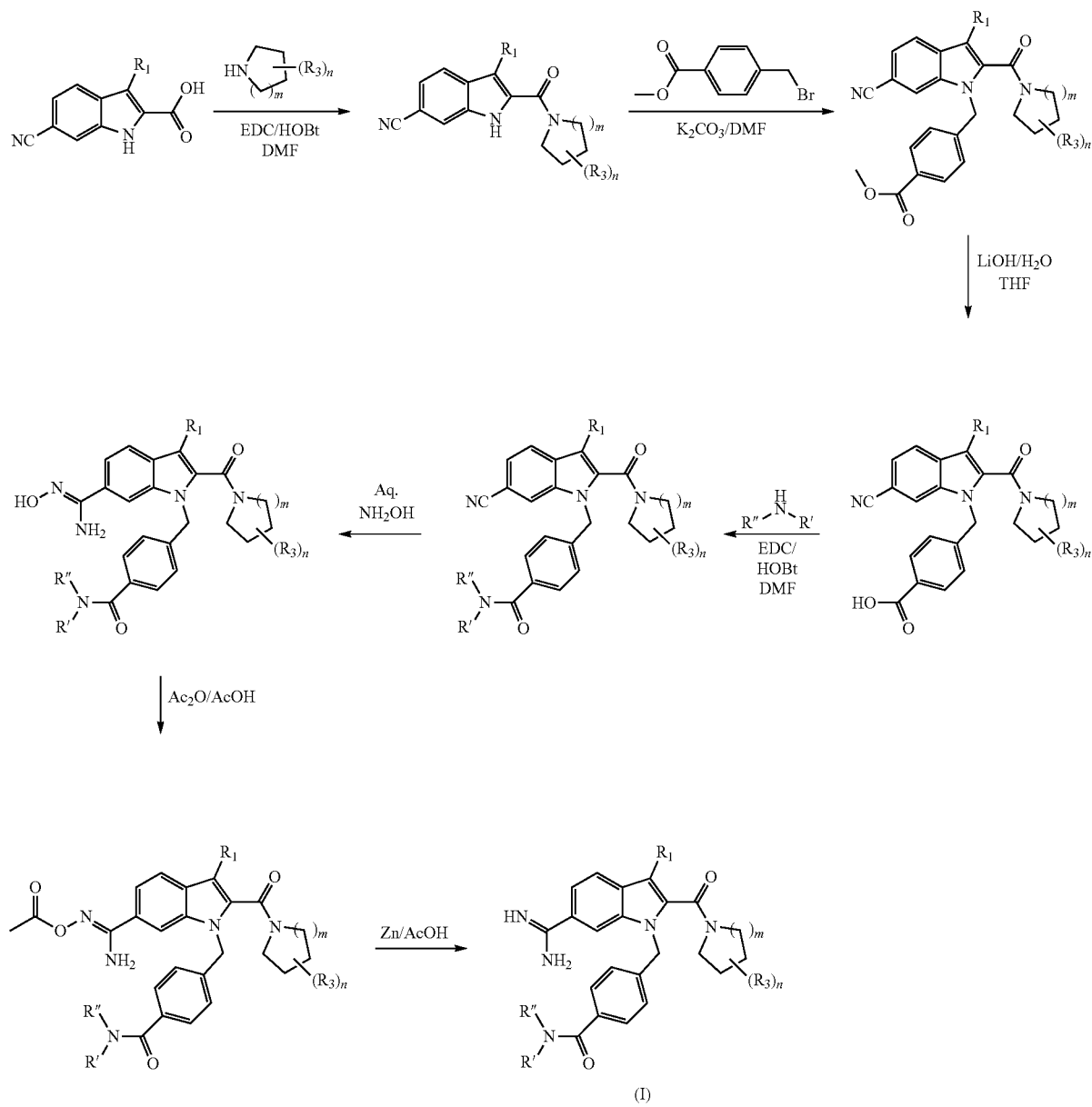
R$_1$ = H; R$_3$, m and n are as defined in formula (I); R′ and R″ are appropriate substitutions as given in the examples below Yet another general approach for the synthesis of compounds of general formula (I) is depicted in general synthetic scheme-13. Following procedures described in the scheme above compounds of Formula (I) were synthesized.

Example 77: Synthesis of Compound I-385

4-((6-Carbamimidoyl-2-(3,3-difluoropyrrolidine-1-carbonyl)-1H-indol-1-yl)methyl)-N-ethylbenzamide

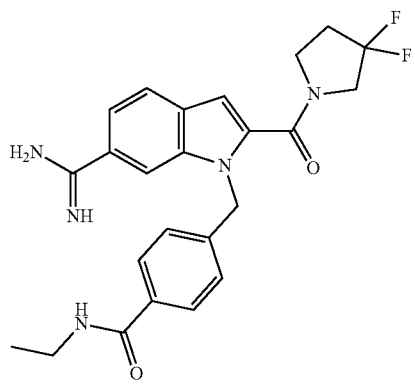 [SMILES: CCNC(=O)c1ccc(Cn2c(C(=O)N3CCC(F)(F)C3)cc3ccc(C(=N)N)cc32)cc1]

Step-1: 2-(3,3-Difluoropyrrolidine-1-carbonyl)-1H-indole-6-carbonitrile

6-Cyano-1H-indole-2-carboxylic acid (1.5 g, 8.06 mmol) and 3,3-difluoropyrrolidine (862 mg, 8.06 mmol) were treated together to afford 1.27 g of the title compound following the procedure described in step-3 of example 68. LCMS: 276.1 (M+1)$^+$.

Step-2: Methyl 4-((6-cyano-2-(3,3-difluoropyrrolidine-1-carbonyl)-1H-indol-1-yl)methyl)-benzoate The product of step-1 of example-77 (1.2 g, 4.34 mmol) was treated with methyl 4-(bromomethyl)benzoate (990 mg, 4.34 mmol) to afford 1.28 g of the title compound following the procedure described in step-1 of example 68. LCMS: 424.1 (M+1)$^+$.

Step-3: 4-((6-Cyano-2-(3,3-difluoropyrrolidine-1-carbonyl)-1H-indol-1-yl)methyl)benzoic Acid The product of step-2 of example-77 (1.2 g, 2.83 mmol) was treated with LiOH (544 mg, 22.7 mmol) to afford 810 mg of the title compound following the procedure described in step-2 of example 68. LCMS: 410.1 (M+1)$^+$.

Step-4: 4-((6-Cyano-2-(3,3-difluoropyrrolidine-1-carbonyl)-1H-indol-1-yl)methyl)-N-ethylbenzamide The product of step-3 of example-77 (800 mg, 1.95 mmol) and tert-butyl (3-aminopropyl)carbamate (340 mg, 1.95 mmol) were treated together to afford 530 mg of the title compound following the procedure described in step-3 of example 68. LCMS: 437.2 (M+1)$^+$.

Step-5: 4-((2-(3,3-Difluoropyrrolidine-1-carbonyl)-6-(N'-hydroxycarbamimidoyl)-1H-indol-1-yl)methyl)-N-ethylbenzamide The product of step-4 of example-77 (500 mg, 1.14 mmol) was treated with aq. NH$_2$OH solution (0.4 mL) to afford 375 mg of the title compound following the procedure described in step-4 of example 69. LCMS: 470.2 (M+1)$^+$.

Step-6: 4-((6-(N'-Acetoxycarbamimidoyl)-2-(3,3-difluoropyrrolidine-1-carbonyl)-1H-indol-1-yl)methyl)-N-ethylbenzamide The product of step-5 of example-77 (250 mg, 0.53 mmol) was treated with Ac$_2$O (435 mg, 4.26 mmol) to afford 180 mg of the title compound following the procedure described in step-5 of example 69 LCMS: 512.2 (M+1)$^+$.

Step-7: 4-((6-Carbamimidoyl-2-(3,3-difluoropyrrolidine-1-carbonyl)-1H-indol-1-yl)methyl)-N-ethylbenzamide The product of step-6 of example-77 (150 mg, 0.29 mmol) was treated with Zn (150 mg, 2.34 mmol) to afford 35 mg of the title compound following the procedure described in step-6 of example 69. LCMS: 454.2 (M+1)$^+$, $^1$H NMR (300 MHz, DMSO-d$_6$): δ 1.06 (m, 3H), 2.29 (s, 2H), 3.22 (m, 2H), 3.68 (m, 2H), 3.89 (m, 2H), 5.67 (d, 2H), 7.10 (m, 3H), 7.54 (d, 2H), 7.73 (m, 2H), 7.86 (d, 1H), 8.40 (m, 1H), 8.95 (brs, 2H), 9.25 (brs, 2H); HPLC: 96.93% (Retention Time 3.264 min).

The following compounds listed in table-18 were prepared according to scheme-13 by following similar procedure as described above for example-77 using appropriate reagents with suitable modifications known to the one skilled in the art.

TABLE 18

| Cpd. ID. | R$_2$ | m | R$_3$ | Characteristic Data |
|---|---|---|---|---|
| I-386 | 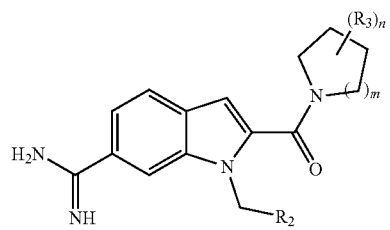 | 1 | —F$_2$ | LCMS (M + 1)$^+$: 454.2<br>$^1$H NMR: δ 2.30 (m, 2H), 2.84 (s, 3H), 2.94 (s, 3H), 3.61 (m, 2H), 3.82 (m, 2H), 5.65 (d, 2H), 7.07 (m, 3H), 7.31 (m, 2H), 7.54 (d, 1H), 7.86 (d, 1H), 8.25 (s, 1H), 8.97 (brs, 2H), 9.26 (brs, 2H); HPLC: 91.12% (Retention Time = 5.557 min). |

TABLE 18-continued

| Cpd. ID. | R₂ | m | R₃ | Characteristic Data |
| --- | --- | --- | --- | --- |
| I-387 | 4-(cyclopropylcarbamoyl)benzyl | 1 | —F₂ | LCMS (M + 1)⁺: 466.2<br>¹H NMR: δ 0.49 (m, 2H), 0.64 (m, 2H), 2.30 (m, 2H), 2.79 (m, 1H), 3.67 (m, 2H), 3.89 (m, 2H), 5.66 (d, 2H), 7.10 (m, 3H), 7.54 (m, 1H), 7.71 (d, 2H), 7.86 (d, 1H), 8.18 (s, 1H), 8.36 (brs, 1H), 8.93 (brs, 2H), 9.25 (brs, 2H); HPLC: 88.64% (Retention Time = 3.448 min). |
| I-388 | 4-(methylcarbamoyl)benzyl | 2 | —F | LCMS (M + 1)⁺: 436.2<br>¹H NMR: δ 1.30 (m, 4H), 2.76 (d, 3H), 3.37 (m, 4H), 4.71 (m, 1H), 5.62 (s, 2H), 6.94 (s, 1H), 7.16 (d, 2H), 7.57 (m, 1H), 7.76 (d, 2H), 7.87 (d, 1H), 8.28 (s, 1H), 8.40 (m, 1H), 8.93 (brs, 2H), 9.25 (brs, 2H); HPLC: 96.44% (Retention Time = 5.308 min). |
| I-389 | 4-(dimethylcarbamoyl)benzyl | 2 | —F | LCMS (M + 1)⁺: 450.2<br>¹H NMR: δ 1.30 (m, 4H), 2.86 (s, 3H), 2.96 (s, 3H), 3.37 (m, 4H), 4.71 (m, 1H), 5.62 (s, 2H), 6.94 (s, 1H), 7.13 (d, 2H), 7.35 (d, 2H), 7.57 (d, 1H), 7.87 (d, 1H), 8.33 (s, 1H), 9.03 (brs, 2H), 9.28 (brs, 2H); HPLC: 95.24% (Retention Time = 5.507 min). |
| I-390 | 4-(ethylcarbamoyl)benzyl | 2 | —F | LCMS (M + 1)⁺: 450.2<br>¹H NMR: δ 1.10 (m, 3H), 1.44 (m, 2H), 1.71 (m, 2H), 2.25 (m, 3H), 3.37 (m, 4H), 4.71 (m, 1H), 5.62 (s, 2H), 6.94 (s, 1H), 7.16 (d, 2H), 7.57 (d, 1H), 7.77 (d, 2H), 7.87 (d, 1H), 8.27 (s, 1H), 8.42 (m, 1H), 8.95 (brs, 2H), 9.26 (brs, 2H); HPLC: 96.31% (Retention Time = 5.506 min). |
| I-391 | 4-(cyclopropylcarbamoyl)benzyl | 2 | —F | LCMS (M + 1)⁺: 462.2<br>¹H NMR: δ 0.54 (m, 2H), 0.68 (m, 2H), 1.30 (m, 4H), 2.82 (m, 1H), 3.37 (m, 4H), 4.71 (m, 1H), 5.62 (s, 2H), 6.95 (s, 1H), 7.16 (d, 2H), 7.57 (d, 1H), 7.75 (d, 2H), 7.87 (d, 1H), 8.26 (s, 1H), 8.39 (d, 1H), 8.96 (brs, 2H), 9.26 (brs, 2H); HPLC: 97.99% (Retention Time = 5.528 min). |
| I-392 | 4-((2-aminoethyl)carbamoyl)benzyl | 1 | —F₂ | LCMS (M + 1)⁺: 469.2<br>¹H NMR: δ 2.92 (m, 2H), 3.67 (m, 4H), 3.87 (m, 4H), 5.67 (d, 2H), 7.15 (m, 3H), 7.55 (d, 1H), 7.77 (m, 4H), 7.89 (d, 1H), 7.18 (s, 1H), 8.52 (brs, 1H), 9.00 (brs, 2H), 9.25 (brs, 2H); HPLC: 90.99% (Retention Time = 4.71 min). |

TABLE 18-continued

| Cpd. ID. | R₂ | m | R₃ | Characteristic Data |
|---|---|---|---|---|
| I-393 | 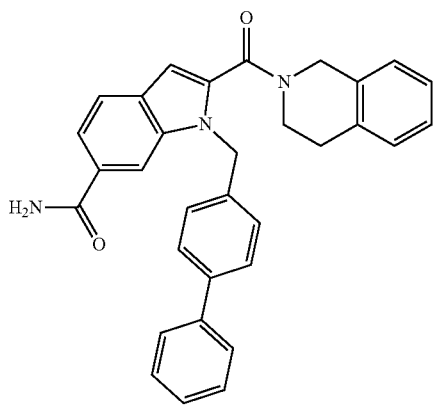 | 2 | —F | LCMS (M + 1)⁺: 465.2<br>¹H NMR: δ 1.41 (m, 4H), 2.82 (m, 2H), 3.37 (m, 6H), 4.71 (m, 1H), 5.61 (s, 2H), 6.91 (d, 1H), 7.18 (d, 2H), 7.55 (d, 1H), 7.77 (m, 4H), 8.23 (s, 1H), 8.58 (m, 1H), 9.11 (brs, 2H), 9.25 (brs, 2H); HPLC: 94.62% (Retention Time = 4.688 min). |

Example 78: Synthesis of Compound I-394

1-([1,1'-Biphenyl]-4-ylmethyl)-2-(1,2,3,4-tetrahydroisoquinoline-2-carbonyl)-1H-indole-6-carboxamide

Step-1: Ethyl 1-([1,1'-biphenyl]-4-ylmethyl)-6-cyano-1H-indole-2-carboxylate Ethyl 6-cyano-1H-indole-2-carboxylate (800 mg, 3.73 mmol) and 4-(bromomethyl)-1,1'-biphenyl (917 mg, 3.73 mmol) were treated together to afford 985 mg of the title compound following the procedure described in step-1 of example 68. LCMS: 381.1 (M+1)⁺.

Step-2: 1-([1,1'-Biphenyl]-4-ylmethyl)-6-cyano-1H-indole-2-carboxylic Acid

The product of step-1 of example-78 (980 mg, 2.57 mmol) was treated with LiOH (495 mg, 20.63 mmol) to afford 630 mg of the title compound following the procedure described in step-2 of example 68. LCMS: 353.1 (M+1)⁺.

Step-3: 1-([1,1'-Biphenyl]-4-ylmethyl)-2-(1,2,3,4-tetrahydroisoquinoline-2-carbonyl)-1H-indole-6-carbonitrile The product of step-2 of example-78 (600 mg, 1.7 mmol) and 1,2,3,4-tetrahydroisoquinoline (226 mg, 1.7 mmol) were treated together to afford 410 mg of the title compound following the procedure described in step-3 of example 68. LCMS: 468.2 (M+1)⁺.

Step-4: 1-([1,1'-Biphenyl]-4-ylmethyl)-2-(1,2,3,4-tetrahydroisoquinoline-2-carbonyl)-1H-indole-6-carboxamide To a solution of the product of step-3 of example-78 (350 mg, 0.75 mmol) in 5 mL of the mixture of MeOH and H₂O (1:1) was added solid NaOH (240 mg, 6.0 mmol). The reaction was stirred at 50° C. Upon reaction completion, the reaction mixture was concentrated to remove methanol and acidified with 2N HCl. The aq mixture was extracted with ethyl acetate and dried over anhydrous sodium sulphate. Solvent was evaporated under vacuum to give crude product which was purified by reverse-phase preparative HPLC and afforded 80 mg of the title compound. LCMS: 486.2 (M+1)⁺, ¹H NMR (300 MHz, DMSO-d₆): δ 2.61 (m, 2H), 3.6 (m, 2H), 4.74 (m, 2H), 4.71 (s, 2H), 5.81 (s, 2H), 6.90 (s, 1H), 7.07 (m, 3H), 7.16 (m, 3H), 7.34 (m, 5H), 7.52 (m, 2H), 7.69 (s, 2H), 7.98 (brs, 2H), 8.26 (brs, 2H); HPLC: 89.33% (Retention Time=5.639 min).

General synthetic scheme - 14

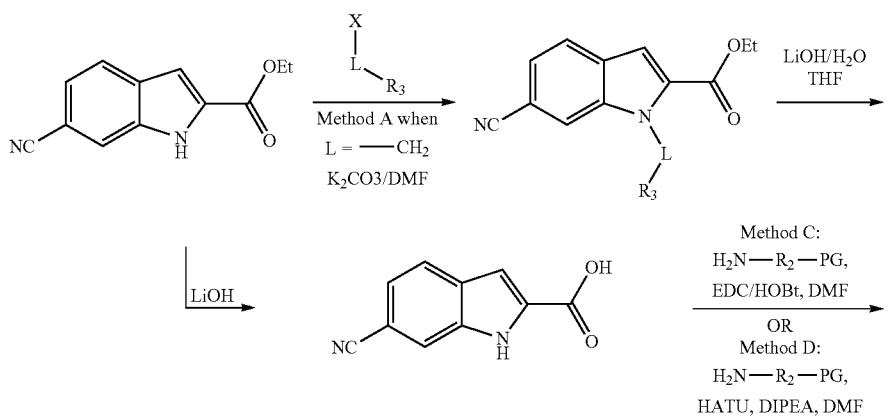

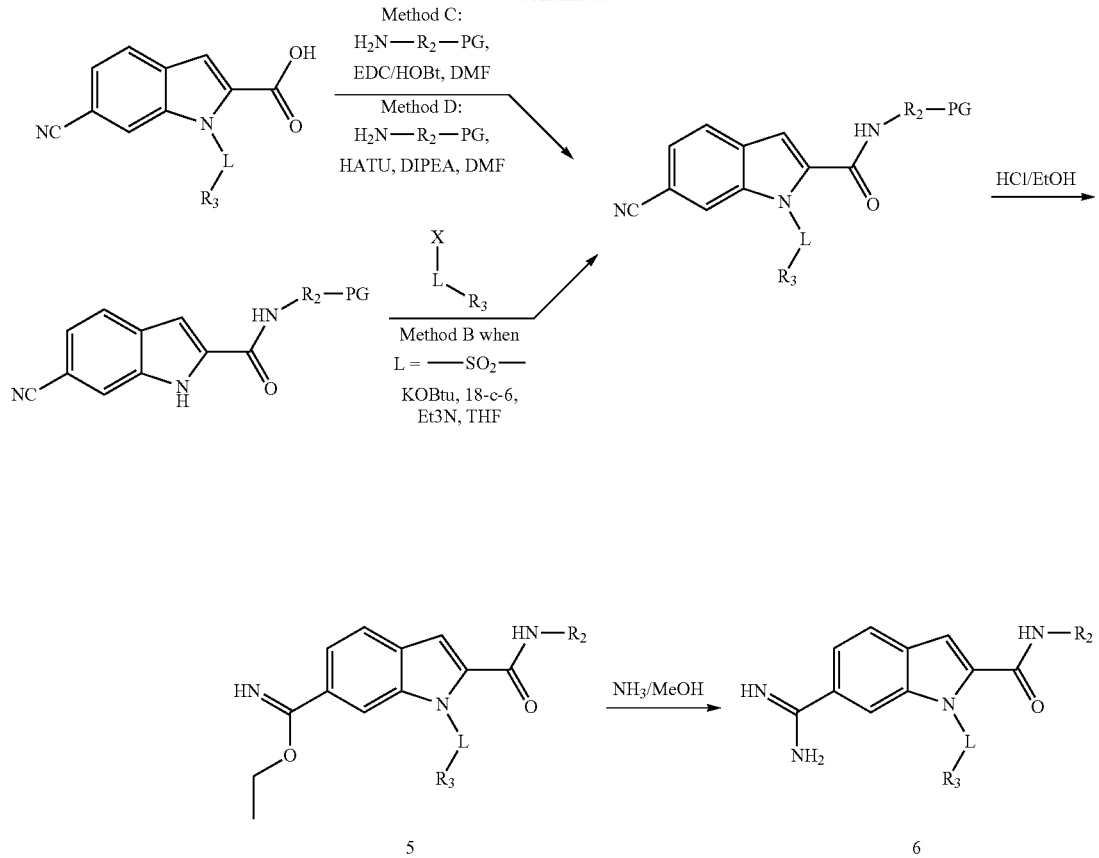

PG = optional protecting group; X = Br or Cl

Example 79: Synthesis of Compound I-395

Carbamimidoyl-N-(4-carbamimidoylbenzyl)-1-(naphthalen-1-ylmethyl)-1H-indole-2-carboxamide)

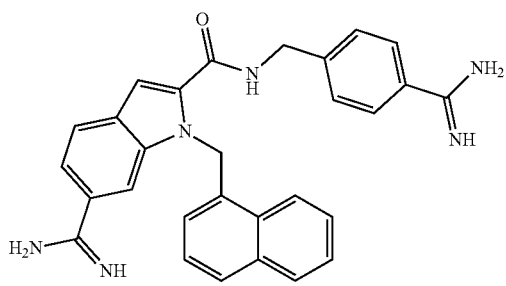 [SMILES: N=C(N)c1ccc(CNC(=O)c2cc3ccc(C(=N)N)cc3n2Cc2cccc3ccccc23)cc1]

Step-1: Ethyl 6-cyano-1-(naphthalen-1-ylmethyl)-1H-indole-2-carboxylate

To a solution of ethyl 6-cyano-1H-indole-2-carboxylate (2.0 g, 8.433 mmol) in DMF (20 ml) was added potassium carbonate (3.90 g, 28.32 mmol), solution of 1-(bromomethyl)naphthalene (3.1 g, 14.15 mmol) dissolved in THF (10 mL) and stirred at room temperature for 3 h. After reaction completion, THF was distilled off, added ice-cold water and precipitated product was filtered off. Thus, obtained solid was dried under vacuum to give title compound (2.2 g, crude) which was proceeded to next step without purification. LCMS: 353.1 (M-1)$^+$.

Step-2: 6-cyano-1-(naphthalen-1-ylmethyl)-1H-indole-2-carboxylic Acid

Product of step-1 of example-79 (1.0 g, 2.8 mmol) was dissolved in mixture of tetrahydrofuran/ethanol/water (10 mL: 5 mL: 3 mL) and added lithium hydroxide monohydrate (155 mg, 2.67 mmol) at room temperature. Resulting mixture was stirred at room temperature for 12 h. Reaction mixture was distilled off and acidified with 2N HCl, precipitated product was filtered off. Thus obtained solid was dried under vacuum to give titled compound (850 mg, crude) which was proceeded to next step. LCMS: 325.2 (M-1)$^+$.

Step-3: 6-cyano-N-(4-cyanobenzyl)-1-(naphthalen-1-ylmethyl)-1H-indole-2-carboxamide Product of step-2 of example 395 (350 mg, 1.01 mmol) was dissolved in 5 mL of N,N-dimethylformamide and added 1-ethyl-3-(3-dimethylaminopropyl)carbodiimide (194 mg, 1.01 mmol), hydroxybenzotriazole (109 mg, 1.01 mmol) and 4-(aminomethyl)benzonitrile (136 mg, 0.81 mmol) and N,N-diisopropylethylamine (0.352 ml, 2.02 mmol) at 0° C. under nitrogen atmosphere and resulting mixture was stirred at room temperature for 12 h. The reaction mixture was quenched with ice-cold water and precipitated product was filtered off and dried under vacuum. The crude solid obtained was purified by combi-flash on silica-gel and eluted with 0.5% methanol in dichloromethane afforded the title compound (235 mg). LCMS: 441.3 (M+1)+.

Step-4: Ethyl 2-((4-(ethoxy(imino)methyl)benzyl)carbamoyl)-1-(naphthalen-1-ylmethyl)-1H-indole-6-carbimidate Product of step-3 of example 79 (170 mg, 0.39 mmol) was dissolved in 10 mL of ethanolic-HCl and 5 mL of dioxane·HCl kept in a glass sealed tube at 0° C. and stirred for 12 h at room temperature. Reaction was not completed. Again added 10 mL 4M soln of HCl in dioxane and stirred for 2 days at RT. After reaction completion, solvent was evaporated under vacuum to afford the title compound (not isolated) and as such crude product proceeded to next step. LCMS: 533.7 (M+1)+.

Step-5: Carbamimidoyl-N-(4-carbamimidoylbenzyl)-1-(naphthalen-1-ylmethyl)-1H-indole-2-carboxamide (TFA Salt)

Product of step-4 of example 79 was dissolved in 50 mL of methanolic-ammonia kept in sealed tube, stirred for 12 h at RT. After reaction completion, solvent was evaporated under vacuum to give crude product which was purified by preparative HPLC instrument with a Kinetex EVO C18 reverse phase column (21.2×150 mm, 5 micron). The mobile phases were 30% acetonitrile in water (0.1% TFA) to 60% acetonitrile (0.1% TFA) which afforded the title compound (100 mg) as a TFA Salt.
LCMS: 475.2 [M+1]+; $^1$HNMR (400 MHz, CD$_3$OD): δ 4.52 (s, 2H), 6.20 (dd, 1H), 6.45 (s, 2H), 7.19 (dd, 1H), 7.27-7.34 (m, 2H), 7.37 (d, 1H), 7.50-7.65 (m, 5H), 7.77 (d, 1H), 7.90-8.02 (m, 3H), 8.16-8.22 (m, 1H). HPLC: 99.45% (Retention Time=4.88 min).

Example 80: Synthesis of Compound I-396

N-((1r,4r)-4-aminocyclohexyl)-6-carbamimidoyl-1-(naphthalen-1-ylsulfonyl)-1H-indole-2-carboxamide

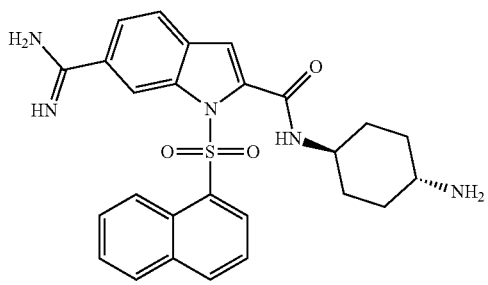 [SMILES: N=C(N)c1ccc2cc(C(=O)N[C@H]3CC[C@H](N)CC3)n(S(=O)(=O)c3cccc4ccccc34)c2c1]

Step-1: 6-cyano-1H-indole-2-carboxylic Acid

Ethyl 6-cyano-1H-indole-2-carboxylate (700 mg, 3.28 mmol) was treated with lithium hydroxide monohydrate (207 mg, 4.92 mmol) to afford 600 mg of title compound following the procedure described in step-2 of example 79. LCMS: 184.9 (M−1)+.

Step-2: tert-butyl ((1r,4r)-4-(6-cyano-1H-indole-2-carboxamido)cyclohexyl)carbamate The product of step-1 of example 80 (600 mg, 3.22 mmol) and tert-butyl ((1r,4r)-4-aminocyclohexyl)carbamate (700 mg, 3.22 mmol) were treated together to afford 1.1 g of the title compound following the procedure described in step-3 of example 79. LCMS: 283.0 (M−100)+.

Step-3: tert-butyl ((1r,4r)-4-(6-cyano-1-(naphthalen-1-ylsulfonyl)-1H-indole-2-carboxamido)cyclohexyl)carbamate To a solution of product of step 2 of example 80 (500 mg, 1.305 mmol) in THF (15 ml) was added potassium tert-butoxide (250 m g, 2.21 mmol) and 18-crown-6 (35 mg, 0.130 mmol) at 0° C. followed by the addition of THF solution (5 mL) of naphthalene-1-sulfonyl chloride (442 mg, 1.958 mmol) at 0° C. The resulting reaction mixture was stirred at room temperature for 12 h. After reaction completion, added ice water and extracted with ethyl acetate (2×50 mL). Separated the organic layers and concentrated under vacuum. The crude residue obtained was purified by combiflash on silica gel eluted with 0.5% methanol in dichloromethane to give title compound (200 mg). LCMS: 517.4 (M−56)+.

Step-4: Ethyl2-(((1r,4r)-4-aminocyclohexyl)carbamoyl)-1-(naphthalen-1-ylsulfonyl)-1H-indole-6-carbimidate The product of step-3 of example 80 (220 mg, 0.384 mmol) was treated with 10 mL of ethanolic-HCl and 4M soln of HCl in dioxane at room temperature for 3 days to afford 250 mg of the title compound following the procedure described in step-4 of example 79. LCMS: 518.8 (M)+. As such crude product proceeded to next step Step-5: N-((1r,4r)-4-aminocyclohexyl)-6-carbamimidoyl-1-(naphthalen-1-ylsulfonyl)-1H-indole-2-carboxamide (TFA Salt)

The product of step-4 of example 80 (250 mg (crude), 0.482 mmol) was treated with 10 mL of ethanolic-NH$_3$ at room temperature as described in the step-5 of example 1 to give the crude product which was purified by preparative HPLC instrument with a LUNA C18 reverse phase column (21.2×150 mm, 5 micron). The mobile phases were 30% acetonitrile in water (0.02% TFA) to 60% acetonitrile (0.02% TFA) which afforded the title compound (50 mg) as a TFA Salt.
LCMS: 490.3 (M+1)+; $^1$HNMR (300 MHz, CD$_3$OD): δ 1.52-1.38 (m, 4H), 2.08-2.05 (m, 4H), 3.08-3.06 (m, 1H), 3.78-3.62 (m, 1H), 7.11 (s, 1H), 7.70-7.54 (m, 4H), 7.90-7.87 (m, 1H), 8.04-8.00 (m, 2H), 8.24-8.21 (d, 1H), 8.49-8.40 (m, 2H); HPLC: 99.5% (Retention Time=4.55 min).

The following compound listed in table-19 prepared according to Scheme-14 by following similar procedure as described above for example 80 using appropriate reagents with suitable modifications known to the one skilled in the art.

TABLE 19
Compounds synthesized using general scheme-14
| Cpd. ID. | Structure | LCMS [M + H]+ | 1H-NMR Data |
|---|---|---|---|
| I-397 | 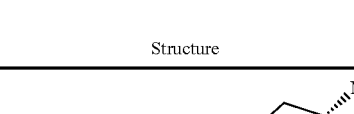 | 490.3 | $^1$HNMR (300 MHz, CD$_3$OD): δ 1.60-1.49 (m, 4H), 1.98 (s, 6H), 2.23-2.13 (m, 4H), 3.20-3.18 (m, 1H), 3.95-3.90 (m, 1H), 7.04 (s, 1H), 7.70-7.63 (m, 3H), 7.81-7.79 (d, 1H), 8.10-7.93 (m, 4H), 8.58 (s, 1H), 8.74 (s, 1H). |
General synthetic scheme-15
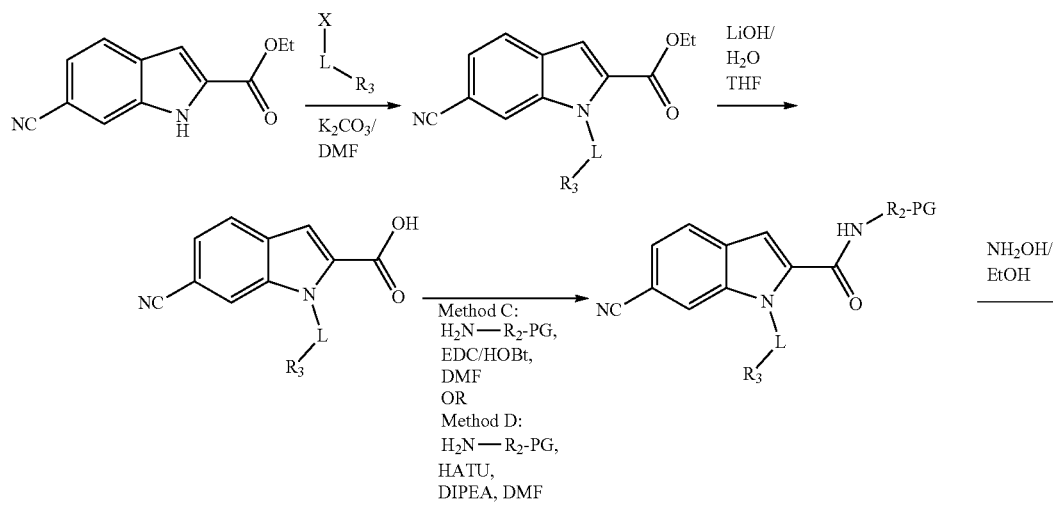
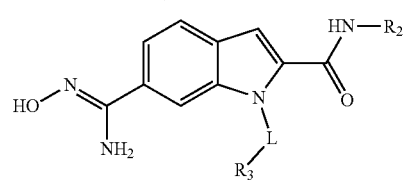

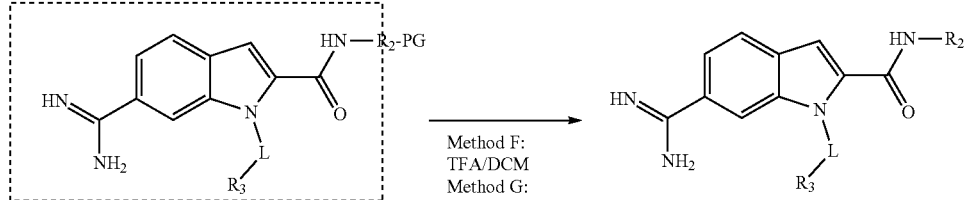

PG = optional protecting group; X = Br or Cl;

Example 81: Synthesis of Compound I-398

6-(N'-hydroxycarbamimidoyl)-1-(naphthalen-2-ylmethyl)-N-(piperidin-4-ylmethyl)-1H-indole-2-carboxamide

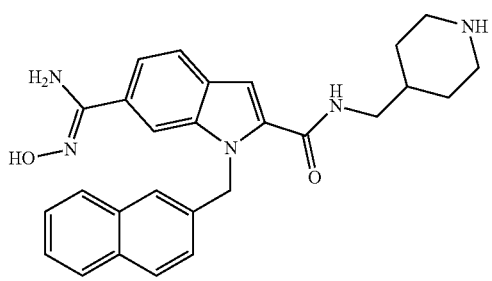 [SMILES: N/C(=N\O)c1ccc2cc(C(=O)NCC3CCNCC3)n(Cc3ccc4ccccc4c3)c2c1]

Step-1: Ethyl 6-cyano-1-(naphthalen-2-ylmethyl)-1H-indole-2-carboxylate

To a solution of ethyl 6-cyano-1H-indole-2-carboxylate (380 mg, 1.77 mmol) in DMF (10 ml) was added potassium carbonate (612 mg, 4.43 mmol) and 2-(bromomethyl)naphthalene (392 mg, 1.77 mmol) at room temperature and stirred for overnight (12 h) at room temperature. After reaction completion, added water and extracted with ethyl acetate, dried over anhydrous sodium sulphate and concentrated to give crude product (720 mg) which was further purified by combiflash on silica gel (40 g column)eluted with 30% ethyl acetate in hexane to give title compound (560 mg). LCMS: 355.2 (M+1)+.

Step-2: 6-cyano-1-(naphthalen-2-ylmethyl)-1H-indole-2-carboxylic Acid

Product of step-1 of example 81 (560 mg, 1.58 mmol) was dissolved in mixture of tetrahydrofuran/ethanol (7 mL: 2 mL) and added aqueous solution of lithium hydroxide monohydrate (66 mg, 1.58 mmol) at room temperature. Resulting mixture was stirred at room temperature for 2 h. Reaction mixture was distilled off and acidified with dilute HCl to pH 4, precipitated product was filtered off. Thus obtained solid was dried under vacuum to give titled compound (460 mg, crude) which was proceeded to next step.

Step-3: tert-butyl-4-((6-cyano-1-(naphthalen-2-ylmethyl)-1H-indole-2-carboxamido)methyl)piperidine-1-carboxylate To a stirred solution of product of step-2 of example 81 (330 mg, 1.01 mmol) in DMF added HATU (403 mg, 1.06 mmol) and N, N-diisopropylethylamine (253 mg, 2.02 mmol) at 0° C. After stirred at RT for 10 min, added tert-butyl 4-(amino methyl) piperidine-1-carboxylate (216 mg, 1.01 mmol) and stirred for 3 h at room temperature. After reaction completion, added water and extracted with ethyl acetate, dried over anhydrous sodium sulphate and concentrated to give crude product (470 mg) which was further purified by combiflash on silica gel (24 g column) eluted with 5% methanol in dichloromethane to give title compound (370 mg). LCMS: 523.6 9 (M+1)+.

Step-4: tert-butyl-4-((6-(N'-hydroxycarbamimidoyl)-1-(naphthalen-2-ylmethyl)-1H-indole-2-carboxamido) methyl)piperidine-1-carboxylate The product of step-3 of example 81 (90 mg, 0.172 mmol) was dissolved in 5 mL of ethanol and added 50% aqueous hydroxylamine solution (1.3 mL) and resulting mixture was refluxed for 2 h at 90° C. Solvent was evaporated under vacuum to get crude, water was added and precipitated solid was filtered off and dried under vacuum to afford the title compound (60 mg). LCMS: 556.6 (M+1)+.

Step-5: 6-(N'-hydroxycarbamimidoyl)-1-(naphthalen-2-ylmethyl)-N-(piperidin-4-ylmethyl)-1H-indole-2-carboxamide (TFA Salt)

To a stirred solution of product of step-4 of example 81 (60 mg, 0.108 mmol) in dichloromethane was added TFA (0.2 mL) at room temperature and stirred for 3 h. Evaporated off reaction mixture under reduced pressure at room temperature to give crude product which was purified by preparative HPLC instrument with a Kinetex C18 reverse phase column (19×150 mm, 5 micron). The mobile phases were 10% acetonitrile in water (0.3% TFA) to 40% acetonitrile (0.3% TFA) which afforded the title compound (90 mg) as a TFA Salt. LCMS: 456.2 (M+1)+; $^1$HNMR (400 MHz, CD$_3$OD): δ1.28-1.09 (m, 2H), 1.54-1.48 (d, 2H), 1.59-1.55 (m, 1H), 2.51-2.44 (m, 2H), 3.01-2.98 (d, 2H), 3.16-3.14 (d, 2H), 6.03 (s, 2H), 7.14-7.12 (d, 1H), 7.20 (s, 1H), 7.33 (s, 1H), 7.43-7.42 (m, 3H), 7.69-7.66 (m, 1H), 7.82-7.75 (m, 2H), 7.93-7.91 (dd, 1H), 8.03 (s, 1H); HPLC: 99.8% (Retention Time=5.11 min)

The following compound listed in table-20 prepared according to general scheme-15 by following similar procedure as described above for example 81 using appropriate reagents with suitable modifications known to the one skilled in the art.

TABLE 20

Compounds synthesized using general scheme-15

| Cpd. ID. | Structure | LCMS [M + H]+ | 1H-NMR Data |
|---|---|---|---|
| I-399 | 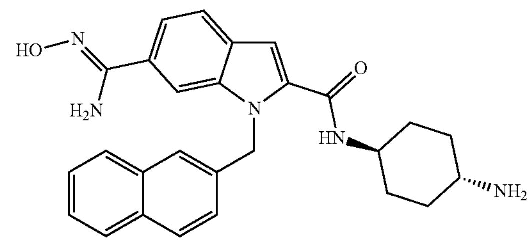 [SMILES: N/C(=N\O)c1ccc2cc(C(=O)N[C@H]3CC[C@H](N)CC3)n(Cc3ccc4ccccc4c3)c2c1] | 456.3 | 1HNMR (400 MHz, CD3OD): δ1.47-1.28 (m, 4H), 2.01-1.88 (m, 4H), 3.05-2.99 (m, 1H), 3.77-3.71 (m, 1H), 6.01 (s, 2H), 7.22-7.17 (m, 2H), 7.44-7.40 (m, 3H), 7.68-7.66 (m, 1H), 7.79-7.74 (m, 2H), 7.90-7.88 (d, 1H), 7.97 (s, 1H), 8.55 (m, 1H). |
| I-400 | 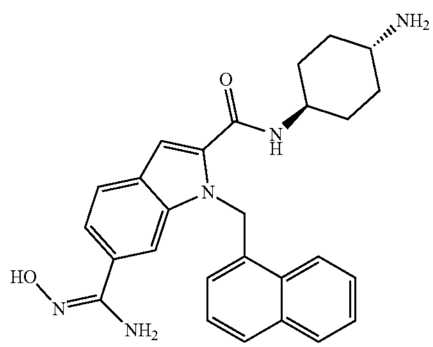 [SMILES: N/C(=N/O)c1ccc2cc(C(=O)N[C@H]3CC[C@H](N)CC3)n(Cc3cccc4ccccc34)c2c1] | 456.3 | 1HNMR (300 MHz, CD3OD): δ1.44-1.36 (m, 4H), 1.99-1.90 (m, 4H), 3.06 (m, 1H), 3.68 (m, 1H), 6.28-6.26 (d, 1H), 6.41 (s, 2H), 7.21-7.16 (t, 1H), 7.28 (s, 1H), 7.45-7.42 (m, 1H), 7.65-7.53 (m, 2H), 7.76-7.73 (d, 1H), 7.82 (s, 1H), 7.96-7.90 (t, 2H), 8.21-8.18 (d, 1H) |
| I-401 | 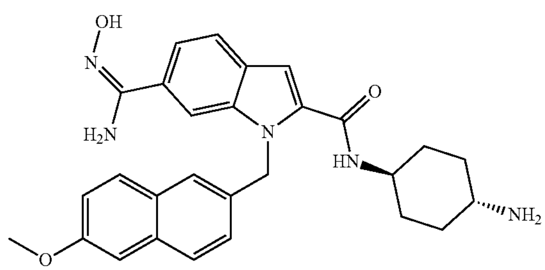 [SMILES: COc1ccc2cc(Cn3c(C(=O)N[C@H]4CC[C@H](N)CC4)cc4ccc(/C(N)=N\O)cc43)ccc2c1] | 486.3 | 1HNMR (400 MHz, CD3OD): δ1.50-1.28 (m, 4H), 2.05-1.85 (m, 4H), 3.06 (m, 1H), 3.68 (m, 1H), 3.86 (s, 3H), 5.96 (s, 2H), 7.08 (dd, 1H), 7.17-7.15 (m, 3H), 7.42-7.38 (m, 2H), 7.58-7.56 (dd, 1H), 7.66-7.64 (dd, 1H), 7.90-7.88 (dd, 1H), 7.98 (s, 1H). |

Example 82: Synthesis of Compound I-402 tert-butyl ((1r,4r)-4-(6-carbamimidoyl-1-(naphthalen-2-ylmethyl)-1H-indole-2-carboxamido) cyclohexyl) carbamate

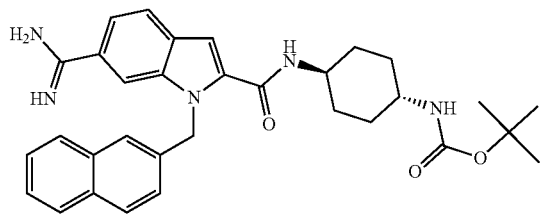 [SMILES: CC(C)(C)OC(=O)N[C@H]1CC[C@H](NC(=O)c2cc3ccc(C(=N)N)cc3n2Cc2ccc3ccccc3c2)CC1]

Step-1: tert-butyl ((1r,4r)-4-(6-cyano-1-(naphthalen-2-ylmethyl)-1H-indole-2-carboxamido)cyclohexyl) carbamate Product of step-2 of example 81 (310 mg, 0.950 mmol) and tert-butyl ((1r,4r)-4-aminocyclohexyl)carbamate (220 mg, 1.1 mmol) were treated together for 1 h at room temperature to afford 370 mg of the title compound following the procedure described in step-3 of example 81. LCMS: 567.15 (M–56)+.

Step-2: tert-butyl ((1r,4r)-4-(6-(—N'-hydroxycarbamimidoyl)-1-(naphthalen-2-ylmethyl)-1H-indole-2-carboxamido)cyclohexyl)carbamate Product of step-1 of example 82 (370 mg, 0.708 mmol) was treated with 50% aqueous hydroxylamine solution (10 mL) to afford the 300 mg of the title compound following the procedure described in step-4 of example 81. LCMS: 555.85 (M+1)+.

Step-3: tert-butyl ((1r,4r)-4-(6-(-N'-acetoxycarbamimidoyl)-1-(naphthalen-2-ylmethyl)-1H-indole-2-carboxamido)cyclohexyl)carbamate To a stirred solution of product of step-2 of example 82 (300 mg, 0.540 mmol) in acetic acid (12 mL) was added acetic anhydride (0.6 mL) at room temperature and resulting reaction mixture was stirred for 4 h. Evaporated off the reaction mixture under reduced pressure at room temperature. The crude obtained was basified with aqueous sodium bicarbonate. The precipitated solid was filtered off and dried under vacuum to give the title compound (270 mg, crude). LCMS: 597.91 (M+1)+.

Step-4: tert-butyl ((1r,4r)-4-(6-carbamimidoyl-1-(naphthalen-2-ylmethyl)-1H-indole-2-carboxamido)cyclohexyl) carbamate To a solution of product of step-3 of example 82 (220 mg, 0.360 mmol) in a mixture of Methanol:THF (1:1) (20 mL) was added 10% Palladium on Carbon (25 mg) and resulted mixture was stirred at room temperature for 5 h under the hydrogen atmosphere (balloon filled with hydrogen gas). After reaction completion, the reaction mixture was filtered through celite bed and filtrate was concentrated under reduced pressure. The crude obtained was purified by preparative HPLC instrument using LUNA C18 reverse phase column (21.2×150 mm, 5 micron). The mobile phases were 15% acetonitrile:Methanol (1:1) in water to 80% acetonitrile:Methanol (1:1) in water which afforded the title compound (140 mg) as a TFA Salt. LCMS: 540.25 (M+1)$^+$; $^1$HNMR (400 MHz, DMSO-d$_6$): δ 1.20-125 (m, 4H), 1.32 (s, 9H), 1.75-178 (m, 4H), 3.14-3.20 (m, 1H), 3.62-3.70 (m, 1H), 6.00 (s, 2H), 6.75 (d, 1H), 7.20 (s, 1H), 7.29 (d, 1H), 7.45-7.47 (s, 2H), 7.52-7.57 (m, 2H), 7.74-7.77 (m, 1H), 7.80-7.85 (m, 3H), 8.22 (s, 1H), 8. 55 (d, 1H). HPLC: 99.13% (Retention Time=6.83 min)

The following compound listed in table-21 prepared according to general scheme-15 by following similar procedure as described above for example 82 using appropriate reagents with suitable modifications known to the one skilled in the art.

TABLE 21

| Cpd. ID. | Structure | LCMS [M + H]$^+$ | $^1$H-NMR Data |
|---|---|---|---|
| I-403 | 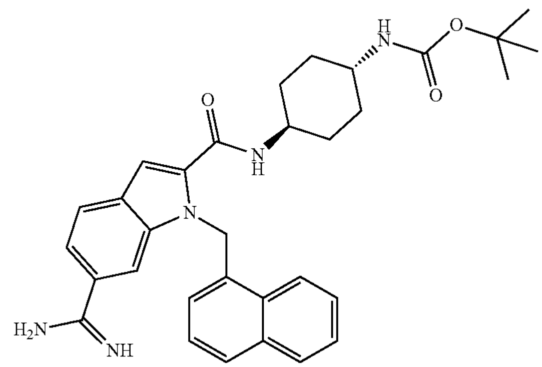 [SMILES: CC(C)(C)OC(=O)N[C@H]1CC[C@H](NC(=O)c2cc3ccc(C(=N)N)cc3n2Cc2cccc3ccccc23)CC1] | 540.1 | $^1$H NMR (300 MHz, DMSO-d$_6$): δ 1.03-1.32 (m, 4H), 1.35 (s, 9H), 1.66-1.74 (m, 6H), 3.15-3.30 (m, 1H), 3.45-3.55 (m, 1H), 6.09 (d, 1H), 6.40 (s, 2H), 6.71 (d, 1H), 7.22 (t, 1H), 7.37 (s, 1H), 7.54-7.72 (m, 3H), 7.78-7.87 (m, 2H), 7.98 (d, 2H), 8.26 (d, 1H), 8.52 (d, 1H), 8.65 (bs, 1H). |
| I-404 | 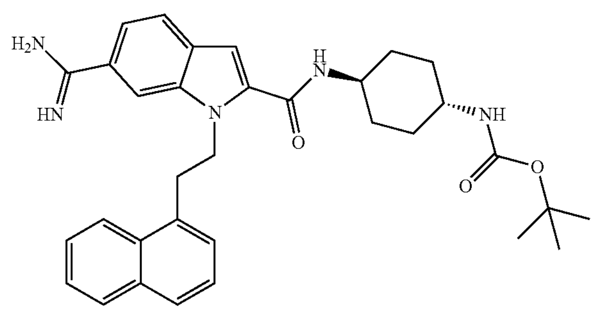 [SMILES: CC(C)(C)OC(=O)N[C@H]1CC[C@H](NC(=O)c2cc3ccc(C(=N)N)cc3n2CCc2cccc3ccccc23)CC1] | 554.2 | $^1$HNMR (400 MHz, DMSO-d$_6$): δ1.35 (m, 3H), 1.38 (s, 9H), 1.73 (s, 2H), 1.83-1.80 (d, 3H), 3.1 (m, 1H), 3.55 (t, 2H), 3.65 (m, 1H), 4.9 (t, 2H), 6.8 (d, 1H), 7.14 (s, 1H), 7.36 (m, 2H), 7.54 (m, 3H), 7.80-7.78 (d, 2H), 7.90 (d, 1H), 8.02 (s, 1H), 8.3 (d, 1H), 8.40 (d, 1H). |
| I-405 | 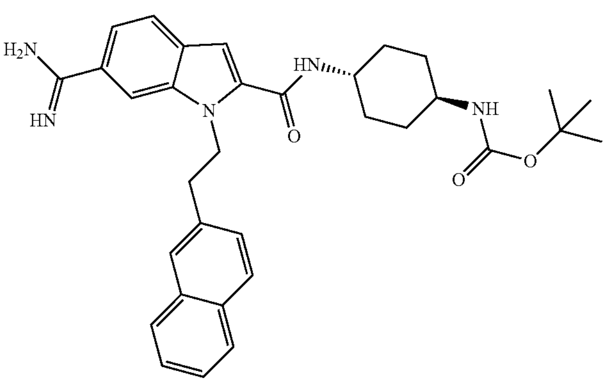 [SMILES: CC(C)(C)OC(=O)N[C@H]1CC[C@H](NC(=O)c2cc3ccc(C(=N)N)cc3n2CCc2ccc3ccccc3c2)CC1] | 554.4 | $^1$HNMR (400 MHz, DMSO-d$_6$): δ1.26-1.20 (m, 4H), 1.35 (s, 9H), 1.75-1.67 (m, 4H), 3.18-3.14 (m, 5H), 3.59 (m, 1H), 4.88 (m, 1H), 6.72-6.71 (d, 1H), 7.11 (s, 1H), 7.48 (m, 3H), 7.68 (s, 1H), 7.84-7.73 (m, 3H), 8.16 (s, 1H), 8.27 (d, 1H). |

Example 83: Synthesis of Compound I-406

6-carbamimidoyl-1-(naphthalen-2-ylmethyl)-N-(piperidin-4-ylmethyl)-1H-indole-2-carboxamide

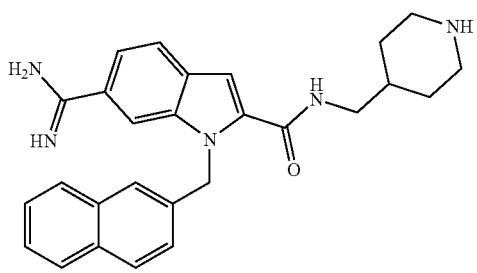 [SMILES: N=C(N)c1ccc2cc(C(=O)NCC3CCNCC3)n(Cc3ccc4ccccc4c3)c2c1]

Step-1: Tert-butyl-4-((6-(N'-acetoxycarbamimidoyl)-1-(naphthalen-2-ylmethyl)-1H-indole-2-carboxamido)methyl)piperidine-1-carboxylate Product of step-4 of example 81 (240 mg, 0.432 mmol) and acetic anhydride (0.5 mL) were treated together to afford 200 mg of the title compound following the procedure described in step-3 of example 82. LCMS: 598.4 (M+1)$^+$.

Step-2: tert-butyl 4-((6-carbamimidoyl-1-(naphthalen-2-ylmethyl)-1H-indole-2-carboxamido)methyl)piperidine-1-carboxylate Product of step-1 of example 83 (200 mg, 0.335 mmol) was treated with 10% Palladium on carbon (40 mg) in presence of hydrogen atmosphere for 6 h afforded 200 mg of the title compound following the procedure described in step-4 of example 82. LCMS: 540.9 (M+1)$^+$.

Step-3: 6-carbamimidoyl-1-(naphthalen-2-ylmethyl)-N-(piperidin-4-ylmethyl)-1H-indole-2-carboxamide Product of step-2 of example 83 (200 mg, 0.335 mmol) was dissolved in ethanol (5 mL) and was added ethanolic HCl (5 mL) at 0° C. and then stirred at room temperature for 5 h. After reaction completion, reaction mixture was concentrated under reduced pressure to give crude product (218 mg), further triturated with pentane and dried under vacuum to afford the title compound (130 mg) as HCl salt. LCMS: 440.4 (M+1)$^+$, $^1$HNMR (400 MHz, CD$_3$OD): δ1.17 (m, 2H), 1.52-1.48 (m, 3H), 2.49-2.48 (t, 2H), 3.01-2.98 (d, 2H), 3.17-3.15 (d, 2H), 6.05 (s, 2H), 7.15- 7.12 (d, 1H), 7.21 (s, 1H), 7.34 (s, 1H), 7.46-7.43 (m, 2H), 7.58-7.55 (m, 2H), 7.70-7.68 (m, 1H), 7.81-7.76 (m, 2H), 7.94-7.92 (d, 11H), 8.17 (s, 1H); HPLC: 95.22% (Retention Time=5.08 min).

The following compounds listed in table-22 prepared according to general scheme-15 by following similar procedure as described above for example 406 using appropriate reagents with suitable modifications known to the one skilled in the art.

TABLE 22

Compounds synthesized using general scheme-15

| Cpd. ID. | Structure | LCMS [M + H]$^+$ | $^1$H-NMR Data |
|---|---|---|---|
| I-407 | 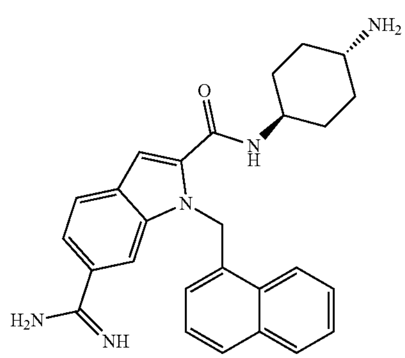 [SMILES: N=C(N)c1ccc2cc(C(=O)N[C@H]3CC[C@H](N)CC3)n(Cc3cccc4ccccc34)c2c1] | 440.4 | $^1$HNMR (300 MHz, CD$_3$OD): δ1.44-1.29 (m, 4H), 1.99-1.89 (m, 4H), 3.06 (m, 1H), 3.68 (m, 1H), 6.27-6.25 (d, 1H), 6.43 (s, 2H), 7.21-7.16 (t, 1H), 7.28 (s, 1H), 7.65-7.53 (m, 3H), 7.76-7.73 (d, 1H), 7.97-7.90 (m, 3H), 8.21-8.1 (d, 1H), 8.61-8.58 (d, 1H) |
| I-408 | 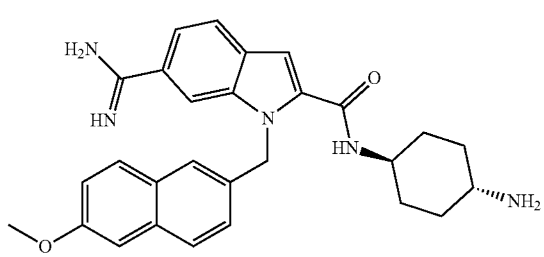 [SMILES: COc1ccc2cc(Cn3c(C(=O)N[C@H]4CC[C@H](N)CC4)cc4ccc(C(=N)N)cc43)ccc2c1] | 470.4 | $^1$HNMR (400 MHz, CD$_3$OD): δ1.48-1.30 (m, 4H), 2.02-1.88 (m, 4H), 3.06 (m, 1H), 3.68 (m, 1H), 3.86 (s, 3H), 5.96 (s, 2H), 7.08-7.05 (dd, 1H), 7.17-7.14 (m, 3H), 7.37 (s, 1H), 7.58-7.51 (m, 2H), 7.66-7.64 (dd, 1H), 7.90-7.87 (dd, 1H), 7.12 (s, 1H), 8.65 (broad s, 1H), 9.2 (broad s, 1H). |

TABLE 22-continued

Compounds synthesized using general scheme-15

| Cpd. ID. | Structure | LCMS [M + H]+ | 1H-NMR Data |
|---|---|---|---|
| I-409 | 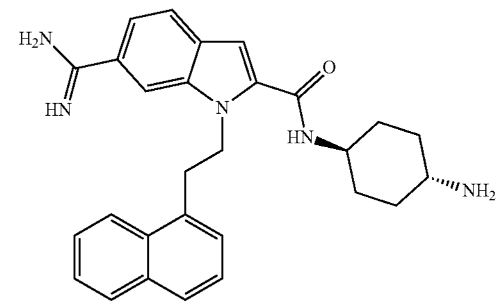 [SMILES: N=C(N)c1ccc2cc(C(=O)N[C@H]3CC[C@H](N)CC3)n(CCc3cccc4ccccc34)c2c1] | 454.2 | $^1$HNMR (400 MHz, DMSO-$d_6$): δ1.48-1.41 (m, 4H), 1.95 (m, 2H), 2.07 (m, 2H), 3.05 (m, 1H), 3.61-3.58 (m, 3H), 5.04-5.02 (t, 2H), 6.86-6.85 (d, 1H), 6.98 (s, 1H), 7.12-7.09 (m, 1H), 7.37-7.35 (d, 1H), 7.50-7.45 (m, 3H), 7.63-7.61 (d, 1H), 7.76-7.70 (d, 1H), 7.81-7.79 (d, 1H), 8.12-8.10 (d, 1H). |
| I-410 | 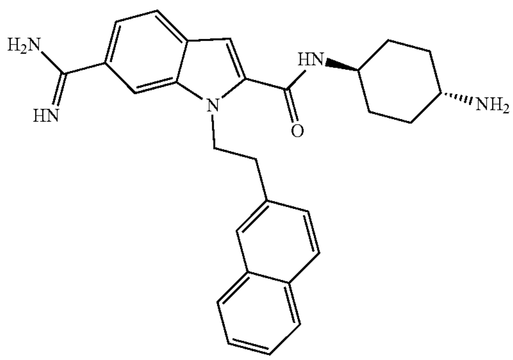 [SMILES: N=C(N)c1ccc2cc(C(=O)N[C@H]3CC[C@H](N)CC3)n(CCc3ccc4ccccc4c3)c2c1] | 454.3 | $^1$HNMR (300 MHz, $CD_3OD$): δ1.45-1.90 (m, 4H), 1.75-1.70 (m, 2H), 2.02-1.98 (m, 2H), 3.00 (m, 1H), 3.24-3.23 (t, 2H), 3.33-3.30 (m, 1H), 5.06-5.01 (t, 2H), 7.03-6.99 (m, 2H), 7.47-7.39 (m, 4H), 7.69-7.62 (m, 2H), 7.81-7.74 (m, 2H), 7.92 (s, 1H). |

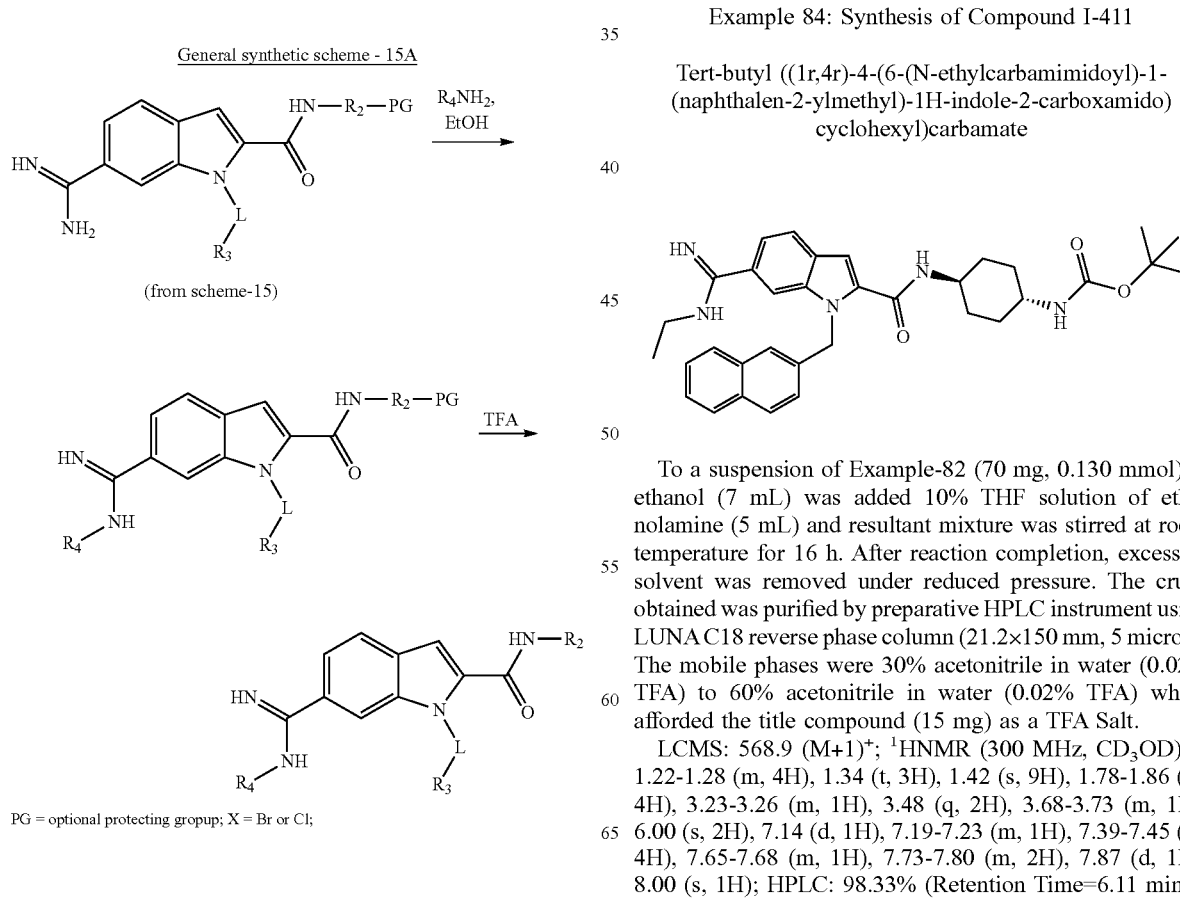

General synthetic scheme - 15A (from scheme-15)

PG = optional protecting gropup; X = Br or Cl;

Example 84: Synthesis of Compound I-411

Tert-butyl ((1r,4r)-4-(6-(N-ethylcarbamimidoyl)-1-(naphthalen-2-ylmethyl)-1H-indole-2-carboxamido) cyclohexyl)carbamate To a suspension of Example-82 (70 mg, 0.130 mmol) in ethanol (7 mL) was added 10% THF solution of ethanolamine (5 mL) and resultant mixture was stirred at room temperature for 16 h. After reaction completion, excess of solvent was removed under reduced pressure. The crude obtained was purified by preparative HPLC instrument using LUNA C18 reverse phase column (21.2×150 mm, 5 micron). The mobile phases were 30% acetonitrile in water (0.02% TFA) to 60% acetonitrile in water (0.02% TFA) which afforded the title compound (15 mg) as a TFA Salt.

LCMS: 568.9 (M+1)+; $^1$HNMR (300 MHz, $CD_3OD$): δ 1.22-1.28 (m, 4H), 1.34 (t, 3H), 1.42 (s, 9H), 1.78-1.86 (m, 4H), 3.23-3.26 (m, 1H), 3.48 (q, 2H), 3.68-3.73 (m, 1H), 6.00 (s, 2H), 7.14 (d, 1H), 7.19-7.23 (m, 1H), 7.39-7.45 (m, 4H), 7.65-7.68 (m, 1H), 7.73-7.80 (m, 2H), 7.87 (d, 1H), 8.00 (s, 1H); HPLC: 98.33% (Retention Time=6.11 min)

The following compound listed in table-23 prepared according to general scheme-15A by following similar procedure as described above for example 84 using appropriate reagents with suitable modifications known to the one skilled in the art.

TABLE 23

Compounds synthesized using general scheme-15A

| Cpd. ID. | Structure | LCMS [M + H]+ | 1H-NMR Data |
|---|---|---|---|
| I-412 | 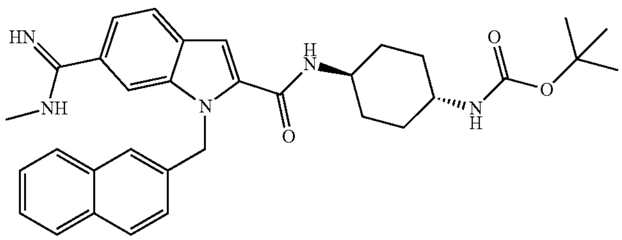 [SMILES: CNC(=N)c1ccc2cc(C(=O)N[C@H]3CC[C@H](NC(=O)OC(C)(C)C)CC3)n(Cc3ccc4ccccc4c3)c2c1] | 554.35 | 1HNMR (300 MHz, CD3OD): δ 1.18-1.28 (m, 4H), 1.42 (s, 9H), 1.78-1.87 (m, 4H), 3.08 (s, 3H) 3.20-3.25 (m, 1H), 3.70-3.75 (m, 1H), 6.01 (s, 2H), 7.15 (s, 1H), 7.21 (d, 1H), 7.44-7.47 (m, 4H), 7.66-7.68 (m, 1H), 7.73-7.80 (m, 2H), 7.87-7.89 (m, 1H), 8.01 (s, 1H). |

Example 85: Synthesis of Compound I-413

N-((1r,4r)-4-aminocyclohexyl)-6-(N-ethylcarbamimidoyl)-1-(naphthalen-2-ylmethyl)-1H-indole-2-carboxamide

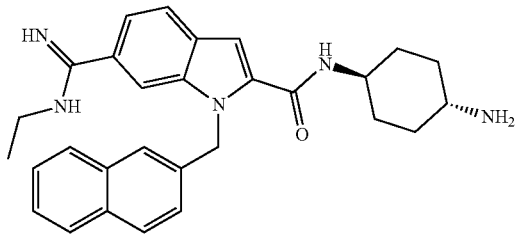 [SMILES: CCNC(=N)c1ccc2cc(C(=O)N[C@H]3CC[C@H](N)CC3)n(Cc3ccc4ccccc4c3)c2c1]

Example 84 (10 mg, 0.02 mmol) was treated with TFA (0.1 mL) afforded 5 mg of title compound as TFA salt following the procedure described in step-5 of example 81. LCMS: 468.04 (M+1)+; 1HNMR (400 MHz, CD3OD): δ 1.27-1.35 (m, 5H), 1.43-1.46 (m, 2H), 1.86-1.89 (m, 2H), 1.98-2.01 (m, 2H), 2.97-3.10 (m, 1H) 3.45-3.47 (m, 2H), 3.71-3.75 (m, 1H), 6.00 (s, 2H), 7.16-7.21 (m, 2H), 7.41-7.45 (m, 4H), 7.63-7.67 (m, 1H), 7.73-7.76 (m, 2H), 7.87 (d, 1H), 8. 01 (s, 1H); HPLC: 96.36% (Retention Time=4.56 min).

The following compound listed in table-24 prepared according to general scheme-15A by following similar procedure as described above for example 85 using appropriate reagents with suitable modifications known to the one skilled in the art.

TABLE 24

Compounds synthesized using Scheme-15A

| Cpd. ID. | Structure | LCMS [M + H]+ | 1H-NMR Data |
|---|---|---|---|
| I-414 | 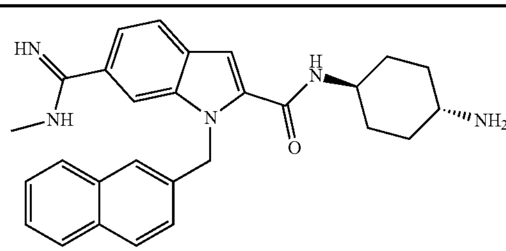 | 454.45 | 1HNMR (400 MHz, CD3OD): δ 1.29-1.33 (m, 2H), 1.43-1.47 (m, 2H), 1.87-1.90 (m, 2H), 1.97-2.01 (m, 2H), 2.95-3.05 (m, 1H), 3.07 (s, 3H), 3.70-3.75 (m, 1H), 6.02 (s, 2H), 7.16 (s, 1H), 7.18-7.21 (m, 1H), 7.40-7.47 (m, 4H), 7.65-7.66 (m, 1H), 7.73-7.79 (m, 2H), 7.88 (d, 1H), 8.01 (s, 1H). |

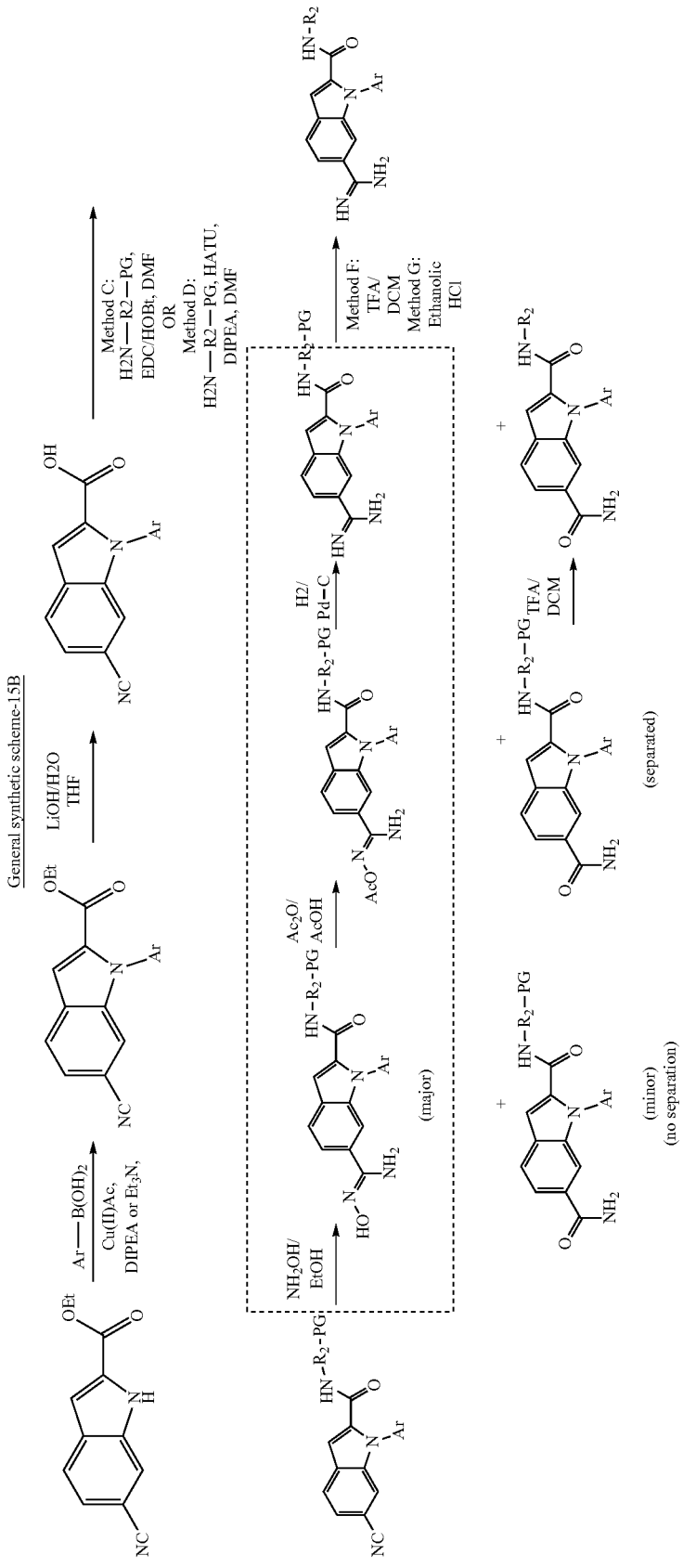
General synthetic scheme-15B
PG = optional protecting group;

Example 86: Synthesis of Compound I-415

N-((1r,4r)-4-aminocyclohexyl)-6-carbamimidoyl-1-(naphthalen-1-yl)-1H-indole-2-carboxamide

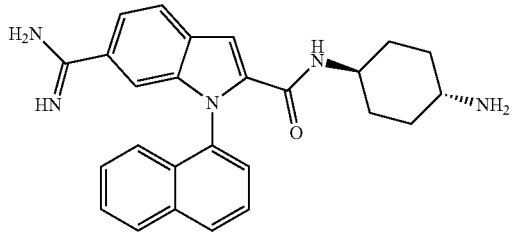 [SMILES: N=C(N)c1ccc2cc(C(=O)N[C@H]3CC[C@H](N)CC3)n(-c3cccc4ccccc34)c2c1]

Step-1: Ethyl 6-cyano-1-(naphthalen-1-yl)-1H-indole-2-carboxylate

To a stirred solution of ethyl 6-cyano-1H-indole-2-carboxylate (2.0 g, 9.34 mmol) in dichloromethane (50 mL) was added naphthalen-1-ylboronic acid (3.1 g, 18.69 mmol), copper (II) acetate (3.25 g, 18.69 mmol) and N,N-diisopropylethylamine (3.6 g, 28.038 mmol) at room temperature. The resulting reaction mixture was stirred at room temperature under atmosphere of oxygen gas (oxygen bladder) for 16 h. After reaction completion, water was added, separated the layers, organic layer concentrated under reduced pressure. The crude obtained above was purified by combiflash on silica gel eluted with 10% ethyl acetate in hexane to give the title product (200 mg). LCMS: 340.9 (M)$^+$

Step-2: 6-cyano-1-(naphthalen-1-yl)-1H-indole-2-carboxylic Acid

Product of step-1 of example 86 (200 mg, 0.588 mmol) was treated with lithium hydroxide monohydrate (38 mg, 0.882 mmol) in THF: Ethanol: water (3:3:1) afforded the 150 mg of title compound following the procedure described in step-2 of example 81. Here the reaction mixture stirred for 12 h at room temperature. LCMS: 311.2 (M−1)$^+$

Step-3: tert-butyl ((1r,4r)-4-(6-cyano-1-(naphthalen-1-yl)-1H-indole-2-carboxamido)cyclohexyl)carbamate Product of step-2 of example 86 (50 mg, 0.160 mmol) and tert-butyl ((1r,4r)-4-aminocyclohexyl)carbamate (42 mg, 0.192 mmol) were treated together afforded the 66 mg of title compound following the procedure described in step-3 of example 81. LCMS: 453.4 (M−56)$^+$

Step-4: tert-butyl ((1r,4r)-4-(6-(N'-hydroxycarbamimidoyl)-1-(naphthalen-1-yl)-1H-indole-2-carboxamido) cyclohexyl)carbamate To a stirred solution of product of step-3 of example 86 (100 mg, 0.196 mmol) and N,N-diisopropylethylamine (152 mg, 1.176 mmol) in ethanol was added hydroxylamine hydrochloride at room temperature. The resulting reaction mixture was stirred at 80° C. for 5 h. After reaction completion distilled off excess solvent, added water, precipitated solid was filtered off and dried under vacuum to give the title compound as crude (100 mg). LCMS: 542.2 [M+1]$^+$.

Also confirmed the formation of amide derivative of title compound as minor product as below which was inseparable by TLC in this step. LCMS: 527.3 [M+1]$^+$.

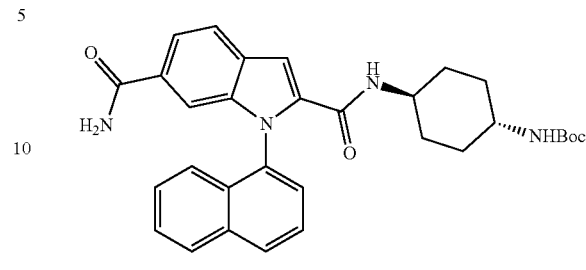

(tert-butyl ((1r,4r)-4-(6-carbamoyl-1-(naphthalen-1-yl)-1H-indole-2-carboxamido)cyclohexyl)carbamate)

This crude mixture of compounds proceeded to next step without purification.

Step-5: tert-butyl ((1r,4r)-4-(6-(N'-acetoxycarbamimidoyl)-1-(naphthalen-1-yl)-1H-indole-2-carboxamido) cyclohexyl)carbamate To a stirred solution of product of step-4 of example 86 (100 mg, 0.184 mmol) in acetic acid (1 mL) was added acetic anhydride (0.2 mL) at room temperature and resulting reaction mixture was stirred for 2 h. Evaporated off the reaction mixture under reduced pressure at room temperature, added ice-cold water. The precipitated solid was filtered off and dried under vacuum. The crude solid obtained was further purified by combiflash on silica gel, eluted with 0.5% methanol in dichloromethane.

The nonpolar compound isolated was confirmed as title compound (50 mg). LCMS: 584.2 (M+1)$^+$.

The polar compound isolated was confirmed as amide derivative which was formed in a step-4 of example 86 (30 mg) as below. LCMS: 527.2 (M+1)$^+$.

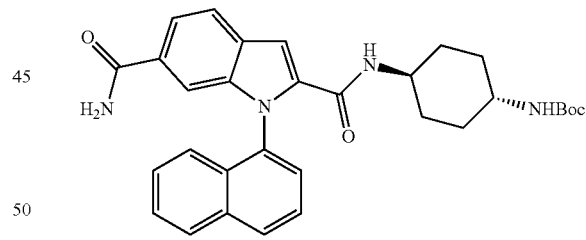

tert-butyl ((1r,4r)-4-(6-carbamoyl-1-(naphthalen-1-yl)-1H-indole-2-carboxamido)cyclohexyl)carbamate) (Polar)

Step-6: tert-butyl ((1r,4r)-4-(6-carbamimidoyl-1-(naphthalen-1-yl)-1H-indole-2-carboxamido)cyclohexyl) carbamate The nonpolar product of step-5 of example 86 (50 mg) was treated with 10% palladium on carbon (15 mg) under hydrogen atmosphere afforded the 40 mg of title compound following the procedure described in step-4 of example 82. Here reaction mixture stirred for 2 h at room temperature. LCMS: 526.4 (M+1)$^+$.

Following compound listed in table-25 prepared according to general scheme-15B by following similar procedure as described above for the product of step-6 of example 86 using appropriate reagents with suitable modifications known to the one skilled in the art.

TABLE 25

Compounds synthesized using general Scheme-15B

| Cpd. ID. | Structure | LCMS [M + H]+ | 1H-NMR Data |
|---|---|---|---|
| I-416 | 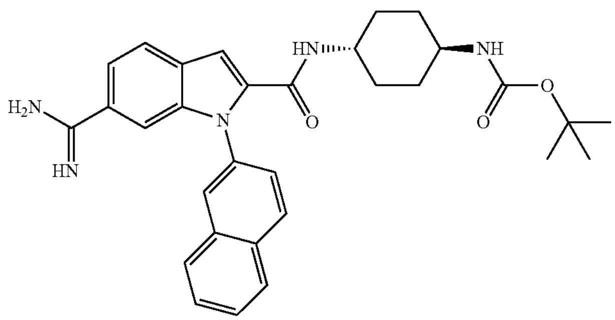 [SMILES: CC(C)(C)OC(=O)N[C@H]1CC[C@H](NC(=O)c2cc3ccc(C(=N)N)cc3n2-c2ccc3ccccc3c2)CC1] | 525.95 | 1HNMR (300 MHz, DMSO-$d_6$): δ1.17-1.16 (m, 4H), 1.36 (s, 9H), 1.68 (s, 3H), 1.77-1.73 (m, 4H), 3.1 (m, 1H), 3.25 (m, 1H), 4.88 (m, 1H), 6.71 (d, 1H), 7.30 (s, 1H), 7.43 (m, 1H), 7.63-7.56 (m, 2H), 7.70 (s, 1H), 8.08-7.90 (m, 4H), 8.6 (d, 1H). |

Step-7: N-((1r,4r)-4-aminocyclohexyl)-6-carbamimidoyl-1-(naphthalen-1-yl)-1H-indole-2-carboxamide Product of step-6 of example 86 (40 mg, 0.069 mmol) was treated with TFA (0.1 mL) afforded the 30 mg of title compound as TFA salt following the procedure described in step-5 of example 81. LCMS: 426.3 (M+1)+; 1HNMR (300 MHz, CD$_3$OD): δ 1.41-1.30 (m, 4H), 1.99-1.75 (m, 4H), 3.02-3.00 (m, 1H), 3.53-3.47 (m, 1H), 7.05-7.02 (d, 1H), 7.41-7.36 (m, 3H), 7.72-7.51 (m, 4H), 8.11-7.99 (m, 3H); HPLC: 95.53% (Retention Time=4.60 min)

Following compound listed in table-25A prepared according to general scheme-15B by following similar procedure as described above for the product of step-7 of example 86 using appropriate reagents with suitable modifications known to the one skilled in the art.

TABLE 25A

Compounds synthesized using general Scheme-15B

| Cpd. Id. | Structure | LCMS [M + H]+ | 1H-NMR Data |
|---|---|---|---|
| I-416A | 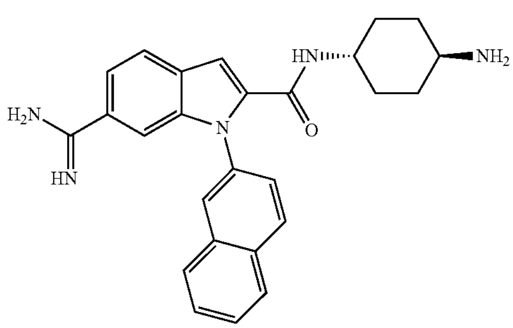 [SMILES: N=C(N)c1ccc2cc(C(=O)N[C@H]3CC[C@H](N)CC3)n(-c3ccc4ccccc4c3)c2c1] | 426.3 | 1HNMR (300 MHz, CD$_3$OD): δ1.46-1.39 (m, 4H), 2.02-1.99 (m, 4H), 3.05 (m, 1H), 3.45 (m, 1H), 7.28-7.27 (s, 1H), 7.50-7.46 (m, 1H), 7.61-7.46 (m, 3H), 7.74-7.73 (m, 1H), 8.01-7.94 (m, 4H), 8.07-8.04 (m, 1H). |

Example 87: Synthesis of Compound I-417
N2-((1r,4r)-4-aminocyclohexyl)-1-(naphthalen-1-yl)-1H-indole-2,6-dicarboxamide
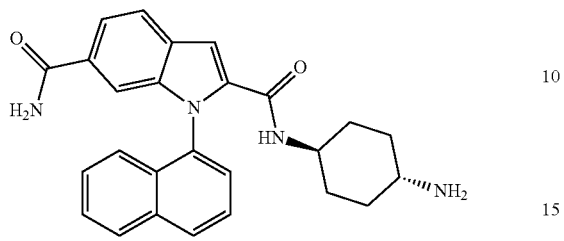
The polar product isolated in step-5 of example 86 (30 mg, 0.057 mmol) was treated with TFA (0.1 mL) afforded the 15 mg of title compound as TFA salt following the procedure described in step-5 of example 81. LCMS: 427.2 $(M+1)^+$; $^1$HNMR (300 MHz, $CD_3OD$): δ 1.38-1.28 (m, 4H), 1.97-1.78 (m, 4H), 3.07-2.99 (m, 1H), 3.53-3.51 (m, 1H), 7.05-7.03 (d, 1H), 7.39-7.32 (m, 2H), 7.71-7.46 (m, 5H), 7.85-7.82 (d, 1H), 8.08-8.00 (m, 2H); HPLC: 99.63% (Retention Time=5.04 min)

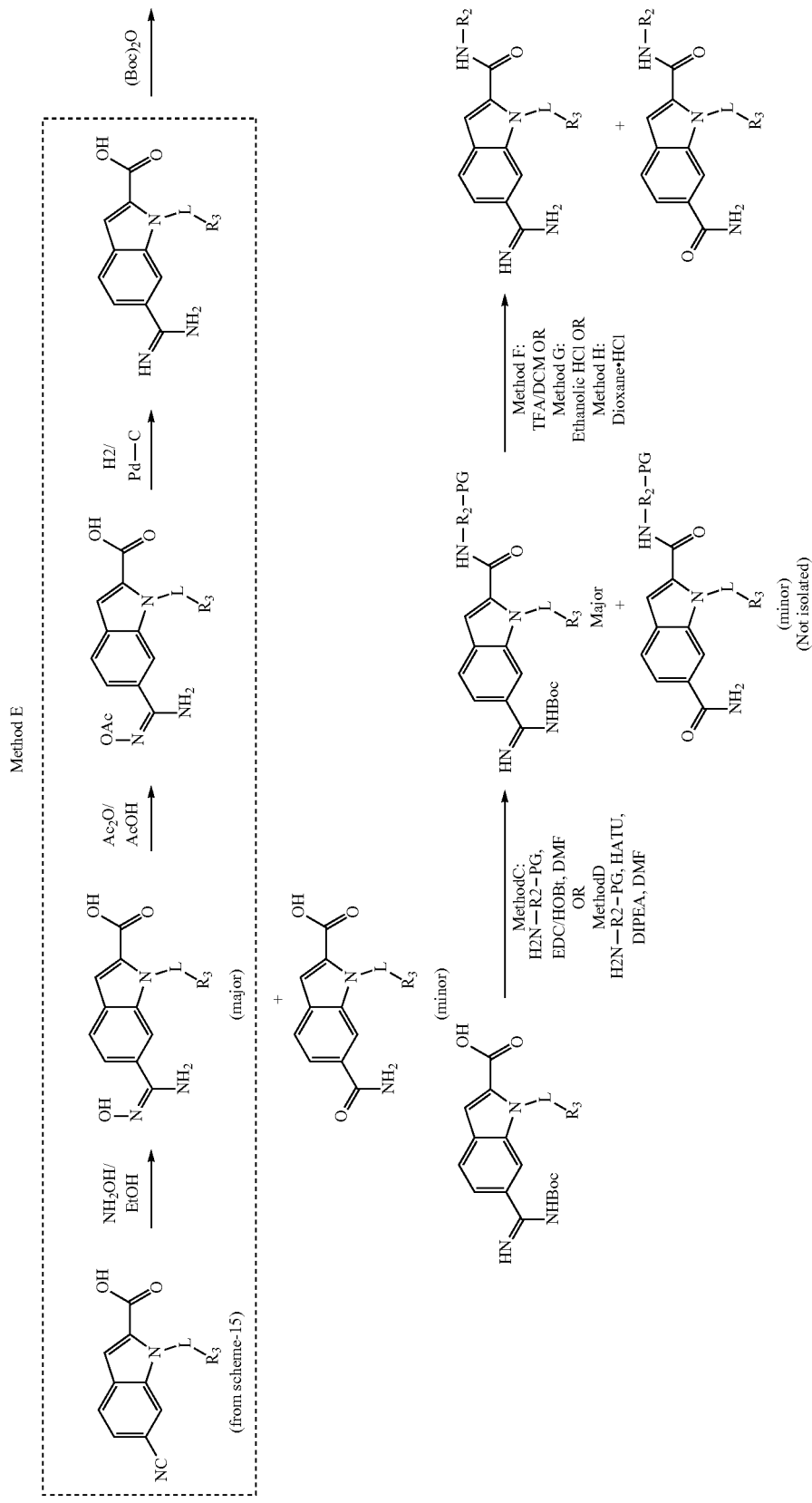

Example 88: Synthesis of Compound I-418

6-carbamimidoyl-1-(naphthalen-1-ylmethyl)-N-(piperidin-4-yl)-1H-indole-2-carboxamide

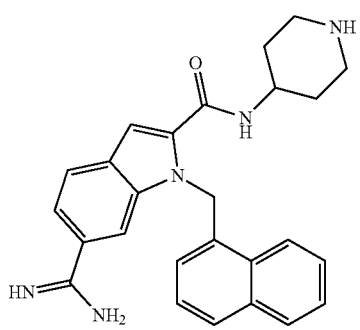 [SMILES: N=C(N)c1ccc2cc(C(=O)NC3CCNCC3)n(Cc3cccc4ccccc34)c2c1]

Step-1: 6-(N'-hydroxycarbamimidoyl)-1-(naphthalen-1-ylmethyl)-1H-indole-2-carboxylic Acid The product of step-2 of example 81 (2.7 g, 8.273 mmol) was dissolved in 50 mL of ethanol and added 50% aqueous hydroxylamine solution (20 mL) and resulting mixture was refluxed for 2 h at 80° C. Solvent was evaporated under vacuum to get crude, water was added and precipitated solid was filtered off. The solid obtained was triturated with cold water followed by n-pentane and dried under vacuum to give the title compound (2.45 g). LCMS: 360.2 (M+1)-.

Step-2: 6-(N'-acetoxycarbamimidoyl)-1-(naphthalen-1-ylmethyl)-1H-indole-2-carboxylic Acid To a stirred solution of product of step-1 of example 88 (2.40 g, 6.678 mmol) in acetic acid (20 mL) was added acetic anhydride (4.09 g, 40.07 mmol) at 0° C. Resulting reaction mixture was stirred at room temperature for 3 h. Evaporated off the reaction mixture under reduced pressure at room temperature. The residue obtained was triturated with diethyl ether, dried under vacuum to give the title compound (2.65 g, crude). LCMS: 402.2 (M+1)$^+$.

Step-3: 6-carbamimidoyl-1-(naphthalen-1-ylmethyl)-1H-indole-2-carboxylic Acid To a stirred suspension of product of step-2 of example 88 (2.65 g, 6.601 mmol) in methanol was added acetic acid (3.0 mL), 10% palladium on carbon (wet) (300 mg) at room temperature and was stirred for 3 h under hydrogen atmosphere (Balloon filled with hydrogen gas). After reaction completion, the reaction mixture was filtered through celite bed and filtrate was concentrated under reduced pressure. The crude obtained was triturated with 50 ml of mixture of diethyl ether: pentane (1:4) and solid obtained was dried under vacuum afforded the title compound (2.40 g). LCMS: 343.7 (M−1)$^+$.

Step-4: 6-(N-(tert-butoxycarbonyl)carbamimidoyl)-1-(naphthalen-1-ylmethyl)-1H-indole-2-carboxylic Acid To a stirred suspension of product of step-3 of example 88 (2.40 g, 6.98 mmol) in methanol was added di-tert-butyl dicarbonate (2.28 mg, 10.48 mmol) and N,N-diisopropylethylamine (2.44 mL, 13.97 mmol) at 0° C. and resulting reaction mixture was stirred at room temperature for 20 h. After reaction completion, reaction mixture was evaporated off under reduced pressure. The residue obtained above was redissolved in water and extracted with equal volume of ethyl acetate and aqueous layer were acidified with citric acid solution and precipitated solid was filtered off and dried to give title compound (2.40 g). LCMS: 444.4 (M+1)$^+$.

Step-5: tert-butyl 4-(6-(N-(tert-butoxycarbonyl)carbamimidoyl)-1-(naphthalen-1-ylmethyl)-1H-indole-2-carboxamido) piperidine-1-carboxylate To a stirred solution of product of step-4 of example 88 (200 mg, 0.441 mmol) in DMF added HATU (251 mg, 0.662 mmol) and N,N-diisopropylethylamine (142 mg, 2.02 mmol) at 0° C. After stirred at room temperature for 10 min, added tert-butyl 4-aminopiperidine-1-carboxylate (105 mg, 0.529 mmol) and stirred for 16 h at room temperature. After reaction completion, added ice cold water, precipitated solid was filtered off and dried to give title compound (340 mg), LCMS: 626.4 (M+1)$^+$.

Following compounds listed in table-26 prepared according to general scheme-15C by following similar procedure as described above for the product of step-5 of example 88 using appropriate reagents with suitable modifications known to the one skilled in the art.

TABLE 26

Compounds synthesized using general scheme-15C

| Cpd. ID. | Structure | LCMS [M + H]+ | 1H-NMR Data |
|---|---|---|---|
| I-419 | 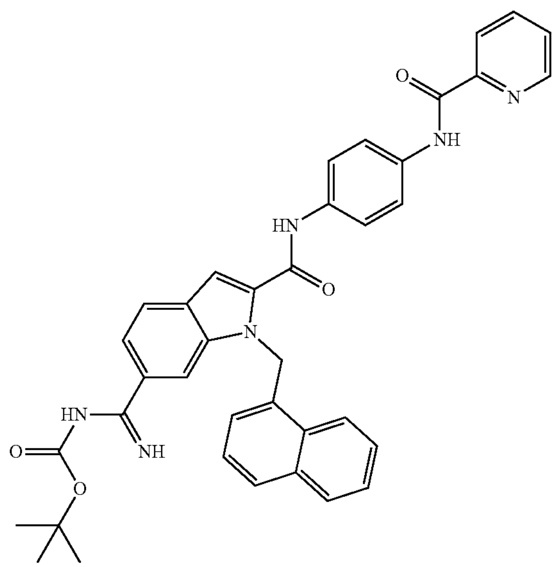 [SMILES: CC(C)(C)OC(=O)NC(=N)c1ccc2cc(C(=O)Nc3ccc(NC(=O)c4ccccn4)cc3)n(Cc3cccc4ccccc34)c2c1] | 639.4 | $^1$HNMR (400 MHz, CD$_3$OD): δ1.45 (s, 9H), 6.36-6.35 (d, 1H), 6.46 (s, 2H), 7.21-7.17 (t, 2H), 7.43 (s, 1H), 7.73-7.52 (m, 7H), 7.90-7.84 (m, 3H), 8.01-7.97 (m, 2H), 8.24-8.17 (m, 2H), 8.68-8.67 (d, 1H). |
| I-420 | 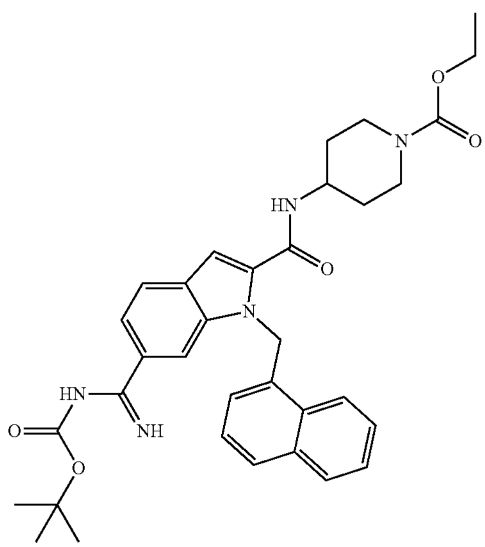 [SMILES: CCOC(=O)N1CCC(NC(=O)c2cc3ccc(C(=N)NC(=O)OC(C)(C)C)cc3n2Cc2cccc3ccccc23)CC1] | 598.4 | $^1$HNMR (400 MHz, CD$_3$OD): δ 1.23 (t, 3H), 1.34-1.38 (m, 2H), 1.44 (s, 9H), 1.71-1.73 (m, 2H), 2.80-2.90 (m, 2H), 3.82-3.85 (m, 1H), 4.00-4.11 (m, 4H), 4.58 (s, 3H), 6.27 (d, 1H), 6.38 (s, 2H), 7.15-7.20 (m, 2H), 7.53-7.63 (m, 3H), 7.71 (d, 1H), 7.78 (d, 1H), 7.89 (d, 1H), 8.00 (s, 1H), 8.19 (d, 1H). |
| I-421 | 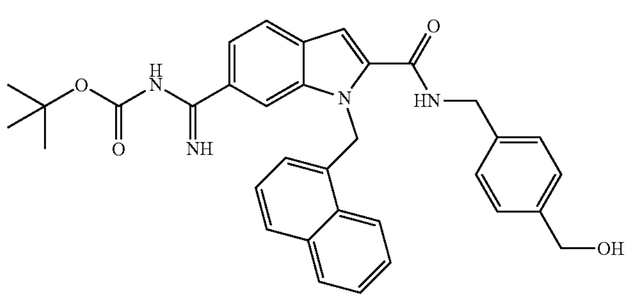 [SMILES: CC(C)(C)OC(=O)NC(=N)c1ccc2cc(C(=O)NCc3ccc(CO)cc3)n(Cc3cccc4ccccc34)c2c1] | 563.25 | $^1$HNMR (400 MHz, CD$_3$OD): δ 1.44 (s, 9H), 4.40 (s, 2H), 4.50 (s, 2H), 6.27 (d, 1H), 6.43 (s, 2H), 7.05-7.16 (m, 5H), 7.23 (s, 1H), 7.50-7.65 (m, 3H), 7.75-7.80 (m, 2H), 7.92 (d, 1H), 8.00 (s, 1H), 8.23 (d, 1H). |

TABLE 26-continued
Compounds synthesized using general scheme-15C
| Cpd. ID. | Structure | LCMS [M + H]+ | 1H-NMR Data |
|---|---|---|---|
| I-422 | 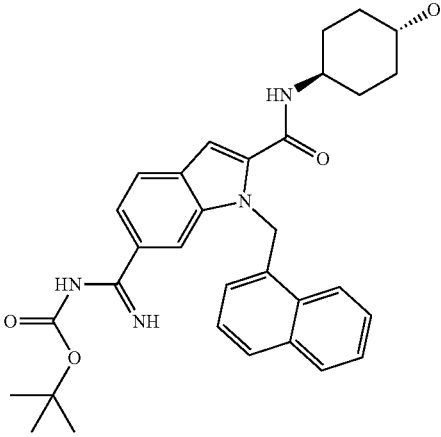 | 541.4 | 1HNMR (400 MHz, CD3OD): δ 1.25-1.37 (m, 4H), 1.45 (s, 9H), 1.76-1.90 (m, 4H), 3.42-3.52 (m, 1H), 3.58-3.68 (m, 1H), 6.29 (d, 1H), 6.39 (s, 2H), 7.14-7.21 (m, 2H), 7.51-7.64 (m, 3H), 7.70-7.80 (m, 2H), 7.91 (d, 1H), 7.99 (s, 1H), 8.22 (d, 1H). |
| I-423 | 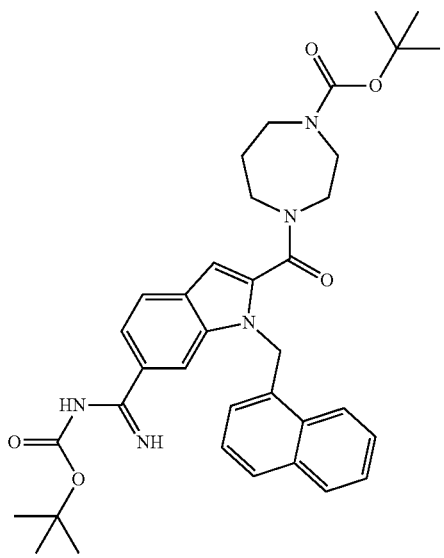 [SMILES: CC(C)(C)OC(=O)NC(=N)c1ccc2cc(C(=O)N3CCCN(C(=O)OC(C)(C)C)CC3)n(Cc3cccc4ccccc34)c2c1] | 626.6 | 1HNMR (400 MHz, CD3OD): δ 1.41 (d, 9H), 1.49 (s, 9H), 1.58-1.66 (m, 2H), 2.90-3.20 (m, 6H), 3.43-3.48 (m, 2H), 6.05 (s, 2H), 6.72-6.88 (m, 2H), 7.34 (t, 1H), 7.45-7.55 (m, 2H), 7.67 (d, 1H), 7.75-7.81 (m, 2H), 7.89-7.96 (m, 2H), 8.24 (d, 1H). |
| I-424 | 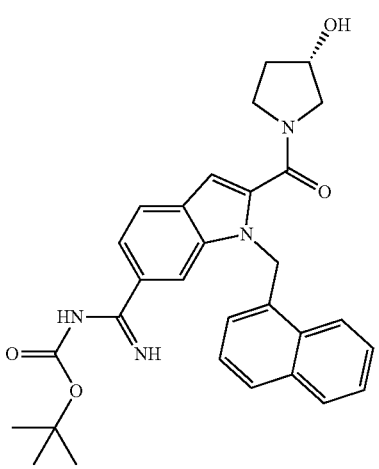 [SMILES: CC(C)(C)OC(=O)NC(=N)c1ccc2cc(C(=O)N3CC[C@H](O)C3)n(Cc3cccc4ccccc34)c2c1] | 513.4 | 1HNMR (400 MHz, CD3OD): δ 1.48 (d, 9H), 1.57-1.62 (m, 1H), 1.76-1.80 (m, 1H), 2.95-3.02 (m, 1H), 3.18-3.28 (m, 1H), 3.35-3.51 (m, 2H), 4.05-4.10 (m, 1H), 4.20-4.25 (m, 1H), 6.04-6.27 (m, 2H), 6.65-6.78 (m, 1H), 6.93 (d, 1H), 7.24-7.30 (m, 1H), 7.43-7.51 (m, 2H), 7.62-7.66 (m, 1H), 7.74-7.77 (m, 2H), 7.86-8.02 (m, 2H), 8.11-8.21 (m, 1H). |

TABLE 26-continued
Compounds synthesized using general scheme-15C
| Cpd. ID. | Structure | LCMS [M + H]+ | 1H-NMR Data |
|---|---|---|---|
| I-425 | 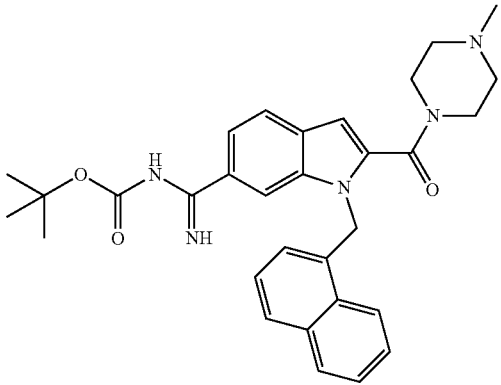 [SMILES: CN1CCN(C(=O)c2cc3ccc(C(=N)NC(=O)OC(C)(C)C)cc3n2Cc2cccc3ccccc23)CC1] | 526.5 | 1HNMR (400 MHz, CD3OD): δ1.49 (s, 9H), 1.60-1.70 (m, 2H), 1.92-2.03 (m, 2H), 2.04 (s, 3H), 3.15-3.25 (m, 2H), 3.40-3.50 (m, 2H), 6.07 (s, 2H), 6.80 (s, 1H), 6.89 (d, 1H), 7.30-7.34 (m, 1H), 7.44-7.52 (m, 2H), 7.68 (d, 1H), 7.75-7.82 (m, 2H), 7.89-7.94 (m, 2H), 8.29 (s, 1H). |
| I-426 | 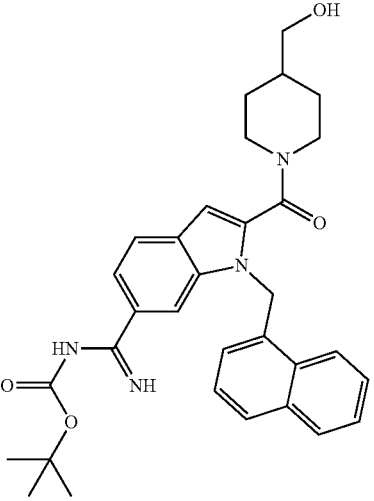 [SMILES: CC(C)(C)OC(=O)NC(=N)c1ccc2cc(C(=O)N3CCC(CO)CC3)n(Cc3cccc4ccccc34)c2c1] | 541.3 | 1HNMR (400 MHz, CD3OD): δ1.29 (m, 4H), 1.50 (s, 9H), 1.52-1.62 (m, 1H), 2.45-2.65 (m, 2H), 3.14 (m, 2H), 3.65-3.75 (m, 1H), 4.30-4.40 (m, 1H), 6.08 (m, 2H), 6.73 (s, 1H), 6.88 (d, 1H), 7.29-7.33 (m, 1H), 7.46-7.50 (m, 2H), 7.67 (dd, 1H), 7.74-7.80 (m, 2H), 7.87-7.96 (m, 2H), 8.27 (s, 1H). |
| I-427 | 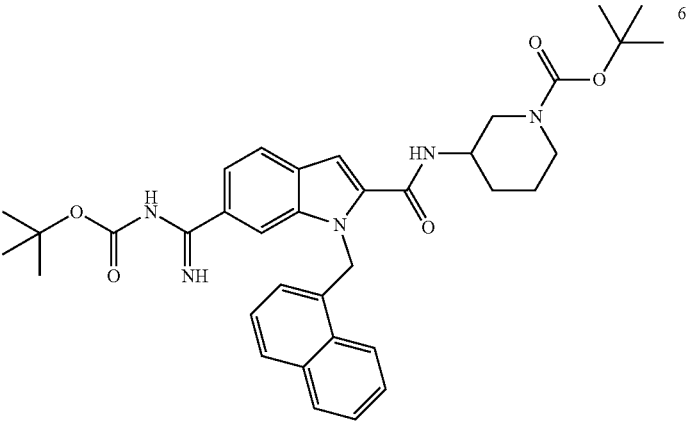 | 626.6 | 1HNMR (400 MHz, CD3OD): δ 1.32 (d, 9H), 1.45 (s, 9H), 1.70-1.60 (m, 2H), 1.90-1.80 (m, 2H), 2.92-2.76 (m, 2H), 3.01-2.96 (m, 1H), 3.80-3.70 (m, 2H), 6.28 (d, 1H), 6.40 (d, 2H), 7.21-7.16 (m, 2H), 7.64-7.51 (m, 3H), 7.73-7.71 (m, 1H), 7.80-7.78 (m, 1H), 7.99-7.88 (m, 1H), 7.99 (s, 1H), 8.21-8.18 (m, 1H). |

TABLE 26-continued

Compounds synthesized using general scheme-15C

| Cpd. ID. | Structure | LCMS [M + H]+ | 1H-NMR Data |
|---|---|---|---|
| I-428 | 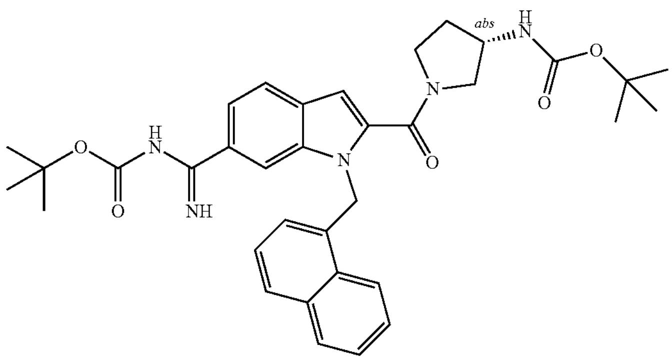 [SMILES: CC(C)(C)OC(=O)NC(=N)c1ccc2cc(C(=O)N3CC[C@H](NC(=O)OC(C)(C)C)C3)n(Cc3cccc4ccccc34)c2c1] | 612.4 | 1HNMR (400 MHz, CD3OD): δ1.47-1.64 (m, 18H), 1.58-1.95 (m, 2H), 2.95-3.10 (m, 2H), 3.32-3.47 (m, 2H), 3.73-3.90 (m, 1H), 6.08-6.18 (m, 2H), 6.64-6.82 (m, 1H), 6.90 (d, 2H), 7.26-7.34 (m, 1H), 7.43-7.51 (m, 2H), 7.74-7.81 (m, 2H), 7.86-7.90 (m, 2H), 7.95-8.23 (m, 1H). |

Step-6: 6-carbamimidoyl-1-(naphthalen-1-ylmethyl)-N-(piperidin-4-yl)-1H-indole-2-carboxamide To a stirred solution of product of step-S of example 88 (340 mg, 0.523 mmol) in dichloromethane was added TFA (0.2 mL) at 0° C. and stirred at room temperature for 4 h. Evaporated off of reaction mixture under reduced pressure to give the crude compound (490 mg). The crude obtained was purified by preparative HPLC instrument using X-Bridge C18 reverse phase column (19×150 mm, 5 micron). The mobile phases were 10% acetonitrile in water (0.02% TFA) to 50% acetonitrile in water (0.02% TFA) which afforded the title compound (100 mg) as a TFA Salt.

LCMS: 426.2 (M+1)+; 1HNMR (400 MHz, CD3OD): δ1.99-1.69 (m, 4H), 3.36-3.00 (m, 4H), 3.95 (m, 1H), 6.26-6.25 (d, 1H), 6.43 (s, 2H), 7.20-7.17 (t, 1H), 7.32 (s, 1H), 7.62-7.55 (m, 3H), 7.75-7.73 (d, 1H), 7.58-7.50 (m, 3H), 8.20-8.18 (d, 1H); HPLC: 99.36% (Retention Time 4.84 min)

Following compounds listed in table-27 prepared according to general scheme-15C by following similar procedure as described above for the example 88 using appropriate reagents with suitable modifications known to the one skilled in the art.

TABLE 27

Compounds synthesized using general scheme-15C

| Cpd. ID. | Structure | LCMS [M + H]+ | 1NMR Data |
|---|---|---|---|
| I-429 | 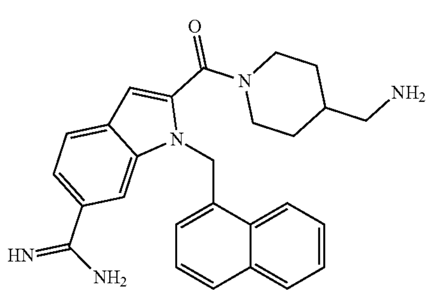 [SMILES: N=C(N)c1ccc2cc(C(=O)N3CCC(CN)CC3)n(Cc3cccc4ccccc34)c2c1] | 440.3 | 1HNMR (300 MHz, CD3OD): δ1.70-1.35 (m, 4H), 2.54 (m, 5H), 3.75 (m, 1H,) 4.40 (m, 1H), 6.12 (d, 2H), 6.84 (s, 2H), 7.36-7.32 (t, 1H), 7.53-7.48 (m, 2H), 7.61-7.59 (d, 1H), 7.83-7.81 (d, 1H), 7.95-7.89 (m, 3H), 8.245-8.241 (s, 1H). |

TABLE 27-continued

Compounds synthesized using general scheme-15C

| Cpd. ID. | Structure | LCMS [M + H]+ | ¹NMR Data |
|---|---|---|---|
| I-430 | 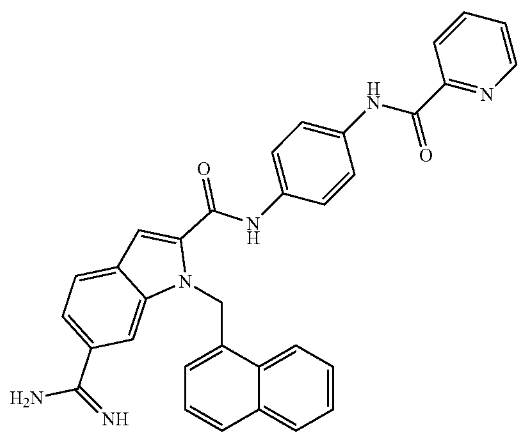 [SMILES: N=C(N)c1ccc2cc(C(=O)Nc3ccc(NC(=O)c4ccccn4)cc3)n(Cc3cccc4ccccc34)c2c1] | 539.4 | ¹HNMR (300 MHz, CD₃OD): δ 6.39-6.37 (d, 1H), 6.49 (s, 2H), 7.24-7.19 (t, 1H), 7.50 (s, 1H), 7.65-7.53 (m, 6H), 7.76-7.72 (m, 3H), 8.03-7.90 (m, 4H), 8.24-8.17 (m, 2H), 8.69-8.68 (d, 1H). |
| I-431 | 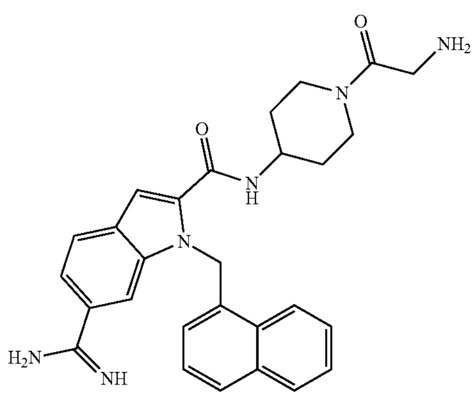 [SMILES: N=C(N)c1ccc2cc(C(=O)NC3CCN(C(=O)CN)CC3)n(Cc3cccc4ccccc34)c2c1] | 469.4 | ¹HNMR (400 MHz, CD₃OD): δ 2.79-2.69 (m, 4H), 3.54-3.46 (m, 4H), 3.86-3.83 (m, 2H), 6.13 (s, 2H), 6.95-6.83 (m, 3H), 7.39-7.32 (m, 1H), 7.62-7.47 (m, 3H), 7.94-7.80 (m, 3H), 8.27-8.24 (d, 1H). |
| I-432 | 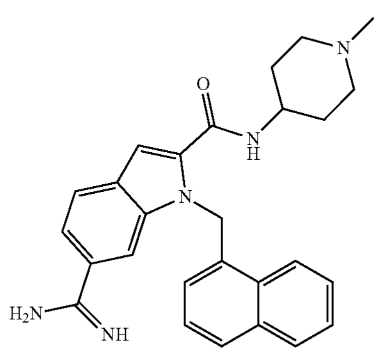 [SMILES: CN1CCC(NC(=O)c2cc3ccc(C(=N)N)cc3n2Cc2cccc3ccccc23)CC1] | 440.3 | ¹HNMR (300 MHz, CD₃OD): δ 2.04-1.72 (m, 4H), 2.82 (s, 3H), 3.07-2.99 (m, 2H), 3.50-3.46 (m, 2H), 3.93-3.90 (m, 1H), 6.25-6.23 (d, 1H), 6.44 (s, 2H), 7.21-7.16 (t, 1H), 7.32 (s, 1H), 7.62-7.54 (m, 3H), 7.76-7.73 (d, 1H), 7.98-7.90 (m, 3H), 8.21-8.18 (d, 1H). |
| I-433 | 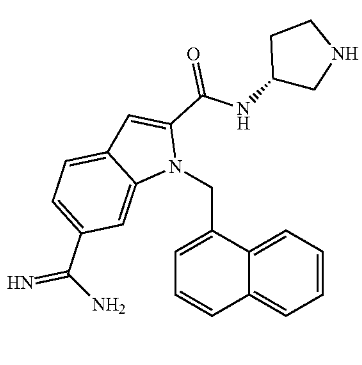 [SMILES: N=C(N)c1ccc2cc(C(=O)N[C@@H]3CCNC3)n(Cc3cccc4ccccc34)c2c1] | 412.1 | ¹HNMR (400 MHz, CD₃OD): δ 2.30-2.00 (m, 2H), 3.30-3.10 (m, 2H), 3.46-3.41 (m, 2H), 4.50-4.45 (m, 1H), 6.25-6.23 (d, 1H), 6.45 (s, 2H), 7.21-7.17 (t, 1H), 7.37 (s, 1H), 7.63-7.55 (m, 3H), 7.76-7.74 (d, 1H), 7.96-7.91 (m, 3H), 8.21-8.19 (d, 1H). |

TABLE 27-continued
| | Compounds synthesized using general scheme-15C | | |
|---|---|---|---|
| Cpd. ID. | Structure | LCMS [M + H]⁺ | ¹NMR Data |
| I-434 | 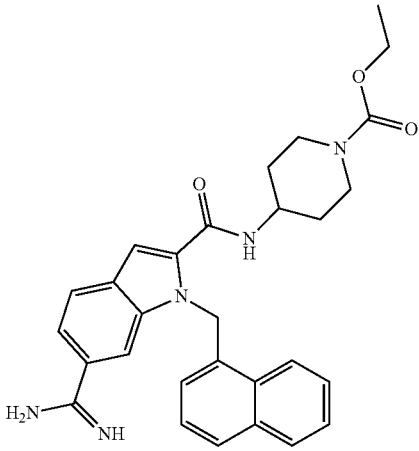 [SMILES: CCOC(=O)N1CCC(NC(=O)c2cc3ccc(C(=N)N)cc3n2Cc2cccc3ccccc23)CC1] | 498.7 | ¹HNMR (400 MHz, CD₃OD): δ 1.24 (t, 3H), 1.28-1.38 (m, 2H), 1.71-1.73 (m, 2H), 2.80-2.90 (m, 2H), 3.82-3.88 (m, 1H), 4.00-4.11 (m, 4H), 6.29 (d, 1H), 6.41 (s, 2H), 7.19 (t, 1H), 7.27 (s, 1H), 7.54-7.63 (m, 3H), 7.74 (d, 1H), 7.90-7.96 (m, 3H), 8.19 (d, 1H), 8.56 (d, 1H). |
| I-435 | 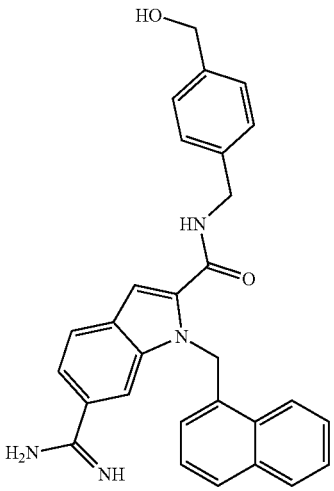 [SMILES: N=C(N)c1ccc2cc(C(=O)NCc3ccc(CO)cc3)n(Cc3cccc4ccccc34)c2c1] | 463.45 | ¹HNMR (400 MHz, CD₃OD): δ 4.41 (s, 2H), 4.50 (s, 2H), 6.25 (d, 1H), 6.45 (s, 2H), 7.04-7.17 (m, 5H), 7.30 (s, 1H), 7.54-7.61 (m, 3H), 7.76 (d, 1H), 7.92-7.96 (m, 3H), 8.20 (d, 1H). |
| I-436 | 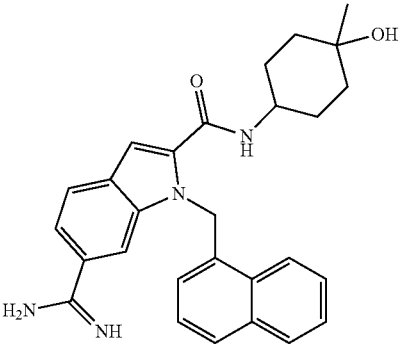 [SMILES: CC1(O)CCC(NC(=O)c2cc3ccc(C(=N)N)cc3n2Cc2cccc3ccccc23)CC1] | 455.2 | ¹HNMR (400 MHz, CD₃OD): δ 1.29 (s, 1.75 H), 1.30 (s, 1.25 H), 1.34-1.50 (m, 4H) 1.58-1.61 (m, 2H), 1.70-1.73 (m, 2H), 3.73-3.74 (m, 1H), 6.16 (d, 0.3H), 6.32 (d, 0.7H), 6.41 (s, 1.4H), 6.51 (s, 0.5H), 7.18-7.23 (m, 1H), 7.27 (s, 1H), 7.55-7.66 (m, 3H), 7.74-7.76 (m, 1H), 7.91-8.01 (m, 3H), 8.19-8.26 (m, 1H). |

TABLE 27-continued
Compounds synthesized using general scheme-15C
| Cpd. ID. | Structure | LCMS [M + H]⁺ | ¹NMR Data |
|---|---|---|---|
| I-437 | 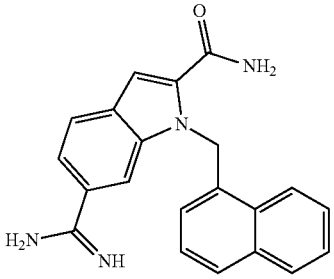 [SMILES: N=C(N)c1ccc2cc(C(N)=O)n(Cc3cccc4ccccc34)c2c1] | 343.1 | ¹HNMR (400 MHz, CD$_3$OD): δ 6.24 (d, 1H), 6.51 (s, 2H), 7.20 (t, 1H), 7.42, (s, 1H), 7.56-7.67 (m, 3H), 7.75 (d, 1H), 7.92-7.98 (m, 3H), 8.24 (d, 1H). |
| I-438 | 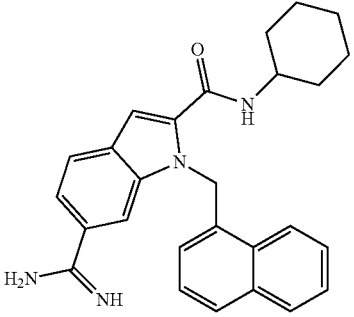 [SMILES: N=C(N)c1ccc2cc(C(=O)NC3CCCCC3)n(Cc3cccc4ccccc34)c2c1] | 425.1 | ¹HNMR (400 MHz, CD$_3$OD): δ 1.11-1.35 (m, 6H), 1.57-1.79 (m, 4H), 3.60-3.70 (m, 1H), 6.30 (dd, 1H), 6.41 (s, 2H), 7.20 (dd, 1H), 7.25 (d, 1H), 7.53-7.63 (m, 3H), 7.74 (d, 1H), 7.89-7.96 (m, 3H), 8.17-8.22 (m, 1H). |
| I-439 | 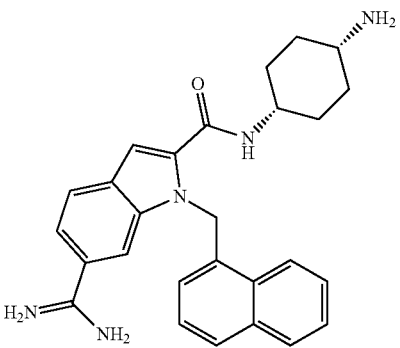 [SMILES: N=C(N)c1ccc2cc(C(=O)N[C@H]3CC[C@@H](N)CC3)n(Cc3cccc4ccccc34)c2c1] | 440.4 | ¹HNMR (400 MHz, CD$_3$OD): δ1.65-1.75 (m, 4H), 1.75-1.80 (m, 4H), 3.18-3.28 (s, 1H), 3.80-3.90 (m, 1H), 6.33 (d, 1H), 6.41 (s, 2H), 7.18-7.30 (m, 1H), 7.32 (s, 1H), 7.53-7.63 (m, 3H), 7.75 (d, 1H), 7.90-7.99 (m, 3H), 8.20 (d, 1H). |
| I-440 | 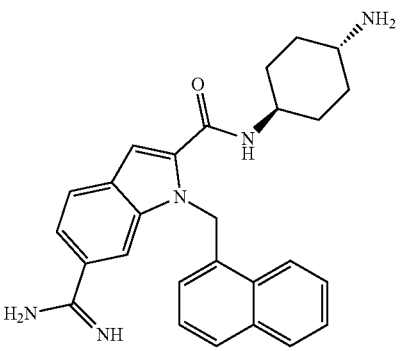 [SMILES: N=C(N)c1ccc2cc(C(=O)N[C@H]3CC[C@H](N)CC3)n(Cc3cccc4ccccc34)c2c1] | 441.6 | ¹HNMR (400 MHz, CD$_3$OD): δ 1.32-1.28 (m, 4H), 1.90-1.76 (m, 4H), 3.45-3.50 (m, 1H), 3.60-3.68 (m, 1H), 6.30 (dd, 1H), 6.41 (s, 2H), 7.17-7.21 (m, 1H), 7.25 (s, 1H), 7.52-7.62 (m, 3H), 7.75 (d, 1H), 7.90-7.95 (m, 3H), 8.20 (d, 1H). |

TABLE 27-continued

Compounds synthesized using general scheme-15C

| Cpd. ID. | Structure | LCMS [M + H]+ | 1NMR Data |
|---|---|---|---|
| I-441 | 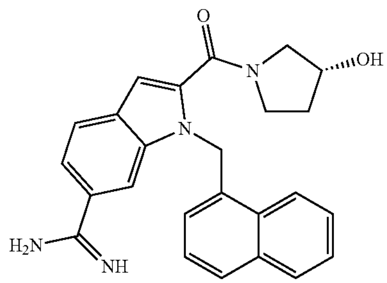 [SMILES: N=C(N)c1ccc2cc(C(=O)N3CC[C@@H](O)C3)n(Cc3cccc4ccccc34)c2c1] | 413.2 | 1HNMR (300 MHz, CD3OD): δ 1.52-1.82 (m, 2H), 2.84-3.26 (m, 2H), 3.37-3.53 (m, 2H), 4.11-4.22 (m, 1H), 6.05-6.29 (m, 2H), 6.66-6.79 (m, 1H), 6.99-7.02 (m, 1H), 7.45-7.59 (m, 4H), 7.78-8.17 (m, 5H). |
| I-442 | 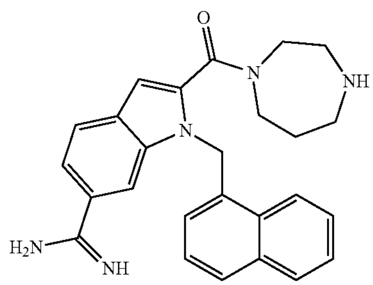 [SMILES: N=C(N)c1ccc2cc(C(=O)N3CCCNCC3)n(Cc3cccc4ccccc34)c2c1] | 426.3 | 1HNMR (400 MHz, CD3OD): δ 1.70-1.95 (m, 2H), 2.62-2.68 (m, 2H), 2.85-3.08 (m, 2H), 3.39-3.50 (m, 2H), 3.62-3.68 (m, 2H), 6.10-6.18 (m, 2H), 6.70-6.75 (m, 1H), 6.90-7.01 (m, 2H), 7.30-7.38 (m, 1H), 7.53-7.62 (m, 3H), 7.89-7.99 (m, 3H), 8.22 (s, 1H). |
| I-443 | 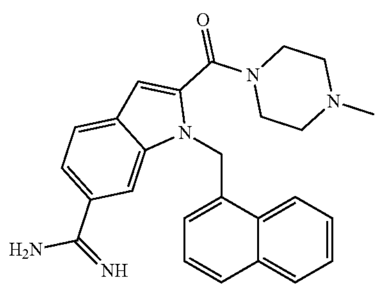 [SMILES: CN1CCN(C(=O)c2cc3ccc(C(=N)N)cc3n2Cc2cccc3ccccc23)CC1] | 426.3 | 1H NMR (600 MHz, D2O): δ 2.42 (s, 3H), 2.57-2.86 (m, 2H), 2.92-3.25 (m, 2H), 3.27-3.64 (m, 2H), 3.86-4.35 (m, 2H), 5.85 (s, 2H), 6.71 (s, 1H), 7.00 (brs, 1H), 7.29-7.52 (m, 5H), 7.76-7.86 (m, 3H), 8.16 (s, 1H). |
| I-444 | 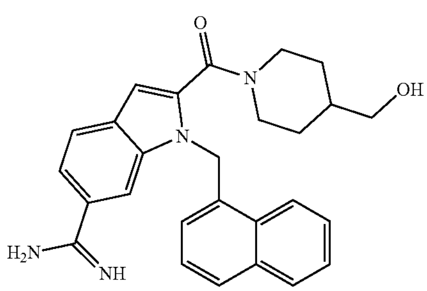 [SMILES: N=C(N)c1ccc2cc(C(=O)N3CCC(CO)CC3)n(Cc3cccc4ccccc34)c2c1] | 441.6 | 1HNMR (400 MHz, CD3OD): δ 0.25-0.40 (m, 1H), 0.55-0.65 (m, 1H), 1.25-1.35 (m, 1H), 1.42-1.62 (m, 2H), 2.44-2.64 (m, 2H), 3.10-3.18 (m, 2H), 3.65-3.71 (m, 1H), 4.31-4.41 (m, 1H), 6.06-6.38 (m, 2H), 6.82-6.87 (m, 2H), 7.31-7.35 (m, 1H), 7.46-7.60 (m, 3H), 7.81-7.94 (m, 4H), 8.22 (s, 1H). |
| I-445 | 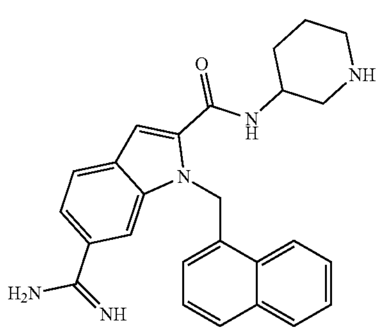 [SMILES: N=C(N)c1ccc2cc(C(=O)NC3CCCNC3)n(Cc3cccc4ccccc34)c2c1] | 426.3 | 1HNMR (400 MHz, CD3OD): δ 1.56-1.80 (m, 2H), 1.92-2.00 (m, 2H), 2.70-2.75 (m, 1H), 2.85-2.90 (m, 1H), 3.25-3.28 (m, 2H), 4.00-4.09 (m, 1H), 6.25 (d, 1H), 6.38-6.49 (m, 2H), 7.19 (t, 1H), 7.35 (s, 1H), 7.54-7.66 (m, 3H), 7.75 (d, 1H), 7.90-8.01 (m, 3H), 8.20 (d, 1H). |

TABLE 27-continued
Compounds synthesized using general scheme-15C
| Cpd. ID. | Structure | LCMS [M + H]⁺ | ¹NMR Data |
|---|---|---|---|
| I-446 | 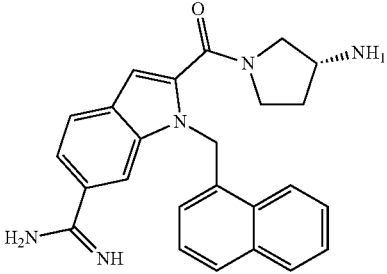 [SMILES: N=C(N)c1ccc2cc(C(=O)N3CC[C@@H](N)C3)n(Cc3cccc4ccccc34)c2c1] | 412.3 | ¹HNMR (400 MHz, CD₃OD): δ1.75-2.20 (m, 3H), 3.23-3.29 (m, 1H), 3.47-3.76 (m, 3H), 6.12-6.28 (m, 2H), 6.64-6.68 (m, 1H), 7.07 (s, 1H), 7.32 (t, 1H), 7.51-7.61 (m, 3H), 7.80-7.82 (d, 1H), 7.90-8.05 (m, 3H), 8.08-8.13 (m, 1H). |
| I-447 | 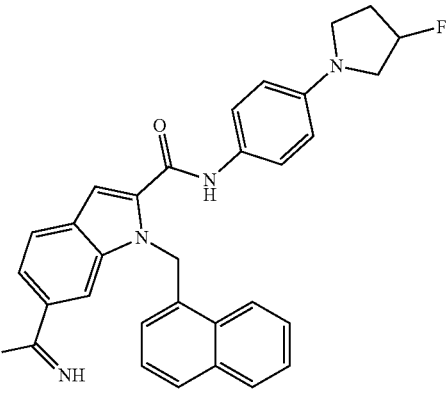 | 506.65 | ¹HNMR (300 MHz, CD₃OD): δ 2.07-2.34 (m, 2H), 3.22-3.60 (m, 4H), 5.24-5.44 (m, 1H), 6.37 (dd, 1H), 6.47-6.56 (m, 4H), 7.18-7.23 (m, 1H), 7.33-7.36 (m, 2H), 7.44 (s, 1H), 7.51-7.65 (m, 3H), 7.74 (d, 1H), 7.88-8.01 (m, 3H), 8.20 (d, 1H). |
| I-448 | 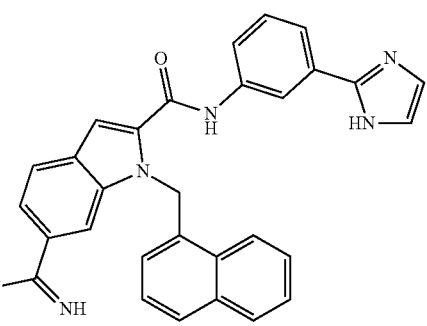 | 485 | ¹HNMR (400 MHz, CD₃OD): δ 6.31-6.37 (m, 1H), 6.55 (s, 2H), 7.20-7.27 (m, 1H), 7.54 (s, 2H), 7.57-7.71 (m, 7H), 7.77 (d, 1H), 7.91-7.98 (m, 1H), 8.01 (s, 1H), 8.06 (d, 1H), 8.27 (d, 1H), 8.47 (s, 1H). |
| I-449 | 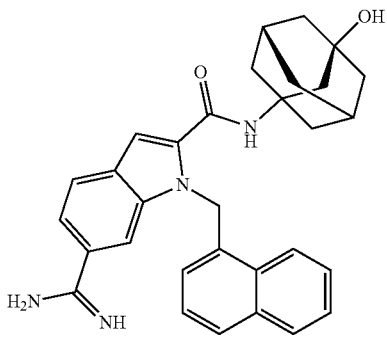 [SMILES: N=C(N)c1ccc2cc(C(=O)NC34CC5C[C@H](C3)C[C@](O)(C5)C4)n(Cc3cccc4ccccc34)c2c1] | 493.65 | ¹HNMR (400 MHz, CD₃OD): δ1.53 (d, 2H), 1.61-1.65 (m, 4H), 1.81-1.90 (m, 4H), 1.95 (s, 2H), 2.14-2.19 (m, 2H), 6.35-6.41 (m, 3H), 7.19-7.27 (m, 2H), 7.54-7.67 (m, 3H), 7.78 (d, 1H), 7.91-7.98 (m, 3H), 8.18-8.22 (m, 1H). |

TABLE 27-continued
Compounds synthesized using general scheme-15C
| Cpd. ID. | Structure | LCMS [M + H]+ | 1NMR Data |
|---|---|---|---|
| I-450 | 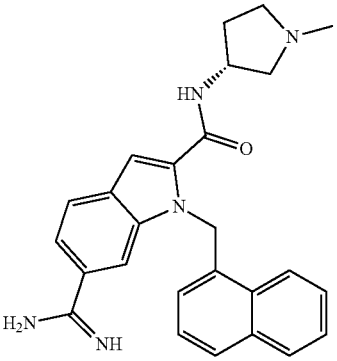 [SMILES: CN1CC[C@@H](NC(=O)c2cc3ccc(C(=N)N)cc3n2Cc2cccc3ccccc23)C1] | 426.2 | 1HNMR (300 MHz, CD3OD): δ 1.99-2.19 (m, 1H), 2.42 (s, 1H), 2.83 (s, 3H), 3.22-3.26 (m, 2H), 3.26-3.38 (m, 2H), 4.42-4.47 (m, 1H), 6.22-6.24 (m, 1H), 6.46 (s, 2H), 7.15-7.20 (m, 1H), 7.37 (s, 1H), 7.55-7.69 (m, 3H), 7.76 (d, 1H), 7.90-8.01 (m, 3H), 8.19-8.25 (m, 1H). |
| I-451 | 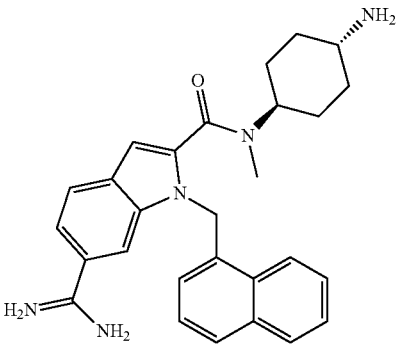 [SMILES: CN(C(=O)c1cc2ccc(C(=N)N)cc2n1Cc1cccc2ccccc12)[C@H]1CC[C@H](N)CC1] | 454.5 | 1H NMR (600 MHz, CD3OD): δ 0.88-0.92 (m, 2H), 1.27-1.45 (m, 4H), 1.76-1.92 (m, 2H), 2.54-2.65 (m, 3H), 2.84-2.93 (m, 1H), 3.44 (brs, 0.5H), 4.06 (brs, 0.5H), 6.09 (d, 2H), 6.77 (m, 1H), 6.87 (s, 1H), 7.30-7.34 (m, 1H), 7.49-7.51 (m, 2H), 7.59-7.6 (m, 1H), 7.81-7.94 (m, 4H), 8.25 (d, 1H) |
| I-452 | 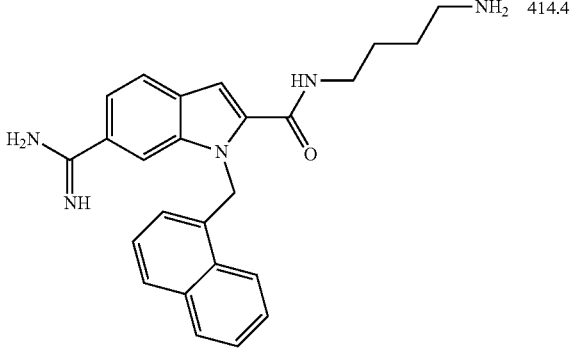 | 414.4 | 1H NMR (600 MHz, CD3OD): δ 1.52-1.53 (m, 4H), 2.78-2.79 (m, 2H), 3.27-3.29 (m, 2H), 6.20 (d, 1H), 6.44 (s, 2H), 7.16-7.18 (m, 1H), 7.29 (s, 1H), 7.54-7.57 (m, 2H), 7.61-7.64 (m, 1H), 7.72-7.74 (m, 1H), 7.90-7.94 (m, 3H), 8.21 (d, 1H). |
| I-453 | 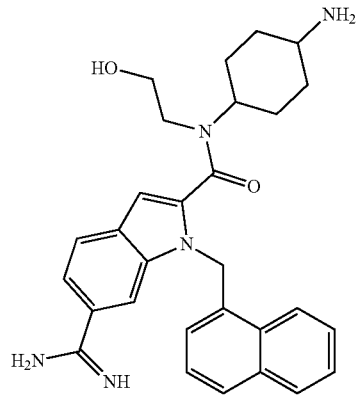 [SMILES: N=C(N)c1ccc2cc(C(=O)N(CCO)C3CCC(N)CC3)n(Cc3cccc4ccccc34)c2c1] | 484.65 | 1H NMR (400 MHz, CD3OD): δ 0.85-1.00 (m, 2H), 1.28-1.48 (m, 3H), 1.60-1.93 (m, 3H), 2.85-3.06 (m, 1H), 3.17-3.54 (m, 5H), 6.09 (s, 2H), 7.34-7.48 (m, 2H), 7.5-7.81 (m, 3H), 7.83-7.93 (m, 4H), 7.96-8.09 (m, 1H), 8.27 (s, 1H). |

TABLE 27-continued

Compounds synthesized using general scheme-15C

| Cpd. ID. | Structure | LCMS [M + H]+ | 1NMR Data |
|---|---|---|---|
| I-454 | 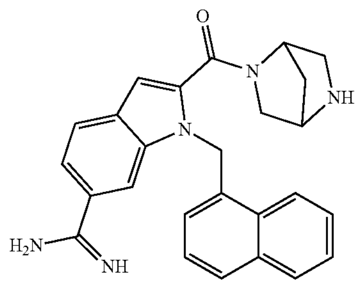 [SMILES: N=C(N)c1ccc2cc(C(=O)N3CC4CC3CN4)n(Cc3cccc4ccccc34)c2c1] | 424.3 | 1HNMR (400 MHz, CD3OD): δ1.42 (m, 1H), 1.90-1.62 (m, 3H), 3.42 (s, 2H), 4.36 (s, 1H), 4.68 (s, 1H), 6.22 (s, 2H), 6.54 (d, 1H), 7.11 (bs, 1H), 7.29 (t, 1H), 7.62-7.53 (m, 3H), 7.82 (d, 1H), 7.98-7.91 (m, 3H), 8.16 (s, 1H). |

Example 89: Synthesis of Compound I-455

1-(naphthalen-1-ylmethyl)-N2-(piperidin-4-yl)-1H-indole-2,6-dicarboxamide

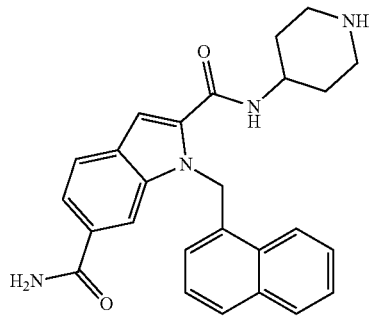 [SMILES: NC(=O)c1ccc2cc(C(=O)NC3CCNCC3)n(Cc3cccc4ccccc34)c2c1]

The above title compound (50 mg) was isolated as TFA salt in the preparative HPLC purification in a step-6 of example 88. LCMS: 428.0 (M+1)+; 1HNMR (400 MHz, CD3OD): δ2.00-1.69 (m, 4H), 3.36-2.96 (m, 4H), 3.93 (m, 1H), 6.242-6.224 (d, 1H), 6.38 (s, 2H), 7.18-7.14 (t, 1H), 7.25 (s, 1H), 7.61-7.51 (m, 2H), 7.71-7.67 (m, 2H), 7.79-7.71 (m, 1H), 7.89-7.87 (m, 1H), 8.00 (s, 1H), 8.19-8.17 (d, 1H); HPLC: 98.45% (Retention Time=5.25 min)

Following compounds listed in table-27A were isolated in final preparative HPLC purification of following similar procedure as described above for the example 89 using appropriate reagents with suitable modifications known to the one skilled in the art.

TABLE 27A

| Cpd. ID. | Structure | LCMS [M + H]+ | 1H-NMR Data |
|---|---|---|---|
| I-456 | 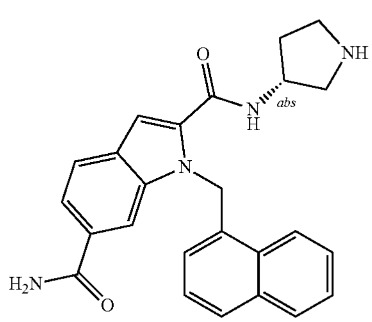 [SMILES: NC(=O)c1ccc2cc(C(=O)N[C@@H]3CCNC3)n(Cc3cccc4ccccc34)c2c1] | 413 | 1HNMR (300 MHz, CD3OD): δ 2.32-2.00 (m, 2H), 3.27-3.16 (m, 2H), 3.47-3.42 (m, 2H), 4.42-4.38 (m, 1H), 6.23-6.20 (d, 1H), 6.41 (s, 2H), 7.19-7.14 (t, 1H), 7.30 (s, 1H), 7.64-7.53 (m, 2H), 7.81-7.68 (m, 3H), 7.98-7.89 (m, 2H), 8.21-8.18 (d, 1H). |

TABLE 27A-continued
| Cpd. ID. | Structure | LCMS [M + H]+ | 1H-NMR Data |
|---|---|---|---|
| I-457 | 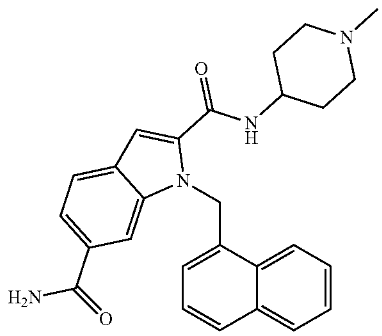 [SMILES: CN1CCC(NC(=O)c2cc3ccc(C(N)=O)cc3n2Cc2cccc3ccccc23)CC1] | 441.4 | 1HNMR (600 MHz, CD3OD): δ 1.74-1.72 (m, 2H), 2.04-2.02 (m, 2H), 2.80 (s, 3H), 3.05-3.00 (m, 2H), 3.47-3.45 (m, 2H), 3.95-3.90 (m, 1H), 6.21-6.20 (d, 1H), 6.39 (s, 2H), 7.16-7.15 (m, 1H), 7.23 (s, 1H), 7.61-7.53 (m, 2H), 7.70-7.67 (m, 2H), 7.78-7.76 (d, 1H), 7.89-7.87 (d, 1H), 7.99 (s, 1H), 8.19-8.18 (d, 1H). |
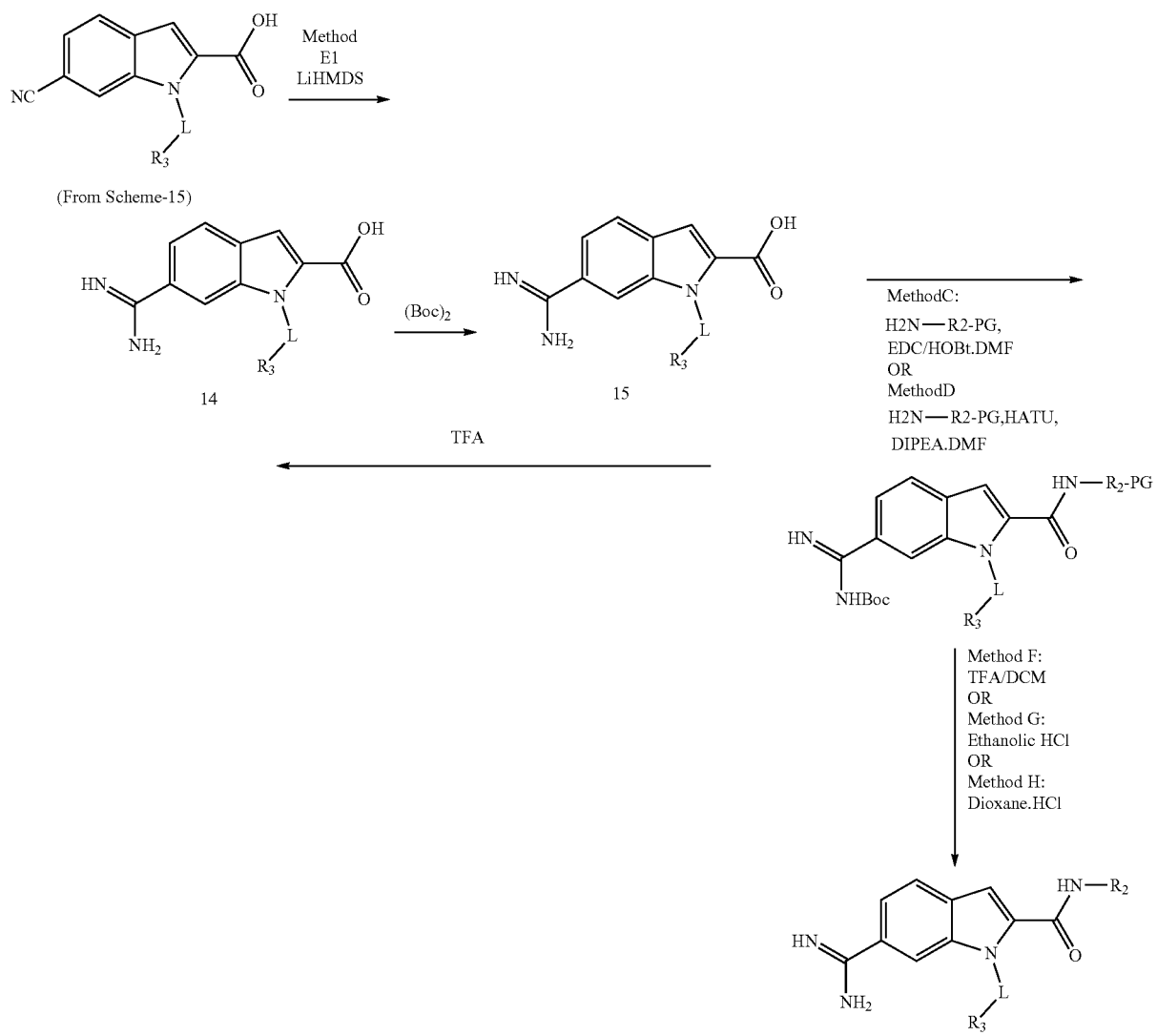
General synthetic scheme-15D
PG = optional protecting group;

Example 90: Synthesis of Compound I-458

6-carbamimidoyl-1-(naphthalen-1-ylmethyl)-1H-indole-2-carboxylic Acid

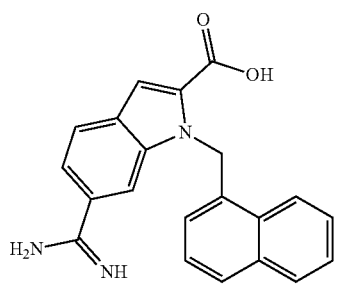 [SMILES: N=C(N)c1ccc2cc(C(=O)O)n(Cc3cccc4ccccc34)c2c1]

Step-1: 6-carbamimidoyl-1-(naphthalen-1-ylmethyl)-1H-indole-2-carboxylic Acid A 0° C. cooled solution of product of step-1 of example 79 (250 m g, 0.766 mmol) in THF (3 mL) maintained under inert atmosphere was added to pre dissolved solution of LiHMDS (solid) (896 mg, 5.367 mmol) in THF (1 mL) at 0° C. under inert atmosphere. The resulting solution was stirred for overnight (16 h) at room temperature. After reaction completion, reaction mixture was quenched with saturated aqueous solution of ammonium chloride. The precipitated product was filtered off and dried to give title compound (180 mg). LCMS: 344.0 (M+1)+.

Step-2: 6-(N-(tert-butoxycarbonyl)carbamimidoyl)-1-(naphthalen-1-ylmethyl)-1H-indole-2-carboxylic Acid To a stirred solution of product of step-1 of example 90 (980 mg, 2.85 mmol) in THF (20 mL) was added 2M aqueous solution of sodium hydroxide (250 mg, 4.28 mmol) followed by addition of di-tert-butyl dicarbonate (932.5 mg, 4.28 mmol) at room temperature and resulting reaction mixture was refluxed at 50° C. for 3 h. After reaction completion, evaporated off the reaction mixture under reduced pressure. The residue obtained was diluted with water and adjusted the pH=6-7 using citric acid solution. The precipitated solid was filtered off and dried to give title compound (1.1 g). LCMS: 443.0 (M+1)+.

Step-2a: 6-carbamimidoyl-1-(naphthalen-1-ylmethyl)-1H-indole-2-carboxylic Acid To a stirred solution of product of step-2 of example 90s (85 mg, 0.191 mmol) in dichloromethane (8 mL) was added predissolved solution of TFA (0.4 mL) in 2 mL of dichloromethane at 0° C. and stirred reaction mixture for 4 h at room temperature. Evaporated off reaction mixture under reduced pressure and the crude obtained was purified by preparative HPLC instrument using X-Bridge C18 reverse phase column (19×150 mm, 5 micron). The mobile phases were 10% acetonitrile in water (0.1% TFA) to 50% acetonitrile in water (0.02% TFA) which afforded the title compound (46 mg) as a TFA Salt. LCMS: 342.0 (M−1)*; $^1$HNMR (600 MHz, CD$_3$OD): δ6.16-6.15 (d, 1H), 6.50 (s, 2H), 7.18 (t, 1H), 7.57-7.53 (m, 3H), 7.64 (t, 1H), 7.74-7.72 (d, 1H), 7.92-7.89 (m, 2H), 7.99-7.97 (d, 1H), 8.24-8.23 (d, 1H); HPLC: 97.95% (Retention Time=5.38 min)

Following compound listed in table-28 prepared according to general scheme-15D by following similar procedure as described above for the example 90 using appropriate reagents with suitable modifications known to the one skilled in the art.

TABLE 28

Compounds synthesized using Scheme-15D

| Cpd. ID. | Structure | LCMS [M + H]+ | $^1$H-NMR Data |
|---|---|---|---|
| I-459 | 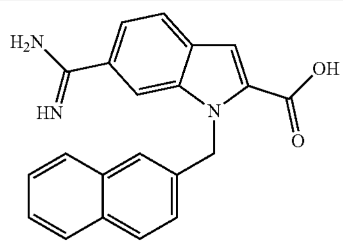 [SMILES: N=C(N)c1ccc2cc(C(=O)O)n(Cc3ccc4ccccc4c3)c2c1] | 344.2 | $^1$HNMR (400 MHz, CD$_3$OD): δ 6.17 (s, 2H), 7.27-7.24 (m, 1H), 7.48-7.39 (m, 3H), 7.55-7.53 (m, 2H), 7.69-7.67 (m, 1H), 7.82-7.79 (m, 2H), 7.98-7.96 (m, 1H), 8.06 (s, 1H). |

Example 91: Synthesis of Compound I-460

6-carbamimidoyl-N-((1-methylpiperidin-4-yl)methyl)-1-(naphthalen-1-ylmethyl)-1H-indole-2-carboxamide

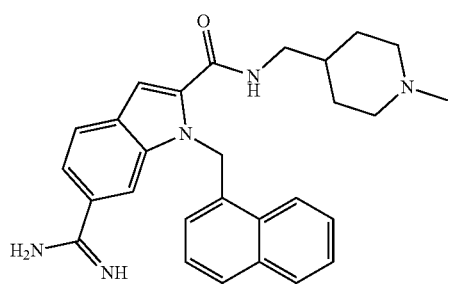 [SMILES: CN1CCC(CNC(=O)c2cc3ccc(C(=N)N)cc3n2Cc2cccc3ccccc23)CC1]

Step-1: tert-butyl (imino(2-(((1-methylpiperidin-4-yl)methyl)carbamoyl)-1-(naphthalen-1-ylmethyl)-1H-indol-6-yl)methyl)carbamate Product of step-2 of example 90 (100 mg, 0.230 mmol) and (1-methylpiperidin-4-yl) methanamine (38 mg, 0.290 mmol) were treated together afforded the title compound (110 mg) as crude following the procedure described in step-3 of example 79. LCMS: 554.85 (M+1)⁺.

Step-2: 6-carbamimidoyl-N-((1-methylpiperidin-4-yl) methyl)-1-(naphthalen-1-ylmethyl)-1H-indole-2-carboxamide To a stirred solution of product of step-1 of example 91 (110 mg, 0.200 mmol) in dichloromethane was added TFA (0.456 mL, 5.96 mmol) at 0° C. under nitrogen atmosphere and stirred at room temperature for 3 h. After completion of reaction, reaction mixture was evaporated off under reduced pressure. The crude obtained was triturated with diethyl ether and dried. The crude obtained was purified by preparative HPLC instrument using Kinetex EVO C18 reverse phase column (21.2×150 mm, 5 micron). The mobile phases were 30% acetonitrile in water (0.1% TFA) to 60% acetonitrile in water (0.1% TFA) which afforded the title compound (50 mg) as a TFA Salt.

LCMS: 453.9 (M+1)⁺; ¹HNMR (400 MHz, CD₃OD): δ 1.24-1.30 (m, 2H), 1.67 (d, 2H), 2.64 (m, 5H), 2.89-2.99 (m, 1H), 3.15 (dd, 2H), 3.29-3.30 (m, 2H), 6.18 (dt, 1H), 6.44 (s, 2H), 7.19 (dd, 1H), 7.28 (d, 1H), 7.56-7.59 (m, 2H), 7.60-7.66 (m, 1H), 7.75 (d, 1H), 7.76-7.96 (m, 2H), 7.99-8.06 (s, 1H), 8.18-8.26 (m, 1H); HPLC: 99.69% (Retention Time=5.11 min)

Following compound listed in table-29 prepared according to general scheme-15D by following similar procedure as described above for the example 91 using appropriate reagents with suitable modifications known to the one skilled in the art.

TABLE 29

| Compounds synthesized using Scheme-15D | | | |
|---|---|---|---|
| Cpd. ID. | Structure | LCMS [M + H]⁺ | ¹H-NMR Data |
| I-461 | | 488.95 | ¹H NMR (400 MHz, CD₃OD): δ 2.04-2.07 (m, 4H), 3.39-3.57 (m, 4H), 6.32 (dd, 1H), 6.45-6.57 (m, 3H), 6.92 (d, 1H), 7.22 (dd, 1H), 7.56-7.77 (m, 6H), 7.92-7.95 (m, 1H), 7.98-8.03 (m, 1H), 8.07 (d, 1H), 8.24-8.31 (m, 1H). |
| I-462 | | 494.2 | ¹H NMR (300 MHz, CD₃OD): δ 1.29-1.51 (m, 4H), 1.85-2.01 (m, 4H), 2.05-2.30 (m, 4H), 3.01-3.20 (m, 3H), 3.49-3.79 (m, 3H), 6.27 (d, 1H), 6.43 (s, 2H), 7.19 (t, 1H), 7.29 (s, 1H), 7.55-7.62 (m, 3H), 7.74 (d, 1H), 7.90-7.97 (m, 3H), 8.20 (d, 1H), 8.59-8.62 (m, 1H). |
| I-463 | | 427.1 | ¹H NMR (400 MHz, CD₃OD): δ 1.50-1.59 (m, 2H), 1.70 (ddd, 2H), 3.41 (td, 2H), 3.87-3.94 (m, 3H), 6.31 (dd, 1H), 6.44 (s, 2H), 7.22 (dd, 1H), 7.31 (d, 1H), 7.54-7.65 (m, 3H), 7.76 (d, 1H), 7.91-7.98 (m, 3H), 8.21 (dd, 1H) |

TABLE 29-continued

Compounds synthesized using Scheme-15D

| Cpd. ID. | Structure | LCMS [M + H]+ | ¹H-NMR Data |
|---|---|---|---|
| I-464 | 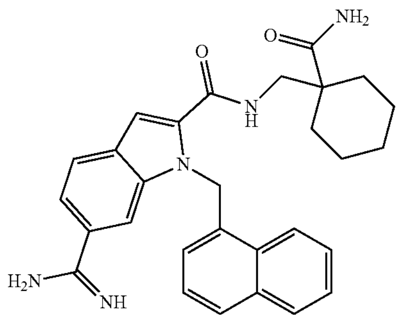 [SMILES: N=C(N)c1ccc2cc(C(=O)NCC3(C(N)=O)CCCCC3)n(Cc3cccc4ccccc34)c2c1] | 482.6 | ¹H NMR (400 MHz, CD₃OD): δ 1.16-1.29 (m, 5H), 1.44-1.50 (m, 3H), 1.84 (d, 2H), 3.35 (d, 2H), 6.21 (d, 1H), 6.43 (s, 2H), 7.15-7.24 (m, 1H), 7.31 (s, 1H), 7.54-7.61 (m, 2H), 7.64 (ddd, 1H), 7.75 (d, 1H), 7.91-7.96 (m, 3H), 8.22 (d, 1H). |
| I-465 | 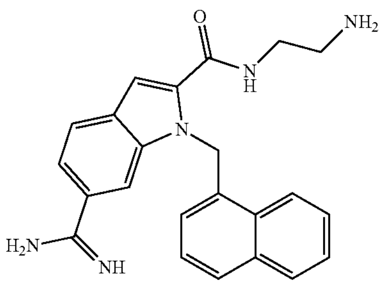 [SMILES: N=C(N)c1ccc2cc(C(=O)NCCN)n(Cc3cccc4ccccc34)c2c1] | 386.2 | ¹H NMR (400 MHz, CD₃OD): δ 3.06 (t, 2H), 3.55 (t, 2H), 6.26 (d, 1H), 6.5 (s, 2H), 7.19-7.22 (m, 1H), 7.43 (s, 1H), 7.57-7.66 (m, 3H), 7.77 (d, 1H), 7.91-8.03 (m, 3H), 8.24 (d, 1H) |
| I-466 | 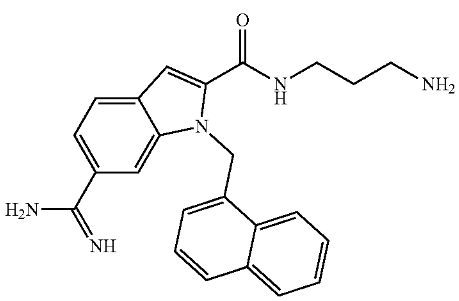 [SMILES: N=C(N)c1ccc2cc(C(=O)NCCCN)n(Cc3cccc4ccccc34)c2c1] | 400.4 | ¹H NMR (400 MHz, CD₃OD): δ 1.84 (m, 2H), 2.83 (t, 2H), 3.38 (qd, 2H), 6.23 (d, 1H), 6.50 (s, 2H), 7.19-7.23 (m, 1H), 7.37 (s, 1H), 7.57-7.66 (m, 3H), 7.77 (d, 1H), 7.93-8.03 (m, 3H), 8.24 (d, 1H), 8.90-9.02 (m, 1H). |
| I-467 | 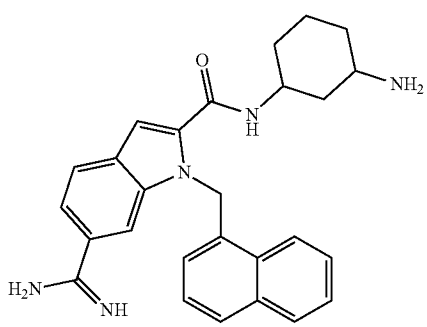 [SMILES: N=C(N)c1ccc2cc(C(=O)NC3CCCC(N)C3)n(Cc3cccc4ccccc34)c2c1] | 440.3 | ¹HNMR (400 MHz, CD₃OD): δ1.34-1.20 (m, 3H), 1.95-2.10 (m, 5H), 3.15-3.00 (m, 1H), 3.80-3.75 (m, 1H), 6.27-6.22 (m, 1H), 6.51-6.37 (m, 2H), 7.21-7.16 (m, 1H), 7.32-7.30 (d, 1H), 7.65-7.54 (m, 3H), 7.75-7.70 (d, 1H), 7.96-7.90 (m, 3H), 8.20-8.18 (d, 1H). |
| I-468 | 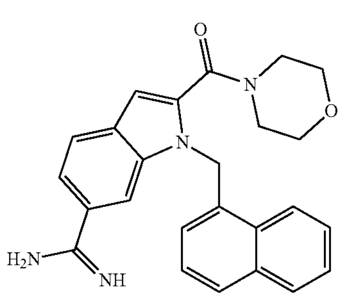 [SMILES: N=C(N)c1ccc2cc(C(=O)N3CCOCC3)n(Cc3cccc4ccccc34)c2c1] | 412.9 | ¹HNMR (400 MHz, CD₃OD): δ2.95-2.88 (m, 2H), 3.29-3.15 (m, 4H), 3.45-3.38 (m, 2H), 6.11 (s, 2H), 6.86-6.84 (d, 2H), 7.36-7.32 (t, 1H), 7.60-7.46 (m, 3H), 7.94-7.84 (m, 4H), 8.23 (s, 1H). |

TABLE 29-continued

Compounds synthesized using Scheme-15D

| Cpd. ID. | Structure | LCMS [M + H]+ | 1H-NMR Data |
|---|---|---|---|
| I-469 | 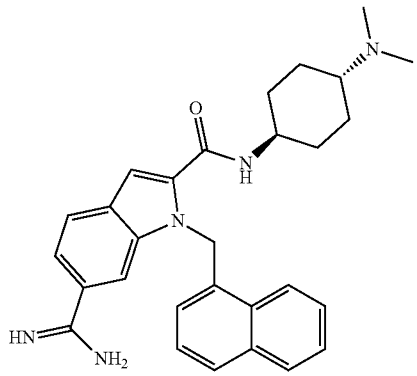 [SMILES: CN(C)[C@H]1CC[C@H](NC(=O)c2cc3ccc(C(=N)N)cc3n2Cc2cccc3ccccc23)CC1] | 468.3 | 1HNMR (400 MHz, CD3OD): δ1.46-1.31 (m, 2H), 1.63-1.53 (m, 2H), 2.17-1.96 (m, 4H), 2.85 (s, 6H), 3.20-3.10 (m, 1H), 4.90-3.67 (m, 1H), 6.27-6.26 (d, 1H), 6.45 (s, 2H), 7.23-7.19 (m, 1H), 7.30 (s, 1H), 7.58-7.56 (m, 2H), 7.59-7.58 (m, 1H), 7.65-7.60 (m, 1H), 8.02-7.90 (m, 3H), 8.23-8.21 (m, 1H). |
| I-470 | 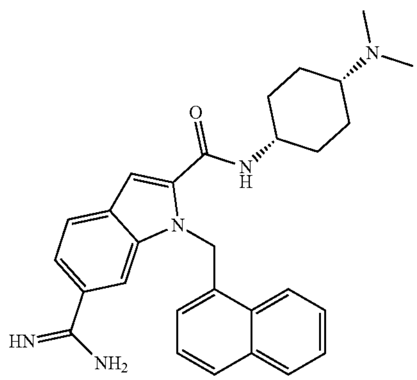 [SMILES: CN(C)[C@H]1CC[C@@H](NC(=O)c2cc3ccc(C(=N)N)cc3n2Cc2cccc3ccccc23)CC1] | 468.3 | 1HNMR (400 MHz, CD3OD): δ1.45-1.30 (m, 1H), 1.70-1.52 (m, 4H), 2.10-1.80 (m, 3H), 2.85 (s, 6H), 3.20-3.10 (m, 1H), 4.05-3.98 (m, 1H), 6.30-6.26 (d, 1H), 6.40 (s, 2H), 7.34-7.21 (m, 2H), 7.68-7.55 (m, 3H), 7.80-7.70 (m, 1H), 8.00-7.90 (m, 2H), 8.05 (s, 1H), 8.25-8.20 (m, 1H). |
| I-471 | 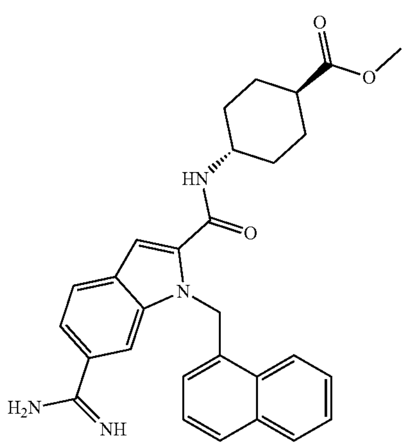 [SMILES: COC(=O)[C@H]1CC[C@H](NC(=O)c2cc3ccc(C(=N)N)cc3n2Cc2cccc3ccccc23)CC1] | 483.3 | 1HNMR (400 MHz, CD3OD): δ1.35-1.28 (m, 2H), 1.50-1.43 (m, 2H), 1.98-1.83 (m, 4H), 2.30-2.24 (m, 1H), 3.64 (s, 3H), 3.68-3.65 (m, 1H), 6.32-6.30 (d, 1H), 6.43 (s, 2H), 7.23-7.19 (m, 1H), 7.28 (s, 1H), 7.65-7.55 (m, 3H), 7.77-7.75 (d, 1H), 7.97-7.92 (m, 3H), 8.22-8.20 (d, 1H). |
| I-472 | 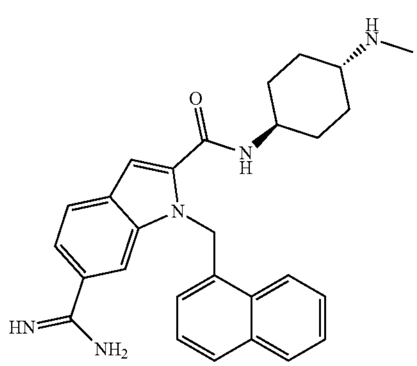 [SMILES: CN[C@H]1CC[C@H](NC(=O)c2cc3ccc(C(=N)N)cc3n2Cc2cccc3ccccc23)CC1] | 454.2 | 1HNMR (400 MHz, CD3OD): δ1.75-1.67 (m, 4H), 1.86-1.80 (m, 4H), 2.70 (s, 3H), 3.15-3.10 (m, 1H), 3.95-3.91 (m, 1H), 6.35-6.34 (d, 1H), 6.43 (s, 2H), 7.24-7.20 (m, 1H), 7.34 (s, 1H), 7.65-7.58 (m, 3H), 7.78-7.76 (d, 1H), 8.01-7.92 (m, 3H), 8.22-8.20 (d, 1H). |

TABLE 29-continued

Compounds synthesized using Scheme-15D

| Cpd. ID. | Structure | LCMS [M + H]+ | 1H-NMR Data |
|---|---|---|---|
| I-473 | 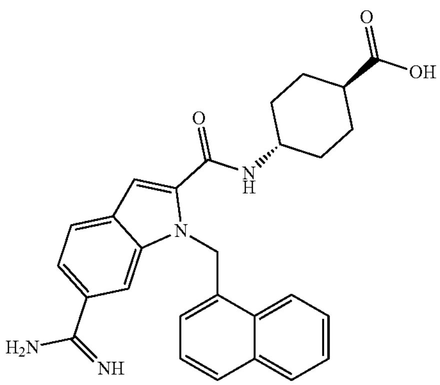 [SMILES: N=C(N)c1ccc2cc(C(=O)N[C@H]3CC[C@H](C(=O)O)CC3)n(Cc3cccc4ccccc34)c2c1] | 469.2 | ¹HNMR (400 MHz, CD₃OD): δ1.32-1.30 (m, 2H), 1.48-1.42 (m, 2H), 2.05-1.85 (m, 4H), 2.25-2.15 (m, 1H), 3.70-3.60 (m, 1H), 6.32-6.30 (d, 1H), 6.43 (s, 2H), 7.23-7.19 (m, 1H), 7.28 (s, 1H), 7.65-7.58 (m, 3H), 7.78-7.76 (d, 1H), 7.97-7.92 (m, 3H), 8.22-8.20 (d, 1H). |
| I-474 | 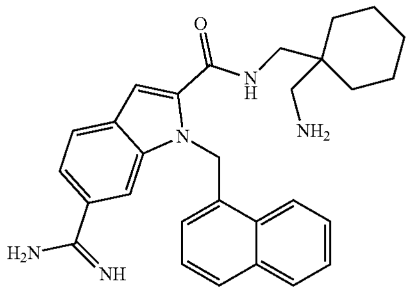 [SMILES: N=C(N)c1ccc2cc(C(=O)NCC3(CN)CCCCC3)n(Cc3cccc4ccccc34)c2c1] | 468.3 | ¹HNMR (400 MHz, CD₃OD): δ1.46-1.28 (m, 10H), 2.44 (s, 2H), 3.25 (s, 2H), 6.22-6.20 (d, 1H), 6.46 (s, 2H), 7.21-7.18 (m, 1H), 7.39 (s, 1H), 7.65-7.57 (m, 3H), 7.77-7.75 (d, 1H), 7.99-7.92 (m, 3H), 8.23-8.21 (d, 1H). |
| I-475 | 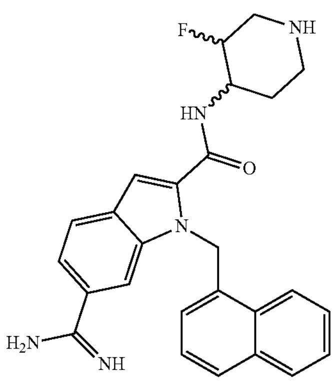 [SMILES: N=C(N)c1ccc2cc(C(=O)NC3CCNCC3F)n(Cc3cccc4ccccc34)c2c1] | 444.1 | ¹HNMR (300 MHz, CD₃OD): δ 1.91-1.86 (m, 1H), 2.20-2.14 (m, 1H), 3.21-3.06 (m, 1H), 3.44-3.41 (m, 1H), 3.65-3.58 (m, 1H), 4.30-4.10 (m, 1H), 4.81-4.78 (m, 1H), 4.96-4.92 (m, 1H), 6.27-6.25 (m, 1H), 6.45 (s, 2H), 7.21-7.16 (t, 1H), 7.39 (s, 1H), 7.66-7.53 (m, 3H), 7.76-7.73 (d, 1H), 7.98-7.90 (m, 3H), 8.22-8.19 (d, 1H). |
| I-476 | 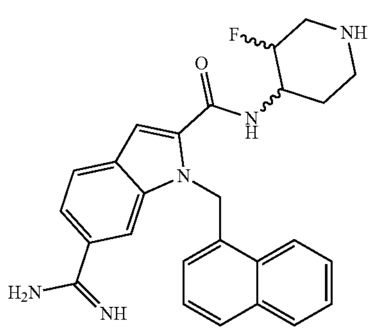 [SMILES: N=C(N)c1ccc2cc(C(=O)NC3CCNCC3F)n(Cc3cccc4ccccc34)c2c1] | 444 | ¹HNMR (300 MHz, CD₃OD): δ 1.79-1.78 (m, 1H), 2.15-2.09 (m, 1H), 3.24-3.06 (m, 2H), 3.45-3.40 (m, 2H), 4.25-4.15 (m, 1H), 4.68-4.60 (m, 1H), 6.31-6.29 (d, 1H), 6.50-6.36 (m, 2H), 7.22-7.17 (t, 1H), 7.38 (s, 1H), 7.65-7.54 (m, 3H), 7.76-7.74 (d, 1H), 7.99-7.90 (m, 3H), 8.21-8.18 (d, 1H). |

TABLE 29-continued
Compounds synthesized using Scheme-15D
| Cpd. ID. | Structure | LCMS [M + H]+ | 1H-NMR Data |
|---|---|---|---|
| I-477 | 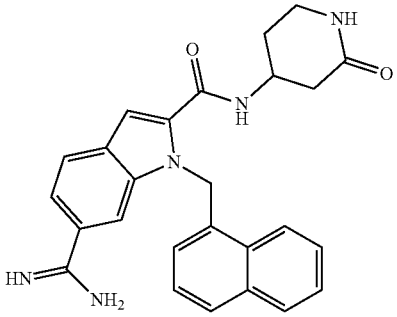 [SMILES: N=C(N)c1ccc2cc(C(=O)NC3CCNC(=O)C3)n(Cc3cccc4ccccc34)c2c1] | 440.1 | 1HNMR (300 MHz, CD3OD): δ1.73-1.62 (m, 1H), 1.87-1.85 (m, 1H), 2.31-2.22 (m, 1H), 2.58-2.50 (m, 1H), 3.24-3.16 (m, 2H), 4.29-4.09 (m, 1H), 6.30-6.27 (m, 1H), 6.42 (s, 2H), 7.22-7.17 (t, 1H), 7.31 (s, 1H), 7.63-7.52 (m, 3H), 7.75-7.72 (m, 1H), 7.97-7.88 (m, 3H), 8.19-8.16 (m, 1H). |
| I-478 | 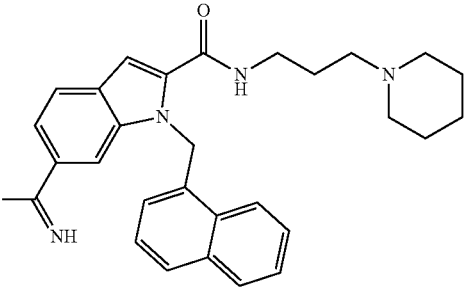 | 468.3 | 1HNMR (400 MHz, CD3OD): δ1.34-1.30 (m, 2H), 1.48-1.40 (m, 2H), 1.66-1.56 (m, 2H), 1.90-1.85 (m, 2H), 2.44-2.37 (m, 2H), 2.70-2.67 (m, 2H), 2.97-2.94 (m, 2H), 3.42-3.36 (m, 2H), 6.17-6.15 (m, 1H), 6.53 (s, 2H), 7.26-722 (t, 1H), 7.41 (s, 1H), 7.63-7.60 (m, 2H), 7.65-7.64 (m, 1H), 7.72-7.68 (m, 1H), 8.06-7.96 (m, 3H), 8.29-8.27 (m, 1H). |
| I-479 | 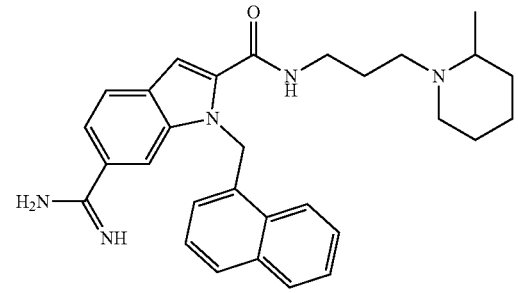 [SMILES: CC1CCCCN1CCCNC(=O)c1cc2ccc(C(=N)N)cc2n1Cc1cccc2ccccc12] | 482.25 | 1HNMR (400 MHz, CD3OD): δ 0.91-0.90 (d, 3H), 1.25-1.20 (m, 2H), 1.68-1.46 (m, 6H), 2.01-1.95 (m, 1H), 2.09 (m, 1H), 2.28-2.24 (m, 1H), 2.69-2.64 (m, 2H), 3.28-3.14 (m, 2H), 6.18-6.16 (d, 1H), 6.48 (s, 2H), 7.21-7.17 (t, 1H), 7.27 (s, 1H), 7.60-7.57 (m, 2H), 7.67-7.64 (m, 1H), 7.77-7.75 (m, 1H), 7.98-7.92 (m, 3H), 8.24-8.22 (m, 1H). |
| I-480 | 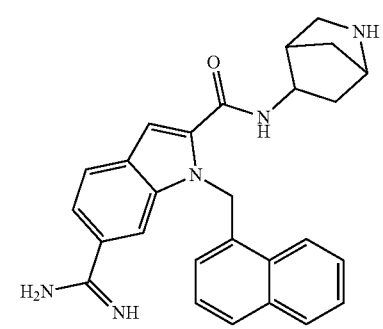 [SMILES: N=C(N)c1ccc2cc(C(=O)NC3CC4CC3CN4)n(Cc3cccc4ccccc34)c2c1] | 438.2 | 1HNMR (400 MHz, CD3OD): δ1.66-1.63 (m, 1H), 1.79-1.76 (m, 1H), 1.92-1.89 (m, 1H), 2.28-2.25 (m, 1H), 2.81 (s, 1H), 2.94-2.90 (m, 1H), 3.21-3.18 (m, 1H), 4.02 (m, 1H), 4.19-4.17 (m, 1H), 6.29-6.28 (m, 1H), 6.51-6.44 (q, 2H), 7.23-7.20 (t, 1H), 7.42 (s, 1H), 7.66-7.56 (m, 3H), 7.78-7.76 (m, 1H), 8.02-7.93 (m, 3H), 8.22-8.20 (m, 1H). |

TABLE 29-continued

| Compounds synthesized using Scheme-15D | | | |
|---|---|---|---|
| Cpd. ID. | Structure | LCMS [M + H]+ | 1H-NMR Data |
| I-481 | | 454.2 | 1HNMR (400 MHz, CD3OD): δ1.74-1.30 (m, 6H), 2.78-2.74 (t, 2H), 3.14-3.11 (t, 2H), 3.40-3.33 (t, 2H), 3.66-3.63 (t, 2H), 6.21-6.19 (m, 1H), 6.51 (s, 2H), 7.23-7.20 (m, 1H), 7.41 (s, 1H), 7.62-7.58 (m, 2H), 7.70-7.65 (m, 1H), 7.79-7.76 (m, 1H), 8.02-7.94 (m, 3H), 8.27-8.25 (m, 1H). |
| I-482 | | 371.15 | 1HNMR (400 MHz, CD3OD): δ2.62 (S. 3H), 2.79 (s, 3H), 6.10 (s, 2H), 6.88-6.85 (m, 2H), 7.37-7.33 (t, 1H), 7.61-7.47 (m, 3H), 7.94-7.83 (m, 4H), 8.19 (s, 1H) |
| I-483 | | 357.15 | 1HNMR (400 MHz, CD3OD): δ2.82 (s, 3H), 6.25 (d, 1H), 6.49 (s, 2H), 7.30 (s, 2H), 7.59-7.58 (m, 2H), 7.65 (t, 1H), 7.75 (d, 1H), 7.96-7.93 (m, 3H), 8.25 (d, 1H) |
| I-484 | | 447.2 | 1HNMR (400 MHz, CD3OD): δ 0.81-0.83 (m, 2H), 1.11-1.12 (m, 2H), 2.78-2.81 (m, 1H), 6.37 (d, 1H), 6.46 (s, 2H), 7.23 (t, 1H), 7.55-7.68 (m, 4H), 7.78 (d, 1H), 7.95 (d, 1H), 8.03-8.05 (m, 2H), 8.26 (d, 1H). |

General synthetic scheme-15D-1

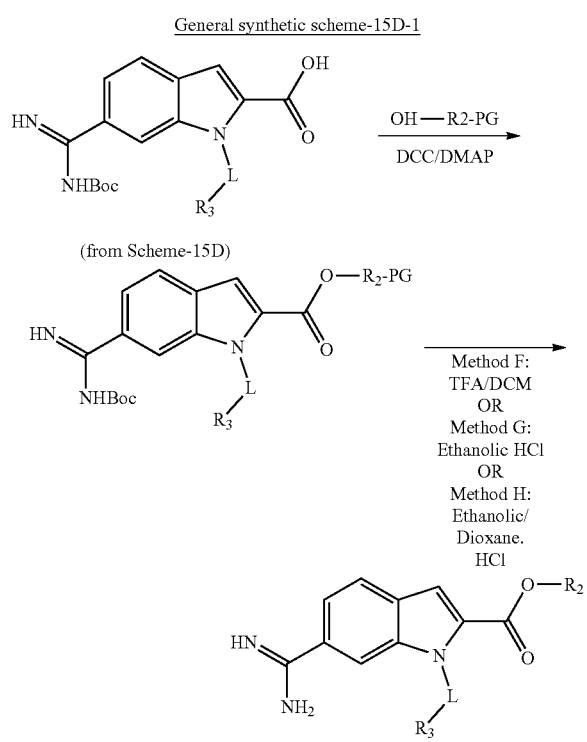

PG = optional protecting group;

Example 92: Synthesis of Compound I-485

(1r,4r)-4-aminocyclohexyl 6-carbamimidoyl-1-(naphthalen-1-ylmethyl)-1H-indole-2-carboxylate

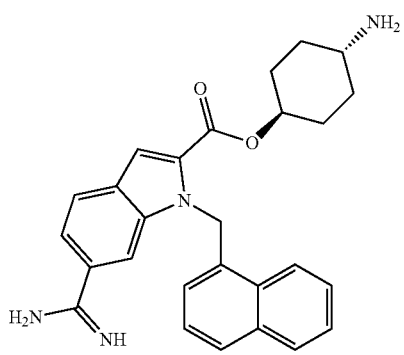 [SMILES: N=C(N)c1ccc2cc(C(=O)O[C@H]3CC[C@H](N)CC3)n(Cc3cccc4ccccc34)c2c1]

Step-1:(1r,4r)-4-((tert-butoxycarbonyl)amino)cyclohexyl 6-(N-(tert-butoxycarbonyl)carbamimidoyl)-1-(naphthalen-1-ylmethyl)-1H-indole-2-carboxylate To a solution of product of step-2 of example 90 (70 mg, 0.150 mmol) in dichloromethane was added 4-dimethylaminopyridine (4 mg, 0.030 mmol) followed by addition of N,N'-dicyclohexylcarbodiimide (40 mg, 0.180 mmol) and tert-butyl ((1r, 4r)-4-hydroxycyclohexyl) carbamate (40 mg, 0.180 mmol) at room temperature and resulting reaction mixture was stirred for 2 h. Reaction mixture was diluted with dichloromethane, washed with water and dried over sodium sulphate. The organic layer was concentrated under reduced pressure afforded the title compound (200 mg). LCMS: 641.2 (M+1)$^+$.

Step-2:(1r,4r)-4-aminocyclohexyl 6-carbamimidoyl-1-(naphthalen-1-ylmethyl)-1H-indole-2-carboxylate Product of step-1 of example 92 (200 mg, 0.300 mmol) was treated with TFA (0.5 mL) afforded the crude product following the procedure described in step-5 of example 81. The crude obtained was purified by preparative HPLC instrument using X-Bridge C18 reverse phase column (19× 150 mm, 5 micron). The mobile phases were 10% acetonitrile in water (0.1% TFA) to 60% acetonitrile in water (0.1% TFA) which afforded the title compound (50 mg) as a TFA Salt.

LCMS: 440.85 (M+1)$^+$; $^1$HNMR (400 MHz, CD$_3$OD): δ 1.37-1.46 (m, 4H), 1.99-2.03 (m, 4H), 3.54-3.58 (m, 1H), 4.78-4.82 (m, 1H), 6.16 (d, 1H), 6.41 (s, 2H), 7.20 (t, 1H), 7.59-7.61 (m, 3H), 7.68 (t, 1H), 7.78 (d, 1H), 7.95-8.02 (m, 3H), 8.27 (d, 1H); HPLC: 98.35% (Retention Time=5.24 min)

General synthetic scheme-15D-2

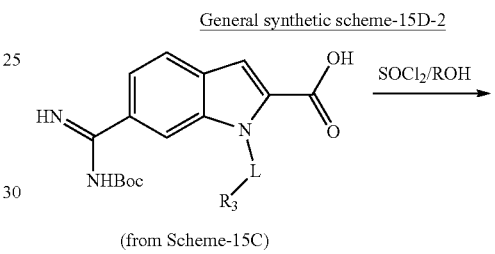

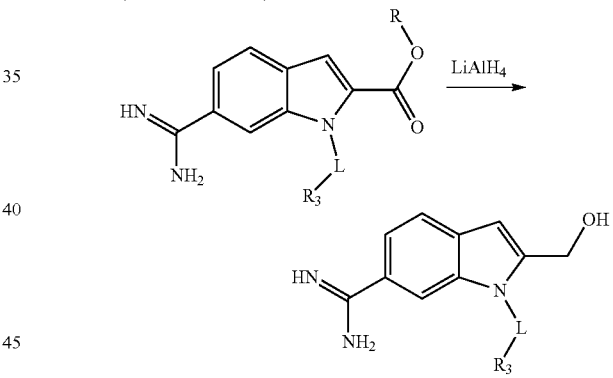

Example 93: Synthesis of Compound I-486

Methyl 6-carbamimidoyl-1-(naphthalen-1-ylmethyl)-1H-indole-2-carboxylate

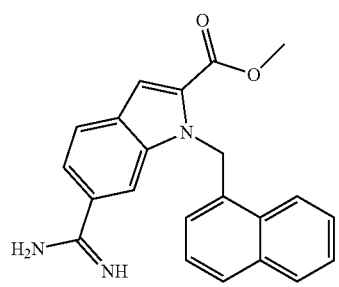 [SMILES: COC(=O)c1cc2ccc(C(=N)N)cc2n1Cc1cccc2ccccc12]

Step-1: Methyl 6-carbamimidoyl-1-(naphthalen-1-ylmethyl)-1H-indole-2-carboxylate To a stirred solution of product of step-2 of example 90 (200 mg, 0.400 mmol) in methanol (5 mL) was added thionyl chloride (0.160 mL, 2.2 mmol) dropwise at 0° C. The resulting reaction mixture was stirred at 65° C. for 2 h. After reaction completion, reaction mixture was concentrated under reduced pressure. The residue obtained was basified with aqueous sodium carbonate solution up to pH 9-10 and extracted with mixture of methanol:dichloromethane (10:90) three times. Combined organic layer was washed with water, dried over anhydrous sodium sulphate and concentrated under reduced pressure. The crude solid obtained was triturated with diethyl ether and dried. The crude obtained was purified by preparative HPLC instrument using X-Bridge C18 reverse phase column (19×150 mm, 5 micron). The mobile phases were 10% acetonitrile in water (0.1% TFA) to 60% acetonitrile in water (0.1% TFA) which afforded the title compound (65 mg) as a TFA Salt.

LCMS: 358.0 (M+1)$^+$; $^1$HNMR (400 MHz, CD$_3$OD): δ3.82 (s, 3H), 6.17-6.15 (d, 1H), 6.51 (s, 2H), 7.22-7.19 (m, 1H), 7.78-7.57 (m, 5H), 8.02-7.94 (m, 3H), 8.28-8.26 (d, 1H); HPLC: 95.95% (Retention Time=5.21 min)

Example 94: Synthesis of Compound I-487

2-(hydroxymethyl)-1-(naphthalen-1-ylmethyl)-1H-indole-6-carboximidamide

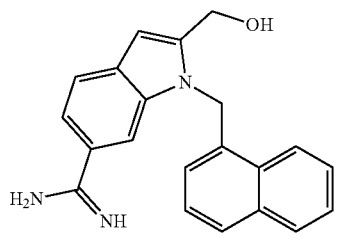 [SMILES: N=C(N)c1ccc2cc(CO)n(Cc3cccc4ccccc34)c2c1]

Step-1: 2-(hydroxymethyl)-1-(naphthalen-1-ylmethyl)-1H-indole-6-carboximidamide To a stirred solution of lithium aluminium hydride (104 mg, 2.6 mmol) in THF (7.5 mL) was added the redissolved solution of product of step-1 of example 93 (250 mg, 0.600 mmol) in THF at 0° C. under inert atmosphere. The resulting reaction mixture was stirred at room temperature for 4 h. After reaction completion reaction mixture was quenched with ethyl acetate (2 mL), water (3 mL) and 15% Aq. NaOH (1 mL) at 0° C., stirred for 10 min. The resulting suspension was filtered through celite bed, washed with ethyl acetate and filtrate was concentrated under reduced pressure to dryness. The crude obtained was purified by preparative HPLC instrument using X-Bridge C18 reverse phase column (19×150 mm, 5 micron). The mobile phases were 20% acetonitrile in water (0.1% TFA) to 60% acetonitrile in water (0.1% TFA) which afforded the title compound (50 mg) as a TFA Salt.

LCMS: 330.15 (M+1)$^+$; $^1$HNMR (400 MHz, CD$_3$OD): δ4.72 (s, 2H), 6.16 (s, 2H), 6.28-6.24 (d, 1H), 6.81 (s, 1H), 7.28-7.20 (m, 1H), 7.90-7.55 (m, 6H), 7.98-7.94 (d, 1H), 8.30-8.25 (d, 1H); HPLC: 98.69% (Retention Time=5.33 min)

General synthetic scheme-15D-3

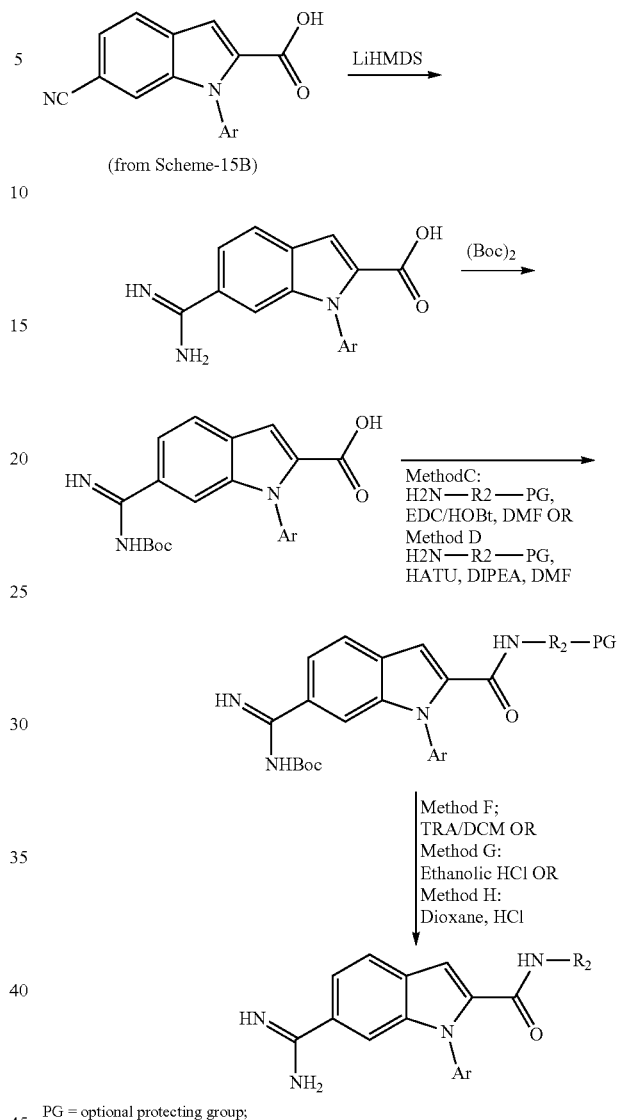

PG = optional protecting group;

Example 95: Synthesis of Compound I-488

6-carbamimidoyl-1-(naphthalen-2-yl)-1H-indole-2-carboxylic Acid

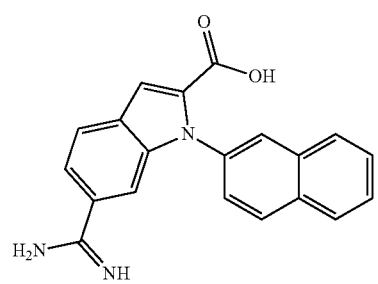 [SMILES: N=C(N)c1ccc2cc(C(=O)O)n(-c3ccc4ccccc4c3)c2c1]

Step-1: ethyl 6-cyano-1-(naphthalen-2-yl)-1H-indole-2-carboxylate

To a predigested (10 min.) solution of ethyl 6-cyano-1H-indole-2-carboxylate (2.0 g, 9.34 mmol) in DMSO (25 mL) was added naphthalen-2-ylboronic acid (3.99 g, 0.023 mmol), trimethylamine (3.77 g, 0.037 mmol) followed by degassing for 5 min and then addition of copper (II) acetate (6.76 g, 0.373 mmol) at room temperature in a sealed tube. The sealed tube closed under nitrogen atmosphere and stirred at room temperature for 2 days. After reaction completion, reaction mixture was diluted with ethyl acetate and filtered through celite bed. The filtrate collected was washed with water, brine and dried over sodium sulphate and concentrated to yield the crude product (2.54 g). The crude obtained was purified by combiflash on silica gel (64 g column) eluted with 10% ethyl acetate in hexane afforded the title compound (1.45 g). LCMS: 340.75 (M+1)$^+$ Step-2: 6-cyano-1-(naphthalen-2-yl)-1H-indole-2-carboxylic Acid Product of step-1 of example 95 (1.45 g, 4.2 mmol) was treated with lithium hydroxide monohydrate (179 mg, 4.2 mmol) in THF: Ethanol: water afforded the 590 mg of title compound as crude following the procedure described in step-2 of example 81. LCMS: 311.4 (M−1)$^+$.

Step-3: 6-carbamimidoyl-1-(naphthalen-2-yl)-1H-indole-2-carboxylic Acid

Product of step-2 of example 95 (200 mg, 0.640 mmol) was treated with solid LiHMDS (750 mg, 4.48 mmol) afforded the 210 mg of title compound following the procedure described in step-1 of example 90. LCMS: 328.2 (M−1)$^+$.

Step-4: 6-(N-(tert-butoxycarbonyl)carbamimidoyl)-1-(naphthalen-2-yl)-1H-indole-2-carboxylic Acid Product of step-3 of example 95 (210 mg, 0.636 mmol) and Di-tert-butyl dicarbonate (207 mg, 0.954 mmol) were treated together afforded the 200 mg of title compound following the procedure described in step-2 of example 90. LCMS: 428.4 (M−1)$^+$.

Step-4a: 6-carbamimidoyl-1-(naphthalen-2-yl)-1H-indole-2-carboxylic Acid

Product of step-4 of example 95 (70 mg, 0.163 mmol) was treated with TFA (0.2 ml) in dichloromethane afforded the initial crude product following the procedure described in step-2a of example 90. The crude obtained was purified by preparative HPLC instrument using X-Bridge C18 reverse phase column (19×150 mm, 5 micron). The mobile phases were 20% acetonitrile in water (0.1% TFA) to 60% acetonitrile in water (0.1% TFA) which afforded the title compound (25 mg) as a TFA Salt.

LCMS: 330.15 (M+1)$^+$; $^1$HNMR (400 MHz, CD$_3$OD): δ7.49-7.46 (dd, 1H), 7.64-7.57 (m, 5H), 8.08-7.97 (m, 5H); HPLC: 99.59% (Retention Time=4.68 min)

Following compound listed in table-30 prepared according to general scheme-15D-3 by following similar procedure as described above for the example 95 using appropriate reagents with suitable modifications known to the one skilled in the art.

TABLE 30

| Cpd. ID | Structure | LCMS [M + H]$^+$ | $^1$H-NMR Data |
|---|---|---|---|
| I-489 | 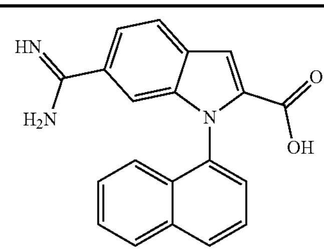 | 330.1 | $^1$HNMR (300 MHz, CD$_3$OD): δ6.97-6.94 (m, 1H), 7.31 (s, 1H), 7.40-7.31(t, 1H), 7.60-7.50 (m, 3H), 7.70-7.68 (m, 2H), 8.10-8.01 (m, 3H). |

Example 96: Synthesis of Compound I-490

6-carbamimidoyl-1-(naphthalen-2-yl)-N-(piperidin-4-ylmethyl)-1H-indole-2-carboxamide

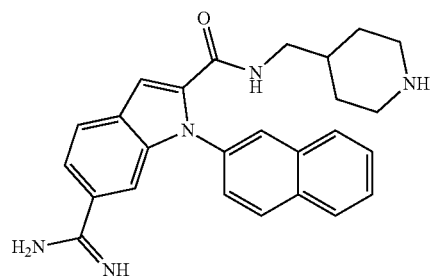 [SMILES: N=C(N)c1ccc2cc(C(=O)NCC3CCNCC3)n(-c3ccc4ccccc4c3)c2c1]

Step-1: tert-butyl-4-((6-(N-(tert-butoxycarbonyl) carbamimidoyl)-1-(naphthalen-2-yl)-1H-indole-2-carboxamido) methyl)piperidine-1-carboxylate Product of step-4 of example 95 (55 mg, 0.128 mmol) and tert-butyl 4-(aminomethyl)piperidine-1-carboxylate (28 mg, 0.129 mmol) were treated together afforded 88 mg of title compound following the procedure described in step-5 of example 25. LCMS: 626.4 (M+1)+.

Step-2: 6-carbamimidoyl-1-(naphthalen-2-yl)-N-(piperidin-4-ylmethyl)-1H-indole-2-carboxamide Product of step-1 of example 96 (88 mg, 0.140 mmol) was treated with TFA (0.5 mL) in dichloromethane afforded the initial crude product following the procedure described in step-2a of example 90. The crude obtained was purified by preparative HPLC instrument using Kinetex EVO C18 reverse phase column (21.2×150 mm, 5 micron). The mobile phases were 30% acetonitrile in water (0.05% TFA) to 70% acetonitrile in water (0.05% TFA) which afforded the title compound (43 mg) as a TFA Salt.

LCMS: 426.2 [M+1]+; $^1$HNMR (400 MHz, CD$_3$OD): δ1.25 (m, 2H), 1.75 (m, 3H), 2.75 (m, 2H), 3.32-3.15 (m, 4H), 7.28 (s, 1H), 7.55 (dd, 1H), 7.60 (m, 3H), 7.75 (s, 1H), 8.13-7.96 (m, 5H); HPLC: 98.11% (Retention Time=4.94 min).

Following compound listed in table-31 prepared according to general scheme-15D-3 by following similar procedure as described above for the example 96 using appropriate reagents with suitable modifications known to the one skilled in the art.

TABLE 31

Compounds synthesized using Scheme-15D-3

| Cpd. ID. | Structure | LCMS [M + H]+ | $^1$H-NMR Data |
|---|---|---|---|
| I-491 | 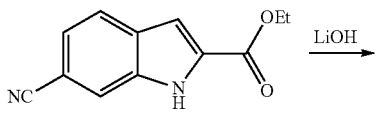 | 425.8 | $^1$HNMR(400 MHz, CD$_3$OD): δ1.76-1.71 (m, 4H), 1.87-1.79 (m, 4H), 3.28-3.24 (m, 1H), 3.94-3.91 (m, 1H), 7.33 (s, 1H), 7.54-7.52 (m, 1H), 7.64-7.60 (m, 3H), 7.78-7.74 (m, 1H), 8.03-7.96 (m, 4H), 8.10-8.07(d, 1H). |

General synthetic scheme-15E

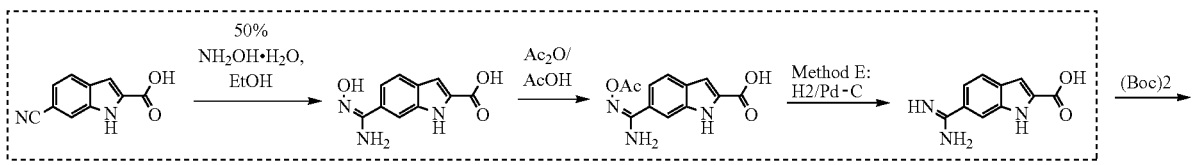

-continued

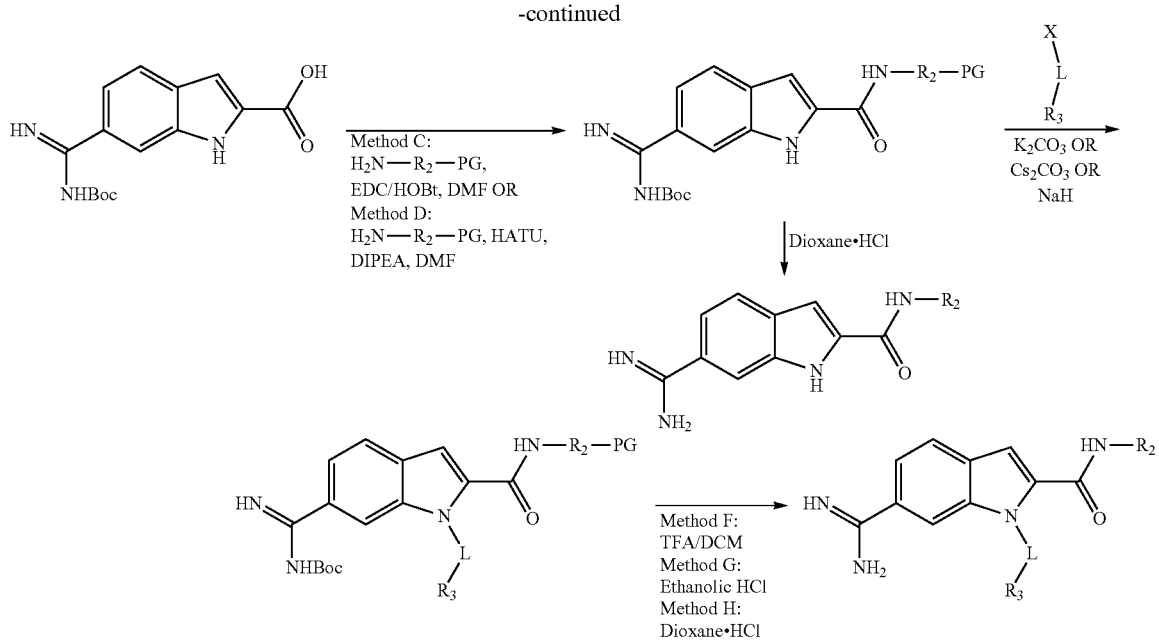

PG = optional protecting group; X = Br or Cl;

Example 97: Synthesis of Compound I-492 tert-butyl 4-((6-(N-(tert-butoxycarbonyl)carbamimidoyl)-1-(naphthalen-1-ylmethyl)-1H-indole-2-carboxamido)methyl)piperidine-1-carboxylate

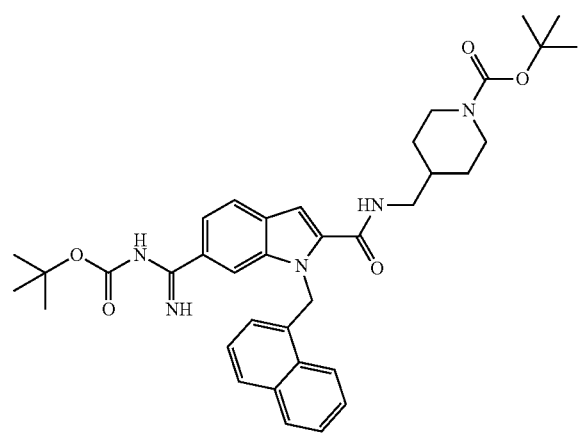 [SMILES: CC(C)(C)OC(=O)NC(=N)c1ccc2cc(C(=O)NCC3CCN(C(=O)OC(C)(C)C)CC3)n(Cc3cccc4ccccc34)c2c1]

Step-1: 6-cyano-1H-indole-2-carboxylic Acid

Ethyl 6-cyano-1H-indole-2-carboxylate (3.5 g, 0.016 mmol) was treated with lithium hydroxide monohydrate (0.86 mg, 0.167 mmol) afforded the title compound (2.95 g) following the procedure described in step-2 of example 79. LCMS: 185.0 [M−1]$^+$.

Step-2: 6-(N'-hydroxycarbamimidoyl)-1H-indole-2-carboxylic Acid

The product of step-1 of example 97 (2.95 g, 15.84 mmol) was treated with 50% aqueous hydroxylamine solution (10 mL) afforded the 4.0 g of title compound following the procedure described in step-1 of example 418. LCMS: 219.9 (M+1)$^+$.

Step-3: 6-(N'-acetoxycarbamimidoyl)-1H-indole-2-carboxylic Acid

The product of step-2 of example 97 (4.0 g, 18.26 mmol) was treated with acetic anhydride (5.58 g, 54.79 mmol) to afford the 7.0 g of title compound following the procedure described in step-2 of example 10. LCMS: 262.0 (M+1)$^+$.

Step-4: 6-carbamimidoyl-1H-indole-2-carboxylic Acid

The product of step-3 of example 97 (3.5 g, 13.39 mmol) was treated with 10% palladium on carbon (400 mg) in an atmosphere of hydrogen gas to afford the title compound (4.0 g) following the procedure described in step-3 of example 88. LCMS: 203.9 (M+1)$^+$.

Step-5: 6-(N-(tert-butoxycarbonyl)carbamimidoyl)-1H-indole-2-carboxylic Acid The product of step-4 of example 97 (4.0 g, 0.019 mmol) was treated with di-tert-butyl dicarbonate (4.29 g, 0.019 mmol) to afford the title compound (1.7 g) following the procedure described in step-4 of example 88. LCMS: 304.0 (M+1)$^+$.

Step-6: tert-butyl 4-((6-(N-(tert-butoxycarbonyl)carbamimidoyl)-1H-indole-2-carboxamido)methyl)piperidine-1-carboxylate The product of step-5 of example 97 (250 mg, 0.825 mmol) and tert-butyl 4-(amino methyl)piperidine-1-carboxylate (211 mg, 0.990 mmol) were treated together afforded the 250 mg of title compound following the procedure described in step-5 of example 88. LCMS: 500.6 (M+1)⁺.

Step-7: tert-butyl 4-((6-(N-(tert-butoxycarbonyl) carbamimidoyl)-1H-indole-2-carboxamido)methyl) piperidine-1-carboxylate To a solution of product of step-6 of example 97 (100 mg, 0.200 mmol) in DMF (3 ml) was added potassium carbonate (82.96 mg, 0.601 mmol) and 1-(bromomethyl) naphthalene (53.1 mg, 0.240 mmol) at room temperature and stirred at 60° C. for 5 h. After reaction completion, added ice cold water, precipitated solid was filtered off and dried. The crude product obtained above was purified by preparative TLC (mobile Phase: 2% methanol in dichloromethane) afforded the title compound (25 mg) as impure which was further purified by preparative HPLC instrument using Gemini-NX C18 reverse phase column (21.2×150 mm, 5 micron). The mobile phases were 40% acetonitrile in water (0.02% ammonia) to 90% acetonitrile in water (0.02% ammonia) which afforded the title compound (10 mg).

LCMS: 640.5 [M+1]⁺; ¹HNMR (400 MHz, CD₃OD): δ 0.87-0.85 (m, 2H), 1.39-1.29 (m, 3H), 1.41 (s, 9H), 1.45 (s, 9H), 2.59-2.49 (m, 2H), 3.20-3.06 (m, 2H), 3.86-3.83 (m, 2H), 6.19-6.17 (d, 1H), 6.39 (s, 2H), 7.18-7.14 (t, 2H), 7.55-7.53 (m, 3H), 7.65-7.63 (m, 1H), 7.81-7.79 (d, 1H), 7.91-7.89 (d, 1H), 8.04 (s, 1H), 8.22-8.20 (d, 1H); HPLC: 98.23% (Retention Time=6.64 min).

Following compound listed in table-32 prepared according to general scheme-15E by following similar procedure as described above for the example 97 using appropriate reagents with suitable modifications known to the one skilled in the art.

TABLE 32

Compounds synthesized using Scheme-15E

| Cpd. ID. | Structure | LCMS [M + H]⁺ | ¹H-NMR Data |
|---|---|---|---|
| I-493 | 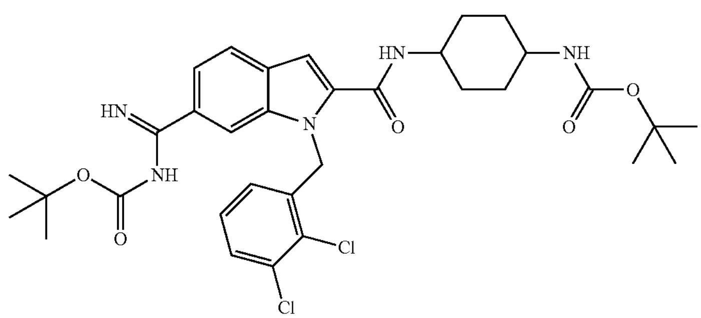 [SMILES: CC(C)(C)OC(=O)NC(=N)c1ccc2cc(C(=O)NC3CCC(NC(=O)OC(C)(C)C)CC3)n(Cc3cccc(Cl)c3Cl)c2c1] | 658.5 | ¹HNMR (400 MHz, DMSO-d₆): δ 1.36-1.17 (m, 4H), 1.33 (s, 9H), 1.36 (s, 9H), 1.77-1.71 (m, 4H), 3.35-3.30 (m, 1H), 3.66-3.50 (m, 1H), 5.80 (s, 2H), 6.675-6.73 (d, 1H), 7.15-7.11 (t, 1H), 7.35 (s, 1H), 7.52-7.50 (d, 1H), 7.78 (s, 1H), 8.09 (s, 1H), 8.48-8.46(d, 1H), 8.89-8.80 (m, 1H). |
| I-494 | 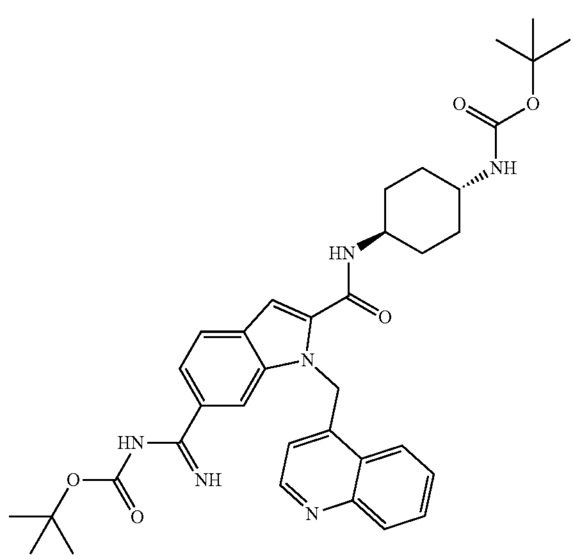 [SMILES: CC(C)(C)OC(=O)NC(=N)c1ccc2cc(C(=O)N[C@H]3CC[C@H](NC(=O)OC(C)(C)C)CC3)n(Cc3ccnc4ccccc34)c2c1] | 641.5 | ¹HNMR(400 MHz, CD₃OD): δ 1.30-1.20 (m, 4H), 1.40 (s, 9H), 1.44 (s, 9H), 1.90-1.80 (m, 4H), 3.70-3.60 (m, 2H), 6.28-6.27(d, 1H), 6.46 (s, 1H), 7.70-7.60(d, 1H), 7.83-7.70 (m, 3H), 8.00 (s, 1H), 8.10-8.05(d, 1H), 8.40-8.30(d, 1H), 8.55-8.54(d, 1H). |

TABLE 32-continued

Compounds synthesized using Scheme-15E

| Cpd. ID. | Structure | LCMS [M + H]+ | 1H-NMR Data |
|---|---|---|---|
| I-495 | 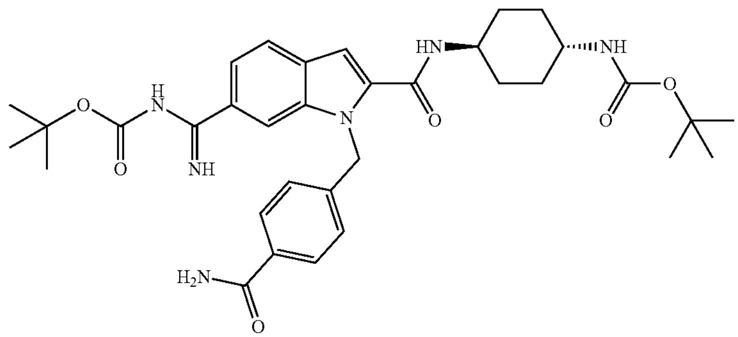 [SMILES: CC(C)(C)OC(=O)NC(=N)c1ccc2cc(C(=O)N[C@H]3CC[C@H](NC(=O)OC(C)(C)C)CC3)n(Cc3ccc(C(N)=O)cc3)c2c1] | 633.9 | 1HNMR (400 MHz, CD3OD): δ 1.40-1.30 (m, 4H), 1.42 (s, 9H), 1.50 (s, 9H), 1.90-1.87 (m, 4H), 3.80-3.70 (m, 2H), 5.90 (s, 2H), 7.12-7.10 (m, 3H), 7.60-7.59(d, 1H), 7.74-7.72(d, 3H), 8.05 (s, 1H). |

Example 98: Synthesis of Compound I-496

6-carbamimidoyl-N-(piperidin-4-ylmethyl)-1H-indole-2-carboxamide

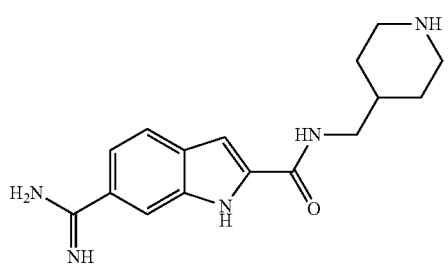 [SMILES: N=C(N)c1ccc2cc(C(=O)NCC3CCNCC3)[nH]c2c1]

Step-1: 6-carbamimidoyl-N-(piperidin-4-ylmethyl)-1H-indole-2-carboxamide

To a solution of product of step-6 of example 97 (60 mg, 0.120 mmol) in 1,4 dioxane (2 mL) was added HCl in 1,4 dioxane (4 mL) at 0° C. and then stirred at room temperature for 3 h. After reaction completion, reaction mixture was concentrated under reduced pressure to give crude product (60 mg). The crude product obtained above was further purified by preparative HPLC instrument using Gemini-NX C18 reverse phase column (21.2×150 mm, 5 micron). The mobile phases were 0.5% acetonitrile in water (0.1% TFA) to 25% acetonitrile in water (0.1% TFA) which afforded the title compound (10 mg) as a TFA salt.

LCMS: 300.0 [M+1]+; 1HNMR (400 MHz, CD3OD): δ 1.54-1.28 (m, 2H), 2.03-1.96 (m, 3H), 3.01-2.95 (m, 2H), 3.43-3.32 (m, 4H), 7.19 (s, 11H), 7.47-7.44 (d, 11H), 7.84-7.82 (d, 1H), 7.97 (s, 1H), 8.78-8.75 (m, 1H); HPLC: 98.94% (Retention Time=4.21 min).

Example 99: Synthesis of Compound I-497

6-carbamimidoyl-1-(naphthalen-1-ylmethyl)-N-(piperidin-4-ylmethyl)-1H-indole-2-carboxamide

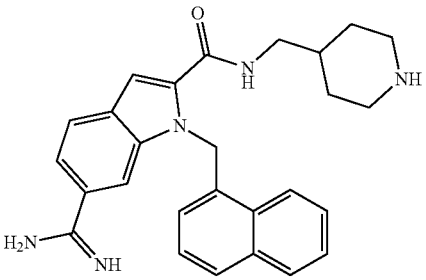 [SMILES: N=C(N)c1ccc2cc(C(=O)NCC3CCNCC3)n(Cc3cccc4ccccc34)c2c1]

Step-1: 6-carbamimidoyl-1-(naphthalen-1-ylmethyl)-N-(piperidin-4-ylmethyl)-1H-indole-2-carboxamide Product of step-7 of example 97 (45 mg, 0.076 mmol) was treated with HCl in 1,4 dioxane afforded the crude product following the procedure described in example 20. The crude product obtained above was further purified by preparative HPLC instrument using Kinetex EVO C18 reverse phase column (21.2×150 mm, 5 micron). The mobile phases were 30% acetonitrile in water (0.1% TFA) to 60% acetonitrile in water (0.1% TFA) which afforded the title compound (19 mg) as a TFA salt.

LCMS: 440.2 [M+1]+; 1HNMR (400 MHz, CD3OD): δ 1.19-1.16 (m, 2H), 1.65-1.58 (m, 3H), 2.71-2.65 (m, 2H), 3.17-3.14 (m, 4H), 6.18-6.16 (d, 1H), 6.44 (s, 2H), 7.27-7.16 (m, 1H), 7.27 (s, 1H), 7.59-7.568 (m, 1H), 7.66-7.62 (m, 1H), 7.76-7.74 (d, 1H), 7.96-7.91 (m, 2H), 8.02 (s, 1H), 8.22-8.21 (d, 1H), 8.85-8.79 (m, 1H); HPLC: 98.97% (Retention Time=4.68 min).

Following compounds listed in table-33 prepared according to general scheme-15E by following similar procedure as described above for the example 99 using appropriate reagents with suitable modifications known to the one skilled in the art

TABLE 33

Compounds synthesized using Scheme-15E

| Cpd. ID. | Structure | LCMS [M + H]+ | 1H-NMR Data |
|---|---|---|---|
| I-498 | 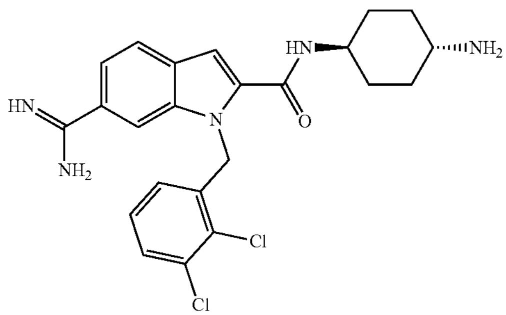 [SMILES: N=C(N)c1ccc2cc(C(=O)N[C@H]3CC[C@H](N)CC3)n(Cc3cccc(Cl)c3Cl)c2c1] | 458.2 | $^1$HNMR(400 MHz, CD$_3$OD): δ 1.50-1.42 (m, 4H), 2.07-1.96 (m, 4H), 3.18-3.12 (m, 1H), 3.80-3.70 (m, 1H), 6.00 (s, 2H), 6.15-6.13(d, 1H), 7.06-7.02(t, 1H), 7.29 (s, 1H), 7.43-7.29 (m, 1H), 7.58-7.55 (m, 1H), 7.95-7.91(t, 2H), 8.60-8.50(d, 1H). |
| I-499 | 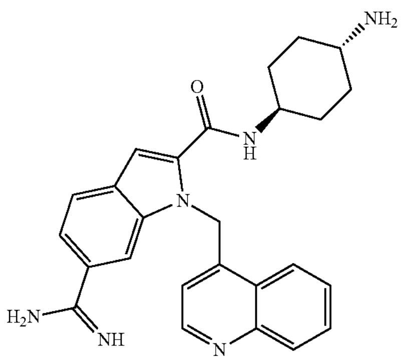 [SMILES: N=C(N)c1ccc2cc(C(=O)N[C@H]3CC[C@H](N)CC3)n(Cc3ccnc4ccccc34)c2c1] | 441.1 | $^1$HNMR(400 MHz, CD$_3$OD): δ 1.45-1.42 (m, 4H), 2.04-1.93 (m, 4H), 3.10-3.00 (m, 1H), 3.70-3.60 (m, 1H), 6.57-6.55(d, 1H), 6.60 (s, 2H), 7.43 (s, 1H), 7.62-7.60 (m, 1H), 8.08-7.96 (m, 4H), 8.22-8.20(d, 1H), 8.54-8.52(d, 1H), 8.75-8.73(d, 1H). |
| I-500 | 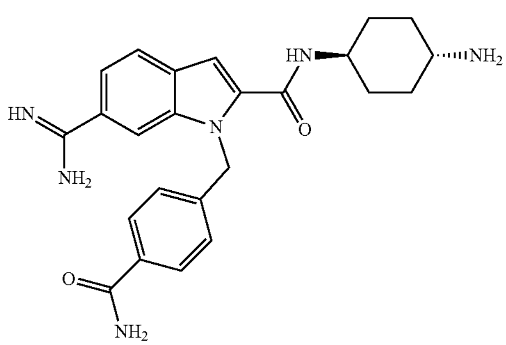 [SMILES: N=C(N)c1ccc2cc(C(=O)N[C@H]3CC[C@H](N)CC3)n(Cc3ccc(C(N)=O)cc3)c2c1] | 433.5 | $^1$HNMR (400 MHz, CD$_3$OD): δ 1.60-1.40 (m, 4H), 2.10-1.90 (m, 4H), 3.20-3.10 (m, 1H), 3.80-3.70 (m, 1H), 5.98 (s, 2H), 7.11-7.09(d, 2H), 7.19 (s, 1H), 7.58-7.52(d, 1H), 7.76-7.74(d, 2H), 7.90-7.87(d, 1H), 8.15 (s, 1H). |
| I-501 | 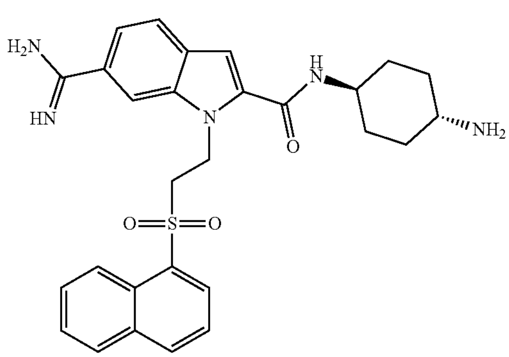 [SMILES: N=C(N)c1ccc2cc(C(=O)N[C@H]3CC[C@H](N)CC3)n(CCS(=O)(=O)c3cccc4ccccc34)c2c1] | 518.3 | $^1$H NMR (300 MHz, CD$_3$OD) δ 1.25-1.59 (m, 4H), 1.91-2.15 (m, 4H), 3.05-3.14 (m, 1H), 3.64-3.72 (m, 1H), 4.08 (t, 2H), 4.96-5.04 (m, 2H), 6.95 (s, 1H), 7.40-7.48 (m, 2H), 7.61-7.77 (m, 4H), 7.87-7.91 (m, 1H), 8.01-8.06 (m, 1H), 8.11-8.21 (m, 1H), 8.54-8.58 (m, 1H). |

TABLE 33-continued

Compounds synthesized using Scheme-15E

| Cpd. ID. | Structure | LCMS [M + H]+ | 1H-NMR Data |
|---|---|---|---|
| I-502 | 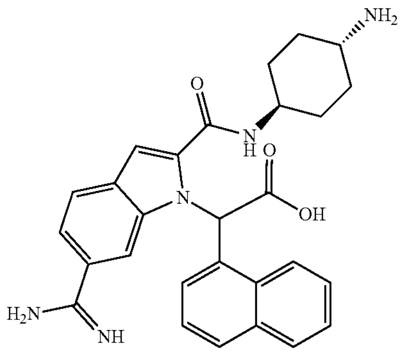 [SMILES: N=C(N)c1ccc2cc(C(=O)N[C@H]3CC[C@H](N)CC3)n(C(C(=O)O)c3cccc4ccccc34)c2c1] | 484.3 | 1HNMR (400 MHz, CD3OD): δ 1.55-1.52 (m, 4H), 2.12-2.11 (m, 4H), 3.20-3.10 (m, 1H), 3.90-3.80 (m, 1H), 7.22 (s, 1H), 7.56-7.30 (m, 4H), 7.77-7.74 (m, 2H), 8.00-7.81 (m, 5H). |
| I-503 | 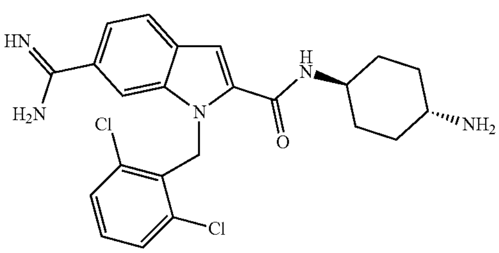 [SMILES: N=C(N)c1ccc2cc(C(=O)N[C@H]3CC[C@H](N)CC3)n(Cc3c(Cl)cccc3Cl)c2c1] | 458.1 | 1HNMR(400 MHz, CD3OD): δ 1.53-1.40 (m, 4H), 2.12-2.00 (m, 4H), 3.15-3.08 (m, 1H), 3.82-3.77 (m, 1H), 6.20 (s, 2H), 7.06 (s, 1H), 7.31-7.27 (m, 1H), 7.40-7.38(d, 2H), 7.48-7.45(d, 1H), 7.85-7.83(d, 1H), 7.92 (s, 1H), 8.68-8.66(d, 1H). |
| I-504 | 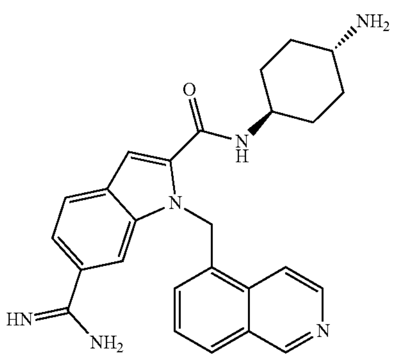 [SMILES: N=C(N)c1ccc2cc(C(=O)N[C@H]3CC[C@H](N)CC3)n(Cc3cccc4cnccc34)c2c1] | 441.3 | 1HNMR(400 MHz, CD3OD): δ 1.46-1.41 (m, 4H), 2.04-1.91 (m, 4H), 3.10-3.00 (m, 1H), 3.70-3.60 (m, 1H), 6.50 (s, 2H), 6.93-6.91(d, 1H), 7.39 (s, 1H), 7.61-7.59 (m, 1H), 7.71-7.68(t, 1H), 7.99-7.97(d, 1H), 8.03 (s, 1H), 8.30-8.28(d, 1H), 8.71-8.63 (m, 2H), 9.70 (s, 1H). |
| I-505 | 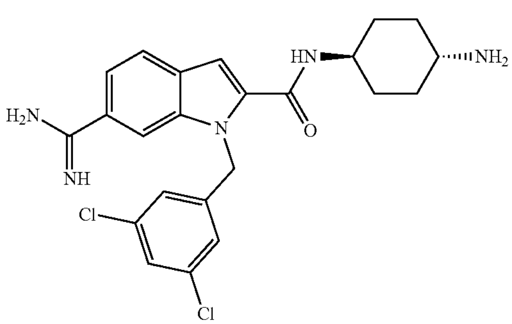 [SMILES: N=C(N)c1ccc2cc(C(=O)N[C@H]3CC[C@H](N)CC3)n(Cc3cc(Cl)cc(Cl)c3)c2c1] | 458.2 | 1HNMR (300 MHz, CD3OD): δ 1.55-1.42 (m, 4H), 2.10-2.00 (m, 4H), 3.20-3.10 (m, 1H), 3.80-3.70 (m, 1H), 5.80 (s, 2H), 6.98 (s, 2H), 7.21 (s, 1H), 7.32 (s, 1H), 7.57-7.54(d, 1H), 7.92-7.89(d, 1H), 8.05 (s, 1H). |

TABLE 33-continued

Compounds synthesized using Scheme-15E

| Cpd. ID. | Structure | LCMS [M + H]+ | 1H-NMR Data |
|---|---|---|---|
| I-506 | 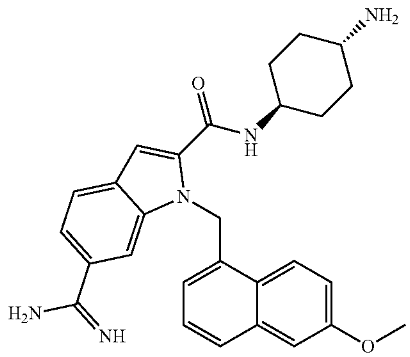 [SMILES: COc1ccc2c(Cn3c(C(=O)N[C@H]4CC[C@H](N)CC4)cc4ccc(C(=N)N)cc43)cccc2c1] | 470.3 | 1HNMR(400 MHz, CD3OD): δ 1.46-1.38 (m, 4H), 2.04-1.89 (m, 4H), 3.10-3.00 (m, 1H), 3.75-3.65 (m, 1H), 3.94 (s, 3H), 6.14-6.12(d, 1H), 6.40 (s, 2H), 7.17-7.13(t, 1H), 7.31-7.28 (m, 3H), 7.58-7.56 (m, 1H), 7.68-7.66(d, 1H), 7.98-7.94 (m, 2H), 8.13-8.11(d, 1H). |
| I-507 | | 441.3 | 1HNMR(400 MHz, CD3OD): δ 1.46-1.41 (m, 4H), 2.03-1.93 (m, 4H), 3.20-3.10 (m, 1H), 3.75-3.65 (m, 1H), 6.46 (s, 2H), 7.36-7.32 (m, 2H), 7.62-7.59 (m, 1H), 7.89-7.85(t, 1H), 8.07-7.97 (m, 3H), 8.33-8.26 (m, 2H), 8.70-8.60 (m, 1H), 9.25 (s, 1H). |
| I-508 | 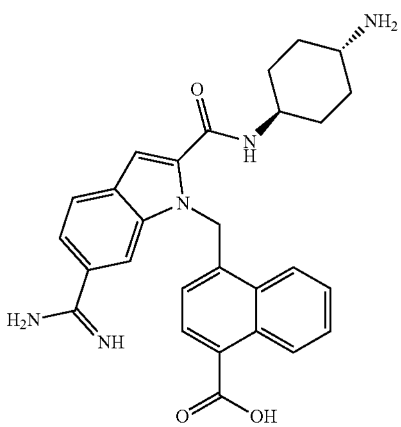 [SMILES: N=C(N)c1ccc2cc(C(=O)N[C@H]3CC[C@H](N)CC3)n(Cc3ccc(C(=O)O)c4ccccc34)c2c1] | 484.2 | 1HNMR(400 MHz, CD3OD): δ 1.42-1.31 (m, 4H), 2.01-1.91 (m, 4H), 3.10-3.06 (m, 1H), 3.77-3.67 (m, 1H), 6.30-6.28(d, 1H), 6.50 (s, 2H), 7.34 (s, 1H), 7.61-7.59(d, 1H), 7.74-7.68 (m, 2H), 7.92-7.90(d, 1H), 8.00-7.97 (m, 2H), 8.33-8.31 (m, 1H), 9.01-8.98(d, 1H). |
| I-509 | 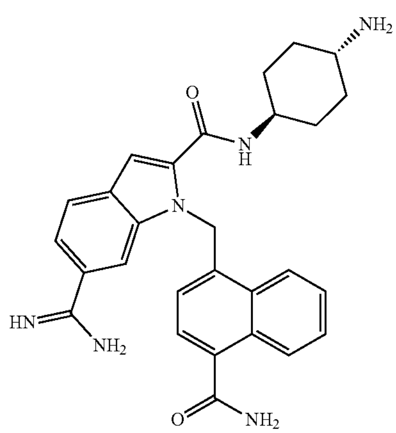 [SMILES: N=C(N)c1ccc2cc(C(=O)N[C@H]3CC[C@H](N)CC3)n(Cc3ccc(C(N)=O)c4ccccc34)c2c1] | 483.6 | 1HNMR(400 MHz, CD3OD): δ 1.46-1.41 (m, 4H), 2.05-1.93 (m, 4H), 3.10-3.00 (m, 1H), 3.75-3.65 (m, 1H), 6.29-6.27(d, 1H), 6.48 (s, 2H), 7.34 (s, 1H), 7.41-7.39(d, 1H), 7.74-7.57 (m, 3H), 7.98-7.95(t, 2H), 8.39-8.29 (m, 2H), 8.70-8.61(d, 1H). |

TABLE 33-continued
Compounds synthesized using Scheme-15E
| Cpd. ID. | Structure | LCMS [M + H]+ | 1H-NMR Data |
|---|---|---|---|
| I-510 | 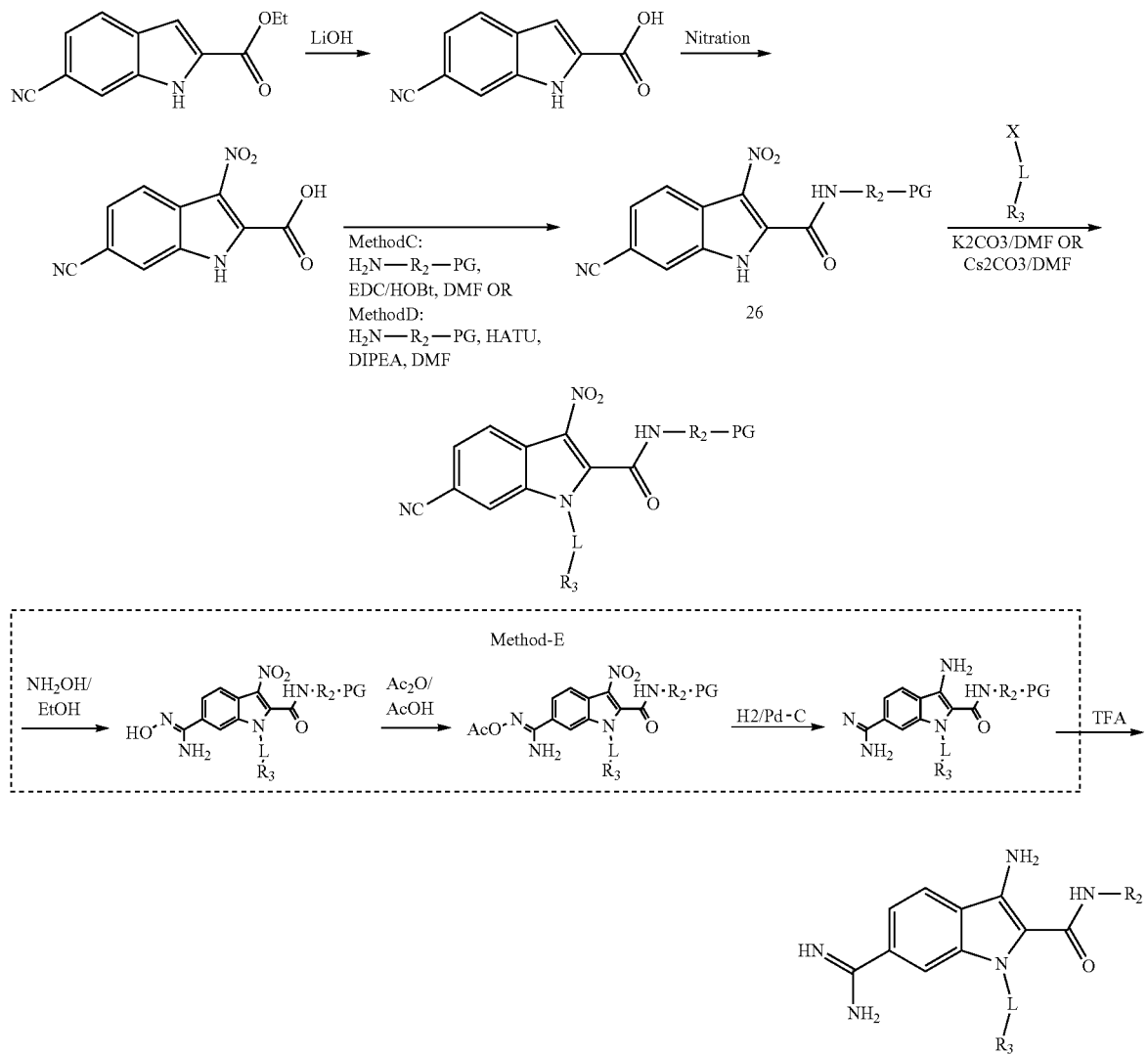 | 466.25 | 1HNMR(400 MHz, CD3OD): δ 1.42-1.54 (m, 4H), 1.98-2.11 (m, 4H), 3.08-3.09 (m, 1H), 3.78-3.80 (m, 1H), 6.49 (d, 1H), 7.12-7.14 (m, 2H), 7.22-7.28 (m, 2H), 7.38-7.49 (m, 6H), 7.62 (s, 1H), 7.84 (d, 1H). |

Example 100: Synthesis of Compound I-511

3-amino-N-((1r,4r)-4-aminocyclohexyl)-6-carbamimidoyl-1-(naphthalen-1-ylmethyl)-1H-indole-2-carboxamide

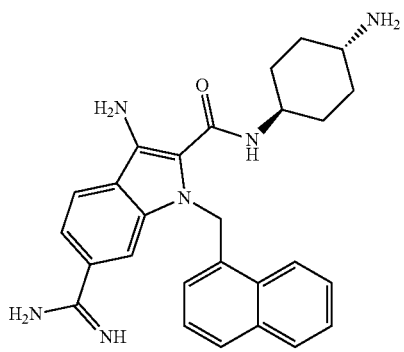 [SMILES: N=C(N)c1ccc2c(N)c(C(=O)N[C@H]3CC[C@H](N)CC3)n(Cc3cccc4ccccc34)c2c1]

Step-1: 6-cyano-3-nitro-1H-indole-2-carboxylic Acid

To a −5° C. precooled acetic anhydride (4.5 mL) was added Conc. nitric acid (0.5 mL) slowly. After being stirred the reaction mixture at same temperature (−5° C.), product of step-1 of example 97 (0.860 g, 4.62 mmol) was added and maintain the temperature −5° C. for 30 min. The reaction mixture gradually brought to room temperature and further stirred for overnight (~16 h). After reaction completion, reaction mixture was poured into water, precipitated solid was filtered off and washed with cold water and dried to afford 700 mg of title compound. LCMS: 230.2 [M−1]$^+$

Step-2: tert-butyl ((1r,4r)-4-(6-cyano-3-nitro-1H-indole-2-carboxamido)cyclohexyl)carbamate Product of step-1 of example 100 (650 mg, 2.81 mmol) and tert-butyl ((1r,4r)-4-aminocyclohexyl)carbamate (662 mg, 3.09 mmol) were treated to give 365 mg crude product following the procedure described in step-3 of example 81. Crude compound was further purified by combiflash on silica gel (24 g column), eluted with 5% methanol in dichloromethane afforded the title compound (300 mg). LCMS: 426.0 (M−1)$^+$.

Step-3: tert-butyl ((1r,4r)-4-(6-cyano-1-(naphthalen-1-ylmethyl)-3-nitro-1H-indole-2-carboxamido)cyclohexyl) carbamate To a solution of product of step-2 of example 100 (300 mg, 0.702 mmol) in DMF (5 ml) was added potassium carbonate (242 mg, 1.756 mmol) and 1-(bromomethyl) naphthalene (204 mg, 0.910 mmol) at room temperature and stirred at for overnight (16 h). After reaction completion, added ice cold water, precipitated solid was filtered off and dried afforded the title compound (320 mg). LCMS: 512.15 (M−56)$^+$.

Step-4: tert-butyl ((1r,4r)-4-(6-(N'-hydroxycarbamimidoyl)-1-(naphthalen-1-ylmethyl)-3-nitro-1H-indole-2-carboxamido)cyclohexyl)carbamate The product of step-3 of example 100 (320 mg, 0.560 mmol) was treated with 50% aqueous hydroxyl amine solution (8 mL) afforded the title compound (270 mg) following the procedure described in step-4 of example 86. LCMS: 601.4 (M+1)$^+$.

Step-5: tert-butyl ((1r,4r)-4-(6-(N'-acetoxycarbamimidoyl)-1-(naphthalen-1-ylmethyl)-3-nitro-1H-indole-2-carboxamido)cyclohexyl)carbamate Product of step-4 of example 100 (270 mg, 0.450 mmol) and acetic anhydride (0.5 mL) were treated together to afford 220 mg of the title compound following the procedure described in step-3 of example 82. LCMS: 643.5 (M+1)$^+$.

Step-6: tert-butyl ((1r,4r)-4-(3-amino-6-carbamimidoyl-1-(naphthalen-1-ylmethyl)-1H-indole-2-carboxamido) cyclohexyl)carbamate Product of step-5 of example 100 (220 mg, 0.340 mmol) was treated with 10% Palladium on carbon (44 mg) in presence of hydrogen atmosphere for overnight afforded 190 mg of the title compound following the procedure described in step-4 of example 82. LCMS: 556.0 (M+1)$^+$.

Step-7: 3-amino-N-((1r,4r)-4-aminocyclohexyl)-6-carbamimidoyl-1-(naphthalen-1-ylmethyl)-1H-indole-2-carboxamide Product of step-6 of example 100 (100 mg, 0.200 mmol) was treated with 1,4 dioxane·HCl afforded the crude product following the procedure described in step-3 of example 83. The crude obtained was purified by preparative HPLC instrument using LUNA C18 reverse phase column (21.2× 150 mm, 5 micron). The mobile phases were 10% acetonitrile in water (0.05% HCl) to 50% acetonitrile in water (0.05% HCl) which afforded the title compound (36 mg) as a HCl Salt.

LCMS: 455.2 [M+1]$^+$; $^1$HNMR (600 MHz, CD$_3$OD): δ 1.17-1.15 (m, 2H), 1.35-1.29 (m, 2H), 1.72-1.70 (m, 2H), 1.90-1.89 (m, 2H), 2.94 (m, 1H), 3.62 (m, 1H), 6.31 (s, 2H), 6.41 (m, 1H), 7.24 (m, 1H), 7.57 (m, 1H), 7.58 (m, 2H), 7.79 (m, 1H), 7.93 (m, 1H), 8.10 (m, 1H), 8.17 (m, 2H), HPLC: 94.45% (Retention Time=5.76 min).

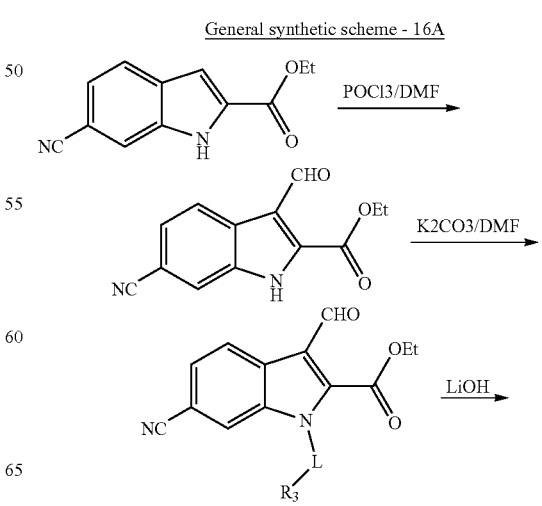

General synthetic scheme - 16A

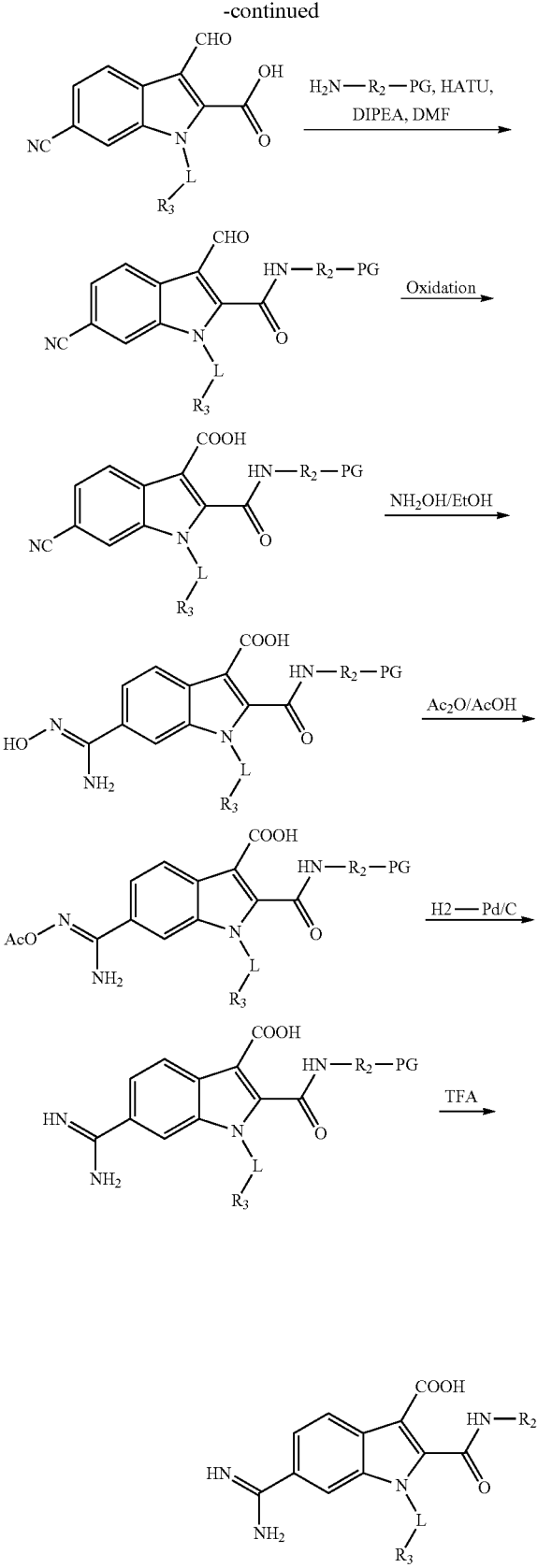

PG = optional protecting group; X = Br or Cl;

Example 101: Synthesis of Compound I-512

2-(((1r,4r)-4-aminocyclohexyl)carbamoyl)-6-carbamimidoyl-1-(naphthalen-1-ylmethyl)-1H-indole-3-carboxylic Acid

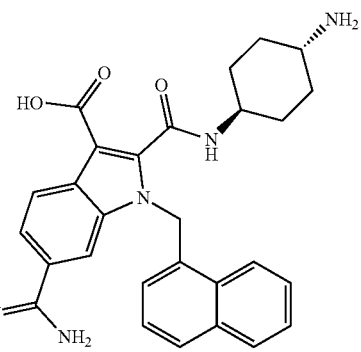

Step-1: Ethyl 6-cyano-3-formyl-1H-indole-2-carboxylate

To a 0° C. cooled solution of N,N-Dimethylformamide (30 mL) was added phosphorus oxychloride (10.72 mL, 0.069 mmol) dropwise under nitrogen atmosphere maintaining the inside temperature below 10° C. The resultant reaction mixture was stirred at 10° C. for 1 h followed by dropwise addition of solution of ethyl 6-cyano-1H-indole-2-carboxylate (5.0 g, 0.023 mmol) dissolved in 15 mL of N,N-Dimethylformamide. The reaction mixture was brought to room temperature gradually and stirred at 70° C. for 6 h. After reaction completion, the reaction mixture was quenched with ice-cold water and neutralised with 2N aq. sodium hydroxide solution (140 mL). The precipitated solid was filtered off and dried to give crude product (5.6 g) which was further purified by combiflash on silica-gel (40 g column) and eluted with neat dichloromethane afforded the title compound (3.9 g). LCMS: 243 (M+1)$^+$.

Step-2: Ethyl 6-cyano-3-formyl-1-(naphthalen-1-ylmethyl)-1H-indole-2-carboxylate Product of step-1 of example 101 (1.35 g, 5.578 mmol) and 1-(bromomethyl) naphthalene (1.60 g, 7.25 mmol) were treated together afforded the crude product following the procedure described in step-3 of example 100. The crude was further purified by combiflash on silica-gel (40 g column) and eluted with neat dichloromethane afforded the title compound (1.95 g). LCMS: 383.1 (M+1)$^+$.

Step-3: 6-cyano-3-formyl-1-(naphthalen-1-ylmethyl)-1H-indole-2-carboxylic Acid Product of step-2 of example 101 (1.75 g, 4.58 mmol) was treated with lithium hydroxide monohydrate (183 mg, 4.58 mmol) in THF: Ethanol: water afforded the 1.57 g of title compound as crude following the procedure described in step-2 of example 1. Here reaction mixture was stirred for 4 h. LCMS: 353.2 (M+1)$^+$.

Step-4: tert-butyl ((1r,4r)-4-(6-cyano-3-formyl-1-(naphthalen-1-ylmethyl)-1H-indole-2-carboxamido)cyclohexyl)carbamate Product of step-3 of example 101 (1.57 g, 4.43 mmol) and tert-butyl ((1r,4r)-4-aminocyclohexyl) carbamate (0.95 g, 4.43 mmol) were treated to give crude product following the procedure described in step-3 of example 79 which was further purified by combiflash on silica gel (24 g column), eluted with 1.5% methanol in dichloromethane afforded the title compound (1.47 g). LCMS: 451.5 (M−100)+.

Step-5: 2-(((1r,4r)-4-((tert-butoxycarbonyl)amino) cyclohexyl)carbamoyl)-6-cyano-1-(naphthalen-1-ylmethyl)-1H-indole-3-carboxylic Acid To a stirred solution of product of step-4 of example 101 (500 mg, 0.909 mmol) in tert-butanol (40 mL) was added 2-Methyl-2-butene (12 mL) at room temperature and cooled to 10° C. Sodium chlorite (740 mg, 8.18 mmol) and sodium dihydrogen phosphate (740 mg, 6.135 mmol) were dissolved in water (7.5 mL) and added dropwise to above preparation at 0° C. Resulting reaction mixture was stirred at room temperature for overnight. TLC monitoring shown the presence of starting material. To above reaction mixture was added THF (40 mL) and acetonitrile (40 mL), cooled to 10° C. and 1.5 equivalent of hydrogen peroxide was added followed by addition of aqueous solution (150 mL) of sodium chlorite and sodium dihydrogen phosphate. The resulting reaction mixture was stirred overnight (~16 h) at room temperature. After reaction completion, the reaction mixture was concentrated under reduced pressure. The residue obtained was diluted with water and acidified to pH 5.0 with citric acid maintaining the temperature 10° C. The precipitated solid was filtered off and dried to afford title compound (510 mg). LCMS: 565.0 (M+1)+.

Step-6: 2-(((1r,4r)-4-((tert-butoxycarbonyl)amino) cyclohexyl)carbamoyl)-6-(N'-hydroxycarbamimidoyl)-1-(naphthalen-1-ylmethyl)-1H-indole-3-carboxylic Acid The product of step-5 of example 101 (150 mg, 0.215 mmol) was treated with hydroxylamine hydrochloride (46 mg, 0.662 mmol) afforded the title compound (158 mg) following the procedure described in step-4 of example 86. LCMS: 599.9 (M+1)+.

Step-7: 6-(N'-acetoxycarbamimidoyl)-2-(((1r,4r)-4-((tert-butoxycarbonyl)amino)cyclohexyl)carbamoyl)-1-(naphthalen-1-ylmethyl)-1H-indole-3-carboxylic Acid The product of step-6 of example 101 (158 mg, 0.215 mmol) and acetic anhydride (0.3 mL) were treated together to afford 148 mg of the title compound following the procedure described in step-3 of example 82. Here reaction mixture was stirred for 8 h. LCMS: 641.8 (M+1)+.

Step-8: 2-(((1r,4r)-4-((tert-butoxycarbonyl)amino) cyclohexyl)carbamoyl)-6-carbamimidoyl-1-(naphthalen-1-ylmethyl)-1H-indole-3-carboxylic Acid The product of step-7 of example 101 (148 mg, 0.230 mmol) was treated with 10% Palladium on carbon (35 mg) in presence of hydrogen atmosphere for 4 h afforded 92 mg of the title compound following the procedure described in step-4 of example 82. LCMS: 582.8.0 (M−1)*.

Step-9: 2-(((1r,4r)-4-aminocyclohexyl)carbamoyl)-6-carbamimidoyl-1-(naphthalen-1-ylmethyl)-1H-indole-3-carboxylic Acid The product of step-8 of example 101 (60 mg, 0.102 mmol) was treated with TFA (0.35 mL) in dichloromethane following the procedure described in step-6 of example 10. Here reaction mixture was stirred for 5 h. The crude obtained was purified by preparative HPLC instrument using X-Bridge C18 reverse phase column (19×150 mm, 5 micron). The mobile phases were 10% acetonitrile in water (0.1% TFA) to 50% acetonitrile in water (0.1% TFA) which afforded the title compound (32 mg) as a TFA Salt.

LCMS: 482.3 (M+1)+; 1HNMR (400 MHz, CD3OD): δ1.16-1.10 (m, 2H), 1.37-1.31 (m, 2H), 1.70-1.67 (d, 2H), 1.92-1.90 (d, 2H), 2.94 (m, 1H), 3.61 (m, 1H), 6.16 (s, 2H), 6.63-6.61 (d, 1H), 7.32-7.28 (m, 1H), 7.64-7.57 (m, 3H), 7.84-7.81 (d, 1H), 7.96-7.94 (d, 1H), 8.06 (s, 1H), 8.18-8.16 (d, 1H), 8.49-8.47 (d, 1H); HPLC: 99.46% (Retention Time=4.56 min)

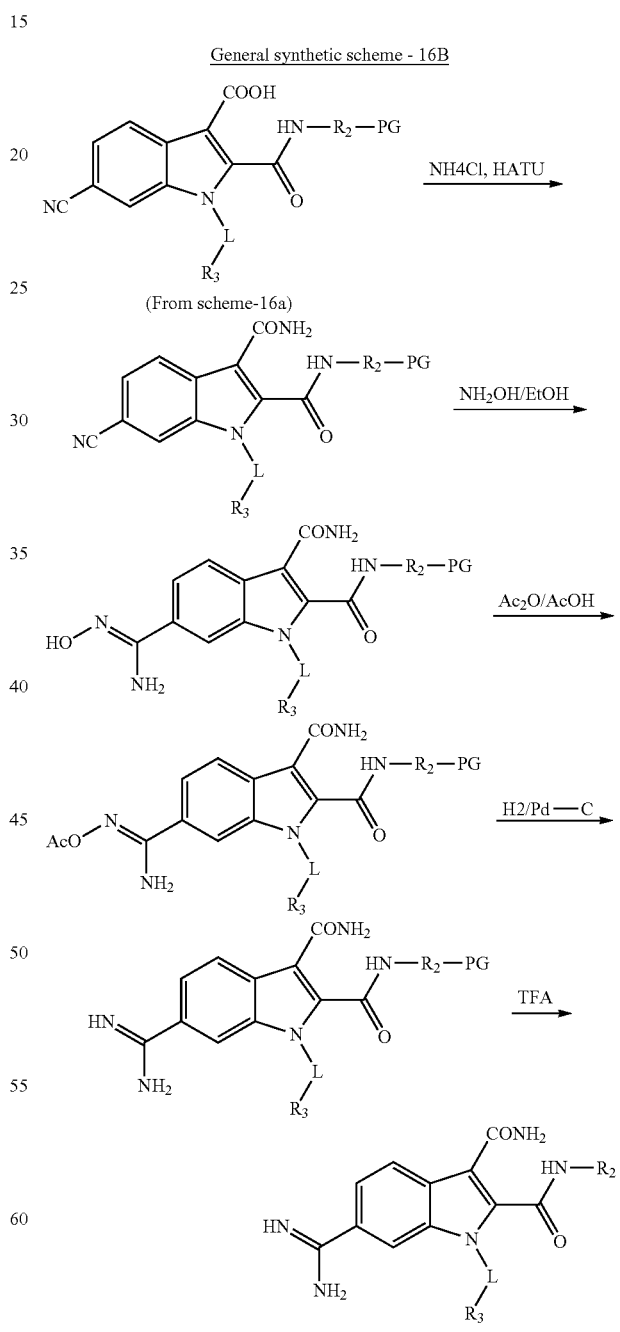

General synthetic scheme - 16B

PG = optional protecting group; X = Br or Cl;

Example 102: Synthesis of Compound I-513

N2-((1r,4r)-4-aminocyclohexyl)-6-carbamimidoyl-1-(naphthalen-1-ylmethyl)-1H-indole-2,3-dicarboxamide

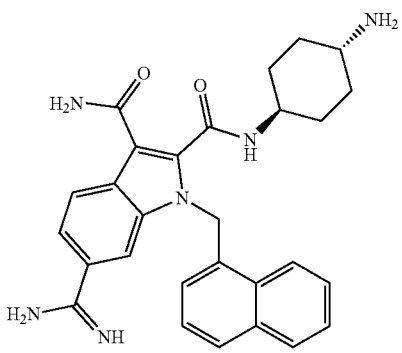 [SMILES: N=C(N)c1ccc2c(C(N)=O)c(C(=O)N[C@H]3CC[C@H](N)CC3)n(Cc3cccc4ccccc34)c2c1]

Step-1: tert-butyl ((1r,4r)-4-(3-carbamoyl-6-cyano-1-(naphthalen-1-ylmethyl)-1H-indole-2-carboxamido)cyclohexyl)carbamate The product of step-5 of example 101 (200 mg, 0.353 mmol) and ammonium chloride (95 mg, 1.766 mmol) were treated to afford the title compound (188 mg) following the procedure described in step-3 of example 79. In this reaction after completion of reaction, ice cold water was added, and precipitated solid was filtered off and dried. LCMS: 566.2 $(M+1)^+$.

Step-2: tert-butyl ((1r,4r)-4-(3-carbamoyl-6-(N'-hydroxycarbamimidoyl)-1-(naphthalen-1-ylmethyl)-1H-indole-2-carboxamido)cyclohexyl)carbamate The product of step-1 of Example 102 (194 mg, 0.343 mmol) was treated with hydroxylamine hydrochloride (82 mg, 1.2 mmol) afforded the title compound (187 mg) following the procedure described in step-4 of example 86. LCMS: 599.4 $(M+1)^+$.

Step-3: tert-butyl ((1r,4r)-4-(6-(N'-acetoxycarbamimidoyl)-3-carbamoyl-1-(naphthalen-1-ylmethyl)-1H-indole-2-carboxamido)cyclohexyl)carbamate The product of step-2 of Example 102 (187 mg, 0.312 mmol) and acetic anhydride (0.32 mL) were treated together to afford 200 mg of the title compound following the procedure described in step-3 of example 82. Here reaction mixture was stirred for 12 h. LCMS: 642 $(M+1)^+$.

Step-4: tert-butyl ((1r,4r)-4-(6-carbamimidoyl-3-carbamoyl-1-(naphthalen-1-ylmethyl)-1H-indole-2-carboxamido)cyclohexyl)carbamate The product of step-3 of Example 102 (200 mg, 0.312 mmol) was treated with 10% Palladium on carbon (50 mg) in presence of hydrogen atmosphere for 4 h afforded 167 mg of the title compound following the procedure described in step-4 of example 82. LCMS: 583.5 $(M+1)^+$.

Step-5: N2-((1r,4r)-4-aminocyclohexyl)-6-carbamimidoyl-1-(naphthalen-1-ylmethyl)-1H-indole-2,3-dicarboxamide The product of step-4 of Example 102 (67 mg, 0.115 mmol) was treated with TFA (0.35 mL) in dichloromethane and the reaction mixture was stirred for 5 h. The crude obtained was purified by preparative HPLC instrument using X-Bridge C18 reverse phase column (19×150 mm, 5 micron). The mobile phases were 10% acetonitrile in water (0.1% TFA) to 50% acetonitrile in water (0.1% TFA) which afforded the title compound (39 mg) as a TFA Salt.

LCMS: 481.4 $(M-1)^+$; $^1$HNMR (600 MHz, CD$_3$OD): δ1.22-1.15 (m, 2H), 1.35-1.31 (m, 2H), 1.75-1.73 (d, 2H), 1.92-1.90 (d, 2H), 2.95 (m, 1H), 3.61 (m, 1H), 6.25 (s, 2H), 6.48-6.47 (d, 1H), 7.24-7.23 (t, 1H), 7.57-7.53 (m, 1H), 7.63-7.61 (m, 1H), 7.69-7.67 (m, 1H), 7.79-7.77 (d, 1H), 7.91 (d, 1H), 8.05 (s, 1H), 8.16-8.15 (d, 1H), 8.26-8.24 (d, 1H); HPLC: 97.58% (Retention Time=4.63 min)

General synthetic scheme-16C

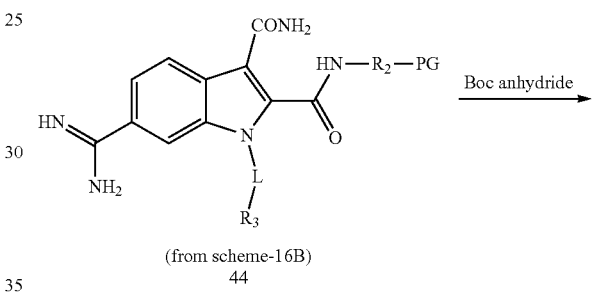

(from scheme-16B)
44

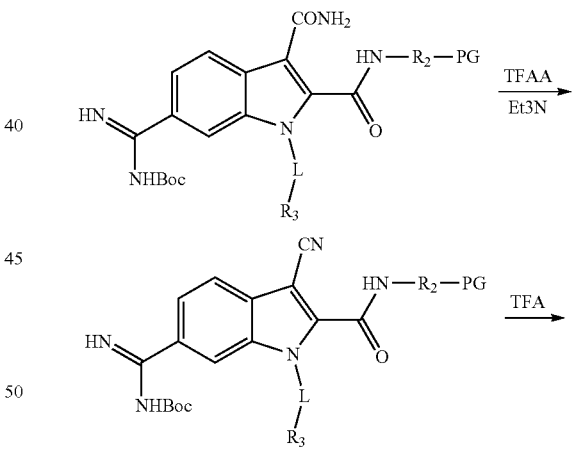

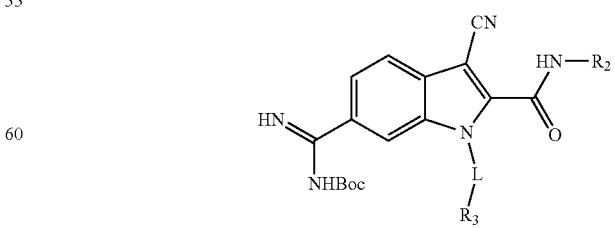

PG = optional protecting group; X = Br or Cl;

Example 103: Synthesis of Compound I-514

N-((1r,4r)-4-aminocyclohexyl)-6-carbamimidoyl-3-cyano-1-(naphthalen-1-ylmethyl)-1H-indole-2-carboxamide

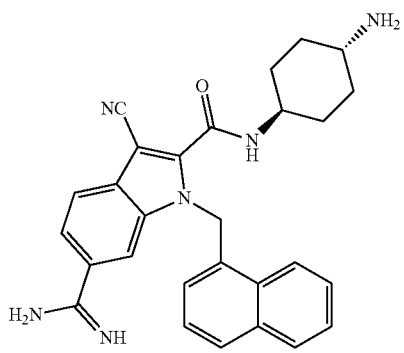 [SMILES: N#Cc1c(C(=O)N[C@H]2CC[C@H](N)CC2)n(Cc2cccc3ccccc23)c2cc(C(=N)N)ccc12]

Step-1: tert-butyl ((1r,4r)-4-(6-(N-(tert-butoxycarbonyl)carbamimidoyl)-3-carbamoyl-1-(naphthalen-1-ylmethyl)-1H-indole-2-carboxamido)cyclohexyl)carbamate To a stirred solution of product of step-4 of Example 103 (80 mg, 0.137 mmol) in THF (5 mL) was added 1N aq. solution of sodium hydroxide (5.5 mg, 0137 mmol) at 10° C. and stirred for 15 min. followed by addition of di-tert-butyl dicarbonate (30 mg, 0.206 mmol). The resulting reaction mixture was stirred for overnight (~16 h) at room temperature. After reaction completion, evaporated off the reaction mixture under reduced pressure. The residue obtained was diluted with water. The precipitated solid was filtered off and dried to give title compound (80 mg). LCMS: 683.05 (M+1)$^+$.

Step-2: tert-butyl ((1r,4r)-4-(6-(N-(tert-butoxycarbonyl)carbamimidoyl)-3-cyano-1-(naphthalen-1-ylmethyl)-1H-indole-2-carboxamido)cyclohexyl)carbamate To a stirred solution of product of step-1 of example 103 (80 mg, 0.137 mmol) and triethylamine (177 mg, 1.759 mmol) in dry dichloromethane (5.0 mL) was added trifluoroacetic anhydride (295 mg, 1.407 mmol) at 10° C. and resulting reaction mixture was stirred at room temperature for overnight (~16 h). After reaction completion, reaction mixture was diluted with dichloromethane washed with aq. sodium bicarbonate solution. The organic layer separated, dried over sodium sulphate and concentrated under reduced pressure afforded the title compound (71 mg). LCMS: 665.4 (M+1)$^+$.

Step-3: N-((1r,4r)-4-aminocyclohexyl)-6-carbamimidoyl-3-cyano-1-(naphthalen-1-ylmethyl)-1H-indole-2-carboxamide

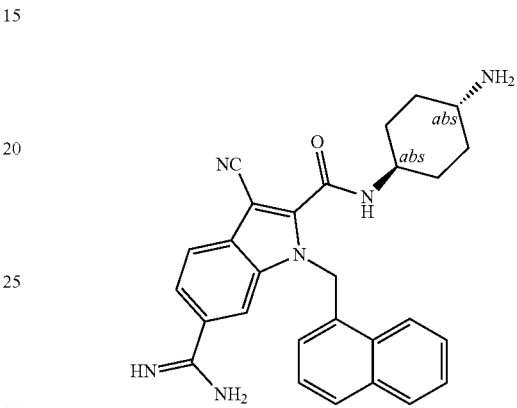

The product of step-2 of example 103 (71 mg, 0.106 mmol) was treated with TFA (0.20 mL) in dichloromethane. The crude obtained was purified by preparative HPLC using X-Bridge C18 reverse phase column (19×150 mm, 5 micron). The mobile phases were 20% acetonitrile in water (0.1% TFA) to 60% acetonitrile in water (0.1% TFA) which afforded the title compound (20 mg) as a TFA Salt.

LCMS: 465.2 (M+1)$^+$; $^1$HNMR (400 MHz, CD$_3$OD): δ1.41-1.26 (m, 4H), 1.81-1.78 (d, 2H), 1.99-1.96 (d, 2H), 2.99 (m, 1H), 3.68 (m, 1H), 6.33 (s, 2H), 6.61-6.60 (d, 1H), 7.32-7.28 (t, 1H), 7.64-7.57 (m, 2H), 7.85-7.78 (m, 2H), 7.96-7.94 (d, 1H), 8.06-8.04 (m, 1H), 8.14-8.12 (d, 1H), 8.243-8.240 (d, 1H); HPLC: 99.50% (Retention Time=4.94 min)

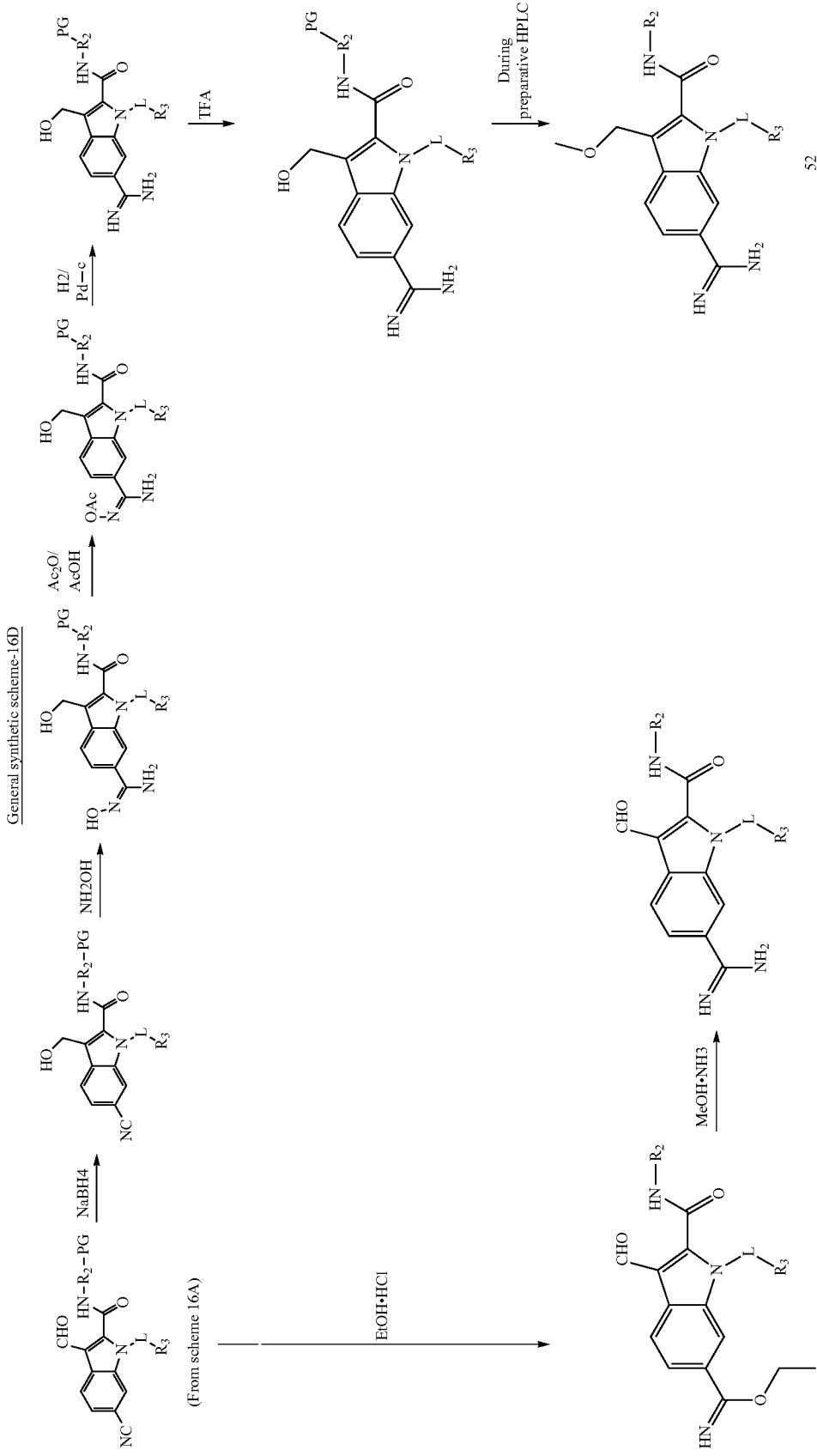

Example 104: Synthesis of Compound I-515

N-((1r,4r)-4-aminocyclohexyl)-6-carbamimidoyl-3-formyl-1-(naphthalen-1-ylmethyl)-1H-indole-2-carboxamide

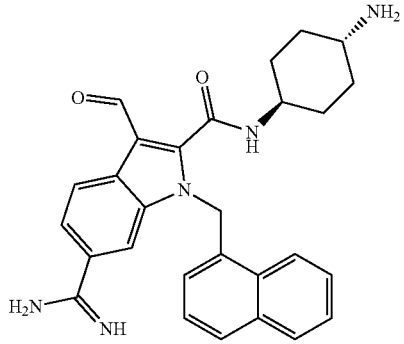 [SMILES: N=C(N)c1ccc2c(C=O)c(C(=O)N[C@H]3CC[C@H](N)CC3)n(Cc3cccc4ccccc34)c2c1]

Step-1: Ethyl 2-(((1r,4r)-4-aminocyclohexyl)carbamoyl)-3-formyl-1-(naphthalen-1-ylmethyl)-11H-indole-6-carbimidate Product of step-4 of example 101 (150 mg, 0.272 mmol) was treated with ethanolic HCl (5 mL) and 1,4 dioxane HCl (10 mL) for 4 days afforded the 235 mg of title compound as crude following the procedure described in step-4 of example 79. LCMS: 497.2 (M+1)$^+$.

Step-2: N-((1r,4r)-4-aminocyclohexyl)-6-carbamimidoyl-3-formyl-1-(naphthalen-1-ylmethyl)-1H-indole-2-carboxamide Product of step-1 of example 104 (135 mg, 0.272 mmol) was treated with methanolic ammonia (20 ml) afforded the 27 mg crude product following the procedure described in step-5 of example 1. The crude obtained was purified by preparative HPLC instrument using Zorbax XDB C18 reverse phase column (21.2×150 mm, 5 micron). The mobile phases were 10% acetonitrile in water (0.1% TFA) to 25% acetonitrile in water (0.1% TFA) which afforded the title compound (3 mg) as a TFA Salt. LCMS: 468.3 (M+1)$^+$; $^1$HNMR (600 MHz, CD$_3$OD): δ1.16-1.10 (m, 2H), 1.35-1.31 (m, 2H), 1.68-1.66 (d, 2H), 1.90-1.88 (d, 2H), 2.90 (m, 1H), 3.63 (m, 1H), 6.25 (s, 2H), 6.62-6.61 (d, 1H), 7.29-7.26 (t, 1H), 7.62-7.55 (m, 2H), 7.77-7.75 (d, 1H), 7.82-7.81 (d, 1H), 7.93-7.92 (d, 1H), 8.13-8.11 (d, 1H), 8.16 (s, 1H), 8.59-8.57 (d, 1H), 10.14 (s, 1H); HPLC: 98.86% (Retention Time=5.08 min).

Example 105: Synthesis of Compound I-516

N-((1r,4r)-4-aminocyclohexyl)-6-carbamimidoyl-3-(hydroxymethyl)-1-(naphthalen-1-ylmethyl)-1H-indole-2-carboxamide

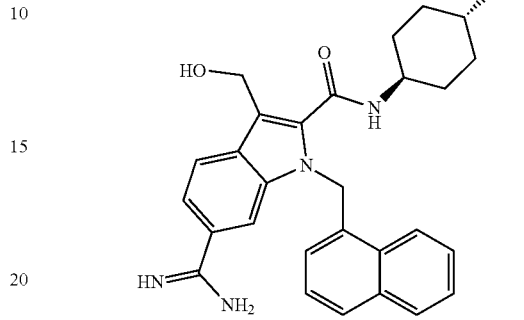

Step-1: tert-butyl((1r,4r)-4-(6-cyano-3-(hydroxymethyl)-1-(naphthalen-1-ylmethyl)-1H-indole-2-carboxamido) cyclohexyl)carbamate To a stirred solution of product of step-4 of example 101 (250 mg, 0.454 mmol) in methanol (30 mL) was added sodium borohydride (86 mg, 2.292 mmol) at 0° C. and resulting reaction mixture was stirred at room temperature for overnight (~16 h). After reaction completion, reaction mixture was concentrated under reduced vacuum. The residue obtained was diluted with water; precipitated solid was filtered off and dried completely afforded 250 mg of title compound. LCMS: 535.75 (M−17)$^+$.

Step-2: tert-butyl ((1r,4r)-4-(6-carbamimidoyl-3-(hydroxymethyl)-1-(naphthalen-1-ylmethyl)-1H-indole-2-carboxamido)cyclohexyl)carbamate The product of step-1 of example 105 (230 mg, 0.416 mmol) was treated consequently in three steps with hydroxyl amine hydrochloride, acetic anhydride followed by hydrogenation with 10% palladium carbon following the procedure described in step-4, step-5 and step-6 of example 100 afforded the 171 mg of title compound. LCMS: 570.3 (M+1)$^+$.

Step-3: N-((1r,4r)-4-aminocyclohexyl)-6-carbamimidoyl-3-(hydroxymethyl)-1-(naphthalen-1-ylmethyl)-1H-indole-2-carboxamide The product of step-2 of example 105 (70 mg, 0.123 mmol) was treated with 4 M solution of HCl in 1,4 dioxane afforded the crude product following the procedure described in step-3 of example 83. The crude obtained was purified by preparative HPLC instrument using Gemini-NX C18 reverse phase column (21.2×150 mm, 5 micron). The mobile phases were 5% acetonitrile in water (0.02% TFA) to 30% acetonitrile in water (0.02% TFA) which afforded the title compound (12 mg) as a TFA Salt.

LCMS: 470.2 (M+1)$^+$; $^1$HNMR (400 MHz, CD$_3$OD): δ1.44-1.23 (m, 4H), 1.98-1.85 (m, 4H), 3.01 (m, 1H), 3.68 (m, 1H), 4.98 (s, 2H), 6.34 (s, 2H), 6.40-6.38 (d, 1H), 7.25-7.21 (t, 1H), 7.65-7.55 (m, 3H), 7.79-7.77 (d, 1H), 7.94-7.92 (d, 1H), 8.03 (s, 1H), 8.10-8.07 (d, 1H), 8.20-8.18 (d, 1H); HPLC: 89.62% (Retention Time=8.17 min).

Example 106: Synthesis of Compound I-517

N-((1r,4r)-4-aminocyclohexyl)-6-carbamimidoyl-3-(methoxymethyl)-1-(naphthalen-1-ylmethyl)-1H-indole-2-carboxamide

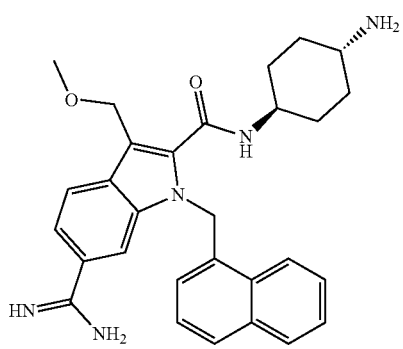 [SMILES: COCc1c(C(=O)N[C@H]2CC[C@H](N)CC2)n(Cc2cccc3ccccc23)c2cc(C(=N)N)ccc12]

While isolation of step-3 of example 105 by preparative HPLC method methanol was added for solubilising purpose which leaded the title compound as side product isolated by preparative HPLC method using Zorbax XDB reverse phase column (21.2×150 mm, 5 micron). The mobile phases were 15% acetonitrile in water (0.1% TFA) to 40% acetonitrile in water (0.1% TFA) which afforded the title compound (1.7 mg) as a TFA Salt.

LCMS: 484.4 (M+1)$^+$; $^1$HNMR (400 MHz, CD$_3$OD): δ1.30-1.24 (m, 2H), 1.43-1.39 (m, 2H), 1.87-1.84 (d, 2H), 2.00-1.97 (d, 2H), 3.04 (m, 1H), 3.46 (s, 3H), 3.67 (m, 1H), 4.85 (s, 2H), 6.33 (s, 2H), 6.41-6.39 (d, 1H), 7.26-7.25 (t, 1H), 7.64-7.57 (m, 3H), 7.79-7.77 (d, 1H), 7.94- 7.92 (d, 1H), 8.08-8.05 (m, 2H), 8.19-8.17 (d, 1H); HPLC: 97.15% (Retention Time=5.01 min).

General synthetic scheme - 17

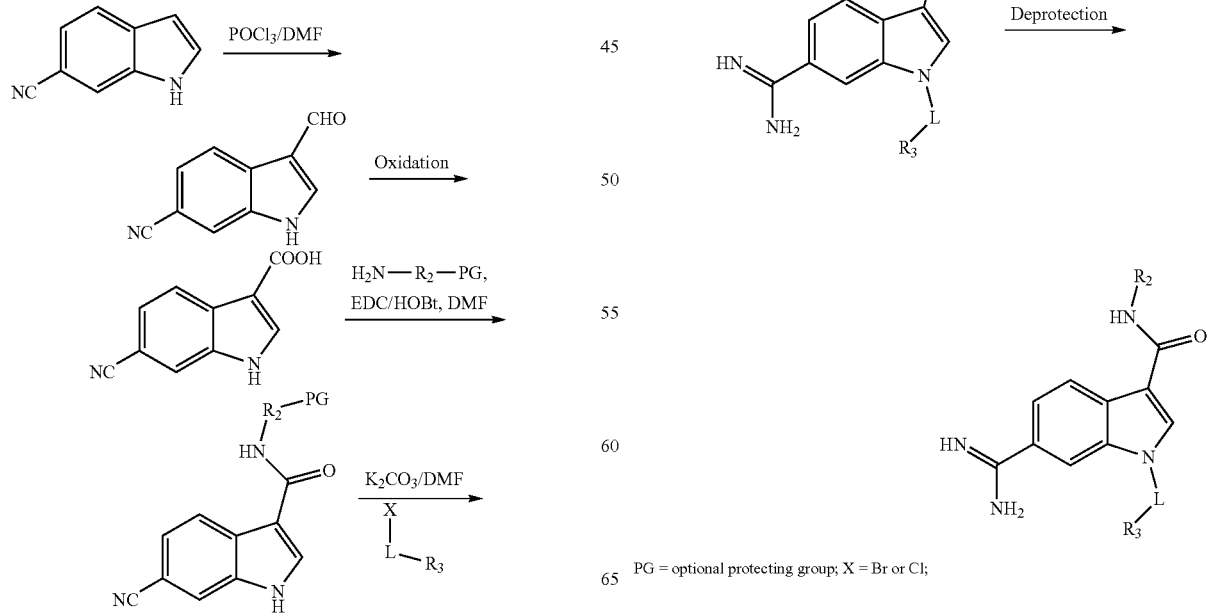

PG = optional protecting group; X = Br or Cl;

Example 107: Synthesis of Compound I-518 tert-butyl ((1r,4r)-4-(6-carbamimidoyl-1-(naphthalen-1-ylmethyl)-1H-indole-3-carboxamido) cyclohexyl) carbamate

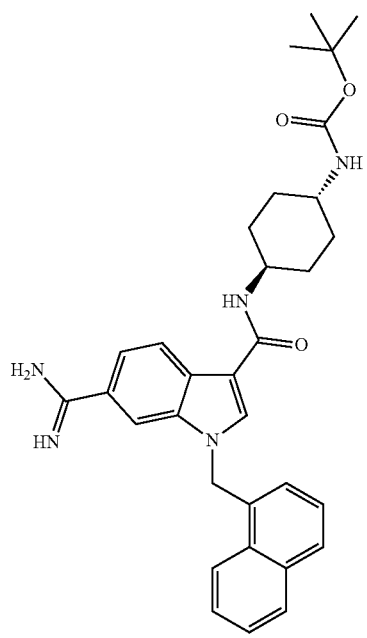 [SMILES: CC(C)(C)OC(=O)N[C@H]1CC[C@H](NC(=O)c2cn(Cc3cccc4ccccc34)c3cc(C(=N)N)ccc23)CC1]

Step-1: 6-cyano-1H-indole-3-carboxylic Acid

The title compound mentioned above was prepared from 1H-indole-6-carbonitrile in two steps as described in literature procedure of *Bioorganic and Medicinal Chemistry Letters*, 1996, vol. 6, 1, p. 81-86.

Step-2: tert-butyl ((1r,4r)-4-(6-cyano-1H-indole-3-carboxamido)cyclohexyl)carbamate The product of step-1 of example 107 (750 mg, 4.02 mmol) and tert-butyl ((1r,4r)-4-amino cyclohexyl) carbamate (879 mg, 4.1 mmol) were treated together to afford 740 mg of the title compound following the procedure described in step-3 of example 79. LCMS: 383.0 (M+1)$^+$.

Step-3: tert-butyl ((1r,4r)-4-(6-cyano-1-(naphthalen-1-ylmethyl)-1H-indole-3-carboxamido)cyclohexyl) carbamate The product of step-2 of example 107 (350 mg, 0.915 mmol) was treated with 1-(bromomethyl) naphthalene (222 mg, 1.006 mmol) afforded the title compound (520 mg) following the procedure described in step-1 of example 79. In this reaction, reaction mixture was stirred for 5 h at room temperature. LCMS: 523.5 (M+1)$^+$.

Step-4: tert-butyl ((1r,4r)-4-(6-carbamimidoyl-1-(naphthalen-1-ylmethyl)-1H-indole-3-carboxamido) cyclohexyl) carbamate The product of step-3 of example 107 (550 mg, 1.05 mmol) was treated consequently in three steps with hydroxyl amine (50% in water), acetic anhydride followed by hydrogenation with 10% palladium carbon following the procedure described in step-1, step-2 and step-3 of example 88 gave the 560 mg of crude compound which was further purified (150 mg) by preparative TLC (mobile phase: 8% methanol in dichloromethane) afforded 55 mg of title compound.

LCMS: 540.0 (M+1)$^+$; $^1$HNMR (CDCl$_3$, 400 MHz): δ0.81-0.71 (m, 4H), 1.33-1.15 (m, 9H), 1.89-1.88 (m, 4H), 3.23 (m, 1H), 3.76 (m, 1H), 5.76 (s, 2H), 6.99-6.97 (dd, 1H), 7.34-7.30 (t, 1H), 7.50-7.41 (m, 3H), 7.64 (s, 1H), 7.85-7.76 (m, 3H), 7.930 (s, 1H), 8.24-8.22 (dd, 1H); HPLC: 94.43% (Retention Time=9.18 min).

Example 108: Synthesis of Compound I-519

N-((1r,4r)-4-aminocyclohexyl)-6-carbamimidoyl-1-(naphthalen-1-ylmethyl)-1H-indole-3-carboxamide

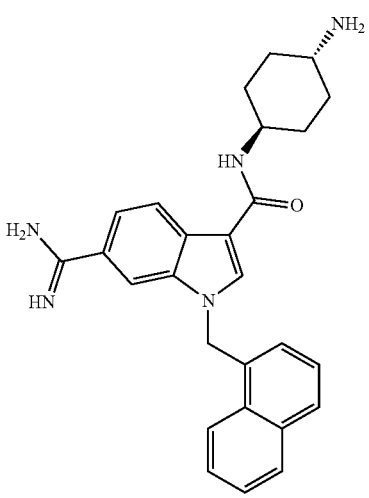 [SMILES: N=C(N)c1ccc2c(C(=O)N[C@H]3CC[C@H](N)CC3)cn(Cc3cccc4ccccc34)c2c1]

Step-1: N-((1r,4r)-4-aminocyclohexyl)-6-carbamimidoyl-1-(naphthalen-1-ylmethyl)-1H-indole-3-carboxamide The product of step-4 of example 108 (100 mg, 0.185 mmol) was treated with TFA (0.5 mL) in dichloromethane following the procedure described in step-6 of example 88. The crude obtained was purified by preparative HPLC instrument using Gemini-NX C18 reverse phase column (21.2×150 mm, 5 micron). The mobile phases were 30% acetonitrile in water (0.1% TFA) to 60% acetonitrile in water (0.1% TFA) which afforded the title compound (45 mg) as a TFA Salt.

LCMS: 440.2 (M+1)$^+$; $^1$HNMR (400 MHz, CD$_3$OD): δ1.53-1.27 (m, 4H), 2.07-2.04 (m, 4H), 3.06 (m, 1H), 3.84 (m, 1H), 6.0 (s, 2H), 7.15-7.13 (dd, 1H), 7.46-7.42 (t, 1H), 7.55-7.46 (m, 2H), 7.66-7.63 (dd, 1H), 7.98-7.91 (m, 4H), 8.177-8.174 (s, 1H), 8.43-8.41 (dd, 1H); HPLC: 95.01% (Retention Time=4.97 min).

Following compound listed in table-34 prepared according to general scheme-17 by following similar procedure as described above for the examples 108 using appropriate reagents with suitable modifications known to the one skilled in the art

TABLE 34

Compounds synthesized using General Scheme-17

| Cpd. ID. | Structure | LCMS [M + H]+ | 1H-NMR Data |
|---|---|---|---|
| I-520 | 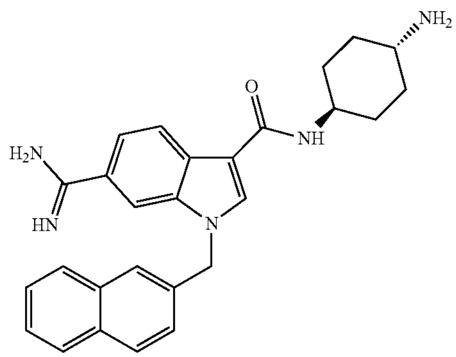 [SMILES: N=C(N)c1ccc2c(C(=O)N[C@H]3CC[C@H](N)CC3)cn(Cc3ccc4ccccc4c3)c2c1] | 440.4 | 1HNMR(400 MHz, CD3OD): δ1.61-1.41 (m, 4H), 2.12-2.08(d, 4H), 3.09-3.06(t, 1H), 3.89-3.86(t, 1H), 5.69 (s, 2H), 7.45-7.34(d, 1H), 7.51-7.46(t, 2H), 7.62-7.59(d, 1H), 7.72 (s, 1H), 7.88-7.72 (m, 3H), 8.10 (s, 1H), 8.22 (s, 1H), 8.41-8.38(d, 1H). |

General synthetic scheme-17A

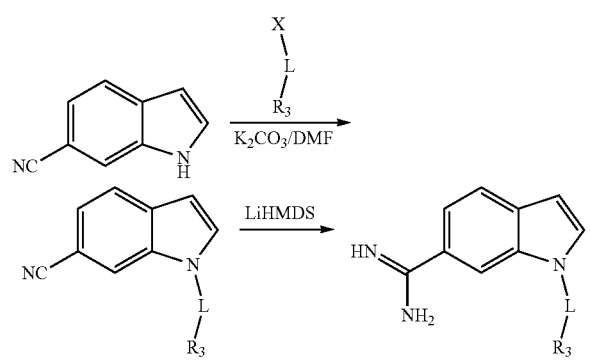

Example 109: Synthesis of Compound I-521

1-(naphthalen-1-ylmethyl)-1H-indole-6-carboximidamide

Step-1:1-(naphthalen-1-ylmethyl)-1H-indole-6-carbonitrile 1H-indole-6-carbonitrile was treated with (300 mg, 2.1 mmol) was treated with 1-(bromomethyl) naphthalene (560 mg, 2.5 mmol) and gave the crude product following the procedure described in step-1 of example 81. The reaction mixture was stirred for overnight at room temperature. The crude product obtained was further purified by combiflash on silica gel (40 g) and eluted with dichloromethane afforded the 530 mg of title compound. LCMS: 283.05 (M+1)+.

Step-2: 1-(naphthalen-1-ylmethyl)-1H-indole-6-carboximidamide

Product of step-1 of example 109 (200 mg, 0.7 mmol) was treated with solid LiHMDS (0.827 mg, 4.9 mmol) afforded crude product (220 mg) following the procedure described in step-1 of example 90. The crude obtained was purified by preparative HPLC instrument using Zorbax XDB C18 reverse phase column (21.2×150 mm, 5 micron). The mobile phases were 20% acetonitrile in water (0.1% TFA) to 60% acetonitrile in water (0.1% TFA) which afforded the title compound (90 mg) as a TFA Salt. LCMS: 300.2 (M+1)+; 1HNMR (400 MHz, CD3OD): δ 6.00 (s, 2H), 6.69-6.70 (m, 1H), 6.89-6.91 (m, 1H), 7.36-7.39 (m, 1H), 7.47-7.57 (m, 4H), 7.83-7.88 (m, 2H), 7.94-8.03 (m, 1H), 8.06 (s, 1H), 8.06-8.08 (m, 1H); HPLC: 99.14% (Retention Time=6.49 min).

General synthetic scheme018

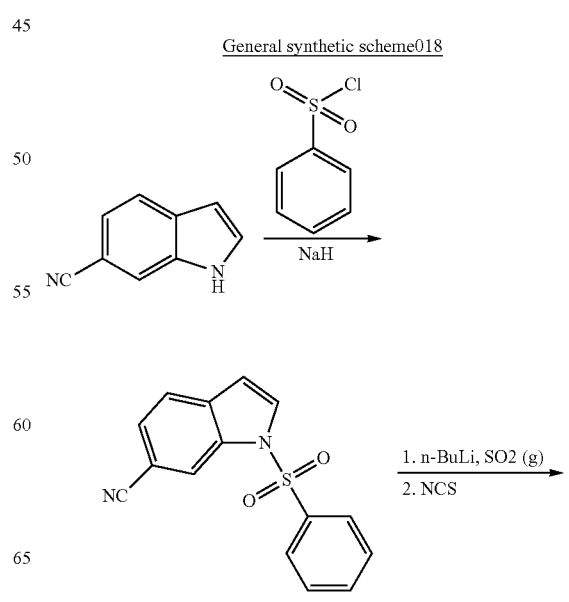

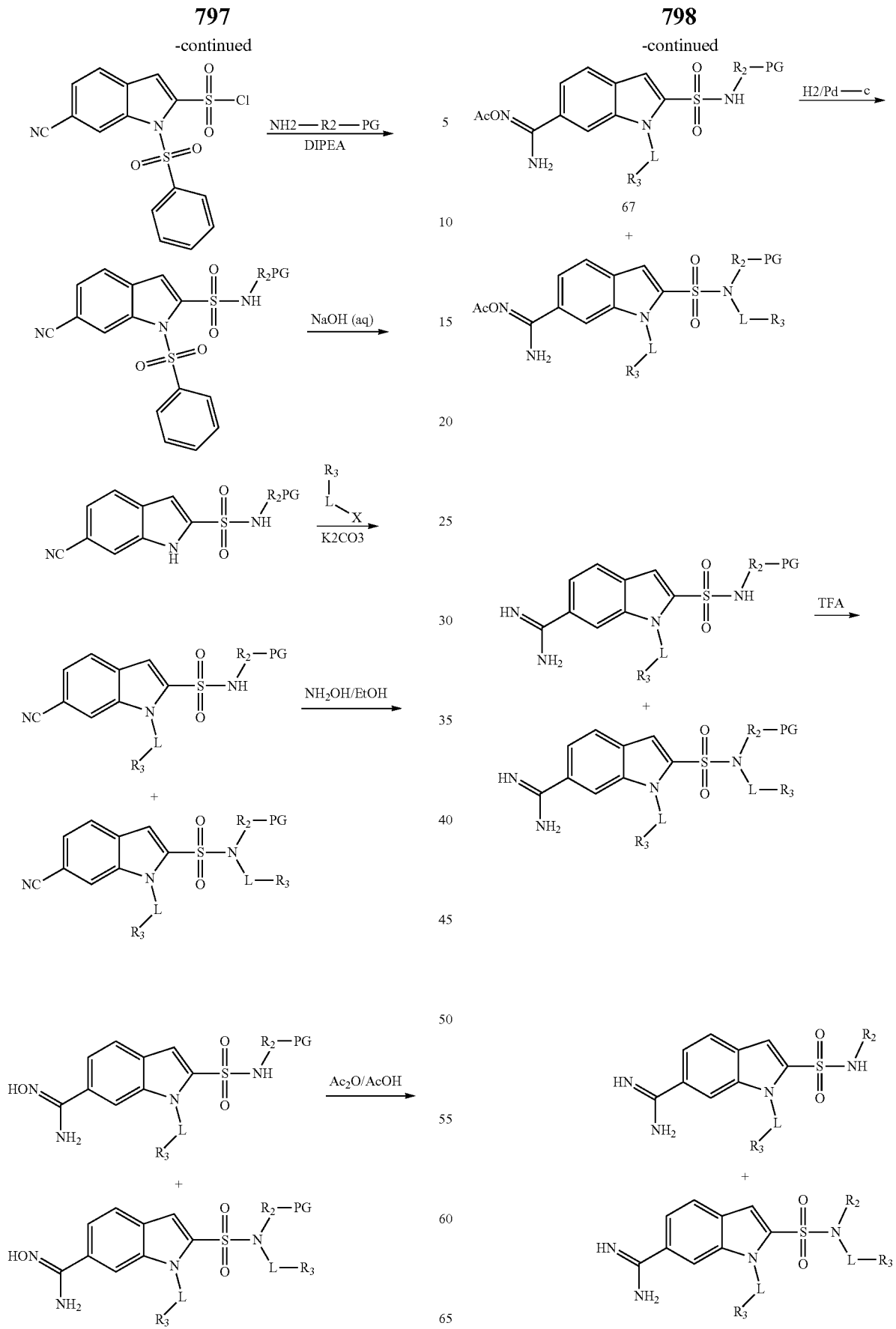

Example 110: Synthesis of Compound I-522

2-(N-((1r,4r)-4-aminocyclohexyl)sulfamoyl)-1-(naphthalen-1-ylmethyl)-1H-indole-6-carboximidamide

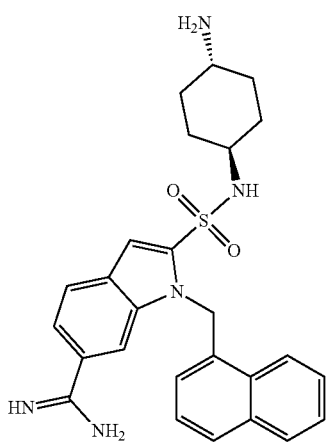 [SMILES: N=C(N)c1ccc2cc(S(=O)(=O)N[C@H]3CC[C@H](N)CC3)n(Cc3cccc4ccccc34)c2c1]

Step-1: 1-(phenylsulfonyl)-1H-indole-6-carbonitrile

The title compound mentioned above was prepared from 1H-indole-6-carbonitrile as described in *Journal of Medicinal Chemistry*, 2015, vol. 58, #24, p. 9480-9497.

Step-2: 6-cyano-1-(phenylsulfonyl)-1H-indole-2-sulfonyl chloride

Stage-1: Product of step-1 of example 110 (1.0 g, 3.546) dissolved in THF (15 mL), cooled to −70° C. under nitrogen atmosphere and was added n-butyl lithium (1.7 M in n-hexane) (2.29 mL, 3.90 mmol) dropwise maintaining the same temperature. The resulting reaction mixture was stirred at −70° C. for 35 min followed by purging of sulphur dioxide gas for 15 min. The reaction mixture was gradually warmed to room temperature over 2 h. After reaction completion, the reaction mixture was diluted with hexane (2×50 mL) and stirred for 15 min and hexane layer was decanted off and dried to give the lithium salt (1.7 g).

Stage-2: To a stirred solution of product of stage-1 (lithium salt) in dichloromethane was added N-chlorosuccinimide (700 mg, 5.319 mmol) at 0° C. and resulting reaction mixture was stirred at room temperature for 12 h. After reaction completion, the reaction mixture was filtered through celite bed and washed with dichloromethane. Collected filtrate was concentrated under reduced pressure, residue obtained was diluted with 20% dichloromethane in hexane, precipitated solid filtered and washed with dichloromethane. The solid was discarded and collected filtrates were concentrated to give title compound as crude (1.25 g). LCMS: 360.6 (M−19, sulphonic acid)$^+$.

Step-3: tert-butyl ((1r,4r)-4-((6-cyano-1H-indole)-2-sulfonamido)cyclohexyl)carbamate Stage-1: To a 0° C. cooled stirred solution of product of step-2 of example 110 (250 mg, 1.1 mmol) in dichloromethane (15 mL) was added triethylamine (0.81 mL, 5.8 mmol), stirred for 5 min followed by addition of tert-butyl ((1r,4r)-4-aminocyclohexyl)carbamate (0.976 g, 2.5 mmol). The resultant reaction mixture was stirred at room temperature for 16 h. After reaction completion, the reaction mixture was concentrated under reduced pressure. The crude obtained (1.8 g) was proceeded to next stage.

Stage-2: To a solution of crude obtained in stage-1 above in ethanol (6 mL) was added 10% sodium hydroxide solution (6 mL) and stirred at 80° C. for 1 h. After reaction completion distilled off ethanol completely and crude obtained was diluted with water and extracted with ethyl acetate. Ethyl acetate layer was washed with water, brine, dried over sodium sulphate and concentrated under reduced pressure. The crude residue obtained above was purified by combiflash on silica gel eluted with 55% ethyl acetate in hexane afforded the title compound (150 mg). LCMS: 557.75 (M+1)$^+$.

Step-4: tert-butyl ((1r,4r)-4-((6-cyano-1-(naphthalen-1-ylmethyl)-1H-indole)-2-sulfonamido) cyclohexyl) carbamate (Polar Compound)

Product of step-3 of example 110 (600 mg, 1.4 mmol) treated with 1-(bromomethyl)naphthalene (317 mg, 1.4 mmol) afforded the crude product following the procedure described in step-7 of example 97. Here reaction was stirred at room temperature for 16 h. The crude obtained above was purified by combiflash on silica gel eluted with 20% ethyl acetate in hexane afforded the title compound (230 mg) from polar fractions. LCMS: 559.3 (M+1)$^+$.

The non-polar compound isolated (400 mg) was confirmed as di alkylated product tert-butyl ((1r,4r)-4-((6-cyano-N,1-bis(naphthalen-1-ylmethyl)-1H-indole)-2-sulfonamido)cyclohexyl) carbamate. LCMS: 643.5 (M−56)$^+$.

Step-5: tert-butyl ((1r,4r)-4-((6-carbamimidoyl-1-(naphthalen-1-ylmethyl)-1H-indole)-2-sulfonamido) cyclohexyl) carbamate The polar product of step-4 of example 110 (200 mg, 0.3 mmol) was treated in consequent three steps with hydroxyl amine (50% in water), acetic anhydride followed by hydrogenation with 10% palladium carbon (here hydrogenation carried out in ethanol at room temperature for 2 h) following the procedure described in step-1, step-2 and step-3 of example 88 afforded the 120 mg of title compound. LCMS: 576.85 (M+1)$^+$.

Step-6: 2-(N-((1r,4r)-4-aminocyclohexyl)sulfamoyl)-1-(naphthalen-1-ylmethyl)-1H-indole-6-carboximidamide Product of step-5 of example 110 (120 mg, 0.2 mmol) was treated with TFA (0.3 mL). The crude obtained was purified by preparative HPLC instrument using Zorbax XDB C18 reverse phase column (21.2×150 mm, 5 micron). The mobile phases were 10% acetonitrile in water (0.1% TFA) to 50% acetonitrile in water (0.1% TFA) which afforded the title compound (45 mg) as a TFA Salt. LCMS: 474.5 (M+1)$^+$; $^1$HNMR (400 MHz, CD$_3$OD): δ1.25-1.20 (m, 4H), 1.76-1.72 (m, 2H), 1.88-1.84 (m, 2H), 2.95-2.88 (m, 1H), 3.10-3.05 (m, 1H), 6.26-6.25 (d, 1H), 6.34 (s, 2H), 7.23-7.19 (t, 1H), 7.43 (s, 1H), 7.60-7.58 (m, 2H), 7.69-7.65 (t, 1H), 7.79-7.76 (m, 2H), 8.01-7.93 (m, 2H), 8.24-8.22 (d, 1H); HPLC: 98.96% (Retention Time=5.46 min).

Following compound listed in table-35 prepared according to general scheme-18 starting from the non-polar product of step-4 of example 110 by following similar procedure as described above for the examples 110 using appropriate reagents with suitable modifications known to the one skilled in the art TABLE 35
Compounds synthesized using General Scheme-18
| Cpd. ID. | Structure | LCMS [M + H]+ | 1H-NMR Data |
|---|---|---|---|
| I-523 | 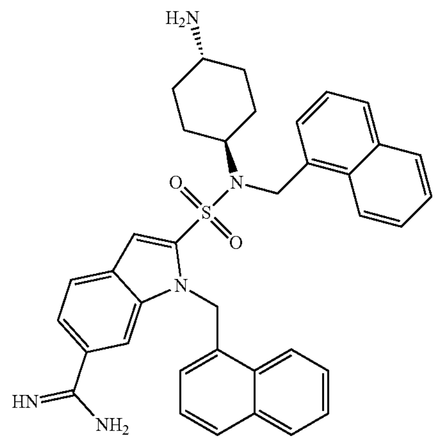 [SMILES: N=C(N)c1ccc2cc(S(=O)(=O)N(Cc3cccc4ccccc34)[C@H]3CC[C@H](N)CC3)n(Cc3cccc4ccccc34)c2c1] | 615.85 | 1HNMR (400 MHz, CD3OD): δ1.45-1.21 (m, 4H), 1.87-1.72 (m, 4H), 2.78-2.72 (m, 1H), 3.90-3.85 (m, 1H), 4.46 (s, 2H), 6.34 (s, 2H), 6.39-6.37(d, 1H), 7.22-7.20(d, 1H), 7.38-7.29 (m, 5H), 7.49-7.47(d, 1H), 8.05-8.03 (m, 1H), 8.16-8.13 (m, 1H). |
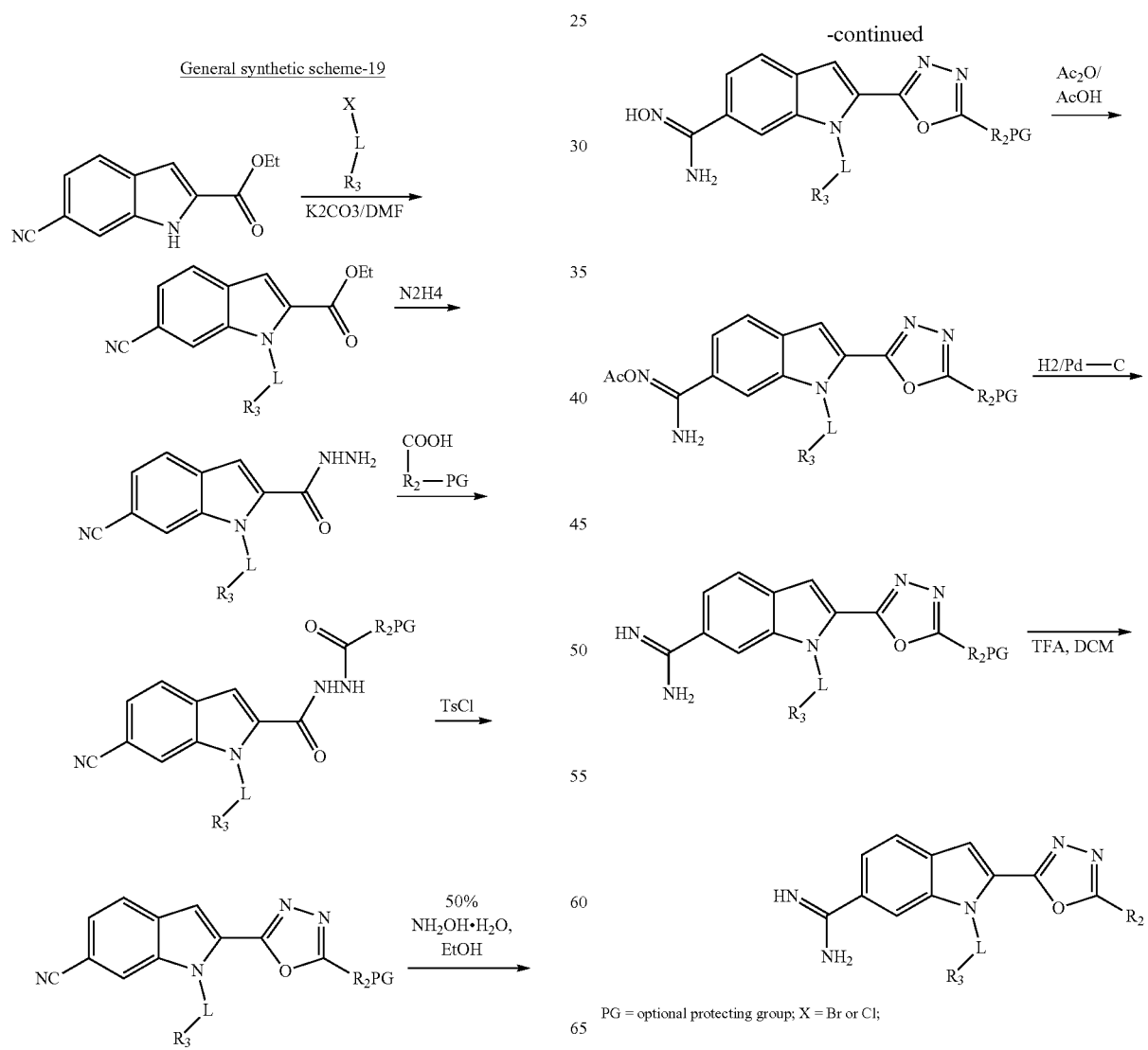
General synthetic scheme-19
PG = optional protecting group; X = Br or Cl;

Example 111: Synthesis of Compound I-524 tert-butyl ((1r,4r)-4-(5-(6-carbamimidoyl-1-(naphthalen-1-ylmethyl)-1H-indol-2-yl)-1,3,4-oxadiazol-2-yl) cyclohexyl)carbamate

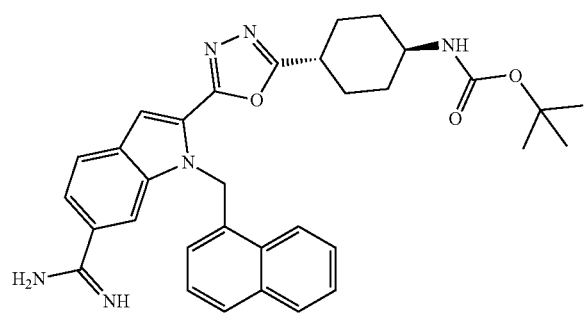 [SMILES: CC(C)(C)OC(=O)N[C@H]1CC[C@H](c2nnc(-c3cc4ccc(C(=N)N)cc4n3Cc3cccc4ccccc34)o2)CC1]

Step-1: 6-cyano-1-(naphthalen-1-ylmethyl)-1H-indole-2-carbohydrazide

To a solution of product of step-1 of example 79 (700 mg, 1.977 mmol) in ethanol (10 mL) was added hydrazine hydrate monohydrate (2 mL) and stirred at 90° C. for overnight (~16 h). Evaporated off the reaction mixture under reduced pressure, diluted with ice cold water, precipitated solid was filtered off and dried to afford the title compound (600 mg) as crude. LCMS: 341.1 (M+1)$^+$.

Step-2: tert-butyl ((1r,4r)-4-(2-(6-cyano-1-(naphthalen-1-ylmethyl)-1H-indole-2-carbonyl)hydrazine-1-carbonyl)cyclohexyl)carbamate To a solution of product of step-1 of example-111 (600 mg, 1.764 mmol) and (1r,4r)-4-((tert-butoxycarbonyl)amino)cyclohexane-1-carboxylic acid (471 mg, 1.941 mmol) in DMF was added TBTU (850 mg, 2.646 mmol) and N, N-Diisopropylethylamine (456 mg, 3.528 mmol) and stirred at room temperature for overnight (~16 h). After reaction completion, ice-cold water was added and the precipitated solid was filtered off to give title compound (1.0 g) as crude. LCMS: 466.3 (M−100)$^+$.

Step-3: tert-butyl ((1r,4r)-4-(5-(6-cyano-1-(naphthalen-1-ylmethyl)-1H-indol-2-yl)-1,3,4-oxadiazole-2-carbonyl)cyclohexyl)carbamate To a solution of product of step-2 of example-111 (1.0 g, 1.769 mmol) in acetonitrile was added N, N-Diisopropylethylamine (456 mg, 3.538 mmol) and 4-Toluenesulfonyl chloride (1.0 g, 5.309 mmol) and stirred for 4 h at room temperature. Evaporated reaction mixture under reduced pressure and crude obtained was purified by combiflash on silica gel, eluted with 0.2% methanol in dichloromethane afforded the title compound (750 mg).

Step-4: tert-butyl ((1r,4r)-4-(5-(6-carbamimidoyl-1-(naphthalen-1-ylmethyl)-1H-indol-2-yl)-1,3,4-oxadiazole-2-carbonyl)cyclohexyl)carbamate The product of step-3 of example-111 (1.0 g, 1.769 mmol) was treated consequently in three steps with hydroxyl amine hydrochloride, acetic anhydride followed by hydrogenation with 10% palladium carbon (here hydrogenation carried out in ethanol and acetic acid at room temperature for 3 h) following the procedure described in step-4, step-5 and step-6 of example 100 afforded the 180 mg of title compound. LCMS: 565.4 (M+1)$^+$; $^1$HNMR (300 MHz, CD$_3$OD): δ 1.29-1.17 (m, 4H), 1.43 (s, 9H), 1.91 (s, 3H), 1.98-1.93 (m, 5H), 2.79-2.75 (m, 1H), 6.22-6.19 (d, 1H), 6.57 (s, 2H), 7.19-7.14 (t, 1H), 7.76-7.57 (m, 5H), 7.95-7.93 (d, 1H), 8.04-8.01 (m, 2H), 8.29- 8.26 (d, 1H); HPLC: 91.35% (Retention Time=7.02 min).

Example 112: Synthesis of Compound I-525

2-(5-((1r,4r)-4-aminocyclohexyl)-1,3,4-oxadiazol-2-yl)-1-(naphthalen-1-ylmethyl)-1H-indole-6-carboximidamide

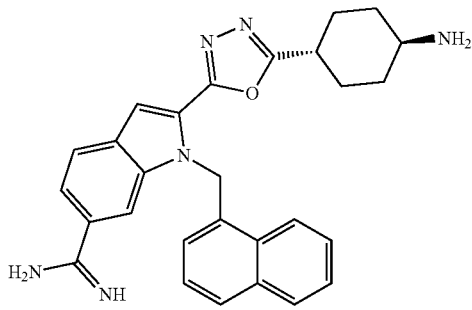 [SMILES: N=C(N)c1ccc2cc(-c3nnc([C@H]4CC[C@H](N)CC4)o3)n(Cc3cccc4ccccc34)c2c1]

The product of step-4 of example-111 (1.0 g, 1.769 mmol) was treated with TFA (0.3 mL) following the procedure described in step-6 of example 88. The crude product obtained was triturated with diethyl ether afforded the title compound (140 mg) as a TFA salt. LCMS: 465.2 (M+1)$^+$; $^1$HNMR (400 MHz, CD$_3$OD): δ 1.45-1.42 (m, 4H), 2.07-2.04 (m, 4H), 3.00-2.80 (m, 2H), 6.35-6.25 (d, 1H), 6.58 (s, 2H), 7.20-7.15 (t, 1H), 7.76-7.61 (m, 5H), 7.95-7.93 (d, 1H), 8.04-8.02 (m, 2H), 8.30-8.28 (d, 1H); HPLC: 95.29% (Retention Time=5.23 min).

General synthetic scheme-19A

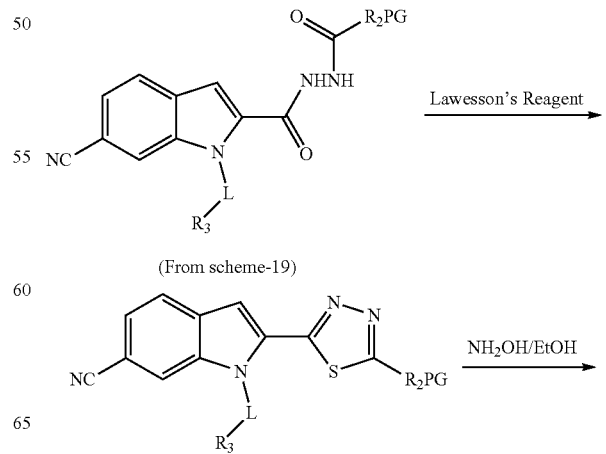

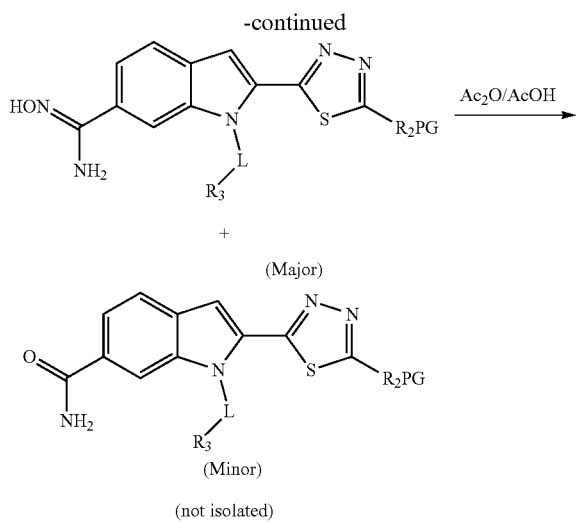

(Major)

(Minor)

(not isolated)

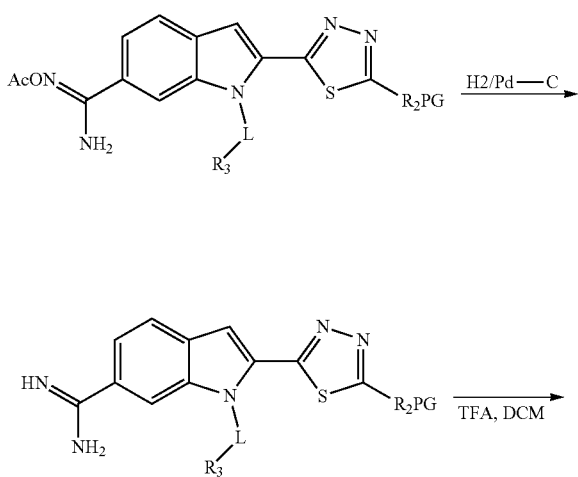

PG = optional protecting group; X = Br or Cl;

Example 113: Synthesis of Compound I-526

2-(5-((1r,4r)-4-aminocyclohexyl)-1,3,4-thiadiazol-2-yl)-1-(naphthalen-1-ylmethyl)-1H-indole-6-carboximidamide

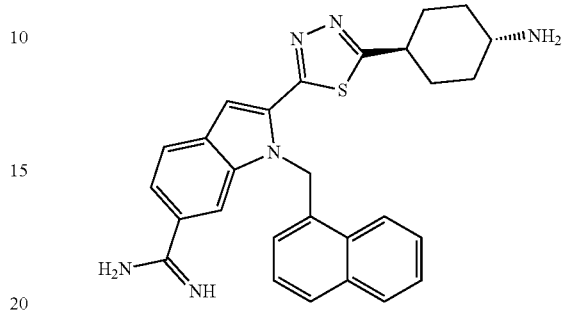

Step-1: tert-butyl ((1r,4r)-4-(5-(6-cyano-1-(naphthalen-1-ylmethyl)-1H-indol-2-yl)-1,3,4-thiadiazole-2-carbonyl)cyclohexyl)carbamate To a solution of product of step-2 of example-111 (450 mg, 0.796 mmol) was added Lawesson's reagent (643 mg, 1.592 mmol) and irradiated in microwave at 120° C. for 1.5 h. After reaction completion, ice cold water was added, extracted with ethyl acetate (2×20 mL). The organic layers separated, dried over sodium sulphate and concentrated under reduced pressure. The crude obtained was purified by combiflash on silica gel, eluted with 30% ethyl acetate in hexane afforded the title compound (30 mg). LCMS: 492.4 (M−100)$^+$.

Step-2: tert-butyl ((1r,4r)-4-(5-(6-carbamimidoyl-1-(naphthalen-1-ylmethyl)-1H-indol-2-yl)-1,3,4-thiadiazole-2-carbonyl)cyclohexyl)carbamate The product of step-1 of example-113 (310 mg, 0.550 mmol) was treated consequently in three steps with hydroxyl amine hydrochloride, acetic anhydride followed by hydrogenation with 10% palladium carbon (here hydrogenation carried out in methanol for 3 h) following the procedure described in step-4, step-5 and step-6 of example 100 afforded the 170 mg of title compound. LCMS: 609.5 (M+1)$^+$.

Step-3: 2-(5-((1r,4r)-4-aminocyclohexyl)-1,3,4-thiadiazol-2-yl)-1-(naphthalen-1-ylmethyl)-1H-indole-6-carboximidamide The product of step-2 of example-113 (170 mg, 0.293 mmol) was treated with TFA (0.3 mL) following the procedure described in step-6 of example 88. The crude obtained was purified by preparative HPLC instrument using Zorbax ECLIPSR XDB C18 reverse phase column (21.2×150 mm, 5 micron). The mobile phases were 10% acetonitrile:methanol (1:1) in water (0.1% TFA) to 50% acetonitrile:methanol (1:1) in water (0.1% TFA) which afforded the title compound (15 mg) as a TFA Salt.

LCMS: 481.3 (M+1)$^+$; $^1$HNMR (400 MHz, CD$_3$OD): δ 1.72-1.53 (m, 4H), 2.27-2.13 (m, 4H), 3.18-3.14 (m, 2H), 6.24-6.22 (d, 1H), 6.66 (s, 2H), 7.19-7.15 (t, 1H), 7.48 (s,

1H), 7.75-7.60 (m, 4H), 8.01-7.92 (m, 3H), 8.26-8.24 (d, 1H); HPLC: 96.46% (Retention Time=4.43 min).

Example 114: Synthesis of Compound I-527

2-(5-((1r,4r)-4-aminocyclohexyl)-1,3,4-thiadiazol-2-yl)-1-(naphthalen-1-ylmethyl)-1H-indole-6-carboxamide

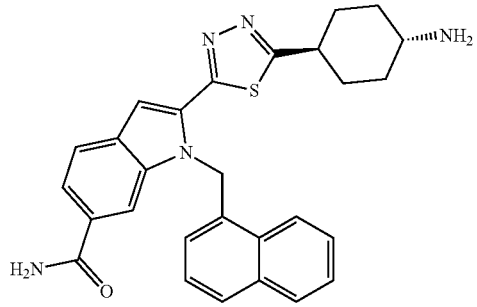 [SMILES: NC(=O)c1ccc2cc(-c3nnc([C@H]4CC[C@H](N)CC4)s3)n(Cc3cccc4ccccc34)c2c1]

The title compound mentioned above was isolated (20 mg) as TFA salt in preparative HPLC purification of product of step-3 of example-113

LCMS: 482.3 (M+1)$^+$; $^1$HNMR (400 MHz, CD$_3$OD): δ 1.70-1.50 (m, 4H), 2.25-2.10 (m, 4H), 3.15-3.07 (m, 2H), 6.21-6.18 (d, 1H), 6.59 (s, 2H), 7.16-7.10 (t, 1H), 7.35 (s, 1H), 7.74-7.54 (m, 4H), 7.91-7.81 (m, 2H), 8.01 (s, 1H), 8.24-8.21 (d, 1H); HPLC: 98.70% (Retention Time=5.99 min).

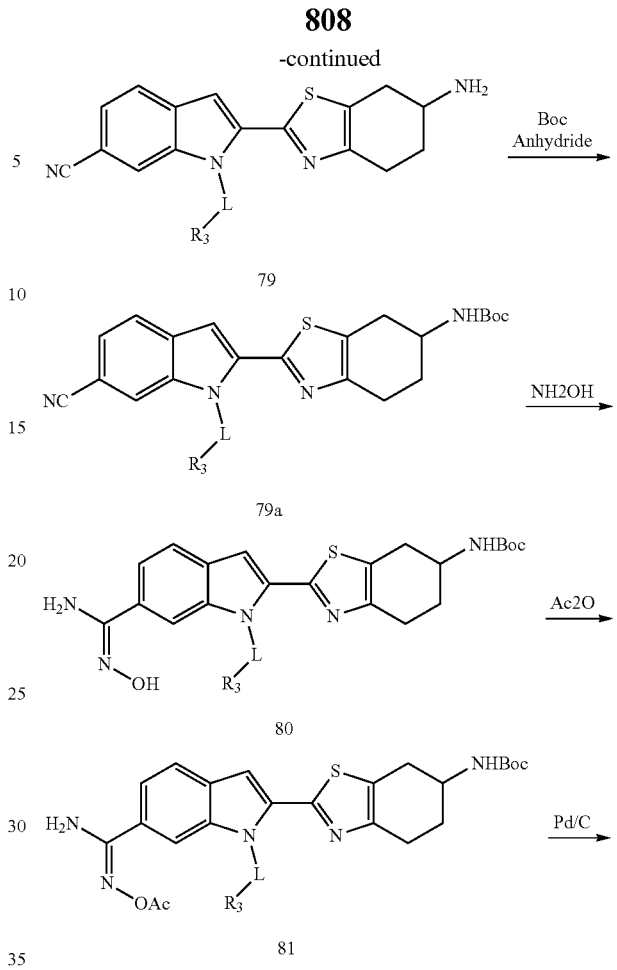

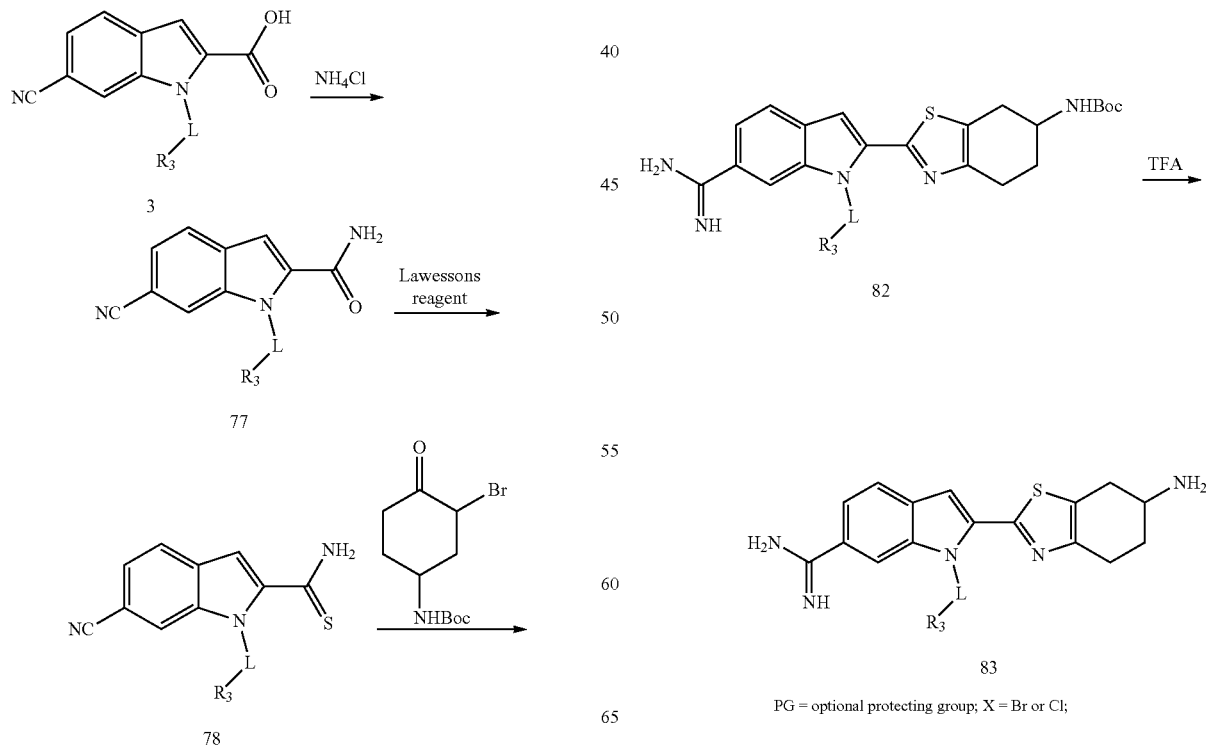

General synthetic scheme-19B

PG = optional protecting group; X = Br or Cl;

Example 115: Synthesis of Compound I-528

2-(5-amino-4,5,6,7-tetrahydrobenzo[d]thiazol-2-yl)-1-(naphthalen-1-ylmethyl)-1H-indole-6-carboximidamide

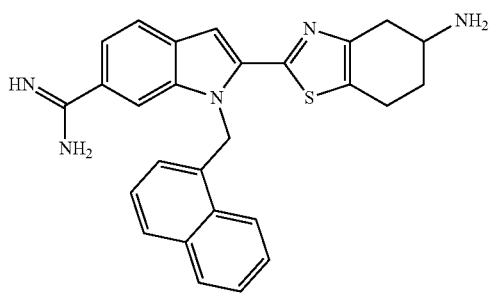 [SMILES: N=C(N)c1ccc2cc(-c3nc4c(s3)CCC(N)C4)n(Cc3cccc4ccccc34)c2c1]

Step-1: 6-cyano-1-(naphthalen-1-ylmethyl)-1H-indole-2-carboxamide

Product of step-2 of example 1 (400 mg, 1.2 mmol) was treated with ammonium chloride (135 mg, 2.4 mmol) following the procedure described in step-6 of example 398 afforded the title compound (400 mg) as crude. LCMS: 324.4 (M+1)$^+$.

Step-2: 6-cyano-1-(naphthalen-1-ylmethyl)-1H-indole-2-carbothioamide

To a solution of product of step-1 of example-115 (350 mg, 1.0 mmol) in THF (5 mL) was added Lawesson's reagent (810 mg, 2.0 mmol) and irradiated in microwave at 150° C. for 1 h. Evaporated the reaction mixture and crude obtained was purified by combiflash on silica gel eluted with 30% ethyl acetate in hexane afforded the title compound (180 mg). LCMS: 342.1 (M+1)$^+$.

Step-3: 2-(5-amino-4,5,6,7-tetrahydrobenzo[d]thiazol-2-yl)-1-(naphthalen-1-ylmethyl)-1H-indole-6-carbonitrile To a solution of product of step-2 of example-115 (50 mg, 0.114 mmol) in ethanol (2 mL) was added tert-butyl (3-bromo-4-oxocyclohexyl)carbamate (50 mg, 0.180 mmol) and resulting reaction mixture was refluxed for 6 h. Evaporated off reaction mixture under reduce pressure afforded the title compound (110 mg) as crude. LCMS: 435.15 (M+1)$^+$.

Step-4: tert-butyl (2-(6-cyano-1-(naphthalen-1-ylmethyl)-1H-indol-2-yl)-4,5,6,7-tetrahydrobenzo[d]thiazol-5-yl)carbamate To a stirred solution of product of step-3 of example 115 (340 mg, 0.78 mmol) and N,N-diisopropylethylamine (0.150 ml, 0.780 mmol) in THF (10 mL) was added di-tert-butyl dicarbonate (0.20 mL, 0.780 mmol). The resulting reaction mixture was stirred for 3 h at room temperature. After reaction completion, water was added and extracted with ethyl acetate. Organic layer separated, dried over sodium sulphate and concentrated under reduced pressure. The crude obtained above was purified by combiflash on silica gel eluted with 20% ethyl acetate in hexane afforded the title compound (80 mg). LCMS: 535.2 (M+1)$^+$.

Step-5: tert-butyl (2-(6-carbamimidoyl-1-(naphthalen-1-ylmethyl)-1H-indol-2-yl)-4,5,6,7-tetrahydrobenzo[d] thiazol-5-yl) carbamate The product of step-4 of example 115 (80 mg, 0.150 mmol) was treated consequently in three steps with hydroxyl amine hydrochloride, acetic anhydride followed by hydrogenation with 10% palladium carbon (here hydrogenation carried out in methanol for 4 h) following the procedure described in step-4, step-5 and step-6 of example 100 afforded the 50 mg of title compound as crude. LCMS: 552.25 (M+1)$^+$.

Step-6: 2-(5-amino-4,5,6,7-tetrahydrobenzo[d]thiazol-2-yl)-1-(naphthalen-1-ylmethyl)-1H-indole-6-carboximidamide The product of step-5 of example 115 (50 mg, 0.01 mmol) was treated with TFA (0.2 mL) following the procedure described in step-6 of example 88. The crude obtained was purified by preparative HPLC instrument using Kinetex C18 reverse phase column (21.2×150 mm, 5 micron). The mobile phases were 10% acetonitrile:methanol (1:1) in water (0.1% TFA) to 55% acetonitrile:methanol (1:1) in water (0.1% TFA) which afforded the title compound (5 mg) as a TFA Salt.

LCMS: 452.3 (M+1)$^+$; $^1$HNMR (400 MHz, CD$_3$OD): δ 1.55-1.16 (m, 2H), 1.86-2.0 (m, 1H), 2.05-2.10 (m, 1H), 2.70-2.90 (m, 2H), 3.22-3.28 (m, 1H), 3.45-3.48 (m, 1H), 3.63-3.65 (m, 1H), 6.25 (d, 1H), 6.66 (s, 2H), 7.16 (t, 1H), 7.34 (s, 1H), 7.58-7.60 (m, 2H), 7.63-7.72 (m, 2H), 7.92-7.96 (m, 3H), 8.26 (d, 1H); HPLC: 96.82% (Retention Time=5.15 min).

General synthetic scheme-20

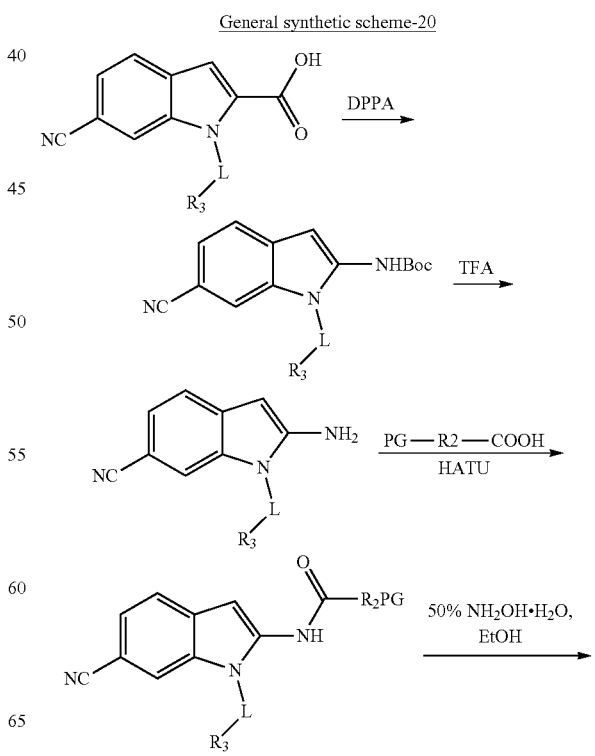

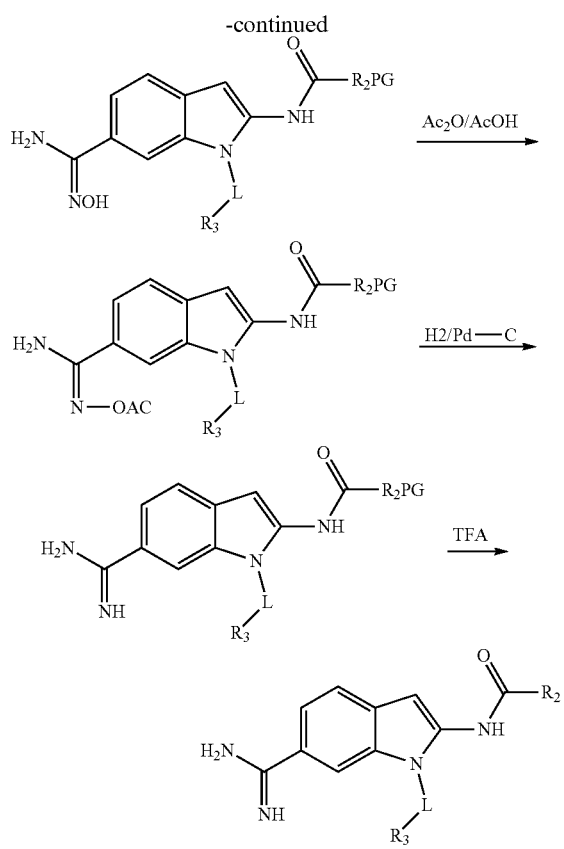

PG = optional protecting group; X = Br or Cl;

Example 116: Synthesis of Compound I-529

(1r,4r)-4-amino-N-(6-carbamimidoyl-1-(naphthalen-1-ylmethyl)-1H-indol-2-yl) cyclohexane-1-carboxamide

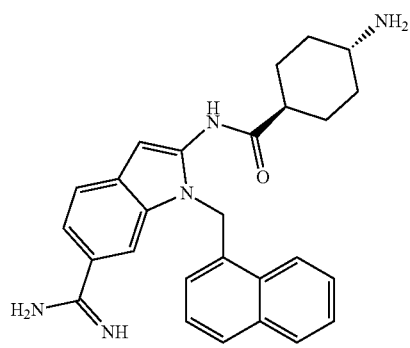 [SMILES: N=C(N)c1ccc2cc(NC(=O)[C@H]3CC[C@H](N)CC3)n(Cc3cccc4ccccc34)c2c1]

Step-1: tert-butyl (6-cyano-1-(naphthalen-1-ylmethyl)-1H-indol-2-yl) carbamate

To a solution of product of step-2 of example 79 (1.0 g, 3.067 mmol) in toluene (5 mL) and tert-butanol (1.0 mL) was added Diphenylphosphoryl azide (338 mg, 1.226 mmol) followed by addition of N,N-diisopropylethylamine (0.352 mL, 2.02 mmol) at room temperature. The resulting reaction mixture was stirred at 80° C. for overnight. After reaction completion evaporated off the reaction mixture, added ice cold water, extracted with ethyl acetate (2×20 mL) and separated organic layer was concentrated. The crude obtained was purified by combiflash on silica gel eluted with 20% ethyl acetate in hexane afforded the 70 mg of title compound. LCMS: 398.2 (M+1)$^+$.

Step-2: 2-amino-1-(naphthalen-1-ylmethyl)-1H-indole-6-carbonitrile

The product of step-1 of example 116 (655 mg, 1.649 mmol) was treated with TFA (1.0 mL) afforded the title compound (500 mg) as a TFA salt following the procedure described in step-6 of example 88. LCMS: 298.1 (M+1)$^+$.

Step-3: tert-butyl ((1r,4r)-4-((6-cyano-1-(naphthalen-1-ylmethyl)-1H-indol-2-yl)carbamoyl)cyclohexyl) carbamate The product of step-2 of example 116 (250 mg, 0.608 mmol) and (1r,4r)-4-((tert-butoxycarbonyl) amino) cyclohexane-1-carboxylic acid (178 mg, 0.729 mmol) treated together afforded the title product following the procedure described in step-3 of example 81, which was purified by combiflash on silica gel eluted with 1% methanol in dichloromethane to give title compound (180 mg). LCMS: 523.3 (M+1)$^+$.

Step-4: tert-butyl ((1r,4r)-4-((6-carbamimidoyl-1-(naphthalen-1-ylmethyl)-1H-indol-2-yl)carbamoyl) cyclohexyl) carbamate The product of step-3 of example 116 (180 mg, 0.344 mmol) was treated consequently in three steps with hydroxyl amine hydrochloride, acetic anhydride followed by hydrogenation with 10% palladium carbon (here hydrogenation carried out in methanol for 2 h) following the procedure described in step-4, step-5 and step-6 of example 100 afforded the 60 mg of title compound as crude. LCMS: 540.4 (M+1)$^-$.

Step-5: (1r,4r)-4-amino-N-(6-carbamimidoyl-1-(naphthalen-1-ylmethyl)-1H-indol-2-yl)cyclohexane-1-carboxamide The product of step-4 of example 116 (60 mg, 0.111 mmol) was treated with TFA (0.2 mL) afforded the crude product following the procedure described in step-6 of example 88. The crude obtained was purified by preparative HPLC instrument using LUNA C18 reverse phase column (20×250 mm, 5 micron). The mobile phases were 10% acetonitrile in water (0.1% TFA) to 50% acetonitrile in water (0.1% TFA) which afforded the title compound (30 mg) as a TFA salt.

LCMS: 440.3 (M+1)$^+$; $^1$HNMR (300 MHz, CD$_3$OD): δ 1.48-1.24 (m, 4H), 1.97-1.71 (m, 4H), 2.29-2.25 (m, 1H), 2.99-2.98 (m, 1H), 6.02 (s, 2H), 6.30-6.28 (d, 1H), 6.82 (s, 1H), 7.25-7.20 (t, 1H), 7.68-7.52 (m, 3H), 7.95-7.77 (m, 4H), 8.20-8.18 (d, 1H); HPLC: 98.03% (Retention Time=5.15 min.)

General synthetic scheme-21

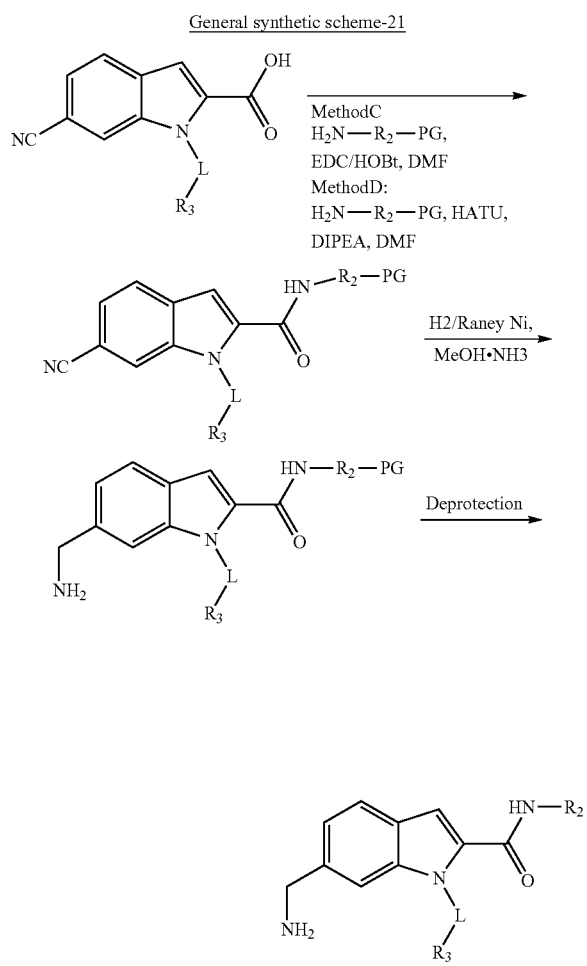

PG = optional protecting group; X = Br or Cl;

Example 117: Synthesis of Compound I-530 tert-butyl ((1r,4r)-4-(6-(aminomethyl)-1-(naphthalen-1-ylmethyl)-1H-indole-2-carboxamido)cyclohexyl) carbamate

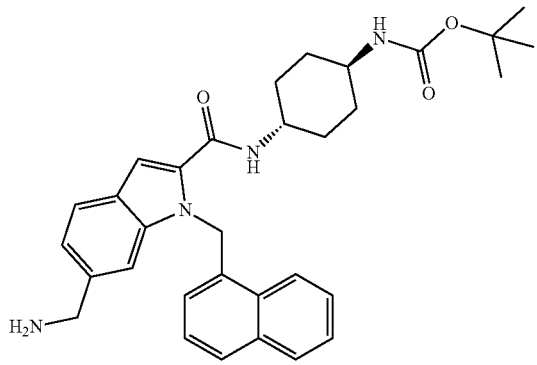 [SMILES: CC(C)(C)OC(=O)N[C@H]1CC[C@H](NC(=O)c2cc3ccc(CN)cc3n2Cc2cccc3ccccc23)CC1]

Step-1: tert-butyl ((1r,4r)-4-(6-cyano-1-(naphthalen-1-ylmethyl)-1H-indole-2-carboxamido) cyclohexyl) carbamate Product of step-2 of example 81 (100 mg, 0.300 mmol) and tert-butyl ((1r,4r)-4-aminocyclohexyl) carbamate (78 mg, 0.300 mmol) were treated together afforded the title compound (150 mg) following the procedure described in step-3 of example 79. (In this step the solid precipitated out was filtered and dried to get the title compound). LCMS: 521.75 (M−1)*.

Step-2: tert-butyl ((1r,4r)-4-(6-(aminomethyl)-1-(naphthalen-1-ylmethyl)-1H-indole-2-carboxamido) cyclohexyl) carbamate To stirred solution of product of step-1 of example 117 (130 mg, 0.200 mmol) in methanol was added Raney Ni (50 mg) and methanolic ammonia (5 mL). The resultant suspension was stirred at room temperature for overnight under the hydrogen atmosphere (balloon filled with hydrogen gas). After reaction completion, the reaction mixture was filtered through celite bed, washed with 10% methanol in dichloromethane and filtrate was concentrated under reduced pressure. The crude obtained was purified by preparative HPLC instrument using XBridge C18 reverse phase column (20.0× 150 mm, 5 micron). The mobile phases were 30% acetonitrile in water (10 mM ammonium bicarbonate) to 70% acetonitrile in water (10 mM ammonium bicarbonate) which afforded the title compound (12 mg).

LCMS: 528.4 (M+1)$^+$; $^1$HNMR (DMSO-d$_6$, 400 MHz): δ1.26-1.11 (m, 4H), 1.33 (s, 9H), 1.74-1.67 (m, 4H), 3.20-3.15 (m, 1H), 3.58-3.51 (m, 1H), 3.72 (s, 2H), 6.12-6.10 (d, 1H), 6.34 (s, 2H), 6.70-6.68 (d, 1H), 7.33-7.10 (m, 4H), 7.67-7.58 (m, 3H), 7.77-7.74 (d, 1H), 7.98-7.96 (d, 1H), 8.31-8.24 (m, 2H); HPLC: 95.15% (Retention Time=6.08 min)

Example 118: Synthesis of Compound I-531

N-((1r,4r)-4-aminocyclohexyl)-6-(aminomethyl)-1-(naphthalen-1-ylmethyl)-1H-indole-2-carboxamide

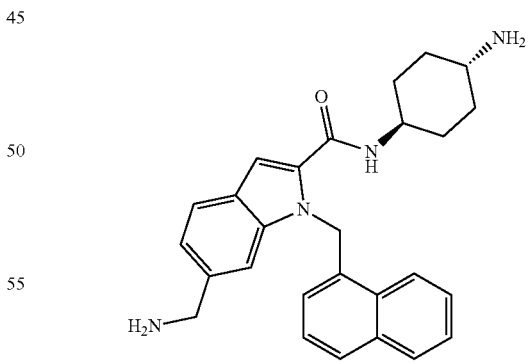

Product of step-2 of example 117 (80 mg, 0.150 mmol) was treated with TFA (0.2 mL) afforded the crude product (130 mg) following the procedure described in step-6 of example 88. The crude obtained was purified by preparative HPLC instrument using Zorbax C18 reverse phase column (21.2×150 mm, 5 micron). The mobile phases were 5% acetonitrile:methanol (1:1) in water (0.05% TFA) to 60% acetonitrile:methanol (1:1) in water (0.05% TFA) which afforded the title compound (45 mg) as a TFA salt. LCMS: 428.3 (M+1)+; ¹HNMR (DMSO-D₂O, 400 MHz): δ1.30-1.29 (m, 4H), 1.91-1.65 (m, 4H), 3.01-2.90 (m, 4H), 3.58-3.50 (m, 4H), 3.99 (s, 2H), 6.07-6.05 (d, 1H), 6.26 (s, 2H), 7.19-7.10 (m, 2H), 7.22 (s, 3H), 7.43 (s, 1H), 7.65-7.50 (m, 2H), 7.78-7.75 (m, 2H), 7.95-7.90 (d, 1H), 8.25-8.20 (d, 1H); HPLC: 99.51% (Retention Time=5.59 min).

The following compound listed in table-36 prepared according to general scheme-21 by following similar procedure as described above for example 118 using appropriate reagents with suitable modifications known to the one skilled in the art.

TABLE 36

Compounds synthesized using General Scheme-21

| Cpd. ID. | Structure | LCMS [M + H]⁺ | ¹H-NMR Data |
|---|---|---|---|
| I-532 | 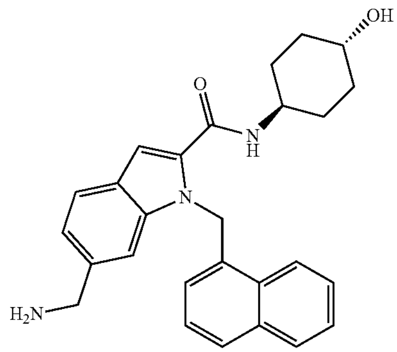 [SMILES: NCc1ccc2cc(C(=O)N[C@H]3CC[C@H](O)CC3)n(Cc3cccc4ccccc34)c2c1] | 411.2 | ¹HNMR(400 MHz, CD₃OD): δ1.40-1.20 (m, 4H), 1.90-1.75 (m, 4H), 3.50-3.45 (m, 1H), 3.70-3.60 (m, 1H), 4.11 (s, 2H), 6.25-6.20(d, 1H), 6.36 (s, 2H), 7.25-7.10 (m, 3H), 7.43 (s, 1H), 7.65-7.55 (m, 2H), 7.90-7.70 (m, 3H), 8.20(d, 1H). |
| I-533 | 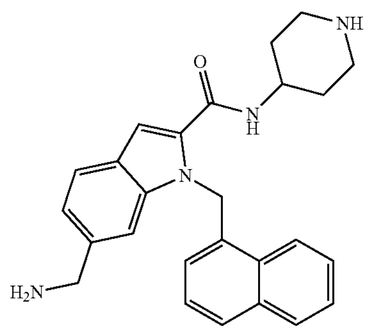 [SMILES: NCc1ccc2cc(C(=O)NC3CCNCC3)n(Cc3cccc4ccccc34)c2c1] | 413.3 | ¹HNMR(300 MHz, CD₃OD): δ1.79-.65(m, 2H), 2.03-1.99(m, 2H), 3.07-2.97(m, 2H), 3.38-3.32(m, 2H), 3.99-3.91(m, 1H), 4.12(s, 2H), 6.21-6.19(d, 1H), 6.38(s, 2H), 7.18-7.12(t, 1H), 7.27-7.22(m, 2H), 7.47 (s, 1H), 7.58-7.53(m, 2H), 7.65-7.58(m, 1H), 7.73-7.70(m, 1H), 7.91-7.89(m, 1H), 8.21-8.19(m, 1H). |
| I-534 | 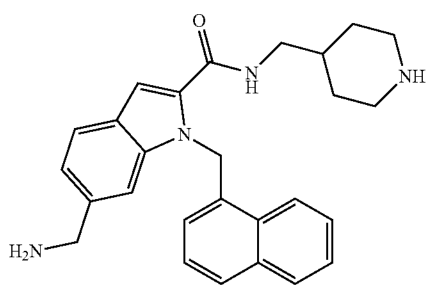 [SMILES: NCc1ccc2cc(C(=O)NCC3CCNCC3)n(Cc3cccc4ccccc34)c2c1] | 427.3 | ¹HNMR(400 MHz, CD₃OD): δ1.29-.20(m, 2H), 1.68-1.63(m, 3H), 2.76-2.67(m, 2H), 3.23-3.14(m, 4H), 4.14(s, 2H), 6.15-6.12 (m, 1H), 6.38(s, 2H), 7.17-7.12(m, 1H), 7.26-7.21(m, 2H), 7.51(s,1H), 7.67-7.54(m, 2H), 7.73-7.71(m, 1H), 7.83-7.80(m, 1H), 7.92-7.90(m, 1H), 8.23-8.20(m, 1H). |
| I-535 | 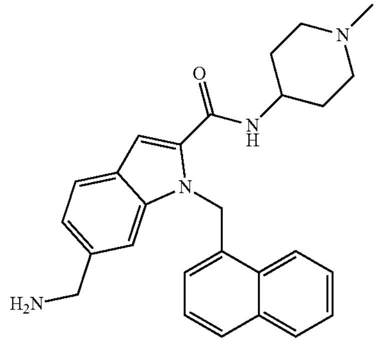 [SMILES: CN1CCC(NC(=O)c2cc3ccc(CN)cc3n2Cc2cccc3ccccc23)CC1] | 426.95 | ¹HNMR(300 MHz, CD₃OD): δ1.56-1.53 (m, 2H), 1.78-1.74 (m, 2H), 2.08-2.00 (m, 2H), 2.22 (s, 3H), 2.81-2.78 (m, 2H), 3.67 (m, 1H), 3.84 (m, 1H), 6.26 (m, 1H), 6.33 (s, 2H), 7.17-7.14 (m, 3H), 7.31 (m, 1H), 7.59-7.55 (m, 2H), 7.70-7.68 (m, 2H), 7.86 (m, 1H), 8.17 (m, 1H). |

General synthetic scheme-21A

General synthetic scheme -21B

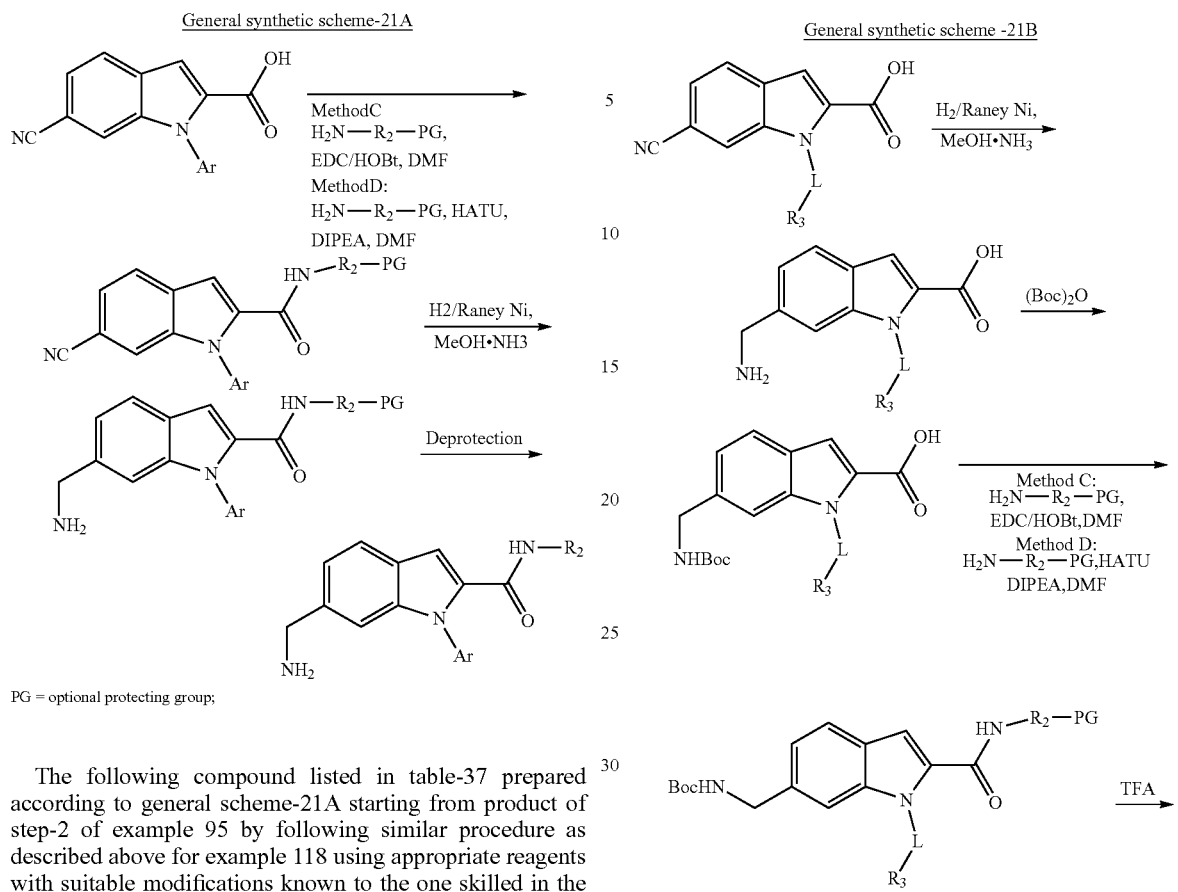

PG = optional protecting group;

The following compound listed in table-37 prepared according to general scheme-21A starting from product of step-2 of example 95 by following similar procedure as described above for example 118 using appropriate reagents with suitable modifications known to the one skilled in the art.

TABLE 37

Compounds synthesized using General Scheme-21A

| Cpd. ID. | Structure | LCMS [M + H]+ | $^1$H-NMR Data |
|---|---|---|---|
| I-536 | 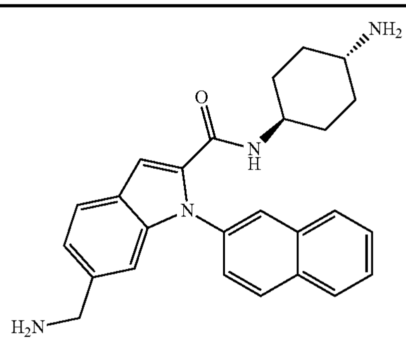 | 414.4 | $^1$HNMR(400 MHz, CD$_3$OD): δ1.48-1.41 (m, 4H), 2.04-1.96 (m, 4H), 3.10-3.00 (m, 1H), 3.70-3.60 (m, 1H), 4.12 (s, 2H), 7.20 (s, 1H), 7.24-7.21(d, 1H), 7.35 (s, 1H), 7.45-7.42 (m, 1H), 7.59-7.57 (m, 2H), 7.81-7.79(d, 1H), 8.00-7.82 (m, 4H). |
| I-537 | 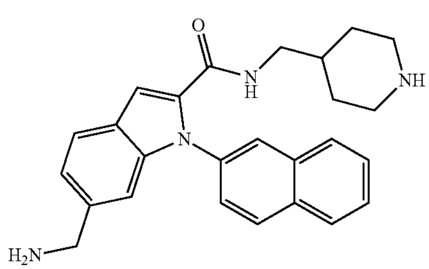 [SMILES: NCc1ccc2cc(C(=O)NCC3CCNCC3)n(-c3ccc4ccccc4c3)c2c1] | 412.95 | $^1$HNMR(400 MHz, CD$_3$OD): δ1.35-1.25 (m, 2H), 1.80-1.70 (m, 3H), 2.75-2.70(t, 2H), 3.25-3.15 (m, 4H), 4.13 (s, 2H), 7.22 (s, 1H), 7.24-7.21(d, 1H), 7.35 (s, 1H), 7.45-7.42 (m, 1H), 7.60-7.58 (m, 2H), 8.05-7.75 (m, 5H). |

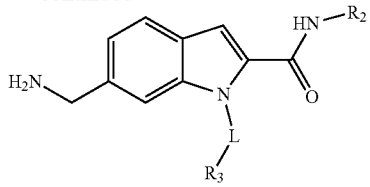

PG = optional protecting group; X = Br or Cl;

Example 119: Synthesis of Compound I-538

6-(aminomethyl)-1-(naphthalen-1-ylmethyl)-1H-indole-2-carboxylic Acid

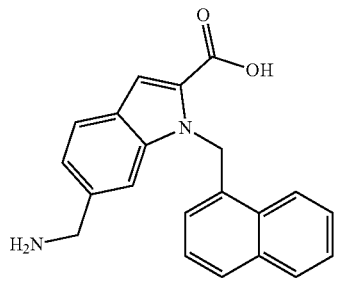 [SMILES: NCc1ccc2cc(C(=O)O)n(Cc3cccc4ccccc34)c2c1]

Step-1: 6-(aminomethyl)-1-(naphthalen-1-ylmethyl)-1H-indole-2-carboxylic Acid

Product of step-2 of example 398 (1.0 g, 3.06 mmol) was treated with Raney Ni (200 mg) in methanolic ammonia (50 mL) under hydrogen atmosphere at room temperature afforded the title compound (1.10 g) following the procedure described in step-2 of example 117. LCMS: 331.1 (M+1)$^+$; $^1$H NMR (400 MHz, CD$_3$OD): δ 4.12 (s, 2H), 6.15 (d, 1H), 6.46 (s, 2H), 7.17 (t, 1H), 7.25 (d, 1H), 7.43 (s, 1H), 7.52 (s, 1H), 7.58 (t, 1H), 7.66 (t, 1H), 7.73 (d, 1H), 7.86-7.92 (dd, 1H), 8.25 (d, 1H); HPLC: 99.61% (Retention Time=5.89 min).

Example 120: Synthesis of Compound I-539

6-(((tert-butoxycarbonyl) amino)methyl)-1-(naphthalen-1-ylmethyl)-1H-indole-2-carboxylic Acid

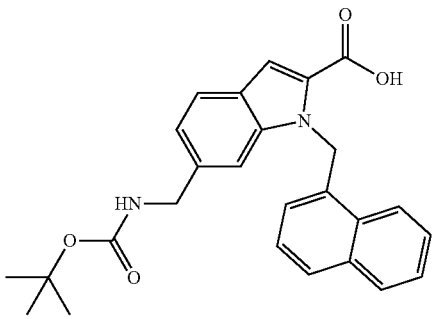 [SMILES: CC(C)(C)OC(=O)NCc1ccc2cc(C(=O)O)n(Cc3cccc4ccccc34)c2c1]

Step-1: 6-(((tert-butoxycarbonyl) amino)methyl)-1-(naphthalen-1-ylmethyl)-1H-indole-2-carboxylic Acid Product of step-1 of example 119 (600 mg, 1.816 mmol) was treated with di-tert-butyl dicarbonate (594 mg, 2.72 mmol) afforded the crude product (506 mg) following the procedure described in step-2 of example 90. The crude obtained above was purified by preparative TLC (Mobile phase: 3% methanol in dichloromethane, run twice) afforded the title compound (14 mg). LCMS: 429.2 (M+1)$^+$; $^1$H NMR (400 MHz, CD$_3$OD): δ1.27-1.30 (d, 9H), 4.24 (s, 2H), 6.20 (d, 1H), 6.43 (s, 2H), 7.04-7.12 (m, 1H), 7.14-7.22 (m, 2H), 7.64 (m, 2H), 7.41 (s, 1H), 7.70 (dd, 2H), 7.91 (d, 1H), 8.25 (d, 1H); HPLC: 97.76% (Retention Time=6.68 min).

The following compound listed in table-38 prepared according to general scheme-21B starting from example 120 by following similar procedure as described above for example 117 and 118 using appropriate reagents with suitable modifications known to the one skilled in the art.

TABLE 38

Compounds synthesized using General Scheme-21B

| Cpd. ID. | Structure | LCMS [M + H]$^+$ | $^1$H-NMR Data |
|---|---|---|---|
| 540 | 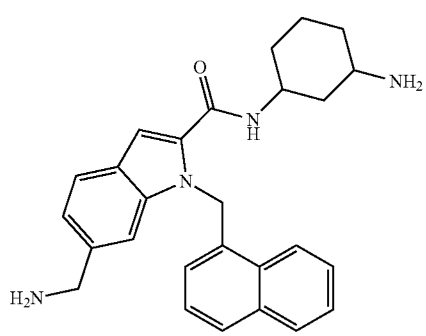 [SMILES: NCc1ccc2cc(C(=O)NC3CCCC(N)C3)n(Cc3cccc4ccccc34)c2c1] | 427.4 | $^1$H NMR(400 MHz, CD$_3$OD): δ 1.25-1.45 (m, 2H), 1.55-1.80 (m, 2H), 1.81-1.91 (m, 2H), 1.95-2.01 (m, 1H), 2.25-2.30 (m, 1H), 3.06-3.17 (m, 1H), 3.75-3.85 (m, 1H), 4.14 (s, 2H), 6.19-6.22 (m, 1H), 6.39-6.49 (m, 2H), 7.15-7.29 (m, 3H), 7.58-7.65 (m, 2H), 7.46 (s, 1H), 7.72-7.74 (d, 1H), 7.81-7.86 (m, 1H), 7.92-7.94 (m, 1H), 8.21-8.24 (m, 1H). |

TABLE 38-continued
Compounds synthesized using General Scheme-21B
| Cpd. ID. | Structure | LCMS [M + H]+ | 1H-NMR Data |
|---|---|---|---|
| 541 | 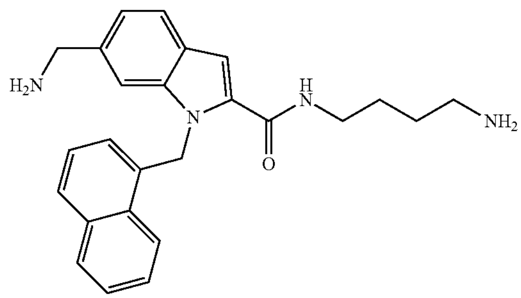 [SMILES: NCCCCNC(=O)c1cc2ccc(CN)cc2n1Cc1cccc2ccccc12] | 401.2 | 1H NMR (400 MHz, CD3OD): δ 1.57-1.59 (m, 4H), 2.79-2.89 (m, 2H), 3.27-3.29 (m, 2H), 4.14 (s, 2H), 6.19 (dd, 1H), 6.43 (s, 2H), 7.14-7.21 (m, 1H), 7.24-7.28 (m, 2H), 7.46 (s, 1H), 7.56-7.68 (m, 2H), 7.74 (d, 1H), 7.83 (d, 1H), 7.90-7.96 (m, 1H), 8.21-8.27 (m, 1H). |
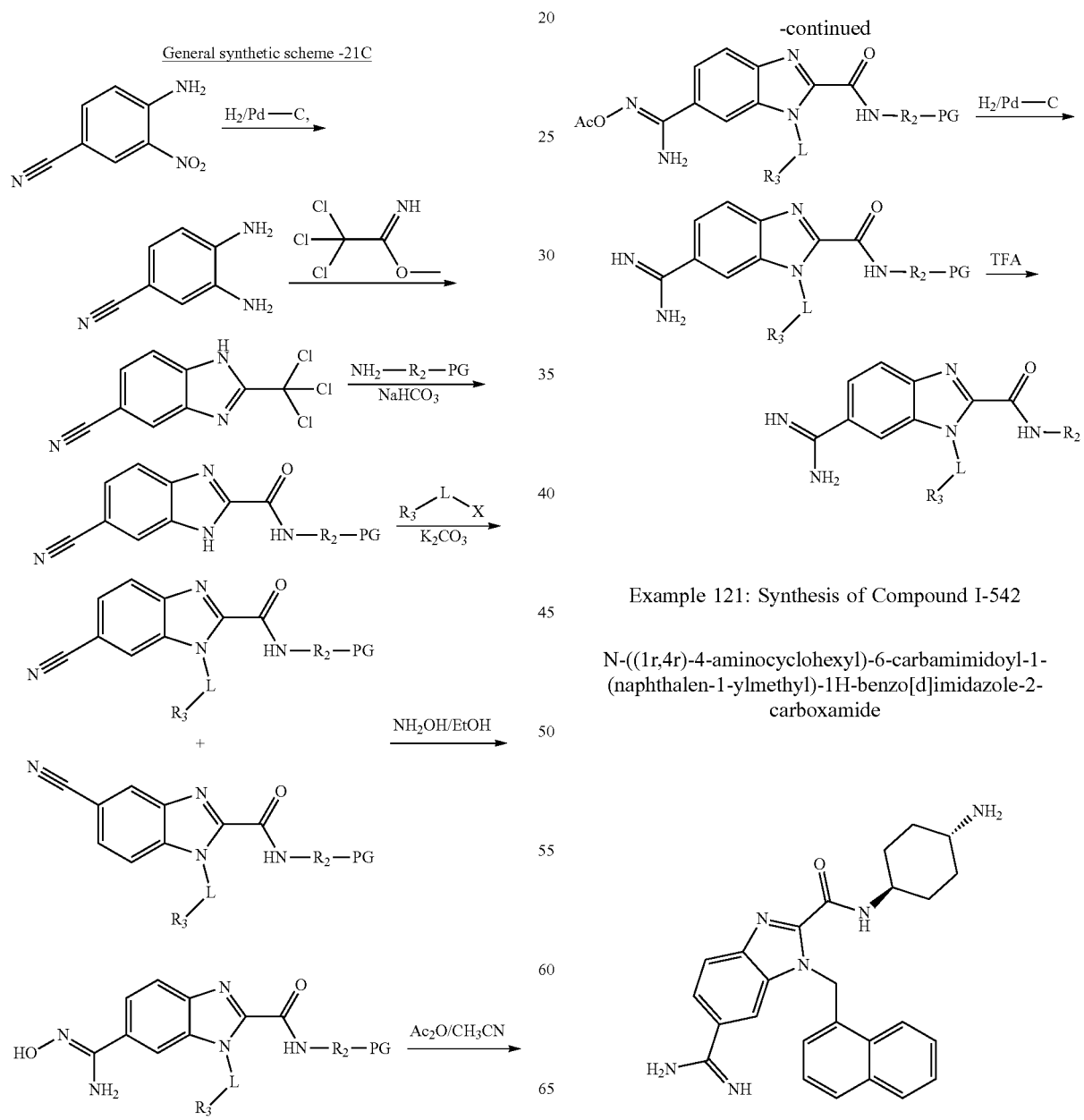
Example 121: Synthesis of Compound I-542
N-((1r,4r)-4-aminocyclohexyl)-6-carbamimidoyl-1-(naphthalen-1-ylmethyl)-1H-benzo[d]imidazole-2-carboxamide

Step-1: 2-(trichloromethyl)-1H-benzo[d]imidazole-6-carbonitrile

The title compound mentioned above was prepared as described in *Bioorganic and Medicinal Chemistry Letters*, 2010, vol. 20, #2, p. 586-590

Step-2: tert-butyl ((1r,4r)-4-(6-cyano-1H-benzo[d]imidazole-2-carboxamido)cyclohexyl)carbamate Product of step-1 of example 121 in 30 mL of THF: Water (2:1) was added sodium bicarbonate (1.6 g, 19.2 mmol), stirred for 10 min at room temperature and was added tert-butyl ((1r,4r)-4-aminocyclohexyl)carbamate (411 mg, 1.92 mmol). The resultant reaction mixture was stirred at room temperature for 4 h. Evaporated off the reaction mixture under reduced pressure, water was added and extracted with dichloromethane. Separated the organic layers, dried over sodium sulphate and concentrated under reduced pressure afforded the title compound (540 mg). LCMS: 382.30 (M−1)$^+$.

Step-3: tert-butyl ((1r,4r)-4-(6-cyano-1-(naphthalen-1-ylmethyl)-1H-benzo[d]imidazole-2-carboxamido)cyclohexyl) carbamate (Polar) & tert-butyl ((1r,4r)-4-(5-cyano-1-(naphthalen-1-ylmethyl)-1H-benzo[d]imidazole-2-carboxamido) cyclohexyl) carbamate (Non-Polar)

Product of step-2 of example 121 (540 mg, 1.40 mmol) and 1-(bromomethyl) naphthalene (467 mg, 2.11 mmol) were treated together afforded the crude product (340 mg) following the procedure described in step-1 of example 22. The crude product was a mixture of both title polar and non-polar compounds which were separated by combiflash on silica gel (40 g column) eluted with 50% ethyl acetate in hexane afforded the title compound (150 mg) from polar fractions. LCMS: 523.85 (M+1)$^+$.

The non-polar compound isolated (120 mg) was confirmed as regioisomer. LCMS: 523.9 (M+1)$^+$.

Step-4: tert-butyl ((1r,4r)-4-(6-carbamimidoyl-1-(naphthalen-1-ylmethyl)-1H-benzo[d]imidazole-2-carboxamido) cyclohexyl) carbamate The polar product of step-3 of example 121 (150 mg, 0.464 mmol) was treated in consequent three steps with hydroxyl amine (50% in water), acetic anhydride followed by hydrogenation with 10% palladium carbon (here hydrogenation carried out in ethanol at room temperature for 5 h) following the procedure described in step-1, step-2 and step-3 of example 88 afforded the 60 mg of title compound. LCMS: 541.75 (M+1)$^+$.

Step-5: N-((1r,4r)-4-aminocyclohexyl)-6-carbamimidoyl-1-(naphthalen-1-ylmethyl)-1H-benzo[d]imidazole-2-carboxamide The product of step-4 of example 121 (60 mg, 0.110 mmol) was treated with TFA (0.3 mL) afforded the crude product (130 mg) following the procedure described in step-5 of example 81.

The crude obtained was purified by preparative HPLC instrument using Kinetex EVO C18 reverse phase column (21.2×150 mm, 5 micron). The mobile phases were 15% acetonitrile in water (0.1% TFA) to 40% acetonitrile in water (0.1% TFA) which afforded the title compound (30 mg) as a TFA Salt.

LCMS: 441.1 (M+1)$^+$; $^1$H NMR (CD$_3$OD, 300 MHz): δ 1.58-1.48 (m, 4H), 2.07-1.99 (m, 4H), 3.10 (m, 1H), 3.81 (m, 1H), 6.46-6.44 (d, 1H), 6.56 (s, 2H), 7.28-7.23 (t, 1H), 7.65-7.58 (m, 2H), 7.81-7.62 (t, 2H), 7.95-7.92 (m, 1H), 8.08-8.00 (m, 2H), 8.23-8.20 (d, 1H); HPLC: 99.13% (Retention Time=4.63 min).

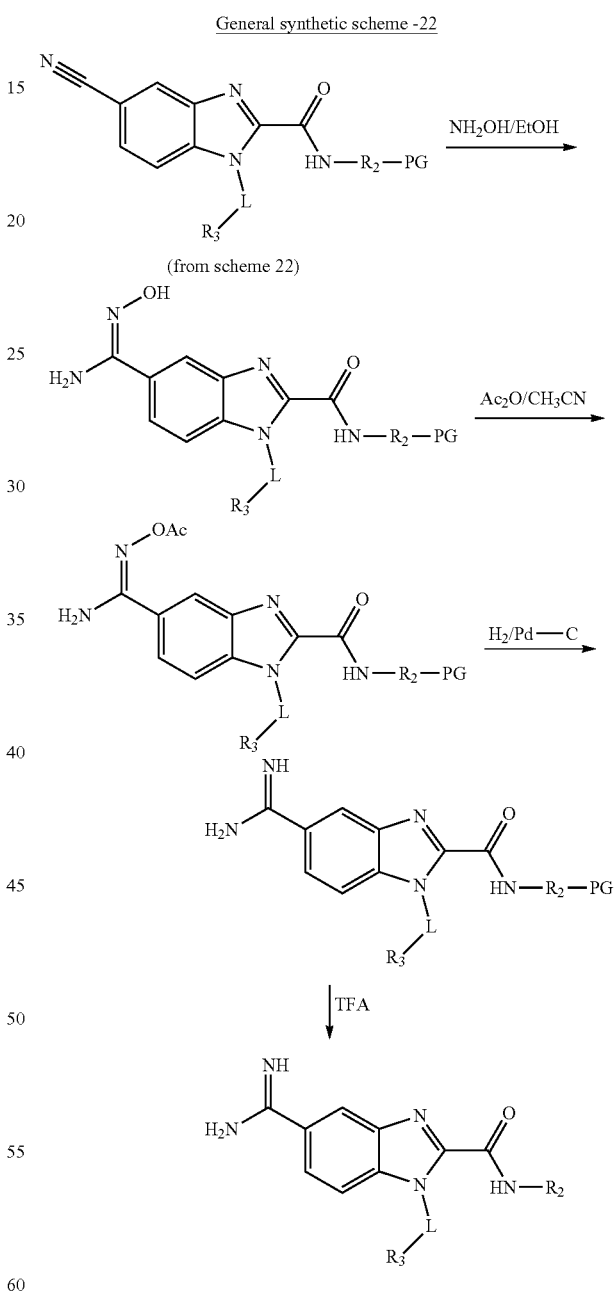

General synthetic scheme -22

The following compound listed in table-39 was prepared according to general scheme-22 starting from non-polar compound isolated (120 mg) in step-3 of example 121 by following similar procedure as described above for example 121 using appropriate reagents with suitable modifications known to the one skilled in the art.

TABLE 39

Compounds synthesized using General Scheme-22

| Cpd. ID. | Structure | LCMS [M + H]+ | 1H-NMR Data |
|---|---|---|---|
| I-543 | 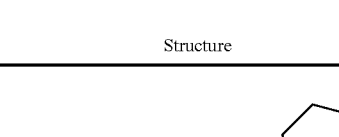 | 441.25 | 1H NMR(CD3OD, 300 MHz): δ 1.57-1.46 (m, 4H), 2.08-2.01 (m, 4H), 3.10 (m, 1H), 3.81 (m, 1H), 6.53-6.50(d, 1H), 6.56 (s, 2H), 7.28-7.22(t, 1H), 7.65-7.57 (m, 4H), 7.81-7.78 (m, 1H), 7.95-7.92 (m, 1H), 8.22-8.19(d, 1H), 8.34-8.33 (s, 1H). |

TABLE 40

Compounds synthesized using general scheme-15.

| ID | Structure | LCMS [M + H]+ | 1H-NMR Data |
|---|---|---|---|
| I-809 | 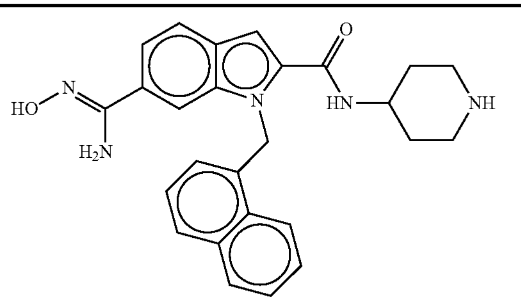 | 442.25 | 1HNMR (CD3OD, 400 MHz): δ 1.75-1.70 (m, 2H), 1.97 (d, 2H), 3.01-3.00 (m, 2H), 3.69-3.33 (d, 2H), 3.95-3.92 (m, 1H), 6.27-6.25 (d, 1H), 6.42 (s, 2H), 7.20-7.17 (t, 1H), 7.32 (s, 1H), 7.46-7.43 (d, 1H), 7.62-7.55 (m, 2H), 7.75-7.73 (m, 1H), 7.83 (S, 1H), 7.96-7.90 (m, 2H), 8.20-8.18 (m, 1H). |
| I-802 | 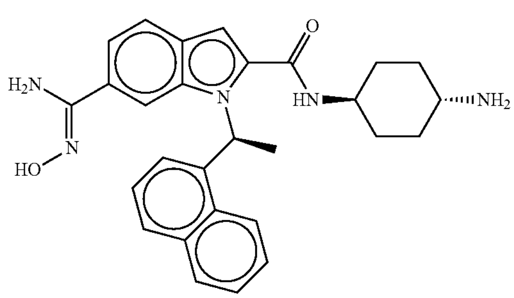 | 470.2 | 1HNMR (CD3OD, 300 MHz): δ 1.47-1.55 (m, 4H), 1.85-1.95 (m, 1H), 2.08-2.11 (m, 3H), 2.18-2.21 (d, 3H), 3.05-3.15 (m, 1H), 3.70-3.85 (m, 1H), 6.96 (s, 1H), 7.14-7.26 (m, 3H), 7.33-7.36 (t, 1H), 7.56-7.61 (m, 2H), 7.71-7.76 (m, 2H), 7.82-7.85 (d, 1H), 7.88-7.91 (d, 1H), 7.95-7.98 (d, 1H). |
| I-795 | 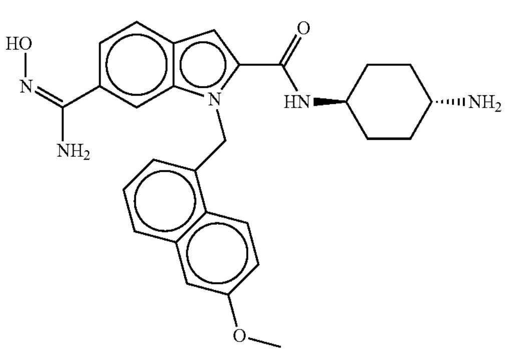 | 486.2 | 1HNMR (CD3OD, 400 MHz): δ 1.44-1.36 (m, 4H), 2.00-1.87 (m, 4H), 3.10-3.02 (m, 1H), 3.60-3.58 (m, 1H), 3.92 (s, 3H), 6.16-6.11 (d, 1H), 6.36 (s, 2H), 7.29-7.11 (m, 4H), 7.44-7.41 (m, 1H), 7.66-7.64 (d, 1H), 7.80 (s, 1H), 7.94-7.92 (d, 1H), 8.11-8.08 (d, 1H). |

TABLE 40-continued

Compounds synthesized using general scheme-15.

| ID | Structure | LCMS [M + H]+ | 1H-NMR Data |
|---|---|---|---|
| I-789 | 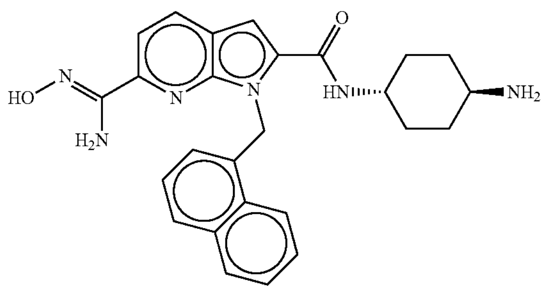 | 457.2 | 1HNMR (CD3OD, 400 MHz): δ 1.27-1.41 (m, 4H), 1.79-1.99 (m, 4H), 2.97-3.07 (m, 1H), 3.59-3.69 (m, 1H), 6.50 (s, 2H), 6.54-6.56 (d, 1H), 7.13 (s, 1H), 7.21-7.25 (m, 1H), 7.48-7.54 (m, 2H), 7.72-7.88 (m, 3H), 8.21-8.32 (m, 2H). |

TABLE 41

Compounds synthesized using general scheme-15.

| ID | Structure | LCMS [M + H]+ | 1H-NMR Data |
|---|---|---|---|
| I-616 | 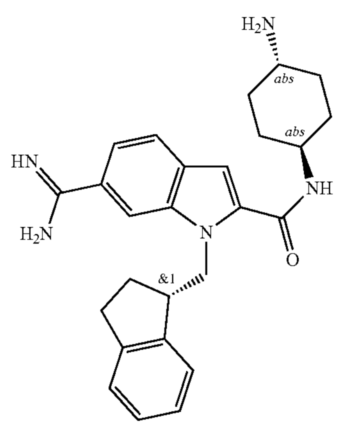 [SMILES: N=C(N)c1ccc2cc(C(=O)N[C@H]3CC[C@H](N)CC3)n(C[C@H]3CCc4ccccc43)c2c1] | 430.3 | 1HNMR (CD3OD, 400 MHz): δ 1.44-1.52 (m, 4H), 1.85-1.95 (m, 2H), 2.05-2.10 (m, 4H), 2.78-2.84 (m, 1H), 3.01-3.05 (m, 1H), 3.07-3.12 (m, 1 H), 3.71-3.73 (m, 2H), 4.74-4.76 (m, 1 H), 4.91-4.93 (m, 1H), 6.51 (d, 1H), 6.91 (t, 1H), 7.09 (t, 2H), 7.09 (d, 1H), 7.50 (d, 1 H), 7.85 (d, 1H), 7.93 (s, 1H). |
| I-634 | 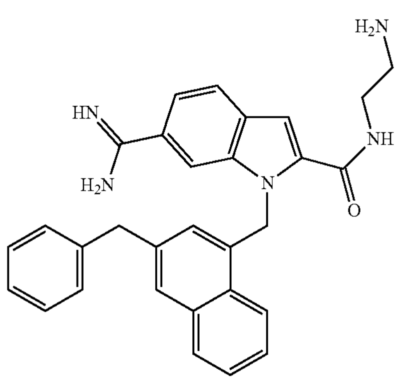 [SMILES: N=C(N)c1ccc2cc(C(=O)NCCN)n(Cc3cc(Cc4ccccc4)cc4ccccc34)c2c1] | 478.4 | 1HNMR (CD3OD, 600 MHz): δ 3.09-3.06 (t, 2H), 3.58-3.55 (t, 2H), 5.9 (s, 1H), 6.49 (S, 2H), 1.78 (d, 2H), 7.05 (t, 1H), 7.12 (s, 1H), 7.25-7.21 (t, 2H), 7.36 (s, 1H), 7.58-7.54 (m, 3H), 7.75 (d, 1H) 7.94-7.92 (d, 2H), 8.2 (d, 1H). |

TABLE 41-continued

Compounds synthesized using general scheme-15.

| ID | Structure | LCMS [M + H]+ | ¹H-NMR Data |
|---|---|---|---|
| I-645 | 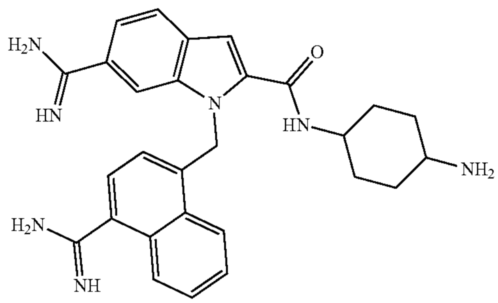 [SMILES: N=C(N)c1ccc2cc(C(=O)NC3CCC(N)CC3)n(Cc3ccc(C(=N)N)c4ccccc34)c2c1] | 482.2 | ¹HNMR (DMSO-d₆, 400 MHz): δ 1.39.1-28 (m, 4H), 1.80-1.77 (m, 4H), 2.89 (s, 1H), 3.58 (s, 1H), 6.15-6.13 (d, 1H), 6.48 (s, 2H), 7.50-7.48 (d, 1H), 7.61-7.59 (s, 1H), 7.48-7.80 (m, 2H), 8.08-7.98 (m, 3H), 8.45-8.39 (m, 3H), 8.66-8.64 (d, 2H), 8.68-8.66 (m, 4H) |
| I-668 | 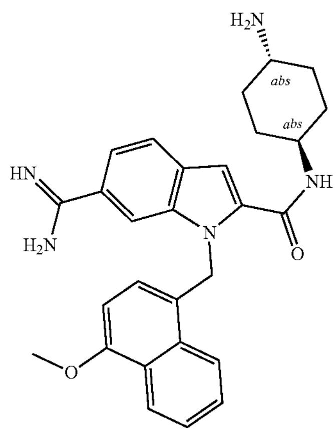 [SMILES: COc1ccc(Cn2c(C(=O)N[C@H]3CC[C@H](N)CC3)cc3ccc(C(=N)N)cc32)c2ccccc12] | 470.25 | ¹HNMR (CD₃OD, 400 MHz): δ 1.29-1.45 (m, 4H), 1.91-2.03 (m, 4H), 3.0-3.1 (m, 1H), 3.6-3.75 (m, 1H), 3.91 (s, 3H), 6.26-6.30 (d, 3H), 6.11-6.63 (d, 1H), 7.23 (s, 1H), 7.51-7.62 (m, 3H), 7.91-7.94 (d, 1H), 7.98 (s, 1H), 8.00-8.10 (d, 1H), 8.26-8.28 (d, 1H). |
| I-694 | 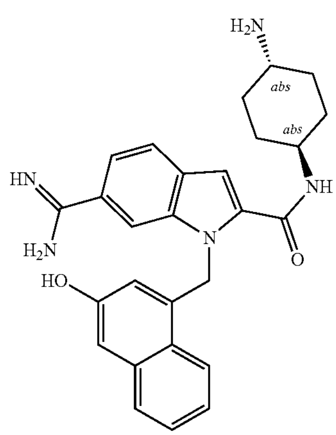 [SMILES: N=C(N)c1ccc2cc(C(=O)N[C@H]3CC[C@H](N)CC3)n(Cc3cc(O)cc4ccccc34)c2c1] | 456.0 | ¹HNMR (CD₃OD, 300 MHz): δ 1.28-1.44 (m, 4H), 1.92-2.00 (m, 4H), 3.0-3.1 (m, 1H), 3.6-3.75 (m, 1H), 5.87 (s, 1H), 6.37 (s, 2H), 6.96-6.97 (d, 1H), 7.29 (s, 1H), 7.38-7.44 (m, 2H), 7.54-7.57 (d, 1H), 7.66-7.68 (d, 1H), 7.93-7.97 (m, 2H), 8.04-8.07 (d, 1H). |

TABLE 41-continued

Compounds synthesized using general scheme-15.

| ID | Structure | LCMS [M + H]+ | ¹H-NMR Data |
|---|---|---|---|
| I-701 | 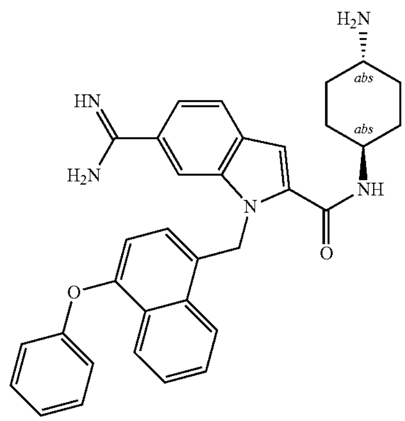 [SMILES: N=C(N)c1ccc2cc(C(=O)N[C@H]3CC[C@H](N)CC3)n(Cc3ccc(Oc4ccccc4)c4ccccc34)c2c1] | 532.3 | ¹HNMR (CD₃OD, 400 MHz): δ 1.39-1.43 (m, 4H), 1.85-2.05 (m, 4H), 3.00-3.10 (m, 1H), 3.62-3.70 (m, 1H), 6.25-6.27 (m, 1H), 6.38 (s, 2H), 6.64-6.66 (d, 1H), 6.93-6.95 (d, 2H), 7.08-7.10 (m, 1H), 7.24-7.33 (m, 3H), 7.54-7.67 (m, 3H), 7.91-7.93 (d, 1H), 8.02 (s, 1H), 8.19-8.23 (m, 2H). |
| I-739 | 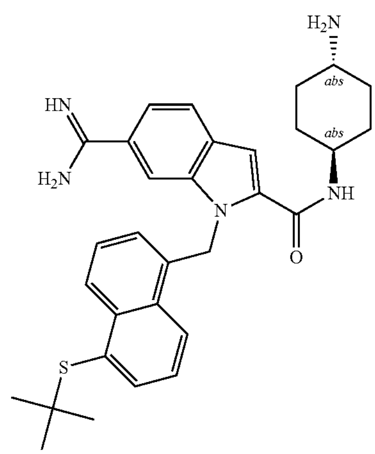 [SMILES: CC(C)(C)Sc1cccc2c(Cn3c(C(=O)N[C@H]4CC[C@H](N)CC4)cc4ccc(C(=N)N)cc43)cccc12] | 528.3 | ¹HNMR (DMSO-d₆, 400 MHz): δ 1.32 (s, 9H), 1.35 (m, 4H), 1.71 (m, 2H), 1.87 (m, 2H), 2.94 (m, 1H), 3.54 (m, 1H), 6.09 (d, 1H), 6.55 (brs, 2H), 7.31 (t, 1H), 7.41 (s, 1H), 7.60 (d, 1H), 7.73 (m, 4H), 7.92 (d, 1H), 8.00 (d, 1H), 8.13 (s, 1H), 8.38 (d, 1H), 8.56 (d, 1H), 8.64 (d, 1H), 8.80 (brs, 2H), 9.15 (brs, 2H); |
| I-742 | 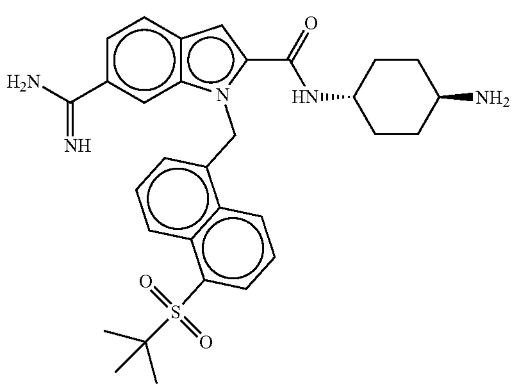 | 560.3 | ¹HNMR (CD₃OD, 300 MHz): δ 1.32 (s, 9H), 1.35 (m, 4H), 1.73 (m, 2H), 1.88 (m, 2H), 2.90 (m, 1H), 3.53 (m, 1H), 6.16 (d, 1H), 6.46 (brs, 2H), 7.46 (m, 2H), 7.61 (d, 1H), 7.70 (m, 3H), 7.93 (t, 1H), 8.01 (s, 1H), 8.13 (s, 1H), 8.33 (d, 1H), 8.65 (d, 1H), 8.74 (d, 1H), 8.79 (brs, 2H), 8.81 (s, 1H), 9.14 (brs, 2H) |
| I-805 | 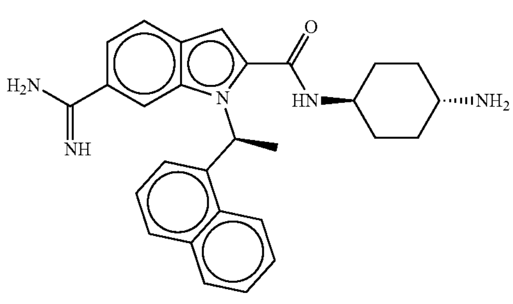 | 454.1 | ¹HNMR (CD₃OD, 400 MHz): δ 1.46-1.61 (m, 4H), 1.91-1.93 (m, 3H), 2.12-2.24 (m, 4H), 3.12-3.129 (m, 1H), 3.94 (m, 1H), 5.92-5.94 (d, 1H), 7.09-7.11 (d, 1H), 7.25-7.35 (m, 3H), 7.50-7.54 (t, 1H), 7.75-7.82 (m, 4H), 8.12-8.14 (d, 1H). |

TABLE 41-continued

Compounds synthesized using general scheme-15.

| ID | Structure | LCMS [M + H]+ | 1H-NMR Data |
|---|---|---|---|
| I-788 | 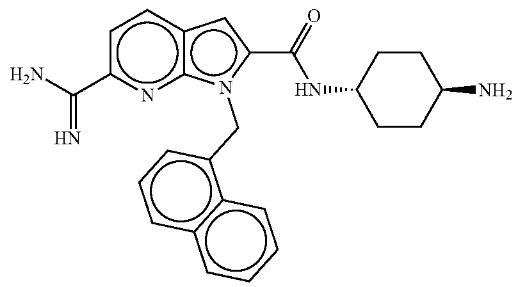 | 441.1 | 1HNMR (CD3OD, 400 MHz): δ 1.25-1.45 (m, 4H), 1.75-2.05 (m, 4H), 2.95-3.05 (m, 1H), 3.62-3.70 (m, 1H), 6.53-6.60 (m, 3H), 7.17-7.23 (m, 2H), 7.50-7.52 (m, 2H), 7.72-7.76 (m, 1H), 7.76-7.78 (m, 1H), 8.00-8.03 (d, 1H), 8.20-8.25 (d, 1H), 8.39-8.41 (d, 1H). |
| I-776 | 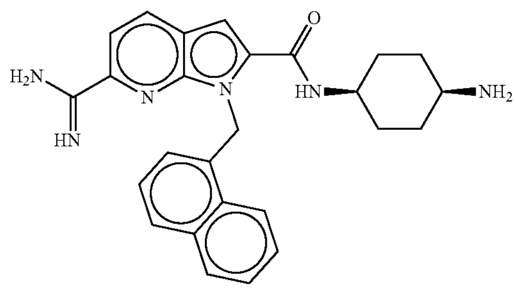 | 457.2 | 1HNMR (CD3OD, 400 MHz): δ 1.27-1.41 (m, 4H), 1.79-1.99 (m, 4H), 2.97-3.07 (m, 1H), 3.59-3.69 (m, 1H), 6.50 (s, 2H), 6.54-6.56 (d, 1H), 7.13 (s, 1H), 7.21-7.25 (m, 1H), 7.48-7.54 (m, 2H), 7.72-7.88 (m, 3H), 8.21-8.32 (m, 2H). |

TABLE 42

Compounds synthesized using general scheme-15C.

| ID | Structure | LCMS [M + H]+ | 1H-NMR Data |
|---|---|---|---|
| I-759 | 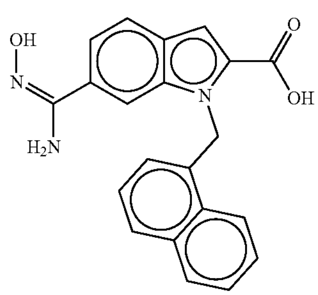 | 360.0 | 1HNMR (DMSO-d6, 400 MHz): δ 6.024-6.042 (d, 1H), 6.408 (s, 2H), 6.52 (bs, 1H), 7.222-7.260 (t, 1H), 7.455 (s, 1H), 7.535-7.558 (d, 2H), 7.608-7.712 (m, 3H), 7.776-7.812 (m, 3H), 7.81-8.004 (d, 1H), 8.292-8.312 (d, 1H), 9.95 (bs, 1H). |
| I-665 | 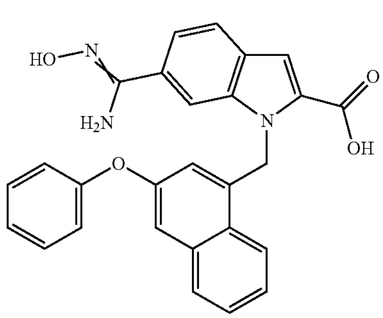 [SMILES: NC(=NO)c1ccc2cc(C(=O)O)n(Cc3cc(Oc4ccccc4)cc4ccccc34)c2c1] | 452.3 | 1HNMR (CD3OD, 400 MHz): δ 5.92 (s, 1H), 6.47 (s, 2H), 6.81-6.83 (d, 2H), 7.05-7.07 (t, 1H), 7.12 (d, 1H), 7.21-7.25 (t, 2H), 7.41-7.43 (d, 1H), 7.48 (s, 1H), 7.52-7.56 (m, 2H), 7.75-7.77 (d, 2H), 7.91-7.93 (d, 1H), 8.18-8.21 (d, 1H). |

TABLE 42-continued

Compounds synthesized using general scheme-15C.

| ID | Structure | LCMS [M + H]+ | 1H-NMR Data |
| --- | --- | --- | --- |
| I-660 | 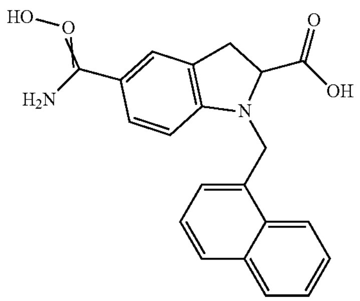 | 360.4 | 1HNMR (CD3OD, 300 MHz): δ 6.16-6.18 (d, 1H), 6.48 (s, 2H), 7.13-7.19 (m, 1H), 7.51-7.74 (m, 6H), 7.90-7.93 (d, 1H), 8.21-8.24 (d, 2H). |
| I-659 | 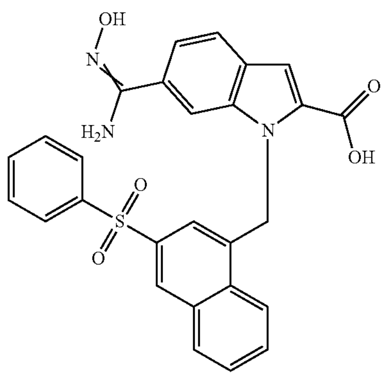 [SMILES: NC(=NO)c1ccc2cc(C(=O)O)n(Cc3cc(S(=O)(=O)c4ccccc4)cc4ccccc34)c2c1] | 500.4 | 1HNMR (DMSO-d6, 400 MHz): δ 6.24 (s, 1H), 6.41 (s, 2H), 7.44-7.59 (m, 6H), 7.80-7.94 (m, 4H), 8.29-8.39 (m, 2H), 8.56 (s, 1H), 13.15 (bs, 1H). |
| I-650 | 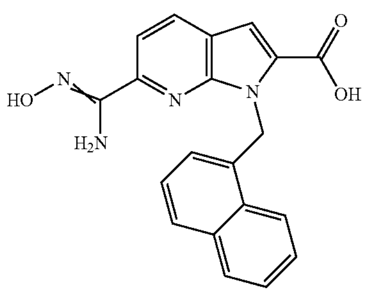 [SMILES: NC(=NO)c1ccc2cc(C(=O)O)n(Cc3cccc4ccccc34)c2n1] | 361.4 | 1HNMR (CD3OD, 300 MHz): δ 6.19-6.21 (d, 1H), 6.61 (s, 2H), 7.16-7.21 (m, 1H), 7.53-7.92 (m, 6H), 8.28-8.31 (d, 1H), 8.46-8.48 (d, 1H). |
| I-641 | 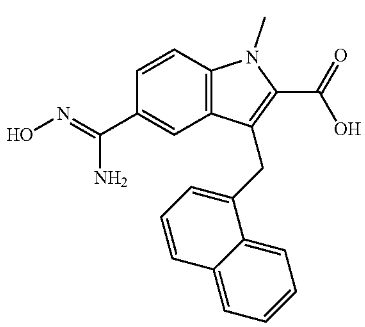 [SMILES: Cn1c(C(=O)O)c(Cc2cccc3ccccc23)c2cc(/C(N)=N/O)ccc21] | 374.1 | 1HNMR (DMSO-d6, 400 MHz): δ 2.06 (s, 2H), 3.87-3.90 (m, 1H), 4.01 (s, 3H), 4.88 (s, 2H), 6.74-6.76 (d, 1H), 7.22-7.26 (t, 1H), 7.50-7.62 (m, 4H), 7.69-7.71 (m, 2H), 7.90-7.92 (d, 1H), 8.34-8.36 (d, 1H). |

TABLE 43

Compounds synthesized using general scheme-15C.

| ID | Structure | LCMS [M + H]+ | ¹H-NMR Data |
|---|---|---|---|
| I-711 | 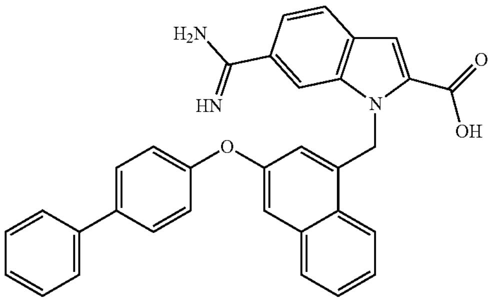 [SMILES: N=C(N)c1ccc2cc(C(=O)O)n(Cc3cc(Oc4ccc(-c5ccccc5)cc4)cc4ccccc34)c2c1] | 512.2 | ¹HNMR (CD₃OD, 300 MHz): δ 5.92 (s, 1H), 6.45 (s, 2H), 6.87-6.90 (d, 2H), 7.20 (s, 1H), 7.31-7.44 (m, 2H), 7.46-7.59 (m, 9H), 7.77-7.80 (m, 1H), 7.88-7.91 (d, 1H), 7.94 (s, 1H), 8.19-8.22 (d, 1H). |
| I-709 | 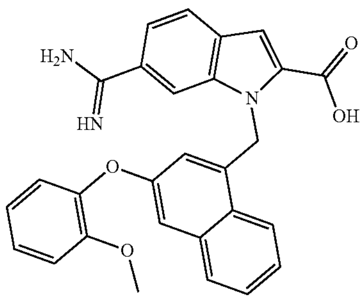 [SMILES: COc1ccccc1Oc1cc(Cn2c(C(=O)O)cc3ccc(C(=N)N)cc32)c2ccccc2c1] | 466.2 | ¹HNMR (CD₃OD, 300 MHz): δ 3.56 (s, 3H), 5.72-5.73 (d, 1H), 6.469 (s, 2H), 6.82-6.85 (m, 2H), 6.92-6.97 (m, 2H), 7.09-7.15 (m, 1H), 7.48-7.56 (m, 4H), 7.68-7.71 (m, 1H), 7.92-7.96 (m, 2H), 8.14-8.17 (t, 1H) |
| I-613 | 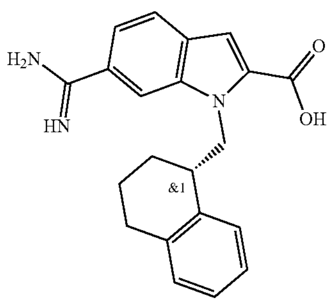 [SMILES: N=C(N)c1ccc2cc(C(=O)O)n(C[C@H]3CCCc4ccccc43)c2c1] | 348.4 | ¹HNMR (CD₃OD, 400 MHz): δ 1.65-1.76 (m, 3H), 2.0-2.1 (m, 1H), 2.75-2.86 (m, 2H), 3.42-3.45 (m, 1H), 4.79-4.98 (m, 2H), 6.69-6.71 (d, 1H), 6.80-6.84 (t, 1H), 7.00-7.07 (m, 2H), 7.41 (s, 1H), 7.46-7.48 (d, 1H), 7.81 (s, 1H), 7.86-7.88 (d, 1H). |
| I-544 | 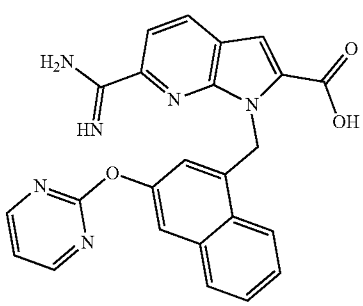 [SMILES: N=C(N)c1ccc2cc(C(=O)O)n(Cc3cc(Oc4ncccn4)cc4ccccc34)c2n1] | 439.1 | ¹HNMR (CD₃OD, 400 MHz): δ 6.02 (s, 1H), 6.63 (s, 2H), 7.12-7.14 (m, 1H), 7.51-7.62 (m, 4H), 7.62-7.97 (m, 2H), 8.31-8.33 (d, 1H), 8.42-8.46 (m, 3H). |
| I-757 | 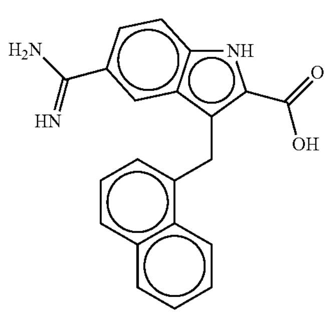 | 344.3 | ¹HNMR (CD₃OD, 400 MHz): δ 5.09 (s, 2H), 7.026 (d, 1H), 7.305 (t, 1H), 7.517 (m, 2H), 7.655-7.663 (m, 2H), 7.727-7.748 (d, 1H), 7.887-7.907 (d, 1H), 7.971 (s, 1H), 8.347-8.368 (d, 1H). |

TABLE 43-continued

Compounds synthesized using general scheme-15C.

| ID | Structure | LCMS [M + H]+ | ¹H-NMR Data |
|---|---|---|---|
| I-689 | 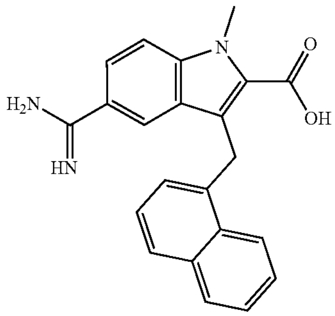 [SMILES: Cn1c(C(=O)O)c(Cc2cccc3ccccc23)c2cc(C(=N)N)ccc21] | 358.03 | ¹HNMR (CD$_3$OD, 300 MHz): δ 4.12 (s, 3H), 4.94 (s, 2H), 6.85-6.87 (d, 1H), 7.21-7.26 (t, 1H), 7.50-7.57 (m, 2H), 7.68-7.74 (m, 3H), 7.86-7.89 (d, 1H), 8.00 (s, 1H), 8.31-8.34 (d, 1H). |
| I-685 | 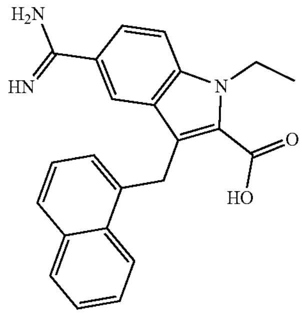 [SMILES: CCn1c(C(=O)O)c(Cc2cccc3ccccc23)c2cc(C(=N)N)ccc21] | 372.2 | ¹HNMR (DMSO-d$_6$, 400 MHz): δ 1.35 (t, 3H), 4.72 (q, 2H), 4.94 (s, 2H), 6.69 (d, 1H), 7.27 (m, 1H), 7.75 (d, 2H), 7.95 (m, 4H), 8.17 (s, 1H), 8.40 (d, 1H), 8.67 (brs, 2H), 9.11 (brs, 2H), 13.36 (brs, 1H); |
| I-637 | 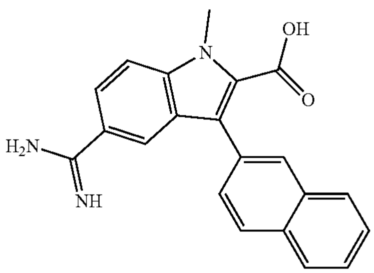 [SMILES: Cn1c(C(=O)O)c(-c2ccc3ccccc3c2)c2cc(C(=N)N)ccc21] | 344.0 | ¹HNMR (CD$_3$OD, 400 MHz): δ 4.16 (S, 3H), 7.52-7.50 (m, 2H), 7.60-7.58 (dd, 1H), 7.81-7.77 (m, 2H), 7.94-7.89 (m, 3H), 7.97 (S, 1H), 8.08-8.07 (d, 1H). |
| I-606 | 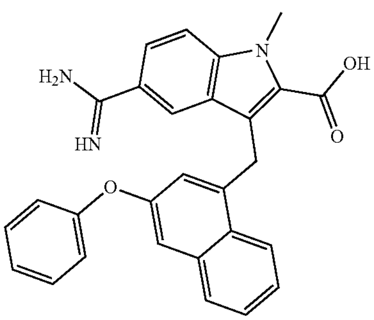 [SMILES: Cn1c(C(=O)O)c(Cc2cc(Oc3ccccc3)cc3ccccc23)c2cc(C(=N)N)ccc21] | 450.1 | ¹HNMR (CD$_3$OD, 400 MHz): δ 4.13 (s, 3H), 5.02 (s, 2H), 6.5 (s, 1H), 6.89-6.87 (d, 2H), 7.06 (d, 2H), 7.24 (t, 2H), 7.483 (d, 2H), 7.74-7.686 (t, 3H), 8.05 (s, 1H), 8.3 (s, 1H). |
| I-588 | 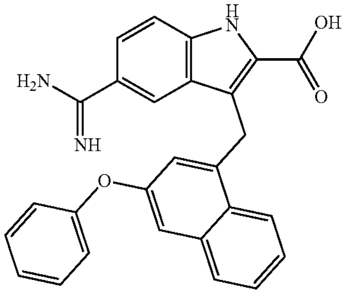 [SMILES: N=C(N)c1ccc2[nH]c(C(=O)O)c(Cc3cc(Oc4ccccc4)cc4ccccc34)c2c1] | 436.1 | ¹HNMR (CD$_3$OD, 400 MHz): δ 5.067 (s, 2H), 6.69 (s, 1H), 6.89-6.91 (d, 2H), 7.05-7.07 (t, 1H), 7.11-7.12 (s, 1H), 7.24-7.28 (t, 2H), 7.46-7.48 (t, 2H), 7.62 (s, 2H), 7.71-7.74 (t, 1H), 8.01 (s, 1H), 8.31-8.33 (d, 1H). |

TABLE 44

Compounds synthesized using general scheme-15C.

| ID | Structure | LCMS [M + H]+ | 1H-NMR Data |
|---|---|---|---|
| I-700 | 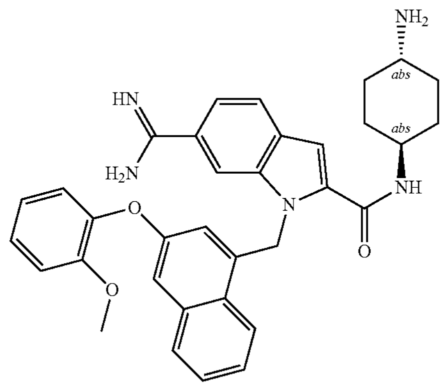 [SMILES: COc1ccccc1Oc1cc(Cn2c(C(=O)N[C@H]3CC[C@H](N)CC3)cc3ccc(C(=N)N)cc32)c2ccccc2c1] | 560.2 | $^1$HNMR (CD$_3$OD, 300 MHz): δ 1.41-1.47 (m, 4H), 1.96-2.02 (m, 4H), 3.06 (s, 1H), 3.59 (s, 3H), 3.71 (s, 1H), 5.93-5094 (d, 1H), 6.43 (s, 2H), 6.85-6.86 (m, 3H), 6.98-7.01 (d, 1H), 7.11-7.15 (m, 1H), 7.28 (s, 1H), 7.47-7.58 (m, 3H), 7.65-7.68 (m, 1H), 7.91-7.97 (m, 2H), 8.12-8.15 (m, 1H) |
| I-594 | 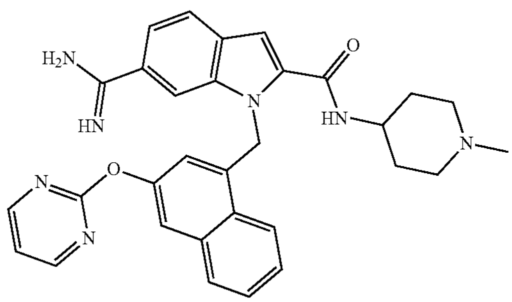 [SMILES: CN1CCC(NC(=O)c2cc3ccc(C(=N)N)cc3n2Cc2cc(Oc3ncccn3)cc3ccccc23)CC1] | 534.2 | $^1$HNMR (CD$_3$OD, 400 MHz): δ 1.79 (m, 2H), 2.06-2.09 (m, 2H), 2.83 (s, 3H), 3.06 (t, 2H), 3.49-3.52 (d, 2H), 3.95 (s, 1H), 6.49 (s, 2H), 7.11 (t, 1H), 7.27 (s, 1H), 7.53-7.57 (m, 2H), 7.61-7.65 (m, 2H), 7.88-7.93 (m, 2H), 8.00 (1H), 8.23-8.25 (d, 1H), 8.38-8.40 (d, 2H) |
| I-590 | 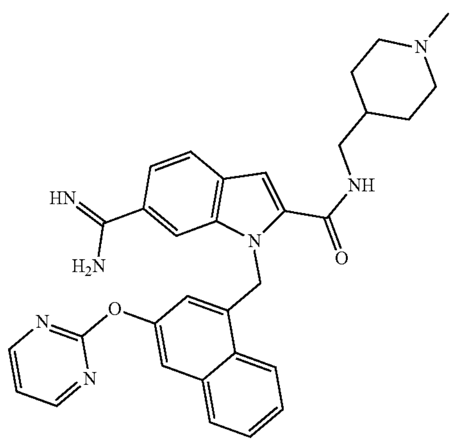 [SMILES: CN1CCC(CNC(=O)c2cc3ccc(C(=N)N)cc3n2Cc2cc(Oc3ncccn3)cc3ccccc23)CC1] | 548.4 | $^1$HNMR (CD$_3$OD, 400 MHz): δ 1.29 (m, 2H), 1.75 (m, 2H), 2.73-2.79 (m, 5H), 3.17-3.19 (d, 1H), 3.35-3.38 (d, 2H), 5.99 (s, 1H), 6.49 (s, 2H), 7.11-7.14 (t, 1H), 7.23 (s,1H), 7.53-7.58 (m, 2H), 7.62-7.66 (m, 2H), 7.88-7.94 (m, 2H), 8.05 (s, 1H), 8.24-8.26 (d, 1H), 8.40-8.41 (d, 2H). |
| I-582 | 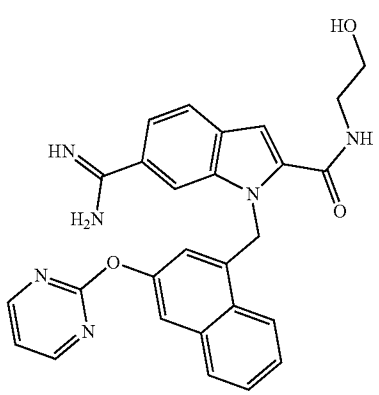 [SMILES: N=C(N)c1ccc2cc(C(=O)NCCO)n(Cc3cc(Oc4ncccn4)cc4ccccc34)c2c1] | 481.2 | $^1$HNMR (CD$_3$OD, 400 MHz): δ 3.38-3.42 (t, 2H), 3.58-3.61 (t, 2H), 5.95 (s, 1H), 6.51 (s, 2H), 7.08-7.11 (t, 1H), 7.28 (s, 1H), 7.5-7.55 (dd, 1H), 7.55-7.6 (bs, 1H), 7.6-7.72 (m, 2H), 7.87-7.89 (d, 1H), 7.90-7.93 (m, 2H), 8.24-8.27 (d, 1H), 8.38-8.39 (d, 2H). |

TABLE 44-continued

Compounds synthesized using general scheme-15C.

| ID | Structure | LCMS [M + H]+ | $^1$H-NMR Data |
|---|---|---|---|
| I-578 | 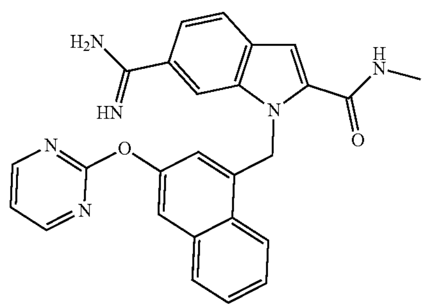 [SMILES: CNC(=O)c1cc2ccc(C(=N)N)cc2n1Cc1cc(Oc2ncccn2)cc2ccccc12] | 451.1 | $^1$HNMR (CD$_3$OD, 300 MHz): δ 2.813 (s, 3H), 5.890 (s, 1H), 6.52 (s, 2H), 7.109 (t, 1H), 7.211 (s, 1H), 7.53-7.63 (m, 4H), 7.86-7.93 (m, 3H), 8.244 (d, 1H), 8.37-8.39 (d, 2H), 8.52 (s, 1H) |
| I-572 | 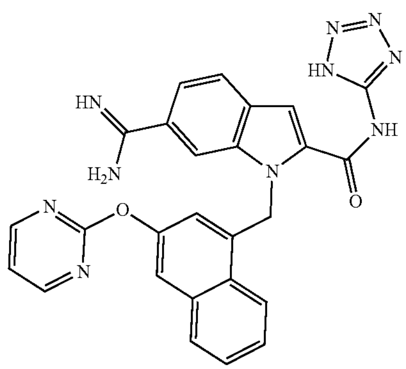 [SMILES: N=C(N)c1ccc2cc(C(=O)Nc3nnn[nH]3)n(Cc3cc(Oc4ncccn4)cc4ccccc34)c2c1] | 505.2 | $^1$HNMR (CD$_3$OD, 400 MHz): δ 5.8 (s, 1H), 6.53 (s, 2H), 7.1 (bs, 1H), 7.49-7.54 (m, 5H), 7.90-7.94 (m, 3H), 8.2-8.3 (d, 1H), 8.38-8.39 (d, 2H). |
| I-564 | 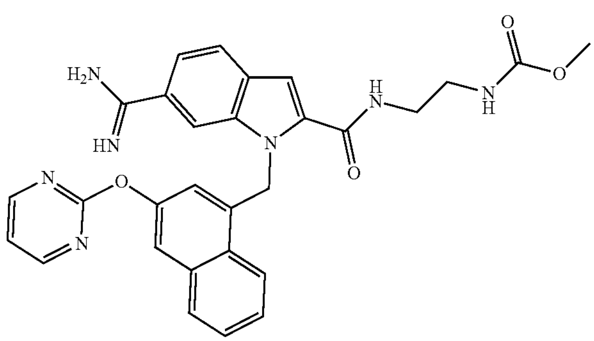 [SMILES: COC(=O)NCCNC(=O)c1cc2ccc(C(=N)N)cc2n1Cc1cc(Oc2ncccn2)cc2ccccc12] | 538.3 | $^1$HNMR (CD$_3$OD, 400 MHz): δ 3.18-3.21 (t, 2H), 3.33-3.36 (t, 2H), 3.52 (s, 3H), 5.99 (s, 1H), 6.48 (s, 2H), 7.09-7.11 (t, 1H), 7.24 (s, 1H), 7.50-7.55 (m, 2H), 7.59-7.64 (m, 2H), 7.86-7.92 (m, 3H), 8.22-8.24 (d, 1H), 8.37-8.39 (d, 2H). |
| I-560 | 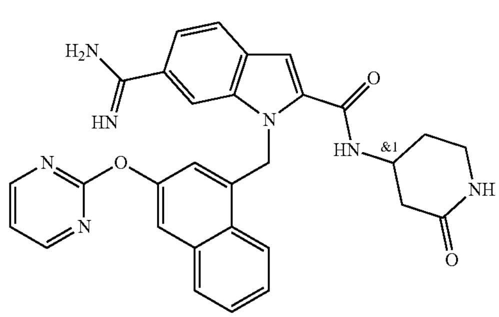 [SMILES: N=C(N)c1ccc2cc(C(=O)NC3CCNC(=O)C3)n(Cc3cc(Oc4ncccn4)cc4ccccc34)c2c1] | 534.2 | $^1$HNMR (DMSO-d$_6$, 300 MHz): δ 1.54-1.59 (m, 1H), 1.76-1.80 (d, 1H), 2.10-2.19 (m, 1H), 2.26-2.36 (m, 3H), 3.06-3.09 (d, 4H), 4.04 (s, 1H), 5.90 (s, 1H), 6.45 (s, 2H), 7.18-7.28 (m, 3H), 7.37 (s, 1H), 7.54-7.57 (d, 2H), 7.63-7.66 (m, 3H), 7.90-7.95 (m, 2H), 8.3 (s, 1H), 8.27-8.29 (d, 1H), 8.42 (s, 1H), 8.49-8.51 (d, 2H), 8.78-8.80 (d, 1H) |

TABLE 44-continued
Compounds synthesized using general scheme-15C.
| ID | Structure | LCMS [M + H]+ | 1H-NMR Data |
|---|---|---|---|
| I-547 | 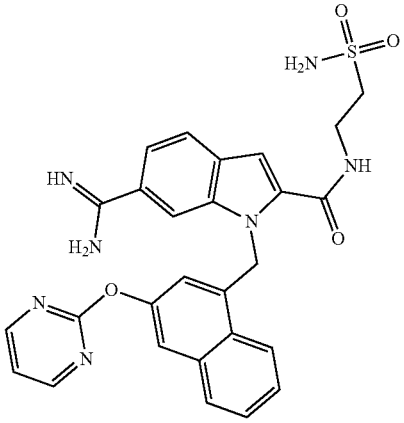 [SMILES: N=C(N)c1ccc2cc(C(=O)NCCS(N)(=O)=O)n(Cc3cc(Oc4ncccn4)cc4ccccc34)c2c1] | 544.2 | $^1$HNMR (CD$_3$OD, 300 MHz): δ 3.22-3.24 (m, 2H), 3.71-3.73 (m, 2H), 5.92 (s, 1H), 6.50 (s, 2H), 7.09-7.15 (m, 1H), 7.25 (s, 1H), 7.51-7.65 (m, 4H), 7.87-7.95 (m, 3H), 8.23-8.26 (d, 1H), 8.40-8.42 (d, 2H), 8.80 (s, 1H). |
| I-851 | 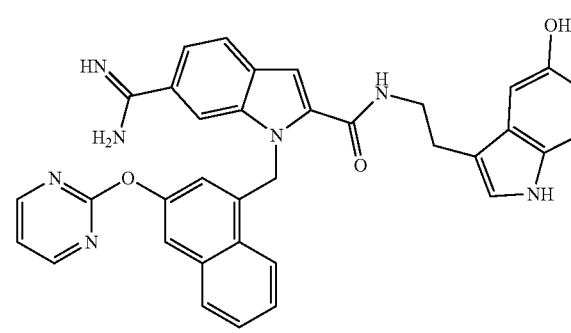 | 596.3 | $^1$HNMR (CD$_3$OD, 400 MHz): δ 2.85 (t, 2H), 3.51 (t, 2H), 5.95 (d, 1H), 6.45 (s, 2H), 6.62-6.65 (m, 1H), 6.90-6.91 (m, 2H), 7.05-7.14 (m, 3H), 7.50-7.67 (m, 4H), 7.8-7.93 (m, 3H), 8.40-8.42 (d, 2H), 8.23 (d, 1H), 8.34 (d, 2H). |
TABLE 45
Compounds synthesized using general scheme-15D.
| ID | Structure | LCMS [M + H]+ | 1H-NMR Data |
|---|---|---|---|
| I-821 | 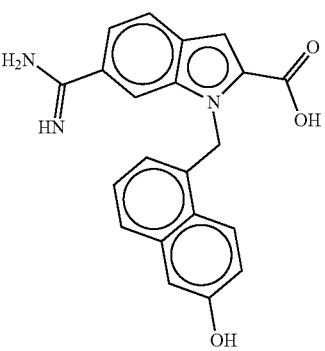 | 360.1 | $^1$HNMR (CD$_3$OD, 400 MHz): δ 5.95-5.94 (d, 1H), 6.45 (s, 2H), 7.24-7.06 (m, 3H), 7.57-7.51 (m, 3H), 7.90 (s, 1H), 8.00-7.98 (d, 1H), 8.12-8.10 (d, 1H). |

TABLE 45-continued

Compounds synthesized using general scheme-15D.

| ID | Structure | LCMS [M + H]+ | 1H-NMR Data |
|---|---|---|---|
| I-746 | 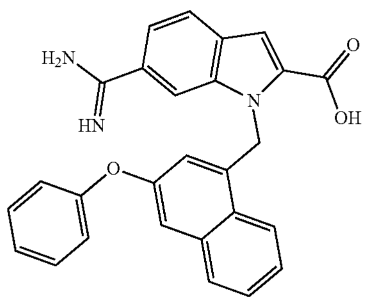 [SMILES: N=C(N)c1ccc2cc(C(=O)O)n(Cc3cc(Oc4ccccc4)cc4ccccc34)c2c1] | 436.3 | 1HNMR (CD3OD, 400 MHz): δ 5.82 (s, 1H), 6.49 (s, 2H), 6.80-6.83 (d, 2H), 7.05-7.25 (m, 4H), 7.48-7.54 (m, 4H), 7.75-7.80 (m, 1H), 7.92-7.94 (d, 2H), 8.19-8.21 (d, 1H). |
| I-730 | 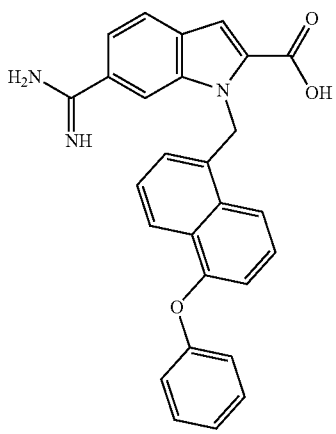 [SMILES: N=C(N)c1ccc2cc(C(=O)O)n(Cc3cccc4c(Oc5ccccc5)cccc34)c2c1] | 436.2 | 1HNMR (CD3OD, 400 MHz): δ 6.21 (d, 1H), 6.51 (s, 2H), 6.98-7.03 (m, 3H), 7.10-7.23 (m, 2H), 7.32-7.39 (m, 2H), 7.54-7.59 (m, 3H), 7.94-8.07 (m, 4H). |
| I-705 | 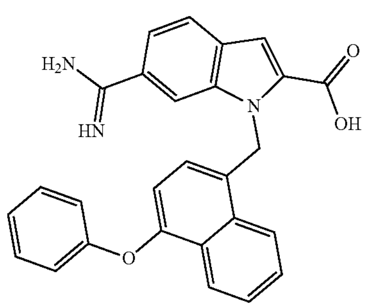 [SMILES: N=C(N)c1ccc2cc(C(=O)O)n(Cc3ccc(Oc4ccccc4)c4ccccc34)c2c1] | 436.2 | 1HNMR (CD3OD, 400 MHz): δ 6.13-6.15 (d, 1H), 6.63-6.65 (d, 1H), 6.49 (s, 2H), 6.93-6.95 (d, 2H), 6.96-7.08 (m, 1H), 7.28-7.32 (m, 2H), 7.50-7.70 (m, 4H), 7.92-7.99 (m, 2H), 8.22-8.30 (m, 2H). |
| I-703 | 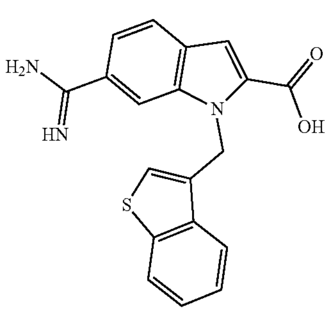 [SMILES: N=C(N)c1ccc2cc(C(=O)O)n(Cc3csc4ccccc34)c2c1] | 350.2 | 1H NMR (CD3OD, 400 MHz): δ 6.17 (s, 2H), 6.63 (s, 1H), 7.43-7.47 (m, 3H), 7.57 (d, 1H), 7.98 (t, 3H), 8.22 (s, 1H), 8.98 (s, 2H), 9.27 (s, 2H). |

TABLE 45-continued
Compounds synthesized using general scheme-15D.
| ID | Structure | LCMS [M + H]⁺ | ¹H-NMR Data |
|---|---|---|---|
| I-672 | 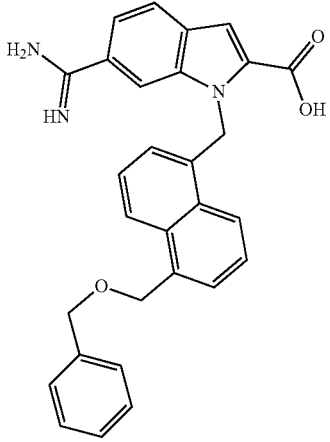 [SMILES: N=C(N)c1ccc2cc(C(=O)O)n(Cc3cccc4c(COCc5ccccc5)cccc34)c2c1] | 464.2 | ¹HNMR (DMSO-d$_6$, 400 MHz): δ 4.63 (s, 2H), 5.00 (s, 2H), 6.02 (d, 1H), 6.45 (brs, 2H), 7.30 (m, 3H), 7.37 (m, 3H), 7.55 (s, 1H), 7.67 (d, 2H), 7.69 (m, 2H), 8.03 (m, 2H), 8.09 (s, 1H), 8.30 (m, 1H), 8.81 (brs, 2H), 9.18 (brs, 2H), 13.35 (brs, 1H) |
| I-585 | 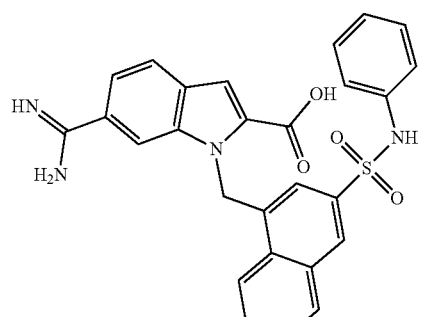 | 499.1 | ¹HNMR (CD$_3$OD, 300 MHz): δ 6.42 (s, 2H), 6.518 (s, 1H), 6.80 (d, 2H), 7.00 (t, 3H), 7.60 (d, 2H), 7.73 (d, 1H), 7.86 (m, 2H), 8.03 (m, 2H), 8.28 (d, 2H). |
| I-766 | 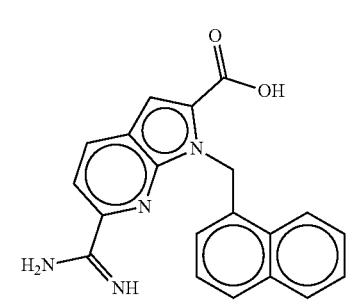 | 345.3 | ¹HNMR (DMSO-d$_6$, 300 MHz): δ 6.14-6.16 (d, 1H), 6.65 (s, 2H), 7.016-7.21 (m, 2H), 7.56-7.73 (m, 3H), 7.91-8.01 (m, 2H), 8.31-8.39 (m, 2H), 9.25-9.31 (bs, 1H), 10.15-10.25 (bs, 1H). |
| I-732 | 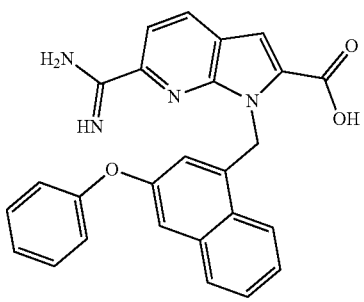 [SMILES: N=C(N)c1ccc2cc(C(=O)O)n(Cc3cc(Oc4ccccc4)cc4ccccc34)c2n1] | 437.2 | ¹HNMR (CD$_3$OD, 400 MHz): δ 5.90 (s, 1H), 6.62 (s, 2H), 6.80-6.83 (d, 2H), 7.03-7.25 (m, 4H), 7.47-7.55 (m, 3H), 7.72-7.78 (m, 1H), 7.95-7.97 (d, 1H), 8.26-8.28 (d, 1H), 8.41-8.43 (d, 1H). |

TABLE 45-continued

Compounds synthesized using general scheme-15D.

| ID | Structure | LCMS [M + H]+ | 1H-NMR Data |
|---|---|---|---|
| I-724 | 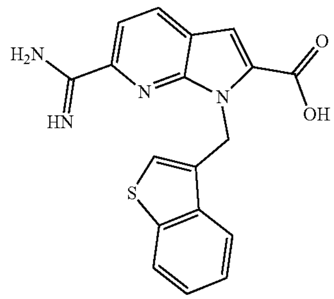 [SMILES: N=C(N)c1ccc2cc(C(=O)O)n(Cc3csc4ccccc34)c2n1] | 350.9 | 1HNMR (DMSO-d6, 300 MHz): δ 6.36 (s, 2H), 6.95 (s, 1H), 7.33-7.43 (m, 3H), 7.94-8.10 (m, 3H), 8.44-8.46 (d, 1H), 9.52-9.61 (bs, 4H). |
| I-679 | 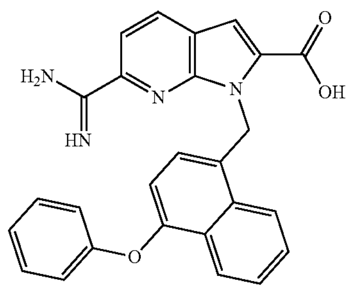 [SMILES: N=C(N)c1ccc2cc(C(=O)O)n(Cc3ccc(Oc4ccccc4)c4ccccc34)c2n1] | 437.0 | 1HNMR (CD3OD, 400 MHz): δ 6.23-6.25 (d, 1H), 6.60-6.66 (m, 3H), 6.92-6.94 (d, 2H), 7.03-7.07 (m, 1H), 7.26-7.31 (m, 2H), 7.54-7.68 (m, 3H), 7.92-8.10 (d, 1H), 8.18-8.20 (d, 1H), 8.34-8.36 (d, 1H), 8.48-8.50 (d, 1H). |
| I-667 | 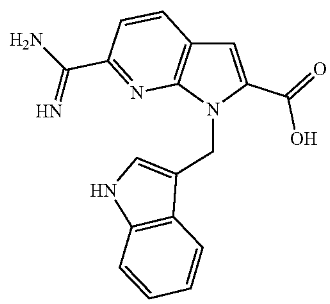 [SMILES: N=C(N)c1ccc2cc(C(=O)O)n(Cc3c[nH]c4ccccc34)c2n1] | 332.2 | 1HNMR (CD3OD, 300 MHz): δ 6.26 (s, 2H), 6.83-7.03 (m, 2H), 7.23-7.34 (m, 3H), 7.56-7.59 (d, 1H), 7.94-7.97 (d, 1H), 8.33-8.36 (d, 1H). |

TABLE 46

Compounds synthesized using general scheme-15D.

| ID | Structure | LCMS [M + H]+ | 1H-NMR Data |
|---|---|---|---|
| I-767 | 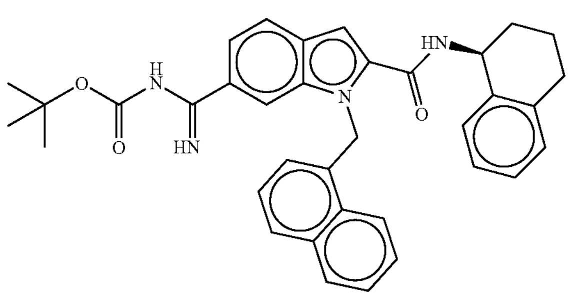 | 573.0 | 1HNMR (CDCl3, 400 MHz): δ 1.49-1.55 (s, 9H), 1.744-1.746 (t, 2H) 1.98 (m, 2H), 2.2 (m, 1H), 2.720-2.738 (m, 2H), 5.17-5.29 (m, 2H), 6.28-6.30 (dd, 2H), 6.34-6.37 (m, 2H), 6.97 (s, 1H), 7.03-7.061 (m, 2H), 7.127-7.258 (m, 2H), 7.511-7.633 (m, 3H), 7.711-7.732 (d, 1H), 7.88-7.89 (m, 1H), 8.13-8.15 (d, 1H). |

TABLE 47
Compounds synthesized using general scheme-15D.
| ID | Structure | LCMS [M + H]+ | 1H-NMR Data |
|---|---|---|---|
| I-771 | 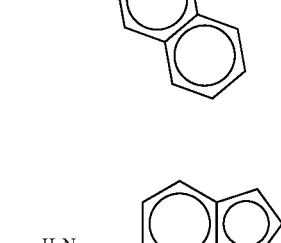 | 470.0 | 1HNMR (CD3OD, 300 MHz): δ 6.20-6.29 (d, 1H), 6.44 (s, 2H), 7.11-7.16 (t, 1H), 7.45-7.65 (m, 5H), 7.72-7.82 (m, 2H), 7.94-8.18 (m, 5H), 8.63-8.69 (m, 2H), 8.87-8.88 (d, 1H). |
| I-764 | 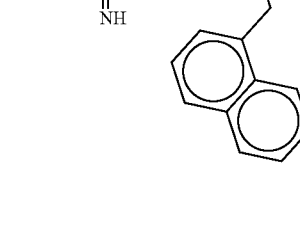 | 473.4 | 1HNMR (CD3OD, 400 MHz): δ 1.695-1.724 (m, 2H), 1.880-1.917 (m, 2H), 2.732-2.771 (m, 2H), 6.281-6.306 (d, 1H), 6.392-6.451 (d, 1H), 6.517-6.576 (d, 1H), 6.763-7.788 (d, 2H), 6.837-6.886 (m, 1H), 7.018-7.061 (m, 2H), 7.182-7.247 (m, 2H), 7.537-7.674 (m, 3H), 7.779-7.806 (d, 1H), 7.920-7.966 (m, 2H), 8.019 (s, 1H), 8.228-8.255 (d, 1H), |
| I-763 | 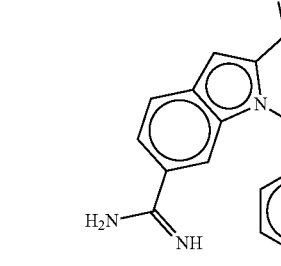 | 420.3 | 1HNMR (CD3OD, 400 MHz): δ 6.26 (d, 1H), 6.51 (s, 2H), 7.18 (t, 1H), 7.58-7.66 (m, 3H), 7.75 (d, 1H), 7.79 (s, 1H), 7.92 (d, 1H), 8.06 (t, 2H), 8.23 (t, 3H), 8.5 (d, 2H). |
| I-760 | 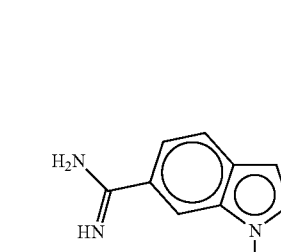 | 477.3 | 1HNMR (CD3OD, 400 MHz): δ 4.195 (s, 4H), 6.351-6.369 (d, 1H), 6.463 (s, 2H), 6.633-6.654 (d, 1H), 6.693-6.733 (t, 1H), 7.210-7.228 (t, 2H), 7.467 (s, 1H), 7.541-7.611 (m, 3H), 7.728-7.749 (d, 1H), 7.892-7.922 (m, 2H), 7.971-7.992 (d, 1H), 8.195-8.217 (d, 1H). |

TABLE 47-continued

Compounds synthesized using general scheme-15D.

| ID | Structure | LCMS [M + H]+ | 1H-NMR Data |
|---|---|---|---|
| I-758 | 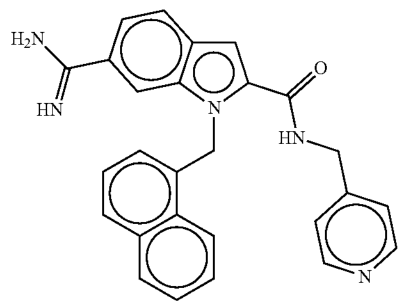 | 434.2 | 1HNMR (CD3OD, 400 MHz): δ 4.63 (S, 2H), 6.16 (d, 1H), 6.44 (s, 2H), 7.22 (t, 1H), 7.43-7.50 (m, 3H), 7.55-7.64 (m, 3H), 7.79 (d, 1H), 7.93-8.05 (m, 3H), 8.17 (d, 1H), 8.38 (t, 2H). |
| I-754 | 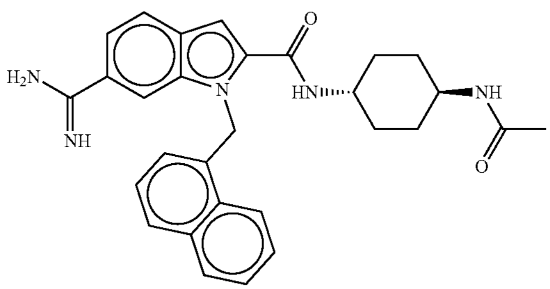 | 482.2 | 1HNMR (CD3OD, 400 MHz): δ 1.21-1.37 (m, 4H), 1.77-1.85 (m, 4H), 1.88 (s, 3H), 3.56-3.65 (m, 2H), 6.28 (d, 1H), 6.41 (s, 2H), 7.18 (t, 1H), 7.27 (s, 1H), 7.53-7.63 (m, 3H), 7.74 (d, 1H), 7.89-7.96 (m, 3H), 8.19 (d, 1H). |
| I-753 | 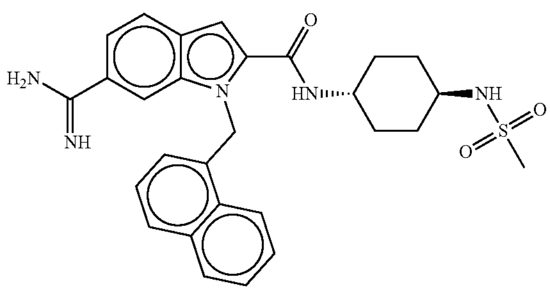 | 518.3 | 1HNMR (CD3OD, 400 MHz): δ 1.28-1.38 (m, 4H), 1.78-1.98 (m, 4H), 2.91 (s, 3H), 3.21-3.29 (m, 1H), 3.58-3.65 (m, 1H), 6.28 (d, 1H), 6.41 (s, 2H), 7.18 (t, 1H), 7.26 (s, 1H), 7.53-7.61 (m, 3H), 7.73 (d, 1H), 7.89-7.95 (m, 3H), 8.18 (d, 1H). |
| I-741 | 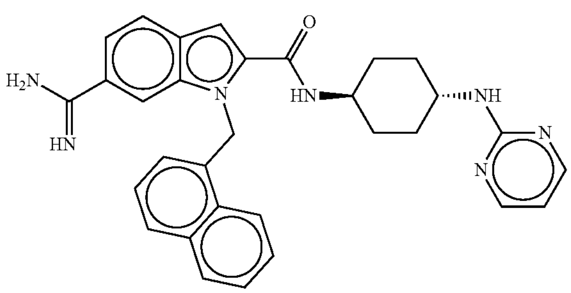 | 518.3 | 1HNMR (CD3OD, 300 MHz): δ 1.29-1.43 (m, 4H), 1.84-2.03 (m, 4H), 3.65-3.85 (m, 2H), 6.29-6.310 (d, 1H), 6.433 (s, 2H), 6.73-6.77 (t, 1H), 7.17-7.28 (m, 2H), 7.54-7.63 (m, 3H), 7.73-7.76 (d, 1H), 7.90-7.96 (m, 3H), 8.19-8.21 (d, 1H) 8.38-8.40 (d, 2H). |
| I-736 | 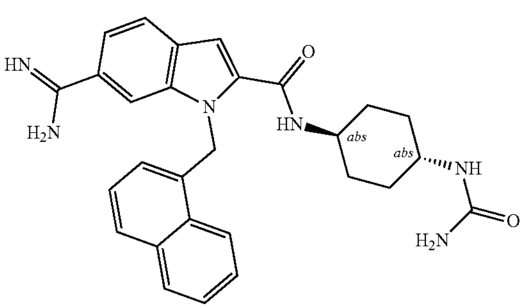 [SMILES: N=C(N)c1ccc2cc(C(=O)N[C@H]3CC[C@H](NC(N)=O)CC3)n(Cc3cccc4ccccc34)c2c1] | 483.2 | 1HNMR (CD3OD, 300 MHz): 1.16-1.38 (m, 5H), 1.76-1.91 (m, 4H), 3.65 (s, 1H), 6.29 (d, 1H), 6.41 (s, 2H), 7.19 (t, 1H), 7.27 (s, 1H), 7.53-7.62 (m, 3H), 7.75 (d, 1H), 7.92 (t, 3H), 8.19 (d, 1H). |

TABLE 47-continued

Compounds synthesized using general scheme-15D.

| ID | Structure | LCMS [M + H]+ | ¹H-NMR Data |
|---|---|---|---|
| I-735 | 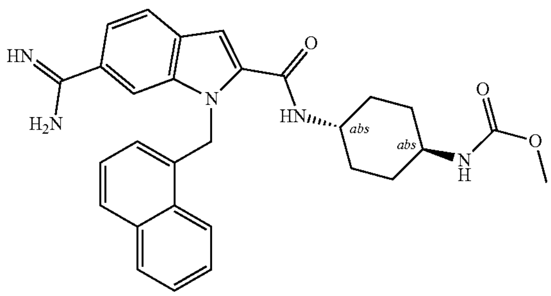 [SMILES: COC(=O)N[C@H]1CC[C@H](NC(=O)c2cc3ccc(C(=N)N)cc3n2Cc2cccc3ccccc23)CC1] | 498.2 | ¹HNMR (CD$_3$OD, 400 MHz): 1.28 (m, 6H), 1.75-1.79 (m, 4H), 3.58 (s, 4H), 6.29 (d, 1H), 6.41 (s, 2H), 7.19 (t, 1H), 7.26 (s, 1H), 7.53-7.61 (m, 3H), 7.74 (d, 1H), 7.90-7.95 (m, 3H), 8.19 (d, 1H), 8.52 (s, 1H). |
| I-734 | 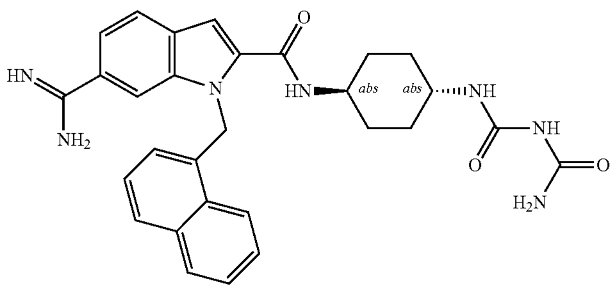 [SMILES: N=C(N)c1ccc2cc(C(=O)N[C@H]3CC[C@H](NC(=O)NC(N)=O)CC3)n(Cc3cccc4ccccc34)c2c1] | 526.4 | ¹HNMR (CD$_3$OD, 400 MHz): δ 1.29 (m, 8H), 1.80 (s, 2H), 1.93 (s, 2H), 2.02 (s, 2H), 3.50 (s, 1H), 3.65 (s, 1H), 6.28 (d, 1H), 6.41 (s, 1H), 7.19 (t, 1H), 7.27 (s, 1H), 7.54 (t, 1H), 7.62 (t, 2H), 7.72 (d, 1H), 7.92 (d, 1H), 7.95 (t, 1H), 8.20 (d, 1H). |
| I-729 | 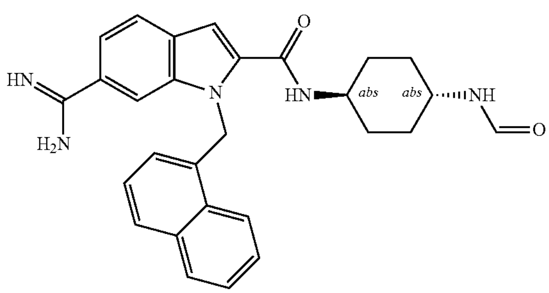 [SMILES: N=C(N)c1ccc2cc(C(=O)N[C@H]3CC[C@H](NC=O)CC3)n(Cc3cccc4ccccc34)c2c1] | 468.2 | ¹HNMR (CD$_3$OD, 300 MHz): δ 1.25-1.39 (m, 4H), 1.79-1.9 (m, 4H), 3.67 (t, 2H), 6.286 (t, 1H), 6.42 (s, 1H), 7.20 (s, 2H), 7.27 (s, 1H), 7.54-7.64 (m, 2H), 7.75 (d, 1H), 7.90-7.96 (m, 3H), 8.20 (d, 1H). |
| I-728 | 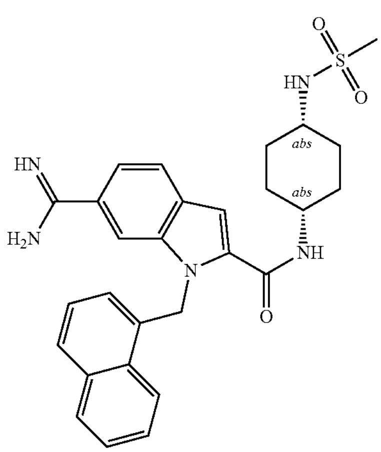 [SMILES: CS(=O)(=O)N[C@H]1CC[C@@H](NC(=O)c2cc3ccc(C(=N)N)cc3n2Cc2cccc3ccccc23)CC1] | 518.2 | ¹HNMR (CD$_3$OD, 400 MHz): δ 1.62-1.66 (m, 6H), 1.75 (s, 2H), 2.93 (s, 3H), 3.44 (s, 1H), 3.74 (s, 1H), 6.33 (d, 1H), 6.41 (s, 2H), 7.20 (t, 1H), 7.28 (s, 1H), 7.53-7.64 (m, 3H), 7.75 (d, 1H), 7.90-7.97 (m, 3H), 8.19 (d, 1H). |

TABLE 47-continued

Compounds synthesized using general scheme-15D.

| ID | Structure | LCMS [M + H]+ | 1H-NMR Data |
|---|---|---|---|
| I-615 | 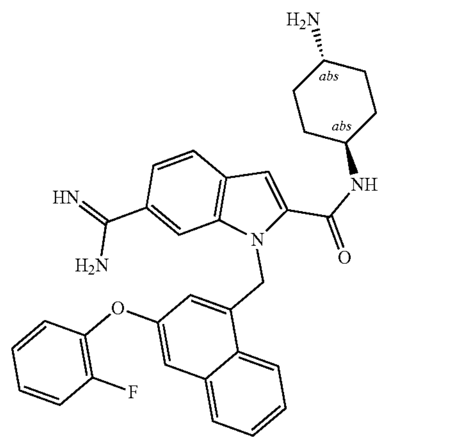 [SMILES: N=C(N)c1ccc2cc(C(=O)N[C@H]3CC[C@H](N)CC3)n(Cc3cc(Oc4ccccc4F)cc4ccccc34)c2c1] | 550.2 | 1HNMR (CD3OD, 300 MHz): δ 1.29-1.47 (m, 4H), 1.95-2.02 (m, 4H), 3.06 (s, 1H), 3.57 (s, 1H), 5.99 (s, 1H), 6.45 (s, 2H), 6.96-7.00 (m, 2H), 7.05-7.09 (m, 1H), 7.12-7.16 (m, 2H), 7.28 (s, 1H), 7.51-7.59 (m, 3H), 7.72-7.75 (m, 1H), 7.91-7.94 (d, 1H), 8.00 (s, 1H), 8.15-8.18 (d, 1H), 8.61-8.63 (s, 1H) |
| I-612 | 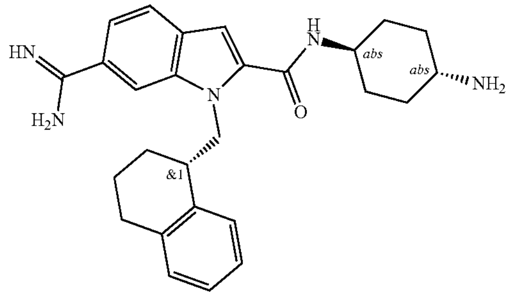 [SMILES: N=C(N)c1ccc2cc(C(=O)N[C@H]3CC[C@H](N)CC3)n(C[C@H]3CCCc4ccccc43)c2c1] | 444.4 | 1HNMR (CD3OD, 300 MHz): δ 1.29-1.75 (m, 6H), 1.75-2.12 (m, 4H), 2.74-2.88 (m, 2H), 3.07-3.11 (m, 1H), 3.299-3.30 (m, 1H), 3.70-3.85 (m, 1H), 4.70-5.03 (m, 2H), 6.64-6.66 (d, 1H), 6.86-6.91 (m, 1H), 7.05-7.09 (m, 3H), 7.49-7.52 (d, 1H), 7.83-7.86 (d, 1H), 7.96 (s, 1H), 8.46 (s, 2H). |
| I-600 | 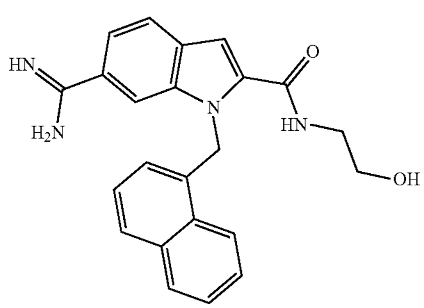 [SMILES: N=C(N)c1ccc2cc(C(=O)NCCO)n(Cc3cccc4ccccc34)c2c1] | 387.2 | 1HNMR (CD3OD, 400 MHz): δ 3.373-3.387 (t, 2H), 3.564-3.592 (t, 2H), 6.256-6.274 (d, 2H), 6.458 (s, 2H), 7.193 (t, 1H), 7.348 (s, 1H), 7.544-7.562 (t, 2H), 7.632 (t, 1H), 7.735-7.756 (d, 1H), 7.908-7.940 (t, 1H), 7.962 (m, 1H), 8.204-8.226 (d, 1H). |
| I-587 | 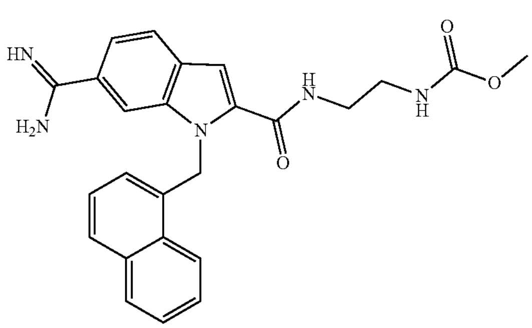 [SMILES: COC(=O)NCCNC(=O)c1cc2ccc(C(=N)N)cc2n1Cc1cccc2ccccc12] | 444.2 | 1HNMR (CD3OD, 400 MHz): δ 3.178-3.208 (t, 2H), 3.297-3.313 (m, 4H), 3.561 (s, 3H), 6.250-6.268 (d, 1H), 6.450 (s, 2H), 7.176-7.214 (m, 1H), 7.309 (s, 1H), 7.540-7.585 (m, 2H), 7.633-7.736 (m, 1H), 7.737-7.757 (d, 1H), 7.908 (s, 1H), 7.929-7.961 (m, 1H), 8.204-8.224 (d, 1H). |

TABLE 47-continued

Compounds synthesized using general scheme-15D.

| ID | Structure | LCMS [M + H]+ | ¹H-NMR Data |
|---|---|---|---|
| I-721 | 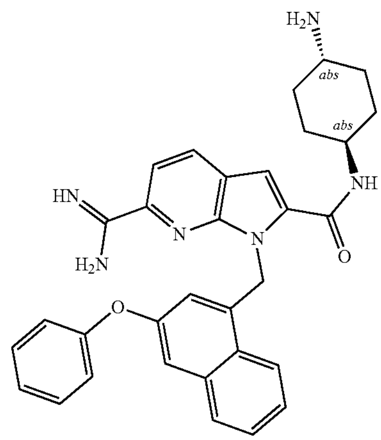 [SMILES: N=C(N)c1ccc2cc(C(=O)N[C@H]3CC[C@H](N)CC3)n(Cc3cc(Oc4ccccc4)cc4ccccc34)c2n1] | 533.2 | ¹HNMR (CD$_3$OD, 300 MHz): δ 1.29-1.47 (m, 4H), 1.89-2.04 (m, 4H), 3.02-3.10 (m, 1H), 3.67-3.75 (m, 1H), 6.34 (s, 1H), 6.55 (s, 2H), 6.85-6.88 (d, 2H), 7.06-7.30 (m, 5H), 7.45-7.49 (m, 2H), 7.71-7.74 (m, 1H), 7.99-8.02 (m, 1H), 8.22-8.25 (m, 1H), 8.36-8.39 (d, 1H). |
| I-723 | 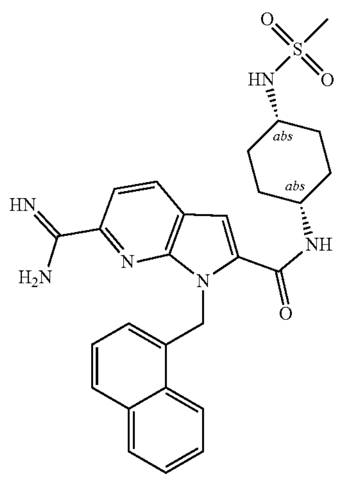 [SMILES: CS(=O)(=O)N[C@H]1CC[C@@H](NC(=O)c2cc3ccc(C(=N)N)nc3n2Cc2cccc3ccccc23)CC1] | 519.2 | ¹HNMR (CD$_3$OD, 400 MHz): δ 1.54-1.75 (m, 8H), 2.94 (s, 3H), 3.40-3.46 (m, 1H), 3.70-3.76 (m, 1H), 6.53 (s, 2H), 6.67-6.72 (d, 1H), 7.18 (s, 1H), 7.26-7.40 (m, 1H), 7.50-7.53 (m, 2H), 7.76-7.78 (d, 1H), 7.88-7.91 (m, 1H), 8.02-8.04 (d, 1H), 8.23-8.25 (m, 1H), 8.41-8.49 (m, 2H). |
| I-722 | 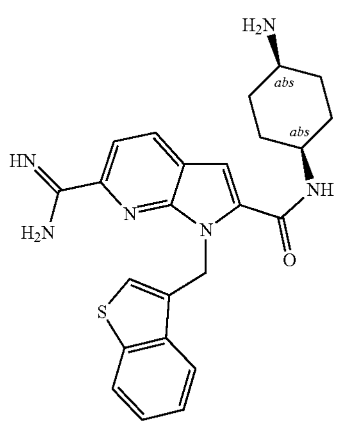 [SMILES: N=C(N)c1ccc2cc(C(=O)N[C@H]3CC[C@@H](N)CC3)n(Cc3csc4ccccc34)c2n1] | 447.1 | ¹HNMR (CD$_3$OD, 400 MHz): δ 1.66-1.84 (m, 8H), 3.22-3.28 (m, 1H), 3.95-4.10 (m, 1H), 6.25 (s, 2H), 7.10 (s, 1H), 7.23-7.29 (m, 3H), 7.76-7.82 (m, 2H), 8.02-8.04 (d, 1H), 8.35-8.37 (d, 1H). |

TABLE 48

Compounds synthesized using general scheme-15D-1.

| ID | Structure | LCMS [M + H]+ | 1H-NMR Data |
|---|---|---|---|
| I-811 | 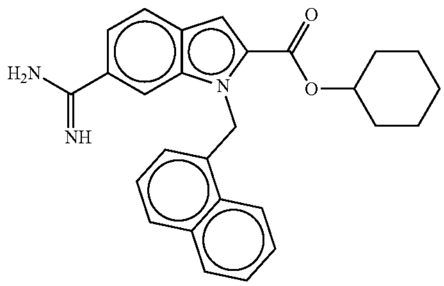 | 426.1 | 1HNMR (CD3OD, 400 MHz): δ 0.86-0.89 (m, 1H), 1.15-1.18 (m, 2H), 1.28-1.43 (m, 7H), 1.57-1.58 (m, 2H), 1.71 (m, 2H), 6.14-6.16 (d, 1H), 6.46 (s, 2H), 7.17-7.21 (t, 1H), 7.55-7.64 (m, 4H), 7.64-7.68 (t, 1H), 7.68-7.76 (d, 1H), 7.92-8.01 (m, 3H), 8.23-8.25 (d, 1H). |
| I-779 | 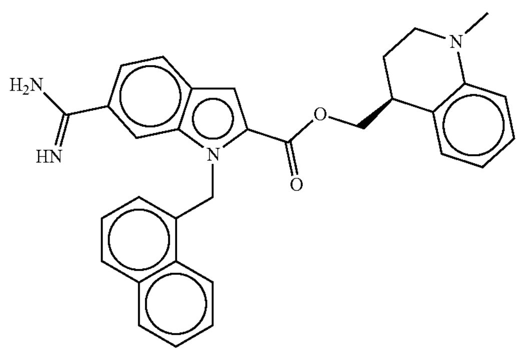 | 503.1 | 1HNMR (CD3OD, 300 MHz): δ 1.74-1.84 (m, 4H), 2.87 (s, 3H), 2.98-3.14 (m, 3H), 4.29-4.38 (m, 2H), 6.20 (d, 1H), 6.46 (s, 2H), 6.65-6.74 (m, 2H), 7.03-7.11 (m, 2H), 7.19-7.23 (t, 1H), 7.58-7.70 (m, 4H), 7.76-7.78 (d, 1H), 7.94-7.99 (m, 2H), 8.02-8.04 (d, 1H), 8.23-8.25 (d, 1H). |
| I-761 | 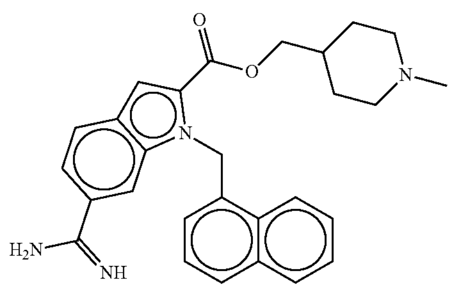 | 455.2 | 1HNMR (CD3OD, 300 MHz): δ 1.35 (d, 2H), 1.75 (d, 3H), 2.69 (s, 2H), 2.75 (s, 3H), 4.12 (d, 2H), 4.81 (s, 1H), 4.94 (s, 1H), 6.15 (d, 1H), 6.47 (s, 2H), 7.19 (t, 1H), 7.57-7.68 (m, 4H), 7.76 (d, 1H), 7.94-8.03 (m, 2H), 8.26 (d, 1H). |
| I-752 | 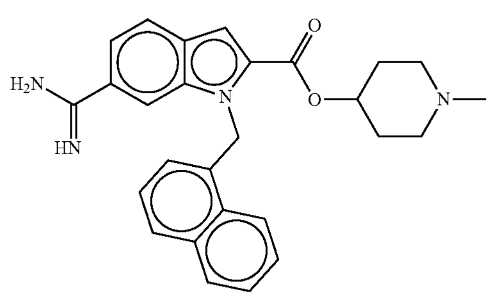 | 441.2 | 1HNMR (CD3OD, 400 MHz): δ 1.95-2.03 (m, 4H), 2.55 (s, 3H), 3.01-3.05 (m, 2H), 3.29-3.33 (m, 2H), 5.15-5.20, (m, 1H), 6.22 (d, 1H), 6.47 (s, 2H), 7.22 (t, 1H), 7.58-7.80 (m, 5H), 7.95-8.04 (m, 3H), 8.27 (d, 1H). |
| I-745 | 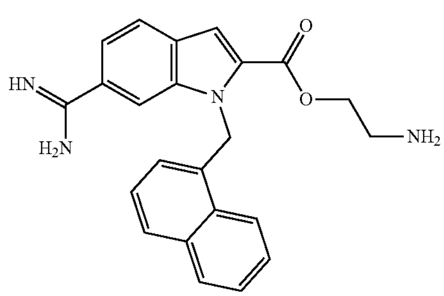 [SMILES: N=C(N)c1ccc2cc(C(=O)OCCN)n(Cc3cccc4ccccc34)c2c1] | 387.2 | 1HNMR (CD3OD, 400 MHz): δ 3.30-3.27 (t, 2H), 4.45-4.43 (t, 2H), 6.20-6.18 (d, 1H), 6.50 (s, 2H), 7.18-7.14 (t, 1H), 7.78-7.57 (m, 5H), 8.03-7.92 (m, 3H), 8.26-8.24 (d, 1H). |

TABLE 48-continued

Compounds synthesized using general scheme-15D-1.

| ID | Structure | LCMS [M + H]+ | ¹H-NMR Data |
|---|---|---|---|
| I-744 | 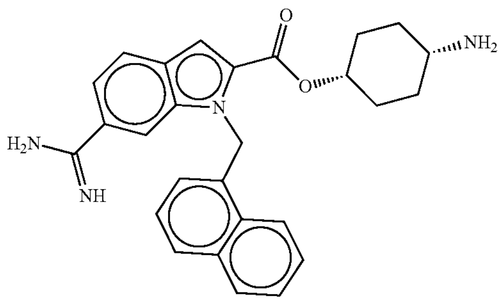 | 441.4 | ¹HNMR (CD₃OD, 400 MHz): δ 5 2.00-1.68 (m, 8H), 3.20-3.10 (m, 1H), 5.20-5.10 (m, 1H), 6.20-6.18 (d, 1H), 6.49 (s, 2H), 7.20-7.16 (t, 1H), 7.76-7.57 (m, 5H), 8.02-7.92 (m, 3H), 8.26-8.23 (d, 1H). |
| I-629 | 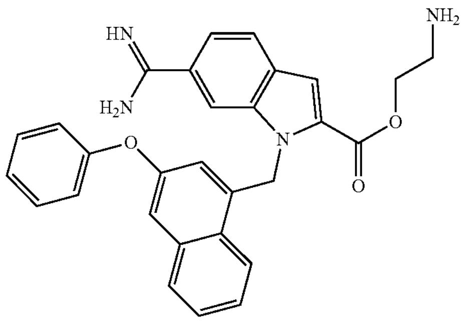 [SMILES: N=C(N)c1ccc2cc(C(=O)OCCN)n(Cc3cc(Oc4ccccc4)cc4ccccc34)c2c1] | 479.2 | ¹HNMR (CD₃OD, 400 MHz): δ 3.297-3.344 (m, 2H), 4.473-4.499 (t, 2H), 5.58 (s, 1H), 6.499 (s, 2H), 6.187-6.839 (d, 2H), 7.10 (t, 1H), 7.116-7.120 (bs, 1H), 7.220-7.242 (t, 2H), 7.568-7.586 (m, 3H), 7.740 (s, 1H), 7.75 (d, 1H), 7.979-7.999 (d, 2H), 8.4 (d, 1H). |
| I-611 | 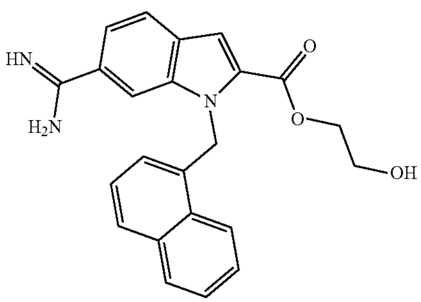 [SMILES: N=C(N)c1ccc2cc(C(=O)OCCO)n(Cc3cccc4ccccc34)c2c1] | 388.5 | ¹HNMR (CD₃OD, 400 MHz): δ 3.74 (t, 2H), 4.27 (t, 2H), 6.20 (d, 1H), 6.49 (s, 2H), 7.15-7.20 (t, 1H), 7.55-7.60 (m, 2H), 7.62-7.68 (m, 2H), 7.75-7.76 (d, 1H), 7.90-7.94 (d, 2H), 8.0 (d, 1H), 8.25-8.3 (d, 1H). |
| I-602 | 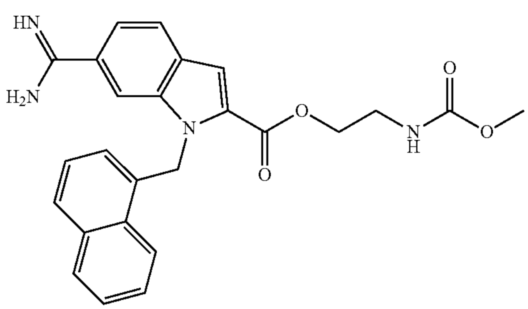 [SMILES: COC(=O)NCCOC(=O)c1cc2ccc(C(=N)N)cc2n1Cc1cccc2ccccc12] | 445.2 | ¹HNMR (CD₃OD, 400 MHz): δ 3.353-3.379 (t, 2H), 3.585 (s, 3H), 4.225-4.253 (t, 2H), 6.05 (s, 1H) 6.482 (s, 2H), 7.170-7.208 (t, 1H), 7.555-7.605 (t, 2H), 7.666 (d, 2H), 7.744-7.643 (d, 1H), 7.927-7.938 (d, 2H), 8.003-8.023 (d, 1H), 8.244-8.265 (d, 1H) |
| I-597 | 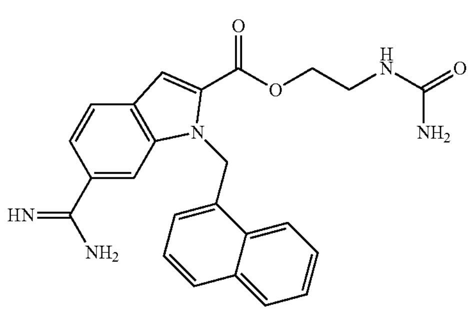 [SMILES: N=C(N)c1ccc2cc(C(=O)OCCNC(N)=O)n(Cc3cccc4ccccc34)c2c1] | 430.1 | ¹HNMR (CD₃OD, 300 MHz): δ 3.38 (t, 2H), 4.21-4.25 (t, 2H), 6.05-6.18 (d, 1H), 6.48 (s, 2H), 7.18 (t, 1H), 7.55-7.76 (m, 5H), 7.93-8.02 (m, 3H), 8.24-8.27 (d, 1H). |

TABLE 48-continued

Compounds synthesized using general scheme-15D-1.

| ID | Structure | LCMS [M + H]⁺ | ¹H-NMR Data |
|---|---|---|---|
| I-596 | 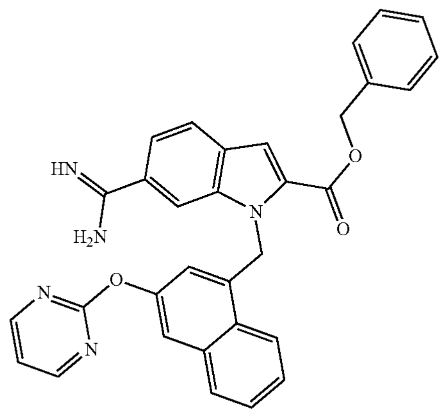 [SMILES: N=C(N)c1ccc2cc(C(=O)OCc3ccccc3)n(Cc3cc(Oc4ncccn4)cc4ccccc34)c2c1] | 528.1 | ¹HNMR (CD₃OD, 400 MHz): δ 5.25 (s, 2H), 6.48 (s, 2H), 7.08 (t, 1H), 7.21-7.22 (m, 4H), 7.54 (d, 1H), 7.56 (s, 1H), 7.62-7.64 (t, 2H), 7.92-7.94 (d, 2H), 7.98 (s, 1H), 8.21 (d, 1H), 8.35-8.36 (d, 2H) |
| I-583 | 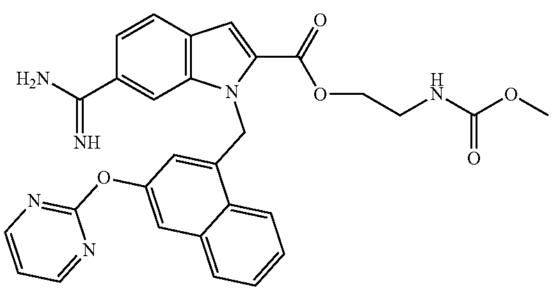 [SMILES: COC(=O)NCCOC(=O)c1cc2ccc(C(=N)N)cc2n1Cc1cc(Oc2ncccn2)cc2ccccc12] | 539.3 | ¹HNMR (CD₃OD, 400 MHz): δ 3.338 (m, 2H), 3.557 (s, 3H), 4.260 (t, 2H), 5.850 (t, 1H), 6.158 (s, 2H), 7.120 (t, 1H), 7.550 (d, 1H), 7.574 (s, 2H), 7.610-7.750 (m, 2H), 7.930-7.957 (d, 2H), 7.983 (s, 1H), 8.300 (d, 1H), 8.397-8.409 (d, 2H). |
| I-568 | 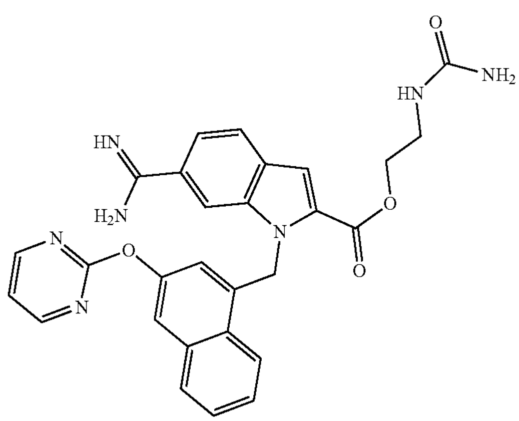 [SMILES: N=C(N)c1ccc2cc(C(=O)OCCNC(N)=O)n(Cc3cc(Oc4ncccn4)cc4ccccc34)c2c1] | 524.2 | ¹HNMR (CD₃OD, 400 MHz): δ 3.37-3.39 (t, 2H), 4.23-4.26 (t, 2H), 5.84 (s, 1H), 6.52 (s, 2H), 7.10-7.13 (t, 1H), 7.52-7.70 (m, 5H), 7.92-7.98 (t, 3H), 8.26-8.29 (d, 1H), 8.39-8.40 (d, 2H). |
| I-565 | 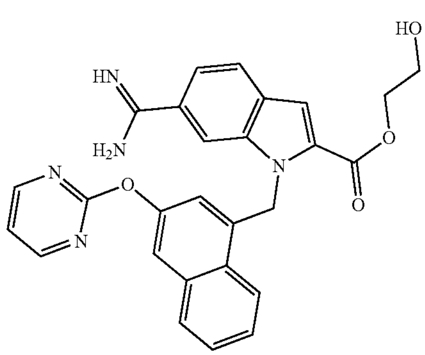 [SMILES: N=C(N)c1ccc2cc(C(=O)OCCO)n(Cc3cc(Oc4ncccn4)cc4ccccc34)c2c1] | 482.1 | ¹HNMR (CD₃OD, 300 MHz): δ 3.71-3.75 (m, 2H), 4.28-4.31 (m, 2H), 5.84 (s, 1H), 6.53 (s, 2H), 7.09-7.13 (m, 1H), 7.52-7.68 (m, 5H), 7.92-7.98 (m, 3H), 8.27-8.30 (d, 1H), 8.39-8.41 (d, 2H), 8.53 (s, 1H). |

TABLE 48-continued

Compounds synthesized using general scheme-15D-1.

| ID | Structure | LCMS [M + H]+ | 1H-NMR Data |
|---|---|---|---|
| I-562 | 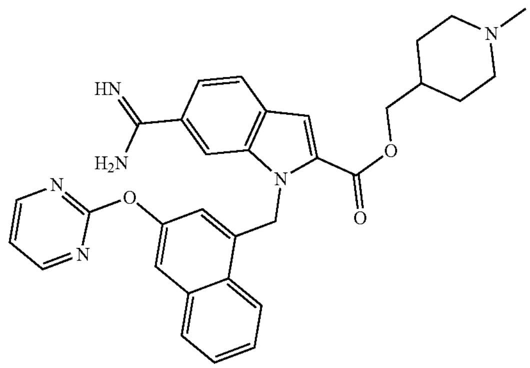 [SMILES: CN1CCC(COC(=O)c2cc3ccc(C(=N)N)cc3n2Cc2cc(Oc3ncccn3)cc3ccccc23)CC1] | 549.1 | 1HNMR (CD3OD, 300 MHz): δ 6.50 (S, 2H), 7.11-7.14 (t, 1H), 7.53-7.73 (m, 5H), 7.92-7.97 (t, 2H), 8.03 (S, 1H), 8.28-8.31 (d, 1H), 8.41 (d, 2H). |
| I-556 | 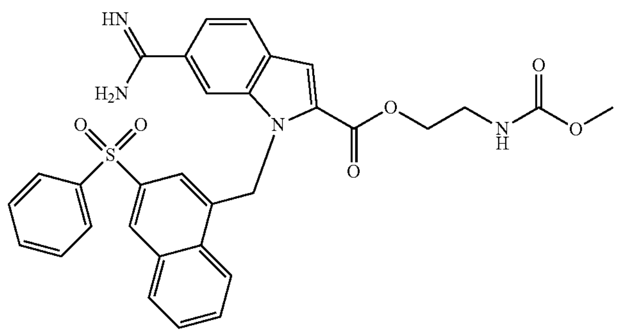 [SMILES: COC(=O)NCCOC(=O)c1cc2ccc(C(=N)N)cc2n1Cc1cc(S(=O)(=O)c2ccccc2)cc2ccccc12] | 585.1 | 1HNMR (CD3OD, 400 MHz): δ 3.325-3.339 (m, 2H), 3.595 (s, 3H), 4.104-4.131 (m, 2H), 6.276 (s, 1H), 6.442 (s, 2H), 7.383-7.423 (m, 2H), 7.538-7.578 (m, 3H), 7.640-7.665 (dd, 1H), 7.706 (s, 1H), 7.747-7.785 (t, 1H), 7.851-7.839 (m, 1H), 7.912 (s, 1H), 8.086-8.107 (d, 1H), 8.164-8.185 (d, 1H), 8.308-8.329 (d, 1H), 8.449 (s, 1H). |
| I-555 | 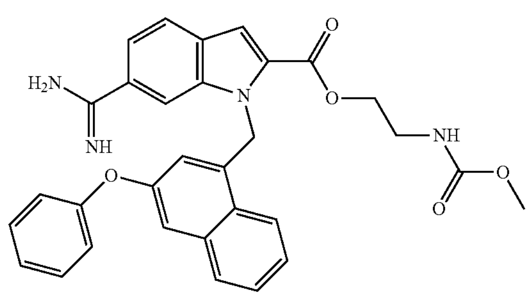 [SMILES: COC(=O)NCCOC(=O)c1cc2ccc(C(=N)N)cc2n1Cc1cc(Oc2ccccc2)cc2ccccc12] | 537.2 | 1HNMR (CD3OD, 400 MHz): δ 3.380-3.407 (m, 2H), 3.588 (s, 3H), 4.250-4.277 (t, 2H), 5.830 (s, 1H), 6.466 (s, 2H), 6.813-6.834 (d, 2H), 7.046-7.084 (t, 1H), 7.133-7.137 (s, 1H), 7.214-7.259 (m, 2H), 7.531-7.577 (m, 4H), 7.595-7.787 (d, 1H), 7.956-7.976 (m, 2H), 8.199-8.218 (d, 1H). |

TABLE 49

Compounds synthesized using general scheme-15D-2.

| ID | Structure | LCMS [M + H]+ | 1H-NMR Data |
|---|---|---|---|
| I-669 | 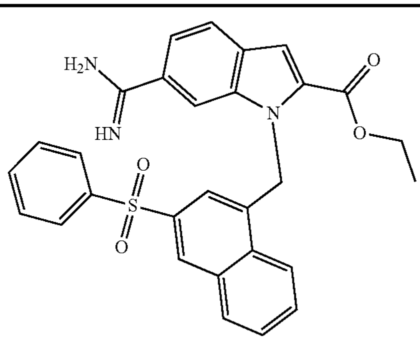 | 512.2 | 1HNMR (CD3OD, 400 MHz ): δ 1.066-1.101 (t, 3H), 4.094-4.111 (q, 2H), 6.280 (s, 2H), 6.435 (s, 2H), 7.404-7.424 (t, 2H), 7.541-7.561 (d, 3H), 7.633-7.644 (d, 2H), 7.763 (t, 1H), 7.800 (t, 1H), 7.926 (s, 1H), 8.076-8.097 (d, 1H), 8.162-8.183 (m, 4H), 8.307-8.327 (d, 1H), 8.498-8.500 (s, 1H). |

TABLE 49-continued

Compounds synthesized using general scheme-15D-2.

| ID | Structure | LCMS [M + H]+ | 1H-NMR Data |
| --- | --- | --- | --- |
| I-662 | 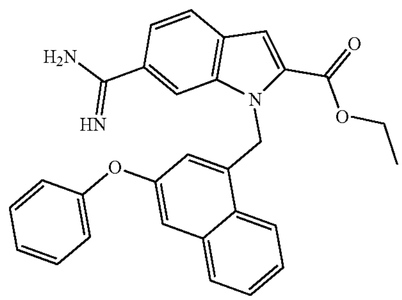 [SMILES: CCOC(=O)c1cc2ccc(C(=N)N)cc2n1Cc1cc(Oc2ccccc2)cc2ccccc12] | 464.2 | 1HNMR (CD3OD, 400 MHz): δ 1.21-1.29 (t, 3H), 4.24-4.29 (q, 2H), 5.92 (s, 1H), 6.46 (s, 2H), 6.80-6.81 (d, 2H), 7.05-7.07 (t, 1H), 7.143-7.148 (d, 1H), 7.21-7.25 (t, 2H), 7.51 (s, 1H), 7.54-7.58 (m, 3H), 7.77-7.79 (d, 1H), 7.94-7.96 (d, 2H), 8.19-8.21 (d, 1H). |
| I-601 | 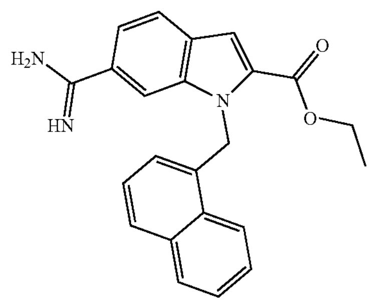 [SMILES: CCOC(=O)c1cc2ccc(C(=N)N)cc2n1Cc1cccc2ccccc12] | 372.1 | 1HNMR (CD3OD, 400 MHz): δ 1.22-1.17 (t, 3H), 4.28-4.20 (q, 2H), 6.16-6.14 (d, 1H), 6.4 (s, 2H), 7.18 (t, 1H), 7.76-7.55 (m, 5H), 8.02-7.92 (d, 3H), 8.26-8.24 (d, 1H). |
| I-708 | 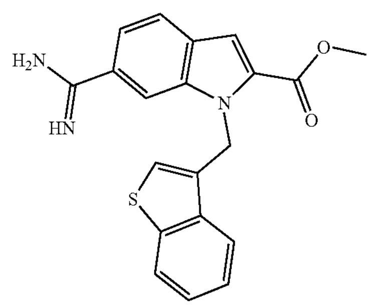 [SMILES: COC(=O)c1cc2ccc(C(=N)N)cc2n1Cc1csc2ccccc12] | 364.0 | 1HNMR (CD3OD, 400 MHz): δ 3.32 (s, 3H), 6.20 (s, 2H), 6.53 (s, 1H), 7.37-7.46 (m, 2H), 7.53-7.55 (m, 2H), 7.86-7.95 (m, 2H), 7.99 (dd, 1H), 8.03 (s, 1H). |

TABLE 50

Compounds synthesized using general scheme-15E.

| ID | Structure | LCMS [M + H]+ | 1H-NMR Data |
| --- | --- | --- | --- |
| I-825 | 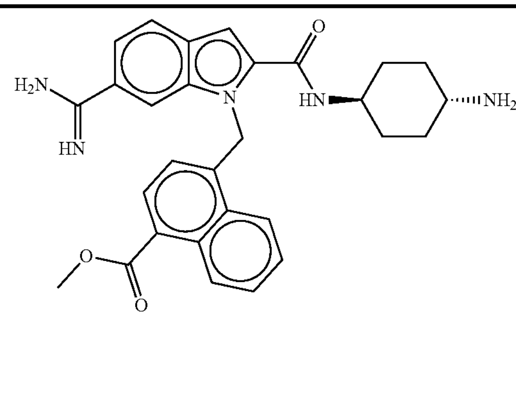 | 498.1 | 1HNMR (CD3OD, 400 MHz): δ 1.42-1.37 (m, 4H), 1.99-1.89 (m, 4H), 3.15-3.00 (m, 1H), 3.72-3.06 (m, 1H), 3.93 (s, 3H), 6.29-6.27 (d, 1H), 6.49 (s, 2H), 7.33 (s, 1H), 7.59-7.57 (m, 1H), 7.73-7.70 (m, 2H), 7.98-7.85 (m, 3H), 8.33-8.30 (m, 1H), 8.92-8.90 (m, 1H). |

TABLE 50-continued

Compounds synthesized using general scheme-15E.

| ID | Structure | LCMS [M + H]+ | 1H-NMR Data |
|---|---|---|---|
| I-824 | 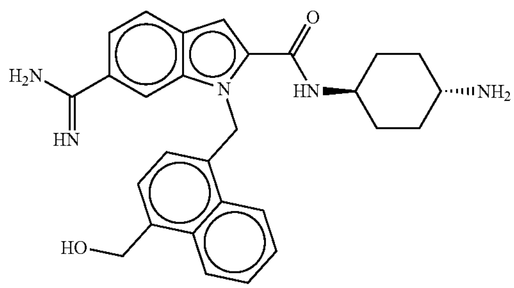 | 470.4 | 1HNMR (CD3OD, 400 MHz): δ 1.40-1.28 (m, 4H), 2.00-1.91 (m, 4H), 3.10-3.00 (m, 1H), 3.70-3.68 (m, 1H), 5.02 (s, 2H), 6.24-6.22 (d, 1H), 6.44 (s, 2H), 7.29-7.22 (m, 2H), 7.66-7.55 (m, 3H), 7.96-7.94 (d, 2H), 8.25-8.18 (m, 2H). |
| I-823 | 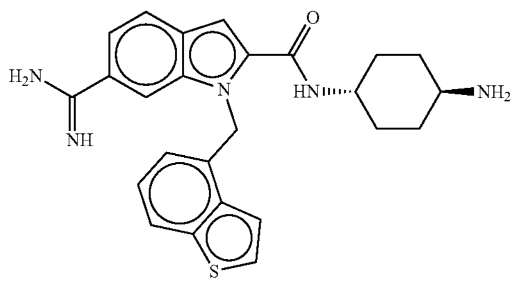 | 446.1 | 1HNMR (CD3OD, 300 MHz): δ 1.25-1.50 (m, 4H), 1.82-2.07 (m, 4H), 2.93-3.03 (m, 1H), 3.62-3.72 (m, 1H), 6.26 (s, 2H), 6.39-6.41 (d, 1H), 7.12-7.14 (t, 1H), 7.21 (s, 1H), 7.53-7.57 (m, 2H), 7.66-7.68 (d, 1H), 7.78-7.80 (d, 1H), 7.90-7.93 (d, 1H), 8.00 (s, 1H). |
| I-822 | 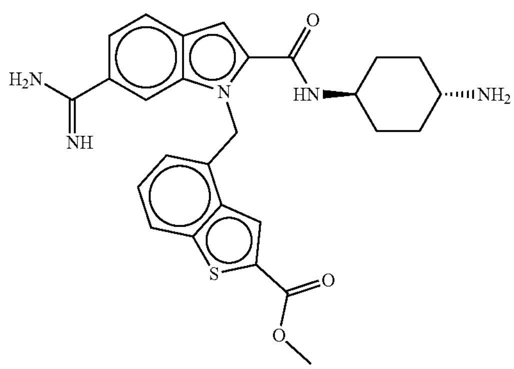 | 504.1 | 1HNMR (CD3OD, 300 MHz): δ 1.30-1.50 (m, 4H), 1.83-2.08 (m, 4H), 2.98-3.09 (m, 1H), 3.65-3.75 (m, 1H), 3.95 (s, 3H), 6.29 (s, 2H), 6.49-6.52 (d, 1H), 7.24-7.28 (m, 2H), 7.54-7.58 (d, 1H), 7.81-7.84 (d, 1H), 7.91-7.94 (d, 1H), 8.05 (s, 1H), 8.34 (s, 1H). |
| I-820 | 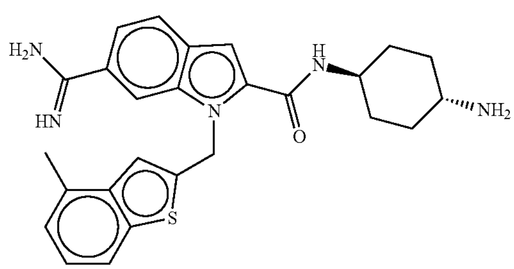 | 460.1 | 1HNMR (CD3OD, 300 MHz): δ 1.42-1.51 (m, 4H), 2.00-2.215 (m, 4H), 2.51 (s, 3H), 3.00-3.15 (m, 1H), 3.80-3.90 (m, 1H), 6.16 (s, 2H), 7.10-7.18 (m, 3H), 7.32 (s, 1H), 7.50-7.56 (m, 2H), 7.86-7.89 (d, 1H), 8.21 (s, 1H). |
| I-819 | 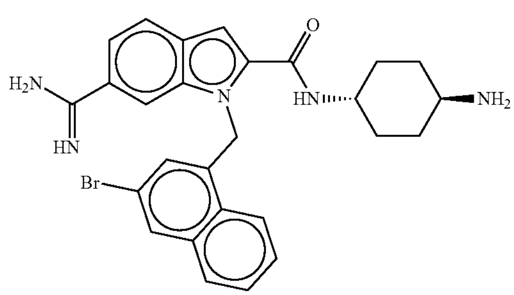 | 520.2 | 1HNMR (DMSO-d6, 400 MHz): δ 1.23-1.36 (m, 4H), 1.75-1.91 (m, 4H), 2.90-3.00 (m, 1H), 3.52-3.60 (m, 1H), 6.13-6.14 (d, 1H), 6.39 (s, 2H), 7.43 (s, 1H), 7.59-7.78 (m, 6H), 7.98-8.01 (d, 2H), 8.11-8.14 (d, 2H), 8.25-8.27 (d, 1H), 8.70-8.74 (d, 1H), 8.95 (s, 2H), 9.18 (s, 2H). |

TABLE 50-continued

Compounds synthesized using general scheme-15E.

| ID | Structure | LCMS [M + H]+ | 1H-NMR Data |
|---|---|---|---|
| I-818 | 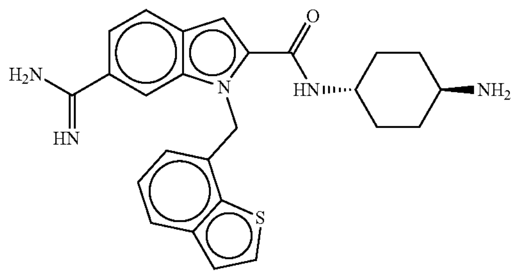 | 446.3 | 1HNMR (CD3OD, 400 MHz): δ 1.48-1.36 (m, 4H), 2.05-1.89 (m, 4H), 3.10-3.06 (m, 1H), 3.70-3.60 (m, 1H), 6.16 (s, 2H), 6.60-6.58 (d, 1H), 7.24-7.20 (m, 2H), 7.44-7.42 (d, 1H), 7.58-7.54 (m, 2H), 7.77-7.75 (m, 1H), 7.94-7.92 (d, 1H), 8.009-8.005 (m, 1H). |
| I-817 | 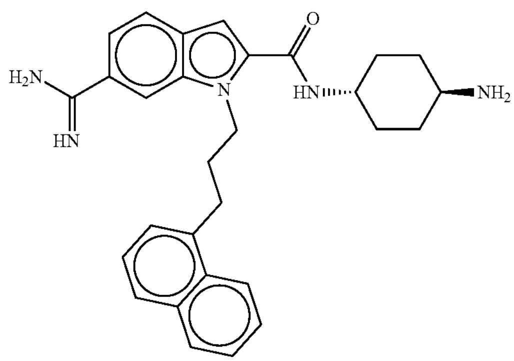 | 468.2 | 1HNMR (CD3OD, 400 MHz): δ 1.56-1.45 (m, 4H), 2.11-2.03 (m, 4H), 2.26-2.22 (m, 2H), 3.09-3.06 (m, 3H), 3.89-3.86 (m, 1H), 4.90-4.77 (t, 2H), 7.12 (s, 1H), 7.51-7.33 (m, 5H), 7.73-7.71 (d, 1H), 7.92-7.83 (m, 4H). |
| I-814 | 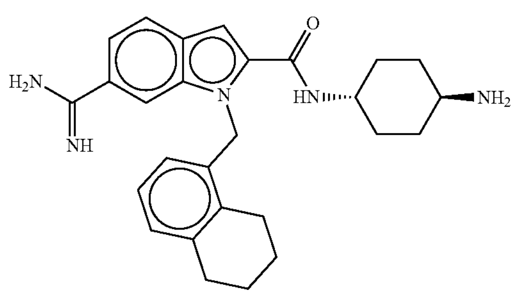 | 444.2 | 1HNMR (CD3OD, 400 MHz): δ 1.39-1.51 (m, 4H), 1.80-1.84 (m, 2H), 1.96-1.90 (m, 3H), 2.07-2.04 (m, 2H), 2.84-2.78 (m, 4H), 3.08-3.07 (m, 1H), 3.74-3.73 (m, 1H), 5.83-5.86 (d, 2H), 6.78-6.82 (t, 1H), 6.91-6.92 (d, 1H), 7.22 (s, 1H), 7.54-7.56 (dd, 1H), 7.91-7.95 (m, 2H), 8.55-8.57 (d, 1H). |
| I-812 | 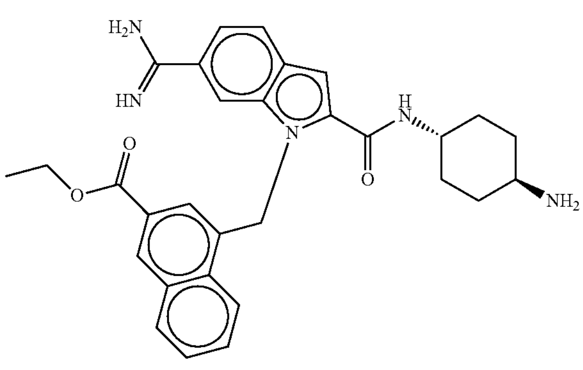 | 512.3 | 1HNMR (DMSO-d6, 400 MHz): δ 1.26-1.29 (m, 3H), 1.38-1.43 (m, 4H), 1.88-2.02 (m, 4H), 3.00-3.10 (m, 1H), 3.62-3.72 (m, 1H), 4.21-4.27 (m, 2H), 6.45 (s, 2H), 6.90 (s, 1H), 7.33 (s, 1H), 7.56-7.77 (m, 4H), 7.95-8.09 (m, 3H), 8.26-8.28 (d, 1H), 8.49 (s, 1H). |

TABLE 50-continued

Compounds synthesized using general scheme-15E.

| ID | Structure | LCMS [M + H]+ | 1H-NMR Data |
|---|---|---|---|
| I-807 | 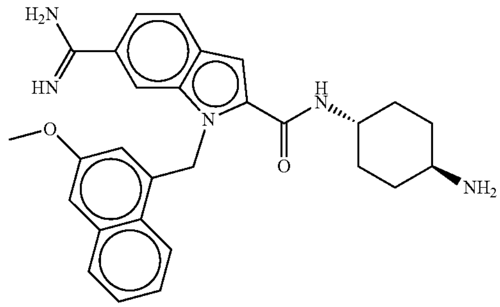 | 470.1 | 1HNMR (CD3OD, 400 MHz): δ 1.40-1.43 (m, 4H), 1.89-2.05 (m, 4H), 3.00-3.10 (m, 1H), 3.62-3.70 (m, 1H), 3.73 (s, 3H), 5.84-5.85 (d, 1H), 6.38 (s, 2H), 7.10-7.11 (d, 1H), 7.29 (s, 1H), 7.45-7.57 (m, 3H), 7.80-7.82 (d, 1H), 7.94-7.96 (d, 2H), 8.07-8.10 (d, 1H). |
| I-799 | 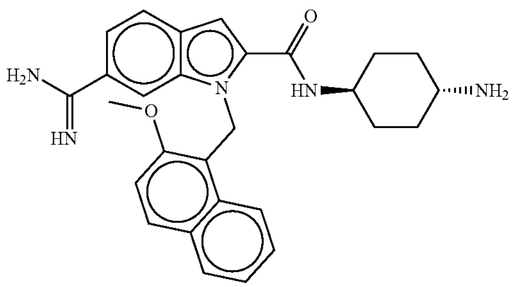 | 470.2 | 1HNMR (CD3OD, 400 MHz): δ 1.53-1.62 (m, 4H), 2.13-2.24 (m, 4H), 3.12-3.20 (m, 1H), 3.98-4.12 (m, 4H), 4.91 (s, 2H), 7.06-7.08 (d, 1H), 7.25-7.45 (m, 4H), 7.75-7.83 (m, 3H), 8.05-8.07 (d, 1H), 8.30 (d, 1H). |
| I-798 | 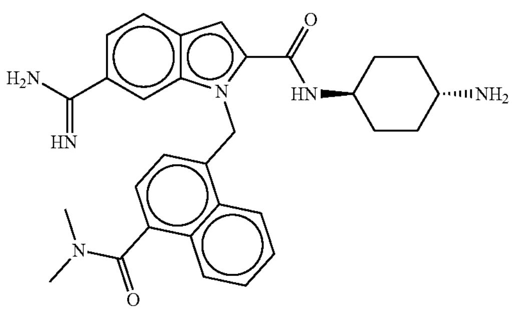 | 511.2 | 1HNMR (CD3OD, 300 MHz): δ 1.41 (m, 4H), 1.95 (m, 4H), 2.79 (s, 3H), 3.05 (s, 1H), 3.20 (s, 3H), 3.71 (s, 1H), 6.3 (d, 1H), 6.47 (s, 2H), 7.14-7.17 (d, 1H), 7.31 (s, 1H), 7.55 (d, 1H), 7.68 (m, H), 7.8 (d, 1H), 7.94-7.96 (d, 2H), 8.31 (d, 1H), 8.6 (d, 1H). |
| I-797 | 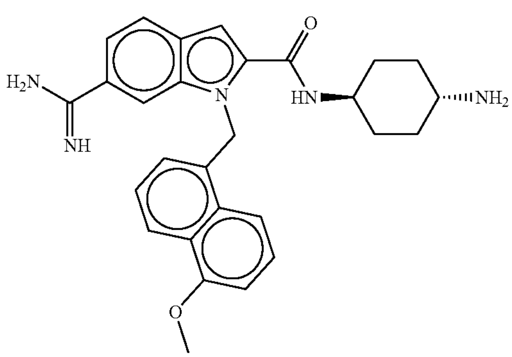 | 470.1 | 1HNMR (CD3OD, 400 MHz): δ 1.29-1.39 (m, 4H), 1.89-1.99 (m, 4H), 3.00-3.10 (m, 1H), 3.62-3.70 (m, 1H), 4.00 (s, 3H), 6.25 (s, 1H), 6.38 (s, 2H), 7.00-7.27 (m, 3H), 7.52-7.60 (m, 2H), 7.72-7.80 (m, 1H), 7.92-8.00 (m, 2H), 8.10-8.15 (m, 1H). |
| I-794 | 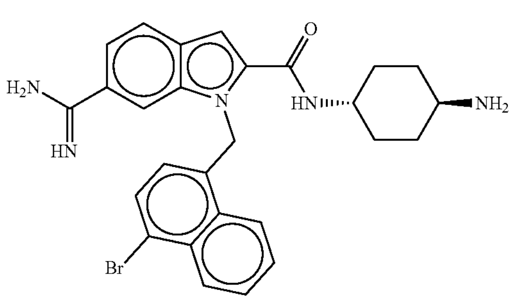 | 518.1 | 1HNMR (CD3OD, 300 MHz): δ 1.39-1.45 (m, 4H), 1.85-2.05 (m, 4H), 3.00-3.10 (m, 1H), 3.60-3.70 (m, 1H), 6.14-6.16 (m, 1H), 6.40 (s, 2H), 7.29 (s, 1H), 7.53-7.58 (m, 2H), 7.70-7.73 (m, 2H), 7.93-7.98 (m, 2H), 8.24-8.32 (m, 2H). |

TABLE 50-continued

Compounds synthesized using general scheme-15E.

| ID | Structure | LCMS [M + H]+ | 1H-NMR Data |
|---|---|---|---|
| I-792 | 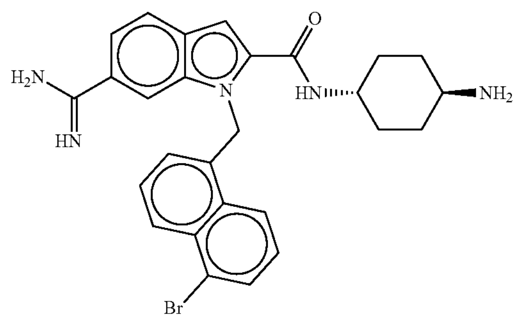 | 520.0 | 1HNMR (CD3OD, 400 MHz): δ 1.28-1.43 (m, 4H), 1.86-2.01 (m, 4H), 3.00-3.10 (m, 1H), 3.62-3.70 (m, 1H), 6.31-6.33 (d, 1H), 6.44 (s, 2H), 7.30-7.35 (m, 2H), 7.50-7.58 (m, 2H), 7.90-7.97 (m, 3H), 8.13-8.15 (d, 1H), 8.24-8.26 (d, 1H), 8.57-8.59 (d, 1H). |
| I-790 | 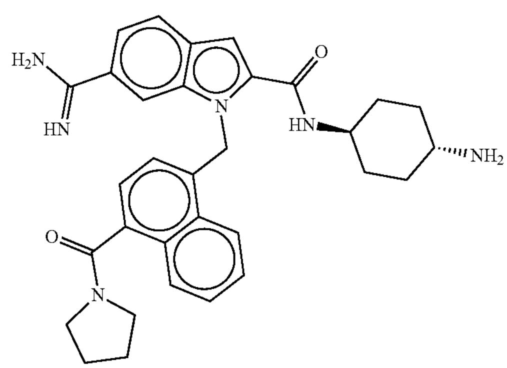 | 537.3 | 1HNMR (CD3OD, 400 MHz): δ 1.42-1.41 (m, 4H), 2.02-1.81 (m, 8H), 3.08-3.07 (m, 3H), 3.71-3.68 (m, 3H), 6.30-6.29 (d, 1H), 6.46 (s, 2H), 7.20-7.18 (d, 1H), 7.31 (s, 1H), 7.71-7.55 (m, 3H), 7.96-7.85 (m, 3H), 8.31-8.29 (d, 1H). |
| I-781 | 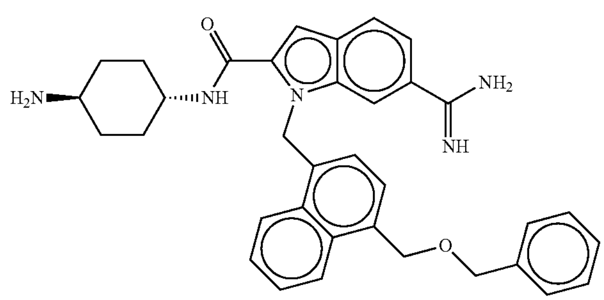 | 560.2 | 1HNMR (CD3OD, 400 MHz): δ 1.43-1.37 (m, 4H), 1.99-1.91 (m, 4H), 3.10-3.01 (m, 1H), 3.70-3.68 (m, 1H), 4.59 (s, 2H), 4.94 (s, 2H), 6.25-6.23 (d, 1H), 6.54 (s, 2H), 7.34-7.24 (m, 7H), 7.69-7.57 (m, 3H), 7.98-7.95 (m, 2H), 8.27-8.19 (m, 2H). |
| I-780 | 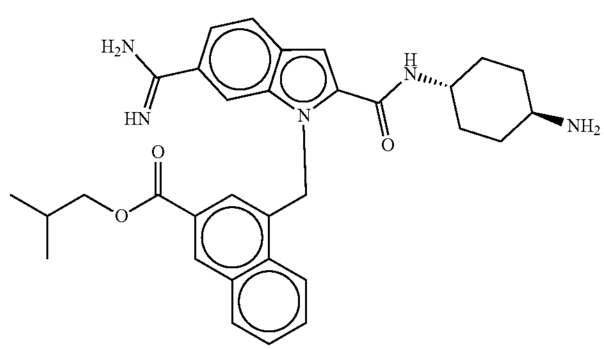 | 540.1 | 1HNMR (CD3OD, 300 MHz): δ 0.88-0.89 (d, 6H), 1.31-1.44 (m, 4H), 1.87-2.01 (m, 5H), 3.00-3.10 (m, 1H), 3.25-3.33 (m, 1H), 3.97-3.98 (d, 2H), 6.49 (s, 2H), 6.89 (s, 1H), 7.38 (s, 1H), 7.59-7.82 (m, 3H), 7.97-8.12 (m, 3H), 8.29-8.32 (d, 1H), 8.50 (s, 1H). |

TABLE 50-continued

Compounds synthesized using general scheme-15E.

| ID | Structure | LCMS [M + H]+ | ¹H-NMR Data |
|---|---|---|---|
| I-778 | 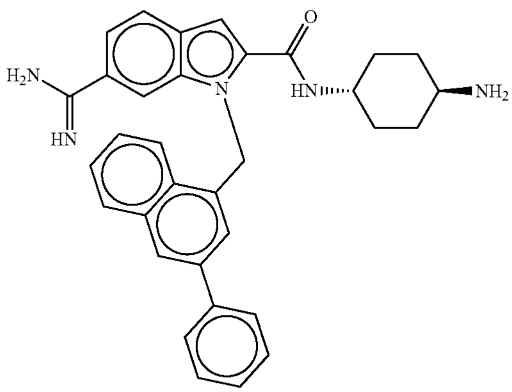 | 516.2 | ¹HNMR (CD$_3$OD, 400 MHz): δ 1.31-1.41 (m, 4H), 1.84-1.98 (m, 4H), 2.95-3.05 (m, 1H), 3.65-3.75 (m, 1H), 6.51 (s, 2H), 6.61 (s, 1H), 7.26-7.42 (m, 6H), 7.57-7.65 (m, 3H), 7.96-8.08 (m, 4H), 8.19-8.22 (d, 1H). |
| I-777 | 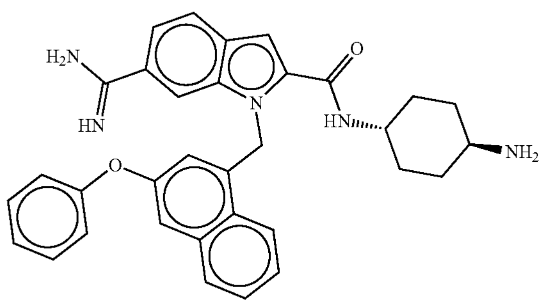 | 532.3 | ¹HNMR (CD$_3$OD, 400 MHz): δ 1.433-1.443 (m, 4H), 1.8-2.2 (m, 4H), 3.1 (bs, 1H), 3.75 (bs, 1H), 6.1 (s, 1H), 6.446 (s, 2H), 6.817-6.836 (d, 2H), 7.05 (t, 1H), 7.132 (s, 1H), 7.219-7.267 (m, 3H), 7.530-7.574 (m, 3H) 7.675 (d, 1H), 7.898-7.920 (d, 1H), 7.978-7.976 (s, 1H), 8.30 (d, 1H). |
| I-775 | 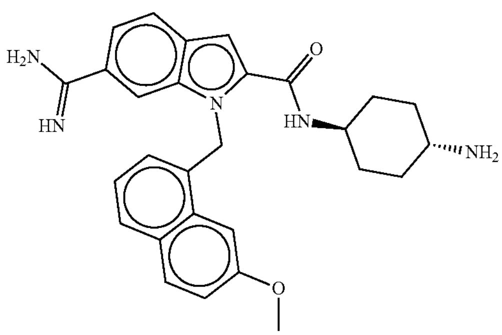 | 470.2 | ¹HNMR (CD$_3$OD, 400 MHz): δ 1.30-1.49 (m, 4H), 1.85-1.88 (m, 2H), 2.01-2.04 (m, 2H), 3.02-3.07 (m, 1H), 3.65-3.69 (m, 2H), 3.84 (s, 3H), 6.33 (s, 2H), 6.45 (d, 1H), 7.10 (t, 1H), 7.17-7.20 (m, 2H), 7.24 (s, 1H), 7.31-7.32 (m, 1H), 7.58 (d, 1H), 7.69 (d, 1H), 7.81 (d, 1H), 7.95 (d, 1H), 8.07 (s, 1H). |
| I-774 | 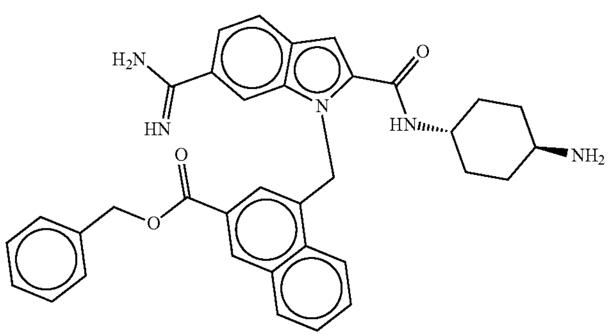 | 574.1 | ¹HNMR (CD$_3$OD, 400 MHz): δ 1.31-1.44 (m, 4H), 1.87-2.01 (m, 4H), 2.95-3.05 (m, 1H), 3.65-3.70 (m, 1H), 5.25 (s, 2H), 6.49 (s, 2H), 6.93 (s, 1H), 7.29-7.36 (m, 6H), 7.59-7.82 (m, 3H), 7.98-8.12 (m, 3H), 8.29-8.32 (d, 1H), 8.54 (s, 1H). |

TABLE 50-continued

Compounds synthesized using general scheme-15E.

| ID | Structure | LCMS [M + H]+ | ¹H-NMR Data |
|---|---|---|---|
| I-773 | 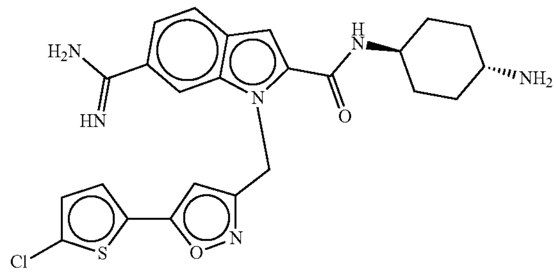 | 497.1 | ¹HNMR (CD₃OD, 400 MHz): δ 1.52-1.57 (m, 4H), 2.11-2.13 (m, 4H), 2.95-3.15 (m, 1H), 3.85-3.95 (m, 1H), 5.96 (s, 2H), 6.53 (s, 1H), 7.06-7.07 (d, 1H), 7.24 (s, 1H), 7.37-7.38 (d, 1H), 7.54-7.57 (dd, 1H), 7.88-7.90 (d, 1H), 8.15 (s, 1H). |
| I-772 | 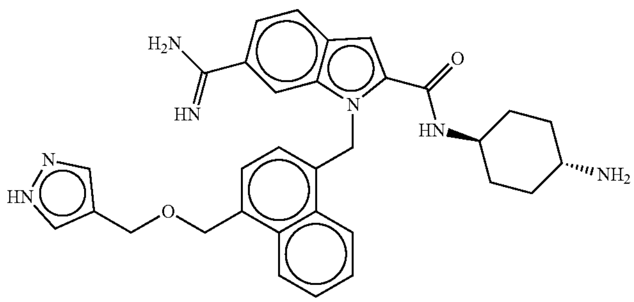 | 550.2 | ¹HNMR (CD₃OD, 400 MHz): δ 1.42-1.40 (m, 4H), 2.00-1.90 (m, 4H), 3.10-3.00 (m, 1H), 3.60-3.55 (m, 1H), 4.56 (s, 2H), 4.91 (s, 2H), 6.24-6.22 (d, 1H), 6.45 (s, 2H), 7.25-7.23 (d, 1H), 7.30 (s, 1H), 7.67-7.56 (m, 5H), 7.97-7.95 (d, 2H), 8.26-8.16 (m, 2H). |
| I-770 | 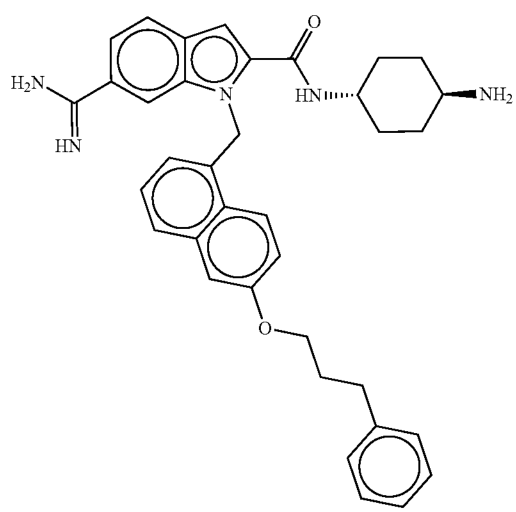 | 574.2 | ¹HNMR (CD₃OD, 400 MHz): δ 1.3-1.6 (m, 4H), 1.9 (bs, 2H), 2.0 (bs, 2H), 2.15-2.25 (m, 2H), 2.88 (t, 2H), 3.0 (bs, 1H), 3.7 (bs, 1H), 4.12 (t, 2H), 6.1 (d, 1H), 6.41 (s, 2H), 7.1-7.2 (m, 2H), 7.25-7.29 (m, 6H), 7.4-7.6 (dd, 2H), 7.6-7.65 (d, 1H), 7.95 (m, 2H), 8.1-8.18 (d, 1H). |
| I-769 | 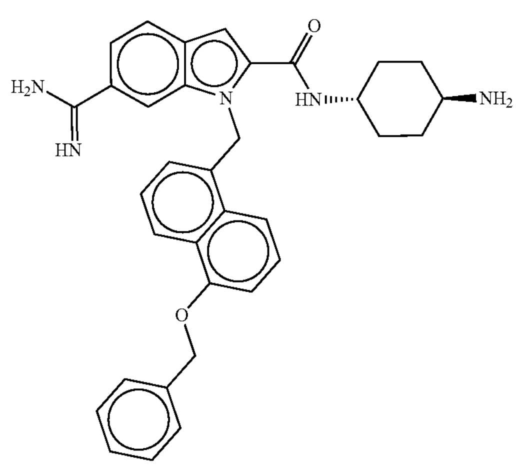 | 546.3 | ¹HNMR (CD₃OD, 400 MHz): δ 1.31-1.42 (m, 4H), 1.91 bs (bs, 2H), 2.00 (bs, 2H), 3.00 (bs, 1H), 3.7 (bs, 1H), 5.32 (s, 2H), 6.27-6.29 (d, 1H), 6.41 (s, 2H), 7.11-7.13 (d, 1H), 7.17-7.21 (t, 1H), 7.29 (s, 1H), 7.35-7.37 (d, 1H), 7.40-7.44 (t, 2H), 7.53-7.59 (m, 4H), 7.77-7.79 (d, 1H), 7.95-7.79 (m, 2H), 8.21-8.24 (d, 1H). |

TABLE 50-continued

Compounds synthesized using general scheme-15E.

| ID | Structure | LCMS [M + H]+ | ¹H-NMR Data |
|---|---|---|---|
| I-768 | 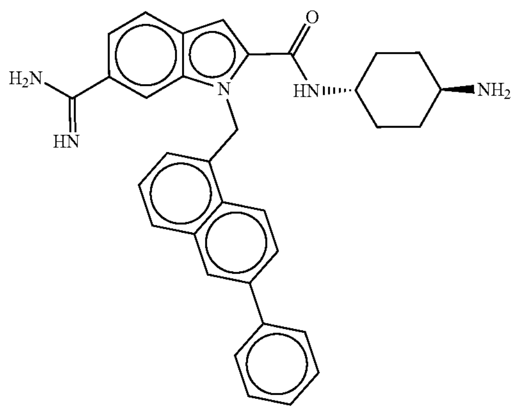 | 516.2 | ¹HNMR (CD₃OD, 400 MHz): δ 1.31-1.41 (m, 4H), 1.91 (bs, 2H), 2.00 (bs, 2H), 3.00 (bs, 1H), 3.7 (bs, 1H), 6.32-6.33 (d, 1H), 6.47 (s, 2H), 7.23-7.27 (t, 1H), 7.30 (s, 1H), 7.41-7.43 (t, 1H), 7.50-7.54 (t, 2H), 7.58-7.60 (dd, 1H), 7.80-7.82 (d, 2H), 7.84-7.86 (d, 1H), 7.94-7.98 (t, 2H), 8.03 (s, 1H), 8.181-8.185 (d, 1H), 8.30-8.32 (d, 1H). |
| I-756 | 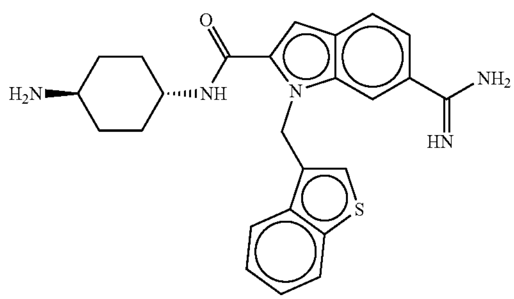 | 446.3 | ¹HNMR (CD₃OD, 400 MHz): δ 1.48-1.37 (m, 4H), 2.05-1.92 (m, 4H), 3.05-3.04 (m, 1H), 3.75-3.74 (m, 1H), 6.76 (s, 1H), 7.17 (s, 1H), 7.39-7.36 (m, 2H), 7.56-7.54 (d, 1H), 7.91-7.79 (m, 3H), 8.12 (s, 1H). |
| I-755 | 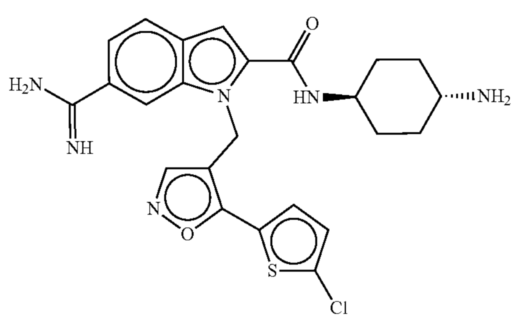 | 497.3 | ¹HNMR (CD₃OD, 400 MHz): δ 1.45-1.48 (m, 4H), 1.99-2.08 (m, 4H), 3.00-3.09 (m, 1H), 3.75-3.81 (m, 1H), 5.88 (s, 2H), 7.17-7.19 (m, 2H), 7.44-7.45 (d, 1H), 7.52-7.54 (dd, 1H), 7.86-7.89 (m, 3H). |
| I-740 | 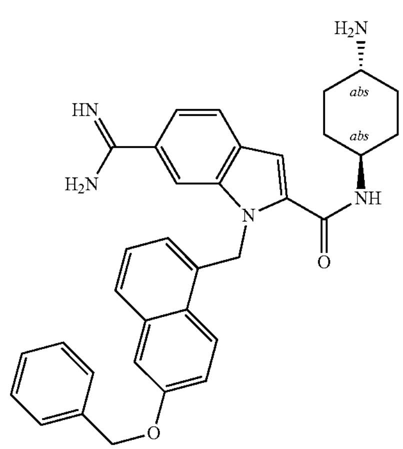 [SMILES: N=C(N)c1ccc2cc(C(=O)N[C@H]3CC[C@H](N)CC3)n(Cc3cccc4cc(OCc5ccccc5)ccc34)c2c1] | 546.25 | ¹HNMR (CD₃OD, 400 MHz): δ 1.29-1.44 (m, 4H), 1.88-1.92 (m, 2H), 2.00-2.02 (m, 2H), 3.03-3.05 (s, 1H), 3.67-3.69 (s, 1H), 5.22 (s, 2H), 6.39 (s, 2H), 7.11-7.15 (m, 1H), 7.27-7.31 (m, 1H), 7.32-7.41 (m, 4H), 7.48-7.56 (m, 2H), 7.54-7.56 (m, 1H), 7.62-7.64 (d, 1H), 7.92-7.97 (m, 2H), 8.11-8.14 (d, 1H) |

TABLE 50-continued

Compounds synthesized using general scheme-15E.

| ID | Structure | LCMS [M + H]+ | ¹H-NMR Data |
|---|---|---|---|
| I-737 | 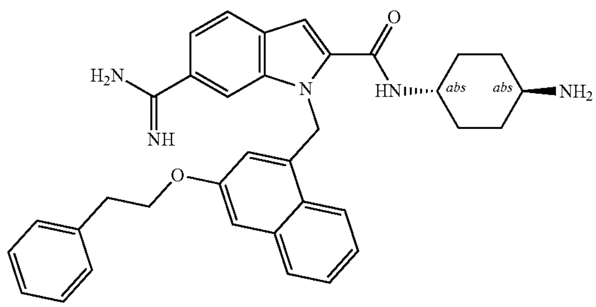 [SMILES: N=C(N)c1ccc2cc(C(=O)N[C@H]3CC[C@H](N)CC3)n(Cc3cc(OCCc4ccccc4)cc4ccccc34)c2c1] | 560.4 | ¹HNMR (CD₃OD, 300 MHz): δ 1.39-1.42 (m, 4H), 1.92-1.99 (m, 4H), 2.93-2.98 (m, 3H), 3.6-3.72 (m, 1H), 4.11-4.16 (t, 2H), 5.87-5.88 (s, 1H), 6.38 (s, 2H), 7.11-7.22 (m, 6H), 7.30 (s, 1H), 7.44-7.49 (m, 2H) 7.56-7.60 (d, 1H), 7.78-7.81 (d, 1H), 7.95-7.97 (m, 2H) 8.08-8.10 (d, 1H). |
| I-733 | 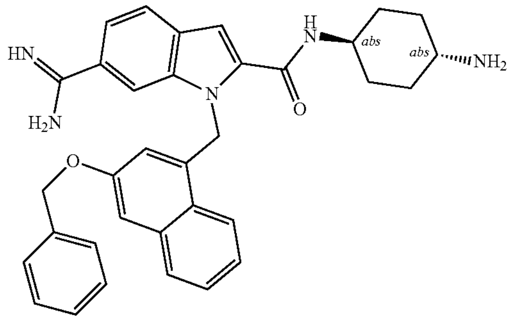 [SMILES: N=C(N)c1ccc2cc(C(=O)N[C@H]3CC[C@H](N)CC3)n(Cc3cc(OCc4ccccc4)cc4ccccc34)c2c1] | 546.3 | ¹HNMR (CD₃OD, 300 MHz): δ 1.28-1.48 (m, 4H), 1.90-2.03 (m, 4H), 3.01-3.05 (m, 1H), 3.67-3.70 (m, 1H), 4.99-5.01 (s, 2H), 5.92-5.93 (s, 1H), 6.39 (s, 2H), 7.21-7.31 (m, 6H), 7.44-7.58 (m, 3H), 7.79-7.80 (d, 1H), 7.93-7.98 (m, 2H), 8.09-8.12 (d, 1H), 8.64-8.66 (d, 1H). |
| I-731 | 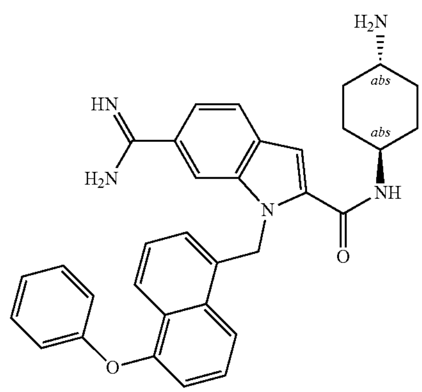 [SMILES: N=C(N)c1ccc2cc(C(=O)N[C@H]3CC[C@H](N)CC3)n(Cc3cccc4c(Oc5ccccc5)cccc34)c2c1] | 532.2 | ¹HNMR (CD₃OD, 400 MHz): δ 1.40-1.47 (m, 4H), 1.85-1.95 (m, 2H), 2.05-2.10 (m, 2H), 3.03-3.07 (m, 1 H), 3.71-3.73 (m, 1H), 6.33 (d, 1H), 6.46 (s, 2H), 7.01-7.04 (m, 3H), 7.15 (t, 1H), 7.23 (t, 1H), 7.31 (s, 1H), 7.36-7.40 (m, 2H), 7.56-7.60 (m, 2H), 7.96-8.02 (m, 3H), 8.09 (d, 1H). |
| I-727 | 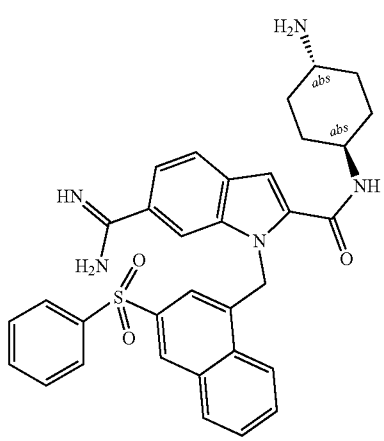 [SMILES: N=C(N)c1ccc2cc(C(=O)N[C@H]3CC[C@H](N)CC3)n(Cc3cc(S(=O)(=O)c4ccccc4)cc4ccccc34)c2c1] | 580.2 | ¹HNMR (CD₃OD, 400 MHz): δ 1.40-1.44 (m, 4H), 1.93-2.05 (m, 4H), 3.05-3.10 (m, 1H), 3.62-3.75 (m, 1H), 5.90 (s, 1H), 6.47 (s, 2H), 7.10-7.13 (m, 1H), 7.23 (s, 1H), 7.50-7.65 (m, 4H), 7.86-7.97 (m, 3H), 8.23-8.25 (d, 1H), 8.28-8.39 (d, 2H). |

TABLE 50-continued

Compounds synthesized using general scheme-15E.

| ID | Structure | LCMS [M + H]+ | 1H-NMR Data |
| --- | --- | --- | --- |
| I-725 | 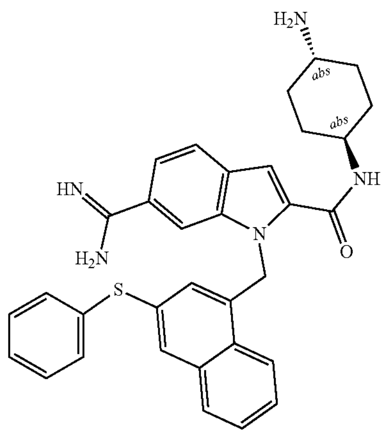 [SMILES: N=C(N)c1ccc2cc(C(=O)N[C@H]3CC[C@H](N)CC3)n(Cc3cc(Sc4ccccc4)cc4ccccc34)c2c1] | 548.3 | 1HNMR (CD3OD, 400 MHz): δ 1.389-1.453 (m, 4H), 1.963-2.044 (m, 4H), 3.045-3.072 (m, 1H), 3.711 (m, 1H), 6.403 (s, 2H), 7.081-7.222 (m, 5H), 7.251 (s, 1H), 7.548-7.657 (m, 3H), 7.703 (s, 1H), 7.825-7.845 (d, 1H), 7.900-7.920 (d, 2H), 8.053 (s, 1H), 8.171-8.197 (d, 1H). |
| I-715 | 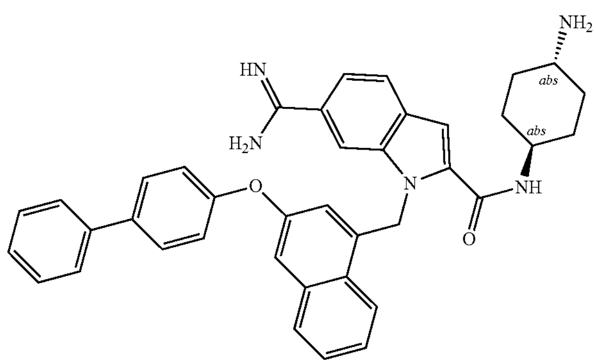 [SMILES: N=C(N)c1ccc2cc(C(=O)N[C@H]3CC[C@H](N)CC3)n(Cc3cc(Oc4ccc(-c5ccccc5)cc4)cc4ccccc34)c2c1] | 608.3 | 1HNMR (CD3OD, 400 MHz): δ 1.41-1.44 (m, 4H), 1.94-2.00 (m, 4H), 3.0-3.05 (m, 1H), 3.69-3.72 (m, 1H), 5.99-5.996 (s, 1H), 6.46 (s, 2H), 6.89-6.91 (m, 2H), 7.21-7.22 (d, 1H), 7.27 (s, 1H), 7.31-7.33 (t, 1H), 7.40-7.56 (m, 9H), 7.78-7.80 (m, 1H) 7.88-7.882 (d, 1H), 7.98-7.99 (s, 1H), 8.18-8.20 (d, 1H). |
| I-707 | 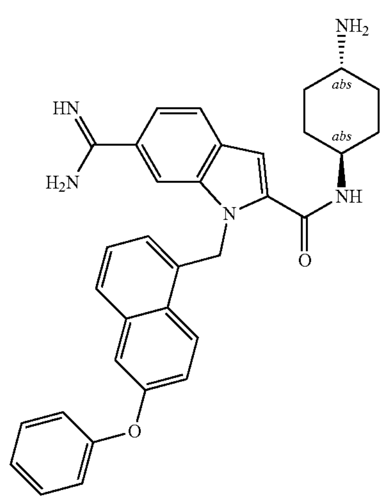 [SMILES: N=C(N)c1ccc2cc(C(=O)N[C@H]3CC[C@H](N)CC3)n(Cc3cccc4cc(Oc5ccccc5)ccc34)c2c1] | 532.2 | 1H NMR (CD3OD, 400 MHz): δ 1.36-1.44 (m, 4H), 1.88 (d, 2H), 2.00 (s, 2H), 3.05 (s, 1H), 3.69 (s, 1H), 6.20 (s, 1H), 6.40 (s, 2H), 7.07 (d, 2H), 7.16 (dd, 2H), 7.28 (s, 1H), 7.33-7.42 (m, 4H), 7.54-7.60 (m, 2H), 7.92 (d, 1H), 7.97 (d, 1H), 8.23 (d, 1H). |

TABLE 50-continued

Compounds synthesized using general scheme-15E.

| ID | Structure | LCMS [M + H]+ | 1H-NMR Data |
|---|---|---|---|
| I-702 | 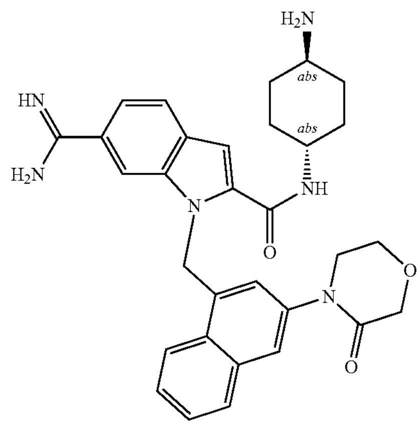 [SMILES: N=C(N)c1ccc2cc(C(=O)N[C@H]3CC[C@H](N)CC3)n(Cc3cc(N4CCOCC4=O)cc4ccccc34)c2c1] | 539.2 | 1HNMR (CD3OD, 400 MHz): δ 1.395-1.417 (m, 4H), 1.922 (m, 2H), 1.997 (m, 2H), 3.05 (m, 1H), 3.686-3.711 (m, 3H), 3.928-3.954 (m, 2H), 4.128 (s, 2H), 6.334-6.339 (s, 1H), 6.411 (s, 2H), 7.265-7.267 (d, 1H), 7.526-7.551 (dd, 1H), 7.609-7.673 (m, 2H), 7.771-7.775 (s, 1H), 7.910-7.958 (m, 3H), 8.216-8.237 (d, 1H). |
| I-691 | 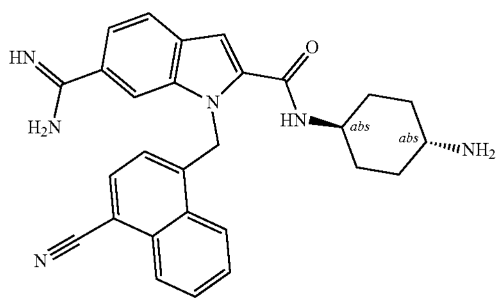 [SMILES: N#Cc1ccc(Cn2c(C(=O)N[C@H]3CC[C@H](N)CC3)cc3ccc(C(=N)N)cc32)c2ccccc12] | 465.3 | 1HNMR (DMSO-d6, 400 MHz ): δ 1.37-1.23 (m, 4H), 1.77-1.74 (d, 2H), 1.90-1.87 (d, 2H), 2.98-2.97 (d, 1H), 3.54-3.49 (t, 1H), 6.15-6.14 (s, 1H), 6.47 (s, 2H), 7.48 (s, 1H), 7.61-7.59 (m, 1H), 7.7478.73 (m, 3H), 7.99-7.91 (m, 3H), 8.01-7.99 (d, 1H), 8.10 (s, 1H), 8.22-8.20 (d, 1H), 8.48-8.46 (d, 1H), 8.68-8.66 (d, 1H), 8.87 (s, 2H), 9.14 (s, 2H). |
| I-670 | 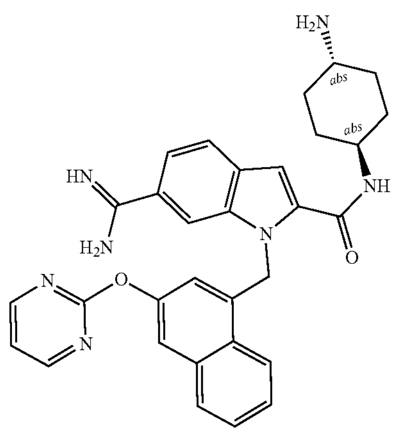 [SMILES: N=C(N)c1ccc2cc(C(=O)N[C@H]3CC[C@H](N)CC3)n(Cc3cc(Oc4ncccn4)cc4ccccc34)c2c1] | 534.5 | 1HNMR (CD3OD, 400 MHz): δ 1.40-1.44 (m, 4H), 1.93-2.05 (m, 4H), 3.05-3.10 (m, 1H), 3.62-3.75 (m, 1H), 5.90 (s, 1H), 6.47 (s, 2H), 7.10-7.13 (m, 1H), 7.23 (s, 1H), 7.50-7.65 (m, 4H), 7.86-7.97 (m, 3H), 8.23-8.25 (d, 1H), 8.28-8.39 (d, 2H). |
| I-666 | 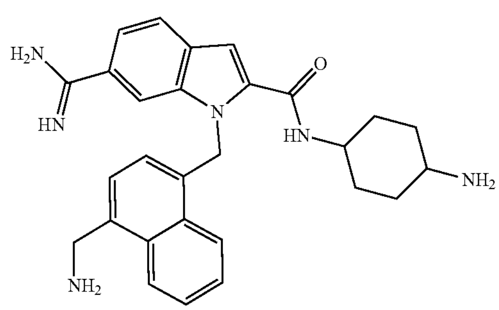 [SMILES: N=C(N)c1ccc2cc(C(=O)NC3CCC(N)CC3)n(Cc3ccc(CN)c4ccccc34)c2c1] | 469.3 | 1HNMR (DMSO-d6, 400 MHz ): δ 1.39-1.12 (m, 3H), 1.80-1.77 (d, 2H), 1.92-1.98 (d, 2H), 2.97-2.89 (d, 1H), 3.58-3.56 (d, 1H), 4.48 (s, 2H), 6.10-6.08 (d, 1H), 6.43 (s, 1H), 7.32-7.30 (d, 1H), 7.47 (S, 1H), 7.62-7.59 (d, 1H), 7.84-7.76 (m, 5H), 8.02-7.98 (t, 2H), 8.36-8.23 (m, 5H), 8.69-8.67 (d, 1H), 9.17-9.07 (m, 3H). |

TABLE 50-continued

Compounds synthesized using general scheme-15E.

| ID | Structure | LCMS [M + H]+ | 1H-NMR Data |
| --- | --- | --- | --- |
| I-652 | 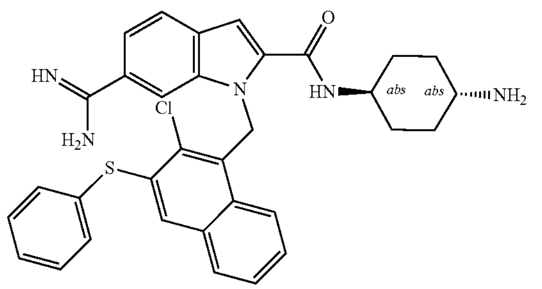 [SMILES: N=C(N)c1ccc2cc(C(=O)N[C@H]3CC[C@H](N)CC3)n(Cc3c(Cl)c(Sc4ccccc4)cc4ccccc34)c2c1] | 582.5 | 1HNMR (CD3OD, 400 MHz): δ 1.45-1.55 (m, 4H), 1.82-2.20 (m, 4H), 3.05-3.15 (m, 1H), 3.62-3.75 (m, 1H), 5.62 (s, 1H), 6.28 (s, 2H), 7.06-7.23 (m, 5H), 7.57-7.89 (m, 6H), 8.18-8.20 (d, 1H), 8.30-8.32 (d, 1H). |
| I-631 | 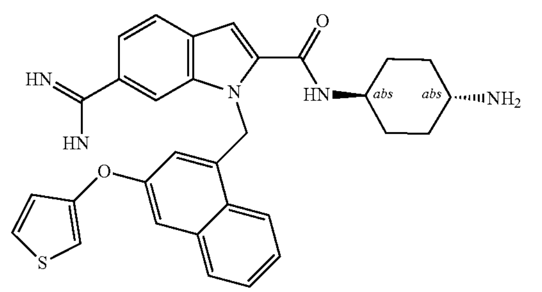 [SMILES: N=C(N)c1ccc2cc(C(=O)N[C@H]3CC[C@H](N)CC3)n(Cc3cc(Oc4ccsc4)cc4ccccc34)c2c1] | 538.5 | 1HNMR (CD3OD, 400 MHz): δ 1.44 (t, 4H), 2.0 (t, 4H), 3.1 (s, 1H), 3.6 (s, 1H), 6 (s, 1H), 6.44 (s, 2H), 6.53 (d, 1H), 6.68 (d, 1H), 7.2-7.19 (d, 1H), 7.29-7.28 (t, 2H), 7.55-7.53 (m, 2H), 7.56 (d, 1H) 7.7 (d, 1H), 7.97-7.92 (s, 2H), 8.2 (d, 1H) |
| I-614 | 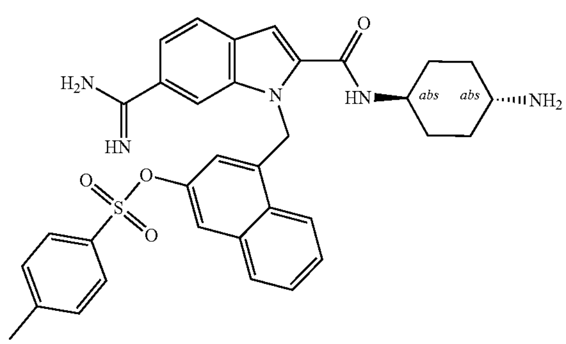 [SMILES: Cc1ccc(S(=O)(=O)Oc2cc(Cn3c(C(=O)N[C@H]4CC[C@H](N)CC4)cc4ccc(C(=N)N)cc43)c3ccccc3c2)cc1] | 610.5 | 1HNMR (CD3OD, 400 MHz): δ 1.40-1.50 (m, 4H), 1.93-2.05 (m, 4H), 2.40 (s, 3H), 3.00-3.10 (m, 1H), 3.19-3.26 (m, 1H), 6.05 (s, 1H), 6.40 (s, 2H), 7.21-7.66 (m, 9H), 7.79-7.99 (m, 3H), 8.20-8.22 (d, 1H). |
| I-599 | 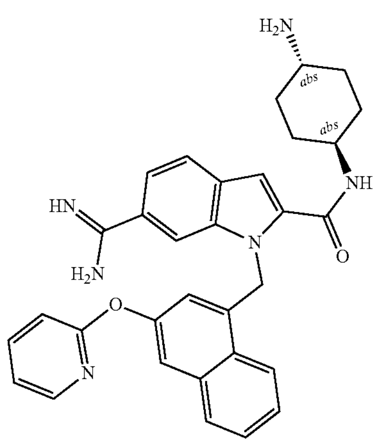 [SMILES: N=C(N)c1ccc2cc(C(=O)N[C@H]3CC[C@H](N)CC3)n(Cc3cc(Oc4ccccn4)cc4ccccc34)c2c1] | 533.2 | 1HNMR (CD3OD, 400 MHz): δ 1.41-1.43 (d, 4H), 1.95 (m, 2H), 2.02 (m, 2H), 3.1 (s, 1H), 3.71 (s, 1H), 6.47 (s, 2H), 6.82-6.84 (d, 1H), 6.98-7.01 (m, 1H), 7.22-7.23 (d, 1H), 7.44-7.45 (d, 1H), 7.516-7.54 (q, 1H), 7.59-7.63 (m, 2H), 7.693-7.73 (m, 1H), 7.77-7.78 (m, 1H), 7.85-7.88 (m, 1H), 7.953-7.955 (d, 1H), 8.22-8.24 (d, 1H) |

TABLE 50-continued

Compounds synthesized using general scheme-15E.

| ID | Structure | LCMS [M + H]+ | 1H-NMR Data |
|---|---|---|---|
| I-608 | 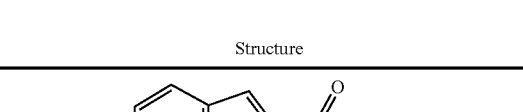 | 596.2 | 1HNMR (CD3OD, 400 MHz): δ 1.453 (m, 4H), 1.957-2.043 (d, 4H), 3.070 (bs, 1H), 3.706 (bs, 1H), 5.98 (s, 1H), 6.378 (s, 2H), 7.319-7.358 (m, 4H), 7.524-7.604 (m, 3H), 7.616-7.669 (m, 2H), 7.819-7.810 (d, 1H), 7.901 (s, 1H), 7.975-7.997 (d, 1H), 8.204-8.225 (d, 1H), 8.59 (d, 1H). |

TABLE 51

Compounds synthesized using general scheme-20.

| ID | Structure | LCMS [M + H]+ | 1H-NMR Data |
|---|---|---|---|
| I-603 | 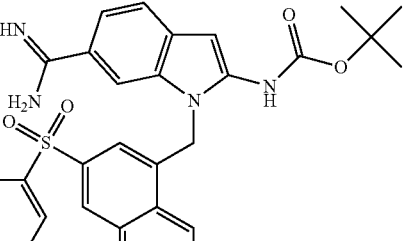 | 555.4 | 1HNMR (CD3OD, 400 MHz): δ 1.41 (s, 9H), 6.01 (s, 2H), 7.37 (t, 2H), 7.56-7.61 (m, 4H), 7.71-7.90 (m, 4H), 8.11-8.20 (d, 2H), 8.20-8.29 (d, 1H), 8.51 (s, 2H). |

TABLE 52

Compounds synthesized using general scheme-21.

| ID | Structure | LCMS [M + H]+ | 1H-NMR Data |
|---|---|---|---|
| I-743 | 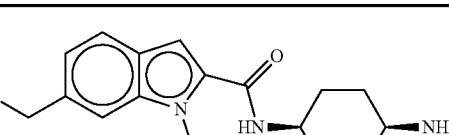 | 427.40 | 1HNMR (CD3OD, 300 MHz): δ 1.66-1.84 (m, 8H), 3.19-3.26 (m, 1H), 3.80-3.86 (m, 1H), 4.12 (s, 2H), 6.24-6.26 (d, 1H), 6.35 (s, 2H), 7.13-7.29 (m, 3H), 7.46-7.90 (m, 6H), 8.18-8.21 (d, 1H). |

TABLE 52-continued

Compounds synthesized using general scheme-21.

| ID | Structure | LCMS [M + H]+ | 1H-NMR Data |
|---|---|---|---|
| I-636 | 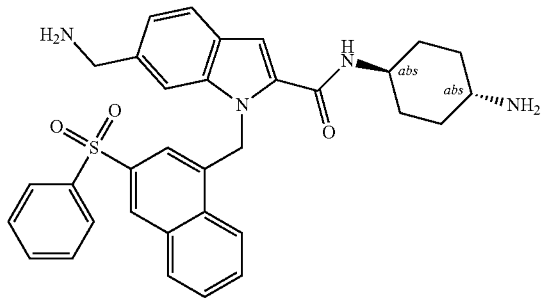 [SMILES: NCc1ccc2cc(C(=O)N[C@H]3CC[C@H](N)CC3)n(Cc3cc(S(=O)(=O)c4ccccc4)cc4ccccc34)c2c1] | 565.20 | 1HNMR (CD3OD, 300 MHz): δ 1.29-1.45 (m, 4H), 1.95 (s, 2H), 2.05 (s, 2H), 3.1 (s, 1H), 3.65 (s, 1H), 4.05 (s, 2H), 6.40 (s, 2H), 6.478 (s, 1H), 7.30 (d, 1H), 7.35 (m, 2H), 7.39-7.42 (d, 2H), 7.54-7.59 (m, 3H), 7.74 (t, 1H), 7.87-7.90 (d, 1H), 8.13 (d, 1H), 8.28 (d, 1H), 8.45 (s, 1H) |
| I-635 | 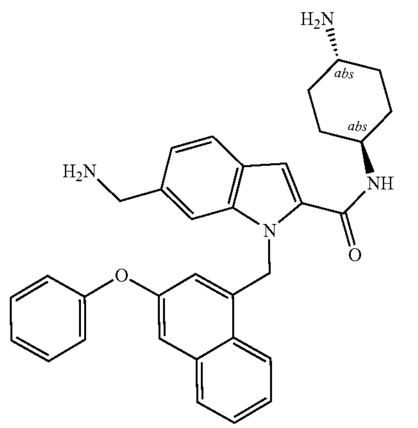 [SMILES: NCc1ccc2cc(C(=O)N[C@H]3CC[C@H](N)CC3)n(Cc3cc(Oc4ccccc4)cc4ccccc34)c2c1] | 519.3 | 1HNMR (CD3OD, 400 MHz): δ 1.42-1.47 (m, 4H), 1.95-2.03 (m, 4H), 3.05-3.12 (m, 1H), 3.65-3.75 (m, 1H), 4.14 (s, 2H), 5.98 (s, 1H), 6.32 (s, 2H), 6.81-6.83 (d, 2H), 7.06-7.08 (m, 2H), 7.21-7.27 (m, 4H), 7.47-7.54 (m, 3H), 7.72-7.78 (m, 2H), 8.171-8.192 (d, 1H). |
| I-605 | 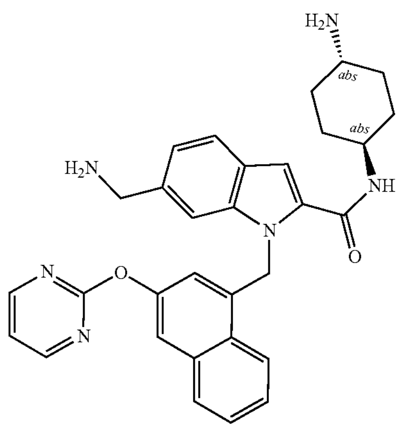 [SMILES: NCc1ccc2cc(C(=O)N[C@H]3CC[C@H](N)CC3)n(Cc3cc(Oc4ncccn4)cc4ccccc34)c2c1] | 521.35 | 1HNMR (DMSO-d6, 300 MHz): δ 1.2-1.4 (m, 5H), 1.95-2.0 (d, 4H), 3.06 (s, 1H), 3.30-3.37 (m, 3H), 4.14 (s, 4H), 5.96 (s, 1H), 6.43 (s, 2H), 7.11-7.22 (m, 3H), 7.48-7.64 (m, 4H), 7.73-7.76 (d, 1H), 7.89-7.91 (d, 1H) 8.23-8.26 (d, 1H) 8.42-8.44 (d, 2H) |
| I-785 | 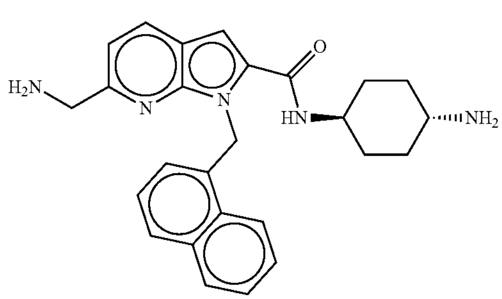 | 428.0 | 1HNMR (CD3OD, 300 MHz): δ 1.26-1.42 (m, 4H), 1.78-1.99 (m, 4H), 2.95-3.05 (m, 1H), 3.55-3.65 (m, 1H), 4.35 (s, 2H), 6.35-6.38 (d, 1H), 6.50 (s, 2H), 7.13-7.28 (m, 3H), 7.50-7.89 (m, 4H), 8.18-8.22 (m, 2H). |

General synthetic scheme -23
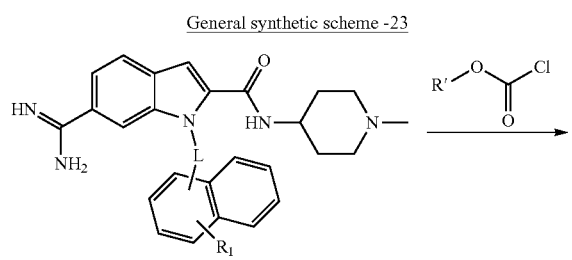 → 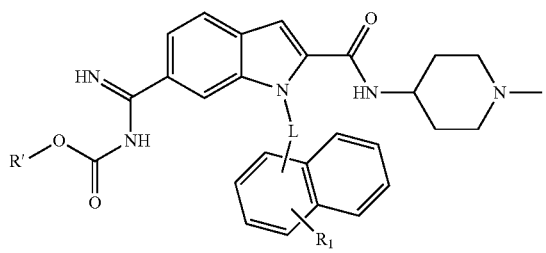
-continued
TABLE 53
Compounds synthesized using general scheme-23.
| ID | Structure | LCMS [M + H]+ | 1H-NMR Data |
|---|---|---|---|
| I-784 | 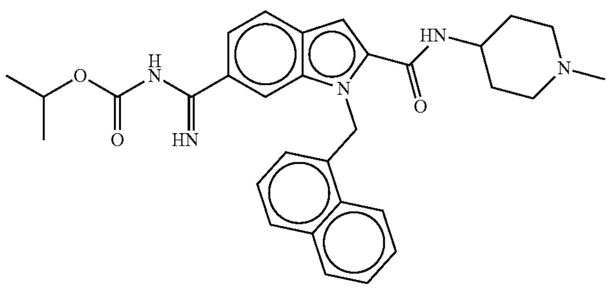 | 526.40 | 1HNMR (CD3OD, 300 MHz): δ 1.33-1.35 (d, 6H), 1.8 (m, 2H), 2.0 (m, 2H), 2.816 (s, 3H), 3.1 (m, 2H), 3.462 (m, 2H), 3.9 (s, 1H), 5.12 (m, 1H), 6.25 (d, 1H), 6.451 (s, 2H), 7.190 (m, 1H), 7.34 (s, 1H), 7.54-7.62 (m, 3H), 7.73 (d, 1H), 7.90-8.02 (m, 3H), 8.18 (d, 1H) |
| I-783 | 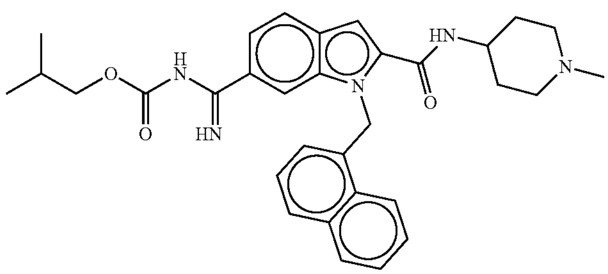 | 540.2 | 1HNMR (CD3OD, 400 MHz): δ 0.94-0.99 (d, 6H), 1.76-1.79 (d, 2H), 2.01-2.04 (m, 3H), 2.84 (s, 3H), 3.05 (s, 2H), 3.48 (S, 2H), 3.959 (s, 1H), 4.10-4.11 (d, 2H), 6.21 (t, 1H), 7.39 (s, 1H), 7.58-7.66 (m, 3H), 7.75-7.78 (d, 1H), 7.92-8.06 (m, 3H), 8.21-8.23 (d, 1H) |
| I-782 | 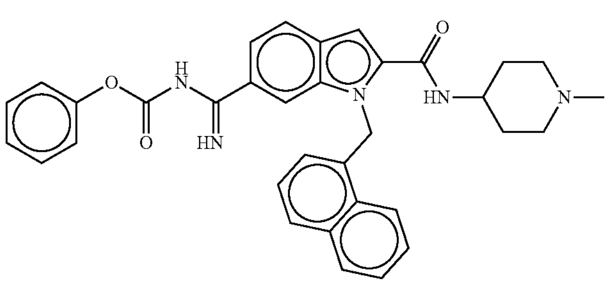 | 560.2 | 1HNMR (CD3OD, 300 MHz): δ 1.54- 1.66 (m, 2H), 1.78-1.81 (m, 2H), 1.91 (s, 1H), 2.25-2.33 (m, 2H), 2.37 (s, 3H), 2.92-2.96 (d, 2H), 3.69-3.76 (m, 1H), 6.24-6.26 (d, 1H), 6.35-6.39 (m, 2H), 7.04-7.09 (m, 3H), 7.14-7.19 (t, 1H), 7.25-7.29 (m, 3H), 7.51-7.63 (m, 2H), 7.70-7.73 (d, 2H), 7.81-7.83 (d, 1H), 7.88-7.94 (m, 1H), 8.06 (s, 1H) 8.16-8.19 (d, 1H) |

TABLE 53-continued
Compounds synthesized using general scheme-23.
| ID | Structure | LCMS [M + H]+ | 1H-NMR Data |
|---|---|---|---|
| I-765 | 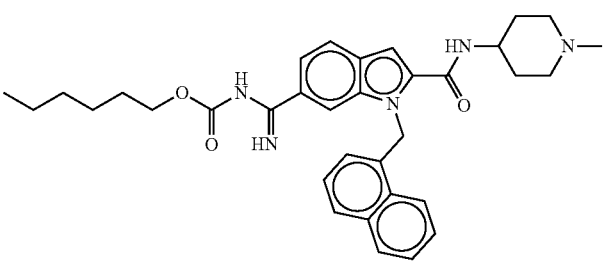 | 568.30 | 1HNMR (CD3OD, 300 MHz): δ 0.893 (t, 3H), 1.28-1.41 (m, 7H), 1.69-1.78 (m, 3H), 1.99-2.03 (d, 2H), 2.81-2.85 (m, 3H), 3.02-3.08 (m, 2H), 3.46-3.50 (d, 2H), 3.9 (m, 1H), 4.31 (t, 2H), 6.25-6.27 (d, 1H), 6.45 (s, 1H), 7.19 (t, 1H), 7.34 (s, 1H), 7.54-7.65 (m, 3H), 7.73-7.76 (d, 1H), 7.90-7.93 (m, 1H), 7.97-8.02 (m, H), 8.18-8.21 (d, 1H) |
| I-557 | 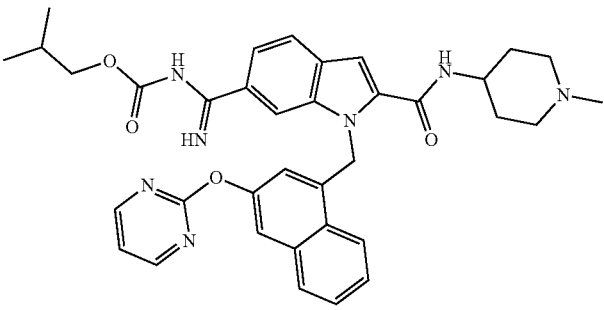 [SMILES: CC(C)COC(=O)NC(=N)c1ccc2cc(C(=O)NC3CCN(C)CC3)n(Cc3cc(Oc4ncccn4)cc4ccccc34)c2c1] | 632.35 | 1HNMR (CD3OD, 400 MHz): δ 0.93-0.95 (d, 6H), 1.68-1.73 (m, 2H), 1.91-1.97 (m, 3H), 2.59 (s, 3H), 2.67 (m, 2H), 3.17 (m, 1H), 3.86-3.88 (d, 3H), 5.98 (s, 1H), 6.45 (s, 2H),7.07-7.09 (t, 1H),7.20 (s, 1H), 7.53 (s, 1H), 7.54-7.66-(m, 4H), 7.74-7.76 (d, 1H), 7.89-7.91 (d, 1H) 8.04 (s, 1H), 8.23-8.25 (d, 1H), 8.37-8.38 (d, 2H). |
| I-553 | 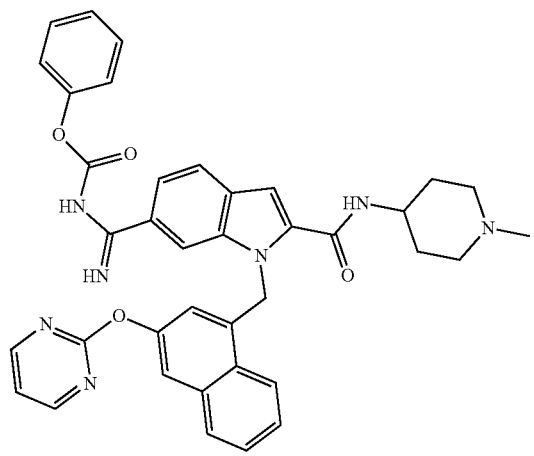 [SMILES: CN1CCC(NC(=O)c2cc3ccc(C(=N)NC(=O)Oc4ccccc4)cc3n2Cc2cc(Oc3ncccn3)cc3ccccc23)CC1] | 654.25 | 1HNMR (CDCl3, 400 MHz): δ 1.422-1.44 (t, 2H), 1.84-1.86 (d, 2H), 2.00-2.05 (t, 2H), 2.22 (s, 3H), 2.69-2.71 (d, 2H), 3.8-3.9 (m, 1H), 6.12-6.16 (t, 2H), 6.39 (s, 2H), 6.93-6.95 (t, 1H), 7.13-7.17 (t, 3H), 7.31-7.35 (t, 1H), 7.54-7.70 (m, 3H) 7.70 (s, 2H) 7.84-7.87 (m, 2H), 8.09-8.11 (d, 1H) 8.36-8.37 (d, 2H), 9.5 (br, 1H). |
| I-549 | 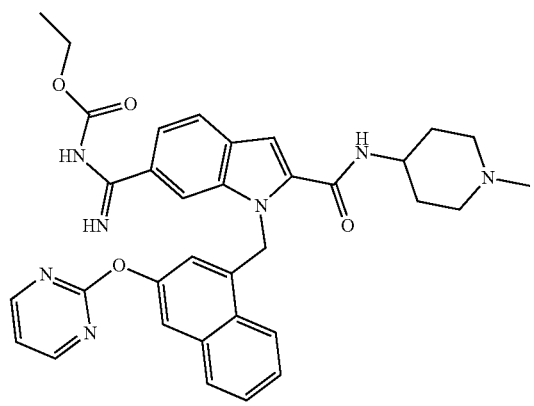 [SMILES: CCOC(=O)NC(=N)c1ccc2cc(C(=O)NC3CCN(C)CC3)n(Cc3cc(Oc4ncccn4)cc4ccccc34)c2c1] | 606.3 | 1HNMR (CD3OD, 300 MHz): δ 1.23-1.28 (t, 3H), 1.56-1.60 (m, 2H), 1.80-1.84 (d, 2H), 2.15-2.23 (t, 2H), 2.31 (s, 3H), 2.87-2.91 (d, 2H), 3.74 (m, 1H), 4.09-4.16 (q, 2H), 5.98 (S, 1H), 6.44 (s, 2H), 7.06-7.09 (t, 1H), 7.18 (s, 1H), 7.53-7.66 (m, 4H), 7.72-7.75 (d, 1H), 7.88-7.91 (d, 1H), 8.02 (s, 1H), 8.22-8.25 (d, 1H), 8.36-8.38 (d, 2H). |

TABLE 53-continued

Compounds synthesized using general scheme-23.

| ID | Structure | LCMS [M + H]+ | 1H-NMR Data |
|---|---|---|---|
| I-545 | 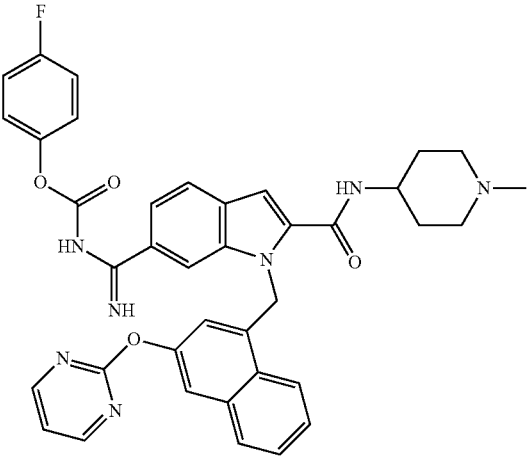 [SMILES: CN1CCC(NC(=O)c2cc3ccc(C(=N)NC(=O)Oc4ccc(F)cc4)cc3n2Cc2cc(Oc3ncccn3)cc3ccccc23)CC1] | 672.25 | 1HNMR (CDCl3, 600 MHz): δ 1.44-1.48 (q, 2H), 1.85-1.871 (d, 2H), 2.20-2.06 (t, 2H), 2.24 (s, 3H), 2.72 (bs, 2H), 3.82 (bs, 1H), 6.13 (s, 1H), 6.16-6.17 (d, 1H), 6.41 (s, 2H), 6.8 (bs, 1H), 6.95-6.97 (m, 2H), 7.01-7.04 (t, 2H), 7.12-7.15 (m, 2H), 7.56-7.61 (m, 3H), 7.68-7.73 (q, 2H), 7.85-7.88 (m, 2H), 8.10-8.12 (d, 1H), 8.37-8.38 (d, 2H), 9.5 (bs, 1H). |

General synthetic scheme -24

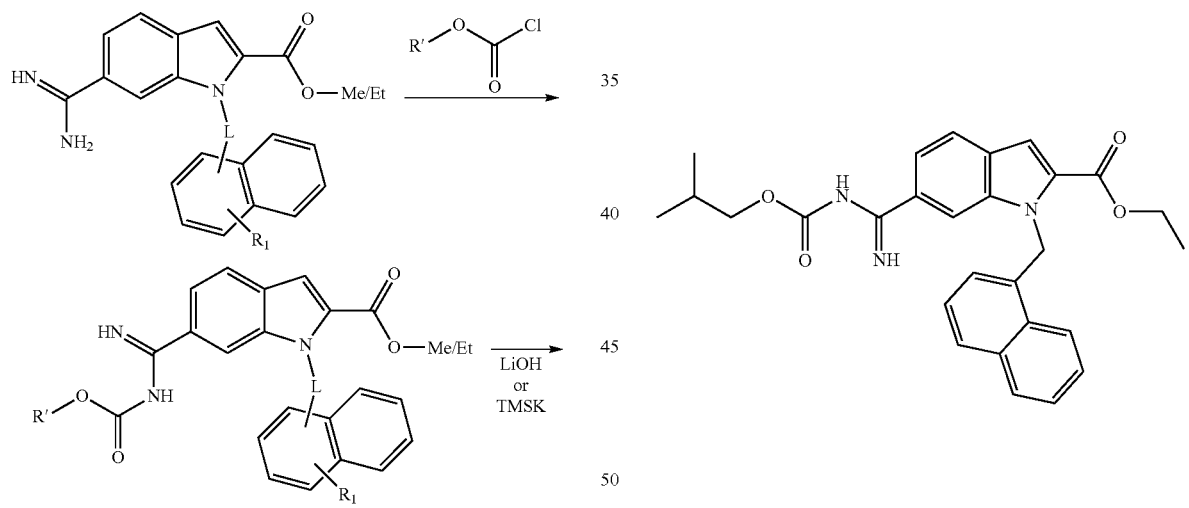

Example 122: Synthesis of Compound I-719

Step-1: Synthesis of Ethyl 6-(N-(isobutoxycarbonyl)carbamimidoyl)-1-(naphthalen-1-ylmethyl)-1H-indole-2-carboxylate Following the experimental protocol of Scheme 2A, ethyl 6-(N-(isobutoxycarbonyl) carbamimidoyl)-1-(naphthalen-1-ylmethyl)-1H-indole-2-carboxylate compound was synthesized. LCMS: 472.2 (M+1)+; 1HNMR (DMSO-d6, 400 MHz): δ 0.85 (d, 6H), 1.14 (t, 3H), 1.87 (m, 1H), 3.75 (d, 2H), 4.19 (q, 2H), 6.03 (d, 1H), 6.41 (brs, 2H), 7.23 (t, 1H), 7.54 (s, 1H), 7.63 (t, 1H), 7.70 (t, 1H), 7.80 (d, 1H), 7.87 (m, 2H), 8.00 (d, 1H), 8.19 (s, 1H), 8.23 (d, 1H), 8.90 (brs, 1H), 9.20 (brs, 1H); HPLC: 96.72% (Retention Time=7.23 min).

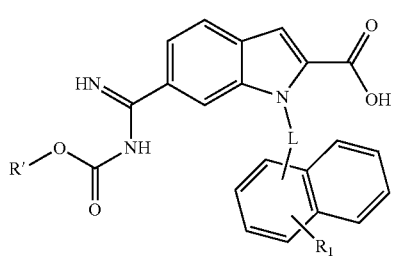

TABLE 54

Compounds synthesized using step 1 of general scheme-24

| ID | Structure | LCMS [M + H]+ | 1H-NMR Data |
|---|---|---|---|
| I-738 | 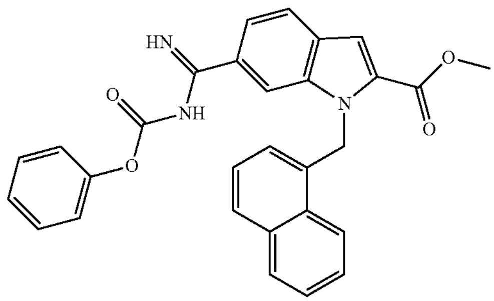 [SMILES: COC(=O)c1cc2ccc(C(=N)NC(=O)Oc3ccccc3)cc2n1Cc1cccc2ccccc12] | 487.20 | 1HNMR (CDCl3, 300 MHz): δ 3.80 (s, 3H), 6.16-6.17 (d, 1H), 6.42 (s, 2H), 6.51-6.58 (bs, 1H), 7.09-7.19 (m, 4H), 7.25-7.32 (m, 2H), 7.50-7.85 (m, 5H), 7.88-7.94 (m, 3H), 8.14-8.16 (d, 1H), 9.55-9.65 (bs, 1H). |
| I-676 | 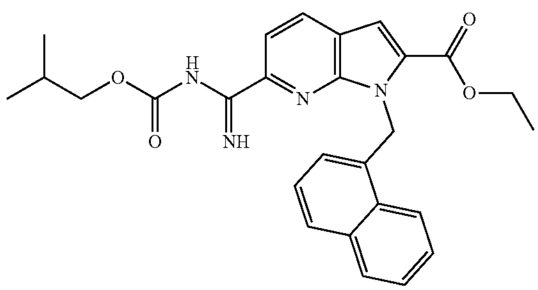 [SMILES: CCOC(=O)c1cc2ccc(C(=N)NC(=O)OCC(C)C)nc2n1Cc1cccc2ccccc12] | 473.10 | 1HNMR (CDCl3, 300 MHz): δ 0.92-1.05 (d, 6H), 1.12-1.15 (m, 3H), 2.00-2.05 (m, 1H), 3.90-3.95 (d, 2H), 4.20-4.25 (m, 2H), 6.34-6.37 (d, 1H), 6.51 (s, 2H), 7.17-7.20 (m, 1H), 7.45-7.73 (m, 4H), 7.89-8.41 (m, 5H), 9.20-9.22 (m, 1H). |
| I-627 | 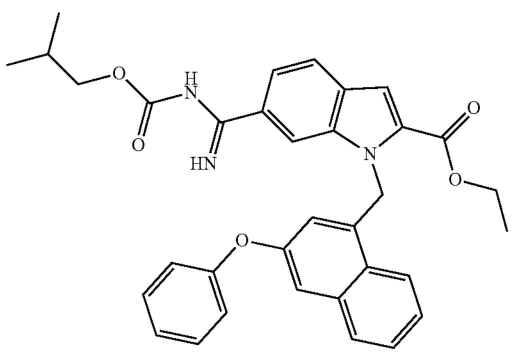 [SMILES: CCOC(=O)c1cc2ccc(C(=N)NC(=O)OCC(C)C)cc2n1Cc1cc(Oc2ccccc2)cc2ccccc12] | 564.20 | 1HNMR (CD3OD, 300 MHz): δ 0.85-0.95 (d, 6H), 1.27 (t, 3H), 1.96-2.05 (m, 1H), 3.88-3.90 (d, 2H), 4.22-4.30 (q, 2H), 6.03 (s, 1H), 6.40 (s, 2H), 6.89-6.92 (d, 2H), 7.04-7.09 (m, 2H), 7.23 (s, 1H), 7.25-7.28 (s, 1H), 7.46-7.60 (m, 4H), 7.68-7.80 (m, 2H), 7.92 (s, 1H), 8.07-8.10 (d, 1H) |
| I-607 | 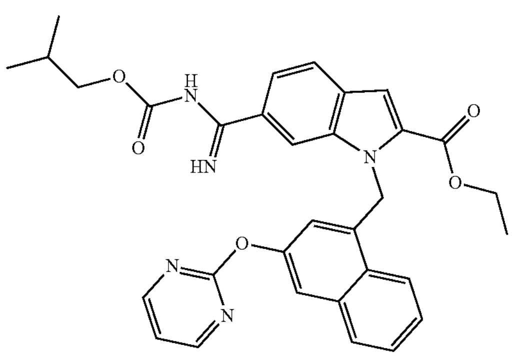 [SMILES: CCOC(=O)c1cc2ccc(C(=N)NC(=O)OCC(C)C)cc2n1Cc1cc(Oc2ncccn2)cc2ccccc12] | 566.3 | 1HNMR (CDCl3, 300 MHz): δ 0.93-0.95 (d, 6H), 1.20-1.27 (t, 3H), 1.98-2.01 (m, 1H), 3.89-3.91(d, 2H), 4.22-4.29 (q,2H), 6.08 (s, 1H), 6.44 (s, 2H), 6.91-6.93 (t, 1H), 7.42 (s, 1H), 7.54-7.64 (m, 4H), 7.73-7.76 (d, 1H), 7.85-7.88 (m, 2H), 8.12-8.14 (d, 1H), 8.35-8.37 (d, 2H). |

TABLE 54-continued

Compounds synthesized using step 1 of general scheme-24

| ID | Structure | LCMS [M + H]+ | ¹H-NMR Data |
|---|---|---|---|
| I-586 | 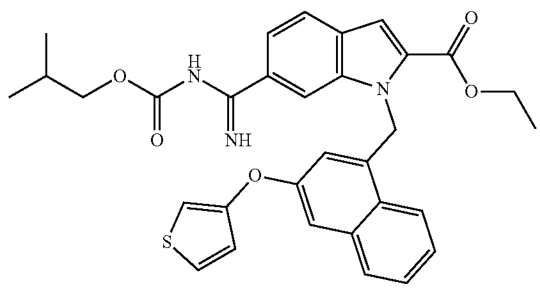 [SMILES: CCOC(=O)c1cc2ccc(C(=N)NC(=O)OCC(C)C)cc2n1Cc1cc(Oc2ccsc2)cc2ccccc12] | 570.20 | ¹HNMR (CDCl₃, 600 MHz): δ 0.92-0.94 (d, 6H), 1.26-1.27 (t, 3H), 1.97-2.01 (m, 1H), 3.88-3.89 (d, 2H), 4.24-4.27 (q, 2H), 6.39 (s, 2H), 6.53 (s, 1H), 6.72-6.73 (d, 1H), 7.01 (s, 1H), 7.17-7.18 (t, 1H), 7.47 (s, 1H), 7.49-7.52 (m, 2H), 7.53-7.54 (m, 1H), 7.58-7.60 (d, 1H), 7.71-7.72 (d, 1H), 7.79-7.81 (d, 1H), 7.91 (s, 1H), 8.07-8.08 (d, 1H). |
| I-581 | 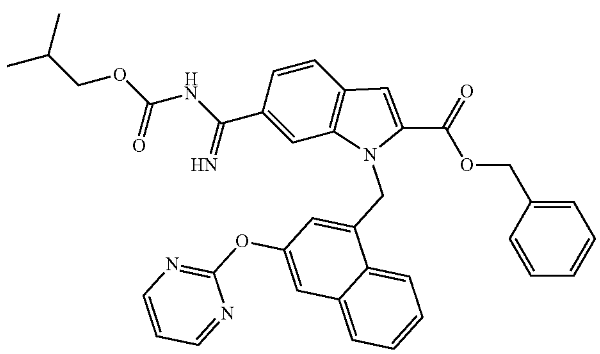 [SMILES: CC(C)COC(=O)NC(=N)c1ccc2cc(C(=O)OCc3ccccc3)n(Cc3cc(Oc4ncccn4)cc4ccccc34)c2c1] | 628.30 | ¹HNMR (CDCl₃, 600 MHz): δ 0.94-0.95 (d, 6H), 1.98-2.03 (m, 1H), 3.89-3.90 (d, 2H), 5.23 (s, 2H), 6.09 (s, 1H), 6.42 (s, 2H), 6.90-6.91 (t, 1H), 7.26-7.27 (s, 4H), 7.47 (s, 1H), 7.55-7.63 (m, 4H), 7.73-7.74 (d, 1H), 7.84 (s, 1H), 7.86-7.87 (d, 2H), 8.07-8.08 (d, 1H), 8.341-8.349 (d, 2H). |
| I-579 | 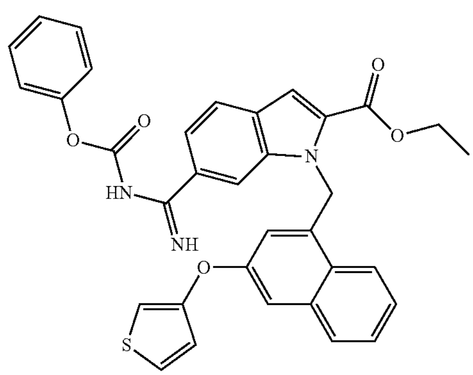 [SMILES: CCOC(=O)c1cc2ccc(C(=N)NC(=O)Oc3ccccc3)cc2n1Cc1cc(Oc2ccsc2)cc2ccccc12] | 590.20 | ¹HNMR (CDCl₃, 600 MHz): δ 1.26-1.31 (t, 3H), 4.25-4.28 (q, 2H), 6.02 (s, 1H), 6.39 (s, 2H), 6.538-6.541 (d, 1H), 6.73-6.74 (t, 1H), 7.11-7.15 (m, 4H), 7.15-7.19 (m, 2H), 7.28-7.31 (t, 1H), 7.48-7.49 (s, 1H), 7.52-7.54 (m, 2H), 7.61-7.63 (d, 1H), 7.72-7.73 (d, 1H) 7.83-7.84 (d, 1H), 7.99 (s, 1H), 8.08-8.10 (d, 1H). |
| I-576 | 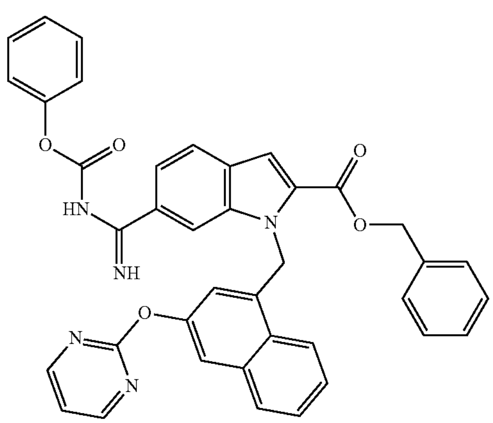 [SMILES: N=C(NC(=O)Oc1ccccc1)c1ccc2cc(C(=O)OCc3ccccc3)n(Cc3cc(Oc4ncccn4)cc4ccccc34)c2c1] | 648.15 | ¹HNMR (CDCl₃, 400 MHz): δ 5.24 (s, 2H), 6.15 (s, 1H), 6.41 (s, 2H), 6.7-6.75 (br, 1H), 6.92 (t, 1H), 7.14-7.16 (d, 3H), 7.26-7.32 (m, 6H), 7.49 (s, 1H), 7.56-7.58 (m, 3H), 7.6-7.7 (d, 1H), 7.75-7.8 (d, 1H), 7.85-7.90 (m, 2H) 8.05-8.10 (d, 1H), 8.35-8.36 (d, 2H) 9.55-9.62 (br, 1H). |

TABLE 54-continued

Compounds synthesized using step 1 of general scheme-24

| ID | Structure | LCMS [M + H]+ | ¹H-NMR Data |
|---|---|---|---|
| I-559 | 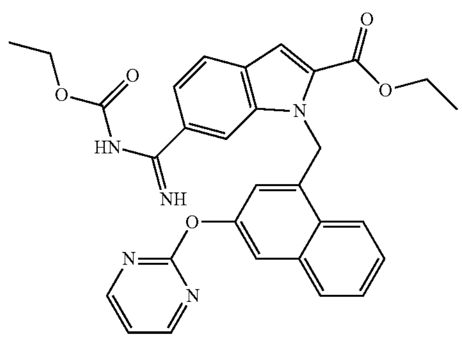 [SMILES: CCOC(=O)NC(=N)c1ccc2cc(C(=O)OCC)n(Cc3cc(Oc4ncccn4)cc4ccccc34)c2c1] | 538.4 | ¹HNMR (CD$_3$OD, 400 MHz): δ 1.17-1.28 (m, 6H), 4.09-4.14 (q, 2H), 4.20-4.26 (q, 2H), 5.86 (s, 1H), 6.46 (s, 2H), 7.06-7.08 (t, 1H), 7.44 (s, 1H), 7.53 (s, 1H), 7.58-7.65 (m, 3H), 7.76-7.79 (d, 1H), 7.90-7.92 (d, 1H), 8.03 (s, 1H), 8.25-8.27 (d, 1H), 8.36-8.38 (d, 2H). |
| I-554 | 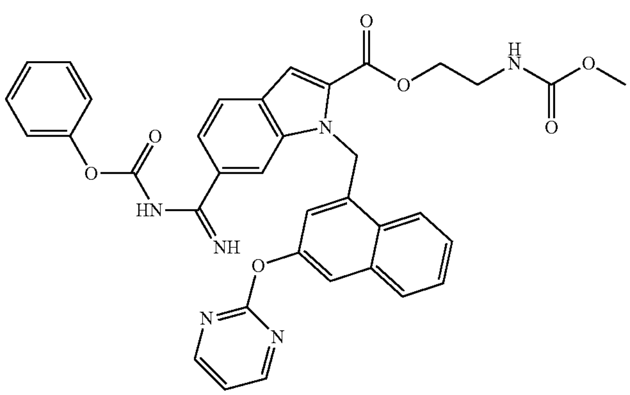 [SMILES: COC(=O)NCCOC(=O)c1cc2ccc(C(=N)NC(=O)Oc3ccccc3)cc2n1Cc1cc(Oc2ncccn2)cc2ccccc12] | 659.20 | ¹HNMR (CDCl$_3$, 400 MHz): δ 3.31-3.32 (d, 2H), 3.54 (s, 3H), 4.27-4.29 (t, 2H), 4.8 (bs, 1H), 6.07 (s, 1H), 6.38 (s, 2H), 6.9 (bs, 1H), 6.94-6.96 (t, 1H), 7.12-7.17 (m, 2H), 7.30-7.34 (m, 2H), 7.47 (s, 1H), 7.56-7.67 (m, 4H), 7.77-7.79 (d, 1H), 7.86-7.88 (d, 1H), 7.95 (s, 1H), 8.10-8.12 (d, 1H), 8.37-8.38 (d, 2H), 9.6 (bs, 1H). |
| I-550 | 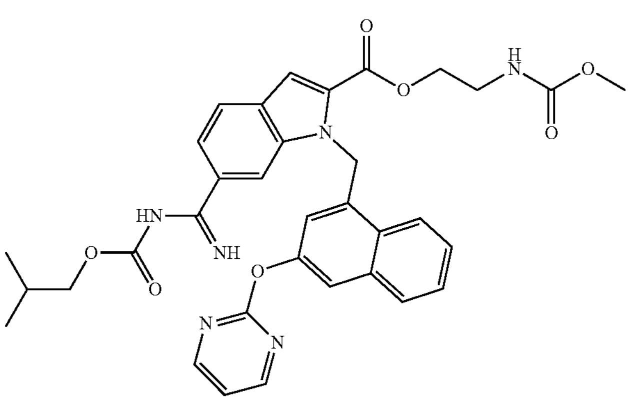 [SMILES: COC(=O)NCCOC(=O)c1cc2ccc(C(=N)NC(=O)OCC(C)C)cc2n1Cc1cc(Oc2ncccn2)cc2ccccc12] | 639.20 | ¹HNMR (CDCl$_3$, 400 MHz): δ 0.94-0.95 (d, 6H), 1.99-2.03 (m, 1H), 3.30-3.31 (d, 2H), 3.54 (s, 2H), 3.89-3.90 (d, 2H), 4.26-4.28 (t, 2H), 4.88 (bs, 1H), 6.07 (s, 1H), 6.37 (s, 2H), 6.93-6.95 (t, 1H), 7.45 (s, 1H), 7.55-7.62 (m, 4H), 7.74-7.75 (d, 1H), 7.86-7.88 (m, 2H), 8.10-8.12 (d, 1H), 8.36-8.37 (d, 2H). |

Step-2: Potassium 6-(N-((hexyloxy)carbonyl)car-bamimidoyl)-1-(naphthalen-1-ylmethyl)-1H-indole-2-carboxylate: (I-720)

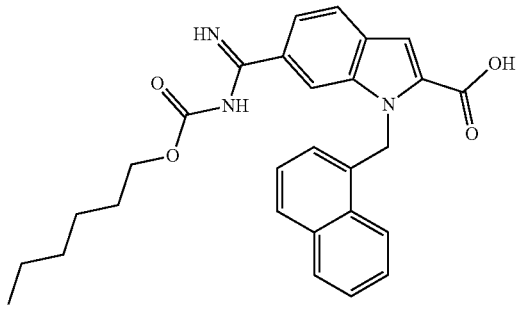 [SMILES: CCCCCCOC(=O)NC(=N)c1ccc2cc(C(=O)O)n(Cc3cccc4ccccc34)c2c1]

To a stirred solution of Step-1 compound (100 mg, 0.20 mmol) in 2 ml of THF was added Potassium trimethylsilanolate (24 mg, 0.19 mmol) at 0° C. in one portion under $N_2$ and the reaction mixture was stirred at room temperature for about 16 h. The reaction mixture was diluted with diethyl ether and the solids obtained were filtered, washed with ether and dried under nitrogen atmosphere further dried using Lyophilization to give 50 mg of title compound as Potassium salt. LCMS: 472.2 (M+1)$^+$; $^1$H NMR (400 MHz, DMSO-d$_6$): δ 0.84 (t, 6H), 1.29-1.20 (m, 6H), 1.52 (m, 1H), 3.90 (t, 2H), 6.06 (d, 1H), 6.66 (brs, 2H), 6.84 (s, 1H), 7.19 (t, 1H), 7.71-7.60 (m, 5H), 7.91 (s, 1H), 7.96 (d, 1H), 8.32 (d, 1H), 8.80 (brs, 1H), 9.20 (brs, 1H); HPLC: 97.12% (Retention Time=7.086 min).

| | Compounds synthesized using step 1 of general scheme-24 | | |
|---|---|---|---|
| ID | Structure | LCMS [M + H]$^+$ | $^1$H-NMR Data |
| I-791 | | 444.25 | $^1$HNMR (CD$_3$OD, 300 MHz): δ 0.92 (d, 6H), 1.56-1.59 (m, 1H), 1.387-1.389 (d, 2H), 6.52-6.53 (d, 1H), 6.574 (s, 2H), 7.15-7.18 (t, 1H), 7.284 (s, 1H), 7.529-7.701 (m, 4H), 7.78-7.81 (d, 2H), 7.87-7.89 (m, 2H), 8.25-8.28 (d, 1H) |
| I-786 | | 430.25 | $^1$HNMR (CD$_3$OD, 300 MHz): δ 1.27-1.29 (d, 6H), 4.986- 5.027 (m, 1H), 6.21-6.24 (d, 1H), 6.558 (s, 2H), 7.13-7.18 (m, 1H), 7.34 (s, 1H), 7.51-7.62 (m, 3H), 7.68-7.71 (d, 1H), 7.885 (t, 3H), 8.24-8.26 (d, 1H) |
| I-712 | | 416.15 | $^1$HNMR (CD$_3$OD, 400 MHz): δ1.25-1.33(m, 3H), 4.18-4.23(m, 2H), 6.02-6.22(d, 1H), 6.54(s, 2H), 7.13-7.17(m, 1H), 7.34(s, 1H), 7.51-7.70(m, 4H), 7.84-7.89(m, 3H), 8.23-8.25(d, 1H). |

-continued

| ID | Structure | LCMS [M + H]+ | ¹H-NMR Data |
|---|---|---|---|
| Compounds synthesized using step 1 of general scheme-24 ||||
| I-698 | 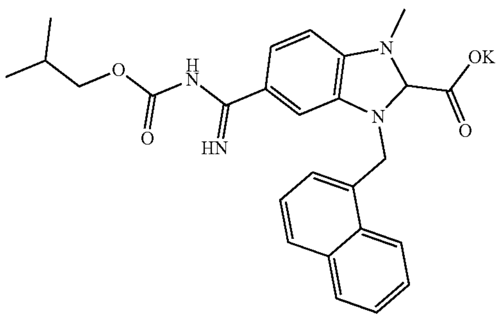 | 458.5 | ¹HNMR (DMSO-$d_6$, 400 MHz): δ 0.87 (d, 6H), 1.88 (m, 1H), 3.74 (d, 2H), 4.01 (s, 3H), 4.94 (s, 2H), 7.05 (d, 1H), 7.26 (t, 1H), 7.40 (d, 1H), 7.68-7.49 (m, 2H), 7.74 (d, 1H), 7.77 (d, 1H), 7.88 (d, 1H), 8.01 (s, 1H), 8.53 (d, 1H), 8.90 (brs, 1H), 9.20 (hrs, 1H); |
| I-674 | 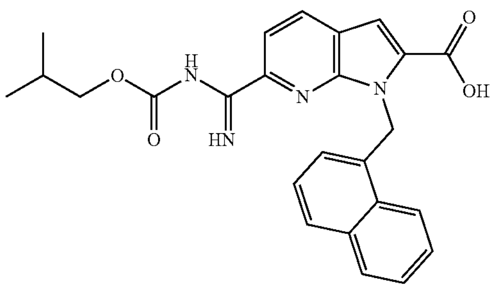 [SMILES: CC(C)COC(=O)NC(=N)c1ccc2cc(C(=O)O)n(Cc3cccc4ccccc34)c2n1] | 445.25 | ¹HNMR (CD$_3$OD, 400 MHz): δ 0.95-0.97 (d, 6H), 2.00-2.05 (m, 1H), 4.09-4.11 (d, 2H), 6.23-6.25 (d, 1H), 6.64 (s, 2H), 7.16-7.20 (m, 1H), 7.53-7.72 (m, 4H), 7.88-7.90 (d, 1H), 8.04-8.06 (d, 1H), 8.28-8.30 (d, 1H), 8.50-8.52 (d, 1H). |
| I-622 | 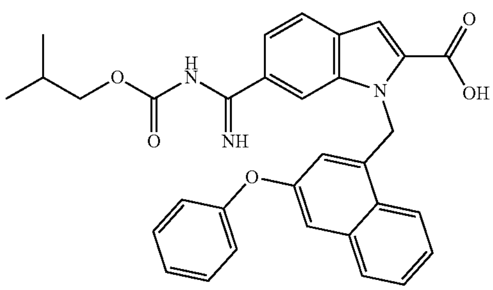 [SMILES: CC(C)COC(=O)NC(=N)c1ccc2cc(C(=O)O)n(Cc3cc(Oc4ccccc4)cc4ccccc34)c2c1] | 536.25 | ¹HNMR (CD$_3$OD, 400 MHz): δ 0.93-0.95 (d, 6H), 1.98 (m, 1H), 3.94-3.97 (d, 2H), 5.95 (s, 1H), 6.54 (s, 2H), 6.80-6.83 (d, 2H), 7.03-7.06 (t, 2H), 7.19-7.24 (t, 2H), 7.31 (s, 1H), 7.50-7.57 (m, 3H), 7.70-7.71 (d, 1H), 7.81-7.83 (d, 1H), 7.92 (s, 1H), 8.19 (d, 1H). |
| I-595 | 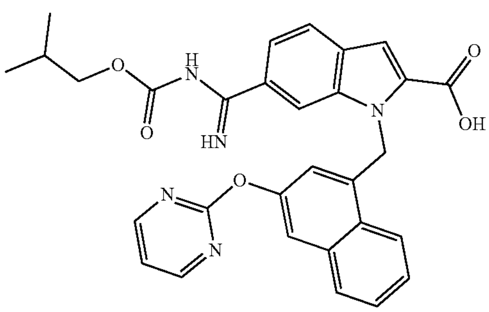 [SMILES: CC(C)COC(=O)NC(=N)c1ccc2cc(C(=O)O)n(Cc3cc(Oc4ncccn4)cc4ccccc34)c2c1] | 538.25 | ¹HNMR (CD$_3$OD, 400 MHz): δ 0.942-0.958 (d, 6H), 1.95 (m, 1H), 3.98-3.99 (d, 2H), 5.95 (s, 1H), 6.61 (s, 2H), 7.07 (t, 1H), 7.29 (s, 1H), 7.25-7.70 (m, 4H), 7.79-7.8 (d, 1H), 7.90-7.917 (d, 2H), 8.29-8.31 (d, 1H), 8.35-8.36 (d, 2H). |
| I-561 | 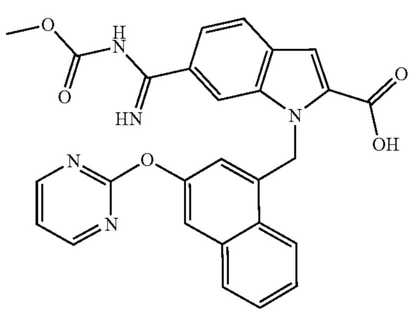 [SMILES: COC(=O)NC(=N)c1ccc2cc(C(=O)O)n(Cc3cc(Oc4ncccn4)cc4ccccc34)c2c1] | 496.15 | ¹HNMR (CD$_3$OD, 400 MHz): δ 3.78 (s, 3H), 5.98 (s, 1H), 6.59 (s, 2H), 7.05 (m, 1H), 7.29(s, 1H), 7.5-7.62 (m, 4H), 7.78 (d, 1H), 7.91 (d, 2H), 8.25 (d, 1H), 8.34-8.36 (d, 2H). |

-continued

Compounds synthesized using step 1 of general scheme-24

| ID | Structure | LCMS [M + H]+ | 1H-NMR Data |
|---|---|---|---|
| I-552 | 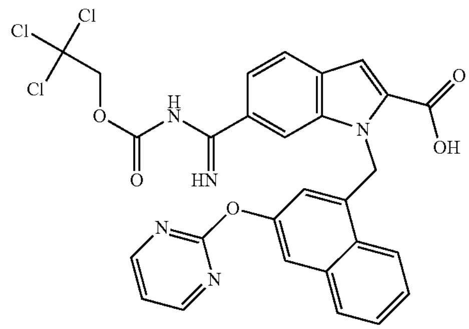 [SMILES: N=C(NC(=O)OCC(Cl)(Cl)Cl)c1ccc2cc(C(=O)O)n(Cc3cc(Oc4ncccn4)cc4ccccc34)c2c1] | 614.05 | 1HNMR (CD3OD, 400 MHz): δ 4.85 (s, 2H), 5.89 (s, 1H), 6.56 (s, 2H), 7.05-7.07 (t, 1H), 7.34 (s, 1H), 7.51 (s, 1H), 7.34-7.66 (m, 3H), 7.75-7.77 (d, 1H), 7.88-7.90 (d, 1H), 8.01 (s, 1H), 8.27-8.29 (d, 1H), 8.35-8.37 (d, 2H). |
| I-551 | 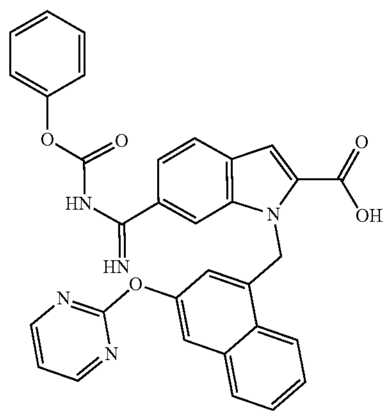 [SMILES: N=C(NC(=O)Oc1ccccc1)c1ccc2cc(C(=O)O)n(Cc3cc(Oc4ncccn4)cc4ccccc34)c2c1] | 558.15 | 1HNMR (CD3OD, 300 MHz): δ 5.88(s, 1H), 6.53(s, 2H), 7.06-7.13(m, 4H), 7.28-7.26(m, 3H), 7.53-8.01(m, 7H), 8.26-8.38(m, 3H). |

General synthetic scheme -25

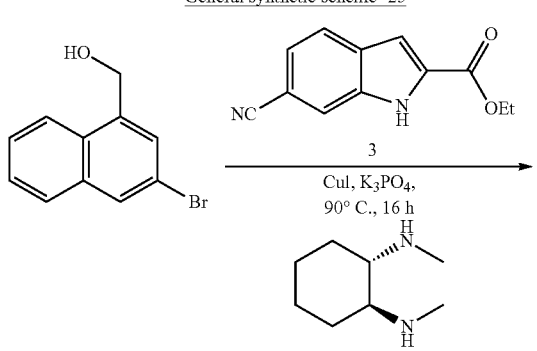

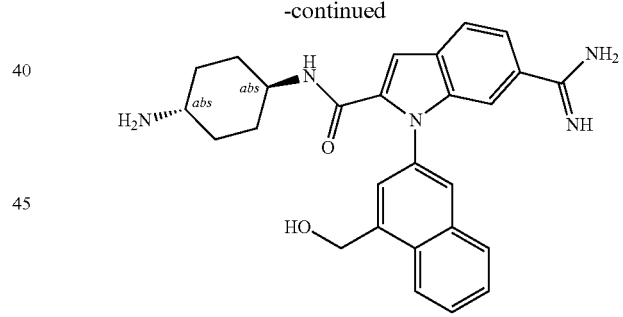

Step-1: Synthesis of Ethyl 6-cyano-1-(4-(hydroxymethyl)naphthalen-2-yl)-1H-indole-2-carboxylate In a sealed tube was added (3-bromonaphthalen-1-yl)methanol (410 mg, 1.74 mmol), K3PO4 (0.4 g, 3.48 mmol,), ethyl 6-cyano-1H-indole-2-carboxylate (377 mg, 1.74 mmol,) and trans-N,N'-Dimethylcyclohexane-1,2-diamine (247 mg, 1.74 mmol), in toluene in presence of argon gas, Copper iodide (165 mg, 0.87 mmol) was added, closed and stirred at 90° C. for 16 h. After completion, the reaction mixture was quenched with water and extracted with ethyl acetate twice. The organic layer was dried over sodium sulphate, filtered and evaporated in vacuum to get a crude compound. It was purified by using combi-flash with 50% EA/Hex, the obtained fractions were concentrated to get 200 mg of ethyl 6-cyano-1-(4-(hydroxymethyl)naphthalen-2-yl)-1H-indole-2-carboxylate.

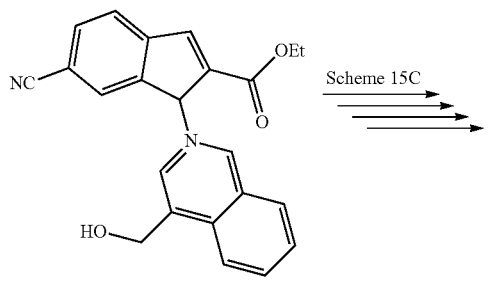

Scheme 15C

TABLE 56
Compounds synthesized using general scheme-25
| ID | Structure | LCMS [M + H]+ | 1H-NMR Data |
|---|---|---|---|
| I-677 | 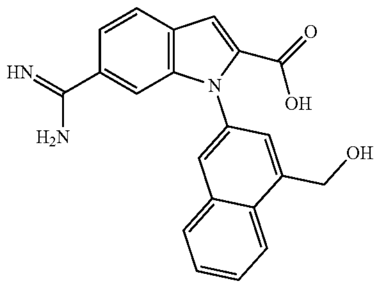 [SMILES: N=C(N)c1ccc2cc(C(=O)O)n(-c3cc(CO)c4ccccc4c3)c2c1] | 360.0 | 1HNMR (CD3OD, 400 MHz): δ 5.17 (s, 2H), 7.54-7.64 (m, 6H), 7.89 (s, 1H), 7.97-7.99 (d, 2H), 8.17-8.19 (d, 1H). |
TABLE 57
Compounds synthesized using general scheme-15C
| ID | Structure | LCMS [M + H]+ | 1H-NMR Data |
|---|---|---|---|
| I-681 | 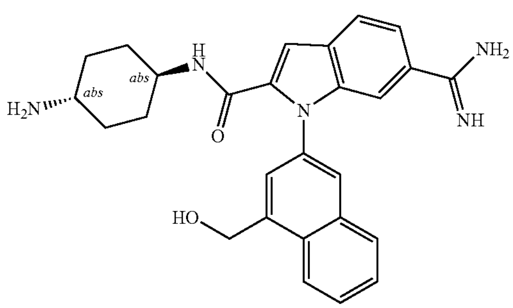 [SMILES: N=C(N)c1ccc2cc(C(=O)N[C@H]3CC[C@H](N)CC3)n(-c3cc(CO)c4ccccc4c3)c2c1] | 456.3 | 1HNMR (CD3OD, 400 MHz): δ 1.14-1.46 (m, 4H), 1.99-2.04 (m, 4H), 3.00-3.10 (m, 1H), 3.62-3.70 (m, 1H), 5.17 (s, 2H), 7.27 (s, 1H), 7.57-7.65 (m, 4H), 7.74 (s, 1H), 7.88-7.97 (m, 3H), 8.14-8.16 (d, 1H). |
General synthetic scheme -26
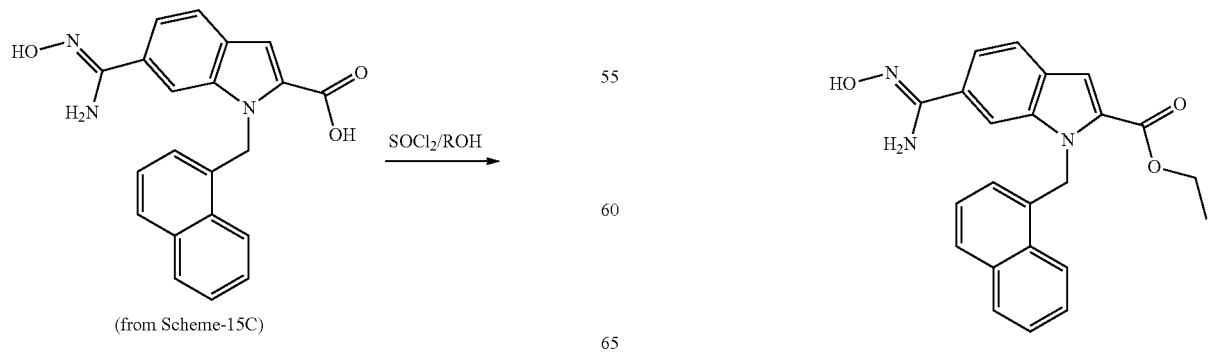

Example 123: Synthesis of Compound I-675

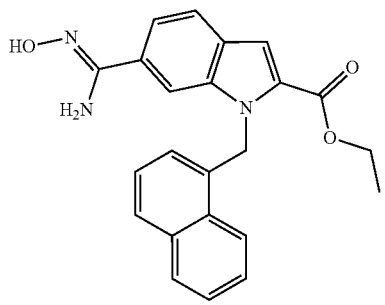 [SMILES: CCOC(=O)c1cc2ccc(/C(N)=N/O)cc2n1Cc1cccc2ccccc12]

Step-1: Synthesis of Ethyl (Z)-6-(N'-hydroxycarbamimidoyl)-1-(naphthalen-1-ylmethyl)-1H-indole-2-carboxylate Following the experimental protocol of Step 1 in Scheme 15D-2, ethyl (Z)-6-(N'-hydroxycarbamimidoyl)-1-(naphthalen-1-ylmethyl)-1H-indole-2-carboxylate was synthesized LCMS: 388.2 (M+1)$^+$, $^1$HNMR (CD$_3$OD, 400 MHz): δ 1.07-1.11 (m, 3H), 4.08-4.14 (m, 2H), 6.05-6.07 (d, 1H), 6.31 (s, 2H), 7.05-7.09 (m, 1H), 7.38-7.69 (m, 7H), 7.81-7.83 (d, 1H), 8.14-8.16 (d, 1H); HPLC: 99.91% (Retention Time=5.54 min).

TABLE 58

Compounds synthesized using general scheme-26

| ID | Structure | LCMS [M + H]$^+$ | $^1$H-NMR Data |
|---|---|---|---|
| I-663 | 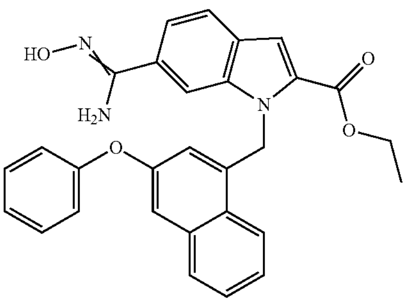 [SMILES: CCOC(=O)c1cc2ccc(C(N)=NO)cc2n1Cc1cc(Oc2ccccc2)cc2ccccc12] | 480.2 | $^1$HNMR (CD$_3$OD, 400 MHz): δ 1.21-1.28 (t, 3H), 4.24-4.29 (q, 2H), 5.92 (s, 1H), 6.44 (s, 2H), 6.80-6.82 (d, 2H), 7.04-7.07 (t, 1H), 7.14 (d, 1H), 7.21-7.25 (t, 2H), 7.42-7.45 (d, 1H), 7.50 (s, 1H), 7.54-7.57 (m, 2H), 7.76-7.81 (m, 2H), 7.92-7.94 (d, 1H), 8.19-8.21 (d, 1H). |
| I-658 | 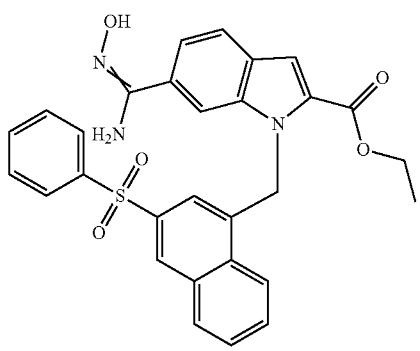 [SMILES: CCOC(=O)c1cc2ccc(C(N)=NO)cc2n1Cc1cc(S(=O)(=O)c2ccccc2)cc2ccccc12] | 528.4 | $^1$HNMR (CD$_3$OD, 400 MHz): δ 1.08-1.10 (m, 3H), 4.08-4.14 (m, 2H), 6.31 (s, 1H), 6.45 (s, 2H). 7.42-7.89 (m, 10H), 8.10-8.35 (m, 3H), 8.52 (s, 1H). |

General synthetic scheme -27
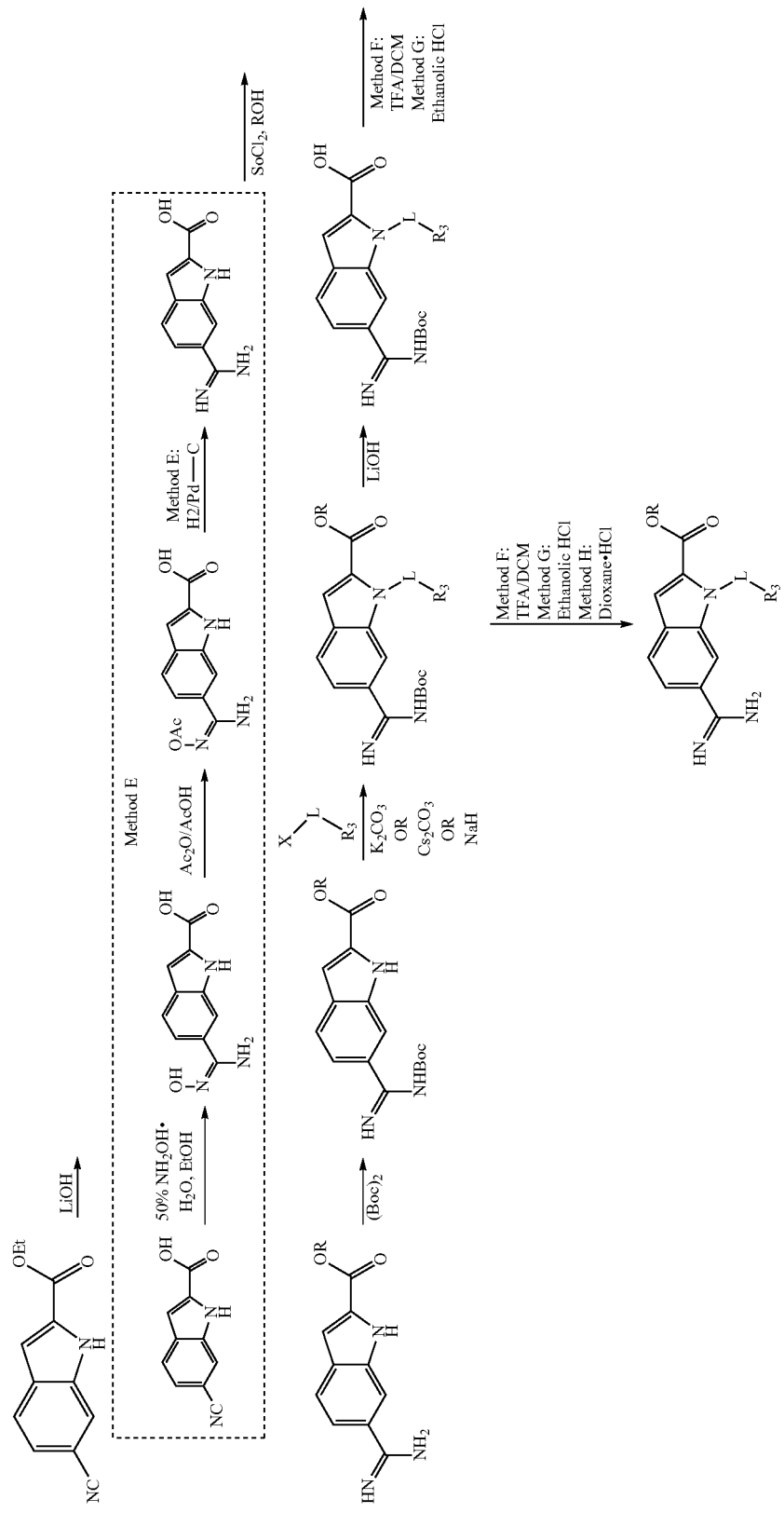

-continued
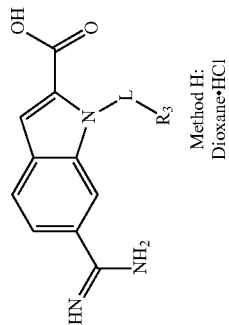
Method H:
Dioxane•HCl
PG = optional protecting group; X = Br or Cl;
R = Me/Et Example 124: Synthesis of Compound I-598

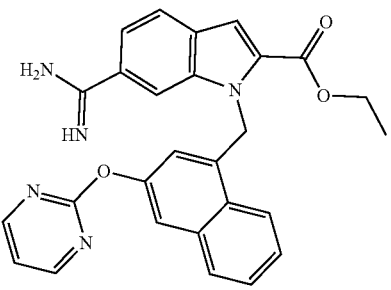 [SMILES: CCOC(=O)c1cc2ccc(C(=N)N)cc2n1Cc1cc(Oc2ncccn2)cc2ccccc12]

Synthesis of 6-cyano-1H-indole-2-carboxylic Acid

To a solution of ethyl 6-cyano-1H-indole-2-carboxylate (15 g, 0.07 mol) in EtOH (150 ml), and THF (150 ml), LiOH·H$_2$O (8.9 g, 0.21 mol) dissolved in water (100 ml) was added and resulting mixture was stirred at rt for 4 h. Excess of solvent was removed under reduce pressure and residue was suspended in 100 ml of ice water. Aqueous layer was further acidified with 1N HCl and resultant solid was filtered and dried to afford title compound (13 g, 99%).

Synthesis of (E)-6-(N'-hydroxycarbamimidoyl)-1H-indole-2-carboxylic Acid

To solution of 6-cyano-1H-indole-2-carboxylic acid (13 g, 0.07 mol) in EtOH (200 ml) and THF (200 ml), DIPEA (226 ml, 1.26 mol) and hydroxyl amine hydrochloride (NH$_2$OH·HCl) was added at 0° C. After addition completed reaction mass was heated at 75° C. for overnight. After cooling to ambient temperature reaction mass was concentrated to dryness under reduce pressure and residue was resuspended in 200 ml ice water. Resultant solid was filtered and dried under vacuum to afford desire compound (14 g, 91%).

Synthesis of (E)-6-(N'-acetoxycarbamimidoyl)-1H-indole-2-carboxylic Acid

To a solution of (E)-6-(N'-hydroxycarbamimidoyl)-1H-indole-2-carboxylic acid (16 g, 0.07 mol) in acetic acid (200 ml) & acetonitrile (400 ml), acetic anhydride (10 ml) was added at 0° C. Reaction mass was stirred at rt for 2 h and after completion of reaction, excess of solvent was removed under vacuum. Residue were resuspended in water and filtered to afford title compound (12 g, 63%).

Synthesis of 6-carbamimidoyl-1H-indole-2-carboxylic Acid (E)-6-(N'-acetoxycarbamimidoyl)-1H-indole-2-carboxylic acid (12 g, 0.04 mol) was dissolved in acetic acid (200 ml) and EtOH (100 ml) mixture. Pd/C (1.2 g) was added and reaction mixture was stirred at rt for 6 h under hydrogen atmosphere. Reaction mass was filtered through celite bed and wash with 2% TFA in MeOH. Combine filtrate was collected and concentrated to afford title compound (9.0 g, 98%).

Synthesis of Ethyl 6-carbamimidoyl-1H-indole-2-carboxylate

To a solution of 6-carbamimidoyl-1H-indole-2-carboxylic acid (6 g, 0.029 mol), in EtOH (100 ml), SOCl$_2$ (7.2 ml) was added at 0° C. After addition completed reaction mass was refluxed for overnight. Excess of solvent was removed under reduce pressure. Residue were resuspended in 200 ml of ice water and resultant solid was filtered, dried to afford title compound (5.5 g, 88%).

Synthesis of Ethyl 6-(N-(tert-butoxycarbonyl)carbamimidoyl)-1H-indole-2-carboxylate To a solution of ethyl 6-carbamimidoyl-1H-indole-2-carboxylate (16 g, 0.073 mol), in THF (100 ml) and water (50 ml), DIPEA (8.5 ml) and Boc$_2$O was added at 0° C. Resulting mixture was stirred at rt for 3 h. Excess of solvent was removed under reduce pressure and residue were resuspended in water (200 ml). Aqueous layer was extracted with EtOAc (2*200 ml) and combined organic layer was dried over Na$_2$SO$_4$ and concentrated to afford crude compound. Crude was further resuspended in 10% EtOAc in Hexane (100 ml), stirred, filtered and dried to afford sufficient pure title compound (5.3 g, 68%).

Synthesis of Ethyl 6-(N-(tert-butoxycarbonyl)carbamimidoyl)-1-((3-(pyrimidin-2-yloxy)naphthalen-1-yl)methyl)-1H-indole-2-carboxylate Following the experimental protocol of Step 1 in Scheme 15, Ethyl 6-(N-(tert-butoxycarbonyl)carbamimidoyl)-1-((3-(pyrimidin-2-yloxy)naphthalen-1-yl)methyl)-1H-indole-2-carboxylate was synthesized Synthesis of Ethyl 6-carbamimidoyl-1-((3-(pyrimidin-2-yloxy)naphthalen-1-yl)methyl)-1H-indole-2-carboxylate Following the experimental protocol of Step 7 in Scheme 15, Ethyl 6-carbamimidoyl-1-((3-(pyrimidin-2-yloxy)naphthalen-1-yl)methyl)-1H-indole-2-carboxylate. LCMS: 466.2 (M+1)$^+$ $^1$HNMR (CD$_3$OD, 400 MHz): δ1.19-1.22 (m, 3H), 4.25-4.27 (m, 2H), 5.90 (s, 1H), 6.51 (s, 2H), 7.12-7.20 (m, 1H), 7.52-7.70 (m, 5H), 7.92-7.94 (m, 3H), 8.28-8.30 (d, 1H), 8.38-8.40 (d, 2H). HPLC: 97.80% (Retention Time=4.68 min)

TABLE 59

Compounds synthesized using general scheme-27

| ID. | Structure | LCMS [M + H]+ | 1H-NMR Data |
|---|---|---|---|
| I-696 | 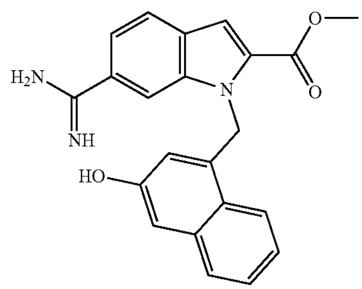 [SMILES: COC(=O)c1cc2ccc(C(=N)N)cc2n1Cc1cc(O)cc2ccccc12] | 374.1 | 1HNMR (CD$_3$OD, 300 MHz): δ 3.82 (s, 3H), 5.75-5.759 (s, 1H), 6.43 (s, 2H), 6.97-6.978 (d, 1H), 7.41-7.47 (m, 2H), 7.54-7.60 (m, 2H), 7.68-7.71 (d, 1H), 7.94 (s, 1H), 7.99-8.02 (d, 1H), 8.09-8.12 (d, 1H). |
| I-592 | 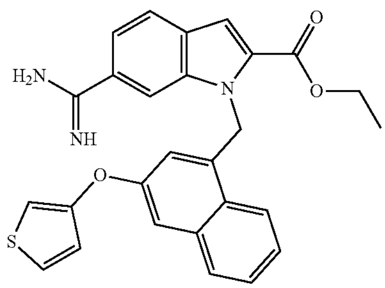 [SMILES: CCOC(=O)c1cc2ccc(C(=N)N)cc2n1Cc1cc(Oc2ccsc2)cc2ccccc12] | 470.15 | 1HNMR (CD$_3$OD, 300 MHz): δ 1.23-1.26 (t, 3H), 4.25-4.30 (q, 2H), 5.8 (s, 1H), 6.46 (s, 2H), 6.55-6.56 (d, 1H), 6.65-6.67 (d, 1H), 7.19 (s, 1H), 7.27-7.30 (m, 1H), 7.55-7.58 (m, 4H), 7.78-7.82 (d, 1H), 7.97-8.00 (m, 2H), 8.19-8.23 (d, 1H). |

Example 125: Synthesis of Compound I-695

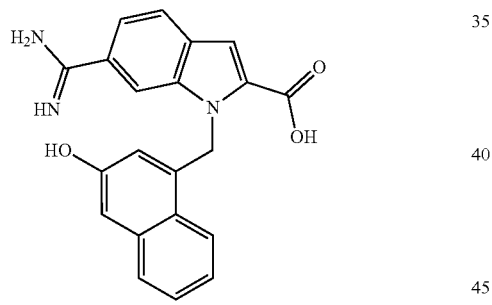

Synthesis of 6-(N-(tert-butoxycarbonyl)carbamimidoyl)-1-((3-hydroxynaphthalen-1-yl)methyl)-1H-indole-2-carboxylic Acid Following the experimental protocol of Step 2 in Scheme 15, 6-(N-(tert-butoxycarbonyl)carbamimidoyl)-1-((3-hydroxynaphthalen-1-yl)methyl)-1H-indole-2-carboxylic acid Synthesis of 6-carbamimidoyl-1-((3-hydroxynaphthalen-1-yl)methyl)-1H-indole-2-carboxylic Acid Following the experimental protocol of Step 7 in Scheme 15, 6-carbamimidoyl-1-((3-hydroxynaphthalen-1-yl)methyl)-1H-indole-2-carboxylic acid. LCMS: 360.1 (M+1)+
1HNMR (CD$_3$OD, 300 MHz): δ 5.79-5.80 (s, 1H), 6.45 (s, 2H), 6.96-6.97 (d, 1H), 7.40-7.45 (m, 2H), 7.53-7.55 (d, 2H), 7.67-7.70 (d, 1H), 7.90 (s, 1H), 7.97-8.00 (d, 1H), 8.09-8.11 (d, 1H). HPLC: 96.73% (Retention Time=5.50 min)

TABLE 60

| | | LCMS | |
|---|---|---|---|
| ID. | Structure | [M + H]⁺ | ¹H-NMR Data |
| I-695 | | 360.1 | ¹HNMR (CD₃OD, 300 MHz): δ 5.79-5.80 (s, 1H), 6.45 (s, 2H), 6.96-6.97 (d, 1H), 7.40-7.45 (m, 2H), 7.53-7.55 (d, 2H), 7.67-7.70 (d, 1H), 7.90 (s, 1H), 7.97-8.00 (d, 1H), 8.09-8.11 (d, 1H). |
| I-693 | | 438.1 | ¹HNMR (CD₃OD, 400 MHz): δ 5.845-5.851 (s, 1H), 6.555 (s, 2H), 7.100-7.124 (t, 1H), 7.477 (s, 1H), 7.502-7.527 (d, 1H), 7.560-7.565 (d, 1H), 7.616-7.671 (m, 2H), 7.904-7.938 (m, 3H), 8.268-8.290 (d, 1H), 8.388-8.400 (d, 2H). |
| I-692 | | 443.25 | ¹HNMR (CD₃OD, 400 MHz): δ 3.684-3.711 (t, 2H), 3.926-3.951 (t, 2H), 4.118 (s, 2H), 6.289 (s, 1H), 6.511 (s, 2H), 7.520-7.564 (m, 2H), 7.630-7.696 (m, 2H), 7.781 (s, 1H), 7.905 (s, 1H), 7.964-7.985 (d, 2H), 8.258-8.279 (d, 1H). |
| I-688 | | 466.2 | ¹HNMR (CD₃OD, 400 MHz): δ 3.78 (s, 3H), 5.80 (s, 1H), 6.48 (s, 2H), 6.80-6.81 (d, 4H), 6.99-7.00 (d, 1H), 7.51-7.57 (m, 4H), 7.71-7.73 (m, 1H), 7.93-7.97 (m, 2H), 8.17-8.19 (m, 1H). |

TABLE 60-continued

Compounds synthesized using general scheme-27

| ID. | Structure | LCMS [M + H]+ | 1H-NMR Data |
|---|---|---|---|
| I-686 | 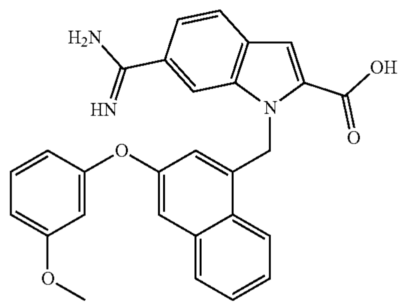 [SMILES: COc1cccc(Oc2cc(Cn3c(C(=O)O)cc4ccc(C(=N)N)cc43)c3ccccc3c2)c1] | 466.05 | 1HNMR (CD3OD, 400 MHz): δ 3.36 (s, 3H), 5.80 (s, 1H), 6.305-6.37 (m, 2H) 6.47 (s, 2H), 6.61 (d, 1H), 7.07-7.17 (m, 2H), 7.50-7.56 (m, 4H), 7.77 (d, 1H), 7.93-7.95 (m, 2H), 8.19 (d, 1H). |
| I-682 | 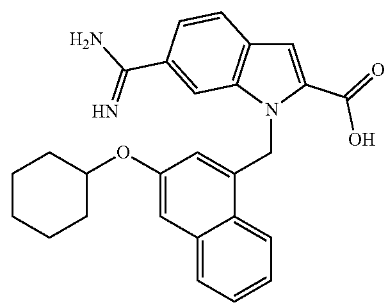 [SMILES: N=C(N)c1ccc2cc(C(=O)O)n(Cc3cc(OC4CCCCC4)cc4ccccc34)c2c1] | 442.0 | 1HNMR (CD3OD, 300 MHz): δ 1.30-1.36 (m, 6H), 1.68 (m, 2H), 1.88 (m, 2H), 4.10-4.20 (m, 1H), 5.71 (s, 1H), 6.44 (s, 2H), 7.08 (s, 1H), 7.45-7.59 (m, 4H), 7.76-7.79 (d, 1H), 7.92 (s, 1H), 7.99-8.02 (d, 1H), 8.10-8.13 (d, 1H). |
| I-680 | 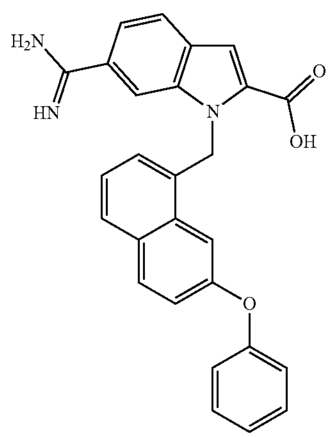 [SMILES: N=C(N)c1ccc2cc(C(=O)O)n(Cc3cccc4ccc(Oc5ccccc5)cc34)c2c1] | 436.05 | 1HNMR (CD3OD, 400 MHz): δ 6.21 (s, 1H), 6.33 (s, 2H), 7.08-7.16 (m, 4H), 7.30 (d, 1H), 7.40 (t, 2H), 7.52-7.53 (m, 2H), 7.72-7.74 (m, 2H), 7.87 (s, 1H), 7.95 (t, 2H). |
| I-678 | 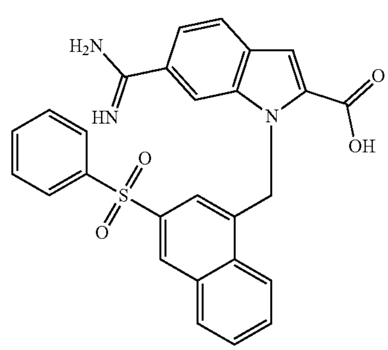 [SMILES: N=C(N)c1ccc2cc(C(=O)O)n(Cc3cc(S(=O)(=O)c4ccccc4)cc4ccccc34)c2c1] | 484.00 | 1HNMR (CD3OD, 400 MHz): δ 6.303-6.303 (s, 1H), 6.471 (s, 2H), 7.377-7.415 (t, 2H), 7.521-7.564 (m, 3H), 7.619-7.638 (d, 2H), 7.640-7.644 (t, 1H), 7.751-7.771 (m, 2H), 8.069-8.089 (d, 1H), 8.147-8.168 (d, 1H), 8.308-8.327 (d, 1H), 8.476 (s, 1H). |

TABLE 60-continued

Compounds synthesized using general scheme-27

| ID. | Structure | LCMS [M + H]+ | 1H-NMR Data |
|---|---|---|---|
| I-661 | 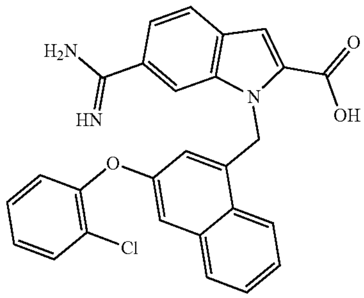 [SMILES: N=C(N)c1ccc2cc(C(=O)O)n(Cc3cc(Oc4ccccc4Cl)cc4ccccc34)c2c1] | 470.02 | 1HNMR (CD3OD, 400 MHz): δ 5.73 (s, 1H), 6.48 (s, 2H), 6.89 (d, 1H), 7.04 (s, 1H), 7.08-7.17 (m, 2H), 7.35 (d, 1H), 7.49-7.56 (m, 4 H), 7.76 (d, 1H), 7.93-7.96 (m, 2H), 8.19 (d, 1H) |
| I-655 | 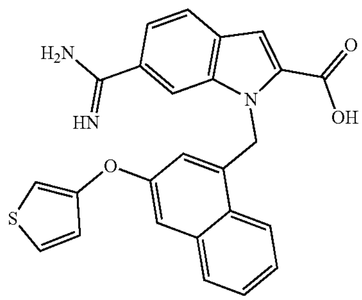 [SMILES: N=C(N)c1ccc2cc(C(=O)O)n(Cc3cc(Oc4ccsc4)cc4ccccc34)c2c1] | 442.3 | 1HNMR (CD3OD, 400 MHz): δ 5.88 (s, 1H), 6.50-6.69 (m, 4H), 7.20 (s, 1H), 7.29-7.32 (m, 1H), 7.56-7.60 (m, 4H), 7.79-7.81 (d, 1H), 7.95-8.00 (m, 2H), 8.20-8.22 (d, 1H). |
| I-653 | 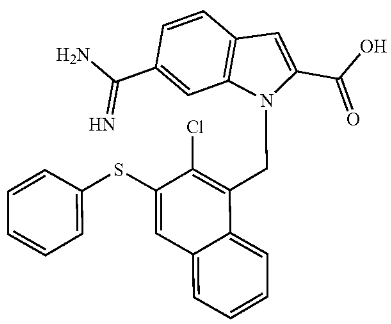 [SMILES: N=C(N)c1ccc2cc(C(=O)O)n(Cc3c(Cl)c(Sc4ccccc4)cc4ccccc34)c2c1] | 486.3 | 1HNMR (CD3OD, 400 MHz): δ 5.45(s, 1H), 6.29(s, 2H), 7.03-7.09(m, 4H), 7.26(s, 2H), 7.53-7.90(m, 5H), 8.18-8.30(m, 2H). |
| I-649 | 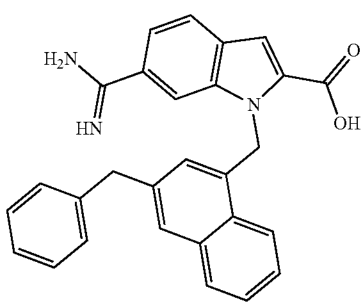 [SMILES: N=C(N)c1ccc2cc(C(=O)O)n(Cc3cc(Cc4ccccc4)cc4ccccc34)c2c1] | 434.6 | 1HNMR (CD3OD, 400 MHz): δ 3.80 (s, 2H), 5.98 (s, 1H), 6.44 (s, 2H), 6.86-6.87 (d, 2H), 7.05-7.06 (d, 3H), 7.52-7.57 (m, 5H), 7.82 (m, 2H), 7.96-7.98 (d, 1H), 8.15-8.20 (d, 1H). |
| I-648 | 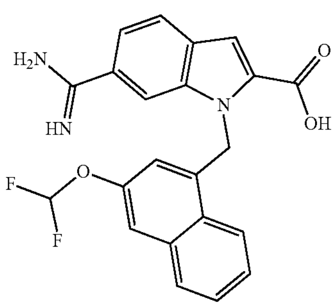 [SMILES: N=C(N)c1ccc2cc(C(=O)O)n(Cc3cc(OC(F)F)cc4ccccc34)c2c1] | 409.95 | 1HNMR (CD3OD, 400 MHz): δ 6.49 (s, 2H), 6.73 (s, 1H)6.98 (s, 1H), 7.44 (s, 1H), 7.56-7.64 (m, 4H), 7.90-7.93 (m, 2H), 8.00-8.03 (d, 1H), 8.23-8.26 (d, 1H) |

TABLE 60-continued
Compounds synthesized using general scheme-27
| ID. | Structure | LCMS [M + H]+ | ¹H-NMR Data |
|---|---|---|---|
| I-647 | 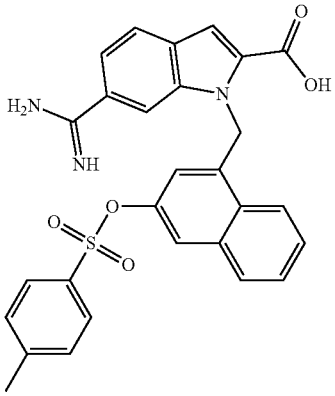 [SMILES: Cc1ccc(S(=O)(=O)Oc2cc(Cn3c(C(=O)O)cc4ccc(C(=N)N)cc43)c3ccccc3c2)cc1] | 514.45 | ¹HNMR (CD₃OD, 300 MHz): δ 2.35 (s, 3H), 5.65-5.66 (d, 1H), 6.30 (s, 2H), 7.11-7.13 (d, 2H), 7.30-7.50 (m, 7H), 7.77-7.79 (d, 2H), 7.91-7.93 (d, 1H), 8.12-8.14 (d, 1H). |
| I-640 | 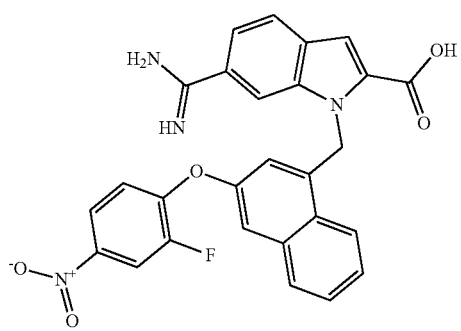 | 499.05 | ¹HNMR (CD₃OD, 300 MHz): δ 3.29-3.31 (m, 2H), 5.78-5.787 (d, 1H), 6.51 (s, 2H), 6.91-6.97 (m, 1H), 7.40-7.41 (d, 1H), 7.50 (d, 1H), 7.53-7.66 (m, 3H), 7.87-7.97 (m, 4H), 8.04-8.08 (q, 1H), 8.25-8.28 (d, 1H) |
| I-639 | 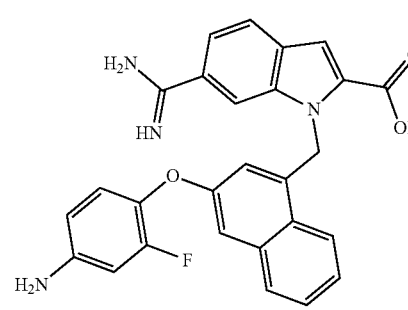 | 469.20 | ¹HNMR (CD₃OD, 300 MHz): δ 5.8 (d, 1H), 6.44 (d, 1H), 6.47 (s, 3H), 6.51-6.52 (d, 1H), 6.73 (t, 1H), 6.91 (s, 1H), 7.49-7.58 (m, 5H), 7.69 (m, 1H), 7.93-8.00 (m, 2H), 8.15 (m, 1H) |
| I-632 | 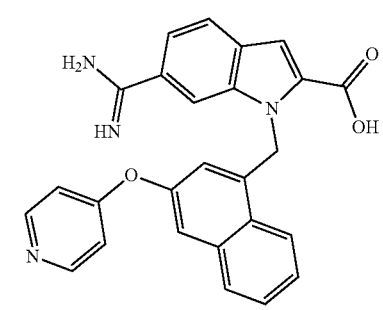 [SMILES: N=C(N)c1ccc2cc(C(=O)O)n(Cc3cc(Oc4ccncc4)cc4ccccc34)c2c1] | 437.15 | ¹HNMR (CD₃OD, 300 MHz): δ 5.963 (s, 1H), 6.54 (s, 2H), 7.18 (s, 1H), 7.51-7.75 (m, 6H), 7.94-7.99 (m, 3H), 8.33-8.36 (d, 1H), 8.51 (s, 1H) |

TABLE 60-continued

Compounds synthesized using general scheme-27

| ID. | Structure | LCMS [M + H]+ | ¹H-NMR Data |
|---|---|---|---|
| I-628 | 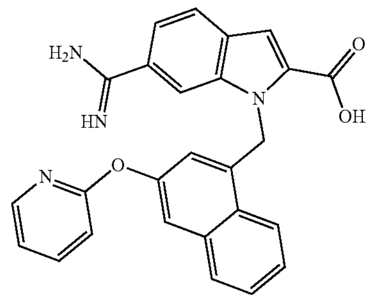 [SMILES: N=C(N)c1ccc2cc(C(=O)O)n(Cc3cc(Oc4ccccn4)cc4ccccc34)c2c1] | 437.4 | ¹HNMR (CD₃OD, 300 MHz): δ 5.70-5.80 (s, 1H), 6.52 (s, 2H), 6.90-6.80 (d, 1H), 7.48 (s, 1H), 7.00 (t, 1H), 7.60-7.50 (s, 1H), 7.60-7.50 (s, 1H), 7.70-7.60 (m, 2H), 7.80-7.70 (m, 1H), 7.90-7.80 (d, 1H), 8.00-7.90 (d, 2H), 8.30-8.20 (d, 1H). |
| I-626 | 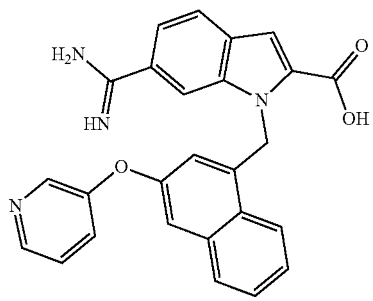 [SMILES: N=C(N)c1ccc2cc(C(=O)O)n(Cc3cc(Oc4cccnc4)cc4ccccc34)c2c1] | 437.4 | ¹HNMR (CD₃OD, 300 MHz): δ 6.51 (s, 2H), 7.39-7.32 (d, 3H), 7.39-7.32 (d, 3H), 7.39-7.32 (d, 3H), 7.96-7.93 (d, 2H), 8.16 (s, 1H), 8.25 (d, 2H). |
| I-625 | 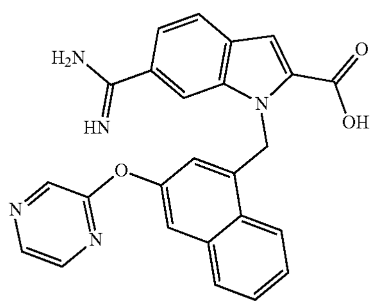 [SMILES: N=C(N)c1ccc2cc(C(=O)O)n(Cc3cc(Oc4cnccn4)cc4ccccc34)c2c1] | 438.1 | ¹HNMR (CD₃OD, 300 MHz): δ6.544 (s, 2H), 5.869 (s, 1H), 8.19-8.8 (m, 3H), 7.879-7.945 (m, 4H), 7.495-7.670 (m, 5H) |
| I-623 | 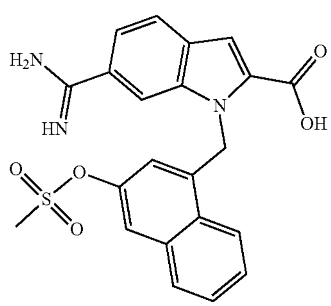 [SMILES: CS(=O)(=O)Oc1cc(Cn2c(C(=O)O)cc3ccc(C(=N)N)cc32)c2ccccc2c1] | 438.10 | ¹HNMR (CD₃OD, 400 MHz): δ 3.04 (s, 3H), 6.05 (s, 1H), 6.52 (s, 2H), 7.05-7.25 (m, 5H), 7.93-8.05 (m, 3H), 8.28-8.30 (d, 1H). |
| I-621 | 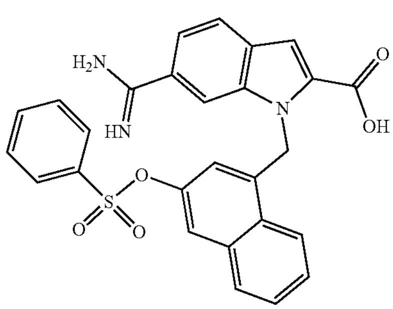 [SMILES: N=C(N)c1ccc2cc(C(=O)O)n(Cc3cc(OS(=O)(=O)c4ccccc4)cc4ccccc34)c2c1] | 500.1 | ¹HNMR (CD₃OD, 400 MHz): δ 5.65 (s, 1H), 6.381 (s, 2H), 7.349-7.370 (t, 2H), 7.45 (s, 1H), 7.517 (m, 3H), 7.536-7.538 (m, 4H), 7.85 (s, 1H), 7.9 (d, 1H), 8.01 (d, 1H), 8.25 (d, 1H). |

TABLE 60-continued

Compounds synthesized using general scheme-27

| ID. | Structure | LCMS [M + H]+ | 1H-NMR Data |
|---|---|---|---|
| I-618 | 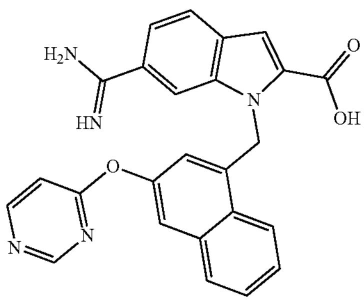 [SMILES: N=C(N)c1ccc2cc(C(=O)O)n(Cc3cc(Oc4ccncn4)cc4ccccc34)c2c1] | 437.7 | 1HNMR (CD3OD, 400 MHz): δ 5.85 (s, 1H), 6.54 (s, 2H), 6.94 (d, 1H), 7.69-7.5 (m, 4H), 7.97-7.92 (m, 3H), 8.28 (d, 1H), 8.42 (s, 1H), 8.51 (d, 1H). |
| I-610 | 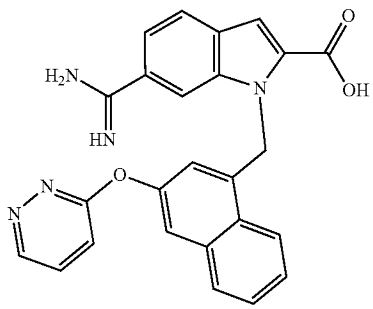 [SMILES: N=C(N)c1ccc2cc(C(=O)O)n(Cc3cc(Oc4cccnn4)cc4ccccc34)c2c1] | 438.2 | 1HNMR (CD3OD, 400 MHz): δ 5.89 (s, 1H), 6.54 (s, 2H), 7.30 (d, 1H), 7.49-7.46 (m, 2H), 7.67-7.57 (m, 4H), 7.94-7.87 (m, 3H), 8.28 (d, 1H), 8.78 (s, 2H). |
| I-589 | 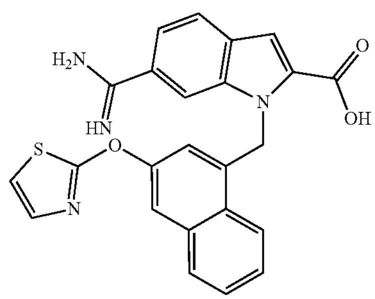 [SMILES: N=C(N)c1ccc2cc(C(=O)O)n(Cc3cc(Oc4nccs4)cc4ccccc34)c2c1] | 443.2 | 1HNMR (CD3OD, 300 MHz): δ 6.54 (s, 2H), 6.96-7.05 (m, 2H), 7.52-7.68 (m, 5H), 7.93-7.96 (d, 3H), 8.27-8.29 (d, 1H). |
| I-584 | 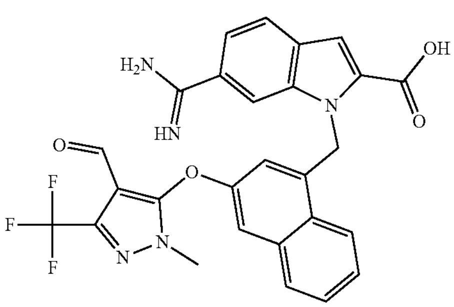 [SMILES: Cn1nc(C(F)(F)F)c(C=O)c1Oc1cc(Cn2c(C(=O)O)cc3ccc(C(=N)N)cc32)c2ccccc2c1] | 536.2 | 1HNMR (CD3OD, 400 MHz): δ 3.63 (s, 3H), 5.73 (d, 1H), 6.56 (s, 3H), 7.34-7.31 (m, 3H), 7.60-7.50 (m, 4H), 7.90-7.82 (m, 4H), 8.23 (d, 2H), 9.23 (s, 1H). |
| I-575 | 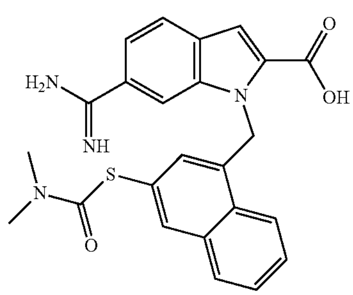 [SMILES: CN(C)C(=O)Sc1cc(Cn2c(C(=O)O)cc3ccc(C(=N)N)cc32)c2ccccc2c1] | 447.15 | 1HNMR (CD3OD, 400 MHz): δ 2.82 (s, 1H), 3.01 (s, 3H), 6.52 (s, 2H), 7.52-7.54 (d, 1H), 7.60 (s, 1H), 7.71-7.78 (m, 1H), 7.60-7.69 (m, 1H), 7.90 (s, 1H), 7.95-8.02 (m, 2H), 8.82-8.29 (d, 1H), |

TABLE 60-continued

Compounds synthesized using general scheme-27

| ID. | Structure | LCMS [M + H]⁺ | ¹H-NMR Data |
|---|---|---|---|
| I-574 | 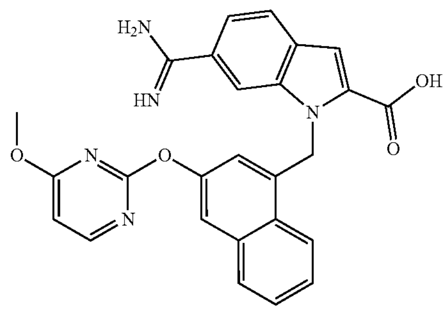 [SMILES: COc1ccnc(Oc2cc(Cn3c(C(=O)O)cc4ccc(C(=N)N)cc43)c3ccccc3c2)n1] | 468.2 | ¹HNMR (DMSO-d$_6$, 300 MHz): δ 3.67 (s, 3H), 5.88 (s, 1H), 6.46-6.48 (d, 1H), 6.54 (s, 2H), 7.52-7.67 (m, 5H), 7.93-8.00 (m, 4H), 8.27-8.29 (d, 1H) |
| I-571 | 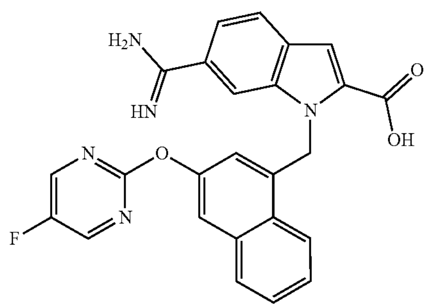 [SMILES: N=C(N)c1ccc2cc(C(=O)O)n(Cc3cc(Oc4ncc(F)cn4)cc4ccccc34)c2c1] | 456.10 | ¹HNMR (CD$_3$OD, 400 MHz): δ 5.866-5.872 (s, 1H), 6.532 (s, 2H), 7.521-7.551 (d, 3H), 7.600-7.700 (m, 2H), 7.935-7.938 (m, 2H), 7.950 (s, 1H), 8.295-8.300 (d, 1H), 8.366 (s, 2H). |
| I-570 | 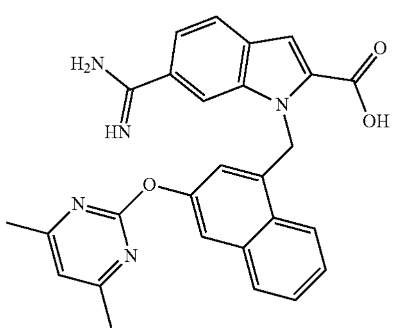 [SMILES: Cc1cc(C)nc(Oc2cc(Cn3c(C(=O)O)cc4ccc(C(=N)N)cc43)c3ccccc3c2)n1] | 466.20 | ¹HNMR (CD$_3$OD, 400 MHz): δ 2.218 (s, 6H), 5.950 (s, 1H), 6.533 (s, 2H), 6.873 (s, 1H), 7.510-7.524 (m, 3H), 7.600-7.700 (m, 2H), 7.933-7.961 (m, 3H), 8.290-8.300 (d, 1H). |
| I-566 | 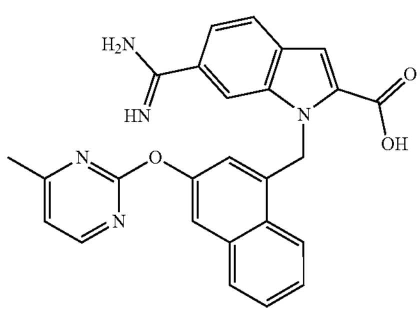 [SMILES: Cc1ccnc(Oc2cc(Cn3c(C(=O)O)cc4ccc(C(=N)N)cc43)c3ccccc3c2)n1] | 452.15 | ¹HNMR (CD$_3$OD, 400 MHz): δ 2.28 (s, 3H), 5.91 (s, 1H), 6.51(s, 2H), 6.97-6.98 (d, 1H), 7.49-7.53 (m, 3H), 7.59-7.62 (m, 2H), 7.89-7.95 (m, 3H), 8.16-8.17 (d, 1H), 8.24-8.26 (d, 1H). |

TABLE 60-continued
Compounds synthesized using general scheme-27
| ID. | Structure | LCMS [M + H]+ | 1H-NMR Data |
|---|---|---|---|
| I-563 | 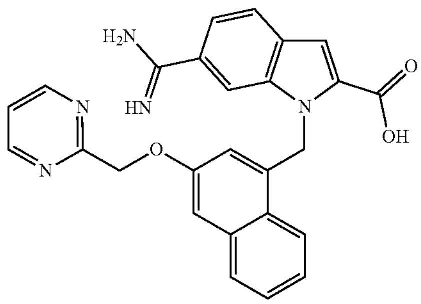 [SMILES: N=C(N)c1ccc2cc(C(=O)O)n(Cc3cc(OCc4ncccn4)cc4ccccc34)c2c1] | 452.2 | 1NMR (DMSO-d6, 400 MHz): δ 5.18 (s, 2H), 5.59 (s, 1H), 6.39 (s, 2H), 7.2-7.24 (m, 1H), 7.41 (t, 1H), 7.61-7.52 (m, 4H), 7.84 (d, 1H), 8.02 (d, 1H), 8.12 (s, 1H), ), 8.19 (d, 1H), 8.74 (d, 2H), 8.86 (s, 2H), 9.21 (s, 2H). |
| I-548 | 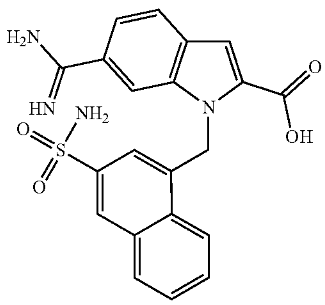 [SMILES: N=C(N)c1ccc2cc(C(=O)O)n(Cc3cc(S(N)(=O)=O)cc4ccccc34)c2c1] | 423.1 | 1HNMR (CD3OD, 400 MHz): δ 6.53 (s, 2H), 6.79 (s, 1H), 7.55 (d, 1H), 7.57 (t, 1H), 7.75 (t, 1H), 7.82 (d, 1H), 7.73 (t, 1H), 7.93 (s, 1H), 8.01 (d, 1H), 8.11 (d, 1H), 8.36 (2s, 2H). |
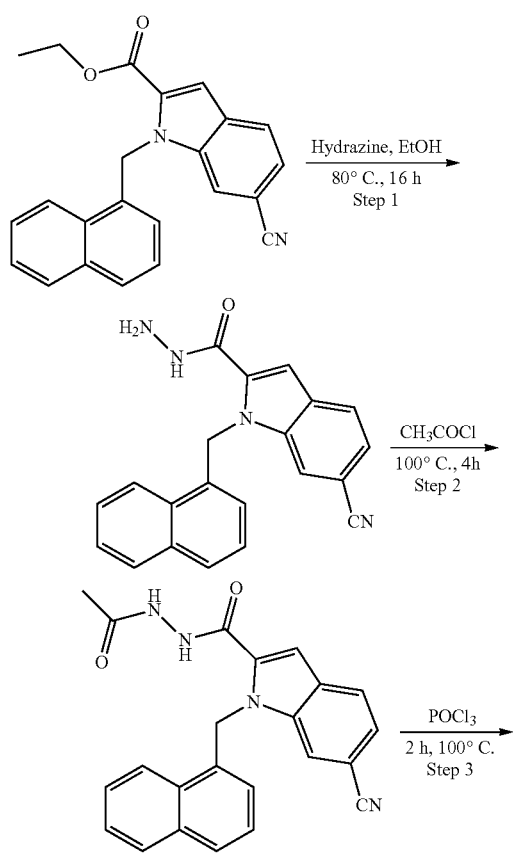
Synthetic Scheme -28

Example 126: Synthesis of Compound I-751

2-(5-methyl-1,3,4-oxadiazol-2-yl)-1-(naphthalen-1-ylmethyl)-1H-indole-6-carboximidamide

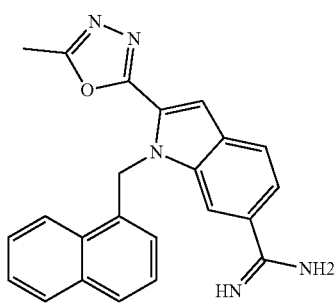 [SMILES: Cc1nnc(-c2cc3ccc(C(=N)N)cc3n2Cc2cccc3ccccc23)o1]

Step 1: 6-cyano-1-(naphthalen-1-ylmethyl)-1H-indole-2-carbohydrazide

To a solution of Ethyl 6-cyano-1-(naphthalen-1-ylmethyl)-1H-indole-2-carboxylate (0.5 g, 1.41 mmol) dissolved in ethanol (5 mL), hydrazine hydrate (5 mL) was added and reaction was heated at 90° C. and stirred at same temperature for 16 h. Reaction mass was evaporated under vacuum and residue was quenched with ice cool water. Resultant solid was filtered and dried under vacuum to afford the title compound (0.35 g). LCMS: 341.05 (M+1)+.

Step 2: N'-acetyl-6-cyano-1-(naphthalen-1-ylmethyl)-1H indole-2-carbohydrazide To 6-cyano-1-(naphthalen-1-ylmethyl)-1H-indole-2-carbohydrazide (0.35 g, 0.91 mmol) was added acetyl chloride (2 mL) and reaction was refluxed for 4 h. Acetyl chloride was removed under vacuum and basified with saturated sodium carbonate solution and extracted with ethyl acetate (2×50 mL). Combined organic layer was washed with brine solution, dried over anhydrous sodium sulphate, concentrated under vacuum to get crude product which was used for the next step without any further purification (0.35 g, crude).

Step 3: 2-(5-methyl-1,3,4-oxadiazol-2-yl)-1-(naphthalen-1-ylmethyl)-1H-indole-6-carbonitrile To N'-acetyl-6-cyano-1-(naphthalen-1-ylmethyl)-1H indole-2-carbohydrazide (0.35 g) was added phosphorous oxychloride (4 mL) and the reaction was refluxed for 1 h. Phosphorous oxychloride was removed under vacuum and neutralized with saturated sodium bicarbonate solution, extracted with ethyl acetate (2×50 mL). The organic layer was washed with brine solution, dried over anhydrous sodium sulphate, concentrated to get the crude product, which was purified through combiflash eluting with 20% ethyl acetate in hexane to afford the desired product (200 mg) LCMS: 365.05 (M+1)+.

Step 4: 2-(5-methyl-1,3,4-oxadiazol-2-yl)-1-(naphthalen-1-ylmethyl)-1H-indole-6-carboximidamide Following experimental protocol of Scheme 15 Method E, above compound have been synthesized. LCMS: 382.0 (M+1)+, 1H NMR (400 MHz, DMSO-$d_6$) δ 9.19 (s, 2H), 8.90-8.72 (bs, 2H), 8.33 (d, J=8.0 Hz, 1H), 8.14 (s, 1H), 8.05-7.99 (m, 2H), 7.79 (d, J=8.40 Hz, 1H), 7.72-7.11 (m, 1H), 7.65 (t, J=7.20 Hz, 2H), 7.59 (s, 1H), 7.20 (t, J=8.0 Hz, 1H), 6.56 (s, 2H), 6.04 (d, J=6.80 Hz, 1H), 2.49 (s, 3H).

Synthetic Scheme -29

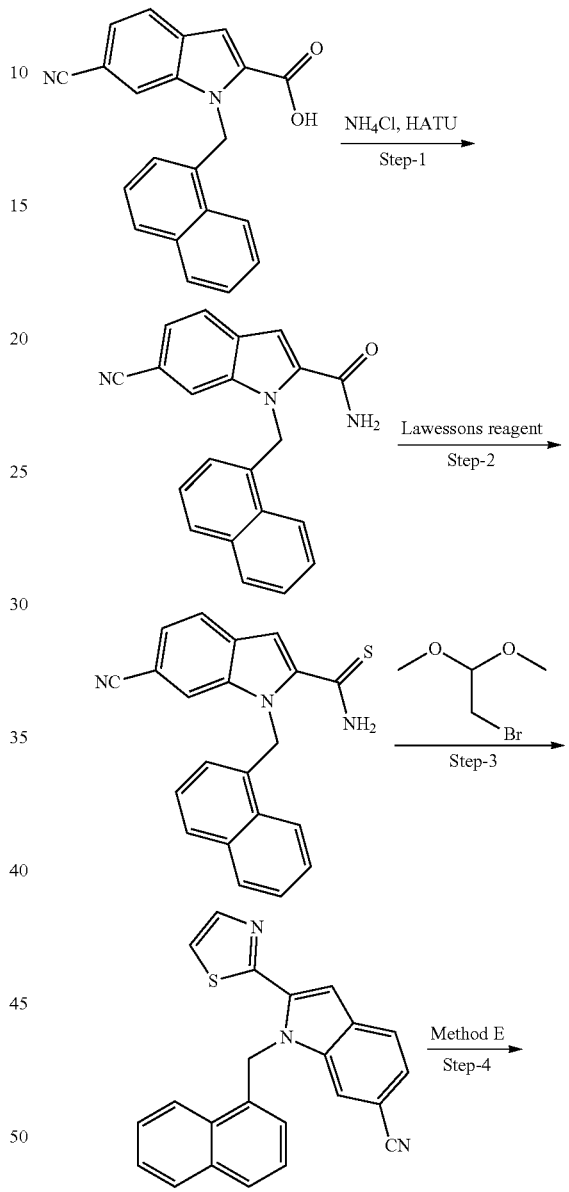

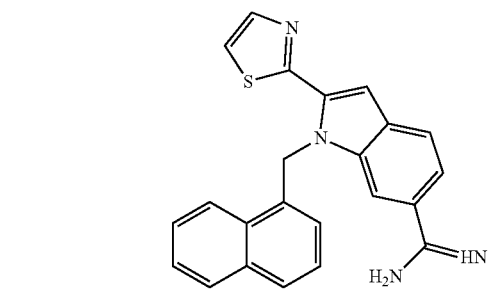

Example 127: Synthesis of Compound I-750

1-(naphthalen-1-ylmethyl)-2-(thiazol-2-yl)-1H-indole-6-carboximidamide

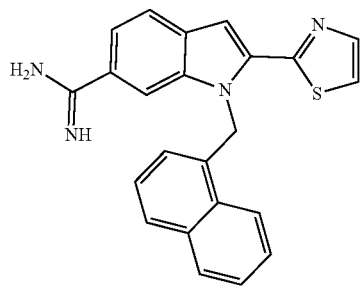 [SMILES: N=C(N)c1ccc2cc(-c3nccs3)n(Cc3cccc4ccccc34)c2c1]

Step 1: 6-cyano-1-(naphthalen-1-ylmethyl)-1H-indole-2-carboxamide

To a stirred solution of 6-cyano-1-(naphthalen-1-ylmethyl)-1H-indole-2-carboxylic acid (1.6 g, 4.87 mmol) in N,N-Dimethylformamide (15.0 mL) was added 1-[Bis(dimethylamino) methylene]-1H-1,2,3-triazolo[4,5-b]pyridinium 3-oxid hexafluorophosphate (2.78 g, 7.31 mmol) and N,N-Diisopropyl ethylamine (2.49 mL, 14.61 mmol). Then after 10 min, added Ammonium chloride (0.391 g, 7.31 mmol) and reaction mixture was stirred at ambient temperature for 16 h. Reaction mass diluted with cold water (100.0 mL) stirred for 15 min, off-white solid was thrown out, which was filtered and dried to get the crude compound. The crude washed with n-Pentane (40 mL×2), to get the title compound as an off-white solid, (1.47 g, 92.8%), LCMS: 326.05 (M+1)⁺.

Step 2: 6-cyano-1-(naphthalen-1-ylmethyl)-1H-indole-2-carbothioamide

Product of Step 1 (0.5 g, 1.53 mmol), Lawesson's reagent (0.62 g, 1.53 mmol) replaced in sealed tube, resulting mixture was stirred and heated at 110° C. for 4 h. After Reaction completion which was diluted with ethyl acetate (50.0 mL) and washed with saturated sodium bicarbonate solution. The organic layer was separated, dried over anhydrous sodium sulfate and concentrated to get the crude compound, which was purified by combi-flash eluting with 10% ethyl acetate in hexane as an eluent to get the title compound as an off-white solid (0.256 g). LCMS: 340.1 (M−1)−.

Step 3: 1-(naphthalen-1-ylmethyl)-2-(thiazol-2-yl)-1H-indole-6-carbonitrile

Product of Step 2 (0.2 g, 0.585 mmol) and 2-bromo-1,1-diethoxyethane (2.0 mL) together replaced in a sealed tube, which was heated at 100° C. for 4 h. Reaction mixture cooled, diluted with ethyl acetate (50.0 mL) and washed with water. The separated organic layer was dried over anhydrous sodium sulfate and concentrated to get the crude compound, which was purified by combi-flash eluting with 10% ethyl acetate in hexane as an eluent to get the title compound as an off-white solid (90.0 mg, 42.13%), LCMS: 366.1 (M+1)⁺.

Step 4: 1-(naphthalen-1-ylmethyl)-2-(thiazol-2-yl)-1H-indole-6-carboximidamide Following experimental protocol of Scheme 15 Method E, 1-(naphthalen-1-ylmethyl)-2-(thiazol-2-yl)-1H-indole-6-carboximidamide have been synthesized and purified by Preparative HPLC. The mobile phases (0.1% Formic acid in water to 100% acetonitrile, compound was lyophilized for 3 days to afford the title compound (5 mg). LCMS: 383.2 (M+1)⁺, ¹HNMR (DMSOd6, 400 MHz): δ 6.13-6.11 (d, 1H), 6.61 (S, 2H), 7.47-7.18 (t, 1H), 7.59 (S, 1H), 7.67-7.62 (m, 2H), 7.71-7.68 (m, 1H), 7.79-7.75 (m, 3H), 7.99-7.97 (m, 2H), 8.07 (S, 1H), 8.31-8.29 (d, 1H), 8.42 (s, 1H), 8.6-9.4 (bs, 1H). HPLC: 99.97% (Retention Time=5.39 min).

Synthetic Scheme -30

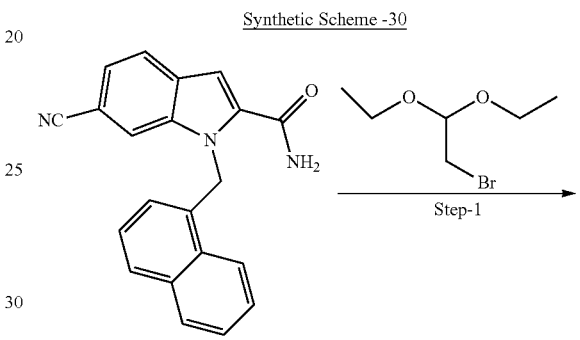

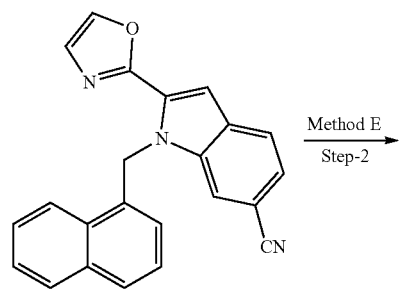

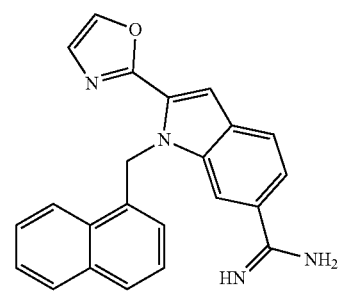

949

Example 128: Synthesis of Compound I-748

1-(naphthalen-1-ylmethyl)-2-(oxazol-2-yl)-1H-indole-6-carboximidamide

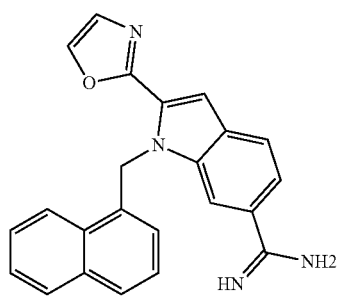 [SMILES: N=C(N)c1ccc2cc(-c3ncco3)n(Cc3cccc4ccccc34)c2c1]

Step 1: 1-(naphthalen-1-ylmethyl)-2-(oxazol-2-yl)-1H-indole-6-carbonitrile 6-cyano-1-(naphthalen-1-ylmethyl)-1H-indole-2-carboxamide (0.4 g, 1.23 mmol) and 2-bromo-1,1-diethoxyethane (4.0 mL) together replaced in a sealed tube and which was heated to 115° C. for 5 h. Reaction mixture cooled, diluted with ethyl acetate (60.0 mL) and washed with water (50.0 mL×3). The separated organic layer was dried over anhydrous sodium sulfate and concentrated to get the crude compound, which was purified by combi-flash eluting with 15% ethyl acetate in hexane as an eluent to get the title compound as an off-white solid (0.19 g, 43.90%), LCMS: 350.1 (M+1)$^+$ Step 2: 1-(naphthalen-1-ylmethyl)-2-(oxazol-2-yl)-1H-indole-6-carboximidamide Following experimental protocol of Scheme 15 Method E, 1-(naphthalen-1-ylmethyl)-2-(oxazol-2-yl)-1H-indole-6-carboximidamide have been synthesized. LCMS: 367.1 (M+1)$^+$, $^1$HNMR (DMSOd6, 400 MHz): δ 6.06-6.04 (d, 1H), 6.61 (S, 2H), 7.22-7.18 (t, 1H), 7.31 (S, 1H), 7.54 (S, 1H), 7.63-7.61 (m, 2H), 7.79-7.70 (m, 2H), 8.01-7.99 (d, 1H), 8.08 (S, 1H), 8.24 (S, 1H), 8.34-8.32 (d, 1H), 8.79 (bS, 2H), 9.16 (bS, 2H), (HPLC: 99.74%, Retention time: 5.33)

Synthetic scheme -31

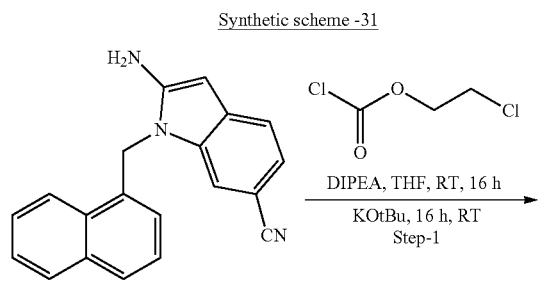

950

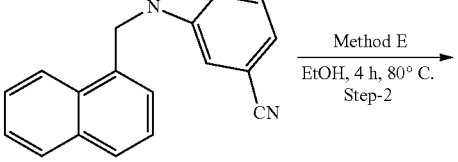

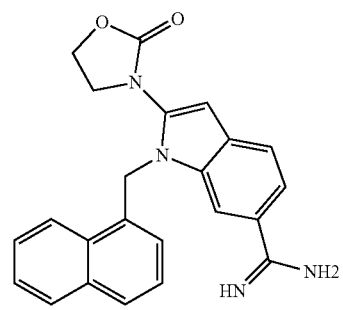

Example 129: Synthesis of Compound I-726

1-(naphthalen-1-ylmethyl)-2-(2-oxooxazolidin-3-yl)-1H-indole-6-carboximidamide

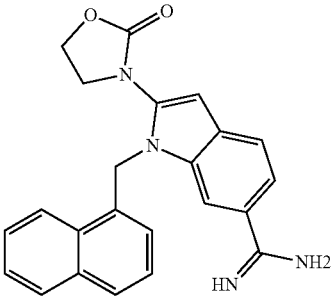 [SMILES: N=C(N)c1ccc2cc(N3CCOC3=O)n(Cc3cccc4ccccc34)c2c1]

Step 1: 1-(naphthalen-1-ylmethyl)-2-(2-oxooxazolidin-3-yl)-1H-indole-6-carbonitrile To as stirred solution of 2-amino-1-(naphthalen-1-ylmethyl)-1H-indole-6-carbonitrile (0.1 g, 0.33 mmol) in THF (5 mL), were added diisopropylethylamine (0.11 mL, 0.67 mmol), 2-chloroethyl chloroformate (0.038 mL, 0.37 mmol) at 0° C. The reaction was stirred for 16 h at rt. To this potassium t-butoxide (0.18 g, 1.68 mmol) was added then the reaction was stirred for 16 h at rt. Water was added to the reaction mixture, extracted with ethyl acetate (2×25 mL). The separated organic layer was washed with brine solution dried over anhydrous sodium sulphate, concentrated under vacuum to give the crude product which was purified through combiflash chromatography eluting with 30% EtOAc in Hexane to afford the desired product (40 mg) LCMS: 368.20 (M+1)$^+$.

Step 2: 1-(naphthalen-1-ylmethyl)-2-(2-oxooxazolidin-3-yl)-1H-indole-6-carboximidamide Following experimental protocol of Scheme 15 Method E, 1-(naphthalen-1-ylmethyl)-2-(2-oxooxazolidin-3-yl)-1H- indole-6-carboximidamide have been synthesized. $^1$H NMR (400 MHz, DMSO-$d_6$) δ 9.12 (s, 2H), 8.70 (bs, 2H), 8.13 (d, J=8.80 Hz, 1H), 8.04-7.99 (m, 2H), 7.87 (d, J=8.40 Hz, 2H), 7.64-7.58 (m, 3H), 7.34-7.31 (m, 1H), 6.82 (s, 1H), 6.42 (d, J=7.20 Hz, 1H), 5.98 (s, 2H), 4.23-4.19 (m, 2H), 3.69-3.65 (m, 2H) LCMS: 392.95 (M+1)$^+$.

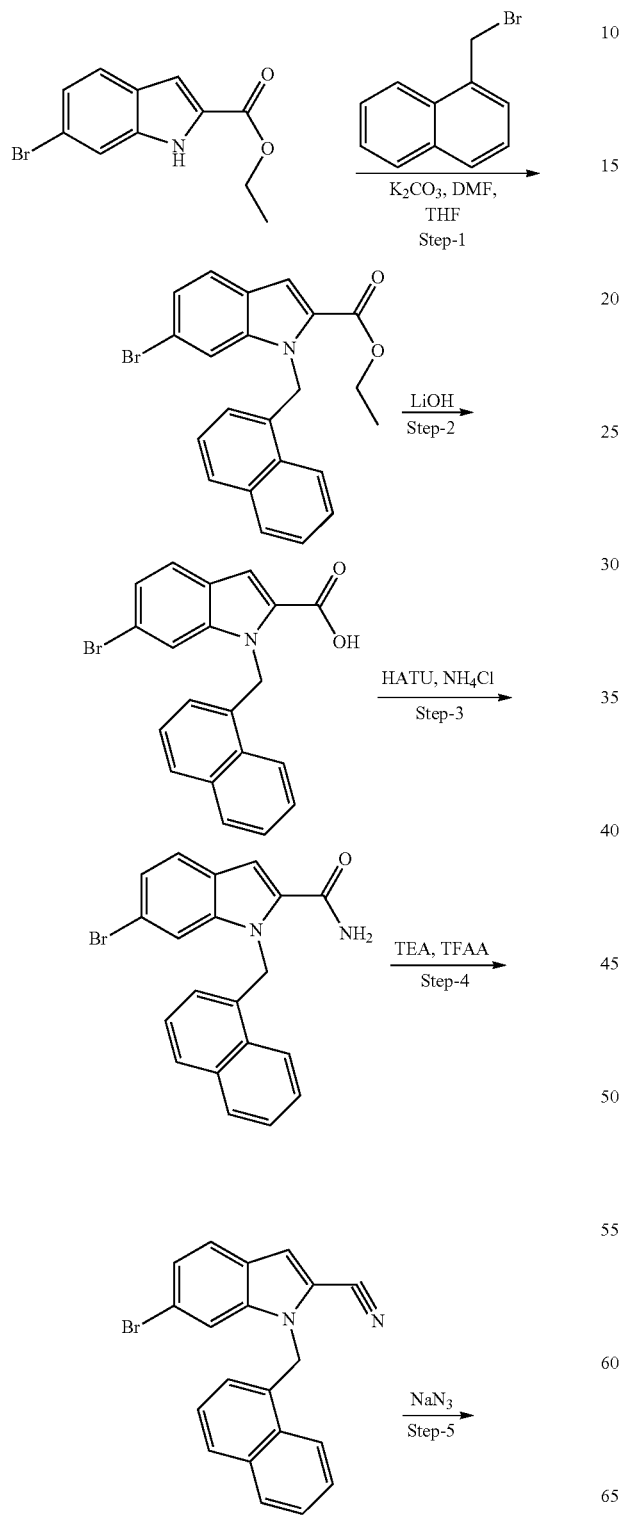

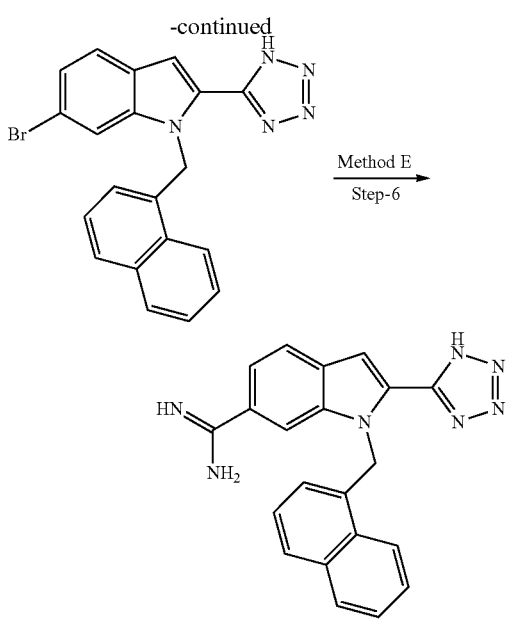

Example 130: Synthesis of Compound I-803

1-(naphthalen-1-ylmethyl)-2-(1H-tetrazol-5-yl)-1H-indole-6-carboximidamide

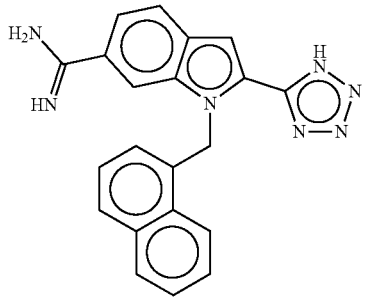

Step 1: Ethyl 6-bromo-1-(naphthalen-1-ylmethyl)-1H-indole-2-carboxylate

To a solution of ethyl 6-bromo-1H-indole-2-carboxylate (0.5 g, 0.0096 mol) in DMF (10 ml) was added potassium carbonate (0.8 g, 0.00577 mol) and solution of 1-(bromomethyl) naphthalene (0.65 g, 0.0029 mol) dissolved in THF (3 mL). Then Reaction mass was stirred at room temperature for 3 h. After reaction completion, THF was distilled off, added ice-cold water and precipitated product was filtered and dried under vacuum to give title compound (0.7 g, 87.5%) which was proceeded to next step without purification. LCMS: 409.1 (M+1)$^+$.

Step 2: 6-bromo-1-(naphthalen-1-ylmethyl)-1H-indole-2-carboxylic Acid

To a stirred solution of Product of Step 1 (600 mg, 0.00147 mol) in tetrahydrofuran & ethanol (5 mL: 10 mL) mixture, was added aqueous lithium hydroxide monohydrate (300 mg, 0.00737 mol) at room temperature. Resulting mixture was stirred at room temperature for 8 h. After reaction completion, THF and ethanol was distilled off, acidified with dilute HCl to pH 4. Precipitated product was filtered off, dried under vacuum to give titled compound (600 mg, crude) which was proceeded to next step, LCMS: 379.9 (M−1).

Step 3: 6-bromo-1-(naphthalen-1-ylmethyl)-1H-indole-2-carboxamide

To a stirred solution of product of Step 2 (100 mg, 0.00026 mol) in DMF added HATU (110 mg, 0.000286 mol) and N, N-diisopropylethylamine (84 mg, 0.00065 mol) at 0° C. After stirred at room temperature for 10 min., added NH₄Cl (21 mg, 0.00039 mol) and stirred for 16 h at room temperature. After reaction completion, added ice cold water, precipitated solid was filtered off and dried to give title compound (80 mg, 81.6%) LCMS: 378.95 (M−1)-.

Step 4: 6-bromo-1-(naphthalen-1-ylmethyl)-1H-indole-2-carbonitrile

To a solution of product of Step 3 (1 g, 0.00263 mol) in DCM (10 mL) was added TEA (1.06 g, 0.0105 mol) and resulting was stirred at RT for 5 min. Then TFAA (1.1 g, 0.00526 mol) was added dropwise at 0° C. and stirred at RT for 2 hr. After completion of reaction by TLC, quenched with aq.NaHCO₃ solution, and extracted with DCM. The separated organic layer was dried and concentrated, purified by combi-flash to give title compound ((0.3 g, 31.5%); (1H-NMR-DMSO-d6); 8.2 (d, 1H), 8.05 (d, 2H), 7.9 (d, 1H), 7.75 (d, 1H), 7.65 (m, 3H), 7.35 (m, 2H), 6.25 (d, 1H), 6.2 (s, 2H).

Step 5: 6-bromo-1-(naphthalen-1-ylmethyl)-2-(1H-tetrazol-5-yl)-1H-indole

To a solution of product of Step 4 (1 g, 0.00276 mol) in DMF (10 mL), were added NaN₃ (3.6 g, 0.0055 mol) & NH₄Cl (1.44 g, 0.0269 mol) at RT and resulting suspension was heated to 120° C. for 4 h. Then cooled to RT and poured into ice water to precipitate the product and solids were collected by filtration to give title compound (1 g, crude) LCMS: 404.1 (M+1)⁺.

Step 6: 1-(naphthalen-1-ylmethyl)-2-(1H-tetrazol-5-yl)-1H-indole-6-carboximidamide Following experimental protocol of general Scheme 15 Method E, 1-(naphthalen-1-ylmethyl)-2-(1H-tetrazol-5-yl)-1H-indole-6-carboximidamide have been synthesized. LCMS: 368.15 (M+1)⁺, 1HNMR (CD3OD, 300 MHz): δ 6.21 (d, 1H), 6.632 (s, 2H), 7.124 (t, 1H), 7.469 (s, 1H), 7.56-7.71 (m, 4H), 7.88-7.98 (m, 3H), 7.135 (d, 1H)

Synthetic Scheme -33

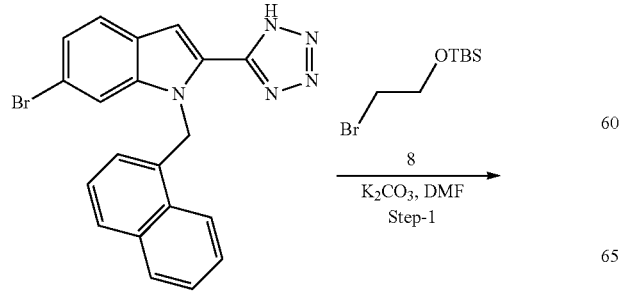

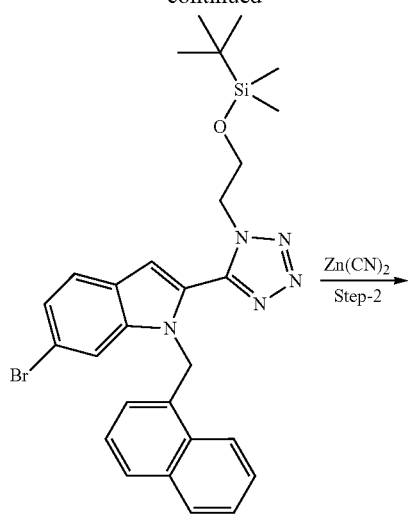

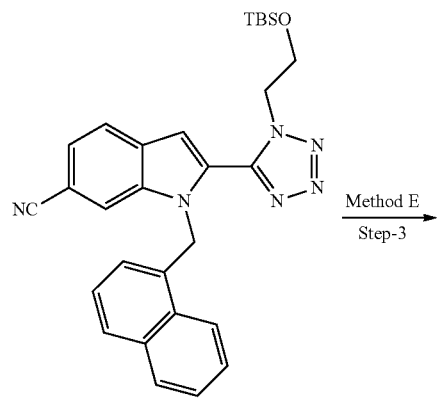

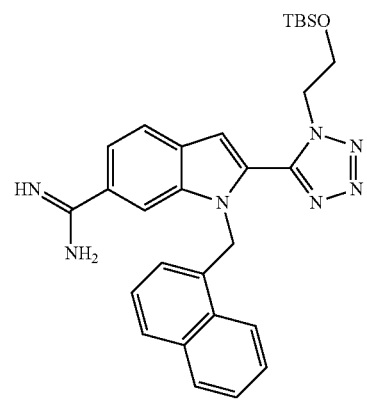

Example 131: Synthesis of Compound I-710

2-(1-(2-((tert-butyldimethylsilyl)oxy)ethyl)-1H-tetrazol-5-yl)-1-(naphthalen-1-ylmethyl)-1H-indole-6-carboximidamide

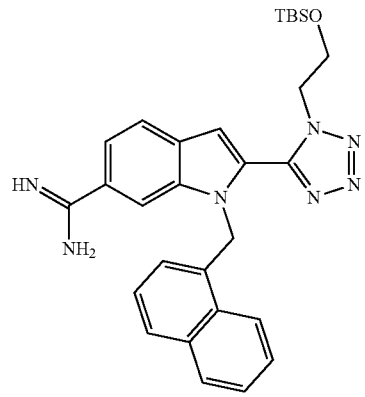 [SMILES: CC(C)(C)[Si](C)(C)OCCn1nnnc1-c1cc2ccc(C(=N)N)cc2n1Cc1cccc2ccccc12]

Step 1: 6-bromo-2-(1-(2-((tert-butyldimethylsilyl)oxy)ethyl)-1H-tetrazol-5-yl)-1-(naphthalen-1-ylmethyl)-1H-indole To a solution of 6-bromo-1-(naphthalen-1-ylmethyl)-2-(1H-tetrazol-5-yl)-1H-indole (0.7 g, 0.00172 mol), (2-bromoethoxy)(tert-butyl)dimethylsilane (0.5 g, 0.00207 mol) in DMF (5 ml), was added $K_2CO_3$ (0.476 g, 0.00344) at RT and resulting suspension was heated to 70° C. for 3 h. After completion of reaction, cooled to RT and ice water was added then extracted with ethylacetate. The organic layer dried over $Na_2SO_4$ and concentrated to give the crude product. Crude purified by combi-flash to give title compound (0.3 g, 31%); LCMS: 564.2 (M+2)$^+$.

Step 2: 2-(1-(2-((tert-butyldimethylsilyl)oxy)ethyl)-1H-tetrazol-5-yl)-1-(naphthalen-1-ylmethyl)-1H-indole-6-carbonitrile To a solution of 6-bromo-2-(1-(2-((tert-butyldimethylsilyl)oxy)ethyl)-1H-tetrazol-5-yl)-1-(naphthalen-1-ylmethyl)-1H-indole (0.3 g, 0.000534 mol) in DMF, was added $Zn(CN)_2$ (0.156 g, 0.00133 mol) and resulting suspension was de-gassed with $N_2$ for 5 min, then $PdCl_2(dppf) \cdot DCM$ (23 mg, 0.05 mol) was added under $N_2$ gas atmosphere. Reaction mixture heated to 150° C. for overnight. After completion of reaction, cooled to RT and ice water was added and resulting solids were collected by filtration to give title compound (0.22 g, 81.4%) LCMS: 509.2 (M+1)$^+$.

Step 3: 2-(1-(2-((tert-butyldimethylsilyl) oxy)ethyl)-1H-tetrazol-5-yl)-1-(naphthalen-1-ylmethyl)-1H-indole-6-carboximidamide Following experimental protocol of Scheme 15 Method E, 2-(1-(2-((tert-butyldimethylsilyl) oxy) ethyl)-1H-tetrazol-5-yl)-1-(naphthalen-1-ylmethyl)-1H-indole-6-carboximidamide have been synthesized. LCMS: 526.1 (M+1)$^+$, $^1$HNMR (DMSO-d$_6$, 400 MHz): δ −0.32 (s, 6H), 0.531 (s, 9H), 3.903 (t, 1H), 4.708 (t, 1H), 5.99-6.01 (d, 1H), 6.578 (s, 2H), 7.159 (t, 1H), 7.517 (s, 1H), 7.62-7.64 (m, 2H), 7.69-7.76 (m, 2H), 7.95-7.98 (m, 2H), 8.13 (s, 1H), 8.31-8.33 (d, 1H), 8.493 (s, 2H).

2-(1-(2-hydroxyethyl)-1H-tetrazol-5-yl)-1-(naphthalen-1-ylmethyl)-1H-indole-6-carboximidamide

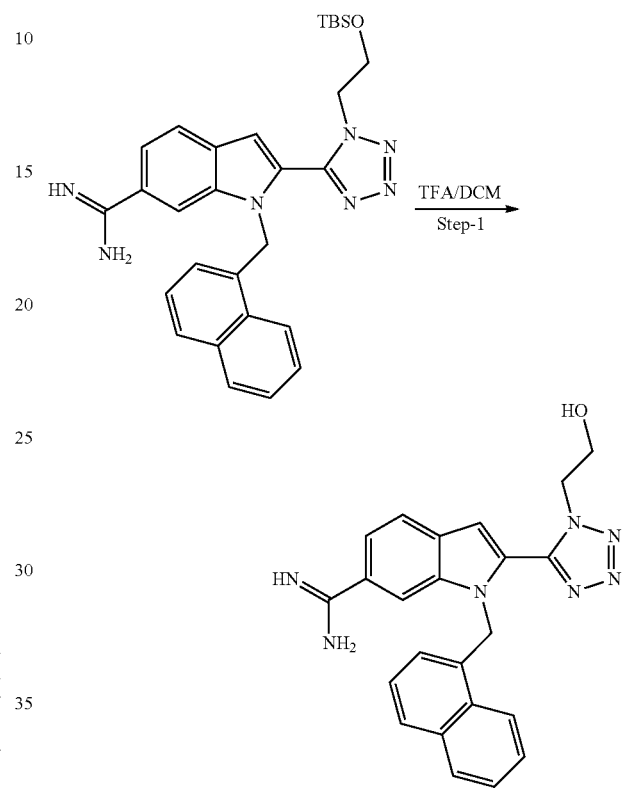

To a solution of 2-(1-(2-((tert-butyldimethylsilyl)oxy)ethyl)-1H-tetrazol-5-yl)-1-(naphthalen-1-ylmethyl)-1H-indole-6-carboximidamide (60 mg, 0.000114 mol) in DCM (5 ml), was added TFA (0.5 g) dropwise at 0° C. and stirred at RT for overnight. After completion of reaction, evaporated the solvent and washed with ether, resulting solid was dried on high vacuum to give title compound (25 mg, 54%); LCMS: 412.2 (M+H)$^+$; $^1$H NMR (400 MHz, DMSO-d$_6$): δ 9.3 (bs, 3H), 8.35 (d, 1H), 8.1 (s, 1H), 8.0 (d, 2H), 7.8 (d, 1H), 7.7 (d, 1H), 7.65 (d, 1H), 7.55 (s, 1H), 7.2 (t, 1H), 6.6 (s, 2H), 6.1 (d, 1H), 5.0 (bs, 1H), 4.7 (t, 2H), 3.8 (bs, 2H); HPLC; 99.9%.

Synthetic Scheme - 34

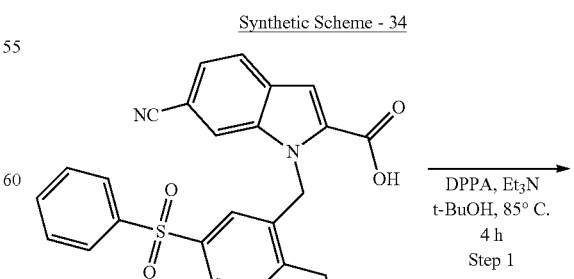

Example 132: Synthesis of Compound I-603 tert-butyl (6-carbamimidoyl-1-((3-(phenylsulfonyl) naphthalen-1-yl) methyl)-1H-indol-2-yl)carbamate

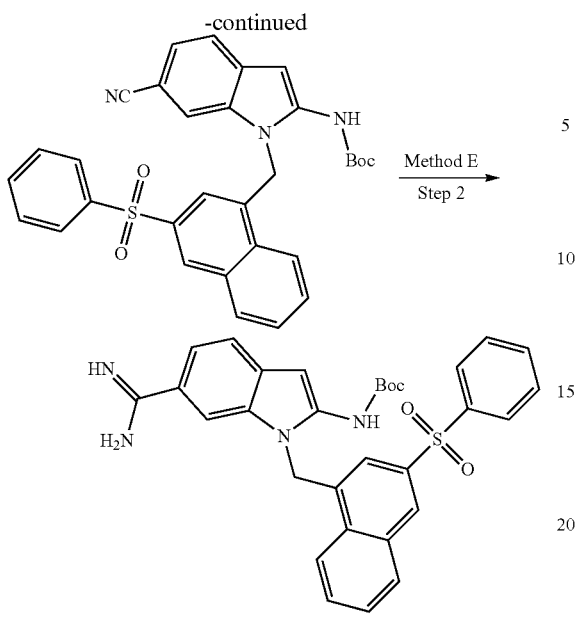

Step 1: tert-butyl (6-cyano-1-((3-(phenylsulfonyl) naphthalen-1-yl)methyl)-1H-indol-2-yl)carbamate Following experimental protocol of Step 1 of general Scheme 20, tert-butyl (6-cyano-1-((3-(phenylsulfonyl)naphthalen-1-yl)methyl)-1H-indol-2-yl)carbamate have been synthesized. LCMS: 536.2 (M−1)⁻.

Step 2: tert-butyl (6-carbamimidoyl-1-((3-(phenylsulfonyl) naphthalen-1-yl) methyl)-1H-indol-2-yl)carbamate Following experimental protocol of general Scheme 15 Method E, tert-butyl (6-carbamimidoyl-1-((3-(phenylsulfonyl) naphthalen-1-yl) methyl)-1H-indol-2-yl)carbamate have been synthesized. LCMS: 555.4 (M+1)⁺, ¹HNMR (CD₃OD, 400 MHz): δ 1.41 (s, 9H), 6.01 (s, 2H), 7.37 (t, 2H), 7.56-7.61 (m, 4H), 7.71-7.90 (m, 4H), 8.11-8.20 (d, 2H), 8.20-8.29 (d, 1H), 8.51 (s, 2H).

Synthetic Scheme-35

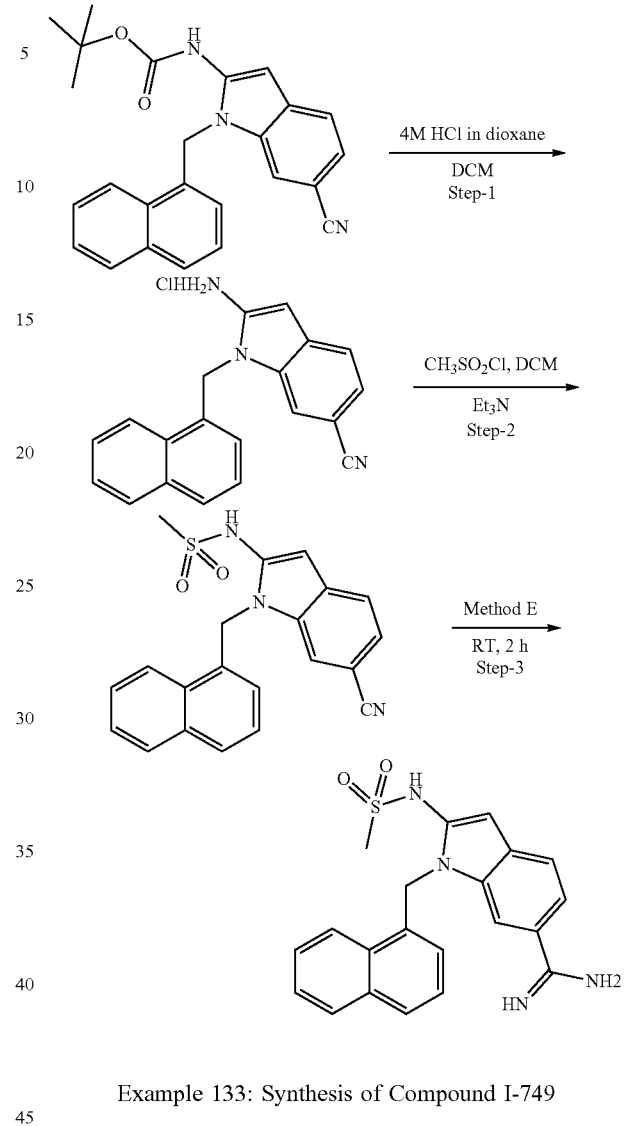

Example 133: Synthesis of Compound I-749

2-(5-methyl-1,3,4-oxadiazol-2-yl)-1-(naphthalen-1-ylmethyl)-1H-indole-6-carboximidamide

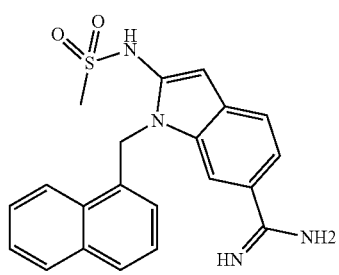 [SMILES: CS(=O)(=O)Nc1cc2ccc(C(=N)N)cc2n1Cc1cccc2ccccc12]

Step 1: 2-amino-1-(naphthalen-1-ylmethyl)-1H-indole-6-carbonitrile hydrochloride tert-butyl (6-cyano-1-(naphthalen-1-ylmethyl)-1H-indol-2-yl)carbamate (0.15 g) in dichloromethane (5 mL) was added 4M Dioxane HCl (5 mL) and the reaction was stirred for 16 h at rt. Excess solvent was removed under vacuum afforded the crude product which was used for the next step without any further purification (150 mg, crude), LCMS: 298.2 (M-Cl)⁻

Step 2: N-(6-cyano-1-(naphthalen-1-ylmethyl)-1H-indol-2-yl)methanesulfonamide 2-amino-1-(naphthalen-1-ylmethyl)-1H-indole-6-carbonitrile hydrochloride (0.13 g, 0.38 mmol) in dichloromethane (3 mL), were added triethyl amine (0.16 mL, 1.55 mmol) and methane sulfonyl chloride (0.036 mL, 0.46 mmol) at 0° C. and stirred for 1 h at the same temperature. Water was added to the reaction mixture, extracted with dichloromethane (2×50 mL). Combined organic layer was washed with brine solution and dried over anhydrous sodium sulphate, concentrated to get the crude product which was purified through combiflash chromatography eluting with 20% EtOAc in hexane to afforded the desired product (95 mg) LCMS: 376.1 (M+1)⁺.

Step 3: 2-(methylsulfonamido)-1-(naphthalen-1-ylmethyl)-1H-indole-6-carboximidamide Following experimental protocol of Scheme 15 Method E, 2-(methylsulfonamido)-1-(naphthalen-1-ylmethyl)-1H-indole-6-carboximidamide have been synthesized. LCMS: 392.95 (M+1)⁺, ¹H NMR (400 MHz, DMSO-d₆) δ 8.97 (bs, 1H), 8.56 (bs, 2H), 8.21 (d, J=6.40 Hz, 1H), 8.02 (d, J=8.0 Hz, 1H), 7.86 (d, J=8.40 Hz, 1H), 7.72-7.63 (m, 5H), 7.35 (t, J=7.60 Hz, 1H), 7.18 (bs, 2H), 6.33 (d, J=6.80 Hz, 1H), 5.92 (s, 2H), 3.31 (s, 3H).

Example 134: Synthesis of Compound I-620

N-((1r,4r)-4-aminocyclohexyl)-6-guanidino-1-(naphthalen-1-ylmethyl)-1H-indole-2-carboxamide

Step 1: N-((1r,4r)-4-aminocyclohexyl)-6-guanidino-1-(naphthalen-1-ylmethyl)-1H-indole-2-carboxamide tert-butyl ((1r,4r)-4-(6-((4,6-dimethoxypyrimidin-2-yl)amino)-1-(naphthalen-1-ylmethyl)-1H-indole-2-carboxamido)cyclohexyl)carbamate (0.3 g, 0.461 mmol) was taken in sealed tube, added Acetic acid (3 mL) and 6N aqueous HCl (5 ml), then stirred at 100° C. for 2 h. All the solvents were evaporated to dryness to get the crude product, which was purified by Prep HPLC (0.01 g). LCMS: 455.3 (M+1)⁺. ¹HNMR (CD₃OD, 400 MHz): δ 1.1-1.20 (m, 2H), 1.45-1.48 (m, 2H), 1.97-2.00 (d, 4H), 2.95-3.05 (m, 1H), 3.7-3.82 (m, 1H), 4.94 (s, 2H), 6.85-6.88 (d, 1H), 7.09-7.11 (d, 1H), 7.27-7.29 (t, 2H), 7.36 (s, 1H), 7.48-7.52 (m, 3H), 7.19-7.74 (d, 1H), 7.86-7.88 (d, 1H), 8.28-8.30 (d, 1H).

Synthetic Scheme-36

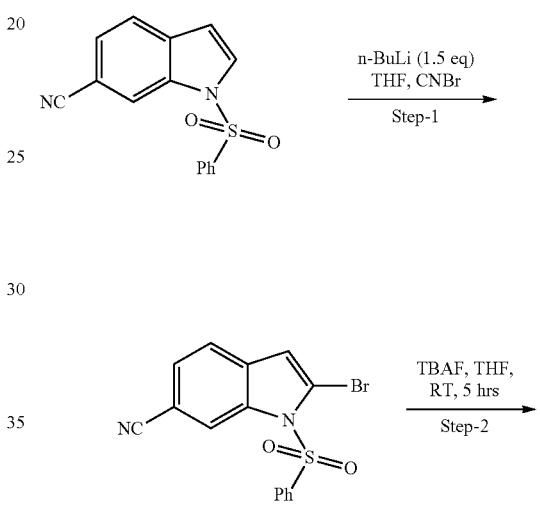

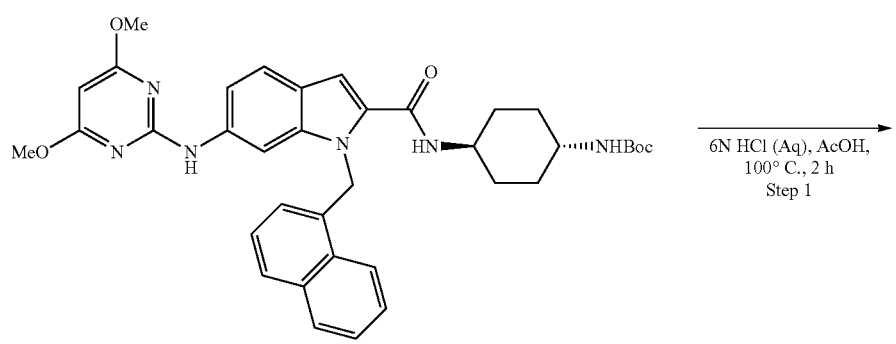

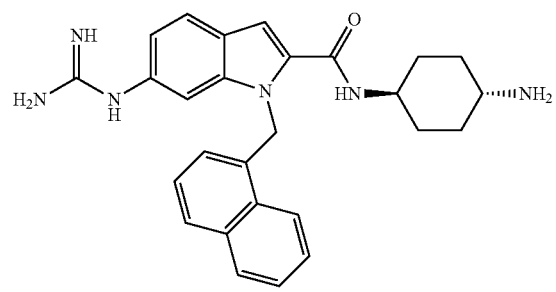

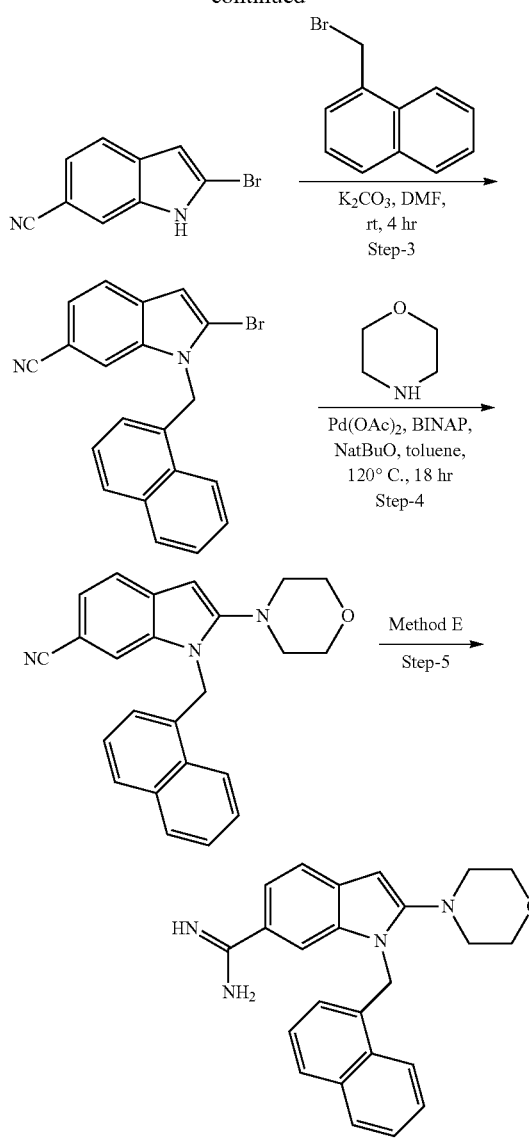

Example 135: Synthesis of Compound I-644

2-morpholino-1-(naphthalen-1-ylmethyl)-1H-indole-6-carboximidamide

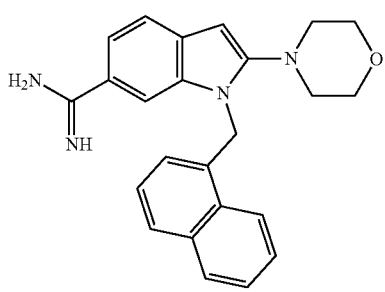 [SMILES: N=C(N)c1ccc2cc(N3CCOCC3)n(Cc3cccc4ccccc34)c2c1]

Step 1: 2-bromo-1-(phenylsulfonyl)-1H-indole-6-carbonitrile 1-(phenylsulfonyl)-1H-indole-6-carbonitrile (600 mg, 2.21 mmol) was dissolved in THF (10 mL) and cooled to −78° C. temperature. Then sec-BuLi was dropwise added into the reaction mixture and gradually raised the temperature to −20° C. and stirred for 1.5 h, then cyanogen bromide in THF (5 ml) was dropwise added into the reaction mixture at −78° C. Reaction mixture gradually brought to room temperature and stirred for 16 hrs. After reaction completion, reaction mixture was quenched with added ice-cold water and extracted with ethyl acetate followed by washed with brine and water and dried over sodium sulphate. Solvent was evaporated under vacuum to give crude compound. Crude product was purified by combi-flash to get compound (140 mg). LCMS: 361 (M+1)$^+$.

Step 2: 2-bromo-1H-indole-6-carbonitrile

Product of Step 1 (140 mg, 0.387 mmol) was dissolved in THF (2 mL) and added TBAF (1.5 mL) at 0° C. then stirred at room temperature for 4 h. After reaction completion, reaction mixture was diluted with ethyl acetate then washed with brine and water. Organic layer dried over sodium sulphate, evaporated under vacuum to give crude compound. (90 mg, crude) which was proceeded to next step. LCMS: 221.1 (M+1)$^+$.

Step 3: 2-bromo-1-(naphthalen-1-ylmethyl)-1H-indole-6-carbonitrile

The product of Step 2 (80 mg, 0.36 mmol) in DMF, was treated with 1-(bromomethyl) naphthalene and potassium carbonate to afford 85 mg of the title compound. LCMS: 361.1 (M+1)$^+$.

Step 4: 2-morpholino-1-(naphthalen-1-ylmethyl)-1H-indole-6-carbonitrile

To a solution of Step 3 product (80 mg, 0.221 mmol), morpholine (38 mg, 0.442 mmol) and KOtBu (74 g, 0.66 mmol), were taken in toluene (10 mL) and degassed for 10 mins. Now palladium acetate (1.5 mg, 0.006 mmol) and BINAP (8.5 mg, 0.13 mmol) were added and heated at 120° C. for 16 h. After reaction completion, reaction mass was diluted with ethyl acetate and washed with brine, dried over sodium sulphate. Solvent was evaporated under vacuum to give crude compound. Crude product was purified by combi-flash to get compound (25 mg). LCMS: 368.1 (M+1)$^+$.

Step 5: 2-morpholino-1-(naphthalen-1-ylmethyl)-1H-indole-6-carboximidamide

Following experimental protocol of general Scheme 15 Method E, above compound have been synthesized. LCMS: 385.1 (M+1)$^+$, $^1$H NMR (400 MHz, DMSO-d$_6$): δ 2.98 (m, 4H), 3.62 (m, 4H), 5.85 (s, 2H), 6.27 (s, 1H), 6.57 (d, 1H), 7.32-7.37 (m, 2H), 7.52 (m, 1H), 7.62-7.70 (m, 4H), 7.84 (d, 1H), 8.01 (d, 1H), 8.30 (d, 1H), 8.47 (s, 1H), 8.83 (bs, 1H); HPLC: 99.3% (Retention Time=5.27 min).

Synthetic Scheme-37
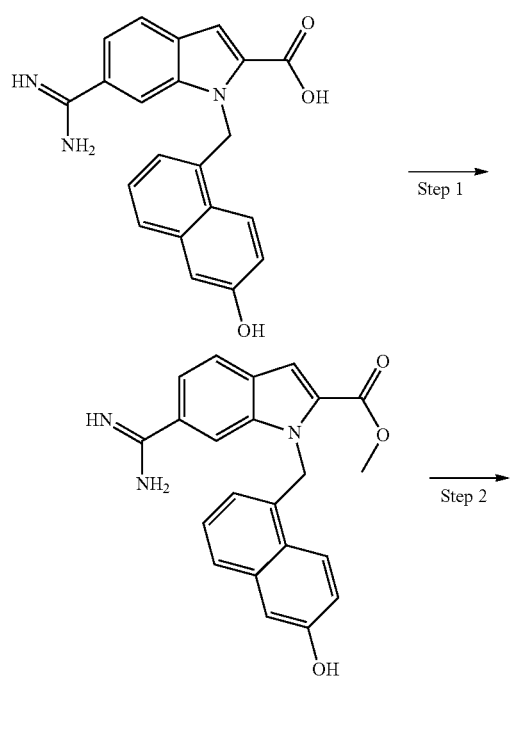
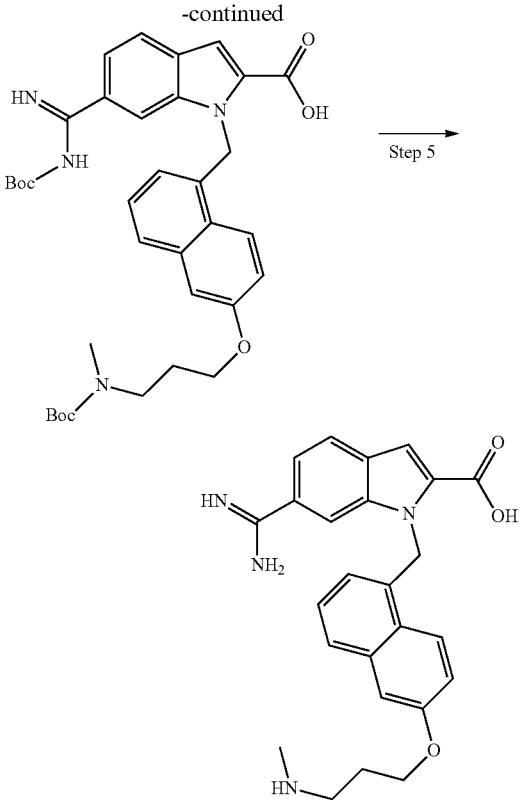
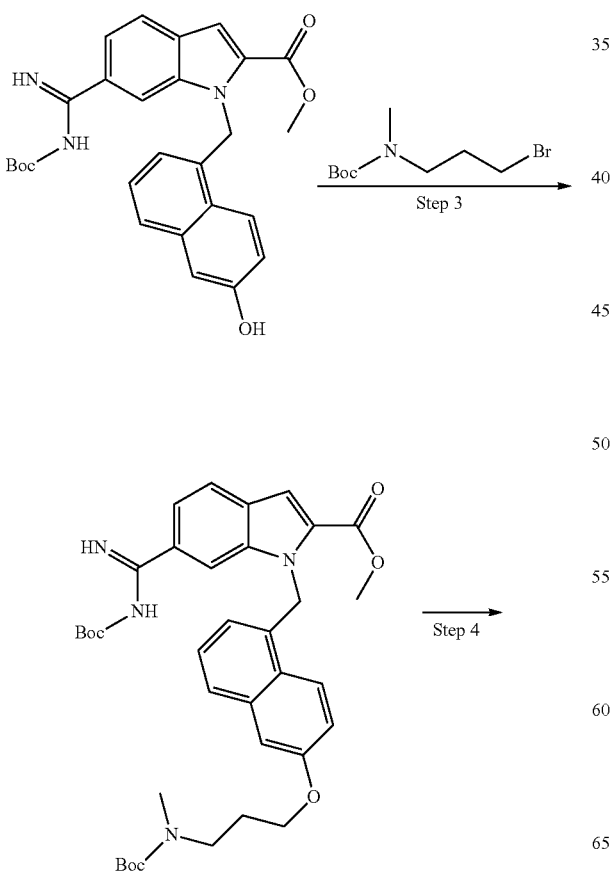
Example 136: Synthesis of Compound I-801
6-carbamimidoyl-1-((6-(3-(methylamino)propoxy)naphthalen-1-yl)methyl)-1H-indole-2-carboxylic Acid
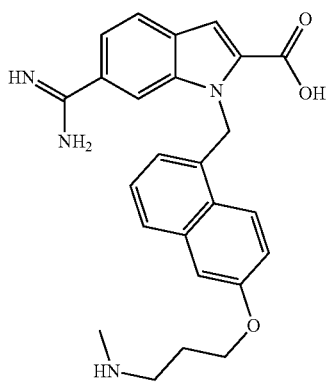 [SMILES: CNCCCOc1ccc2c(Cn3c(C(=O)O)cc4ccc(C(=N)N)cc43)cccc2c1]
Step 1: methyl 6-carbamimidoyl-1-((6-hydroxynaphthalen-1-yl)methyl)-1H-indole-2-carboxylate
Following experimental protocol of Step 1 in Scheme 15D-2, above compound have been prepared. LCMS: 374.0 (M+1)$^+$

Step 2: methyl 6-(N-(tert-butoxycarbonyl)carbamimidoyl)-1-((6-hydroxynaphthalen-1-yl)methyl)-1H-indole-2-carboxylate Following experimental protocol of Step 2 in Scheme 15D, above compound have been prepared. LCMS: 474.2 (M+1)⁺

Step 3: 6-carbamimidoyl-1-((6-hydroxynaphthalen-1-yl)methyl)-1H-indole-2-carboxylic Acid To a stirred solution of methyl 6-(N-(tert-butoxycarbonyl)carbamimidoyl)-1-((6-hydroxynaphthalen-1-yl)methyl)-1H-indole-2-carboxylate (120 mg, 0.25 mmol) and tert-butyl (3-bromopropyl)(methyl)carbamate (95.8 mg, 0.38 mmol) in THF:DMF (2 mL:2 mL) was added $K_2CO_3$ (105 mg, 0.76 mmol) at room temperature and stirred the reaction mixture at 80° C. for 5 hours. Once the reaction was completed, reaction mixture poured into ice cold water, solid obtained was filtered and dried to afford the title compound (120 mg). LCMS: 645.1 (M+1)⁺.

Step 4: 1-((6-(3-((tert-butoxycarbonyl)(methyl)amino)propoxy)naphthalen-1-yl)methyl)-6-(N-(tert-butoxycarbonyl)carbamimidoyl)-1H-indole-2-carboxylic Acid Following experimental protocol of Step 2 in Scheme 15, above compound have been prepared. LCMS: 631.1 (M+1)⁺.

Step 5: 6-carbamimidoyl-1-((6-(3-(methylamino)propoxy)naphthalen-1-yl)methyl)-1H-indole-2-carboxylic Acid Following experimental protocol of method F, above compound have been prepared. LCMS: 431.1 (M+1)⁺, 1HNMR (CD3OD, 400 MHz): δ 2.28-2.24 (m, 2H), 2.76 (s, 3H), 3.27-3.26 (t, 2H), 4.27-4.24 (t, 2H), 6.04-6.02 (d, 1H), 6.47 (s, 2H), 7.33-7.14 (m, 3H), 7.65-7.52 (m, 3H), 7.89 (s, 1H), 7.98-7.96 (d, 1H), 8.18-8.16 (m, 1H).

TABLE 61

Compounds synthesized using synthetic scheme-37

| ID | Structure | LCMS [M + H]⁺ | ¹H-NMR Data |
|---|---|---|---|
| I-808 | 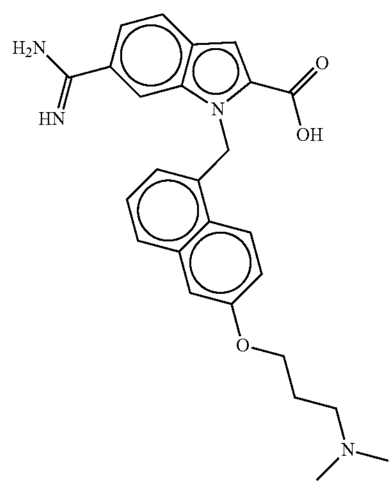 | 445.2 | ¹HNMR (CD₃OD, 400 MHz): δ 2.23-2.28 (m, 2H), 3.10 (s, 6H), 3.43-3.39 (t, 2H), 4.26-4.24 (t, 2H), 6.03-6.01 (m, 1H), 6.46 (s, 2H), 7.16-7.13 (m, 1H), 7.33-7.31 (m, 2H), 7.66-7.53 (m, 3H), 7.90 (s, 1H), 7.99-7.97 (d, 1H), 8.18-8.16 (d, 1H). |
| I-793 | 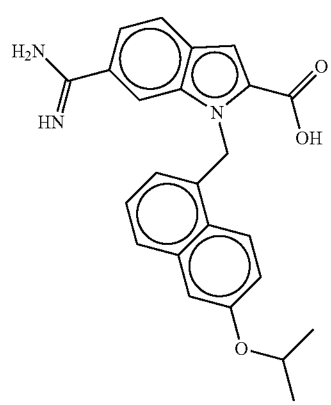 | 402.2 | ¹HNMR (CD₃OD, 400 MHz): δ 1.40-1.38 (d, 6H), 4.78-4.77 (m, 1H), 6.00-5.99 (m, 1H), 6.45 (s, 2H), 7.13-7.09 (t, 1H), 7.29-7.24 (m, 2H), 7.66-7.52 (m, 3H), 7.89 (s, 1H)( 7.99-7.97 (d, 1H), 8.15-8.12 (d, 1H). |

Example 137: Synthesis of Compound I-804

N-((1r,4r)-4-aminocyclohexyl)-6-carbamimidoyl-1-((6-(3-(dimethylamino)propoxy) naphthalen-1-yl)methyl)-1H-indole-2-carboxamide

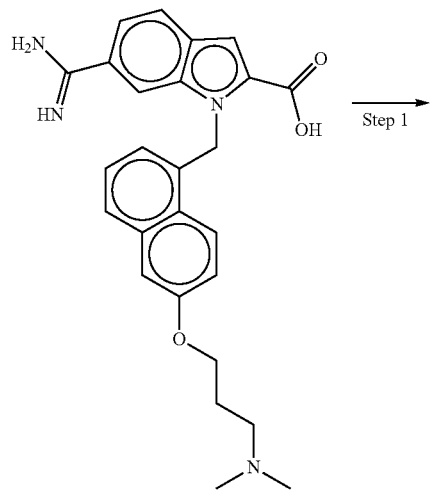

Synthetic Scheme-38

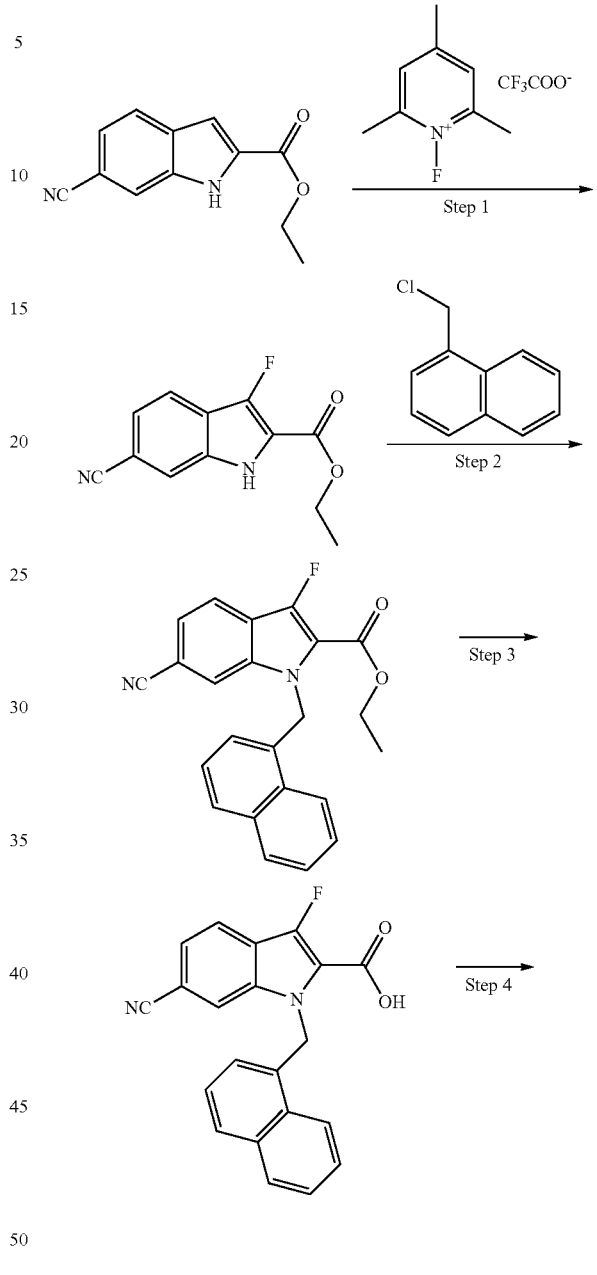

Step 1: N-((1r,4r)-4-aminocyclohexyl)-6-carbamimidoyl-1-((6-(3-(dimethylamino)propoxy) naphthalen-1-yl)methyl)-1H-indole-2-carboxamide Following experimental procedure of Scheme 15 D, above compound have been prepared. LCMS: 541.3 (M+1)$^+$, 1HNMR (CD3OD, 400 MHz): δ 1.50-1.41 (m, 4H), 2.00-1.90 (m, 4H), 2.35-2.30 (m, 2H), 2.97 (s, 6H), 3.10-3.07 (m, 1H), 3.44-3.40 (t, 1H), 3.70-3.60 (m, 1H), 4.26-4.14 (t, 2H), 6.10-6.09 (d, 1H), 6.39 (s, 2H), 7.20-7.14 (m, 1H), 7.33-7.29 (m, 3H), 7.66-7.54 (m, 2H), 7.95-7.92 (d, 2H), 8.15-8.13 (d, 1H).

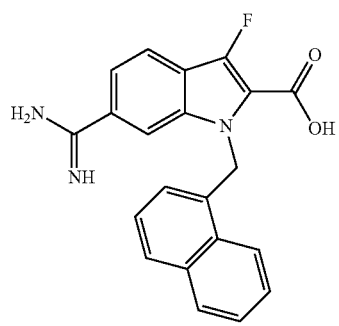

Example 138: Synthesis of Compound I-577

6-carbamimidoyl-3-fluoro-1-(naphthalen-1-ylmethyl)-1H-indole-2-carboxylic Acid

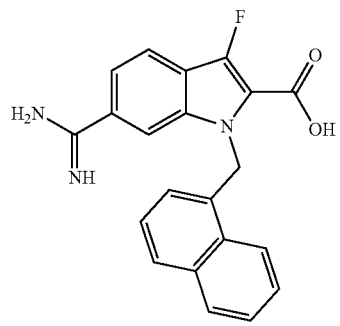 [SMILES: N=C(N)c1ccc2c(F)c(C(=O)O)n(Cc3cccc4ccccc34)c2c1]

Step 1: ethyl 6-cyano-3-fluoro-1H-indole-2-carboxylate

To a mixture of N-fluoro-2,4,6-trimethylpyridinium triflate (658 mg, 2.28 mmol) and ethyl 6-cyano-1H-indole-2-carboxylate (150 mg, 0.70 mmol) was added 1,1,2,2-tetrachloroethane (3 mL) and heated to 100° C. for 16 h. After completion of reaction, mixture was allowed to cool to rt. Then diluted with EtOAc and washed with water. The organic layer was dried and evaporated to get the crude, which was azeotrope with toluene to remove residual 1,1,2,2-tetrachloroethane, then purified by combi flash using 20% Ethyl acetate in Hexane as an eluent. LCMS: 231.05 (M−1)−.

Step 2-3: 6-cyano-3-fluoro-1-(naphthalen-1-ylmethyl)-1H-indole-2-carboxylic Acid Following experimental protocol of Step 1 and Step 2 of Scheme 15, above compound have been prepared. LCMS: 343.1 (M−1)−.

Step 4: 6-carbamimidoyl-3-fluoro-1-(naphthalen-1-ylmethyl)-1H-indole-2-carboxylic Acid Following experimental protocol of Scheme 15C, above compound have been prepared. LCMS: 360.15 (M−1)−; $^1$HNMR (CD$_3$OD, 300 MHz): δ 6.21 (d, 1H), 6.44 (s, 1H), 6.510 (s, 1H), 7.22 (m, 1H), 7.556-7.595 (m, 2H), 7.649-7.652 (m, 1H), 7.744 (d, 1H), 7.916-7.916 (d, 2H), 7.938-7.945 (d, 1H), 7.991-8.016 (m, 1H).

Synthetic Scheme-39

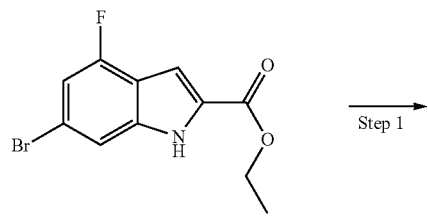

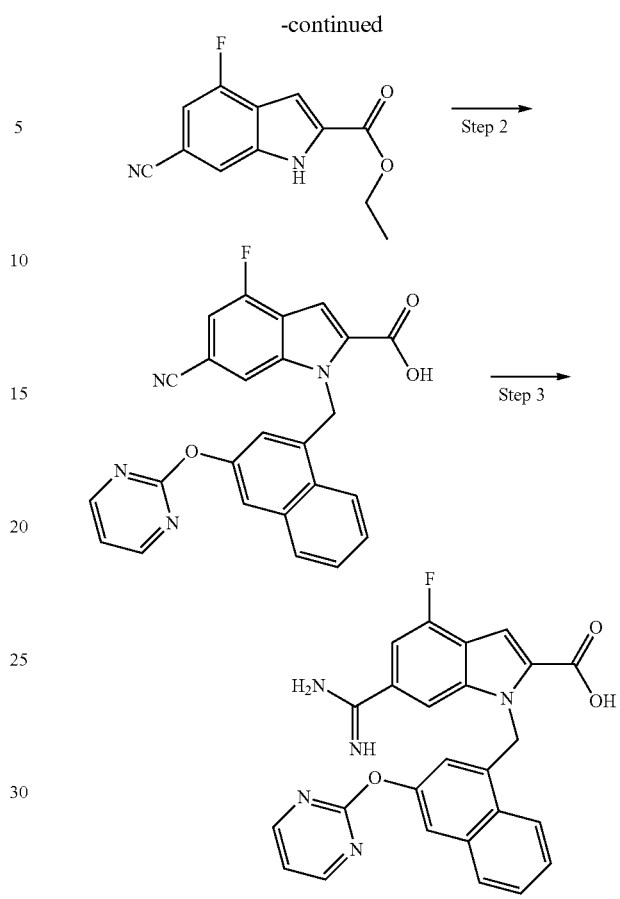

Example 139: Synthesis of Compound I-569

6-carbamimidoyl-4-fluoro-1-((3-(pyrimidin-2-yloxy)naphthalen-1-yl)methyl)-1H-indole-2-carboxylic Acid

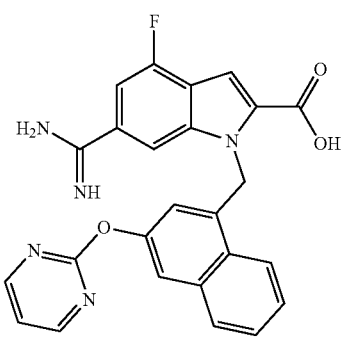 [SMILES: N=C(N)c1cc(F)c2cc(C(=O)O)n(Cc3cc(Oc4ncccn4)cc4ccccc34)c2c1]

Step 1: ethyl 6-cyano-4-fluoro-1H-indole-2-carboxylate

To a stirred solution of ethyl 6-bromo-4-fluoro-1H-indole-2-carboxylate (240 mg, 0.83 mmol) in DMF (10 mL) under argon was added CuCN (300 mg, 3.35 mmol) and heated to 155° C. for 16 h. After completion of reaction, Reaction mixture was poured in water, solid obtain was filtered, dried which was dissolved in THF and filter through celite bed. Filtrate was concentrated to get the crude. Crude was purified by combi flash using DCM as an eluent. (190 mg) LCMS: 231.15 (M−1)−.

Step 2: 6-cyano-4-fluoro-1-((3-(pyrimidin-2-yloxy) naphthalen-1-yl)methyl)-1H-indole-2-carboxylic Acid Following experimental protocol of Step 1 and Step 2 of Scheme 15, above compound have been prepared. LCMS: 439.10 (M+1)+.

Step 3: 6-carbamimidoyl-4-fluoro-1-((3-(pyrimidin-2-yloxy)naphthalen-1-yl)methyl)-1H-indole-2-carboxylic Acid Following experimental protocol of Scheme 15C, above compound have been prepared. LCMS: 456.1 (M+1)+; $^1$HNMR (CD$_3$OD, 400 MHz): δ 5.890 (s, 1H), 6.551 (s, 2H), 7.122-7.146 (t, 1H), 7.269-7.295 (d, 1H), 7.533 (s, 1H), 7.581-7.676 (m, 3H), 7.833 (s, 1H), 7.927-7.947 (d, 1H), 8.526-8.276 (d, 1H), 8.415-8.427 (d, 2H).

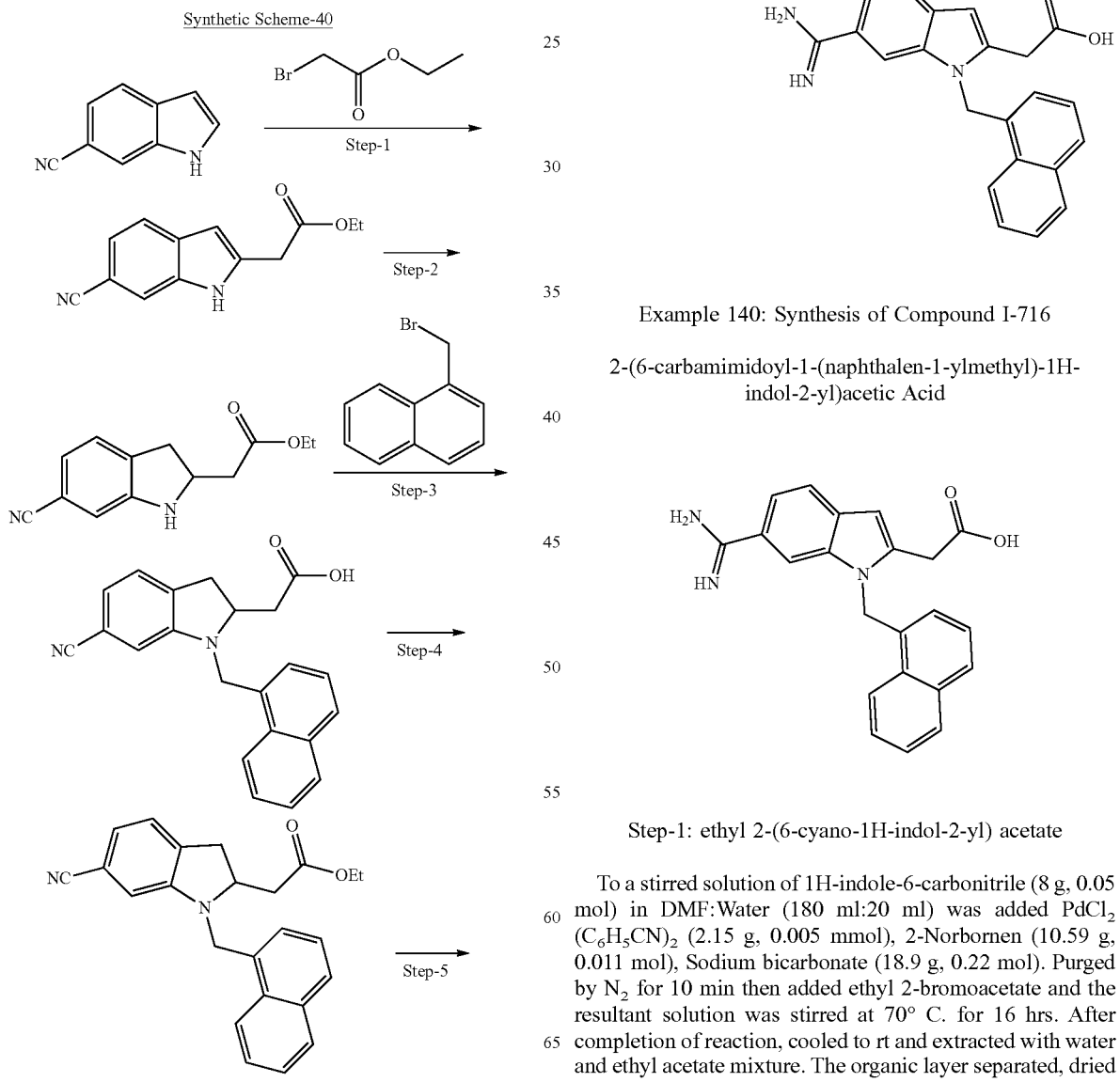

Synthetic Scheme-40

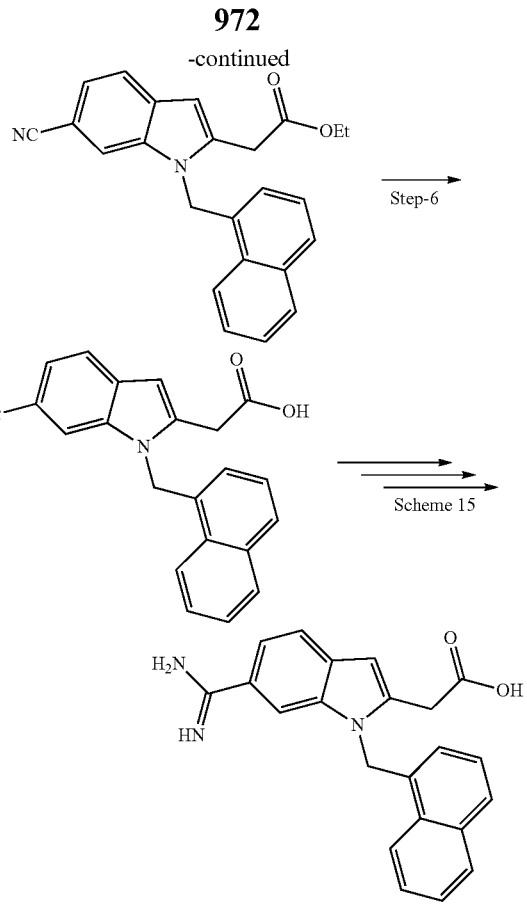

Example 140: Synthesis of Compound I-716

2-(6-carbamimidoyl-1-(naphthalen-1-ylmethyl)-1H-indol-2-yl)acetic Acid

Step-1: ethyl 2-(6-cyano-1H-indol-2-yl) acetate

To a stirred solution of 1H-indole-6-carbonitrile (8 g, 0.05 mol) in DMF:Water (180 ml:20 ml) was added PdCl$_2$(C$_6$H$_5$CN)$_2$ (2.15 g, 0.005 mmol), 2-Norbornen (10.59 g, 0.011 mol), Sodium bicarbonate (18.9 g, 0.22 mol). Purged by N$_2$ for 10 min then added ethyl 2-bromoacetate and the resultant solution was stirred at 70° C. for 16 hrs. After completion of reaction, cooled to rt and extracted with water and ethyl acetate mixture. The organic layer separated, dried over sodium sulphate and evaporated under reduced pressure to afford the crude product, which was purified using combiflash and 20% Ethyl acetate in Hexane as an eluent. Yield-6.5 gm. LCMS: 229.2 (M+1)⁺.

Step-2: ethyl 2-(6-cyanoindolin-2-yl) acetate

To a stirred solution of ethyl 2-(6-cyano-1H-indol-2-yl) acetate (6.5 g, 0.02 mol) in Acetic acid (100 ml) was added sodium cyano borohydride (14.14 g, 0.22 mol) at 0° C. and stirred at rt for 4 hrs. After completion of reaction, cooled 0° C. and neutralises with Aq. Sodium bicarbonate then extracted with ethyl acetate. The organic layer separated, dried over sodium sulphate and evaporated under reduced pressure, to afford the crude product, which was purified using combiflash and 10% Ethyl acetate in Hexane as an eluent. Yield-2.2 gm LCMS: 230.9 (M+1)⁺.

Step-3: 2-(6-cyano-1-(naphthalen-1-ylmethyl)indolin-2-yl)acetic Acid

To a solution of ethyl 2-(6-cyanoindolin-2-yl)acetate (1.2 g, 0.0052 mol) in THF was added sodium hydride (0.374 g, 0.0078 mol) and 1-(bromomethyl)naphthalene (1.72 g, 0.0078 mol) at 0° C. and stirred rt for 16 hrs. After completion of reaction, extracted with water and ethyl acetate mixture. The organic layer separated, dried over sodium sulphate and evaporated under reduced pressure, to afford the crude product, which was purified using combiflash and 1% Methanol in DCM as an eluent. Yield-0.58 gm, LCMS: 343.05 (M+1)⁺.

Step-4: ethyl 2-(6-cyano-1-(naphthalen-1-ylmethyl)indolin-2-yl)acetate

To a solution of 2-(6-cyano-1-(naphthalen-1-ylmethyl) indolin-2-yl)acetic acid (0.58 g, 1.69 mmol) in ethanol (15 ml) was added thionyl chloride (0.24 ml g, 3.39 mmol) at 0° C. and heated to 85° C. for 2 hrs. After completion of reaction, cooled to 0° C. and neutralises with Aq. Sodium bicarbonate then extracted with ethyl acetate. The organic layer separated, dried over sodium sulphate and evaporated under reduced pressure, to afford the crude product. Yield- 0.68 gm LCMS: 371.3 (M+1)⁺.

Step-5: ethyl 2-(6-cyano-1-(naphthalen-1-ylmethyl)-1H-indol-2-yl)acetate

To a stirred solution of ethyl 2-(6-cyano-1-(naphthalen-1-ylmethyl)indolin-2-yl)acetate (0.76 g, 2.05 mmol) in THF (15 ml) was added DDQ (0.699 mg, 3.08 mmol) at 0° C. and stirred rt for 16 hrs. After completion of reaction, cooled 0° C. and neutralised with Aq. Sodium bicarbonate then extracted with ethyl acetate. The organic layer separated, dried over sodium sulphate and evaporated under reduced pressure, to afford the crude product, which was purified using combiflash and 15% Ethyl acetate in Hexane as an eluent LCMS: 369.1 (M+1)⁺.

Step-6: 2-(6-cyano-1-(naphthalen-1-ylmethyl)-1H-indol-2-yl) acetic Acid

Following experimental protocol of Step 2 in Scheme 15, 2-(6-cyano-1-(naphthalen-1-ylmethyl)-1H-indol-2-yl)acetic acid have been prepared. LCMS: 358.2 (M+1)⁺, ¹HNMR (CD₃OD, 400 MHz): δ 3.77 (s, 2H), 6.20 (s, 2H), 6.25-6.24 (d, 1H), 6.75 (s, 1H), 7.23-7.19 (t, 1H), 7.67-7.49 (m, 3H), 7.83-7.79 (m, 3H), 7.94-7.93 (d, 1H), 8.21-8.19 (d, 1H).

Synthetic Scheme-41

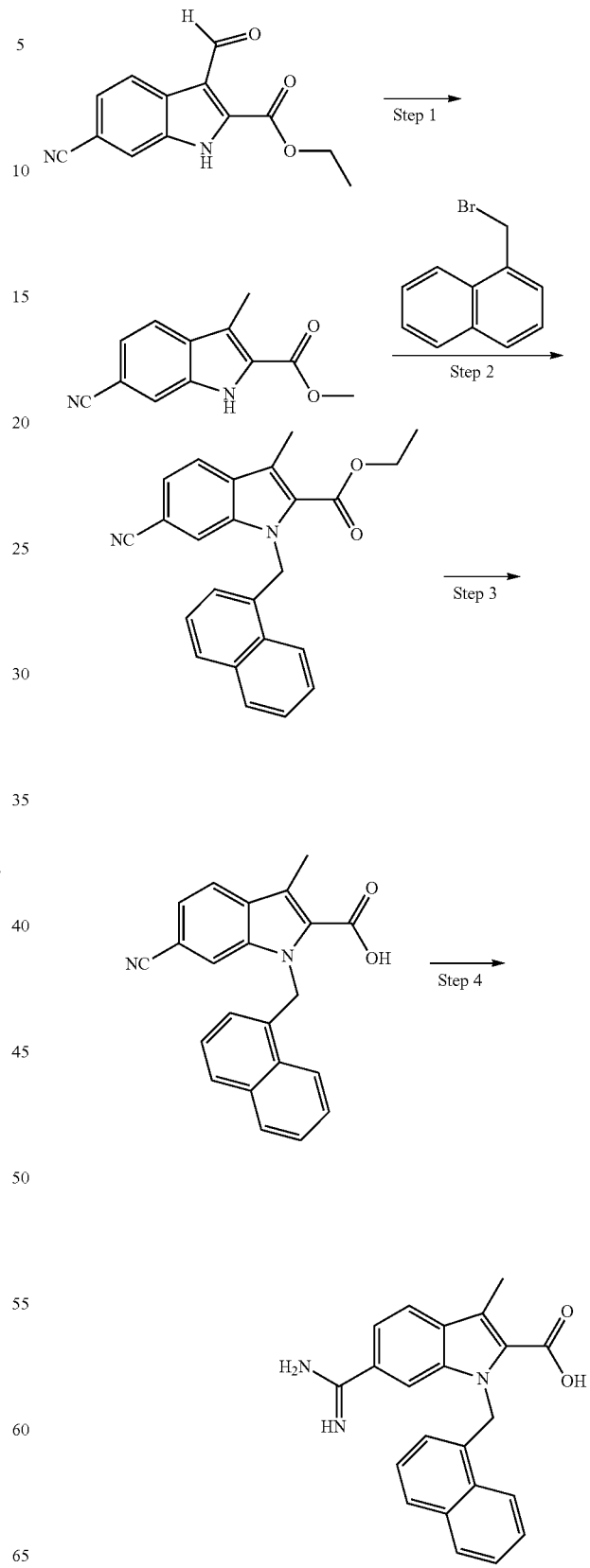

Example 141: Synthesis of Compound I-638

6-carbamimidoyl-3-methyl-1-(naphthalen-1-ylmethyl)-1H-indole-2-carboxylic Acid

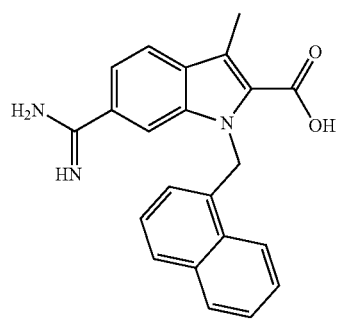 [SMILES: Cc1c(C(=O)O)n(Cc2cccc3ccccc23)c2cc(C(=N)N)ccc12]

Step 1: methyl 6-cyano-3-methyl-1H-indole-2-carboxylate

To a stirred solution of ethyl 6-cyano-3-formyl-1H-indole-2-carboxylate (0.8 g, 3.3057 mmol) in TFA (1 mL) was added Triethylsilane (1.34 g, 11.57 mmol) at 0° C. Reaction mixture was stirred at room temperature for 16 h. After completion of reaction, reaction mixture was diluted with hexane, filtered the solid and dried to get the product. (400 mg). $^1$HNMR (CD$_3$OD, 400 MHz): δ 1.38-1.35 (t, 3H), 2.55 (s, 3H), 4.40-4.35 (q, 2H), 7.40-7.38 (dd, 1H), 7.87-7.84 (m, 2H), 12.05 (s, 1H).

Step 2-3: 6-cyano-3-methyl-1-(naphthalen-1-ylmethyl)-1H-indole-2-carboxylic Acid Following experimental protocol of Step 1 and 2 of Scheme 15, above compound have been prepared. $^1$HNMR (DMSO-d$_6$, 400 MHz): δ 2.57 (s, 3H), 6.04-6.05 (d, 1H), 6.47 (s, 2H), 7.20-7.24 (t, 1H), 7.36-7.38 (d, 1H), 7.59-7.65 (m, 2H), 7.74-7.76 (d, 1H), 7.82-7.84 (d, 1H), 7.92-7.97 (t, 2H), 8.24-8.26 (d, 1H), 4.40-4.35 (q, 2H), 7.40-7.38 (dd, 1H), 12.05 (bs, 1H).

Step 4: 6-carbamimidoyl-3-methyl-1-(naphthalen-1-ylmethyl)-1H-indole-2-carboxylic Acid Following experimental protocol of Step 1 of Scheme 15D, above compound have been prepared. LCMS: 358.1 (M+1)$^+$; $^1$HNMR (CD$_3$OD, 400 MHz): δ 2.63 (s, 3H), 6.06-6.08 (d, 1H), 6.35 (s, 2H), 7.07-7.10 (m, 1H), 7.44-7.64 (m, 4H), 7.78-7.92 (d, 3H), 8.12-8.14 (d, 1H).

Synthetic Scheme-42

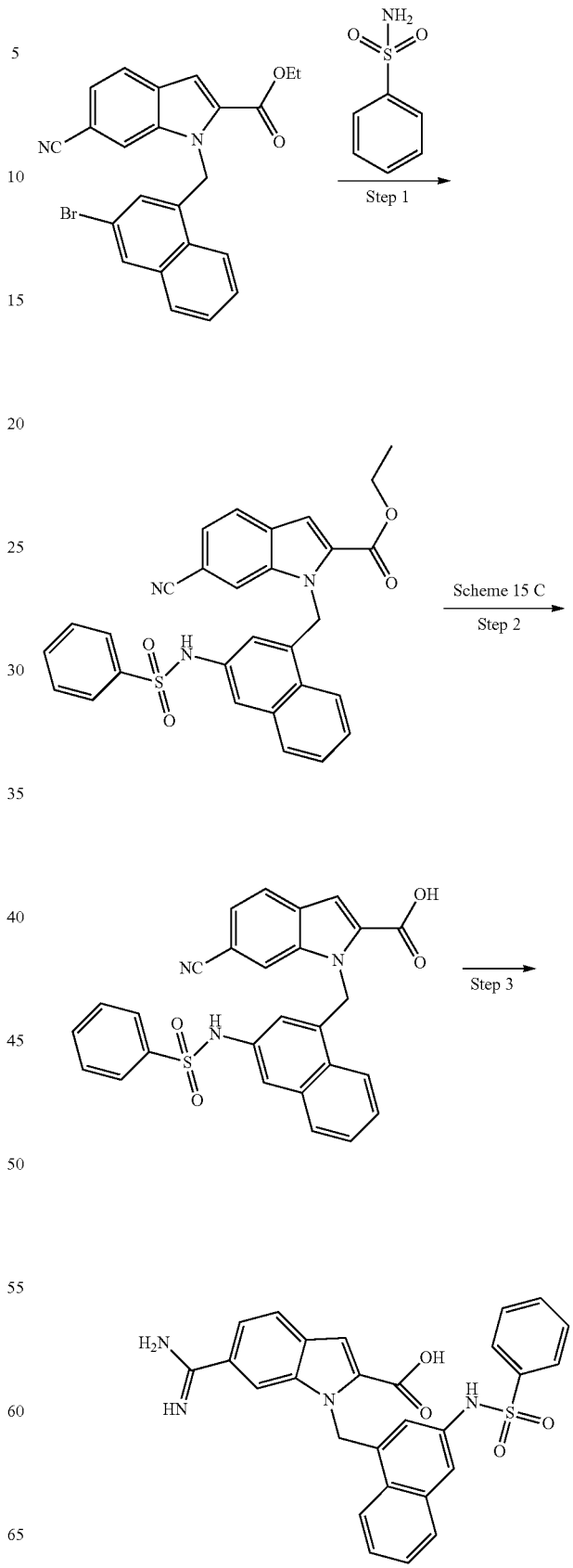

Example 142: Synthesis of Compound I-567

6-carbamimidoyl-1-((3-(phenylsulfonamido)naphthalen-1-yl)methyl)-1H-indole-2-carboxylic Acid

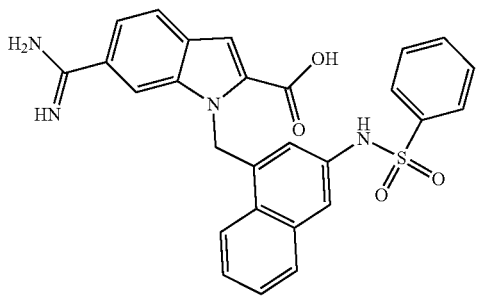 [SMILES: N=C(N)c1ccc2cc(C(=O)O)n(Cc3cc(NS(=O)(=O)c4ccccc4)cc4ccccc34)c2c1]

Step 1: ethyl 6-cyano-1-((3-(phenylsulfonamido)naphthalen-1-yl)methyl)-1H-indole-2-carboxylate To a stirred solution of compound ethyl 1-((3-bromonaphthalen-1-yl)methyl)-6-cyano-1H-indole-2-carboxylate (440 mg, 1.01 mmol) in 1-4 Dioxane (6 mL) and water (2 mL) was added benzene sulfonamide (176 mg, 1.12 mmol) and $K_3PO_4$ (422 mg, 1.99 mmol). Resultant solution was purged with argon for 5 min. To this [Pd(cinnamyl) Cl]$_2$ (35 mg, 0.062 mmol) and t-Bu-Xphos (70 mg, 1.165 mmol) was added and heated to 100° C. for 18 h. After completion of reaction the reaction mixture was filtered through celite bed and the filtrate was concentrated to give the crude product, which was purified using combi flash and 20% ethyl acetate in hexane as an eluent to afford title compound. (450 mg). LCMS: 510.14 (M+1)$^+$.

Step 2: 6-cyano-1-((3-(phenylsulfonamido)naphthalen-1-yl)methyl)-1H-indole-2-carboxylic Acid Following experimental protocol Step 2 of Scheme 15C, above compound have been prepared. LCMS: 480.5 (M−1)$^−$

Step 3: 6-carbamimidoyl-1-((3-(phenylsulfonamido)naphthalen-1-yl)methyl)-1H-indole-2-carboxylic Acid Following experimental protocol method E of Scheme 15C, above compound have been prepared. LCMS: 499.0 (M−1), $^1$HNMR (CD$_3$OD, 300 MHz): δ 6.19 (S, 1H), 6.39 (S, 1H), 7.25-7.31 (t, 3H), 7.41-7.74 (m, 9H), 7.87 (S, 1H), 8.01-8.04 (d, 1H), 8.11-8.14 (d, 1H).

TABLE 62

Compounds synthesized using synthetic scheme-42

| ID | Structure | LCMS [M + 1]$^+$ | 1H-NMR Data |
|---|---|---|---|
| I-546 | 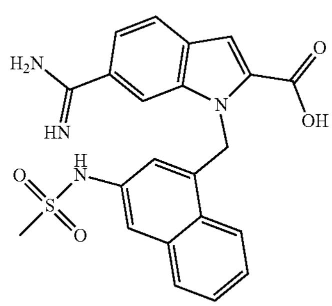 [SMILES: CS(=O)(=O)Nc1cc(Cn2c(C(=O)O)cc3ccc(C(=N)N)cc32)c2ccccc2c1] | 437.18 | $^1$HNMR (DMSO-d$_6$, 400 MHz): δ 2.781 (s, 3H), 6.095 (s, 1H), 6.260 (s, 2H), 6.996 (s, 1H), 7.447-7.502 (m, 4H), 7.762 (d, 1H), 7.829 (s, 2H), 8.170 (d, 1H). |
| I-656 | 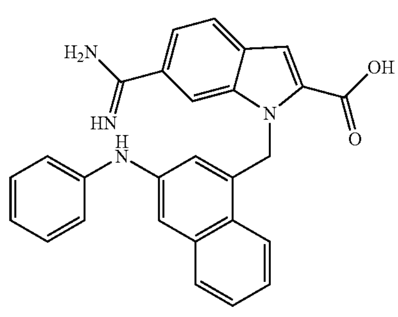 [SMILES: N=C(N)c1ccc2cc(C(=O)O)n(Cc3cc(Nc4ccccc4)cc4ccccc34)c2c1] | 435.5 | $^1$HNMR (CD$_3$OD, 300 MHz): δ 6.02 (s, 1H), 6.51 (s, 2H), 6.74 (t, 1H), 6.81-6.83 (d, 2H), 7.01-7.06 (t, 2H), 7.22-7.26 (d, 2H), 7.34-7.40 (m, 2H), 7.47-7.50 (d, 1H), 7.60-7.63 (d, 1H), 7.84-7.87 (d, 2H), 8.06 (d, 1H). |

TABLE 63

Compounds synthesized using synthetic scheme-37

| ID. | Structure | LCMS [M + H]+ | 1H-NMR Data |
|---|---|---|---|
| I-717 | 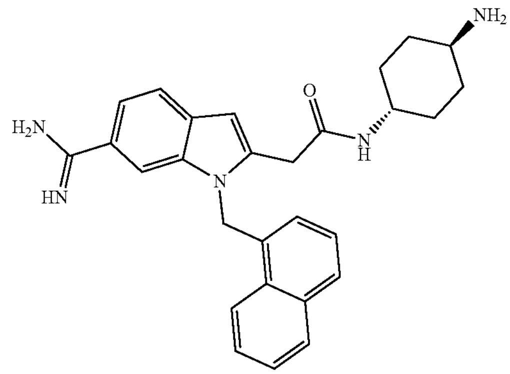 [SMILES: N=C(N)c1ccc2cc(CC(=O)N[C@H]3CC[C@H](N)CC3)n(Cc3cccc4ccccc34)c2c1] | 454.3 | $^1$HNMR (CD$_3$OD, 400 MHz): δ 1.07-1.03 (m, 2H), 1.33-1.29 (m, 3H), 1.91-1.62 (m, 4H), 3.00-2.93 (m, 1H), 3.69 (s, 2H), 6.20 (s, 2H), 6.27-6.25 (d, 1H), 6.73 (s, 1H), 7.22-7.18 (t, 1H), 7.66-7.50 (m, 3H), 7.81-7.76 (m, 3H), 7.95-7.93 (d, 1H), 8.23-8.21 (d, 1H). |
| I-591 | 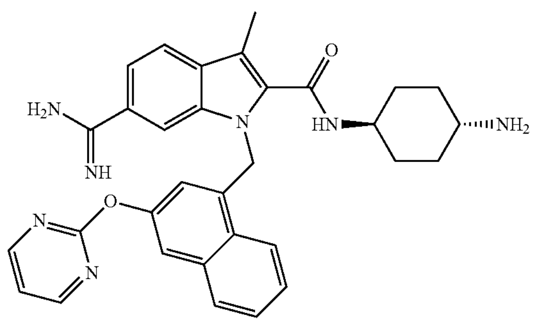 [SMILES: Cc1c(C(=O)N[C@H]2CC[C@H](N)CC2)n(Cc2cc(Oc3ncccn3)cc3ccccc23)c2cc(C(=N)N)ccc12] | 548.4 | $^1$HNMR (CD$_3$OD, 400 MHz): δ 1.2-1.5 (m, 4H), 1.80-2.0 (m, 4H), 2.45 (s, 3H), 2.98-3.05 (m, 1H), 3.65-3.75 (m, 1H), 6.21-6.23 (d, 3H), 7.13-7.15 (t, 1H), 7.52-7.55 (d, 1H), 7.59-7.61 (m, 3H), 7.83-7.85 (d, 1H), 7.90 (d, 1H), 8.004- 8.007 (d, 1H), 8.16 (d, 1H), 8.42-8.44 (d, 2H). |
| I-633 | 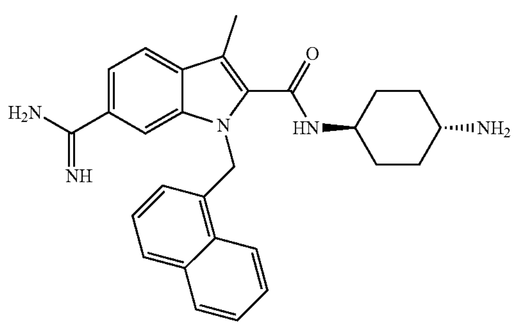 [SMILES: Cc1c(C(=O)N[C@H]2CC[C@H](N)CC2)n(Cc2cccc3ccccc23)c2cc(C(=N)N)ccc12] | 454.2 | $^1$HNMR (CD$_3$OD, 400 MHz): δ 1.12-1.39 (m, 4H), 1.70-1.90 (m, 4H), 2.50 (s, 3H), 2.95-3.01 (m, 1H), 3.62-3.70 (m, 1H), 6.18 (s, 2H), 6.48-6.50 (d, 1H), 7.21-7.25 (m, 1H), 7.55-7.58 (m, 3H), 7.75-7.78 (d, 1H), 7.90-7.92 (d, 2H), 8.02 (s, 1H) 8.12-8.15 (d, 1H). |

Example 143: Synthesis of Compound I-573

6-carbamimidoyl-1-(naphthalen-1-ylmethyl)-N-(pyrimidin-2-yl)-1H-indole-2-carboxamide

Synthetic Scheme-43

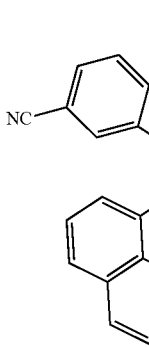
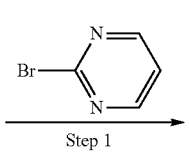
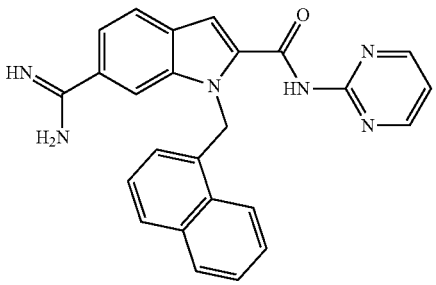 [SMILES: N=C(N)c1ccc2cc(C(=O)Nc3ncccn3)n(Cc3cccc4ccccc34)c2c1]
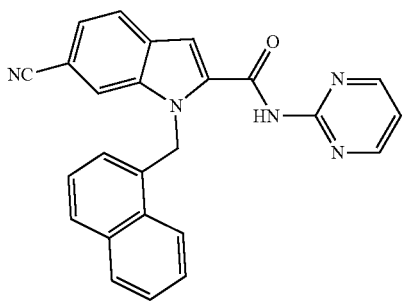
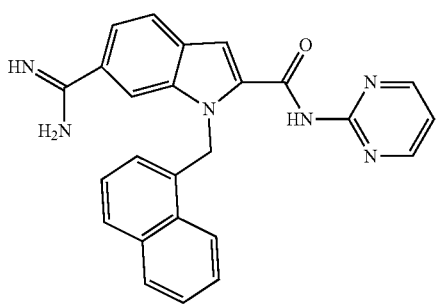

Step 1: 6-cyano-1-(naphthalen-1-ylmethyl)-N-(pyrimidin-2-yl)-1H-indole-2-carboxamide To a stirred solution of 6-cyano-1-(naphthalen-1-ylmethyl)-1H-indole-2-carboxamide (300 mg, 0.92 mmol) in 1,4 Dioxane (10 mL) was added Bromopyrimidine (126 mg, 1.10 mmol) and cesium Carbonate (421 mg, 0.046 mmol), resultant reaction mixture was purged with argon for 5 min. To this Xanthphos (80 mg, 0.138 mmol) and Pd$_2$(dba)$_3$ (42 mg, 0.046 mmol), was added and stirred at 100° C. for 16 h. After completion of reaction, Reaction mixture was filtered through celite bed and concentrated. Crude purified by combi flash using 5% MeOH in DCM. LCMS: 404.1 (M+1)$^+$.

Step 2: 6-carbamimidoyl-1-(naphthalen-1-ylmethyl)-N-(pyrimidin-2-yl)-1H-indole-2-carboxamide Following experimental protocol of Method E of Scheme 15 above compound have been prepared. LCMS: 421.20 (M+1)$^+$; $^1$HNMR (CD3OD, 400 MHz): δ 6.30-6.32 (d, 1H), 6.50 (s, 2H), 7.15-7.22 (m, 2H), 7.55-7.62 (m, 3H), 7.66 (s, 1H), 7.72-7.74 (d, 1H), 7.89-7.91 (d, 1H), 7.98-7.985 (s, 1H), 8.03-8.05 (d, 1H), 8.21-8.23 (d, 1H), 8.59-8.60 (d, 2H).

TABLE 64

Compounds synthesized using synthetic scheme-43

| ID. | Structure | LCMS [M + H]$^+$ | 1H-NMR Data |
|---|---|---|---|
| I-854 | 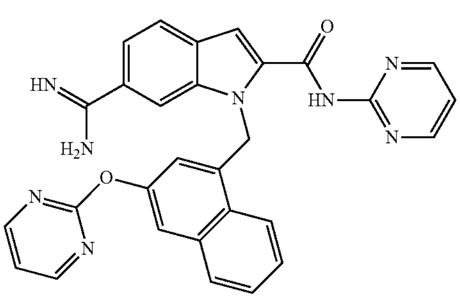 [SMILES: N=C(N)c1ccc2cc(C(=O)Nc3ncccn3)n(Cc3cc(Oc4ncccn4)cc4ccccc34)c2c1] | 515.2 | 1HNMR (CD3OD, 400 MHz): 6.04-6.09 (s, 1H), 6.53 (s, 2H), 7.07-7.09 (t, 1H), 7.16-7.17 (t,1H), 7.53-7.63 (m, 5H), 7.88-7.90 (m, 1H), 7.95 - 7.97 (d, 1H), 8.01-8.02 (s, 1H), 8.23-8.25 (d, 1H), 8.35-8.36 (d, 2H), 8.59-8.60 (d, 2H). |

Synthetic Scheme-44

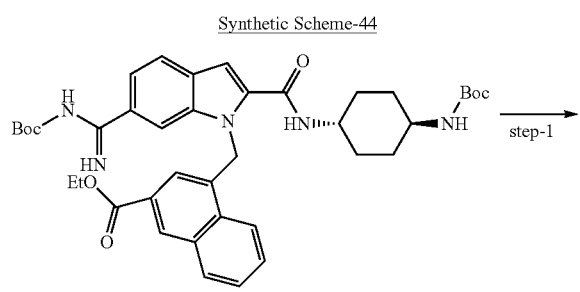

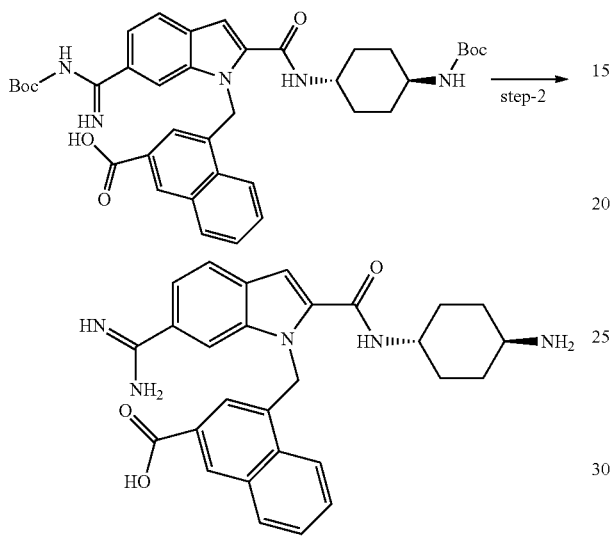

Example 144: Synthesis of Compound I-806

4-((2-(((1r,4r)-4-aminocyclohexyl)carbamoyl)-6-carbamimidoyl-1H-indol-1-yl)methyl) benzo[b]thiophene-2-carboxylic Acid

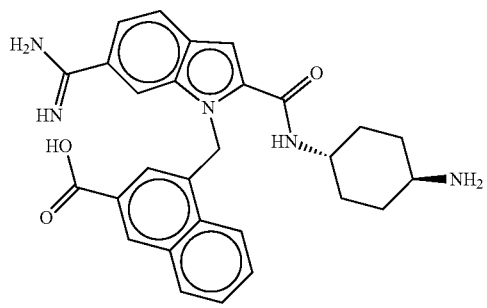

Step-1: 4-((2-(((1r,4r)-4-((tert-butoxycarbonyl)amino)cyclohexyl)carbamoyl)-6-(N-(tert-butoxycarbonyl)carbamimidoyl)-1H-indol-1-yl)methyl)-2-naphthoic Acid Following experimental protocols of Step 2 of general Scheme 15, above compound have been synthesized. LCMS: 684.2 (M+1)⁺.

Step-2: 4-((2-(((1r, 4r)-4-aminocyclohexyl)carbamoyl)-6-carbamimidoyl-1H-indol-1-yl)methyl)benzo[b]thiophene-2-carboxylic Acid Following experimental protocols of method F, above compound have been synthesized. LCMS: 484.1 (M+1)⁺, $^1$HNMR (CD$_3$OD, 400 MHz): δ 1.37-1.40 (m, 4H), 1.85-2.05 (m, 4H), 2.95-3.09 (m, 1H), 3.62-3.72 (m, 1H), 6.46 (s, 2H), 6.90 (s, 1H), 7.32 (s, 1H), 7.55-7.77 (m, 3H), 7.95-8.08 (m, 3H), 8.26-8.29 (d, 1H), 8.50 (s, 1H).

Synthetic Scheme-45

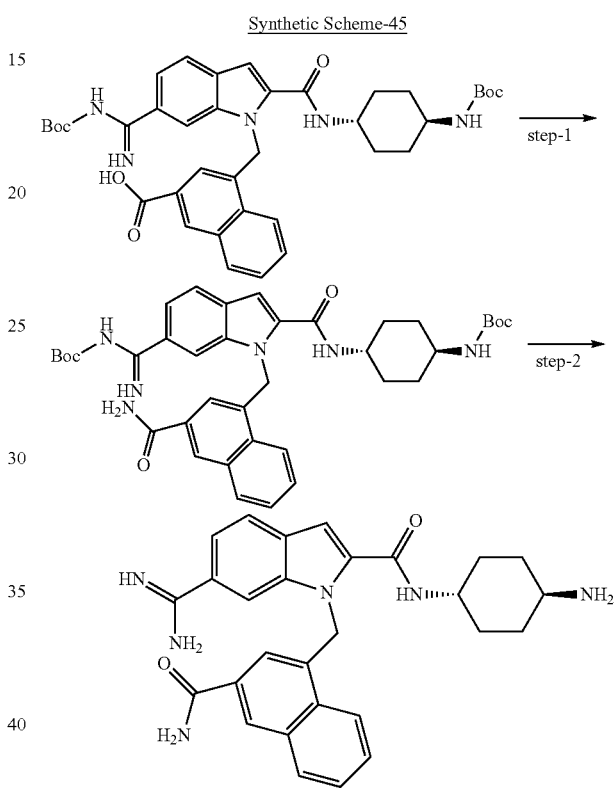

Example 145: Synthesis of Compound I-796

N-((1r, 4r)-4-aminocyclohexyl)-6-carbamimidoyl-1-((3-carbamoylnaphthalen-1-yl)methyl)-1H-indole-2-carboxamide

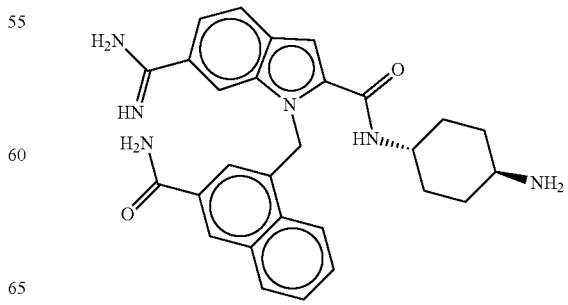

Step-1: tert-butyl ((2-(((1r, 4r)-4-((tert-butoxycarbonyl)amino)cyclohexyl)carbamoyl)-1-((3-carbamoylnaphthalen-1-yl)methyl)-1H-indol-6-yl)(imino)methyl)carbamate Following experimental protocols of Step 1 of general Scheme 15E, method C, above compound have been synthesized. LCMS 683.2 (M+1)$^+$.

Step-2: N-((1r, 4r)-4-aminocyclohexyl)-6-carbamimidoyl-1-((3-carbamoylnaphthalen-1-yl) methyl)-1H-indole-2-carboxamide Following experimental protocols of method F, above compound have been synthesized. LCMS: 483.3 (M+1)$^+$, $^1$HNMR (CD$_3$OD, 300 MHz): δ 1.29-1.39 (m, 4H), 1.86-1.96 (m, 4H), 2.95-3.05 (m, 1H), 3.60-3.70 (m, 1H), 6.43 (s, 2H), 6.86 (s, 1H), 7.54-7.74 (m, 2H), 7.93-8.06 (m, 3H), 8.25-8.30 (m, 2H).

Synthetic Scheme-46

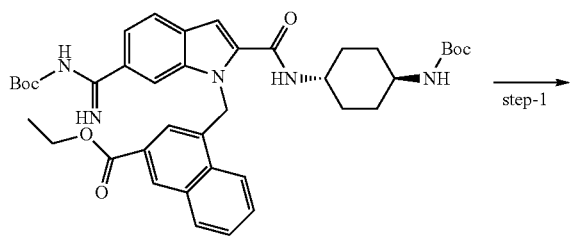

Example 146: Synthesis of Compound I-800

N-((1r,4r)-4-aminocyclohexyl)-6-carbamimidoyl-1-((3-(hydroxymethyl)naphthalen-1-yl)methyl)-1H-indole-2-carboxamide

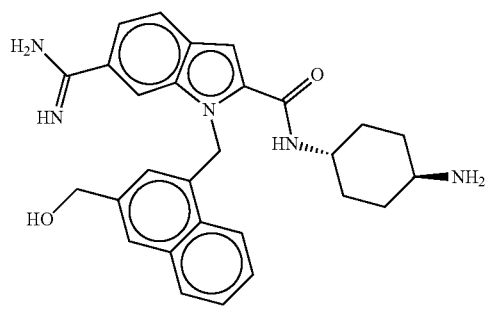

Step-1: tert-butyl ((2-(((1r,4r)-4-((tert-butoxycarbonyl)amino)cyclohexyl)carbamoyl)-1-((3-(hydroxymethyl)naphthalen-1-yl)methyl)-1H-indol-6-yl)(imino)methyl)carbamate Following experimental protocols of Step 2 of Scheme 15D-2, above compound have been synthesized. LCMS 670.4 (M+1)$^+$.

Step-2: N-((1r,4r)-4-aminocyclohexyl)-6-carbamimidoyl-1-((3-(hydroxyl methyl) naphthalen-1-yl) methyl)-1H-indole-2-carboxamide Following experimental protocols of method F tert-butyl ((2-(((1r,4r)-4-((tert-butoxycarbonyl)amino)cyclohexyl)carbamoyl)-1-((3-(hydroxymethyl)naphthalen-1-yl)methyl)-1H-indol-6-yl)(imino)methyl)carbamate have been synthesized. LCMS: 470.3 (M+1)$^+$, $^1$HNMR (CD$_3$OD, 400 MHz): δ 1.28-1.39 (m, 4H), 1.87-1.97 (m, 4H), 2.90-3.00 (m, 1H), 3.62-3.70 (m, 1H), 4.47 (s, 2H), 4.61 (s, 1H), 6.38 (s, 1H), 6.41 (s, 2H), 7.27 (s, 1H), 7.54-7.70 (m, 4H), 7.89-7.97 (m, 3H), 8.17-8.19 (d, 1H), 8.53 (s, 2H).

Example 147: Synthesis of Compound I-815

4-((2-(((1r,4r)-4-aminocyclohexyl)carbamoyl)-6-carbamimidoyl-1H-indol-1-yl)methyl) benzo[b]thiophene-2-carboxylic Acid

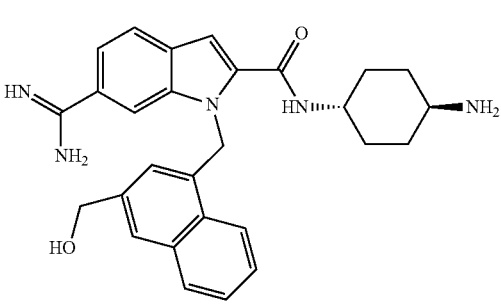

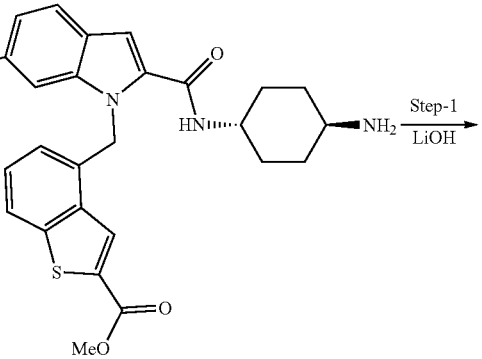

987  988
-continued  -continued

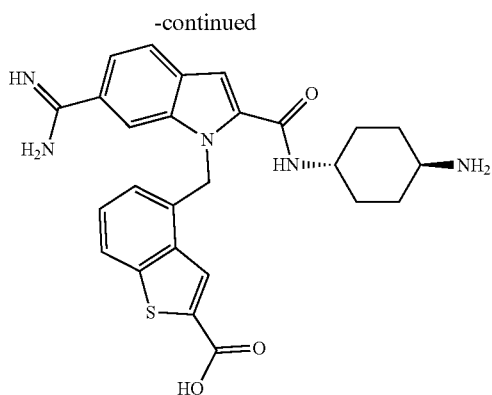

Step-1: 4-((2-(((1r,4r)-4-aminocyclohexyl)carbamoyl)-6-carbamimidoyl-1H-indol-1-yl) methyl)benzo[b]thiophene-2-carboxylic Acid Following experimental protocols of Step 2 of general Scheme 15, above compound have been synthesized. LCMS: 358.2 (M+1)+, ¹HNMR (CD₃OD, 400 MHz): δ 1.30-1.50 (m, 4H), 1.88-2.05 (m, 4H), 3.06-3.11 (m, 1H), 3.69-3.79 (m, 1H), 6.30 (s, 2H), 6.49-6.51 (d, 1H), 7.24-7.28 (m, 2H), 7.56-7.58 (d, 1H), 7.81-7.84 (d, 1H), 7.92-7.94 (d, 1H), 8.06 (s, 1H), 8.28 (s, 1H), 8.56-8.58 (d, 1H).

Synthetic Scheme - 47

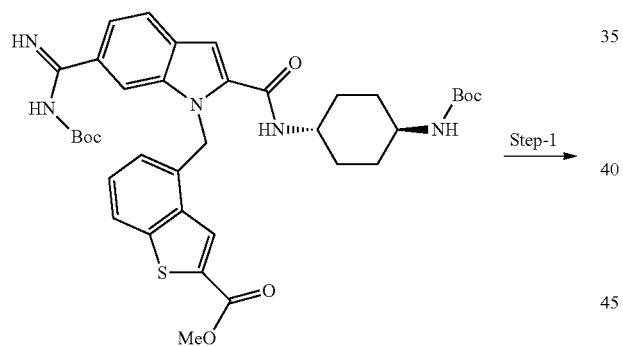

Step-1 →

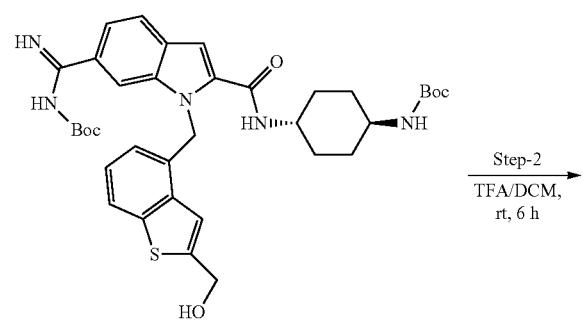

Step-2 →
TFA/DCM,
rt, 6 h

Example 148: Synthesis of Compound I-813

N-((1r,4r)-4-aminocyclohexyl)-6-carbamimidoyl-1-((2-(hydroxymethyl)benzo[b]thiophen-4-yl)methyl)-1H-indole-2-carboxamide

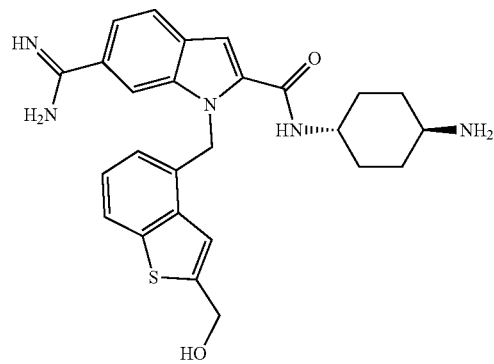 [SMILES: N=C(N)c1ccc2cc(C(=O)N[C@H]3CC[C@H](N)CC3)n(Cc3cccc4sc(CO)cc34)c2c1]

Step-1: tert-butyl ((2-(((1r,4r)-4-((tert-butoxycarbonyl)amino)cyclohexyl)carbamoyl)-1-((2-(hydroxymethyl)benzo[b]thiophen-4-yl)methyl)-1H-indol-6-yl)(imino)methyl)carbamate Following experimental protocols of Step 2 of general Scheme 15D-2, above compound have been synthesized. LCMS 676.1 (M+1)+.

Step-2: N-((1r,4r)-4-aminocyclohexyl)-6-carbamimidoyl-1-((2-(hydroxymethyl) benzo[b]thiophen-4-yl)methyl)-1H-indole-2-carboxamide Following experimental protocols of method F, N-((1r,4r)-4-aminocyclohexyl)-6-carbamimidoyl-1-((2-(hydroxymethyl)benzo[b]thiophen-4-yl)methyl)-1H-indole-2-carboxamide have been synthesized. LCMS: 476.2 (M+1)+, ¹HNMR (CD₃OD, 300 MHz): δ 1.38-1.45 (m, 4H), 1.92-2.01 (m, 4H), 3.00-3.10 (m, 1H), 3.62-3.72 (m, 1H), 4.11 (s, 2H), 6.20-6.28 (d, 1H), 6.37 (s, 2H), 7.15-7.23 (m, 3H), 7.45-7.90 (m, 6H), 8.18-8.21 (d, 1H).

Example 149: Synthesis of Compound I-643

(Z)-6-(N'-hydroxycarbamimidoyl)-1-((3-(pyrimidin-2-yloxy)naphthalen-1-yl)methyl)-1H-indole-2-carboxylic Acid

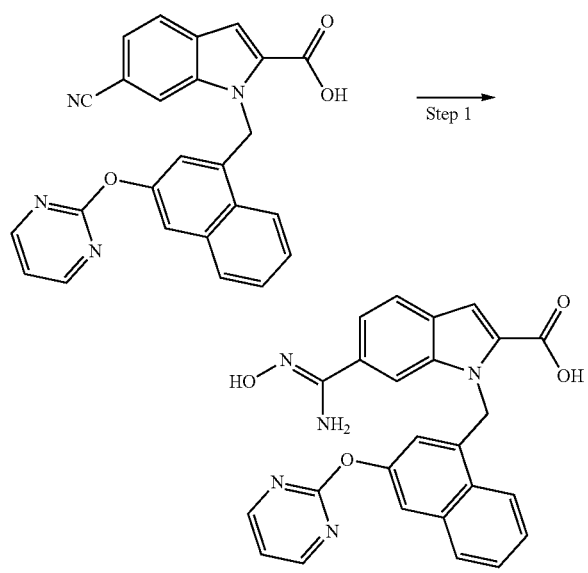

Step 1: (Z)-6-(N'-hydroxycarbamimidoyl)-1-((3-(pyrimidin-2-yloxy)naphthalen-1-yl)methyl)-1H-indole-2-carboxylic Acid Following experimental protocol of Step 1 of Scheme 15C, above compound have been prepared. LCMS: 454.3 (M+1)⁺; ¹HNMR (CD₃OD, 400 MHz): δ 5.85 (s, 1H), 6.53 (s, 2H), 7.12-7.15 (m, 1H), 7.40-7.70 (m, 5H), 7.81 (s, 1H), 7.91-7.94 (d, 2H), 8.25-8.28 (d, 1H), 8.39-8.41 (d, 2H).

Example 150: Synthesis of Compound I-630

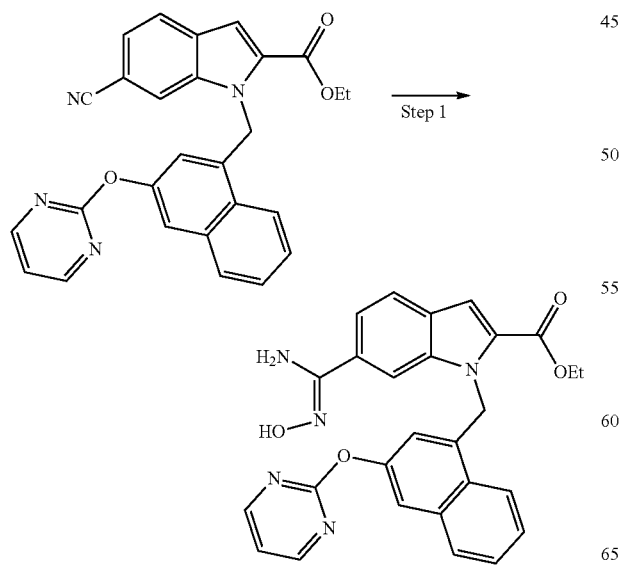

Step 1: ethyl (Z)-6-(N'-hydroxycarbamimidoyl)-1-((3-(pyrimidin-2-yloxy)naphthalen-1-yl)methyl)-1H-indole-2-carboxylate Following experimental protocol of Step 1 of Scheme 15C, above compound have been prepared. LCMS: 482.4 (M+1)⁺; ¹HNMR (CD₃OD, 400 MHz): δ1.19-1.26 (m, 3H), 4.27-4.26 (m, 2H), 5.90 (s, 1H), 6.50 (s, 2H), 7.11-7.12 (m, 1H), 7.40-7.80 (m, 5H), 7.85-7.95 (m, 3H), 8.26-8.41 (m, 3H).

Synthetic Scheme-48

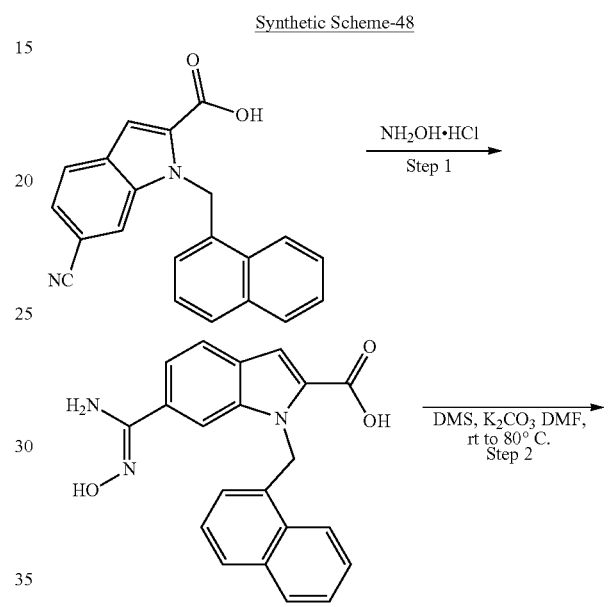

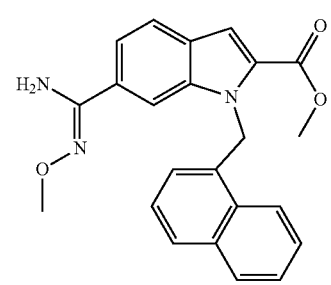

Example 151: Synthesis of Compound I-718 methyl (E)-6-(N'-methoxycarbamimidoyl)-1-(naphthalen-1-ylmethyl)-1H-indole-2-carboxylate

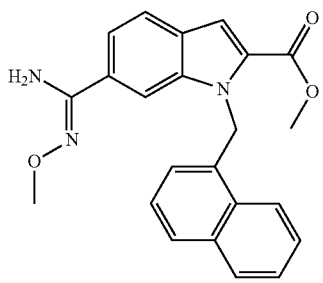

Step 1: (E)-6-(N'-hydroxycarbamimidoyl)-1-(naphthalen-1-ylmethyl)-1H-indole-2-carboxylic Acid To a stirred solution of 6-cyano-1-(naphthalen-1-ylmethyl)-1H-indole-2-carboxylic acid (0.35 g, 1.07 mmol) in ethanol (10.0 mL) was added 50% hydroxyl amine in water (1.0 mL) then which heated at 90° C. for 16 h. All the solvents were evaporated, crude washed with n-pentane to get the title crude compound as an off-white solid, (280.0 mg, crude, 72.61%), LC-MS: 360.1, (M+1).

Step 2: Methyl (E)-6-(N'-hydroxycarbamimidoyl)-1-(naphthalen-1-ylmethyl)-1H-indole-2-carboxylate To a stirred solution of product of Step 1 (0.175 g, 0.48 mmol) in DMF (5.0 mL) were added potassium carbonate (0.134 g, 0.973 mmol) and Dimethyl sulphate (0.093 mL, 0.973 mmol). Then reaction mixture was heated at 80° C. for 36 h. Reaction mass cooled and diluted with cold water, off-white solid was thrown out which was filtered and dried to get the title compound. (0.14 g, 77.96%) LC-MS: 374.1, (M+1).

Step 3: methyl (E)-6-(N'-methoxycarbamimidoyl)-1-(naphthalen-1-ylmethyl)-1H-indole-2-carboxylate To a stirred solution of Product of Step 2 (100.0 mg, 0.262 mmol) in DMF (1.0 mL) was added sodium hydride (12.0 mg, 0.285 mmol) in portions for 2 min at 0° C. Then added methyl iodide (41.0 mg, 0.288 mmol) and stirred the reaction mixture was stirred at the same temperature for another 10 min. Reaction mixture was diluted with cold water (30.0 mL) and extracted into ethyl acetate. The separated organic layer dried over anhydrous sodium sulphate and concentrated to get the crude compound. Crude compound was purified by combi-flash eluting with 15-20% ethyl acetate in hexane as an eluent. (10.8 mg, 8.8%) LCMS: 387.95 (M+1), HPLC: 95%, $^1$HNMR (CD3OD, 400 MHz): δ 3.70 (S, 3H), 3.66 (S, 3H), 6.05-6.03 (d, 2H), 6.33 (S, 2H), 7.09-7.05 (t, 1H), 7.41-7.38 (m, 3H), 7.55-7.47 (m, 3H), 7.70-7.68 (d, 1H), 7.83-7.81 (d, 1H), 8.17-8.15 (d, 1H).

Example 152: Synthesis of Compound I-699

(E)-6-(N'-methoxycarbamimidoyl)-1-(naphthalen-1-ylmethyl)-1H-indole-2-carboxylic Acid

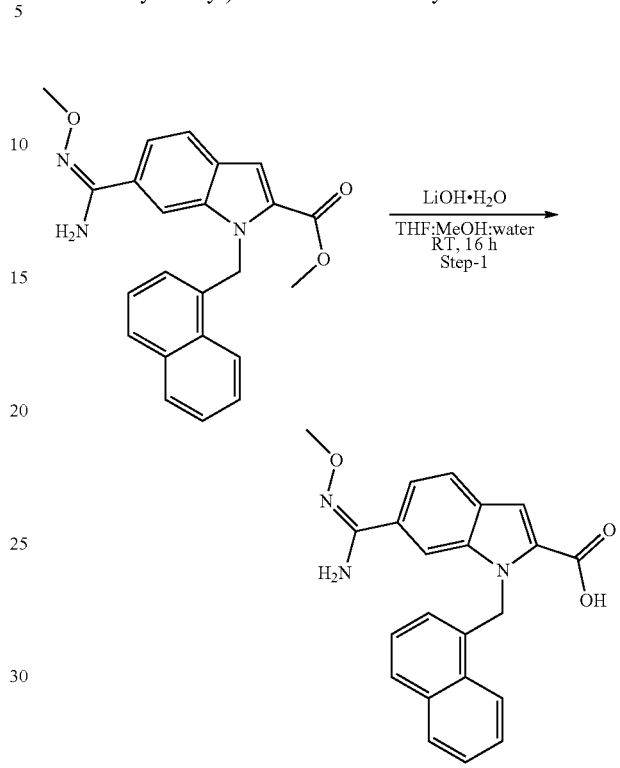

Step 1: (E)-6-(N'-methoxycarbamimidoyl)-1-(naphthalen-1-ylmethyl)-1H-indole-2-carboxylic Acid Following experimental protocol of Step 2 of general Scheme 15, (E)-6-(N'-methoxycarbamimidoyl)-1-(naphthalen-1-ylmethyl)-1H-indole-2-carboxylic acid have been synthesized. $^1$HNMR (DMSOd6, 400 MHz): δ 3.68 (S, 3H), 6.02-5.99 (m, 3H), 6.41 (S, 2H), 7.25-7.21 (t, 1H), 7.37 (S, 1H), 7.53-7.50 (d, 1H), 7.78-7.60 (m, 6H), 7.99-7.97 (d, 1H), 8.15 (S, 1H), 8.31-8.29 (d, 1H). HPLC: 99.70%.

Example 153: Synthesis of Compound I-704

(Z)-6-(N'-methoxycarbamimidoyl)-1-(naphthalen-1-ylmethyl)-1H-pyrrolo[2,3-b]pyridine-2-carboxylic Acid

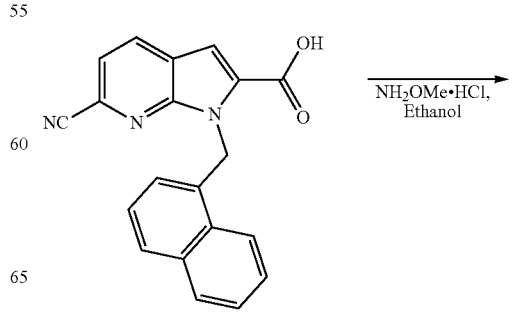

-continued

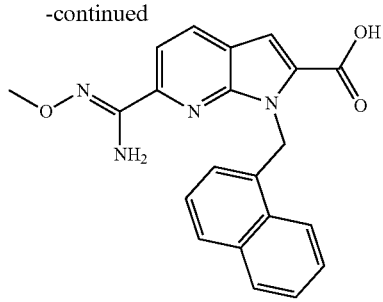

To a stirred suspension of 6-cyano-1-(naphthalen-1-ylmethyl)-1H-pyrrolo[2,3-b]pyridine-2-carboxylic acid (0.200 mg, 0.6110 mmol) in Ethanol were added NH₂OMe·HCl (0.357 g, 4.277 mmol) and DIPEA (0.86 mL, 4.888 mmol) at 0° C. Reaction mixture was stirred at room temperature for 6 h. After reaction completion, Reaction mixture was evaporated under reduced pressure, obtained residue was triturated with ice water and precipitated solid was collected by filtration which was purified by RPHPLC method to give the desired product as off white solid (0.025 g, 30%) LCMS: 375.05 (M+1)⁺, HPLC: 96.33% (RRT: 5.553), ¹HNMR (CD₃OD, 400 MHz): δ 3.14 (s, 3H), 6.23-6.25 (d, 1H), 6.54 (s, 2H), 7.14-7.18 (m, 1H), 7.54-7.72 (m, 5H), 7.90-7.92 (d, 1H), 8.26-8.28 (d, 1H), 8.46-8.48 (d, 1H).

Example 154: Synthesis of Compound I-697

Methyl (Z)-6-(N'-methoxycarbamimidoyl)-1-(naphthalen-1-ylmethyl)-1H-pyrrolo[2,3-b]pyridine-2-carboxylate

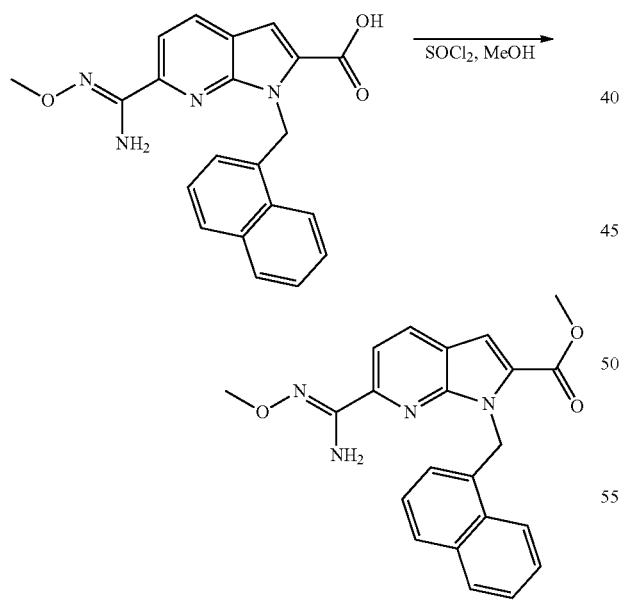

To a stirred suspension of 6-(N'-methoxycarbamimidoyl)-1-(naphthalen-1-ylmethyl)-1H-pyrrolo[2,3-b] pyridine-2-carboxylic acid (0.100 g, 0.2671 mmol) in Methanol was added SOCl₂ (0.2 mL, 2.671 mmol) at 0° C. Reaction mixture was heated to 60° C. for 16 h. After reaction completion, Reaction mixture was evaporated under reduced pressure, obtained residue was re dissolved in ice water, pH was adjusted to 7 and precipitated solid was collected by filtration. Obtained solid was purified by RPHPLC method to give the desired product as off white solid (0.090 g, 92%) LCMS: 389.15 (M+1)⁺, HPLC: 97.59% (RRT: 4.637), 1HNMR (CD3OD, 300 MHz): δ 3.15 (s, 3H), 3.82 (s, 3H), 6.21-6.23 (d, 1H), 6.52 (s, 2H), 7.13-7.18 (m, 1H), 7.57-7.74 (m, 5H), 7.90-7.93 (d, 1H), 8.26-8.29 (d, 1H), 8.47-8.50 (d, 1H).

Example 155: Synthesis of Compound I-684

Methyl(Z)-5-(N'-methoxycarbamimidoyl)-1-methyl-3-(naphthalen-1-ylmethyl)-1H-indole-2-carboxylate

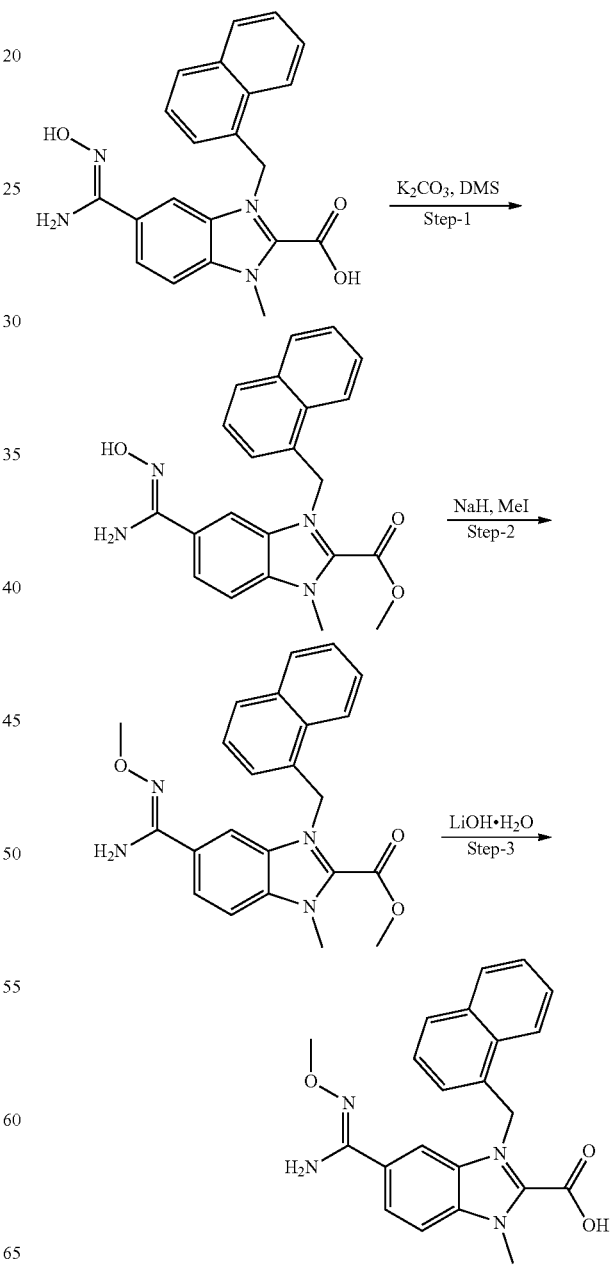

Step 1: Methyl(Z)-5-(N'-hydroxycarbamimidoyl)-1-methyl-3-(naphthalen-1-ylmethyl)-1H-indole-2-carboxylate To the stirred solution of product of step-1 (250 mg, 0.67 mmol) in DMF was added potassium carbonate (184 mg, 1.34 mmol), then stirred for 10 min, then added dimethyl sulphate (168 mg, 1.34 mmol). Reaction mixture was stirred at 70° C. for 16 h. After reaction completion, reaction mixture was cooled to RT, diluted with water and extracted with ethyl acetate (2*50 ml). Organic layer separated, dried over anhydrous sodium sulphate and concentrated to get the crude compound, which was washed with n-pentane and dried to get the desired compound, which was directly used for the next step (180 mg), LCMS: 388.1 (M+1)$^+$.

Step 2: Methyl(Z)-5-(N'-methoxycarbamimidoyl)-1-methyl-3-(naphthalen-1-ylmethyl)-1H-indole-2-carboxylate To the stirred solution of product of step-2 (180 mg, 0.46 mmol) in DMF was added sodium hydride (24 mg, 0.511 mmol) at 0° C. Then added methyl iodide (72 mg, 0.511 mmol) at 0° C. and then stirred for 15 min. Reaction mixture was diluted with cold water and extracted with ethyl acetate (2*25 ml), separated organic layer dried over anhydrous sodium sulphate and concentrated to get the crude compound was purified by Combi-flash to get desired compound (105 mg). LCMS: 402.1 (M+1)$^+$.

Step 3: Synthesis of Methyl(Z)-5-(N'-methoxycarbamimidoyl)-1-methyl-3-(naphthalen-1-ylmethyl)-1H-indole-2-carboxylate Following experimental protocol of Step 2 of Scheme 15, Methyl(Z)-5-(N'-methoxycarbamimidoyl)-1-methyl-3-(naphthalen-1-ylmethyl)-1H-indole-2-carboxylate have been synthesized (30 mg), LCMS: 388.2 (M+1)$^+$, HPLC: 99.3% (Retention Time=5.72 min), $^1$H NMR (400 MHz, DMSO-d$_6$): δ 3.66 (s, 3H), 4.04 (s, 3H), 4.91 (s, 2H), 5.91 (s, 2H), 6.81 (bs, 1H), 7.26 (t, 1H), 7.52-7.63 (m, 3H), 7.71 (d, 1H), 7.76 (bs, 1H), 7.93 (d, 1H), 8.40 (d, 1H).

Example 156: Synthesis of Compound I-558 ethyl (Z)-6-(N'-cyanocarbamimidoyl)-1-((3-(pyrimidin-2-yloxy)naphthalen-1-yl)methyl)-1H-indole-2-carboxylate

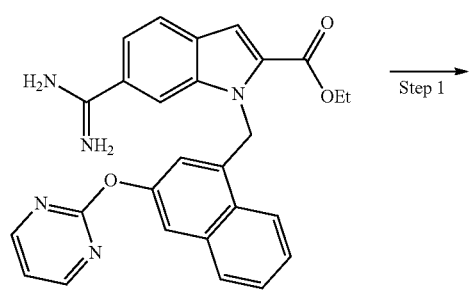
Step 1

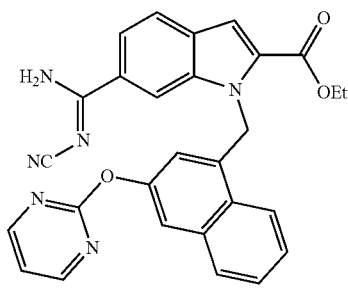

To a stirred solution of ethyl 6-carbamimidoyl-1-((3-(pyrimidin-2-yloxy)naphthalen-1-yl)methyl)-1H-indole-2-carboxylate (80 mg, 0.172 mmol) in DCM (3 mL) was added DIPEA (0.17 mL, 0.86 mmol) followed by CNBr (270 mg, 2.58 mmol). Reaction mixture was stirred at rt for 3 h. After completion of reaction, Reaction mixture was concentrated to get the crude, which was purified by washing with Diethyl ether and DCM (5:1) mixture. LCMS: 491.2 (M+1)$^+$; $^1$HNMR (DMSO-d$_6$, 400 MHz): δ 1.10-1.14 (t, 3H), 4.17-4.18 (q, 2H), 6.42 (s, 2H), 7.2 (bs, 1H), 7.46 (s, 1H), 7.60-7.70 (m, 4H), 7.8-7.82 (d, 1H), 7.9-8.0 (d, 1H), 8.2 (bs, 1H), 8.23-8.32 (d, 1H), 8.45-8.46 (d, 2H).

Synthetic Scheme-49

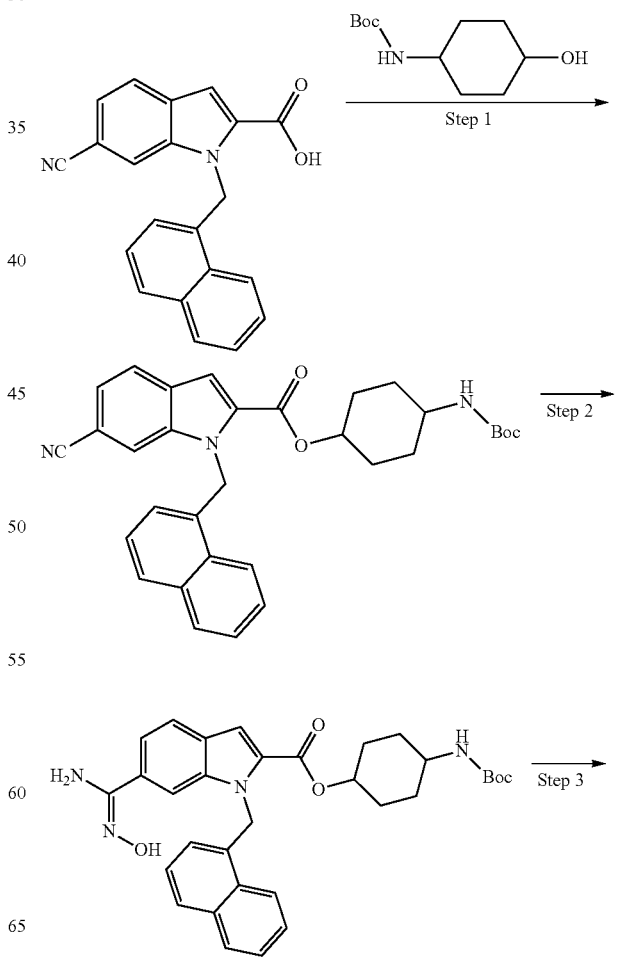

-continued

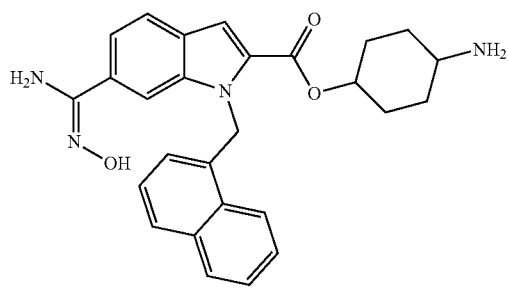

Example 157: Synthesis of Compound I-810

(1r,4r)-4-aminocyclohexyl 6-((Z)—N'-hydroxycarbamimidoyl)-1-(naphthalen-1-ylmethyl)-1H-indole-2-carboxylate

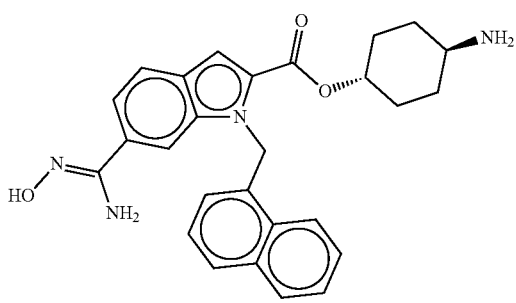

Step 1: 4-((tert-butoxycarbonyl)amino)cyclohexyl 6-cyano-1-(naphthalen-1-ylmethyl)-1H-indole-2-carboxylate Following experimental protocol of Step 1 of Scheme 15D-1, 4-((tert-butoxycarbonyl)amino)cyclohexyl 6-cyano-1-(naphthalen-1-ylmethyl)-1H-indole-2-carboxylate have been prepared. LCMS 524.1 (M+1)$^+$.

Step 2-3: 4-aminocyclohexyl (E)-6-(N'-hydroxycarbamimidoyl)-1-(naphthalen-1-ylmethyl)-1H-indole-2-carboxylate Following experimental protocol of Step 4 and 5 in Scheme 15, above compound have been prepared. LCMS: 457.15 (M+1)$^+$, $^1$HNMR (CD3OD, 400 MHz): δ 1.36-1.45 (m, 4H), 1.95-2.01 (m, 4H), 2.97 (m, 1H), 4.79 (m, 1H), 6.14-6.157 (d, 1H), 6.44 (s, 2H), 7.207-7.169 (t, 1H), 7.47-7.44 (dd, 1H), 7.57-7.61 (m, 2H), 7.65-7.69 (m, 1H), 7.74-7.76 (d, 1H), 7.84 (S, 1H), 7.93-7.95 (d, 1H), 7.99-8.01 (d, 1H), 8.24-8.26 (d, 1H).

Example 158: Synthesis of Compound I-762

6-(N-acetylcarbamimidoyl)-N-(1-methylpiperidin-4-yl)-1-(naphthalen-1-ylmethyl)-1H-indole-2-carboxamide

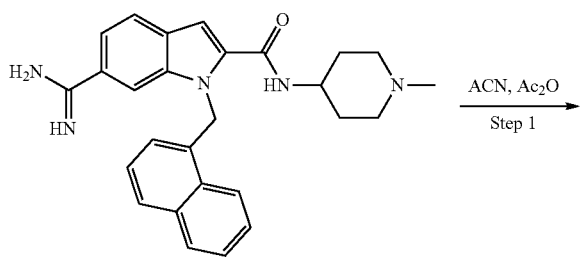

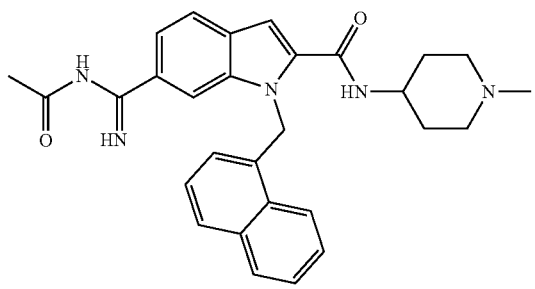

Step 1: 6-(N-acetylcarbamimidoyl)-N-(1-methylpiperidin-4-yl)-1-(naphthalen-1-ylmethyl)-1H-indole-2-carboxamide To a stirred solution of 6-carbamimidoyl-N-(1-methylpiperidin-4-yl)-1-(naphthalen-1-ylmethyl)-1H-indole-2-carboxamide (200 mg, 0.95 mmol) in acetonitrile (4 mL) was added Ac$_2$O (93 mg, 0.91 mmol) dropwise at room temperature. Reaction mixture was stirred at rt for 6 h. After completion of reaction, reaction mixture was concentrated, purified by prep HPLC. LCMS: 483.3 (M+1)$^+$, $^1$HNMR (CD3OD, 300 MHz): δ 2.01 (s, 3H), 2.33 (s, 3H), 2.83 (d, 3H), 3.03 (s, 2H), 3.48 (d, 2H), 3.93 (s, 1H), 6.23 (d, 1H), 6.42 (s, 2H), 7.17 (t, 1H), 7.25 (s, 1H), 7.54-7.61 (m, 2H), 7.70-7.75 (m, 2H), 7.83 (d, 1H), 7.90 (d, 1H), 8.09 (s, 1H), 8.20 (d, 1H).

Synthetic Scheme-50

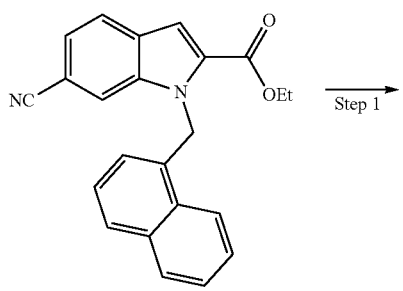

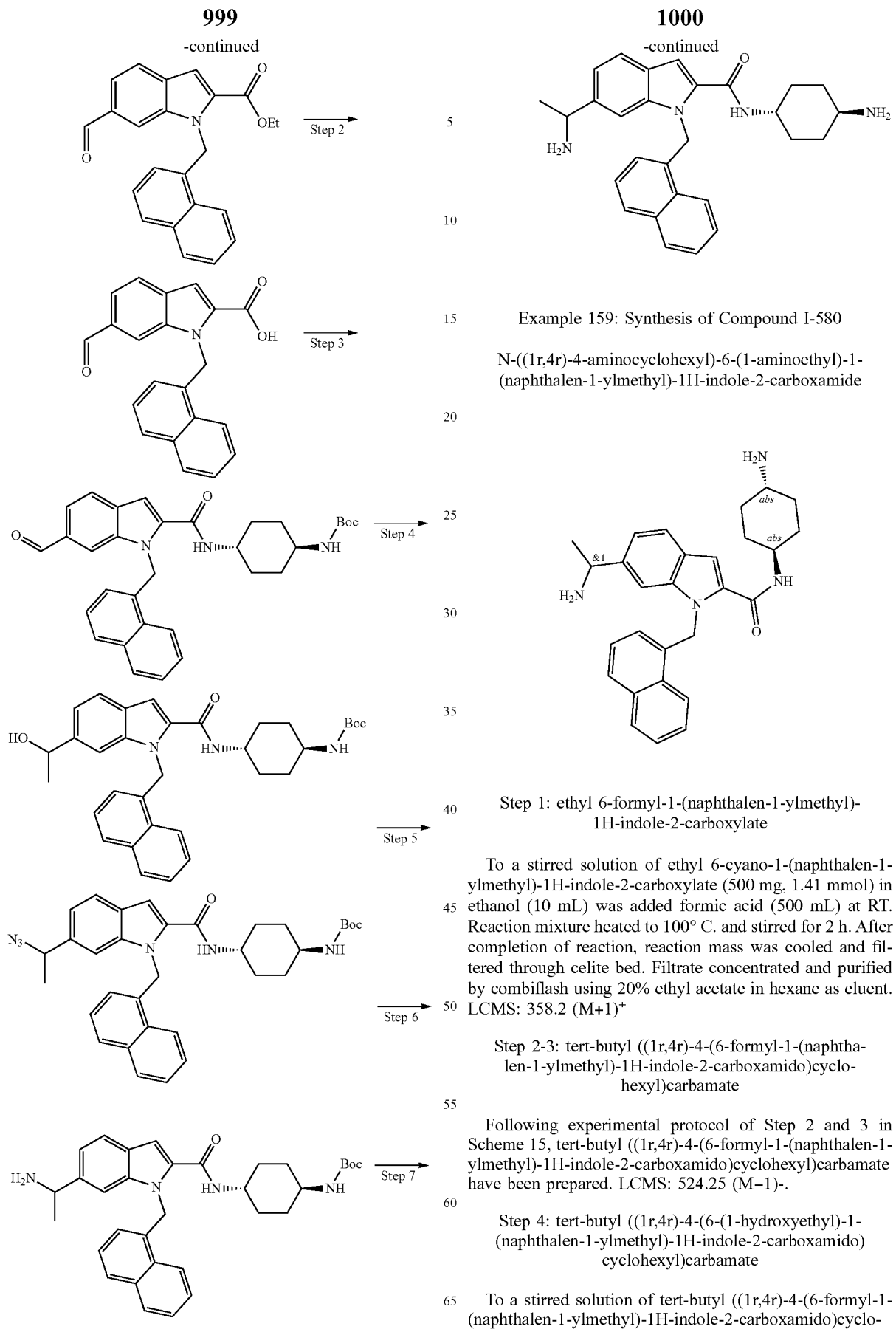

Example 159: Synthesis of Compound I-580

N-((1r,4r)-4-aminocyclohexyl)-6-(1-aminoethyl)-1-(naphthalen-1-ylmethyl)-1H-indole-2-carboxamide Step 1: ethyl 6-formyl-1-(naphthalen-1-ylmethyl)-1H-indole-2-carboxylate To a stirred solution of ethyl 6-cyano-1-(naphthalen-1-ylmethyl)-1H-indole-2-carboxylate (500 mg, 1.41 mmol) in ethanol (10 mL) was added formic acid (500 mL) at RT. Reaction mixture heated to 100° C. and stirred for 2 h. After completion of reaction, reaction mass was cooled and filtered through celite bed. Filtrate concentrated and purified by combiflash using 20% ethyl acetate in hexane as eluent. LCMS: 358.2 (M+1)$^+$ Step 2-3: tert-butyl ((1r,4r)-4-(6-formyl-1-(naphthalen-1-ylmethyl)-1H-indole-2-carboxamido)cyclohexyl)carbamate Following experimental protocol of Step 2 and 3 in Scheme 15, tert-butyl ((1r,4r)-4-(6-formyl-1-(naphthalen-1-ylmethyl)-1H-indole-2-carboxamido)cyclohexyl)carbamate have been prepared. LCMS: 524.25 (M−1)-.

Step 4: tert-butyl ((1r,4r)-4-(6-(1-hydroxyethyl)-1-(naphthalen-1-ylmethyl)-1H-indole-2-carboxamido)cyclohexyl)carbamate To a stirred solution of tert-butyl ((1r,4r)-4-(6-formyl-1-(naphthalen-1-ylmethyl)-1H-indole-2-carboxamido)cyclohexyl)carbamate (400 mg, 0.76 mmol) in THF (10 mL) was added MeLi (1.5 mL) at 0° C. and stirred at same temperature for 1 h. After completion of reaction, reaction mixture was quenched with saturated NH₄Cl, extracted with ethyl acetate, dried over anhydrous Na₂SO₄, and concentrated. Crude was purified by combi flash using 2% MeOH in DCM as an eluent. LCMS: 540.30 (M−1)-.

Step 5: tert-butyl ((1r,4r)-4-(6-(1-azidoethyl)-1-(naphthalen-1-ylmethyl)-1H-indole-2-carboxamido)cyclohexyl)carbamate To the stirred solution of tert-butyl ((1r,4r)-4-(6-(1-hydroxyethyl)-1-(naphthalen-1-ylmethyl)-1H-indole-2-carboxamido)cyclohexyl)carbamate (150 mg, 0.27 mmol) in DCM (10 mL) was added azidotrimethylsilane (0.3 mL) and Cu(OTf)₂ (15 mL) at rt. Reaction mixture was stirred at room temperature for 1 h. After completion of reaction, reaction mixture was diluted with ice cold water and extracted with DCM to get the crude, which taken to next step without purification. LCMS: 565.3 (M−1)-.

Step 6: tert-butyl ((1r,4r)-4-(6-(1-aminoethyl)-1-(naphthalen-1-ylmethyl)-1H-indole-2-carboxamido)cyclohexyl)carbamate To a stirred solution of tert-butyl ((1r,4r)-4-(6-(1-azidoethyl)-1-(naphthalen-1-ylmethyl)-1H-indole-2-carboxamido)cyclohexyl)carbamate (160 mg, 0.17 mmol) in methanol was added Pd/C (10 mg). Reaction mixture was stirred at room temperature under hydrogen atmosphere for 16 h. After completion of reaction, reaction mixture was filtered through celite bed and filtrate was concentrated to get the product. LCMS: 539.25 (M−1)-.

Step 7: N-((1r,4r)-4-aminocyclohexyl)-6-(1-aminoethyl)-1-(naphthalen-1-ylmethyl)-1H-indole-2-carboxamide Following experimental protocol of method F in Scheme 15, above compound have been prepared. LCMS: 439.15 (M+1)⁺, ¹HNMR (CD3OD, 400 MHz): δ 1.39-1.45 (m, 4H), 1.56-1.58 (d, 3H), 1.90-2.03 (m, 4H), 3.00-3.10 (m, 1H), 3.60-3.70 (m, 1H), 4.45-4.48 (m, 1H), 6.20-6.22 (d, 1H), 6.40 (s, 2H), 7.14-7.26 (m, 3H), 7.45 (s, 1H), 7.55-7.91 (m, 5H), 8.20-8.22 (d, 1H).

Synthetic Scheme-51

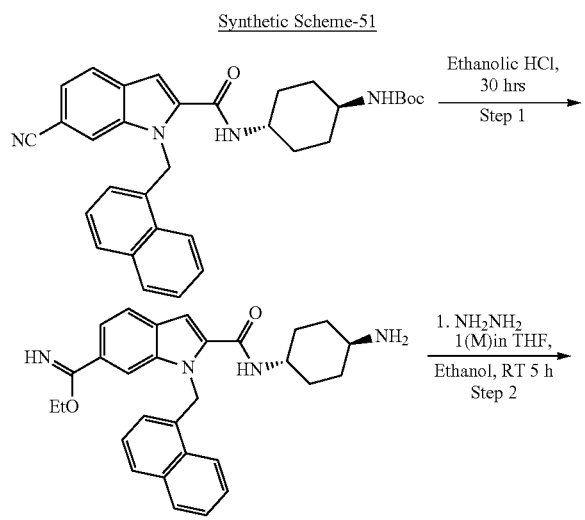

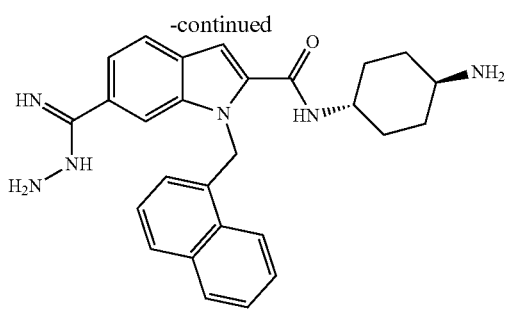

Example 160: Synthesis of Compound I-827

N-((1r,4r)-4-aminocyclohexyl)-6-(hydrazineyl(imino)methyl)-1-(naphthalen-1-ylmethyl)-1H-indole-2-carboxamide

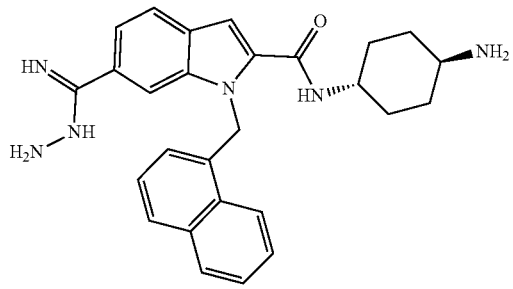 [SMILES: N=C(NN)c1ccc2cc(C(=O)N[C@H]3CC[C@H](N)CC3)n(Cc3cccc4ccccc34)c2c1]

Step 1: ethyl 2-(((1r,4r)-4-aminocyclohexyl)carbamoyl)-1-(naphthalen-1-ylmethyl)-1H-indole-6-carbimidate tert-butyl ((1r,4r)-4-(6-cyano-1-(naphthalen-1-ylmethyl)-1H-indole-2-carboxamido) cyclohexyl) carbamate (0.25 g, 0.478 mmol) was replaced in sealed tube added ethanol (20.0 mL) then passed dry HCl gas at 0° C. for 15 min, then stirred at RT for 16 h. After reaction completion, all the solvents were evaporated to dryness, washed with n-pentane to get the crude desired compound. (0.24 g, crude) LCMS: 469.3 (M+1)⁺.

Step 2: N-((1r,4r)-4-aminocyclohexyl)-6-(hydrazineyl(imino)methyl)-1-(naphthalen-1-ylmethyl)-1H-indole-2-carboxamide Product of Step 1 (0.469 g, 0.512 mmol), 1.0 M Hydrazine in THF (5.0 mL) and Ethanol (2.0 mL) replaced in sealed tube then stirred at RT for 5 h. After reaction completion, all the solvents were evaporated to dryness to get the crude, which purified by preparative HPLC. (15.0 mg). LCMS: 455.3 (M+1)⁺. ¹HNMR (CD3OD, 400 MHz): δ 1.45-1.40 (m, 4H), 1.99-1.91 (m, 2H), 2.15-2.14 (m, 3H), 3.06-3.03 (m, 1H), 3.69-3.68 (m, 1H), 6.27-6.25 (d, 1H), 6.42 (S, 2H), 7.21-7.17 (m, 1H), 7.28 (S, 2H), 7.48-7.46 (dd, 1H), 7.63-7.57 (m, 2H), 7.76-7.74 (d, 1H), 7.84 (S, 1H), 7.95-7.93 (m, 2H), 8.22-8.17 (m, 1H). HPLC: 93.20%.

TABLE 65
Compounds synthesized using synthetic scheme-51
| ID | Structure | LCMS [M + H]+ | $^1$H-NMR Data |
|---|---|---|---|
| I-664 | 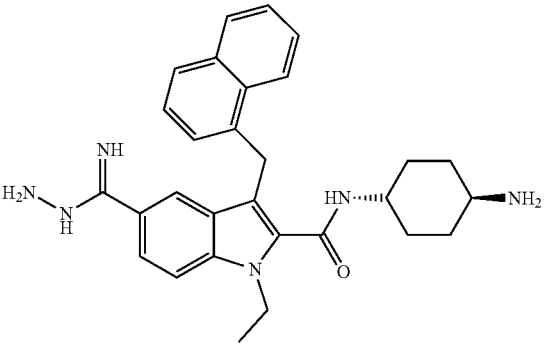 | 483.3 | $^1$H NMR (400 MHz, DMSO-d$_6$): δ 1.2-1.45 (m, 8H), 1.7-1.8 (m, 2H), 1.8-1.9 (m, 2H), 4.35-4.45 (m, 2H), 4.65 (s, 2H), 5.15-5.2 (m, 1H), 6.5 (s, 2H), 6.95-6.98 (d, 1H), 7.31-7.35 (m, 1H), 7.5-7.6 (m, 3H), 7.65-7.8 (m, 5H), 7.95 (d, 1H), 8.0 (s, 1H), 8.2-8.22 (m, 1H), 8.6-8.7 (m, 2H), 9.25 (s, 1H), 10.7 (s, 1H). |
| I-747 | 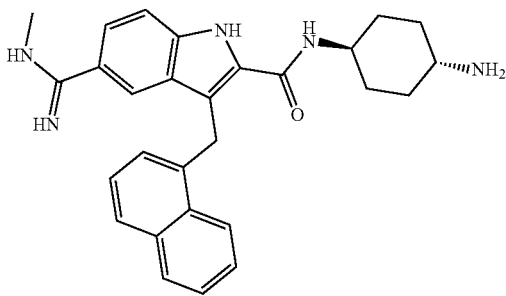 [SMILES: CNC(=N)c1ccc2[nH]c(C(=O)N[C@H]3CC[C@H](N)CC3)c(Cc3cccc4ccccc34)c2c1] | 454.2 | $^1$HNMR (CD$_3$OD, 400 MHz): δ 1.1-1.25 (q, 2H), 1.35-1.55 (q, 2H), 1.92-1.98 (t, 4H), 2.90-3.0 (m, 1H), 3.021 (s, 3H), 3.7-3.8 (m, 1H), 4.98 (s, 2H), 6.98-7.0 (d, 1H), 7.25-7.29 (t, 1H), 7.51-7.58 (m, 3H), 7.62-7.65 (d, 1H), 7.72-7.74 (d, 1H), 7.88-7.90 (d, 1H), 7.96 (s, 1H), 8.31-8.33 (d, 1H). |
Synthetic Scheme-52
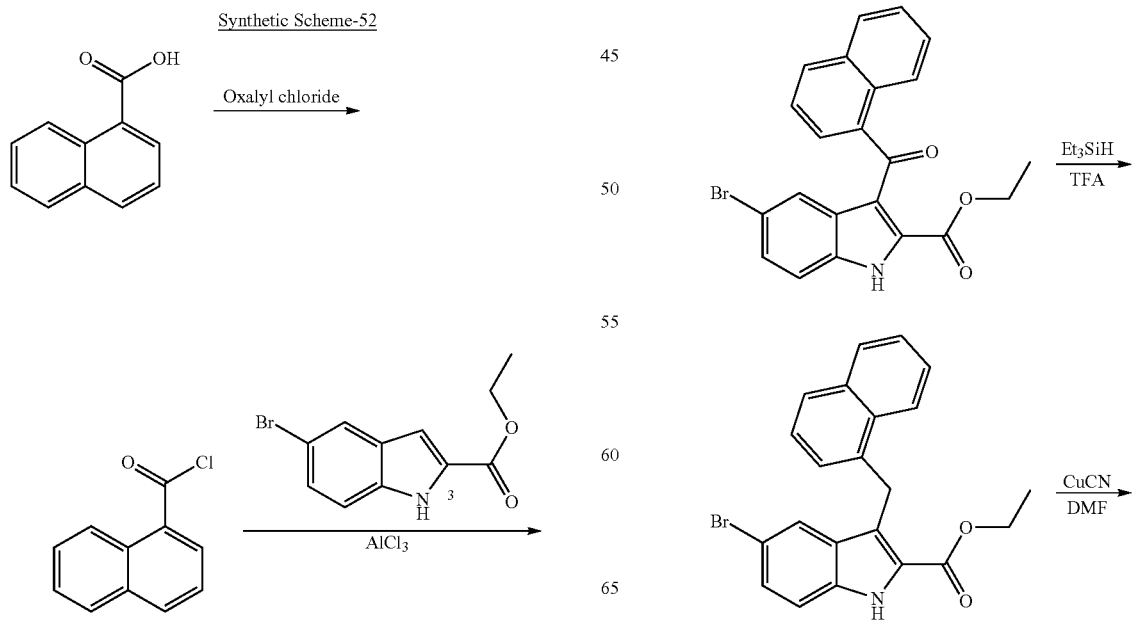

-continued

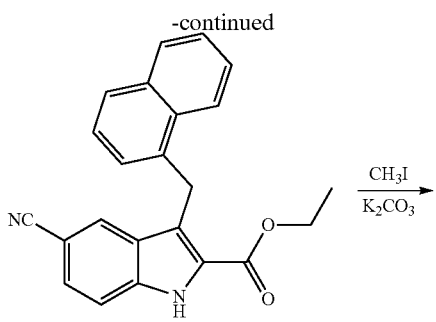

CH₃I, K₂CO₃ →

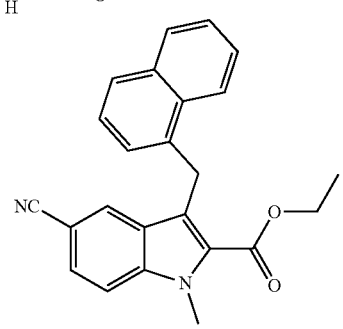

Step-1: 1-Naphthoyl Chloride

To a stirred solution of 1-Napthoic acid (5.0 g, 29.0 mmol) in DCM, was added oxalyl chloride (1.0 mL) and catalytic amount of DMF. Then reaction mixture stirred for 3 hrs at rt. After completion of reaction, evaporated under vacuum and used for the next step without any purification and analysis. (5.1 g, crude).

Step-2: ethyl 3-(1-naphthoyl)-5-bromo-1H-indole-2-carboxylate

To a stirred solution of 1-naphthoyl chloride (5.0 g, 18.6 mmol) in DCM was added Aluminium trichloride (3.96 g, 29.80 mmol) at 0° C. and stirred for 15 minutes at 0° C. Ethyl 5-bromo-1H-indole-2-carboxylate (5.67 g, 29.80 mmol) was added and reaction mixture heated to 40° C. for 8 hrs. After completion of the reaction diluted with DCM and washed with water, sodium bicarbonate solution. Organic layer dried over sodium sulphate and evaporated to get the crude product, which purified using combi flash with 10% Ethyl acetate in Hexane as an eluent. (4.6 g, 42%). LCMS: 424.0 (M+2)⁺.

Step-3: ethyl 5-bromo-3-(naphthalen-1-ylmethyl)-1H-indole-2-carboxylate

To a stirred solution of Ethyl 5-bromo-1H-indole-2-carboxylate (4.6 g, 10.9 mmol) in TFA (25 mL) was added Triethyl silane (125 mL) and the reaction was stirred for 48 hr at rt. After reaction completion, diluted with Hexane (100 mL). The resulting solid was filtered and dried under vacuum to give the crude product which was preceded for next step (4.0 g). LCMS: 407.95 (M−1)⁻

Step-4: ethyl 5-cyano-3-(naphthalen-1-ylmethyl)-1H-indole-2-carboxylate

In a sealed tube, Ethyl 5-bromo-3-(naphthalen-1-ylmethyl)-1H-indole-2-carboxylate (4.0 g, 9.82 mmol) was taken with DMF (50 mL) and copper cyanide (2.2 g, 24.5 mmol). Reaction mixture was stirred for 16 h at 140° C. After completion of the reaction, filtered through celite, water was added to the filtrate and extracted with ethyl acetate (2*100 mL). Combined organic layer was washed with brine solution, dried over anhydrous sodium sulphate and concentrated under vacuum to give the crude product which was proceeded for next step (3.8 g). LCMS: 353.10 (M−1)-.

Step-5: ethyl 5-cyano-1-methyl-3-(naphthalen-1-ylmethyl)-1H-indole-2-carboxylate To a stirred solution of Ethyl 5-cyano-3-(naphthalen-1-ylmethyl)-1H-indole-2-carboxylate (3.60 g, 10.16 mmol) in DMF (50 mL) were added potassium carbonate (4.20 g, 20.33 mmol) and methyl iodide (1.3 mL, 30.4 mmol). Then reaction was stirred for 6 h at 40° C. After completion of the reaction, water was added to the reaction mass and extracted with ethyl acetate (2*100 mL). Combined organic layer was washed with brine solution, dried over anhydrous sodium sulphate and concentrated under vacuum to give the crude product which purified using combi flash with 10% Ethyl acetate in Hexane as an eluent to get pure compound (2.1 g, 56.0%).

Synthetic Scheme-53

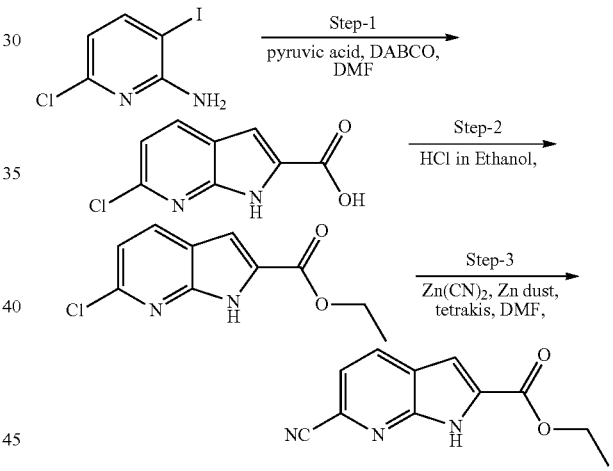

Step-1: 6-chloro-1H-pyrrolo[2,3-b]pyridine-2-carboxylic Acid 6-chloro-3-iodopyridin-2-amine (1.2 g, 4.71 mmol), Pyruvic acid (1.25 g, 14.19 mmol) and DABCO (1.59 g, 14.19 mmol) were taken in DMF (10 mL) and degassed for 10 mins with N₂ followed by palladium acetate (0.06 g, 0.23 mmol) was added and heated at 110° C. for 3 h. After reaction completion, cooled to room temperature, quenched with ice cold 1N HCl and precipitated solid was collected by filtration. Crude compound as such used for the next step without further purification (706 mg, crude). LCMS: 197.15 (M+1)⁺.

Step-2: ethyl 6-chloro-1H-pyrrolo[2,3-b]pyridine-2-carboxylate 6-chloro-1H-pyrrolo[2,3-b] pyridine-2-carboxylic acid (700 mg, 3.56 mmol) was taken in 1M HCl in ethanol (20 mL) and heated at 70° C. for 16 h. After reaction completion, evaporated under reduced pressure and separated between ethyl acetate and aqueous NaHCO$_3$ solution. The organic layer washed with water, dried over sodium sulphate and evaporated under reduced pressure to give the titled compound (750 mg, crude), which used further without purification. LCMS: 225.05 (M+1)$^+$.

Step-3: ethyl 6-cyano-1H-pyrrolo[2,3-b] pyridine-2-carboxylate

To a solution of ethyl 6-chloro-1H-pyrrolo[2,3-b] pyridine-2-carboxylate (500 mg, 2.22 mmol) in DMF (5 mL) were added zinc cyanide (264 mg, 2.24 mmol) and Zinc dust (15 mg, 0.22 mmol). After 10 mins degassed with N$_2$, Pd(dppf)Cl2·DCM complex (92 mg, 0.11 mmol) Was added. Reaction mixture was heated at 110° C. for 1 h. After reaction completion, cooled to room temperature, diluted with water: ethyl acetate (1:1) mixture. The organic layer washed with water, dried over sodium sulphate and evaporated under reduced pressure to give the crude compound which purified using combi flash with 30% Ethyl acetate in Hexane as an eluent to get pure compound. (300 mg, 63%). LCMS: 216.15 (M+1)$^+$.

Synthetic Scheme-54

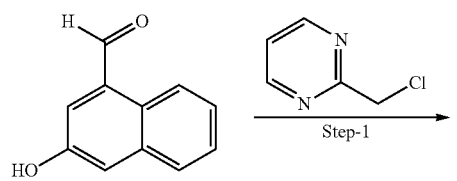

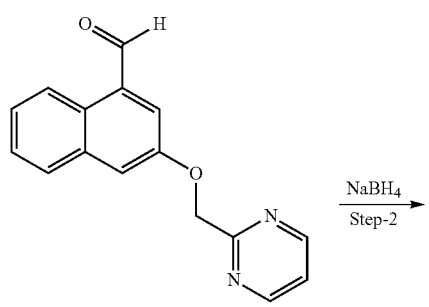

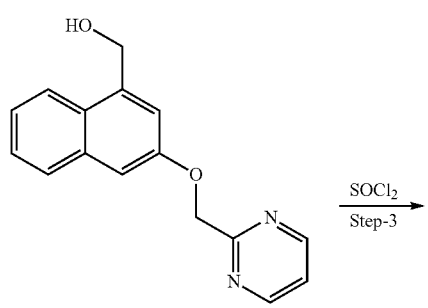

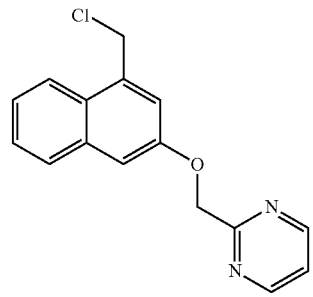

Step-1: Synthesis of 3-(pyrimidin-2-ylmethoxy)-1-naphthaldehyde

To a stirred a solution of 3-hydroxy-1-naphthaldehyde (250 mg, 1.45 mmol) in DMF (6.0 mL) was added cesium carbonate (1.5 g, 4.36 mmol) followed by 2-(chloromethyl) pyrimidine hydrogen chloride (238 mg, 1.45 mmol). The reaction mixture was stirred at room temperature. After reaction completion, quenched with water and extracted with ethyl acetate. The organic layer was dried over sodium sulphate and evaporated under reduced pressure to give the crude compound which purified using combi flash with 30% Ethyl acetate in Hexane as an eluent to get pure compound. 250 mg, LCMS: 265 (M+1)$^+$.

Step-2: (3-(pyrimidin-2-ylmethoxy)naphthalen-1-yl)methanol

To a stirred a solution of 3-(pyrimidin-2-ylmethoxy)-1-naphthaldehyde (250 mg, 0.94 mmol) in methanol (6.0 mL), was added sodium borohydride (113 mg, 2.84 mmol) under nitrogen atmosphere at 0° C. The resultant reaction mixture was stirred at RT for 2 h. After reaction completion, evaporated to dryness and quenched with water, which was extracted with ethyl acetate. The organic layer was dried over sodium sulphate and evaporated under reduced pressure to give the crude compound 225 mg, LCMS: 267 (M+1)$^+$.

Step-3: 2-(((4-(chloromethyl)naphthalen-2-yl)oxy) methyl)pyrimidine

To a stirred a solution of 3-(pyrimidin-2-ylmethoxy) naphthalen-1-yl)methanol (225 mg, 0.93 mmol) in DCM (5.0 mL), was added SOCl$_2$ (0.6 mL)) at 0° C. and the reaction mixture was stirred at RT for 1 h. After reaction completion, which was quenched with water and extracted with DCM. The organic layer was dried over sodium sulphate and evaporated under reduced pressure to give the crude compound 210 mg, $^1$HNMR (DMSO-d$_6$, 300 MHz): δ 5.22 (s, 2H), 5.41 (s, 2H), 7.36-7.37 (m, 2H), 7.43-7.49 (m, 4H), 7.78-7.81 (m, 1H), 8.04-8.07 (m, 1H), 8.83 (d, 2H). Similarly, following above experimental procedure listed below compounds have been synthesized.

TABLE 66

Compounds synthesized using synthetic scheme-54

| S. No | Compounds | Analytical data |
|---|---|---|
| 1 | ![structure] | $^1$HNMR (CDCl$_3$, 300 MHz): δ 5.05 (s, 2H), 7.07 (s, 2H), 7.5 (s, 1H), 7.57-7.641 (m, 3H), 7.86 (d, 1H), 8.14 (d, 1H), 8.648 (s, 1H) 8.83 (d, 1H). |
| 2 | ![structure] | $^1$HNMR (CDCl$_3$, 300 MHz): δ 5.05 (s, 2H), 6.68 (d, 1H), 7.25 (s, 1H), 7.57-7.641 (m, 3H), 7.79 (s, 1H), 7.81 (d, 1H), 8.11 (s, 1H) |
| 3 | ![structure] | $^1$HNMR (CDCl$_3$, 300 MHz): δ 3.35 (s, 3H) 5.05 (s, 2H), 7.57-7.641 (m, 3H), 7.79 (s, 1H), 7.81 (d, 1H), 8.11 (s, 1H), 9.58 (s, 1H) |
| 4 | ![structure] | $^1$HNMR (CDCl$_3$, 300 MHz): δ 3.90 (s, 3H) 5.05 (s, 2H), 6.53 (s, 1H) 7.45-7.67 (m, 4H) 7.86 (d, 1H), 8.14 (d, 1H), 8.25 (s, 1H). |
| 5 | ![structure] | 1HNMR (CDCl3, 600 MHz): δ 2.510 (s, 3H) 5.05 (s, 2H), 6.53 (s, 1H) 7.45-7.67 (m, 4H) 7.86 (d, 1H), 8.14 (d, 1H), 8.25 (s, 1H). |

TABLE 66-continued

Compounds synthesized using synthetic scheme-54

| S. No | Compounds | Analytical data |
|---|---|---|
| 6 | (naphthalene with CH2Cl and O-pyrimidine) | ¹HNMR (CDCl₃, 300 MHz): δ 5.25 (s, 2H), 7.40 (s, 1H), 7.54-7.641 (m, 3H), 7.86 (d, 1H), 8.14 (d, 2H), 8.31 (d, 1H) 8.50 (s, 1H). |
| 7 | (naphthalene with CH2Cl and O-SO2-phenyl) | ¹HNMR (DMSO-d₆, 300 MHz): δ 4.95 (s, 2H), 7.14 (s, 1H), 7.47-7.76 (m, 6H), 7.86 (d, 1H), 8.07 (d, 1H). |
| 8 | (naphthalene with CH2Cl and O-SO2-tolyl) | ¹HNMR (DMSO-d₆, 400 MHz): δ 2.42 (s, 3H), 5.25 (s, 2H), 7.39-7.48 (m, 3H), 7.59-7.68 (m, 3H), 7.76-7.78 (d, 2H), 7.94-7.96 (d, 1H), 8.15-8.17 (d, 1H). |
| 9 | (naphthalene with CH2Cl and O-SO2-Me) | ¹HNMR (CDCl₃, 300 MHz): δ 3.21 (s, 3H), 4.92 (s, 2H), 7.49-7.76 (m, 4H), 7.88-7.91 (d, 1H), 8.14-8.17 (d, 1H). |
| 10 | (naphthalene with CH2OH and O-5-fluoropyrimidine) | ¹HNMR (CDCl₃, 600 MHz): δ 5.16 (s, 2H), 7.40 (s, 1H), 7.46-7.48 (m, 2H), 7.50-7.53 (m, 2H), 7.57 (s 1H) 7.83-7.85 (m 1H) 8.03-8.05 (m 2H), 8.41 (d, 1H). |
| 11 | (naphthalene with CH2OH and O-4,6-dimethylpyrimidine) | ¹HNMR (CDCl₃, 300 MHz): δ 2.40 (s 6H) 5.16 (s, 2H), 6.78 (s 1H) 7.42 (d, 1H), 7.49-7.52 (m, 2H), 7.59 (d, 1H), 7.81-7.84 (m 1H) 8.07-8.10 (m 1H). |
| 12 | (naphthalene with CH2Cl and O-pyrazine) | ¹HNMR (CDCl₃, 300 MHz): δ 5.05 (s, 2H), 7.40 (s, 1H), 7.54-7.641 (m, 3H), 7.86 (d, 1H), 8.14 (d, 2H), 8.31 (d, 1H) 8.50 (s, 1H). |

Synthetic Scheme - 55

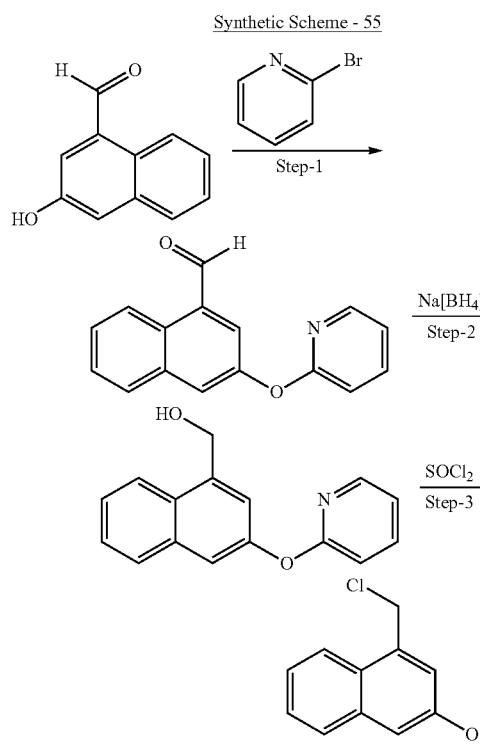

Step-1: 2-((4-(chloromethyl)naphthalen-2-yl)oxy)pyridine

To a stirred solution of 3-hydroxy-1-naphthaldehyde (250 mg, 1.45 mmol) in DMSO, were added potassium phosphate (630 mg, 2.90 mmol), 2-bromopyridine (455 mg, 2.90 mmol) Copper iodide (26.6 mg, 0.14 mmol) and picolinic acid (17.2 mg, 0.14 mmol). Then the reaction mixture stirred at 120° C. for 16 h. After reaction completion, cooled to rt, quenched with water and extracted with ethyl acetate. The organic layer was dried over sodium sulphate and evaporated under reduced pressure to give the crude compound which purified using combi flash with 25% Ethyl acetate in Hexane as an eluent to get pure compound 100 mg, LCMS: 250.1 (M+1)+.

Step-2: (3-(pyridin-2-yloxy)naphthalen-1-yl)methanol

Following experimental protocol of step-2 of synthetic scheme-54, above compound have been synthesized. LCMS: 252.1 (M+1)+.

Step-3: 2-((4-(chloromethyl)naphthalen-2-yl)oxy)pyridine

Following experimental protocol of step-3 of synthetic Scheme-54, above compound have been synthesized. ¹HNMR (CDCl₃, 400 MHz): δ 5.10 (s, 2H), 6.95-7.08 (m, 2H), 7.35 (s, 1H), 7.43-7.60 (m, 3H), 7.71 (t, 1H), 7.88 (d, 1H), 8.14 (d, 1H) 8.23 (s, 1H).

TABLE 67

Compounds synthesized using synthetic scheme-55

| S.No | Compounds | Analytical data |
|---|---|---|
| 1 | *[structure with 2-F-phenoxy]* | ¹HNMR (CDCl₃, 300 MHz): δ 5.02 (s, 2H), 7.15-7.24 (m, 5H) 7.38 (d, 1H) 7.46-7.50 (m, 2H), 7.69-7.72 (m, 1H) 8.071-8.10 (m 1H). |
| 2 | *[structure with 3-OMe-phenoxy]* | ¹HNMR (CDCl₃, 300 MHz): δ 3.76 (s 3H) 4.95(s, 2H) 6.8-6.88 (m, 2H), 6.97-6.99 (m, 2H) 7.08 (d, 1H) 7.26 (d, 1H), 7.39-7.41 (m, 1H) 7.60-7.62 (m 1H) 7.98-8.01 (m 1H). |
| 3 | *[structure with 4-OMe-phenoxy]* | ¹HNMR (CDCl₃, 300 MHz): δ 3.76 (s 3H) 4.95(s, 2H) 6.8-6.88 (m, 2H), 6.97-6.99 (m, 2H) 7.08 (d, 1H) 7.26 (d, 1H), 7.39-7.41 (m, 1H) 7.60-7.62 (m 1H) 7.98-8.01 (m 1H). |
| 4 | *[structure with 2-Cl-phenoxy]* | ¹HNMR (CDCl₃, 300 MHz): δ 5.02 (s, 2H) 7.09-7.30 (m, 4H), 7.37 (d, 1H) 7.49-7.53 (m, 3H) 7.70-7.72 (m, 1H), 8.08-8.11 (m, 1H). |

TABLE 67-continued
Compounds synthesized using synthetic scheme-55
| S.No | Compounds | Analytical data |
|---|---|---|
| 5 | | $^1$HNMR (CDCl$_3$, 300 MHz): δ 5.05 (s, 2H), 7.35 (s, 2H) 7.32-7.59 (m, 5H) 7.75-7.78 (m, 1H), 8.10-8.13 (m, 1H) 8.50 (b 1H) |
| 6 | | $^1$HNMR (CDCl$_3$, 300 MHz): δ 5.05 (s, 2H), 7.04 (s, 1H) 7.02-7.06 (m, 1H) 7.58-7.64 (m, 3H), 7.85 (d, 1H), 8.15 (d, 1H), 8.61-8.66 (m, 1H) 8.829.05 (d, 1H). |
| 7 | | $^1$HNMR (CDCl$_3$, 300 MHz): δ 5.05 (s, 2H), 7.35 (s, 2H) 7.32-7.59 (m, 5H) 7.75-7.78 (m, 1H), 8.10-8.13 (m, 1H) 8.50 (b 1H) |
| 8 | | $^1$HNMR (DMSO-d$_6$), 300 MHz): δ 5.30 (s, 2H), 7.42 (d 2H) 7.64-7.70 (m, 3H), 7.91 (s, 1H), 8.0 (d, 1H), 8.20 (d, 1H) 8.73(d, 2H). |
| 9 | | $^1$HNMR (CDCl$_3$, 300 MHz): δ 5.28 (s, 2H), 7.58-7.64 (m, 4H), 7.86-7.85 (m, 2H), 8.98 (d, 1H), 8.20 (d, 1H) 9.05 (d, 1H). |
| 10 | | $^1$HNMR (CDCl$_3$, 300 MHz): δ 5.01 (s, 2H), 7.08 (d, 2H) 7.17 (t, 1H) 7.26-7.41 (m, 4H), 7.49-7.51 (m, 2H) 7.71-7.74 (m 1H) 8.08-8.11 (m, 1H) |
Syntetic Scheme-56
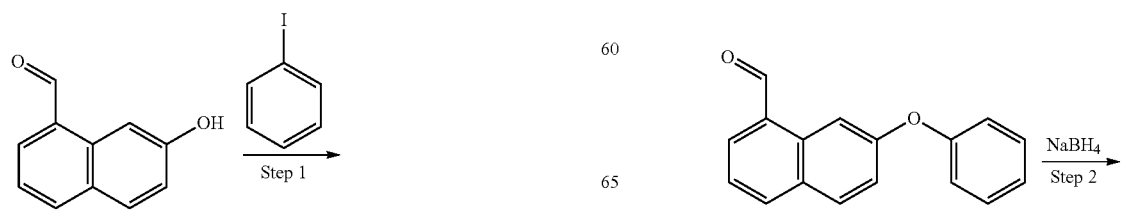

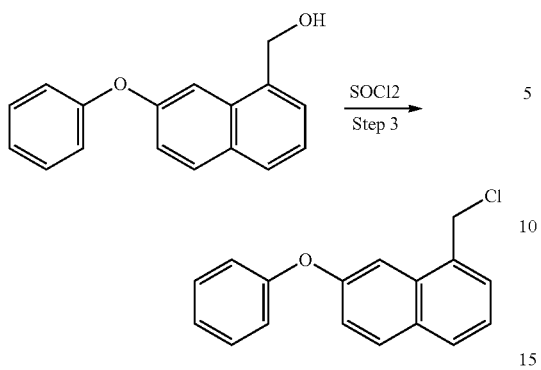
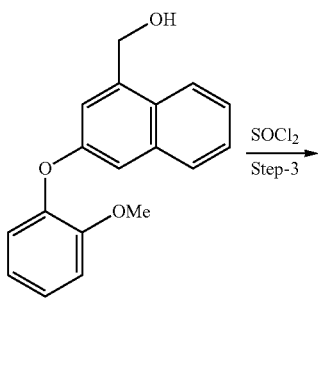

Step-1: 7-phenoxy-1-naphthaldehyde

Following experimental protocol of step-1 of synthetic Scheme-55, above compound have been synthesised. $^1$HNMR (DMSO-d$_6$, 300 MHz): δ (s, 2H), 7.36-7.37 (m, 2H), 7.43-7.49 (m, 4H), 7.78-7.81 (m, 1H), 8.04-8.07 (m, 1H), 8.83 (d, 2H).

Step-2: (7-phenoxynaphthalen-1-yl)methanol

Following experimental protocol of step-2 of synthetic Scheme-54 above compound have been synthesized. $^1$HNMR (DMSO-d$_6$, 300 MHz): δ 5.01 (s, 2H), 7.36-7.37 (m, 2H), 7.43-7.49 (m, 4H), 7.78-7.81 (m, 1H), 8.04-8.07 (m, 1H), 8.83 (d, 2H).

Step-3: 1-(chloromethyl)-7-phenoxynaphthalene

Following experimental protocol of step-3 of synthetic Scheme-54, above compound have been synthesised. $^1$HNMR (DMSO-d$_6$, 300 MHz): δ 4.91 (s, 2H), 7.36-7.37 (m, 2H), 7.43-7.49 (m, 4H), 7.78-7.81 (m, 1H), 8.04-8.07 (m, 1H), 8.83 (d, 2H).

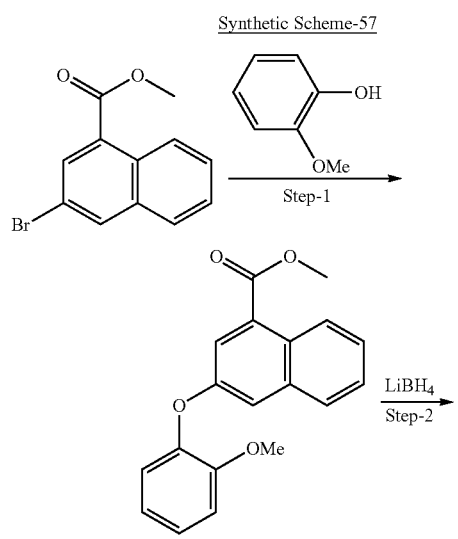

Synthetic Scheme-57

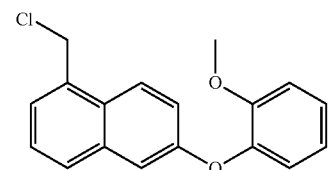

Step-1: methyl 3-(2-methoxyphenoxy)-1-naphthoate

To a solution of methyl 3-bromo-1-naphthoate (1 g, 0.380 mmol) in toluene (10 mL), were added K3PO4 (0.152 mmol) and 2-methoxyphenol (0.462 mmol). After 10 mins degassed with N$_2$, Pd(OAc)$_2$ (0.02 mmol) and t-Bu-Xphos (0.03 mmol) was added. Then the reaction mixture stirred at 100° C. for 16 h. After reaction completion, cooled to rt, quenched with water and extracted with ethyl acetate. The organic layer was dried over sodium sulphate and evaporated under reduced pressure to give the crude compound which purified using combi flash with 5% Ethyl acetate in Hexane as an eluent to get pure compound 480 mg, LCMS: 309.1 (M+1)$^+$.

Step-2: (3-(2-methoxyphenoxy)naphthalen-1-yl)methanol

To a stirred a solution of methyl 3-(2-methoxyphenoxy)-1-naphthoate (480 mg, 1.55 mmol) in Methanol (6.0 mL), was added 2.0M Lithium borohydride (2.3 ml, 4.63 mmol) under nitrogen atmosphere at 0° C. and stirred at RT for 2 h. After reaction completion, cooled to rt, quenched with water and extracted with ethyl acetate. The organic layer was dried over sodium sulphate and evaporated under reduced pressure to give the crude compound 350 mg, LCMS: 344.5 (M+1)$^+$.

Step-3: 1-(chloromethyl)-3-(2-methoxyphenoxy)naphthalene

Following experimental protocol of step-3 of synthetic Scheme-54, above compound have been synthesized. $^1$HNMR (CDCl3, 300 MHz): δ 3.83 (s, 3H), 5.01 (s, 2H), 6.97-7.12 (m, 4H), 7.18-7.21 (m, 1H), 7.36-7.48 (m, 2H), 7.62-7.73 (m, 1H), 8.05-8.12 (m, 1H).

TABLE 68

Compounds synthesized using synthetic scheme-57

| S.No | Compounds | Analytical data |
|------|-----------|-----------------|
| 1 | naphthalene with CH2OH, O-linked biphenyl | ¹HNMR (CDCl₃, 300 MHz): δ 5.167(s 3H) 7.12(d, 2H) 7.32 (d, 2H), 6.97-6.99 (m, 2H) 7.08 (d, 2H) 7.371-7.60 (m, 10H), 7.742 (d, 1H) 8.07 (d 1H). |
| 2 | naphthalene with CH2OH, O-linked methoxyphenyl | ¹HNMR (CDCl₃, 300 MHz): δ 3.76 (s 3H) 4.95(s, 2H) 6.81-6.88 (m, 2H), 6.97-6.99 (m, 2H) 7.08 (d, 1H) 7.26 (d, 1H), 7.39-7.41 (m, 1H) 7.60-7.62 (m 1H) 7.98-8.01 (m 1H). |

Synthetic Scheme-58

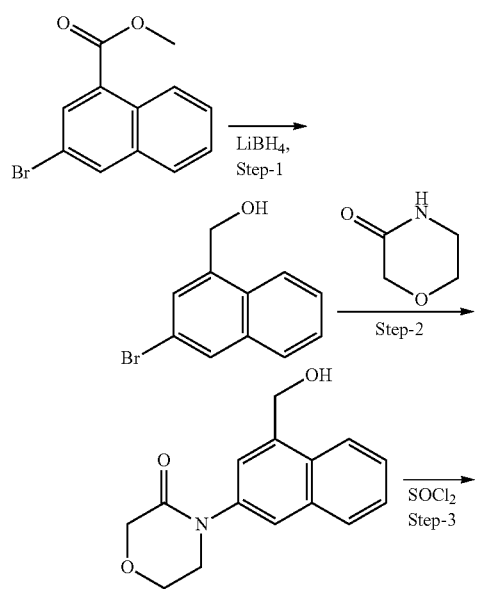

Step-1; (3-bromonaphthalen-1-yl)methanol

Following experimental protocol of step-2 of synthetic Scheme-57, above compound have been synthesized. LCMS: 238.5 (M+1)⁺.

Step-2: 4-(4-(hydroxymethyl)naphthalen-2-yl)morpholin-3-one

To a solution of (3-bromonaphthalen-1-yl)methanol (1 g, 0.005 mol) in toluene (10 mL), were added K3PO4 (0.4 g, 0.0004 mol), morpholin-3-one (0.6 g, 0.0062 mmol), trans-N,N'-Dimethylcyclohexane-1,2-diamine (0.2 g 0.0015 mol) and Copper iodide (0.2 g, 0.0002 mol) was added. Then the reaction mixture stirred at 90° C. for 16 h. After reaction completion, cooled to rt, quenched with water and extracted with ethyl acetate. The organic layer was dried over sodium sulphate and evaporated under reduced pressure to give the crude compound which purified using combi flash with 10% Ethyl acetate in Hexane as an eluent to get pure compound 500 mg. LCMS: 258.2 (M+1)⁺.

Step-3: 4-(4-(chloromethyl)naphthalen-2-yl)morpholin-3-one

Following experimental protocol of step-3 of synthetic Scheme-54, above compound have been synthesized. ¹HNMR (CDCl₃, 300 MHz): δ 3.85-3.89 (m, 2H), 4.07-4.10 (m, 2H), 4.39 (s, 2H), 5.15 (d, 2H), 7.53-7.57 (m, 3H), 7.72 (d, 1H), 7.83-7.91 (m, 1H), 8.03-8.09 (m, 1H).

Synthetic Scheme-59

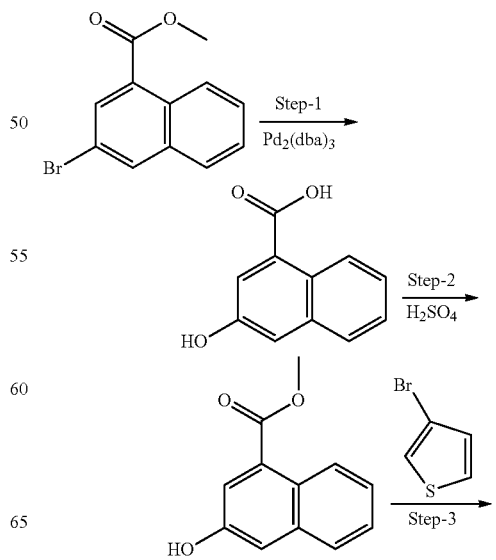

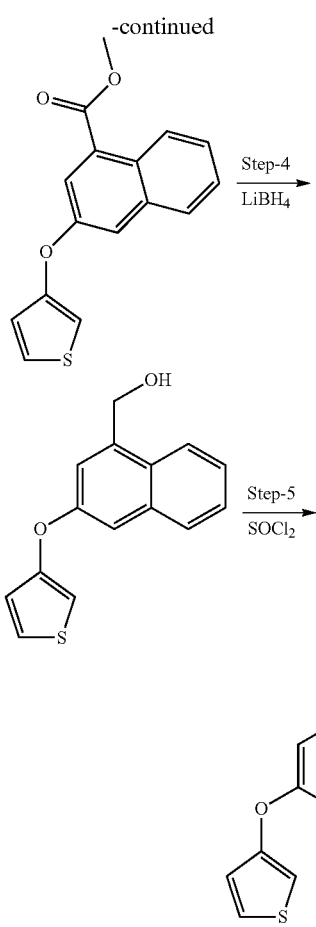

Step-1: 3-hydroxy-1-naphthoic Acid

To a stirred solution of methyl 3-bromo-1-naphthoate (5 g, 1.259 mmol) in dioxane (50 ml), KOH (3.2 g, 0.57 mmol) dissolved in water was added. After 10 mins degassed with argon Pd(dba)₃ (0.4 g 0.019 mmol) and t-Bu-Xphos (2.4 g, 0.057 mmol) was added. Then the reaction mixture stirred at 90° C. for 1 h. After reaction completion, cooled to rt, quenched with water, acidified with 1N HCl to $_p$H 3 and extracted with ethyl acetate. The organic layer was dried over sodium sulphate and evaporated under reduced pressure to give 3.3 g of the crude compound. LCMS: 238.2 (M+1)⁺.

Step-2: methyl 3-hydroxy-1-naphthoate

To a stirred a solution of 3-hydroxy-1-naphthoic acid (3.3 g, 0.017 mol) in methanol, was added H2SO4 (1.5 ml,) at 0° C. and the reaction mixture was stirred at 60° C. for 6 h. After reaction completion, the mixture was evaporated and extracted with water and ethyl acetate mixture. The organic layer was dried over sodium sulphate and evaporated under reduced pressure to give the crude compound, which was purified by using combi-flash to give 2 g of the pure compound. LCMS: 238.1 (M+1)⁺.

Step-3: methyl 3-(thiophen-3-yloxy)-1-naphthoate

In a microwave vial, methyl 3-hydroxy-1-naphthoate (1.0 g, 0.490 mmol) was taken in dioxane (25 ml). Then to that potassium carbonate (2.0 g, 0.014 mol), 3-bromothiophene (0.95 g, 0.55 mmol), and copper (0.56 g, 0.25 mmol) was added and which was irradiated with micro wave 120° C. for 16 h. After reaction completion, reaction mass cooled to rt, quenched with water and extracted with ethyl acetate. The organic layer was dried over sodium sulphate and evaporated under reduced pressure to give the crude compound, which was purified by using combi-flash to give 260 mg of pure compound. LCMS: 238.1 (M+1)⁺.

Step-4: (3-(thiophen-3-yloxy)naphthalen-1-yl)methanol

Following experimental protocol of step-2 of synthetic Scheme-57 above compound have been synthesized.

Step-5: 3-((4-(chloromethyl)naphthalen-2-yl)oxy)thiophene

Following experimental protocol of step-3 of synthetic Scheme-57 above compound have been synthesized. ¹HNMR (CDCl₃, 600 MHz): δ 5.01 (s, 2H), 6.72 (d, 1H), 6.91 (d, 1H), 7.31-7.32 (m, 1H), 7.38 (d, 1H), 7.42-7.50 (m, 2H), 7.73-7.75 (m, 1H) 7.92 (d, 1H) 8.08 (d, 1H).

Synthetic Scheme-60

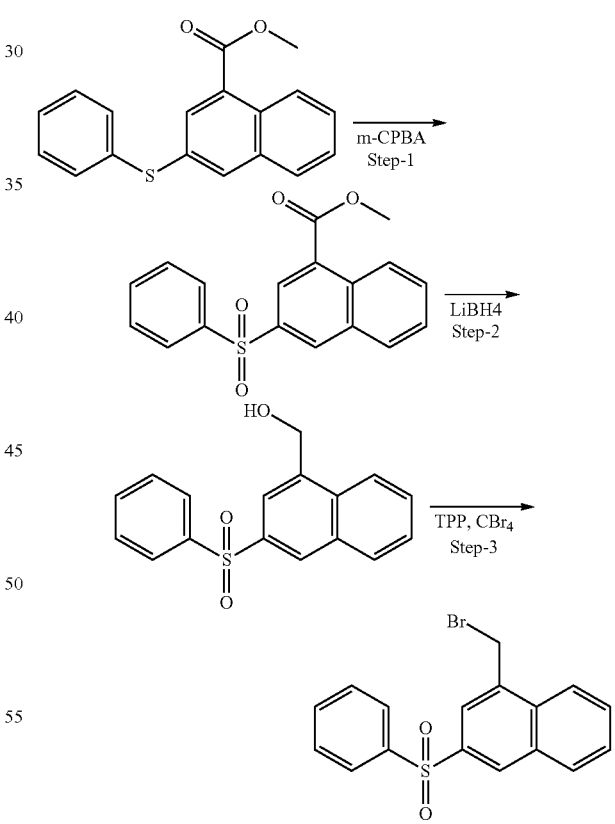

Step-1: methyl 3-(phenylsulfonyl)-1-naphthoate

To a stirred a solution of methyl 3-(phenylthio)-1-naphthoate (300 mg, 1.02 mmol) in DCM (4.0 ml), was added m-CPBA (438 mg, 2.55 mmol) under nitrogen atmosphere at 0° and stirred at room temperature for 2 h. After reaction completion, quenched with water, extracted with ethyl acetate. The organic layer washed with sodium bicarbonate, dried over sodium sulphate, evaporated under reduced pressure to get 210 mg of the desired product. LCMS: 327.1 (M+1)⁺.

Step-2: (3-(phenylsulfonyl)naphthalen-1-yl)methanol

Following experimental protocol of step-2 of synthetic Scheme-57 above compound have been synthesized.

Step-3: 1-(bromomethyl)-3-(phenylsulfonyl)naphthalene

To a stirred a solution of (3-(phenylsulfonyl)naphthalen-1-yl)methanol (140 mg, 0.56 mmol) in DCM, were added triphenylphosphine (295 mg, 1.22 mmol) and CBr₄ (372 mg, 1.22 mmol) at 0° C. Reaction mixture was stirred at reflux condition for 16 h. After reaction completion, quenched with water and extracted with ethyl acetate. The organic layer dried over sodium sulphate and evaporated under reduced pressure to give the crude compound, which was purified by using combi-flash to give 150 mg of 1-(bromomethyl)-3-(phenylsulfonyl)naphthalene. ¹HNMR (CDCl₃, 300 MHz): δ 4.92 (s, 2H), 7.45-7.62 (m, 4H), 7.64-7.74 (m, 1H), 7.81 (t, 1H), 7.93 (d, 1H), 8.02-8.19 (m, 2H), 8.20 (d, 1H) 8.52 (s, 1H).

Step-1; (3-chloro-4-(chloromethyl)naphthalen-2-yl)(phenyl)sulfane

To a stirred a solution of (3-(phenylsulfinyl)naphthalen-1-yl)methanol (100 mg, 0.35 mmol) in DCM (5.0 mL), was added SOCl₂ (0.6 mL)) at 0° C. and the reaction mixture was stirred at RT for 1 h. After reaction completion, quenched with water and extracted with DCM. The organic layer was dried over sodium sulphate and evaporated under reduced pressure to get 210 mg of a desired compound. ¹HNMR (CDCl₃, 300 MHz): δ 4.92 (s, 2H), 7.08 (s, 1H), 7.37-7.47 (m, 3H), 7.48-7.65 (m, 4H), 8.05 (d, 1H), 8.33 (d, 1H).

TABLE 69

Compounds synthesized using synthetic scheme-60

| S.No | Compounds | Analytical data |
|---|---|---|
| 1 | ![structure] | ¹HNMR (CDCl₃, 300 MHz): δ 4.92 (s 2H) 7.25-7.33(m, 3H) 7.34-7.41 (m, 2H), 7.47 (s, 1H) 7.51 (t, 1H) 7.51 (t, 1H), 7.75-7.77 (m, 2H) 8.01 (d 1H). |
| 2 | ![structure] | ¹HNMR (CDCl₃, 400 MHz): δ 4.86 (s, 2H) 7.30-7.41 (m, 5H), 7.48-7.62 (m, 3H) 7.66-7.80 (m, 2H) 8.12 (d, 1H). |

Synthetic Scheme-61

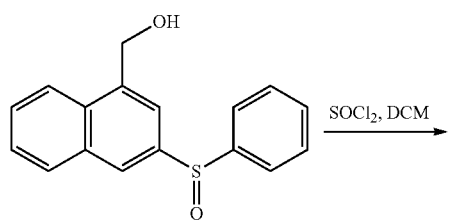

Synthetic Scheme-62

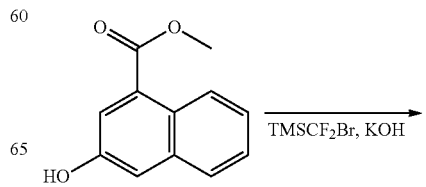

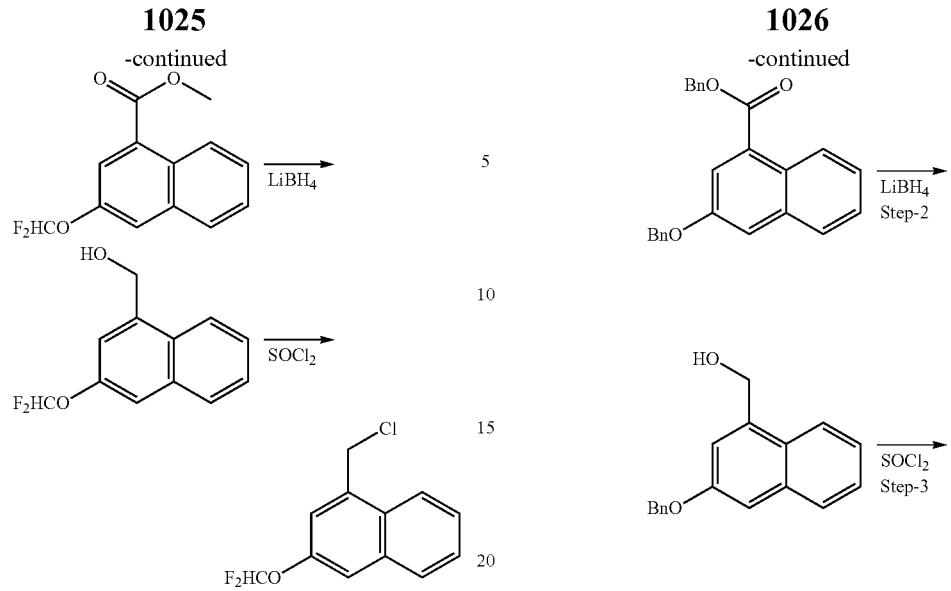

Step-1: 3-((4-(chloromethyl)naphthalen-2-yl)oxy) thiophene

To a stirred a solution of methyl 3-hydroxy-1-naphthoate (450 mg, 2.20 mmol) in DCM (5 ml) were added potassium hydroxide (370 mg, 6.63 mmol) and (Bromodifluoromethyl) trimethylsilane (670 mg, 3.32 mmol) at 0° C. The reaction mixture was stirred at rt for 3 h. After reaction completion, quenched with water and extracted with ethyl acetate. The organic layer was dried over sodium sulphate and evaporated under reduced pressure to get a crude compound, which was purified by using combi-flash, to get 130 mg of 1-(chloromethyl)-3-(difluoromethoxy) naphthalene.

Step-2: (3-(difluoromethoxy) naphthalen-1-yl)methanol

Following experimental protocol of step-2 of synthetic Scheme-57 (3-(difluoromethoxy) naphthalen-1-yl) methanol have been synthesized.

Step-3: 1-(chloromethyl)-3-(difluoromethoxy) naphthalene

Following experimental protocol of step-3 of synthetic Scheme-57 1-(chloromethyl)-3-(difluoromethoxy) naphthalene have been synthesized. $^1$HNMR (CDCl$_3$, 300 MHz): δ 4.02 (s, 3H), 6.42 (s, 0.3H), 6.66 (d, 0.3H), 6.83 (s, 0.3H) 7.54-7.60 (m, 2H), 7.71 (d, 1H), 7.82-7.87 (m, 1H), 7.98 (d, 1H) 8.89 (d, 1H) 8.08 (d, 1H).

Synthetic Scheme-63

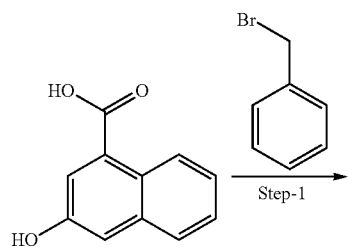

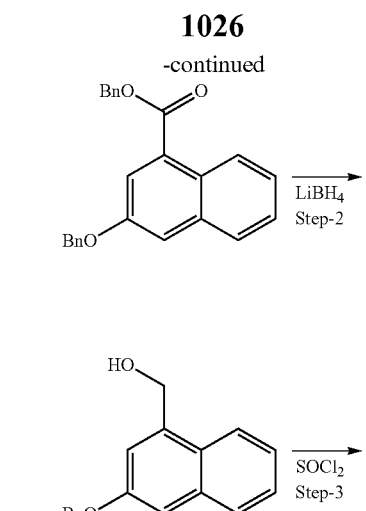

Step-1: benzyl 3-(benzyloxy)-1-naphthoate

To a stirred a solution of 3-hydroxy-1-naphthoic acid (310 mg, 1.64 mmol) in DMF (4.0 ml), was added potassium carbonate (682 mg, 4.94 mmol) followed by (bromomethyl) benzene (352 mg, 1.97 mmol). The reaction mixture was stirred at room temperature for 4 h. After reaction completion, quenched with water and extracted with ethyl acetate. The organic layer was dried over sodium sulphate and evaporated in under reduced pressure to get a crude compound, which was purified by using combi-flash with 30% EA/Hex, to get 250 mg of benzyl 3-(benzyloxy)-1-naphthoate. LCMS: 253.1 (M+1)$^+$.

Step-2: (3-(benzyloxy)naphthalen-1-yl)methanol

Following experimental protocol of step-2 of synthetic Scheme-57 (3-(benzyloxy)naphthalen-1-yl)methanol have been synthesized. $^1$HNMR (CDCl$_3$, 300 MHz): δ 5.01 (s, 2H), 6.72 (d, 1H), 6.91 (d, 1H), 7.31-7.32 (m, 1H), 7.38 (d, 1H), 7.42-7.50 (m, 2H), 7.73-7.75 (m, 1H) 7.92 (d, 1H) 8.08 (d, 1H).

Step-3: 3-(benzyloxy)-1-(chloromethyl)naphthalene

Following experimental protocol of step-3 of synthetic Scheme-57 3-(benzyloxy)-1-(chloromethyl) naphthalene have been synthesized. $^1$HNMR (CDCl$_3$, 300 MHz): δ 5.21 (s, 2H), 6.72 (d, 1H), 6.91 (d, 1H), 7.31-7.32 (m, 1H), 7.38 (d, 1H), 7.42-7.50 (m, 2H), 7.73-7.75 (m, 1H) 7.92 (d, 1H) 8.08 (d, 1H).

TABLE 70

Compounds synthesized using synthetic scheme-63

| S.No | Compounds | Analytical data |
|---|---|---|
| 1 | | $^1$HNMR (CDCl$_3$, 300 MHz): δ 3.17 (t 2H) 4.30 (t 2H) 5.10 (d 2H) 7.08 (d, 9H) 7.23-7.48 (m, 6H), 7.71 (d, 1H) 7.99 (d, 1H). |
| 2 | | $^1$HNMR (CDCl$_3$, 300 MHz): δ 2.13-2.22 (m 2H) 2.84-2.89 (m 2H) 4.06-4.11 (m 2H) 5.01 (s, 2H) 7.13-7.40 (m, 9H) 7.68-7.72 (m, 1H), 8.06 (d, 1H). |

Synthetic Scheme-64

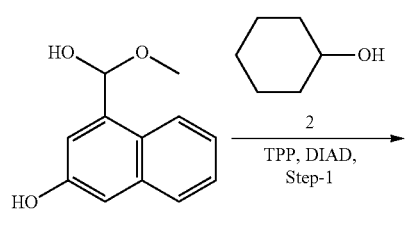

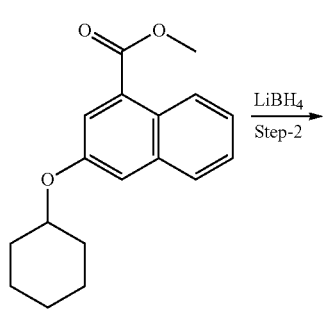

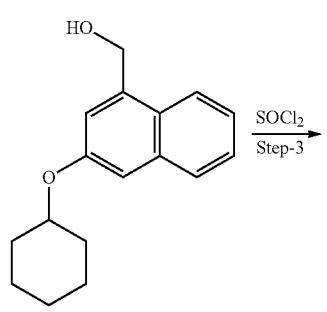

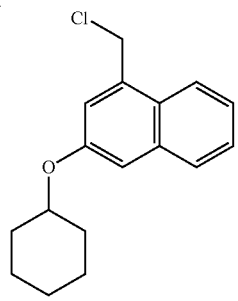

Step-1: 3-(cyclohecyloxy)-1-naphthoate

To a stirred a solution of methyl 3-hydroxy-1-naphthoate (500 mg, 2.47 mmol) in toluene (5.0 ml), was added cyclohexanol (321 mg, 3.2 mmol), triphenyl phosphene (970 mg, 3.7 mmol) followed by Diisopropyl azodicarboxylate (748 mg, 3.7 mmol) under nitrogen atmosphere and heated at 80° C. for 16 h. After reaction completion, quenched with water and extracted with ethyl acetate. The organic layer was dried over sodium sulphate and evaporated under reduced pressure to get 210 mg of methyl 3-(cyclohexyloxy)-1-naphthoate. LCMS: 286.1 (M+1)$^+$.

Step-2: (3-(cyclohexyloxy)naphthalen-1-yl)methanol

Following experimental protocol of step-2 of synthetic Scheme-57 (3-(cyclohexyloxy)naphthalen-1-yl)methanol have been synthesized. $^1$HNMR (CDCl$_3$, 300 MHz): δ 1.23-1.48 (m, 3H), 1.5-1.6 (m, 2H), 1.8 (d, 2H), 2.08 (d, 2H), 5.06 (s, 2H), 7.10 (d, 1H), 7.22-7.40 (m, 3H) 7.74 (d, 1H) 7.97 (d, 1H).

Step-3: 1-(chloromethyl)-3-(cyclohexyloxy)naphthalene

Following experimental protocol of step-3 of synthetic Scheme-57 3-(benzyloxy)-1-(chloromethyl)naphthalene have been synthesized. $^1$HNMR (CDCl$_3$, 300 MHz): δ 1.23-1.48 (m, 3H), 1.5-1.6 (m, 2H), 1.8 (d, 2H), 2.08 (d, 2H), 4.96 (s, 2H), 7.10 (d, 1H), 7.22-7.40 (m, 3H) 7.74 (d, 1H) 7.97 (d, 1H).

Synthetic Scheme-65

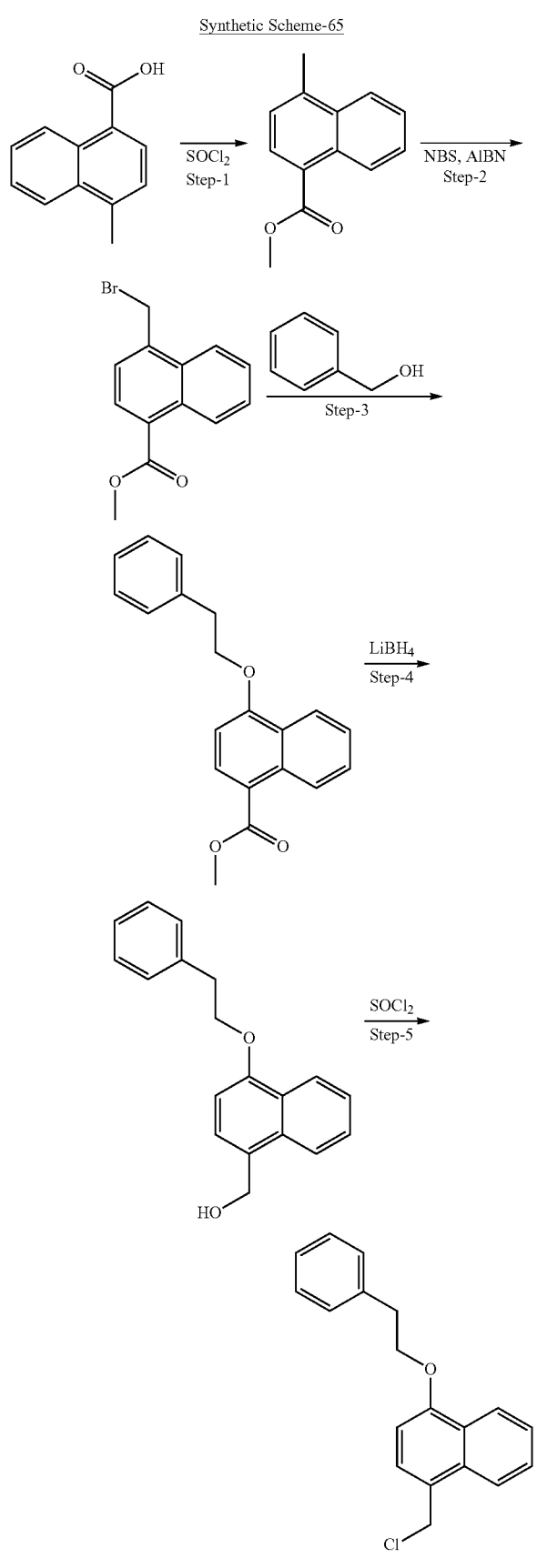

Step-1: methyl 4-methyl-1-naphthoate

To a stirred a solution of 4-methyl-1-naphthoic acid (2.0 g, 0.001 mol) in methanol (20 ml), was added $SOCl_2$ (0.8 ml) at 0° C. and the reaction mixture was stirred at 60° C. for 4 h. After reaction completion, methanol was evaporated, quenched with water and extracted with ethyl acetate. The organic layer was dried over sodium sulphate and evaporated under reduced pressure to get a crude compound, which was purified by using combi-flash, to get 2.1 g of methyl 4-methyl-1-naphthoate. LCMS: 201.1 $(M+1)^+$.

Step-2: methyl 4-(bromomethyl)-1-naphthoate

To a stirred solution of 4-methyl-1-naphthoate (2.1 g, 0.01 mol) in CCl4 (20 ml), was added azobisisobutyronitrile (2.6 g, 0.015 mol) and NBS (1.8 g, 0.015 mol). The reaction mixture was stirred at 60° C. for 4 h. After reaction completion, reaction mixture was evaporated, quenched with water and extracted with ethyl acetate. The organic layer was dried over sodium sulphate and evaporated under reduced pressure to get a crude compound. It was purified by using combi-flash with 18% Ethyl acetate in Hexane as an eluent to get 2.3 g of methyl 4-(bromomethyl)-1-naphthoate. LCMS: 277.1 $(M+1)^+$.

Step-3: methyl 4-((benzyloxy)methyl)-1-naphthoate

To a suspension of NaH (400 mg, 8.5 mol) in THF was added phenyl methanol (550 mg, 5.1 mmol) at 0° C. and the resulting mixture was stirred at rt for 10 mins. Then, methyl 4-(bromomethyl)-1-naphthoate (850 mg, 4.25 mmol) was added and the reaction mixture was stirred at rt for 3 h. After reaction completion, quenched with water and extracted with ethyl acetate. The organic layer was dried over sodium sulphate and evaporated under reduced pressure to get a crude compound. It was purified by using combi-flash, to get a 550 mg of methyl 4-((benzyloxy)methyl)-1-naphthoate. LCMS: 306.1 $(M+1)^+$.

Step-4: (4-((benzyloxy)methyl)naphthalen-1-yl)methanol

Following experimental protocol of step-2 of synthetic Scheme-57 (4-((benzyloxy)methyl)naphthalen-1-yl)methanol have been synthesized. LCMS: 297.2 $(M+1)^+$.

Step-5: 1-((benzyloxy)methyl)-4-(chloromethyl)naphthalene

Following experimental protocol of step-3 of synthetic Scheme-57 1-((benzyloxy)methyl)-4-(chloromethyl)naphthalene have been synthesized. $^1$HNMR (CDCl3, 300 MHz): δ 4.96 (s, 2H), 5.0 (s, 2H), 5.05 (s, 2H), 7.32-7.63 (m, 9H), 8.14-8.20 (m, 2H).

TABLE 71

Compounds synthesized using synthetic scheme-65

| S.No | Compounds | Analytical data |
|---|---|---|
| 1 | ![compound] | ¹HNMR (CDCl₃, 300 MHz): δ 4.06 (s 2H), 4.92 (s, 2H), 5.03 (s 2H), 7.13-7.17 (m, 6H), 7.26-7.32 (m, 9H), 7.39- 7.61 (m, 6H), 7.69 (s 1H), 8.08-8.18 (m 2H) |

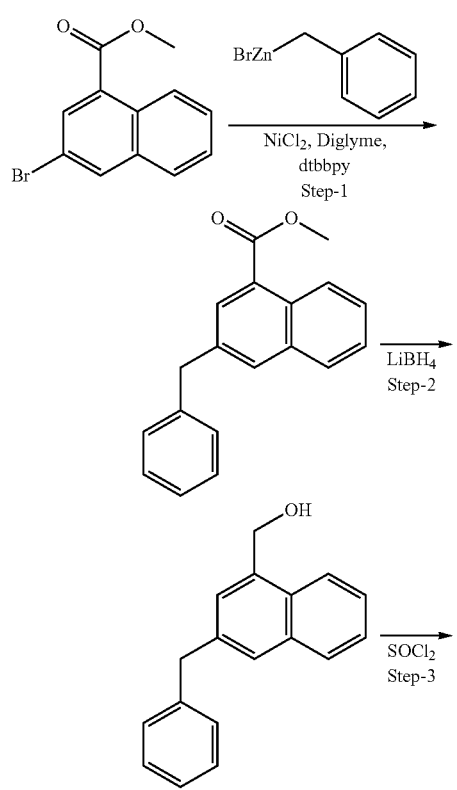

Synthetic Scheme-66

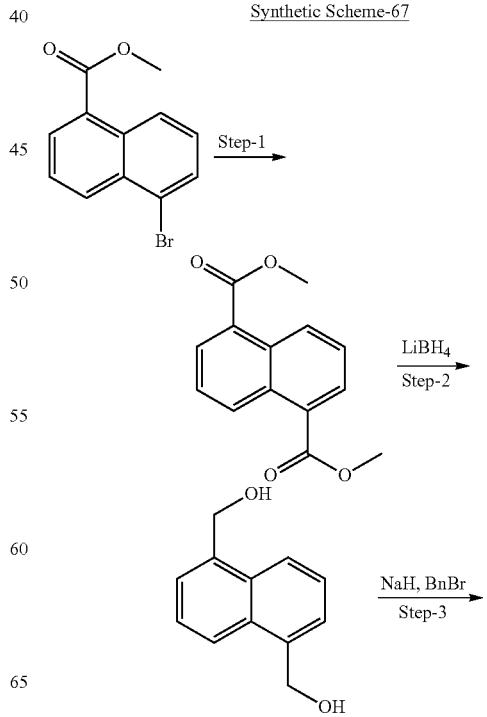

Synthetic Scheme-67

Step-1: methyl 3-benzyl-1-naphthoate

To a stirred a solution of methyl 3-bromo-1-naphthoate (228 mg, 0.867 mmol) in THF (5 ml) was added benzyl zinc(II) bromide (3.5 ml, 1.73 mmol) and degaussed with nitrogen for 5 mins. Then NiCl₂·Diglyme (3 mg, 0.03 mmol), 4,4'-Di-tert-butyl-2,2'-dipyridyl (8 mg 0.015 mmol) was added and kept under photo irradiation for 3 h. After reaction completion, the reaction mixture was diluted with ammonium chloride solution and extracted with ethyl acetate. The organic layer was dried over sodium sulphate and evaporated under reduced pressure to get a crude compound. It was purified by using combi-flash with Ethyl acetate in hexane as an eluent, to get pure compound methyl 3-benzyl-1-naphthoate.

Step-2: (3-benzylnaphthalen-1-yl)methanol

Following experimental protocol of step-2 of synthetic Scheme-57 (3-benzylnaphthalen-1-yl)methanol have been synthesized.

Step-3: 3-benzyl-1-(chloromethyl)naphthalene

Following experimental protocol of step-3 of synthetic Scheme-57 3-benzyl-1-(chloromethyl)naphthalene have been synthesised. ¹HNMR (CDCl₃, 300 MHz): δ 4.13 (s, 2H), 5.09 (d, 2H) 7.22-7.32 (m, 5H), 7.37 (s, 1H), 7.36 (s, 1H), 7.49 (t, 1H) 7.612 (s, 1H), 7.80 (d, 1H) 8.08 (d, 1H).

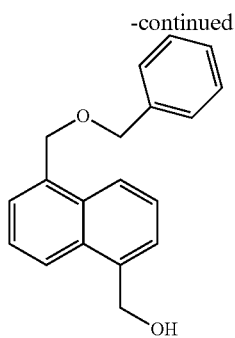

CBr₄, PPh₃
Step-4

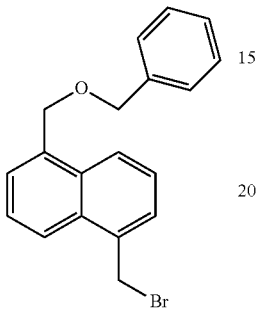

Step-1: dimethyl naphthalene-1,5-dicarboxylate

In a steel bomb, methyl 5-bromo-1-naphthoate (500 mg, 2.31 mmol), DIPEA (1.5 g, 14.2 mmol,) was taken in methanol, and degaussed with $N_2$ gas for 15 min. Pd(dppf)Cl₂ (88 mg, 0.212) was added and stirred under 80 PSI at 80° C. for 16 h. After reaction completion, the reaction mixture was diluted with water and extracted with ethyl acetate. The organic layer was dried over sodium sulphate and evaporated under reduced pressure to get a crude compound. It was purified by using combi-flash with Ethyl acetate in Hexane, to get pure compound dimethyl naphthalene-1,5-dicarboxylate. LCMS: 244.1 (M−1)⁺.

Step-2: naphthalene-1,5-diyldimethanol

Following experimental protocol of step-2 of synthetic Scheme-57, (5-((benzyloxy)methyl)naphthalen-1-yl)methanol compound have been synthesized.

Step-3: (5-((benzyloxy)methyl)naphthalen-1-yl)methanol

To a suspension of NaH (200 mg, 4.255 mmol) in DMF was added naphthalene-1,5-diyldimethanol (400 mg, 2.1277 mmol) at 0° C. and the resulting mixture was stirred at rt for 10 mins. Then benzyl bromide (545 mg, 3.19 mmol) was added and stirred at rt for 16 h. After reaction completion, quenched with water and extracted with ethyl acetate. The organic layer was dried over sodium sulphate and evaporated under reduced pressure to get a crude compound. It was purified by using combi-flash to get a (5-((benzyloxy)methyl)naphthalen-1-yl)methanol. LCMS: 276 (M−1)⁺.

Step-4: 1-((benzyloxy)methyl)-5-(bromomethyl)naphthalene

Following experimental protocol of step-3 of synthetic Scheme-60, 1-((benzyloxy)methyl)-5-(bromomethyl)naphthalene have been synthesized. ¹HNMR (CDCl₃, 400 MHz): δ 4.62 (s, 2H), 4.99 (s, 2H) 5.23 (s, H) 7.35 (d, 5H), 7.52 (t, 1H), 7.626 (t, 2H), 7.73 (d, 1H) 8.119 (d, 2H).

TABLE 72

Compounds synthesized using synthetic scheme-67

| S.No | Compounds | Analytical data |
|---|---|---|
| 1 | ![structure] | 1HNMR (CDCl₃, 300 MHz): δ 5.06 (s 2H) 5.43 (s, 2H) 7.35-7.45 (m, 4H), 7.48-7.50 (m, 2H) 7.60-7.72 (m, 1H) 7.99 (d, 1H), 8.13-8.19 (m, 2H) 8.64 (s 1H). |
| 2 | ![structure] | 1HNMR (CDCl₃, 300 MHz): δ 1.078 (d 6H) 2.172 (d 1H) 4.19 (s 2H) 7.53-7.69 (m, 2H), 8.02 (d, 1H) 8.12 (t, 2H) 8.577 (d, 1H). |

Synthetic Scheme-68

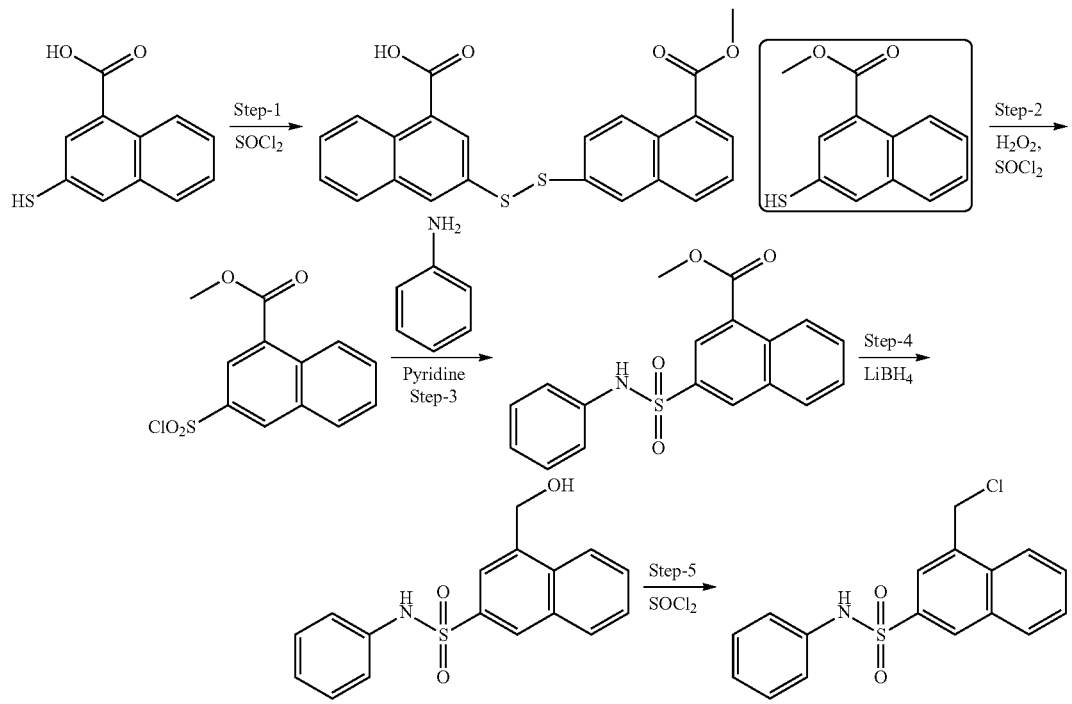

Step-1: dimethyl 3,3'-disulfanediylbis(1-naphthoate)

To a stirred a solution 3-mercapto-1-naphthoic acid (0.7 g) in 5 ml of Methanol was added SOCl2 (0.2 ml, 0.013 mmol) at 0° C. under nitrogen atmosphere and the reaction mixture was heated at 80° C. for 16 h. After reaction completion, evaporated to remove methanol and which was dissolved with water and extracted with ethyl acetate. The organic layer dried over $Na_2SO_4$ and evaporated under reduced pressure to get crude. It was purified with 20% EA/Hexane by using combi-flash to get dimethyl 3,3'-disulfanediylbis (1-naphthoate) (0.2 g) & methyl 3-mercapto-1-naphthoate (0.25 g). $^1$HNMR (CDCl$_3$, 300 MHz): δ 3.65 (s, 1H) 4.00 (s, 3H), 7.52 (t, 2H), 7.64 (d, 1H), 7.91 (s, 1H), 8.13 (d, 1H), 8.9 (d, 1H).

Step-2: methyl 3-(chlorosulfonyl)-1-naphthoate

To a stirred a solution of dimethyl 3,3'-disulfanediylbis (1-naphthoate) (0.2 g, 0.001 mmol) in acetonitrile was added SOCl$_2$ (0.1 ml) and H$_2$O$_2$ (0.5 ml) under nitrogen atmosphere at 0° C. Reaction mixture was stirred at RT for 4 h. After reaction completion, the reaction mixture was taken as such for next step.

Step-3: methyl 3-(chlorosulfonyl)-1-naphthoate

To the reaction mass of step 2 was added aniline (2 ml) in pyridine (2 ml). Then the reaction mixture was continued for 12 h. After reaction completion, which was diluted with water, neutralized with 2N HCl and extracted with ethyl acetate. The organic layer washed with water, dried over Na$_2$SO$_4$ and evaporated under reduced pressure to get crude, which was purified by combi-Flash to get 0.2 g of methyl 3-(chlorosulfonyl)-1-naphthoate. $^1$HNMR (CDCl$_3$, 300 MHz): δ 3.65 (s, 1H) 4.00 (s, 3H), 6.52 (s, 1H) 7.06-7.23 (m, 6H), 7.64 (d, 1H), 7.81 (s, 1H), 7.93 (d, 1H), 8.02-8.19 (m, 2H), 8.20 (d, 1H).

Step-4: 4-(hydroxymethyl)-N-phenylnaphthalene-2-sulfonamide

Following experimental protocol of step-2 of synthetic Scheme-57, 4-(hydroxymethyl)-N-phenylnaphthalene-2-sulfonamide have been synthesized. $^1$HNMR (CDCl$_3$, 300 MHz): δ 4.96 (s, 2H) 6.52 (s, 1H) 7.06-7.23 (m, 6H), 7.64 (d, 1H), 7.81 (s, 1H), 7.93 (d, 1H), 8.02-8.19 (m, 2H), 8.20 (d, 1H).

Step-5: 4-(chloromethyl)-N-phenylnaphthalene-2-sulfonamide

Following experimental protocol of step-3 of synthetic Scheme-57, 4-(chloromethyl)-N-phenylnaphthalene-2-sulfonamide have been synthesized. $^1$HNMR (CDCl$_3$, 300 MHz): δ 5.14 (s, 2H) 6.52 (s, 1H) 7.06-7.23 (m, 6H), 7.64 (d, 1H), 7.81 (s, 1H), 7.93 (d, 1H), 8.02-8.19 (m, 2H), 8.20 (d, 1H).

Synthetic Scheme-69

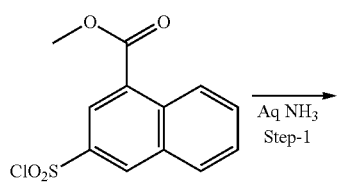

1037

-continued

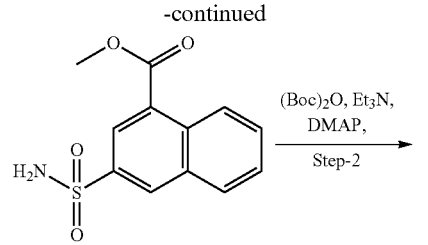

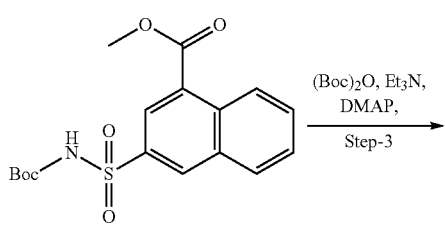

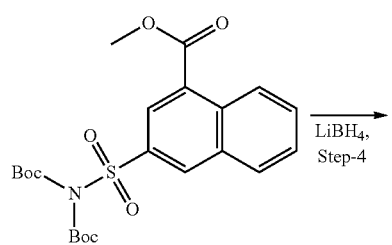

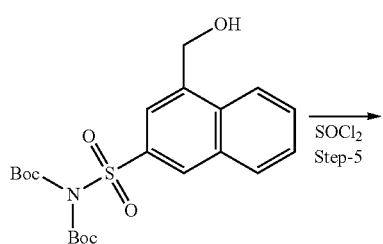

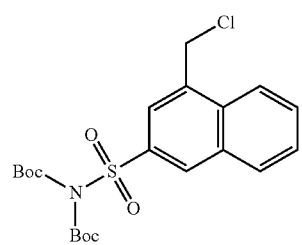

1038

Step-1: methyl 3-sulfamoyl-1-naphthoate

To the reaction mass of step 2 of Synthetic Scheme-68 (after reaction completion), was quenched with aqueous ammonia solution (10 ml). Then the reaction mixture stirred for 12 h. After reaction completion, which was diluted with water and neutralized with 2N HCl. Then extracted with ethyl acetate, washed with water, dried over $Na_2SO_4$ and evaporated under reduced pressure to get crude. It was purified using combi-Flash, to get 0.2 g of methyl 3-sulfamoyl-1-naphthoate. $^1$HNMR (CDCl3, 300 MHz): δ 6.52 (s, 1H) 7.06-7.23 (m, 6H), 7.64 (d, 1H), 7.81 (s, 1H), 7.93 (d, 1H), 8.02-8.19 (m, 2H), 8.20 (d, 1H).

Step-2: methyl 3-(N-(tert-butoxycarbonyl)sulfamoyl)-1-naphthoate

To a stirred a solution of methyl 3-sulfamoyl-1-naphthoate (500 mg, 1.362 mmol) in DCM (4.0 ml), were added tri ethyl amine (0.5 ml, 2.55 mmol) and catalytic amount of DMAP (10 mg, 0.055 mmol) under nitrogen atmosphere at 0° C. The resultant reaction mixture was stirred at room temperature for 12 h. After reaction completion, quenched with water, extracted with ethyl acetate. The organic layer washed with sodium bicarbonate, dried over sodium sulphate and evaporated under reduced pressure to get 500 mg methyl 3-(N-(tert-butoxycarbonyl)sulfamoyl)-1-naphthoate. LCMS: 364.1 (M−1)$^+$.

Step-3: methyl 3-(N,N-bis(tert-butoxycarbonyl)sulfamoyl)-1-naphthoate

To a stirred a solution of methyl 3-sulfamoyl-1-naphthoate (500 mg, 1.362 mmol) in DCM (4.0 ml), were added tri ethyl amine (0.5 ml, 2.55 mmol) and DMAP (334 mg, 0.54 mmol) under nitrogen atmosphere at 0° C. The resultant reaction mixture was stirred at room temperature for 12 h. After reaction completion, quenched with water, extracted with ethyl acetate. The organic layer washed with sodium bicarbonate, dried over sodium sulphate and evaporated under reduced pressure to get 450 mg methyl 3-(N,N-bis(tert-butoxycarbonyl)sulfamoyl)-1-naphthoate. LCMS: 364.1 (M−1)$^+$.

Step-4: 4-(hydroxymethyl)-N-phenylnaphthalene-2-sulfonamide

Following experimental protocol of step-2 of synthetic Scheme-57, 4-(hydroxymethyl)-N-phenylnaphthalene-2-sulfonamide have been synthesized. $^1$HNMR (CDCl$_3$, 300 MHz): δ 4.96 (s, 21H) 7.62-7.9 (m, 2H), 8.01 (d, 1H), 8.02 (t, 2H), 8.54 (d, 1H).

Step-5: 4-(chloromethyl)-N-phenylnaphthalene-2-sulfonamide

Following experimental protocol of step-3 of synthetic Scheme-57, 4-(chloromethyl)-N-phenylnaphthalene-2-sulfonamide have been synthesized. $^1$HNMR (CDCl$_3$, 300 MHz): δ 5.14 (s, 25) 4.96 (s, 24) 7.62-7.9 (m, 2H), 8.01 (d, 1H), 8.02 (t, 2H), 8.54 (d, 1H).

Additional Exemplary Compounds:

| Cpd. ID. | Structure | LCMS (M + 1) | ¹H-NMR Data |
|---|---|---|---|
| I-828 | 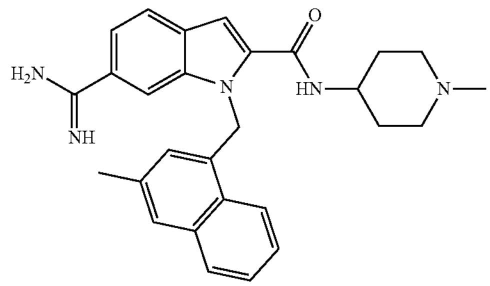 [SMILES: Cc1cc(Cn2c(C(=O)NC3CCN(C)CC3)cc3ccc(C(=N)N)cc32)c2ccccc2c1] | 454.20 | 1HNMR (CD3OD, 400 MHz): δ 1.70-1.81 (m, 2H), 2.00-2.04 (m, 2H), 2.20 (s, 3H), 2.82 (s, 3H), 3.00-3.07 (m, 2H), 3.47-3.50 (m, 2H), 3.94-4.00 (m, 1H), 6.14 (s, 1H), 6.40 (s, 2H), 7.31 (s, 1H), 7.49-7.58 (m, 4H), 7.80-7.82 (m, 1H), 7.94-7.99 (m, 2H), 8.11-8.14 (d, 1H). |
| I-829 | 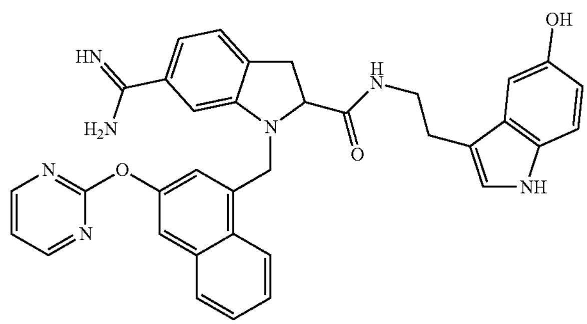 [SMILES: N=C(N)c1ccc2c(c1)N(Cc1cc(Oc3ncccn3)cc3ccccc13)C(C(=O)NCCc1c[nH]c3ccc(O)cc13)C2] | 596.3 | 1HNMR (CD3OD, 400 MHz): δ 2.83-2.86 (t, 2H), 3.50-3.53 (t, 2H), 5.94-5.95 (d, 1H), 6.456 (s, 2H), 6.62-6.65 (d, 1H), 6.90-6.91 (s, 2H), 7.05-7.14 (m, 3H), 7.50-7.52 (d, 1H), 7.57-7.67 (m, 3H), 7.84-7.86 (d, 1H), 7.91-7.93 (d, 2H), 8.22-8.24 (d, 1H), 8.34-8.35 (d, 2H). |
| I-830 | 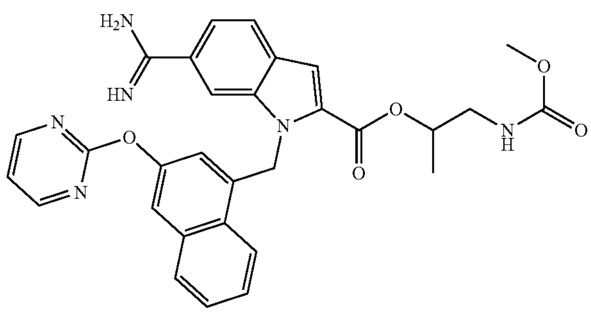 [SMILES: COC(=O)NCC(C)OC(=O)c1cc2ccc(C(=N)N)cc2n1Cc1cc(Oc2ncccn2)cc2ccccc12] | 553.1 | 1HNMR (CD3OD, 400 MHz): δ 1.05-1.07(d, 3H), 3.12-3.24(m, 2H), 3.52(s, 3H), 5.04-5.10(m, 1H), 5.86(s, 1H), 6.48-6.51(d, 2H), 7.10-7.13(t, 1H), 7.51-7.71(m, 5H), 7.92-8.00(m, 3H), 8.28-8.30(d, 1H), 8.38-8.41(d, 2H). |
| I-831 | 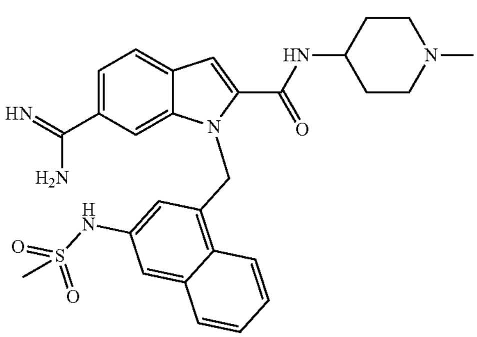 [SMILES: CN1CCC(NC(=O)c2cc3ccc(C(=N)N)cc3n2Cc2cc(NS(C)(=O)=O)cc3ccccc23)CC1] | 533.25 | ¹HNMR (CD3OD, 400 MHz): δ 1.775-1.812 (m, 2H), 2.058-2.093 (d, 2H), 2.780 (s, 3H), 2.830-2.872 (d, 3H), 3.027-3.086 (t, 2H), 3.489-3.521 (d, 2H), 6.332-6.327 (s, 1H), 7.518 (s, 1H), 7.548-7.584 (m, 3H), 7.834-7.858 (m, 1H), 7.942-7.964 (m, 1H), 8.000 (s, 1H), 8.140-8.164 (m, 1H). |
| I-832 | 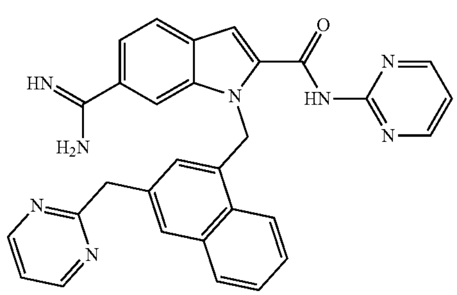 [SMILES: N=C(N)c1ccc2cc(C(=O)Nc3ncccn3)n(Cc3cc(Cc4ncccn4)cc4ccccc34)c2c1] | 515.2 | 1HNMR (CD3OD, 400 MHz): 6.04-6.09 (s, 1H), 6.53 (s, 2H), 7.07-7.09 (t, 1H), 7.16-7.17 (t, 1H), 7.53-7.63 (m, 5H), 7.88-7.90 (m, 1H), 7.95-7.97 (d, 1H), 8.01-8.02 (s, 1H), 8.23-8.25 (d, 1H), 8.35-8.36 (d, 2H), 8.59-8.60 (d, 2H). |

-continued

| Cpd. ID. | Structure | LCMS (M + 1) | ¹H-NMR Data |
|---|---|---|---|
| I-833 | 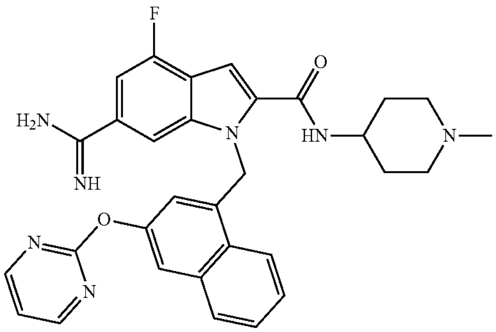 [SMILES: CN1CCC(NC(=O)c2cc3c(F)cc(C(=N)N)cc3n2Cc2cc(Oc3ncccn3)cc3ccccc23)CC1] | 552.3 | 1HNMR (CD3OD, 400 MHz): δ 1.758-1.795 (m, 2H), 2.066-2.102 (d, 2H), 2.837 (s, 3H), 3.037-3.096 (m, 2H), 3.47-3.52 (d, 2H), 3.97-3.402 (m, 1H), 5.96-5.97 (s, 1H), 6.49-6.51 (d, 2H), 7.12-7.15 (t, 1H), 7.28-7.31 (d, 1H), 7.36 (s, 1H), 7.58-7.67 (m, 3H), 7.88-7.94 (m, 2H), 8.21-8.23 (d, 1H), 8.41-8.42 (d, 2H). |
| I-834 | 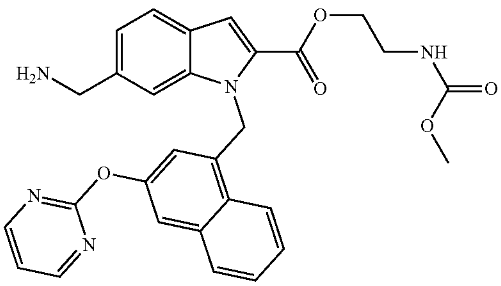 [SMILES: COC(=O)NCCOC(=O)c1cc2ccc(CN)cc2n1Cc1cc(Oc2ncccn2)cc2ccccc12] | 526.2 | ¹HNMR (CD$_3$OD, 300 MHz): δ 3.55 (s, 3H), 4.14 (s, 2H), 4.23 (t, 2H), 5.86 (s, 1H), 6.44 (s, 2H), 7.13-7.24 (m, 2H), 7.49-7.54 (m, 3H), 7.61-7.67 (m, 2H), 7.79-7.81 (d, 1H), 7.91-7.93 (d 1H), 8.26-8.29 (d, 1H), 8.43-8.45 (d, 2H). |
| I-835 | 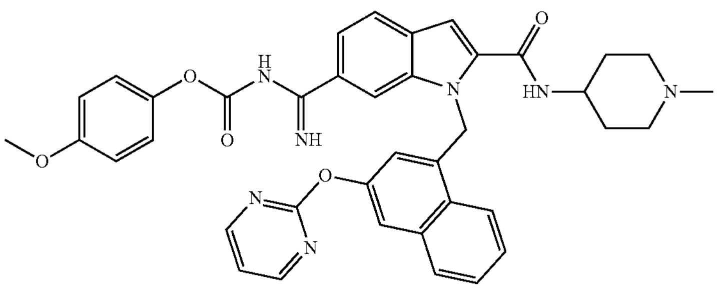 | 684.25 | 1HNMR (CDCl3, 400 MHz): δ 1.41-1.48(m, 2H), 1.80-1.83 (m, 2H), 2.00-2.06 (m, 2H), 2.23 (s, 3H), 2.69-2.72 (m, 2H), 3.76 (s, 3H), 3.80-3.82 (m, 1H), 6.09 (s, 1H), 6.27-6.33 (m, 3H), 6.85-6.94 (m, 4H), 7.06-7.09 (d, 2H), 7.51-7.53 (m, 3H), 7.62-7.68 (m, 2H), 7.79-7.88 (d, 1H), 7.88 (s, 1H), 7.99-8.02 (d, 1H), 8.31-8.34 (d, 2H), 9.4 (bs, 1H). |
| I-836 | 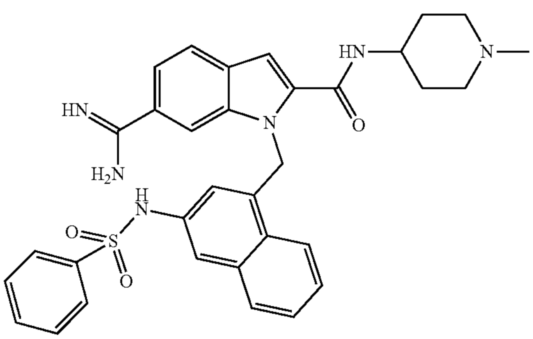 [SMILES: CN1CCC(NC(=O)c2cc3ccc(C(=N)N)cc3n2Cc2cc(NS(=O)(=O)c3ccccc3)cc3ccccc23)CC1] | 595.20 | ¹HNMR (CD3OD, 300 MHz): δ 1.84 (d, 2H), 2.08 (d, 2H), 2.83 (s, 3H), 3.06 (t, 2H), 3.49 595.20 (d, 2H), 6.39 (s, 2H), 6.41 (s, 1H), 7.23 (t, 3H), 7.37-7.55 (m, 6H), 7.62-7.72 (m, 2H), 7.93 (s, 2H), 8.03 (d, 3H), 8.13 (d, 2H). |
| I-837 | 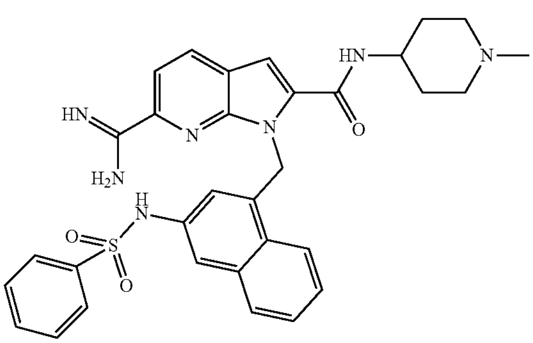 [SMILES: CN1CCC(NC(=O)c2cc3ccc(C(=N)N)nc3n2Cc2cc(NS(=O)(=O)c3ccccc3)cc3ccccc23)CC1] | 596.20 | ¹HNMR (CD3OD, 300 MHz): δ 1.75-2.05 (m, 2H), 2.00-2.04 (m, 2H), 2.80 (s, 3H), 2.95-3.15 (m, 2H), 3.35-3.45 (m, 2H), 3.95-4.05 (m, 1H), 6.50-6.55 (d, 3H), 7.18-7.47 (m, 9H), 7.65-7.68 (m, 1H), 8.05-8.17 (m, 2H), 8.47-8.49 (d, 1H). |

| Cpd. ID. | Structure | LCMS (M + 1) | ¹H-NMR Data |
|---|---|---|---|
| I-838 | 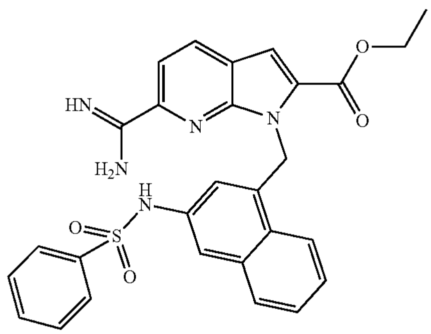 [SMILES: CCOC(=O)c1cc2ccc(C(=N)N)nc2n1Cc1cc(NS(=O)(=O)c2ccccc2)cc2ccccc12] | 527.3 | ¹HNMR (CD3OD, 400 MHz): δ 1.139-1.176 (t, 3H), 4.193-4.246 (q, 2H), 6.626-6.632 (s, 1H), 6.366 (s, 2H), 7.261-7.301 (m, 3H), 7.412-7.433 (m, 3H), 7.518-7.558 (m, 2H), 7.606-7.637 (d, 2H), 7.735-7.758 (d, 1H), 7.916 (s, 1H), 8.041-8.062 (d, 1H), 8.314-8.154 (d, 1H). |
| I-839 | 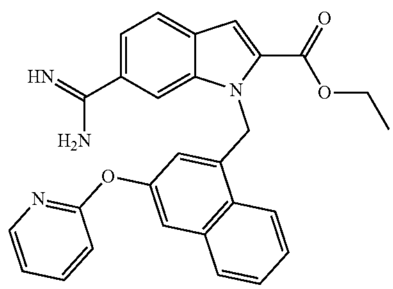 [SMILES: CCOC(=O)c1cc2ccc(C(=N)N)cc2n1Cc1cc(Oc2ccccn2)cc2ccccc12] | 465.3 | ¹HNMR (CD$_3$OD, 400 MHz): δ 1.21-1.24 (t, 3H), 4.23-4.28 (q, 2H), 5.73 (s, 1H), 6.49 (s, 2H), 6.82-6.84 (d, 1H), 6.98-7.01 (m, 1H), 7.43 (s, 1H), 7.49-7.53 (m, 2H), 7.59-.64 (m, 3H), 7.71 (m, 1H), 7.76-7.77 (m, 2H), 7.88-7.95 (m, 1H), 8.23-8.25(d, 1H). |
| I-840 | 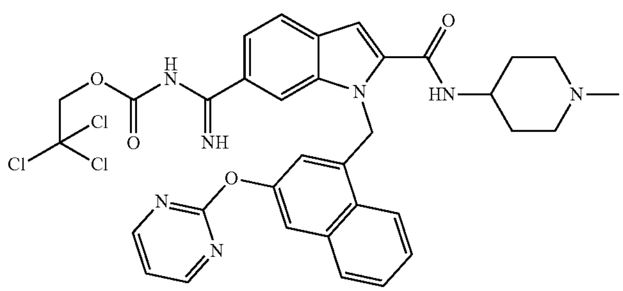 [SMILES: CN1CCC(NC(=O)c2cc3ccc(C(=N)NC(=O)OCC(Cl)(Cl)Cl)cc3n2Cc2cc(Oc3ncccn3)cc3ccccc23)CC1] | 710.10 | ¹HNMR (CD$_3$OD, 300 MHz): δ 1.53-1.60 (m, 2H), 1.76-1.80 (m, 2H), 2.02-2.09 (m, 2H), 2.23 (s, 3H), 2.78-2.82 (m, 2H), 3.66-3.73 (m, 1H), 4.84 (s, 2H), 5.95-6.00 (s, 1H), 6.43 (s, 2H), 7.05-7.08 (t, 1H), 7.17 (s, 1H), 7.52-7.76 (m, 5H), 7.86-7.90 (d, 1H) 8.07 (s, 1H), 8.20-8.23 (d, 1H), 8.36-8.38 (d, 2H). |
| I-841 | 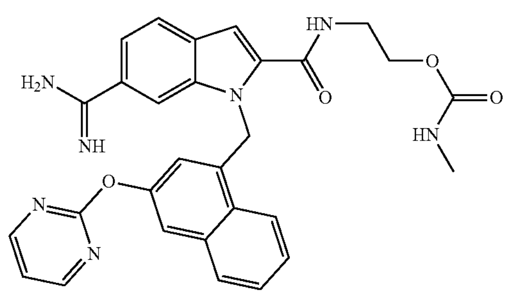 [SMILES: CNC(=O)OCCNC(=O)c1cc2ccc(C(=N)N)cc2n1Cc1cc(Oc2ncccn2)cc2ccccc12] | 538.25 | ¹HNMR (CD3OD, 400 MHz): δ 2.55 (s, 3H), 3.48-3.50 (m, 2H), 4.07 (t, 2H), 5.89 (s, 1H), 3.06-3.09 (d, 4H), 6.50 (s, 2H), 7.10 (t, 1H), 7.24 (s, 1H), 7.51-7.67 (m, 4H), 7.87-7.93 (m, 3H), 8.24 (d, 1H), 8.39 (d, 2H). |
| I-842 | 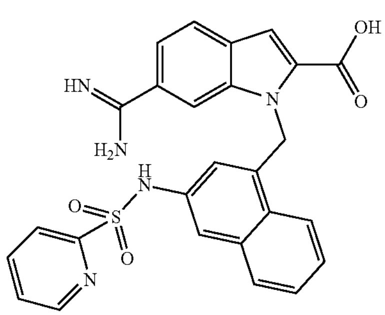 [SMILES: N=C(N)c1ccc2cc(C(=O)O)n(Cc3cc(NS(=O)(=O)c4ccccn4)cc4ccccc34)c2c1] | 500.15 | ¹HNMR (CD3OD, 400 MHz): 6.15 (s, 1H), 6.49 (s, 2H), 7.07 (s, 1H), 7.36 (s, 2H), 7.48-7.54 (m, 4H), 7.60-7.62 (m, 1H), 7.75 -7.78 (m, 5H), 8.15 (s, 1H), 8.36-8.37 (d, 1H), 8.96 (s, 1H), 9.45 (s, 1H). |

| Cpd. ID. | Structure | LCMS (M + 1) | ¹H-NMR Data |
|---|---|---|---|
| I-843 | 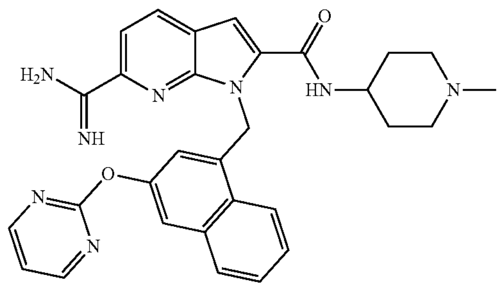 [SMILES: CN1CCC(NC(=O)c2cc3ccc(C(=N)N)nc3n2Cc2cc(Oc3ncccn3)cc3ccccc23)CC1] | 535.30 | ¹HNMR (CD3OD, 400 MHz): δ 1.70-1.81 (m, 2H), 1.95-2.05 (m, 2H), 2.83 (s, 3H), 3.00-3.10 (m, 2H), 3.45-3.55 (m, 2H), 3.90-4.00 (m, 1H), 6.42 (s, 1H), 6.56 (s, 2H), 7.15-7.20 (m, 2H), 7.50-7.55 (m, 3H), 7.84-7.87 (m, 1H), 7.99-8.01 (d, 1H), 8.24-8.26 (m, 1H), 8.36-8.38 (m, 1H), 8.48-8.50 (m, 2H). |
| I-844 | 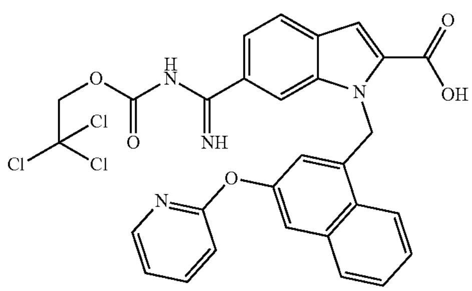 [SMILES: N=C(NC(=O)OCC(Cl)(Cl)Cl)c1ccc2cc(C(=O)O)n(Cc3cc(Oc4ccccn4)cc4ccccc34)c2c1] | 613.05 | ¹HNMR (CD$_3$OD, 400 MHz): δ 4.84 (s, 2H), 5.815-5.819 (s, 1H), 6.533 (s, 2H), 6.72-6.74 (d, 1H), 6.96-6.99 (m, 1H), 7.31 (s, 1H), 7.38-7.39 (s, 1H), 7.537-7.666 (m, 4H), 7.73-7.75 (d, 1H), 7.83-7.86 (m, 2H), 7.989 (s, 1H), 8.24-8.259 (d, 1H). |

Method A:

Test compounds were evaluated for their potential to inhibit Human Recombinant Matriptase 2 (in-house and commercial protein from Enzo Life Sciences—cat log -ALX-201-752-1) using fluorescence based assay. The concentration of Recombinant Matriptase 2 and the substrate used in the assay was: 7 nM (commercial) and 15 nM (Inhouse Matriptase 2) and 100 μM (Boc-Gln-Ala-Arg-7-amido-4-methyl coumarin hydrobromide—Cat log: B4153-Sigma) respectively. The assay buffer used was 100 mM TRIS pH 9, 1 mg/mL BSA. The assay was performed using 384 well black flat bottom plate from grenier (Cat log: 781076) at 25° C. The enzyme and compound was preincubated for 30 mins, plate was read 60 mins after substrate addition at wavelength Ex: 360/Em: 480 nm. The final assay volume was 20 μl. Stock solution of compounds were initially prepared in DMSO and appropriate dilutions were made for screening and IC50 determination (final DMSO conc in the assay was 1%). All the measurements were carried out using the Spectramax M5, Molecular devices. The compounds were screened at 1 and 10 μM concentration and IC50 was determined for the interested compounds.

To determine IC$_{50}$ values, dose response curves were generated by plotting percentage inhibition as a function of inhibitor concentration and the data was fitted to sigmoidal non-linear regression equation (variable slope) using Graph Pad prism software V7.

Method B:

Test compounds were evaluated for their potential to inhibit Human Recombinant Matriptase 2 (in-house and commercial protein from Enzo Life Sciences—cat log -ALX-201-752-1) using fluorescence based assay. The concentration of Recombinant Matriptase 2 and the substrate used in the assay was: 7 nM (commercial) and 15 nM (Inhouse Matriptase 2) and 100 μM (Boc-Gln-Ala-Arg-7-amido-4-methyl coumarin hydrobromide—Cat log: B4153-Sigma and I-1550 from Bachem) respectively. The assay buffer used was 50 mM TRIS pH 7.5, 150 mM NaCl, 0.01% gelatin (G1393 Sigma). The assay was performed using 384 well black flat bottom plate from grenier (Cat log: 781076) at 25° C. The enzyme and compound preincubated for 30 mins, plate was read 60 mins after substrate addition at wavelength Ex: 360/Em:480 nm. The final assay volume of was 20 μl. Stock solution of compounds were initially prepared in DMSO and appropriate dilutions were made for screening and IC50 determination (final DMSO conc in the assay was 1%). All the measurements were carried out using the Spectramax M5, Molecular devices. The compounds were screened at 1 and 10 μM concentration and IC50 was determined for the interested compounds.

To determine IC$_{50}$ values, dose response curves were generated by plotting percentage inhibition as a function of inhibitor concentration and the data was fitted to sigmoidal non-linear regression equation (variable slope) using Graph Pad prism software V7.

Table A above lists % inhibition (I) at 1 uM for certain exemplary compounds, wherein A represents 0%≤I≤25%; B represents 25%≤I≤50%; C represents 50%≤I≤75%; and D represents 75%≤I≤100%.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:
1. A compound of Formula IV:

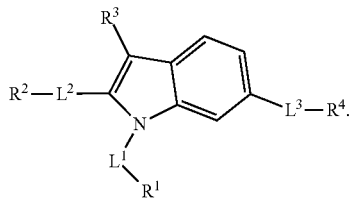

(IV)

or a pharmaceutically acceptable salt thereof, wherein
$L^1$ is a bond, or an optionally substituted bivalent $C_{1-8}$ saturated or unsaturated, straight or branched hydrocarbon chain, wherein 1, 2, or 3 methylene units of the hydrocarbon chain are optionally and independently replaced by —C(O)— or —O—;
$R^1$ is an optionally substituted ring selected from phenyl, a 5-6 membered heteroaromatic ring having 1-4 heteroatoms independently selected from nitrogen, oxygen, and sulfur, an 8-10 membered bicyclic aromatic carbocyclic ring, and an 8-10 membered bicyclic heteroaromatic ring having 1-4 heteroatoms independently selected from nitrogen, oxygen, and sulfur;
$L^2$ is an optionally substituted bivalent $C_{1-8}$ saturated or unsaturated, straight or branched hydrocarbon chain, wherein 1, 2, or 3 methylene units of the hydrocarbon chain are independently replaced by —NR—C(O)—, —C(O)—NR—, —C(O)—, —C(O)—O—, —O—C(O)—, —NR—S(O)$_2$—, —S(O)$_2$—NR—, or -Cy-,
-Cy- is an optionally substituted bivalent 4-6 membered monocyclic heterocyclic ring having 1-4 heteroatoms independently selected from nitrogen, oxygen, and sulfur;
$R^2$ is an optionally substituted ring selected from a 4-7 membered monocyclic carbocyclic ring, a 4-7 membered monocyclic heterocyclic ring having 1-4 heteroatoms independently selected from nitrogen, oxygen, and sulfur, a 7-10 membered bicyclic carbocyclic ring, a 7-10 membered bicyclic heterocyclic ring having 1-4 heteroatoms independently selected from nitrogen, oxygen, and sulfur, phenyl, 5-6 membered monocyclic heteroaromatic ring having 1-4 heteroatoms independently selected from nitrogen, oxygen, and sulfur, an 8-10 membered bicyclic aromatic ring, an 8-10 membered bicyclic heteroaromatic ring having 1-4 heteroatoms independently selected from nitrogen, oxygen, and sulfur, and adamantyl;
$R^3$ is H, —OH, halogen, —CN, —C(O) H, —NH$_2$, —NO$_2$, —COOH, —CONH$_2$, —NH—C(O)—O—C$_{1-6}$aliphatic, C$_{1-6}$aliphatic, or —C(O)—C$_{1-6}$aliphatic, wherein the C$_{1-6}$aliphatic is optionally substituted;
$L^3$ is an optionally substituted bivalent $C_{1-8}$ saturated or unsaturated, straight or branched hydrocarbon chain, wherein 1, 2, or 3 methylene units of the hydrocarbon chain are optionally replaced by —CO—;
$R^4$ is —NHR, —C(N—R)—NHR, —NH—C(N—R)—NHR, or —OH; and
each R is independently H, —OH, —OC$_{1-8}$alkyl, —C(O)—C$_{1-8}$alkyl, —C(O)—OC$_{1-8}$alkyl, —O-(4-7 membered monocyclic carbocyclyl), —C(O)-(4-7 membered monocyclic carbocyclyl), —C(O)—O-(4-7 membered monocyclic carbocyclyl), phenyl, —O-phenyl, —C(O)-phenyl, —C(O)—O-phenyl, 8-10 membered bicyclic aryl, —O-(8-10 membered bicyclic aryl), —C(O)-(8-10 membered bicyclic aryl), or —C(O)—O-(8-10 membered bicyclic aryl), wherein each of the C$_{1-8}$alkyl, 4-7 membered monocyclic carbocyclyl, phenyl, and 8-10 membered bicyclic aryl is optionally and independently substituted.

2. The compound of claim 1, or a pharmaceutically acceptable salt thereof, wherein $L^1$ is an optionally substituted C$_{1-8}$ bivalent hydrocarbon chain, wherein 1 methylene unit of the hydrocarbon chain is optionally replaced by —C(O)— or —O—.

3. The compound of claim 1, or a pharmaceutically acceptable salt thereof, wherein $R^1$ is an optionally substituted phenyl, or an optionally substituted 8-10 membered bicyclic aromatic carbocyclic ring.

4. The compound of claim 1, or a pharmaceutically acceptable salt thereof, wherein $R^1$ is an optionally substituted 5-6 membered heteroaromatic ring having 1-4 heteroatoms independently selected from nitrogen, oxygen, and sulfur, or an optionally substituted 8-10 membered bicyclic heteroaromatic ring having 1-4 heteroatoms independently selected from nitrogen, oxygen, and sulfur.

5. The compound of claim 1, or a pharmaceutically acceptable salt thereof, wherein $L^2$ is an optionally substituted C$_{1-8}$ bivalent hydrocarbon chain, wherein 1 methylene unit of the hydrocarbon chain is replaced by —NR—C(O)—, —C(O)—NR—, —C(O)—, —C(O)—O—, —O—C(O)—, —NR—S(O)$_2$—, —S(O)$_2$—NR—, or -Cy-.

6. The compound of claim 1, or a pharmaceutically acceptable salt thereof, wherein $R^2$ is an optionally substituted ring selected from phenyl, 5-6 membered monocyclic heteroaromatic ring having 1-4 heteroatoms independently selected from nitrogen, oxygen, and sulfur, an 8-10 membered bicyclic aromatic ring, and an 8-10 membered bicyclic heteroaromatic ring having 1-4 heteroatoms independently selected from nitrogen, oxygen, and sulfur.

7. The compound of claim 1, or a pharmaceutically acceptable salt thereof, wherein $R^3$ is —OH, —NH$_2$, —NO$_2$, —COOH, —NH—C(O)—O—C$_{1-6}$aliphatic, C$_{1-6}$aliphatic, or —C(O)—C$_{1-6}$aliphatic, wherein the C$_{1-6}$aliphatic is optionally substituted.

8. The compound of claim 1, or a pharmaceutically acceptable salt thereof, wherein $L^3$ is an optionally substituted C$_{1-8}$ bivalent hydrocarbon chain, wherein 1 methylene unit of the hydrocarbon chain is optionally replaced by —CO—.

9. The compound of claim 1, or a pharmaceutically acceptable salt thereof, wherein $R^4$ is —NHR or —C(N—R)NHR.

10. A compound selected from:

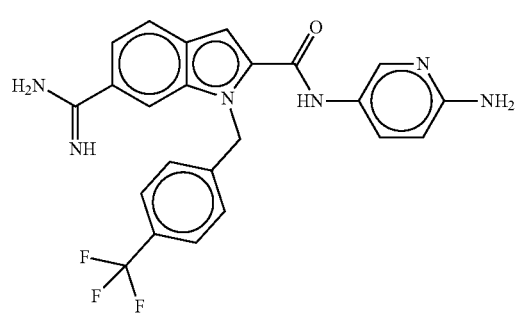

I-1

I-2
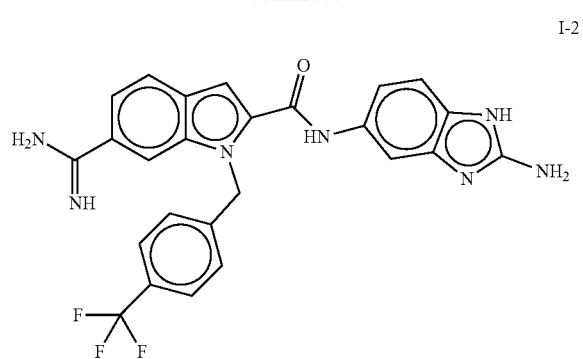
I-3
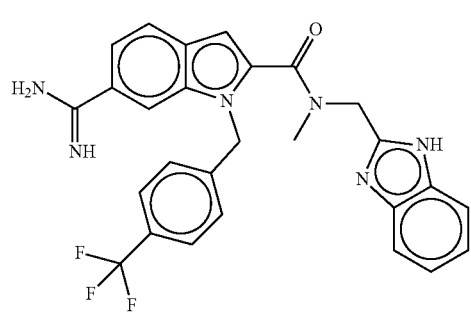
I-4
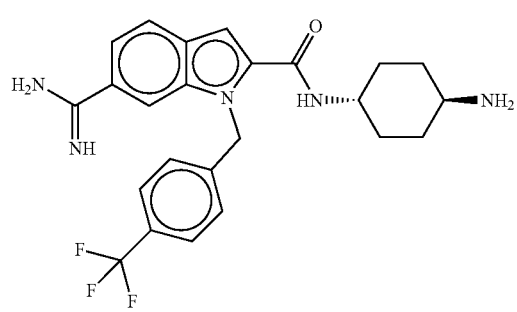
I-5
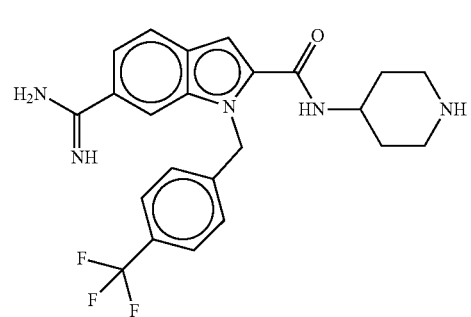
I-6
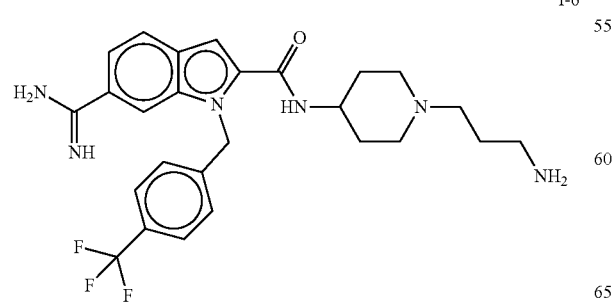
I-7
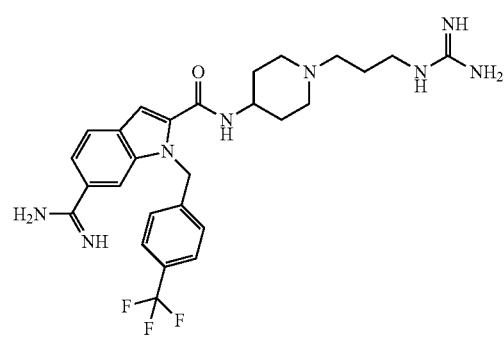
I-8
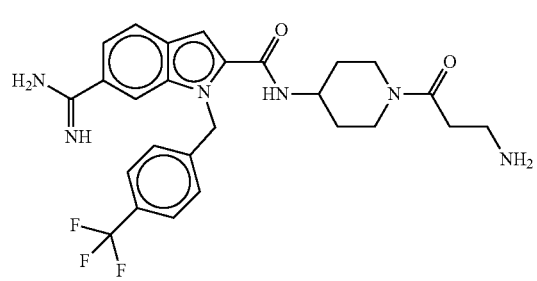
I-9
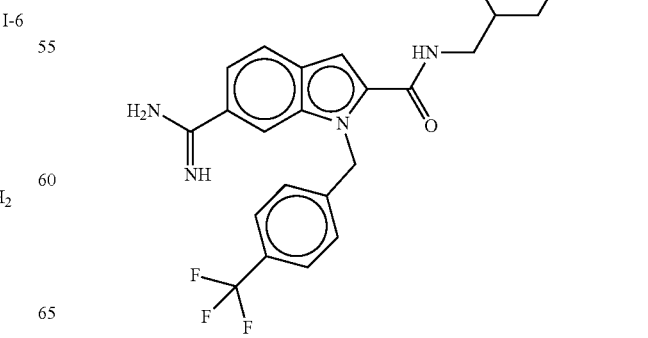
I-10
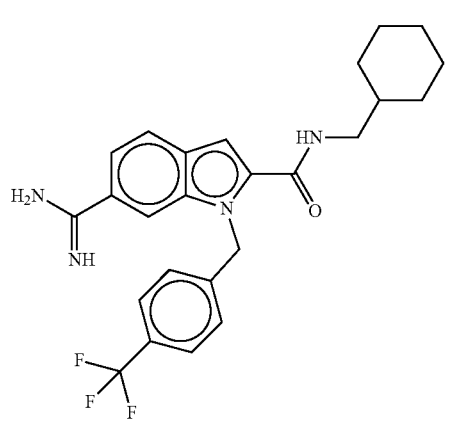

-continued
I-11
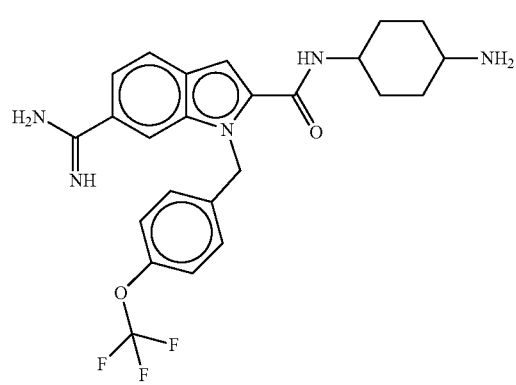
I-12
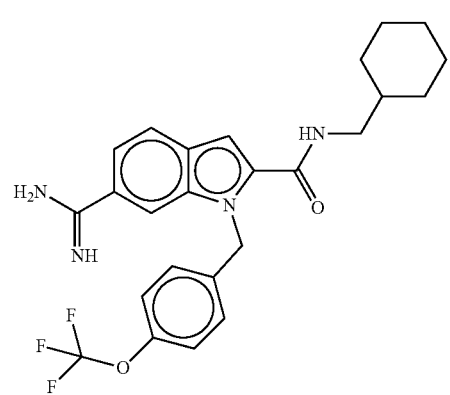
I-13
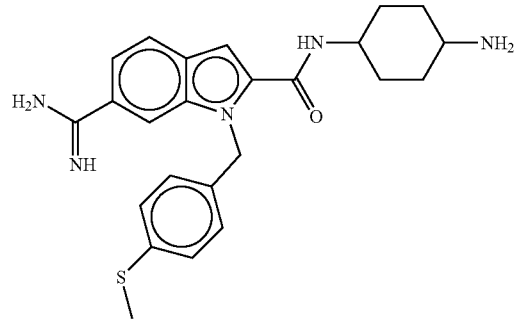
I-14
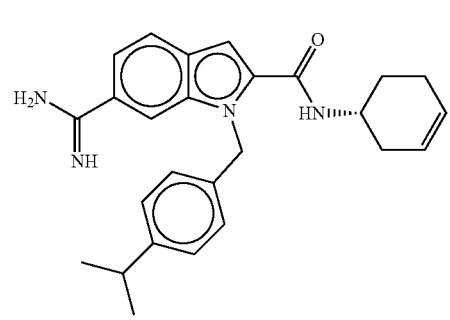
-continued
I-15
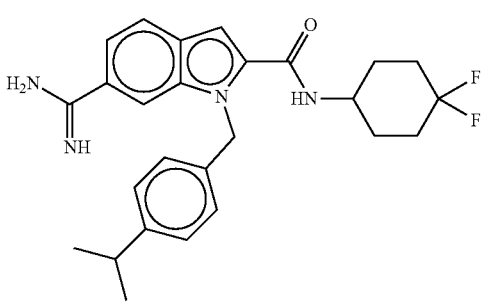
I-16
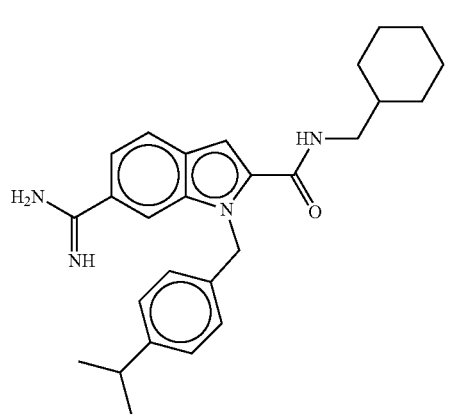
I-17
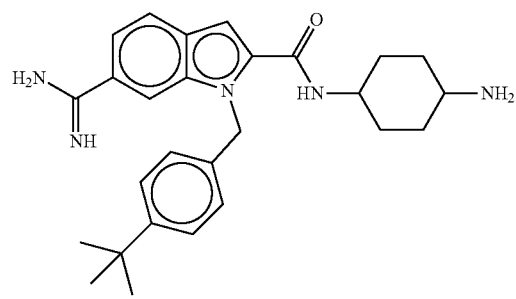
I-18
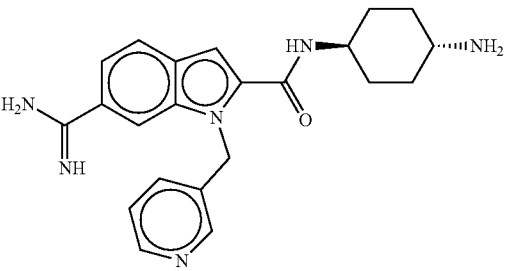
I-19
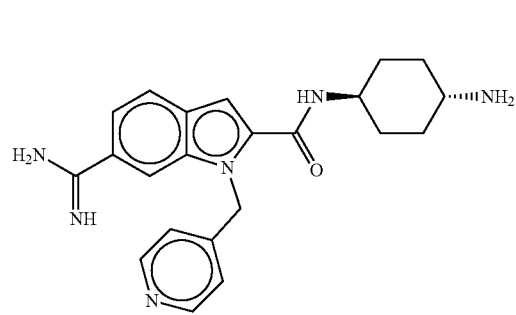

1053
-continued
I-20
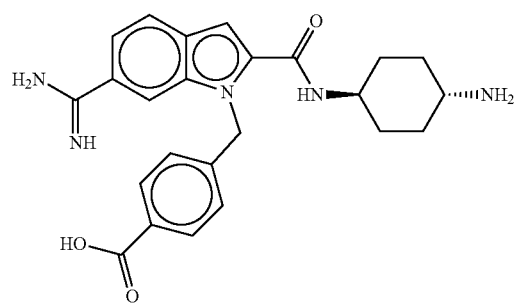
I-21
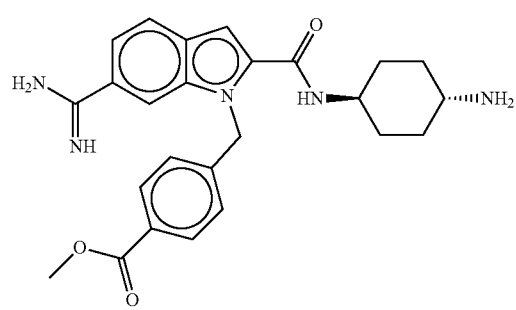
I-22
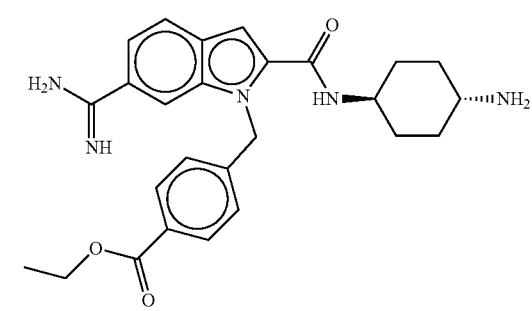
I-23
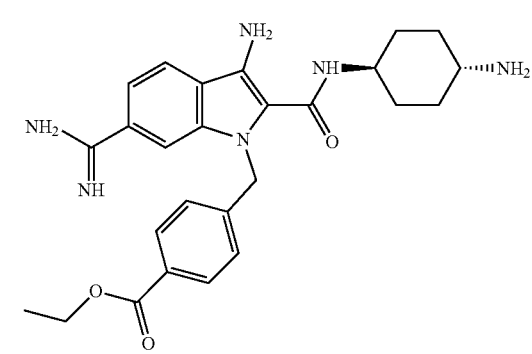
I-24
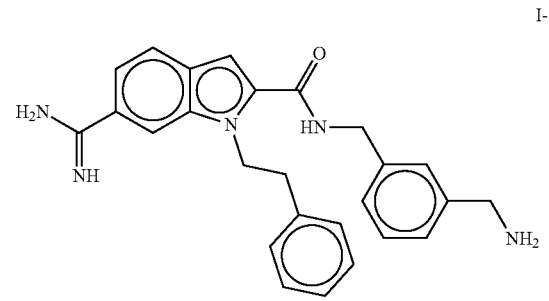
1054
-continued
I-25
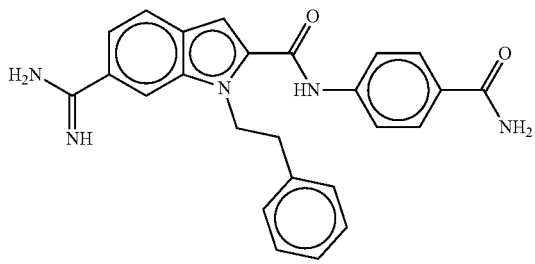
I-26
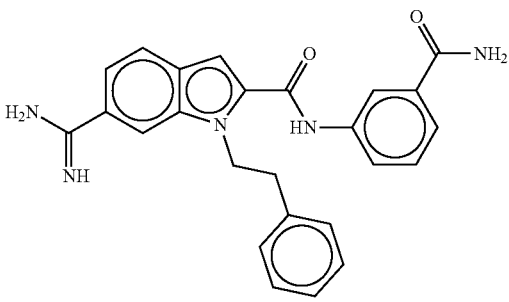
I-27
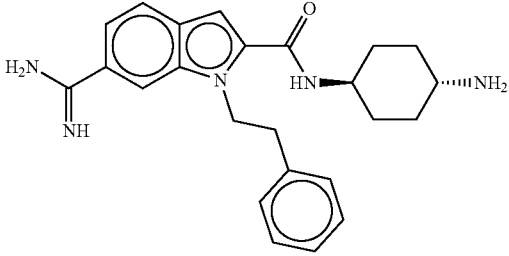
I-28
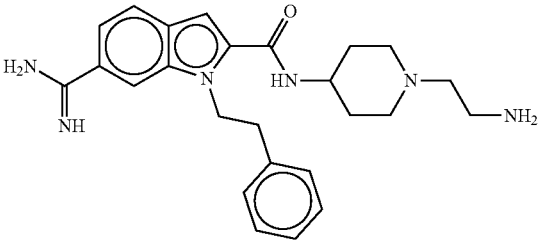
I-29
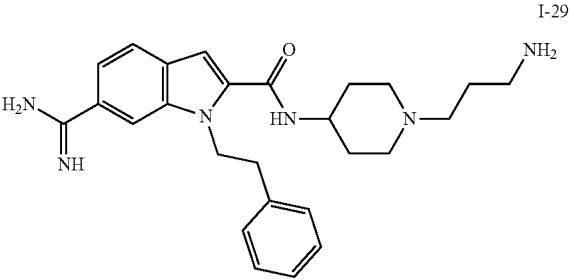

| 1055 -continued | 1056 -continued |
|---|---|
| I-30 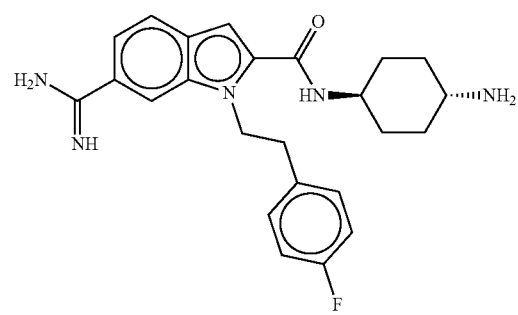 | I-35 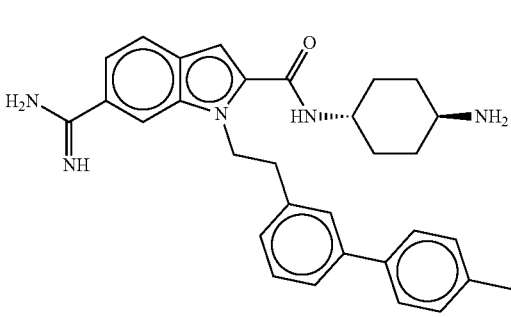 |
| I-31 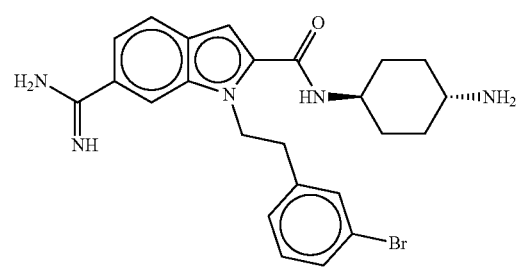 | I-36 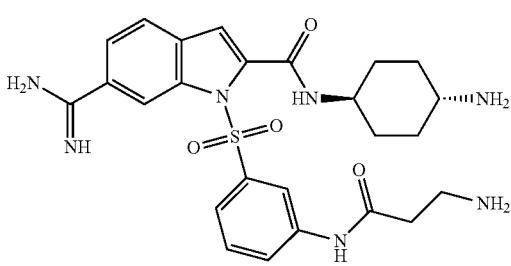 |
| I-32 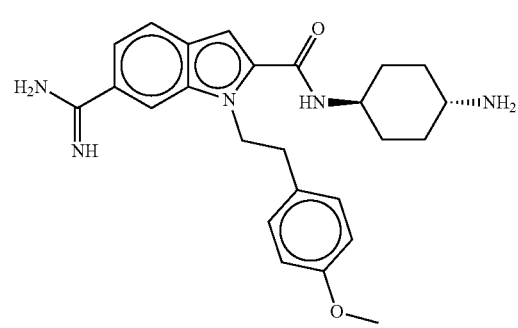 | I-37 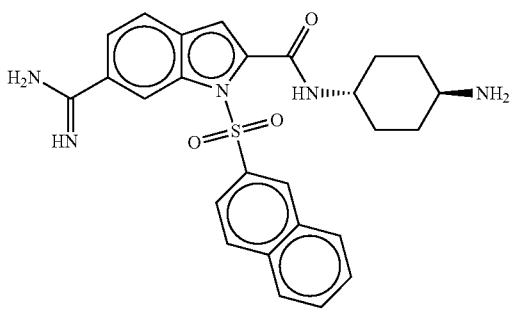 |
| I-33 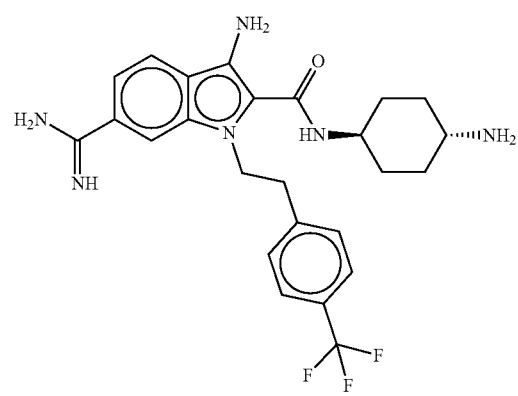 | I-38 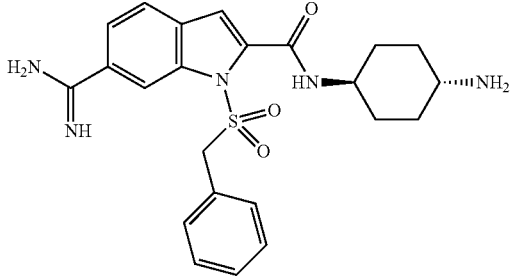 |
| I-34 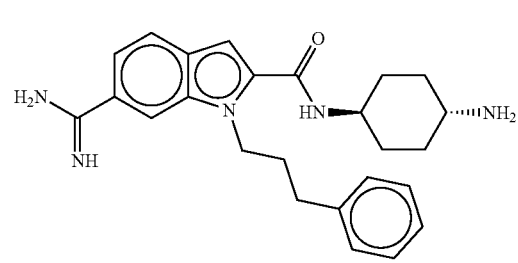 | I-39 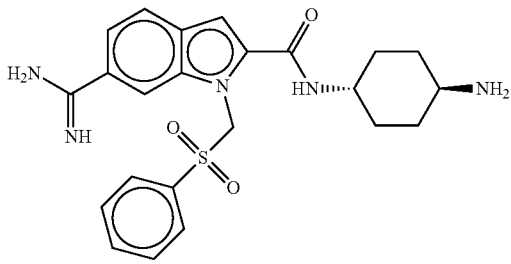 |

I-40
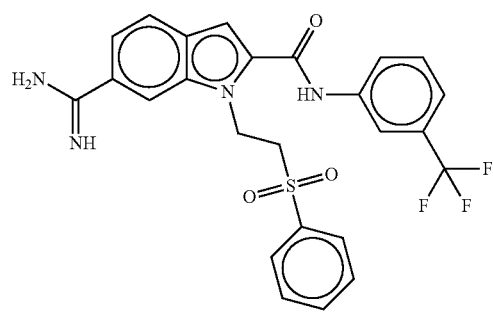
I-41
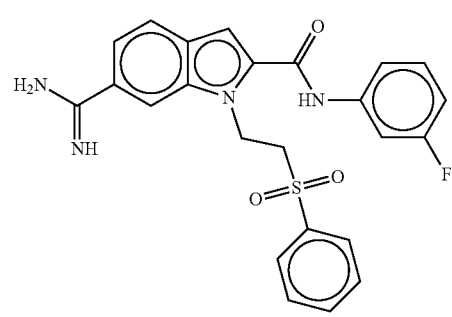
I-42
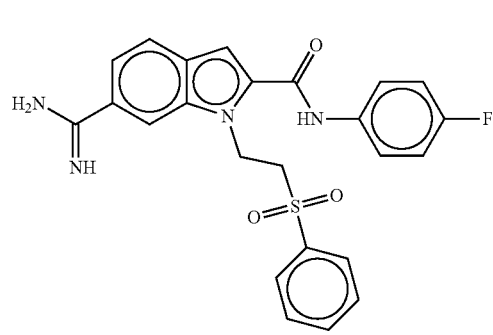
I-43
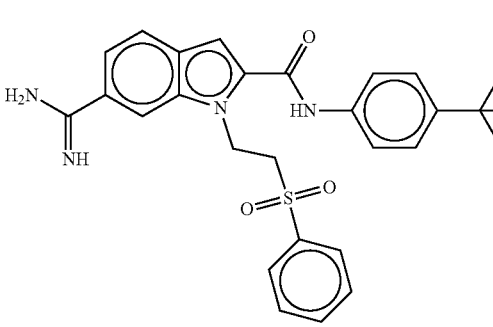
I-44
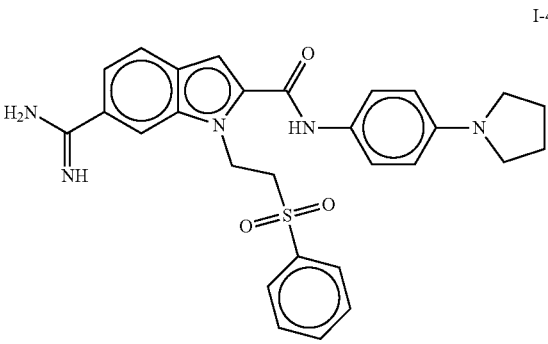
I-45
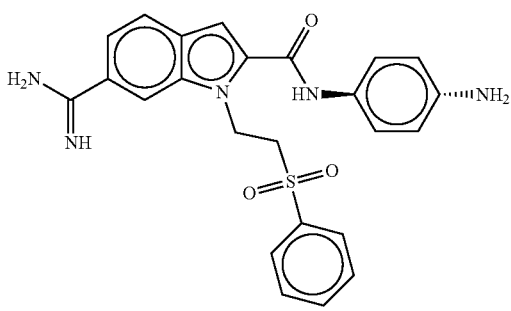
I-46
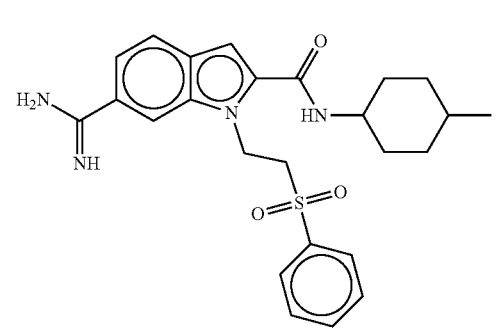
I-47
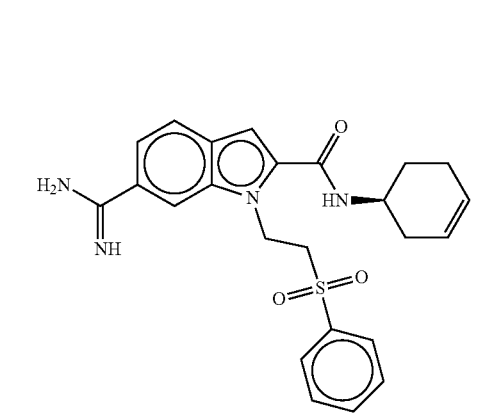
I-48
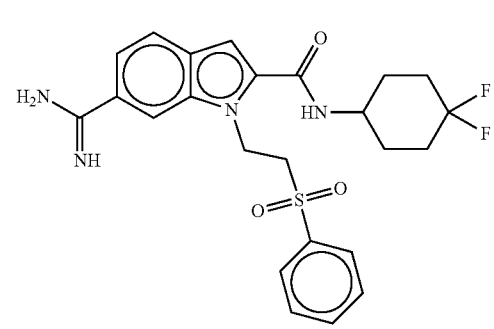

| 1059 -continued | 1060 -continued |
|---|---|
| I-49 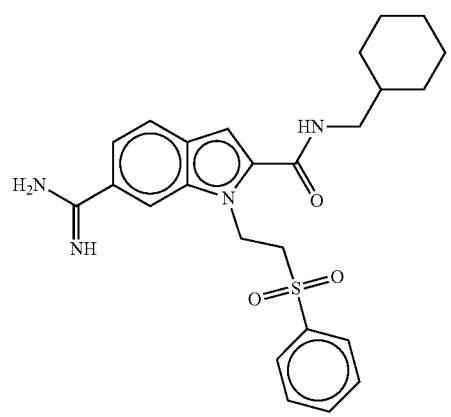 | I-52 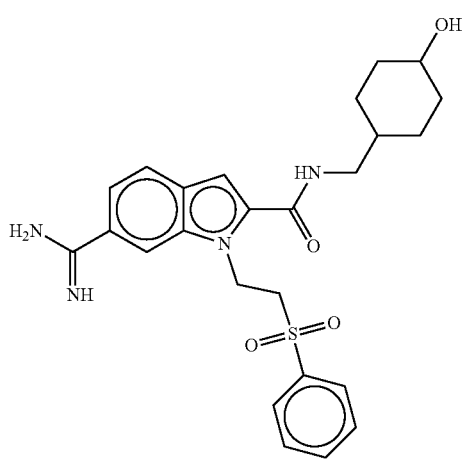 |
| I-50 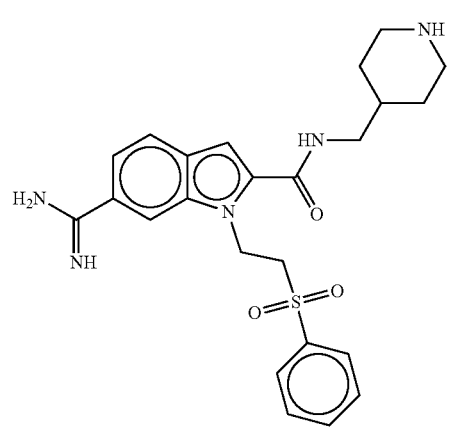 | I-53 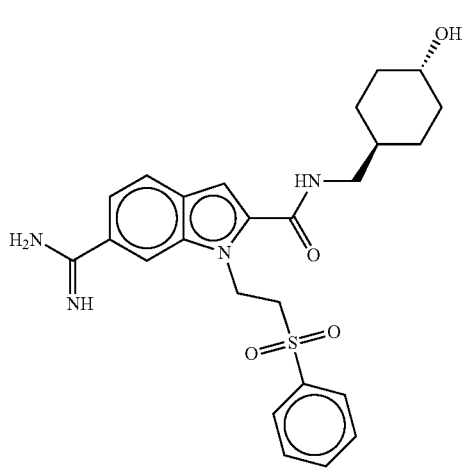 |
| I-51 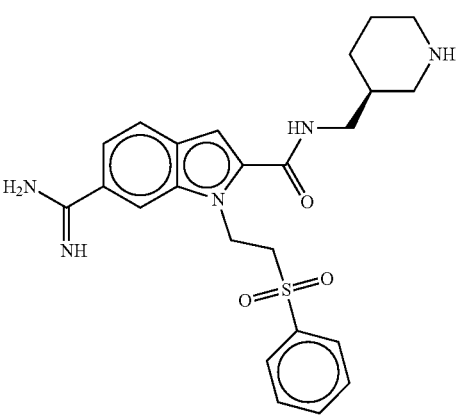 | I-54 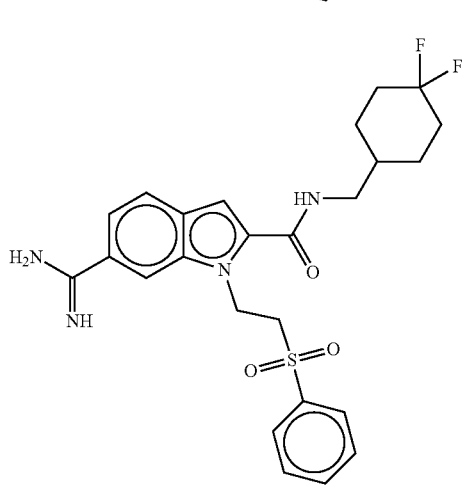 |

I-55
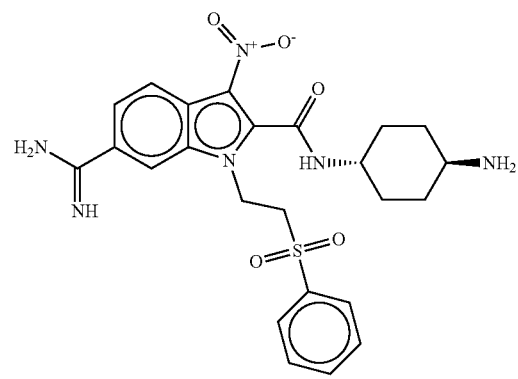
I-56
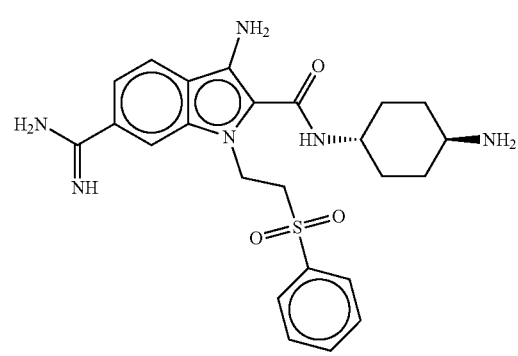
I-57
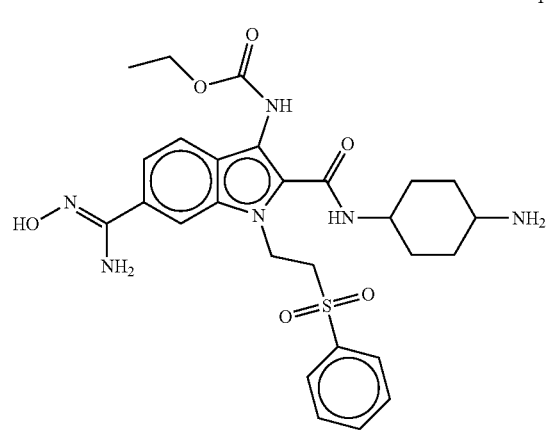
I-58
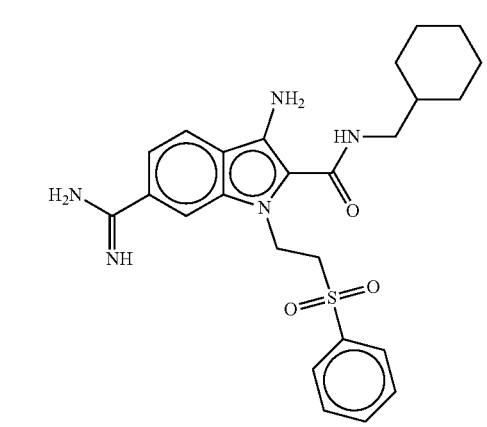
I-59
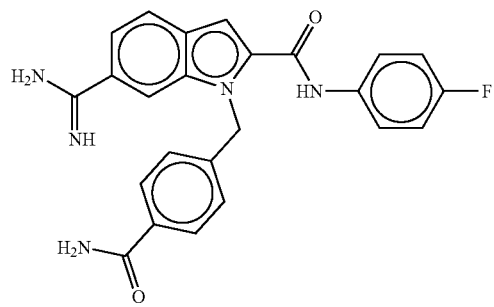
I-60
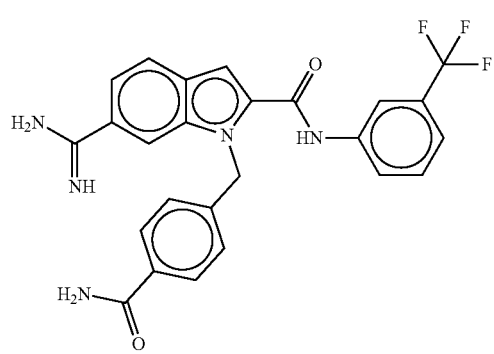
I-61
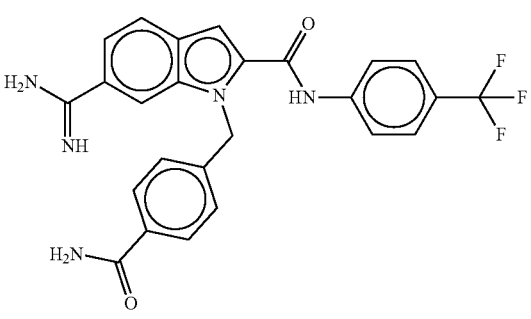
I-62
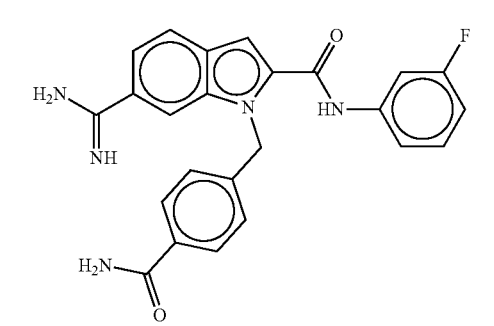
I-63
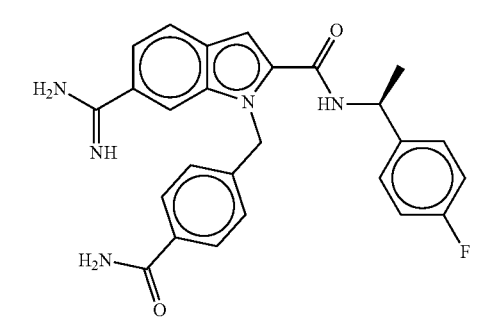

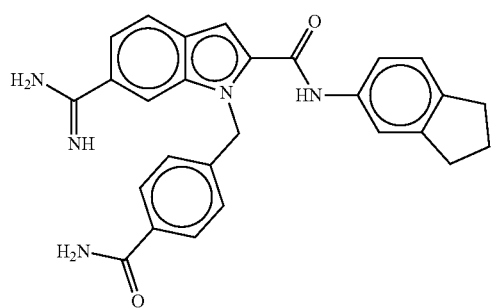
I-64
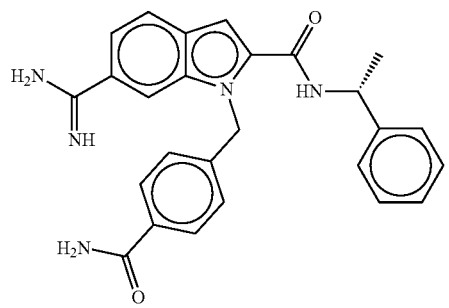
I-69
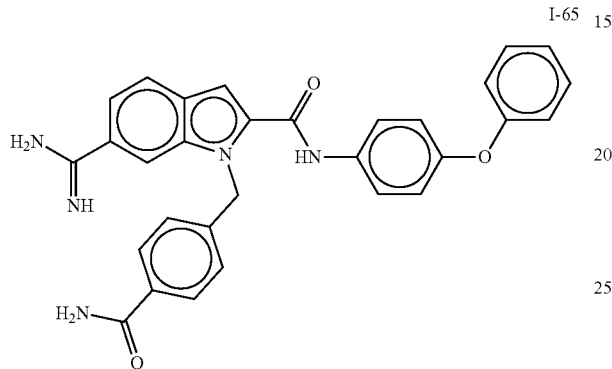
I-65
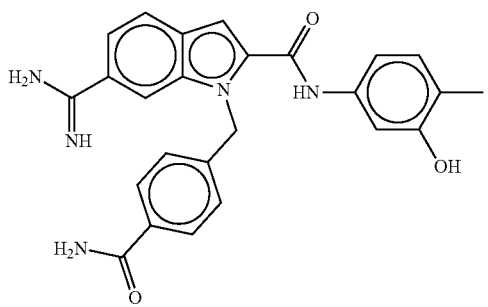
I-70
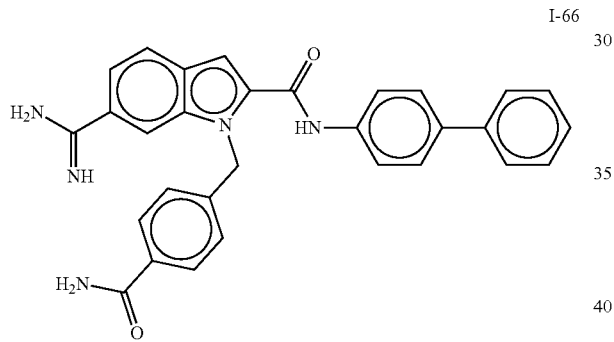
I-66
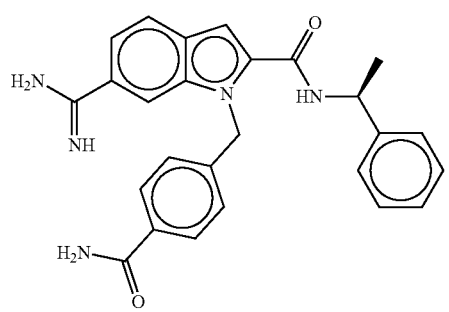
I-71
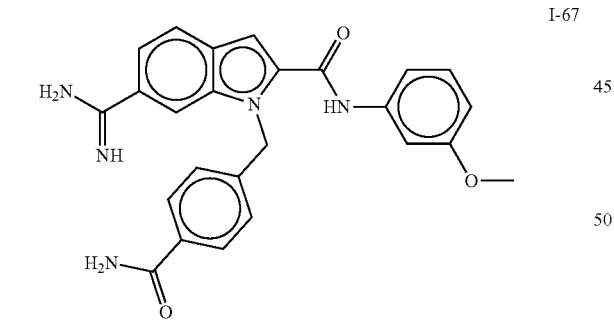
I-67
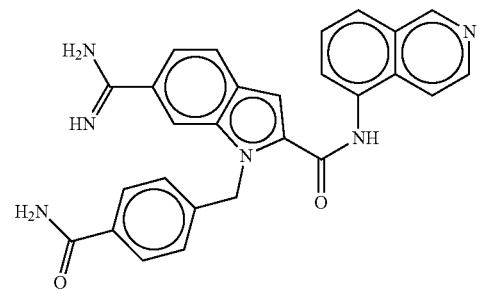
I-72
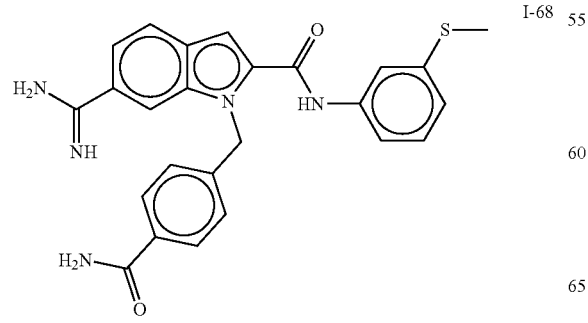
I-68
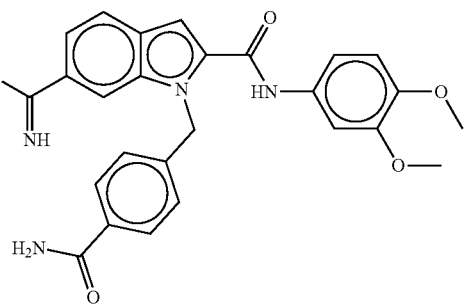
I-73

I-74
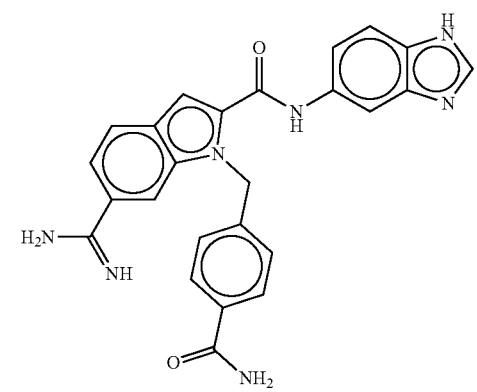
I-75
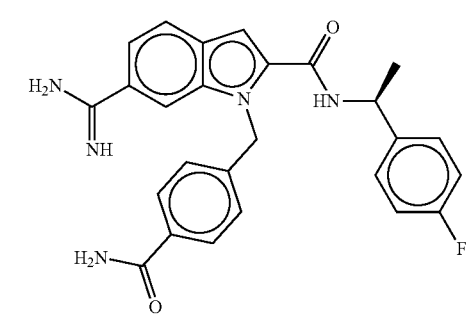
I-76
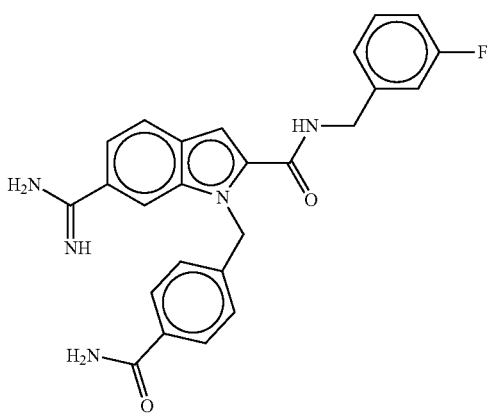
I-77
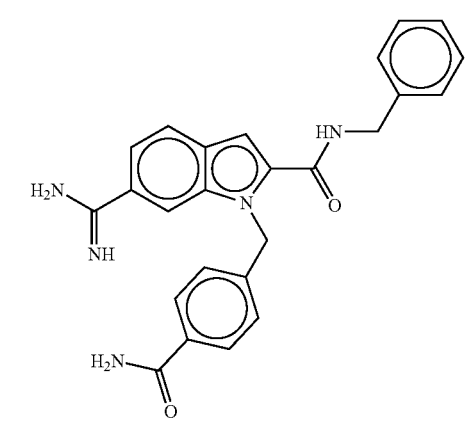
I-78
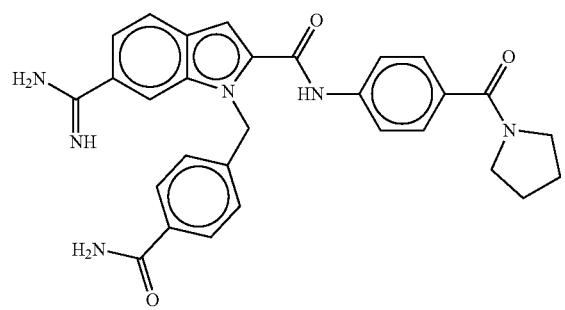
I-79
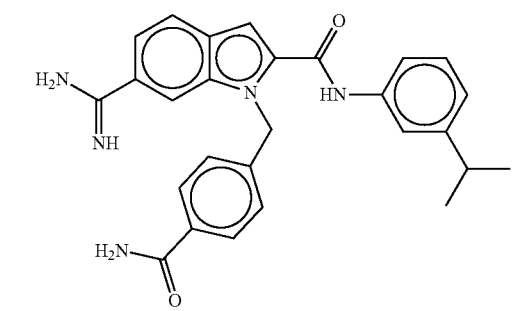
I-80
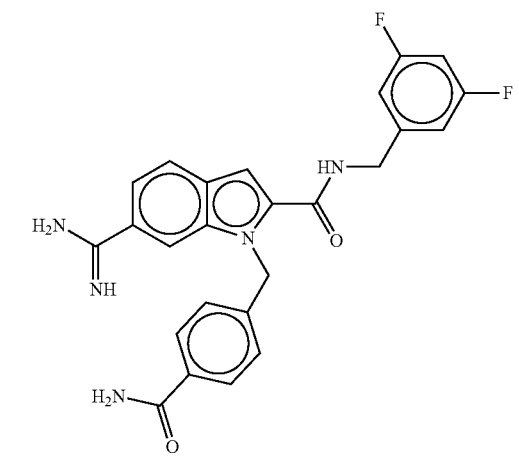
I-81
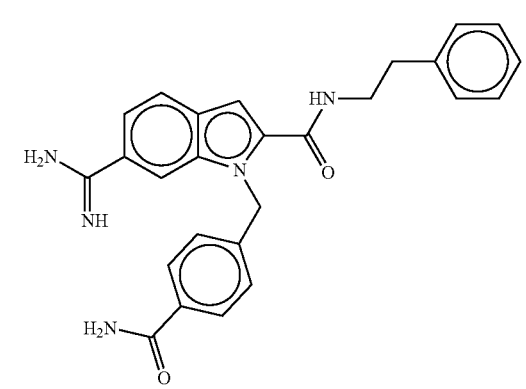

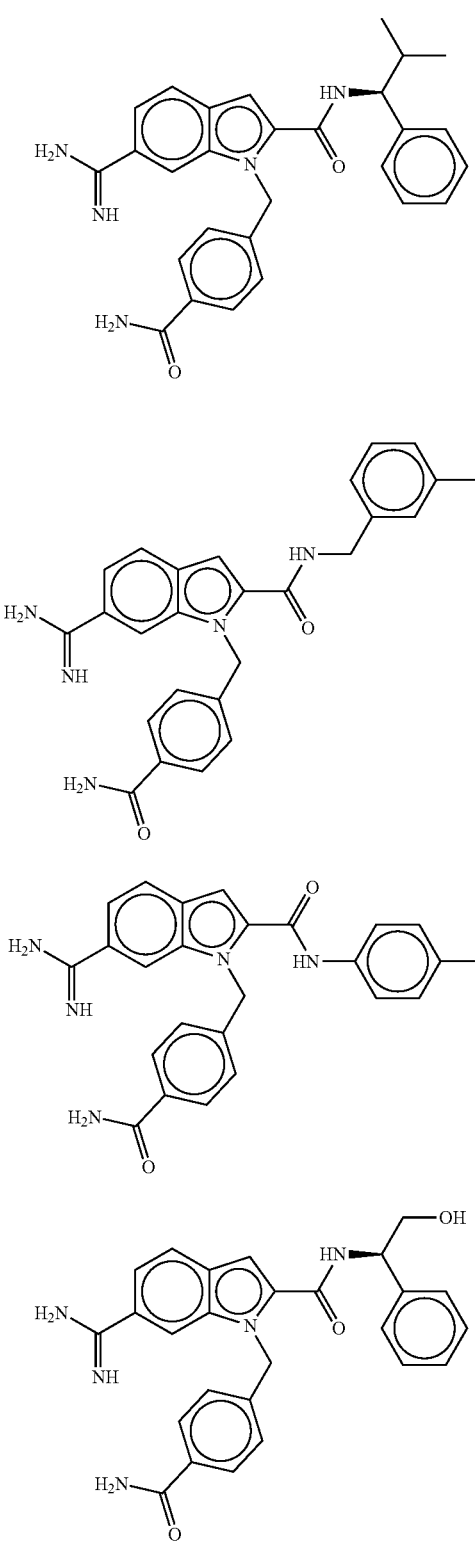
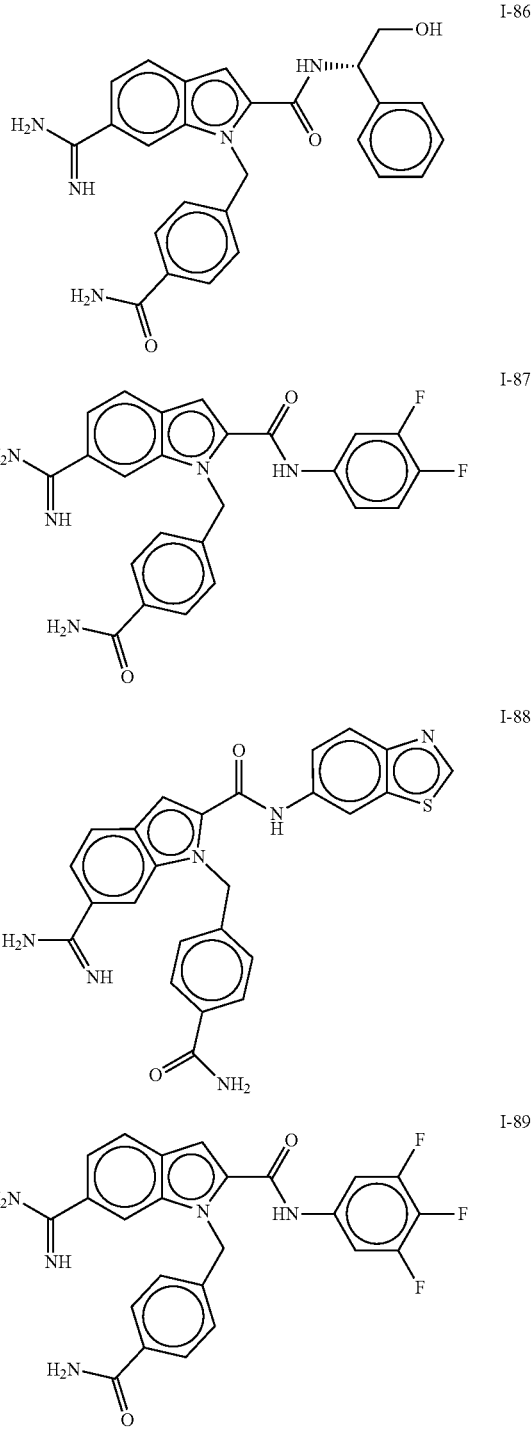

I-90
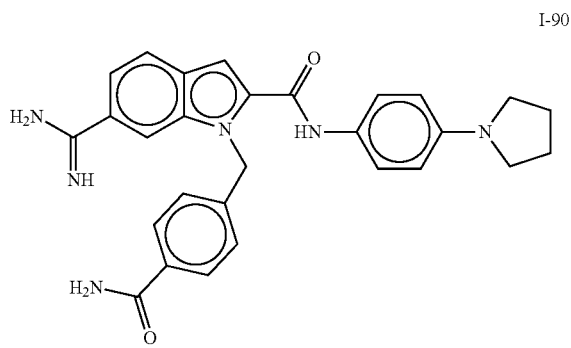
I-91
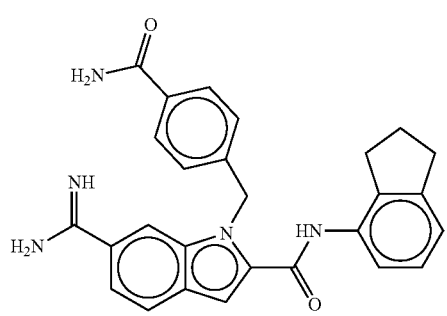
I-92
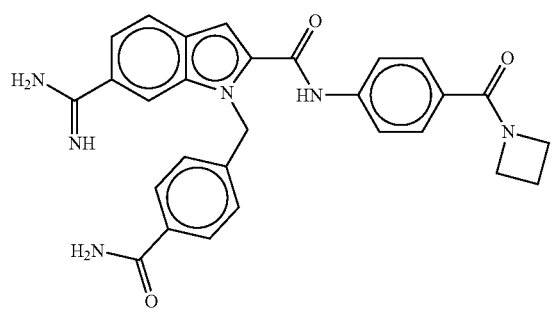
I-93
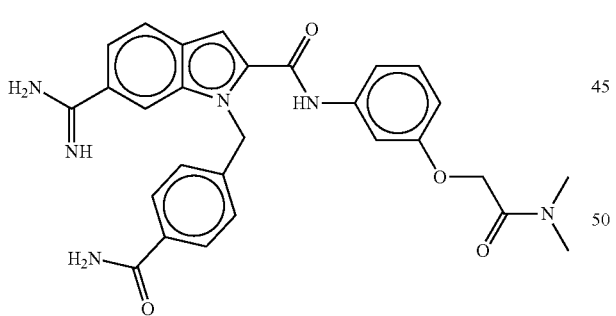
I-94
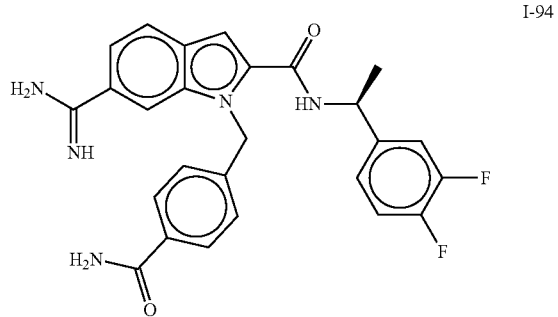
I-95
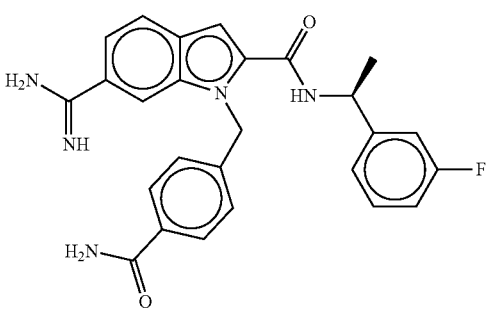
I-96
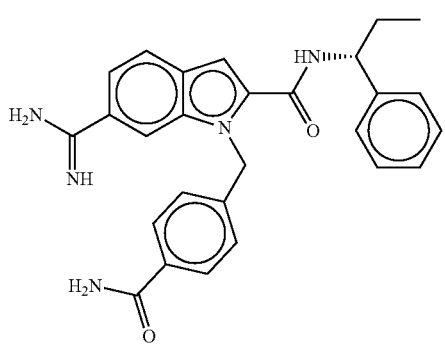
I-97
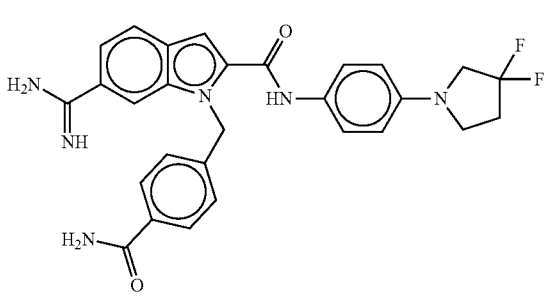
I-98
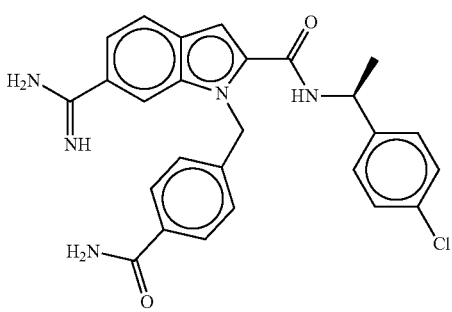
I-99
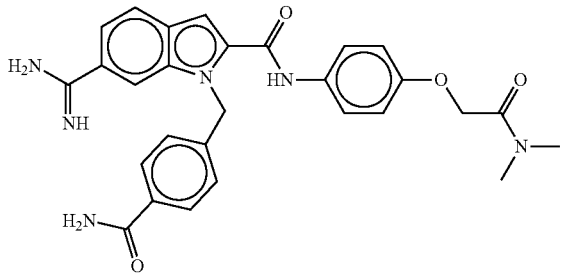

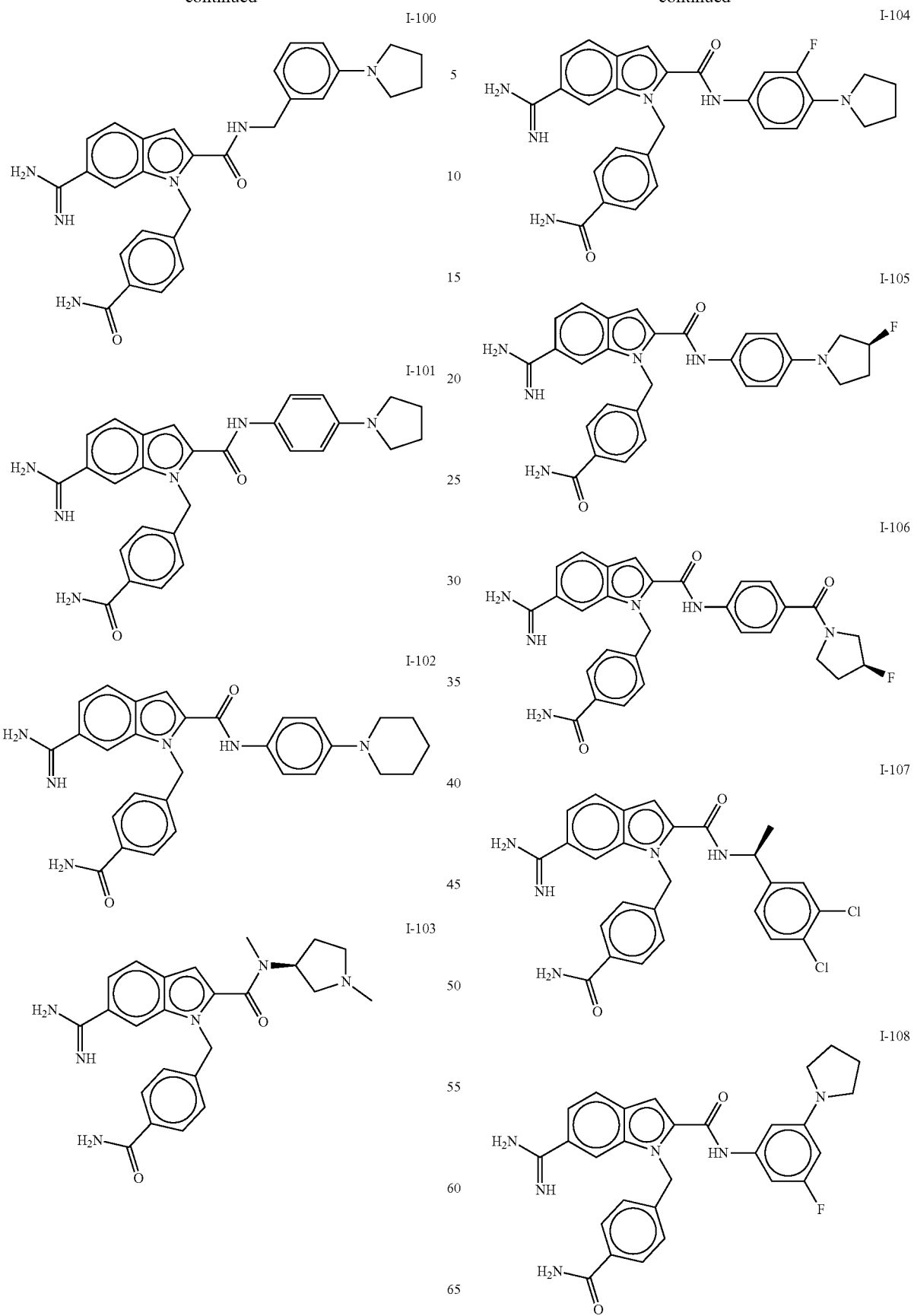

I-109
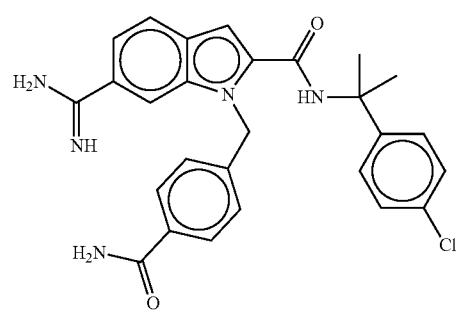
I-110
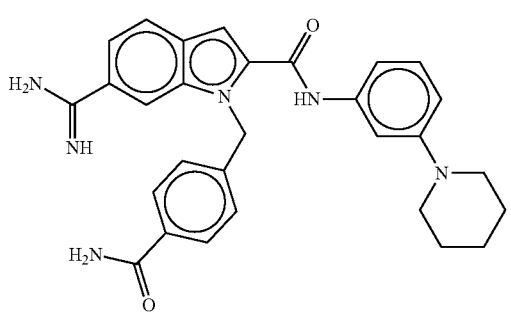
I-111
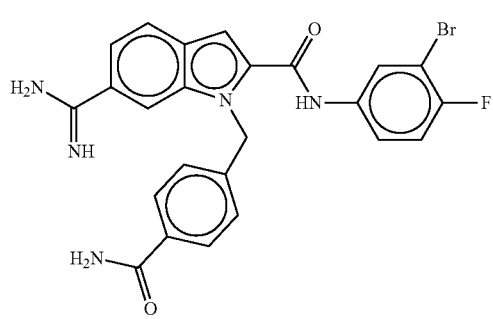
I-112
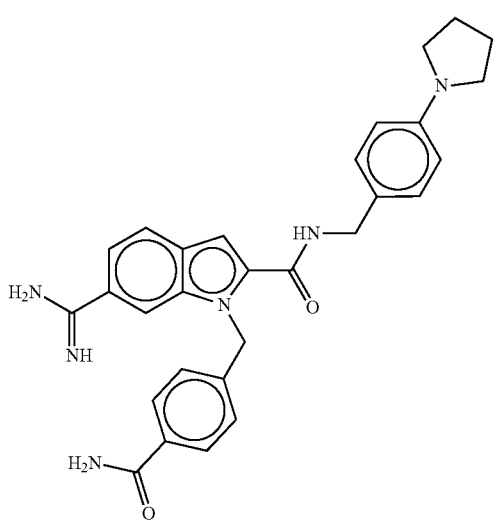
I-113
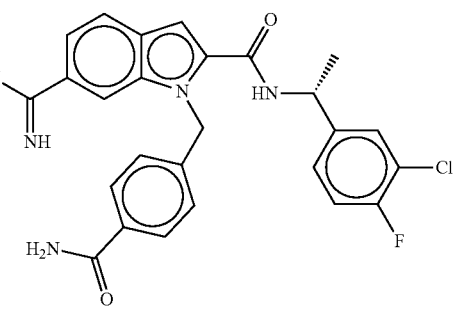
I-114
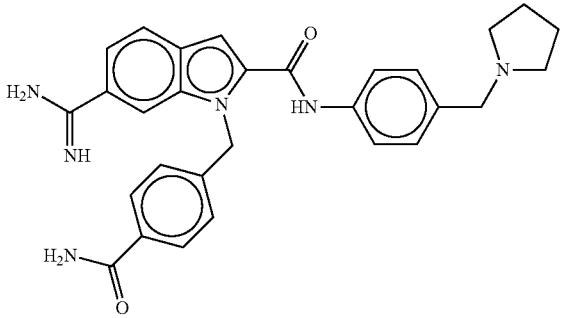
I-115
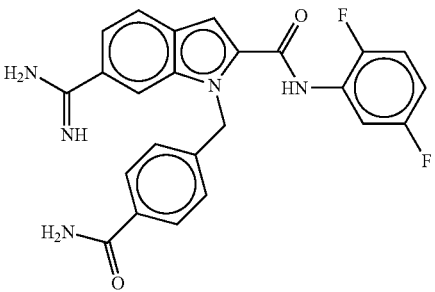
I-116
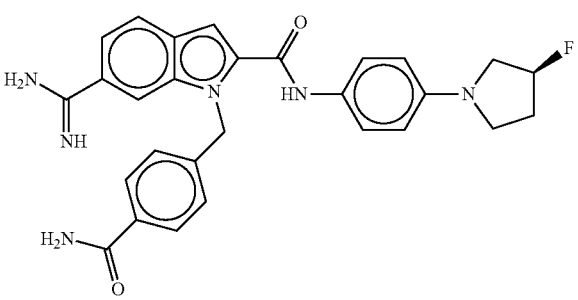

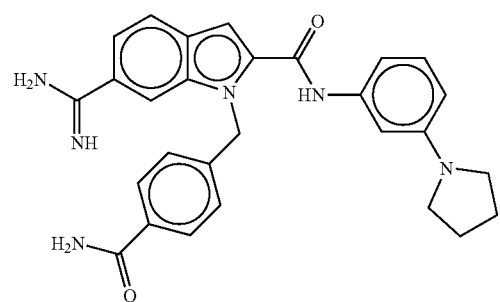
I-117
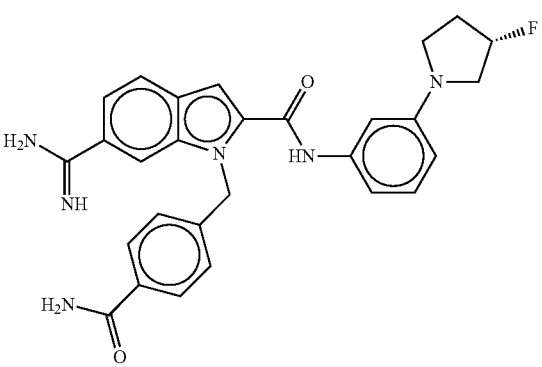
I-122
I-118
I-123
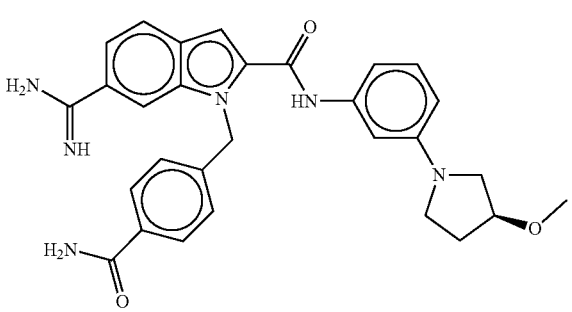
I-119
I-124
I-120
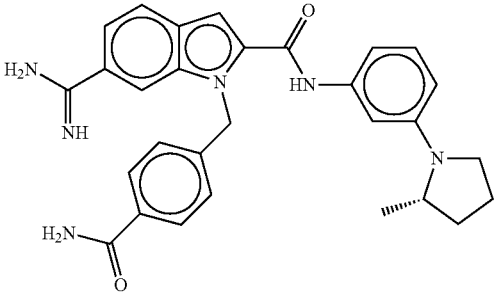
I-125
I-121
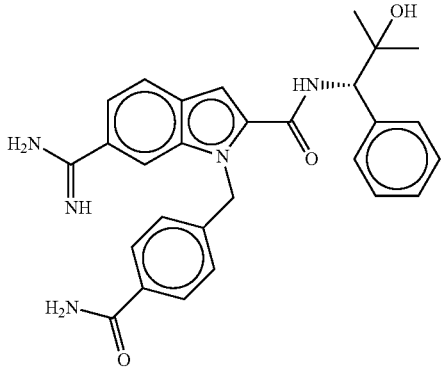

I-126 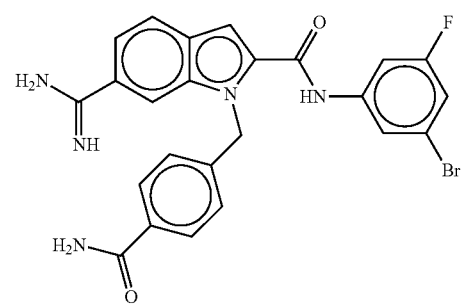
I-127 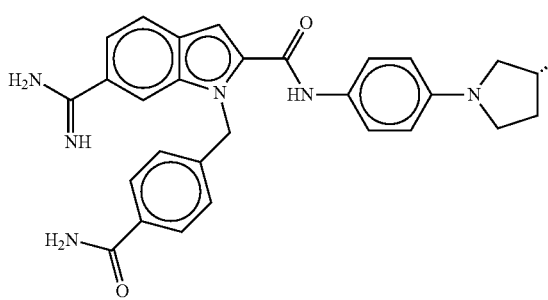
I-128 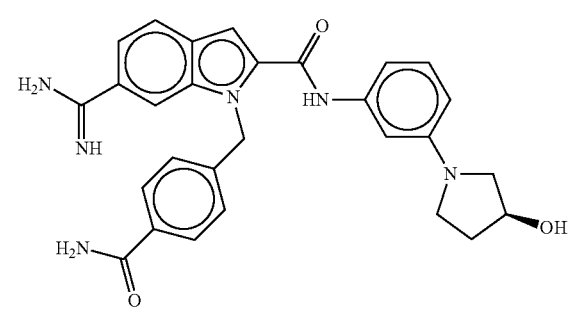
I-129 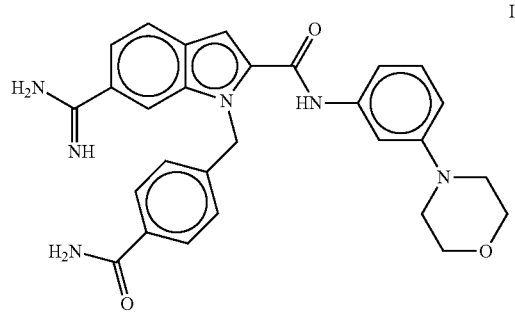
I-130 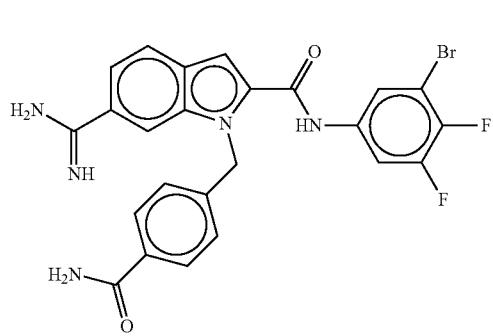
I-131 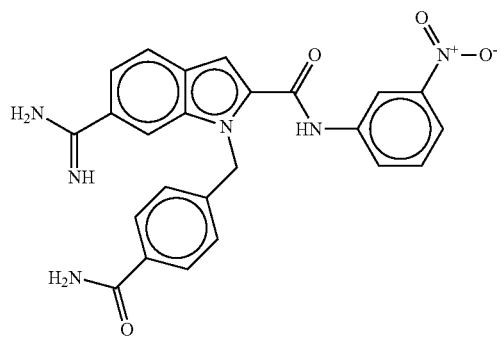
I-132 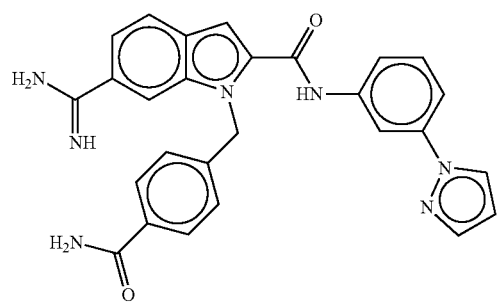
I-133 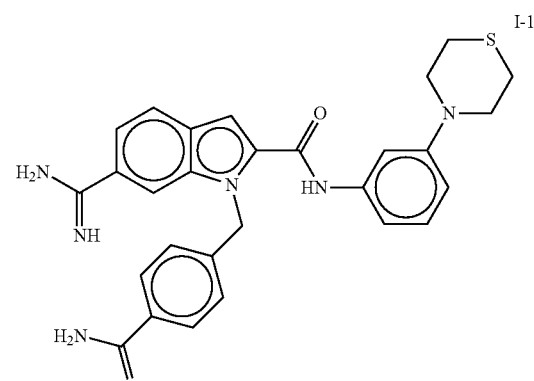
I-134 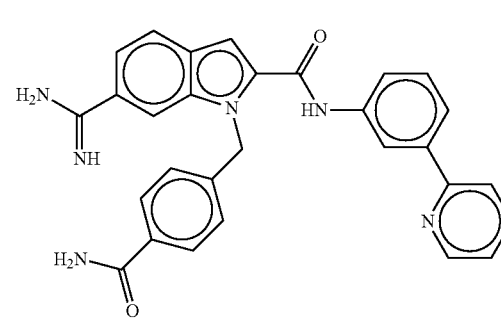
I-135 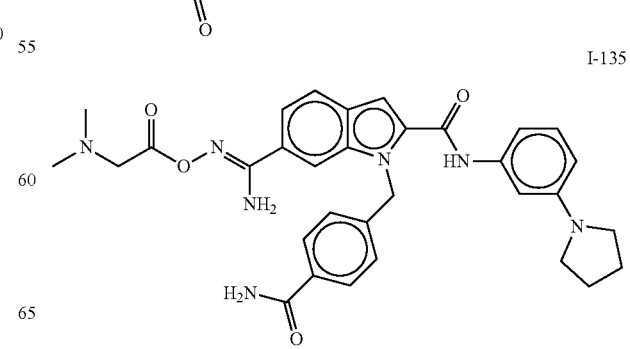

1079
-continued
I-136
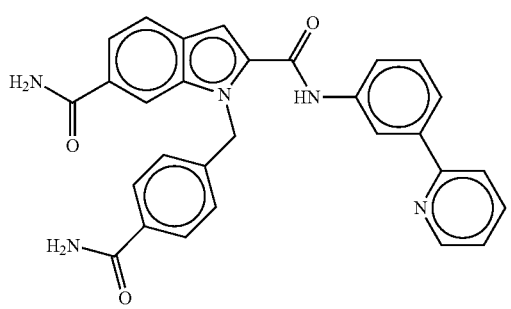
I-137
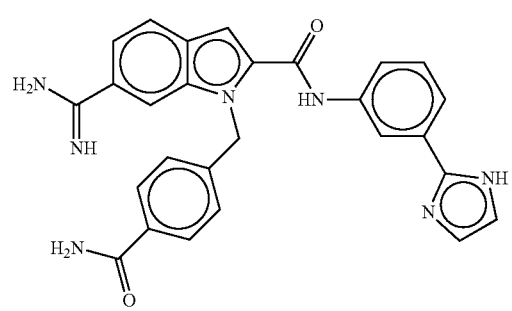
I-138
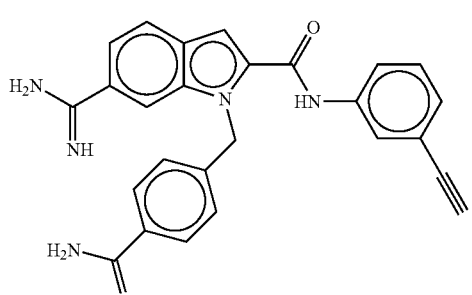
I-139
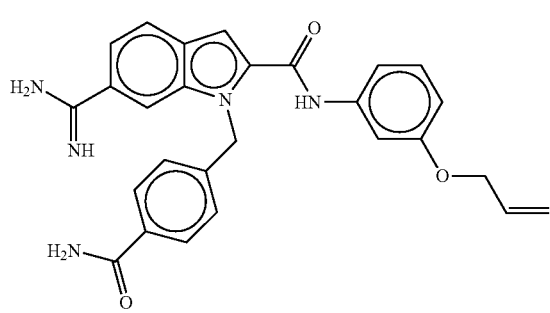
I-140
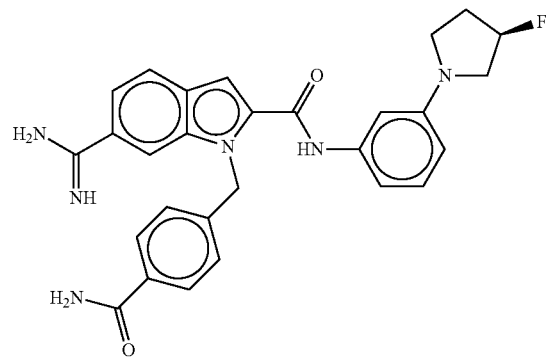
1080
-continued
I-141
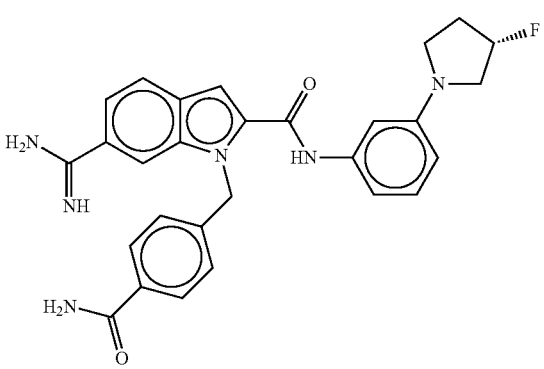
I-142
I-143
I-144
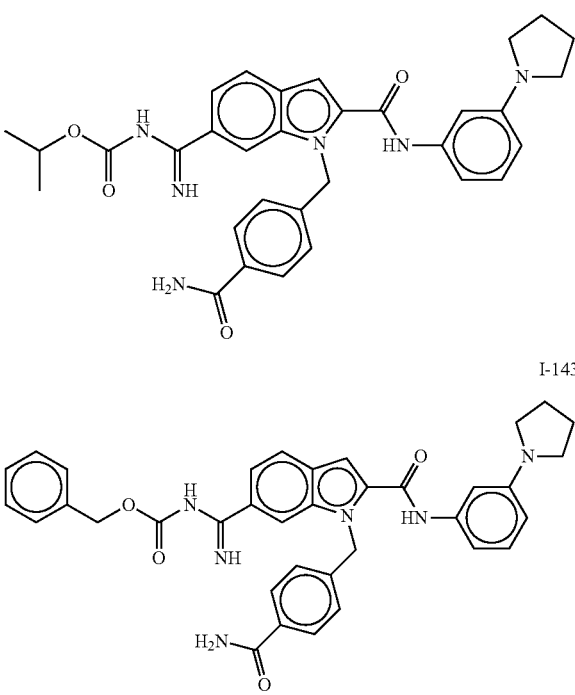

I-145
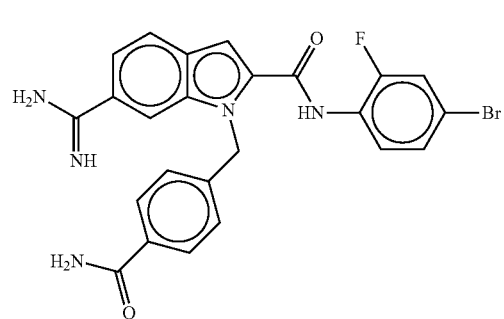
I-146
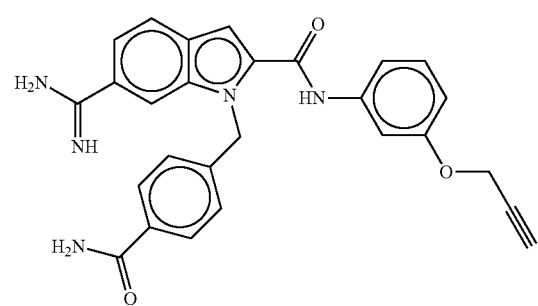
I-147
I-148
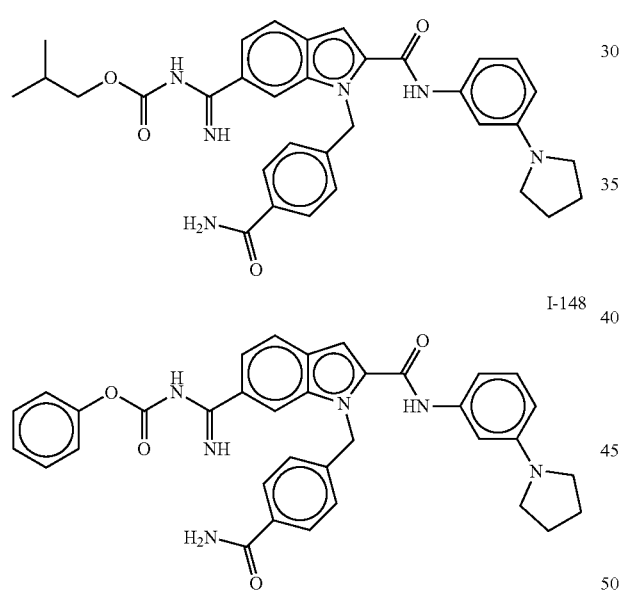
I-149
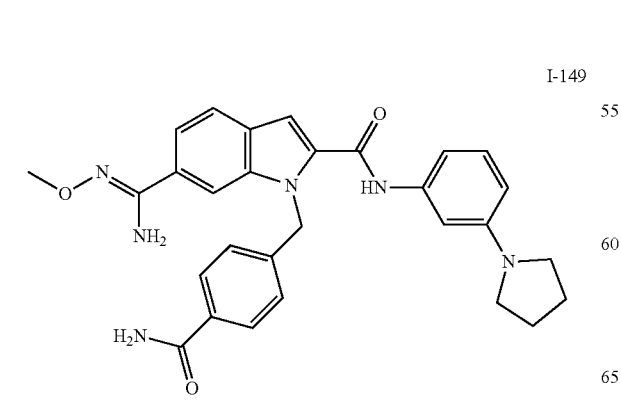
I-150
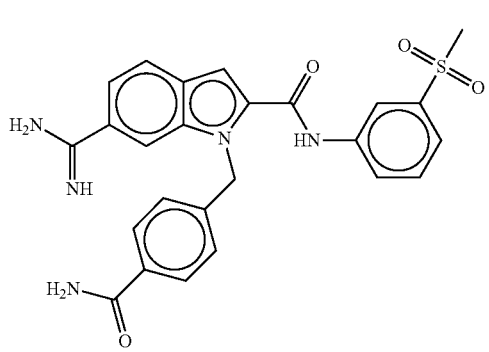
I-151
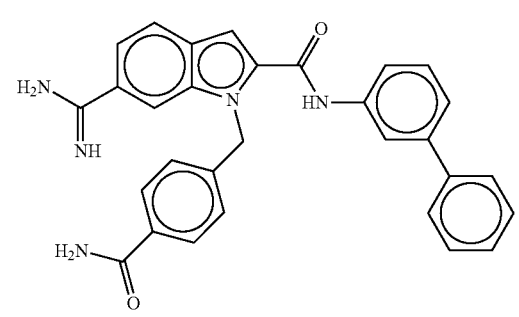
I-152
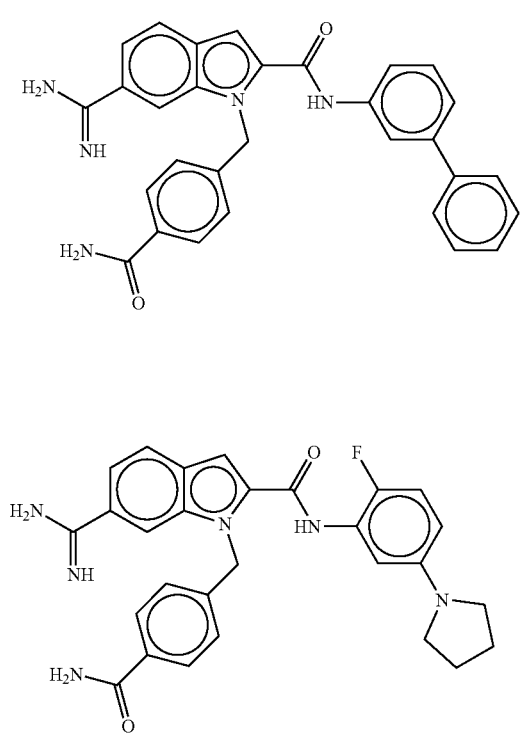
I-153
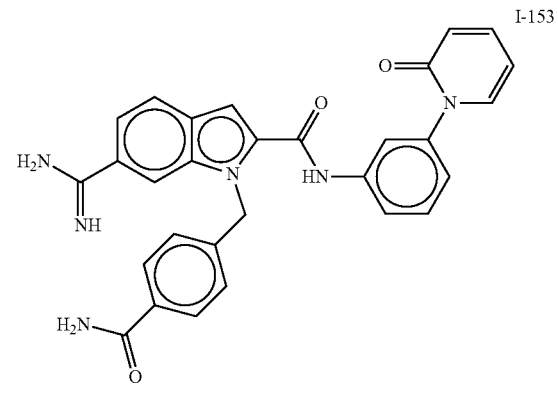

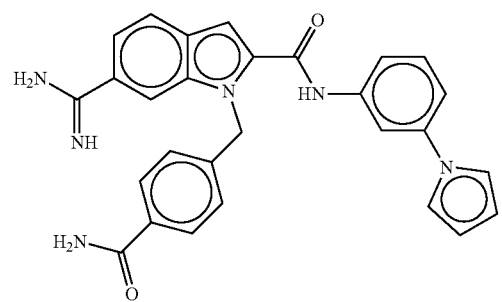
I-154
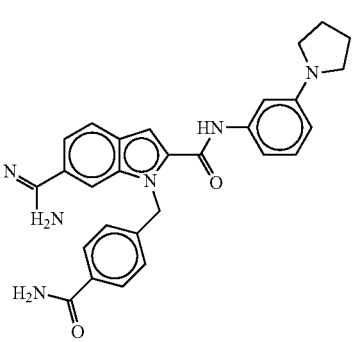
I-158
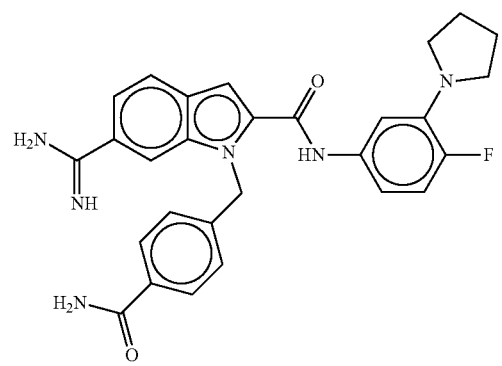
I-155
I-159
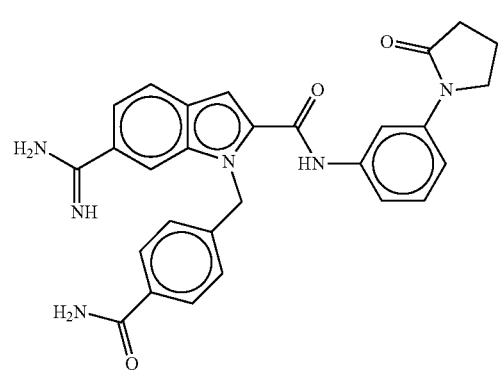
I-156
I-160
I-161
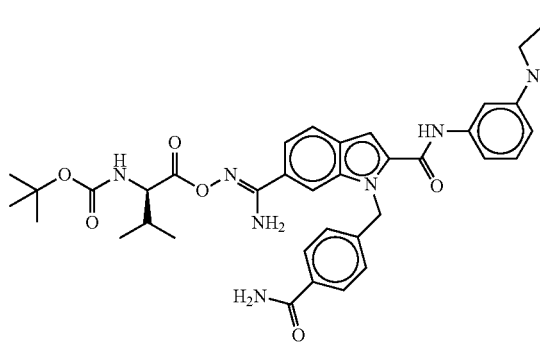
I-157
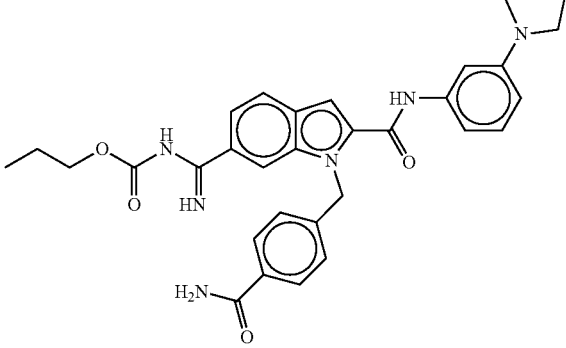
I-162

I-163
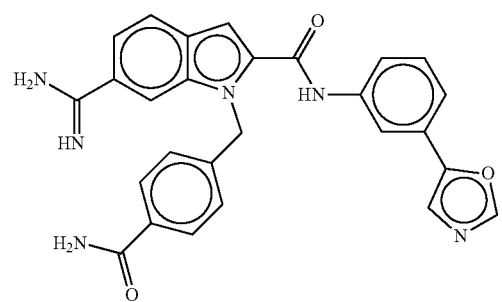
I-164
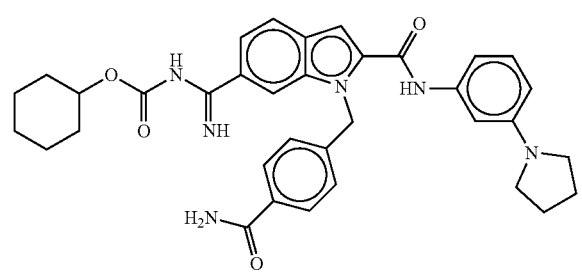
I-165
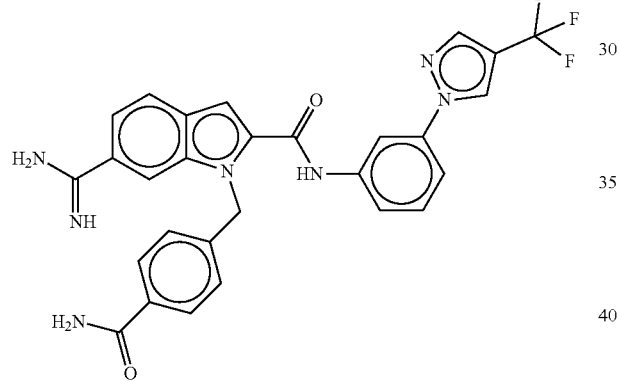
I-166
I-167
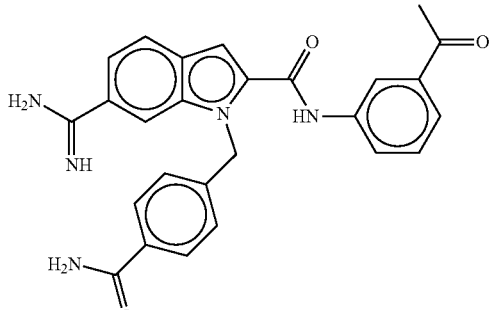
I-168
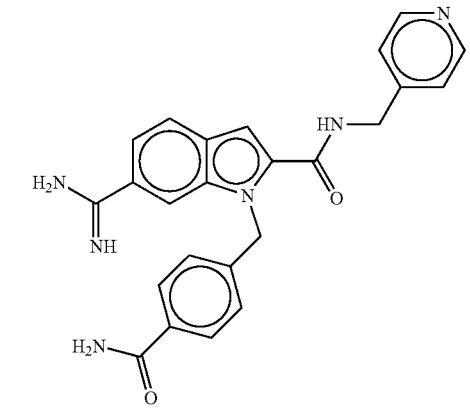
I-169
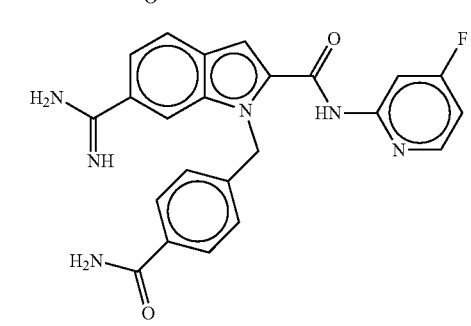
I-170
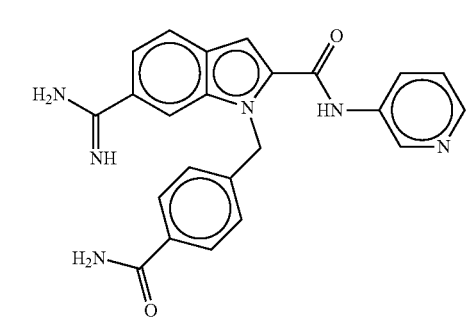
I-171
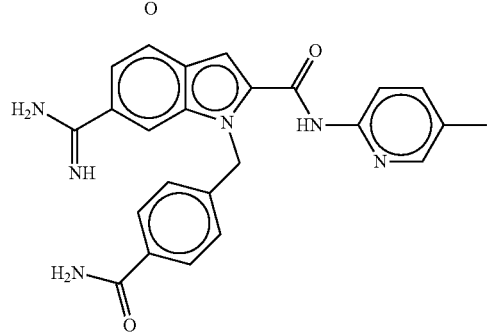

I-172
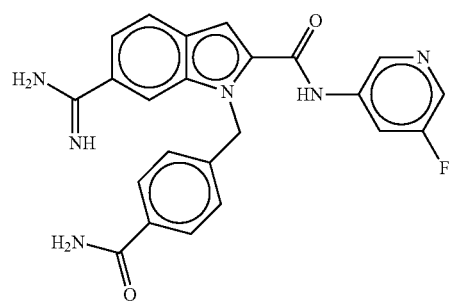
I-173
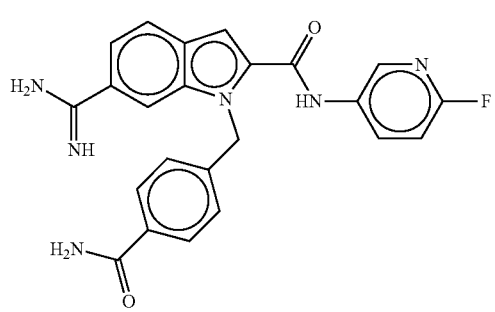
I-174
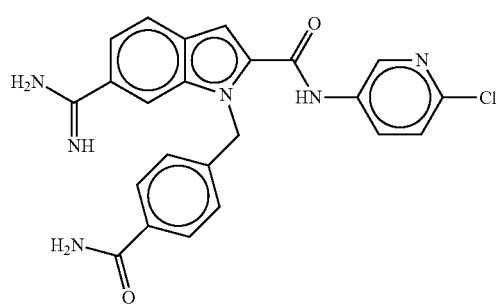
I-175
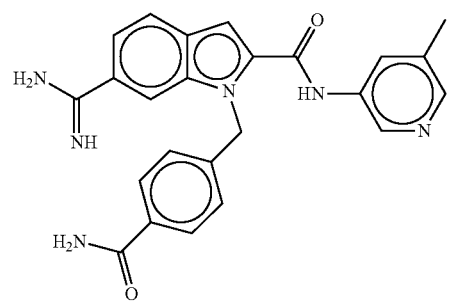
I-176
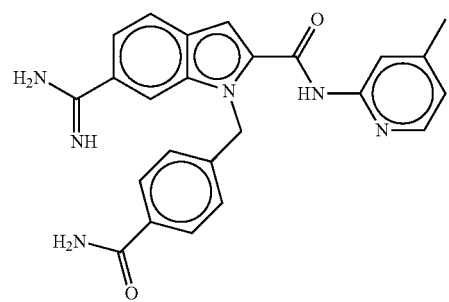
I-177
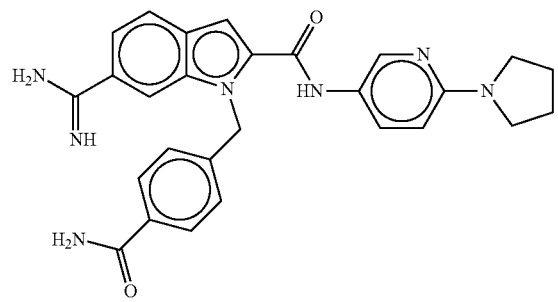
I-178
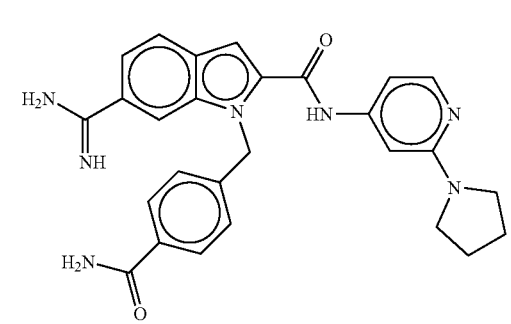
I-179
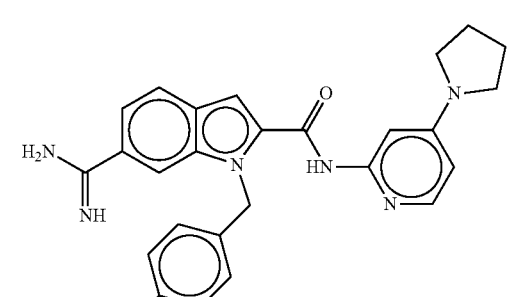
I-180
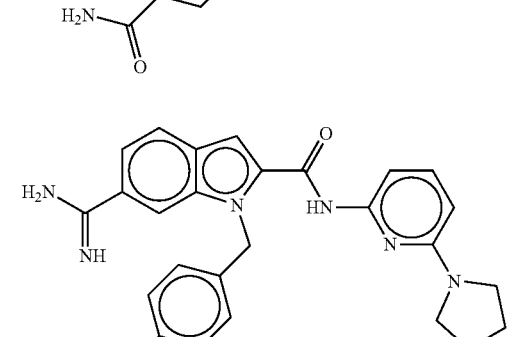
I-181
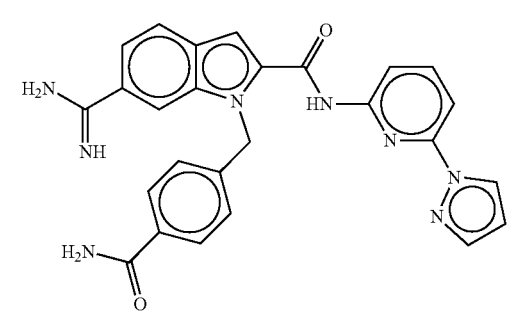

I-182
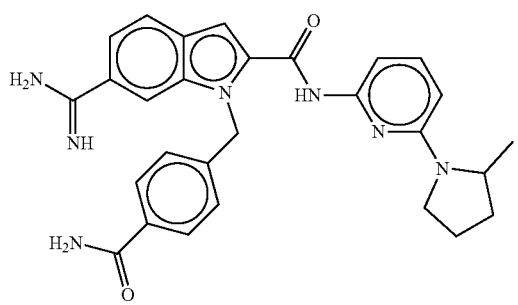
I-187
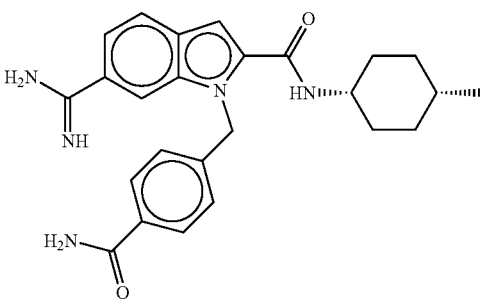
I-183
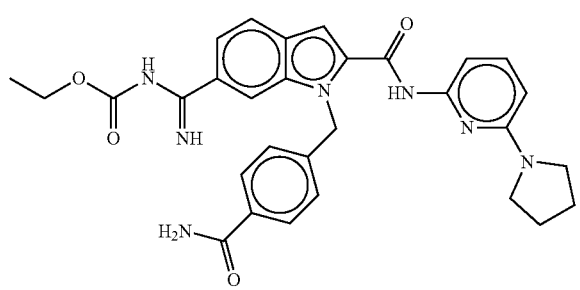
I-188
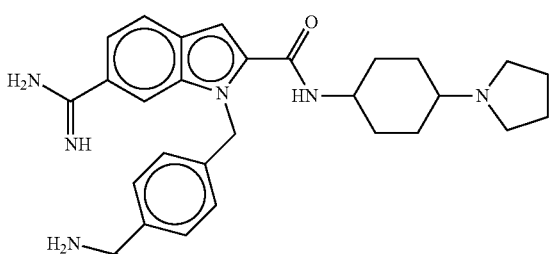
I-184
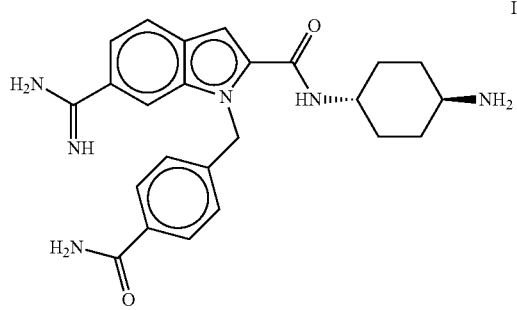
I-189
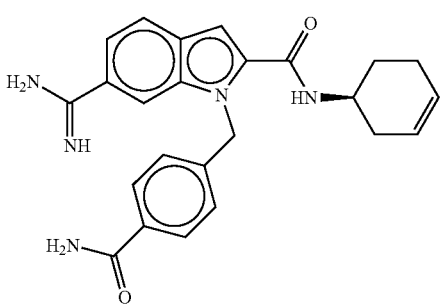
I-185
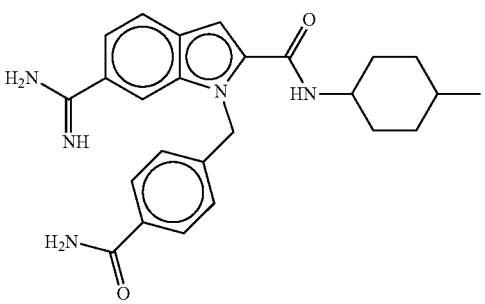
I-186
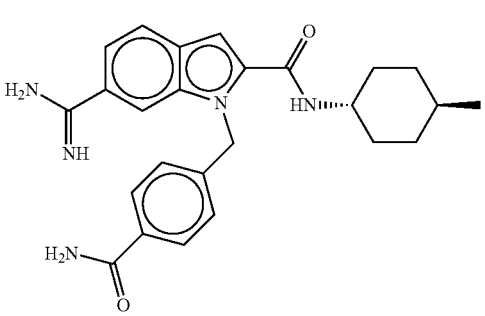
I-190
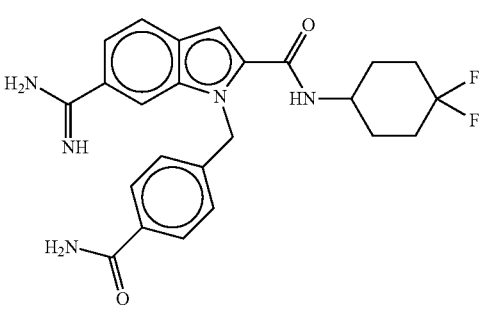

I-191 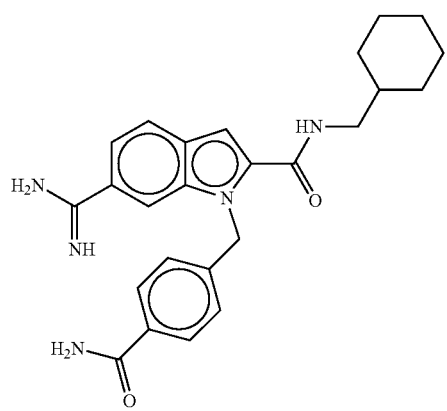
I-192 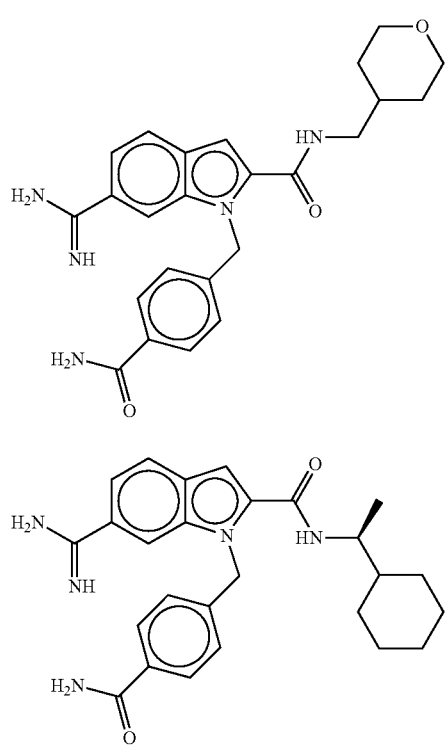
I-193 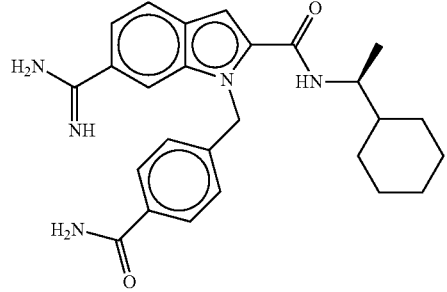
I-194 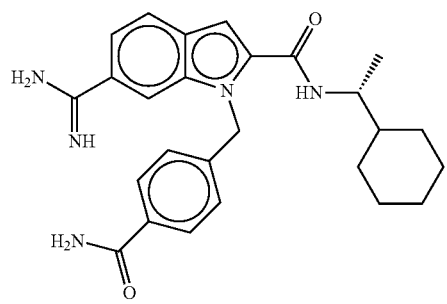
I-195 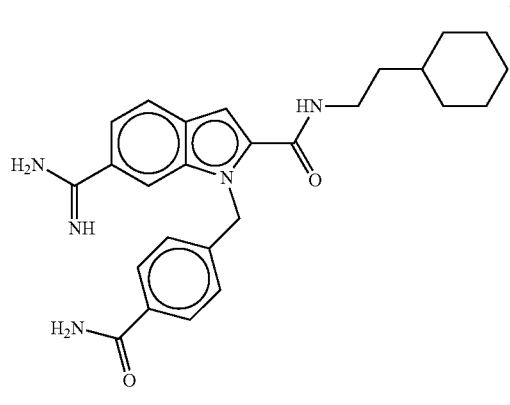
I-196 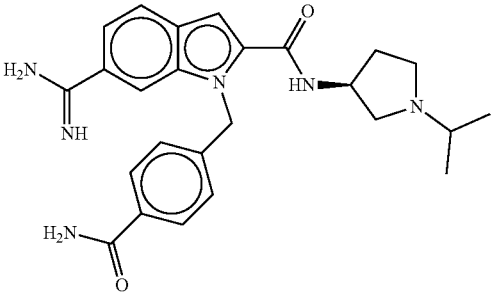
I-197 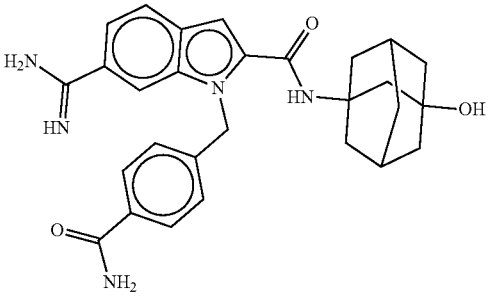
I-198 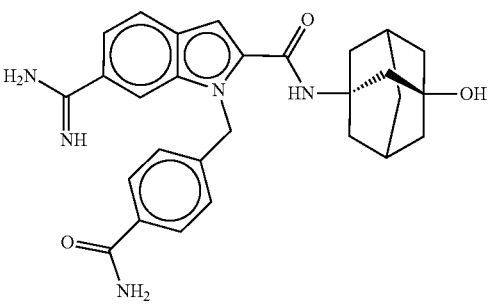
I-199 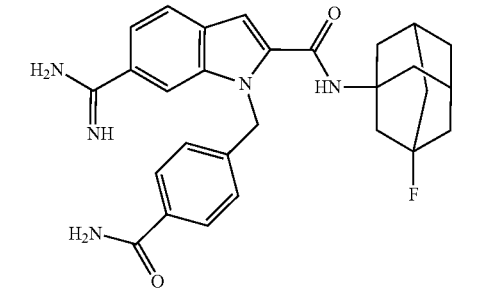

1093
-continued
I-200
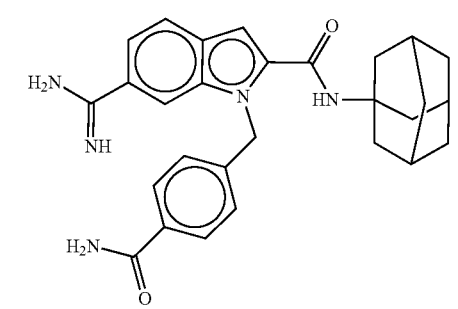
I-201
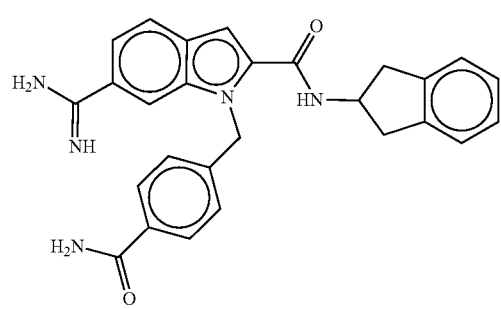
I-202
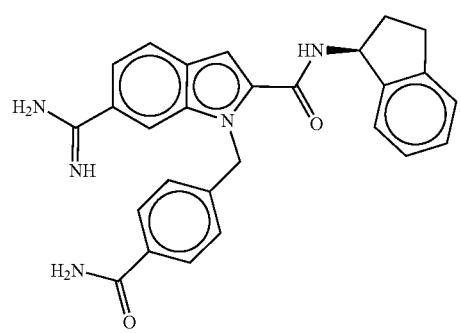
I-203
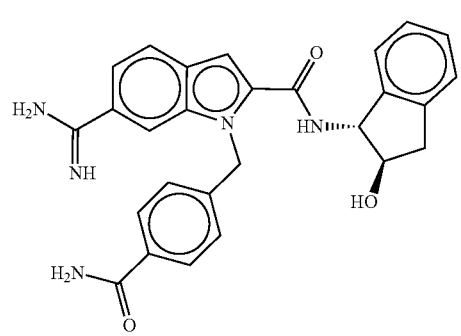
I-204
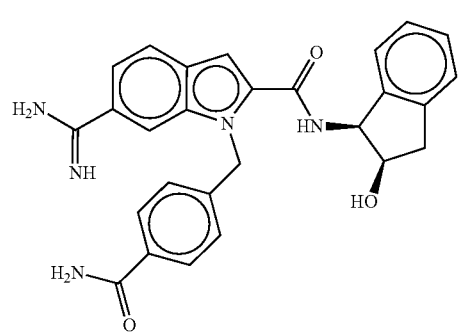
1094
-continued
I-205
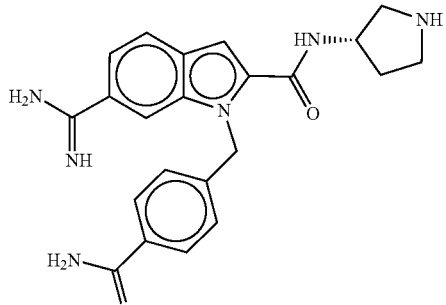
I-206
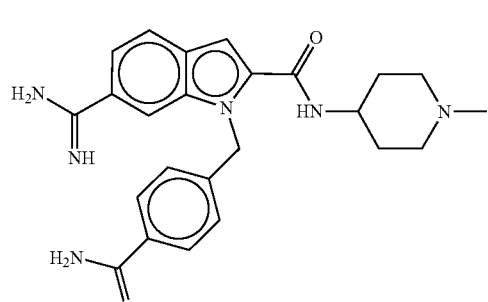
I-207
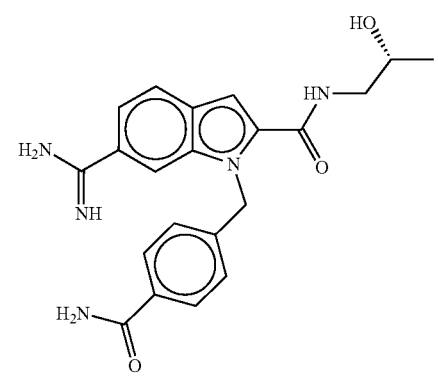
I-208
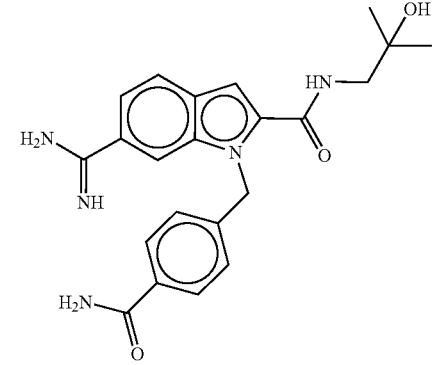

I-209
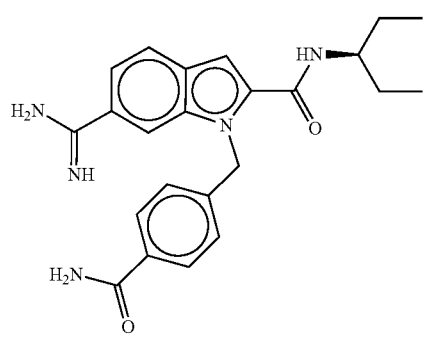
I-210
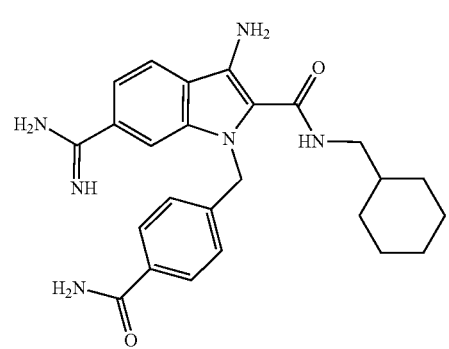
I-211
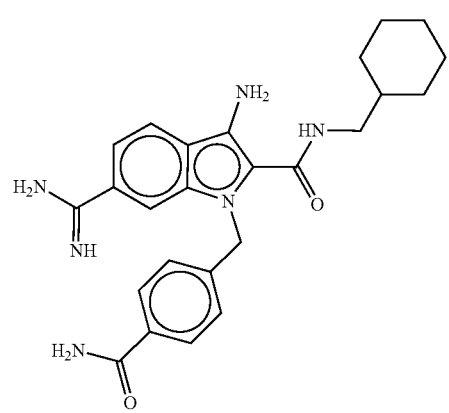
I-212
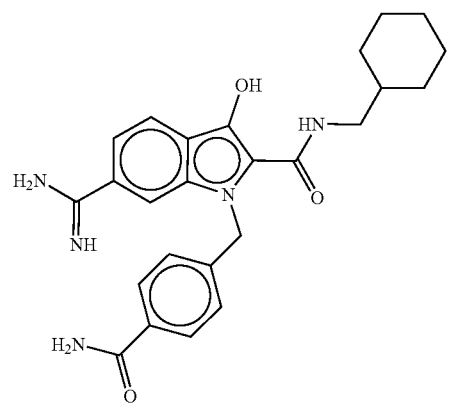
I-213
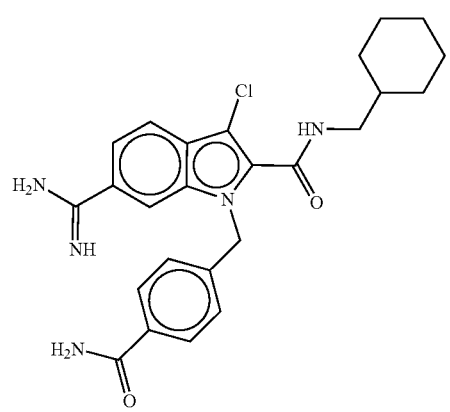
I-214
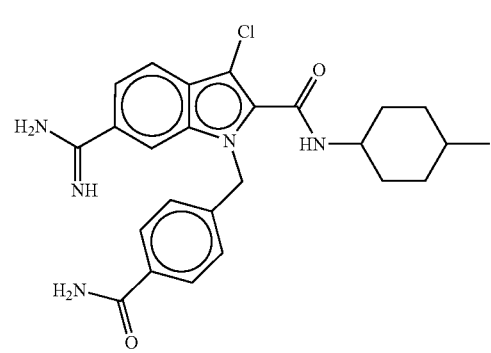
I-215
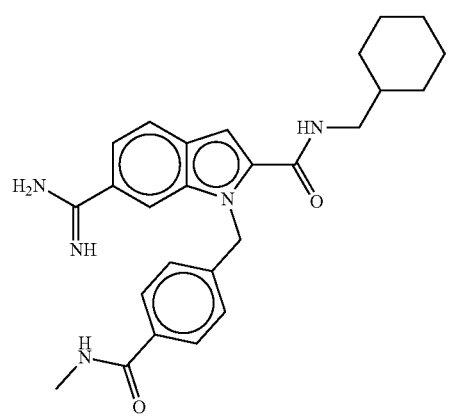
I-216
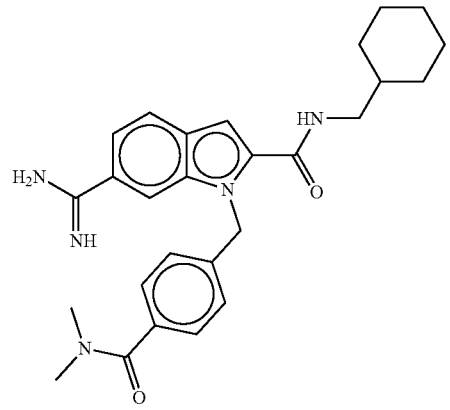

I-217 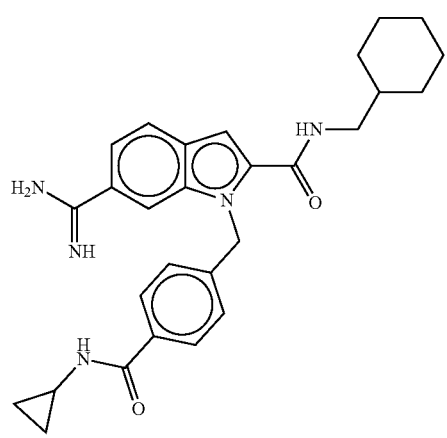
I-218 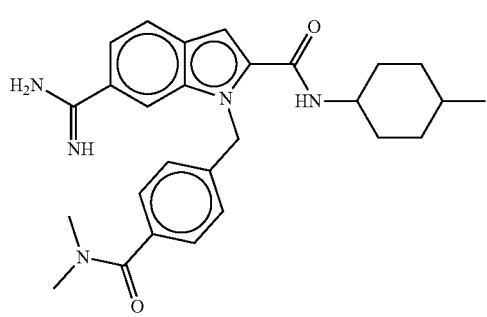
I-219 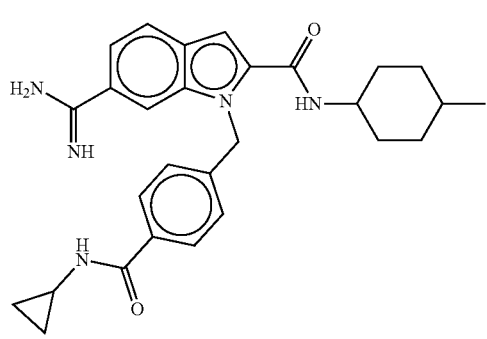
I-220 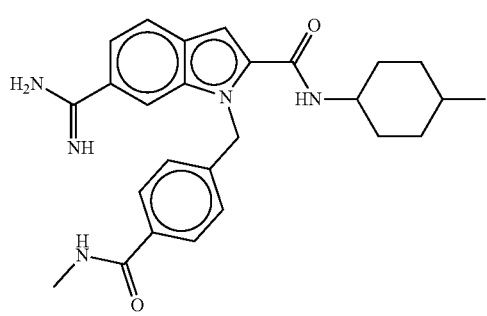
I-221 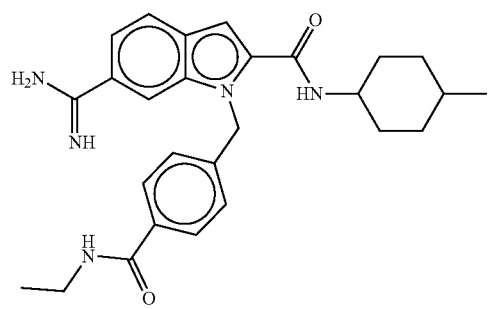
I-222 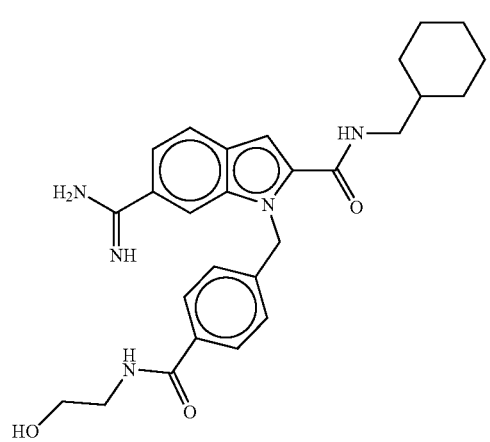
I-223 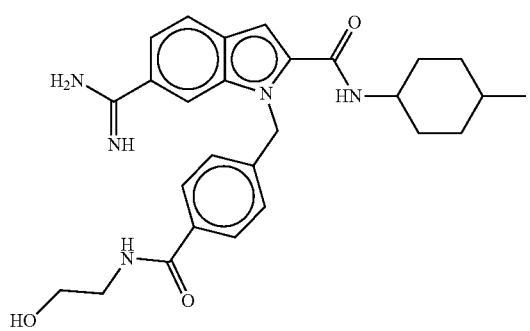
I-224 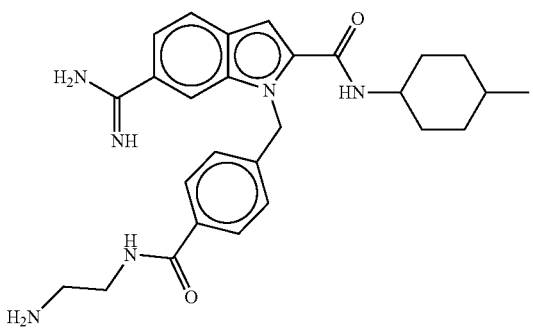

I-225
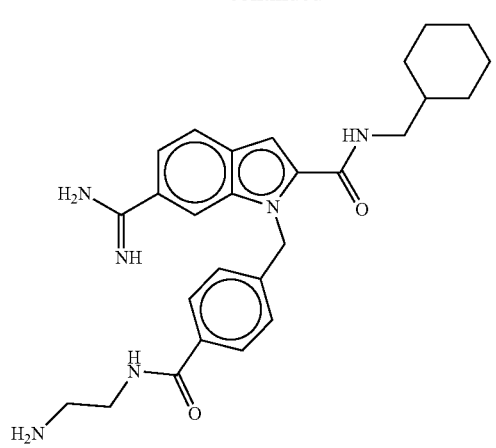
I-229
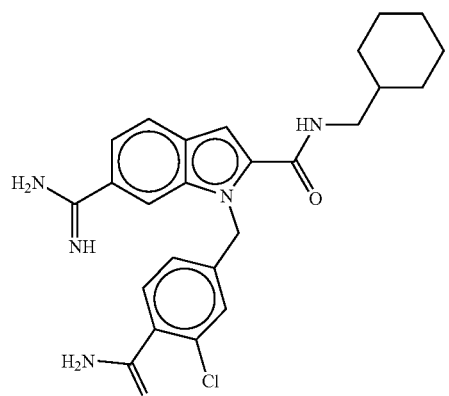
I-226
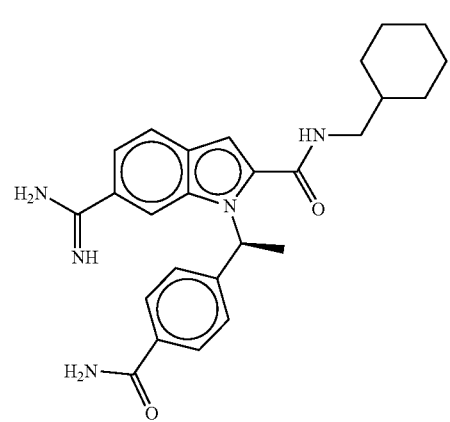
I-230
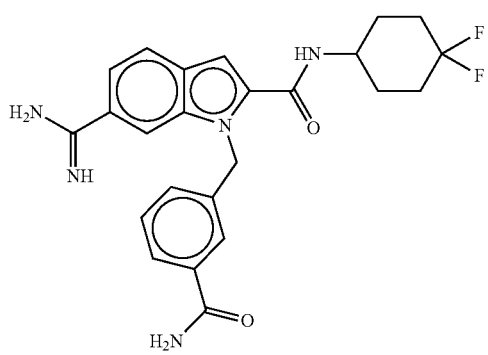
I-227
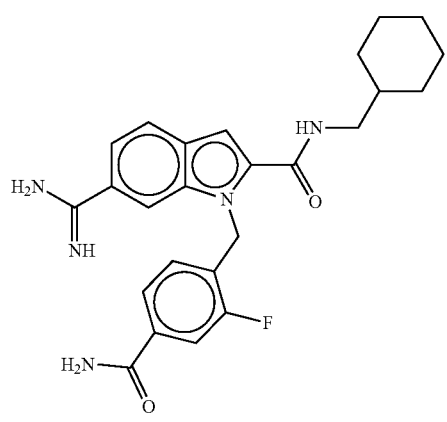
I-231
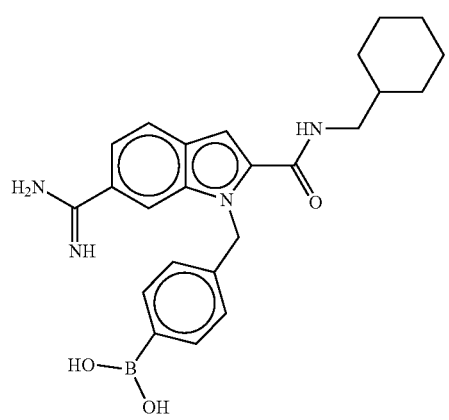
I-228
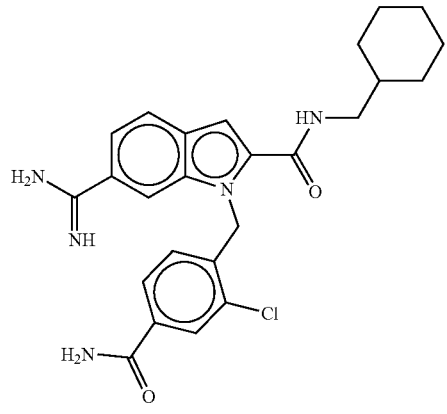
I-232
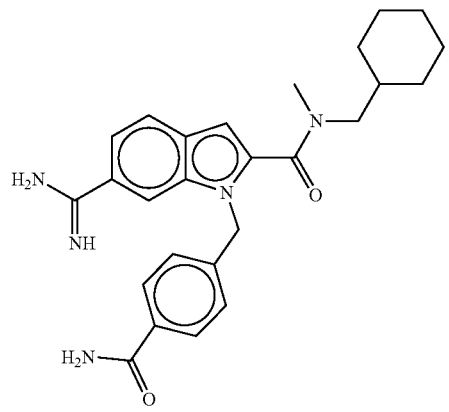

I-233
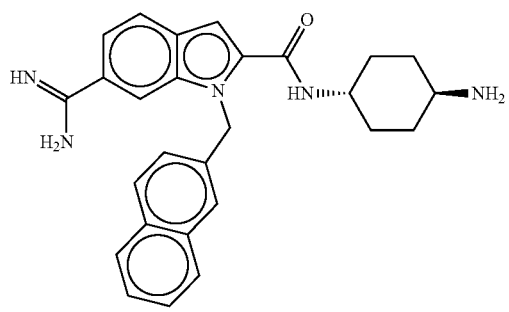
I-234
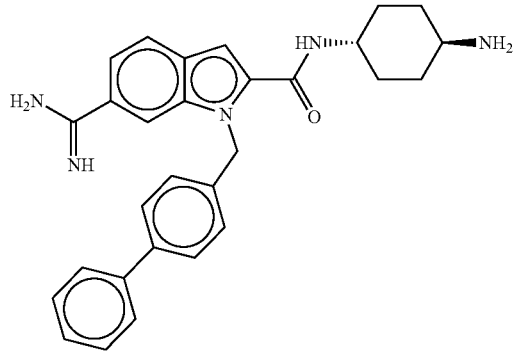
I-235
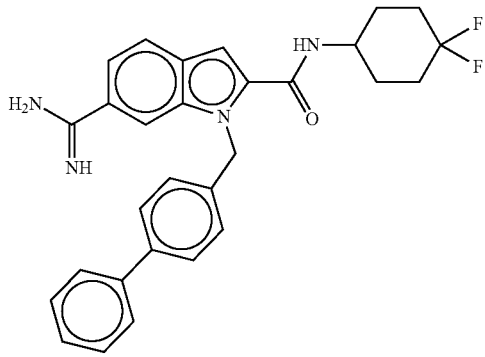
I-236
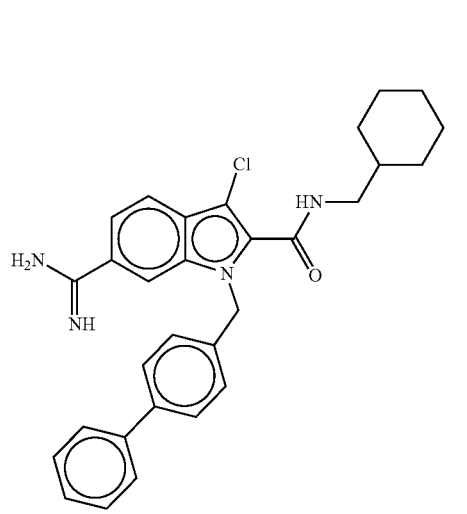
I-237
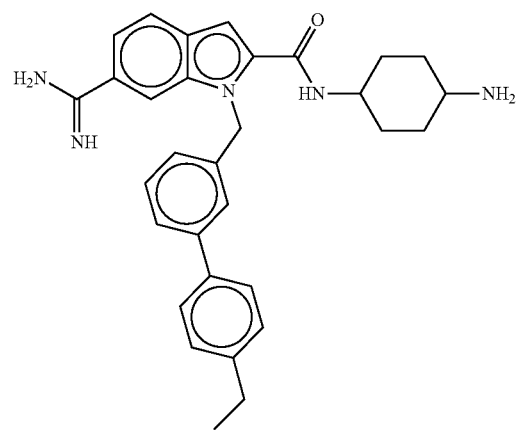
I-238
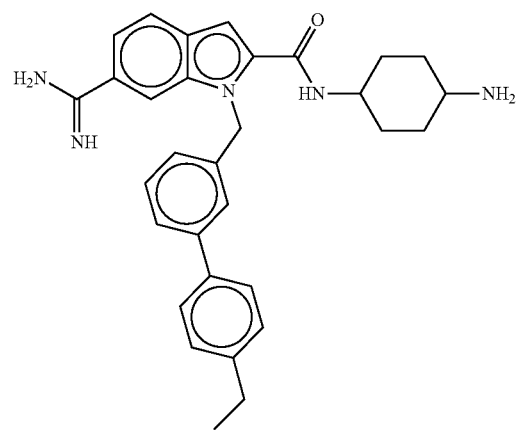
I-239
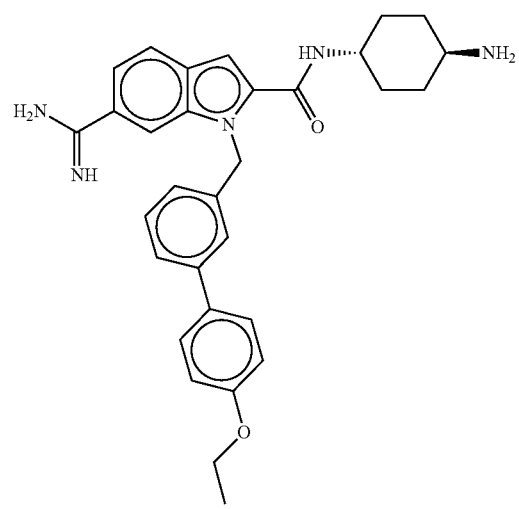

| 1103 -continued | 1104 -continued |
|---|---|
| I-240 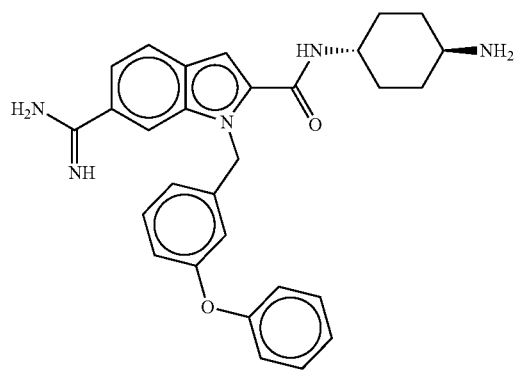 | I-243 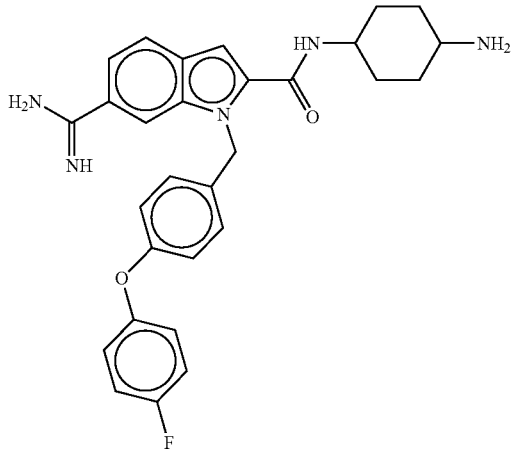 |
| I-241 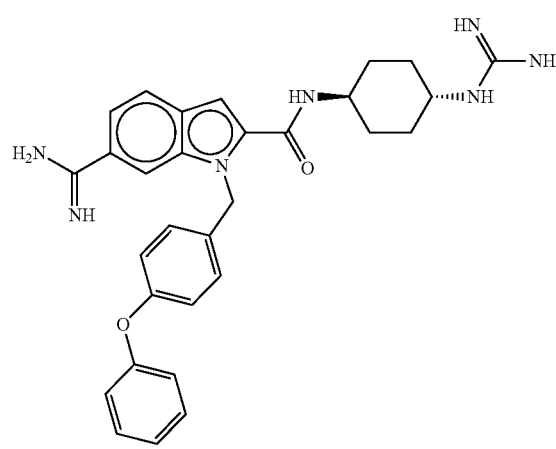 | I-244, I-245, I-246 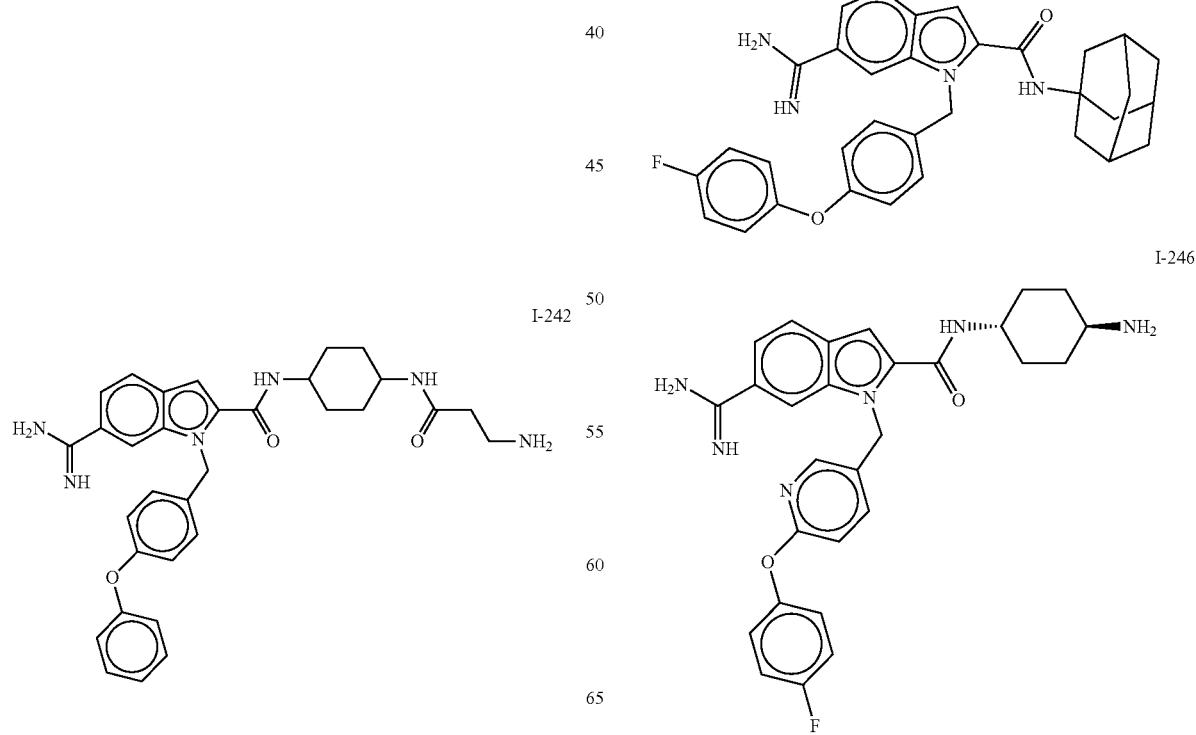 |
| I-242 | |

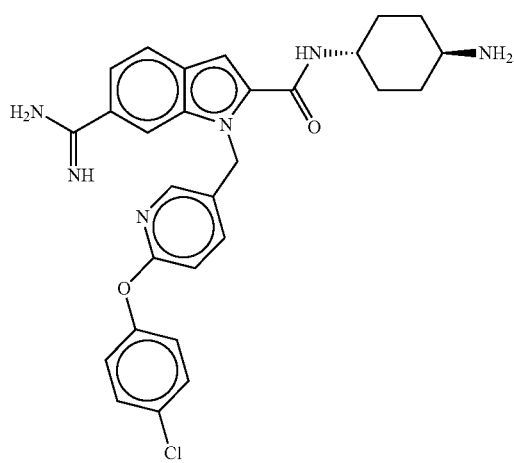
I-247
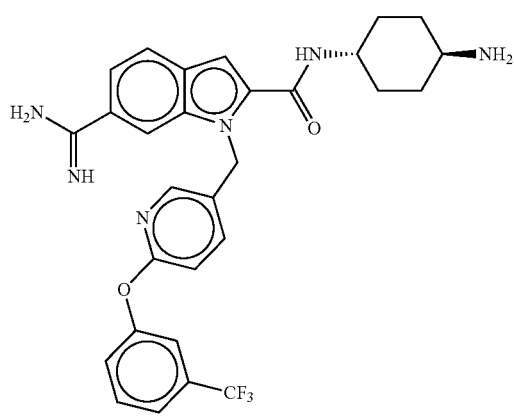
I-248
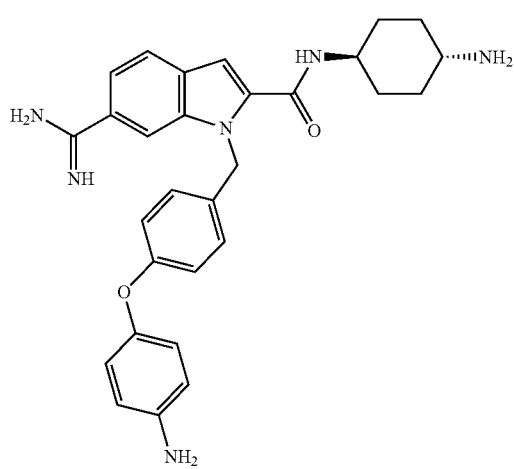
I-249
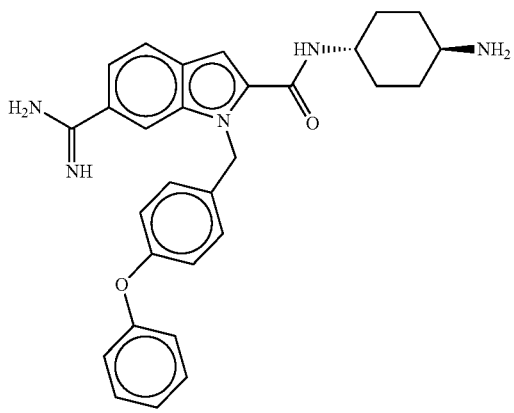
I-250
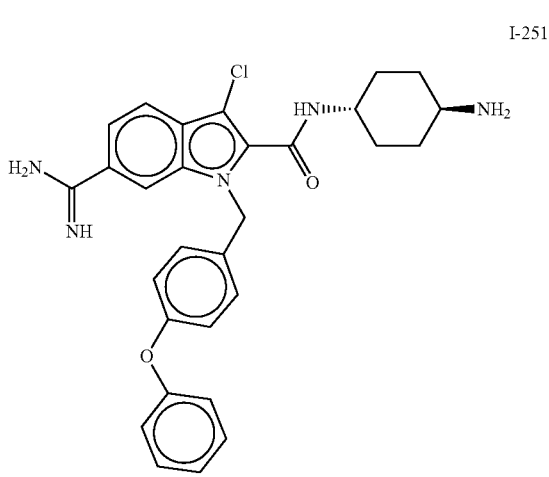
I-251
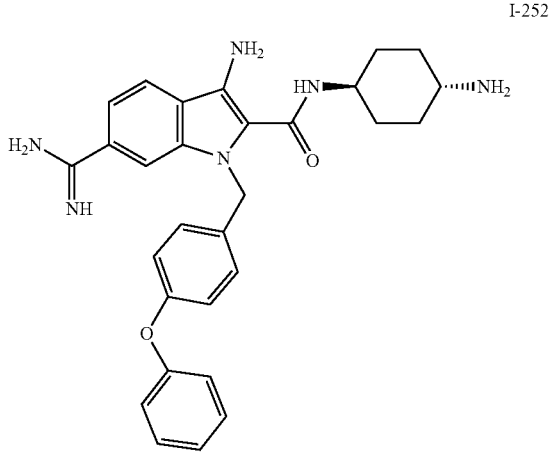
I-252

1107 -continued
I-253
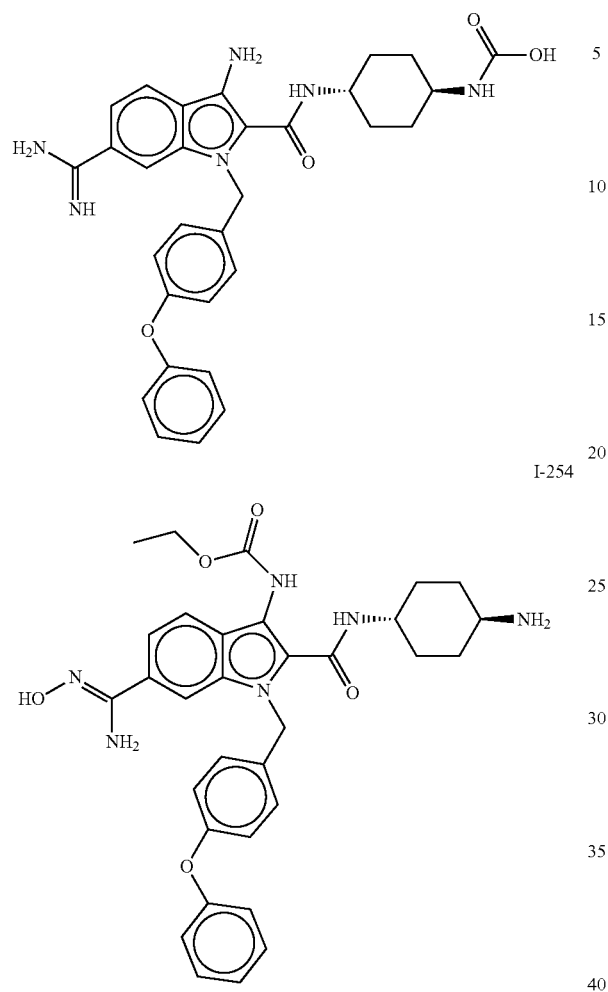
I-254
I-255
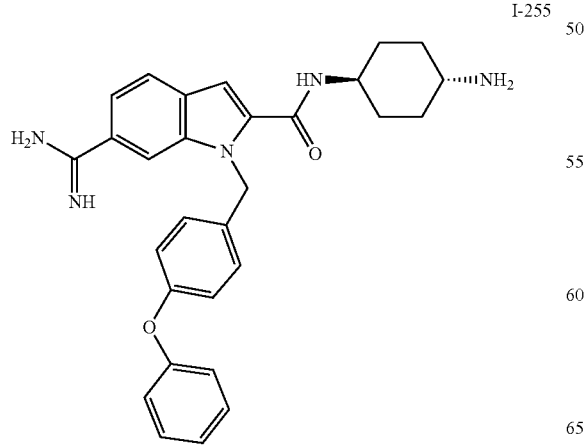
1108 -continued
I-256
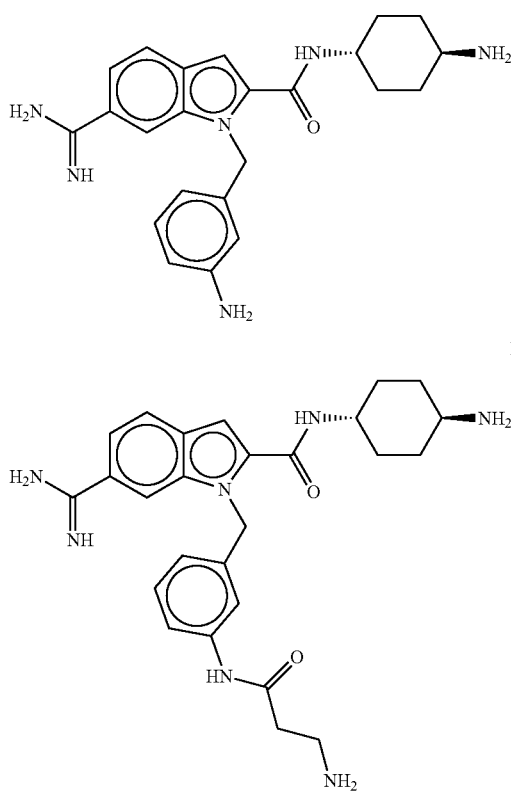
I-257
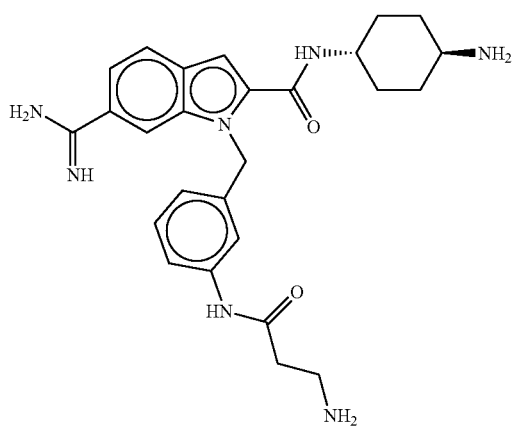
I-258
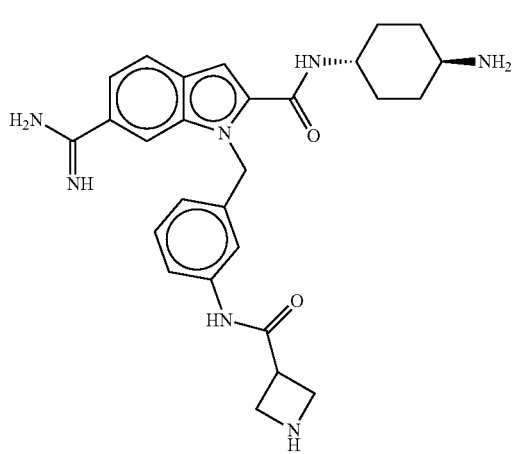

1109
-continued
I-259
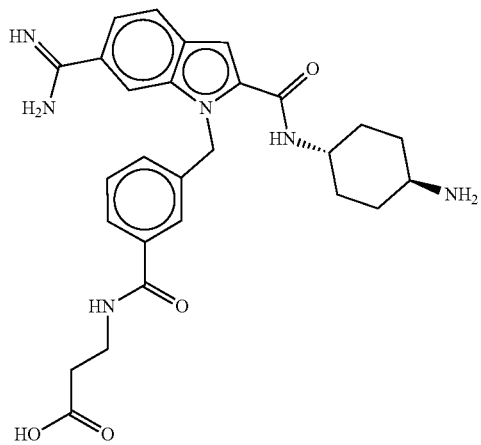
I-260
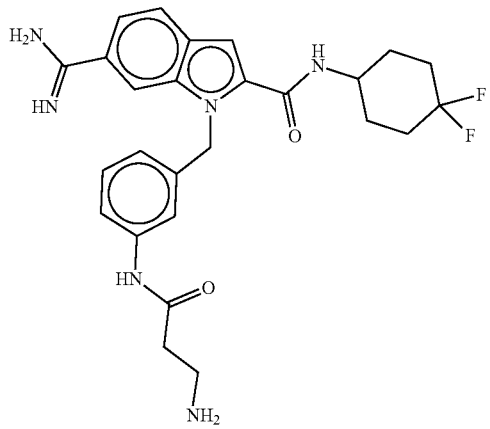
I-261
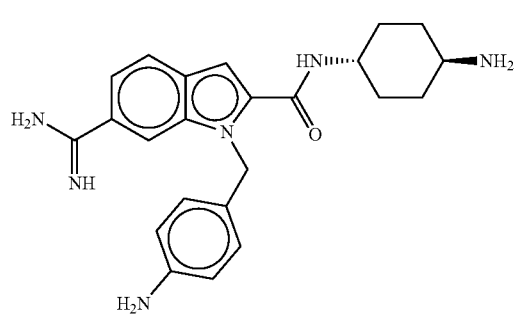
1110
-continued
I-262
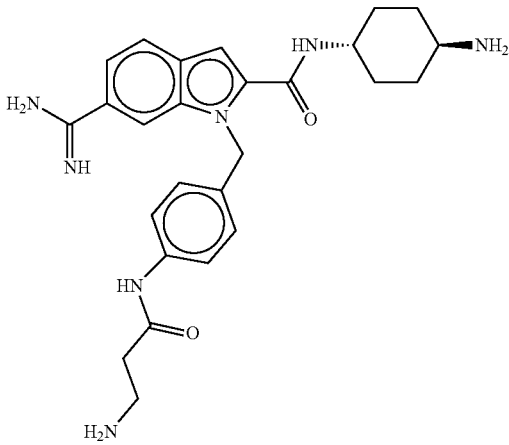
I-s263
I-264
I-265
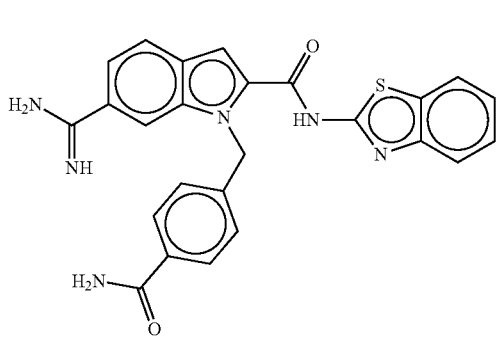

I-266
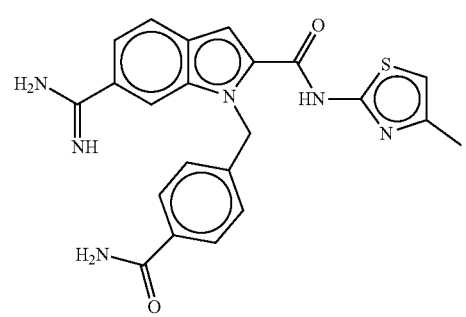
I-267
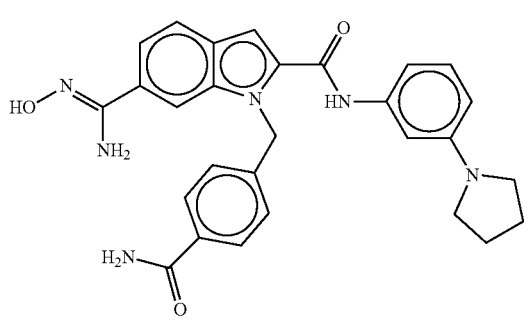
I-268
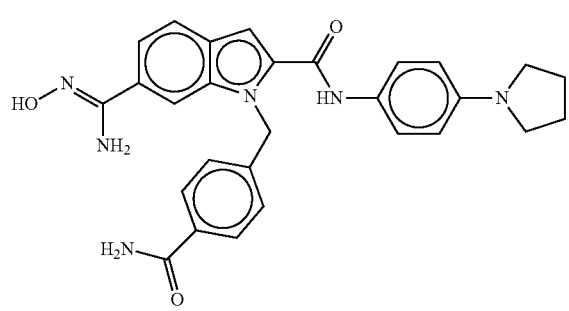
I-269
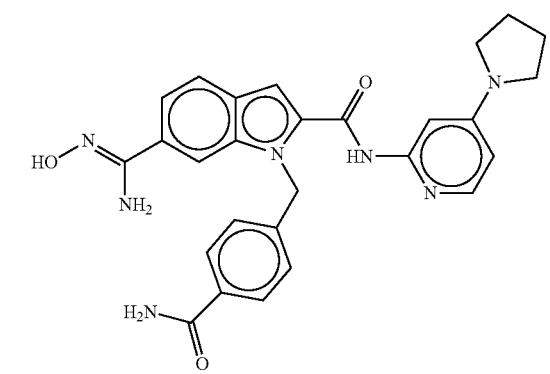
I-270
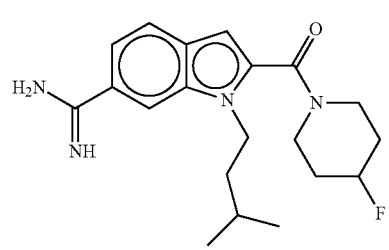
I-271
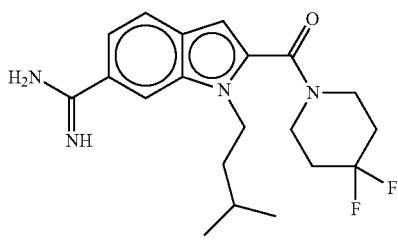
I-272
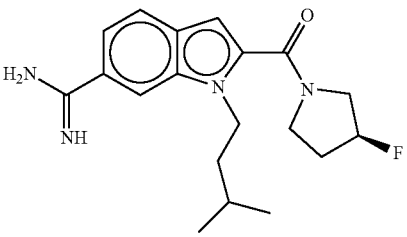
I-273
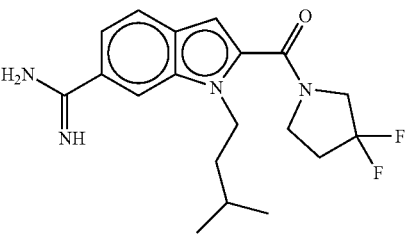
I-274
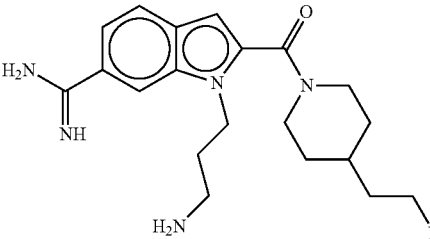
I-275
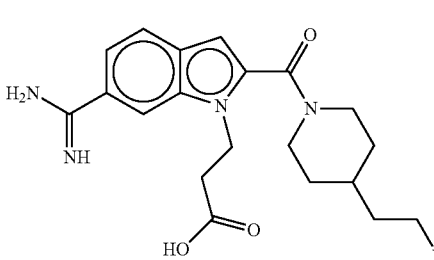
I-276
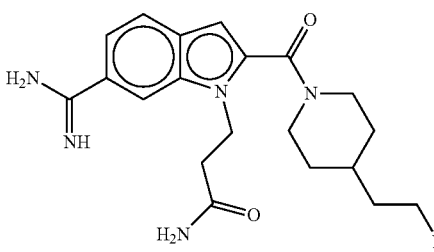

1113
-continued
I-277
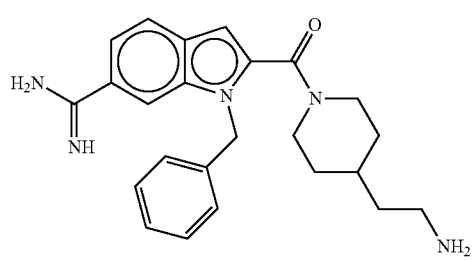
I-278
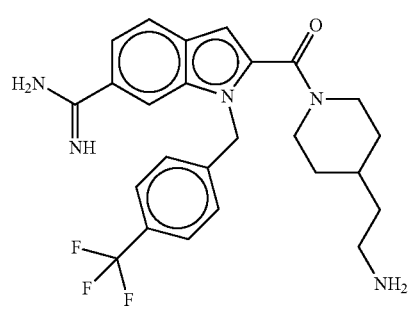
I-279
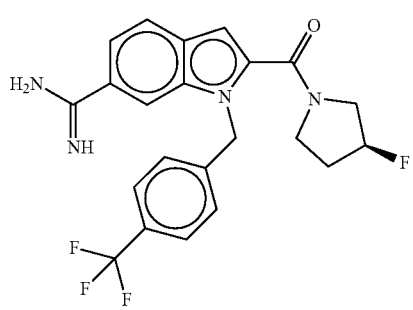
I-280
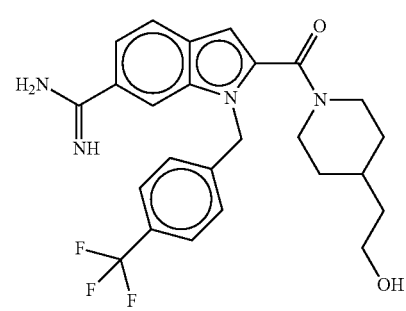
I-281
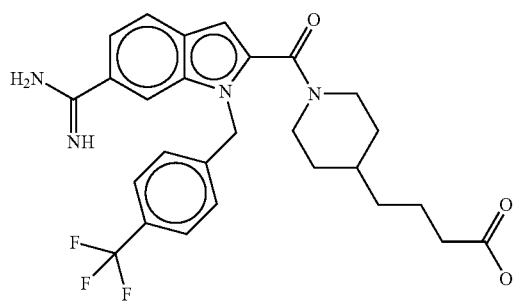
1114
-continued
I-282
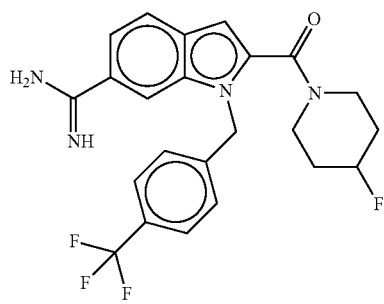
I-283
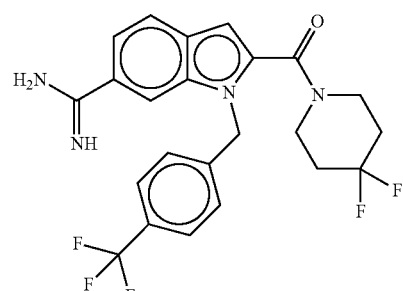
I-284
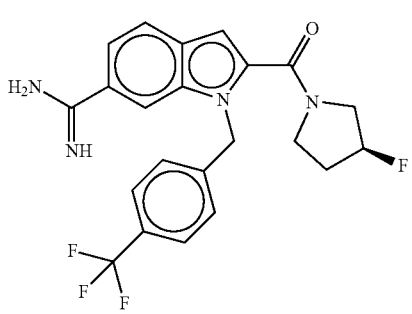
I-285
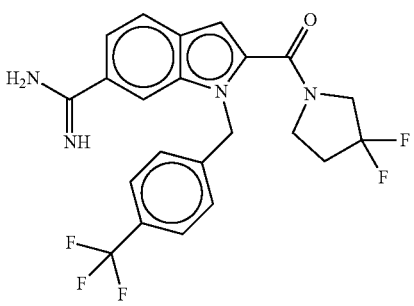

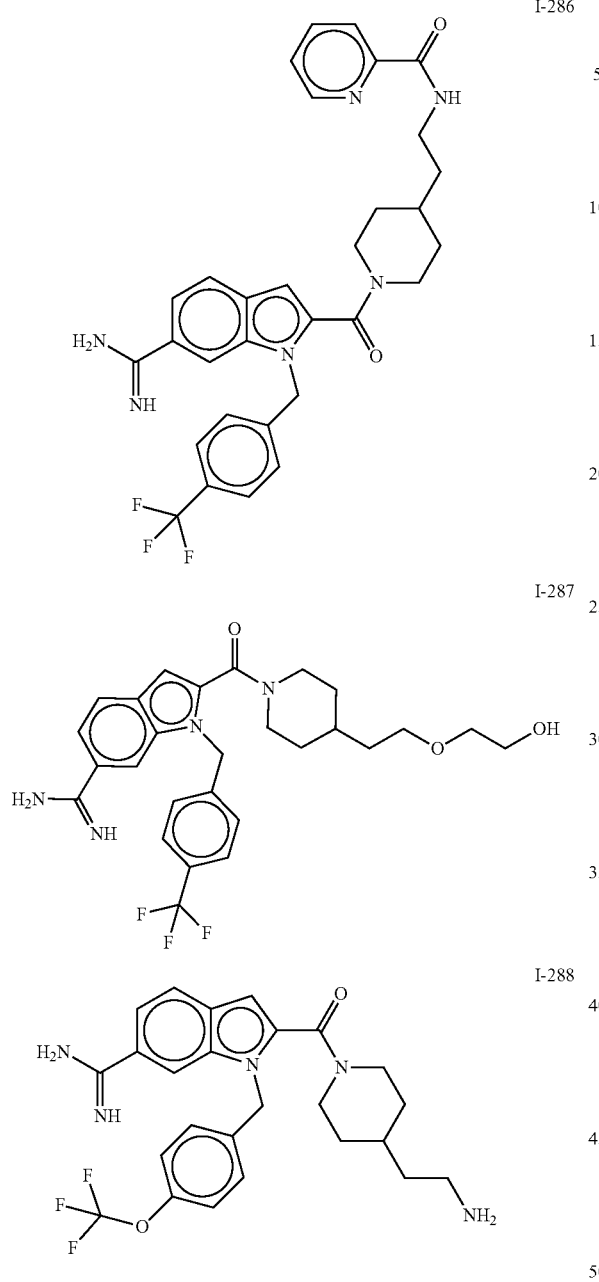
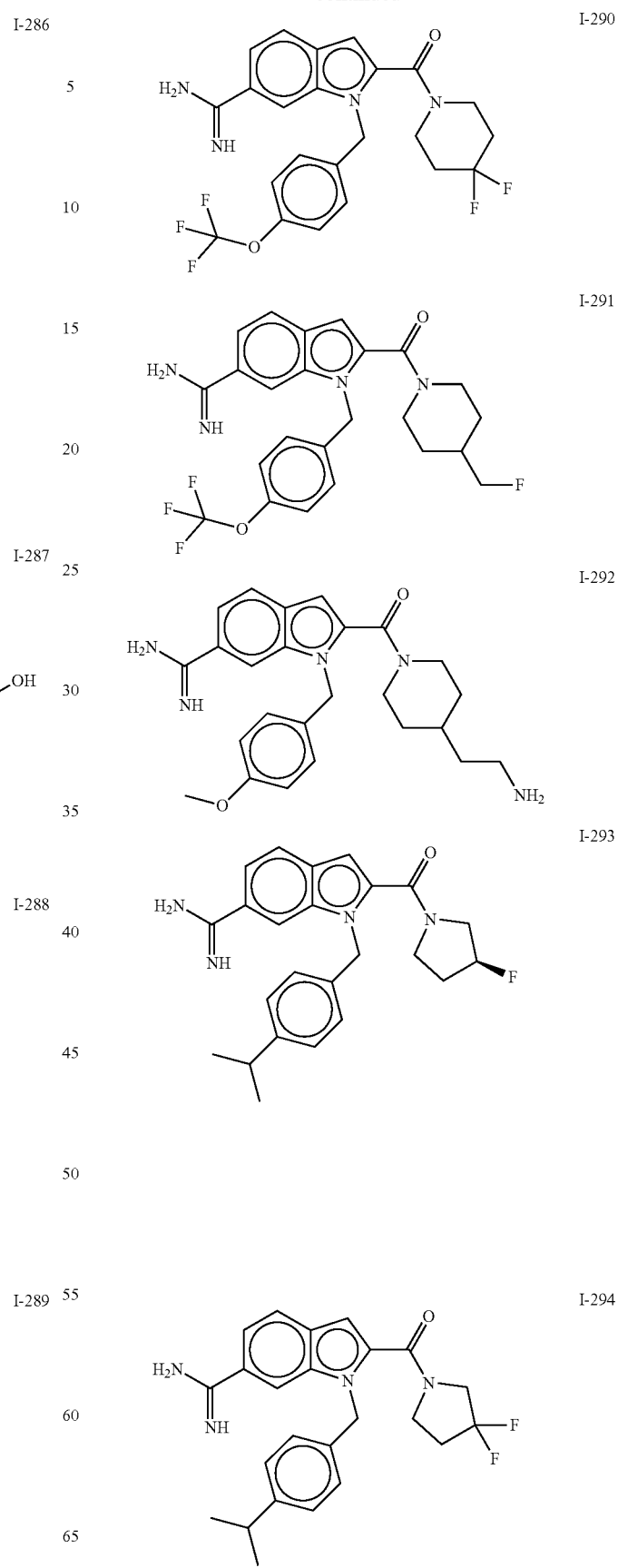

I-295
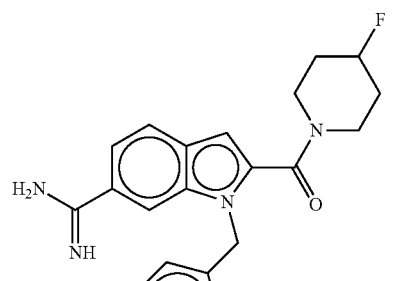
I-296
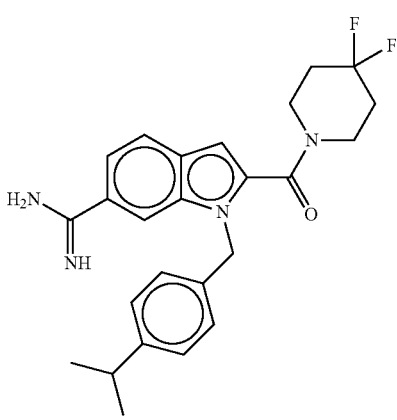
I-297
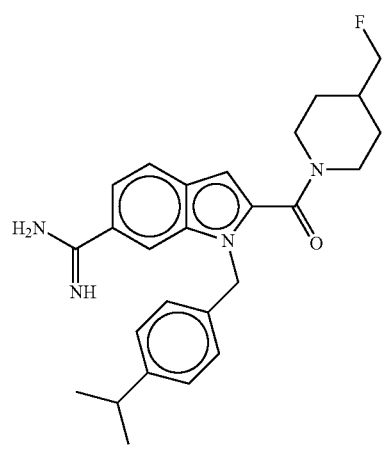
I-298
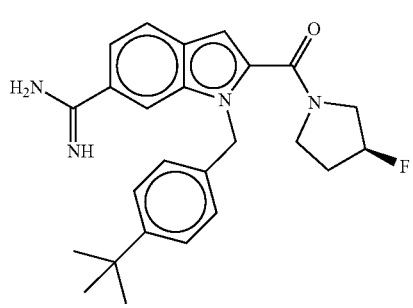
I-299
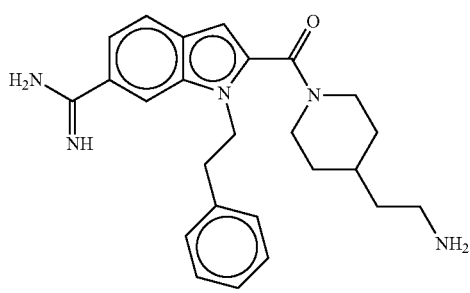
I-300
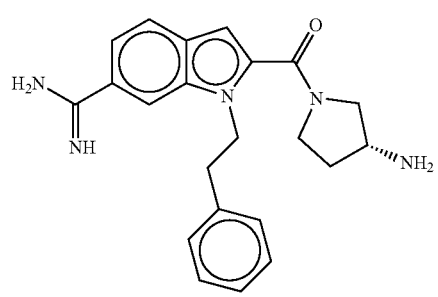
I-301
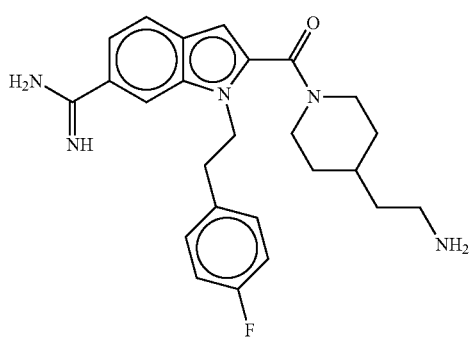
I-302
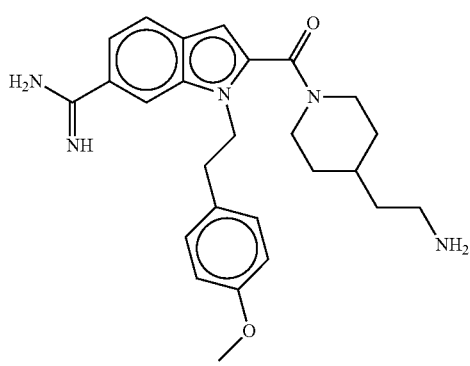
I-303
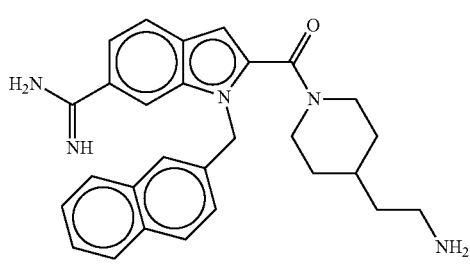

1119 -continued
I-304
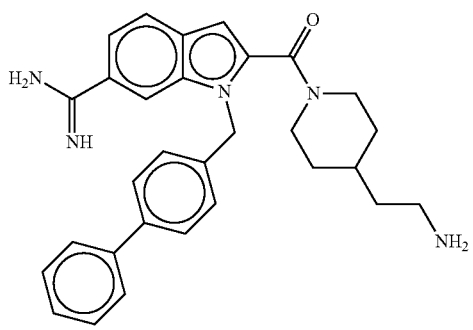
I-305
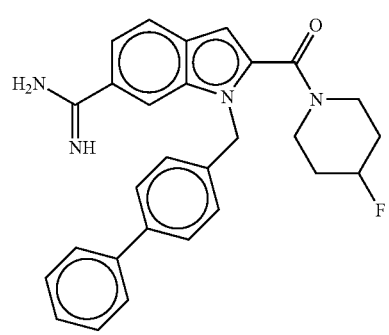
I-306
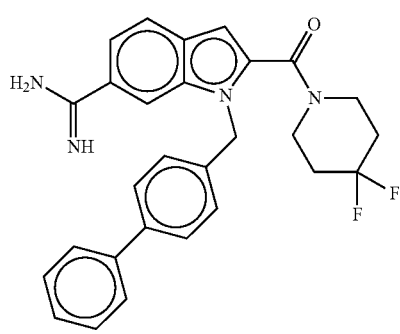
I-307
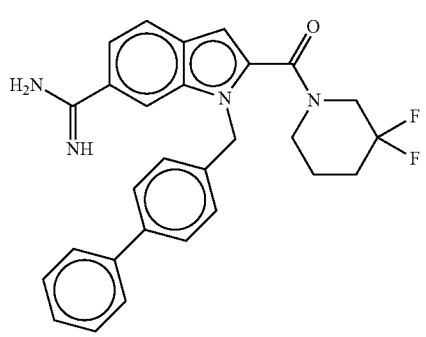
I-308
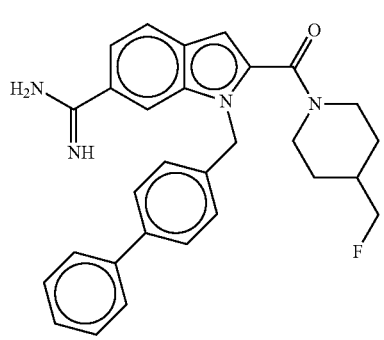
1120 -continued
I-309
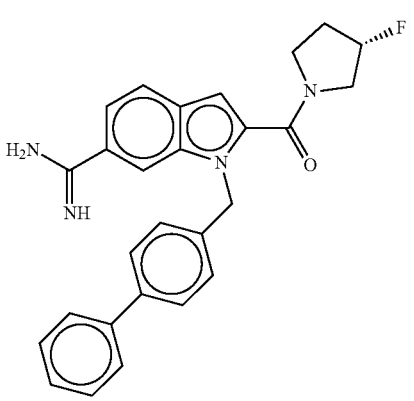
I-310
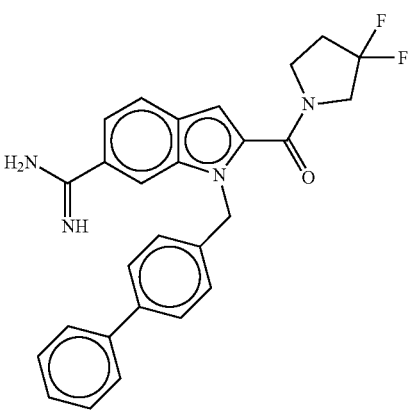
I-311
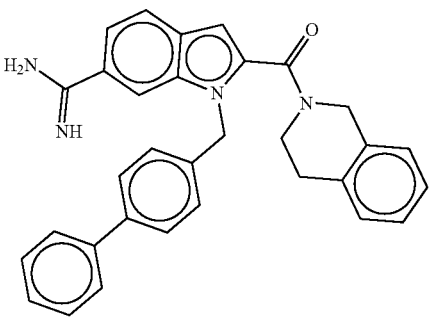
I-312
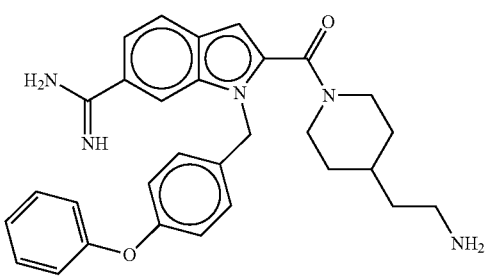

| 1121 -continued | 1122 -continued |
|---|---|
| I-313 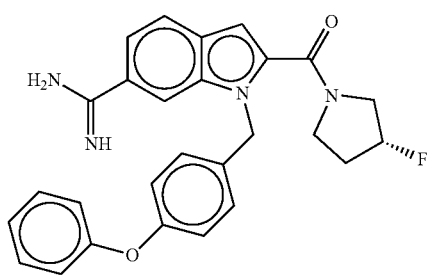 | I-318 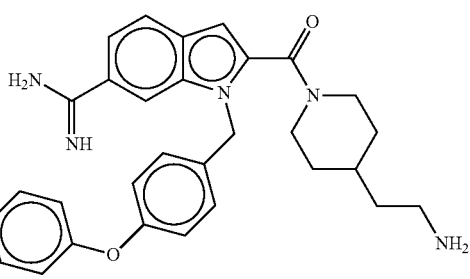 |
| I-314 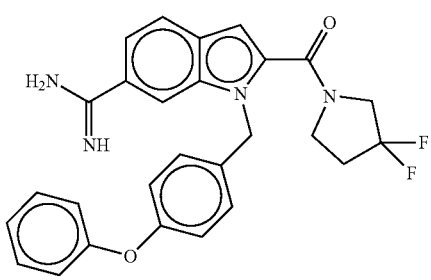 | I-319 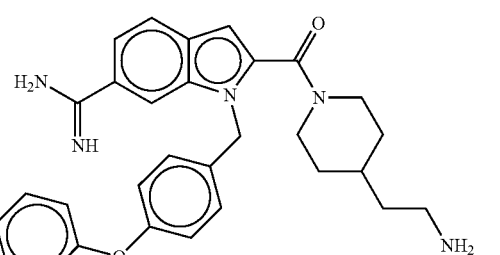 |
| I-315 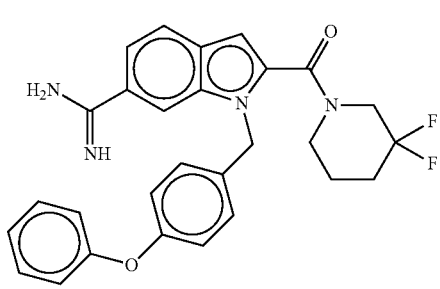 | I-320 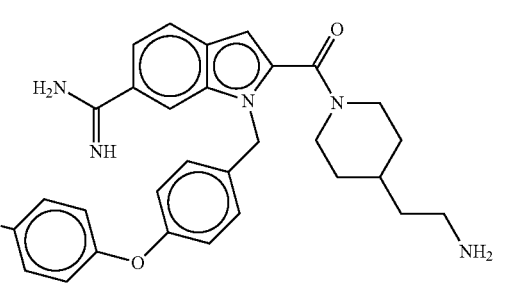 |
| I-316 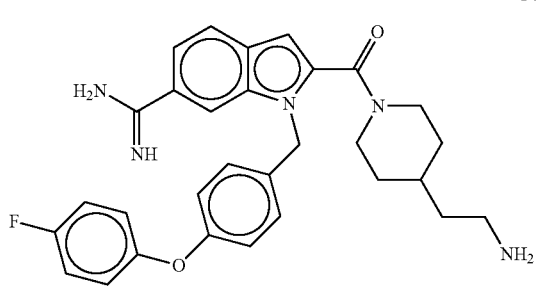 | I-321 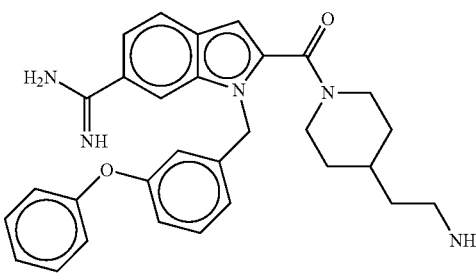 |
| I-317 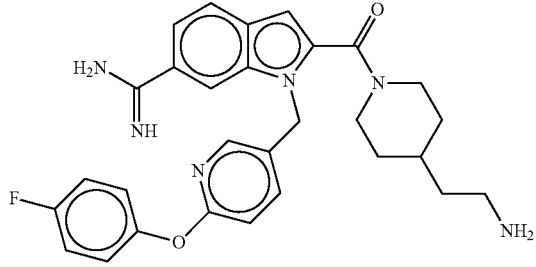 | I-322 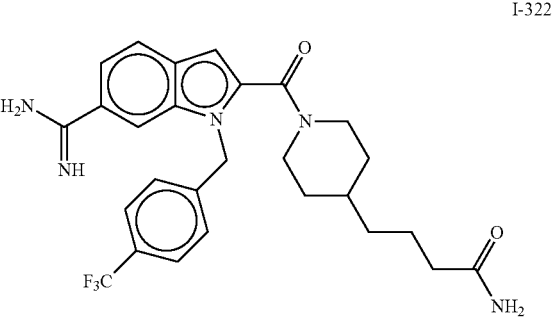 |

I-323
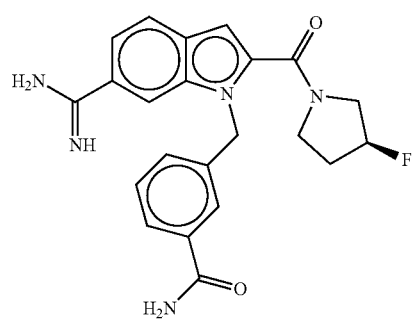
I-324
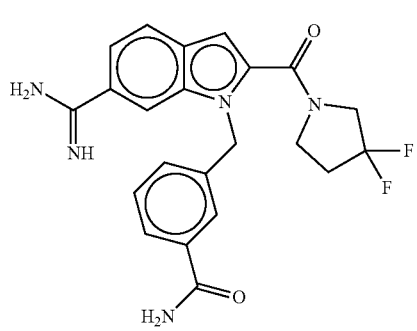
I-325
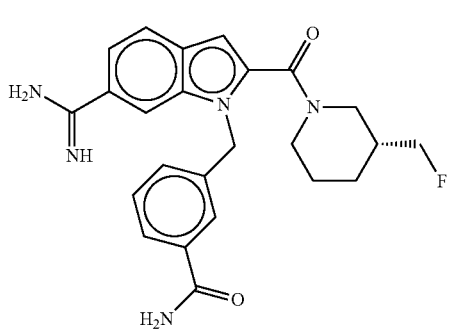
I-326
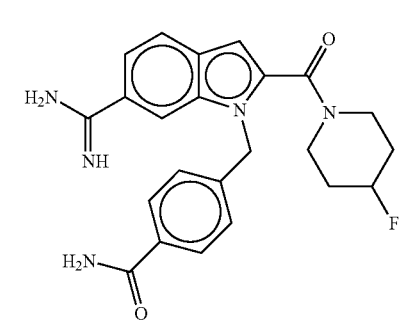
I-327
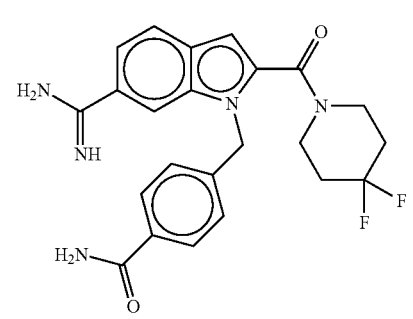
I-328
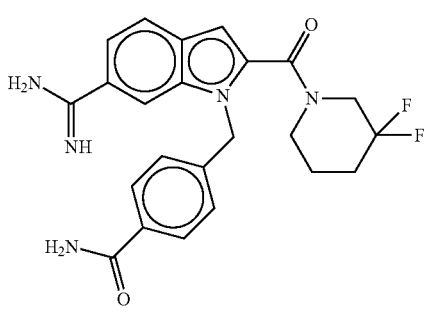
I-329
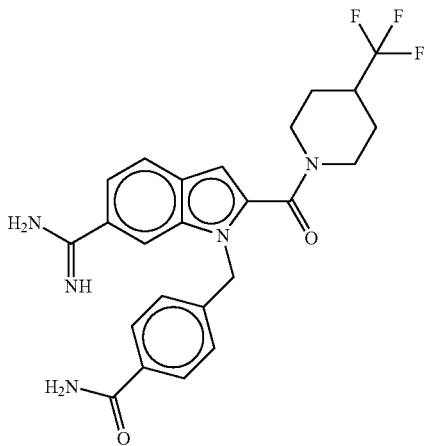
I-330
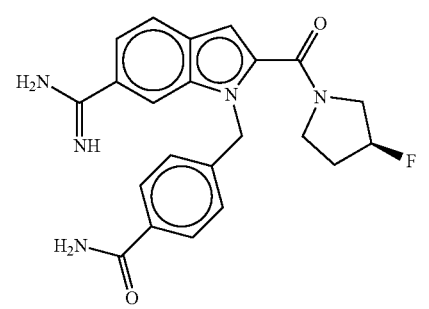
I-331
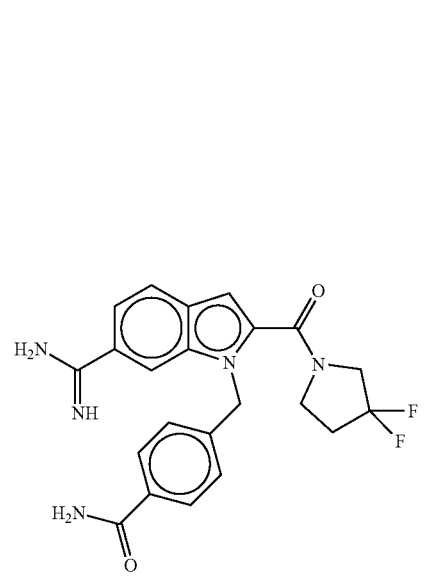

I-332
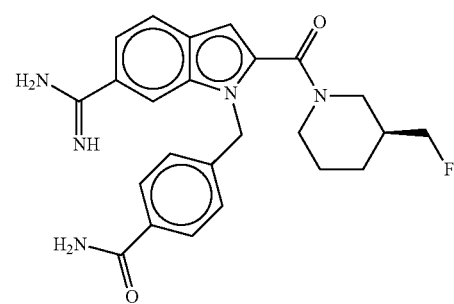
I-333
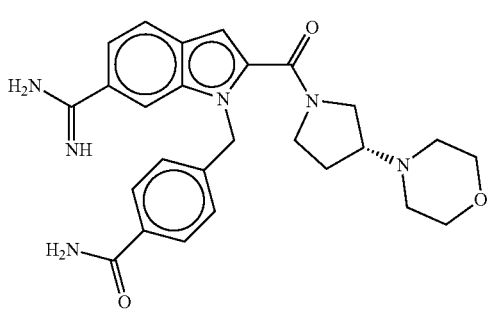
I-334
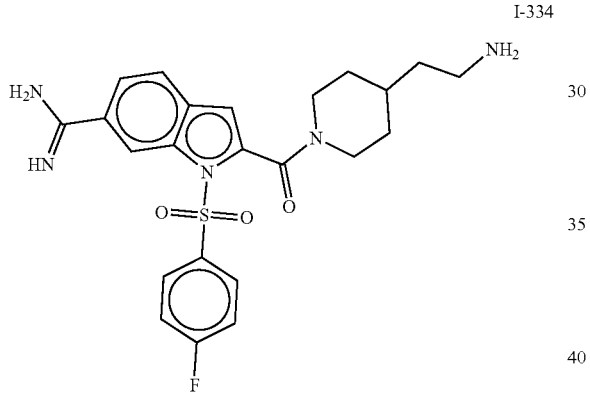
I-335
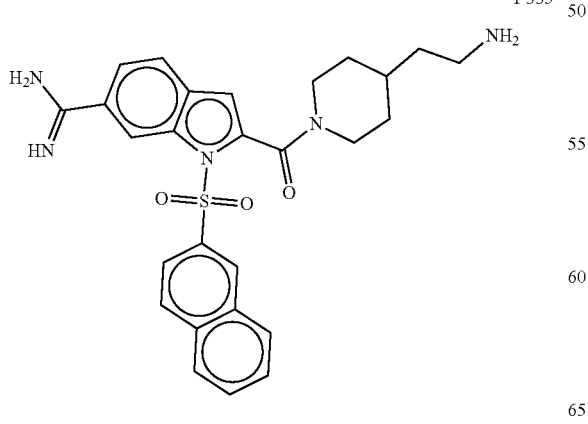
I-336
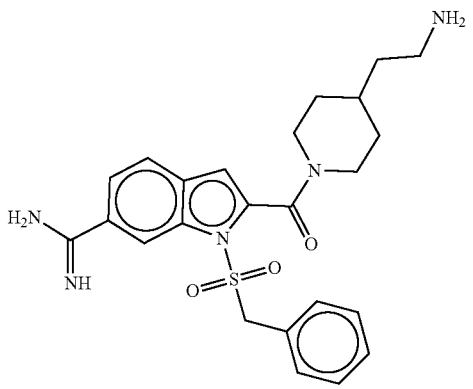
I-337
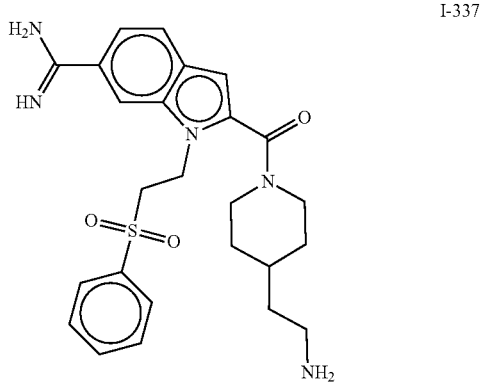
I-338
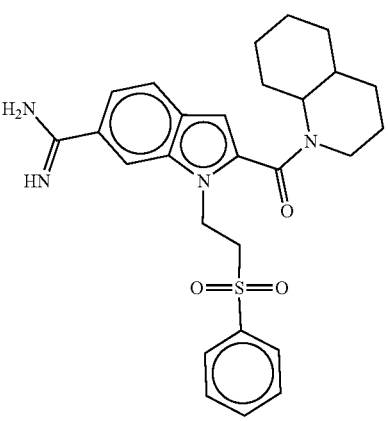
I-339
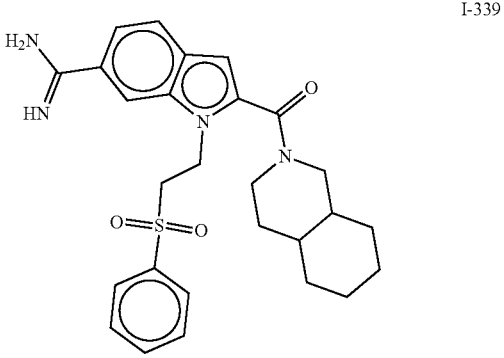

| 1127 -continued | | 1128 -continued | |
|---|---|---|---|
| 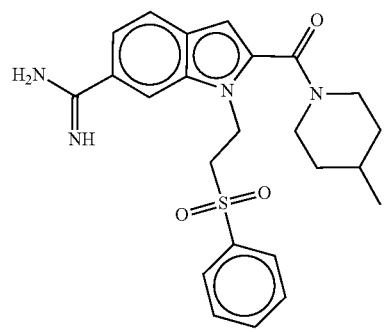 | I-340 | 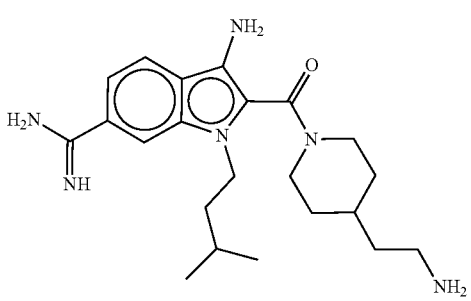 | I-344 |
| 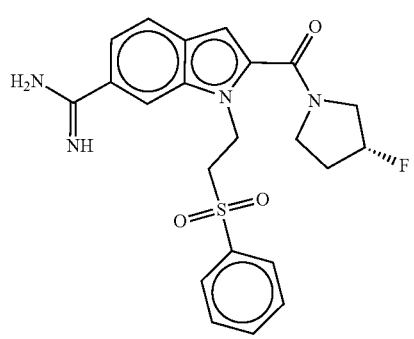 | I-341 | | I-345 |
| 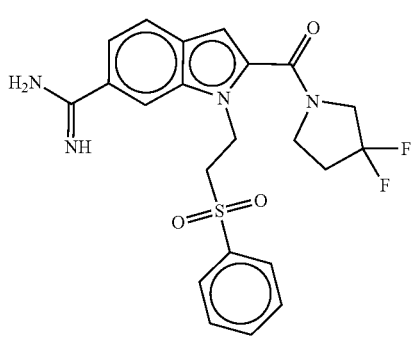 | I-342 | | I-346 |
| 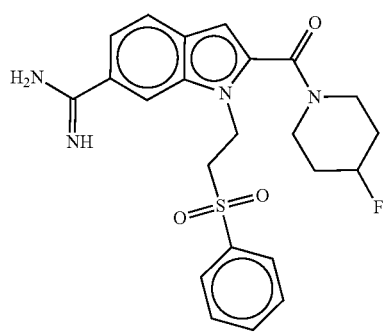 | I-343 | 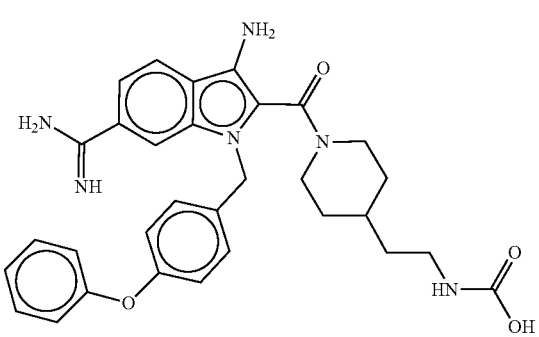 | I-347 |

-continued
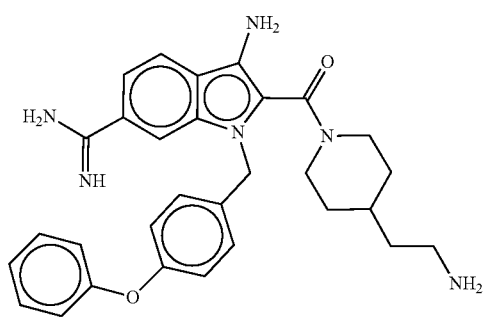
I-348
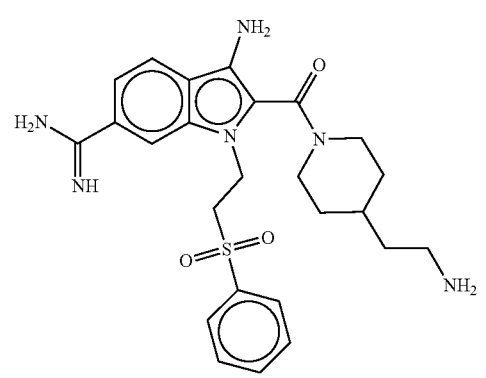
I-349
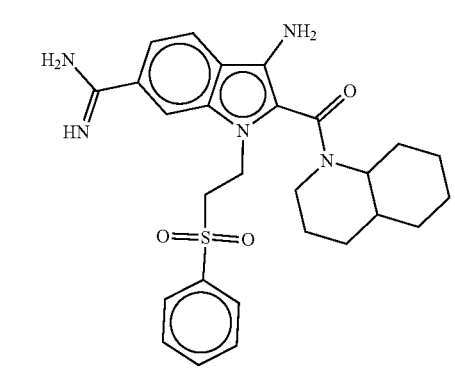
I-350
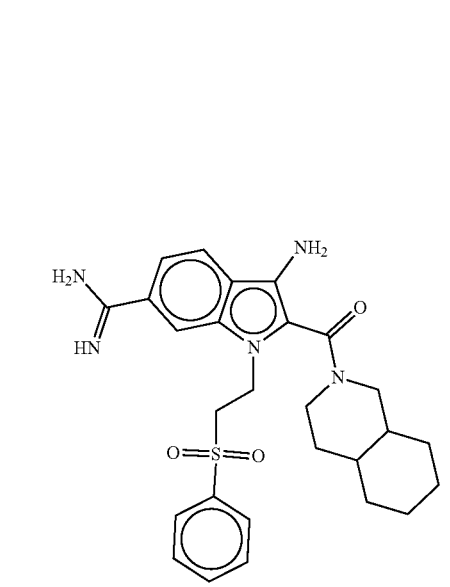
I-351
-continued
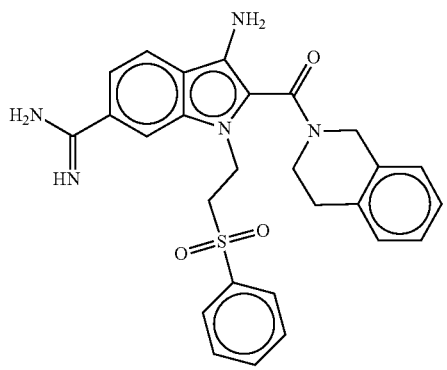
I-352
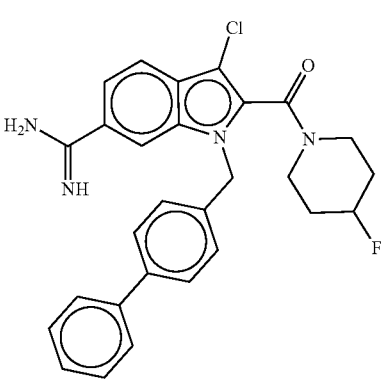
I-353
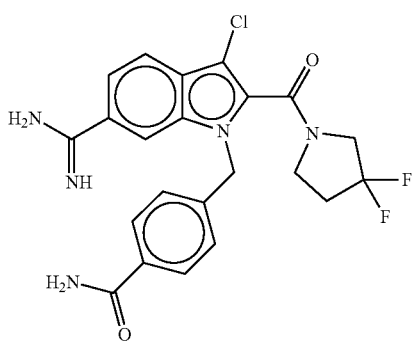
I-354
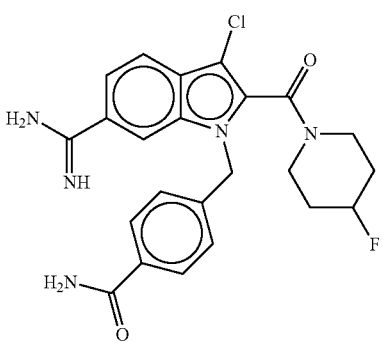
I-355

I-356
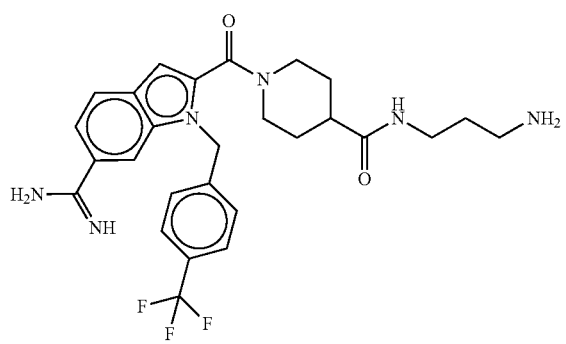
I-357
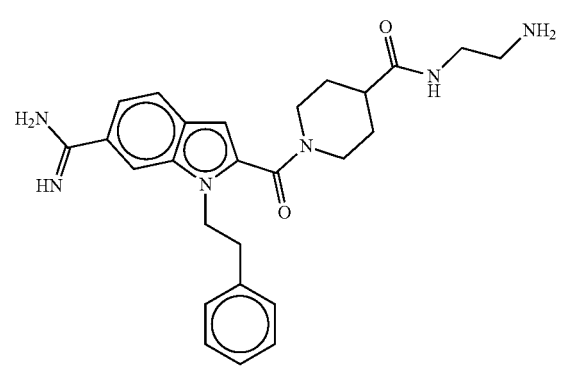
I-358
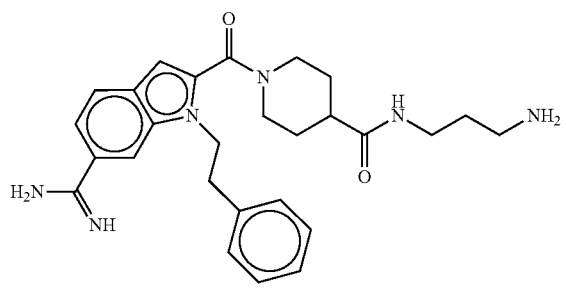
I-359
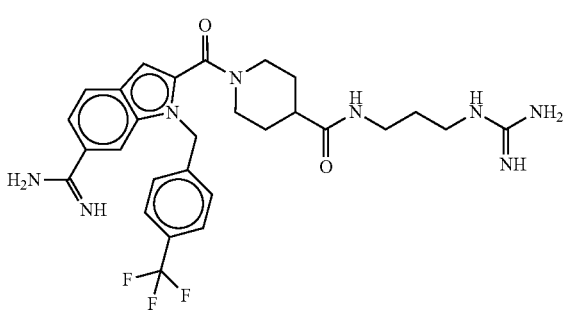
I-360
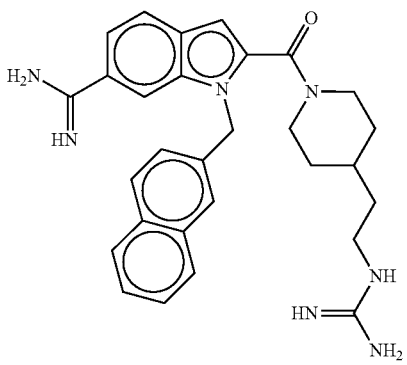
I-361
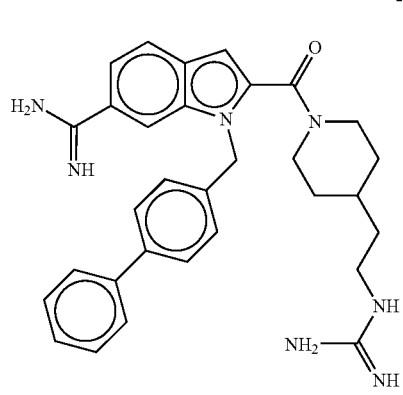
I-362
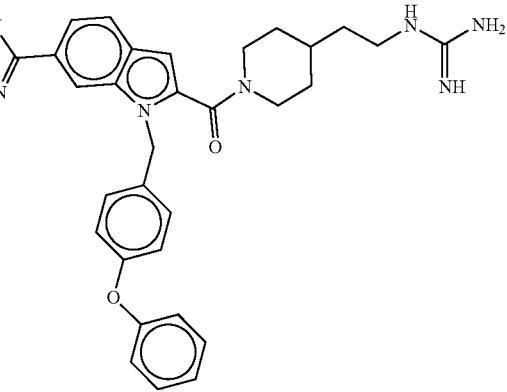
I-363
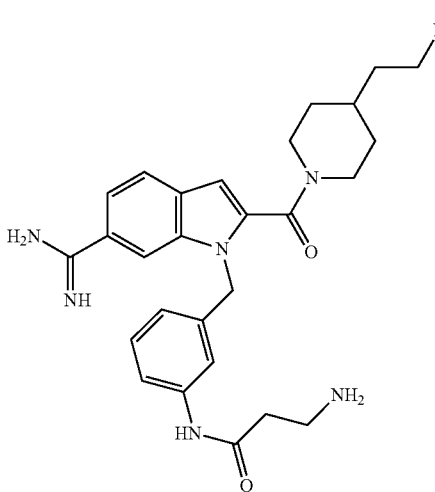

I-364
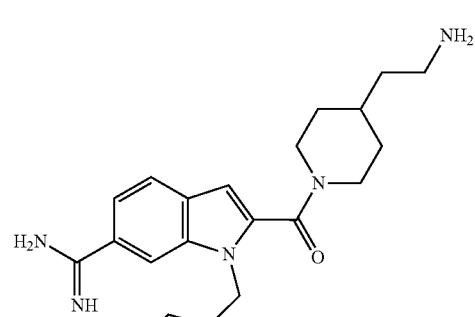
I-365
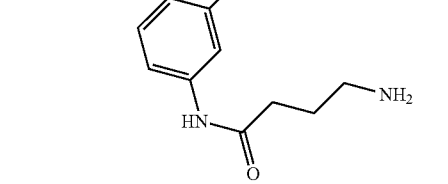
I-366
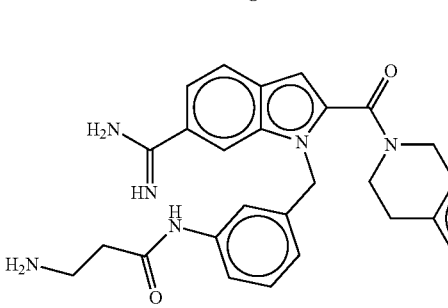
I-367
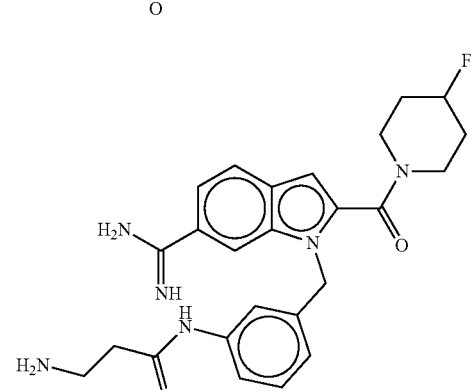
I-368
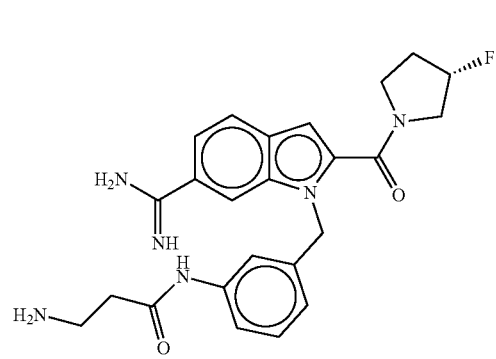
I-369
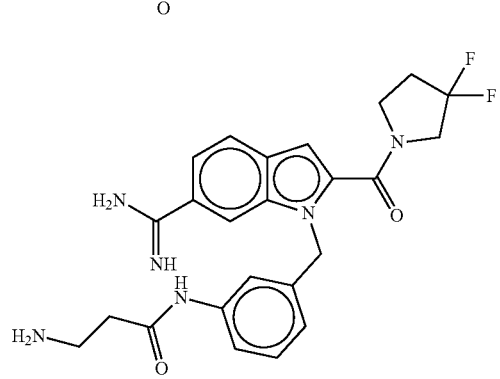
I-370
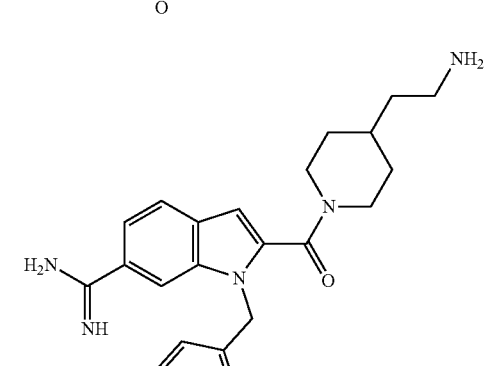
I-371
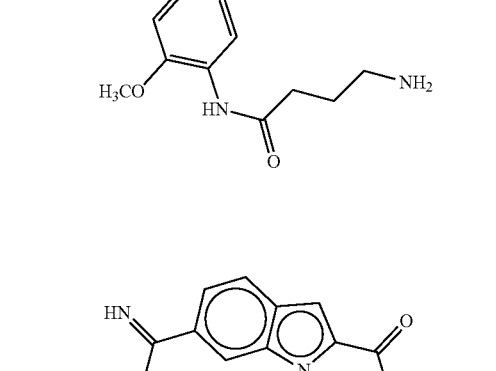

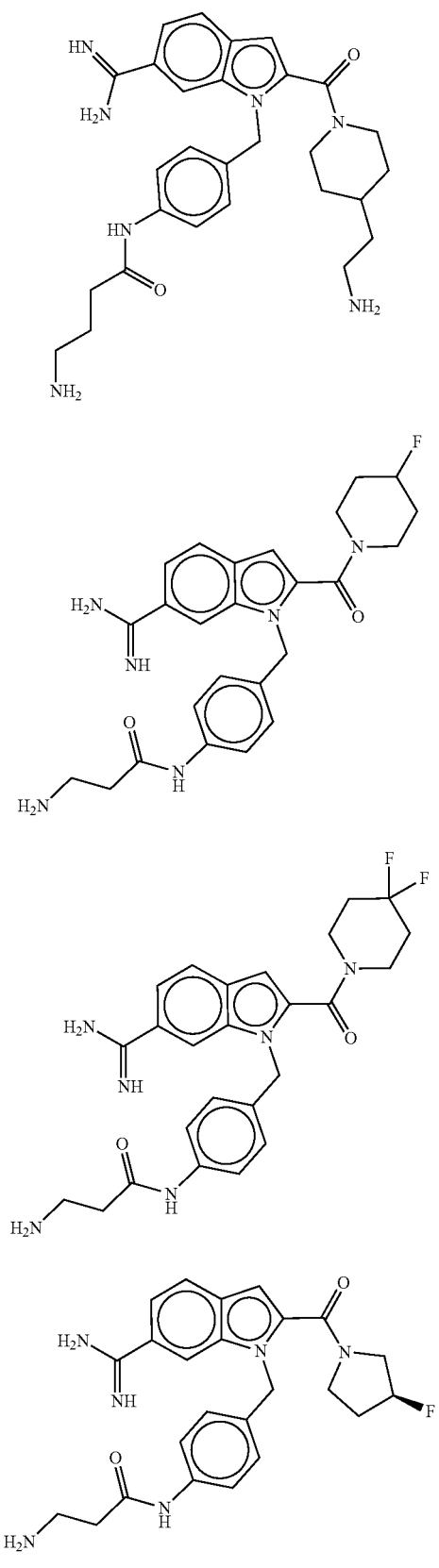
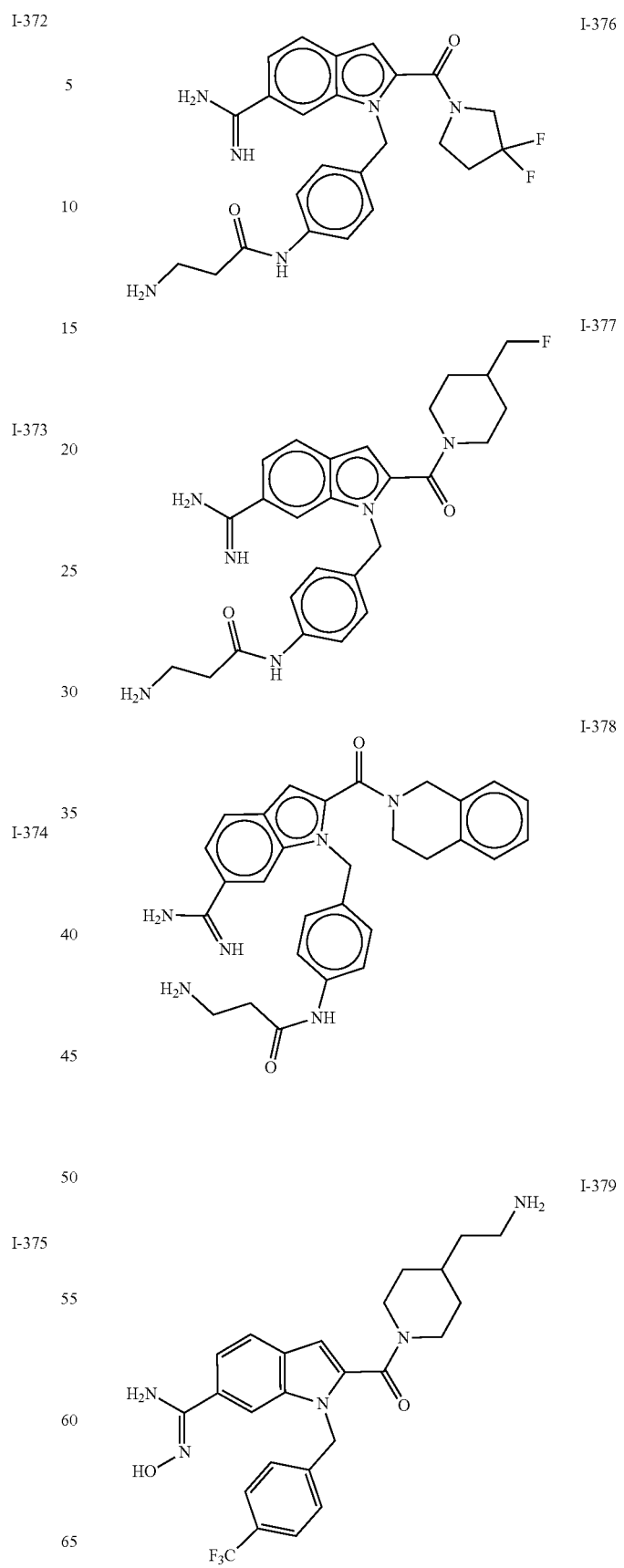

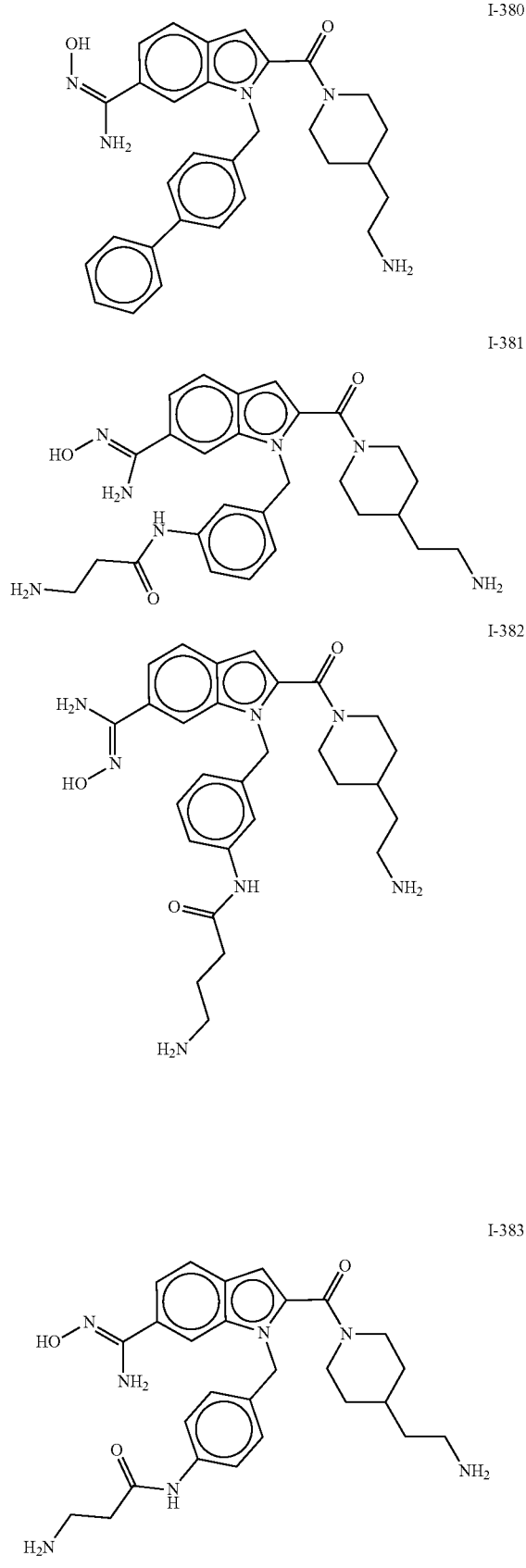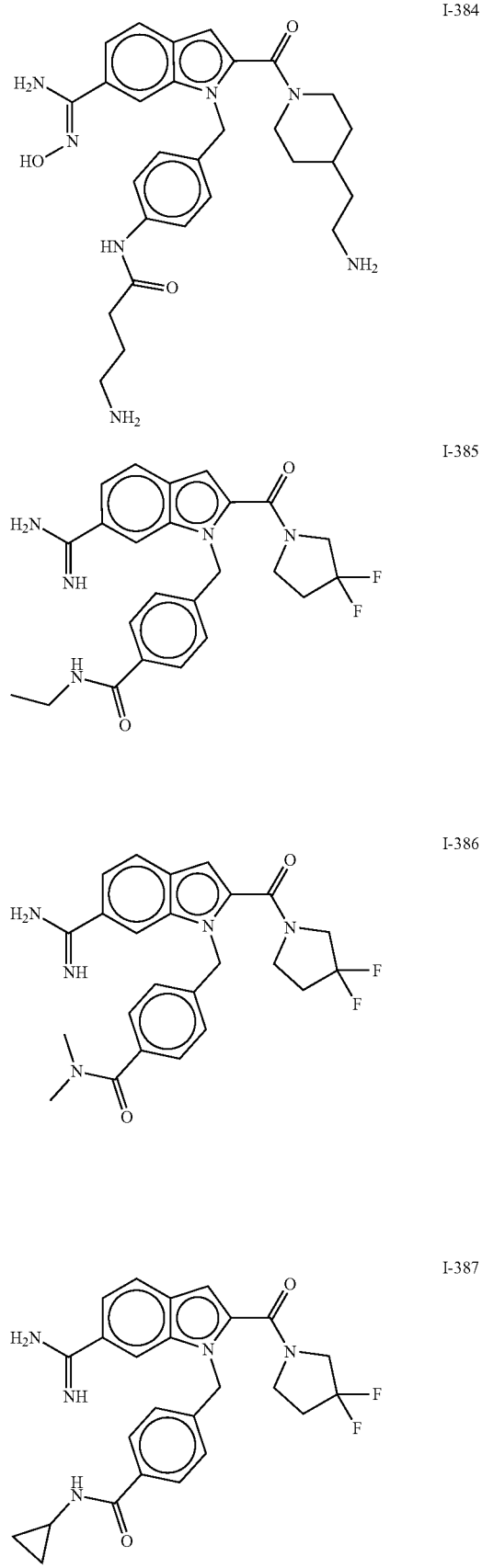

I-388
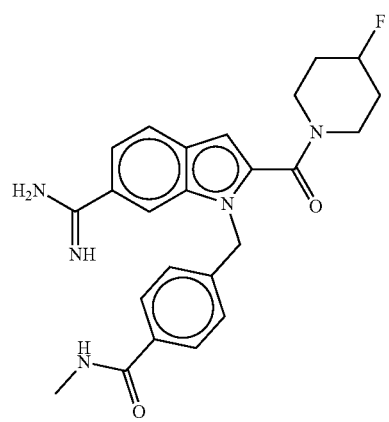
I-389
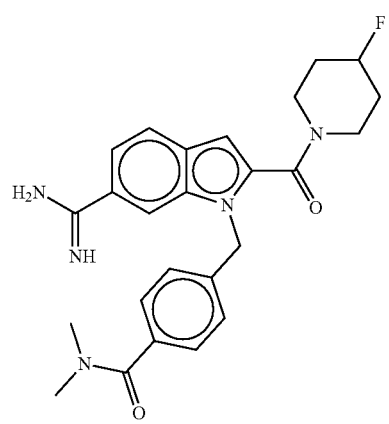
I-390
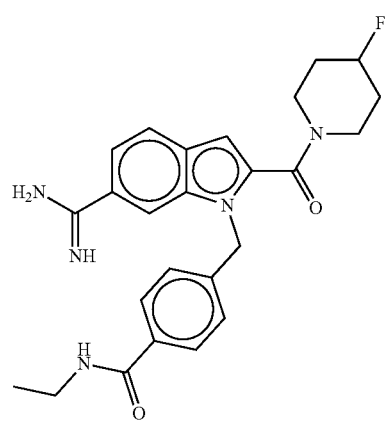
I-391
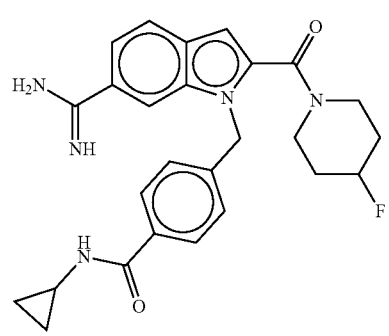
I-392
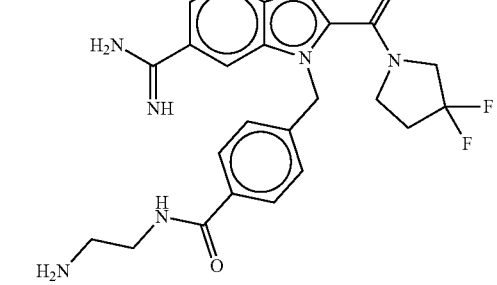
I-393
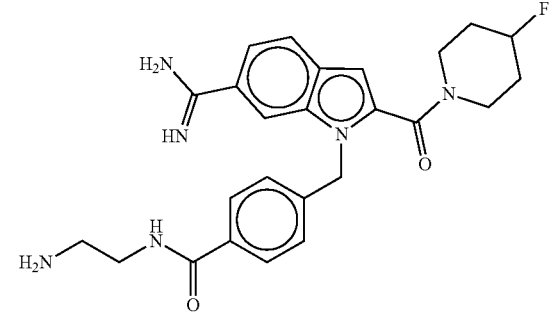
I-394
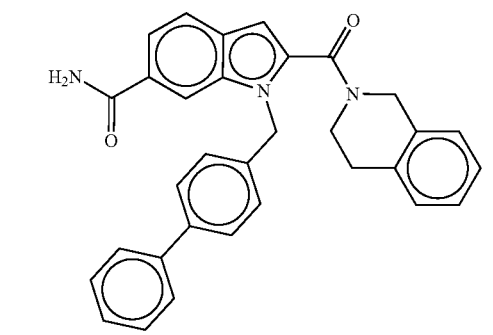
I-395
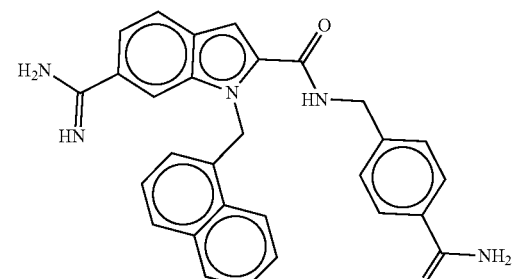
I-396
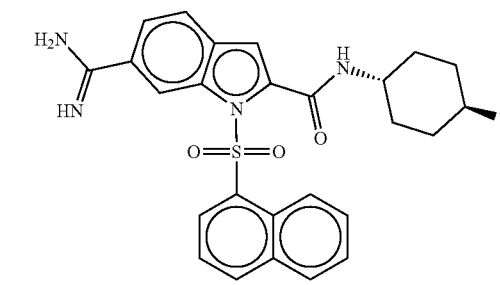

I-397
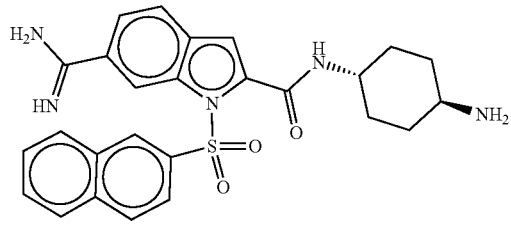
I-398
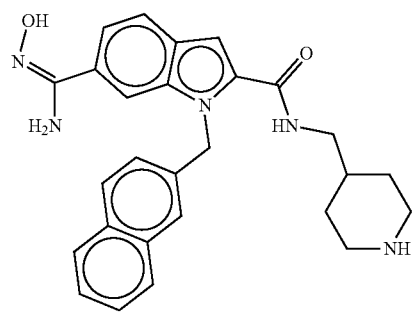
I-399
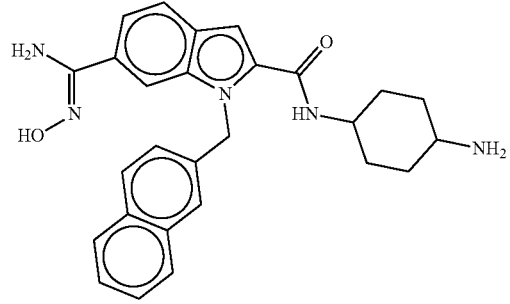
I-400
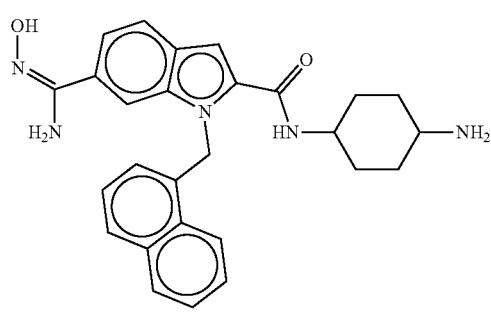
I-401
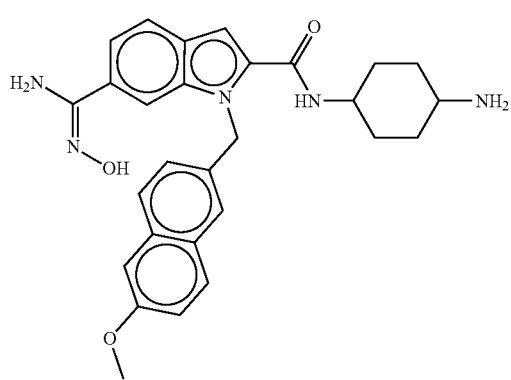
I-402
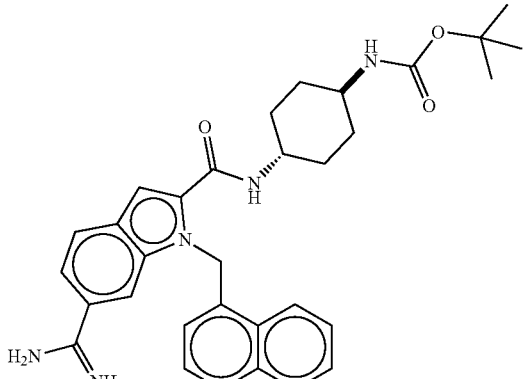
I-403
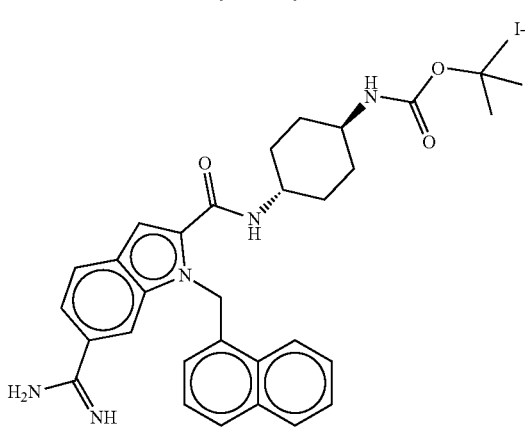
I-404
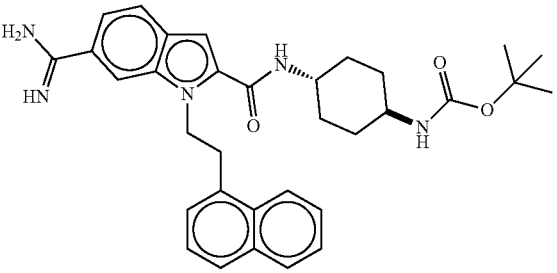
I-405
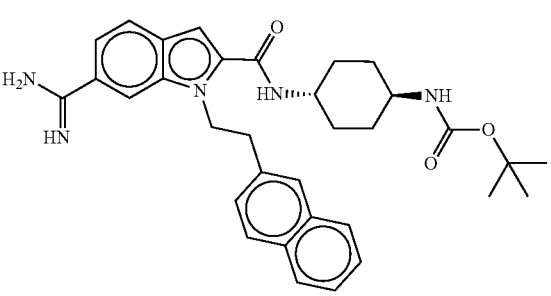

I-406
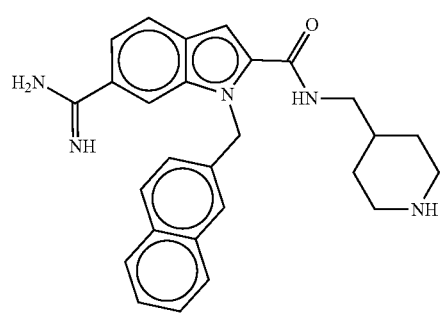
I-407
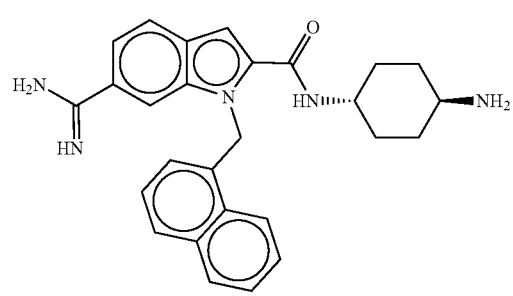
I-408
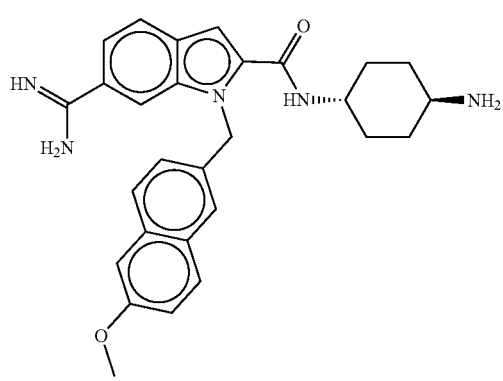
I-409
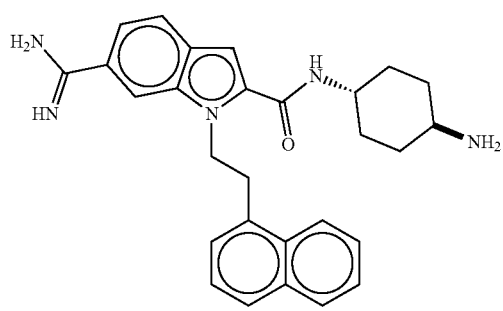
I-410
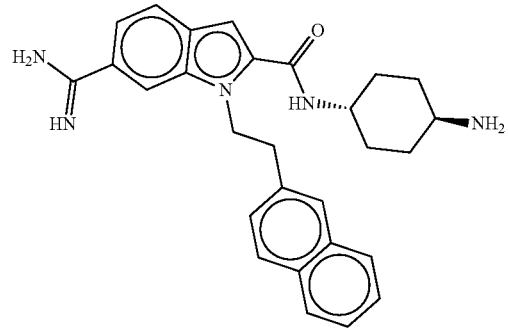
I-411
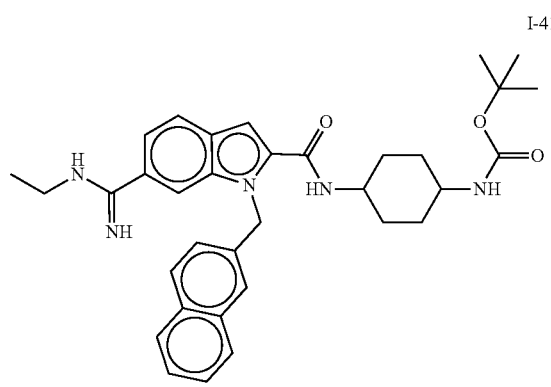
I-412
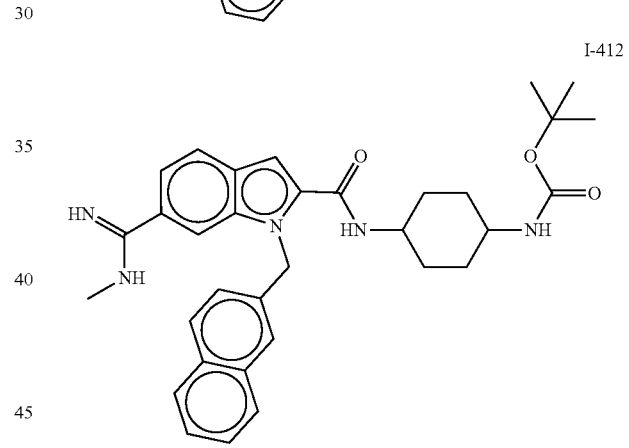
I-413
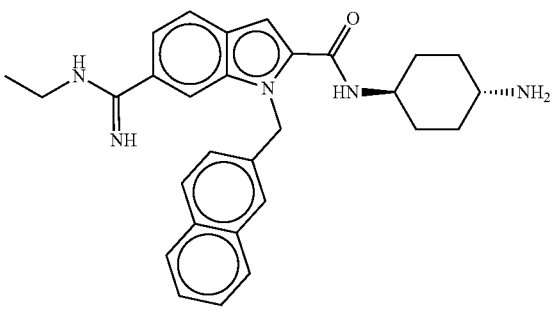

I-414
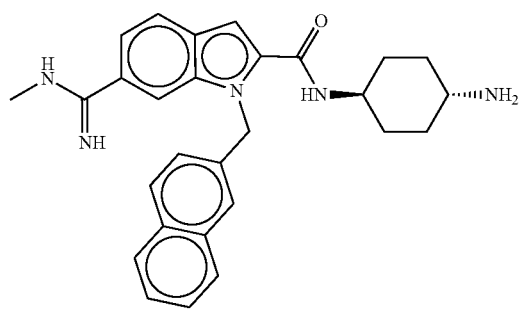
I-419
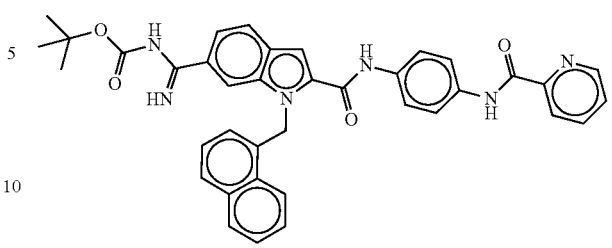
I-415
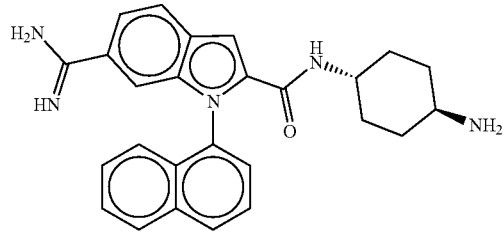
I-420
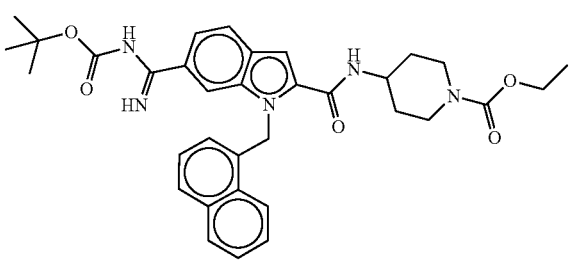
I-416
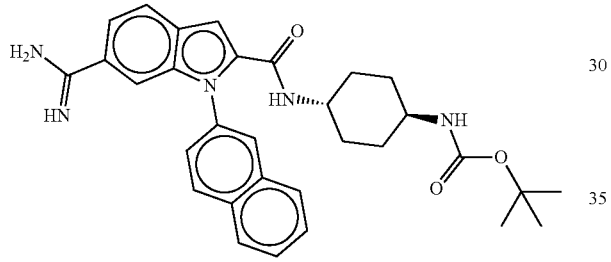
I-421
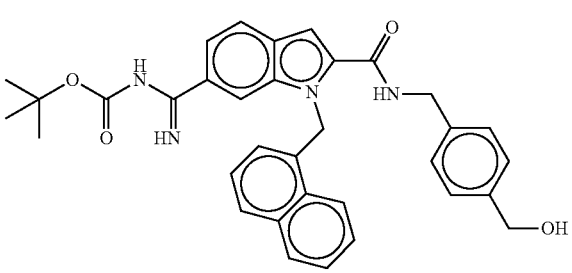
I-417
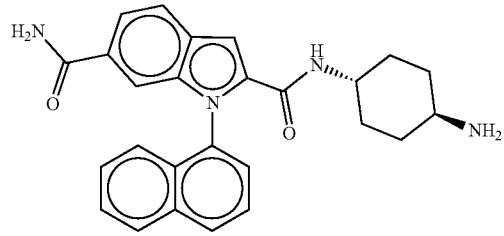
I-422
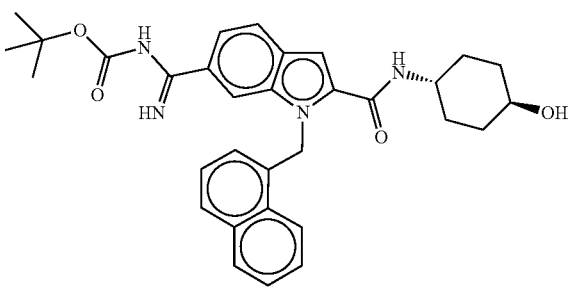
I-418
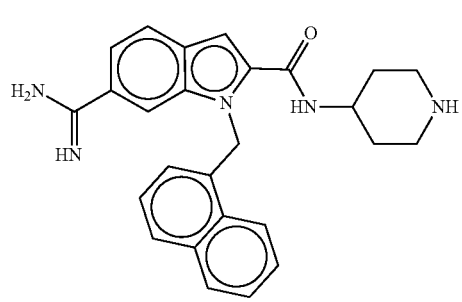
I-423
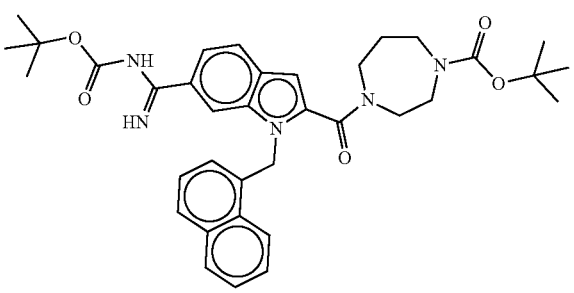

I-424
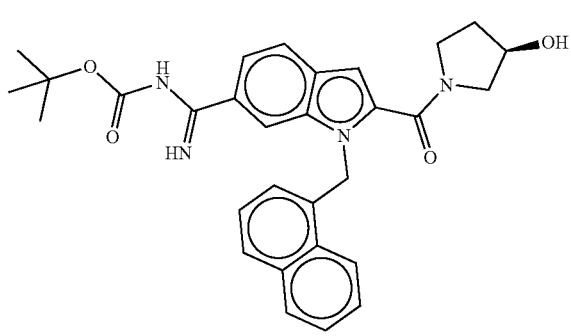
I-425
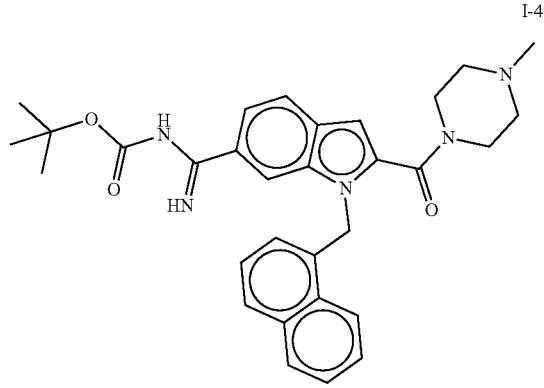
I-426
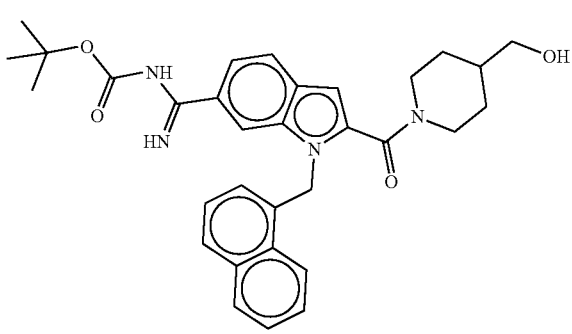
I-427
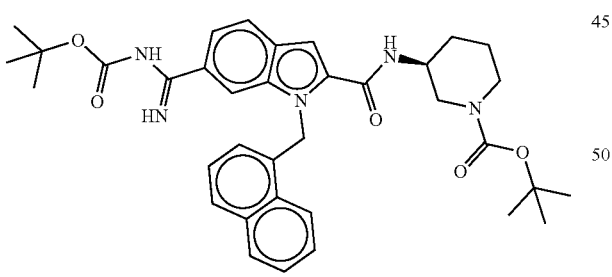
I-428
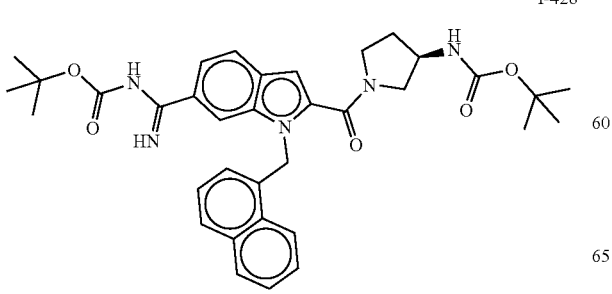
I-429
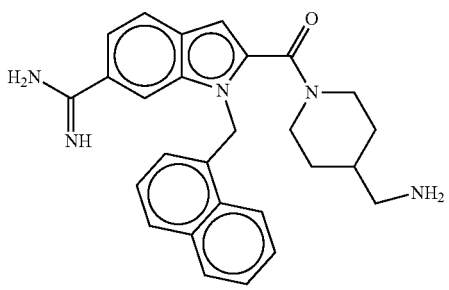
I-430
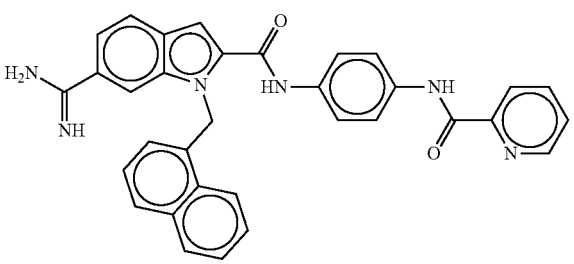
I-431
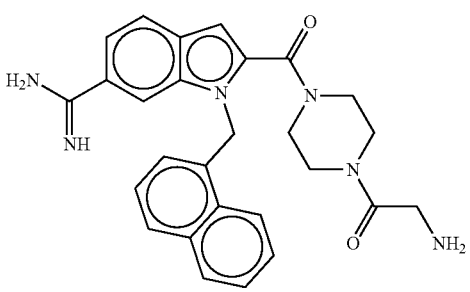
I-432
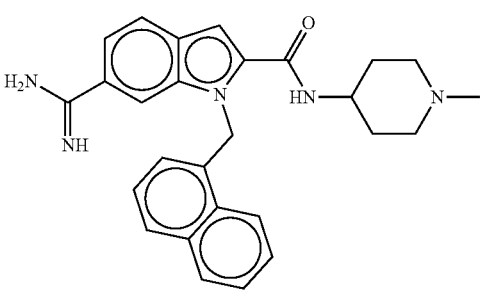
I-433
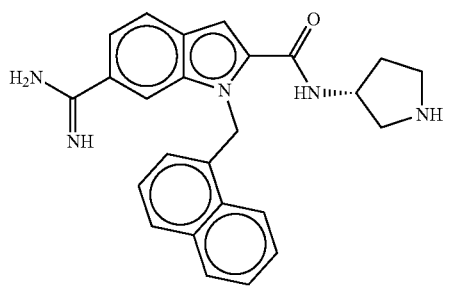

I-434
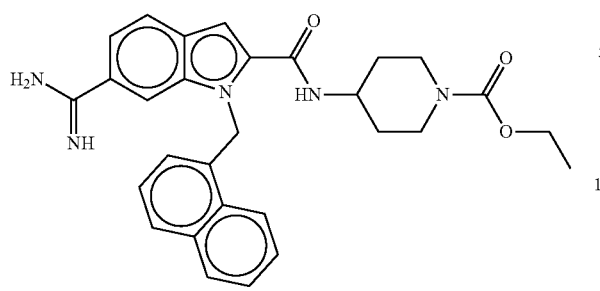
I-439
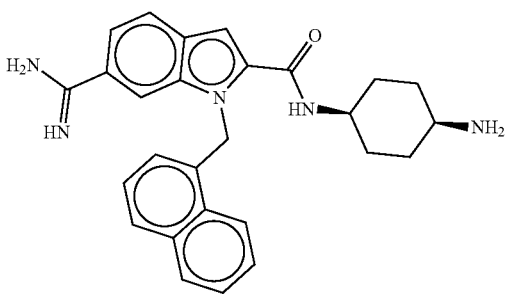
I-435
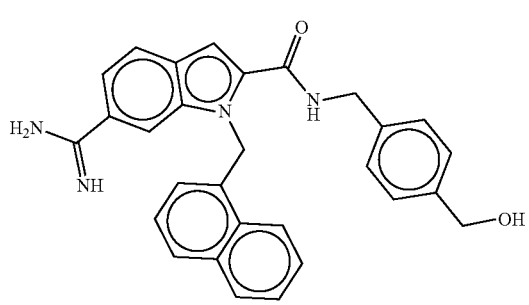
I-440
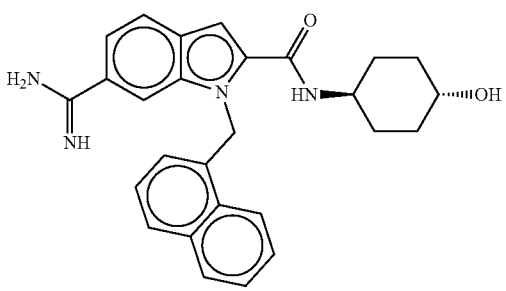
I-436
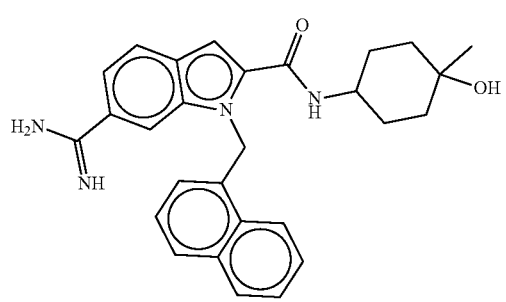
I-441
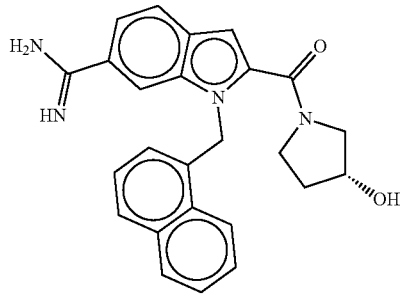
I-437
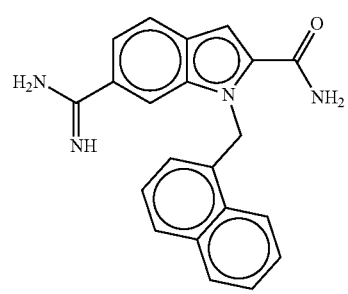
I-442
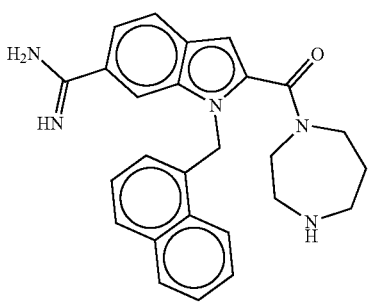
I-438
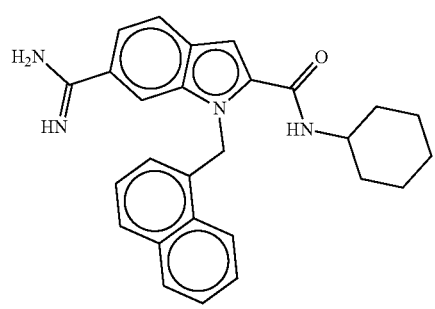
I-443
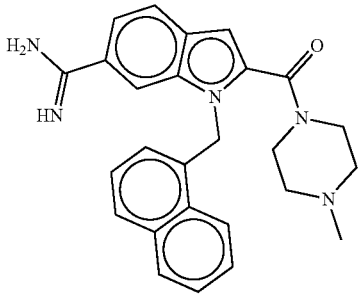

I-444
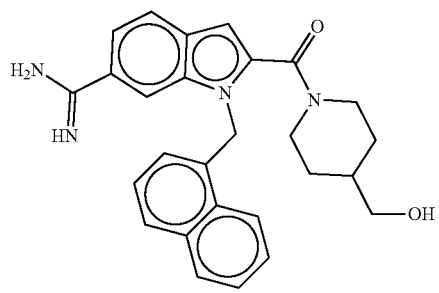
I-449
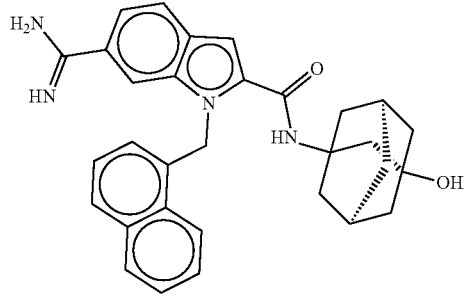
I-445
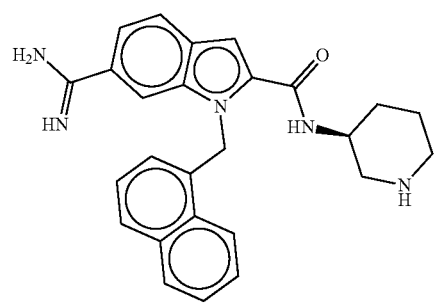
I-450
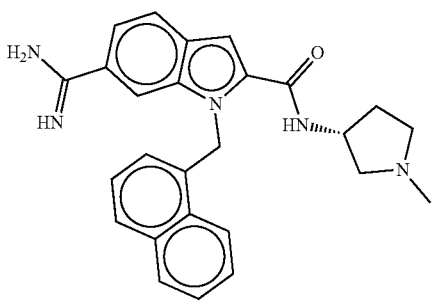
I-446
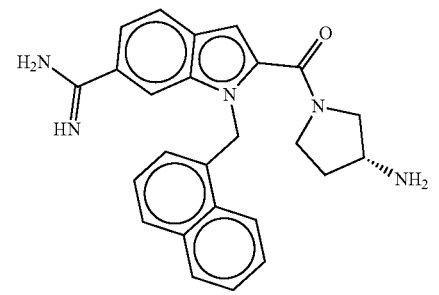
I-451
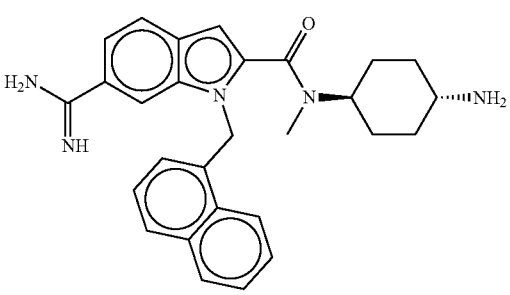
I-447
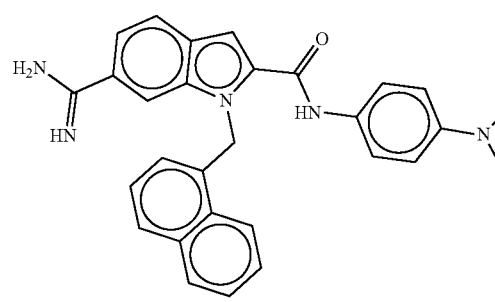
I-452
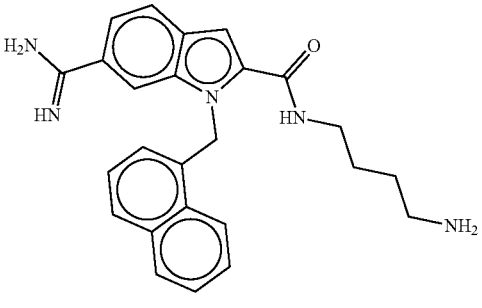
I-448
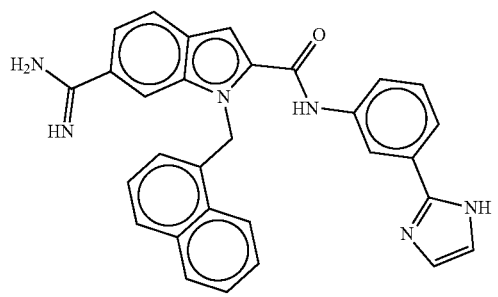
I-453
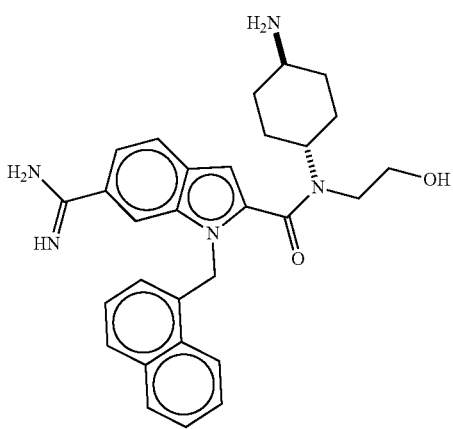

I-454
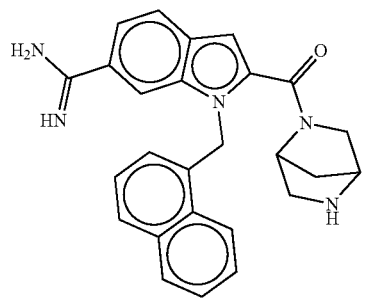
I-455
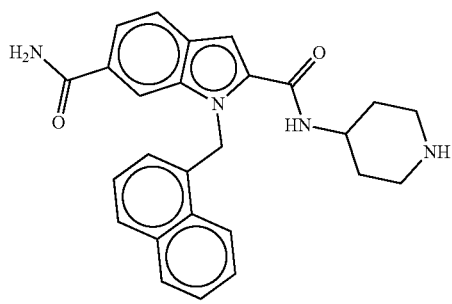
I-456
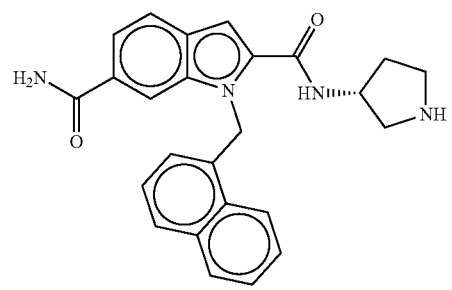
I-457
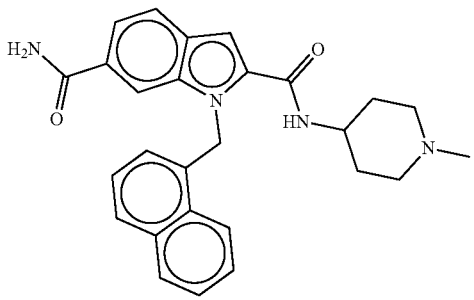
I-458
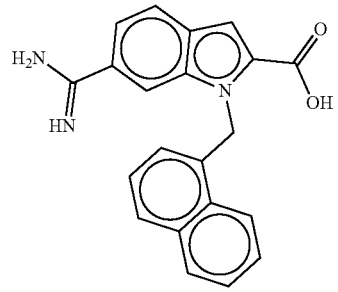
I-459
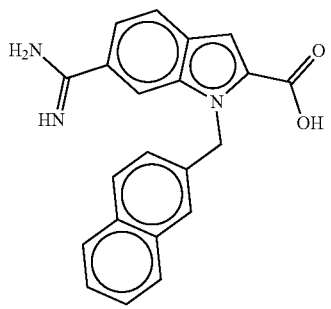
I-460
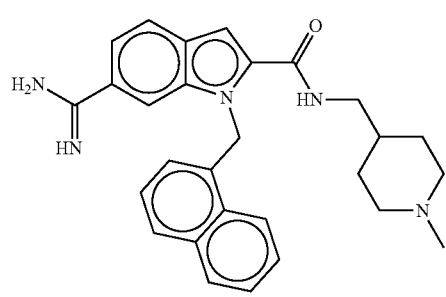
I-461
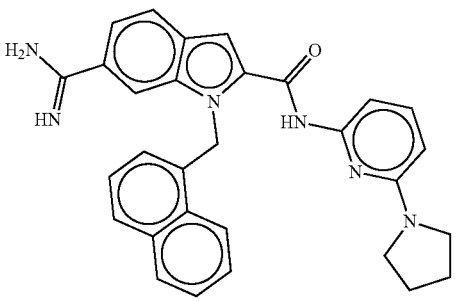
I-462
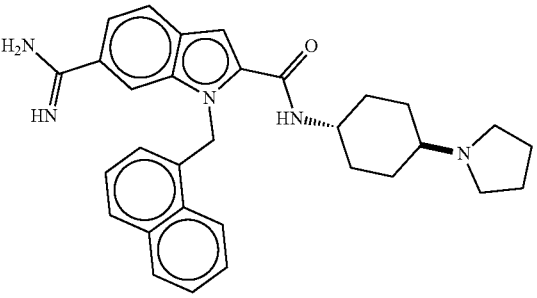
I-463
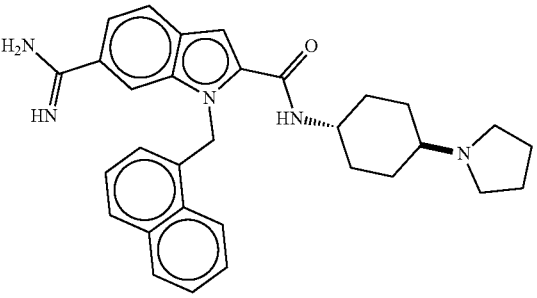

I-464
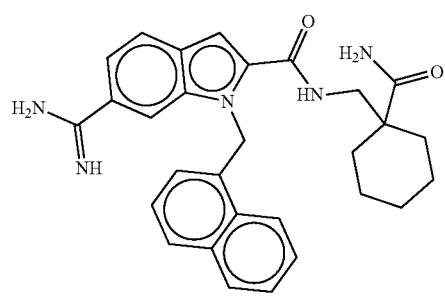
I-465
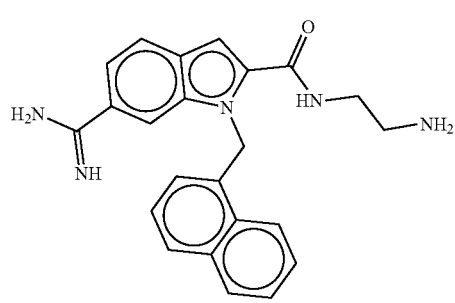
I-466
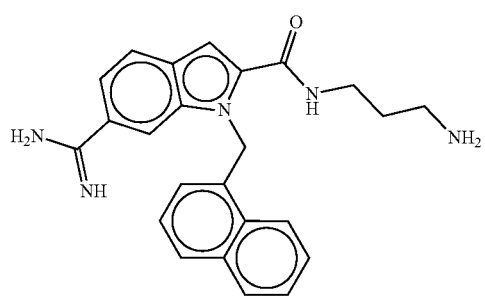
I-467
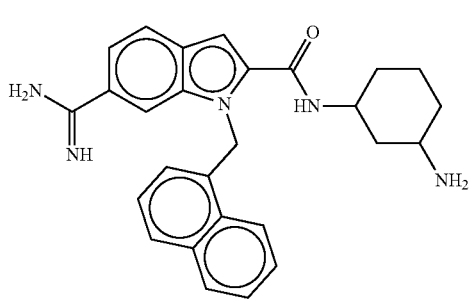
I-468
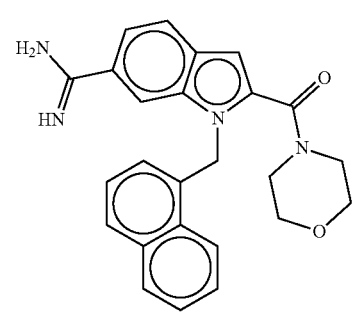
I-469
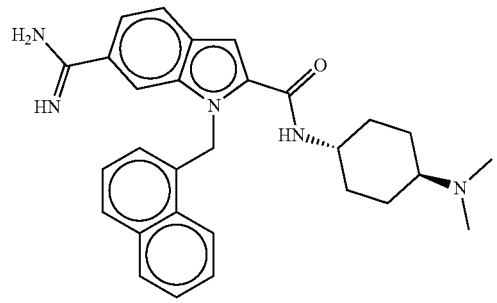
I-470
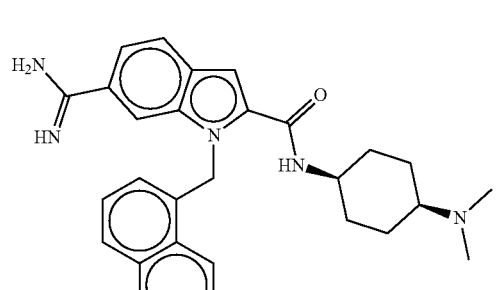
I-471
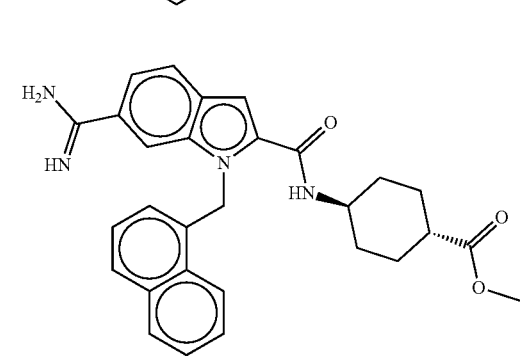
I-472
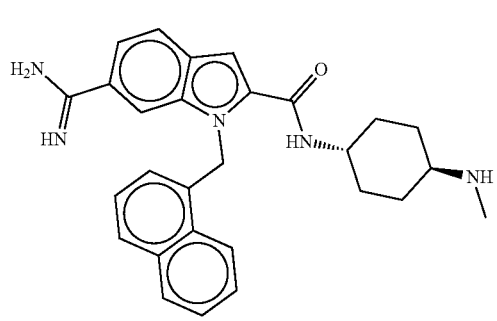
I-473
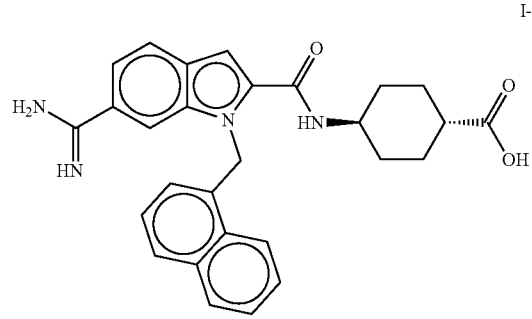

1157 1158
I-474
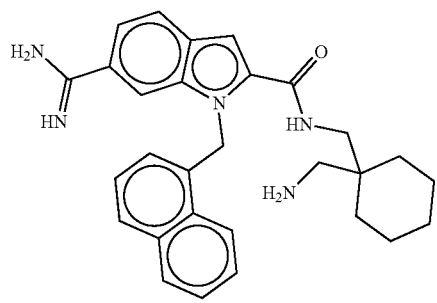
I-479
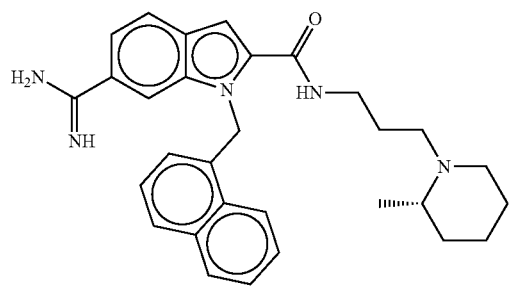
I-475
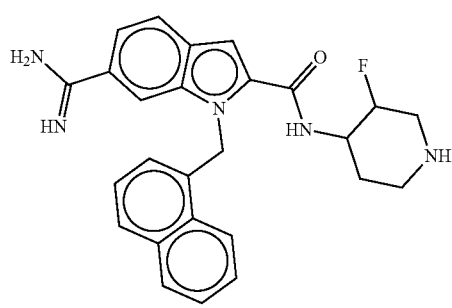
I-480
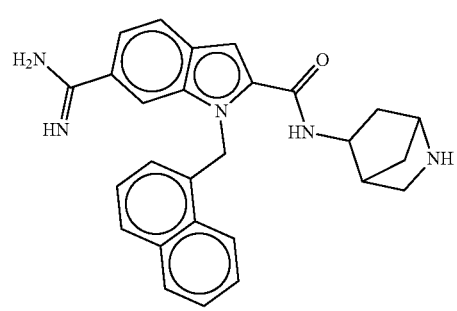
I-476
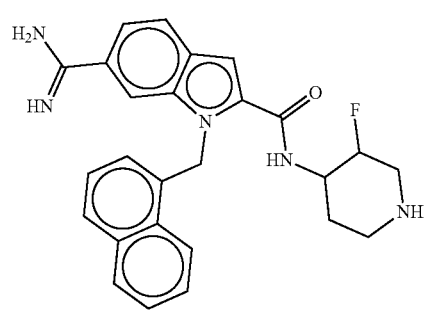
I-481
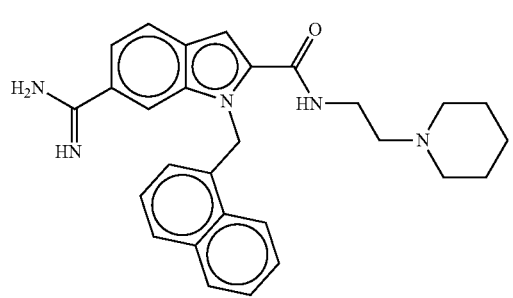
I-477
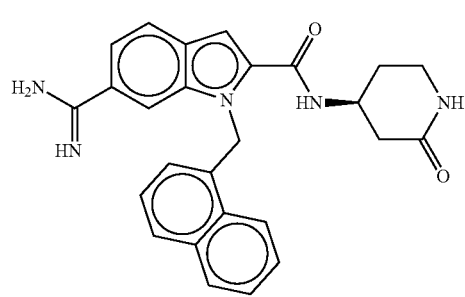
I-482
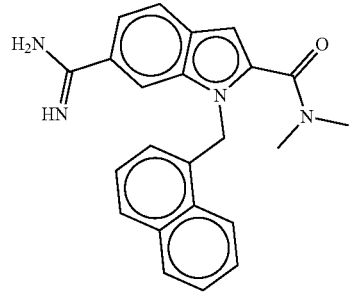
I-478
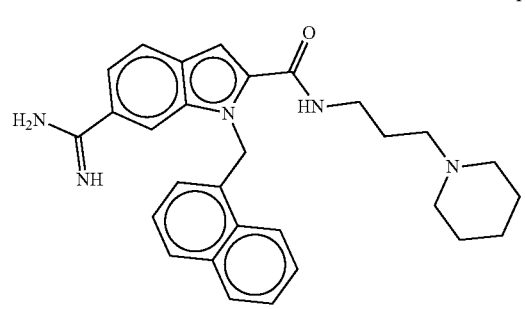
I-483
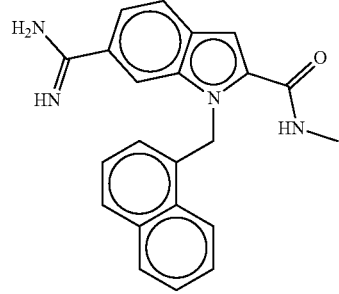

| 1159 -continued | 1160 -continued |
|---|---|
| I-484 | I-489 |
| I-485 | I-490 |
| I-486 | I-491 |
| I-487 | I-492 |
| I-488 | I-493 |

I-494
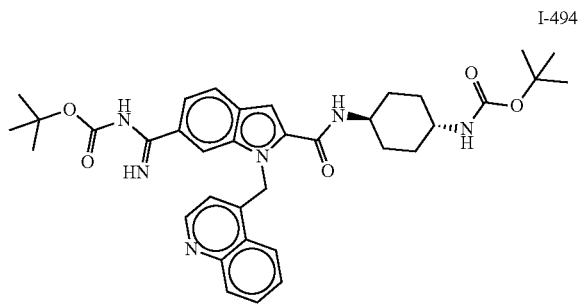
I-500
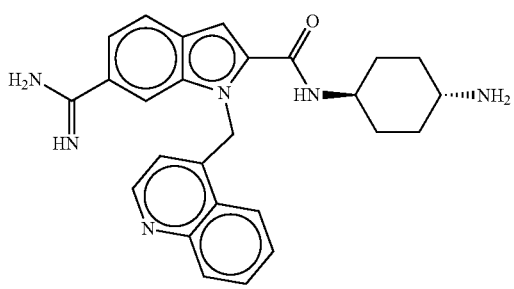
I-495
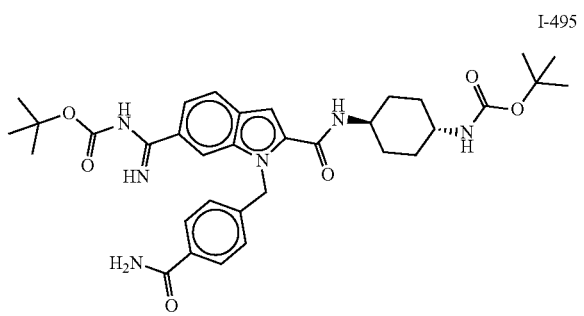
I-501
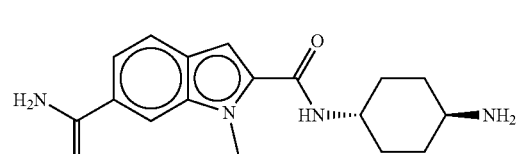
I-496
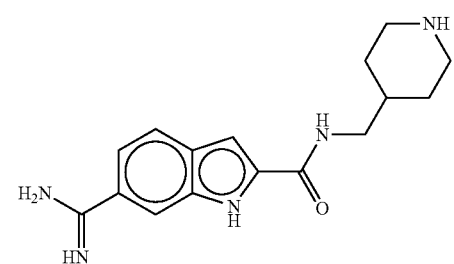
I-502
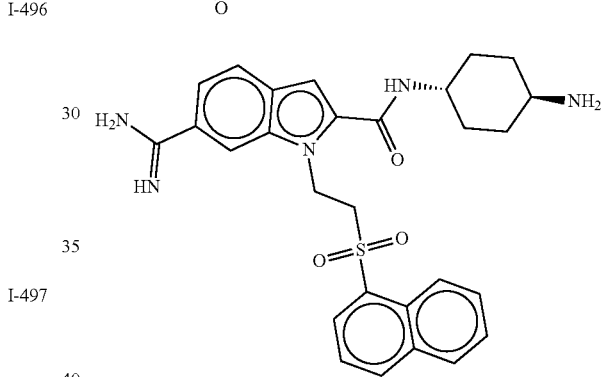
I-497
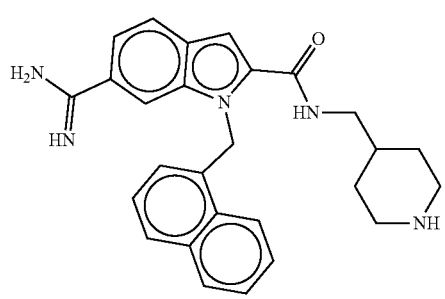
I-503
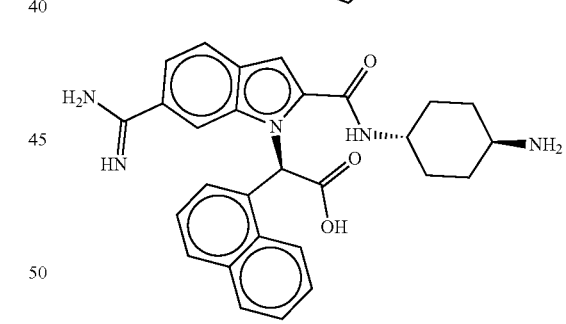
I-498
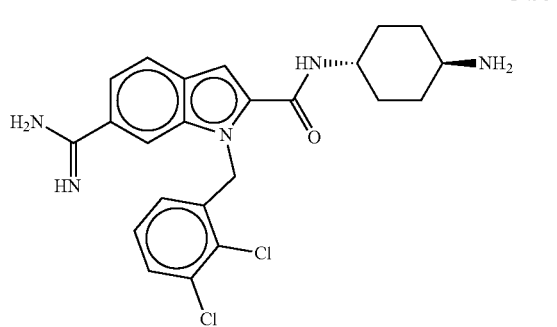
I-504
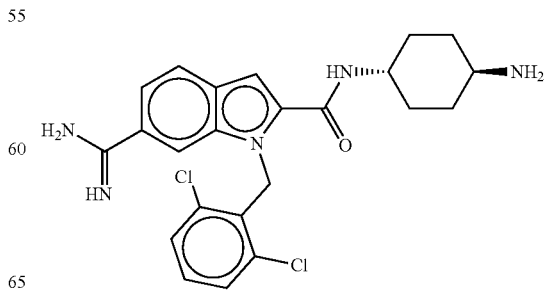

I-505
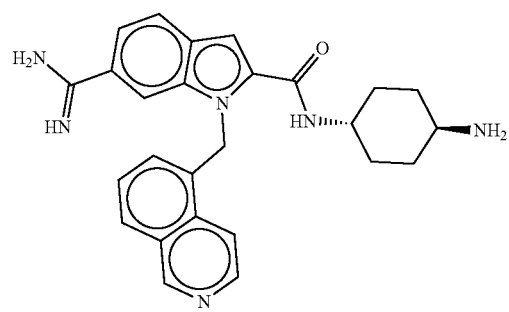
I-506
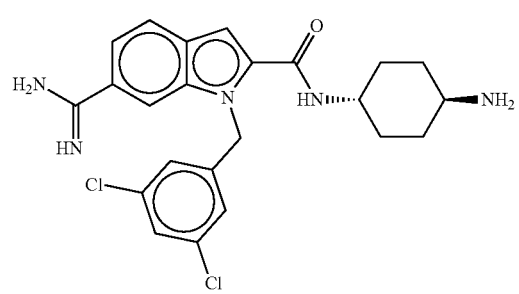
I-507
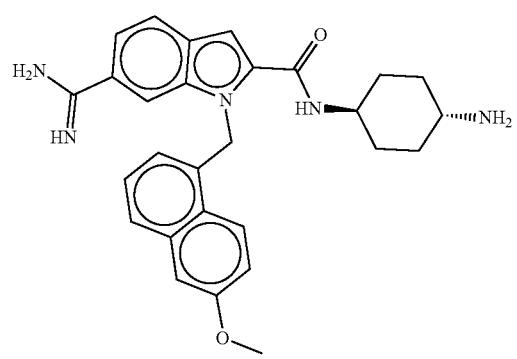
I-508
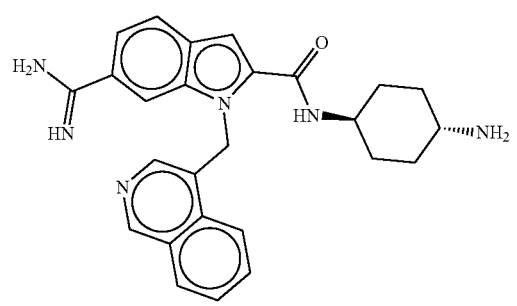
I-509
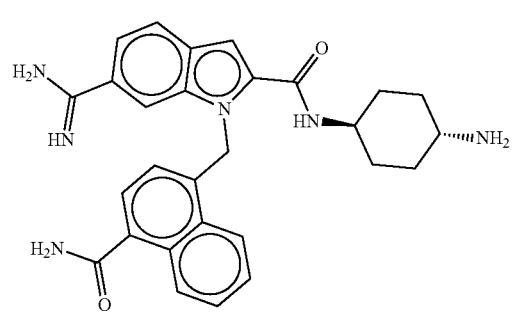
I-510
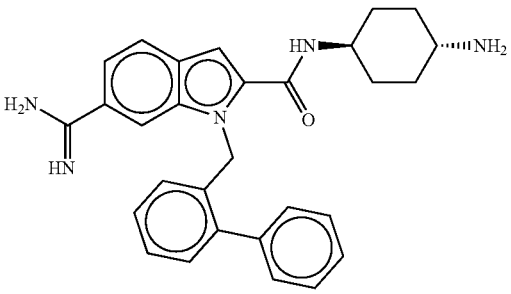
I-511
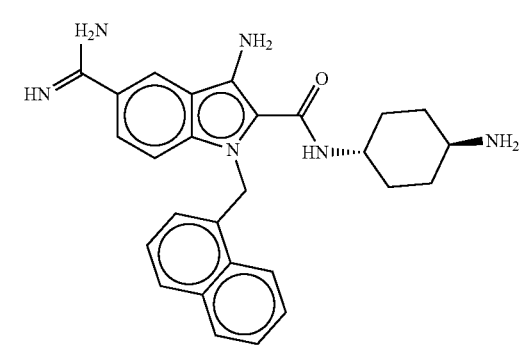
I-512
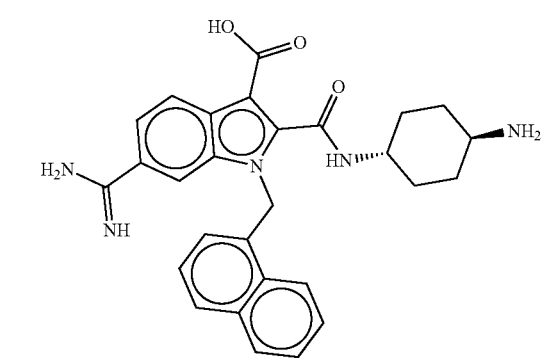
I-513
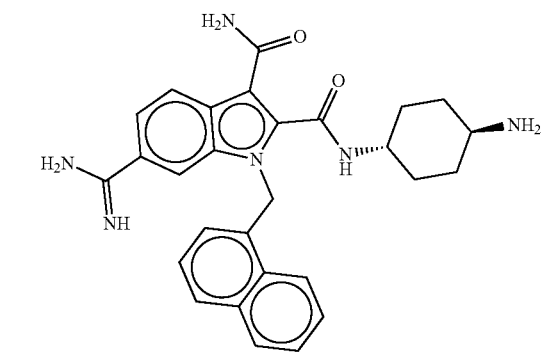

-continued
I-514
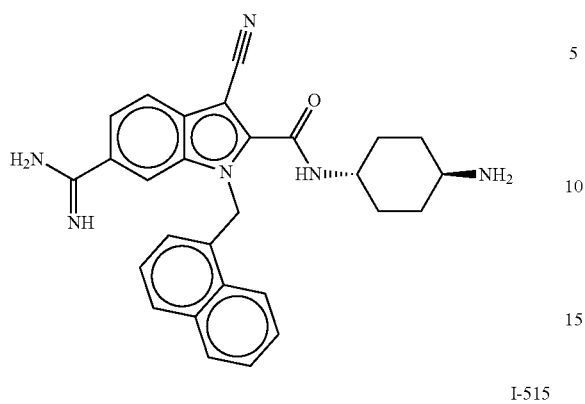
I-515
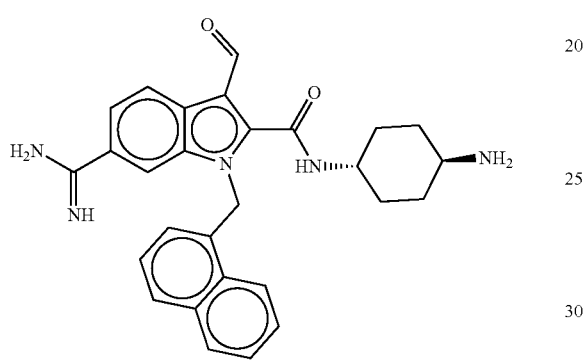
I-516
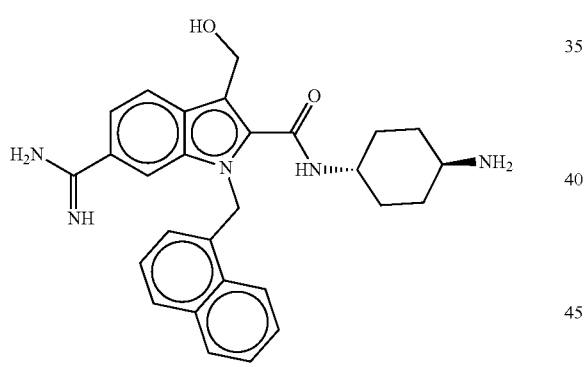
I-5-17
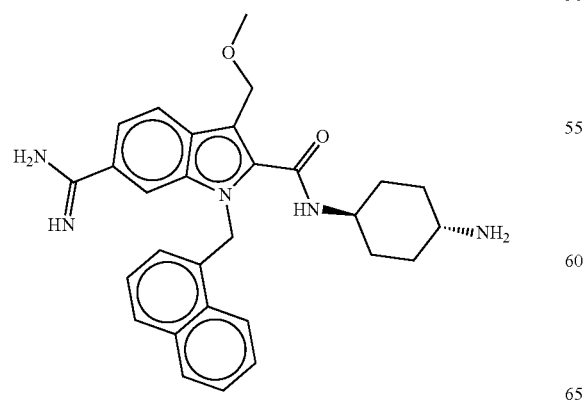
-continued
I-518
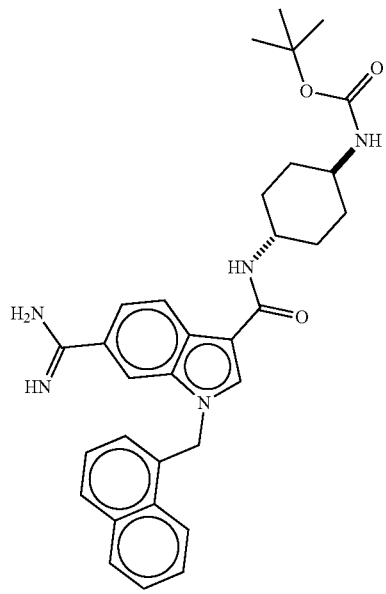
I-519
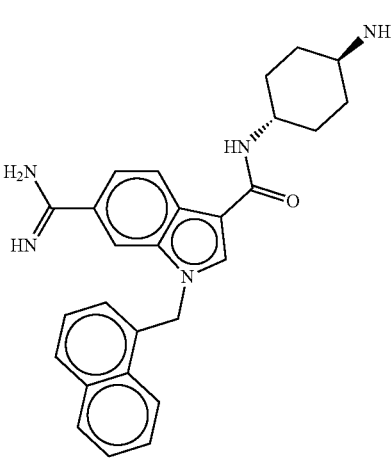
I-520
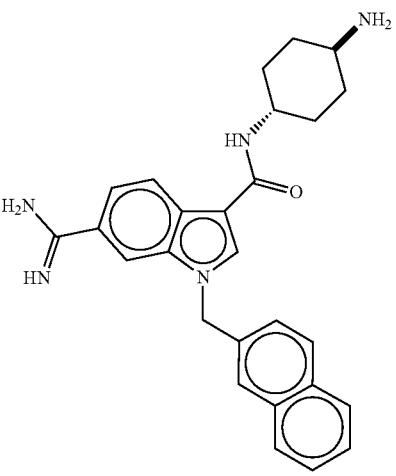

I-521
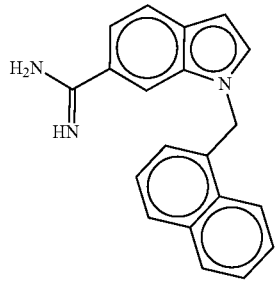
I-522
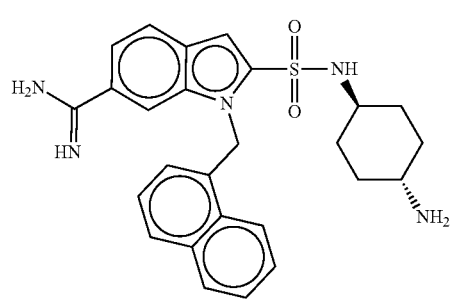
I-523
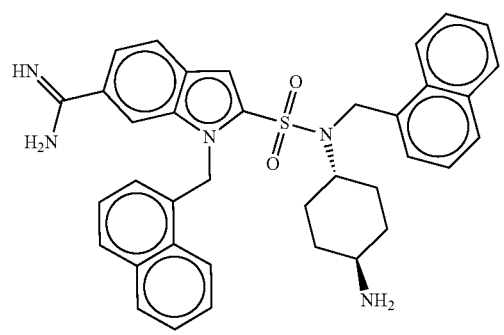
I-524
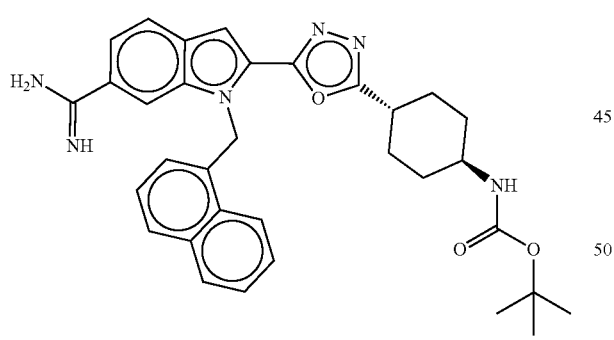
I-525
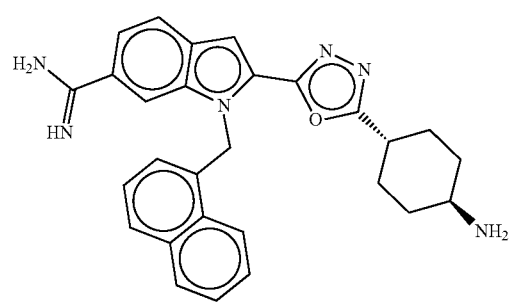
I-526
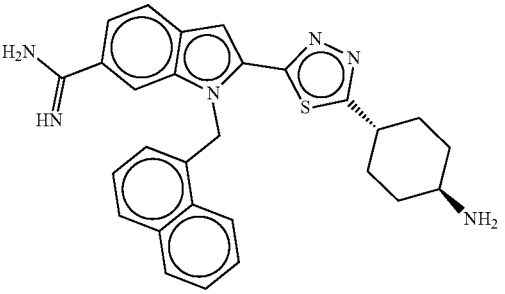
I-527
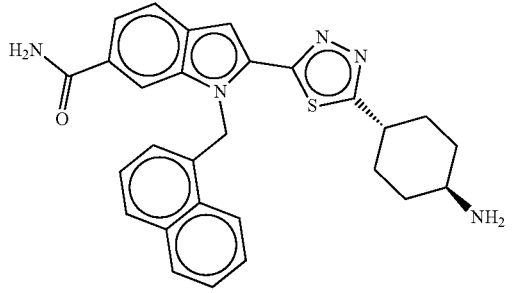
I-528
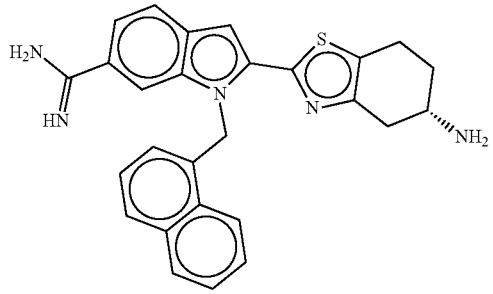
I-529
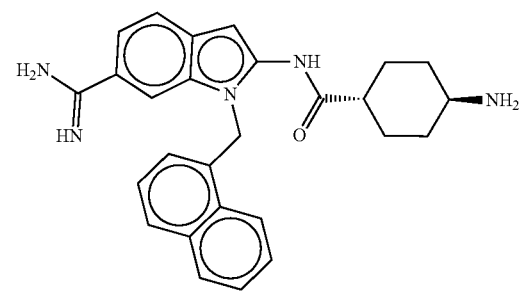

I-530
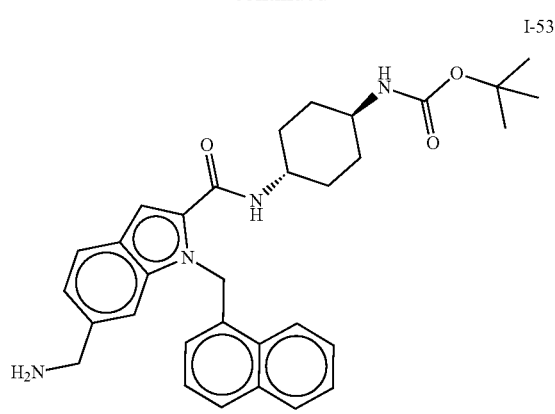
I-531
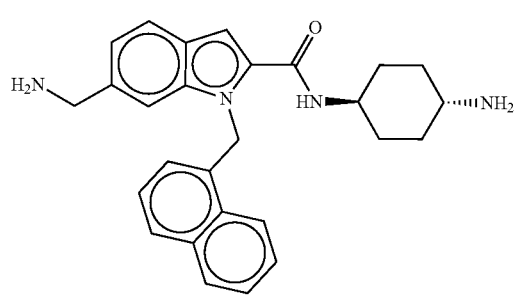
I-532
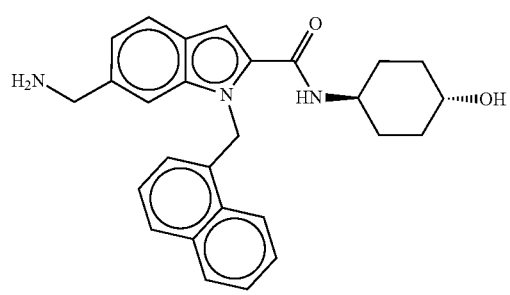
I-533
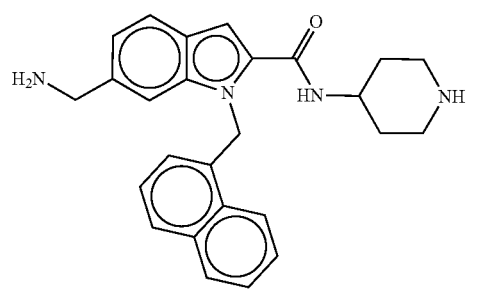
I-534
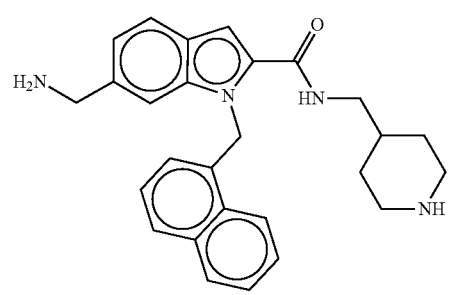
I-535
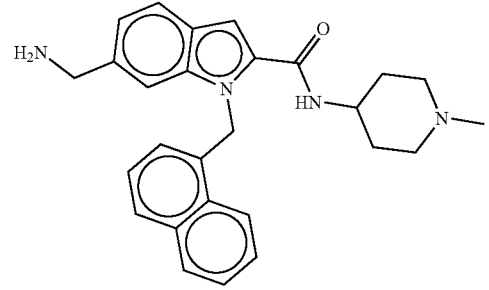
I-536
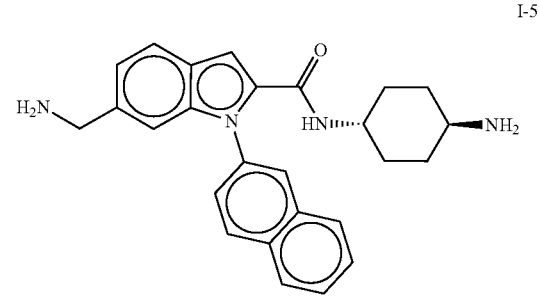
I-537
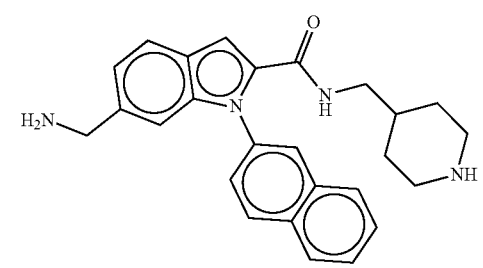
I-538
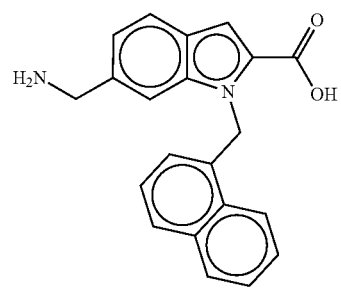
I-539
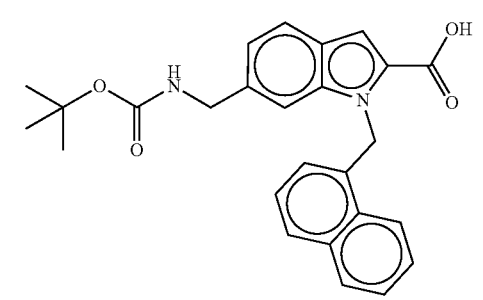

I-540
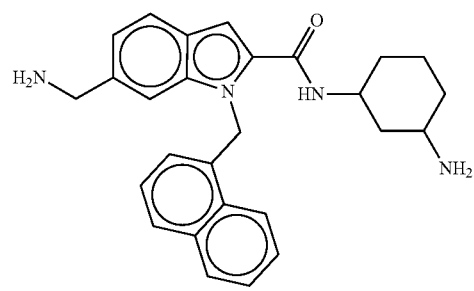
I-541
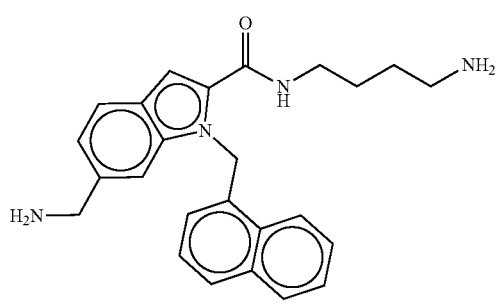
I-542
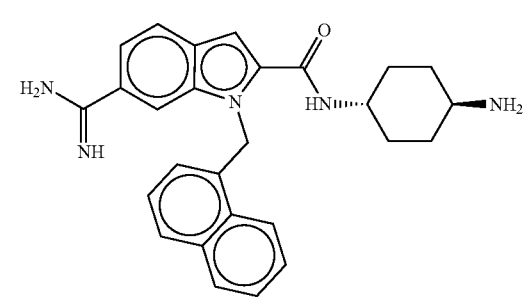
I-543
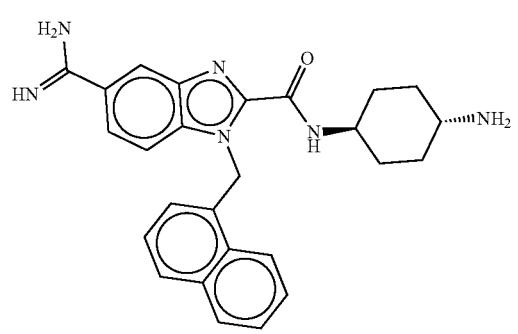
I-544
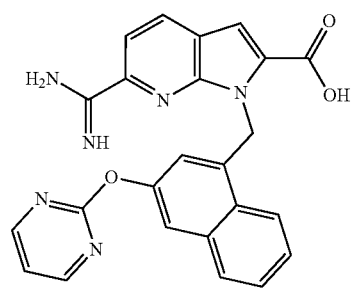
I-545
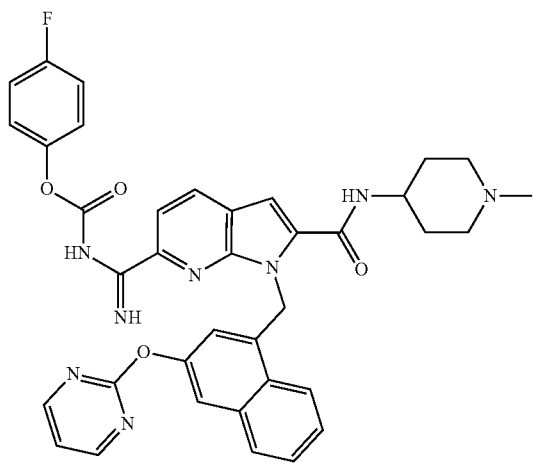
I-546
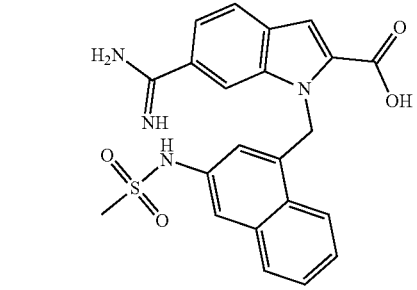
I-547
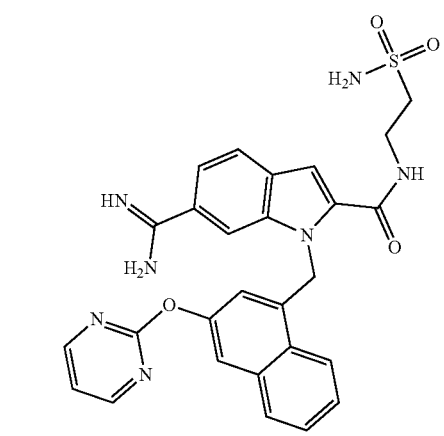
I-548
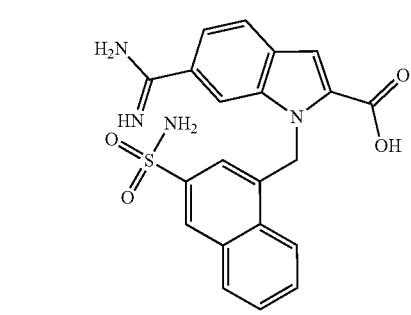

I-549
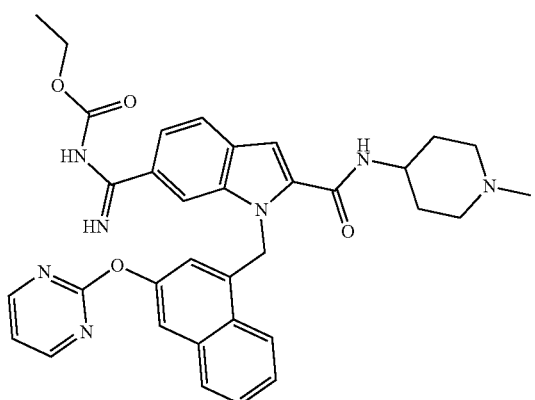
I-553
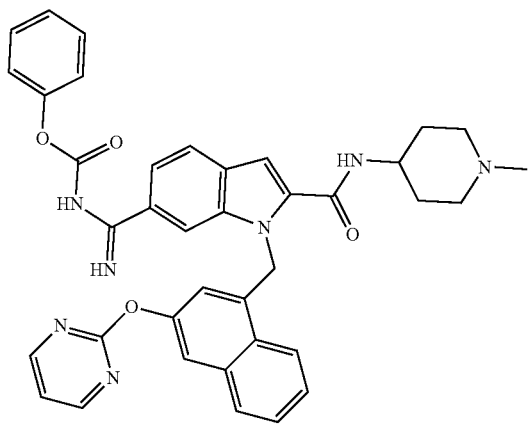
I-550
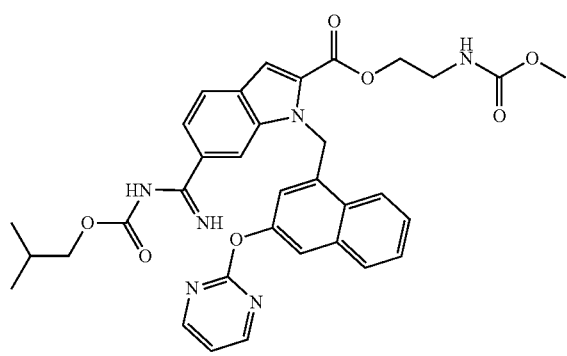
I-554
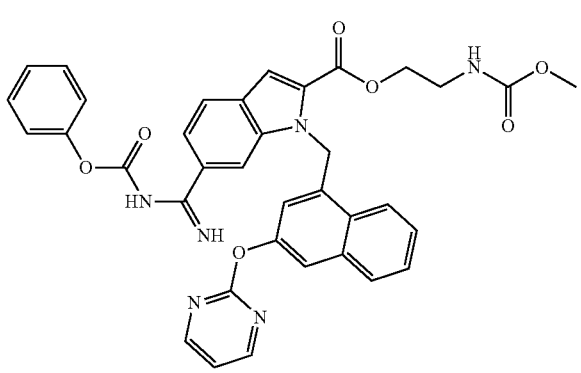
I-551
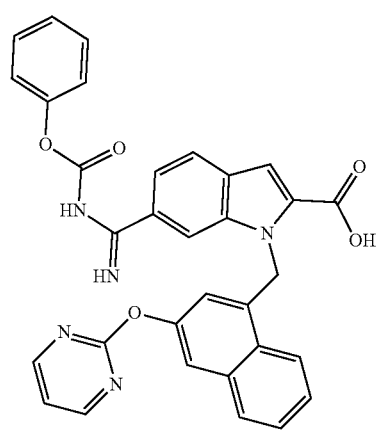
I-555
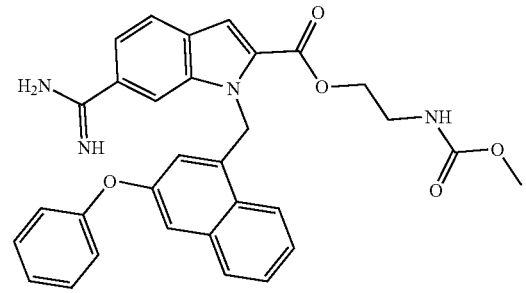
I-552
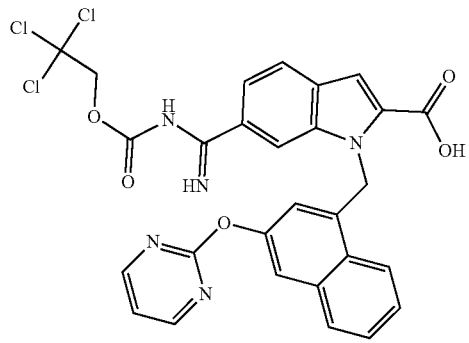
I-556
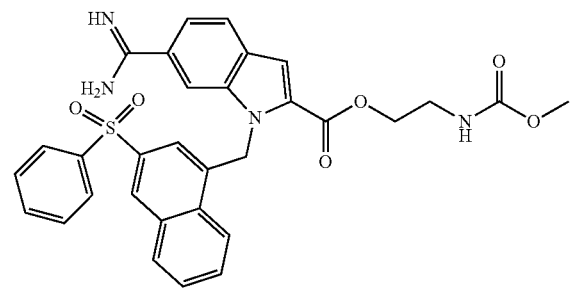

I-557
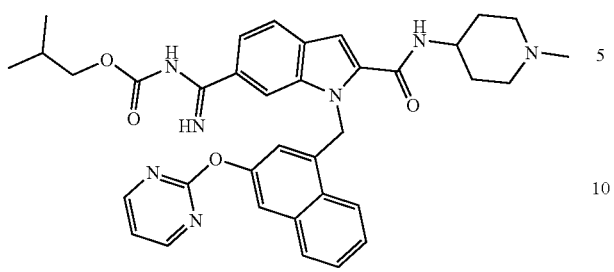
I-558
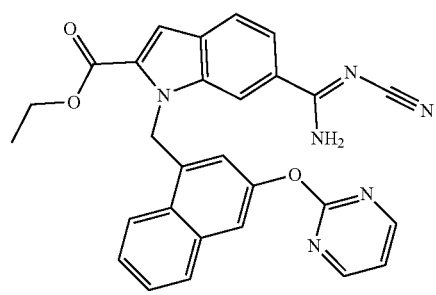
I-559
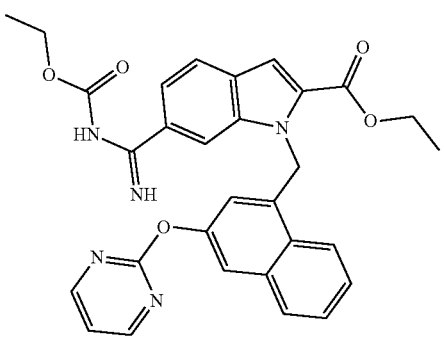
I-560
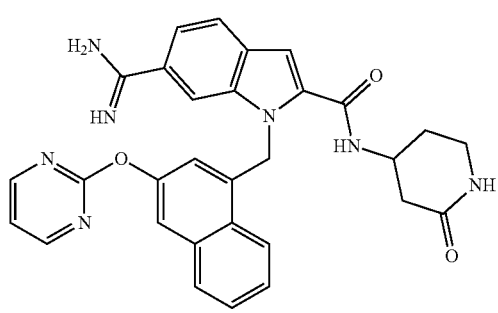
I-561
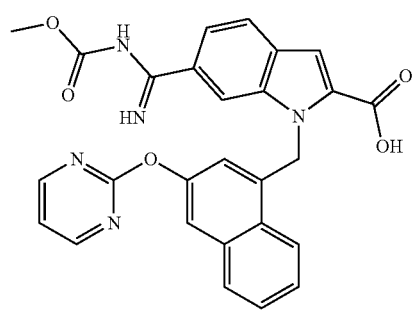
I-562
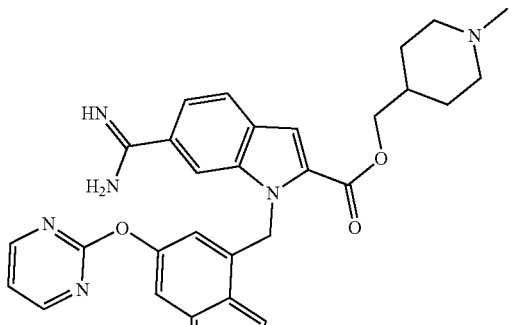
I-563
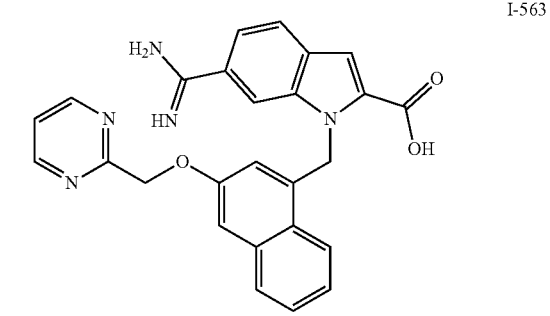
I-564
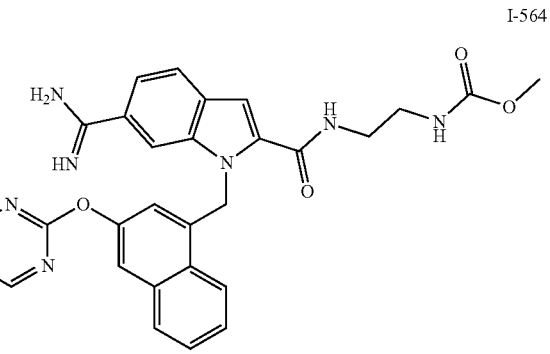
I-565
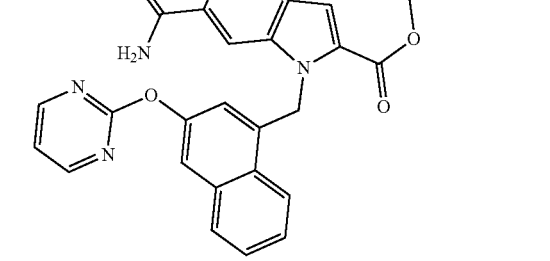

I-566
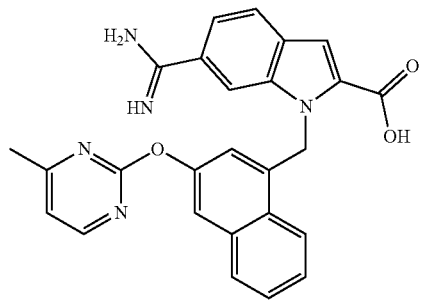
I-567
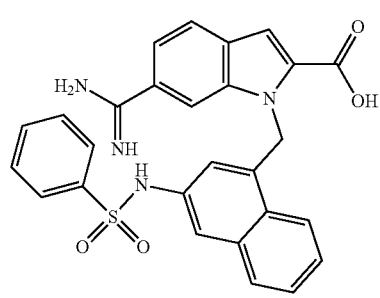
I-568
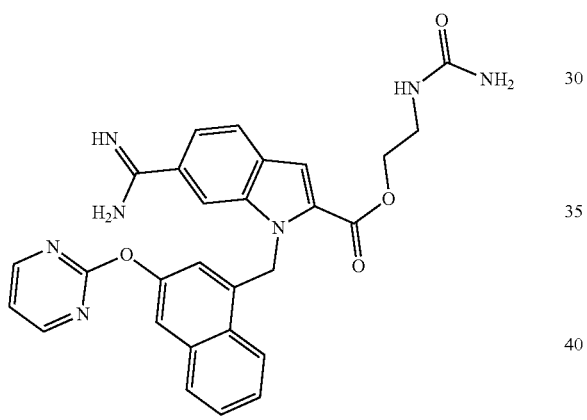
I-569
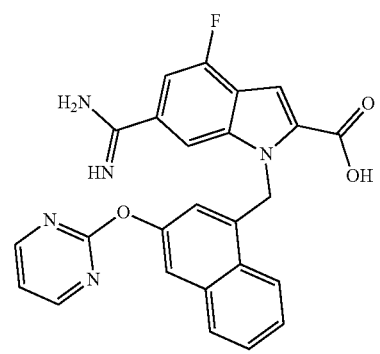
I-570
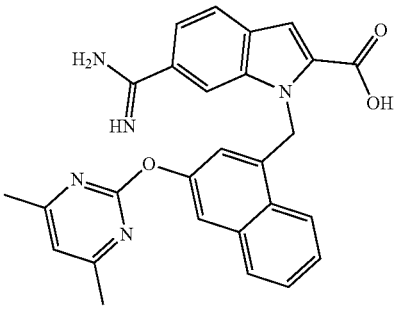
I-571
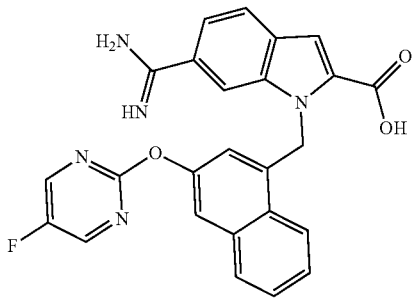
I-572
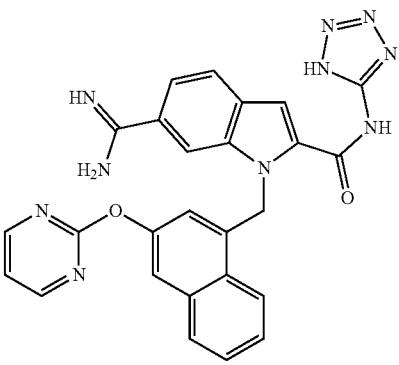
I-573
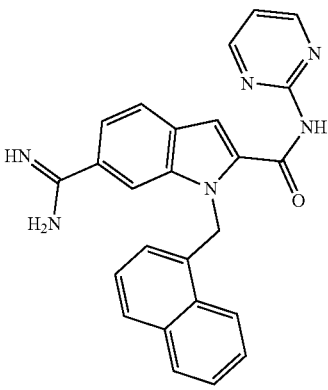

I-574
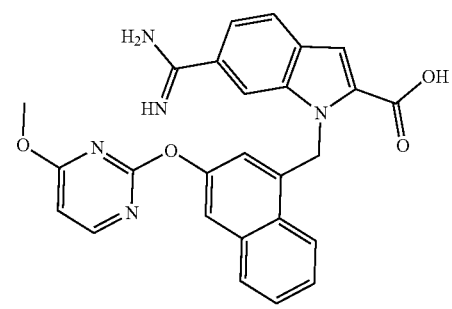
I-575
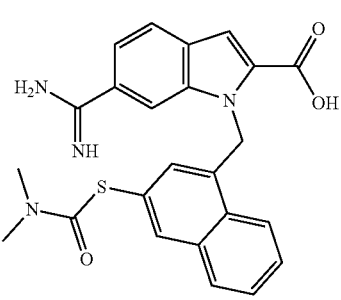
I-576
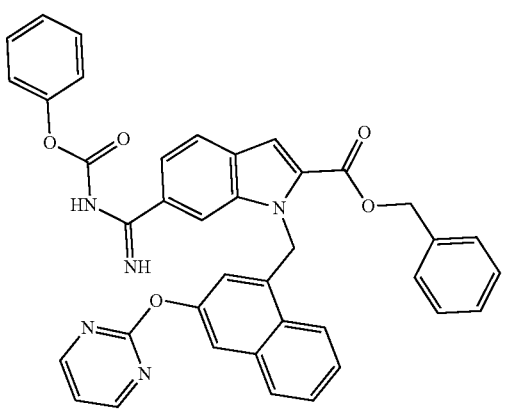
I-577
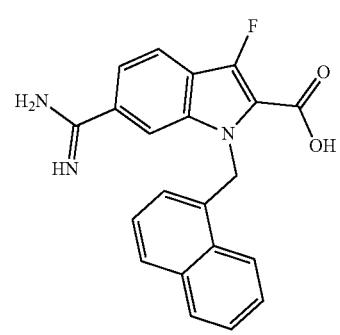
I-578
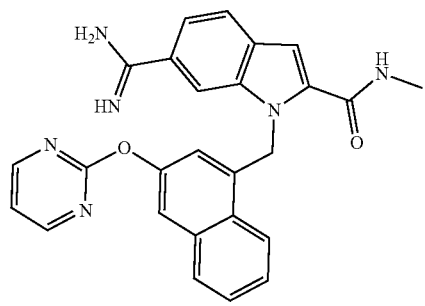
I-579
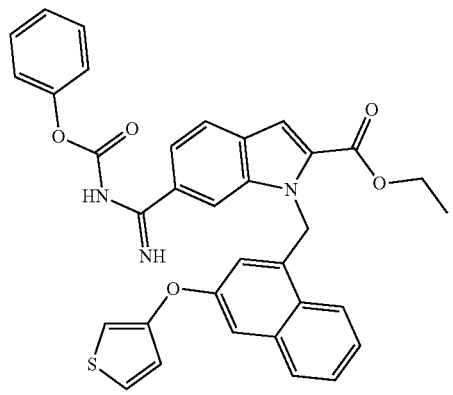
I-580
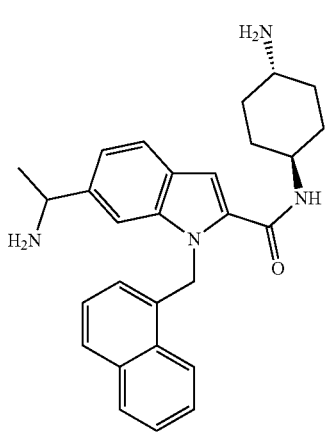
I-581
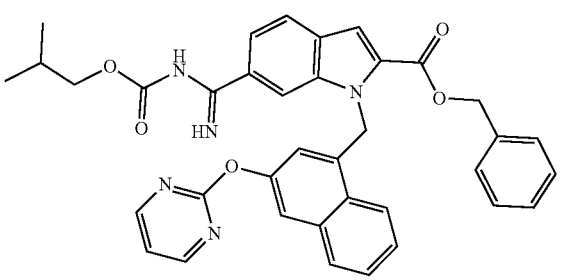
I-582
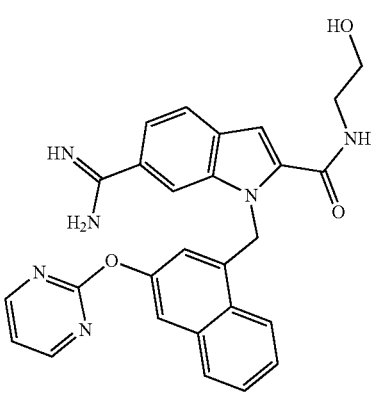

I-583 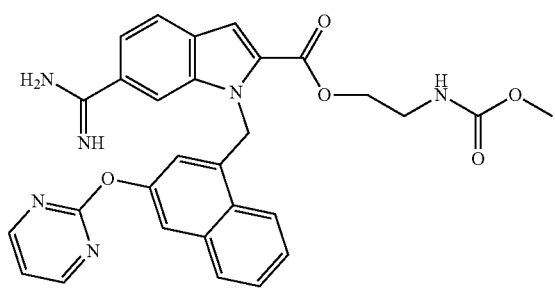
I-584 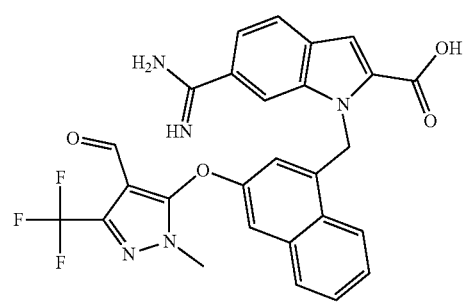
I-585 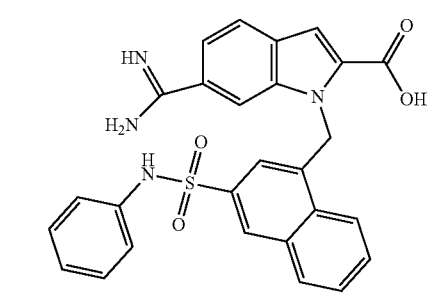
I-588 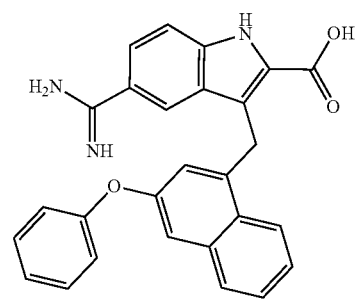
I-589 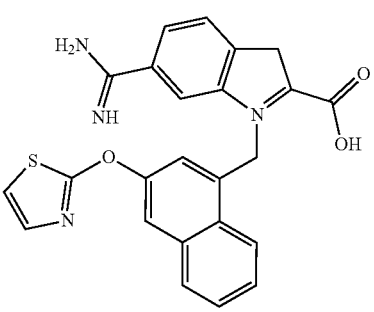
I-590 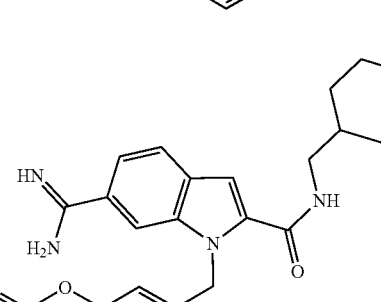
I-586 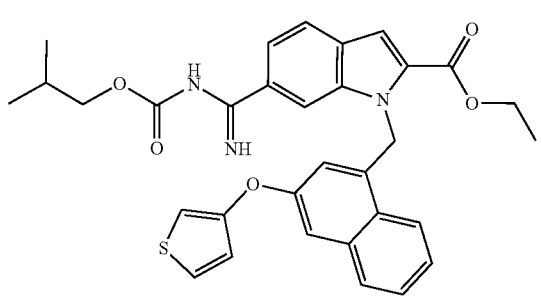
I-591 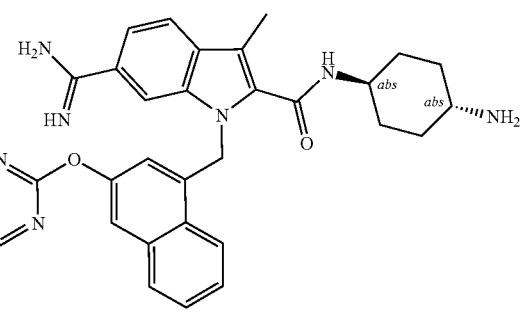
I-587 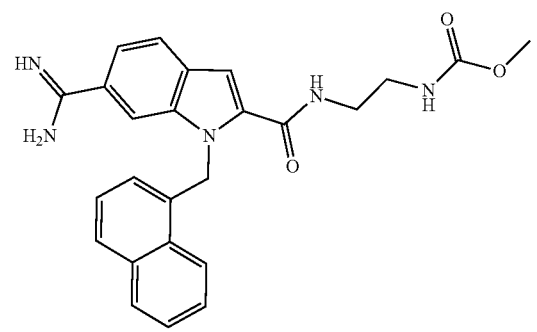
I-592 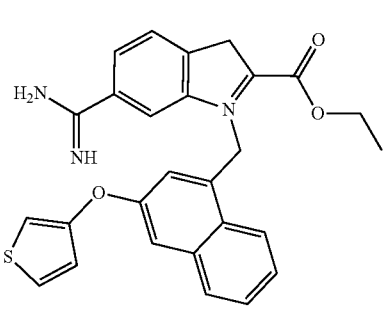

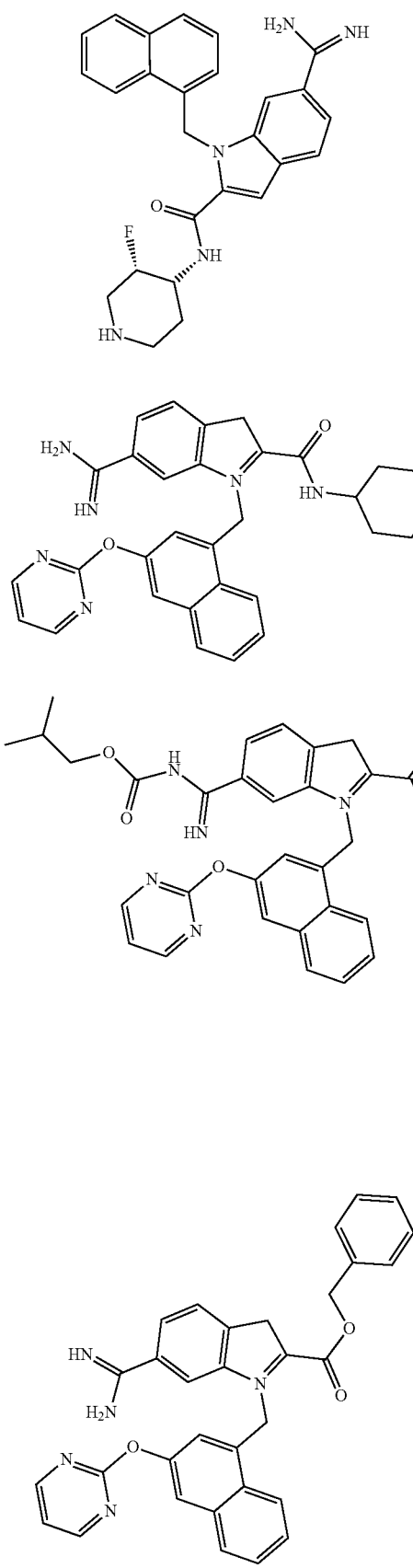
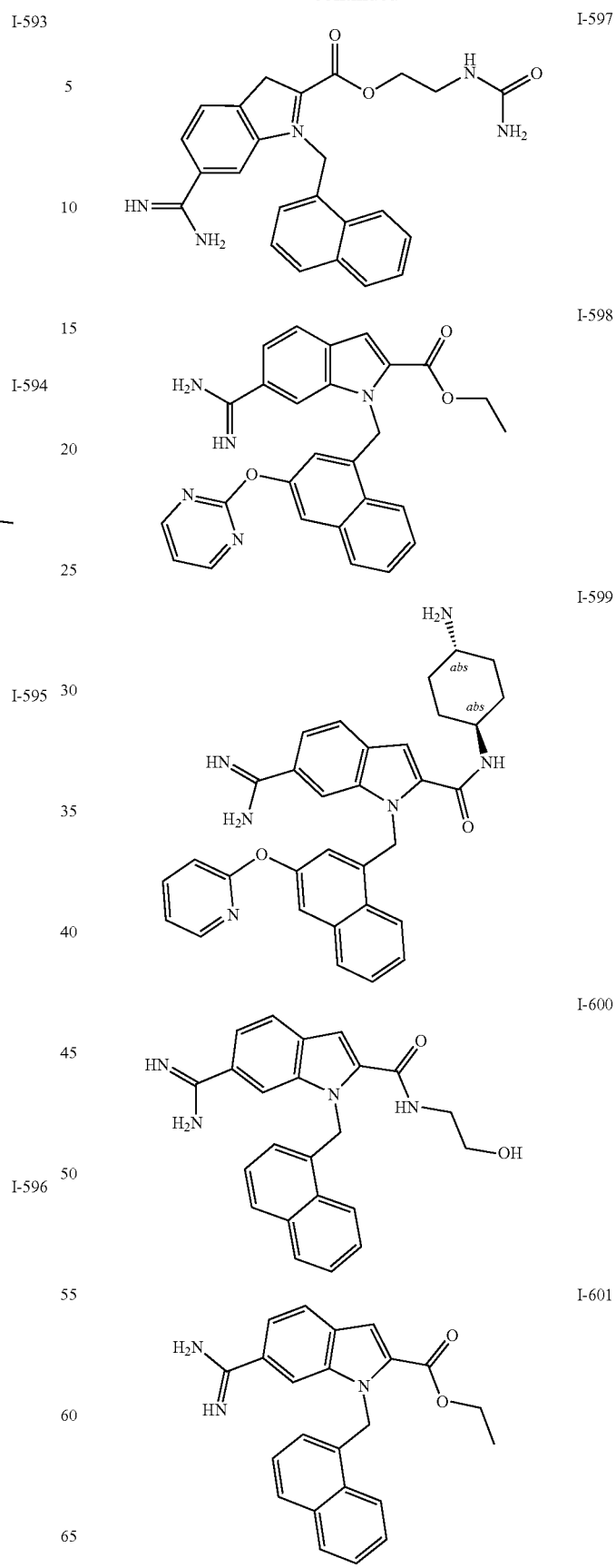

I-602
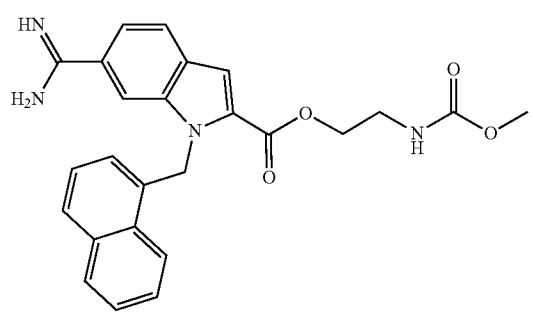
I-603
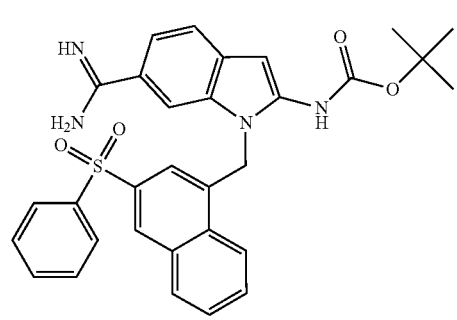
I-604
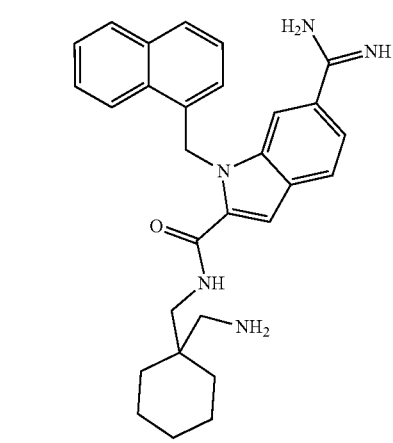
I-605
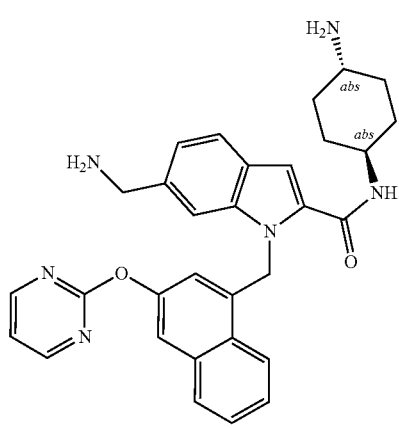
I-606
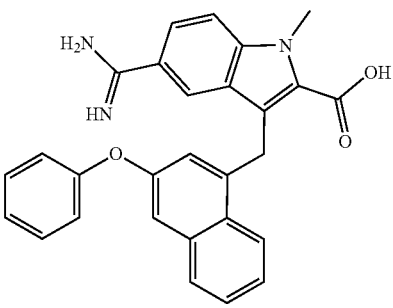
I-607
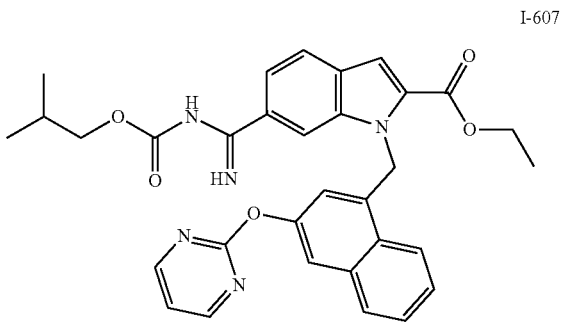
I-608
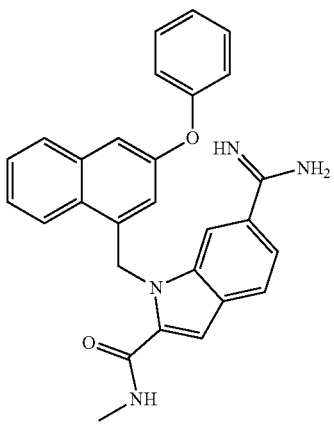
I-609

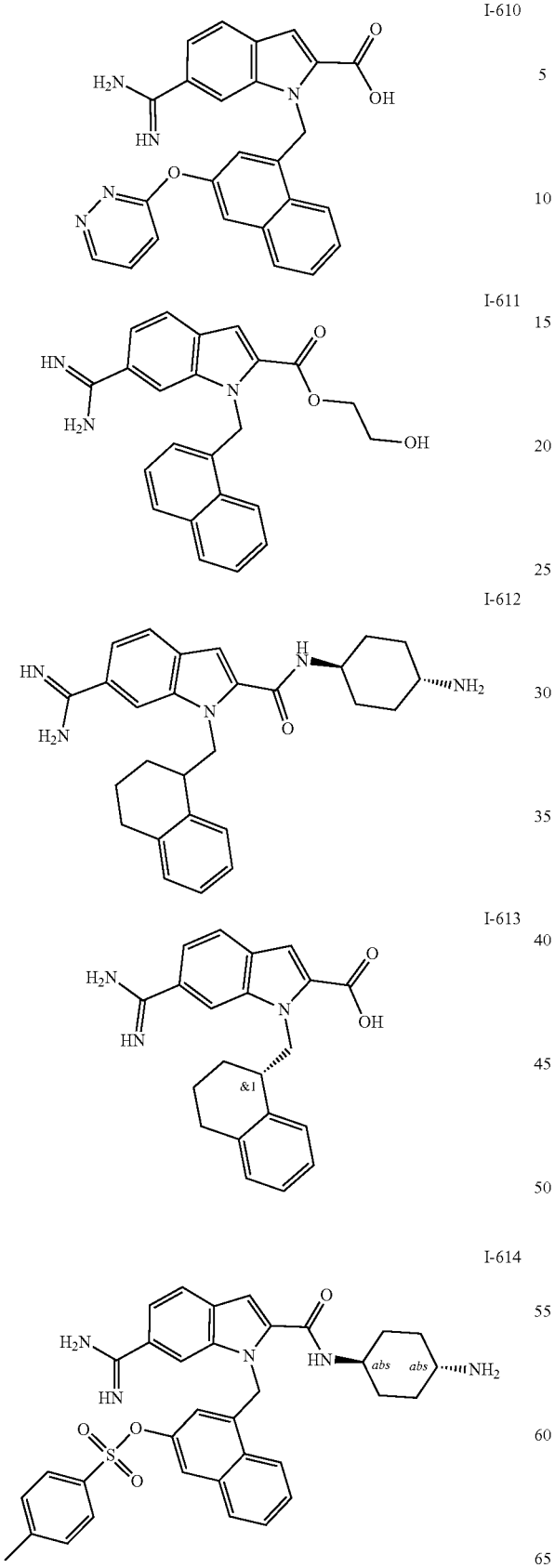
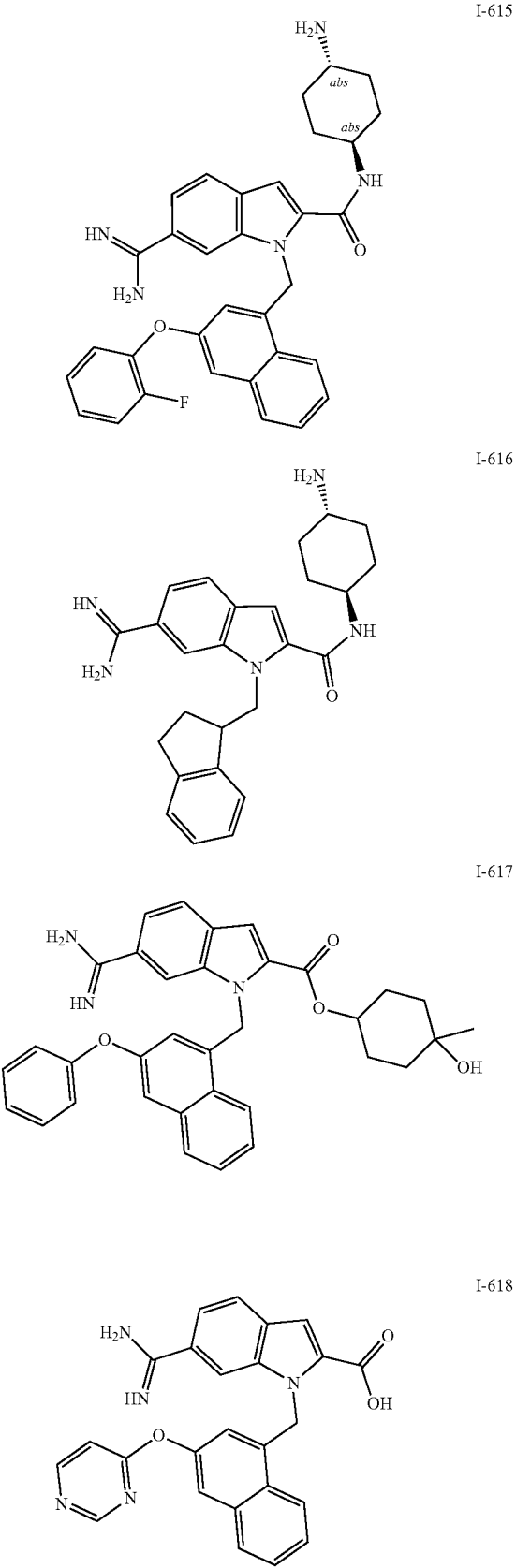

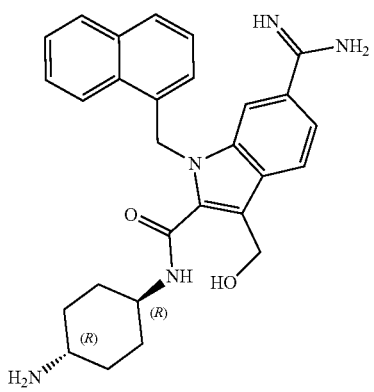
I-619
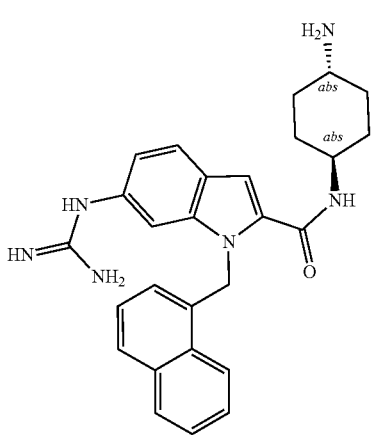
I-620
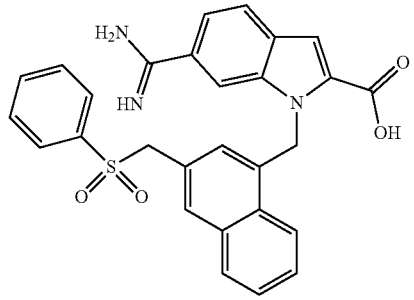
I-621
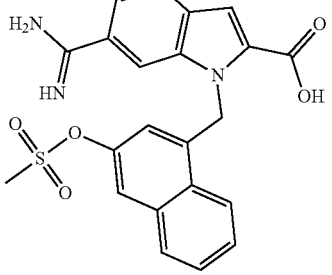
I-622
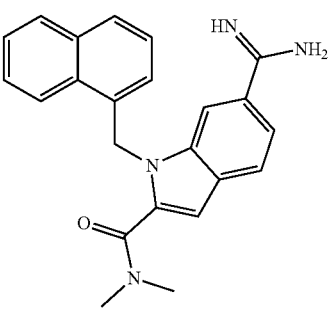
I-623
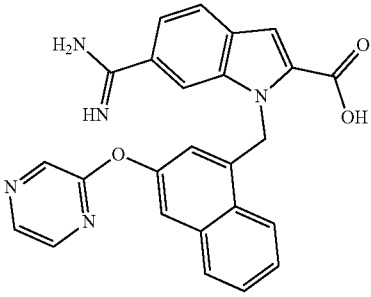
I-624
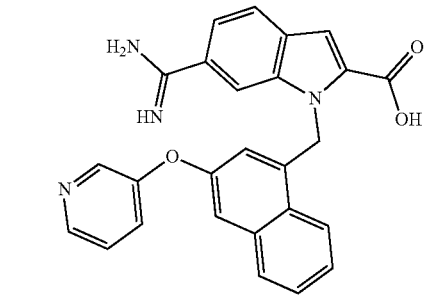
I-625
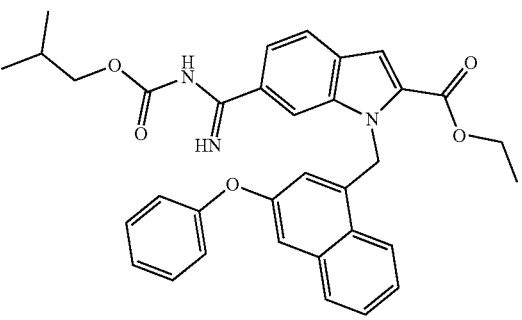
I-626
I-627

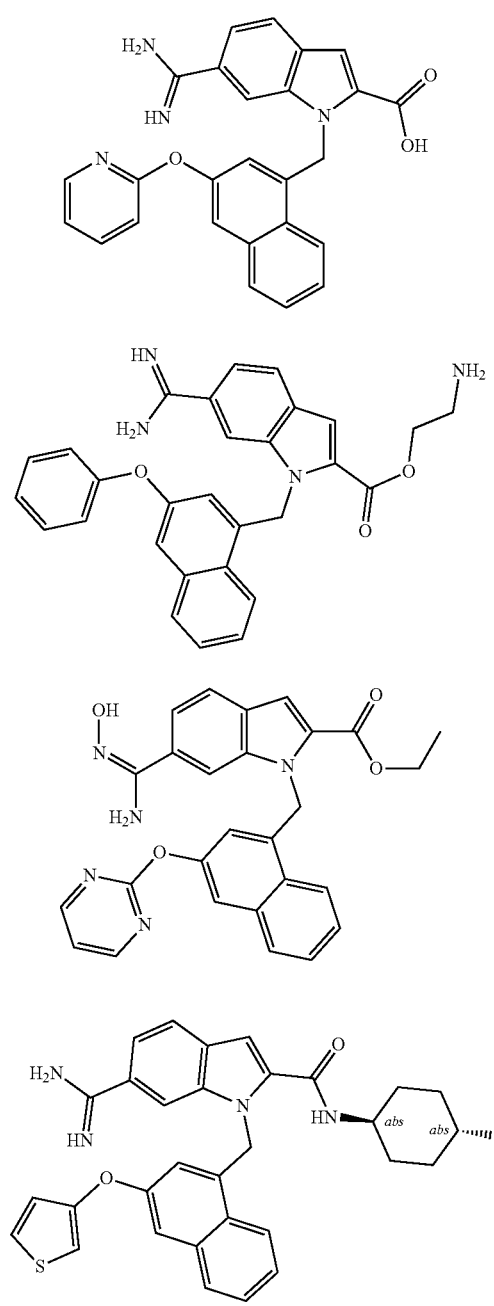
I-628
I-629
I-630
I-631
I-632
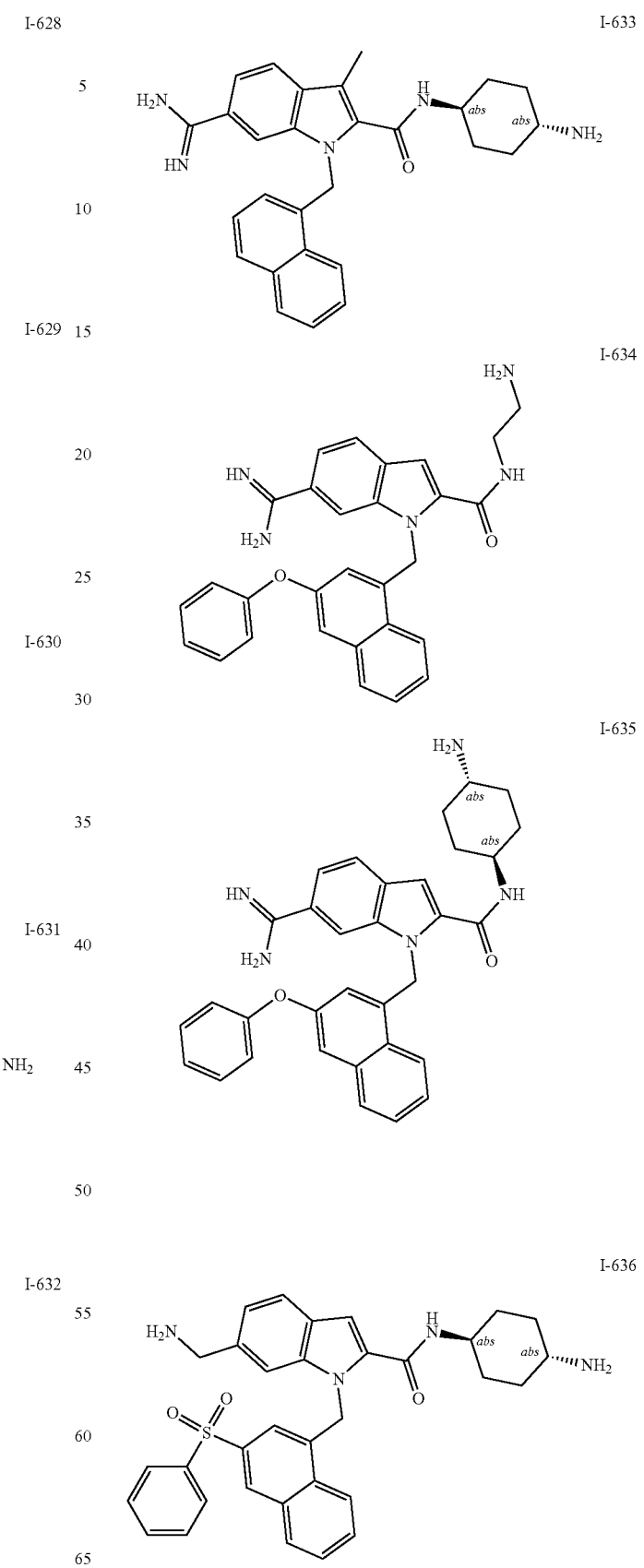
I-633
I-634
I-635
I-636

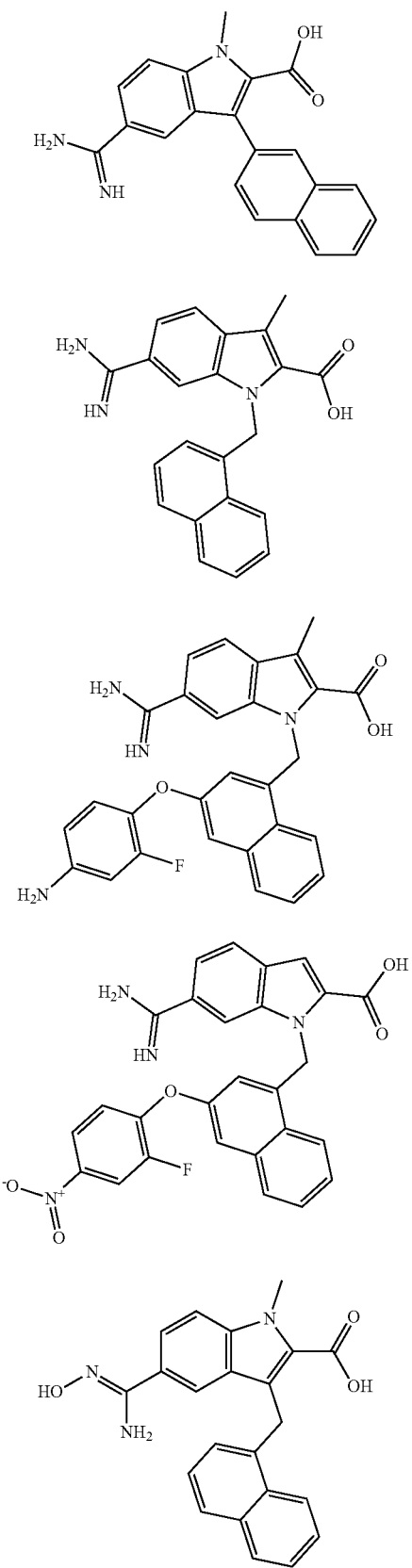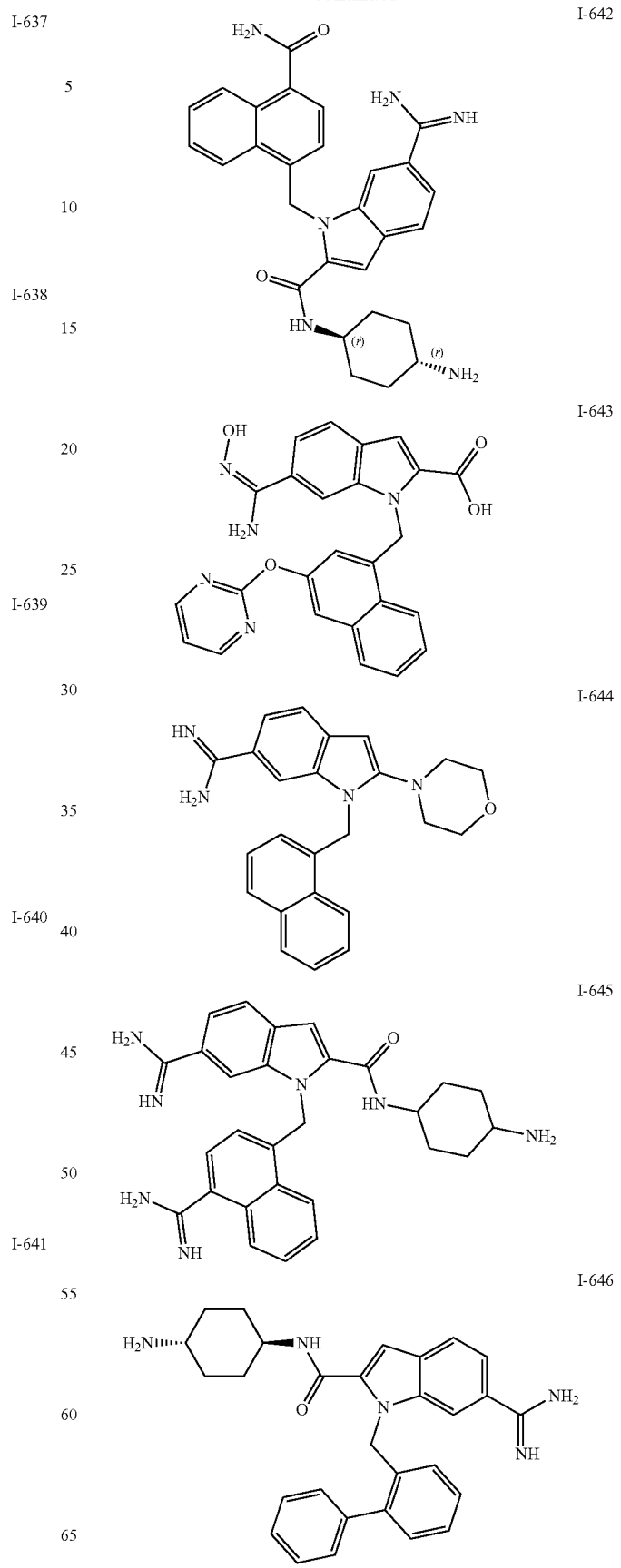

I-647 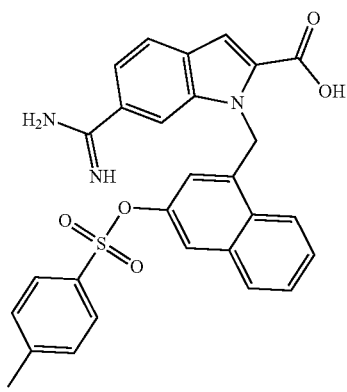
I-648 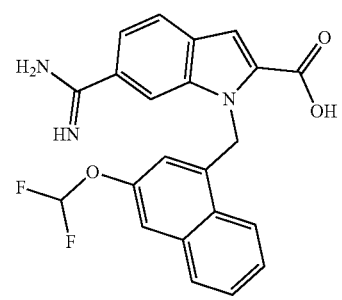
I-649 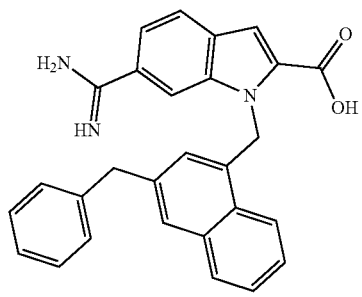
I-650 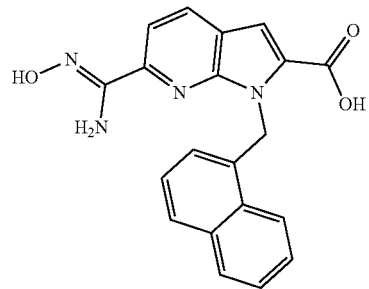
I-651 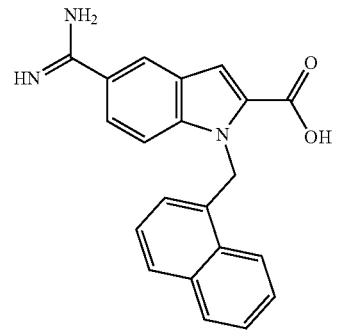
I-652 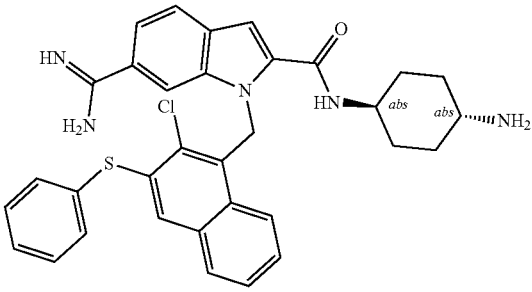
I-653 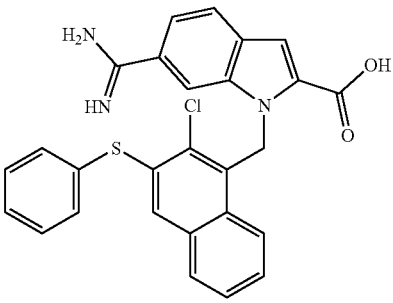
I-654 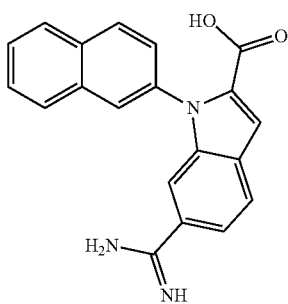
I-655 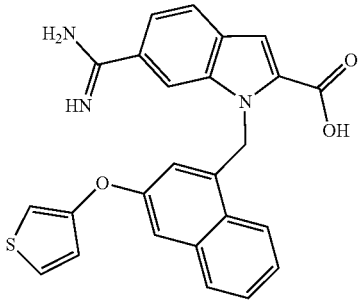
I-656 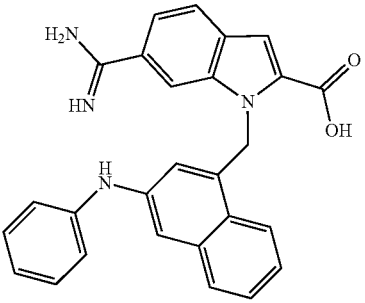

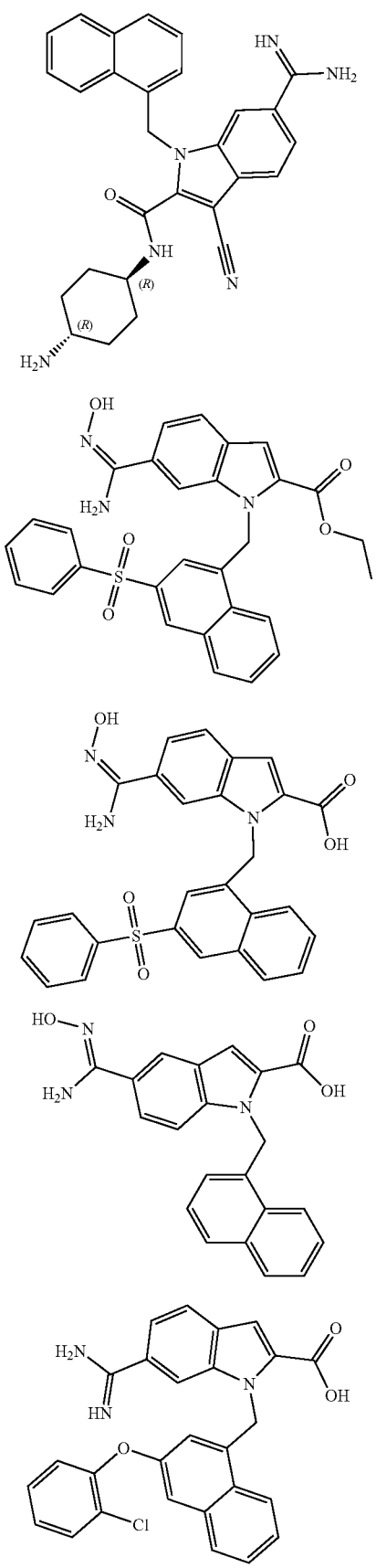
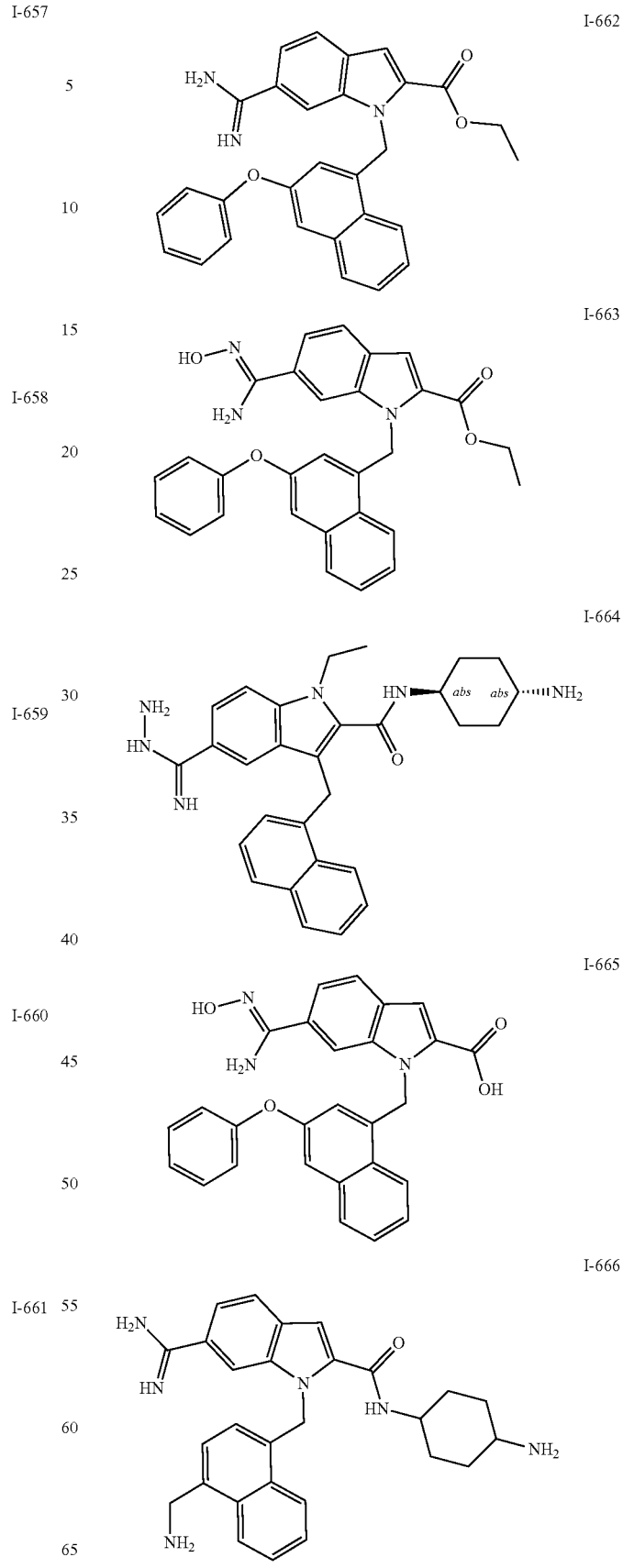

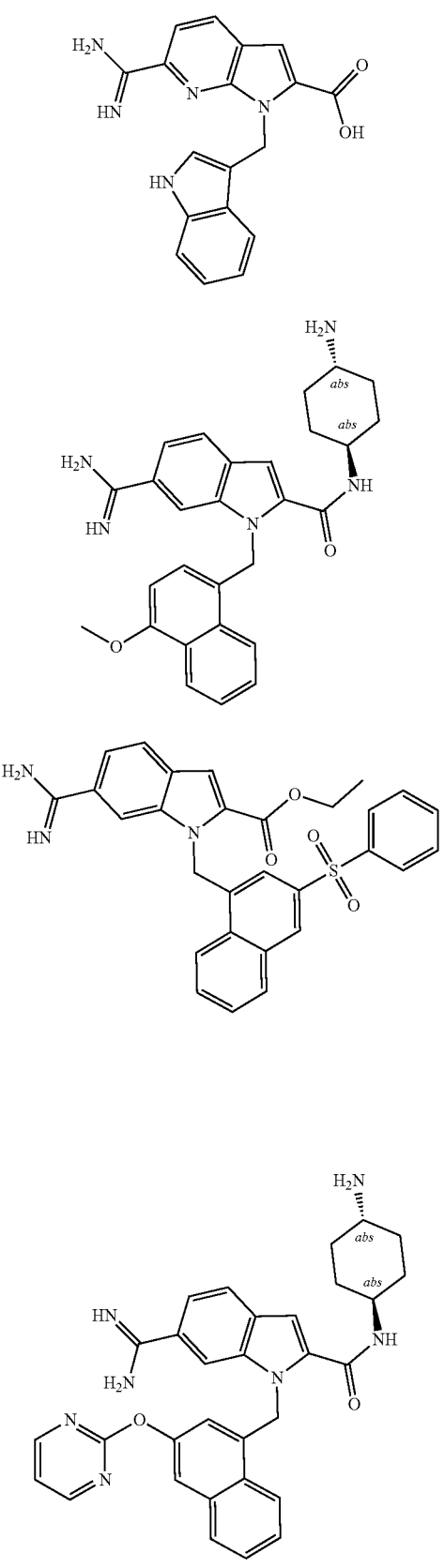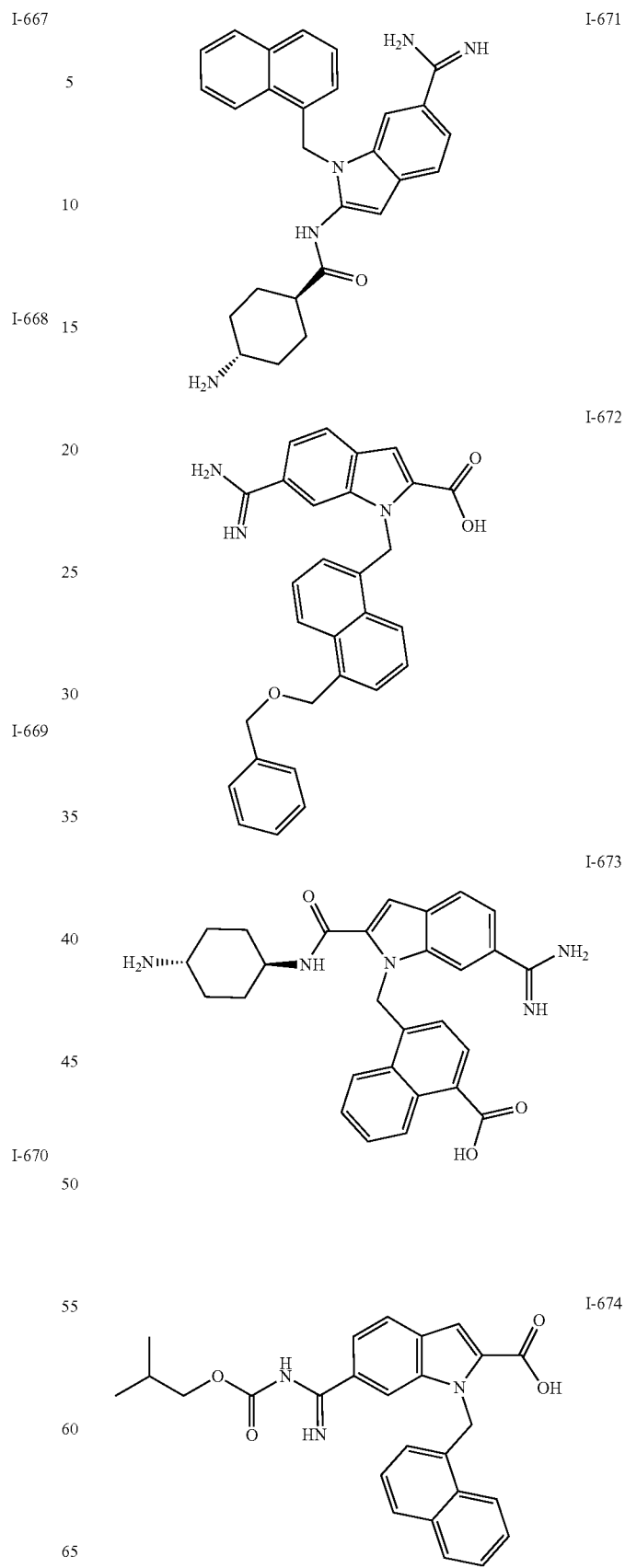

1201
-continued
I-675
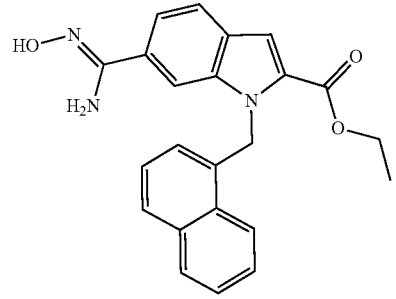
I-676
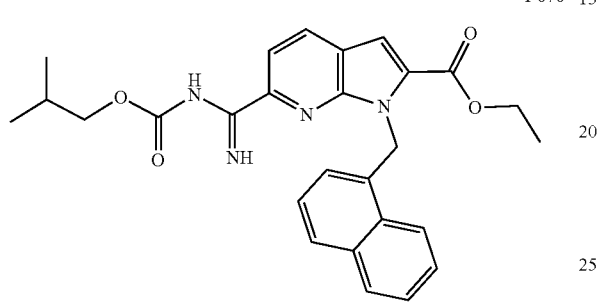
I-677
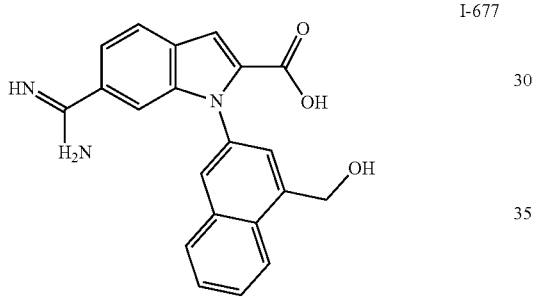
I-678
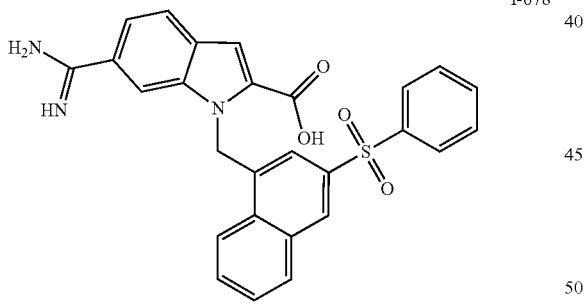
I-679
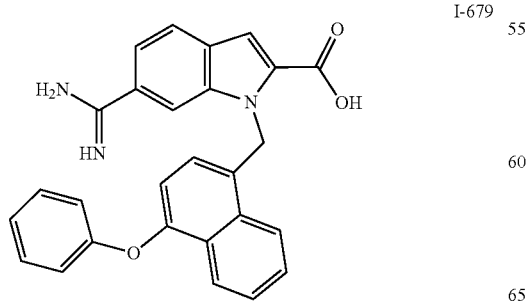
1202
-continued
I-680
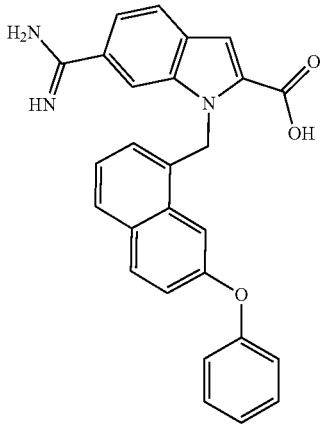
I-681
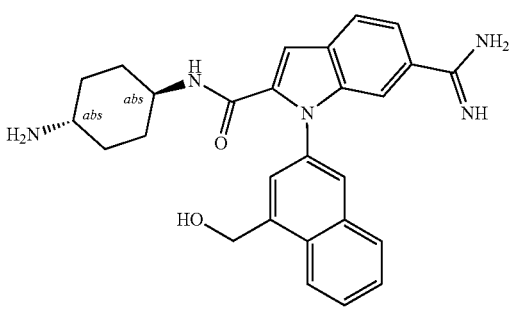
I-682
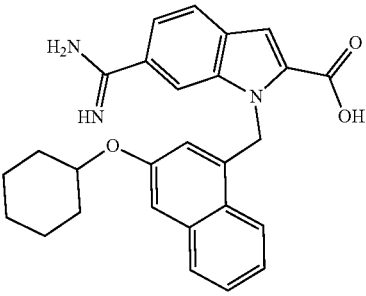
I-683
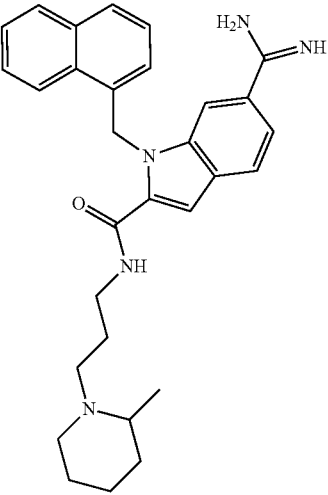

I-684
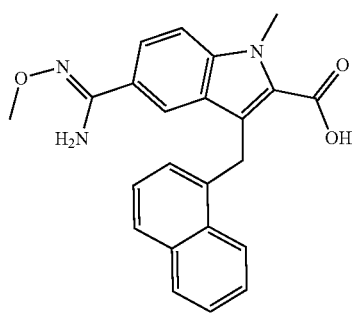
I-685
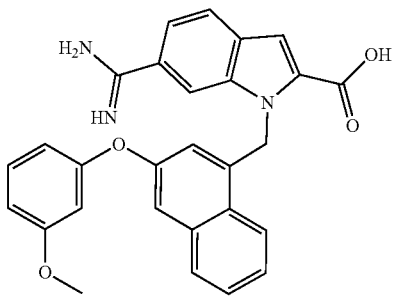
I-688
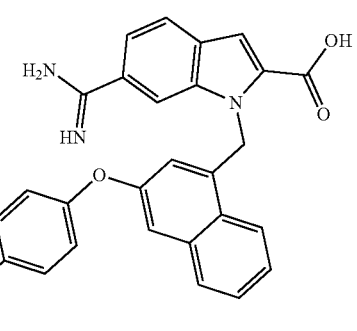
I-689
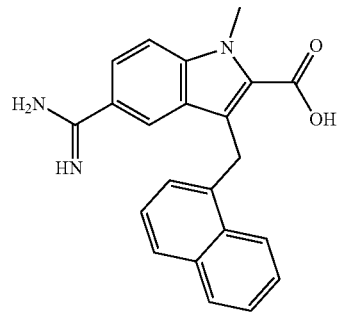
I-690
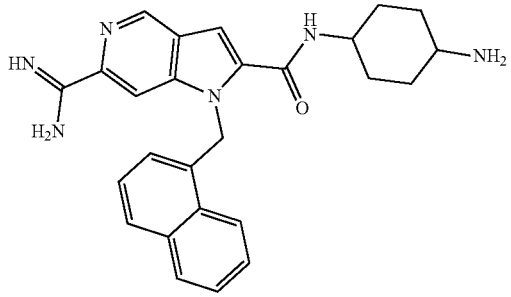
I-691
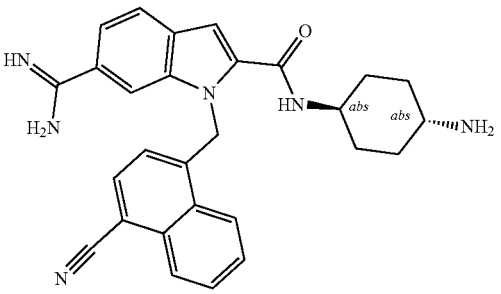
I-692
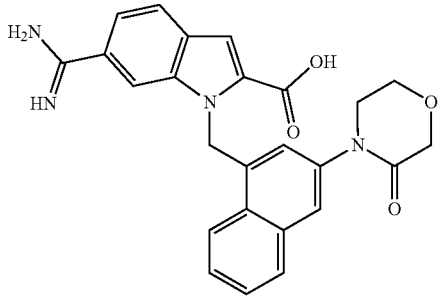
I-686
I-687

I-693
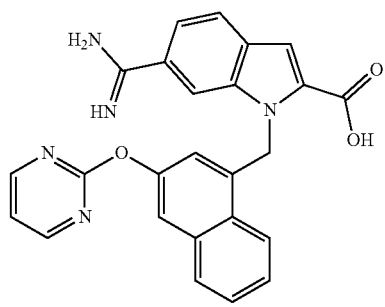
I-694
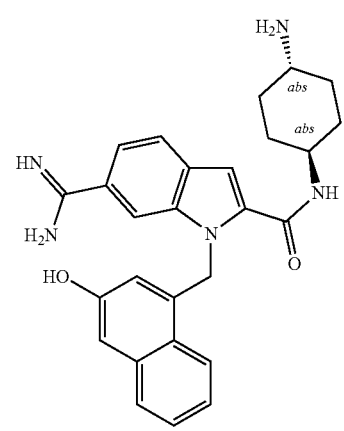
I-695
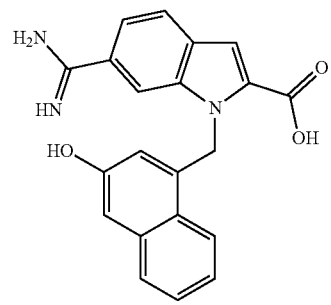
I-696
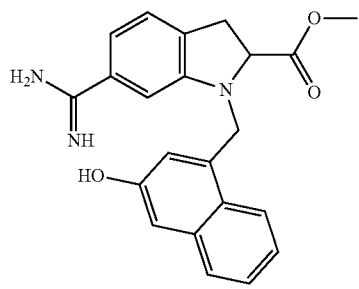
I-697
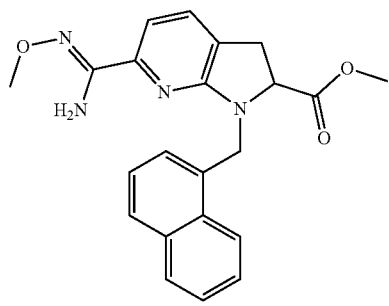
I-698
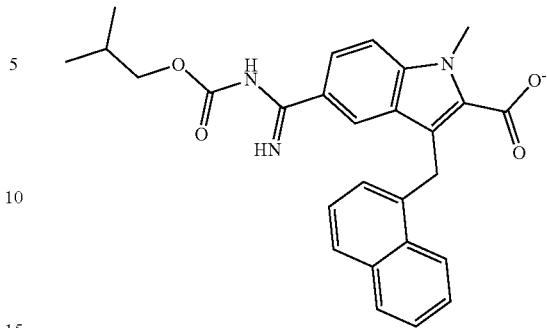
I-699
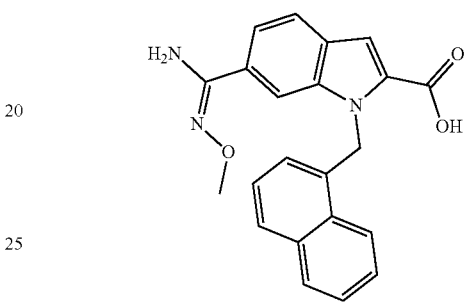
I-700
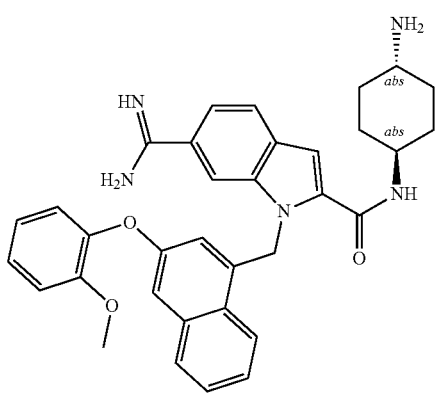
I-701
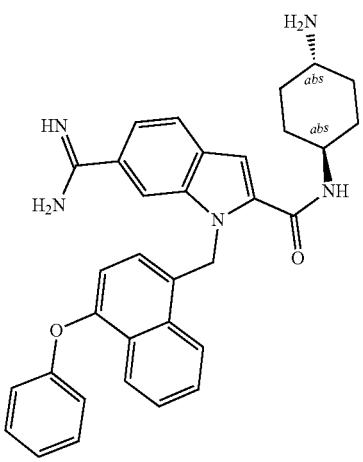

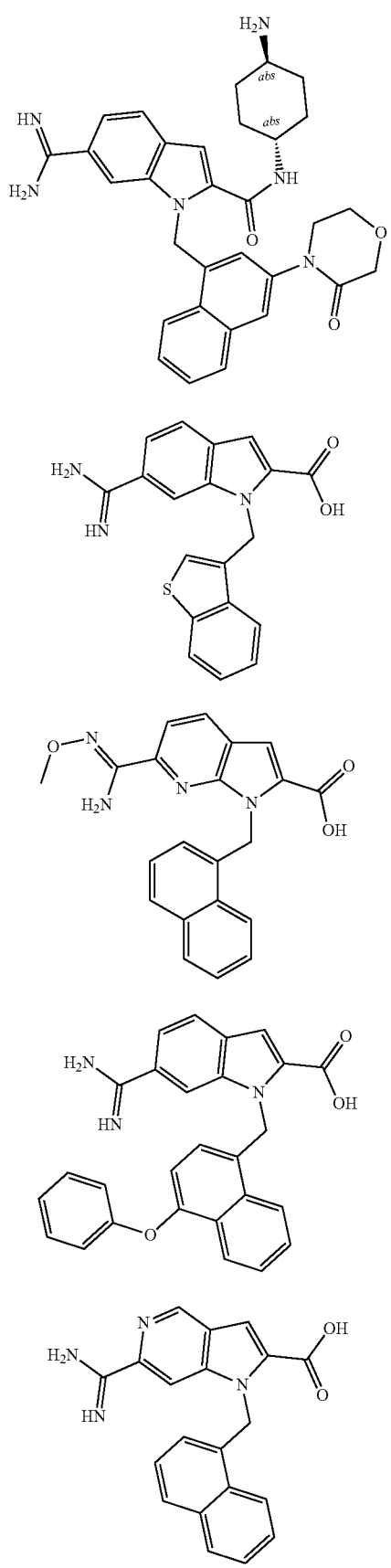
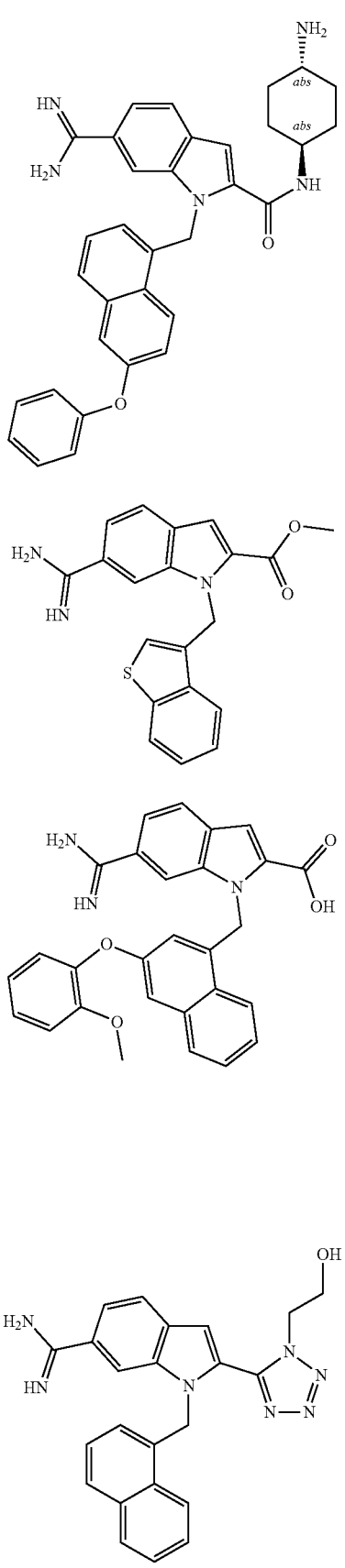

1209 -continued
I-711
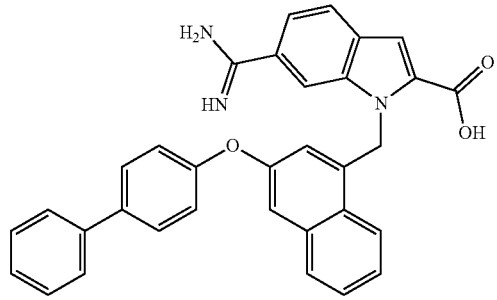
I-712
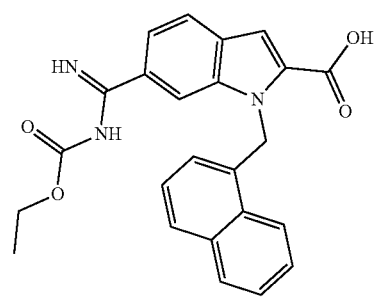
I-713
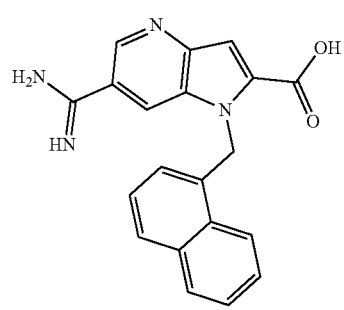
I-714
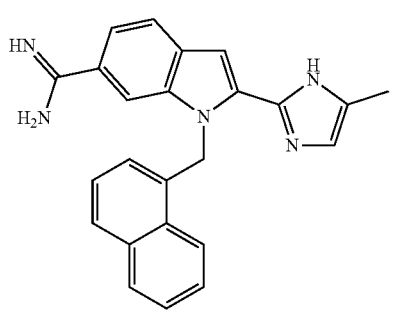
I-715
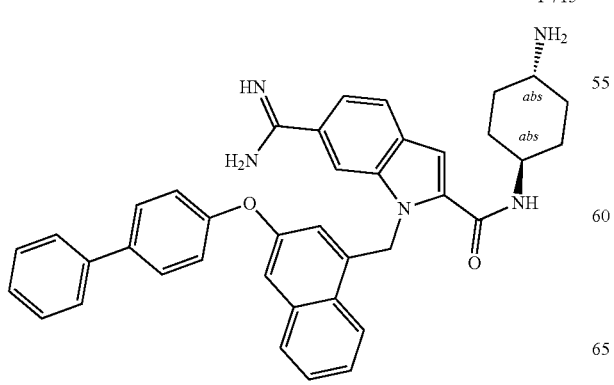
1210 -continued
I-716
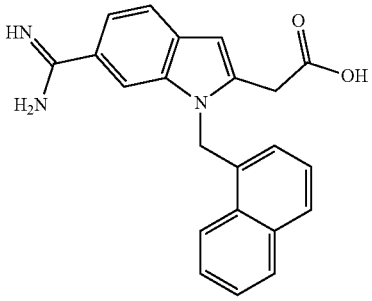
I-717
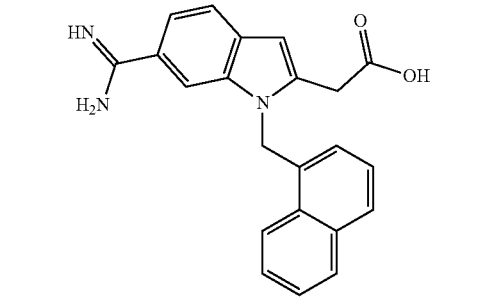
I-718
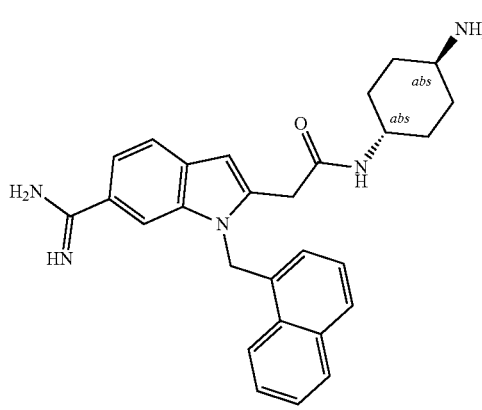
I-719
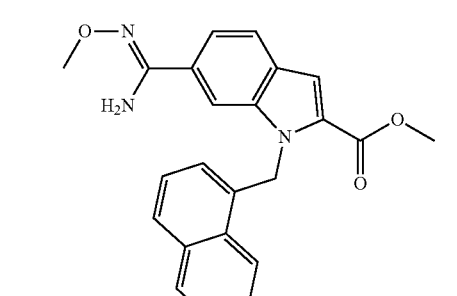

I-720
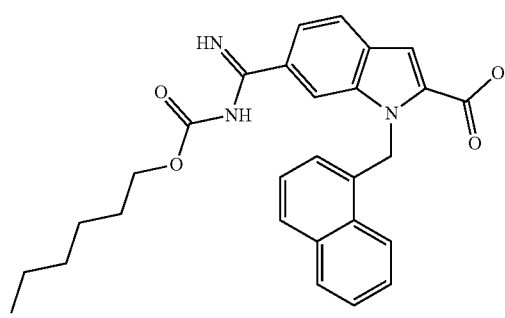
I-721
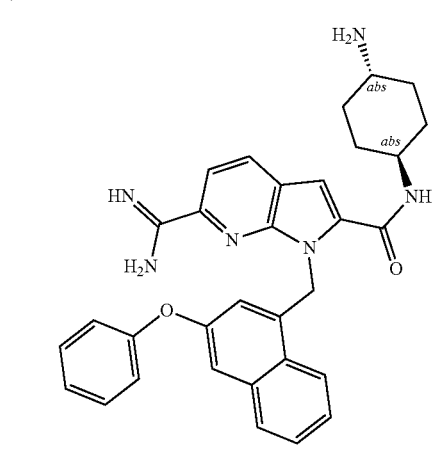
I-722
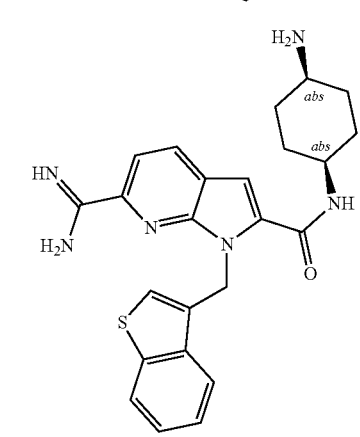
I-723
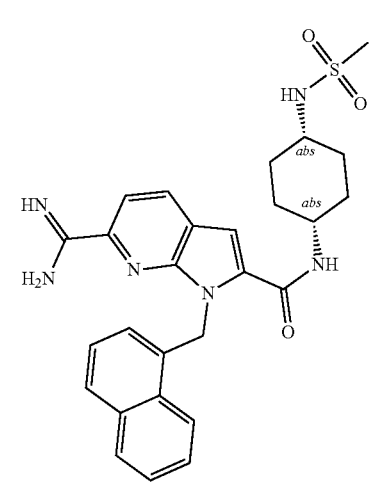
I-724
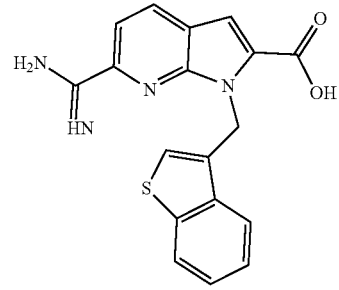
I-725
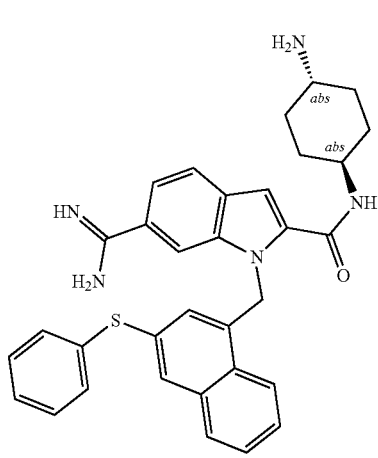
I-726
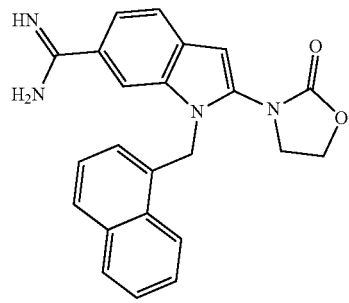
I-727
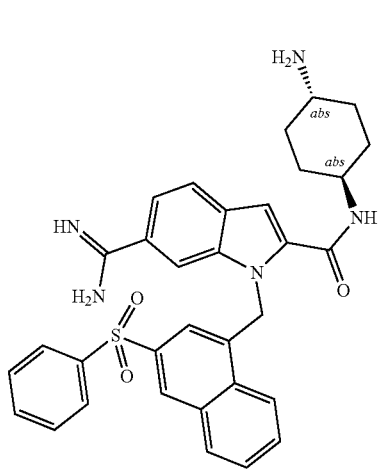

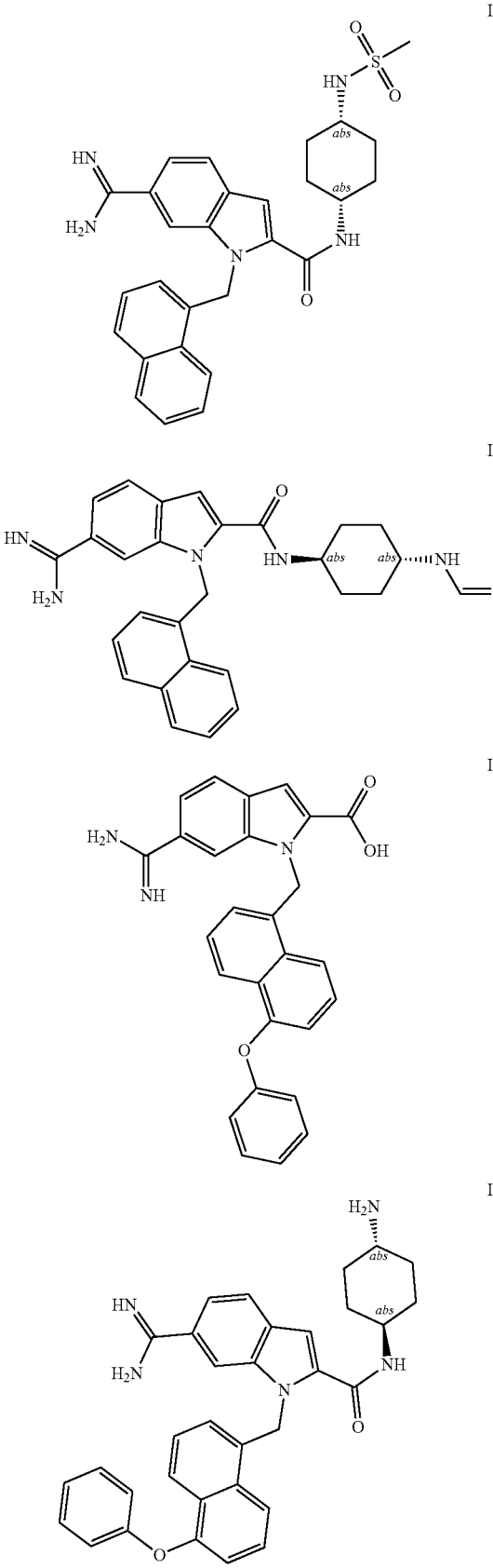
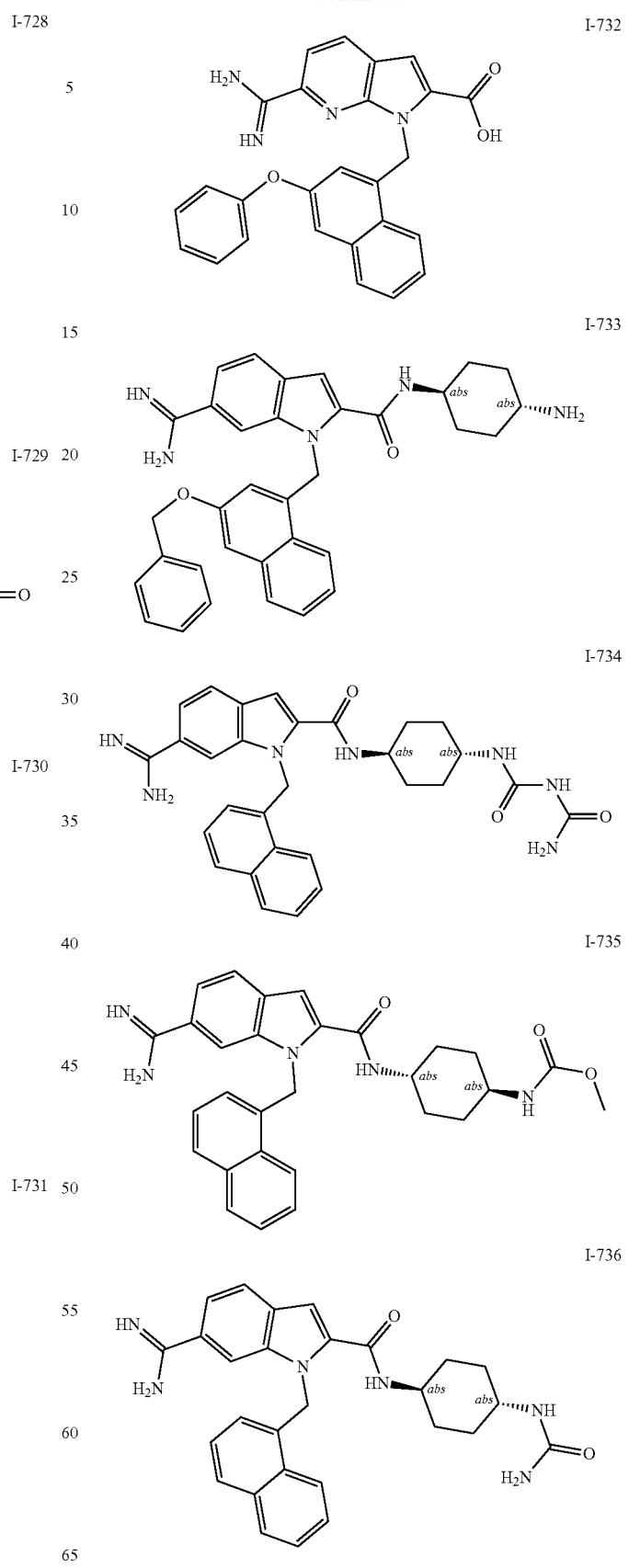

1215
-continued
I-737
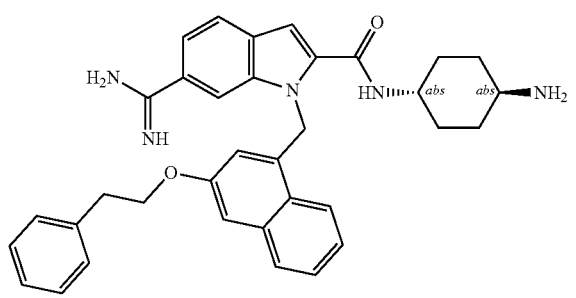
I-738
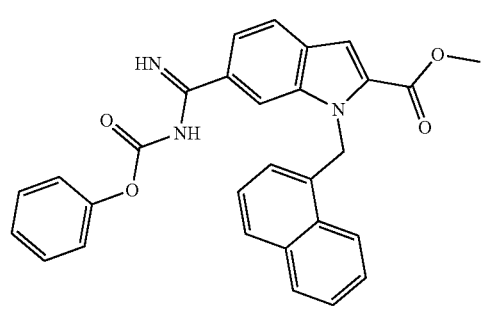
I-739
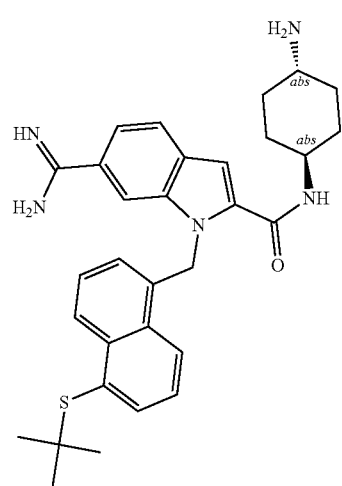
I-740
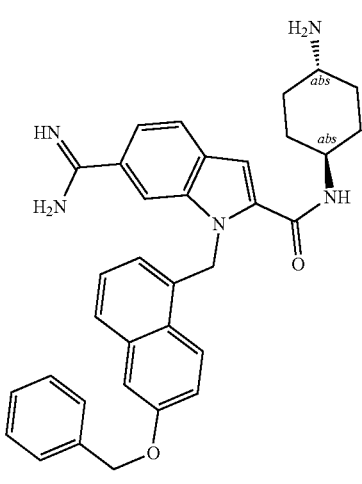
1216
-continued
I-741
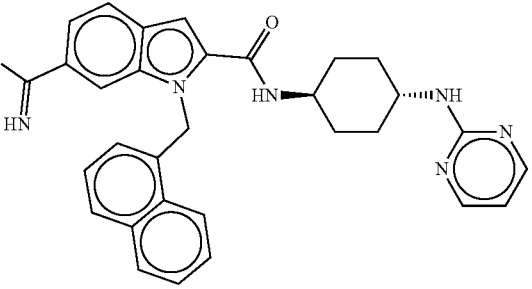
I-742
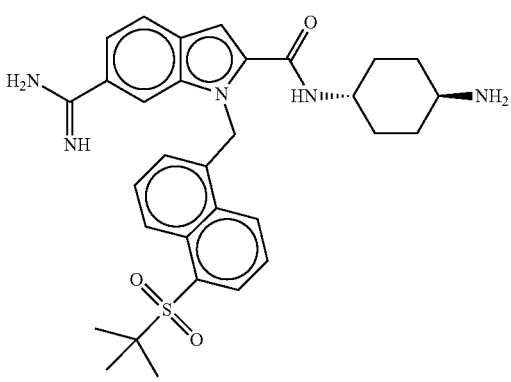
I-743
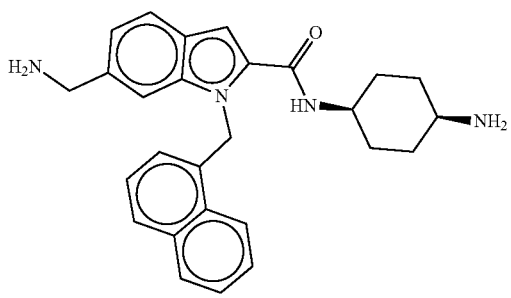
I-744
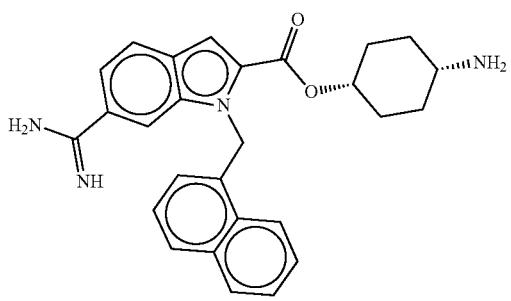
I-745
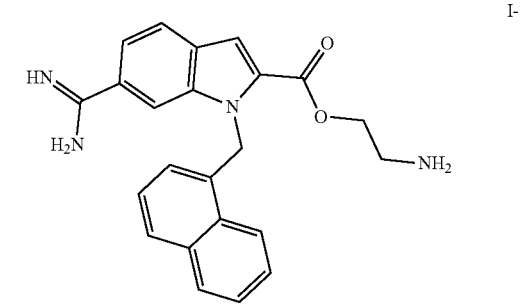

I-746
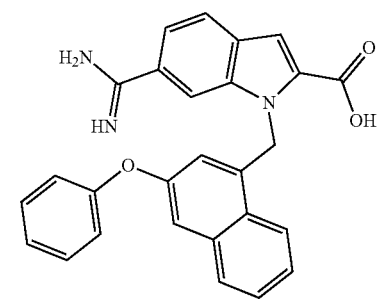
I-747
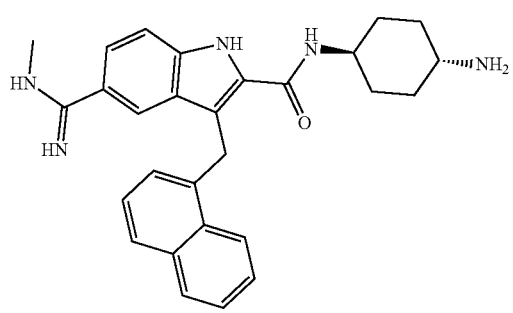
I-748
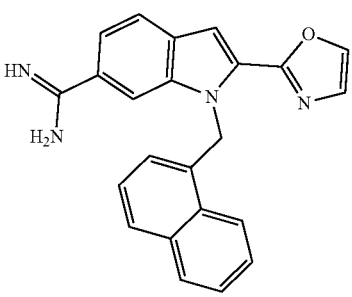
I-749
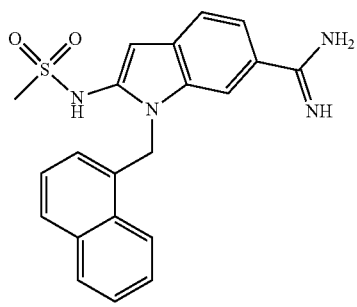
I-750
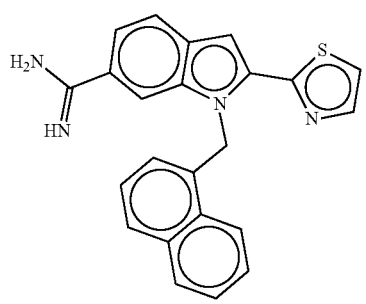
I-751
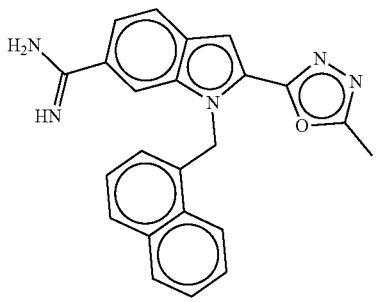
I-752
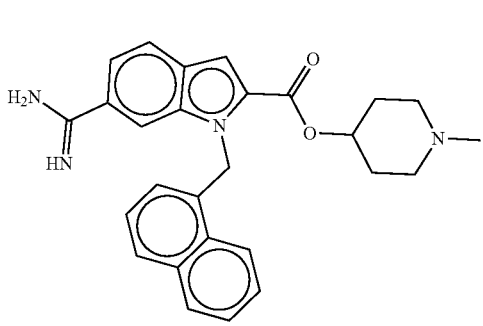
I-753
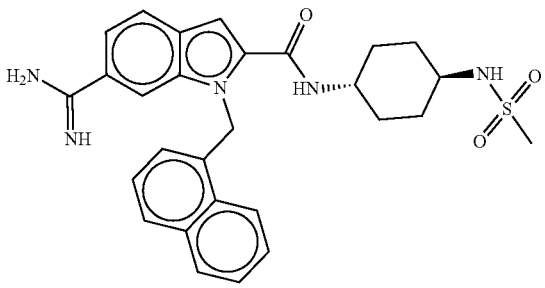
I-754
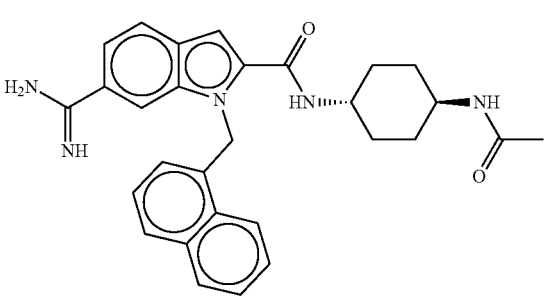
I-755
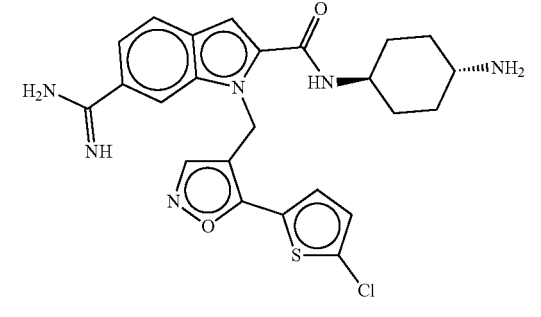

I-756
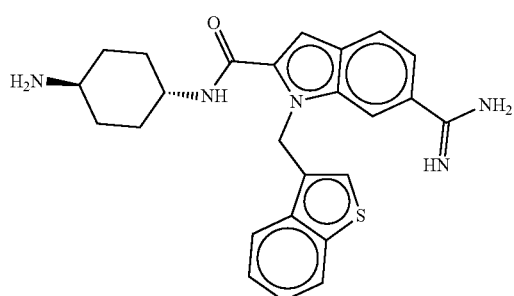
I-757
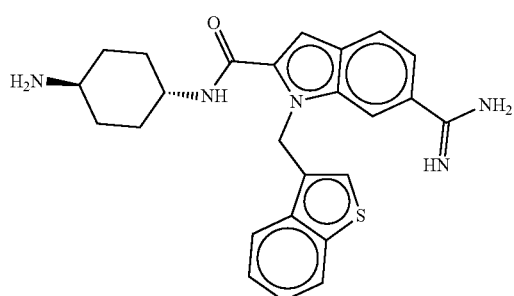
I-758
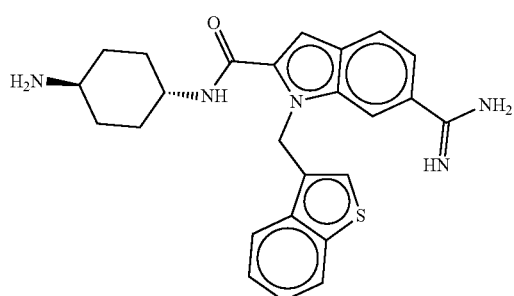
I-759
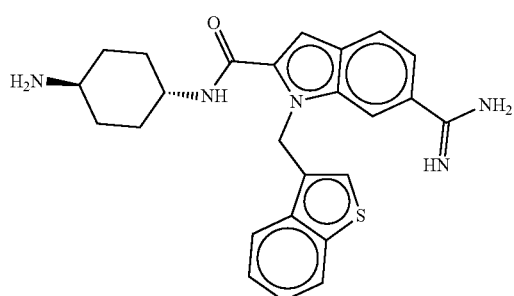
I-760
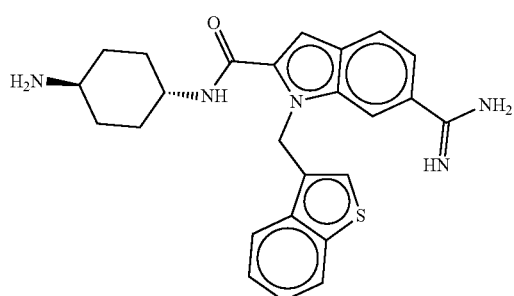
I-761
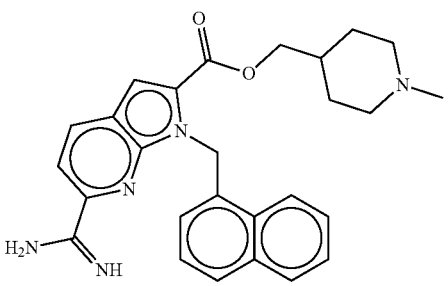
I-763
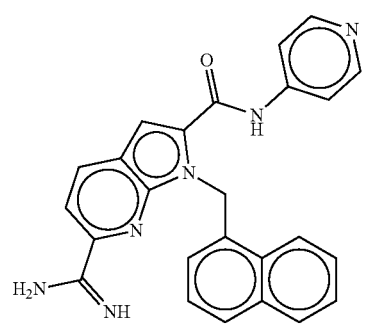
I-764
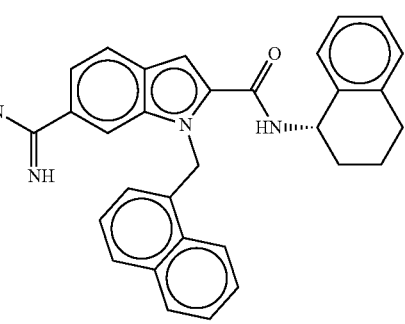
I-765
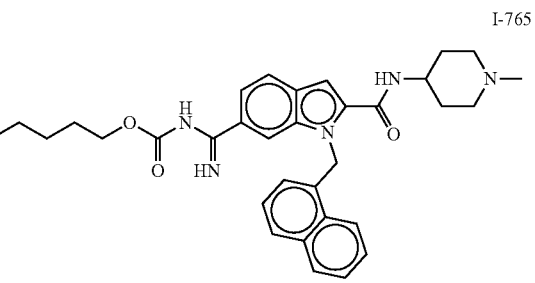
I-766
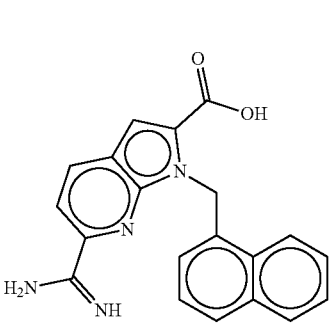

1221
I-767
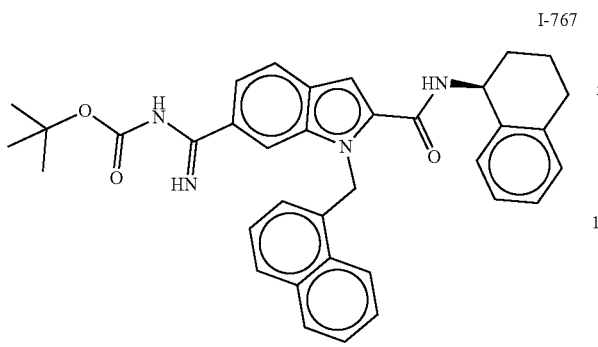
I-768
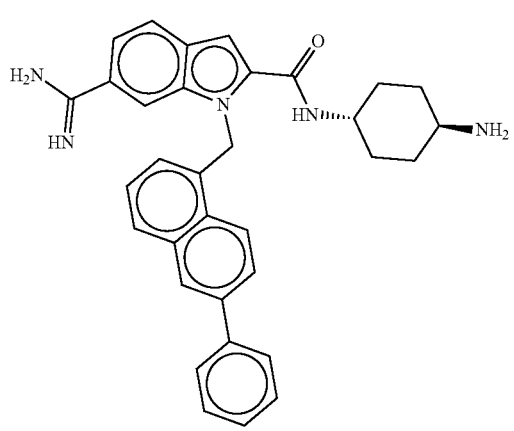
I-769
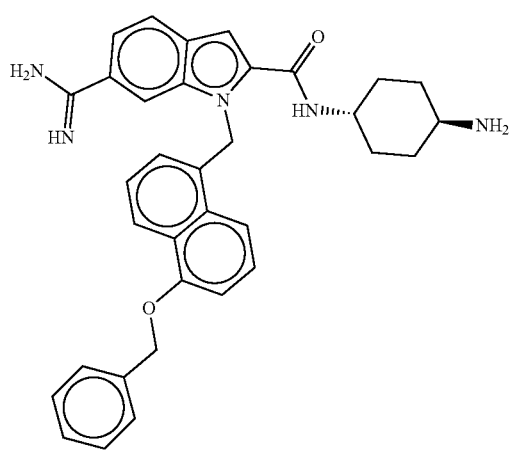
1222
-continued
I-770
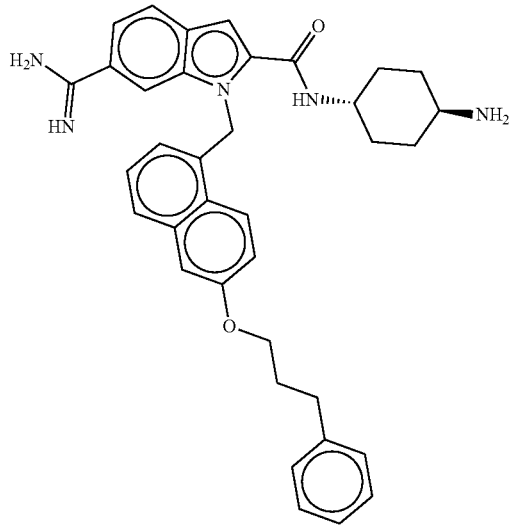
I-771
I-772
I-773
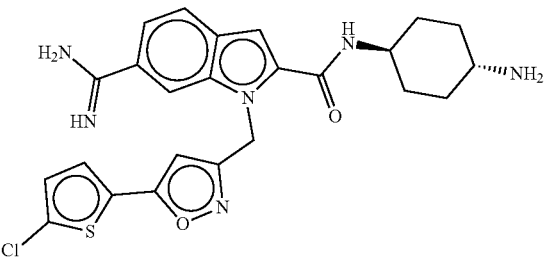

1223
-continued
I-774
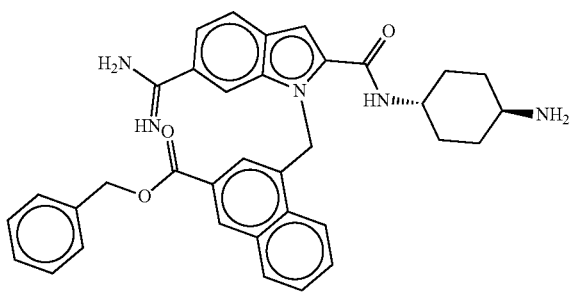
I-775
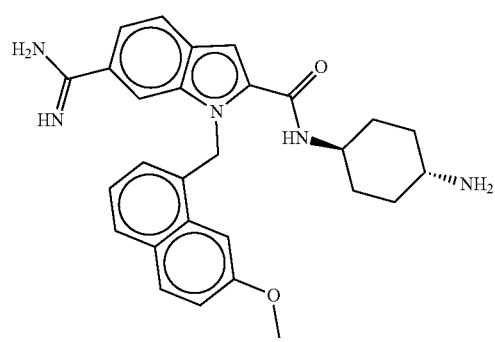
I-776
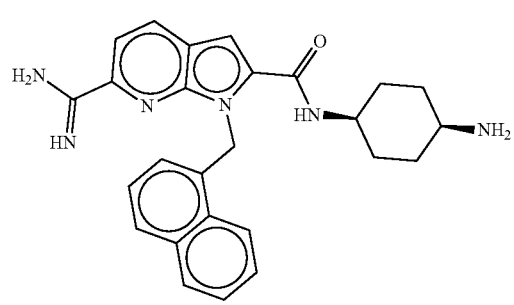
I-777
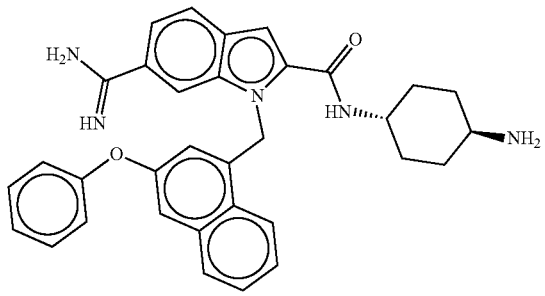
1224
-continued
I-778
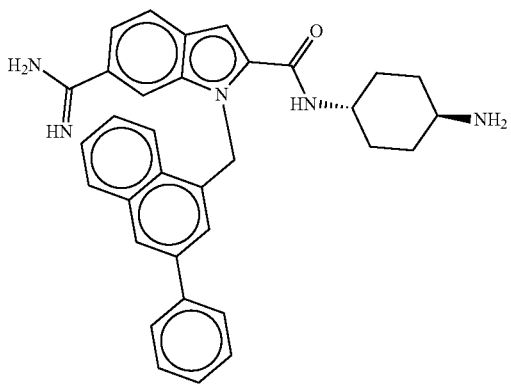
I-779
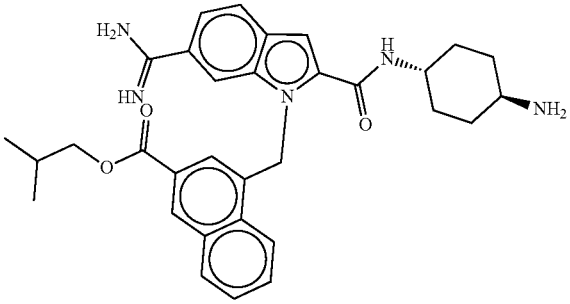
I-780
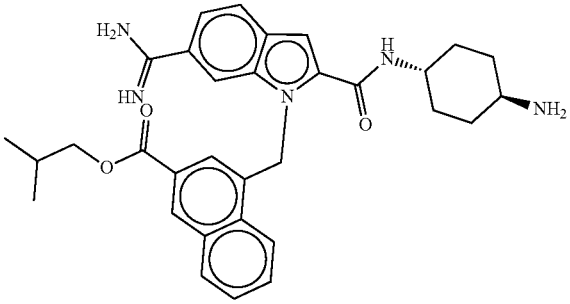
I-781
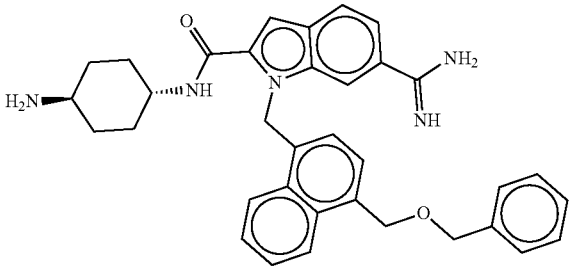

1225
-continued
I-782
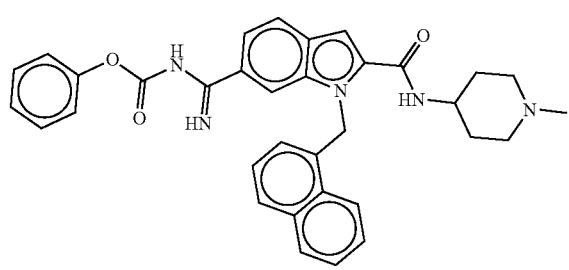
I-783
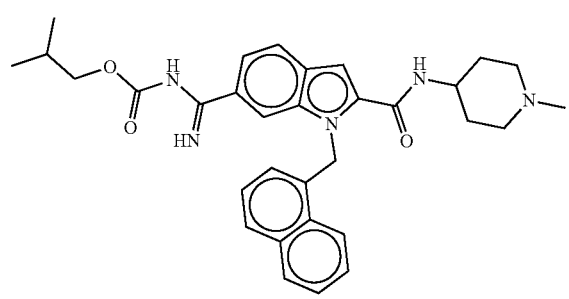
I-784
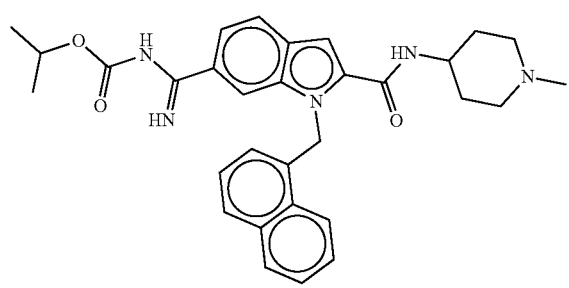
I-785
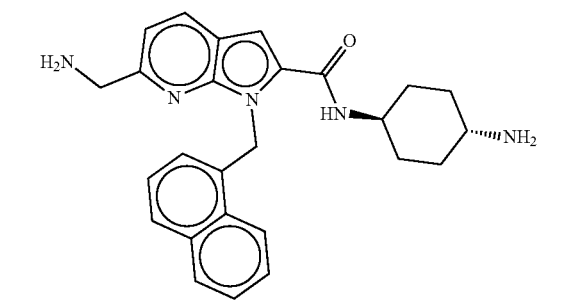
I-786
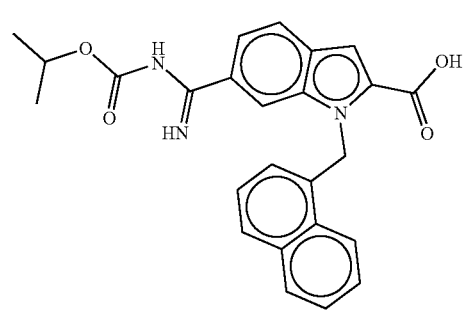
1226
-continued
I-787
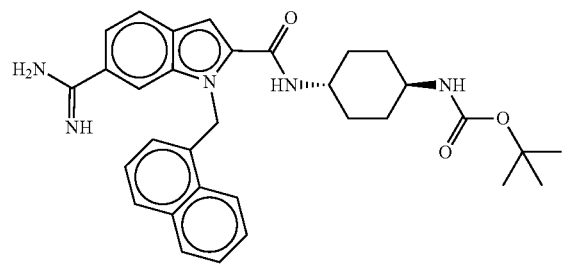
I-788
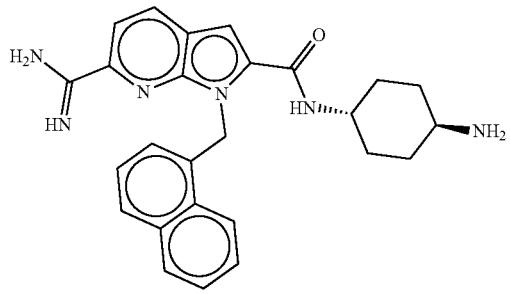
I-789
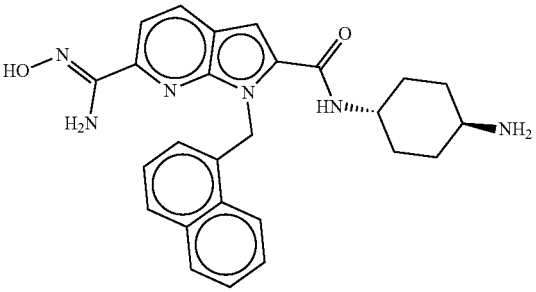
I-790
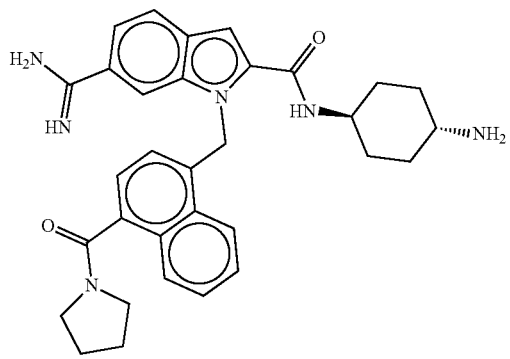
I-791
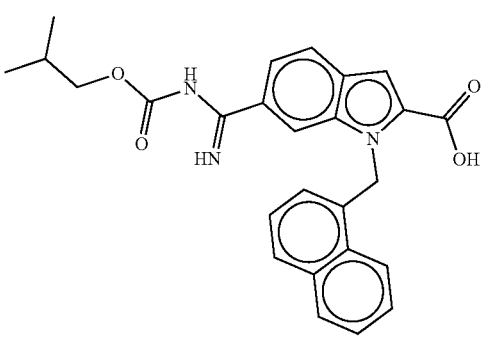

I-792
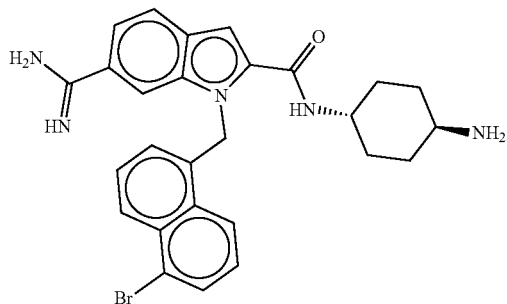
I-793
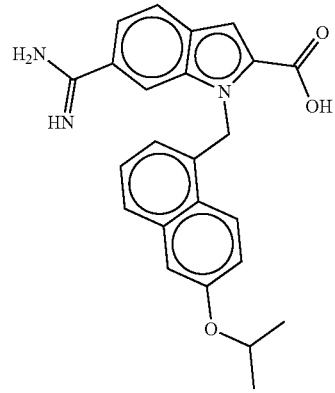
I-794
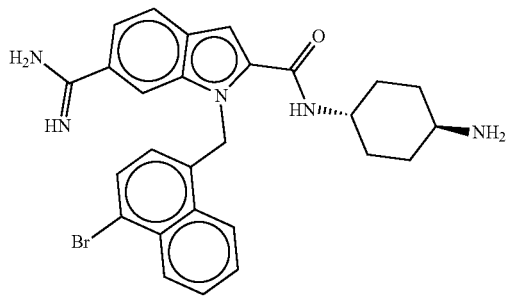
I-795
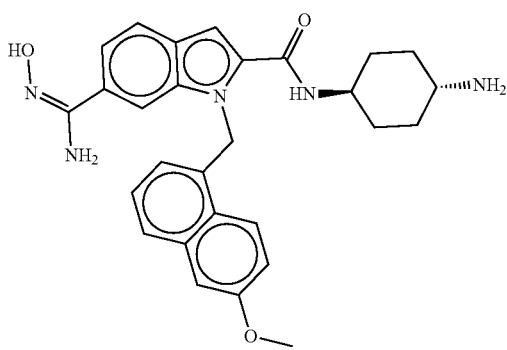
I-796
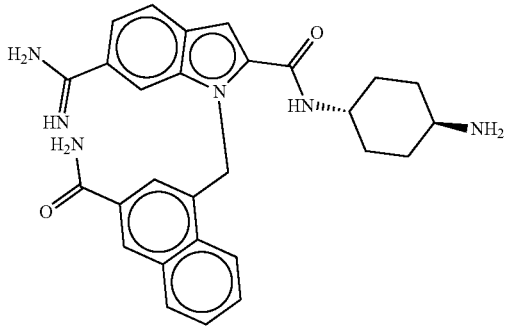
I-797
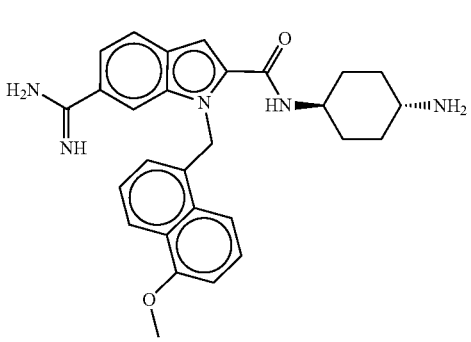
I-798
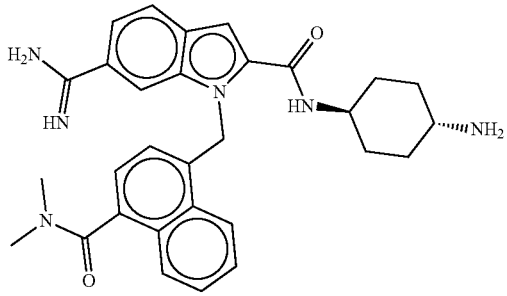
I-799
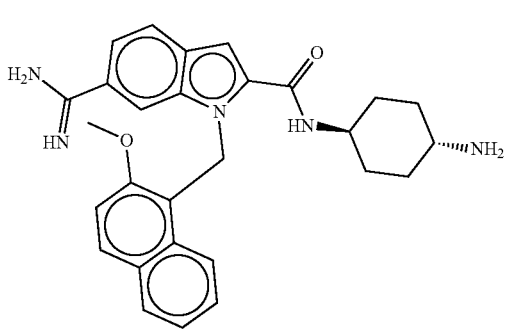

I-800
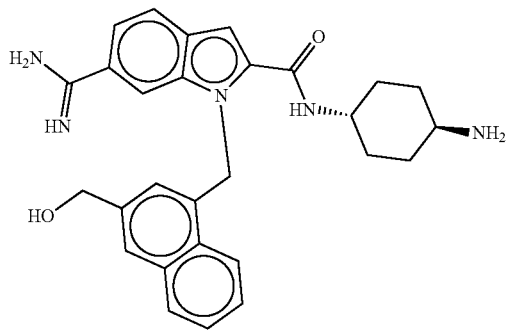
I-801
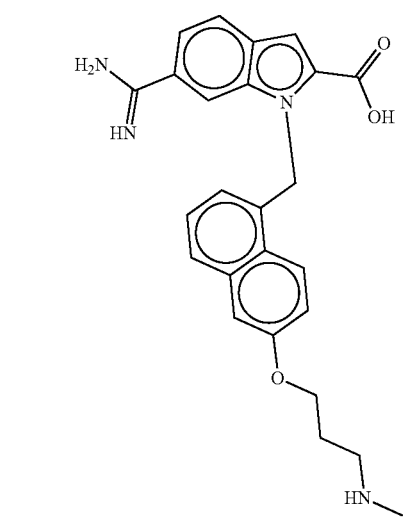
I-802
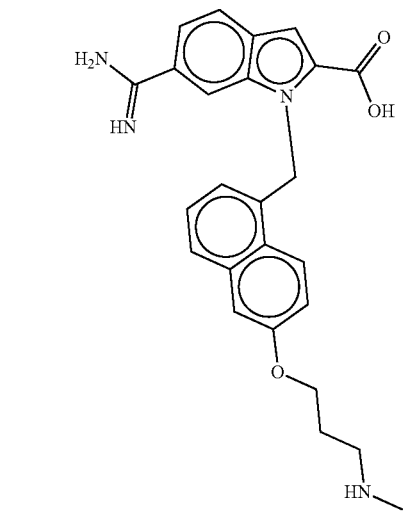
I-803
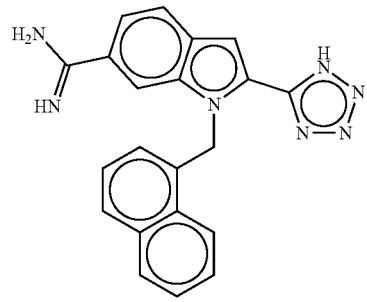
I-804
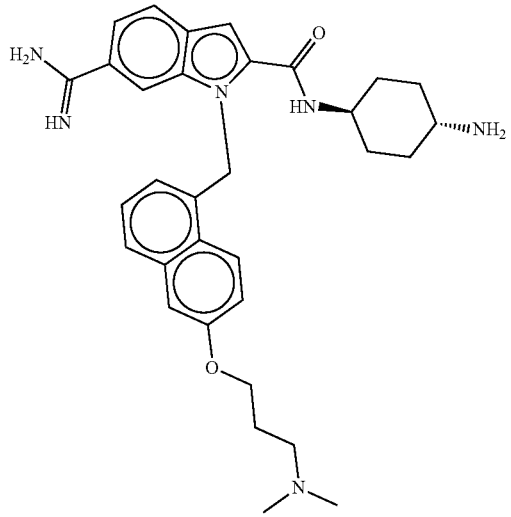
I-805
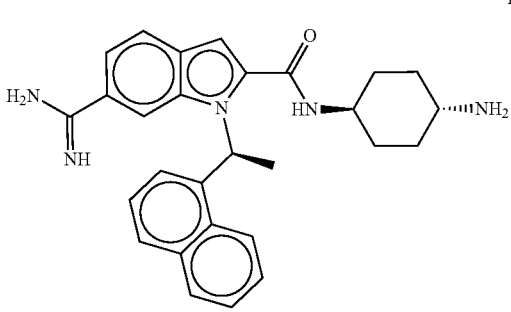
I-806
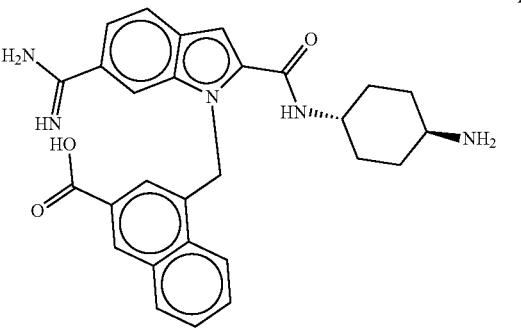
I-807
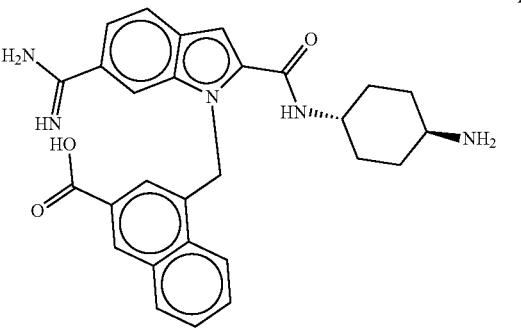

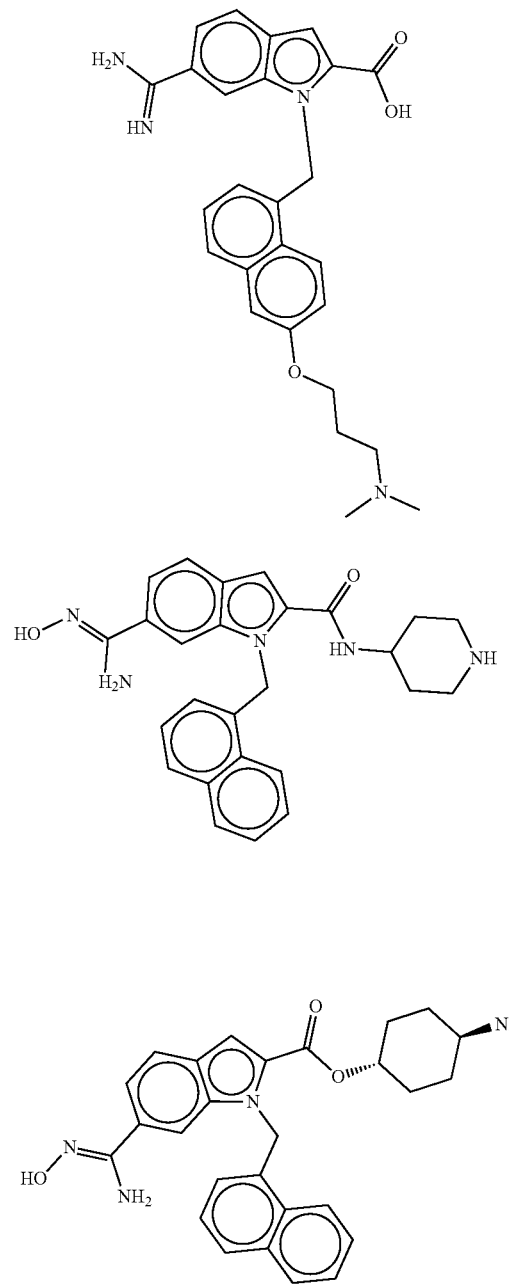
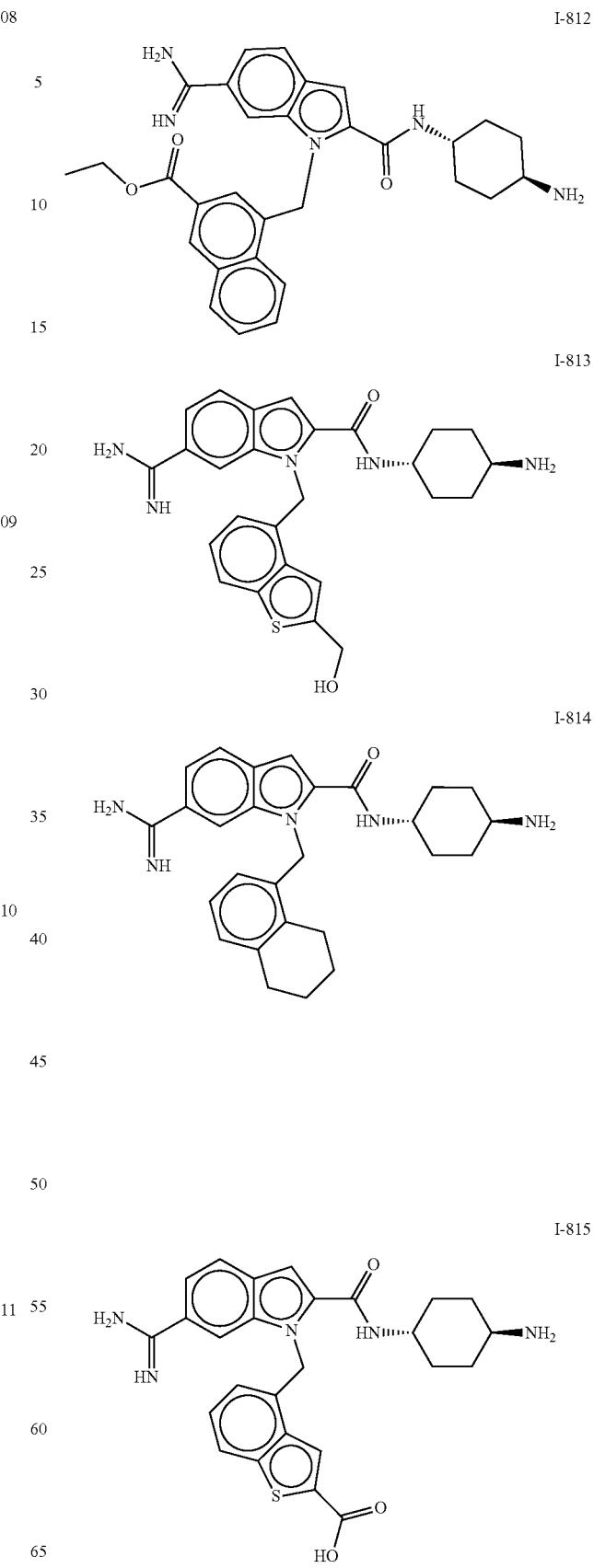

I-816
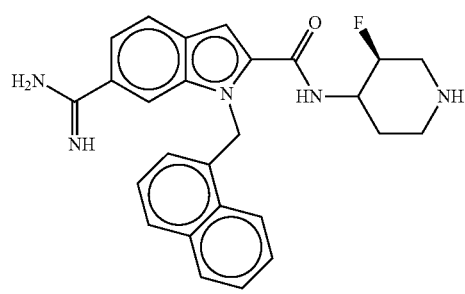
I-821
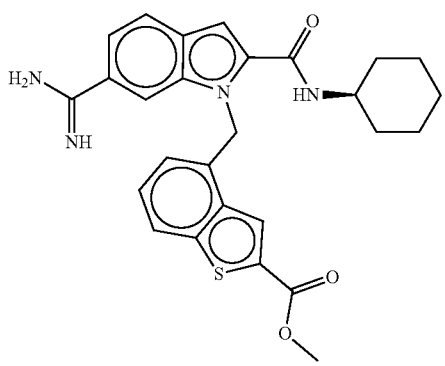
I-817
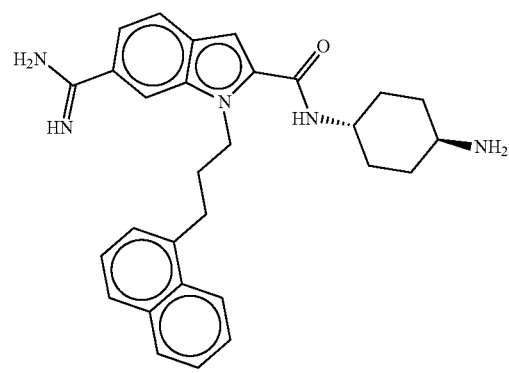
I-822
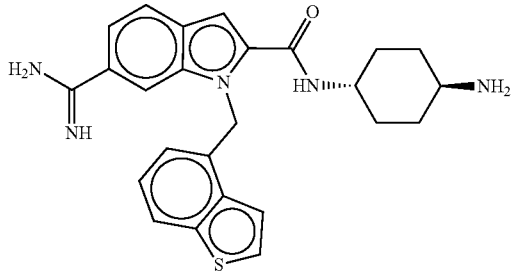
I-818
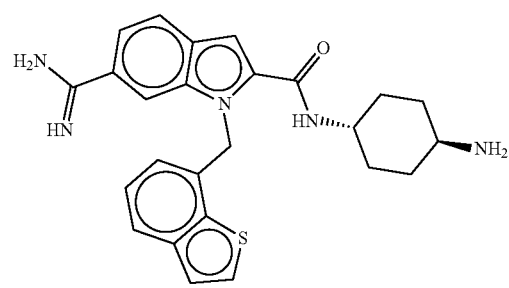
I-823
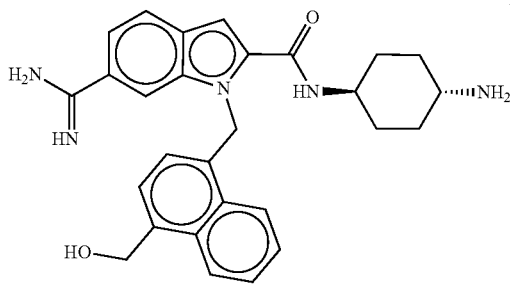
I-819
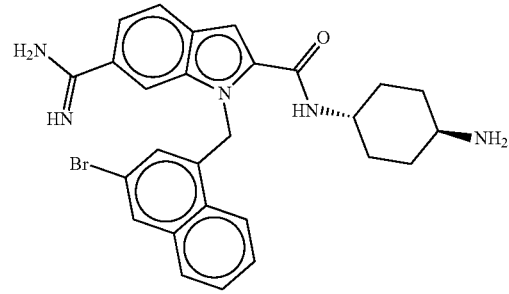
I-824
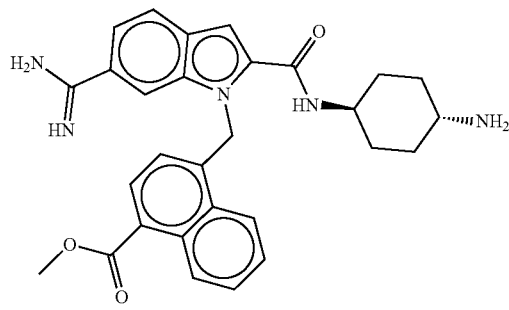
I-820
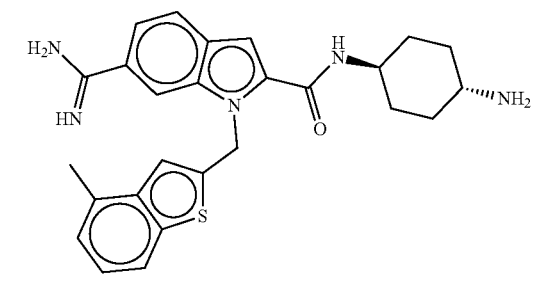
I-825

I-826
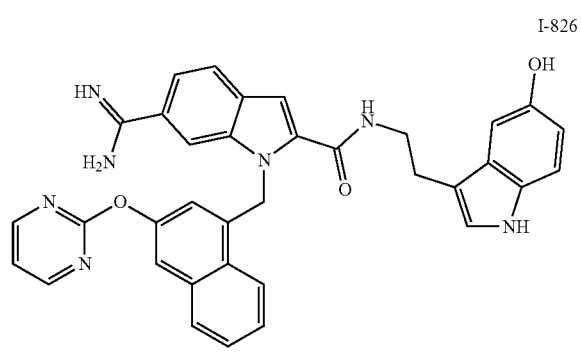
I-827
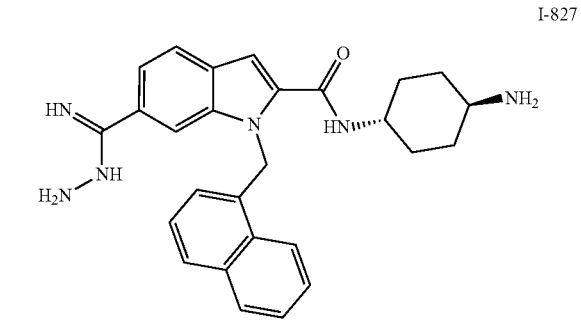
I-828
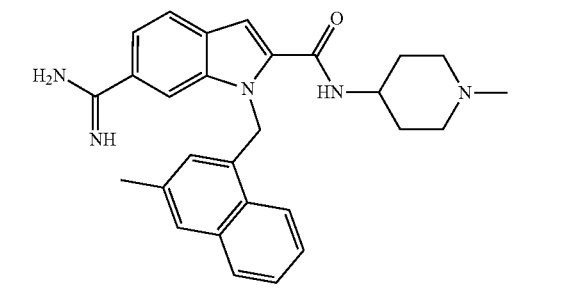
I-829
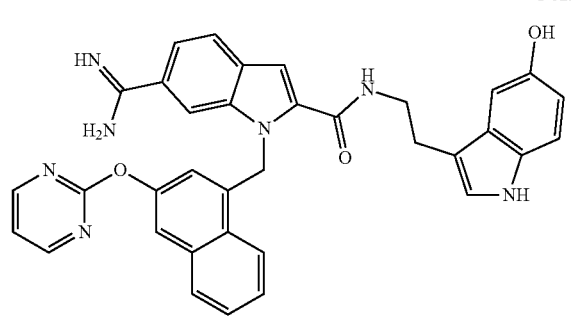
I-830
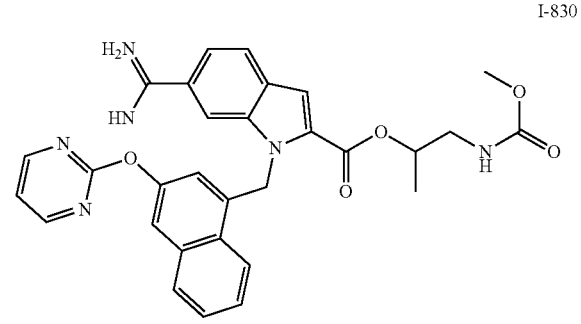
I-831
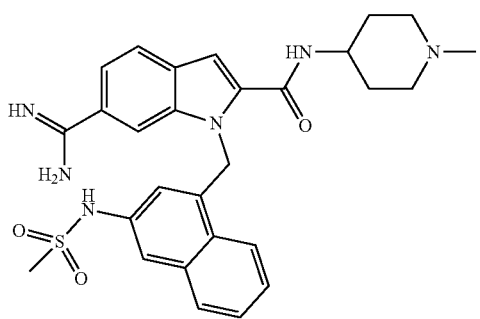
I-832
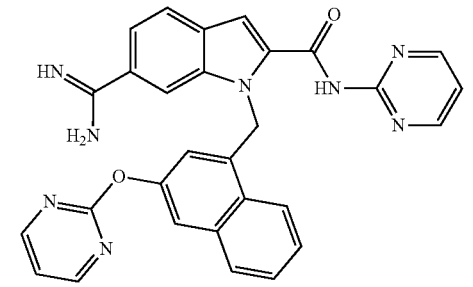
I-833
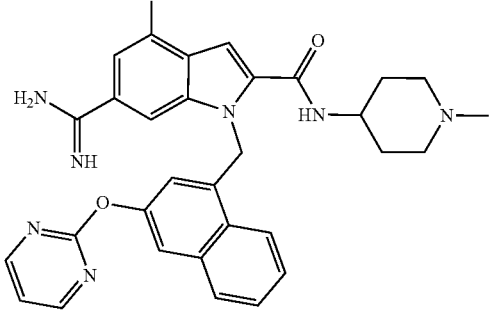
I-834
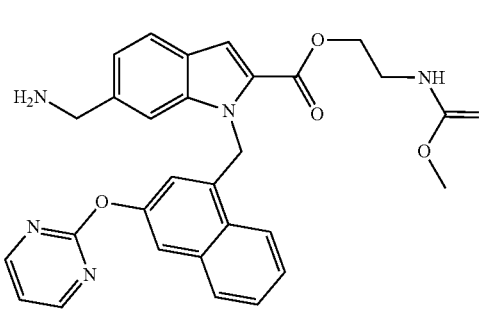
I-835
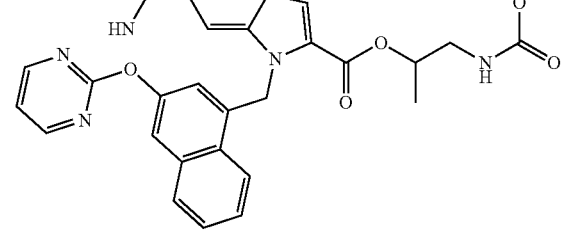

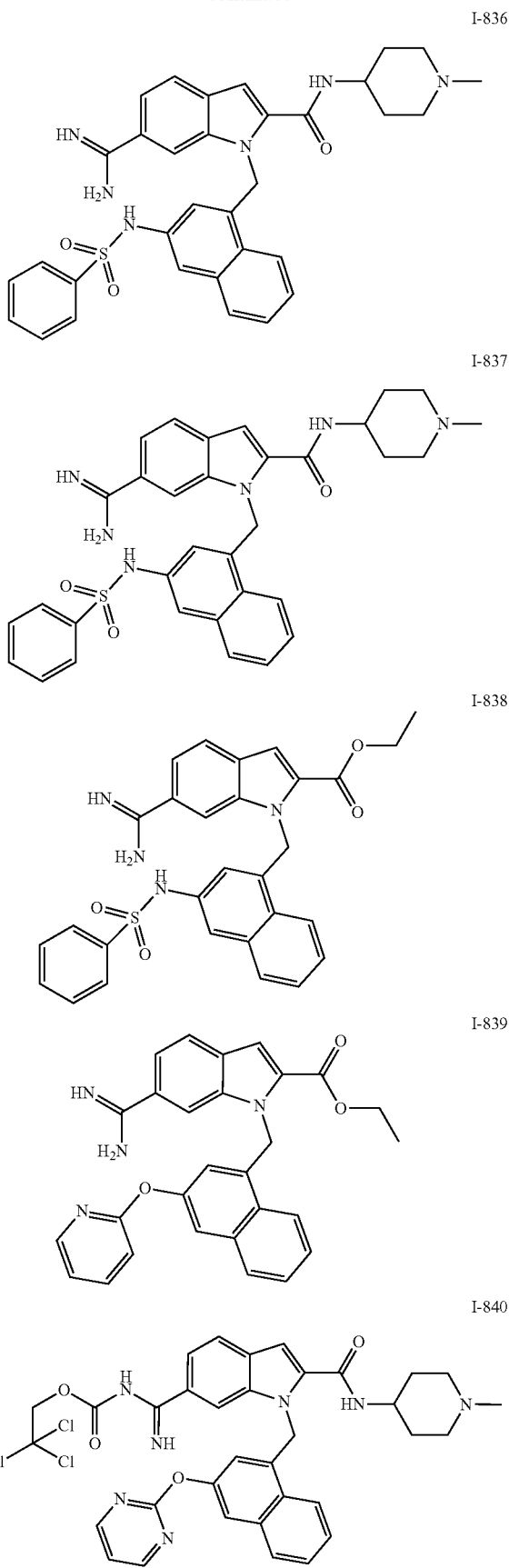

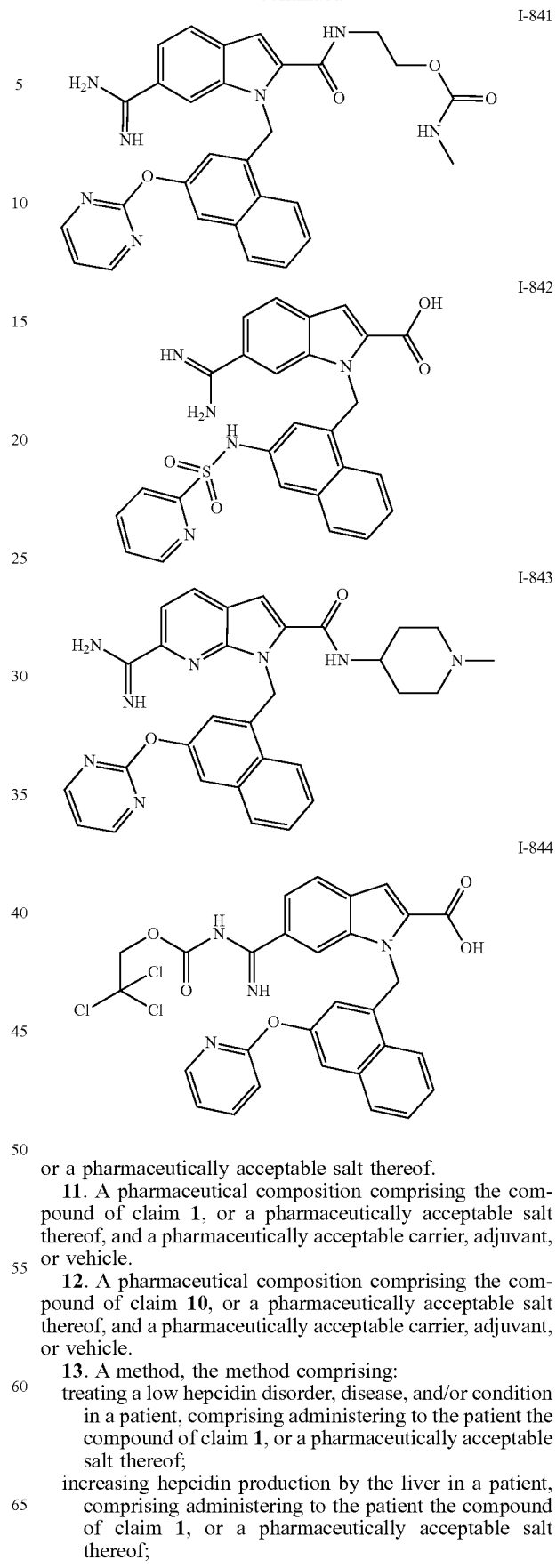

or a pharmaceutically acceptable salt thereof.

11. A pharmaceutical composition comprising the compound of claim 1, or a pharmaceutically acceptable salt thereof, and a pharmaceutically acceptable carrier, adjuvant, or vehicle.

12. A pharmaceutical composition comprising the compound of claim 10, or a pharmaceutically acceptable salt thereof, and a pharmaceutically acceptable carrier, adjuvant, or vehicle.

13. A method, the method comprising:
   treating a low hepcidin disorder, disease, and/or condition in a patient, comprising administering to the patient the compound of claim 1, or a pharmaceutically acceptable salt thereof;
   increasing hepcidin production by the liver in a patient, comprising administering to the patient the compound of claim 1, or a pharmaceutically acceptable salt thereof;

treating an iron overload disorder, disease, and/or condition in a patient, comprising administering to the patient the compound of claim 1, or a pharmaceutically acceptable salt thereof;

treating an iron loading anemia in a patient, comprising administering to the patient the compound of claim 1, or a pharmaceutically acceptable salt thereof;

treating a hematological disease, disorder, and/or condition in a patient, comprising administering to the patient the compound of claim 1, or a pharmaceutically acceptable salt thereof;

treating a liver disease in a patient, comprising administering to the patient the compound of claim 1, or a pharmaceutically acceptable salt thereof;

treating a metabolic disease in a patient, comprising administering to the patient the compound of claim 1, or a pharmaceutically acceptable salt thereof;

treating a neurodegenerative disorder in a patient, comprising administering to the patient the compound of claim 1, or a pharmaceutically acceptable salt thereof;

treating an infectious disease in a patient, comprising administering to the patient the compound of claim 1, or a pharmaceutically acceptable salt thereof; or inhibiting matriptase 2, or a mutant thereof, in a biological sample, comprising contacting the sample with the compound of claim 1, or a pharmaceutically acceptable salt thereof, wherein the patient of any of the foregoing is a patient in need thereof.

14. A method, the method comprising:

treating a low hepcidin disorder, disease, and/or condition in a patient, comprising administering to the patient the pharmaceutical composition of claim 11;

increasing hepcidin production by the liver in a patient, comprising administering to the patient the pharmaceutical composition of claim 11;

treating an iron overload disorder, disease, and/or condition in a patient, comprising administering to the patient the pharmaceutical composition of claim 11, wherein the iron overload disorder, disease, and/or condition is optionally selected from the group consisting of hemochromatosis Type 1, hemochromatosis Type 2a, hemochromatosis Type 2b, hemochromatosis Type 3, Hfe hemochromatosis, juvenile hemochromatosis, hepcidin deficiency, transfusional iron overload, African iron overload, and iron overload cardiomyopathy;

treating an iron loading anemia in a patient, comprising administering to the patient the pharmaceutical composition of claim 11, wherein the iron loading anemia is optionally selected from the group consisting of beta-thalassemia, HbE/thalassemia, thalassemia major, thalassemia intermedia, thalassemia minor, non-transfusion dependent thalassemia, transfusion-dependent thalassemia, alpha thalassemia, congenital dyserythropoietic anemia Type I, congenital dyserythropoietic anemia Type II, pyruvate kinase deficiency, myelodysplasia, myelodysplastic syndrome, and RARS SF3B1 associated MDS;

treating a hematological disease, disorder, and/or condition in a patient, comprising administering to the patient the pharmaceutical composition of claim 11, wherein the hematological disease, disorder, and/or condition is optionally selected from the group consisting of sickle cell disease, sickle cell anemia, polycythemia vera, sideroblastic anemia, and bone marrow transplantation;

treating a liver disease in a patient, comprising administering to the patient the pharmaceutical composition of claim 11, wherein the liver disease is optionally selected from the group consisting of Hepatitis B, Hepatitis C, alcoholic liver disease, cirrhosis of the liver, epahtocellular carcinoma, and non-alcoholic steatohepatitis (NASH);

treating a metabolic disease in a patient, comprising administering to the patient the pharmaceutical composition of claim 11, wherein the metabolic disease is optionally selected from the group consisting of metabolic syndrome, insulin resistance, Type II diabetes, porphyria, porphyria cutanea tarda, Wilson's Disease, and acute iron overdose;

treating a neurodegenerative disorder in a patient, comprising administering to the patient the pharmaceutical composition of claim 11;

treating an infectious disease in a patient, comprising administering to the patient the pharmaceutical composition of claim 11, wherein the infectious disease is optionally a siderophilic infection; or inhibiting matriptase 2, or a mutant thereof, in a biological sample, comprising contacting the sample with the pharmaceutical composition of claim 11, wherein the patient of any of the foregoing is a patient in need thereof.

15. A method, the method comprising:

treating a low hepcidin disorder, disease, and/or condition in a patient, comprising administering to the patient the pharmaceutical composition of claim 12;

increasing hepcidin production by the liver in a patient, comprising administering to the patient the pharmaceutical composition of claim 12;

treating an iron overload disorder, disease, and/or condition in a patient, comprising administering to the patient the pharmaceutical composition of claim 12;

treating an iron loading anemia in a patient, comprising administering to the patient the pharmaceutical composition of claim 12;

treating a hematological disease, disorder, and/or condition in a patient, comprising administering to the patient the pharmaceutical composition of claim 12;

treating a liver disease in a patient, comprising administering to the patient the pharmaceutical composition of claim 12;

treating a metabolic disease in a patient, comprising administering to the patient the pharmaceutical composition of claim 12;

treating a neurodegenerative disorder in a patient, comprising administering to the patient the pharmaceutical composition of claim 12;

treating an infectious disease in a patient, comprising administering to the patient the pharmaceutical composition of claim 12; or inhibiting matriptase 2, or a mutant thereof, in a biological sample, comprising contacting the sample with the pharmaceutical composition of claim 12, wherein the patient of any of the foregoing is a patient in need thereof.

16. The compound of claim 1, or a pharmaceutically acceptable salt thereof, wherein $R^2$ is an optionally substituted ring selected from a 4-7 membered monocyclic carbocyclic ring, a 4-7 membered monocyclic heterocyclic ring having 1-4 heteroatoms independently selected from nitrogen, oxygen, and sulfur, a 7-10 membered bicyclic heterocyclic ring having 1-4 heteroatoms independently selected from nitrogen, oxygen, and sulfur, phenyl, and a 5-6 membered monocyclic heteroaromatic ring having 1-4 heteroatoms independently selected from nitrogen, oxygen, and sulfur.

17. The compound of claim 1, or a pharmaceutically acceptable salt thereof, wherein the compound is of Formula IV-a:

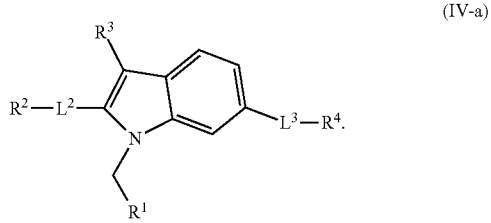

(IV-a)

18. The compound of claim 1, or a pharmaceutically acceptable salt thereof, wherein the compound is of Formula IV-c:

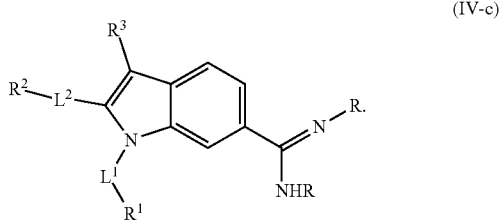

(IV-c)

19. The compound of claim 1, or a pharmaceutically acceptable salt thereof, wherein the compound is of Formula III-e:

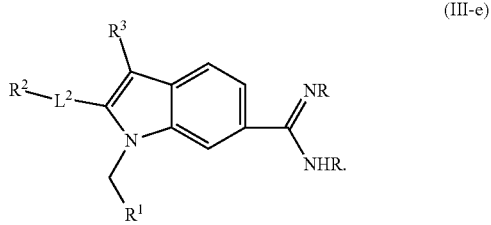

(III-e)

20. The compound of claim 1, or a pharmaceutically acceptable salt thereof, wherein -$L^3$ is an optionally substituted $C_1$ hydrocarbon chain, and $R^4$ is —NHR.

21. The method of claim 13, wherein the iron overload disorder, disease, and/or condition is selected from the group consisting of hemochromatosis Type 1, hemochromatosis Type 2a, hemochromatosis Type 2b, hemochromatosis Type 3, Hfe hemochromatosis, juvenile hemochromatosis, hepcidin deficiency, transfusional iron overload, African iron overload, and iron overload cardiomyopathy.

22. The method of claim 13, wherein the iron loading anemia is selected from the group consisting of beta thalassemia, HbE/thalassemia, thalassemia major, thalassemia intermedia, thalassemia minor, non-transfusion dependent thalassemia, transfusion-dependent thalassemia, alpha thalassemia, congenital dyserythropoietic anemia Type I, congenital dyserythropoietic anemia Type II, pyruvate kinase deficiency, myelodysplasia, myelodysplastic syndrome, and RARS SF3B1 associated MDS.

23. The method of claim 13, wherein the hematological disease, disorder, and/or condition is selected from the group consisting of sickle cell disease, sickle cell anemia, polycythemia vera, sideroblastic anemia, and bone marrow transplantation.

24. The method of claim 13, wherein the liver disease is selected from the group consisting of Hepatitis B, Hepatitis C, alcoholic liver disease, cirrhosis of the liver, hepatocellular carcinoma, and non-alcoholic steatohepatitis (NASH).

25. The method of claim 13, wherein the metabolic disease is selected from the group consisting of metabolic syndrome, insulin resistance, Type II diabetes, porphyria, porphyria cutanea tarda, Wilson's Disease, and acute iron overdose.

26. The method of claim 13, wherein the infectious disease is a siderophilic infection.

27. The method of claim 15, wherein the iron overload disorder, disease, and/or condition is selected from the group consisting of hemochromatosis Type 1, hemochromatosis Type 2a, hemochromatosis Type 2b, hemochromatosis Type 3, Hfe hemochromatosis, juvenile hemochromatosis, hepcidin deficiency, transfusional iron overload, African iron overload, and iron overload cardiomyopathy.

28. The method of claim 15, wherein the iron loading anemia is selected from the group consisting of beta thalassemia, HbE/thalassemia, thalassemia major, thalassemia intermedia, thalassemia minor, non-transfusion dependent thalassemia, transfusion-dependent thalassemia, alpha thalassemia, congenital dyserythropoietic anemia Type I, congenital dyserythropoietic anemia Type II, pyruvate kinase deficiency, myelodysplasia, myelodysplastic syndrome, and RARS SF3B1 associated MDS.

29. The method of claim 15, wherein the hematological disease, disorder, and/or condition is selected from the group consisting of sickle cell disease, sickle cell anemia, polycythemia vera, sideroblastic anemia, and bone marrow transplantation.

30. The method of claim 15, wherein the liver disease is selected from the group consisting of Hepatitis B, Hepatitis C, alcoholic liver disease, cirrhosis of the liver, hepatocellular carcinoma, and non-alcoholic steatohepatitis (NASH).

31. The method of claim 15, wherein the metabolic disease is selected from the group consisting of metabolic syndrome, insulin resistance, Type II diabetes, porphyria, porphyria cutanea tarda, Wilson's Disease, and acute iron overdose.

32. The method of claim 15, wherein the infectious disease is a siderophilic infection.

\* \* \* \* \*